United States Patent
Ashcraft et al.

(10) Patent No.: US 10,899,746 B2
(45) Date of Patent: Jan. 26, 2021

(54) BISAMIDE SARCOMERE ACTIVATING COMPOUNDS AND USES THEREOF

(71) Applicants: AMGEN INC., Thousand Oaks, CA (US); CYTOKINETICS, INC., South San Francisco, CA (US)

(72) Inventors: Luke Ashcraft, San Francisco, CA (US); Alessandro Boezio, Somerville, MA (US); John Butler, Somerville, MA (US); Aroop Chandra, South San Francisco, CA (US); Chihyuan Chuang, Millbrae, CA (US); Scott E. Collibee, San Carlos, CA (US); Mikkel V. Debenedetto, Shrewsbury, MA (US); Vincent DiMassa, South San Francisco, CA (US); Russell Graceffa, Hampton, NH (US); Justin Malinowski, Charlestown, MA (US); David Moebius, Westwood, MA (US); Bradley Paul Morgan, Moraga, CA (US); Joshua Payette, Santa Clara, CA (US); Antonio Romero, San Mateo, CA (US); David St. Jean, Jr., Natick, MA (US); Richard Vargas, Bedford, MA (US); John Yeoman, Medford, MA (US); Hanmo Zhang, Chestnut Hill, MA (US); Alan Cheng, San Francisco, CA (US); Felix Gonzalez Lopez De Turiso, Cambridge, MA (US); Michael Garrett Johnson, San Francisco, CA (US)

(73) Assignees: AMGEN INC., Thousand Oaks, CA (US); CYTOKINETICS, INC., South San Francisco, CA (US)

(*) Notice: Subject to any disclaimer, the term of this patent is extended or adjusted under 35 U.S.C. 154(b) by 8 days.

(21) Appl. No.: 16/833,336

(22) Filed: Mar. 27, 2020

(65) Prior Publication Data
US 2020/0223830 A1  Jul. 16, 2020

Related U.S. Application Data

(62) Division of application No. 16/129,862, filed on Sep. 13, 2018.

(Continued)

(51) Int. Cl.

| | | |
|---|---|---|
| C07D 403/12 | (2006.01) |
| C07D 401/14 | (2006.01) |
| C07D 401/12 | (2006.01) |
| C07D 413/14 | (2006.01) |
| C07D 207/16 | (2006.01) |
| C07D 405/12 | (2006.01) |
| C07D 417/14 | (2006.01) |
| C07D 401/06 | (2006.01) |
| C07D 403/14 | (2006.01) |
| C07D 209/02 | (2006.01) |
| C07D 209/52 | (2006.01) |
| A61P 9/00 | (2006.01) |
| C07D 413/12 | (2006.01) |

(52) U.S. Cl.
CPC .............. *C07D 403/12* (2013.01); *A61P 9/00* (2018.01); *C07D 207/16* (2013.01); *C07D 209/02* (2013.01); *C07D 209/52* (2013.01); *C07D 401/06* (2013.01); *C07D 401/12* (2013.01); *C07D 401/14* (2013.01); *C07D 403/14* (2013.01); *C07D 405/12* (2013.01); *C07D 413/12* (2013.01); *C07D 413/14* (2013.01); *C07D 417/14* (2013.01)

(58) Field of Classification Search
None
See application file for complete search history.

(56) References Cited

U.S. PATENT DOCUMENTS

| 4,904,680 A | 2/1990 | Matsui et al. |
|---|---|---|
| 5,952,307 A | 9/1999 | Powers et al. |

(Continued)

FOREIGN PATENT DOCUMENTS

| JP | 2005/298628 A | 10/2005 |
|---|---|---|
| KR | 2016/0108281 A | 9/2016 |

(Continued)

OTHER PUBLICATIONS

CAS Registry No. 1322226-14-1, 2-Pyrrolidinecarboxamide, 1-[3-(methylsulfonyl)benzoyl]-N-(phenylmethyl)-,(2S), Aug. 24, 2011.

(Continued)

*Primary Examiner* — Kamal A Saeed
(74) *Attorney, Agent, or Firm* — Marshall, Gerstein & Borun LLP

(57) ABSTRACT

The present invention provides a compound of formula (I) or a pharmaceutically acceptable salt thereof, pharmaceutical compositions comprising a compound of the invention, a method for manufacturing compounds of the invention and therapeutic uses thereof.

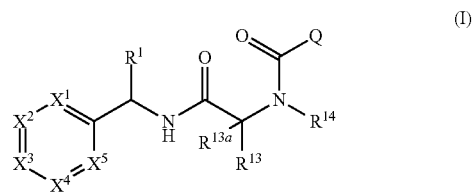

(I)

27 Claims, No Drawings

Related U.S. Application Data

(60) Provisional application No. 62/557,846, filed on Sep. 13, 2017.

(56) References Cited

U.S. PATENT DOCUMENTS

| | | | |
|---|---|---|---|
| 8,604,025 B2 * | 12/2013 | Morgan | C07D 295/26 514/227.5 |
| 9,676,802 B2 | 6/2017 | Qiu et al. | |
| 2002/0022716 A1 | 2/2002 | Hartman et al. | |
| 2005/0176761 A1 | 8/2005 | Pregel et al. | |
| 2007/0066626 A1 | 3/2007 | Morgan et al. | |
| 2007/0078126 A1 | 4/2007 | Morgan et al. | |
| 2009/0192168 A1 | 7/2009 | Muci et al. | |
| 2010/0069370 A1 | 3/2010 | Morgan et al. | |
| 2014/0356322 A1 | 12/2014 | Crews et al. | |

FOREIGN PATENT DOCUMENTS

| | | |
|---|---|---|
| KR | 2017/0000426 A | 1/2017 |
| WO | WO 1996/22966 | 8/1996 |
| WO | WO-2001/29062 A2 | 4/2001 |
| WO | WO-2001/54498 A1 | 8/2001 |
| WO | WO-2001/60798 A1 | 8/2001 |
| WO | WO-2002/46419 A2 | 6/2002 |
| WO | WO-2003/059258 A2 | 7/2003 |
| WO | WO-2003/059265 A2 | 7/2003 |
| WO | WO-2004/064730 A2 | 8/2004 |
| WO | WO-2004/086865 A1 | 10/2004 |
| WO | WO-2004/094610 A2 | 11/2004 |
| WO | WO-2006/009726 A2 | 1/2006 |
| WO | WO-2007/070626 A2 | 6/2007 |
| WO | WO-2007/070683 A2 | 6/2007 |
| WO | WO-2007/078815 A2 | 7/2007 |
| WO | WO-2007/078839 A2 | 7/2007 |
| WO | WO-2007/089336 A2 | 8/2007 |
| WO | WO-2007/089805 A2 | 8/2007 |
| WO | WO-2008/110008 A1 | 9/2008 |
| WO | WO-2008/136695 A1 | 11/2008 |
| WO | WO-2013/059278 A2 | 4/2013 |
| WO | WO-2013/106643 A2 | 7/2013 |
| WO | WO-2013/106646 A2 | 7/2013 |
| WO | WO-2014/152198 A1 | 9/2014 |
| WO | WO-2015/103527 A1 | 7/2015 |
| WO | WO-2015/142001 A2 | 9/2015 |
| WO | WO-2016/118774 A1 | 7/2016 |
| WO | WO-2016/149668 A1 | 9/2016 |
| WO | WO-2016/210240 A1 | 12/2016 |
| WO | WO-2017/035360 A1 | 3/2017 |

OTHER PUBLICATIONS

Cuny et al., Palladium- and copper-catalyzed synthesis of medium- and large-sized ring-fused dihydroazaphenanthrenes and 1,4-benzodiazepine-2,5-diones. control of reaction pathway by metal-switching, *J. Am. Chem. Soc.* 126:14475-84 (2004).

Ellman et al., N-tert-butanesulfinyl imines: versatile intermediates for the asymmetric synthesis of amines, *Acc. Chem. Res.* 35:984-5.

Genaro, Remington's Pharmaceutical Sciences, Mack Printing Company, pp. 1289-1329 (18th ed. 1990).

Greene et al., Protective Groups in Organic Synthesis, Wiley, New York (3rd ed. 1999).

Gross et al., The Peptides, Academic Press, London and New York (1981).

International Search Report and Written Opinion, PCT/US2018/050793 (Nov. 30, 2018).

NCBI Accession No. 10984090, LQRWPDLJGYDVCD-UHFFFAOYSA-N, Oct. 26, 2006.

NCBI Accession No. 20954608, 1-Benzoyl-N-(4-methoxybenzyl)indoline-2-carboxamide, Dec. 5, 2007.

NCBI Accession No. 9893412, GMVOINVPXQBMCP-UHFFFAOYSA-N, Oct. 25, 2006.

Jackson et al., Synthesis and evaluation of diphenyl phosphonate esters as inhibitors of the trypsin-like granzymes A and K and mast cell tryptase, *J. Med. Chem.* 41:2289-301 (1998).

Buckley et al., Small-molecule inhibitors of the interaction between the E3 ligase VHL and HIF1α, *Angew Chem. Int. Ed. Engl.* 51:11463-7 (2012).

CAS Search 3, SciFinder, American Chemical Society (May 2017).

CAS Search 5, SciFinder, American Chemical Society (May 2017).

* cited by examiner

BISAMIDE SARCOMERE ACTIVATING COMPOUNDS AND USES THEREOF

FIELD OF THE INVENTION

The invention relates to substituted bis amide derivatives, particularly to chemical entities that selectively modulate the cardiac sarcomere. More particularly, the invention relates to substituted bis-amide derivatives that are troponin activators, and specifically to said compounds, pharmaceutical compositions and methods of treatment for heart disease.

BACKGROUND OF THE INVENTION

The "sarcomere" is an elegantly organized cellular structure found in cardiac and skeletal muscle made up of interdigitating thin and thick filaments; it comprises nearly 60% of cardiac cell volume. The thick filaments are composed of "myosin," the protein responsible for transducing chemical energy (ATP hydrolysis) into force and directed movement. Myosin and its functionally related cousins are called motor proteins. The thin filaments are composed of a complex of proteins. One of these proteins, "actin" (a filamentous polymer) is the substrate upon which myosin pulls during force generation. Bound to actin are a set of regulatory proteins, the "troponin complex" and "tropomyosin," which make the actin-myosin interaction dependent on changes in intracellular $Ca^{2+}$ levels. With each heartbeat, $Ca^{2+}$ levels rise and fall, initiating cardiac muscle contraction and then cardiac muscle relaxation Each of the components of the sarcomere contributes to its contractile response.

Myosin is the most extensively studied of all the motor proteins. Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes. Myosin-II consists of two globular head domains linked together by a long alpha-helical coiled-coiled tail that assembles with other myosin-IIs to form the core of the sarcomeres thick filament. The globular heads have a catalytic domain where the actin binding and ATP functions of myosin take place. Once bound to an actin filament, the release of phosphate (cf. ATP to ADP) leads to a change in structural conformation of the catalytic domain that in turn alters the orientation of the light-chain binding lever arm domain that extends from the globular head; this movement is termed the powerstroke. This change in orientation of the myosin head in relationship to actin causes the thick filament of which it is a part to move with respect to the thin actin filament to which it is bound. Un-binding of the globular head from the actin filament (also $Ca^{2+}$ modulated) coupled with return of the catalytic domain and light chain to their starting conformation/orientation completes the contraction and relaxation cycle.

Mammalian heart muscle consists of two forms of cardiac myosin, alpha and beta, and they are well characterized. The beta form is the predominant form (>90 percent) in adult human cardiac muscle. Both have been observed to be regulated in human heart failure conditions at both transcriptional and translational levels, with the alpha form being down-regulated in heart failure.

The sequences of all of the human skeletal, cardiac, and smooth muscle myosins have been determined. While the cardiac alpha and beta myosins are very similar (93% identity), they are both considerably different from human smooth muscle (42% identity) and more closely related to skeletal myosins (80% identity). Conveniently, cardiac muscle myosins are incredibly conserved across mammalian species. For example, both alpha and beta cardiac myosins are >96% conserved between humans and rats, and the available 250-residue sequence of porcine cardiac beta myosin is 100% conserved with the corresponding human cardiac beta myosin sequence. Such sequence conservation contributes to the predictability of studying myosin based therapeutics in animal based models of heart failure.

The components of the cardiac sarcomere present targets for the treatment of heart failure, for example by increasing contractility or facilitating complete relaxation to modulate systolic and diastolic function, respectively.

Congestive heart failure ("CHF") is not a specific disease, but rather a constellation of signs and symptoms, all of which are caused by an inability of the heart to adequately respond to exertion by increasing cardiac output. The dominant pathophysiology associated with CHF is systolic dysfunction, an impairment of cardiac contractility (with a consequent reduction in the amount of blood ejected with each heartbeat). Systolic dysfunction with compensatory dilation of the ventricular cavities results in the most common form of heart failure, "dilated cardiomyopathy," which is often considered to be one in the same as CHF. The counterpoint to systolic dysfunction is diastolic dysfunction, an impairment of the ability to fill the ventricles with blood, which can also result in heart failure even with preserved left ventricular function. Congestive heart failure is ultimately associated with improper function of the cardiac myocyte itself, involving a decrease in its ability to contract and relax.

Many of the same underlying conditions can give rise to systolic and/or diastolic dysfunction, such as atherosclerosis, hypertension, viral infection, valvular dysfunction, and genetic disorders. Patients with these conditions typically present with the same classical symptoms: shortness of breath, edema and overwhelming fatigue. In approximately half of the patients with dilated cardiomyopathy, the cause of their heart dysfunction is ischemic heart disease due to coronary atherosclerosis. These patients have had either a single myocardial infarction or multiple myocardial infarctions; here, the consequent scarring and remodeling results in the development of a dilated and hypocontractile heart. At times the causative agent cannot be identified, so the disease is referred to as "idiopathic dilated cardiomyopathy." Irrespective of ischemic or other origin, patients with dilated cardiomyopathy share an abysmal prognosis, excessive morbidity and high mortality.

The prevalence of CHF has grown to epidemic proportions as the population ages and as cardiologists have become more successful at reducing mortality from ischemic heart disease, the most common prelude to CHF. Roughly 4.6 million people in the United States have been diagnosed with CHF; the incidence of such diagnosis is approaching 10 per 1000 after 65 years of age. Hospitalization for CHF is usually the result of inadequate outpatient therapy. Hospital discharges for CHF rose from 377,000 (in 1979) to 970,000 (in 2002) making CHF the most common discharge diagnosis in people age 65 and over. The five-year mortality from CHF approaches 50%. Hence, while therapies for heart disease have greatly improved and life expectancies have extended over the last several years, new and better therapies continue to be sought, particularly for CHF.

"Acute" congestive heart failure (also known as acute "decompensated" heart failure) involves a precipitous drop in cardiac function resulting from a variety of causes. For example in a patient who already has congestive heart failure, a new myocardial infarction, discontinuation of medications, and dietary indiscretions may all lead to accumulation of edema fluid and metabolic insufficiency even in the resting state. A therapeutic agent that increases cardiac function during such an acute episode could assist in relieving this metabolic insufficiency and speeding the removal of edema, facilitating the return to the more stable "compensated" congestive heart failure state. Patients with very advanced congestive heart failure particularly those at the end stage of the disease also could benefit from a therapeutic agent that increases cardiac function, for example, for stabilization while waiting for a heart transplant. Other potential benefits could be provided to patients coming off a bypass pump, for example, by administration of an agent that assists the stopped or slowed heart in resuming normal function. Patients who have diastolic dysfunction (insufficient relaxation of the heart muscle) could benefit from a therapeutic agent that modulates relaxation.

Inotropes are drugs that increase the contractile ability of the heart. As a group, all current inotropes have failed to meet the gold standard for heart failure therapy, i.e., to prolong patient survival. In addition, current agents are poorly selective for cardiac tissue, in part leading to recognized adverse effects that limit their use. Despite this fact, intravenous inotropes continue to be widely used in acute heart failure (e.g., to allow for reinstitution of oral medications or to bridge patients to heart transplantation) whereas in chronic heart failure, orally given digoxin is used as an inotrope to relieve patient symptoms, improve the quality of life, and reduce hospital admissions.

Current inotropic therapies improve contractility by increasing the calcium transient via the adenylyl cyclase pathway, or by delaying cAMP degradation through inhibition of phosphodiesterase (PDE), which can be detrimental to patients with heart failure.

New approaches are needed to improve cardiac function in congestive heart failure. There remains a need for agents that exploit different mechanisms of action and may have better outcomes in terms of relief of symptoms, safety, and patient mortality, both short-term and long-term.

SUMMARY OF THE INVENTION

The present invention provides new compounds which activate the cardiac sarcomere. In particular, compounds of the invention may bind to the Troponin C/Troponin I interface to increase activity of the cardiac sarcomere.

The invention provides, in one aspect, bis-amide compounds which modulate the activity of cardiac sarcomere. Preferably, the bis-amide compounds of the invention are troponin activators interface to increase activity of the cardiac sarcomere. In some embodiments, the bis-amide compounds of the invention are troponin activators that activate the cardiac sarcomere. In some embodiments, the bis-amide compounds of the invention are troponin activators that increase the activity of the cardiac sarcomere. In certain preferred applications, the bis-amide compounds of the invention are compounds that activate the cardiac sarcomere by binding to the Troponin C and Troponin I interface.

The bis-amide compounds of the invention are compounds and salts according Formula (I):

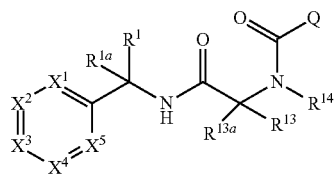

Also provided is a pharmaceutical composition comprising a pharmaceutically acceptable excipient, carrier or adjuvant and at least one compound of formula (I) or subformulae thereof.

Also provided is a packaged pharmaceutical composition, comprising a pharmaceutical composition comprising a pharmaceutically acceptable excipient, carrier or adjuvant and at least one compound of formula (I) or subformulae thereof, and instructions for using the composition to treat a patient suffering from a heart disease.

Also provided is a method of treating heart disease in a mammal which method comprises administering to a mammal in need thereof a therapeutically effective amount of at least one compound of formula (I) or subformulae thereof or a pharmaceutical composition comprising a pharmaceutically acceptable excipient, carrier or adjuvant and at least one compound of formula (I) or subformulae thereof.

Also provided is a method for modulating the cardiac sarcomere in a mammal which method comprises administering to a mammal in need thereof a therapeutically effective amount of at least one compound of formula (I) or subformulae thereof or a pharmaceutical composition comprising a pharmaceutically acceptable excipient, carrier or adjuvant and at least one compound of formula (I) or subformulae thereof.

Also provided is a method for potentiating Troponin C, Troponin I or the interface of Troponin C and Troponin I to increase activity of the cardiac sarcomere in a mammal which method comprises administering to a mammal in need thereof a therapeutically effective amount of at least one compound of formula (I) or subformulae thereof or a pharmaceutical composition comprising a pharmaceutically acceptable excipient, carrier or adjuvant and at least one compound of formula (I) or subformulae thereof.

Also provided is the use, in the manufacture of a medicament for treating heart disease, of at least one compound of formula I or subformulae thereof.

Other aspects and embodiments will be apparent to those skilled in the art form the following detailed description.

DETAILED DESCRIPTION OF THE INVENTION

The invention related generally to compounds of Formula I and salts and tautomers thereof which activate the cardiac sarcomere. Compounds and salts thereof according to Formula I are generally represented by the structure:

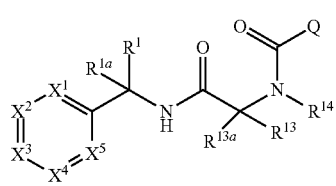

wherein

Q is 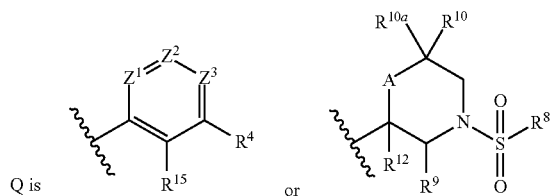

or a 5-member heteroaryl having 1 or 2 ring heteroatoms independently selected from N, O, and S which is optionally substituted with 1 or 2 groups selected from $C_1$-$C_6$alkyl and halo $C_1$-$C_6$alkyl;

A is absent, oxygen, N(H), N($C_1$-$C_6$alkyl) or $CR^{11}R^{11a}$;

$X^1$ is N or $CR^2$;

$X^2$, $X^3$, $X^4$ and $X^5$ are each independently selected from N and $CR^3$ provided that 0, 1, or 2 of $X^1$, $X^2$, $X^3$, $X^4$ and $X^5$ are N and the remainder are $CR^2$ or $CR^3$;

$R^1$ is selected from the group consisting of hydrogen, $C_1$-$C_6$alkyl, halo $C_1$-$C_6$alkyl, hydroxy $C_1$-$C_6$alkyl, $C_2$-$C_6$alkenyl, $C_2$-$C_6$alkynyl, $C_3$-$C_7$cycloalkyl optionally substituted with 1 or 2 groups selected from hydroxy, halogen, and $C_1$-$C_4$alkyl, hydroxy $C_3$-$C_7$cycloalkyl, $C_3$-$C_7$cycloalkyl$C_1$-$C_4$alkyl, hydroxy $C_3$-$C_7$cycloalkyl$C_1$-$C_4$alkyl, and 4 to 7 member heterocycloalkyl having 1 or 2 ring heteroatoms independently selected from N, O and S, which heterocycloalkyl is optionally substituted with 1 or 2 groups selected from oxo, hydroxy, halogen and $C_1$-$C_4$alkyl;

$R^{1a}$ is selected from the group consisting of hydrogen, $C_1$-$C_6$alkyl and halogen;

$R^2$ is selected from the group consisting of hydrogen, halogen, $C_1$-$C_6$alkyl, halo$C_1$-$C_6$alkyl, $C_2$-$C_6$alkenyl, $C_2$-$C_6$alkynyl, $C_3$-$C_7$cycloalkyl, $C_3$-$C_7$cycloalkyl$C_1$-$C_4$alkyl, $C_1$-$C_6$alkoxy, halo$C_1$-$C_6$alkoxy and $SF_5$; or $R^1$ and $R^2$, taken in combination form a divalent group selected from —$CH_2$—, —$CH_2CH_2$—, —$CH_2CH_2CH_2$—, —$OCH_2$—, —$CH_2OCH_2$—, —$OCH_2CH_2$—, —$CH_2N(H)CH_2$— and —$CH_2N(C_1$-$C_4$alkyl$)CH_2$—, each of which is optionally substituted with $C_1$-$C_4$alkyl or hydroxy$C_1$-$C_4$alkyl and wherein the oxygen of —$OCH_2CH_2$— or —$OCH_2$— is attached to the $CR^2$ carbon;

$R^3$ is independently selected from the group consisting of hydrogen, halogen, $C_1$-$C_6$alkyl, halo$C_1$-$C_6$alkyl, $C_2$-$C_6$alkenyl, $C_2$-$C_6$alkynyl, $C_3$-$C_7$cycloalkyl, $C_3$-$C_7$cycloalkyl$C_1$-$C_4$alkyl, $C_1$-$C_6$alkoxy, halo$C_1$-$C_6$alkoxy and $SF_5$ $Z^1$ is N or $CR^5$;

$Z^2$ is N or $CR^6$;

$Z^3$ is N or $CR^7$, wherein 0, 1, or 2 of $Z^1$, $Z^2$ and $Z^3$ can be N;

$R^4$ is hydrogen, halogen, $C_1$-$C_6$alkyl, $C_1$-$C_6$alkoxy, halo$C_1$-$C_6$alkyl, $C_3$-$C_7$cycloalkyl, cyano, benzoyl, $SO_2$—$R^8$ or 4 to 7 member heterocycloalkyl having a ring heteroatom selected from N, O and S which heterocycloalkyl is substituted with 0, 1 or 2 groups independently selected from the group consisting of halogen, oxo, $C_1$-$C_6$alkyl, C(O)$C_1$-$C_6$alkyl, and $SO_2R^8$, and wherein when $R^4$ is $C_1$-$C_6$alkyl, halo$C_1$-$C_6$alkyl, or $C_3$-$C_7$cycloalkyl, it is optionally substituted with one or two groups independently selected from hydroxy, cyano, $CO_2H$, $CO_2C_1$-$C_6$alkyl and C(O)$NH_2$;

$R^5$ is hydrogen, $C_1$-$C_6$alkyl, $C_1$-$C_6$alkoxy, $C_1$-$C_6$alkoxy, amino, mono- or di-$C_1$-$C_6$alkylamino, $C_3$-$C_7$cycloalkylamino or —N(H)C(O)$C_1$-$C_4$alkyl, where each alkyl or cycloalkyl is optionally substituted with hydroxy;

$R^6$ is hydrogen, $C_1$-$C_6$alkyl, halo$C_1$-$C_6$alkyl or halogen;

$R^5$ and $R^6$, taken in combination with the interposed atoms, form a 5- or 6-membered heteroaryl having 1 or 2 ring heteroatoms selected from N, O, and S;

$R^7$ and $R^8$ taken in combination form a divalent group selected from —$CH_2CH_2$— and —$CH_2CH_2CH_2$—; or $R^7$ is hydrogen, $C_1$-$C_6$alkyl, or $SO_2C_1$-$C_6$alkyl; $R^8$ is $C_1$-$C_6$alkyl, $NR^{8d}R^{8e}$, $C_3$-$C_7$cycloalkyl, halo$C_1$-$C_6$alkyl or benzyl, wherein each alkyl, cycloalkyl or haloalkyl is optionally substituted with hydroxy, $CO_2H$, $CO_2C_1$-$C_6$alkyl or C(O)$NH_2$; or $R^8$ is a group of the formula:

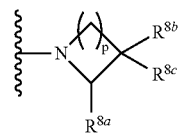

wherein p is 1 or 2;

$R^{8a}$ is hydrogen, $C_1$-$C_6$alkyl, benzyl, or phenyl optionally substituted with $C_1$-$C_6$alkyl or halogen;

$R^{8b}$ is hydrogen, halogen, $C_1$-$C_6$alkyl, $C_2$-$C_6$alkenyl, $C_2$-$C_6$alkynyl, halo$C_1$-$C_6$alkyl, $C_1$-$C_6$alkoxy, $C_1$-$C_6$alkoxy$C_1$-$C_4$alkyl, $C_3$-$C_7$cycloalkyl, cyano, amino, N(H)C(O)$C_1$-$C_6$alkyl, N(H)C(O)$C_3$-$C_7$cycloalkyl, N(H)C(O)halo$C_1$-$C_6$alkyl, $CO_2H$, C(O)$NH_2$, C(O)NH($C_1$-$C_6$alkyl), C(O)N($C_1$-$C_6$alkyl$)_2$, C(O)$C_1$-$C_6$alkyl, C(O)halo$C_1$-$C_6$alkyl, $SO_2C_1$-$C_6$alkyl, phenyl optionally substituted with halogen, $C_1$-$C_4$alkyl or halo$C_1$-$C_4$alkyl, benzyl optionally substituted with halogen, phenoxy optionally substituted with halogen, 4 to 7 member heterocycloalkyl having 1 or 2 ring heteroatoms selected from N, O and S, or 5 or 6 member heteroaryl having 1 ring heteroatom selected from N, O or S and 0, 1 or 2 additional ring nitrogen atoms, which heteroaryl is optionally substituted with 1 or 2 $C_1$-$C_6$alkyl, and wherein the alkoxy is optionally substituted with halogen, phenyl or halogen substituted phenyl;

$R^{8c}$ is hydrogen, halogen, hydroxy or $C_1$-$C_6$alkyl; or $CR^{8b}R^{8c}$, taken in combination, forms a spirocyclic 3 to 6 member carboxycle or a 4 to 6 member heterocycle having a ring heteroatom selected from N, O and S, which spirocycle is optionally substituted with hydroxy, $C_1$-$C_4$alkyl, halo$C_1$-$C_4$alkyl or $C_1$-$C_4$alkoxy;

$R^{8d}$ is hydrogen, $C_1$-$C_6$alkyl, halo$C_1$-$C_6$alkyl, $C_3$-$C_7$cycloalkyl, or 4 to 7 member heterocycloalkyl having 1 ring heteroatom selected from N, O and S and 0 or 1 additional ring nitrogen atoms, which heterocycloalkyl is optionally substituted with 1 or 2 substituents independently selected from hydroxy, halogen, oxo, $C_1$-$C_6$alkyl, and $C_1$-$C_6$alkoxy;

$R^{8e}$ is hydrogen or $C_1$-$C_6$alkyl; or $NR^{8d}R^{8e}$, taken in combination, forms a 4 to 7 member heterocycloalkyl optionally comprising an additional ring heteroatom selected from N, O and S, which heterocycloalkyl is optionally substituted with 1 or 2 substituents independently selected from hydroxy, halogen, oxo, $C_1$-$C_6$alkyl, $C_1$-$C_6$alkoxy and heteroaryl, which heteroaryl has 5 or 6 ring atoms and has one ring heteroatom selected from N, O and S and 0 or 1 additional ring nitrogen atom, or $NR^{8d}R^{8e}$, taken in combination, forms a 5 or 6 member heteroaryl, optionally comprising 1 additional ring heteroatom selected from N, O and S;
$R^9$ is hydrogen or $C_1$-$C_6$alkyl;
$R^{10}$ and $R^{10a}$ are each independently selected from the group consisting of hydrogen, halogen and $C_1$-$C_6$alkyl; or
$R^9$ and $R^{10}$, taken in combination, form a divalent bridge selected from O, $CH_2$, and $CH_2CH_2$ and $R^{10a}$ is hydrogen;
$R^{11a}$ is hydrogen or halogen;
$R^{12}$ is hydrogen or halogen;
$R^{11}$ is selected from the group consisting of hydrogen, halogen, $C_1$-$C_6$alkyl, $N(H)C_1$-$C_6$alkyl and $N(H)C_3$-$C_7$cycloalkyl; or
$R^{11}$ and $R^{12}$, taken in combination, form a double bond;
$R^{13a}$ is hydrogen or $C_1$-$C_6$alkyl;
$R^{13}$ is $C_1$-$C_6$alkyl, $C_3$-$C_7$cycloalkyl or $C_3$-$C_7$cycloalkyl$C_1$-$C_6$alkyl;
$R^{14}$ is $C_1$-$C_5$alkyl, $C_3$-$C_7$cycloalkyl or $C_3$-$C_7$cycloalkyl$C_1$-$C_6$alkyl; or
$R^{13}$ and $R^{14}$, taken in combination with the interposed C and N atoms, form a saturated or partially unsaturated 4 to 7 member heterocycle which heterocycle further comprises 0 or 1 additional ring heteroatoms selected from N, O and S, which heterocycle is optionally fused to a benzo ring or a saturated carbocycle having 3 to 7 ring atoms, or which heterocycle is optionally taken together with a saturated carbocycle having 3 to 7 ring atoms to form a spirocyclic ring, and wherein the heterocycle is optionally substituted with 0, 1, 2, or 3 substituents independently selected from the group consisting of halogen, hydroxy, oxo, $C_1$-$C_6$alkyl, $C_2$-$C_6$alkenyl, $C_2$-$C_6$alkynyl, halo$C_1$-$C_6$alkyl, $C_1$-$C_6$alkoxy, $C_3$-$C_7$cycloalkyl, O—C(O)pyridine substituted with $C_1$-$C_4$alkyl and halo$C_1$-$C_4$alkyl; and
$R^{15}$ is hydrogen or halogen;
with the proviso that
(1) when $R^4$ is $SO_2CH_3$, then at least one occurrence of $R^1$, $R^2$ or $R^3$ is not hydrogen;
(2) when $R^4$ is halogen, trifluoromethyl or cyano and $R^6$ is hydrogen or halogen, then at least one occurrence of $R^1$ or $R^2$ is not hydrogen or $R^1$ is not methyl;
(3) when $R^5$ is $C_1$-$C_6$alkoxy, then $R^4$ is not hydrogen or halogen; and
(4) when $R^4$ is $C_1$-$C_5$alkoxy or $C_1$-$C_6$alkyl, then $R^2$ is not hydrogen.

In certain aspects of the first embodiment, compound of Formula I include compounds wherein Q is

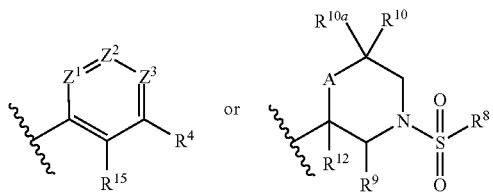

and all other variables are as defined in the first embodiment. In certain aspects, Q is

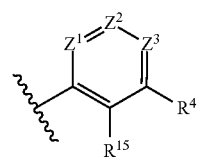

and all other variables are as defined in the first embodiment. In certain aspects, Q is

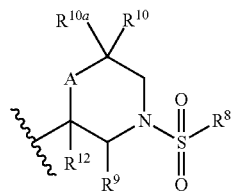

and all other variables are as defined in the first embodiment.

In certain aspects of the first embodiment, compounds of Formula I include compounds of Formula Ia:

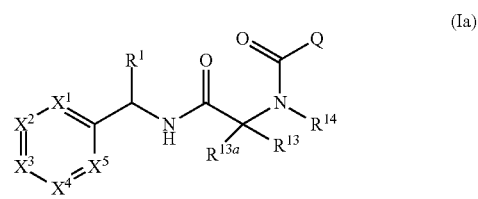

(Ia)

where variables Q, $X^1$, $X^2$, $X^3$, $X^4$, $X^5$, $R^1$, $R^{13}$, $R^{13a}$ and $R^{14}$ are as defined in the first embodiment.

In other aspects of the first embodiment, compounds of Formula I include compounds of Formula Ib:

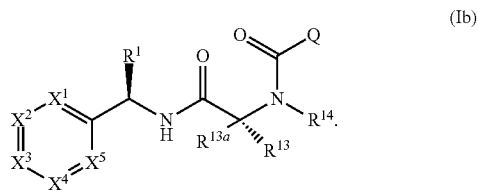

(Ib)

where variables Q, $X^1$, $X^2$, $X^3$, $X^4$, $X^5$, $R^1$, $R^{13}$, $R^{13a}$ and $R^{14}$ are as defined in the first embodiment.

In a second embodiment, the invention provides compounds of the first embodiment in which $X^1$ is $CR^2$, $X^2$ is N or $CR^3$, $X^3$ is $CR^{3a}$, $X^4$ is N or $CR^3$ and $X^5$ is $CR^3$;
$R^2$ is hydrogen, halogen, $C_1$-$C_4$alkyl, cyclopropyl, halo$C_1$-$C_4$alkyl, $C_1$-$C_4$alkoxy or halo$C_1$-$C_4$alkoxy;
$R^3$ is independently selected at each occurrence from the group consisting of hydrogen, halogen, $C_1$-$C_4$alkyl, cyclopropyl, halo$C_1$-$C_4$alkyl, $C_1$-$C_4$alkoxy and halo$C_1$-$C_4$alkoxy; and
$R^{3a}$ is halogen, $C_1$-$C_6$alkyl, halo$C_1$-$C_6$alkyl, $C_2$-$C_6$alkenyl, $C_2$-$C_6$alkynyl, $C_3$-$C_7$cycloalkyl, $C_3$-$C_7$cycloalkyl$C_1$-$C_4$alkyl, $C_1$-$C_6$alkoxy, halo$C_1$-$C_6$alkoxy or $SF_5$.

In a third embodiment, the invention provides compounds of the first or second embodiment in which $X^1$ is $CR^2$; $R^2$ is hydrogen, halogen, $C_1$-$C_4$alkyl or $C_1$-$C_4$alkoxy; $X^2$ is CH or N; $X^3$ is $CR^{3a}$; $R^{3a}$ is halogen, $C_1$-$C_4$alkyl, halo$C_1$-$C_4$alkyl, halo$C_1$-$C_6$alkoxy or $SF_5$; $X^4$ is $CR^3$ or N; $R^3$ is hydrogen or halogen; and $X^5$ is CH.

In a fourth embodiment, the invention provides compounds of any one of the first to third embodiment in which $R^2$ is hydrogen, halogen, methyl, ethyl, methoxy or ethoxy; $X^2$ and $X^5$ are each CH; $X^3$ is $CR^{3a}$; $R^{3a}$ is halogen, methyl, ethyl, fluoromethyl, difluoromethyl, trifluoromethyl, trifluormethoxy or $SF_5$; $X^4$ is $CR^3$; and $R^3$ is hydrogen or halogen.

In some aspects, $R^{3a}$ is fluoro, chloro, $CH_2F$, $CHF_2$, or $CF_3$. In certain aspects, $X^1$ is $CR^2$; $R^2$ is halogen; $X^2$ and $X^5$ are each CH; $X^3$ is $CR^{3a}$; $R^{3a}$ is halogen or trifluoromethyl; $X^4$ is $CR^3$; and $R^3$ is halogen.

In a fifth embodiment, the invention provides compounds of any one of the first to fourth embodiment in which $R^1$ is selected from the group consisting of hydrogen, $C_1$-$C_6$alkyl, halo $C_1$-$C_6$alkyl, $C_3$-$C_7$cycloalkyl, $C_3$-$C_7$cycloalkylmethyl, and 4 to 6 member heterocycloalkyl having a ring heteroatom selected from N and O, which heterocycloalkyl is optionally substituted with 1 or 2 groups selected from oxo, halogen, and hydroxy, and wherein the alkyl or cycloalkyl is optionally substituted with hydroxy. In an embodiment, the invention provides compounds of any one of the first to fourth embodiments in which $R^1$ is selected from the group consisting of $C_2$-$C_6$alkyl, halo $C_1$-$C_6$alkyl, $C_2$-$C_6$alkenyl, $C_2$-$C_6$alkynyl, $C_3$-$C_7$cycloalkyl, $C_3$-$C_7$cycloalkyl$C_1$-$C_4$alkyl, and 4 to 7 member heterocycloalkyl having 1 or 2 ring heteroatoms independently selected from N, O and S, which heterocycloalkyl is optionally substituted with 1 or 2 groups selected from oxo, hydroxy, halogen and $C_1$-$C_4$alkyl and wherein the alkyl or cycloalkyl is optionally substituted with hydroxy;

In a sixth embodiment, the invention provides compounds of any one of the first to fifth embodiment in which $R^1$ is $C_1$-$C_4$alkyl, trifluoromethyl, $C_3$-$C_5$cycloalkyl, $C_3$-$C_5$cycloalkylmethyl, oxetanyl, tetrahydrofuryl, or azetidinyl, wherein each alkyl, cycloalkyl, oxetanyl or azetidinyl is optionally substituted with hydroxy or halogen.

In a seventh embodiment, the invention provides compounds of any one of the first to sixth embodiment in which $R^1$ is methyl, isopropyl, cyclopropyl, cyclopropylmethyl, cyclobutyl, oxetanyl or 1-hydroxycyclopropyl. In certain aspects of the seventh embodiment, $R^1$ is methyl, isopropyl, cyclopropyl or oxetanyl. In certain preferred aspects of the seventh embodiment, $R^1$ is cyclopropyl. In certain aspects, $R^1$ is methyl, isopropyl, cyclopropyl, cyclopropylmethyl, cyclobutyl, oxetanyl, difluoromethyl, 1-hydroxycyclopropyl, 3-hydroxycyclobutyl, 3-hydroxy-3-methylcyclobutyl, 3-fluorooxetanyl or oxopyrrolidinyl.

In an eighth embodiment, the invention provides compounds of any one of the first to seventh embodiment in which $R^{13}$ and $R^{14}$ are each independently selected from the group consisting of $C_1$-$C_4$alkyl, $C_3$-$C_5$cycloalkyl and $C_3$-$C_5$cycloalkylmethyl; and $R^{13a}$ is hydrogen.

In a ninth embodiment, the invention provides compounds of any one of the first to eighth embodiment in which $R^{13}$ and $R^{14}$ are each methyl and $R^{13a}$ is hydrogen.

In a tenth embodiment, the invention provides compounds of any one of the first to seventh embodiment in which $R^{13a}$ is hydrogen; and $R^{13}$ and $R^{14}$, taken in combination with the interposed C and N atoms, form a saturated or partially unsaturated 4 to 6 member heterocycle, which heterocycle further comprises 0 or 1 additional ring heteroatoms selected from N, O and S, wherein the heterocycle is optionally fused to a saturated carbocycle having 3 to 7 ring atoms, or which heterocycle is optionally taken together with a saturated carbocyle having 3 to 7 ring atoms to form a spirocyclic ring, and wherein the heterocycle is optionally substituted with 0, 1, 2, or 3 substituents independently selected from the group consisting of halogen, hydroxy, $C_1$-$C_6$alkyl, halo$C_1$-$C_6$alkyl, $C_1$-$C_6$alkoxy and $C_3$-$C_7$cycloalkyl.

In an eleventh embodiment, the invention provides compounds of any one of the first to seventh and tenth embodiment in which $R^{13a}$ is hydrogen; and $R^{13}$ and $R^{14}$, taken in combination with the interposed C and N atoms, form a heterocyclic ring selected from the group consisting of azetidine, pyrrolidine, thiazolidine, piperidine and morpholine, wherein the heterocyclic ring is optionally fused to a cyclopropyl ring and the heterocyclic ring is further optionally substituted with 1 or 2 substituents independently selected from the group consisting of halogen, hydroxy, methyl, hydroxymethyl, methoxy and cyclopropyl.

In a twelfth embodiment, the invention provides compounds of any one of the first to seventh, tenth and eleventh embodiment in which $R^{13a}$ is hydrogen; and $R^{13}$ and $R^{14}$, taken in combination with the interposed C and N atoms, form a pyrrolidine ring, wherein the pyrrolidine ring is optionally fused with to a cyclopropyl ring and the pyrrolidine ring is further optionally substituted with 1 or 2 substituents independently selected from the group consisting of halogen, hydroxy, methyl, hydroxymethyl and cyclopropyl. In certain aspects of the twelfth embodiment, $R^{13a}$ is hydrogen; and $R^{13}$ and $R^{14}$, taken in combination with the interposed C and N atoms, form a pyrrolidine ring, wherein the pyrrolidine ring is fused to a cyclopropyl ring and the pyrrolidine ring is unsubstituted. In certain aspects of the twelfth embodiment, $R^{13a}$ is hydrogen; $R^{13}$ and $R^{14}$, taken in combination with the interposed C and N atoms, form a pyrrolidine ring, wherein the pyrrolidine ring is fused to a cyclopropyl ring and the pyrrolidine ring is unsubstituted; $X^1$ is $CR^2$; $R^2$ is halogen; $X^2$ and $X^5$ are each CH; $X^3$ is $CR^{3a}$; $R^{3a}$ is halogen or trifluoromethyl; $X^4$ is $CR^3$; and $R^3$ is halogen. In certain aspects of the twelfth embodiment, $R^{13a}$ is hydrogen; $R^{13}$ and $R^{14}$, taken in combination with the interposed C and N atoms, form a pyrrolidine ring, wherein the pyrrolidine ring is fused to a cyclopropyl ring and the pyrrolidine ring is unsubstituted, and $R^1$ is cyclopropyl.

In a thirteenth embodiment, the invention provides compounds of any one of the first to twelfth embodiment in which Q in which Q is

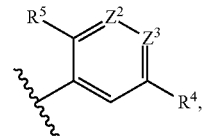

wherein $Z^2$ is N or $CR^6$; $Z^3$ is N or $CR^7$, wherein 0 or 1 of $Z^2$ and $Z^3$ can be N; $R^4$ is $C_1$-$C_4$alkyl, $C_1$-$C_4$alkoxy, cyano, $SO_2$—$R^8$, or 4 to 7 member heterocycloalkyl having a ring heteroatom selected from N, O and S which heterocycloalkyl is substituted with 0, 1 or 2 groups independently selected from the group consisting of halogen, oxo, $C_1$-$C_6$alkyl, $C(O)C_1$-$C_6$alkyl, and $SO_2R^8$ and wherein each alkyl or cycloalkyl is optionally substituted with hydroxy, cyano, $CO_2H$ or $C(O)NH_2$; $R^5$ is hydrogen, $C_1$-$C_4$alkyl, amino, mono- and di-$C_1$-$C_4$alkylamino, $C_3$-$C_6$cycloalkylamino or —N(H)C(O)$C_1$-$C_4$alkyl, where each alkyl or cycloalkyl is optionally substituted with hydroxy; $R^6$ is hydrogen, $C_1$-$C_4$alkyl, halo$C_1$-$C_6$alkyl or halogen; $R^7$ is hydrogen or $C_1$-$C_4$alkyl; $R^8$ is $C_1$-$C_6$alkyl, $NR^{8d}R^{8e}$, $C_3$-$C_7$cycloalkyl or halo$C_1$-$C_6$alkyl, wherein each alkyl, cycloalkyl or haloalkyl is optionally substituted with hydroxy, $CO_2H$, $CO_2C_1$-$C_6$alkyl or $C(O)NH_2$; or $R^8$ is a group of the formula:

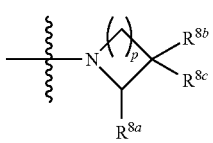

wherein p is 1 or 2; $R^{8a}$ is hydrogen, $C_1$-$C_6$alkyl or phenyl substituted with halogen; $R^{8b}$ is hydrogen, halogen, $C_1$-$C_4$alkyl, halo$C_1$-$C_4$alkyl, $C_1$-$C_4$alkoxy, $C_3$-$C_5$cycloalkyl, cyano, amino or $SO_2C_1$-$C_6$alkyl;

$R^{8c}$ is hydrogen, halogen, hydroxy or $C_1$-$C_6$alkyl; or $CR^{8b}R^{8c}$, taken in combination form a spirocyclic 3 to 6 member carboxycle or a 4 to 6 member heterocycle having a ring heteroatom selected from N, O or S, which spirocycle is optionally substituted with hydroxy, $C_1$-$C_4$alkyl, halo$C_1$-$C_4$alkyl or $C_1$-$C_4$alkoxy; $R^{8d}$ is hydrogen, $C_1$-$C_6$alkyl, halo$C_1$-$C_6$alkyl, $C_3$-$C_7$cycloalkyl, 4 to 7 member heterocycloalkyl having 1 ring heteroatoms selected from N, O or S and 0 or 1 additional ring nitrogen atoms, which heterocycloalkyl is optionally substituted with 1 or 2 substituents independently selected from hydroxy, halogen, oxo, $C_1$-$C_6$alkyl, or $C_1$-$C_6$alkoxy; $R^{8e}$ is hydrogen or $C_1$-$C_6$alkyl; or $NR^{8d}R^{8e}$, taken in combination, form a 4 to 7 member heterocycloalkyl optionally comprising an additional ring heteroatom selected from N, O or S, which heterocycloalkyl is optionally substituted with 1 or 2 substituents independently selected from hydroxy, halogen, oxo, $C_1$-$C_6$alkyl, $C_1$-$C_6$alkoxy and heteroaryl, which heteroaryl has 5 or 6 ring atoms and has one ring heteroatom selected from N, O and S and 0 or 1 additional ring nitrogen atom, or $NR^{8d}R^{8e}$, taken in combination, forms a 5 or 6 member heteroaryl, which heteroaryl optionally comprises 1 additional ring heteroatom selected from N, O and S.

In a fourteenth embodiment, the invention provides compounds of any one of the first to thirteenth embodiment in which Q is

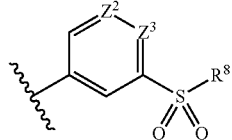

wherein $Z^2$ is CH or N; $Z^3$ is CH or N; $R^8$ is $C_1$-$C_6$alkyl, $C_3$-$C_7$cycloalkyl or halo$C_1$-$C_6$alkyl; or $R^8$ is a group of the formula:

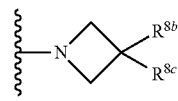

wherein $R^{8b}$ is halogen, $C_1$-$C_4$alkyl, halo$C_1$-$C_4$alkyl, $C_1$-$C_4$alkoxy, $C_3$-$C_5$cycloalkyl, cyano, or amino; $R^{8c}$ is hydrogen, halogen, hydroxy or $C_1$-$C_6$alkyl; or $CR^{8b}R^{8c}$, taken in combination, forms a spirocyclic 3 to 4 member carboxycle or a 4 or 5 member heterocycle having a ring heteroatom selected from N, O and S, which spirocycle is optionally substituted with hydroxy, $C_1$-$C_4$alkyl, halo$C_1$-$C_4$alkyl or $C_1$-$C_4$alkoxy. In certain aspects of the fourteenth embodiment, Q is

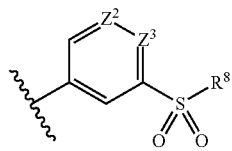

wherein $Z^2$ is N; $Z^3$ is CH; and $R^8$ is $C_1$-$C_6$alkyl. In certain aspects of the fourteenth embodiment, Q is

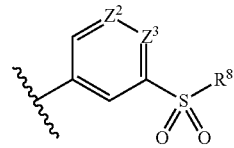

wherein $Z^2$ is CH; $Z^3$ is N; and $R^8$ is $C_1$-$C_6$alkyl. In certain aspects of the fourteenth embodiment, Q is

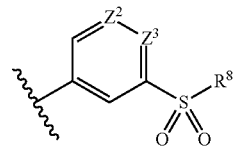

wherein $Z^2$ is N; $Z^3$ is CH; $R^8$ is $C_1$-$C_6$alkyl; $R^{13a}$ is hydrogen; and $R^{13}$ and $R^{14}$, taken in combination with the interposed C and N atoms, form a pyrrolidine ring, wherein the pyrrolidine ring is fused to a cyclopropyl ring and the pyrrolidine ring is unsubstituted. In certain aspects of the fourteenth embodiment, Q is

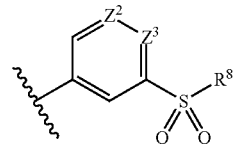

wherein $Z^2$ is CH; $Z^3$ is N; $R^8$ is $C_1$-$C_6$alkyl; $R^{13a}$ is hydrogen; and $R^{13}$ and $R^{14}$, taken in combination with the interposed C and N atoms, form a pyrrolidine ring, wherein the pyrrolidine ring is fused to a cyclopropyl ring and the pyrrolidine ring is unsubstituted. In certain aspects of the fourteenth embodiment, Q is

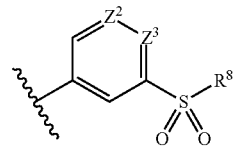

wherein $Z^2$ is N; $Z^3$ is CH; $R^8$ is $C_1$-$C_6$alkyl; $X^1$ is $CR^2$; $R^2$ is halogen; $X^2$ and $X^5$ are each CH; $X^3$ is $CR^{3a}$; $R^{3a}$ is halogen or trifluoromethyl; $X^4$ is $CR^3$; and $R^3$ is halogen. In certain aspects of the fourteenth embodiment, Q is

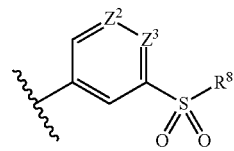

wherein $Z^2$ is CH; $Z^3$ is N; $R^8$ is $C_1$-$C_6$alkyl; $X^1$ is $CR^2$; $R^2$ is halogen; $X^2$ and $X^5$ are each CH; $X^3$ is $CR^{3a}$; $R^{3a}$ is halogen or trifluoromethyl; $X^4$ is $CR^3$; and $R^3$ is halogen. In certain aspects of the fourteenth embodiment, Q is

[Structure: aromatic ring with $Z^2$, $Z^3$ positions and $SO_2R^8$ substituent]

wherein $Z^2$ is N; $Z^3$ is CH; $R^8$ is $C_1$-$C_6$alkyl; and $R^1$ is cyclopropyl. In certain aspects of the fourteenth embodiment, Q is

[Structure: aromatic ring with $Z^2$, $Z^3$ positions and $SO_2R^8$ substituent]

wherein $Z^2$ is CH; $Z^3$ is N; $R^8$ is $C_1$-$C_6$alkyl; and $R^1$ is cyclopropyl.

In a fifteenth embodiment, the invention provides compounds of any one of the first to third embodiment in which the compound is a compound according to the Formula (II):

(II)

[Structure of Formula (II)]

wherein
$R^1$ is selected from the group consisting of hydrogen, $C_1$-$C_6$alkyl, halo $C_1$-$C_6$alkyl, $C_3$-$C_7$cycloalkyl, $C_3$-$C_7$cycloalkylmethyl, and 4 to 6 member heterocycloalkyl having a ring heteroatom selected from N and O, which heterocycloalkyl is optionally substituted with 1 or 2 groups selected from oxo and hydroxy, and wherein the alkyl or cycloalkyl is optionally substituted with hydroxy;
$R^2$ is hydrogen, halogen, $C_1$-$C_4$alkyl or $C_1$-$C_4$alkoxy;
$R^3$ is halogen, $C_1$-$C_4$alkyl, halo$C_1$-$C_4$alkyl or $SF_5$;
$X^4$ is $CR^3$ or N;
$R^3$ is hydrogen or halogen;
$Z^2$ is CH or N;
$Z^3$ is CH or N;
$R^8$ is $C_1$-$C_6$alkyl, $C_3$-$C_7$cycloalkyl or halo$C_1$-$C_6$alkyl; or
$R^8$ is a group of the formula:

[Structure: azetidine with $R^{8b}$ and $R^{8c}$]

wherein
$R^{8b}$ is halogen, $C_1$-$C_4$alkyl, halo$C_1$-$C_4$alkyl, $C_1$-$C_4$alkoxy, $C_3$-$C_5$cycloalkyl, cyano, or amino; $R^{8c}$ is hydrogen, halogen, hydroxy or $C_1$-$C_6$alkyl; or
$CR^{8b}R^{8c}$, taken in combination form a spirocyclic 3 to 4 member carbocycle or a 4 or 5 member heterocycle having a ring heteroatom selected from N, O or S, which spirocycle is optionally substituted with hydroxy, $C_1$-$C_4$alkyl, halo$C_1$-$C_4$alkyl or $C_1$-$C_4$alkoxy;
W is a bond, $CH_2$, $CH_2CH_2$ or $CH_2O$, where the oxygen is adjacent to $CR^{15a}R^{15b}$;
$R^{15a}$ and $R^{15b}$ are independently selected from the group consisting of hydrogen, halogen, hydroxy, $C_1$-$C_4$alkyl, hydroxy$C_1$-$C_4$alkyl, $C_1$-$C_4$alkoxy and $C_3$-$C_6$cycloalkyl; or $R^{15a}$ and $R^{15b}$, taken in combination with the carbon atom to which they are attached, form a spirocyclic cyclopropyl ring;
$R^{16}$ is hydrogen; or
$R^{15a}$ and $R^{16}$, taken in combination with the carbon atoms to which they are attached, form a fused cyclopropyl ring.

In certain aspects of the fifteenth embodiment, compounds of Formula (II) are provided according to Formula (IIa):

(IIa)

[Structure of Formula (IIa)]

where variables $X^4$, $Z^2$, $Z^3$, $R^1$, $R^2$, $R^{3a}$, $R^8$, $R^{15}$, $R^{15a}$ and $R^{16}$ are as defined in the fifteenth embodiment. In some aspects of the fifteenth embodiment, $X^4$ is $CR^3$; $R^3$ is hydrogen or halogen; W is $CH_2$; $Z^2$ is N; and $Z^3$ is CH. In certain aspects of the compounds of Formula (IIa), $R^8$ is $C_1$-$C_6$alkyl. In certain aspects of the compounds of Formula (IIa), $R^1$ is $C_3$-$C_7$cycloalkyl. In certain aspects of the compounds of Formula (IIa), $R^8$ is $C_1$-$C_6$alkyl and $R^1$ is $C_3$-$C_7$cycloalkyl. In certain aspects of the compounds of Formula (IIa), $R^1$ is $C_3$-$C_7$cycloalkyl; $R^2$ is halogen; $R^{3a}$ is halogen or halo$C_1$-$C_4$alkyl; $X^4$ is $CR^3$; $R^3$ is halogen; $Z^2$ is N; $Z^3$ is CH; and $R^8$ is $C_1$-$C_6$alkyl.

In certain other aspects of the fifteenth embodiment, compounds of Formula (II) are provided according to Formula (IIb):

(IIb)

[Structure of Formula (IIb)]

where variables $X^4$, $Z^2$, $Z^3$, $R^1$, $R^2$, $R^{3a}$ and $R^8$ are as defined in the fifteenth embodiment. In certain aspects of the compounds of Formula (IIb), $Z^2$ is N and $Z^3$ is CH. In certain aspects of the compounds of Formula (IIb), $Z^2$ is CH and $Z^3$ is N. In certain aspects of the compounds of Formula (IIb), $R^8$ is $C_1$-$C_6$alkyl. In certain aspects of the compounds of Formula (IIb), $R^1$ is $C_3$-$C_7$cycloalkyl. In certain aspects of the compounds of Formula (IIb), $R^8$ is $C_1$-$C_6$alkyl and $R^1$ is $C_3$-$C_7$cycloalkyl. In certain aspects of the compounds of Formula (IIb), $R^1$ is $C_3$-$C_7$cycloalkyl; $R^2$ is halogen; $R^{3a}$ is halogen or halo$C_1$-$C_4$alkyl; $X^4$ is $CR^3$; $R^3$ is halogen; $Z^2$ is N; $Z^3$ is CH; and $R^8$ is $C_1$-$C_6$alkyl.

In a sixteenth embodiment, the invention provides compounds of any one of the first to twelfth embodiment in which Q is

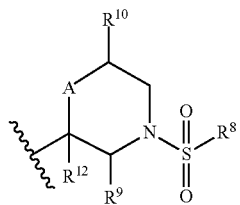

wherein A is oxygen, N(H), or $CHR^{11}$; $R^8$ is $C_1$-$C_6$alkyl, $NR^{8d}R^{8e}$, $C_3$-$C_7$cycloalkyl, halo$C_1$-$C_6$alkyl or benzyl, and wherein each alkyl, cycloalkyl or haloalkyl is optionally substituted with hydroxy, $CO_2H$, $CO_2C_1$-$C_6$alkyl or $C(O)NH_2$; or $R^8$ is a group of the formula:

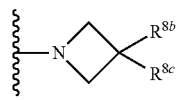

wherein $R^{8b}$ is hydrogen, $C_1$-$C_4$alkyl, halo $C_1$-$C_4$alkyl, $C_1$-$C_4$alkoxy, $C_3$-$C_6$cycloalkyl, cyano, or amino; $R^{8c}$ is hydrogen, hydroxy or $C_1$-$C_6$alkyl; $R^{8d}$ is hydrogen, $C_1$-$C_6$alkyl, halo$C_1$-$C_6$alkyl, or $C_3$-$C_7$cycloalkyl; $R^{8e}$ is hydrogen or $C_1$-$C_6$alkyl; $R^9$ is hydrogen; $R^{10}$ is hydrogen; or $R^9$ and $R^{10}$, taken in combination, form a divalent methylene bridge; and $R^{11}$ is hydrogen or $C_1$-$C_6$alkyl.

In a seventeenth embodiment, the invention provides compounds of any one of the first to third embodiment in which the compound is a compound according to the formula:

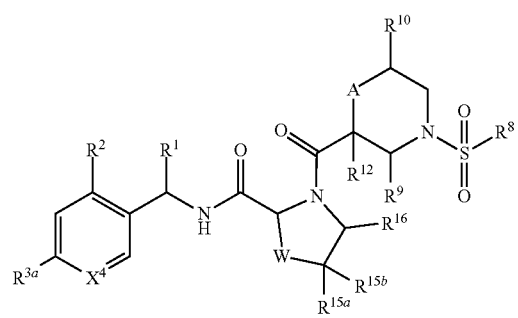

wherein
$R^1$ is selected from the group consisting of hydrogen, $C_1$-$C_6$alkyl, halo $C_1$-$C_6$alkyl, $C_3$-$C_7$cycloalkyl, $C_3$-$C_7$cycloalkylmethyl, and 4 to 6 member heterocycloalkyl having a ring heteroatom selected from N and O, which heterocycloalkyl is optionally substituted with 1 or 2 groups selected from oxo and hydroxy, and wherein the alkyl or cycloalkyl is optionally substituted with hydroxy;

$R^2$ is hydrogen, halogen, $C_1$-$C_4$alkyl or $C_1$-$C_4$alkoxy;

$R^{3a}$ is halogen, $C_1$-$C_4$alkyl, halo$C_1$-$C_4$alkyl or $SF_5$;

$X^4$ is $CR^3$ or N;

$R^3$ is hydrogen or halogen;

$Z^2$ is CH or N;

$Z^3$ is CH or N;

$R^8$ is $C_1$-$C_6$alkyl, $C_3$-$C_7$cycloalkyl or halo$C_1$-$C_6$alkyl; or $R^8$ is a group of the formula:

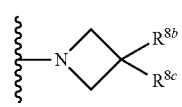

$R^{8b}$ is halogen, $C_1$-$C_4$alkyl, halo$C_1$-$C_4$alkyl, $C_1$-$C_4$alkoxy, $C_3$-$C_5$cycloalkyl, cyano, or amino;

$R^{8c}$ is hydrogen, halogen, hydroxy or $C_1$-$C_6$alkyl; or $CR^{8b}R^{8c}$, taken in combination, forms a spirocyclic 3 to 4 member carboxycle or a 4 or 5 member heterocycle having a ring heteroatom selected from N, O and S, which spirocycle is optionally substituted with hydroxy, $C_1$-$C_4$alkyl, halo$C_1$-$C_4$alkyl or $C_1$-$C_4$alkoxy; W is a bond, $CH_2$, $CH_2CH_2$ or $CH_2O$, where the oxygen is adjacent to $CR^{15a}R^{15b}$;

$R^{15a}$ and $R^{15b}$ are independently selected from the group consisting of hydrogen, halogen, hydroxy, $C_1$-$C_4$alkyl, hydroxy$C_1$-$C_4$alkyl, $C_1$-$C_4$alkoxy and $C_3$-$C_6$cycloalkyl; or $R^{15a}$ and $R^{15b}$, taken in combination with the carbon atom to which they are attached, form a spirocyclic cyclopropyl ring; and $R^{16}$ is hydrogen; or $R^{15a}$ and $R^{16}$, taken in combination with the carbon atoms to which they are attached, form a fused cyclopropyl ring, and $R^{15b}$ is selected from the group consisting of hydrogen, halogen, hydroxy, $C_1$-$C_4$alkyl, hydroxy$C_1$-$C_4$alkyl, $C_1$-$C_4$alkoxy and $C_3$-$C_6$cycloalkyl.

In certain aspects of the seventeenth embodiment, compounds of Formula (III) are provided according to Formula (IIIa):

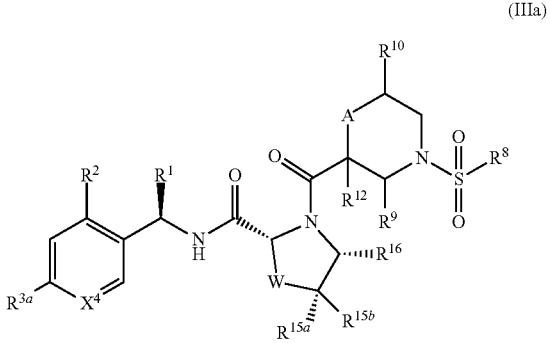

where variables A, W, $X^4$, $R^1$, $R^2$, $R^{3a}$, $R^9$, $R^{10}$, $R^{12}$, $R^{15}$, $R^{15a}$ and $R^{16}$ are as defined in the seventeenth embodiment.

In an Eighteenth Embodiment, the Invention Provides Compounds as Recited in the Below Table A, or a Pharmaceutically Acceptable Salt Thereof:

TABLE A 1-(3-((3-cyano-1-azetidinyl)sulfonyl)benzoyl)-N-((1R)-2-cyclopropyl-1-(4-(trifluoromethyl)phenyl)ethyl)-D-prolinamide;
N—((R)-(4-chloro-2-fluorophenyl)(cyclopropyl)methyl)-1-(((3S)-1-((3-cyano-1-azetidinyl)sulfonyl)-3-piperidinyl)carbonyl)-D-prolinamide;
1-(3-((3-cyano-1-azetidinyl)sulfonyl)benzoyl)-N-((1R)-1-(4-(trifluoromethyl)phenyl)propyl)-D-prolinamide;
1-(((3S)-1-((3-cyano-1-azetidinyl)sulfonyl)-3-piperidinyl)carbonyl)-N-((1R)-1-(2-fluoro-4-(trifluoromethyl)phenyl)propyl)-D-prolinamide;
(1R,2R,5S)-3-((3-((3-cyano-1-azetidinyl)sulfonyl)phenyl)carbonyl)-N-(4-(trifluoromethyl)benzyl)-3-azabicyclo[3.1.0]hexane-2-carboxamide;
1-((3-((3-cyano-1-azetidinyl)sulfonyl)phenyl)carbonyl)-4,4-difluoro-N-((1R)-1-(4-(trifluoromethyl)phenyl)ethyl)-D-prolinamide;
1-(3-((3-cyano-1-azetidinyl)sulfonyl)benzoyl)-N-((1R)-3,3,3-trifluoro-1-(4-(trifluoromethyl)phenyl)propyl)-D-prolinamide;
1-((3-((3-cyano-1-azetidinyl)sulfonyl)phenyl)carbonyl)-4,4-difluoro-N-(4-(trifluoromethyl)benzyl)-D-prolinamide;
1-(((3S)-1-((3-cyano-1-azetidinyl)sulfonyl)-3-piperidinyl)carbonyl)-N-((1R)-1-(2-fluoro-4-(trifluoromethyl)phenyl)-2-methylpropyl)-D-prolinamide;
1-(3-((3-cyano-1-azetidinyl)sulfonyl)benzoyl)-N-((1R)-1-(2-fluoro-4-(trifluoromethyl)phenyl)-2-methylpropyl)-D-prolinamide;
1-(((3S)-1-((3-cyano-1-azetidinyl)sulfonyl)-3-piperidinyl)carbonyl)-N—((R)-cyclopropyl(4-(trifluoromethyl)phenyl)methyl)-D-prolinamide;
1-(3-((3-cyano-1-azetidinyl)sulfonyl)benzoyl)-N-((1R)-1-(2-fluoro-4-(trifluoromethyl)phenyl)propyl)-D-prolinamide;
(2R)-1-((3-((3-cyano-1-azetidinyl)sulfonyl)phenyl)carbonyl)-N-((1R)-1-(3,4-dichlorophenyl)ethyl)-2-piperidinecarboxamide;
1-(((3S)-1-((3-cyano-1-azetidinyl)sulfonyl)-3-piperidinyl)carbonyl)-N-((1R)-2-cyclopropyl-1-(4-(trifluoromethyl)phenyl)ethyl)-D-prolinamide;
(6R)-5-((3-((3-cyano-1-azetidinyl)sulfonyl)phenyl)carbonyl)-N-(4-(trifluoromethyl)benzyl)-5-azaspiro[2.4]heptane-6-carboxamide;
1-((3-((3-cyano-1-azetidinyl)sulfonyl)-5-fluorophenyl)carbonyl)-N-((1R)-1-(4-(trifluoromethyl)phenyl)ethyl)-D-prolinamide;
1-(((3S)-1-((3-cyano-1-azetidinyl)sulfonyl)-3-piperidinyl)carbonyl)-N-((1R)-1-(4-(trifluoromethyl)phenyl)propyl)-D-prolinamide;
(2R)—N-((1R)-1-(4-chlorophenyl)ethyl)-1-((3-((3-cyano-1-azetidinyl)sulfonyl)phenyl)carbonyl)-2-piperidinecarboxamide;
(3R)-4-((3-((3-cyano-1-azetidinyl)sulfonyl)phenyl)carbonyl)-N-((1R)-1-(4-(trifluoromethyl)phenyl)ethyl)-3-morpholinecarboxamide;
N-(4-chloro-2,5-difluorobenzyl)-1-(((3S)-1-((3-cyano-1-azetidinyl)sulfonyl)-3-piperidinyl)carbonyl)-D-prolinamide;
1-((3-((3-cyano-1-azetidinyl)sulfonyl)phenyl)carbonyl)-N-(4-(trifluoromethyl)benzyl)-D-prolinamide;
1-((3-((3-cyano-1-azetidinyl)sulfonyl)phenyl)carbonyl)-N-(3,4-dichlorobenzyl)-D-prolinamide;
(1R,3R,5R)-2-(2-(ethylamino)-5-methylbenzoyl)-N—((R)-(2-fluoro-4-(trifluoromethyl)phenyl)(3-oxetanyl)methyl)-2-azabicyclo[3.1.0]hexane-3-carboxamide;
N-((1S)-1-(4-chloro-3-fluorophenyl)-2-hydroxyethyl)-1-(3-((3-cyano-1-azetidinyl)sulfonyl)benzoyl)-D-prolinamide;
1-(((3S)-1-((3-cyano-1-azetidinyl)sulfonyl)-3-piperidinyl)carbonyl)-4,4-difluoro-N-(4-(trifluoromethyl)benzyl)-D-prolinamide;
1-(2-(cyclopropylamino)-5-(methylsulfonyl)benzoyl)-N—((R)-cyclopropyl(2-fluoro-4-(trifluoromethyl)phenyl)methyl)-D-prolinamide;
(2R)-1-((3-((3-cyano-1-azetidinyl)sulfonyl)phenyl)carbonyl)-N-(4-(trifluoromethyl)benzyl)-2-piperidinecarboxamide;
(2S)-1-((3-((3-cyano-1-azetidinyl)sulfonyl)phenyl)carbonyl)-N-(4-(trifluoromethyl)benzyl)-2-piperidinecarboxamide;
1-(((3S)-1-((3-cyano-1-azetidinyl)sulfonyl)-3-piperidinyl)carbonyl)-N-((1R)-3,3,3-trifluoro-1-(4-(trifluoromethyl)phenyl)propyl)-D-prolinamide;
1-(((3S)-1-((3-cyano-1-azetidinyl)sulfonyl)-3-piperidinyl)carbonyl)-N-((1R)-1-(2-fluoro-4-(trifluoromethyl)phenyl)ethyl)-D-prolinamide;
1-(3-((3-cyano-1-azetidinyl)sulfonyl)benzoyl)-N—((R)-cyclopropyl(4-(trifluoromethyl)phenyl)methyl)-D-prolinamide;
1-(3-((3-cyano-1-azetidinyl)sulfonyl)benzoyl)-N-((1S)-2-hydroxy-1-(4-(trifluoromethyl)phenyl)ethyl)-D-prolinamide;
1-(((3S)-1-((3-cyano-1-azetidinyl)sulfonyl)-3-piperidinyl)carbonyl)-N-(3-fluoro-4-(trifluoromethyl)benzyl)-D-prolinamide;
(1R,3R,5R)-2-(((3S)-1-((3-cyano-1-azetidinyl)sulfonyl)-3-piperidinyl)carbonyl)-N-(2-fluoro-4-(trifluoromethyl)benzyl)-2-azabicyclo[3.1.0]hexane-3-carboxamide;
(4R)—N—((R)-(4-chloro-2,5-difluorophenyl)(3-oxetanyl)methyl)-1-(2-(ethylamino)-5-methylbenzoyl)-4-hydroxy-D-prolinamide;
1-(((3S)-1-((3-cyano-1-azetidinyl)sulfonyl)-3-piperidinyl)carbonyl)-N—((R)-cyclopropyl(2,5-difluoro-4-(trifluoromethyl)phenyl)methyl)-D-prolinamide;
1-(((3S)-1-((3-cyano-1-azetidinyl)sulfonyl)-3-piperidinyl)carbonyl)-N-((1R)-3-hydroxy-1-(4-(trifluoromethyl)phenyl)propyl)-D-prolinamide;
1-(3-((3-cyano-1-azetidinyl)sulfonyl)benzoyl)-N—((S)-cyclopropyl(4-(trifluoromethyl)phenyl)methyl)-D-prolinamide;
N-(3-chloro-4-(trifluoromethyl)benzyl)-1-(((3S)-1-((3-cyano-1-azetidinyl)sulfonyl)-3-piperidinyl)carbonyl)-D-prolinamide;
N—((R)-(4-chloro-2,5-difluorophenyl)(cyclopropyl)methyl)-1-(((3S)-1-((3-cyano-1-azetidinyl)sulfonyl)-3-piperidinyl)carbonyl)-D-prolinamide;
(1R,3R,5R)-2-(2-(cyclobutylamino)-5-(methylsulfonyl)benzoyl)-N—((R)-cyclopropyl(2-fluoro-4-(trifluoromethyl)phenyl)methyl)-2-azabicyclo[3.1.0]hexane-3-carboxamide;
1-((3-((3-cyano-1-azetidinyl)sulfonyl)phenyl)carbonyl)-N-((1R)-1-(4-(trifluoromethyl)phenyl)ethyl)-D-prolinamide;
1-((3-((3-cyano-1-azetidinyl)sulfonyl)phenyl)carbonyl)-N-(2-fluoro-4-(trifluoromethyl)benzyl)-D-prolinamide;
N-(4-chlorobenzyl)-1-((3-((3-cyano-1-azetidinyl)sulfonyl)phenyl)carbonyl)-D-prolinamide; 1-(2-(cyclobutylamino)-5-(methylsulfonyl)benzoyl)-N—((R)-cyclopropyl(2-fluoro-4-(trifluoromethyl)phenyl)methyl)-D-prolinamide;

1-(3-((3-cyano-1-azetidinyl)sulfonyl)benzoyl)-N-((1R)-3-methyl-1-(4-(trifluoromethyl)phenyl)butyl)-D-prolinamide;

1-((3-((3-cyano-1-azetidinyl)sulfonyl)phenyl)carbonyl)-N-((1R)-1-(2-fluoro-4-methylphenyl)ethyl)-D-prolinamide;

N—((S)-3-azetidinyl(4-chloro-2,5-difluorophenyl)methyl)-1-(((3S)-1-((3-cyano-1-azetidinyl)sulfonyl)-3-piperidinyl)carbonyl)-D-prolinamide;

N-((1R)-1-(4-chloro-2,5-difluorophenyl)ethyl)-1-(((3S)-1-((3-cyano-1-azetidinyl)sulfonyl)-3-piperidinyl)carbonyl)-D-prolinamide;

1-((3-((3-cyano-1-azetidinyl)sulfonyl)phenyl)carbonyl)-N-((1R)-1-(4-(difluoromethyl)-2-fluorophenyl)ethyl)-D-prolinamide;

(1R,3R,5R)—N—((R)-cyclopropyl(2-fluoro-4-(trifluoromethyl)phenyl)methyl)-2-(2-(ethylamino)-5-(methylsulfonyl)benzoyl)-2-azabicyclo[3.1.0]hexane-3-carboxamide;

N-(4-chloro-3-fluorobenzyl)-1-(((3S)-1-((3-cyano-1-azetidinyl)sulfonyl)-3-piperidinyl)carbonyl)-D-prolinamide;

1-(3-((3-cyano-1-azetidinyl)sulfonyl)benzoyl)-N—((R)-cyclopropyl(4-(pentafluoro-lambda~6~-sulfanyl)phenyl)methyl)-D-prolinamide;

1-((3-((3-cyano-1-azetidinyl)sulfonyl)-5-fluorophenyl)carbonyl)-N-(4-(trifluoromethyl)benzyl)-D-prolinamide;

(3R)-4-(((3S)-1-((3-cyano-1-azetidinyl)sulfonyl)-3-piperidinyl)carbonyl)-N-((1R)-1-(2-fluoro-4-(trifluoromethyl)phenyl)ethyl)-3-morpholinecarboxamide;

1-(3-((3-cyano-1-azetidinyl)sulfonyl)benzoyl)-N-(3,5-difluorobenzyl)-D-prolinamide; (4S)-1-(((3S)-1-((3-cyano-1-azetidinyl)sulfonyl)-3-piperidinyl)carbonyl)-4-fluoro-N-(4-(trifluoromethyl)benzyl)-D-prolinamide;

N-((1S)-1-(4-chlorophenyl)-2-hydroxyethyl)-1-(3-((3-cyano-1-azetidinyl)sulfonyl)benzoyl)-D-prolinamide;

N—(R)-cyclopropyl(2-fluoro-4-(trifluoromethyl)phenyl)methyl)-1-(3-(dimethylsulfamoyl)benzoyl)-D-prolinamide; 1-(((3S)-1-((cis-3-cyanocyclobutyl)sulfonyl)-3-piperidinyl)carbonyl)-N-(4-(trifluoromethyl)benzyl)-D-prolinamide;

1-(((3S)-1-((3-cyano-1-azetidinyl)sulfonyl)-3-piperidinyl)carbonyl)-N-(2-methyl-4-(trifluoromethyl)benzyl)-D-prolinamide;

(1R,3R,5R)—N—((R)-cyclopropyl(2-fluoro-4-(trifluoromethyl)phenyl)methyl)-2-(5-(methylsulfonyl)-2-(2-propanylamino)benzoyl)-2-azabicyclo[3.1.0]hexane-3-carboxamide;

1-(((3S)-1-((3-cyano-1-azetidinyl)sulfonyl)-3-piperidinyl)carbonyl)-N-(2-fluoro-4-(trifluoromethyl)benzyl)-D-prolinamide;

N-(2-chloro-4-(trifluoromethyl)benzyl)-1-(((3S)-1-((3-cyano-1-azetidinyl)sulfonyl)-3-piperidinyl)carbonyl)-D-prolinamide;

N-(4-chloro-3-fluorobenzyl)-1-((3-((3-cyano-1-azetidinyl)sulfonyl)phenyl)carbonyl)-D-prolinamide;

(2R)-1-(((3S)-1-((3-cyano-1-azetidinyl)sulfonyl)-3-piperidinyl)carbonyl)-N-(4-(trifluoromethyl)benzyl)-2 piperidinecarboxamide;

(1R,3R,5R)—N—(R)-(4-chloro-2,5-difluorophenyl)(3-oxetanyl)methyl)-2-(3-(ethylsulfonyl)benzoyl)-2-azabicyclo[3.1.0]hexane-3-carboxamide;

1-(((3S)-1-((3-cyano-1-azetidinyl)sulfonyl)-3-piperidinyl)carbonyl)-N-(4-(trifluoromethyl)benzyl)-D-prolinamide;

1-(((3S)-1-((3-cyano-1-azetidinyl)sulfonyl)-3-piperidinyl)carbonyl)-N-((1R)-3-methyl-1-(4-(trifluoromethyl)phenyl)butyl)-D-prolinamide;

N-((1R)-1-(4-chloro-3-fluorophenyl)ethyl)-1-(((3S)-1-((3-cyano-1-azetidinyl)sulfonyl)-3-piperidinyl)carbonyl)-D-prolinamide;

N-(4-chloro-2-fluorobenzyl)-1-(((3S)-1-((3-cyano-1-azetidinyl)sulfonyl)-3-piperidinyl)carbonyl)-D-prolinamide;

N-((1R)-1-(4-chlorophenyl)ethyl)-1-((3-((3-cyano-1-azetidinyl)sulfonyl)phenyl)carbonyl)-D-prolinamide;

1-(((3S)-1-((3-(methylsulfonyl)-1-azetidinyl)sulfonyl)-3-piperidinyl)carbonyl)-N-(4-(trifluoromethyl)benzyl)-D-prolinamide;

1-(((2S)-4-((3-cyano-1-azetidinyl)sulfonyl)-2-morpholinyl)carbonyl)-N-((1R)-1-(2-fluoro-4-(trifluoromethyl)phenyl)ethyl)-D-prolinamide;

(1R,3R,5R)—N—((R)-(4-chloro-2,5-difluorophenyl)(3-oxetanyl)methyl)-2-(3-(methylsulfonyl)benzoyl)-2-azabicyclo[3.1.0]hexane-3-carboxamide;

1-((3-((3-cyano-1-azetidinyl)sulfonyl)phenyl)carbonyl)-N-methyl-N-(4-(trifluoromethyl)benzyl)-D-prolinamide;

1-((3-((3-cyano-1-azetidinyl)sulfonyl)phenyl)carbonyl)-N-(2-fluoro-4-methylbenzyl)-D-prolinamide;

1-(((3R)-1-((3-cyano-1-azetidinyl)sulfonyl)-5,5-difluoro-3-piperidinyl)carbonyl)-N-(4-(trifluoromethyl)benzyl)-D-prolinamide;

1-(((3S)-1-((3-cyano-1-azetidinyl)sulfonyl)-5,5-difluoro-3-piperidinyl)carbonyl)-N-(4-(trifluoromethyl)benzyl)-D-prolinamide;

N-((1S)-1-(4-chloro-3-fluorophenyl)-2-hydroxyethyl)-1-(((3S)-1-((3-cyano-1-azetidinyl)sulfonyl)-3-piperidinyl)carbonyl)-D-prolinamide;

N—((R)-cyclopropyl(2-fluoro-4-(trifluoromethyl)phenyl)methyl)-1-(2-(ethylamino)-5-(methylsulfonyl)benzoyl)-D-prolinamide;

methyl (3-((((1R,3R,5R)-3-(((R)-cyclopropyl(2,5-difluoro-4-(trifluoromethyl)phenyl)methyl)carbamoy)-2-azabicyclo[3.1.0]hexan-2-yl)carbonyl)phenyl)sulfonyl)acetate;

N—((R)-cyclopropyl(2-fluoro-4-(trifluoromethyl)phenyl)methyl)-1-(5-(methylsulfonyl)-2-(2-propanylamino)benzoyl)-D-prolinamide;

1-(((3S,4R)-1-((3-cyano-1-azetidinyl)sulfonyl)-4-methyl-3-piperidinyl)carbonyl)-N-(4-(trifluoromethyl)benzyl)-D-prolinamide;

(1R,3R,5R)—N—((R)-(4-chloro-2,5-difluorophenyl)(3-oxetanyl)methyl)-2-(3-fluoro-5-(methylsulfonyl)benzoyl)-2-azabicyclo[3.1.0]hexane-3-carboxamide;

1-(((3S)-1-((3-cyano-1-azetidinyl)sulfonyl)-3-piperidinyl)carbonyl)-N-((1R)-1-(4-(trifluoromethyl)phenyl)ethyl)-D-prolinamide;

1-(3-((3-cyano-1-azetidinyl)sulfonyl)benzoyl)-N-((1S)-1-(4-(trifluoromethyl)phenyl)propyl)-D-prolinamide;

(2R)-1-((3-((3-cyano-1-azetidinyl)sulfonyl)phenyl)carbonyl)-N-((1S)-1-(3,4-dichlorophenyl)ethyl)-2-piperidinecarboxamide;

1-(((3S)-1-((3-cyano-1-azetidinyl)sulfonyl)-3-piperidinyl)carbonyl)-N-(3-fluoro-4-methylbenzyl)-D-prolinamide;

1-(((3S)-1-((3-cyano-1-azetidinyl)sulfonyl)-3-piperidinyl)carbonyl)-N-((1S)-2-hydroxy-1-(4-(trifluoromethyl)phenyl)ethyl)-D-prolinamide;

(2R)—N—((R)-cyclopropyl(2-fluoro-4-(trifluoromethyl)phenyl)methyl)-1-(3-(propylsulfonyl)benzoyl)-2-piperidinecarboxamide;

(1R,2R,5S)-3-(((3S)-1-((3-cyano-1-azetidinyl)sulfonyl)-3-piperidinyl)carbonyl)-N-(4-(trifluoromethyl)benzyl)-3-azabicyclo[3.1.0]hexane-2-carboxamide;

1-(((3S)-1-((3-cyano-1-azetidinyl)sulfonyl)-3-piperidinyl)carbonyl)-N-(3,4-dichlorobenzyl)-D-prolinamide;

(1R,3R,5R)—N—((R)-(4-chloro-2,5-difluorophenyl)(cy-clopropyl)methyl)-2-(3-(cyclopropylsulfonyl)benzoyl)-2-azabicyclo[3.1.0]hexane-3-carboxamide;

(1R)-2-((3-((3-cyano-1-azetidinyl)sulfonyl)phenyl)carbonyl)-N-(4-(trifluoromethyl)benzyl)-2,3-dihydro-1H-isoindole-1-carboxamide;

(1S)-2-((3-((3-cyano-1-azetidinyl)sulfonyl)phenyl)carbonyl)-N-(4-(trifluoromethyl)benzyl)-2,3-dihydro-1H-isoindole-1-carboxamide;

(1R,3R,5R)—N—((R)-(4-chloro-2,5-difluorophenyl)(3-oxetanyl)methyl)-2-(3-((2-hydroxyethyl)sulfonyl)benzoyl)-2-azabicyclo[3.1.0]hexane-3-carboxamide;

1-((3-((3-cyano-1-azetidinyl)sulfonyl)phenyl)carbonyl)-4,4-difluoro-N-((6-(trifluoromethyl)-3-pyridinyl)methyl)-D-prolinamide;

(2R)-1-((3-((3-cyano-1-azetidinyl)sulfonyl)phenyl)carbonyl)-N-(4-(trifluoromethyl)benzyl)-2-azepanecarboxamide;

(2S)-1-((3-((3-cyano-1-azetidinyl)sulfonyl)phenyl)carbonyl)-N-(4-(trifluoromethyl)benzyl)-2-azepanecarboxamide;

N-((1R)-1-(4-chlorophenyl)-2-methoxyethyl)-1-(((3S)-1-((3-cyano-1-azetidinyl)sulfonyl)-3-piperidinyl)carbonyl)-D-prolinamide;

N-((1S)-1-(4-chlorophenyl)-2-methoxyethyl)-1-(((3S)-1-((3-cyano-1-azetidinyl)sulfonyl)-3-piperidinyl)carbonyl)-D-prolinamide;

1-(((3S)-1-((3-cyano-1-azetidinyl)sulfonyl)-3-piperidinyl)carbonyl)-N-((1R)-1-(2-fluoro-4-methylphenyl)ethyl)-D-prolinamide;

1-(((3S)-1-((3-cyano-1-azetidinyl)sulfonyl)-3-piperidinyl)carbonyl)-N-(2,4-dichlorobenzyl)-D-prolinamide;

1-(3-((3-cyano-1-azetidinyl)sulfonyl)benzoyl)-N-(2,3,5-trifluorobenzyl)-D-prolinamide;

(1R,3R,5R)—N—(R)-cyclopropyl(2-fluoro-4-(trifluoromethyl)phenyl)methyl)-2-(2-((2-methyl-2-propanyl)amino)-5-(methylsulfonyl)benzoyl)-2-azabicyclo[3.1.0]hexane-3-carboxamide;

1-((3-((3-cyano-1-azetidinyl)sulfonyl)phenyl)carbonyl)-N-(4-(difluoromethyl)benzyl)-D-prolinamide;

1-(((1R,4R,6R)-2-((3-cyano-1-azetidinyl)sulfonyl)-2-azabicyclo[2.2.1]hept-6-yl)carbonyl)-N-(2-fluoro-4-(trifluoromethyl)benzyl)-D-prolinamide;

1-(((3S)-1-((3-cyano-1-azetidinyl)sulfonyl)-3-piperidinyl)carbonyl)-N-((1R)-1-(4-(difluoromethyl)-2-fluorophenyl)ethyl)-D-prolinamide;

N-((1R)-1-(4-chloro-3-fluorophenyl)-2-hydroxyethyl)-1-(3-((3-cyano-1-azetidinyl)sulfonyl)benzoyl)-D-prolinamide;

1-((3-((3-cyano-1-azetidinyl)sulfonyl)phenyl)carbonyl)-N-(4-methylbenzyl)-D-prolinamide;

1-(((3S)-1-((3-cyano-1-azetidinyl)sulfonyl)-3-piperidinyl)carbonyl)-N-((S)-cyclopropyl(4-(trifluoromethyl)phenyl)methyl)-D-prolinamide;

N—(R)-cyclopropyl(2-fluoro-4-(trifluoromethyl)phenyl)methyl)-1-(2-(ethylamino)-5-methylbenzoyl)-D-prolinamide;

(3R)-4-(((3S)-1-((3-cyano-1-azetidinyl)sulfonyl)-3-piperidinyl)carbonyl)-N-(4-(trifluoromethyl)benzyl)-3-morpholinecarboxamide;

(4S)—N—((R)-(4-chloro-2,5-difluorophenyl) (3-oxetanyl)methyl)-1-(2-(ethylamino)-5-methylbenzoyl)-4-hydroxy-D-prolinamide;

N—((R)-(4-chloro-2,5-difluorophenyl)(3-oxetanyl)methyl)-1-(3-(methylsulfonyl)benzoyl)-D-prolinamide;

(1R,3R,5R)—N—((R)-(4-chloro-2,5-difluorophenyl)(cyclopropyl)methyl)-2-(3-((2-hydroxyethyl)sulfonyl)benzoyl)-2-azabicyclo[3.1.0]hexane-3-carboxamide;

(2R)—N—((R)-(4-chloro-2,5-difluorophenyl) (cyclopropyl)methyl)-1-(3-(methylsulfonyl)benzoyl)-2-piperidinecarboxamide;

N—((R)-(4-chloro-3-fluorophenyl) (cyclopropyl)methyl)-1-(3-(dimethylsulfamoyl)benzoyl)-D-prolinamide;

(1R,3R,5R)—N—((R)-cyclopropyl(2,5-difluoro-4-(trifluoromethyl)phenyl)methyl)-2-(3-(trifluoromethyl)benzoyl)-2-azabicyclo[3.1.0]hexane-3-carboxamide;

1-(((2S)-4-((3-cyano-1-azetidinyl)sulfonyl)-2-morpholinyl)carbonyl)-N-(2-fluoro-4-(trifluoromethyl)benzyl)-D-prolinamide;

1-(((3S)-1-((3-cyano-1-azetidinyl)sulfonyl)-3-piperidinyl)carbonyl)-N—((R)-cyclopropyl(4-(pentafluoro-lambda~6~-sulfanyl)phenyl)methyl)-D-prolinamide;

(1R,3R,5R)—N—((R)-cyclopropyl(2-fluoro-4-(trifluoromethyl)phenyl)methyl)-2-(2-((2-hydroxyethyl)amino)-5-(methylsulfonyl)benzoyl)-2-azabicyclo[3.1.0]hexane-3-carboxamide;

N-(4-chloro-2-methylbenzyl)-1-(((3S)-1-((3-cyano-1-azetidinyl)sulfonyl)-3-piperidinyl)carbonyl)-D-prolinamide;

1-((3-((3-cyano-1-azetidinyl)sulfonyl)phenyl)carbonyl)-N-((1R)-1-(4-(difluoromethyl)phenyl)ethyl)-D-prolinamide;

3-((3-cyano-1-azetidinyl)sulfonyl)-N-methyl-N-((1R)-1-methyl-2-oxo-2-(((1R)-1-(4-(trifluoromethyl)phenyl)ethyl)amino)ethyl)benzamide;

(4R)-1-((3-((3-cyano-1-azetidinyl)sulfonyl)phenyl)carbonyl)-4-fluoro-N-(4-(trifluoromethyl)benzyl)-D-prolinamide;

1-((1-((3-cyano-1-azetidinyl)sulfonyl)-1H-pyrazol-4-yl)carbonyl)-N-(4-(trifluoromethyl)benzyl)-D-prolinamide;

1-(3-((3-cyano-1-azetidinyl)sulfonyl)benzoyl)-N-((1R)-1-(3,5-difluorophenyl)propyl)-D-prolinamide;

(2R)—N—((R)-(4-chloro-2,5-difluorophenyl) (cyclopropyl)methyl)-1-((6-(methylsulfonyl)-3-pyridinyl)carbonyl)-2-piperidinecarboxamide;

(4R)-1-((3-((3-cyano-1-azetidinyl)sulfonyl)phenyl)carbonyl)-4-hydroxy-N-(4-(trifluoromethyl)benzyl)-D-prolinamide;

(1R,3R,5R)—N—((R)-(4-chloro-2,5-difluorophenyl)(cyclopropyl)methyl)-2-(3-(trifluoromethyl)benzoyl)-2-azabicyclo[3.1.0]hexane-3-carboxamide;

(1R,3R,5R)-2-(3-(ethylsulfonyl)benzoyl)-N—((R)-(2-fluoro-4-(trifluoromethyl)phenyl)(3-oxetanyl)methyl)-2-azabicyclo[3.1.0]hexane-3-carboxamide;

(4S)—N—((R)-cyclopropyl(2-fluoro-4-(trifluoromethyl)phenyl)methyl)-3-(3-(methylsulfonyl)benzoyl)-1,3-thiazolidine-4-carboxamide;

N-(3-chloro-4-methylbenzyl)-1-(((3S)-1-((3-cyano-1-azetidinyl)sulfonyl)-3-piperidinyl)carbonyl)-D-prolinamide;

1-((3-((3-cyano-1-azetidinyl)sulfonyl)phenyl)carbonyl)-N-((6-(trifluoromethyl)-3-pyridinyl)methyl)-D-prolinamide;

N—(R)-(4-chlorophenyl)((2R)-tetrahydro-2-furanyl)methyl)-1-(((3S)-1-((3-cyano-1-azetidinyl)sulfonyl)-3-piperidinyl)carbonyl)-D-prolinamide & N—((R)-(4-chlorophenyl)((2S)-tetrahydro-2-furanyl)methyl)-1-(((3S)-1-((3-cyano-1-azetidinyl)sulfonyl)-3-piperidinyl)carbonyl)-D-prolinamide & N—((S)-(4-chlorophenyl)((2R)-tetrahydro-2-furanyl)methyl)-1-(((3S)-1-((3-cyano-1-azetidinyl)sulfonyl)-3-piperidinyl)carbonyl)-D-prolinamide & N—((S)-(4-chlorophenyl)((2S)-tetrahydro-2-furanyl)methyl)-1-(((3S)-1-((3-cyano-1-azetidinyl)sulfonyl)-3-piperidinyl)carbonyl)-D-prolinamide; (1R,3R,5R)—N—((R)-(4-chloro-2,5-difluorophenyl)(cyclopropyl)methyl)-2-((4-(ethylsulfonyl)-2-pyridinyl)carbonyl)-2-azabicyclo[3.1.0]hexane-3-carboxamide;

1-(((3S)-1-((3-cyano-1-azetidinyl)sulfonyl)-3-piperidinyl)carbonyl)-N-((1R)-2-hydroxy-1-(4-(trifluoromethyl)phenyl)ethyl)-D-prolinamide;

1-(((3S)-1-((3-cyano-1-azetidinyl)sulfonyl)-3-piperidinyl)carbonyl)-N-((1S)-2-hydroxy-1-(4-(trifluoromethyl)phenyl)ethyl)-D-prolinamide;

N-((1R)-1-(4-chlorophenyl)ethyl)-1-(((3S)-1-((3-cyano-1-azetidinyl)sulfonyl)-3-piperidinyl)carbonyl)-D-prolinamide;

1-((3-((3-cyano-1-azetidinyl)sulfonyl)phenyl)carbonyl)-N-((2-(trifluoromethyl)-5-pyrimidinyl)methyl)-D-prolinamide;

N-(4-chloro-3-methylbenzyl)-1-(((3S)-1-((3-cyano-1-azetidinyl)sulfonyl)-3-piperidinyl)carbonyl)-D-prolinamide;

(1R,3R,5R)—N—((R)-(4-chloro-2,5-difluorophenyl)(cyclopropyl)methyl)-2-((4-(cyclopropylsulfonyl)-2-pyridinyl)carbonyl)-2-azabicyclo[3.1.0]hexane-3-carboxamide;

(1R,3R,5R)—N—((R)-(4-chloro-2,5-difluorophenyl)(cyclopropyl)methyl)-2-(3-sulfamoylbenzoyl)-2-azabicyclo[3.1.0]hexane-3-carboxamide;

(1R,3R,5R)—N—((R)-(4-chloro-2,5-difluorophenyl)(3-oxetanyl)methyl)-2-(3-methyl-5-(methylsulfonyl)benzoyl)-2-azabicyclo[3.1.0]hexane-3-carboxamide;

(4S)—N—((R)-(4-chloro-2,5-difluorophenyl)(3-oxetanyl)methyl)-4-fluoro-1-(3-(methylsulfonyl)benzoyl)-D-prolinamide;

1-((2-((3-cyano-1-azetidinyl)sulfonyl)-4-pyridinyl)carbonyl)-N-(2-fluoro-4-(trifluoromethyl)benzyl)-D-prolinamide;

1-(((3S)-1-((3-cyano-1-azetidinyl)sulfonyl)-4,4-difluoro-3-piperidinyl)carbonyl)-N-(4-(trifluoromethyl)benzyl)-D-prolinamide;

1-(((2S)-4-((3-cyano-1-azetidinyl)sulfonyl)-2-piperazinyl)carbonyl)-N-((1R)-1-(2-fluoro-4-(trifluoromethyl)phenyl)ethyl)-D-prolinamide;

1-(((3S)-1-((3-cyano-1-azetidinyl)sulfonyl)-3-piperidinyl)carbonyl)-N-(2-methyl-3-(trifluoromethyl)benzyl)-D-prolinamide;

1-(3-(dimethylsulfamoyl)benzoyl)-N-((1R)-1-(2-fluoro-4-(trifluoromethyl)phenyl)propyl)-D-prolinamide;

N—((R)-cyclopropyl(2,5-difluoro-4-(trifluoromethyl)phenyl)methyl)-1-(3-(methylsulfonyl)benzoyl)-D-prolinamide;

(1R,3R,5R)—N—((R)-cyclopropyl(2-fluoro-4-(trifluoromethyl)phenyl)methyl)-2-(2-(methylamino)-5-(methylsulfonyl)benzoyl)-2-azabicyclo[3.1.0]hexane-3-carboxamide;

1-(((2S)-4-((3-cyano-1-azetidinyl)sulfonyl)-2-morpholinyl)carbonyl)-N-(4-(trifluoromethyl)benzyl)-D-prolinamide;

N-((1R)-1-(4-chlorophenyl)ethyl)-1-(((3S)-1-((3-(methylsulfonyl)-1-azetidinyl)sulfonyl)-3-piperidinyl)carbonyl)-D-prolinamide;

N-(2-fluoro-4-(trifluoromethyl)benzyl)-1-(((3S)-1-((3-(1H-1,2,3-triazol-1-yl)-1-azetidinyl)sulfonyl)-3-piperidinyl)carbonyl)-D-prolinamide;

N-(3-chloro-2-methylbenzyl)-1-(((3S)-1-((3-cyano-1-azetidinyl)sulfonyl)-3-piperidinyl)carbonyl)-D-prolinamide;

1-(((3S)-1-((3-cyano-1-azetidinyl)sulfonyl)-3-piperidinyl)carbonyl)-N-(3,4,5-trifluorobenzyl)-D-prolinamide;

N—((R)-cyclopropyl(2-fluoro-4-(trifluoromethyl)phenyl)methyl)-1-(2-((2-hydroxyethyl)amino)-5-(methylsulfonyl)benzoyl)-D-prolinamide;

1-(((3S)-1-((3-cyano-1-azetidinyl)sulfonyl)-3-piperidinyl)carbonyl)-N-((1R)-1-(3-fluoro-4-methylphenyl)ethyl)-D-prolinamide;

1-(((3S)-1-((3-cyano-1-azetidinyl)sulfonyl)-3-piperidinyl)carbonyl)-N-((1S)-1-(3-fluoro-4-methylphenyl)ethyl)-D-prolinamide;

1-(((3S)-1-((3-cyano-3-methyl-1-azetidinyl)sulfonyl)-3-piperidinyl)carbonyl)-N-(4-(trifluoromethyl)benzyl)-D-prolinamide;

1-((3-((3-cyano-1-azetidinyl)sulfonyl)phenyl)carbonyl)-N-(4-(fluoromethyl)benzyl)-D-prolinamide;

1-(3-((3-cyano-1-azetidinyl)sulfonyl)benzoyl)-N-((1S)-2-hydroxy-1-(3-(trifluoromethyl)phenyl)ethyl)-D-prolinamide;

(2R)—N—((R)-(4-chloro-2,5-difluorophenyl)(cyclopropyl)methyl)-1-((4-(methylsulfonyl)-2-pyridinyl)carbonyl)-2-piperidinecarboxamide;

(1R,3R,5R)—N—((R)-(4-chloro-2,5-difluorophenyl)(cyclopropyl)methyl)-2-((5-(ethylsulfonyl)-3-pyridinyl)carbonyl)-2-azabicyclo[3.1.0]hexane-3-carboxamide;

(1R,3R,5R)—N—((R)-cyclobutyl(2-fluoro-4-(trifluoromethyl)phenyl)methyl)-2-(3-(methylsulfonyl)benzoyl)-2-azabicyclo[3.1.0]hexane-3-carboxamide;

N-(4-chlorobenzyl)-1-((3-((3-cyano-1-azetidinyl)sulfonyl)phenyl)carbonyl)-N-methyl-D-prolinamide;

N-(4-chlorobenzyl)-1-((3-((3-cyano-1-azetidinyl)sulfonyl)phenyl)carbonyl)-N-methyl-L-prolinamide;

(1R,3R,5R)—N—((R)-(4-chloro-2,5-difluorophenyl)(cyclopropyl)methyl)-2-((5-(cyclopropylsulfonyl)-3-pyridinyl)carbonyl)-2-azabicyclo[3.1.0]hexane-3-carboxamide;

N-(4-chlorobenzyl)-1-(((3S)-1-((3-cyano-1-azetidinyl)sulfonyl)-3-piperidinyl)carbonyl)-D-prolinamide;

1-(3-((3-cyano-1-azetidinyl)sulfonyl)benzoyl)-N-((1S)-1-(3,5-difluorophenyl)propyl)-D-prolinamide;

1-(((3S)-1-(((2R)-2-(3-fluorophenyl)-1-azetidinyl)sulfonyl)-3-piperidinyl)carbonyl)-N-(4-(trifluoromethyl)benzyl)-D-prolinamide;

1-(((3S)-1-(((2S)-2-(3-fluorophenyl)-1-azetidinyl)sulfonyl)-3-piperidinyl)carbonyl)-N-(4-(trifluoromethyl)benzyl)-D-prolinamide;

3-((3-cyano-1-azetidinyl)sulfonyl)-N-methyl-N-((1R)-1-methyl-2-oxo-2-(((1S)-1-(4-(trifluoromethyl)phenyl)ethyl)amino)ethyl)benzamide;

1-((1-((3-cyano-1-azetidinyl)sulfonyl)-4-fluoro-1,2,5,6-tetrahydro-3-pyridinyl)carbonyl)-N-(4-(trifluoromethyl)benzyl)-D-prolinamide;

N-((1S)-1-(4-chlorophenyl)-2-hydroxyethyl)-1-(((3S)-1-((3-cyano-1-azetidinyl)sulfonyl)-3-piperidinyl)carbonyl)-D-prolinamide;

1-(((3R,4S)-1-((3-cyano-1-azetidinyl)sulfonyl)-4-methyl-3-piperidinyl)carbonyl)-N-(4-(trifluoromethyl)benzyl)-D-prolinamide;

1-(((3S,4R)-1-((3-cyano-1-azetidinyl)sulfonyl)-4-methyl-3-piperidinyl)carbonyl)-N-(4-(trifluoromethyl)benzyl)-D-prolinamide;

(1R,3R,5R)—N—((R)-(4-chloro-2,5-difluorophenyl)(3-oxetanyl)methyl)-2-((2-(trifluoromethyl)-4-pyridinyl)carbonyl)-2-azabicyclo[3.1.0]hexane-3-carboxamide;

1-(((1R,4R,6R)-2-((3-cyano-1-azetidinyl)sulfonyl)-2-azabicyclo[2.2.1]hept-6-yl)carbonyl)-N-(4-(trifluoromethyl)benzyl)-D-prolinamide;

(4S)—N—((R)-cyclopropyl(2,5-difluoro-4-(trifluoromethyl)phenyl)methyl)-4-fluoro-1-(3-(methylsulfonyl)benzoyl)-D-prolinamide;

N-(4-chloro-3-fluorobenzyl)-1-(((2S)-4-((3-cyano-1-azetidinyl)sulfonyl)-2-piperazinyl)carbonyl)-D-prolinamide;

(3R)-4-(((3S)-1-((3-cyano-1-azetidinyl)sulfonyl)-3-piperidinyl)carbonyl)-N-((1R)-1-(4-(trifluoromethyl)phenyl)ethyl)-3-morpholinecarboxamide;

N-(4-chloro-2-methoxybenzyl)-1-(((3S)-1-((3-cyano-1-azetidinyl)sulfonyl)-3-piperidinyl)carbonyl)-D-prolinamide;

(1S,2R,5R)-3-(((3S)-1-((3-cyano-1-azetidinyl)sulfonyl)-3-piperidinyl)carbonyl)-N-(4-(trifluoromethyl)benzyl)-3-azabicyclo[3.1.0]hexane-2-carboxamide;

(1R,3R,5R)—N—((R)-cyclopropyl(4-(difluoromethyl)-2,5-difluorophenyl)methyl)-2-(3-(ethylsulfonyl)benzoyl)-2-azabicyclo[3.1.0]hexane-3-carboxamide;

N—((R)-(3-fluoro-4-(trifluoromethyl)phenyl)(3-oxetanyl)methyl)-1-(3-(methylsulfonyl)benzoyl)-D-prolinamide;

1-(((3S)-1-(((2R)-2-(3-bromophenyl)-1-azetidinyl)sulfonyl)-3-piperidinyl)carbonyl)-N-(4-(trifluoromethyl)benzyl)-D-prolinamide;

1-(((3S)-1-(((2S)-2-(3-bromophenyl)-1-azetidinyl)sulfonyl)-3-piperidinyl)carbonyl)-N-(4-(trifluoromethyl)benzyl)-D-prolinamide;

1-(((3S)-1-((3-cyano-1-azetidinyl)sulfonyl)-3-piperidinyl)carbonyl)-N-(2-fluoro-4-methylbenzyl)-D-prolinamide;

(1R,3R,5R)—N—((R)-(2-fluoro-4-(trifluoromethyl)phenyl)(3-oxetanyl)methyl)-2-(3-(methylsulfonyl)benzoyl)-2-azabicyclo[3.1.0]hexane-3-carboxamide;

1-(((3S)-1-((3-cyano-1-azetidinyl)sulfonyl)-3-fluoro-3-piperidinyl)carbonyl)-N-(4-(trifluoromethyl)benzyl)-D-prolinamide or 1-(((3R)-1-((3-cyano-1-azetidinyl)sulfonyl)-3-fluoro-3-piperidinyl)carbonyl)-N-(4-(trifluoromethyl)benzyl)-D-prolinamide;

(1R,3R,5R)-2-(3-(1-carbamoylcyclopropyl)benzoyl)-N—((R)-(4-chloro-2,5-difluorophenyl)(3-oxetanyl)methyl)-2-azabicyclo[3.1.0]hexane-3-carboxamide;

1-(3-(dimethylsulfamoyl)benzoyl)-N-((1R)-1-(2-fluoro-4-(trifluoromethyl)phenyl)-2-methylpropyl)-D-prolinamide;

N—((R)-cyclopropyl(2-fluoro-4-(trifluoromethyl)phenyl)methyl)-1-(2-((2-methyl-2-propanyl)amino)-5-(methylsulfonyl)benzoyl)-D-prolinamide;

N-(4-chloro-2-fluorobenzyl)-1-(((2S)-4-((3-cyano-1-azetidinyl)sulfonyl)-2-morpholinyl)carbonyl)-O-prolinamide;

1-(3-((3-cyano-1-azetidinyl)sulfonyl)benzoyl)-N-((1R)-2-hydroxy-1-(4-(trifluoromethyl)phenyl)ethyl)-D-prolinamide;

1-(((1R,4R,6R)-2-((3-cyano-1-azetidinyl)sulfonyl)-2-azabicyclo[2.2.1]hept-6-yl)carbonyl)-N-(2-fluoro-4-(trifluoromethyl)benzyl)-D-prolinamide;

1-(((1S,4S,6S)-2-((3-cyano-1-azetidinyl)sulfonyl)-2-azabicyclo[2.2.1]hept-6-yl)carbonyl)-N-(2-fluoro-4-(trifluoromethyl)benzyl)-D-prolinamide;

N-(3-chlorobenzyl)-1-((3-((3-cyano-1-azetidinyl)sulfonyl)phenyl)carbonyl)-D-prolinamide;

N-(2-chloro-4-methylbenzyl)-1-(((3S)-1-((3-cyano-1-azetidinyl)sulfonyl)-3-piperidinyl)carbonyl)-D-prolinamide;

1-(((3S)-1-(((3S)-3-cyano-1-pyrrolidinyl)sulfonyl)-3-piperidinyl)carbonyl)-N-(4-(trifluoromethyl)benzyl)-D-prolinamide;

(1R,3R,5R)—N—(R)-(3-fluoro-4-(trifluoromethyl)phenyl)(3-oxetanyl)methyl)-2-(3-(methylsulfonyl)benzoyl)-2-azabicyclo[3.1.0]hexane-3-carboxamide;

(2R)—N—((R)-(4-chloro-2,5-difluorophenyl) (cyclopropyl)methyl)-1-(3-sulfamoylbenzoyl)-2-piperidinecarboxamide;

1-(((3S)-1-((3-cyano-1-azetidinyl)sulfonyl)-3-piperidinyl)carbonyl)-N-((1S)-1-(4-(trifluoromethyl)phenyl)propyl)-D-prolinamide;

1-(((3S)-1-((3-ethynyl-3-hydroxy-1-azetidinyl)sulfonyl)-3-piperidinyl)carbonyl)-N-(2-fluoro-4-(trifluoromethyl)benzyl)-D-prolinamide;

(1R,3R,5R)—N—((R)-cyclopropyl(4-(difluoromethyl)-2,5-difluorophenyl)methyl)-2-(3-(methylsulfonyl)benzoyl)-2-azabicyclo[3.1.0]hexane-3-carboxamide;

1-(((3S)-1-((3-cyano-1-azetidinyl)sulfonyl)-3-piperidinyl)carbonyl)-N-((1S)-2,2,2-trifluoro-1-(4-(trifluoromethyl)phenyl)ethyl)-D-prolinamide;

1-(((3S)-1-((3-cyclopropyl-3-hydroxy-1-azetidinyl)sulfonyl)-3-piperidinyl)carbonyl)-N-(2-fluoro-4-(trifluoromethyl)benzyl)-D-prolinamide;

1-(((2S)-4-((3-cyano-1-azetidinyl)sulfonyl)-2-piperazinyl)carbonyl)-N-(2-fluoro-4-(trifluoromethyl)benzyl)-D-prolinamide;

(4S)—N—((R)-(4-chloro-2,5-difluorophenyl)(cyclopropyl)methyl)-4-fluoro-1-(3-(methylsulfonyl)benzoyl)-D-prolinamide;

(1R,3R,5R)—N—((R)-(4-chloro-2,5-difluorophenyl)(cyclopropyl)methyl)-2-((4-(methylsulfonyl)-2-pyridinyl)carbonyl)-2-azabicyclo[3.1.0]hexane-3-carboxamide;

1-(((3S)-1-((3-(1H-1,2,3-triazol-1-yl)-1-azetidinyl)sulfonyl)-3-piperidinyl)carbonyl)-N-(4-(trifluoromethyl)benzyl)-D-prolinamide;

1-(3-((3-cyano-1-azetidinyl)sulfonyl)benzoyl)-N-((1S)-1-(2-fluoro-4-(trifluoromethyl)phenyl)propyl)-D-prolinamide;

1-(3-((3-cyano-1-azetidinyl)sulfonyl)benzoyl)-N-((1R)-1-(3,5-difluorophenyl)ethyl)-D-prolinamide;

1-(((3S)-1-((3-cyano-1-azetidinyl)sulfonyl)-3-piperidinyl)carbonyl)-N-(2,3-dichlorobenzyl)-D-prolinamide;

(1R,3R,5R)—N—((R)-(4-chloro-2-fluorophenyl)(3-oxetanyl)methyl)-2-(3-(methylsulfonyl)benzoyl)-2-azabicyclo[3.1.0]hexane-3-carboxamide;

(2R)—N—((R)-cyclopropyl(2-fluoro-4-(trifluoromethyl)phenyl)methyl)-1-(3-((2R)-1,1,1-trifluoro-2-hydroxy-2-propanyl)benzoyl)-2-piperidinecarboxamide;

(2R)—N—((R)-cyclopropyl(2-fluoro-4-(trifluoromethyl)phenyl)methyl)-1-(3-((2S)-1,1,1-trifluoro-2-hydroxy-2-propanyl)benzoyl)-2-piperidinecarboxamide;

(3S)-1-((3-cyano-1-azetidinyl)sulfonyl)-N-((2R)-1-(((1R)-1-(2-fluoro-4-(trifluoromethyl)phenyl)ethyl)amino)-1-oxo-2-propanyl)-N-methyl-3-piperidinecarboxamide;

1-(((3S)-1-((3-((4-chlorobenzyl)oxy)-1-azetidinyl)sulfonyl)-3-piperidinyl)carbonyl)-N-(4-(trifluoromethyl)benzyl)-D-prolinamide;

(1R,3R,5R)—N—((R)-cyclopropyl(2-fluoro-4-(trifluoromethyl)phenyl)methyl)-2-(3-(cyclopropylsulfonyl)benzoyl)-2-azabicyclo[3.1.0]hexane-3-carboxamide;

N—((R)-cyclopropyl(2-fluoro-4-(trifluoromethyl)phenyl)methyl)-1-(3-(ethylsulfonyl)benzoyl)-D-prolinamide;

(1R,3R,5R)—N—((R)-(2-fluoro-4-(trifluoromethyl)phenyl)(3-oxetanyl)methyl)-2-(3-(2-methyl-2-propanyl)benzoyl)-2-azabicyclo[3.1.0]hexane-3-carboxamide;

(1R,3R,5R)—N—((R)-cyclopropyl(2,5-difluoro-4-(trifluoromethyl)phenyl)methyl)-2-((5-(methylsulfonyl)-3-pyridinyl)carbonyl)-2-azabicyclo[3.1.0]hexane-3-carboxamide;

N—((R)-(4-chloro-2,5-difluorophenyl)(cyclopropyl)methyl)-1-((6-(methylsulfonyl)-3-pyridinyl)carbonyl)-D-prolinamide;

(4R)-1-(((3S)-1-((3-cyano-1-azetidinyl)sulfonyl)-3-piperidinyl)carbonyl)-4-fluoro-N-(4-(trifluoromethyl)benzyl)-D-prolinamide;

(1R,3R,5R)-2-(2-(ethylamino)benzoyl)-N—((R)-(2-fluoro-4-(trifluoromethyl)phenyl) (3-oxetanyl)methyl)-2-azabicyclo[3.1.0]hexane-3-carboxamide;

(1R,3R,5R)—N—((R)-(4-chloro-2,5-difluorophenyl)(cyclopropyl)methyl)-2-((5-(methylsulfonyl)-3-pyridinyl)carbonyl)-2-azabicyclo[3.1.0]hexane-3-carboxamide;

(1R,3R,5R)-2-(3-fluoro-5-(methylsulfonyl)benzoyl)-N—((R)-(2-fluoro-4-(trifluoromethyl)phenyl)(3-oxetanyl)methyl)-2-azabicyclo[3.1.0]hexane-3-carboxamide;

1-(3-((3-cyano-1-azetidinyl)sulfonyl)benzoyl)-N-((1S)-1-(2-fluoro-4-(trifluoromethyl)phenyl)-2-methylpropyl)-D-prolinamide;

1-(((3S)-1-((3-cyano-1-azetidinyl)sulfonyl)-3-piperidinyl)carbonyl)-N-(3,4-difluorobenzyl)-D-prolinamide;

N—((R)-(4-chloro-2,5-difluorophenyl)(cyclopropyl)methyl)-1-((4-(methylsulfonyl)-2-pyridinyl)carbonyl)-D-prolinamide;

N—((R)-cyclopropyl(2-fluoro-4-(trifluoromethyl)phenyl)methyl)-1-(3-(cyclopropylsulfonyl)benzoyl)-D-prolinamide;

N—((R)-(4-chloro-2,5-difluorophenyl)(cyclopropyl)methyl)-1-(3-sulfamoylbenzoyl)-D-prolinamide;

(1R,3R,5R)—N—((R)-cyclopropyl(2,5-difluoro-4-(trifluoromethyl)phenyl)methyl)-2-((2-(trifluoromethyl)-4-pyridinyl)carbonyl)-2-azabicyclo[3.1.0]hexane-3-carboxamide;

3-((3-cyano-1-azetidinyl)sulfonyl)-N-methyl-N-((1R)-1-methyl-2-oxo-2-((4-(trifluoromethyl)benzyl)amino)ethyl)benzamide;

1-(((3S)-1-((3-(1,2-oxazol-3-yl)-1-azetidinyl)sulfonyl)-3-piperidinyl)carbonyl)-N-(4-(trifluoromethyl)benzyl)-D-prolinamide;

N—((R)-cyclopropyl(2-fluoro-4-(trifluoromethyl)phenyl)methyl)-1-(2-(methylamino)-5-(methylsulfonyl)benzoyl)-D-prolinamide;

1-(((3S)-1-((3-cyano-1-azetidinyl)sulfonyl)-3-piperidinyl)carbonyl)-N-((1S)-1-(2-fluoro-4-(trifluoromethyl)phenyl)-2-methylpropyl)-D-prolinamide;

(1R,3R,5R)-2-((5-(cyclobutylamino)-2-methyl-4-pyridinyl)carbonyl)-N—((R)-cyclopropyl(2-fluoro-4-(trifluoromethyl)phenyl)methyl)-2-azabicyclo[3.1.0]hexane-3-carboxamide;

(1R,3R,5R)—N—((R)-(4-chloro-2,5-difluorophenyl)(cyclopropyl)methyl)-2-((2-(trifluoromethyl)-4-pyridinyl)carbonyl)-2-azabicyclo[3.1.0]hexane-3-carboxamide;

N—((R)-(2-fluoro-4-(trifluoromethyl)phenyl)(3-oxetanyl)methyl)-1-(3-(methylsulfonyl)benzoyl)-D-prolinamide;

(1R,3R,5R)—N—((R)-(4-chloro-2,5-difluorophenyl)(3-oxetanyl)methyl)-2-((4-(trifluoromethyl)-2-pyridinyl)carbonyl)-2-azabicyclo[3.1.0]hexane-3-carboxamide;

1-((3-((3,3-dimethyl-1-azetidinyl)sulfonyl)phenyl)carbonyl)-N-(4-(trifluoromethyl)benzyl)-D-prolinamide;

N—((R)-cyclobutyl(2-fluoro-4-(trifluoromethyl)phenyl)methyl)-1-(3-(methylsulfonyl)benzoyl)-D-prolinamide;

(3S)—N—((R)-cyclopropyl(2,5-difluoro-4-(trifluoromethyl)phenyl)methyl)-1-((5-(methylsulfonyl)-3-pyridinyl)carbonyl)-3-(trifluoromethyl)-L-prolinamide;

1-(((3S)-1-((3-(2-fluoroethoxy)-1-azetidinyl)sulfonyl)-3-piperidinyl)carbonyl)-N-(2-fluoro-4-(trifluoromethyl)benzyl)-D-prolinamide;

N-(4-chloro-3-fluorobenzyl)-1-(3-((3,3-difluoro-1-azetidinyl)sulfonyl)benzoyl)-D-prolinamide;

1-(((2S)-4-((3-cyano-1-azetidinyl)sulfonyl)-2-piperazinyl)carbonyl)-N-(4-(trifluoromethyl)benzyl)-D-prolinamide;

(4R)-1-(((3S)-1-((3-cyano-1-azetidinyl)sulfonyl)-3-piperidinyl)carbonyl)-4-hydroxy-N-(4-(trifluoromethyl)benzyl)-D-prolinamide;

(3R)—N—((R)-cyclopropyl(2,5-difluoro-4-(trifluoromethyl)phenyl)methyl)-1-((5-(methylsulfonyl)-3-pyridinyl)carbonyl)-3-(trifluoromethyl)-D-prolinamide;

(3S)—N—((R)-cyclopropyl(2,5-difluoro-4-(trifluoromethyl)phenyl)methyl)-1-((5-(methylsulfonyl)-3-pyridinyl)carbonyl)-3-(trifluoromethyl)-L-prolinamide;

1-(((3S)-1-((3-cyano-1-azetidinyl)sulfonyl)-3-piperidinyl)carbonyl)-N-((1R)-4-methoxy-2,3-dihydro-1H-inden-1-yl)-D-prolinamide;

1-(((3S)-1-((3-cyano-1-azetidinyl)sulfonyl)-3-piperidinyl)carbonyl)-N-((1S)-4-methoxy-2,3-dihydro-1H-inden-1-yl)-D-prolinamide;

1-(((3S)-1-((3-cyano-1-azetidinyl)sulfonyl)-3-piperidinyl)carbonyl)-N-(4-methylbenzyl)-D-prolinamide;

(1R,3R,5R)—N—((R)-(2-fluoro-4-(trifluoromethyl)phenyl)((3R)-5-oxo-3-pyrrolidinyl)methyl)-2-(3-(methylsulfonyl)benzoyl)-2-azabicyclo[3.1.0]hexane-3-carboxamide;

1-(((3S)-1-((3-cyano-1-azetidinyl)sulfonyl)-3-piperidinyl)carbonyl)-N-((1R)-1-(3,5-difluorophenyl)propyl)-D-prolinamide;

(1R,3R,5R)—N—((R)-cyclopropyl(2-fluoro-4-(trifluoromethyl)phenyl)methyl)-2-(3-(ethylsulfonyl)benzoyl)-2-azabicyclo[3.1.0]hexane-3-carboxamide;

N—((R)-cyclopropyl(2-fluoro-4-(trifluoromethyl)phenyl)methyl)-1-(3-(1-(cyclopropylsulfonyl)-3-fluoro-3-azetidinyl)benzoyl)-D-prolinamide;

1-(((3S)-1-((3-cyano-1-azetidinyl)sulfonyl)-3-piperidinyl)carbonyl)-N-((1R)-1-(4-(difluoromethyl)phenyl)ethyl)-D-prolinamide;

(1R,3R,5R)—N—((R)-cyclopropyl(2-fluoro-4-(trifluoromethyl)phenyl)methyl)-2-(3-((2-hydroxyethyl)sulfonyl)benzoyl)-2-azabicyclo[3.1.0]hexane-3-carboxamide;

1-((3-((3-cyano-1-azetidinyl)sulfonyl)phenyl)carbonyl)-N-(4-cyanobenzyl)-D-prolinamide;

(4S)-1-((3-((3-cyano-1-azetidinyl)sulfonyl)phenyl)carbonyl)-4-hydroxy-N-(4-(trifluoromethyl)benzyl)-D-prolinamide;

N—((R)-cyclopropyl(2-fluoro-4-(trifluoromethyl)phenyl)methyl)-1-(3-(trifluoromethyl)benzoyl)-D-prolinamide;

(2R)—N—((R)-cyclopropyl(2-fluoro-4-(trifluoromethyl)phenyl)methyl)-1-(3-(methylsulfonyl)benzoyl)-2-piperidinecarboxamide;

N-((1R)-1-(4-chloro-2-fluorophenyl)ethyl)-1-(((2S)-4-((3-cyano-1-azetidinyl)sulfonyl)-2-piperazinyl)carbonyl)-D-prolinamide;

N—((R)-(4-chloro-3-fluorophenyl) (3-oxetanyl)methyl)-1-(3-(methylsulfonyl)benzoyl)-D-prolinamide; 1-(((3S)-1-((3-cyano-1-azetidinyl)sulfonyl)-3-piperidinyl)carbonyl)-N-(2,4-dimethylbenzyl)-D-prolinamide;

1-(((2S)-4-((3-cyano-1-azetidinyl)sulfonyl)-2-piperazinyl)carbonyl)-N-(3,4-dichlorobenzyl)-D-prolinamide;

1-((3-((3-methoxy-1-azetidinyl)sulfonyl)phenyl)carbonyl)-N-(4-(trifluoromethyl)benzyl)-D-prolinamide;

N-((1R)-1-(4-chloro-3-fluorophenyl)propyl)-1-(3-(dimethylsulfamoyl)benzoyl)-D-prolinamide;

N-((6-chloro-3-pyridinyl)methyl)-1-((3-((3-cyano-1-azetidinyl)sulfonyl)phenyl)carbonyl)-D-prolinamide;

1-(((3S)-1-((3-cyano-1-azetidinyl)sulfonyl)-3-piperidinyl)carbonyl)-N-(4-(difluoromethyl)benzyl)-D-prolinamide;

(4S)—N—((R)-(4-chloro-2,5-difluorophenyl) (cyclopropyl)methyl)-4-fluoro-1-((6-(methylsulfonyl)-3-pyridinyl)carbonyl)-D-prolinamide;

(1R,3R,5R)-2-(3-(1-amino-2-methyl-1-oxo-2-propanyl)benzoyl)-N—((R)-(4-chloro-2,5-difluorophenyl)(3-oxetanyl)methyl)-2-azabicyclo[3.1.0]hexane-3-carboxamide;

(1R,3R,5R)—N—((R)-(4-chloro-3-fluorophenyl)(3-oxetanyl)methyl)-2-(3-(methylsulfonyl)benzoyl)-2-azabicyclo[3.1.0]hexane-3-carboxamide;

(2R)—N-((1S)-1-(4-chlorophenyl)ethyl)-1-((3-((3-cyano-1-azetidinyl)sulfonyl)phenyl)carbonyl)-2-piperidinecarboxamide;

(1R,3R,5R)—N—((R)-(4-chloro-2,5-difluorophenyl)(cyclopropyl)methyl)-2-((4-(trifluoromethyl)-2-pyridinyl)carbonyl)-2-azabicyclo[3.1.0]hexane-3-carboxamide;

(1R,3R,5R)—N—((R)-(4-chloro-2,5-difluorophenyl)(3-oxetanyl)methyl)-2-((2-(difluoromethyl)-4-pyridinyl)carbonyl)-2-azabicyclo[3.1.0]hexane-3-carboxamide;

N—((R)-(4-chlorophenyl)(phenyl)methyl)-1-(((3S)-1-((3-cyano-1-azetidinyl)sulfonyl)-3-piperidinyl)carbonyl)-D-prolinamide & N—((S)-(4-chlorophenyl)(phenyl)methyl)-1-(((3S)-1-((3-cyano-1-azetidinyl)sulfonyl)-3-piperidinyl)carbonyl)-D-prolinamide;

(4S)—N—((R)-(4-chloro-2,5-difluorophenyl) (cyclopropyl)methyl)-4-fluoro-1-((4-(methylsulfonyl)-2-pyridinyl)carbonyl)-D-prolinamide;

(1R,3R,5R)—N—((R)-cyclopropyl(2-fluoro-4-(trifluoromethyl)phenyl)methyl)-2-(3-(methylsulfonyl)benzoyl)-2-azabicyclo[3.1.0]hexane-3-carboxamide;

1-(((2S,3S)-1-((3-cyano-1-azetidinyl)sulfonyl)-2-methyl-3-piperidinyl)carbonyl)-N-(4-(trifluoromethyl)benzyl)-D-prolinamide;

N-(3-chloro-4-fluorobenzyl)-1-(((3S)-1-((3-cyano-1-azetidinyl)sulfonyl)-3-piperidinyl)carbonyl)-D-prolinamide;

(4S)-4-fluoro-N—((R)-(3-fluoro-4-(trifluoromethyl)phenyl)(3-oxetanyl)methyl)-1-(3-(methylsulfonyl)benzoyl)-D-prolinamide;

1-(((3S)-1-((3-(difluoromethyl)-1-azetidinyl)sulfonyl)-3-piperidinyl)carbonyl)-N-(4-(trifluoromethyl)benzyl)-D-prolinamide;

(1R,3R,5R)-2-(3-(ethylsulfonyl)benzoyl)-N—((R)-3-oxetanyl(4-(trifluoromethyl)phenyl)methyl)-2-azabicyclo[3.1.0]hexane-3-carboxamide;

1-(((3S)-1-((3-cyano-1-azetidinyl)sulfonyl)-3-piperidinyl)carbonyl)-N-((1R,3R)-3-(hydroxymethyl)-2,3-dihydro-1H-inden-1-yl)-D-prolinamide;

1-(((3S)-1-((3-cyano-1-azetidinyl)sulfonyl)-3-piperidinyl)carbonyl)-N-((1R,3S)-3-(hydroxymethyl)-2,3-dihydro-1H-inden-1-yl)-D-prolinamide;

1-(((3S)-1-((3-cyano-1-azetidinyl)sulfonyl)-3-piperidinyl)carbonyl)-N-((1S,3R)-3-(hydroxymethyl)-2,3-dihydro-1H-inden-1-yl)-D-prolinamide;

1-(((3S)-1-((3-cyano-1-azetidinyl)sulfonyl)-3-piperidinyl)carbonyl)-N-((1S,3S)-3-(hydroxymethyl)-2,3-dihydro-1H-inden-1-yl)-D-prolinamide;

(1R,3R,5R)—N—((R)-(4-chloro-2,5-difluorophenyl)(cyclopropyl)methyl)-2-(((3S)-1-(methylsulfonyl)-3-piperidinyl)carbonyl)-2-azabicyclo[3.1.0]hexane-3-carboxamide;

(1R,3R,5R)—N—((R)-(4-chloro-3,5-difluorophenyl)(cyclopropyl)methyl)-2-(3-(methylsulfonyl)benzoyl)-2-azabicyclo[3.1.0]hexane-3-carboxamide;

(1R,3R,5R)—N—((R)-cyclopropyl(2,5-difluoro-4-(trifluoromethyl)phenyl)methyl)-2-((2-(methylsulfonyl)-4-pyridinyl)carbonyl)-2-azabicyclo[3.1.0]hexane-3-carboxamide;

(4S)—N—((R)-(4-chloro-2,5-difluorophenyl) (cyclopropyl)methyl)-4-fluoro-1-(3-sulfamoylbenzoyl)-D-prolinamide;

N—((R)-cyclopropyl(2-fluoro-4-(trifluoromethyl)phenyl)methyl)-1-(3-((2,2,2-trifluoroethyl)sulfonyl)benzoyl)-D-prolinamide;

(1R,3R,5R)—N—((R)-(4-chloro-2,5-difluorophenyl)(3-oxetanyl)methyl)-2-((5-(trifluoromethyl)-3-pyridinyl)carbonyl)-2-azabicyclo[3.1.0]hexane-3-carboxamide;

1-(3-((3-cyano-1-azetidinyl)sulfonyl)phenyl)carbonyl)-N-(4-cyclopropylbenzyl)-D-prolinamide;

N-(2-chloro-4-fluorobenzyl)-1-(((3S)-1-((3-cyano-1-azetidinyl)sulfonyl)-3-piperidinyl)carbonyl)-D-prolinamide;

1-(((3S)-1-((3-cyano-1-azetidinyl)sulfonyl)-3-piperidinyl)carbonyl)-N-((1R)-1-(4-methylphenyl)ethyl)-D-prolinamide;

N—((R)-cyclopropyl(2-fluoro-4-(trifluoromethyl)phenyl)methyl)-1-(3-(3-fluoro-1-(methylsulfonyl)-3-azetidinyl)benzoyl)-D-prolinamide;

1-(((3S)-1-((3-cyano-1-azetidinyl)sulfonyl)-3-piperidinyl)carbonyl)-N-(3,5-difluorobenzyl)-D-prolinamide;

1-(((3S)-1-((3-cyano-1-azetidinyl)sulfonyl)-3-piperidinyl)carbonyl)-N-(3-fluoro-2-methylbenzyl)-D-prolinamide;

(1R,3R,5R)—N—((R)-cyclopropyl(2,5-difluoro-4-(trifluoromethyl)phenyl)methyl)-2-((4-(trifluoromethyl)-2-pyridinyl)carbonyl)-2-azabicyclo[3.1.0]hexane-3-carboxamide;

N-(4-chloro-2-fluorobenzyl)-1-(((2S)-4-((3-cyano-1-azetidinyl)sulfonyl)-2-piperazinyl)carbonyl)-D-prolinamide;

N-((1R)-1-(4-chlorophenyl)ethyl)-1-(((2S)-4-((3-cyano-1-azetidinyl)sulfonyl)-2-morpholinyl)carbonyl)-D-prolinamide;

(2R)—N—((R)-(4-chloro-2,5-difluorophenyl) (cyclopropyl)methyl)-1-((5-(methylsulfonyl)-3-pyridinyl)carbonyl)-2-piperidinecarboxamide;

1-(((3S)-1-((3-cyano-1-azetidinyl)sulfonyl)-3-piperidinyl)carbonyl)-N-((1S)-1-(2-fluoro-4-(trifluoromethyl)phenyl)propyl)-D-prolinamide;

(4R)—N—((R)-cyclopropyl(2-fluoro-4-(trifluoromethyl)phenyl)methyl)-4-methyl-1-(3-(methylsulfonyl)benzoyl)-D-prolinamide;

(1R,3R,5R)—N—((R)-(4-chloro-2,5-difluorophenyl)(cyclopropyl)methyl)-2-((2-(cyclopropylsulfonyl)-4-pyridinyl)carbonyl)-2-azabicyclo[3.1.0]hexane-3-carboxamide;

1-(((3S)-1-((3-(difluoromethyl)-3-hydroxy-1-azetidinyl)sulfonyl)-3-piperidinyl)carbonyl)-N-(2-fluoro-4-(trifluoromethyl)benzyl)-D-prolinamide;

1-(((3S)-1-((3-cyano-1-azetidinyl)sulfonyl)-3-piperidinyl)carbonyl)-N-(4-fluoro-3-(trifluoromethyl)benzyl)-D-prolinamide;

N-((1R)-2-(((1R)-1-(4-chlorophenyl)ethyl)amino)-1-methyl-2-oxoethyl)-3-((3-cyano-1-azetidinyl)sulfonyl)-N-methylbenzamide;

N-((1R)-2-(((1S)-1-(4-chlorophenyl)ethyl)amino)-1-methyl-2-oxoethyl)-3-((3-cyano-1-azetidinyl)sulfonyl)-N-methylbenzamide;

(2S)-4-((3-cyano-1-azetidinyl)sulfonyl)-N-((2R)-1-(((1R)-1-(2-fluoro-4-(trifluoromethyl)phenyl)ethyl)amino)-1-oxo-2-propanyl)-N-methyl-2-morpholinecarboxamide;

(2R)—N—((R)-cyclopropyl(3-fluoro-4-(trifluoromethyl)phenyl)methyl)-1-(3-(methylsulfonyl)benzoyl)-2-piperidinecarboxamide;

1-(((3S)-1-((3-cyano-1-azetidinyl)sulfonyl)-3-piperidinyl)carbonyl)-N-((1R)-1-(3,4-difluorophenyl)ethyl)-D-prolinamide;

1-(((3S)-1-(((2R)-2-(2-fluorophenyl)-1-azetidinyl)sulfonyl)-3-piperidinyl)carbonyl)-N-(4-(trifluoromethyl)benzyl)-D-prolinamide;

1-(((3S)-1-(((2S)-2-(2-fluorophenyl)-1-azetidinyl)sulfonyl)-3-piperidinyl)carbonyl)-N-(4-(trifluoromethyl)benzyl)-D-prolinamide;

N-(4-chloro-3-fluorobenzyl)-1-(3-(dimethylsulfamoyl)benzoyl)-D-prolinamide;

N—((R)-(4-chloro-2-fluorophenyl) (3-oxetanyl)methyl)-1-(3-(methylsulfonyl)benzoyl)-D-prolinamide;

N-((1R)-1-(4-chlorophenyl)-2-hydroxyethyl)-1-(3-((3-cyano-1-azetidinyl)sulfonyl)benzoyl)-D-prolinamide;

((3-(((1R,3R,5R)-3-(((R)-cyclopropyl(2,5-difluoro-4-(trifluoromethyl)phenyl)methyl)carbamoyl)-2-azabicyclo[3.1.0]hexan-2-yl)carbonyl)phenyl)sulfonyl)acetic acid;

(1R,3R,5R)—N—((R)-cyclopropyl(3-fluoro-4-(trifluoromethyl)phenyl)methyl)-2-(3-(methylsulfonyl)benzoyl)-2-azabicyclo[3.1.0]hexane-3-carboxamide;
N-((1S)-1-(4-chlorophenyl)-2,2,2-trifluoroethyl)-1-(((3S)-1-((3-cyano-1-azetidinyl)sulfonyl)-3-piperidinyl)carbonyl)-D-prolinamide;
(1R,3R,5R)—N—((R)-cyclopropyl(2-methoxy-4-(trifluoromethyl)phenyl)methyl)-2-(3-(methylsulfonyl)benzoyl)-2-azabicyclo[3.1.0]hexane-3-carboxamide;
(1R,3R,5R)—N—((R)-cyclopropyl(3-fluoro-4-(trifluoromethyl)phenyl)methyl)-2-(3-(cyclopropylsulfonyl)benzoyl)-2-azabicyclo[3.1.0]hexane-3-carboxamide;
1-(((3S)-1-((3-(2,2-difluoroethoxy)-1-azetidinyl)sulfonyl)-3-piperidinyl)carbonyl)-N-(4-(trifluoromethyl)benzyl)-D-prolinamide;
(6R)-5-((3-(5-azaspiro[2.3]hex-5-ylsulfonyl)phenyl)carbonyl)-N-(4-(trifluoromethyl)benzyl)-5-azaspiro[2.4]heptane-6-carboxamide;
N-(3-chloro-5-fluorobenzyl)-1-(((3S)-1-((3-cyano-1-azetidinyl)sulfonyl)-3-piperidinyl)carbonyl)-D-prolinamide;
(1R,3R,5R)—N—((R)-(4-chloro-2,5-difluorophenyl)(cyclopropyl)methyl)-2-((2-(methylsulfonyl)-4-pyridinyl)carbonyl)-2-azabicyclo[3.1.0]hexane-3-carboxamide;
1-(3-(methyl(2-propanyl)sulfamoyl)benzoyl)-N-(4-(trifluoromethyl)benzyl)-D-prolinamide;
(1R,3R,5R)—N—((S)-(4-chloro-2,5-difluorophenyl)(1-hydroxycyclopropyl)methyl)-2-(3-(methylsulfonyl)benzoyl)-2-azabicyclo[3.1.0]hexane-3-carboxamide;
(3S)—N-((2R)-1-(((1R)-1-(4-chloro-2-fluorophenyl)ethyl)amino)-1-oxo-2-propanyl)-1-((3-cyano-1-azetidinyl)sulfonyl)-N-methyl-3-piperidinecarboxamide;
(2R)—N—((R)-(4-chloro-2,5-difluorophenyl) (cyclopropyl)methyl)-1-((2-(methylsulfonyl)-4-pyridinyl)carbonyl)-2-piperidinecarboxamide;
1-(((3S)-1-(((3R)-3-cyano-1-pyrrolidinyl)sulfonyl)-3-piperidinyl)carbonyl)-N-(4-(trifluoromethyl)benzyl)-D-prolinamide;
N—(R)-cyclopropyl(2-fluoro-4-(trifluoromethyl)phenyl)methyl)-4,4-difluoro-1-(3-(methylsulfonyl)benzoyl)-D-prolinamide;
N-((1R)-1-(2,4-difluorophenyl)ethyl)-1-(((3S)-1-((3-(methylsulfonyl)-1-azetidinyl)sulfonyl)-3-piperidinyl)carbonyl)-D-prolinamide;
(2R)—N—((R)-cyclopropyl(2-fluoro-4-(trifluoromethyl)phenyl)methyl)-1-(3-(2,2,2-trifluoro-1,1-dihydroxyethyl)benzoyl)-2-piperidinecarboxamide;
(1R,3R,5R)—N—((R)-(2-fluoro-4-(trifluoromethyl)phenyl)(3-oxetanyl)methyl)-2-(3-methyl-5-(methylsulfonyl)benzoyl)-2-azabicyclo[3.1.0]hexane-3-carboxamide;
(1R)-2-((3-((3-cyano-1-azetidinyl)sulfonyl)phenyl)carbonyl)-N-(4-(trifluoromethyl)benzyl)-1,2,3,4-tetrahydro-1-isoquinolinecarboxamide;
(1S)-2-((3-((3-cyano-1-azetidinyl)sulfonyl)phenyl)carbonyl)-N-(4-(trifluoromethyl)benzyl)-1,2,3,4-tetrahydro-1-isoquinolinecarboxamide;
1-(((3S)-1-((3-cyano-1-azetidinyl)sulfonyl)-3-piperidinyl)carbonyl)-N-((1R)-1-(2,4-difluorophenyl)ethyl)-D-prolinamide;
(1R,3R,5R)-2-(((3S)-1-((3-cyano-1-azetidinyl)sulfonyl)-3-piperidinyl)carbonyl)-N-((6-(trifluoromethyl)-3-pyridinyl)methyl)-2-azabicyclo[3.1.0]hexane-3-carboxamide;
1-(((3S)-1-((3-cyano-3-fluoro-1-azetidinyl)sulfonyl)-3-piperidinyl)carbonyl)-N-(2-fluoro-4-(trifluoromethyl)benzyl)-D-prolinamide;
(3R)—N—((R)-(4-chloro-2,5-difluorophenyl) (cyclopropyl)methyl)-4-(3-(methylsulfonyl)benzoyl)-3-morpholinecarboxamide;
1-((3-(2-oxa-6-azaspiro[3.3]hept-6-ylsulfonyl)phenyl)carbonyl)-N-(4-(trifluoromethyl)benzyl)-D-prolinamide;
N-((1S)-1-(4-chlorophenyl)ethyl)-1-((3-((3-cyano-1-azetidinyl)sulfonyl)phenyl)carbonyl)-D-prolinamide;
N-((1R)-2-(((1S)-1-(4-chlorophenyl)ethyl)amino)-1-methyl-2-oxoethyl)-3-((3-cyano-1-azetidinyl)sulfonyl)-N-methylbenzamide;
N-(2-fluoro-4-(trifluoromethyl)benzyl)-1-(((3S)-1-((3-hydroxy-3-(2-propanyl)-1-azetidinyl)sulfonyl)-3-piperidinyl)carbonyl)-D-prolinamide;
N-(4-chloro-3-(trifluoromethyl)benzyl)-1-(((3S)-1-((3-cyano-1-azetidinyl)sulfonyl)-3-piperidinyl)carbonyl)-D-prolinamide;
1-(((2S)-4-((3-cyano-1-azetidinyl)sulfonyl)-2-piperazinyl)carbonyl)-N-(3-fluoro-4-methylbenzyl)-D-prolinamide;
1-(((3S)-1-((3-cyano-1-azetidinyl)sulfonyl)-3-piperidinyl)carbonyl)-N-(2-fluoro-3-(trifluoromethyl)benzyl)-D-prolinamide;
1-(((3S)-1-((3-cyano-1-azetidinyl)sulfonyl)-3-piperidinyl)carbonyl)-N-(3,4-dimethylbenzyl)-D-prolinamide;
N-((1R)-2-((4-chlorobenzyl)amino)-1-methyl-2-oxoethyl)-3-((3-cyano-1-azetidinyl)sulfonyl)-N-methylbenzamide;
1-(((3S)-1-((3-cyano-1-azetidinyl)sulfonyl)-3-piperidinyl)carbonyl)-N-(pentafluorobenzyl)-D-prolinamide;
1-(((3S)-1-(((2R)-2-phenyl-1-azetidinyl)sulfonyl)-3-piperidinyl)carbonyl)-N-(4-(trifluoromethyl)benzyl)-D-prolinamide;
1-(((3S)-1-(((2S)-2-phenyl-1-azetidinyl)sulfonyl)-3-piperidinyl)carbonyl)-N-(4-(trifluoromethyl)benzyl)-D-prolinamide;
(1R,2R,5S)—N—((R)-(4-chloro-2,5-difluorophenyl) (cyclopropyl)methyl)-3-(3-sulfamoylbenzoyl)-3-azabicyclo[3.1.0]hexane-2-carboxamide;
3-((3-cyano-1-azetidinyl)sulfonyl)-N-((1R)-2-((3,4-dichlorobenzyl)amino)-1-methyl-2-oxoethyl)-N-methylbenzamide;
(4S)—N—((R)-cyclopropyl(2-fluoro-4-(trifluoromethyl)phenyl)methyl)-3-((5-(methylsulfonyl)-3-pyridinyl)carbonyl)-1,3-thiazolidine-4-carboxamide;
1-(((3S)-1-((3-(difluoromethoxy)-1-azetidinyl)sulfonyl)-3-piperidinyl)carbonyl)-N-(4-(trifluoromethyl)benzyl)-D-prolinamide;
(1R,3R,5R)—N—((R)-(4-chloro-2-fluorophenyl)(cyclopropyl)methyl)-2-(3-(methylsulfonyl)benzoyl)-2-azabicyclo[3.1.0]hexane-3-carboxamide;
1-(2-amino-5-(methylsulfonyl)benzoyl)-N—((R)-cyclopropyl(2-fluoro-4-(trifluoromethyl)phenyl)methyl)-D-prolinamide;
methyl N-methyl-N-((3-(((2R)-2-((4-(trifluoromethyl)benzyl)carbamoyl)-1-pyrrolidinyl)carbonyl)phenyl)sulfonyl)glycinate;
(2R)—N—((R)-cyclopropyl(2-fluoro-4-(trifluoromethyl)phenyl)methyl)-1-(3-((1R)-2,2,2-trifluoro-1-hydroxyethyl)benzoyl)-2-piperidinecarboxamide;
(2R)—N—((R)-cyclopropyl(2-fluoro-4-(trifluoromethyl)phenyl)methyl)-1-(3-((1S)-2,2,2-trifluoro-1-hydroxyethyl)benzoyl)-2-piperidinecarboxamide;
(1R,3R,5R)-2-(((3S)-1-((3-cyano-1-azetidinyl)sulfonyl)-3-piperidinyl)carbonyl)-N-((5-(trifluoromethyl)-2-pyridinyl)methyl)-2-azabicyclo[3.1.0]hexane-3-carboxamide;
(1R,3R,5R)-2-(3-(1-carbamoylcyclopropyl)benzoyl)-N—((R)-(2-fluoro-4-(trifluoromethyl)phenyl)(3-oxetanyl)methyl)-2-azabicyclo[3.1.0]hexane-3-carboxamide;
1-((3-(5-azaspiro[2.3]hex-5-ylsulfonyl)phenyl)carbonyl)-N-(4-(trifluoromethyl)benzyl)-D-prolinamide;

(1R,3R,5R)—N—((R)-(2-fluoro-4-(trifluoromethyl)phenyl) (3-oxetanyl)methyl)-2-(2-(2,2,2-trifluoroacetamido)benzoyl)-2-azabicyclo[3.1.0]hexane-3-carboxamide;
(4S)—N—((R)-(4-chloro-2-fluorophenyl)(3-oxetanyl) methyl)-4-fluoro-1-(3-(methylsulfonyl)benzoyl)-D-prolinamide;
1-(((3S)-1-((3-cyano-1-azetidinyl)sulfonyl)-3-piperidinyl) carbonyl)-N-(3-(trifluoromethyl)benzyl)-D-prolinamide;
(4R)—N—((R)-cyclopropyl(2-fluoro-4-(trifluoromethyl) phenyl)methyl)-4-(difluoromethyl)-1-(3-(methylsulfonyl)benzoyl)-D-prolinamide;
(2R)-1-((3-((trans-3-cyanocyclobutyl)sulfonyl)phenyl)carbonyl)-N-((6-(trifluoromethyl)-3-pyridinyl)methyl)-2-piperidinecarboxamide;
1-(((3S)-1-((3-cyano-1-azetidinyl)sulfonyl)-3-piperidinyl) carbonyl)-N-(2,3,5-trifluorobenzyl)-D-prolinamide;
1-(((3S)-1-((3-cyano-1-azetidinyl)sulfonyl)-3-piperidinyl) carbonyl)-N-((3R)-4,6-difluoro-2,3-dihydro-1-benzofuran-3-yl)-D-prolinamide;
1-(((3S)-1-((3-cyano-1-azetidinyl)sulfonyl)-3-piperidinyl) carbonyl)-N-((3S)-4,6-difluoro-2,3-dihydro-1-benzofuran-3-yl)-D-prolinamide;
1-(((3S)-1-((3-cyano-1-azetidinyl)sulfonyl)-3-piperidinyl) carbonyl)-N-(3-methyl-5-(trifluoromethyl)benzyl)-D-prolinamide;
(2R)—N—((R)-cyclopropyl(2-fluoro-4-(trifluoromethyl) phenyl)methyl)-1-(3-sulfamoylbenzoyl)-2-piperidinecarboxamide;
1-(((3S)-1-((3-cyano-1-azetidinyl)sulfonyl)-3-piperidinyl) carbonyl)-N-(2,4-difluorobenzyl)-D-prolinamide;
(1R,3R,5R)—N—((R)-cyclopropyl(2,5-difluoro-4-(trifluoromethyl)phenyl)methyl)-2-((5-(trifluoromethyl)-3-pyridinyl)carbonyl)-2-azabicyclo[3.1.0]hexane-3-carboxamide;
N—((R)-(4-chloro-2,5-difluorophenyl)(cyclopropyl) methyl)-1-((5-(methylsulfonyl)-3-pyridinyl)carbonyl)-D-prolinamide;
1-(((3S)-1-((3-cyano-1-azetidinyl)sulfonyl)-3-piperidinyl) carbonyl)-N-methyl-N-(4-(trifluoromethyl)benzyl)-D-prolinamide;
(R)—N—((R)-cyclopropyl(2-fluoro-4-(trifluoromethyl) phenyl)methyl)-1-(3-(methylsulfonyl)benzoyl)pyrrolidine-2-carboxamide;
(4S)—N—((R)-(4-chloro-3-fluorophenyl)(3-oxetanyl) methyl)-4-fluoro-1-(3-(methylsulfonyl)benzoyl)-D-prolinamide;
(1R,3R,5R)-2-(3-cyanobenzoyl)-N—((R)-(2-fluoro-4-(trifluoromethyl)phenyl)(3-oxetanyl)methyl)-2-azabicyclo [3.1.0]hexane-3-carboxamide;
1-(((3S)-1-((3-(1H-pyrrol-1-yl)-1-azetidinyl)sulfonyl)-3-piperidinyl)carbonyl)-N-(4-(trifluoromethyl)benzyl)-D-prolinamide;
N-(2-fluoro-4-(trifluoromethyl)benzyl)-1-(3-((3-hydroxy-3-methyl-1-azetidinyl)sulfonyl)benzoyl)-D-prolinamide;
1-(3-cyclopropylbenzoyl)-N—((R)-cyclopropyl(2-fluoro-4-(trifluoromethyl)phenyl)methyl)-D-prolinamide;
1-(3-(methylsulfonyl)benzoyl)-N—((R)-3-oxetanyl(4-(trifluoromethyl)phenyl)methyl)-D-prolinamide;
1-(((3S)-1-((3-hydroxy-3-phenyl-1-azetidinyl)sulfonyl)-3-piperidinyl)carbonyl)-N-(4-(trifluoromethyl)benzyl)-D-prolinamide;
(1R,3R,5R)-2-(2-acetamidobenzoyl)-N—((R)-cyclopropyl (2-fluoro-4-(trifluoromethyl)phenyl)methyl)-2-azabicyclo[3.1.0]hexane-3-carboxamide;
1-(((3S)-1-((3-cyano-1-azetidinyl)sulfonyl)-3-piperidinyl) carbonyl)-N-((5-(trifluoromethyl)-2-pyridinyl)methyl)-D-prolinamide;
(1R,3R,5R)—N—((R)-(4-chloro-2,5-difluorophenyl)(cyclopropyl)methyl)-2-((5-(trifluoromethyl)-3-pyridinyl) carbonyl)-2-azabicyclo[3.1.0]hexane-3-carboxamide;
(1R,3R,5R)-2-(3-(methylsulfonyl)benzoyl)-N—((R)-3-oxetanyl(4-(trifluoromethyl)phenyl)methyl)-2-azabicyclo [3.1.0]hexane-3-carboxamide;
N-((5-chloro-1,3-thiazol-2-yl)methyl)-1-((3-((3-cyano-1-azetidinyl)sulfonyl)phenyl)carbonyl)-D-prolinamide;
(2R)—N—((R)-cyclopropyl(2-fluoro-4-(trifluoromethyl) phenyl)methyl)-1-(3-(methylsulfonyl)benzoyl)-2,3-dihydro-1H-pyrrole-2-carboxamide;
1-(3-chlorobenzoyl)-N—((R)-cyclopropyl(2-fluoro-4-(trifluoromethyl)phenyl)methyl)-D-prolinamide;
1-(((3S)-1-((3-cyano-1-azetidinyl)sulfonyl)-3-piperidinyl) carbonyl)-N-(3-fluoro-5-(trifluoromethyl)benzyl)-D-prolinamide;
1-(((3S)-1-((3-(trifluoromethyl)-1-azetidinyl)sulfonyl)-3-piperidinyl)carbonyl)-N-(4-(trifluoromethyl)benzyl)-D-prolinamide;
1-(((3S)-1-((3-cyano-1-azetidinyl)sulfonyl)-3-piperidinyl) carbonyl)-N-(4-fluoro-2-methylbenzyl)-D-prolinamide;
(1R,3R,5R)-2-(3-(ethylsulfonyl)benzoyl)-N—((S)-(2-fluoro-4-(trifluoromethyl)phenyl)(1-hydroxycyclopropyl)methyl)-2-azabicyclo[3.1.0]hexane-3-carboxamide;
(1R,3R,5R)—N—((R)-cyclopropyl(2-fluoro-4-(trifluoromethyl)phenyl)methyl)-2-((5-(ethylamino)-2-methyl-4-pyridinyl)carbonyl)-2-azabicyclo[3.1.0]hexane-3-carboxamide;
N-(4-(trifluoromethyl)benzyl)-1-(((3S)-1-(((3S)-3-(trifluoromethyl)-1-pyrrolidinyl)sulfonyl)-3-piperidinyl)carbonyl)-D-prolinamide;
1-(3-((3-hydroxy-3-methyl-1-azetidinyl)sulfonyl)benzoyl)-N-(4-(trifluoromethyl)benzyl)-D-prolinamide;
1-(3-((3-cyano-1-azetidinyl)sulfonyl)benzoyl)-N-((1R)-2-hydroxy-1-(3-(trifluoromethyl)phenyl)ethyl)-D-prolinamide;
1-(((3S)-1-((3-cyano-1-azetidinyl)sulfonyl)-3-piperidinyl) carbonyl)-N-(3-methoxy-4-methylbenzyl)-D-prolinamide;
1-(((3S)-1-((3-cyano-1-azetidinyl)sulfonyl)-3-piperidinyl) carbonyl)-N-((1R)-2-methoxy-1-(3-(trifluoromethyl)phenyl)ethyl)-D-prolinamide;
1-(((3S)-1-((3-cyano-1-azetidinyl)sulfonyl)-3-piperidinyl) carbonyl)-N-((1S)-2-methoxy-1-(3-(trifluoromethyl)phenyl)ethyl)-D-prolinamide;
(1R,3R,5R)—N—((R)-(4-chloro-2,5-difluorophenyl)(cyclopropyl)methyl)-2-((2-(ethylsulfonyl)-4-pyridinyl)carbonyl)-2-azabicyclo[3.1.0]hexane-3-carboxamide;
1-(((3S)-1-((3-cyano-1-azetidinyl)sulfonyl)-3-piperidinyl) carbonyl)-N-(3,5-dichlorobenzyl)-D-prolinamide;
1-(((3S)-1-((3-cyano-1-azetidinyl)sulfonyl)-3-piperidinyl) carbonyl)-N-((1R)-1-(3,5-difluorophenyl)ethyl)-D-prolinamide;
(1R,3R,5R)—N—((R)-(2-fluoro-4-(trifluoromethyl)phenyl) (3-oxetanyl)methyl)-2-((2-(trifluoromethyl)-4-pyridinyl) carbonyl)-2-azabicyclo[3.1.0]hexane-3-carboxamide;
(1R,2R,5S)—N—((R)-(4-chloro-2,5-difluorophenyl) (cyclopropyl)methyl)-3-((2-(methylsulfonyl)-4-pyridinyl) carbonyl)-3-azabicyclo[3.1.0]hexane-2-carboxamide;
1-(((3S)-1-((3-cyano-1-azetidinyl)sulfonyl)-3-piperidinyl) carbonyl)-N-(2,5-difluorobenzyl)-D-prolinamide;
(1R,3R,5R)—N-((1S,2S)-1-(4-chloro-2,5-difluorophenyl)-2-hydroxypropyl)-2-(3-(ethylsulfonyl)benzoyl)-2-azabicyclo[3.1.0]hexane-3-carboxamide;
N-(2-chlorobenzyl)-1-((3-((3-cyano-1-azetidinyl)sulfonyl) phenyl)carbonyl)-D-prolinamide;

(4R)—N—((R)-(4-chloro-2,5-difluorophenyl) (cyclopropyl)methyl)-4-hydroxy-1-((2-(trifluoromethyl)-4-pyridinyl)carbonyl)-D-prolinamide;

1-(((3S)-1-((3-(3-chlorophenyl)-1-azetidinyl)sulfonyl)-3-piperidinyl)carbonyl)-N-(4-(trifluoromethyl)benzyl)-D-prolinamide;

(4R)—N—((R)-(4-chloro-2,5-difluorophenyl) (3-oxetanyl)methyl)-4-hydroxy-1-((2-(trifluoromethyl)-4-pyridinyl)carbonyl)-D-prolinamide;

1-(((3S)-1-((3-cyano-1-azetidinyl)sulfonyl)-3-piperidinyl)carbonyl)-N-((2-(trifluoromethyl)-5-pyrimidinyl)methyl)-D-prolinamide;

(2R)—N—((R)-cyclopropyl(2-fluoro-4-(trifluoromethyl)phenyl)methyl)-1-(3-(methylsulfonyl)benzoyl)-2,5-dihydro-1H-pyrrole-2-carboxamide;

(2R,4S)—N—((R)-cyclopropyl(2-fluoro-4-(trifluoromethyl)phenyl)methyl)-4-fluoro-1-(3-(methylsulfonyl)benzoyl)pyrrolidine-2-carboxamide;

(1R,3R,5R)—N—((R)-(4-chlorophenyl)(3-oxetanyl)methyl)-2-(3-(ethylsulfonyl)benzoyl)-2-azabicyclo[3.1.0]hexane-3-carboxamide;

1-(((3S)-1-((3-cyano-1-azetidinyl)sulfonyl)-3-piperidinyl)carbonyl)-N-((1S)-2-hydroxy-1-(3-(trifluoromethyl)phenyl)ethyl)-D-prolinamide;

(1R,3R,5R)—N-((1S,2S)-1-(4-chloro-2,5-difluorophenyl)-2-hydroxypropyl)-2-(3-(methylsulfonyl)benzoyl)-2-azabicyclo[3.1.0]hexane-3-carboxamide;

N-(3-chloro-2-fluorobenzyl)-1-(((3S)-1-((3-cyano-1-azetidinyl)sulfonyl)-3-piperidinyl)carbonyl)-D-prolinamide;

(1R,2R,5S)—N—((R)-cyclopropyl(2-fluoro-4-(trifluoromethyl)phenyl)methyl)-3-(3-(methylsulfonyl)benzoyl)-3-azabicyclo[3.1.0]hexane-2-carboxamide;

N—((S)-(4-chloro-3-fluorophenyl)(cyclopropyl)methyl)-1-(3-(dimethylsulfamoyl)benzoyl)-D-prolinamide;

(1R,3R,5R)—N—((R)-(2-fluoro-4-(trifluoromethyl)phenyl)(3-oxetanyl)methyl)-2-((4-(trifluoromethyl)-2-pyridinyl)carbonyl)-2-azabicyclo[3.1.0]hexane-3-carboxamide;

1-(((3S)-1-((3-cyano-1-azetidinyl)sulfonyl)-3-piperidinyl)carbonyl)-N-((6-(trifluoromethyl)-3-pyridinyl)methyl)-D-prolinamide;

(4S)-1-((3-((3-cyano-1-azetidinyl)sulfonyl)phenyl)carbonyl)-4-fluoro-N-((1R)-1-(3-(trifluoromethyl)phenyl)ethyl)-D-prolinamide;

(1R,3R,5R)-2-(3-(2-cyano-2-propanyl)benzoyl)-N—((R)-(2-fluoro-4-(trifluoromethyl)phenyl)(3-oxetanyl)methyl)-2-azabicyclo[3.1.0]hexane-3-carboxamide;

1-(((3S)-1-((3-cyano-1-azetidinyl)sulfonyl)-3-piperidinyl)carbonyl)-N-(4-(fluoromethyl)benzyl)-D-prolinamide;

N—((R)-cyclopropyl(2-fluoro-4-(trifluoromethyl)phenyl)methyl)-1-(3-(2-propanyl)benzoyl)-D-prolinamide;

(3S)-1-((3-cyano-1-azetidinyl)sulfonyl)-N-methyl-N-((1R)-1-methyl-2-oxo-2-(((1R)-1-(4-(trifluoromethyl)phenyl)ethyl)amino)ethyl)-3-piperidinecarboxamide;

(4S)—N—((R)-cyclopropyl(2,5-difluoro-4-(trifluoromethyl)phenyl)methyl)-4-fluoro-1-((2-(methylsulfonyl)-4-pyridinyl)carbonyl)-D-prolinamide;

1-(((3S)-1-((3-cyano-1-azetidinyl)sulfonyl)-3-piperidinyl)carbonyl)-N-(2-methoxy-4-methylbenzyl)-D-prolinamide;

N-(2-chloro-3-fluorobenzyl)-1-(((3S)-1-((3-cyano-1-azetidinyl)sulfonyl)-3-piperidinyl)carbonyl)-D-prolinamide;

(2S)—N-((2R)-1-(((1R)-1-(4-chloro-2-fluorophenyl)ethyl)amino)-1-oxo-2-propanyl)-4-((3-cyano-1-azetidinyl)sulfonyl)-N-methyl-2-morpholinecarboxamide;

(2R)—N-((6-chloro-3-pyridinyl)methyl)-1-((3-((trans-3-cyanocyclobutyl)sulfonyl)phenyl)carbonyl)-2-piperidinecarboxamide;

N—((R)-(4-chloro-2,5-difluorophenyl)(cyclopropyl)methyl)-1-((2-(methylsulfonyl)-4-pyridinyl)carbonyl)-D-prolinamide;

(1R,3R,5R)—N—((R)-cyclopropyl(2-fluoro-4-(trifluoromethyl)phenyl)methyl)-2-(3-(3-fluoro-1-(methylsulfonyl)-3-azetidinyl)benzoyl)-2-azabicyclo[3.1.0]hexane-3-carboxamide;

1-(((3S)-1-((3-cyano-1-azetidinyl)sulfonyl)-3-piperidinyl)carbonyl)-N-(2,3,4,6-tetrafluorobenzyl)-D-prolinamide;

1-(((3S)-1-((3-(4-chlorophenoxy)-1-azetidinyl)sulfonyl)-3-piperidinyl)carbonyl)-N-(4-(trifluoromethyl)benzyl)-D-prolinamide;

1-(((3S)-1-((cis-3-carbamoylcyclobutyl)sulfonyl)-3-piperidinyl)carbonyl)-N-(4-(trifluoromethyl)benzyl)-D-prolinamide;

N—((R)-(4-chloro-3-fluorophenyl) (cyclopropyl)methyl)-1-(3-(methylsulfonyl)benzoyl)-D-prolinamide;

(4S)-1-(((3S)-1-((3-cyano-1-azetidinyl)sulfonyl)-3-piperidinyl)carbonyl)-4-fluoro-N-(3-(trifluoromethyl)benzyl)-D-prolinamide;

1-(((2S)-4-((3-cyano-1-azetidinyl)sulfonyl)-2-piperazinyl)carbonyl)-N-((1R)-1-(4-(trifluoromethyl)phenyl)ethyl)-D-prolinamide;

N-(3,5-difluorobenzyl)-1-(((3S)-1-((3-(methylsulfonyl)-1-azetidinyl)sulfonyl)-3-piperidinyl)carbonyl)-D-prolinamide;

(4S)—N—((R)-cyclopropyl(2,5-difluoro-4-(trifluoromethyl)phenyl)methyl)-4-fluoro-1-((5-(methylsulfonyl)-3-pyridinyl)carbonyl)-D-prolinamide;

1-(((3S)-1-((3-cyano-1-azetidinyl)sulfonyl)-3-piperidinyl)carbonyl)-N-((1S)-1-(4-(trifluoromethyl)phenyl)ethyl)-D-prolinamide;

(3S)-1-((3-cyano-1-azetidinyl)sulfonyl)-N-methyl-N-((1R)-1-methyl-2-oxo-2-((4-(trifluoromethyl)benzyl)amino)ethyl)-3-piperidinecarboxamide;

1-(((3S)-1-((3-cyano-1-azetidinyl)sulfonyl)-3-piperidinyl)carbonyl)-N-(2,3-dimethylbenzyl)-D-prolinamide;

1-((3-(5-azaspiro[2.3]hex-5-ylsulfonyl)phenyl)carbonyl)-N-((1R)-1-(4-(trifluoromethyl)phenyl)ethyl)-D-prolinamide;

1-(((3S)-1-((3-cyano-1-azetidinyl)sulfonyl)-3-piperidinyl)carbonyl)-N-(4-(difluoromethoxy)benzyl)-D-prolinamide;

1-(3-(dimethylsulfamoyl)benzoyl)-N-((1R)-1-(4-(trifluoromethyl)phenyl)ethyl)-D-prolinamide;

1-(((3S)-1-((3-cyano-1-azetidinyl)sulfonyl)-3-piperidinyl)carbonyl)-N-(4-fluorobenzyl)-D-prolinamide;

N-(3-chlorobenzyl)-1-(((3S)-1-((3-cyano-1-azetidinyl)sulfonyl)-3-piperidinyl)carbonyl)-D-prolinamide;

1-(((3S)-1-((3-cyano-1-azetidinyl)sulfonyl)-3-piperidinyl)carbonyl)-N-(4-fluoro-3-methylbenzyl)-D-prolinamide;

N-(2-chloro-5-fluorobenzyl)-1-(((3S)-1-((3-cyano-1-azetidinyl)sulfonyl)-3-piperidinyl)carbonyl)-D-prolinamide;

N-((1R)-1-(4-chloro-3-fluorophenyl)-2-hydroxyethyl)-1-(((3S)-1-((3-cyano-1-azetidinyl)sulfonyl)-3-piperidinyl)carbonyl)-D-prolinamide;

1-(((3S)-1-((3-cyano-1-azetidinyl)sulfonyl)-3-piperidinyl)carbonyl)-N-((1R)-2,3-dihydro-1H-inden-1-yl)-D-prolinamide;

1-(((3S)-1-((3-cyano-1-azetidinyl)sulfonyl)-3-piperidinyl)carbonyl)-N-((1S)-2,3-dihydro-1H-inden-1-yl)-D-prolinamide;

N-(3-chloro-5-methylbenzyl)-1-(((3S)-1-((3-cyano-1-azetidinyl)sulfonyl)-3-piperidinyl)carbonyl)-D-prolinamide;

(1R,3R,5R)—N—((R)-cyclopropyl(2-fluoro-4-(trifluoromethyl)phenyl)methyl)-2-(4-(methylsulfonyl)picolinoyl)-2-azabicyclo[3.1.0]hexane-3-carboxamide;

1-(((3S)-1-((3-cyano-1-azetidinyl)sulfonyl)-3-piperidinyl)carbonyl)-N-(4-fluoro-3,5-dimethylbenzyl)-D-prolinamide;

N—((R)-cyclopropyl(2-fluoro-4-(trifluoromethyl)phenyl)methyl)-4,4-difluoro-1-(3-sulfamoylbenzoyl)-D-prolinamide;

1-(((3S)-1-((3-cyano-1-azetidinyl)sulfonyl)-3-piperidinyl)carbonyl)-N-(4-cyclopropylbenzyl)-D-prolinamide;

(3R)-4-(((3S)-1-((3-cyano-1-azetidinyl)sulfonyl)-3-piperidinyl)carbonyl)-N-(4-(difluoromethyl)benzyl)-3-morpholinecarboxamide;

N-(2-fluoro-4-(trifluoromethyl)benzyl)-1-(3-((3-hydroxy-1-azetidinyl)sulfonyl)benzoyl)-D-prolinamide;

1-(((3S)-1-((3-cyclopropyl-3-fluoro-1-azetidinyl)sulfonyl)-3-piperidinyl)carbonyl)-N-(4-(trifluoromethyl)benzyl)-D-prolinamide;

N—((R)-cyclopropyl(2-fluoro-4-(trifluoromethyl)phenyl)methyl)-1-(3-(3-fluoro-1-(3-oxetanylsulfonyl)-3-azetidinyl)benzoyl)-D-prolinamide;

1-(((3S)-1-((3-cyano-1-azetidinyl)sulfonyl)-3-piperidinyl)carbonyl)-N-((1R)-1-(4-methylphenyl)ethyl)-D-prolinamide;

1-(((3S)-1-((3-cyano-1-azetidinyl)sulfonyl)-3-piperidinyl)carbonyl)-N-((1S)-1-(4-methylphenyl)ethyl)-D-prolinamide;

N-((1R)-1-(4-chloro-2,5-difluorophenyl)propyl)-1-(3-(methylsulfonyl)benzoyl)-D-prolinamide;

1-(3-(benzylsulfonyl)benzoyl)-N-(4-(trifluoromethyl)benzyl)-D-prolinamide;

3-((3-cyano-1-azetidinyl)sulfonyl)-N-methyl-N-((1R)-1-methyl-2-oxo-2-((3-(trifluoromethyl)benzyl)amino)ethyl)benzamide;

(1R,3R,5R)-2-(3-(1-cyanocyclopropyl)benzoyl)-N—((R)-(2-fluoro-4-(trifluoromethyl)phenyl)(3-oxetanyl)methyl)-2-azabicyclo[3.1.0]hexane-3-carboxamide;

1-(((3S)-1-((3-cyano-1-azetidinyl)sulfonyl)-3-piperidinyl)carbonyl)-N-(3-fluoro-4-methoxybenzyl)-D-prolinamide;

(1R,3R,5R)-2-((5-(cyclopropylamino)-2-methyl-4-pyridinyl)carbonyl)-N—((R)-cyclopropyl(2-fluoro-4-(trifluoromethyl)phenyl)methyl)-2-azabicyclo[3.1.0]hexane-3-carboxamide;

1-(3-(dimethylsulfamoyl)benzoyl)-N-(2-fluoro-4-(trifluoromethyl)benzyl)-D-prolinamide;

(2R)-1-((3-((cis-3-cyanocyclobutyl)sulfonyl)phenyl)carbonyl)-N-((6-(trifluoromethyl)-3-pyridinyl)methyl)-2-piperidinecarboxamide;

(2R)-1-((3-((trans-3-cyanocyclobutyl)sulfonyl)phenyl)carbonyl)-N-((6-(trifluoromethyl)-3-pyridinyl)methyl)-2-piperidinecarboxamide;

1-((3-((3,3-difluoro-1-azetidinyl)sulfonyl)phenyl)carbonyl)-N-(4-(trifluoromethyl)benzyl)-D-prolinamide;

N-((1S)-1-(4-chloro-3-fluorophenyl)ethyl)-1-(((3S)-1-((3-cyano-1-azetidinyl)sulfonyl)-3-piperidinyl)carbonyl)-D-prolinamide;

1-(((3S)-1-((3-fluoro-3-phenyl-1-azetidinyl)sulfonyl)-3-piperidinyl)carbonyl)-N-(4-(trifluoromethyl)benzyl)-D-prolinamide;

N—((R)-cyclopropyl(2-fluoro-4-(trifluoromethyl)phenyl)methyl)-1-(2-fluoro-5-(methylsulfonyl)benzoyl)-D-prolinamide;

1-(((3S)-1-((3-cyano-1-azetidinyl)sulfonyl)-3-piperidinyl)carbonyl)-N-((1R)-1-(3-(trifluoromethyl)phenyl)ethyl)-D-prolinamide;

1-(3-((3-hydroxy-3-methyl-1-azetidinyl)sulfonyl)benzoyl)-N-((1R)-1-(4-(trifluoromethyl)phenyl)ethyl)-D-prolinamide;

1-(((3S)-1-((3-hydroxy-3-(trifluoromethyl)-1-azetidinyl)sulfonyl)-3-piperidinyl)carbonyl)-N-(4-(trifluoromethyl)benzyl)-D-prolinamide;

1-(((3S)-1-((3-cyano-1-azetidinyl)sulfonyl)-3-piperidinyl)carbonyl)-N-((1S)-1-(3,5-difluorophenyl)propyl)-D-prolinamide;

1-(((3S)-1-((3-((4-fluorophenyl)amino)-1-azetidinyl)sulfonyl)-3-piperidinyl)carbonyl)-N-(4-(trifluoromethyl)benzyl)-D-prolinamide;

1-(((3S)-1-((3-cyano-1-azetidinyl)sulfonyl)-3-pyrrolidinyl)carbonyl)-N-(2-fluoro-4-(trifluoromethyl)benzyl)-D-prolinamide;

(1R,3R,5R)—N—((R)-(4-chloro-2,5-difluorophenyl)(3-oxetanyl)methyl)-2-((4-cyclopropyl-2-pyridinyl)carbonyl)-2-azabicyclo[3.1.0]hexane-3-carboxamide;

(1R,3R,5R)—N—((R)-(4-chloro-2,5-difluorophenyl)(3-oxetanyl)methyl)-2-(4-methyl-3-(methylsulfonyl)benzoyl)-2-azabicyclo[3.1.0]hexane-3-carboxamide;

1-(((3S)-1-(((3R)-2-oxo-3-azepanyl)sulfamoyl)-3-piperidinyl)carbonyl)-N-(4-(trifluoromethyl)benzyl)-D-prolinamide;

1-(((3S)-1-(((3S)-2-oxo-3-azepanyl)sulfamoyl)-3-piperidinyl)carbonyl)-N-(4-(trifluoromethyl)benzyl)-D-prolinamide;

1-((3-((4-methoxy-1-piperidinyl)sulfonyl)phenyl)carbonyl)-N-(4-(trifluoromethyl)benzyl)-D-prolinamide;

(1R)—N—((R)-cyclopropyl(2-fluoro-4-(trifluoromethyl)phenyl)methyl)-2-(3-(methylsulfonyl)benzoyl)-2-azaspiro[3.3]heptane-1-carboxamide;

(3R,5R)-5-(((R)-(4-chloro-2,5-difluorophenyl)(3-oxetanyl)methyl)carbamoyl)-1-((2-(difluoromethyl)-4-pyridinyl)carbonyl)-3-pyrrolidinyl 2-(difluoromethyl)-4-pyridinecarboxylate;

1-(((3S)-1-((3-(4-fluorophenyl)-1-azetidinyl)sulfonyl)-3-piperidinyl)carbonyl)-N-(4-(trifluoromethyl)benzyl)-D-prolinamide;

(1R,2R,5S)-3-(3-(dimethylsulfamoyl)benzoyl)-N-(4-(trifluoromethyl)benzyl)-3-azabicyclo[3.1.0]hexane-2-carboxamide;

N—((R)-(4-chloro-2-fluorophenyl)(cyclopropyl)methyl)-1-(3-(methylsulfonyl)benzoyl)-D-prolinamide;

(1R,3R,5R)-2-((2-(difluoromethyl)-4-pyridinyl)carbonyl)-N—((R)-(2-fluoro-4-(trifluoromethyl)phenyl)(3-oxetanyl)methyl)-2-azabicyclo[3.1.0]hexane-3-carboxamide;

(2R)-1-((3-((3-cyano-1-azetidinyl)sulfonyl)phenyl)carbonyl)-N-(4-(trifluoromethyl)benzyl)-2,3-dihydro-1H-indole-2-carboxamide;

(2S)-1-((3-((3-cyano-1-azetidinyl)sulfonyl)phenyl)carbonyl)-N-(4-(trifluoromethyl)benzyl)-2,3-dihydro-1H-indole-2-carboxamide;

1-(3-(methylsulfonyl)benzoyl)-N—((R)-((3R)-5-oxo-3-pyrrolidinyl)(4-(trifluoromethyl)phenyl)methyl)-D-prolinamide;

1-(((3S)-1-((3-cyclobutyl-1-azetidinyl)sulfonyl)-3-piperidinyl)carbonyl)-N-(4-(trifluoromethyl)benzyl)-D-prolinamide;

(1S,2R,5R)—N—((R)-cyclopropyl(2-fluoro-4-(trifluoromethyl)phenyl)methyl)-3-(3-(methylsulfonyl)benzoyl)-3-azabicyclo[3.1.0]hexane-2-carboxamide;

(1R,3R,5R)—N—((R)-(4-chloro-3-fluorophenyl)(cyclopropyl)methyl)-2-(3-(methylsulfonyl)benzoyl)-2-azabicyclo[3.1.0]hexane-3-carboxamide;

1-(3-(1-azetidinylsulfonyl)benzoyl)-N-(4-(trifluoromethyl)benzyl)-D-prolinamide;

(1R,3R,5R)—N—((R)-(4-chloro-2,5-difluorophenyl)(3-oxetanyl)methyl)-2-((6-(trifluoromethyl)-4-pyrimidinyl)carbonyl)-2-azabicyclo[3.1.0]hexane-3-carboxamide;

(4S)—N—((R)-(4-chloro-2,5-difluorophenyl) (cyclopropyl)methyl)-4-fluoro-1-((5-(methylsulfonyl)-3-pyridinyl)carbonyl)-D-prolinamide;

1-(((3S)-1-((3-((trifluoroacetyl)amino)-1-azetidinyl)sulfonyl)-3-piperidinyl)carbonyl)-N-(4-(trifluoromethyl)benzyl)-D-prolinamide;

(1R,3R,5R)—N—((R)-cyclopropyl(2-fluoro-4-(trifluoromethyl)phenyl)methyl)-2-((6-(methylsulfonyl)-3-pyridinyl)carbonyl)-2-azabicyclo[3.1.0]hexane-3-carboxamide;

(1R,3R,5R)—N—((R)-cyclopropyl(3-fluoro-4-(trifluoromethyl)phenyl)methyl)-2-((5-(cyclopropylsulfonyl)-3-pyridinyl)carbonyl)-2-azabicyclo[3.1.0]hexane-3-carboxamide;

1-(((3S)-1-((3-methoxy-1-azetidinyl)sulfonyl)-3-piperidinyl)carbonyl)-N-(4-(trifluoromethyl)benzyl)-D-prolinamide;

(3R,5R)-5-(((R)-(4-chloro-2,5-difluorophenyl) (3-oxetanyl)methyl)carbamoyl)-1-((2-(trifluoromethyl)-4-pyridinyl)carbonyl)-3-pyrrolidinyl 2-(trifluoromethyl)-4-pyridinecarboxylate;

(4S)-1-(((3S)-1-((3-cyano-1-azetidinyl)sulfonyl)-3-piperidinyl)carbonyl)-4-fluoro-N-((1R)-1-(3-(trifluoromethyl)phenyl)ethyl)-D-prolinamide;

(1R,3R,5R)—N—((R)-cyclopropyl(2-fluoro-4-(trifluoromethyl)phenyl)methyl)-2-((2-(trifluoromethyl)-4-pyridinyl)carbonyl)-2-azabicyclo[3.1.0]hexane-3-carboxamide;

1-(((3S)-1-((3-cyano-1-azetidinyl)sulfonyl)-3-piperidinyl)carbonyl)-N-(3-fluorobenzyl)-D-prolinamide;

(1R,3R,5R)-2-(3-(1-amino-2-methyl-1-oxo-2-propanyl)benzoyl)-N—((R)-(2-fluoro-4-(trifluoromethyl)phenyl)(3-oxetanyl)methyl)-2-azabicyclo[3.1.0]hexane-3-carboxamide;

1-(((3S)-1-((3-cyano-1-azetidinyl)sulfonyl)-3-piperidinyl)carbonyl)-N-(3-fluoro-5-methylbenzyl)-D-prolinamide;

1-(((3S)-1-((3-(methylsulfonyl)-1-azetidinyl)sulfonyl)-3-piperidinyl)carbonyl)-N-((5-(trifluoromethyl)-2-pyridinyl)methyl)-D-prolinamide;

(1R,3R,5R)—N—((R)-(4-chloro-2,5-difluorophenyl)(3-oxetanyl)methyl)-2-((2-(trifluoromethyl)-4-pyrimidinyl)carbonyl)-2-azabicyclo[3.1.0]hexane-3-carboxamide;

(4R)—N—((R)-(4-chloro-2,5-difluorophenyl) (3-oxetanyl)methyl)-1-((2-(difluoromethyl)-4-pyridinyl)carbonyl)-4-hydroxy-D-prolinamide;

1-(((3S)-1-((3-cyano-1-azetidinyl)sulfonyl)-3-piperidinyl)carbonyl)-N-((4R)-3,4-dihydro-2H-chromen-4-yl)-D-prolinamide;

1-(((3S)-1-((3-cyano-1-azetidinyl)sulfonyl)-3-piperidinyl)carbonyl)-N-((4S)-3,4-dihydro-2H-chromen-4-yl)-D-prolinamide;

1-(((1R,4S,5R)-2-((3-cyano-1-azetidinyl)sulfonyl)-2-azabicyclo[3.1.0]hex-4-yl)carbonyl)-N-(4-(trifluoromethyl)benzyl)-D-prolinamide;

1-(((1S,4R,5S)-2-((3-cyano-1-azetidinyl)sulfonyl)-2-azabicyclo[3.1.0]hex-4-yl)carbonyl)-N-(4-(trifluoromethyl)benzyl)-D-prolinamide;

(1R,3R,5R)—N—((R)-(4-chloro-2,5-difluorophenyl)(3-oxetanyl)methyl)-2-((2-(2-propanyl)-4-pyridinyl)carbonyl)-2-azabicyclo[3.1.0]hexane-3-carboxamide;

N—((R)-cyclopropyl(2-fluoro-4-(trifluoromethyl)phenyl)methyl)-1-((6-(methylsulfonyl)-3-pyridinyl)carbonyl)-D-prolinamide;

(4R)—N—((R)-cyclopropyl(2-fluoro-4-(trifluoromethyl)phenyl)methyl)-4-hydroxy-1-(3-(methylsulfonyl)benzoyl)-D-prolinamide;

1-((3-((cis-3-cyanocyclobutyl)sulfonyl)phenyl)carbonyl)-N-((6-(trifluoromethyl)-3-pyridinyl)methyl)-D-prolinamide;

1-((3-((trans-3-cyanocyclobutyl)sulfonyl)phenyl)carbonyl)-N-((6-(trifluoromethyl)-3-pyridinyl)methy)-D-prolinamide;

1-(((3S)-1-((3-cyano-1-azetidinyl)sulfonyl)-3-piperidinyl)carbonyl)-N-(5-fluoro-2-methylbenzyl)-D-prolinamide;

1-(((3S)-1-((3-ethyl-3-hydroxy-1-azetidinyl)sulfonyl)-3-piperidinyl)carbonyl)-N-(2-fluoro-4-(trifluoromethyl)benzyl)-D-prolinamide;

(4S)—N—((R)-(4-chloro-2,5-difluorophenyl) (cyclopropyl)methyl)-4-fluoro-1-((2-(methylsulfonyl)-4-pyridinyl)carbonyl)-D-prolinamide;

N-((1R)-1-(4-chlorophenyl)ethyl)-1-(((2S)-4-((3-cyano-1-azetidinyl)sulfonyl)-2-piperazinyl)carbonyl)-D-prolinamide;

(1R,2R,5S)—N—((R)-(4-chloro-2,5-difluorophenyl)(cyclopropyl)methyl)-3-((5-(methylsulfonyl)-3-pyridinyl)carbonyl)-3-azabicyclo[3.1.0]hexane-2-carboxamide;

(1R,3R,5R)—N-((1R)-1-(4-chloro-2,5-difluorophenyl)ethyl)-2-(3-(ethylsulfonyl)benzoyl)-2-azabicyclo[3.1.0]hexane-3-carboxamide;

1-(((3R)-1-((3-cyano-1-azetidinyl)sulfonyl)-3-fluoro-3-piperidinyl)carbonyl)-N-(4-(trifluoromethyl)benzyl)-D-prolinamide or 1-(((3S)-1-((3-cyano-1-azetidinyl)sulfonyl)-3-fluoro-3-piperidinyl)carbonyl)-N-(4-(trifluoromethyl)benzyl)-D-prolinamide;

1-(((3S)-1-((3-cyano-1-azetidinyl)sulfonyl)-3-piperidinyl)carbonyl)-N-((3-fluoro-5-(trifluoromethyl)-2-pyridinyl)methyl)-D-prolinamide;

1-(((3S)-1-((3-cyano-1-azetidinyl)sulfonyl)-3-piperidinyl)carbonyl)-N-(2,3-difluorobenzyl)-D-prolinamide;

1-(((2S)-4-((3-cyano-1-azetidinyl)sulfonyl)-2-morpholinyl)carbonyl)-N-(3,5-difluorobenzyl)-D-prolinamide;

methyl cis-3-(((3S)-3-(((2R)-2-((4-(trifluoromethyl)benzyl)carbamoyl)-1-pyrrolidinyl)carbonyl)-1-piperidinyl)sulfonyl)cyclobutanecarboxylate;

methyl trans-3-(((3S)-3-(((2R)-2-((4-(trifluoromethyl)benzyl)carbamoyl)-1-pyrrolidinyl)carbonyl)-1-piperidinyl)sulfonyl)cyclobutanecarboxylate;

(1R,3R,5R)—N—((S)-(2-fluoro-4-(trifluoromethyl)phenyl)((3R)-1-methyl-5-oxo-3-pyrrolidinyl)methyl)-2-(3-(methylsulfonyl)benzoyl)-2-azabicyclo[3.1.0]hexane-3-carboxamide;

1-(3-((3-cyano-1-azetidinyl)sulfonyl)benzoyl)-N-((5-methyl-2-pyridinyl)methyl)-D-prolinamide;

N—((R)-cyclopropyl(2-fluoro-4-(trifluoromethyl)phenyl)methyl)-1-(2-(ethylamino)benzoyl)-D-prolinamide;

(1R,3R,5R)-2-(3-(ethylsulfonyl)benzoyl)-N—((S)-(1-hydroxycyclobutyl)(4-(trifluoromethyl)phenyl)methyl)-2-azabicyclo[3.1.0]hexane-3-carboxamide;

N—((R)-cyclopropyl(2-fluoro-4-(trifluoromethyl)phenyl)methyl)-1-(3-(2,2,2-trifluoro-1,1-dihydroxyethyl)benzoyl)-D-prolinamide;

1-(((3S)-1-((3-cyano-1-azetidinyl)sulfonyl)-3-piperidinyl)carbonyl)-N-((1R)-1-(2,5-difluorophenyl)-2,2-difluoroethyl)-D-prolinamide;

1-(((3S)-1-((3-cyano-1-azetidinyl)sulfonyl)-3-piperidinyl)carbonyl)-N-((1S)-1-(2,5-difluorophenyl)-2,2-difluoroethyl)-D-prolinamide;

(2R)—N—((R)-cyclopropyl(2-fluoro-4-(trifluoromethyl)phenyl)methyl)-4,4-difluoro-1-(3-(methylsulfonyl)benzoyl)-2-piperidinecarboxamide & (2S)—N—((R)-cyclopropyl(2-fluoro-4-(trifluoromethyl)phenyl)methyl)-4,4-difluoro-1-(3-(methylsulfonyl)benzoyl)-2-piperidinecarboxamide;

N—((R)-cyclopropyl(2-fluoro-4-(trifluoromethyl)phenyl)methyl)-1-((4-(methylsulfonyl)-2-pyridinyl)carbonyl)-D-prolinamide;

(1R,3R,5R)—N—((R)-(2-fluoro-4-(trifluoromethyl)phenyl)(3-oxetanyl)methyl)-2-((5-(trifluoromethyl)-3-pyridinyl)carbonyl)-2-azabicyclo[3.1.0]hexane-3-carboxamide;

(4S)-4-fluoro-N—((R)-(2-fluoro-4-(trifluoromethyl)phenyl)(3-oxetanyl)methyl)-1-(3-(methylsulfonyl)benzoyl)-D-prolinamide;

(1R,3R,5R)—N—((R)-(4-chloro-2,5-difluorophenyl)(3-oxetanyl)methyl)-2-((6-(trifluoromethyl)-2-pyridinyl)carbonyl)-2-azabicyclo[3.1.0]hexane-3-carboxamide;

1-(3-cyclobutylbenzoyl)-N—((R)-cyclopropyl(2-fluoro-4-(trifluoromethyl)phenyl)methyl)-D-prolinamide;

(4S)—N—((R)-cyclopropyl(2-fluoro-4-(trifluoromethyl)phenyl)methyl)-4-fluoro-1-(3-sulfamoylbenzoyl)-D-prolinamide;

N-(3-chloro-5-(trifluoromethyl)benzyl)-1-(((3S)-1-((3-cyano-1-azetidinyl)sulfonyl)-3-piperidinyl)carbonyl)-D-prolinamide;

1-(3-(1-carbamoylcyclopropyl)benzoyl)-N—((R)-cyclopropyl(2-fluoro-4-(trifluoromethyl)phenyl)methyl)-D-prolinamide;

(1R,3R,5R)—N-((1R)-1-(4-chloro-2,5-difluorophenyl)ethyl)-2-(3-(methylsulfonyl)benzoyl)-2-azabicyclo[3.1.0]hexane-3-carboxamide;

1-(((3S)-1-((3-(trifluoromethoxy)-1-azetidinyl)sulfonyl)-3-piperidinyl)carbonyl)-N-(4-(trifluoromethyl)benzyl)-D-prolinamide;

1-(((3S)-1-((3-(pentyloxy)-1-azetidinyl)sulfonyl)-3-piperidinyl)carbonyl)-N-(4-(trifluoromethyl)benzyl)-D-prolinamide;

(3R)-4-((3-(5-azaspiro[2.3]hex-5-ylsulfonyl)phenyl)carbonyl)-N-(4-(trifluoromethyl)benzyl)-3-morpholinecarboxamide;

(1R,3R,5R)—N—((R)-cyclopropyl(2-fluoro-4-(trifluoromethyl)phenyl)methyl)-2-((5-(methylsulfonyl)-3-pyridinyl)carbonyl)-2-azabicyclo[3.1.0]hexane-3-carboxamide;

1-(((3R)-1-((3-cyano-1-azetidinyl)sulfonyl)-3-piperidinyl)carbonyl)-N-(2-fluoro-4-(trifluoromethyl)benzyl)-D-prolinamide;

1-(((3S)-1-((3-cyano-1-azetidinyl)sulfonyl)-3-piperidinyl)carbonyl)-N-((1R)-1-(4-cyanophenyl)ethyl)-D-prolinamide;

(1R,3R,5R)—N—((R)-(2-fluoro-4-(trifluoromethyl)phenyl)(3-oxetanyl)methyl)-2-((5-((2-hydroxyethyl)amino)-2-methyl-4-pyridinyl)carbonyl)-2-azabicyclo[3.1.0]hexane-3-carboxamide;

(2R)-1-((3-((3-cyano-1-azetidinyl)sulfonyl)phenyl)carbonyl)-N-(4-(trifluoromethyl)benzyl)-2-azetidinecarboxamide;

(4R)—N—((R)-cyclopropyl(2-fluoro-4-(trifluoromethyl)phenyl)methyl)-3-(3-(methylsulfonyl)benzoyl)-2-oxo-1,3-oxazolidine-4-carboxamide;

1-(((3S)-1-((3-cyano-1-azetidinyl)sulfonyl)-3-piperidinyl)carbonyl)-N-(4-methyl-3-(trifluoromethyl)benzyl)-D-prolinamide;

(1R,3R,5R)—N—((R)-cyclopropyl(2-fluoro-4-(trifluoromethyl)phenyl)methyl)-2-((5-((2-hydroxyethyl)amino)-2-methyl-4-pyridinyl)carbonyl)-2-azabicyclo[3.1.0]hexane-3-carboxamide;

(4S)-4-fluoro-1-(3-(methylsulfonyl)benzoyl)-N—((R)-3-oxetanyl(4-(trifluoromethyl)phenyl)methyl)-D-prolinamide;

(1R,3R,5R)—N—((R)-cyclopropyl(2-fluoro-4-(trifluoromethyl)phenyl)methyl)-2-(3-((1R)-2,2,2-trifluoro-1-hydroxyethyl)benzoyl)-2-azabicyclo[3.1.0]hexane-3-carboxamide;

(1R,3R,5R)—N—((R)-cyclopropyl(2-fluoro-4-(trifluoromethyl)phenyl)methyl)-2-(3-((1S)-2,2,2-trifluoro-1-hydroxyethyl)benzoyl)-2-azabicyclo[3.1.0]hexane-3-carboxamide;

(1R,3R,5R)—N—((R)-cyclopropyl(3-fluoro-4-(trifluoromethyl)phenyl)methyl)-2-((5-(methylsulfonyl)-3-pyridinyl)carbonyl)-2-azabicyclo[3.1.0]hexane-3-carboxamide;

N-(5-chloro-2-fluorobenzyl)-1-(((3S)-1-((3-cyano-1-azetidinyl)sulfonyl)-3-piperidinyl)carbonyl)-D-prolinamide;

1-(2-(3-cyano-1-azetidinyl)-5-(methylsulfonyl)benzoyl)-N—((R)-cyclopropyl(2-fluoro-4-(trifluoromethyl)phenyl)methyl)-D-prolinamide;

1-(((3S)-1-((3-cyano-1-azetidinyl)sulfonyl)-3-piperidinyl)carbonyl)-N-(4-cyanobenzyl)-D-prolinamide;

(3R)—N—((R)-cyclopropyl(2-fluoro-4-(trifluoromethyl)phenyl)methyl)-4-(3-(methylsulfonyl)benzoyl)-3-thiomorpholinecarboxamide;

(3S)—N—((R)-cyclopropyl(2-fluoro-4-(trifluoromethyl)phenyl)methyl)-4-(3-(methylsulfonyl)benzoyl)-3-thiomorpholinecarboxamide;

(1R,3R,5R)—N—((R)-cyclopropyl(2-fluoro-4-(trifluoromethyl)phenyl)methyl)-2-(2-(2,2,2-trifluoroacetamido)benzoyl)-2-azabicyclo[3.1.0]hexane-3-carboxamide;

N—((R)-cyclopropyl(2-fluoro-4-(trifluoromethyl)phenyl)methyl)-1-(2-ethoxy-5-(methylsulfonyl)benzoyl)-D-prolinamide;

(1R,3R,5R)—N—((R)-(4-chloro-2,5-difluorophenyl)(3-oxetanyl)methyl)-2-((4-ethyl-2-pyridinyl)carbonyl)-2-azabicyclo[3.1.0]hexane-3-carboxamide;

N—((R)-cyclopropyl(2-fluoro-4-(trifluoromethyl)phenyl)methyl)-1-(3-((1R)-2,2,2-trifluoro-1-hydroxyethyl)benzoyl)-D-prolinamide;

N—((R)-cyclopropyl(2-fluoro-4-(trifluoromethyl)phenyl)methyl)-1-(3-((1S)-2,2,2-trifluoro-1-hydroxyethyl)benzoyl)-D-prolinamide;

1-(((3S)-1-((3-cyano-1-azetidinyl)sulfonyl)-3-piperidinyl)carbonyl)-N-(2-fluoro-4-methoxybenzyl)-D-prolinamide;

N—((R)-3-azetidinyl(4-chloro-2,5-difluorophenyl)methyl)-1-(((3S)-1-((3-cyano-1-azetidinyl)sulfonyl)-3-piperidinyl)carbonyl)-D-prolinamide;

(1R,3R,5R)—N—((S)-(2-fluoro-4-(trifluoromethyl)phenyl)(1-hydroxycyclopropyl)methyl)-2-(3-(methylsulfonyl)benzoyl)-2-azabicyclo[3.1.0]hexane-3-carboxamide;

1-((3-(((3R)-3-hydroxy-1-pyrrolidinyl)sulfonyl)phenyl)carbonyl)-N-(4-(trifluoromethyl)benzyl)-D-prolinamide;

1-((3-(((3S)-3-hydroxy-1-pyrrolidinyl)sulfonyl)phenyl)carbonyl)-N-(4-(trifluoromethyl)benzyl)-D-prolinamide;

1-(((3S)-1-((3-cyano-1-azetidinyl)sulfonyl)-3-piperidinyl)carbonyl)-N-((1R)-2-hydroxy-1-(4-(trifluoromethyl)phenyl)ethyl)-D-prolinamide;

1-(((3S)-1-((3-(1H-imidazol-1-yl)-1-azetidinyl)sulfonyl)-3-piperidinyl)carbonyl)-N-(4-(trifluoromethyl)benzyl)-D-prolinamide;

N—((R)-cyclopropyl(2-fluoro-4-(trifluoromethyl)phenyl)methyl)-1-(2,6-difluoro-3-(methylsulfonyl)benzoyl)-D-prolinamide;

1-(3-(diethylsulfamoyl)benzoyl)-N-(4-(trifluoromethyl)benzyl)-D-prolinamide;

N-((7S)-bicyclo[4.2.0]octa-1,3,5-trien-7-yl)-1-(((3S)-1-((3-cyano-1-azetidinyl)sulfonyl)-3-piperidinyl)carbonyl)-D-prolinamide;

N—((R)-cyclopropyl(2-fluoro-4-(trifluoromethyl)phenyl)methyl)-1-(2-fluoro-5-sulfamoylbenzoyl)-D-prolinamide;

N—((R)-cyclopropyl(2-fluoro-4-(trifluoromethyl)phenyl)methyl)-1-((5-(methylsulfonyl)-2-thiophenyl)carbonyl)-D-prolinamide;

1-((3-(dimethylsulfamoyl)phenyl)carbonyl)-N-(4-(trifluoromethyl)benzyl)-D-prolinamide;

N—((R)-cyclopropyl(2-fluoro-4-(trifluoromethyl)phenyl)methyl)-1-((6-(methylsulfonyl)-3-pyridinyl)carbonyl)-D-prolinamide;

N—((S)-cyclopropyl(2-fluoro-4-(trifluoromethyl)phenyl)methyl)-1-((6-(methylsulfonyl)-3-pyridinyl)carbonyl)-D-prolinamide;

(1R,3R,5R)—N—((R)-(4-cyano-2,5-difluorophenyl)(cyclopropyl)methyl)-2-(3-(methylsulfonyl)benzoyl)-2-azabicyclo[3.1.0]hexane-3-carboxamide;

1-(((3S)-1-((3-cyano-1-azetidinyl)sulfonyl)-3-piperidinyl)carbonyl)-N-(2-methylbenzyl)-D-prolinamide;

(1R,2R,5S)-3-(3-(dimethylsulfamoyl)benzoyl)-N-((1R)-1-(4-(trifluoromethyl)phenyl)ethyl)-3-azabicyclo[3.1.0]hexane-2-carboxamide;

(1R,3R,5R)—N—((R)-cyclopropyl(2-fluoro-4-(trifluoromethyl)phenyl)methyl)-2-((4-(trifluoromethyl)-2-pyridinyl)carbonyl)-2-azabicyclo[3.1.0]hexane-3-carboxamide;

N-(2-chlorobenzyl)-1-(((3S)-1-((3-cyano-1-azetidinyl)sulfonyl)-3-piperidinyl)carbonyl)-D-prolinamide;

(1R,3R,5R)—N—((R)-(2-fluoro-4-(trifluoromethyl)phenyl)((3R)-1-methyl-5-oxo-3-pyrrolidinyl)methyl)-2-(3-(methylsulfonyl)benzoyl)-2-azabicyclo[3.1.0]hexane-3-carboxamide;

(3R)—N—((R)-cyclopropyl(2-fluoro-4-(trifluoromethyl)phenyl)methyl)-4-(3-(methylsulfonyl)benzoyl)-3-morpholinecarboxamide;

N—((R)-cyclopropyl(2-fluoro-4-(trifluoromethyl)phenyl)methyl)-1-(3-(3-fluoro-3-oxetanyl)benzoyl)-D-prolinamide;

(2R)—N—((R)-cyclopropyl(4-(difluoromethyl)-2-fluorophenyl)methyl)-1-(3-(methylsulfonyl)benzoyl)-2-piperidinecarboxamide;

N-((3R)-4-chloro-2,3-dihydro-1-benzofuran-3-yl)-1-(((3S)-1-((3-cyano-1-azetidinyl)sulfonyl)-3-piperidinyl)carbonyl)-D-prolinamide & N-((3S)-4-chloro-2,3-dihydro-1-benzofuran-3-yl)-1-(((3S)-1-((3-cyano-1-azetidinyl)sulfonyl)-3-piperidinyl)carbonyl)-D-prolinamide;

1-(((3S)-1-((3-(4-pyridinyloxy)-1-azetidinyl)sulfonyl)-3-piperidinyl)carbonyl)-N-(4-(trifluoromethyl)benzyl)-D-prolinamide;

(4S)-1-(((3S)-1-((3-cyano-1-azetidinyl)sulfonyl)-3-piperidinyl)carbonyl)-4-hydroxy-N-(4-(trifluoromethyl)benzyl)-D-prolinamide;

1-(((3S)-1-((3-(1H-pyrazol-1-yl)-1-azetidinyl)sulfonyl)-3-piperidinyl)carbonyl)-N-(4-(trifluoromethyl)benzyl)-D-prolinamide;

N-(2-chloro-3-methoxybenzyl)-1-(((3S)-1-((3-cyano-1-azetidinyl)sulfonyl)-3-piperidinyl)carbonyl)-D-prolinamide;

N—((R)-cyclopropyl(2-fluoro-4-(trifluoromethyl)phenyl)methyl)-1-(3-(dimethylamino)benzoyl)-D-prolinamide;

1-(((3S)-1-((3-cyano-1-azetidinyl)sulfonyl)-3-piperidinyl)carbonyl)-N-((1R)-1-(3-fluoro-4-methoxyphenyl)ethyl)-D-prolinamide;

1-(((3S)-1-((3-cyano-1-azetidinyl)sulfonyl)-3-piperidinyl)carbonyl)-N-((1S)-1-(3-fluoro-4-methoxyphenyl)ethyl)-D-prolinamide;

(5R)—N—((R)-cyclopropyl(2-fluoro-4-(trifluoromethyl)phenyl)methyl)-5-methyl-1-(3-(methylsulfonyl)benzoyl)-D-prolinamide;

1-(((3S)-1-((trans-3-cyanocyclobutyl)sulfonyl)-3-piperidinyl)carbonyl)-N-(4-(trifluoromethyl)benzyl)-D-prolinamide;

N—((R)-cyclopropyl(4-(trifluoromethyl)phenyl)methyl)-1-(3-(methylsulfonyl)benzoyl)-D-prolinamide;

(3R)—N—((R)-cyclopropyl(2-fluoro-4-(trifluoromethyl)phenyl)methyl)-3-fluoro-1-(3-(methylsulfonyl)benzoyl)-D-prolinamide;

1-(((3S)-1-((3-cyano-1-azetidinyl)sulfonyl)-3-piperidinyl)carbonyl)-N-((cis-4-(trifluoromethyl)cyclohexyl)methyl)-D-prolinamide;

1-(((3S)-1-((3-cyano-1-azetidinyl)sulfonyl)-3-piperidinyl)carbonyl)-N-((4-(trifluoromethyl)cyclohexyl)methyl)-D-prolinamide;

N-(3-chloro-4-methoxybenzyl)-1-(((3S)-1-((3-cyano-1-azetidinyl)sulfonyl)-3-piperidinyl)carbonyl)-D prolinamide;

1-(((3S)-1-((3-cyano-1-azetidinyl)sulfonyl)-3-piperidinyl)carbonyl)-N-((1R)-1-(4-fluoro-3-methylphenyl)ethyl)-D-prolinamide;

1-(((3S)-1-((3-cyano-1-azetidinyl)sulfonyl)-3-piperidinyl)carbonyl)-N-((1S)-1-(4-fluoro-3-methylphenyl)ethyl)-D-prolinamide;

(1R,3R,5R)—N—((R)-cyclopropyl(2,5-difluoro-4-(trifluoromethyl)phenyl)methyl)-2-((4-cyclopropyl-2-pyridinyl)carbonyl)-2-azabicyclo[3.1.0]hexane-3-carboxamide;

1-(((3S)-1-((3-cyano-1-azetidinyl)sulfonyl)-3-piperidinyl)carbonyl)-N-((1R)-1-(4-(difluoromethoxy)phenyl)ethyl)-D-prolinamide;

1-(((3S)-1-((3-cyano-1-azetidinyl)sulfonyl)-3-piperidinyl)carbonyl)-N-((1S)-1-(4-(difluoromethoxy)phenyl)ethyl)-D-prolinamide;

1-((3-(5-azaspiro[2.3]hex-5-ylsulfonyl)phenyl)carbonyl)-N-((1R)-1-(4-chlorophenyl)ethyl)-D-prolinamide;

(1R,3R,5R)—N—((R)-cyclopropyl(4-(trifluoromethyl)phenyl)methyl)-2-(3-(methylsulfonyl)benzoyl)-2-azabicyclo[3.1.0]hexane-3-carboxamide;

N-((1R)-1-(2-fluoro-4-(trifluoromethyl)phenyl)ethyl)-1-(((3S)-1-((3-hydroxy-3-methyl-1-azetidinyl)sulfonyl)-3-piperidinyl)carbonyl)-D-prolinamide;

(1S,3R,5S)—N—((R)-cyclopropyl(2,5-difluoro-4-(trifluoromethyl)phenyl)methyl)-2-((5-(methylsulfonyl)-3-pyridinyl)carbonyl)-2-azabicyclo[3.1.0]hexane-3-carboxamide;

(4S)—N—((R)-cyclopropyl(2-fluoro-4-(trifluoromethyl)phenyl)methyl)-4-fluoro-1-(3-(3-fluoro-3-oxetanyl)benzoyl)-D-prolinamide;

(1R,3R,5R)—N—((R)-(4-chloro-2,5-difluorophenyl)(3-oxetanyl)methyl)-2-((4-methyl-2-pyridinyl)carbonyl)-2-azabicyclo[3.1.0]hexane-3-carboxamide;

(1R,3R,5R)—N-((1S,2S)-1-(2-fluoro-4-(trifluoromethyl)phenyl)-2-hydroxypropyl)-2-(3-(methylsulfonyl)benzoyl)-2-azabicyclo[3.1.0]hexane-3-carboxamide;

N—((R)-cyclopropyl(2-fluoro-4-(trifluoromethyl)phenyl)methyl)-1-(2-methoxy-5-(methylsulfonyl)benzoyl)-D-prolinamide;

(1R,3R,5R)—N—((R)-(4-chloro-2,5-difluorophenyl)(3-oxetanyl)methyl)-2-((2,6-dimethyl-4-pyridinyl)carbonyl)-2-azabicyclo[3.1.0]hexane-3-carboxamide;

1-(3-(1-cyanocyclopropyl)benzoyl)-N—((R)-cyclopropyl(2-fluoro-4-(trifluoromethyl)phenyl)methyl)-D prolinamide;

(1R,3R,5R)—N—((R)-cyclopropyl(2-fluoro-4-(trifluoromethyl)phenyl)methyl)-2-((2-(difluoromethyl)-4-pyridinyl)carbonyl)-2-azabicyclo[3.1.0]hexane-3-carboxamide;

1-(((3S)-1-((3-cyano-1-azetidinyl)sulfonyl)-3-piperidinyl)carbonyl)-N-(2-fluoro-3-methylbenzyl)-D-prolinamide;

1-(((3S)-1-((3-cyano-1-azetidinyl)sulfonyl)-3-piperidinyl)carbonyl)-N-(2-fluoro-6-methylbenzyl)-D-prolinamide;

(1R,3R,5R)-2-(3-benzoylbenzoyl)-N—((R)-(4-chloro-2,5-difluorophenyl)(cyclopropyl)methyl)-2-azabicyclo[3.1.0]hexane-3-carboxamide;

(1R)—N—((R)-cyclopropyl(2-fluoro-4-(trifluoromethyl)phenyl)methyl)-2-(3-(methylsulfonyl)benzoyl)-2-azaspiro[3.3]heptane-1-carboxamide;

(1S)—N—((R)-cyclopropyl(2-fluoro-4-(trifluoromethyl)phenyl)methyl)-2-(3-(methylsulfonyl)benzoyl)-2-azaspiro[3.3]heptane-1-carboxamide;

N-(2-fluoro-4-(trifluoromethyl)benzyl)-1-(((3S)-1-((3-hydroxy-1-azetidinyl)sulfonyl)-3-piperidinyl)carbonyl)-D-prolinamide;

(1R,3R,5R)-2-((5-cyclopropyl-3-pyridinyl)carbonyl)-N—((R)-(2-fluoro-4-(trifluoromethyl)phenyl)(3-oxetanyl)methyl)-2-azabicyclo[3.1.0]hexane-3-carboxamide;

(1R,3R,5R)—N—((R)-cyclopropyl(2-fluoro-4-(trifluoromethyl)phenyl)methyl)-2-(2-methoxy-5-(methylsulfonyl)benzoyl)-2-azabicyclo[3.1.0]hexane-3-carboxamide;

N-((6-chloro-3-pyridinyl)methyl)-1-(((3S)-1-((3-cyano-1-azetidinyl)sulfonyl)-3-piperidinyl)carbonyl)-D-prolinamide;

1-(((3S)-1-((3-cyano-1-azetidinyl)sulfonyl)-3-piperidinyl)carbonyl)-N-(4-methoxy-2-methylbenzyl)-D-prolinamide;

(1R,3R,5R)—N—((R)-cyclopropyl(2,5-difluoro-4-(trifluoromethyl)phenyl)methyl)-2-((6-(trifluoromethyl)-2-pyridinyl)carbonyl)-2-azabicyclo[3.1.0]hexane-3-carboxamide;

(5R)—N—((R)-cyclopropyl(2-fluoro-4-(trifluoromethyl)phenyl)methyl)-5-methyl-1-(3-(methylsulfonyl)benzoyl)-L-prolinamide;

(1R,3R,5R)—N-(4-chloro-2,5-difluorobenzyl)-2-(3-(ethylsulfonyl)benzoyl)-2-azabicyclo[3.1.0]hexane-3-carboxamide;

N-(5-chloro-2-methylbenzyl)-1-(((3S)-1-((3-cyano-1-azetidinyl)sulfonyl)-3-piperidinyl)carbonyl)-D-prolinamide;

(4R)—N—((R)-cyclopropyl(2-fluoro-4-(trifluoromethyl)phenyl)methyl)-4-fluoro-1-(3-(methylsulfonyl)benzoyl)-D-prolinamide;

(2R)—N-((6-chloro-3-pyridinyl)methyl)-1-((3-((cis-3-cyanocyclobutyl)sulfonyl)phenyl)carbonyl)-2-piperidinecarboxamide;

(2R)—N-((6-chloro-3-pyridinyl)methyl)-1-((3-((trans-3-cyanocyclobutyl)sulfonyl)phenyl)carbonyl)-2-piperidinecarboxamide;

(1R,3R,5R)—N—((R)-(4-chloro-2,5-difluorophenyl)(3-oxetanyl)methyl)-2-((2-methyl-4-pyridinyl)carbonyl)-2-azabicyclo[3.1.0]hexane-3-carboxamide;

1-(((3S)-1-((3-cyano-1-azetidinyl)sulfonyl)-3-piperidinyl)carbonyl)-N-((1R)-5-fluoro-6-methoxy-2,3-dihydro-1H-inden-1-yl)-D-prolinamide;

1-(((3S)-1-((3-cyano-1-azetidinyl)sulfonyl)-3-piperidinyl)carbonyl)-N-((1S)-5-fluoro-6-methoxy-2,3-dihydro-1H-inden-1-yl)-D-prolinamide;

1-(((3S)-1-((3-cyano-1-azetidinyl)sulfonyl)-3-piperidinyl)carbonyl)-N-(2,3,5,6-tetrafluorobenzyl)-D-prolinamide;

(4S)—N—((R)-cyclopropyl(2-fluoro-4-(trifluoromethyl)phenyl)methyl)-4-methyl-1-(3-(methylsulfonyl)benzoyl)-D-prolinamide;

1-(((3S)-1-((3-cyano-1-azetidinyl)sulfonyl)-3-piperidinyl)carbonyl)-N-((1R)-1-(4-methoxyphenyl)propyl)-D-prolinamide;

1-(((3S)-1-((3-cyano-1-azetidinyl)sulfonyl)-3-piperidinyl)carbonyl)-N-((1S)-1-(4-methoxyphenyl)propyl)-D-prolinamide;

1-(((3S)-1-((trans-3-carbamoylcyclobutyl)sulfonyl)-3-piperidinyl)carbonyl)-N-(4-(trifluoromethyl)benzyl)-D-prolinamide;

1-(3-((3-cyano-1-azetidinyl)sulfonyl)benzoyl)-N-((1R)-2,2-dimethyl-1-(4-(trifluoromethyl)phenyl)propyl)-D-prolinamide;

(1R,3R,5R)—N—((R)-(4-chloro-3-fluorophenyl)(cyclopropyl)methyl)-2-((5-(methylsulfonyl)-3-pyridinyl)carbonyl)-2-azabicyclo[3.1.0]hexane-3-carboxamide;

N-((1S)-1-(4-chloro-3-fluorophenyl)propyl)-1-(3-(dimethylsulfamoyl)benzoyl)-D-prolinamide;

N-((1R)-1-(2-fluoro-4-(trifluoromethyl)phenyl)propyl)-1-(3-(methylsulfonyl)benzoyl)-D-prolinamide;

1-(((3S)-1-((3-hydroxy-1-azetidinyl)sulfonyl)-3-piperidinyl)carbonyl)-N-(4-(trifluoromethyl)benzyl)-D-prolinamide;

1-(((3S)-1-((3-cyano-1-azetidinyl)sulfonyl)-3-piperidinyl)carbonyl)-N-((1R)-1-(4-(difluoromethoxy)-3-methoxyphenyl)ethyl)-D-prolinamide;

1-(((3S)-1-((3-cyano-1-azetidinyl)sulfonyl)-3-piperidinyl)carbonyl)-N-((1S)-1-(4-(difluoromethoxy)-3-methoxyphenyl)ethyl)-D-prolinamide;

1-(((3S)-1-((3-cyano-1-azetidinyl)sulfonyl)-3-piperidinyl)carbonyl)-N-((1R)-1-(5-fluoro-2-methoxyphenyl)ethyl)-D-prolinamide;

1-(((3S)-1-((3-cyano-1-azetidinyl)sulfonyl)-3-piperidinyl)carbonyl)-N-((1S)-1-(5-fluoro-2-methoxyphenyl)ethyl)-D-prolinamide;

N-((1S)-1-(4-chloro-3-fluorophenyl)-2-hydroxyethyl)-1-(3-(dimethylsulfamoyl)benzoyl)-D-prolinamide;

1-((3-(5-azaspiro[2.3]hex-5-ylsulfonyl)phenyl)carbonyl)-N-((1R)-1-(3,4-dichlorophenyl)ethyl)-D-prolinamide;

N-((1R)-1-(4-chloro-2,5-difluorophenyl)ethyl)-1-(3-(methylsulfonyl)benzoyl)-D-prolinamide;

(1R,3R,5R)—N—((R)-cyclopropyl(2-fluoro-4-(trifluoromethyl)phenyl)methyl)-2-((2-(methylsulfonyl)-4-pyridinyl)carbonyl)-2-azabicyclo[3.1.0]hexane-3-carboxamide;

(4R)—N—((R)-(4-chloro-2,5-difluorophenyl)(3-oxetanyl)methyl)-4-hydroxy-1-((5-(trifluoromethyl)-3-pyridinyl)carbonyl)-D-prolinamide;

1-(((2R)-4-((3-cyano-1-azetidinyl)sulfonyl)-1-methyl-2-piperazinyl)carbonyl)-N-(4-(trifluoromethyl)benzyl)-D-prolinamide;

1-(((2S)-4-((3-cyano-1-azetidinyl)sulfonyl)-1-methyl-2-piperazinyl)carbonyl)-N-(4-(trifluoromethyl)benzyl)-D-prolinamide;

(1R,3R,5R)—N—((R)-(4-chloro-2,5-difluorophenyl)(cyclopropyl)methyl)-2-((4-ethyl-2-pyridinyl)carbonyl)-2-azabicyclo[3.1.0]hexane-3-carboxamide;

(4R)—N—((R)-(4-chloro-2,5-difluorophenyl) (cyclopropyl)methyl)-4-hydroxy-1-((5-(trifluoromethyl)-3-pyridinyl)carbonyl)-D-prolinamide;

1-(((3S)-1-((3-cyano-1-azetidinyl)sulfonyl)-3-piperidinyl)carbonyl)-N-(2-fluoro-5-methylbenzyl)-D-prolinamide;

1-(((3S)-1-((3-cyano-1-azetidinyl)sulfonyl)-3-piperidinyl)carbonyl)-N-(3-methylbenzyl)-D-prolinamide 1-((3-((3-cyano-1-azetidinyl)sulfonyl)phenyl)carbonyl)-N-((5-(trifluoromethyl)-2-pyridinyl)methyl)-D-prolinamide;

1-(((3S)-1-((1,1-dioxido-3-thietanyl)sulfamoyl)-3-piperidinyl)carbonyl)-N-(4-(trifluoromethyl)benzyl)-D-prolinamide;

(2R)—N—((R)-cyclopropyl(2-fluoro-4-(trifluoromethyl)phenyl)methyl)-1-(2-methoxy-5-(methylsulfonyl)benzoyl)-2-piperidinecarboxamide;

(1R,3R,5R)—N—((R)-(2-fluoro-4-(trifluoromethyl)phenyl)(3-oxetanyl)methyl)-2-((2-(2-methyl-2-propanyl)4-pyridinyl)carbonyl)-2-azabicyclo[3.1.0]hexane-3-carboxamide;

1-(((3S)-1-((3-cyano-1-azetidinyl)sulfonyl)-3-pyrrolidinyl)carbonyl)-N-(4-(trifluoromethyl)benzyl)-D-prolinamide;

1-(3-(methoxy(methyl)sulfamoyl)benzoyl)-N-(4-(trifluoromethyl)benzyl)-D-prolinamide;
(1S,3R,5S)—N—((R)-(4-chloro-2,5-difluorophenyl)(cyclopropyl)methyl)-2-((5-(methylsulfonyl)-3-pyridinyl)carbonyl)-2-azabicyclo[3.1.0]hexane-3-carboxamide;
1-(((3S)-1-((3-cyano-1-azetidinyl)sulfonyl)-3-piperidinyl)carbonyl)-N-(2,5-dichlorobenzyl)-D-prolinamide;
1-(((3S)-1-((3-cyano-1-azetidinyl)sulfonyl)-3-piperidinyl)carbonyl)-N-(4-fluoro-2-(trifluoromethyl)benzyl)-D-prolinamide;
(2R)—N—((R)-cyclopropyl(2-fluoro-4-(trifluoromethyl)phenyl)methyl)-1-((1,1-dioxido-2,3-dihydro-1-benzothiophen-6-yl)carbonyl)-2-piperidinecarboxamide;
1-(((3S)-1-(1-oxa-6-azaspiro[3.3]hept-6-ylsulfonyl)-3-piperidinyl)carbonyl)-N-(4-(trifluoromethyl)benzyl)-D-prolinamide;
1-((3-((3-cyano-1-azetidinyl)sulfonyl)phenyl)carbonyl)-N-((6-(trifluoromethyl)-2-pyridinyl)methyl)-D-prolinamide;
(4S)—N—((R)-cyclopropyl(2-fluoro-4-(trifluoromethyl)phenyl)methyl)-4-(difluoromethyl)-1-(3-(methylsulfonyl)benzoyl)-D-prolinamide;
1-(((3S)-1-((3-cyano-1-azetidinyl)sulfonyl)-3-piperidinyl)carbonyl)-N-((3R)-5-(trifluoromethyl)-2,3-dihydro-1-benzofuran-3-yl)-D-prolinamide & 1-(((3S)-1-((3-cyano-1-azetidinyl)sulfonyl)-3-piperidinyl)carbonyl)-N-((3S)-5-(trifluoromethyl)-2,3-dihydro-1-benzofuran-3-yl)-D-prolinamide;
(1R,3R,5R)—N—((R)-cyclopropyl(2,5-difluoro-4-(trifluoromethyl)phenyl)methyl)-2-((4-methyl-2-pyridinyl)carbonyl)-2-azabicyclo[3.1.0]hexane-3-carboxamide;
1-(((3S)-1-((3-cyano-1-azetidinyl)sulfonyl)-3-piperidinyl)carbonyl)-N-(2-fluoro-6-(trifluoromethyl)benzyl)-D-prolinamide;
N-(2-chloro-5-methylbenzyl)-1-(((3S)-1-((3-cyano-1-azetidinyl)sulfonyl)-3-piperidinyl)carbonyl)-D-prolinamide;
(1R,3R,5R)—N—((R)-cyclopropyl(2,5-difluoro-4-(trifluoromethyl)phenyl)methyl)-2-((4-ethyl-2-pyridinyl)carbonyl)-2-azabicyclo[3.1.0]hexane-3-carboxamide;
N—((R)-cyclopropyl(2-fluoro-4-(trifluoromethyl)phenyl)methyl)-1-((5-(methylsulfonyl)-3-pyridinyl)carbonyl)-D-prolinamide;
N-(4-chloro-3-fluorobenzyl)-1-(((3S)-1-((3-hydroxy-3-methyl-1-azetidinyl)sulfonyl)-3-piperidinyl)carbonyl)-D-prolinamide;
1-(((3S)-1-(3-oxetanylsulfonyl)-3-piperidinyl)carbonyl)-N-(4-(trifluoromethyl)benzyl)-D-prolinamide;
(1R,3R,5R)—N—((R)-cyclopropyl(3-fluoro-4-(trifluoromethyl)phenyl)methyl)-2-((2-(methylsulfonyl)-4-pyridinyl)carbonyl)-2-azabicyclo[3.1.0]hexane-3-carboxamide;
N—((R)-cyclopropyl(2-fluoro-4-(trifluoromethyl)phenyl)methyl)-1-(2-methyl-5-(methylsulfonyl)benzoyl)-D-prolinamide;
(1R,3R,5R)—N—((R)-(4-chloro-2,5-difluorophenyl)(cyclopropyl)methyl)-2-((6-(trifluoromethyl)-2-pyridinyl)carbonyl)-2-azabicyclo[3.1.0]hexane-3-carboxamide;
1-(((3S)-1-((3-hydroxy-3-methyl-1-azetidinyl)sulfonyl)-3-piperidinyl)carbonyl)-N-((1R)-1-(4-(trifluoromethyl)phenyl)propyl)-D-prolinamide;
1-(((3S)-1-((3-hydroxy-3-methyl-1-azetidinyl)sulfonyl)-3-piperidinyl)carbonyl)-N-((1S)-1-(4-(trifluoromethyl)phenyl)propyl)-D-prolinamide;
N-(2-fluoro-4-(trifluoromethyl)benzyl)-1-(((3S)-1-((3-hydroxy-3-methyl-1-azetidinyl)sulfonyl)-3-piperidinyl)carbonyl)-D-prolinamide;
(2S)—N—((R)-cyclopropyl(2,5-difluoro-4-(trifluoromethyl)phenyl)methyl)-2-methyl-1-(3-(methylsulfonyl)benzoyl)-2-azetidinecarboxamide;
(3R)-2-((3-((3-cyano-1-azetidinyl)sulfonyl)phenyl)carbonyl)-N-(4-(trifluoromethyl)benzyl)-1,2,3,4-tetrahydro-3-isoquinolinecarboxamide;
(3S)-2-((3-((3-cyano-1-azetidinyl)sulfonyl)phenyl)carbonyl)-N-(4-(trifluoromethyl)benzyl)-1,2,3,4-tetrahydro-3-isoquinolinecarboxamide;
1-(((3S)-1-((3-cyano-1-azetidinyl)sulfonyl)-3-piperidinyl)carbonyl)-N-(4-methoxy-3-methylbenzyl)-D-prolinamide;
N—((S)-(3-fluoro-3-oxetanyl)(2-fluoro-4-(trifluoromethyl)phenyl)methyl)-1-(3-(methylsulfonyl)benzoyl)-D-prolinamide;
1-(((3S)-1-((3-cyano-1-azetidinyl)sulfonyl)-3-piperidinyl)carbonyl)-N-(2-fluoro-5-(trifluoromethyl)benzyl)-D-prolinamide;
N—((R)-cyclopropyl(2-fluoro-4-(trifluoromethyl)phenyl)methyl)-1-((2-(methylsulfonyl)-4-pyridinyl)carbonyl)-D-prolinamide;
(1R,3R,5R)—N—((S)-(3-fluoro-3-oxetanyl)(2-fluoro-4-(trifluoromethyl)phenyl)methyl)-2-(3-(methylsulfonyl)benzoyl)-2-azabicyclo[3.1.0]hexane-3-carboxamide;
(2R)-1-((3-(dimethylsulfamoyl)phenyl)carbonyl)-N-(4-(trifluoromethyl)benzyl)-2-piperidinecarboxamide;
(2S)-1-((3-(dimethylsulfamoyl)phenyl)carbonyl)-N-(4-(trifluoromethyl)benzyl)-2-piperidinecarboxamide;
1-(3-(dimethylsulfamoyl)benzoyl)-N-((1S)-2-hydroxy-1-(4-(trifluoromethyl)phenyl)ethyl)-D-prolinamide;
1-(((3S)-1-((3-(1H-1,2,4-triazol-1-yl)-1-azetidinyl)sulfonyl)-3-piperidinyl)carbonyl)-N-(4-(trifluoromethyl)benzyl)-D-prolinamide;
(1R,3R,5R)—N—((R)-cyclopropyl(2-fluoro-4-(trifluoromethyl)phenyl)methyl)-2-((5-(trifluoromethyl)-3-pyridinyl)carbonyl)-2-azabicyclo[3.1.0]hexane-3-carboxamide;
1-(((3S)-1-((3-cyano-1-azetidinyl)sulfonyl)-3-piperidinyl)carbonyl)-N-(3-fluoro-5-methoxybenzyl)-D-prolinamide;
(4R)—N—((R)-cyclopropyl(2-fluoro-4-(trifluoromethyl)phenyl)methyl)-4-(difluoromethyl)-1-((5-(methylsulfonyl)-3-pyridinyl)carbonyl)-D-prolinamide;
(4S)-4-fluoro-1-(((3S)-1-((3-hydroxy-3-methyl-1-azetidinyl)sulfonyl)-3-piperidinyl)carbonyl)-N-(4-(trifluoromethyl)benzyl)-D-prolinamide;
1-(((3S)-1-((3-cyano-1-azetidinyl)sulfonyl)-3-piperidinyl)carbonyl)-N-(2-fluorobenzyl)-D-prolinamide;
(1R,3R,5R)—N—((S)-(2-fluoro-4-(trifluoromethyl)phenyl)((3S)-5-oxo-3-pyrrolidinyl)methyl)-2-(3-(methylsulfonyl)benzoyl)-2-azabicyclo[3.1.0]hexane-3-carboxamide;
(1R,3R,5R)—N—((R)-cyclopropyl(3-fluoro-4-(trifluoromethyl)phenyl)methyl)-2-((2-(cyclopropylsulfonyl)-4-pyridinyl)carbonyl)-2-azabicyclo[3.1.0]hexane-3-carboxamide;
1-(2-chloro-5-sulfamoylbenzoyl)-N—((R)-cyclopropyl(2-fluoro-4-(trifluoromethyl)phenyl)methyl)-D-prolinamide;
1-(((3S)-1-((3-(3-methyl-1,2,4-oxadiazol-5-yl)-1-azetidinyl)sulfonyl)-3-piperidinyl)carbonyl)-N-(4-(trifluoromethyl)benzyl)-D-prolinamide;
1-((3-((3-cyano-1-azetidinyl)sulfonyl)phenyl)carbonyl)-N-(2-(3-(trifluoromethyl)-1H-pyrazol-1-yl)ethyl)-D-prolinamide;
N—((R)-cyclopropyl(2-fluoro-4-(trifluoromethyl)phenyl)methyl)-1-(4-fluoro-3-(methylsulfonyl)benzoyl)-D-prolinamide;
N—((R)-cyclopropyl(2-fluoro-4-(trifluoromethyl)phenyl)methyl)-1-(3-(3-methyl-3-oxetanyl)benzoyl)-D-prolinamide;
1-(((3S)-1-((3-((methoxyacetyl)amino)-1-azetidinyl)sulfonyl)-3-piperidinyl)carbonyl)-N-(4-(trifluoromethyl)benzyl)-D-prolinamide;

(4R)—N—((R)-cyclopropyl(2-fluoro-4-(trifluoromethyl) phenyl)methyl)-1-methyl-3-(3-(methylsulfonyl)benzoyl)-2-oxo-4-imidazolidinecarboxamide;
1-(((3S)-1-((3-cyano-1-azetidinyl)sulfonyl)-3-piperidinyl) carbonyl)-N-(3,5-difluorobenzyl)-L-prolinamide;
(1R,3R,5R)—N—((R)-(4-chloro-2,5-difluorophenyl)(3-oxetanyl)methyl)-2-((5-methyl-3-pyridinyl)carbonyl)-2-azabicyclo[3.1.0]hexane-3-carboxamide;
(4R)—N—((R)-cyclopropyl(2-fluoro-4-(trifluoromethyl) phenyl)methyl)-1-methyl-3-(3-(methylsulfonyl)benzoyl)-2-oxo-4-imidazolidinecarboxamide;
(4S)—N—((R)-cyclopropyl(2-fluoro-4-(trifluoromethyl) phenyl)methyl)-1-methyl-3-(3-(methylsulfonyl)benzoyl)-2-oxo-4-imidazolidinecarboxamide;
1-(((3S)-1-(((2R)-2-(4-chlorophenyl)-1-azetidinyl)sulfonyl)-3-piperidinyl)carbonyl)-N-(4-(trifluoromethyl)benzyl)-D-prolinamide;
1-(((3S)-1-(((2S)-2-(4-chlorophenyl)-1-azetidinyl)sulfonyl)-3-piperidinyl)carbonyl)-N-(4-(trifluoromethyl)benzyl)-D-prolinamide;
1-(((3S)-1-((3-cyano-1-azetidinyl)sulfonyl)-3-piperidinyl) carbonyl)-N-((1R)-1-(2-(difluoromethoxy)-4-fluorophenyl)ethyl)-D-prolinamide;
1-(((3S)-1-((3-(4-chlorobenzyl)-1-azetidinyl)sulfonyl)-3-piperidinyl)carbonyl)-N-(4-(trifluoromethyl)benzyl)-D-prolinamide;
1-(((3S)-1-((3-cyano-1-azetidinyl)sulfonyl)-3-piperidinyl) carbonyl)-N-(5-fluoro-2-methoxybenzyl)-D-prolinamide;
1-(3-cyanobenzoyl)-N—((R)-cyclopropyl(2-fluoro-4-(trifluoromethyl)phenyl)methyl)-D-prolinamide;
(1R,3R,5R)—N—((R)-(4-chloro-2,5-difluorophenyl)(cyclopropyl)methyl)-2-((4-methyl-2-pyridinyl)carbonyl)-2-azabicyclo[3.1.0]hexane-3-carboxamide;
1-(((3S)-1-((3,3-difluoro-1-azetidinyl)sulfonyl)-3-piperidinyl)carbonyl)-N-(4-(trifluoromethyl)benzyl)-D-prolinamide;
N—((R)-cyclopropyl(2-fluoro-4-(trifluoromethyl)phenyl) methyl)-1-(3-(1-(methylsulfonyl)-3-azetidinyl)benzoyl)-D-prolinamide;
N-((7R)-bicyclo[4.2.0]octa-1,3,5-trien-7-yl)-1-(((3S)-1-((3-cyano-1-azetidinyl)sulfonyl)-3-piperidinyl)carbonyl)-D-prolinamide;
N-((7S)-bicyclo[4.2.0]octa-1,3,5-trien-7-yl)-1-(((3S)-1-((3-cyano-1-azetidinyl)sulfonyl)-3-piperidinyl)carbonyl)-D-prolinamide;
(4S)-4-fluoro-N—((S)-(3-fluoro-3-oxetanyl)(2-fluoro-4-(trifluoromethyl)phenyl)methyl)-1-(3-(methylsulfonyl) benzoyl)-D-prolinamide;
1-(((3S)-1-((3-(2-pyridinyl)-1-azetidinyl)sulfonyl)-3-piperidinyl)carbonyl)-N-(4-(trifluoromethyl)benzyl)-D-prolinamide;
1-(((3S)-1-((3-cyano-1-azetidinyl)sulfonyl)-3-piperidinyl) carbonyl)-N-(4-ethoxy-3-fluorobenzyl)-D-prolinamide;
1-(((3S)-1-((3-cyano-1-azetidinyl)sulfonyl)-3-piperidinyl) carbonyl)-N-(2,6-dimethylbenzyl)-D-prolinamide;
1-(((3S)-1-((3-((cyclopropylcarbonyl)amino)-1-azetidinyl) sulfonyl)-3-piperidinyl)carbonyl)-N-(4-(trifluoromethyl) benzyl)-D-prolinamide;
1-(((3S)-1-((3-cyano-1-azetidinyl)sulfonyl)-3-piperidinyl) carbonyl)-N-((4R)-2-methyl-1,2,3,4-tetrahydro-4-isoquinolinyl)-D-prolinamide;
1-(((3S)-1-((3-cyano-1-azetidinyl)sulfonyl)-3-piperidinyl) carbonyl)-N-((4S)-2-methyl-1,2,3,4-tetrahydro-4-isoquinolinyl)-D-prolinamide;
1-(((3S)-1-((3-(dimethylcarbamoyl)-1-azetidinyl)sulfonyl)-3-piperidinyl)carbonyl)-N-(4-(trifluoromethyl)benzyl)-D-prolinamide;
(1R,3R,5R)—N—((R)-(4-chloro-2,5-difluorophenyl)(cyclopropyl)methyl)-2-((4-cyclopropyl-2-pyridinyl)carbonyl)-2-azabicyclo[3.1.0]hexane-3-carboxamide;
1-(((3S)-1-((3-cyano-1-azetidinyl)sulfonyl)-3-piperidinyl) carbonyl)-N-(2-methyl-5-(trifluoromethyl)benzyl)-D-prolinamide;
N—((R)-cyclopropyl(2-fluoro-4-(trifluoromethyl)phenyl) methyl)-1-(3-methylbenzoyl)-D-prolinamide;
N—((R)-cyclopropyl(2-fluoro-4-(trifluoromethyl)phenyl) methyl)-1-(2-methyl-5-sulfamoylbenzoyl)-D-prolinamide;
(1R,3R,5R)—N—((R)-cyclopropyl(2,5-difluoro-4-(trifluoromethyl)phenyl)methyl)-2-((2-methyl-4-pyridinyl)carbonyl)-2-azabicyclo[3.1.0]hexane-3-carboxamide;
(1R,3R,5R)-2-((4-cyclopropyl-2-pyridinyl)carbonyl)-N—((R)-(2-fluoro-4-(trifluoromethyl)phenyl)(3-oxetanyl) methyl)-2-azabicyclo[3.1.0]hexane-3-carboxamide;
N-(2-chloro-6-fluorobenzyl)-1-(((3S)-1-((3-cyano-1-azetidinyl)sulfonyl)-3-piperidinyl)carbonyl)-D-prolinamide;
1-(((3S)-1-(((2R)-2-benzyl-1-azetidinyl)sulfonyl)-3-piperidinyl)carbonyl)-N-(4-(trifluoromethyl)benzyl)-D-prolinamide;
1-(((3S)-1-(((2S)-2-benzyl-1-azetidinyl)sulfonyl)-3-piperidinyl)carbonyl)-N-(4-(trifluoromethyl)benzyl)-D-prolinamide;
N—((R)-cyclopropyl(4-(difluoromethyl)-2-fluorophenyl) methyl)-1-(3-(methylsulfonyl)benzoyl)-D-prolinamide;
3-((3-cyano-1-azetidinyl)sulfonyl)-N-methyl-N-((1R)-1-methyl-2-oxo-2-(((2-(trifluoromethyl)-4-pyridinyl) methyl)amino)ethyl)benzamide;
(4S)—N—((R)-(4-chloro-2,5-difluorophenyl) (3-oxetanyl) methyl)-4-hydroxy-1-((2-(trifluoromethyl)-4-pyridinyl) carbonyl)-D-prolinamide;
(1R,3R,5R)—N—((R)-(4-chloro-2,5-difluorophenyl)(cyclopropyl)methyl)-2-(((2S)-4-(methylsulfonyl)-2-piperazinyl)carbonyl)-2-azabicyclo[3.1.0]hexane-3-carboxamide;
1-((3-((3-cyano-1-azetidinyl)sulfonyl)phenyl)carbonyl)-N-((5-(trifluoromethyl)-2-pyrimidinyl)methyl)-D-prolinamide;
N—((R)-cyclopropyl(2-fluoro-4-(trifluoromethyl)phenyl) methyl)-1-(3-(3-thiophenyl)benzoyl)-D-prolinamide;
(1R,3R,5R)—N—((R)-(2-fluoro-4-(trifluoromethyl)phenyl) (3-oxetanyl)methyl)-2-(4-methyl-3-(methylsulfonyl)benzoyl)-2-azabicyclo[3.1.0]hexane-3-carboxamide;
(1R,3R,5R)—N—((R)-(2,4-difluorophenyl)(3-oxetanyl) methyl)-2-(3-(methylsulfonyl)benzoyl)-2-azabicyclo [3.1.0]hexane-3-carboxamide;
1-(((3S)-1-((3-cyano-1-azetidinyl)sulfonyl)-3-piperidinyl) carbonyl)-N-((1R)-1-(4-fluorophenyl)ethyl)-D-prolinamide;
1-(((3S)-1-((3-cyano-1-azetidinyl)sulfonyl)-3-piperidinyl) carbonyl)-N-((1S)-1-(4-fluorophenyl)ethyl)-D-prolinamide;
1-(((3S)-1-((3-hydroxy-3-methyl-1-azetidinyl)sulfonyl)-3-piperidinyl)carbonyl)-N-(4-(trifluoromethyl)benzyl)-D-prolinamide;
(1S,3R,5S)—N—((R)-cyclopropyl(2,5-difluoro-4-(trifluoromethyl)phenyl)methyl)-2-((2-(methylsulfonyl)-4-pyridinyl)carbonyl)-2-azabicyclo[3.1.0]hexane-3-carboxamide;
(2S)—N—((R)-(4-chloro-2,5-difluorophenyl) (cyclopropyl) methyl)-1-(3-(methylsulfonyl)benzoyl)-2-azetidinecarboxamide;
N-((1R)-1-(4-chlorophenyl)-2-hydroxyethyl)-1-(((3S)-1-((3-cyano-1-azetidinyl)sulfonyl)-3-piperidinyl)carbonyl)-D-prolinamide;

1-(((3S)-1-((3-tert-butoxy-1-azetidinyl)sulfonyl)-3-piperidinyl)carbonyl)-N-(4-(trifluoromethyl)benzyl)-D-prolinamide;

1-(((3S)-1-((3-pentyl-1-azetidinyl)sulfonyl)-3-piperidinyl)carbonyl)-N-(4-(trifluoromethyl)benzyl)-D-prolinamide;

(1R,3R,5R)—N—((R)-(4-chloro-2,5-difluorophenyl)(cyclopropyl)methyl)-2-((2-methyl-4-pyridinyl)carbonyl)-2-azabicyclo[3.1.0]hexane-3-carboxamide;

N—((R)-cyclopropyl(2-fluoro-4-(trifluoromethyl)phenyl)methyl)-1-(3-(1H-pyrazol-4-yl)benzoyl)-D-prolinamide;

(1R,3R,5R)—N—((R)-(4-chloro-2-fluorophenyl)(3-oxetanyl)methyl)-2-((2-(2-methyl-2-propanyl)-4-pyridinyl)carbonyl)-2-azabicyclo[3.1.0]hexane-3-carboxamide;

1-(((3S)-1-((3-((3R)-tetrahydro-3-furanyl)-1-azetidinyl)sulfonyl)-3-piperidinyl)carbonyl)-N-(4-(trifluoromethyl)benzyl)-D-prolinamide;

1-(((3S)-1-((3-((3S)-tetrahydro-3-furanyl)-1-azetidinyl)sulfonyl)-3-piperidinyl)carbonyl)-N-(4-(trifluoromethyl)benzyl)-D-prolinamide;

1-(((3S)-1-((3-cyano-1-azetidinyl)sulfonyl)-3-piperidinyl)carbonyl)-N-((1R)-2,2-dimethyl-1-(4-(trifluoromethyl)phenyl)propyl)-D-prolinamide;

1-(((3S)-1-((3-cyano-1-azetidinyl)sulfonyl)-3-piperidinyl)carbonyl)-N-(5-methyl-2-(trifluoromethyl)benzyl)-D-prolinamide;

1-(3-(methylsulfonyl)benzoyl)-N-((1R)-5-(trifluoromethyl)-2,3-dihydro-1H-inden-1-yl)-D-prolinamide;

1-(((3S)-1-((6-hydroxy-6-(trifluoromethyl)-2-azaspiro[3.3]hept-2-yl)sulfonyl)-3-piperidinyl)carbonyl)-N-(4-(trifluoromethyl)benzyl)-D-prolinamide;

1-(((3S)-1-(dimethylsulfamoyl)-3-piperidinyl)carbonyl)-N-(4-(trifluoromethyl)benzyl)-D-prolinamide;

N—((R)-cyclopropyl(2-fluoro-4-(trifluoromethyl)phenyl)methyl)-1-(3-(1H-pyrazol-3-yl)benzoyl)-D-prolinamide;

1-(((3S)-1-((3-cyano-1-azetidinyl)sulfonyl)-3-piperidinyl)carbonyl)-N-(2-(trifluoromethyl)benzyl)-D-prolinamide;

(1R,3R,5R)—N—((R)-cyclopropyl(2,5-difluoro-4-methoxyphenyl)methyl)-2-(3-(methylsulfonyl)benzoyl)-2-azabicyclo[3.1.0]hexane-3-carboxamide;

(1R,3R,5R)—N—((R)-(2-fluoro-4-(trifluoromethyl)phenyl)(3-oxetanyl)methyl)-2-((2-(2-propanyl)-4-pyridinyl)carbonyl)-2-azabicyclo[3.1.0]hexane-3-carboxamide;

1-(3-(methyl(2-propyn-1-yl)sulfamoyl)benzoyl)-N-((1R)-1-(4-(trifluoromethyl)phenyl)ethyl)-D-prolinamide;

1-(((3S)-1-(((6R)-6-hydroxy-2-azaspiro[3.4]oct-2-yl)sulfonyl)-3-piperidinyl)carbonyl)-N-(4-(trifluoromethyl)benzyl)-D-prolinamide;

1-(((3S)-1-(((6S)-6-hydroxy-2-azaspiro[3.4]oct-2-yl)sulfonyl)-3-piperidinyl)carbonyl)-N-(4-(trifluoromethyl)benzyl)-D-prolinamide;

(1R,5R)—N—((R)-cyclopropyl(2-fluoro-4-(trifluoromethyl)phenyl)methyl)-2-(3-(methylsulfonyl)benzoyl)-2-azabicyclo[3.1.0]hexane-1-carboxamide;

(1R,3R,5R)—N—((R)-(4-chloro-2,5-difluorophenyl)(cyclopropyl)methyl)-2-(3-(S-methylsulfonimidoyl)benzoyl)-2-azabicyclo[3.1.0]hexane-3-carboxamide;

(1R,3R,5R)—N-((1R)-5-chloro-2,3-dihydro-1H-inden-1-yl)-2-(3-(methylsulfonyl)benzoyl)-2-azabicyclo[3.1.0]hexane-3-carboxamide;

1-(((3S)-1-((3-((cyclobutylcarbonyl)amino)-1-azetidinyl)sulfonyl)-3-piperidinyl)carbonyl)-N-(4-(trifluoromethyl)benzyl)-D-prolinamide;

(1R,3R,5R)-2-(2-aminobenzoyl)-N—((R)-cyclopropyl(2-fluoro-4-(trifluoromethyl)phenyl)methyl)-2-azabicyclo[3.1.0]hexane-3-carboxamide;

(3R)—N—((R)-cyclopropyl(4-(trifluoromethyl)phenyl)methyl)-3-fluoro-1-(3-(methylsulfonyl)benzoyl)-D-prolinamide;

(1R,3R,5R)—N-((1S,2R)-1-(4-chloro-2,5-difluorophenyl)-2-hydroxypropyl)-2-(3-(methylsulfonyl)benzoyl)-2-azabicyclo[3.1.0]hexane-3-carboxamide;

N-benzyl-1-(((3S)-1-((3-cyano-1-azetidinyl)sulfonyl)-3-piperidinyl)carbonyl)-D-prolinamide;

1-((3-((3-cyano-1-azetidinyl)sulfonyl)phenyl)carbonyl)-N-(cis-3-(trifluoromethyl)cyclobutyl)-D-prolinamide;

1-((3-((3-cyano-1-azetidinyl)sulfonyl)phenyl)carbonyl)-N-(trans-3-(trifluoromethyl)cyclobutyl)-D-prolinamide;

1-(((3S)-1-((3-fluoro-3-(trifluoromethyl)-1-azetidinyl)sulfonyl)-3-piperidinyl)carbonyl)-N-(4-(trifluoromethyl)benzyl)-D-prolinamide;

N—((R)-cyclopropyl(2-fluoro-4-(trifluoromethyl)phenyl)methyl)-1-((2-(methylsulfonyl)-4-pyridinyl)carbonyl)-D-prolinamide;

N—((S)-cyclopropyl(2-fluoro-4-(trifluoromethyl)phenyl)methyl)-1-((2-(methylsulfonyl)-4-pyridinyl)carbonyl)-D-prolinamide;

(1S,3R,5S)—N—((R)-cyclopropyl(2-fluoro-4-(trifluoromethyl)phenyl)methyl)-2-(3-(methylsulfonyl)benzoyl)-2-azabicyclo[3.1.0]hexane-3-carboxamide;

1-(((3S)-1-((3-cyano-1-azetidinyl)sulfonyl)-3-piperidinyl)carbonyl)-N-((1R)-1-(2,3-difluorophenyl)ethyl)-D-prolinamide;

1-(((3S)-1-((3-cyano-1-azetidinyl)sulfonyl)-3-piperidinyl)carbonyl)-N-((1S)-1-(2,3-difluorophenyl)ethyl)-D-prolinamide;

methyl N-((3-(((2R)-2-((4-(trifluoromethyl)benzyl)carbamoyl)-1-pyrrolidinyl)carbonyl)phenyl)sulfonyl)glycinate;

1-(((3S)-1-((3-cyano-1-azetidinyl)sulfonyl)-3-piperidinyl)carbonyl)-N-(2,5-dimethylbenzyl)-D-prolinamide;

1-(((3S)-1-((3R)-tetrahydro-3-furanylsulfonyl)-3-piperidinyl)carbonyl)-N-(4-(trifluoromethyl)benzyl)-D-prolinamide;

1-(((3S)-1-((3S)-tetrahydro-3-furanylsulfonyl)-3-piperidinyl)carbonyl)-N-(4-(trifluoromethyl)benzyl)-D-prolinamide;

(2R)—N—((R)-cyclopropyl(2,5-difluoro-4-(trifluoromethyl)phenyl)methyl)-3,3-difluoro-1-((5-(methylsulfonyl)-3-pyridinyl)carbonyl)-2-azetidinecarboxamide;

(2S)—N—((R)-cyclopropyl(2,5-difluoro-4-(trifluoromethyl)phenyl)methyl)-3,3-difluoro-1-((5-(methylsulfonyl)-3-pyridinyl)carbonyl)-2-azetidinecarboxamide;

1-(((3S)-1-((3-cyano-1-azetidinyl)sulfonyl)-3-piperidinyl)carbonyl)-N-((1R)-2,2,2-trifluoro-1-(4-(trifluoromethyl)phenyl)ethyl)-D-prolinamide;

1-(((3S)-1-(((2R)-2-methyl-1-azetidinyl)sulfonyl)-3-piperidinyl)carbonyl)-N-(4-(trifluoromethyl)benzyl)-D-prolinamide;

1-(((3S)-1-(((2S)-2-methyl-1-azetidinyl)sulfonyl)-3-piperidinyl)carbonyl)-N-(4-(trifluoromethyl)benzyl)-D-prolinamide;

N-(5-chloro-2-methoxybenzyl)-1-(((3S)-1-((3-cyano-1-azetidinyl)sulfonyl)-3-piperidinyl)carbonyl)-D-prolinamide;

N-(4-(trifluoromethyl)benzyl)-1-(((3S)-1-((3-(3-(trifluoromethyl)phenyl)-1-azetidinyl)sulfonyl)-3-piperidinyl)carbonyl)-D-prolinamide;

N-((1R)-1-(4-chloro-3-fluorophenyl)propyl)-1-(3-(methylsulfonyl)benzoyl)-D-prolinamide;

1-(((3S)-1-((3,3-difluoro-1-pyrrolidinyl)sulfonyl)-3-piperidinyl)carbonyl)-N-(4-(trifluoromethyl)benzyl)-D-prolinamide;

1-(((3S)-1-(((5-methyl-1,3,4-oxadiazol-2-yl)methyl)sulfamoyl)-3-piperidinyl)carbonyl)-N-(4-(trifluoromethyl)benzyl)-D-prolinamide;

methyl trans-3-(((3S)-3-(((2R)-2-((4-(trifluoromethyl)benzyl)carbamoyl)-1-pyrrolidinyl)carbonyl)-1-piperidinyl)sulfonyl)cyclobutanecarboxylate;

1-(((3S)-1-((3-cyano-1-azetidinyl)sulfonyl)-3-piperidinyl)carbonyl)-N-((1S)-2,2,2-trifluoro-1-(3-fluoro-4-methoxyphenyl)ethyl)-D-prolinamide;

1-(2-chloro-4-fluoro-5-sulfamoylbenzoyl)-N—((R)-cyclopropyl(2-fluoro-4-(trifluoromethyl)phenyl)methyl)-D-prolinamide;

3-((3-cyano-1-azetidinyl)sulfonyl)-N-methyl-N-((1S)-1-methyl-2-oxo-2-((4-(trifluoromethyl)benzyl)amino)ethyl)benzamide;

(1S,3R,5S)—N—((R)-(4-chloro-2,5-difluorophenyl)(cyclopropyl)methyl)-2-((2-(methylsulfonyl)-4-pyridinyl)carbonyl)-2-azabicyclo[3.1.0]hexane-3-carboxamide;

1-(((3S)-1-(cyclobutylsulfonyl)-3-piperidinyl)carbonyl)-N-(4-(trifluoromethyl)benzyl)-D-prolinamide;

1-(((3S)-1-((3-cyano-1-azetidinyl)sulfonyl)-3-piperidinyl)carbonyl)-N-(3-(difluoromethoxy)benzyl)-D-prolinamide;

1-(((3S)-1-((3-(acetylamino)-1-azetidinyl)sulfonyl)-3-piperidinyl)carbonyl)-N-(4-(trifluoromethyl)benzyl)-D-prolinamide;

1-(((3S)-1-((3-cyano-1-azetidinyl)sulfonyl)-3-piperidinyl)carbonyl)-N-((4R)-6-methoxy-3,4-dihydro-2H-chromen-4-yl)-D-prolinamide;

N—((R)-cyclopropyl(2-fluoro-4-(trifluoromethyl)phenyl)methyl)-1-(3-methoxybenzoyl)-D-prolinamide;

1-((3-((3-cyano-1-azetidinyl)sulfonyl)phenyl)carbonyl)-N-((1R)-1-phenylethyl)-D-prolinamide;

(1R,3R,5R)-2-((4-ethyl-2-pyridinyl)carbonyl)-N—((R)-(2-fluoro-4-(trifluoromethyl)phenyl)(3-oxetanyl)methyl)-2-azabicyclo[3.1.0]hexane-3-carboxamide;

1-(((3S)-1-((3-(2,2,2-trifluoroethyl)-1-azetidinyl)sulfonyl)-3-piperidinyl)carbonyl)-N-(4-(trifluoromethyl)benzyl)-D-prolinamide;

1-(((3S)-1-((3-(methoxymethyl)-1-azetidinyl)sulfonyl)-3-piperidinyl)carbonyl)-N-(4-(trifluoromethyl)benzyl)-D-prolinamide;

(1R,3R,5R)—N—((R)-(2-fluoro-4-(trifluoromethyl)phenyl)(3-oxetanyl)methyl)-2-((6-(trifluoromethyl)-2-pyridinyl)carbonyl)-2-azabicyclo[3.1.0]hexane-3-carboxamide;

1-(((2S)-4-((3-cyano-1-azetidinyl)sulfonyl)-2-piperazinyl)carbonyl)-N-(3,5-dichlorobenzyl)-D-prolinamide;

(5S)—N—((R)-cyclopropyl(2-fluoro-4-(trifluoromethyl)phenyl)methyl)-5-methyl-1-(3-(methylsulfonyl)benzoyl)-D-prolinamide;

(4S)—N—((R)-cyclopropyl(3-fluoro-4-methylphenyl)methyl)-4-fluoro-1-(3-(methylsulfonyl)benzoyl)-D-prolinamide;

1-(3-(ethylsulfonyl)benzoyl)-N-(4-(trifluoromethyl)benzyl)-D-prolinamide;

N—((R)-cyclopropyl(2-fluoro-4-(trifluoromethyl)phenyl)methyl)-1-(3-(2-hydroxy-2-propanyl)benzoyl)-D-prolinamide;

(1R,3R,5R)—N—((R)-(4-chloro-3-fluorophenyl)(cyclopropyl)methyl)-2-((2-(methylsulfonyl)-4-pyridinyl)carbonyl)-2-azabicyclo[3.1.0]hexane-3-carboxamide;

1-(3-(1-acetyl-3-fluoro-3-azetidinyl)benzoyl)-N—((R)-cyclopropyl(2-fluoro-4-(trifluoromethyl)phenyl)methyl)-D-prolinamide;

(1R,3R,5R)—N—((R)-cyclopropyl(2,5-difluoro-4-(trifluoromethyl)phenyl)methyl)-2-((5-methyl-3-pyridinyl)carbonyl)-2-azabicyclo[3.1.0]hexane-3-carboxamide;

(2R)-1-((3-((3,3-difluoro-1-azetidinyl)sulfonyl)phenyl)carbonyl)-N-((6-(trifluoromethyl)-3-pyridinyl)methyl)-2-piperidinecarboxamide;

1-(((3S)-1-((3-cyano-1-azetidinyl)sulfonyl)-3-piperidinyl)carbonyl)-N-((1R,2R)-2-(trifluoromethyl)cyclobutyl)-D-prolinamide;

1-(((3S)-1-((3-cyano-1-azetidinyl)sulfonyl)-3-piperidinyl)carbonyl)-N-((1R,2S)-2-(trifluoromethyl)cyclobutyl)-D-prolinamide;

1-(((3S)-1-((3-cyano-1-azetidinyl)sulfonyl)-3-piperidinyl)carbonyl)-N-((1S,2R)-2-(trifluoromethyl)cyclobutyl)-D-prolinamide;

1-(((3S)-1-((3-cyano-1-azetidinyl)sulfonyl)-3-piperidinyl)carbonyl)-N-((1S,2S)-2-(trifluoromethyl)cyclobutyl)-D-prolinamide;

1-(((3S)-1-(1-azaspiro[3.3]hept-1-ylsulfonyl)-3-piperidinyl)carbonyl)-N-(4-(trifluoromethyl)benzyl)-D-prolinamide;

(1R,3S,5R)-2-(((3S)-1-((3-cyano-1-azetidinyl)sulfonyl)-3-piperidinyl)carbonyl)-N-(4-(trifluoromethyl)benzyl)-2-azabicyclo[3.1.0]hexane-3-carboxamide;

N—((S)-cyclopropyl(2-fluoro-4-(trifluoromethyl)phenyl)methyl)-1-(3-(dimethylsulfamoyl)benzoyl)-D-prolinamide;

N-((1S)-1-(4-chlorophenyl)ethyl)-1-(((3S)-1-((3-cyano-1-azetidinyl)sulfonyl)-3-piperidinyl)carbonyl)-D-prolinamide;

1-(((3S)-1-((3-cyano-1-azetidinyl)sulfonyl)-3-piperidinyl)carbonyl)-N-((1R)-1-(2-methoxyphenyl)propyl)-D-prolinamide;

1-(((3S)-1-((3-cyano-1-azetidinyl)sulfonyl)-3-piperidinyl)carbonyl)-N-((1S)-1-(2-methoxyphenyl)propyl)-D-prolinamide;

1-(4-amino-3-(methylsulfonyl)benzoyl)-N—((R)-cyclopropyl(2-fluoro-4-(trifluoromethyl)phenyl)methyl)-D-prolinamide;

1-(((3S)-1-((1-acetyl-3-azetidinyl)sulfamoyl)-3-piperidinyl)carbonyl)-N-(4-(trifluoromethyl)benzyl)-D-prolinamide;

N-((1R)-1-(2-fluoro-4-(trifluoromethyl)phenyl)-2-methylpropyl)-1-(3-(methylsulfonyl)benzoyl)-D-prolinamide;

(1R,3R,5R)-2-(2-methoxy-5-(methylsulfonyl)benzoyl)-N—((R)-3-oxetanyl(4-(trifluoromethyl)phenyl)methyl)-2-azabicyclo[3.1.0]hexane-3-carboxamide;

N—((R)-cyclopropyl(2-fluoro-4-(trifluoromethyl)phenyl)methyl)-1-((5-(methylsulfonyl)-3-pyridinyl)carbonyl)-D-prolinamide;

N—((S)-cyclopropyl(2-fluoro-4-(trifluoromethyl)phenyl)methyl)-1-((5-(methylsulfonyl)-3-pyridinyl)carbonyl)-D-prolinamide;

(1R,3R,5R)—N—((R)-cyclopropyl(3-fluoro-4-methylphenyl)methyl)-2-(3-(methylsulfonyl)benzoyl)-2-azabicyclo[3.1.0]hexane-3-carboxamide;

(1R,3R,5R)—N—((S)-(4-chloro-2,5-difluorophenyl)(3-fluorooxetan-3-yl)methyl)-2-(3-(methylsulfonyl)benzoyl)-2-azabicyclo[3.1.0]hexane-3-carboxamide;

(1R,3R,5R)-2-(2-amino-5-(methylsulfonyl)benzoyl)-N—((R)-cyclopropyl(2-fluoro-4-(trifluoromethyl)phenyl)methyl)-2-azabicyclo[3.1.0]hexane-3-carboxamide;

(1R,3R,5R)—N—((R)-cyclopropyl(2,5-difluoro-4-(trifluoromethyl)phenyl)methyl)-2-(2-(hydroxymethyl)-5-(methylsulfonyl)benzoyl)-2-azabicyclo[3.1.0]hexane-3-carboxamide;

(1R,3R,5R)—N—((R)-(2,5-difluoro-4-(trifluoromethyl)phenyl)(oxetan-3-yl)methyl)-2-(2-methoxyisonicotinoyl)-2-azabicyclo[3.1.0]hexane-3-carboxamide;

(1R,3R,5R)—N—((R)-(2,5-difluoro-4-(trifluoromethyl)phenyl)(oxetan-3-yl)methyl)-2-(5-methylthiophene-2-carbonyl)-2-azabicyclo[3.1.0]hexane-3-carboxamide;

(1R,3R,5R)—N—((S)-1-(4-chloro-2,5-difluorophenyl)-2,2-difluoroethyl)-2-(5-(methylsulfonyl)nicotinoyl)-2-azabicyclo[3.1.0]hexane-3-carboxamide;

(1R,3R,5R)—N—((R)-(2,5-difluoro-4-(trifluoromethyl)phenyl)(oxetan-3-yl)methyl)-2-(1,4-dimethyl-1H-pyrazole-5-carbonyl)-2-azabicyclo[3.1.0]hexane-3-carboxamide;

(1R,3R,5R)—N—((R)-(2,5-difluoro-4-(trifluoromethyl)phenyl)(oxetan-3-yl)methyl)-2-(3-(2-hydroxypropan-2-yl)benzoyl)-2-azabicyclo[3.1.0]hexane-3-carboxamide;

(1R,3R,5R)—N—((R)-(2,5-difluoro-4-(trifluoromethyl)phenyl)(oxetan-3-yl)methyl)-2-(5-methyl-1H-indazole-7-carbonyl)-2-azabicyclo[3.1.0]hexane-3-carboxamide;

(1R,3R,5R)-2-(5-chloro-1H-indazole-7-carbonyl)-N—((R)-cyclopropyl(2,5-difluoro-4-(trifluoromethyl)phenyl)methyl)-2-azabicyclo[3.1.0]hexane-3-carboxamide;

(1R,3R,5R)—N—((R)-cyclopropyl(2,5-difluoro-4-(trifluoromethyl)phenyl)methyl)-2-(5-(1-hydroxyethyl)-2-methylisonicotinoyl)-2-azabicyclo[3.1.0]hexane-3-carboxamide;

(1R,3R,5R)—N—((R)-(2,5-difluoro-4-(trifluoromethyl)phenyl)(oxetan-3-yl)methyl)-2-(5-(trifluoromethyl)isoxazole-3-carbonyl)-2-azabicyclo[3.1.0]hexane-3-carboxamide;

(1R,3R,5R)—N—((R)-(2,5-difluoro-4-(trifluoromethyl)phenyl)(oxetan-3-yl)methyl)-2-(3,4-dimethylisoxazole-5-carbonyl)-2-azabicyclo[3.1.0]hexane-3-carboxamide;

(1R,3R,5R)—N—((R)-(2,5-difluoro-4-(trifluoromethyl)phenyl)(oxetan-3-yl)methyl)-2-(3,5-dimethylisoxazole-4-carbonyl)-2-azabicyclo[3.1.0]hexane-3-carboxamide;

(1R,3R,5R)—N—((R)-(2,5-difluoro-4-(trifluoromethyl)phenyl)(oxetan-3-yl)methyl)-2-(3-(trifluoromethyl)isoxazole-5-carbonyl)-2-azabicyclo[3.1.0]hexane-3-carboxamide;

(R)—N—((R)-(2,5-difluoro-4-(trifluoromethyl)phenyl)((1s,3S)-3-hydroxycyclobutyl)methyl)-1-(3-(methylsulfonyl)benzoyl)pyrrolidine-2-carboxamide;

(R)—N—((R)-(2,5-difluoro-4-(trifluoromethyl)phenyl)((1r,3R)-3-hydroxycyclobutyl)methyl)-1-(3-(methylsulfonyl)benzoyl)pyrrolidine-2-carboxamide;

(1R,3R,5R)—N—((R)-(2,5-difluoro-4-(trifluoromethyl)phenyl)((1r,3R)-3-hydroxy-3-methylcyclobutyl)methyl)-2-(3-(methylsulfonyl)benzoyl)-2-azabicyclo[3.1.0]hexane-3-carboxamide;

(1R,3R,5R)—N—((R)-(2,5-difluoro-4-(trifluoromethyl)phenyl)((1 s, 3S)-3-hydroxycyclobutyl)methyl)-2-(2-(difluoromethyl)isonicotinoyl)-2-azabicyclo[3.1.0]hexane-3-carboxamide;

(1R,3R,5R)—N—((R)-(2,5-difluoro-4-(trifluoromethyl)phenyl)((1r,3R)-3-hydroxycyclobutyl)methyl)-2-(2-(difluoromethyl)isonicotinoyl)-2-azabicyclo[3.1.0]hexane-3-carboxamide;

(1R,3R,5R)—N—((S)-(2,5-difluoro-4-(trifluoromethyl)phenyl)((R)-5-oxopyrrolidin-3-yl)methyl)-2-(2-(trifluoromethyl)isonicotinoyl)-2-azabicyclo[3.1.0]hexane-3-carboxamide;

(1R,3R,5R)—N—((R)-cyclopropyl(2,5-difluoro-4-(trifluoromethoxy)phenyl)methyl)-2-(3-(methylsulfonyl)benzoyl)-2-azabicyclo[3.1.0]hexane-3-carboxamide; and 1-(((3S)-1-((3-cyano-1-azetidinyl)sulfonyl)-3-piperidinyl)carbonyl)-N-(2-(4-(trifluoromethyl)phenyl)ethyl)-D-prolinamide or a pharmaceutically acceptable salt thereof.

In a Nineteenth Embodiment, the Invention Provides a Compound as Recited in Table B, or a Pharmaceutically Acceptable Salt Thereof:

TABLE B (1R,3R,5R)-2-(((3S)-1-((3-cyano-1-azetidinyl)sulfonyl)-3-piperidinyl)carbonyl)-N-(2-fluoro-4-(trifluoromethyl)benzyl)-2-azabicyclo[3.1.0]hexane-3-carboxamide;

1-(((3S)-1-((3-cyano-1-azetidinyl)sulfonyl)-3-piperidinyl)carbonyl)-N—((R)-cyclopropyl(2,5-difluoro-4-(trifluoromethyl)phenyl)methyl)-D-prolinamide;

(1R,3R,5R)—N—((R)-cyclopropyl(2-fluoro-4-(trifluoromethyl)phenyl)methyl)-2-(2-(ethylamino)-5-(methylsulfonyl)benzoyl)-2-azabicyclo[3.1.0]hexane-3-carboxamide;

(1R,3R,5R)—N—((R)-(4-chloro-2,5-difluorophenyl)(3-oxetanyl)methyl)-2-(3-(methylsulfonyl)benzoyl)-2-azabicyclo[3.1.0]hexane-3-carboxamide;

(1R,3R,5R)—N—((R)-(4-chloro-2,5-difluorophenyl)(cyclopropyl)methyl)-2-(3-(cyclopropylsulfonyl)benzoyl)-2-azabicyclo[3.1.0]hexane-3-carboxamide;

N—((R)-(4-chloro-2,5-difluorophenyl)(3-oxetanyl)methyl)-1-(3-(methylsulfonyl)benzoyl)-D-prolinamide;

(1R,3R,5R)—N—((R)-cyclopropyl(2,5-difluoro-4-(trifluoromethyl)phenyl)methyl)-2-(3-(trifluoromethyl)benzoyl)-2-azabicyclo[3.1.0]hexane-3-carboxamide;

(1R,3R,5R)-2-(3-(ethylsulfonyl)benzoyl)-N—((R)-(2-fluoro-4-(trifluoromethyl)phenyl)(3-oxetanyl)methyl)-2-azabicyclo[3.1.0]hexane-3-carboxamide;

(1R,3R,5R)—N—((R)-(4-chloro-2,5-difluorophenyl)(cyclopropyl)methyl)-2-(3-sulfamoylbenzoyl)-2-azabicyclo[3.1.0]hexane-3-carboxamide;

(4S)—N—((R)-(4-chloro-2,5-difluorophenyl)(3-oxetanyl)methyl)-4-fluoro-1-(3-(methylsulfonyl)benzoyl)-D-prolinamide;

N—((R)-cyclopropyl(2,5-difluoro-4-(trifluoromethyl)phenyl)methyl)-1-(3-(methylsulfonyl)benzoyl)-D-prolinamide;

(1R,3R,5R)—N—((R)-cyclobutyl(2-fluoro-4-(trifluoromethyl)phenyl)methyl)-2-(3-(methylsulfonyl)benzoyl)-2-azabicyclo[3.1.0]hexane-3-carboxamide;

(1R,3R,5R)—N—((R)-(4-chloro-2,5-difluorophenyl)(cyclopropyl)methyl)-2-((5-(cyclopropylsulfonyl)-3-pyridinyl)carbonyl)-2-azabicyclo[3.1.0]hexane-3-carboxamide;

(4S)—N—((R)-cyclopropyl(2,5-difluoro-4-(trifluoromethyl)phenyl)methyl)-4-fluoro-1-(3-(methylsulfonyl)benzoyl)-D-prolinamide;

(1R,3R,5R)—N—((R)-(2-fluoro-4-(trifluoromethyl)phenyl)(3-oxetanyl)methyl)-2-(3-(methylsulfonyl)benzoyl)-2-azabicyclo[3.1.0]hexane-3-carboxamide;

1-(((2S)-4-((3-cyano-1-azetidinyl)sulfonyl)-2-piperazinyl)carbonyl)-N-(2-fluoro-4-(trifluoromethyl)benzyl)-D-prolinamide;

(4S)—N—((R)-(4-chloro-2,5-difluorophenyl)(cyclopropyl)methyl)-4-fluoro-1-(3-(methylsulfonyl)benzoyl)-D-prolinamide;

(1R,3R,5R)—N—((R)-cyclopropyl(2-fluoro-4-(trifluoromethyl)phenyl)methyl)-2-(3-(cyclopropylsulfonyl)benzoyl)-2-azabicyclo[3.1.0]hexane-3-carboxamide;

(1R,3R,5R)—N—((R)-cyclopropyl(2,5-difluoro-4-(trifluoromethyl)phenyl)methyl)-2-((5-(methylsulfonyl)-3-pyridinyl)carbonyl)-2-azabicyclo[3.1.0]hexane-3-carboxamide;

(1R,3R,5R)—N—((R)-(4-chloro-2,5-difluorophenyl)(cyclopropyl)methyl)-2-((5-(methylsulfonyl)-3-pyridinyl)carbonyl)-2-azabicyclo[3.1.0]hexane-3-carboxamide;

(4S)—N—((R)-(4-chloro-2,5-difluorophenyl) (cyclopropyl)methyl)-4-fluoro-1-((6-(methylsulfonyl)-3-pyridinyl)carbonyl)-D-prolinamide;

(1R,3R,5R)—N—((R)-cyclopropyl(2-fluoro-4-(trifluoromethyl)phenyl)methyl)-2-(3-(methylsulfonyl)benzoyl)-2-azabicyclo[3.1.0]hexane-3-carboxamide;

(1R,3R,5R)—N—((R)-cyclopropyl(2,5-difluoro-4-(trifluoromethyl)phenyl)methyl)-2-((2-(methylsulfonyl)-4-pyridinyl)carbonyl)-2-azabicyclo[3.1.0]hexane-3-carboxamide;

(1R,3R,5R)—N—((R)-(4-chloro-2,5-difluorophenyl)(3-oxetanyl)methyl)-2-((5-(trifluoromethyl)-3-pyridinyl)carbonyl)-2-azabicyclo[3.1.0]hexane-3-carboxamide;

1-(((3S)-1-((3-cyano-1-azetidinyl)sulfonyl)-3-piperidinyl)carbonyl)-N-(3,5-difluorobenzyl)-D-prolinamide;

(1R,3R,5R)—N—((R)-cyclopropyl(3-fluoro-4-(trifluoromethyl)phenyl)methyl)-2-(3-(methylsulfonyl)benzoyl)-2-azabicyclo[3.1.0]hexane-3-carboxamide;

(1R,3R,5R)—N—((S)-(4-chloro-2,5-difluorophenyl)(1-hydroxycyclopropyl)methyl)-2-(3-(methylsulfonyl)benzoyl)-2-azabicyclo[3.1.0]hexane-3-carboxamide;

N—((R)-cyclopropyl(2-fluoro-4-(trifluoromethyl)phenyl)methyl)-4,4-difluoro-1-(3-(methylsulfonyl)benzoyl)-D-prolinamide;

(1R,2R,5S)—N—((R)-(4-chloro-2,5-difluorophenyl) (cyclopropyl)methyl)-3-(3-sulfamoylbenzoyl)-3-azabicyclo[3.1.0]hexane-2-carboxamide;

(1R,3R,5R)—N—((R)-(4-chloro-2-fluorophenyl)(cyclopropyl)methyl)-2-(3-(methylsulfonyl)benzoyl)-2-azabicyclo[3.1.0]hexane-3-carboxamide;

N—((R)-(4-chloro-2,5-difluorophenyl)(cyclopropyl)methyl)-1-((5-(methylsulfonyl)-3-pyridinyl)carbonyl)-D-prolinamide;

(R)—N—((R)-cyclopropyl(2-fluoro-4-(trifluoromethyl)phenyl)methyl)-1-(3-(methylsulfonyl)benzoyl)pyrrolidine-2-carboxamide;

(2R,4S)—N—((R)-cyclopropyl(2-fluoro-4-(trifluoromethyl)phenyl)methyl)-4-fluoro-1-(3-(methylsulfonyl)benzoyl) pyrrolidine-2-carboxamide;

(1R,3R,5R)—N-((1S,2S)-1-(4-chloro-2,5-difluorophenyl)-2-hydroxypropyl)-2-(3-(methylsulfonyl)benzoyl)-2-azabicyclo[3.1.0]hexane-3-carboxamide;

(1R,2R,5S)—N—((R)-cyclopropyl(2-fluoro-4-(trifluoromethyl)phenyl)methyl)-3-(3-(methylsulfonyl)benzoyl)-3-azabicyclo[3.1.0]hexane-2-carboxamide;

(4S)—N—((R)-cyclopropyl(2,5-difluoro-4-(trifluoromethyl)phenyl)methyl)-4-fluoro-1-((5-(methylsulfonyl)-3-pyridinyl)carbonyl)-D-prolinamide;

(4S)—N—((R)-(4-chloro-2,5-difluorophenyl) (cyclopropyl)methyl)-4-fluoro-1-((5-(methylsulfonyl)-3-pyridinyl)carbonyl)-D-prolinamide;

(1R,2R,5S)—N—((R)-(4-chloro-2,5-difluorophenyl)(cyclopropyl)methyl)-3-((5-(methylsulfonyl)-3-pyridinyl)carbonyl)-3-azabicyclo[3.1.0]hexane-2-carboxamide;

(1R,3R,5R)—N—((R)-cyclopropyl(2-fluoro-4-(trifluoromethyl)phenyl)methyl)-2-((5-(methylsulfonyl)-3-pyridinyl)carbonyl)-2-azabicyclo[3.1.0]hexane-3-carboxamide;

(1R,3R,5R)—N—((R)-cyclopropyl(3-fluoro-4-(trifluoromethyl)phenyl)methyl)-2-((5-(methylsulfonyl)-3-pyridinyl)carbonyl)-2-azabicyclo[3.1.0]hexane-3-carboxamide; and (1S,3R,5R)—N—((R)-cyclopropyl(2,5-difluoro-4-(trifluoromethyl)phenyl)methyl)-2-((5-(methylsulfonyl)-3-pyridinyl)carbonyl)-2-azabicyclo[3.1.0]hexane-3-carboxamide, or a pharmaceutically acceptable salt thereof.

In a Twentieth Embodiment, the Invention Provides a Compound as Recited in Table C, or a Pharmaceutically Acceptable Salt Thereof:

TABLE C

N—((R)-cyclopropyl(2,5-difluoro-4-(trifluoromethyl)phenyl)methyl)-1-(3-(methylsulfonyl)benzoyl)-D-prolinamide;

(1R,3R,5R)—N—((R)-(4-chloro-2,5-difluorophenyl)(cyclopropyl)methyl)-2-((5-(cyclopropylsulfonyl)-3-pyridinyl)carbonyl)-2-azabicyclo[3.1.0]hexane-3-carboxamide;

(4S)—N—((R)-cyclopropyl(2,5-difluoro-4-(trifluoromethyl)phenyl)methyl)-4-fluoro-1-(3-(methylsulfonyl)benzoyl)-D-prolinamide;

(1R,3R,5R)—N—((R)-(2-fluoro-4-(trifluoromethyl)phenyl)(3-oxetanyl)methyl)-2-(3-(methylsulfonyl)benzoyl)-2-azabicyclo[3.1.0]hexane-3-carboxamide;

(4S)—N—((R)-(4-chloro-2,5-difluorophenyl)(cyclopropyl)methyl)-4-fluoro-1-(3-(methylsulfonyl)benzoyl)-D-prolinamide;

(1R,3R,5R)—N—((R)-cyclopropyl(2,5-difluoro-4-(trifluoromethyl)phenyl)methyl)-2-((5-(methylsulfonyl)-3-pyridinyl)carbonyl)-2-azabicyclo[3.1.0]hexane-3-carboxamide;

(1R,3R,5R)—N—((R)-(4-chloro-2,5-difluorophenyl)(cyclopropyl)methyl)-2-((5-(methylsulfonyl)-3-pyridinyl)carbonyl)-2-azabicyclo[3.1.0]hexane-3-carboxamide;

(1R,3R,5R)—N—((R)-cyclopropyl(2-fluoro-4-(trifluoromethyl)phenyl)methyl)-2-(3-(methylsulfonyl)benzoyl)-2-azabicyclo[3.1.0]hexane-3-carboxamide;

(1R,3R,5R)—N—((R)-cyclopropyl(2,5-difluoro-4-(trifluoromethyl)phenyl)methyl)-2-((2-(methylsulfonyl)-4-pyridinyl)carbonyl)-2-azabicyclo[3.1.0]hexane-3-carboxamide;

(R)—N—((R)-cyclopropyl(2-fluoro-4-(trifluoromethyl)phenyl)methyl)-1-(3-(methylsulfonyl)benzoyl) pyrrolidine-2-carboxamide;

(2R,4S)—N—((R)-cyclopropyl(2-fluoro-4-(trifluoromethyl)phenyl)methyl)-4-fluoro-1-(3-(methylsulfonyl)benzoyl)pyrrolidine-2-carboxamide;

(4S)—N—((R)-cyclopropyl(2,5-difluoro-4-(trifluoromethyl)phenyl)methyl)-4-fluoro-1-((5-(methylsulfonyl)-3-pyridinyl)carbonyl)-D-prolinamide; and (4S)—N—((R)-(4-chloro-2,5-difluorophenyl) (cyclopropyl)methyl)-4-fluoro-1-((5-(methylsulfonyl)-3-pyridinyl)carbonyl)-D-prolinamide, or a pharmaceutically acceptable salt thereof.

In further embodiments, provided herein are compounds as disclosed herein in the form of a pharmaceutically acceptable salt.

In a further embodiment, the invention provides methods of making compounds of formula I or a subformulae thereof.

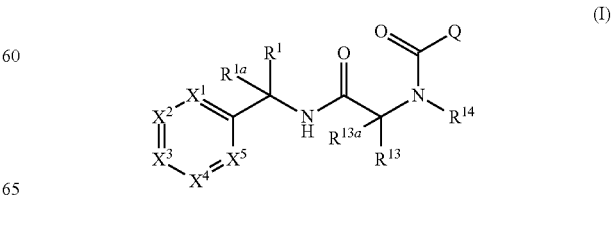

(I)

The method comprising the synthetic steps of:

(a) Coupling protected amino acid,

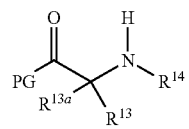

with carboxylic acid, Q-CO$_2$H, under conditions conducive to amide bond formation to generate intermediate:

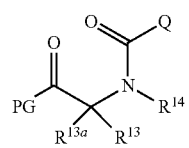

wherein PG represents a carboxylic acid protecting group stable to the amide coupling reaction conditions;

(b) Removing protecting group, PG, to generate free acid:

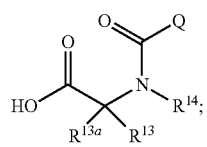

(c) Coupling the carboxylic acid generated in step (b) with a primary amine,

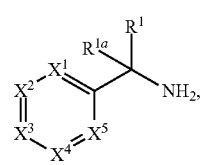

under conditions conducive to amide bond formation to generate the compound of formula (I), wherein variables Q, $X^1$, $X^2$, $X^3$, $X^4$, $X^5$, $R^1$, $R^{1a}$, $R^{13}$, $R^{13a}$ and $R^{14}$ have the definitions provided in the first embodiment.

In a further embodiment, the invention provides methods of making compounds of formula I or a subformulae thereof.

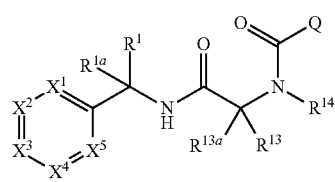
(I)

The method comprising the synthetic steps of:

(a) Coupling protected amino acid,

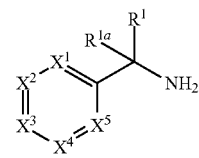

with primary amine

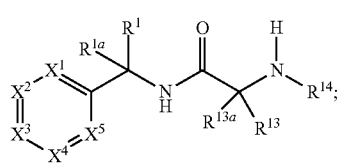

under conditions conducive to amide bond formation to generate intermediate:

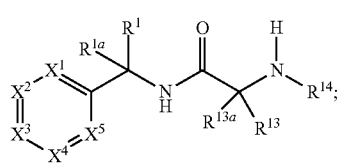

wherein PG represents an amide protecting group stable to the amide coupling reaction conditions;

(b) Removing protecting group, PG, to generate free amine (c) Coupling the amine generated in step (b) with a carboxylic acid, Q-CO$_2$H under conditions conducive to amide bond formation to generate the compound of formula (I), wherein variables Q, $X^1$, $X^2$, $X^3$, $X^4$, $X^5$, $R^1$, $R^{1a}$, $R^{13}$, $R^{13a}$ and $R^{14}$ have the definitions provided in the first embodiment.

In a further embodiment, the invention provides other methods of making compounds of the fifteenth embodiment, e.g., compounds of formula II or a subformulae thereof.

(II)

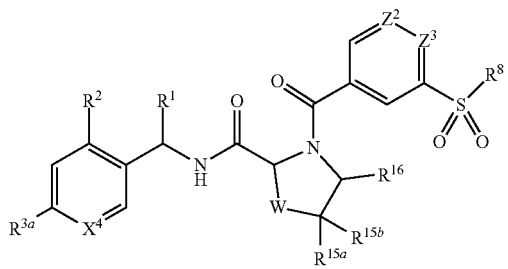

The method comprising the synthetic steps of:
(a) Coupling protected amino acid,

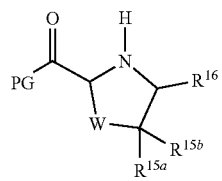

with carboxylic acid,

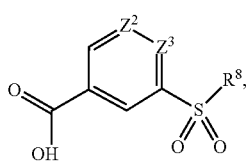

under conditions conducive to amide bond formation to generate intermediate:

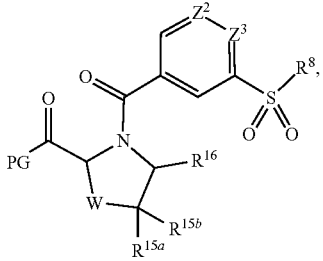

wherein PG represents a carboxylic acid protecting group stable to the amide coupling reaction conditions;
(b) Removing protecting group, PG, to generate free acid:

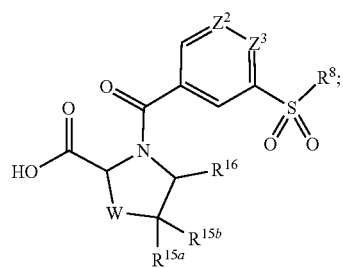

(c) Coupling the carboxylic acid generated in step (b) with a primary amine,

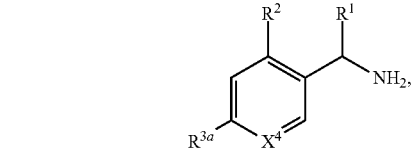

under conditions conducive to amide bond formation to generate the compound of Formula (II), wherein variables W, $X^4$, $Z^2$, $Z^3$, $R^1$, $R^2$, $R^{3a}$, $R^8$, $R^{15a}$, $R^{15b}$ and $R^{16}$ have the definitions provided in the fifteenth embodiment.

In a further embodiment, the invention provides methods of making compounds of formula II or a subformulae thereof.

(II)

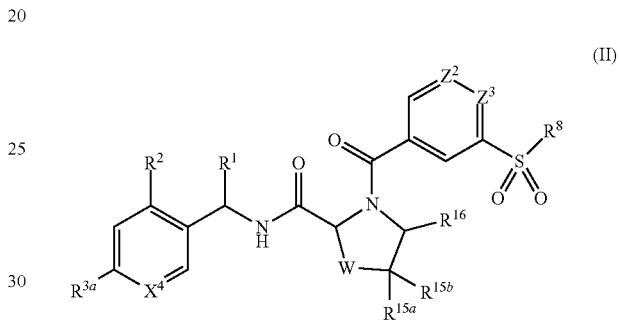

The method comprising the synthetic steps of:
(a) Coupling protected amino acid,

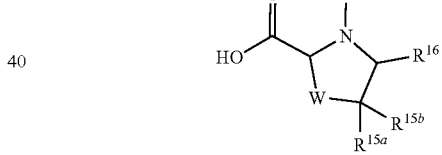

with primary amine

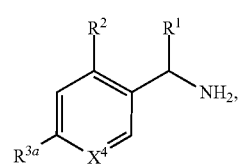

under conditions conducive to amide bond formation to generate intermediate:

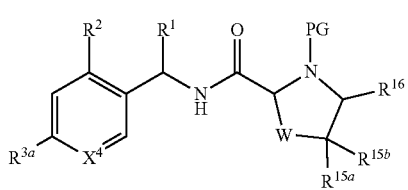

wherein PG represents an amide protecting group stable to the amide coupling reaction conditions;

(b) Removing protecting group, PG, to generate free amine:

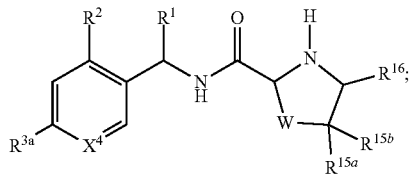

(c) Coupling the amine generated in step (b) with a carboxylic acid,

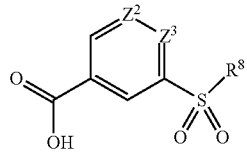

under conditions conducive to amide bond formation to generate the compound of formula (I), wherein variables W, $X^4$, $Z^2$, $Z^3$, $R^1$, $R^2$, $R^{3a}$, $R^8$, $R^{15a}$, $R^{15b}$ and $R^{16}$ have the definitions provided in the fifteenth embodiment.

In a further embodiment, the invention provides other methods of making compounds of the fifteenth embodiment, e.g., compounds of formula IIa.

(IIa)

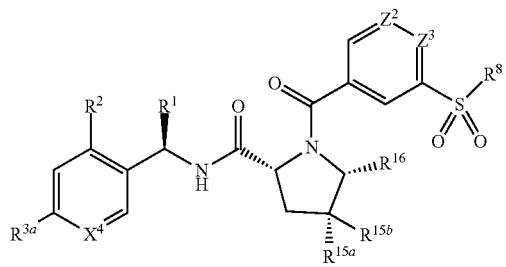

the method comprising the synthetic steps of:
(a) Coupling protected amino acid,

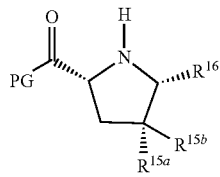

with carboxylic acid,

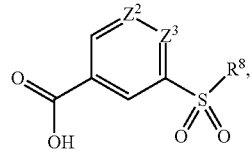

under conditions conducive to amide bond formation to generate intermediate:

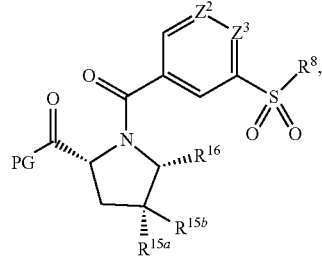

wherein PG represents a carboxylic acid protecting group stable to the amide coupling reaction conditions;
(b) Removing protecting group, PG, to generate free acid:

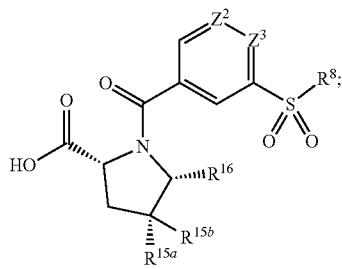

(c) Coupling the carboxylic acid generated in step (b) with a primary amine,

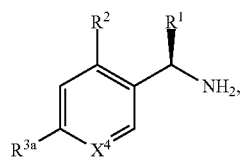

under conditions conducive to amide bond formation to generate the compound of Formula (IIa), wherein variables $X^4$, $Z^2$, $Z^3$, $R^1$, $R^2$, $R^{3a}$, $R^8$, $R^{15a}$, $R^{15b}$ and $R^{16}$ have the definitions provided in the fifteenth embodiment.

In a further embodiment, the invention provides other methods of making compounds of the fifteenth embodiment, e.g., compounds of formula IIa.

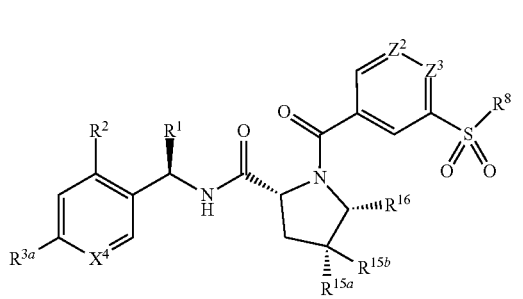

(IIa)

The method comprising the synthetic steps of:

(a) Coupling protected amino acid,

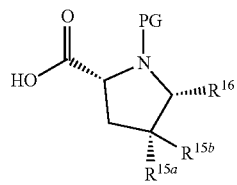

with amine,

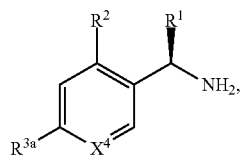

under conditions conducive to amide bond formation to generate intermediate:

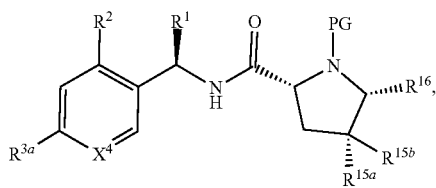

wherein PG represents a carboxylic acid protecting group stable to the amide coupling reaction conditions;

(b) Removing protecting group, PG, to generate free acid:

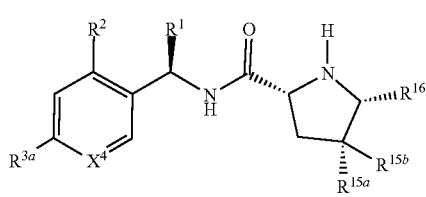

(c) Coupling the carboxylic acid generated in step (b) with a primary amine,

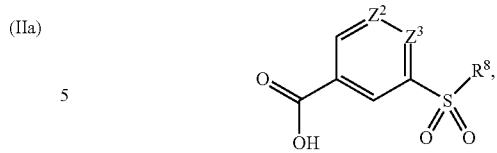

under conditions conducive to amide bond formation to generate the compound of Formula (IIa), wherein variables $X^4$, $Z^2$, $Z^3$, $R^1$, $R^2$, $R^{3a}$, $R^8$, $R^{15a}$, $R^{15b}$ and $R^{16}$ have the definitions provided in the fifteenth embodiment.

In a further embodiment, the invention provides other methods of making compounds of the fifteenth embodiment, e.g., compounds of formula IIb.

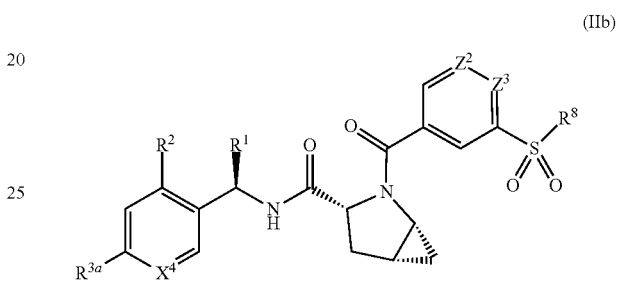

(IIb)

The method comprising the synthetic steps of:

(a) Coupling protected amino acid,

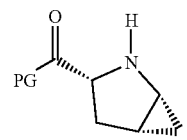

with carboxylic acid,

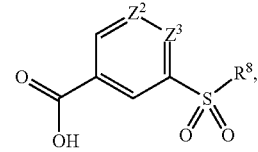

under conditions conducive to amide bond formation to generate intermediate:

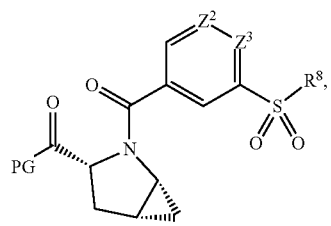

wherein PG represents a carboxylic acid protecting group stable to the amide coupling reaction conditions;

(b) Removing protecting group, PG, to generate free acid:

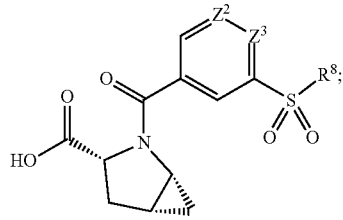

(c) Coupling the carboxylic acid generated in step (b) with a primary amine,

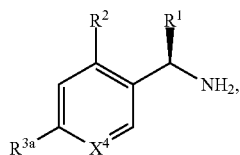

under conditions conducive to amide bond formation to generate the compound of Formula (IIb), wherein $X^4$, $Z^2$, $Z^3$, $R^1$, $R^2$, $R^{3a}$ and $R^8$ have the definitions provided in the fifteenth embodiment.

In a further embodiment, the invention provides other methods of making compounds of the fifteenth embodiment, e.g., compounds of formula IIb.

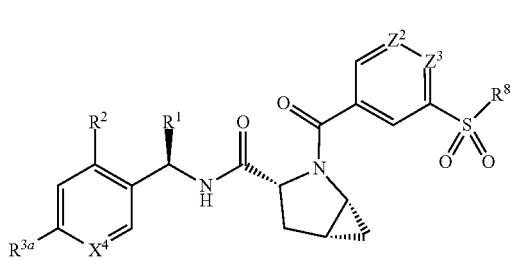

(IIb)

The method comprising the synthetic steps of:
(a) Coupling protected amino acid,

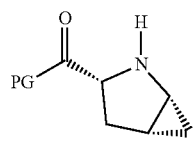

with primary amine

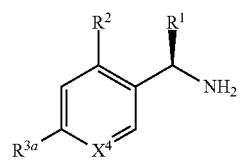

under conditions conducive to amide bond formation to generate intermediate:

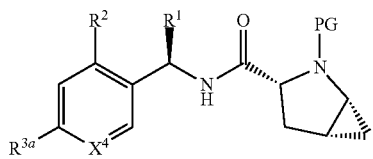

wherein PG represents an amide protecting group stable to the amide coupling reaction conditions;

(b) Removing protecting group, PG, to generate free amine:

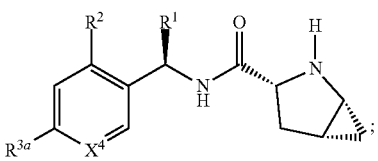

(c) Coupling the amine generated in step (b) with a carboxylic acid,

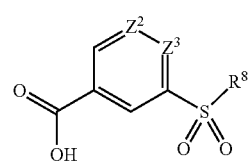

under conditions conducive to amide bond formation to generate the compound of formula (IIb), wherein variables $X^4$, $Z^2$, $Z^3$, $R^1$, $R^2$, $R^{3a}$ and $R^8$ have the definitions provided in the fifteenth embodiment.

In a further embodiment, the invention provides other methods of making compounds of the seventeenth embodiment, e.g., compounds of formula III or a subformulae thereof.

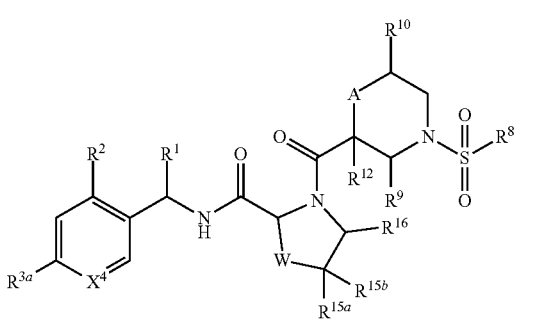

(III)

The method comprising the synthetic steps of:

(a) Coupling protected amino acid,

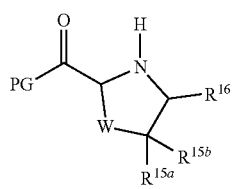

with carboxylic acid,

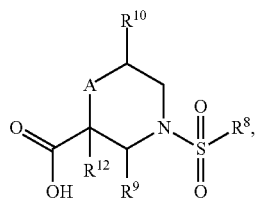

under conditions conducive to amide bond formation to generate intermediate:

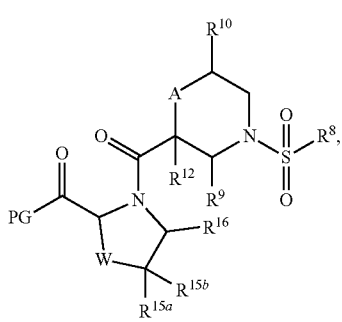

wherein PG represents a carboxylic acid protecting group stable to the amide coupling reaction conditions;

(b) Removing protecting group, PG, to generate free acid:

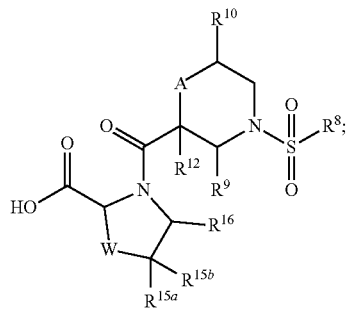

(c) Coupling the carboxylic acid generated in step (b) with a primary amine,

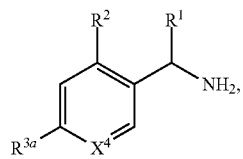

under conditions conducive to amide bond formation to generate the compound of Formula (III), wherein variables A, W, $X^4$, $R^1$, $R^2$, $R^{3a}$, $R^8$, $R^9$, $R^{10}$, $R^{12}$, $R^{15a}$, $R^{15b}$ and $R^{16}$ have the definitions provided in the seventeenth embodiment. In certain compounds of formula (III), when A is NH, the amine may be optionally masked with a suitable protecting group during transformations (a), (b) and/or (c).

In a further embodiment, the invention provides methods of making compounds of formula III or a subformulae thereof.

(III)

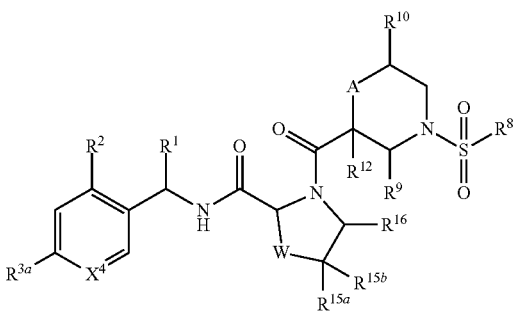

The method comprising the synthetic steps of:

(a) Coupling protected amino acid,

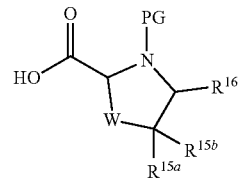

with primary amine

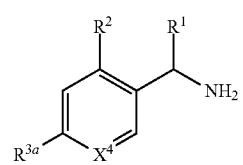

under conditions conducive to amide bond formation to generate intermediate:

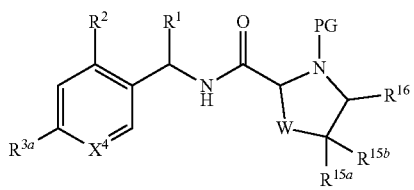

wherein PG represents an amide protecting group stable to the amide coupling reaction conditions;

(b) Removing protecting group, PG, to generate free amine:

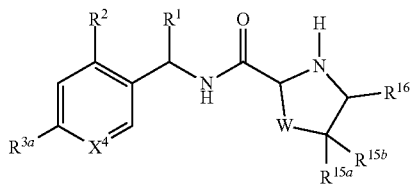

(c) Coupling the amine generated in step (b) with a carboxylic acid,

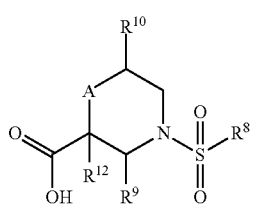

under conditions conducive to amide bond formation to generate the compound of Formula (III), wherein variables A, W, $X^4$, $R^1$, $R^2$, $R^{3a}$, $R^8$, $R^9$, $R^{10}$, $R^{12}$, $R^{15a}$, $R^{15b}$ and $R^{16}$ have the definitions provided in the seventeenth embodiment. In certain compounds of formula (III), when A is NH, the amine may be optionally masked with a suitable protecting group during transformation (c).

In a further embodiment, the invention provides other methods of making compounds of the seventeenth embodiment, e.g., compounds of formula IIIa:

(IIIa)

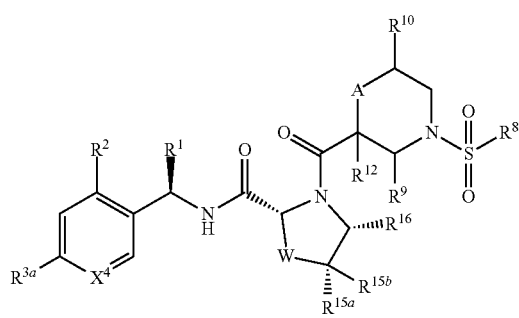

The method comprising the synthetic steps of:
(a) Coupling protected amino acid,

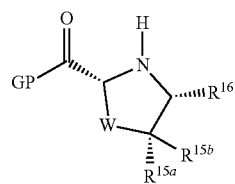

with carboxylic acid,

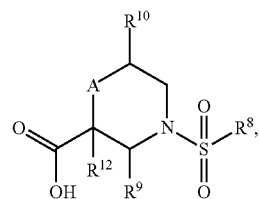

under conditions conducive to amide bond formation to generate intermediate:

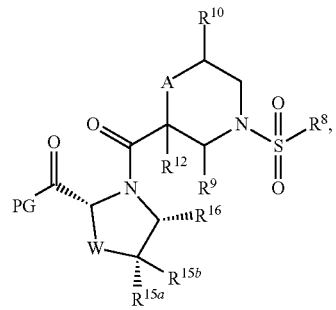

wherein PG represents a carboxylic acid protecting group stable to the amide coupling reaction conditions;

(b) Removing protecting group, PG, to generate free acid:

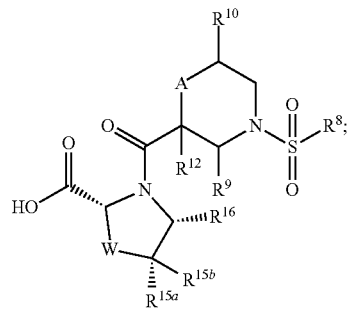

(c) Coupling the carboxylic acid generated in step (b) with a primary amine,

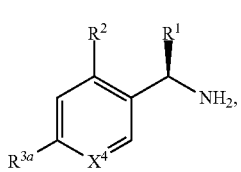

under conditions conducive to amide bond formation to generate the compound of Formula (III), wherein variables A, W, $X^4$, $R^1$, $R^2$, $R^{3a}$, $R^9$, $R^{10}$, $R^{12}$, $R^{15a}$, $R^{15b}$ and $R^{16}$ have the definitions provided in the seventeenth embodiment. In certain compounds of formula (III), when A is NH, the amine may be optionally masked with a suitable protecting group during transformations (a), (b) and/or (c).

In a further embodiment, the invention provides methods of making compounds of formula IIIa or a subformulae thereof.

(IIIa)

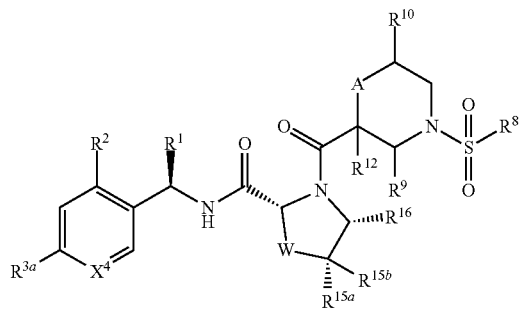

The method comprising the synthetic steps of:

(a) Coupling protected amino acid,

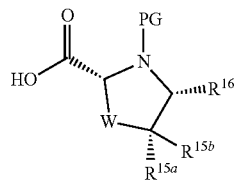

with primary amine

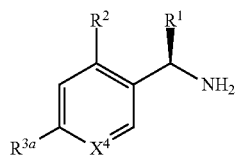

under conditions conducive to amide bond formation to generate intermediate:

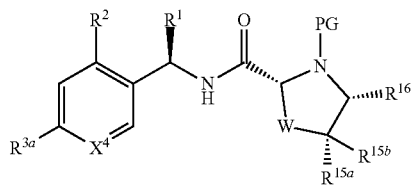

wherein PG represents an amide protecting group stable to the amide coupling reaction conditions;

(b) Removing protecting group, PG, to generate free amine:

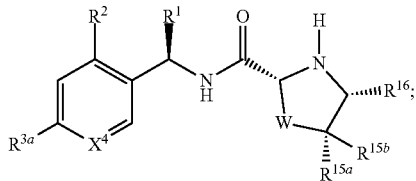

(c) Coupling the amine generated in step (b) with a carboxylic acid,

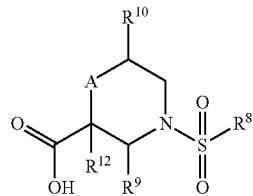

under conditions conducive to amide bond formation to generate the compound of Formula (III), wherein variables A, W, $X^4$, $R^1$, $R^2$, $R^{3a}$, $R^8$, $R^9$, $R^{10}$, $R^{12}$, $R^{15a}$, $R^{15b}$ and $R^{16}$ have the definitions provided in the seventeenth embodiment. In certain compounds of formula (III), when A is NH, the amine may be optionally masked with a suitable protecting group during transformation (c).

In another embodiment, pharmaceutical compositions are provided which comprise one or more pharmaceutically acceptable carriers and a therapeutically effective amount of a compound of any one of formulae I or a subformulae thereof. In some aspects, the composition is formulated in a form selected from the group consisting of an injectable fluid, an aerosol, a tablet, a pill, a capsule, a syrup, a cream, a gel and a transdermal patch.

In another embodiment, combinations, in particular pharmaceutical combinations, are provided which comprise a therapeutically effective amount of the compound any one of formulae I or a subformulae thereof.

In another embodiment, methods of modulating cardiac sarcomere activity in a subject are provided which methods comprise administering to the subject a therapeutically effective amount of Formula I or a subformulae thereof. In preferred aspects of the embodiment, methods of activating cardiac sarcomere activity in a subject are provided, which methods comprise administering to the subject a therapeutically effective amount of a compound of Formula I or subformulae thereof.

In yet other embodiments, methods of treating a disorder or a disease in a subject mediated by cardiac sarcomere activity, in particular methods of treating a disease or disorder in which activation of the cardiac sarcomere would be beneficial, are provided. The methods comprise administering to the subject a therapeutically effective amount of the compound of Formula I or a subformulae thereof.

In another embodiment, methods of treating heart failure, or more preferably systolic heart failure, in a subject are provided which methods comprise administering to the subject a therapeutically effective amount of the compound of Formula I or a subformulae thereof. In certain aspects, the invention provides methods of treating systolic heart failure which method comprises the step of administering to a subject in need of therapy a therapeutically effective amount of a compound or salt of Formula I or a subformulae thereof.

In another aspect, the invention provides for the use of compounds of Formula I or a subformulae thereof for use in the preparation of a medicament and more particularly for use in the manufacture of a medicament for the treatment of a disorder or disease in a subject mediated by cardiac sarcomere activity. In certain other aspects, the invention provides for the use of a compound according of any one of formulae I or a subformulae thereof in the treatment of heart failure and more preferably in the treatment of systolic heart failure. In certain aspects, the invention provides the use of a compound according of any one of formulae I or a subformulae thereof in the treatment of systolic dysfunction.

In one embodiment, the invention provides a combination, in particular a pharmaceutical combination, comprising a therapeutically effective amount of the compound according to the definition of formula I or subformulae thereof or any one of the specifically disclosed compounds of the invention and one or more therapeutically active agents (preferably selected from those listed infra).

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 20 carbon atoms, 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. Unless otherwise provided, alkylene refers to moieties having 1 to 20 carbon atoms, 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, which is substituted with one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. It is understood that haloalkyl can be used to describe haloalkyl groups having a particular number of carbon atoms. For example, a haloalkyl group containing 1 to 6 carbon atoms may be referred to as "halo$C_1$-$C_6$alkyl."

As used herein, the term "hydroxy alkyl" refers to an alkyl as defined herein which is substituted with one or more hydroxy groups. The term "hydroxy cycloalkyl-alkyl" refers to an alkyl group that is substituted with a cycloalkyl group, as defined herein, and further substituted with a hydroxy group. The hydroxy group can be on the alkyl group, the cycloalkyl group, or on each of the alkyl and cycloalkyl groups.

The term "aryl" refers to an aromatic hydrocarbon group having 6-20 carbon atoms in the ring portion. Typically, aryl is monocyclic, bicyclic or tricyclic aryl having 6-20 carbon atoms. Furthermore, the term "aryl" as used herein, refers to an aromatic substituent which can be a single aromatic ring, or multiple aromatic rings that are fused together. Non-limiting examples include phenyl, naphthyl or tetrahydronaphthyl, each of which may optionally be substituted with 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocycle," "heterocycloalkyl" or "heterocyclo" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran, dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, azetidine, thiazolidine, morpholine, and the like.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms, each of which can be optionally substituted with one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like. The term "hydroxy cycloalkyl" refers specifically to a cycloalkyl group substituted with one or more hydroxy groups.

As used herein, the term "heteroaryl" refers to a 5-14 membered monocyclic- or bicyclic- or tricyclic-aromatic ring system, having 1 to 8 heteroatoms selected from N, O and S. In certain preferred aspects, the heteroaryl is a 5-10 membered ring system (e.g., 5-7 membered monocycle or an 8-10 membered bicycle) or a 5-7 membered ring system. Exemplary monocyclic heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, and 5-pyrimidinyl. Exemplary bicyclic heteroaryl groups include 1-, 3-, 4-, 5-, 6-, 7-, or 8-isoquinolinyl, 2-, 3-, 4-, 5-, 6-, 7-, or 8-quinolinyl, 1-, 3-, 4-, 5-, 6-, 7-, or 8-isoquinolinyl, 1-, 2-, 4-, 5-, 6-, 7-, or 8-benzimidazolyl and 1-, 2-, 3-, 4-, 5-, 6-, 7-, or 8-indolyl.

The term "heteroaryl" also refers to a group in which a heteroaromatic ring is fused to one or more aryl, cycloaliphatic, or heterocyclyl rings, where the radical or point of attachment is on the heteroaromatic ring As used herein, the term "halogen" or "halo" refers to fluoro, chloro, bromo, and iodo.

As used herein, the term "optionally substituted" unless otherwise specified refers to a group that is unsubstituted or is substituted with one or more, typically 1, 2, 3 or 4, suitable non-hydrogen substituents. If the identity of the "optional substituent" is not clearly defined in context of the optionally substituted group, then each optional substituent is independently selected from the group consisting of: alkyl, hydroxy, halogen, oxo, amino, alkylamino, dialkylamino, alkoxy, cycloalkyl, $CO_2H$, heterocycloalkyloxy (which denotes a heterocyclic group bonded through an oxygen bridge), —$CO_2$alkyl, mercapto, nitro, cyano, sulfamoyl, sulfonamide, aryl, —OC(O)alkyl, —OC(O)aryl, aryl-S—, aryloxy; alkylthio, formyl (i.e., HC(O)—), —C(O)$NH_2$, aralkyl (alkyl substituted with aryl), aryl and aryl substituted with alkyl, cycloalkyl, alkoxy, hydroxy, amino, alkyl-C(O)—NH—, alkylamino, dialkylamino or halogen. It is understood that where a group is indicated to be optionally substituted, the disclosure includes embodiments in which the group is unsubstituted as well as embodiments in which the group is substituted.

The point of attachment of a given moiety to the parent structure can be readily determined by one of skill in art. Thus, although the point of attachment may not be explicitly shown, it would be evident to the skilled artisan based on common general knowledge in the chemical arts. For example, N(H)C(O)$C_3$-$C_7$cycloalkyl would be understood to be attached to the parent structure at the available valency on the nitrogen atom.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. The use of "rel" indicates that the diastereomeric orientation is known but the absolute stereochemistry is not. In cases where the absolute stereochemistry has not been determined the optical rotation and/or chiral chromatography conditions will indicate which isomer is present.

"Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line or retention time on chiral chromatography separation. Certain of the compounds described herein contain one or more asymmetric centers or axes and may thus give rise to enantiomers, diastereomers, and other stereoisomeric forms that may be defined, in terms of absolute stereochemistry, as (R)- or (S)-, or with the (+) or (−) sign. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

It is understood that for any compound provided herein, including any compound of Formula (I), or any embodiment thereof, or any compound of Table A, B, or C, or a salt of any of the foregoing, the compound may exist in any stereochemical form, such as a single enantiomer, diastereomer, or tautomer or a mixture of one or more enantiomers, diastereomers, and tautomers in any ratio.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, benzenesuflonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper. In certain other embodiments, the salts are selected from ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds as disclosed herein in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds as disclosed herein in $C_1$-$C_4$alkyl sufonic acid, benzenesulfonic acid or mono-, di- or tri-$C_1$-$C_4$alkyl substituted benzene sufonic acid addition salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{124}I$, $^{125}I$ respectively. The invention includes various isotopically labeled compounds as defined herein, for example those into which radioactive isotopes, such as $^3H$, $^{13}C$, and $^{14}O$, are present. Such isotopically labelled compounds are useful in metabolic studies (with $^{14}O$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and salts thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has at least 50% deuterium incorporation at each designated deuterium atom, 60% deuterium incorporation, at least 75% deuterium incorporation, at least 90% deuterium incorporation, at least 95% deuterium incorporation, at least 99% deuterium incorporation, or at least 99.5% deuterium incorporation.

The compounds of the present invention may inherently or by design form solvates with solvents (including water). Therefore, it is intended that the invention embrace both solvated and unsolvated forms. The term "solvate" refers to a molecular complex of a compound of the present invention (including salts thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or biological process (i) mediated by cardiac sarcomere activity, or (ii) associated with cardiac sarcomere activity; or (2) increasing the activity of cardiac sarcomere. In another non-limiting embodiment, the term "a therapeutically effective amount" refers to the amount of the compound of the present invention that, when administered to a cell, or a tissue, or a non-cellular biological material, or a medium, is effective to at least partially increase cardiac sarcomere activity.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

As used herein, the term "prevent," "preventing" or "prevention" of any disease or disorder refers in one embodiment, to delay or avoidance of onset of the disease or disorder (i.e., slowing or preventing the onset of the disease or disorder in a patient susceptible to development of the disease or disorder).

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O-p-toluoyl tartaric acid, mandelic acid, malic acid or camphor-10-sulfonic acid. Racemic products can also be resolved by chiral chromatography, e.g., high performance liquid chromatography (HPLC) or supercritical fluid chromatography (SFC) using a chiral adsorbent.

Mixtures of isomers obtainable according to the invention can be separated in a manner known to those skilled in the art into the individual isomers; diastereoisomers can be separated, for example, by partitioning between polyphasic solvent mixtures, recrystallization and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Within the scope of this text, a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Intermediates and final products can be worked up and/or purified according to standard methods, e.g. using chromatographic methods, distribution methods, (re-) crystallization, and the like.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any process steps disclosed herein can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+form, depending on the nature of the reaction and/or of the reactants at reduced, normal or elevated temperature, for example in a temperature range of from about −100° C. to about 250° C., including, for example, from approximately −80° C. to approximately 250° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington® Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

Typically, the pharmaceutical compositions are tablets or gelatin capsules comprising the active ingredient together with one or more of: a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners. Tablets may be either film coated or enteric coated according to methods known in the art. Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient. Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin. Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives. As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Prophylactic and Therapeutic Uses

The compounds disclosed herein in free form or in pharmaceutically acceptable salt form, exhibit valuable pharmacological properties, e.g. cardiac sarcomere modulating properties and more particularly cardiac sarcomere activating properties e.g. as indicated in in vitro and in vivo tests as provided in the next sections and are therefore indicated for therapy.

The present invention provides methods of treating a disease or disorder associated with heart muscle contractility by administering to a subject in need thereof an effective amount of a compound disclosed herein. In certain aspects, methods are provided for the treatment of diseases associated with increasing activity of the cardiac sarcomere.

In a specific embodiment, the present invention provides a method of treating or preventing heart failure by administering to a subject in need thereof an effective amount of a compound disclosed herein. In certain embodiments, patients who are currently asymptomatic but are at risk of developing heart failure are suitable for administration with a compound of the invention. The methods of treating or preventing heart failure include, but are not limited to, methods of treating or preventing systolic heart failure.

In some embodiments, the present invention provides methods of treating a disease or disorder associated with decreased ejection fraction from the heart, e.g., heart failure by administering to a subject in need thereof an effective amount of a compound disclosed herein. Examples of known heart failure patient populations associated with reduced or compromised ejection fraction include systolic heart failure.

In some embodiments, the compounds disclosed herein are used in the treatment or prevention of heart failure with reduced ejection fraction (HFrEF) or systolic heart failure, dilated cardiomyopathy, postpartum cardiomyopathy, idiopathic cardiomyopathy, pediatric HFrEF, chemotherapy-induced heart failure, heart failure associated with muscular dystrophy, bi-ventricular HFrEF, HFrEF with pulmonary hypertension, heart failure with preserved ejection fraction (HFpEF) with right ventricular dysfunction, pulmonary hypertension with right ventricular dysfunction, scleroderma with pulmonary hypertension, right ventricular dysfunction, Chagas disease, or myocarditis. In some embodiments, provided herein are methods of treating or preventing heart failure with reduced ejection fraction or systolic heart failure, dilated cardiomyopathy, postpartum cardiomyopathy, idiopathic cardiomyopathy, pediatric HFrEF, chemotherapy-induced heart failure, heart failure associated with muscular dystrophy, bi-ventricular HFrEF, HFrEF with pulmonary hypertension, heart failure with preserved ejection fraction (HFpEF) with right ventricular dysfunction, pulmonary hypertension with right ventricular dysfunction, scleroderma with pulmonary hypertension, right ventricular dysfunction, Chagas disease, or myocarditis, which methods comprise administering to a subject in need thereof an effective amount of one or more compounds disclosed herein. Also provided herein is the use of one or more compounds disclosed herein in the manufacture of a medicament for the treatment or prevention of heart failure with reduced ejection fraction or systolic heart failure, dilated cardiomyopathy, postpartum cardiomyopathy, idiopathic cardiomyopathy, pediatric HFrEF, chemotherapy-induced heart failure, heart failure associated with muscular dystrophy, bi-ventricular HFrEF, HFrEF with pulmonary hypertension, heart failure with preserved ejection fraction (HFpEF) with right ventricular dysfunction, pulmonary hypertension with right ventricular dysfunction, scleroderma with pulmonary hypertension, right ventricular dysfunction, Chagas disease, or myocarditis.

In some embodiments, the dilated cardiomyopathy is selected from the group consisting of genetic dilated cardiomyopathy, peripartum cardiomyopathy (e.g., post-partum cardiomyopathy), idiopathic dilated cardiomyopathy, post-infectious dilated cardiomyopathy, toxin-induced dilated cardiomyopathy, and nutritional deficiency dilated cardiomyopathy. In some embodiments, the pediatric HFrEF occurs in pediatric patients with univentricular hearts or a single ventricle or patients post Fontan or Fontan-Kreutzer procedure. In some embodiments, the pediatric HFrEF is pediatric heart failure associated with congenital heart disease. In some embodiments, the chemotherapy-induced heart failure is selected from the group consisting of chemotherapy-induced left ventricular dysfunction, radiation-induced heart failure, heart failure resulting from anthracycline treatment (including but not limited to doxorubicin, epirubicin, and daunorubicin), heart failure resulting from antiERBB2 treatment (including but not limited to trastuzumab and lapatinib), heart failure resulting from VEGF inhibitor treatment (including but not limited to bevacizumab), and heart failure resulting from tyrosine-kinase inhibitor treatment (including but not limited to imatinib, dasatinib, nilotinim, sorafenib, and sunitinib). In some embodiments, the heart failure associated with muscular dystrophy is selected from the group consisting of heart failure associated with Duchenne muscular dystrophy, heart failure associated with Becker muscular dystrophy, heart failure associated with myotonic dystrophy (e.g., Steinert's disease), heart failure associated with laminopathies such as Emery-Dreifuss muscular dystrophy (EDMD), including both X-linked EDMD and autosomal dominant EDMD, heart failure associated with facioscapulohumeral muscular dystrophy (FSHMD), heart failure associated with Limb-girdle muscular dystrophy, including sarcoglycanopathies and the autosomal dominant form of the disease, and heart failure associated with congenital muscular dystrophy. In some embodiments, the pulmonary hypertension with right ventricular dysfunction is associated with high left ventricular (diastolic) pressure in HFrEF or high left ventricular (diastolic) pressure in HFpEF.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by in vitro & in vivo methods, such as those described in the examples below.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound disclosed herein and at least one other therapeutic agent as a combined preparation for simultaneous, separate or sequential use in therapy. In one embodiment, the therapy is the treatment of a disease or condition mediated by the cardiac sarcomere. In preferred aspects, the therapy is a treatment for heart failure having reduced or compromised ejection fraction. Products provided as a combined preparation include a composition comprising the compound disclosed herein and the other therapeutic agent(s) together in the same pharmaceutical composition, or the compound disclosed herein and the other therapeutic agent(s) in separate form, e.g. in the form of a kit.

In one embodiment, the invention provides a pharmaceutical composition comprising a compound as disclosed herein and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound as disclosed herein for treating a disease or condition mediated by the cardiac sarcomere wherein the medicament is prepared for administration with another therapeutic agent. The invention also provides the use of another therapeutic agent for treating a disease or condition mediated by the cardiac sarcomere, wherein the medicament is administered with a compound as disclosed herein. In another aspect, the invention provides the use of a compound as disclosed herein for treating a heart failure having reduced or compromised ejection fraction wherein the medicament is prepared for administration with another therapeutic agent. The invention also provides the use of another therapeutic agent for treating heart failure having reduced or compromised ejection fraction, wherein the medicament is administered with a compound as disclosed herein.

The invention also provides a compound as disclosed herein for use in a method of treating a disease or condition mediated by the cardiac sarcomere or in the treating of heart failure having reduced or compromised ejection fraction, wherein the compound is prepared for administration with another therapeutic agent. The invention also provides another therapeutic agent for use in a method of treating a disease or condition mediated by the cardiac sarcomere or in the treating of heart failure having reduced or compromised ejection fraction, wherein the other therapeutic agent is prepared for administration with a compound as disclosed herein. The invention also provides a compound as disclosed herein for use in a method of treating a disease or condition mediated by the cardiac sarcomere or in the treating of heart failure having reduced or compromised ejection fraction, wherein the compound is administered with another therapeutic agent. The invention also provides another therapeutic agent for use in a method of treating a disease or condition mediated by the cardiac sarcomere or in the treating of heart failure having reduced or compromised ejection fraction, wherein the other therapeutic agent is administered with a compound as disclosed herein.

The invention also provides the use of a compound as disclosed herein for treating a disease or condition mediated by the cardiac sarcomere or in the treating of heart failure having reduced or compromised ejection fraction wherein the patient has previously (e.g. within 24 hours) been treated with another therapeutic agent. The invention also provides the use of another therapeutic agent for treating a disease or condition mediated by the cardiac sarcomere or in the treating of heart failure having reduced or compromised ejection fraction wherein the patient has previously (e.g. within 24 hours) been treated with a compound as disclosed herein.

The pharmaceutical compositions can be administered alone or in combination with other molecules known to have a beneficial effect on heart failure including molecules capable of increasing the contractility of the heart and/or increasing the ejection fraction in patients suffering from or susceptible to heart failure.

A combination therapy regimen may be additive, or it may produce synergistic results (e.g., increases in cardiac contractility or increased cardiac ejection fraction which is more than expected for the combined use of the two agents). In some embodiments, the present invention provide a combination therapy for preventing and/or treating heart failure or more particularly systolic heart failure disease as described above with a compound of the invention and a second therapeutic agent. Suitable additional active agents include, for example: therapies that retard the progression of heart failure by down-regulating neurohormonal stimulation of the heart and attempt to prevent cardiac remodeling (e.g., ACE inhibitors or P-blockers); therapies that improve cardiac function by stimulating cardiac contractility (e.g., positive inotropic agents, such as the P-adrenergic agonist dobutamine or the phosphodiesterase inhibitor milrinone); therapies that reduce cardiac preload (e.g., diuretics, such as furosemide), agents that reduce afterload such as nephrilysin inhibitors/angiotensin receptor blockers, as well as drugs that slow heart rate, such as ivabradine; angiotensin receptor blockers (e.g., without nephrilysin inhibitors); aldosterone antagonists (e.g. spironolactone, eplerenone); hydralizine-nitrates; and digoxin. Suitable additional active agents also include, for example, agents that improve mitochondrial function.

In one embodiment, the invention provides a method of modulating activity of the cardiac sarcomere in a subject, wherein the method comprises administering to the subject a therapeutically effective amount of the compound according to the definition of Formula (I). The invention further provides methods of modulating the activity of the cardiac sarcomere in a subject by administering a compound as disclosed herein which bind to the Troponin C/Troponin I interface to increase activity of the cardiac sarcomere, wherein the method comprises administering to the subject a therapeutically effective amount of the compound as disclosed herein.

In one embodiment, the invention provides a compound as disclosed herein, for use as a medicament.

In one embodiment, the invention provides the use of a compound as disclosed herein for the treatment of a disorder or disease in a subject characterized by reduced cardiac function. In particular, the invention provides the use of a compound as disclosed herein for the treatment of a disorder or disease mediated by reduced cardiac sarcomere function, e.g., heart failure or more particularly systolic heart failure.

In one embodiment, the invention provides the use of a compound as disclosed herein in the manufacture of a medicament for the treatment of a disorder or disease in a subject characterized by reduced cardiac function. More particularly in the manufacture of a medicament for the treatment of a disease or disorder in a subject characterized by reduced cardiac sarcomere function, e.g., heart failure or more particularly systolic heart failure.

In one embodiment, the invention provides the use of a compound as disclosed herein for the treatment of a disorder or disease in a subject characterized by reduced cardiac function. More particularly, the invention provides uses of the compounds provided herein in the treatment of a disease or disorder characterized by reduced cardiac sarcomere function, e.g., heart failure or more particularly systolic heart failure. In certain embodiments, the use is in the treatment of a disease or disorder is selected from heart failure or systolic heart failure.

In a specific embodiment, the present invention provides use of the compounds of the invention for treating or preventing heart failure or systolic heart failure. In certain embodiments, patients who are currently asymptomatic but are at risk of developing a symptomatic heart failure or systolic heart failure are suitable for administration with a compound of the invention. The use in treating or preventing heart failure or systolic heart failure include, but are not limited to, uses in treating or preventing one or more symptoms or aspects of heart failure selected from reduced heart contractility and reduced ejection fraction.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure materials.

The following examples are intended to illustrate the invention and are not to be construed as being limitations thereon. Temperatures are given in degrees centigrade (° C.). If not mentioned otherwise, all evaporations are performed under reduced pressure, typically between about 15 mm Hg and 100 mm Hg (20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art.

| ABREVIATIONS | FULL NAME |
|---|---|
| DAST | Diethylaminosulfur trifluoride |
| DBU | 1,8-Diazabicyclo[5.4.0]undec-7-ene |
| DCM | Dichloromethane |
| DIPEA | N,N-Diisopropylethylamine, or Hünig's base |
| DMF | Dimethylformamide |
| EDC | N-(3-Dimethylaminopropyl)-N-ethylcarbodiimide hydrochloride |
| HBTU | 2-(1H-benzotriazol-1-yl)-1,1,3,3-tetramethyluronium hexaFLuorophosphate |
| HMPT | Tris(dimethylamino)phosphine |
| HOBT | Hydroxybenzotriazole |
| HPLC | High-performance liquid chromatography |
| MCPBA | meta-Chloroperoxybenzoic acid |
| MPLC | Medium pressure liquid chromatography |
| MTBE | Methyl tert-butyl ether |
| NMP | N-Methyl-2-pyrrolidone |
| RT | Room temperature (~23° C.) |
| TBAF | Tetra-n-butylammonium fluoride |
| TBTU | 2-(1H-Benzotriazole-1-yl)-1,1,3,3-tetramethylaminium tetrafluoroborate |
| TFA | Trifluoroacetic acid |
| TFAA | Trifluoroacetic anhydride |

Intermediate 1.0: Preparation of ((S)-1-((3-cyano-azetidin-1-yl)sulfonyl)piperidine-3-carbonyl)-D-proline

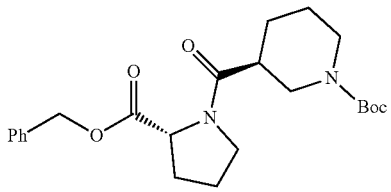 [SMILES: CC(C)(C)OC(=O)N1CCC[C@H](C(=O)N2CCC[C@@H]2C(=O)OCc2ccccc2)C1]

Step 1: Preparation of tert-butyl (S)-3-((R)-2-((benzyloxy)carbonyl)pyrrolidine-1-carbonyl)piperidine-1-carboxylate To a 0° C. solution of (S)-1-(tert-butoxycarbonyl)piperidine-3-carboxylic acid (71 g, 310 mmol, Combi-Blocks, Inc.) in DCM (750 mL), was added TBTU (99 g, 310 mmol) j by the addition of DIPEA (151 mL, 867 mmol). The mixture was allowed to stir at 0° C. for 10 minutes then (R)-benzylpyrrolidine-2-carboxylate hydrochloride (73 g, 302 mmol, Sibian) was added in single portion. After an additional 5 minutes at 0° C., the reaction mixture was allowed to warm to rt and stirred for 2 h. The mixture was diluted with DCM (200 mL) and quenched with saturated aqueous NaHCO₃ solution. The organics were washed with saturated aqueous NH₄Cl, dried over anhydrous Na₂SO₄, filtered, and concentrated. The crude material was purified by MPLC using silica gel (230-400 mesh) and eluted with 100% DCM to afford tert-butyl (S)-3-((R)-2-((benzyloxy)-carbonyl)pyrrolidine-1-carbonyl)piperidine-1-carboxylate (90 g) as a colorless gum. $^1$H NMR (400 MHz, chloroform-d) δ 7.41-7.31 (m, 5H), 5.22 (d, J=12.3 Hz, 1H), 5.11 (d, J=12.3 Hz, 1H), 4.55 (dd, J=8.7, 3.9 Hz, 1H), 4.15 (s, 2H), 3.75-3.55 (m, 2H), 2.87 (s, 1H), 2.70 (s, 1H), 2.51 (br s, 1H), 2.20 (q, J=9.6, 6.9 Hz, 2H), 2.10-1.90 (m, 4H), 1.71 (d, J=13.9 Hz, 2H), and 1.47 (m, 10H). LCMS-ESI (POS.) m/z: 417.0 (M+H)+.

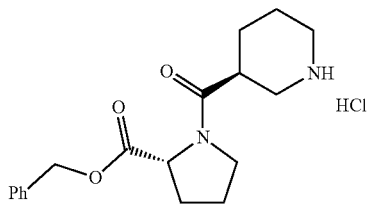 [SMILES: O=C(OCc1ccccc1)[C@H]1CCCN1C(=O)[C@H]1CCCNC1 ; Cl]

Step 2: Preparation of benzyl ((S)-piperidine-3-carbonyl)-D-prolinate hydrochloride To a 0° C. solution of tert-butyl (S)-3-((R)-2-((benzyloxy) carbonyl)pyrrolidine-1-carbonyl) piperidine-1-carboxylate (128 g, 307 mmol) in 1,4-dioxane (100 mL) was slowly added 4M HCl in dioxane (990 mL, 3.96 mol). The solution was allowed to warm to rt and stirred for 3 h, concentrated under reduced pressure, and azeotroped with toluene (200 mL×3). The residue was then triturated with petroleum ether (300 mL) to afford benzyl ((S)-piperidine-3-carbonyl)-D-prolinate hydrochloride (105 g) as white solid. $^1$H NMR (400 MHz, chloroform-d) δ 9.81 (s, 1H), 9.14 (s, 1H), 7.39-7.31 (m, 5H), 5.19 (d, J=12.3 Hz, 1H), 5.07 (d, J=12.3 Hz, 1H), 4.53 (dd, J=8.6, 4.1 Hz, 1H), 3.69 (dt, J=10.3, 6.9 Hz, 1H), 3.61 (dt, J=9.9, 6.5 Hz, 1H), 3.44-3.34 (m, 2H), 3.26-3.16 (m, 2H), 2.95 (m, 1H), 2.65 (s, 1H), 2.22 (ddt, J=14.8, 8.7, 6.1 Hz, 1H), 1.99 (dt, J=9.0, 5.2 Hz, 4H), 1.87 (s, 1H), and 1.66 (dq, J=9.9, 5.4, 4.5 Hz, 1H). LCMS-ESI (POS.) m/z: 317.2 (M+H)+.

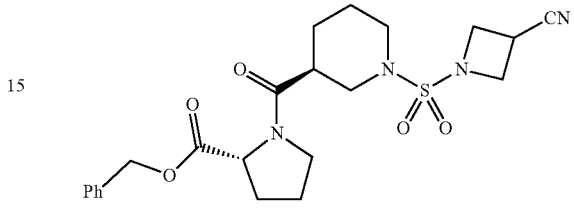

Step 3: Preparation of benzyl ((S)-1-((3-cyanoazetidin-1-yl)sulfonyl)piperidine-3-carbonyl)-D-prolinate To a solution of benzyl ((S)-piperidine-3-carbonyl)-D-prolinate hydrochloride (77 g, 218 mmol) in DCM (570 mL) at rt was added DIPEA (152 mL, 873 mmol) and then 3-cyanoazetidine-1-sulfonyl chloride (59.1 g, 327 mmol, Synthonix). After stirring at rt for 3 h, the mixture was diluted with saturated aqueous NH₄Cl (500 mL) and DCM (300 mL). The organic layer was separated and washed successively with 1N HCl solution (100 mL) and brine (500 mL). After drying over anhydrous Na₂SO₄, the suspension was filtered and concentrated under reduced pressure. The crude material was purified by MPLC using silica gel (230-400 mesh) and eluted with 1% methanol in DCM, to provide benzyl ((S)-1-((3-cyanoazetidin-1-yl)sulfonyl)piperidine-3-carbonyl)-D-prolinate (74 g) as brown oil. $^1$H NMR (300 MHz, chloroform-d) δ 7.44-7.32 (m, 5H), 5.28-5.17 (m, 1H), 5.11 (d, J=12.3 Hz, 1H), 4.54 (dd, J=8.6, 3.7 Hz, 1H), 4.42-4.34 (m, 1H), 4.13-4.05 (m, 4H), 3.83-3.72 (m, 2H), 3.70-3.59 (m, 2H), 3.48-3.35 (m, 1H), 3.04-2.94 (m, 1H), 2.72 (dtt, J=18.8, 11.4, 3.5 Hz, 2H), 2.22 (tdd, J=10.7, 6.6, 4.0 Hz, 1H), 2.02 (dddd, J=14.3, 10.5, 6.6, 4.5 Hz, 4H), and 1.70-1.58 (m, 2H). LCMS-ESI (POS.) m/z: 461.4 (M+H)+.

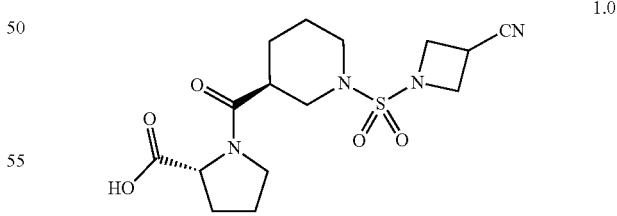

1.0

Step 4: Preparation of ((S)-1-((3-cyanoazetidin-1-yl)sulfonyl)piperidine-3-carbonyl)-D-proline, Intermediate 1.0

To a solution of benzyl ((S)-1-((3-cyanoazetidin-1-yl) sulfonyl)piperidine-3-carbonyl)-D-prolinate (72 g, 156 mmol) in methanol (750 mL) at rt was added 10% Pd/C (8.32 g, 78 mmol). The resulting mixture was stirred under hydrogen atmosphere (1 atm) for 3 h. The mixture was then filtered and the reaction was subjected to another lot of 10% Pd/C (8.32 g, 78 mmol). After 3 h, the reaction mixture was filtered through a pad of Celite and the filtrate was concentrated under reduced pressure to afford ((S)-1-((3-cyanoazetidin-1-yl)sulfonyl)piperidine-3-carbonyl)-D-proline (51 g) as an off white solid. $^1$H NMR (400 MHz, DMSO-d$_6$) δ 12.54 (s, 1H), 4.21 (dd, J=8.8, 4.2 Hz, 1H), 4.09-4.03 (m, 2H), 3.94 (ddd, J=8.0, 5.9, 3.0 Hz, 2H), 3.84-3.76 (m, 1H), 3.56 (dt, J=18.1, 5.8 Hz, 4H), 2.90-2.74 (m, 2H), 2.65 (td, J=7.4, 3.6 Hz, 1H), 2.24-2.08 (m, 1H), 1.97-1.77 (m, 4H), 1.74-1.66 (m, 1H), and 1.54-1.36 (m, 2H). LCMS-ESI (POS.) m/z: 371.0 (M+H)+.

The intermediates in the following table were synthesized following the procedure described for Intermediate 1.0 using known starting material replacements as described.

TABLE 1

| Intermediate | Reagents | Structure, Name and Data |
| --- | --- | --- |
| 1.1 | 3-(methylsulfonyl)azetidine hydrochloride (Advanced Chem Blocks) | 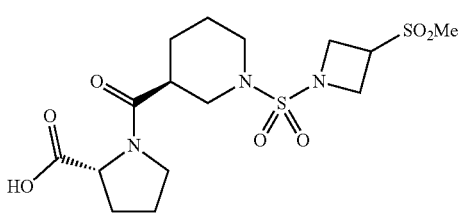 [SMILES: CS(=O)(=O)C1CN(S(=O)(=O)N2CCC[C@H](C(=O)N3CCC[C@@H]3C(=O)O)C2)C1]<br>(R)-1-((S)-1-((3-(methylsulfonyl)azetidin-1-yl)sulfonyl)piperidine-3-carbonyl)pyrrolidine-2-carboxylic acid. LCMS-ESI (POS.) m/z: 424.0 (M + H)+. |
| 1.2 | 3-methylazetidin-3-ol-hydrochloride (Astatech) | 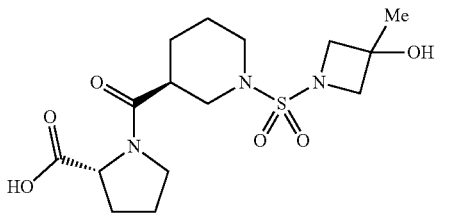 [SMILES: CC1(O)CN(S(=O)(=O)N2CCC[C@H](C(=O)N3CCC[C@@H]3C(=O)O)C2)C1]<br>(R)-1-((S)-1-((3-hydroxy-3-methylazetidin-1-yl)sulfonyl)piperidine-3-carbonyl)pyrrolidine-2-carboxylic acid. LCMS-ESI (POS.) m/z: 376.2 (M + H)+. |
| 1.3 | (S)-1-(tert-butoxycarbonyl)-4-((3-cyanoazetidin-1-yl)sulfonyl)piperazine-2-carboxylic acid (Ark pharm) | 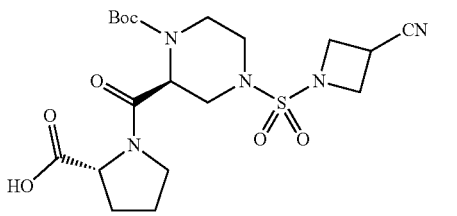 [SMILES: CC(C)(C)OC(=O)N1CCN(S(=O)(=O)N2CC(C#N)C2)C[C@H]1C(=O)N1CCC[C@@H]1C(=O)O]<br>(R)-1-((S)-1-(tert-butoxycarbonyl)-4-((3-cyanoazetidin-1-yl)sulfonyl)piperazine-2-carbonyl)pyrrolidine-2-carboxylic acid. LCMS-ESI (POS.) m/z: 472.2 (M + H)+. |

Intermediate 2.0: Preparation of (S)-1-((3-cyanoazetidin-1-yl)sulfonyl)piperidine-3-carboxylic Acid

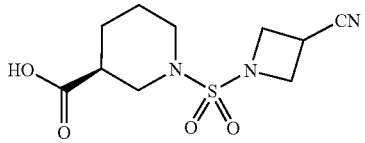

(S)-1-((3-cyanoazetidin-1-yl)sulfonyl)piperidine-3-carboxylic Acid, Intermediate 2.0

To a stirred solution of (S)-piperidine-3-carboxylic acid (90.0 g, 697 mmol, Combi-Blocks, Inc.) in THF (1 L) and water (1 L) at rt was added $Na_2SO_4$ (222 g, 2.10 mol), and 3-cyanoazetidine-1-sulfonyl chloride (138 g, 767 mmol, Synthonix). After stirring at rt for 18 h, the reaction was quenched with water (250 mL) and extracted with ethyl acetate (2×1 L). The pH of the aqueous layer was adjusted to approximately 2 with 6N HCl and then extracted with ethyl acetate (2×1.5 L). The combined organic extracts were washed with water (500 mL), saturated brine solution (500 mL), dried over anhydrous $Na_2SO_4$, and concentrated under reduced pressure to provide (S)-1-((3-cyanoazetidin-1-yl)sulfonyl)-piperidine-3-carboxylic acid (141 g) as white solid. $^1$H NMR (400 MHz, DMSO-$d_6$) δ 12.48 (s, 1H), 4.06 (s, 2H), 3.96-3.93 (m, 2H), 3.79 (td, J=6.1, 3.1 Hz, 1H), 3.56 (dd, J=12.2, 3.9 Hz, 1H), 3.38 (s, 1H), 2.99 (d, J=2.5 Hz, 1H), 2.90-2.84 (m, 1H), 2.49 (m, 1H), 1.88 (q, J=4.5, 4.0 Hz, 1H), 1.70 (q, J=4.8 Hz, 1H), and 1.51-1.45 (m, 2H).

Intermediate 3.0: Preparation of (3-((3-cyanoazetidin-1-yl)sulfonyl)benzoyl)-D-proline

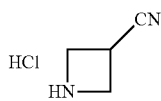

Step 1: Preparation of azetidine-3-carbonitrile hydrochloride

To a solution of tert-butyl 3-cyanoazetidine-1-carboxylate (300 g, 1.65 mol, Pharma Blocks) in 1,4-dioxane (300 mL) at 0° C. was added 4M HCl in dioxane (1.25 L, 5.0 mol). The mixture was allowed to warm to rt and stirred for an additional 4 h. The reaction mixture was then concentrated under reduced pressure and azeotroped with toluene (3×250 mL). The residue was slurried with hexanes (500 mL) and dried under high vacuum to give azetidine-3-carbonitrile hydrochloride (195 g) as a white solid. $^1$H NMR (400 MHz, DMSO-$d_6$): δ 9.87 (bs, 2H), 4.22-4.08 (m, 4H), 4.05-3.95 (m, 1H).

Step 2: Preparation of 3-((3-cyanoazetidin-1-yl)sulfonyl)benzoic Acid, Intermediate 3.1

To a suspension of azetidine-3-carbonitrile hydrochloride (275 g, 2.32 mol) in DCM (2.8 L) at 0° C. was added triethylamine (1.3 L, 9.28 mol). The mixture was stirred for 10 min at 0° C. then 3-(chlorosulfonyl)benzoic acid (563 g, 2.56 mol, Arbor Chemicals) was slowly added in portions over the period of 1 h (Caution: Exotherm). The reaction mixture was stirred at rt for 3 h and then cooled to 0° C. and quenched with 1N aqueous HCl (4 L). The precipitate was collected by filtration, washed with water (2 L) and dried under vacuum to give 3-((3-cyanoazetidin-1-yl)sulfonyl)benzoic acid (475 g) as a white solid. $^1$H NMR (400 MHz, DMSO-$d_6$): δ 13.65 (bs, 1H), 8.33 (d, J=7.8 Hz, 1H), 8.26 (s, 1H), 8.10 (d, J=8.1 Hz, 1H), 7.87 (dd, J=8.1, 7.8 Hz, 1H), 4.02 (dd, J=8.5, 5.8 Hz, 2H), 3.89 (dd, J=8.5, 5.8 Hz, 2H), 3.68-3.60 (m, 1H). LCMS-ESI (NEG) m/z: 265.0 (M−H)−.

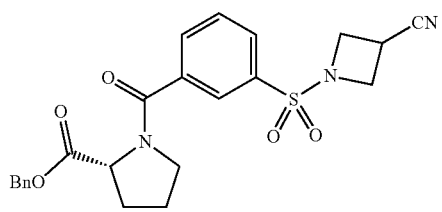 [SMILES: N#CC1CN(S(=O)(=O)c2cccc(C(=O)N3CCC[C@@H]3C(=O)OCc3ccccc3)c2)C1]

Step 3: Preparation of benzyl (3-((3-cyanoazetidin-1-yl)sulfonyl)benzoyl)-D-prolinate To a solution of 3-((3-cyanoazetidin-1-yl)sulfonyl)benzoic acid (220 g, 826 mmol) in DCM (2.2 L) at 0° C. was added TBTU (279 g, 868 mmol) and DIPEA (418 mL, 2396 mmol). After 10 min at 0° C., (R)-benzyl pyrrolidine-2-carboxylate hydrochloride (200 g, 826 mmol, TCI) was added and stirred at rt for 2 h. The reaction mixture was quenched with water (1 L) and extracted with DCM (2×1000 mL). The organic layer was washed consecutively with 10% aqueous $NaHCO_3$ solution (500 mL) and brine (500 mL). The organic layer was dried over $Na_2SO_4$, filtered, and concentrated under reduced pressure. The crude material was adsorbed onto silica gel (60-120 mesh) and purified by column chromatography (silica gel, 230-400 mesh) using 1% MeOH in DCM to give benzyl (3-((3-cyanoazetidin-1-yl)sulfonyl)benzoyl)-D-prolinate (210 g) as a thick brown oil. $^1$H NMR (400 MHz, chloroform-d): δ 8.04 (s, 1H), 7.92 (d, J=8.0 Hz, 1H), 7.87 (d, J=7.6 Hz, 1H), 7.68 (dd, J=8.0, 7.6 Hz, 1H), 7.40-7.32 (m, 5H), 5.30-5.18 (m, 2H), 4.76-4.70 (m, 1H), 4.10-3.97 m, 3H), 3.65 (dd, J=11.6, 5.3 Hz, 1H), 3.51 (dt, J=10.2, 6.4 Hz, 1H), 3.37-3.30 (m, 1H), 2.50-2.29 (m, 1H), 2.10-1.88 (m, 4H). LCMS-ESI (POS.) m/z: 454.0 (M+H)+.

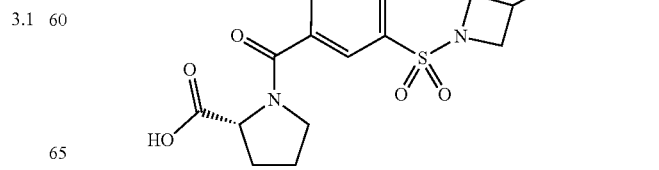

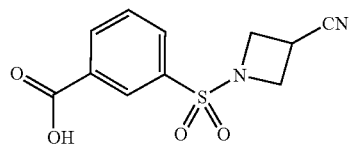

Step 4: Preparation of (3-((3-cyanoazetidin-1-yl)sulfonyl)benzoyl)-D-proline, Intermediate 3.0

A 5 L autoclave was charged with a solution of benzyl (3-((3-cyanoazetidin-1-yl)sulfonyl)benzoyl)-D-prolinate (140 g, 309 mmol) in methanol (1.8 L). The autoclave was purged with nitrogen gas for 5 min then 10% Pd/C (3.29 g) was added and the mixture was stirred under hydrogen pressure (20 psi) at rt for 4 h. The reaction mixture was filtered through a bed of Celite and concentrated under reduced pressure. The crude material was then adsorbed onto silica gel (60-120 mesh) and purified by column chromatography (silica gel, 230-400 mesh) using 3% MeOH in DCM to give (3-((3-cyanoazetidin-1-yl)sulfonyl)benzoyl)-D-proline (70 g) as a white solid. $^1$H NMR (400 MHz, DMSO-$d_6$): δ 12.67 (bs, 1H), 8.00-7.76 (m, 4H), 4.45-4.37 (m, 1H), 4.06-3.85 (m, 4H), 3.69-3.52 (m, 3H), 2.31-2.27 (m, 1H), 2.01-1.87 (m, 3H). LCMS-ESI (NEG) m/z: 362.0 (M−H)−.

Intermediate 4.0: Preparation of (3-(methylsulfonyl)benzoyl)-D-proline

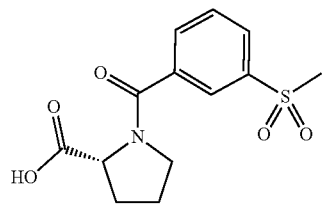

4.0

Preparation of (3-(methylsulfonyl)benzoyl)-D-proline, Intermediate 4.0

The above titled compound was made following the procedure described for the synthesis of Intermediate 14.0 replacing 3-(N,N-dimethylsulfamoyl)benzoic acid with 3-(methylsulfonyl)benzoic acid (Combi-Blocks, Inc.). LCMS-ESI (POS.). m/z: 298.2 (M+H)+.

Intermediate 5.0: Preparation of (1R,3R,5R)-2-(3-(methylsulfonyl)benzoyl)-2-azabicyclo[3.1.0]hexane-3-carboxylic Acid

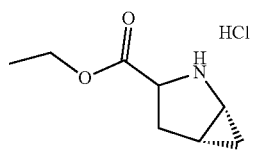

Step 1: Preparation of (1R,3R,5R)-ethyl 2-azabicyclo[3.1.0]hexane-3-carboxylate hydrochloride A 100 mL round-bottom flask was charged with (1R,3R,5R)-2-tert-butyl 3-ethyl 2-azabicyclo[3.1.0]hexane-2,3-dicarboxylate (1.0 g, 3.92 mmol, Synthonix, Inc.) and DCM (13.0 mL). To that solution was added 4.0M HCl in dioxane (4.90 mL, 19.6 mmol). After 2.5 hours at rt, the mixture was concentrated under reduced pressure and azeotroped with methanol (×2, 10 mL) to give (1R,3R,5R)-ethyl 2-azabicyclo[3.1.0]hexane-3-carboxylate hydrochloride (0.751 g, 100%) as a foam. LCMS-ESI (POS.). m/z: 156.2 (M+H)+.

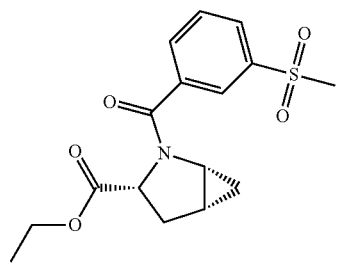 [SMILES: CCOC(=O)[C@H]1C[C@H]2C[C@H]2N1C(=O)c1cccc(S(C)(=O)=O)c1]

Step 2: Preparation of (1R,3R,5R)-ethyl 2-(3-(methylsulfonyl)benzoyl)-2-azabicyclo[3.1.0]hexane-3-carboxylate A 100 mL round-bottom flask was charged with (1R,3R,5R)-ethyl 2-azabicyclo[3.1.0]hexane-3-carboxylate hydrochloride (0.75 g, 3.9 mmol) and DCM (20 mL). To that stirring solution at rt was added 3-(methylsulfonyl)benzoic acid (1.2 g, 5.9 mmol, Combi-Blocks, Inc.), TBTU (1.9 g, 5.9 mmol) and DIPEA (3.4 mL, 19.6 mmol). After 24 hours, the reaction mixture was concentrated under reduced pressure. The resulting oil was diluted with DCM, and purified by MPLC on silica gel, eluting with 0-50% ethyl acetate in heptane to provide (1R,3R,5R)-ethyl 2-(3-(methylsulfonyl)benzoyl)-2-azabicyclo[3.1.0]hexane-3-carboxylate (1.1 g, 83%). LCMS-ESI (POS.). m/z: 338.0 (M+H)+.

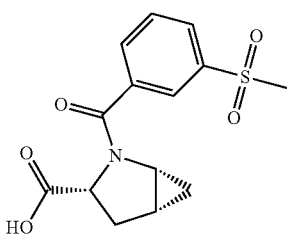

5.0

Step 3: Preparation of (1R,3R,5R)-2-(3-(methylsulfonyl)benzoyl)-2-azabicyclo[3.1.0]hexane-3-carboxylic Acid, Intermediate 5.0

To a 50 mL round-bottom flask was added (1R,3R,5R)-ethyl 2-(3-(methylsulfonyl)benzoyl)-2-azabicyclo[3.1.0]hexane-3-carboxylate (1.0 g, 3.0 mmol), lithium hydroxide (0.14 g, 14.8 mmol) in 1,4-dioxane (10 mL) and water (10 mL). The reaction mixture was stirred at rt for 1 h, then diluted with water and acidified to pH=2 with 1N HCl. The mixture was extracted with 3:1 DCM/MeOH, and the combined organic extracts were washed with brine, dried over MgSO$_4$, filtered, and concentrated under reduced pressure to afford (1R,3R,5R)-2-(3-(methylsulfonyl)benzoyl)-2-azabicyclo[3.1.0]hexane-3-carboxylic acid (0.81 g) as white solid. LCMS-ESI (POS.). m/z: 310.0 (M+H)+.

Intermediate 6.0: Preparation of 3-((3-cyanoazetidin-1-yl)sulfonyl)-5-fluorobenzoic Acid

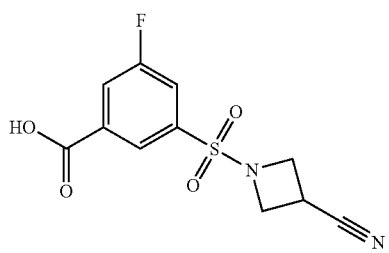

6.0

3-((3-cyanoazetidin-1-yl)sulfonyl)-5-fluorobenzoic acid, Intermediate 6.0. A 40 mL pressure vial was charged with 3-(chlorosulfonyl)-5-fluorobenzoic acid (500 mg, 2.10 mmol, Enamine) and 3-cyanoazetidine hydrochloride (497 mg, 4.19 mmol, Synthonix, Inc.). To that mixture was added DCM (10.5 mL) followed by triethylamine (1.17 mL, 8.38 mmol). After 2 hours at rt, the mixture was transferred to a separatory funnel and the pH was adjusted to ~10 using saturated aqueous solution NaHCO$_3$. The layers were separated and the aqueous was carefully acidified with concentrated HCl (pH=3) upon which a white solid precipitated from the solution. The solid was collected by filtration and lyophilized to give 3-((3-cyanoazetidin-1-yl)sulfonyl)-5-fluorobenzoic acid (349 mg) as a white solid. 1H NMR (500 MHz, DMSO-d$_6$) δ ppm 3.64 (tt, J=8.94, 5.86 Hz, 1H) 3.96 (dd, J=8.69, 5.84 Hz, 2H) 4.06 (t, J=8.82 Hz, 2H) 8.03 (dt, J=7.85, 1.98 Hz, 1H) 8.07-8.11 (m, 2H) 13.92 (brs, 1H). LCMS-ESI (POS.) m/z: 285.2 (M+H)+.

Intermediate 7.0: Preparation of Sodium (S)-4-((3-cyanoazetidin-1-yl)sulfonyl)morpholine-2-carboxylate

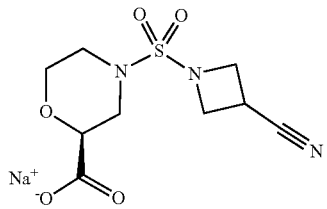

7.0

Sodium (S)-4-((3-cyanoazetidin-1-yl)sulfonyl)morpholine-2-carboxylate, Intermediate 7.0

A 100 mL round-bottom flask was charged with (S)-morpholine-2-carboxylic acid hydrochloride (1.5 g, 8.95 mmol, Ark Pharma, Inc.) and a 1:1 mixture of THF (15 mL) and water (15 mL). To that rt solution was added Na$_2$CO$_3$, anhydrous (2.85 g, 27.0 mmol) followed by 3-cyanoazetidine-1-sulfonyl chloride (1.94 g, 10.7 mmol, Synthonix, Inc). The turbid solution was stirred overnight at rt and then transferred into a separatory funnel and diluted with water and ethyl acetate. The aqueous layer was extracted with ethyl acetate (×3) and then transferred into an Erlenmeyer flask and acidified to a pH of 2 using 1.0 N HCl. The aqueous was then extracted with ethyl acetate (×4, 20 mL) to yield 1.41 g (5.4 mmol). The sticky oil was then dissolved in water and sodium hydroxide. While at rt, 1.0 N NaOH (5.4 mL, 5.4 mmol) was added and the mixture was stirred for 30 minutes and then lyophilized overnight to give sodium (S)-4-((3-cyanoazetidin-1-yl)sulfonyl)morpholine-2-carboxylate (1.49 g) as a fluffy white solid. $^1$H NMR (500 MHz, DMSO-d$_6$) δ ppm 4.08 (q, J=7.83 Hz, 2H), 3.92-3.97 (m, 2H), 3.86-3.91 (m, 1H), 3.77-3.86 (m, 1H), 3.54 (br d, J=12.07 Hz, 1H), 3.45 (dd, J=9.73, 2.85 Hz, 1H), 3.33-3.40 (m, 1H), 3.21 (br d, J=11.68 Hz, 1H), 2.77-2.84 (m, 1H), 2.69-2.76 (m, 1H). LCMS-ESI (POS.) m/z: 298.2 (M+Na)+.

Intermediate 8.0: Preparation of (R)-cyclopropyl(2,5-difluoro-4-(trifluoromethyl)phenyl) methanamine hydrochloride

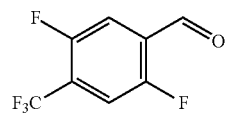

Step 1: Preparation of 2,5-difluoro-4-(trifluoromethyl)benzaldehyde

To a solution of 1-bromo-2,5-difluoro-4-(trifluoromethyl)benzene (130 g, 498 mmol, Oakwood, Inc.) in THF (1.3 L) was added isopropylmagnesium chloride (2M solution in THF, 274 mL, 548 mmol) drop-wise under nitrogen atmosphere at −45° C. The reaction mixture was stirred at −45° C. for 30 min and then DMF (174 mL, 2.24 mol) was slowly added and stirred for 20 min. The reaction mixture was allowed to warm to 0° C. and quenched with saturated aqueous NH$_4$Cl solution (500 mL), diluted with water (1.5 L), and extracted with EtOAc (3×2 L). The organic layer was washed with brine (2.0 L) and dried over Na$_2$SO$_4$, filtered, and concentrated under reduced pressure to give 2,5-difluoro-4-(trifluoromethyl)benzaldehyde (65 g) as a colorless oil. $^1$H NMR (400 MHz, chloroform-d): δ 10.38 (s, 1H), 7.71 (dd, J=9.2, 5.2 Hz, 1H), 7.52 (dd, J=9.2, 5.2 Hz, 1H).

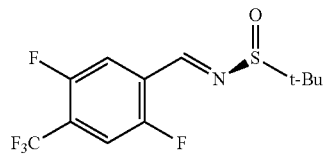

Step 2: Preparation of (S,E)-N-(2,5-difluoro-4-(trifluoromethyl)benzylidene)-2-methylpropane-2-sulfinamide To a suspension of copper(II) sulfate (228 g, 1.43 mol) and 2-methylpropane-2-sulfinamide (130 g, 1.07 mol) in 1,2-dichloroethane (2.2 L) was added 2,5-difluoro-4-(trifluoromethyl)benzaldehyde (150 g, 0.714 mol) at rt. The reaction mixture was heated 80° C. and stirred for 18 h. The mixture was filtered through a pad of Celite and the filter cake was washed with 1,2-dichloroethane (500 mL). The filtrate was concentrated under reduced pressure. The crude residue was absorbed onto a plug of silica gel (60-120 mesh)

and purified by column chromatography (silica gel, 60-120 mesh), eluting with 4% to 10% EtOAc in hexanes to provide (S,E)-N-(2,5-difluoro-4-(trifluoromethyl)benzylidene)-2-methylpropane-2-sulfinamide (195 g) as a pale brown viscous oil. ¹H NMR (400 MHz, chloroform-d): 68.88 (s, 1H), 7.85 (dd, J=9.6, 5.6 Hz, 1H), 7.47 (dd, J=9.2, 5.2 Hz, 1H), 1.31 (s, 9H).

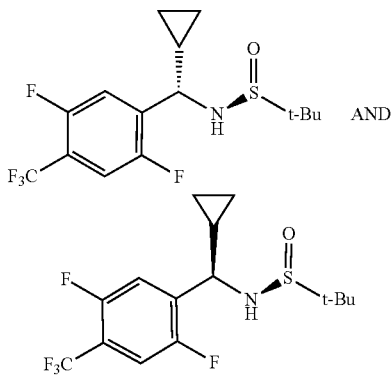

Step 3: Preparation of (S)—N—((S)-cyclopropyl(2,5-difluoro-4-(trifluoromethyl)phenyl)methyl)-2-methylpropane-2-sulfinamide and (S)—N—((R)-cyclopropyl(2,5-difluoro-4-(trifluoromethyl)phenyl)methyl)-2-methylpropane-2-sulfinamide A solution of (S,E)-N-(2,5-difluoro-4-(trifluoromethyl)benzylidene)-2-methylpropane-2-sulfinamide (195 g, 622 mmol) in DCM (3.6 L) was cooled to −78° C. Cyclopropylmagnesium bromide (0.5M in THF, 1.87 L, 934 mmol) was then added dropwise over 1 h. The reaction mixture was stirred at −78° C. for an additional 1 h and allowed to warm to rt over 2 h. The rt reaction mixture was quenched with saturated aqueous NH₄Cl solution (700 mL) and extracted with DCM (3×700 mL). The organic layer was washed with water (500 mL), brine (500 mL), dried over Na₂SO₄, and concentrated under reduced pressure. The crude residue was absorbed onto a plug of silica gel (60-120 mesh) and purified by column chromatography (silica gel, 230-400 mesh) using 5-15% EtOAc in hexanes. The first eluting peak (minor) was assigned as (S)—N—((S)-cyclopropyl(2,5-difluoro-4-(trifluoromethyl)phenyl)methyl)-2-methylpropane-2-sulfinamide (16 g) and collected as a brown oil. ¹H NMR (400 MHz, DMSO-d₆): δ 7.78-7.65 (m, 2H), 5.95 (d, J=8.0 Hz, 1H), 3.87 (dd, J=8.0, 7.4 Hz, 1H), 1.27-1.20 (m, 1H), 1.12 (s, 9H), 0.65-0.60 (m, 1H), 0.52-0.46 (m, 2H), 0.37-0.33 (m, 1H). LCMS-ESI (POS.) m/z: 356.1 (M+H)+. The second eluting peak (major) was assigned as (R)—N—((R)-cyclopropyl(2,5-difluoro-4-(trifluoromethyl)phenyl)methyl)-2-methylpropane-2-sulfinamide (95 g) and collected as a brown oil. ¹H NMR (400 MHz, DMSO-d₆): δ 7.78-7.70 (m, 2H), 5.73 (d, J=6.8 Hz, 1H), 3.87 (dd, J=8.0, 6.8 Hz, 1H), 1.32-1.27 (m, 1H), 1.08 (s, 9H), 0.65-0.61 (m, 1H), 0.52-0.46 (m, 2H), 0.37-0.33 (m, 1H). LCMS-ESI (POS.) m/z: 356.2 (M+H)⁺. The stereochemistry was assigned based on literature precedent (see Ellman, J. A.; Owens, T. D.; Tang, T. P. Acc. Chem. Res. 2002, 35, 984).

8.0

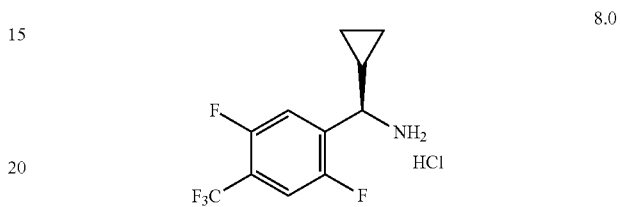

Step 4: Preparation of (R)-cyclopropyl(2,5-difluoro-4-(trifluoromethyl)phenyl)methanamine hydrochloride, Intermediate 8.0

To a solution of (S)—N—((R)-cyclopropyl(2,5-difluoro-4-(trifluoromethyl)phenyl)methyl)-2-methylpropane-2-sulfinamide (95 g, 268 mmol) in methanol (450 mL) was added HCl (4M solution in dioxane, 134 mL, 535 mmol) at 0° C. and stirred at rt for 2 h. The reaction mixture was concentrated under reduced pressure and azeotroped with DCM (500 mL). The residual solid was triturated with diethyl ether (500 mL) and filtered and dried under vacuum to give (R)-cyclopropyl(2,5-difluoro-4-(trifluoromethyl)phenyl)methanamine hydrochloride (73 g) as an off-white solid. ¹H NMR (400 MHz, DMSO-d₆): δ9.10 (s, 3H), 8.19 (dd, J=10.8, 5.6 Hz, 1H), 7.88 (dd, J=8.4, 6.4 Hz, 1H), 3.87 (d, J=8.8 Hz, 1H), 1.46-1.38 (m, 1H), 0.78-0.68 (m, 2H), 0.57-0.53 (m, 1H), 0.39-0.33 (m, 1H). LCMS-ESI (POS.) m/z: 252.1 (M+H)+.

The compounds set forth in the following table were synthesized following the procedure described for Intermediate 8.0 starting from Step 1 or Step 2 using known starting material replacements. The diastereomeric ratios ranged from 4:1 to >95:5 favoring the desired isomer. The stereochemistry was tentatively assigned based on literature precedent (see Ellman, J. A.; Owens, T. D.; Tang, T. P. Acc. Chem. Res. 2002, 35, 984).

TABLE 2

| Intermediate | Reagents | Structure, Name and Data |
|---|---|---|
| 9.0 | 4-chloro-2-fluorobenzaldehyde (Matrix Scientific) and 3.4M methylmagnesium bromide in 2-MeTHF | (R)-1-(4-chloro-2-fluorophenyl)ethanamine hydrochloride. ¹H NMR (500 MHz, DMSO-d₆) δ ppm 8.50 (3H, br s) 7.66 (1H, br t, J = 8.15 Hz) 7.55 (1H, dd, J = 10.38, 1.95 Hz) 7.43 (1H, dd, J = 8.37, 1.88 Hz) 4.60 (1H, q, J = 6.83 Hz) 1.50 (3H, d, J = 6.88 Hz). LCMS (POS.) m/z: 157.2 (M − NH₂)+. |

TABLE 2-continued

| Intermediate | Reagents | Structure, Name and Data |
|---|---|---|
| 9.1 | 3,5-difluorobenzaldehyde and 3.4M methyl magnesium bromide in 2-MeTHF | 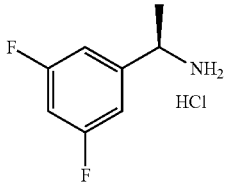<br>(R)-1-(3,5-difluorophenyl)ethanamine hydrochloride. LCMS (POS.) m/z: 141.2 (M − NH$_2$)+. |
| 9.2 | 4-chloro-2,5-difluorobenzaldehyde (Combi-Blocks, Inc.) | 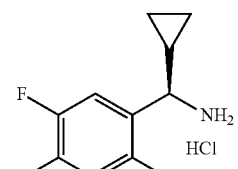<br>(R)-(4-chloro-2,5 difluorophenyl)(cyclopropyl)methanamine hydrochloride. $^1$H NMR (400 MHz, DMSO-d$_6$) δ ppm 8.88 (br s, 3H), 7.99 (dd, J = 9.85, 6.32 Hz, 1H), 7.77 (dd, J = 9.43, 6.22 Hz, 1H), 3.79 (br d, J = 8.50 Hz, 1H), 1.35-1.44 (m, 1H), 0.64-0.72 (m, 2H), 0.48-0.57 (m, 1H), 0.28-0.35 (m, 1H). LCMS (POS.) m/z: 201.2 (M − NH$_2$)+. |
| 9.3 | 3-fluoro-4-(trifluoromethyl)benzaldehyde (Combi-Blocks, Inc.) | 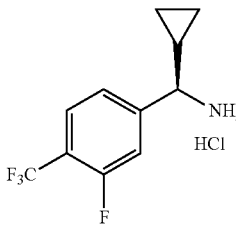<br>(R)-cyclopropyl(3-fluoro-4-(trifluoromethyl)phenyl)methanamine hydrochloride. $^1$H NMR (500 MHz, chloroform-d) δ ppm 9.09-9.34 (m, 3H), 7.65-7.71 (m, 1H), 7.55 (br d, J = 10.64 Hz, 1H), 7.42-7.47 (m, 1H), 3.56-3.67 (m, 1H), 1.40-1.50 (m, 1H), 0.71-0.82 (m, 3H), 0.46 (br dd, J = 8.63, 3.70 Hz, 1H. LCMS (POS.) m/z: 217.2 (M − NH$_2$)+. |
| 9.4 | 4-chloro-2-fluorobenzaldehyde (Matrix Scientific) | 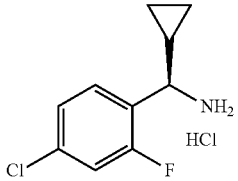 [SMILES: N[C@@H](c1ccc(Cl)cc1F)C1CC1 ; Cl]<br>(R)-(4-chloro-2-fluorophenyl)(cyclopropyl)methanamine hydrochloride. $^1$H NMR (500 MHz, chloroform-d) δ ppm 9.16 (br d, J = 1.56 Hz, 3H) 7.74 (t, J = 8.17 Hz, 1H) 7.23-7.28 (m, 2H) 3.94-4.03 (m, 1H) 1.50-1.59 (m, 1H) 0.77-0.87 (m, 2H) 0.68-0.76 (m, 1H) 0.47-0.56 (m, 1H). LCMS-ESI (POS.). m/z: 183.2 (M − NH$_2$)+. |
| 9.5 | 2-fluoro-4-(trifluoromethyl)benzaldehyde (Combi-Blocks, Inc.) | 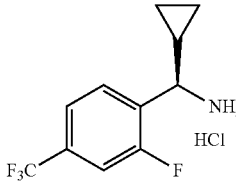<br>(R)-cyclopropyl(2-fluoro-4-(trifluoromethyl)phenyl)methanamine hydrochloride. $^1$H NMR (500 MHz, chloroform-d) δ ppm 9.03-9.31 (m, 3H), 7.86 (t, J = 7.46 Hz, 1H), 7.37-7.46 (m, 2H), 3.95 (br dd, J = 9.54, 5.25 Hz, 1H), 1.41-1.50 (m, 1H), 0.68-0.76 (m, 2H), 0.60-0.68 (m, 1H), 0.46 (dq, J = 9.93, 5.17 Hz, 1H). LCMS-ESI (POS.). m/z: 217.2 (M − NH$_2$)+. |

TABLE 2-continued

| Intermediate | Reagents | Structure, Name and Data |
|---|---|---|
| 9.6 | 4-(trifluoromethyl)benzaldehyde | (R)-cyclopropyl(4-(trifluoromethyl)phenyl)methanamine hydrochloride. LCMS-ESI (POS.). m/z: 199.0 (M − NH$_2$)+. |
| 9.7 | 2-fluoro-4-(trifluoromethyl)benzaldehyde (Combi-Blocks, Inc.) and 4-cyclobutylmagnesium chloride, 0.5M in THF (Oakwood Products, Inc.). | (R)-cyclobutyl(2-fluoro-4-(trifluoromethyl)phenyl)methanamine hydrochloride. $^1$H NMR (500 MHz, chloroform-d) δ ppm 8.92 (br s, 3H) 7.70 (t, J = 7.46 Hz, 1H) 7.43 (d, J = 8.30 Hz, 1H) 7.39 (d, J = 3.73 Hz, 1H) 4.55 (br d, J = 5.06 Hz, 1H) 2.88-3.00 (m, 1H) 1.99-2.16 (m, 2H) 1.79-1.94 (m, 3H) 1.66-1.78 (m, 1H). LCMS-ESI (POS.). m/z: 248.2 (M + H)+. |
| 9.8 | 4-chloro-3,5-difluorobenzaldehyde (Aurum Pharmatech, LLC.) | (R)-(4-chloro-3,5-difluorophenyl)(cyclopropyl)methanamine hydrochloride. $^1$H NMR (500 MHz, DMSO-d$_6$) δ ppm 8.60 (br s, 3H), 7.57 (s, 1H), 7.55 (s, 1H), 3.64 (br d, J = 9.99 Hz, 1H), 1.25-1.34 (m, 1H), 0.66-0.74 (m, 1H), 0.59 (dq, J = 9.63, 5.05 Hz, 1H, 0.49-0.56 (m, 1H), 0.44 (dq, J =9.83, 4.94 Hz, 1H). LCMS-ESI (POS.). m/z: 201.2 (M − NH$_2$)+. |
| 9.9 | 2,5-difluoro-4-methoxybenzaldehyde (Combi-Blocks, Inc.). | (R)-cyclopropyl(2,5-difluoro-4-methoxyphenyl)methanamine hydrochloride. $^1$H NMR (500 MHz, DMSO-d$_6$) δ ppm 8.29-8.73 (m, 3H), 7.55-7.72 (m, 1H), 7.22 (br dd, J = 11.48, 7.33 Hz, 1H), 3.87 (s, 3H), 3.74 (br d, J = 9.34 Hz, 1H), 1.31-1.39 (m, 1H), 0.68 (br s, 1H), 0.60 (br d, J = 4.41 Hz, 1H), 0.52 (br d, J = 4.41 Hz, 1H), 0.28 (br dd, J = 9.67, 5.00 Hz, 1H). LCMS-ESI (POS.). m/z: 197.2 (M − NH$_2$)+. |
| 9.10 | 4-(difluoromethyl)benzaldehyde (Enamine, Ltd.) and 3.4M methylmagnesium bromide in 2-MeTHF | (R)-1-(4-(difluoromethyl)phenyl)ethan-1-amine hydrochloride. LCMS (POS.) m/z: 172.2 (M + H)+. |

TABLE 2-continued

| Intermediate | Reagents | Structure, Name and Data |
|---|---|---|
| 9.11 | 2-fluoro-4-methylbenzaldehyde (AstaTech) and 3.4M methylmagnesium bromide in 2-MeTHF | 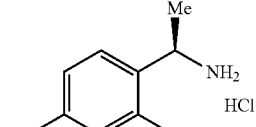<br>(R)-1-(2-fluoro-4-methylphenyl)ethan-1-amine hydrochloride.<br>$^1$H NMR (500 MHz, chloroform-d) δ ppm 8.63-8.99 (m, 3H), 7.44-7.58 (m, 1H), 6.87-7.02 (m, 2H), 4.66-4.83 (m, 1H), 2.35 (s, 3H), 1.67-1.74 (m, 3H). LCMS (POS.) m/z: 137.2 (M − NH$_2$)+. |
| 9.12 | 4-(trifluoromethyl)benzaldehyde and 3.0M ethylmagnesium bromide in diethyl ether | 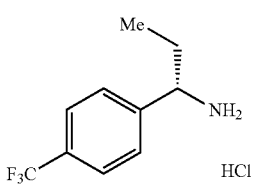<br>(S)-1-(4-(trifluoromethyl)phenyl)propan-1-amine hydrochloride. LCMS (POS.) m/z: 204.2 (M + H)+. |
| 9.13 | 4-(trifluoromethyl)benzaldehyde and 3.0M ethylmagnesium bromide in diethyl ether | 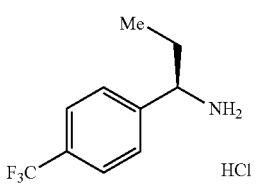 [SMILES: CC[C@@H](N)c1ccc(C(F)(F)F)cc1 ; Cl]<br>(R)-1-(4-(trifluoromethyl)phenyl)propan-1-amine hydrochloride. LCMS (POS.) m/z: 204.2 (M + H)+. |
| 9.14 | 4-(trifluoromethyl)benzaldehyde | 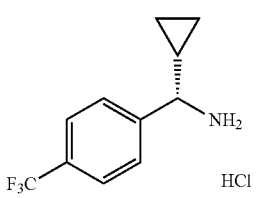<br>(S)-cyclopropyl(4-(trifluoromethyl)phenyl) methanamine hydrochloride. LCMS (POS.) m/z: 199.2 (M − NH$_2$)+. |
| 9.15 | 2-fluoro-4-(trifluoromethyl)benzaldehyde (Sigma-Aldrich) and 3.0M ethylmagnesium bromide in diethyl ether | 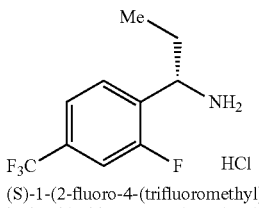<br>(S)-1-(2-fluoro-4-(trifluoromethyl)phenyl)propan-1-amine hydrochloride. LCMS (POS.) m/z: 222.2 (M + H)+. |
| 9.16 | 2-fluoro-4-(trifluoromethyl)benzaldehyde and 3.0M ethylmagnesium bromide in diethyl ether | 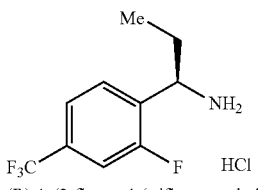<br>(R)-1-(2-fluoro-4-(trifluoromethyl)phenyl)propan-1-amine hydrochloride. LCMS (POS.) m/z: 222.2 (M + H)+. |

TABLE 2-continued

| Intermediate | Reagents | Structure, Name and Data |
|---|---|---|
| 9.17 | 2-fluoro-4-(trifluoromethyl)benzaldehyde and 1.0M isopropylmagnesium bromide in THF | 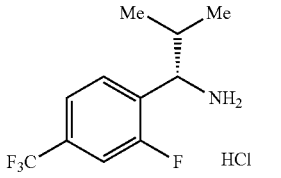 [SMILES: CC(C)[C@H](N)c1ccc(C(F)(F)F)cc1F ; Cl]<br>(S)-1-(2-fluoro-4-(trifluoromethyl)phenyl)-2-methylpropan-1-amine hydrochloride. LCMS (POS.) m/z: 236.2 (M + H)+. |
| 9.18 | 2-fluoro-4-(trifluoromethyl)benzaldehyde and 1.0M isopropylmagnesium bromide in THF | 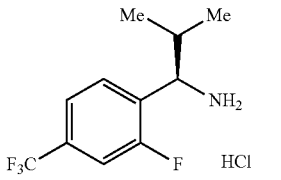 [SMILES: CC(C)[C@@H](N)c1ccc(C(F)(F)F)cc1F ; Cl]<br>(R)-1-(2-fluoro-4-(trifluoromethyl)phenyl)-2-methylpropan-1-amine hydrochloride. LCMS (POS.) m/z: 236.2 (M + H)+. |
| 9.19 | 4-chloro-3-fluorobenzaldehyde (Combi-Blocks Inc.) and 3.0M ethylmagnesium bromide in diethyl ether | 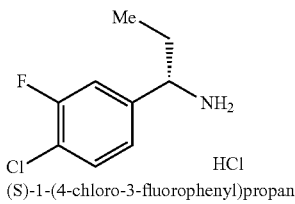<br>(S)-1-(4-chloro-3-fluorophenyl)propan-1-amine hydrochloride. LCMS (POS.) m/z: 171.0 (M − NH$_2$)+. |
| 9.20 | 4-chloro-3-fluorobenzaldehyde (Combi-Blocks Inc.) and 3.0M ehtylmagnesium bromide in diethyl ether | 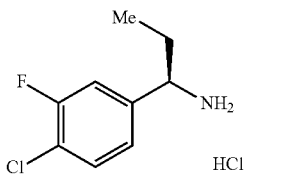 [SMILES: CC[C@@H](N)c1ccc(Cl)c(F)c1 ; Cl]<br>(R)-1-(4-chloro-3-fluorophenyl)propan-1-amine hydrochloride. LCMS (POS.) m/z: 171.2 (M − NH$_2$)+. |
| 9.21 | 3,5-difluorobenzaldehyde and 3.0M ethylmagnesium bromide in diethyl ether | 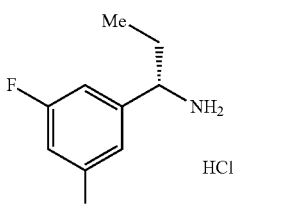<br>(S)-1-(3,5-difluorophenyl)propan-1-amine hydrochloride. LCMS (POS.) m/z: 172.2 (M + H)+. |
| 9.22 | 3,5-difluorobenzaldehyde and 3.0M ethylmagnesium bromide in diethyl ether | 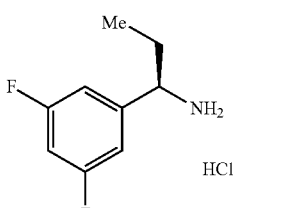<br>(R)-1-(3,5-difluorophenyl)propan-1-amine hydrochloride. LCMS (POS.) m/z: 172.2 (M + H)+. |

TABLE 2-continued

| Intermediate | Reagents | Structure, Name and Data |
|---|---|---|
| 9.23 | 4-chloro-2,5-difluorobenzaldehyde (Combi-Blocks) and 3.0M ethylmagnesium bromide in diethyl ether | 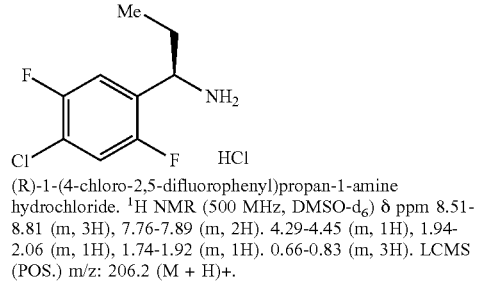<br>(R)-1-(4-chloro-2,5-difluorophenyl)propan-1-amine hydrochloride. $^1$H NMR (500 MHz, DMSO-$d_6$) δ ppm 8.51-8.81 (m, 3H), 7.76-7.89 (m, 2H). 4.29-4.45 (m, 1H), 1.94-2.06 (m, 1H), 1.74-1.92 (m, 1H). 0.66-0.83 (m, 3H). LCMS (POS.) m/z: 206.2 (M + H)+. |
| 9.24 | 4-chloro-3-fluorobenzaldehyde (Combi-Blocks) | 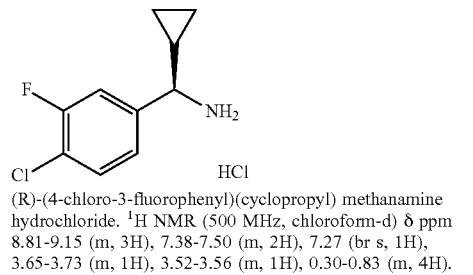<br>(R)-(4-chloro-3-fluorophenyl)(cyclopropyl) methanamine hydrochloride. $^1$H NMR (500 MHz, chloroform-d) δ ppm 8.81-9.15 (m, 3H), 7.38-7.50 (m, 2H), 7.27 (br s, 1H), 3.65-3.73 (m, 1H), 3.52-3.56 (m, 1H), 0.30-0.83 (m, 4H). |
| 9.25 | 4-chloro-2,5-difluorobenzaldehyde (Combi-Blocks) and 3.4M methylmagnesium bromide with 2-MeTHF | 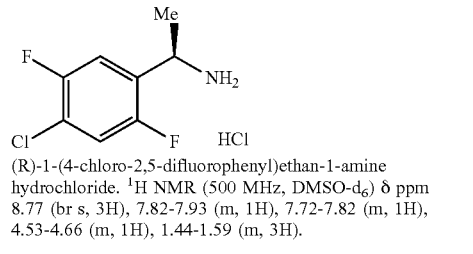<br>(R)-1-(4-chloro-2,5-difluorophenyl)ethan-1-amine hydrochloride. $^1$H NMR (500 MHz, DMSO-$d_6$) δ ppm 8.77 (br s, 3H), 7.82-7.93 (m, 1H), 7.72-7.82 (m, 1H), 4.53-4.66 (m, 1H), 1.44-1.59 (m, 3H). |
| 9.26 | 1-bromo-4-(difluoromethyl)-2-fluorobenzene and 3.4M methylmagnesium bromide with 2-MeTHF | 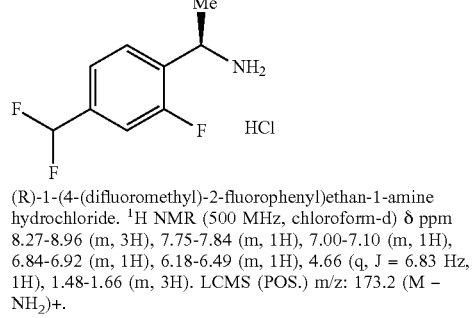<br>(R)-1-(4-(difluoromethyl)-2-fluorophenyl)ethan-1-amine hydrochloride. $^1$H NMR (500 MHz, chloroform-d) δ ppm 8.27-8.96 (m, 3H), 7.75-7.84 (m, 1H), 7.00-7.10 (m, 1H), 6.84-6.92 (m, 1H), 6.18-6.49 (m, 1H), 4.66 (q, J = 6.83 Hz, 1H), 1.48-1.66 (m, 3H). LCMS (POS.) m/z: 173.2 (M − NH$_2$)+. |
| 9.27 | 1-bromo-4-(difluoromethy)-2-fluorobenzene | 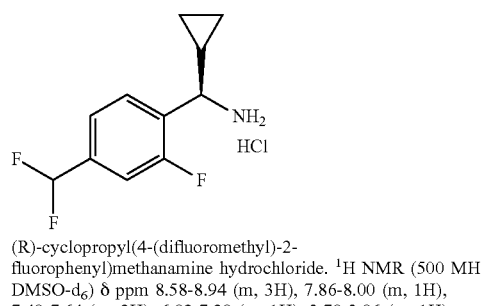<br>(R)-cyclopropyl(4-(difluoromethyl)-2-fluorophenyl)methanamine hydrochloride. $^1$H NMR (500 MHz, DMSO-$d_6$) δ ppm 8.58-8.94 (m, 3H), 7.86-8.00 (m, 1H), 7.48-7.64 (m, 2H), 6.92-7.29 (m, 1H), 3.79-3.96 (m, 1H), 3.27-3.51 (m, 1H), 1.31-1.48 (m, 1H), 0.60-0.79 (m, 2H), 0.45-0.58 (m, 1H), 0.26-0.40 (m, 1H). |

TABLE 2-continued

| Intermediate | Reagents | Structure, Name and Data |
|---|---|---|
| 9.28 | 2-fluoro-4-(trifluoromethyl)benzaldehyde with 3.4M methylmagnesium bromide in 2-MeTHF | 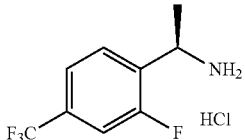<br>(R)-1-(2-fluoro-4-(trifluoromethyl)phenyl)ethanamine hydrochloride. LCMS (POS.) m/z: 208.2 (M + H)+. |
| 9.29 | 2-methoxy-4-(trifluoromethyl)benzaldehyde (Alfa Aesar) | 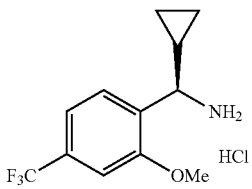 [SMILES: COc1cc(C(F)(F)F)ccc1[C@H](N)C1CC1 ; Cl]<br>(R)-cyclopropyl(2-methoxy-4-(trifluoromethyl)phenyl) methanamine hydrochloride. LCMS (POS.) m/z: 229.0 (M − NH$_2$)+. |
| 9.30 | 3-fluoro-4-methylbenzaldehyde | 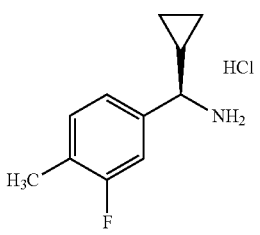<br>(R)-cyclopropyl(3-fluoro-4-methylphenyl) methanamine hydrochloride. $^1$H NMR (400 MHz, DMSO-d6) δ ppm 8.46 (s, 3H), 7.31-7.39 (m, 2H), 7.24 (dd, J = 1.8, 7.7 Hz, 1H), 3.57 (d, J = 9.8 Hz, 1H), 2.25 (d, J = 1.9 Hz, 3H), 1.21-1.31 (m, 1H), 0.64-0.73 (m, 1H), 0.47-0.60 (m, 2H), 0.38 (ddd, J = 4.6, 9.0, 10.4 Hz, 1H). |
| 9.31 | 1-bromo-2,5-difluoro-4-(trifluoromethoxy)benzene | <br>(R)-cyclopropyl(2,5-difluoro-4-(trifluoromethoxy)phenyl)methanamine hydrochloride. $^1$H NMR (500 MHz, DMSO-d6) δ ppm 8.73 (br s, 3H) 8.03 (dd, J = 10.90, 6.49 Hz, 1H) 7.83 (dd, J = 9.21, 6.62 Hz, 1H) 3.83 (br d, J = 9.86 Hz, 1H) 1.35 -1.44 (m, 1H) 0.64-0.74 (m, 2H) 0.51-0.58 (m, 1H) 0.34 (dq, J = 9.70, 4.98 Hz, 1H). LCMS-ESI (POS.) m/z: 267.0 (M + H)+. |

Intermediate 10.0: Preparation of 5-(trifluoromethyl)-2,3-dihydro-1H-inden-2-amine

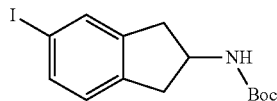 [SMILES: CC(C)(C)OC(=O)NC1Cc2ccc(I)cc2C1]

Step 1: Preparation of (5-iodo-2,3-dihydro-1H-inden-2-yl)carbamate

A 250 mL round-bottom flask was charged with 5-iodo-2,3-dihydro-1H-inden-2-amine (5.20 g, 20.0 mmol, Combi-Blocks, Inc.), Boc$_2$O (4.4 g 20.0 mmol) and 20 mL of DCM. While at rt, 1-methylimidazole (2.1 g, 26.1 mmol) was added and the resulting mixture was allowed to stir at rt for 1 h. The reaction was then concentrated under reduced pressure and purified by silica gel column chromatography (0-50% EtOAc/heptane) to give tert-butyl (5-iodo-2,3-dihydro-1H-inden-2-yl)carbamate (8.04 g). LCMS-ESI (POS.). m/z: 382.0 (M+Na)+.

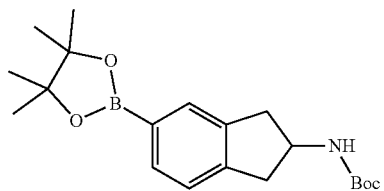 [SMILES: CC(C)(C)OC(=O)NC1Cc2ccc(B3OC(C)(C)C(C)(C)O3)cc2C1]

Step 2: Preparation of (5-(4,4,5,5-tetramethyl-1,3,2-dioxaborolan-2-yl)-2,3-dihydro-1H-inden-2-yl)carbamate A solution of bis(pinacolato)diboron (5.05 g, 19.91 mmol, Sigma-Aldrich), tert-butyl (5-iodo-2,3-dihydro-1H-inden-2-yl)carbamate (6.50 g, 18.10 mmol), PdCl$_2$(dppf)-CH$_2$Cl$_2$ (0.739 g, 0.905 mmol), and potassium acetate (7.10 g, 72.4 mmol) in 30 mL DMF was heated to 100° C. for 12 h. The reaction mixture was partially concentrated and then purified directly by silica gel column chromatography (0-50% EtOAc/heptane) to provide tert-butyl (5-(4,4,5,5-tetramethyl-1,3,2-dioxaborolan-2-yl)-2,3-dihydro-1H-inden-2-yl)carbamate (6.02 g). LCMS-ESI (POS.). m/z: 382.0 (M+Na)+.

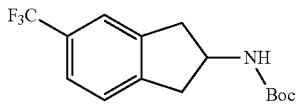

Step 3: Preparation of tert-butyl (5-(trifluoromethyl)-2,3-dihydro-1H-inden-2-yl)carbamate A solution of tert-butyl (5-(4,4,5,5-tetramethyl-1,3,2-dioxaborolan-2-yl)-2,3-dihydro-1H-inden-2-yl)carbamate (6.02 g, 16.76 mmol) in 100 mL MeCN and 20 mL DMF was heated to 80° C. in a crystalizing dish. (1,10-phenanthroline)(trifluoromethyl)copper(I) (7.86 g, 25.1 mmol) was added in 1 g portions over one hour. The reaction mixture was then diluted with saturated aqueous Rochelle® salt and was extracted with DCM. The organics were dried over MgSO$_4$ and concentrated. Purification of the crude residue by silica gel column chromatography (0-50% EtOAc/heptane) gave tert-butyl (5-(trifluoromethyl)-2,3-dihydro-1H-inden-2-yl)carbamate (2.46 g). $^1$H NMR (400 MHz, acetonitrile-d$_3$) δ ppm 7.14-7.55 (m, 3H), 5.47-5.66 (m, 1H), 4.31-4.42 (m, 1H), 3.16-3.31 (m, 2H), 2.74-2.92 (m, 2H), 1.41-1.49 (m, 9H).

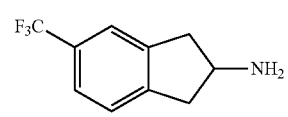

10.0

Step 4: Preparation of 5-(trifluoromethyl)-2,3-dihydro-1H-inden-2-amine, Intermediate 10.0

A solution of tert-butyl (5-(trifluoromethyl)-2,3-dihydro-1H-inden-2-yl)carbamate (2.1 g, 7.0 mmol) in 10 mL DCM was treated with TFA (5.40 mL, 70.0 mmol) and was allowed to stir at rt for 12 h. The reaction mixture was concentrated and purified by reverse phase column chromatography (Puriflash C18, 10-100% (0.1% NH$_4$OH in MeOH)/(0.1% NH$_4$OH in water)] gave 5-(trifluoromethyl)-2,3-dihydro-1H-inden-2-amine (0.49 g). LCMS-ESI (POS.). m/z: 202.2 (M+H)+.

Intermediate 11.0: Preparation of tert-butyl 3-(amino(4-chloro-2,5-difluorophenyl)methyl)azetidine-1-carboxylate

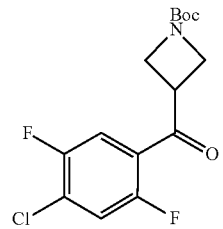 [SMILES: CC(C)(C)OC(=O)N1CC(C(=O)c2cc(F)c(Cl)cc2F)C1]

Step 1: Preparation of tert-butyl 3-(4-chloro-2,5-difluorobenzoyl)azetidine-1-carboxylate Zinc (0.60 g, 9.18 mmol) was added to a 100 mL round-bottom flask and suspended in THF (20 mL). 1,2-dibromoethane (0.073 mL, 0.848 mmol) was then added and the reaction was heated to 65° C. for 5 min and then cooled to rt. Chlorotrimethylsilane (0.090 mL, 0.706 mmol) was added and the reaction was stirred an additional 30 min at rt and 1-boc-3-iodoazetidine (1.23 g, 7.06 mmol) was then added dropwise. After 45 min, the reaction was cooled to −10° C., and lithium chloride (0.90 g, 21.19 mmol, Sigma-Aldrich) and copper(I) cyanide (0.325 g, 10.60 mmol) were introduced. This was stirred for 15 min followed by the addition of 4-chloro-2,5-difluorobenzoyl chloride (1.20 g, 8.83 mmol). The reaction was then warmed to rt and stirred 1.5 hours. The reaction was quenched with sat. sodium bicarbonate and extracted with EtOAc, dried with Na₂SO₄, filtered, and concentrated. Purified via column chromatography (10-20% EtOAc in heptane) to yield the desired product as a white solid (1.6 g). $^1$H NMR (500 MHz, chloroform-d) δ ppm 7.76 (br d, J=2.72 Hz, 1H), 7.26 (d, J=5.71 Hz, 1H), 4.15-4.25 (m, 4H), 3.90-4.06 (m, 1H), 1.39-1.46 (m, 9H). LCMS-ESI (POS.). m/z: 354.2 (M+Na)+.

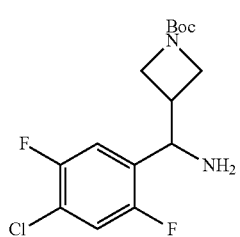

11.0

Step 2: Preparation of tert-butyl 3-(amino(4-chloro-2,5-difluorophenyl)methyl)azetidine-1-carboxylate, Example 11.0 tert-butyl 3-(4-chloro-2,5-difluorobenzoyl)azetidine-1-carboxylate (1.6 g, 4.8 mmol) was dissolved in MeOH at rt. Added ammonium acetate (3.47 g, 48.2 mmol) followed by sodium cyanoborohydride (0.91 g, 14.5 mmol) in portions. The mixture was then heated at reflux for 1 h and then cooled to rt, concentrated, and then dissolved in saturated aqueous NaHCO₃ and EtOAc. The organics were dried with Na₂SO₄, filtered, and concentrated to colorless oil. Purification via column chromatography (10-100% EtOAc/heptanes) provided the desired product (0.88 g). $^1$H NMR (500 MHz, chloroform-d) δ ppm 7.26-7.30 (m, 1H), 7.09-7.18 (m, 1H), 5.06-5.14 (m, 1H), 3.84-3.95 (m, 3H), 3.70-3.80 (m, 1H), 2.79-2.93 (m, 1H), 1.38-1.46 (m, 9H).

Intermediate 12.0: Preparation of 4-(methylsulfonyl)picolinic Acid

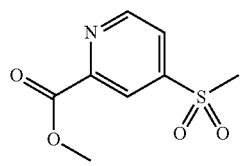

Step 1: Preparation of methyl 4-(methylsulfonyl)picolinate

To a solution of methyl 4-chloropicolinate (5.0 g, 29.1 mmol, Combi-Blocks, Inc.) in NMP (45 mL) were added sodium methanesulfinate (3.72 g, 36.4 mmol, Oakwood Chemical, Inc.), quinoline (0.345 g, 2.91 mmol) and copper (II) chloride (0.392 g, 2.91 mmol). The reaction mixture was stirred at 150° C. for 5 h then allowed to cool to rt and quenched with water (50 mL). The reaction mixture was extracted with DCM (3×50 mL), washed with water (2×100 mL), and brine (100 mL). The organic layer was dried over Na₂SO₄, filtered, and concentrated under reduced pressure. The crude material was purified using silica gel (60-120 mesh) eluting with 55-70% EtOAc/hexanes to give methyl 4-(methylsulfonyl)picolinate (2.5 g) as a pale yellow solid. $^1$H NMR (400 MHz, chloroform-d): δ 9.07 (d, J=4.8 Hz, 1H), 8.62 (s, 1H), 8.02 (d, J=4.8 Hz, 1H), 4.08 (s, 3H), 3.15 (s, 3H). LCMS-ESI (POS.). m/z: 216.1 (M+H)+.

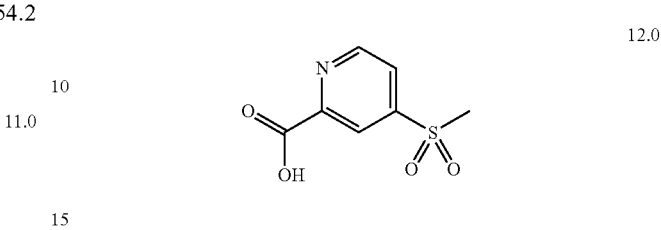

12.0

Step 2: Preparation of Synthesis of 4-(methylsulfonyl)picolinic Acid, Intermediate 12.0

To a solution of methyl 4-(methylsulfonyl)picolinate (1.0 g, 4.65 mmol) in EtOH (12 mL) was added a solution of 1.5M NaOH in water (12 mL). The reaction mixture was stirred at rt for 1 h and then concentrated under reduced pressure. The remaining aqueous solution was cooled to 10° C. and acidified to pH 2 using 3N HCl. The precipitated solid was collected by filtration, washed with water (2×20 mL), and dried under vacuum to give 4-(methylsulfonyl) picolinic acid (0.65 g) as an off-white solid. $^1$H NMR (400 MHz, DMSO-d₆): δ 13.77 (s, 1H), 9.06 (d, J=5.2 Hz, 1H), 8.42 (s, 1H), 8.14 (d, J=5.2 Hz, 1H), 3.41 (s, 3H). LCMS-ESI (NEG). m/z: 200.1 (M–H)+.

Intermediate 13.0: Preparation of 3-(N,N-dimethylsulfamoyl)benzoic Acid

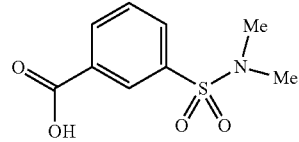

13.0

Preparation of 3-(N,N-dimethylsulfamoyl)benzoic Acid, Intermediate 13.0

To a round-bottom flask was added dimethylamine (2.0M in THF, 9.1 mL, 18.2 mmol) and DCM (40 mL). The solution was cooled to 0° C. and DIPEA (7.88 mL, 45.3 mmol) was added followed by 3-(chlorosulfonyl)benzoic acid (4.0 g, 18.1 mmol) in portions maintaining the temperature <5° C. The reaction was stirred at 0° C. for 2 h then 1N NaOH (50 mL) was added and the phases were separated. The organics were washed with 1N NaOH (2×50 mL) and the aqueous extracts were collected and acidified with conc. HCl to pH 2. The resulting precipitate was collected by filtration and dried under reduced pressure to give the desired product (2.93 g). $^1$H NMR (500 MHz, DMSO-d₆) δ ppm 13.55 (br s, 1H), 8.23-8.29 (m, 1H), 8.18-8.22 (m, 1H), 7.95-8.06 (m, 1H), 7.74-7.85 (m, 1H), 2.63 (s, 6H). LCMS-ESI (POS.). m/z: 230.2 (M+H)+.

The compounds set forth in the following table were synthesized following the procedure described for Intermediate 13.0 using known starting material replacements as described.

TABLE 3

| Intermediate | Reagents | Structure, Name and Data |
|---|---|---|
| 13.1 | 3,3-difluoroazetidine hydrochloride (Synthonix, Inc.) | 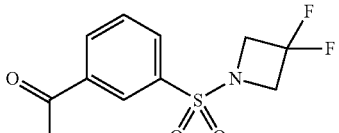<br>3-((3,3-difluoroazetidin-1-yl)sulfonyl)benzoic acid. LCMS-ESI (POS.). m/z: 278.0 (M + H)+. |
| 13.2 | N-isopropylmethylamine (Acros Organics) | 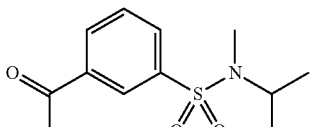<br>3-(N-isopropyl-N-methylsulfamoyl)benzoic acid. LCMS-ESI (POS.). m/z: 258.2 (M + H)+. |
| 13.3 | Azetidine (Matrix Scientific) | 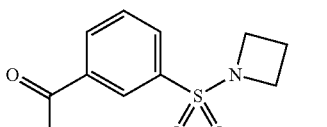<br>3-(azetidin-1-ylsulfonyl)benzoic acid. LCMS-ESI (POS.). m/z: 242.0 (M + H)+. |
| 13.4 | N,O-dimethylhydroxylamine hydrochloride (ACROS Organics) | 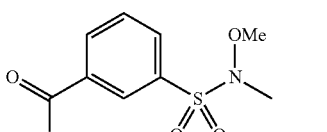<br>3-(N-methoxy-N-methylsulfamoyl)benzoic acid. LCMS-ESI (POS.). m/z: 246.0 (M + H)+. |
| 13.5 | Diethylamine | 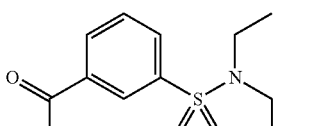<br>3-(N,N-diethylsulfamoyl)benzoic acid. LCMS-ESI (POS.). m/z: 258.2 (M + H)+. |
| 13.6 | (2,2,2-trifluoroethyl)methylamine (Oakwood Products) | 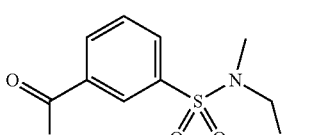<br>3-(N-methyl-N-(2,2,2-trifluoroethyl)sulfamoyl) benzoic acid.<br>LCMS-ESI (POS). m/z: 298.0 (M + H)+. |
| 13.7 | 3-hydroxy-3-methylazetidine hydrochloride (Matrix Scientific) | 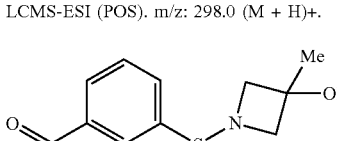<br>3-((3-hydroxy-3-methylazetidin-1-yl)sulfonyl) benzoic acid. $^1$H NMR (400 MHz. DMSO-$d_6$) δ 13.58 (br s, 1H), 8.30 (td, J = 1.31, 7.85 Hz, 1H), 8.24 (t, J = 1.55 Hz, 1H), 8.00-8.10 (m, 1H), 7.84 (t, J = 7.77 Hz, 1H), 5.61 (br s, 1H), 3.60 (d, J = 8.50 Hz, 2H), 3.46 (d, J = 8.19 Hz, 2H), 1.21 (s, 3H). |

TABLE 3-continued

| Intermediate | Reagents | Structure, Name and Data |
|---|---|---|
| 13.8 | 2-(chlorosulfonyl) isonicotinic acid hydrochloride (Astatech) 3-cyano-azetidine hydrochloride (Advanced Chem Blocks) | 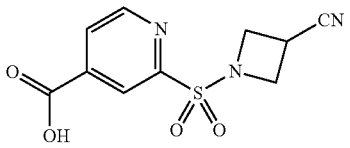 [SMILES: N#CC1CN(S(=O)(=O)c2cc(C(=O)O)ccn2)C1] 2-((3-cyanoazetidin-1-yl)sulfonyl)isonicotinic acid. LCMS-ESI (POS.). m/z: 268.0 (M + H)+. |
| 13.9 | 2-oxo-6-azaspiro[3.3]-heptane (JW Pharma Lab) | 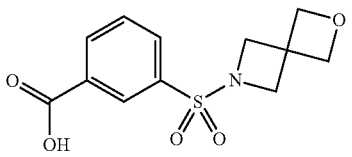 [SMILES: O=C(O)c1cccc(S(=O)(=O)N2CC3(COC3)C2)c1] 3-(2-oxa-6-azaspiro[3.3]heptan-6-ylsulfonyl) benzoic acid. LCMS-ESI (POS.). m/z: 284.2 (M + H)+. |
| 13.10 | 3-methoxyazetidine hydrochloride (JW Pharma Lab) | 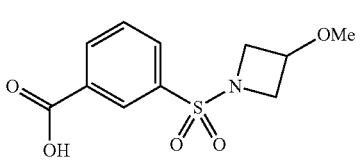 [SMILES: COC1CN(S(=O)(=O)c2cccc(C(=O)O)c2)C1] 3-((3-methoxyazetidin-1-yl)sulfonyl)benzoic acid. LCMS-ESI (POS.). m/z: 272.2 (M + H)+. |

Intermediate 14.0: Preparation of 3-(N,N-dimethylsulfamoyl)benzoic Acid

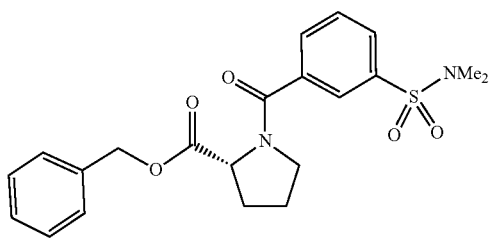 [SMILES: CN(C)S(=O)(=O)c1cccc(C(=O)N2CCC[C@@H]2C(=O)OCc2ccccc2)c1]

Step 1: Preparation of benzyl (3-(N,N-dimethylsulfamoyl)benzoyl)-D-prolinate

To a 250 mL round-bottom flask was added 3-(N,N-dimethylsulfamoyl)benzoic acid (1.8 g, 7.9 mmol), TBTU (2.5 g, 7.9 mmol), (R)-benzyl pyrrolidine-2-carboxylate hydrochloride (1.9 g, 7.9 mmol) and dichloromethane (40 mL). After cooling to 0° C., DIPEA (4.1 mL, 23.6 mmol) was added. The reaction was allowed to warm to 23° C. and stirred for an additional 5 h then 1N HCl (20 mL) was added. The organics were separated and concentrated under reduced pressure and the crude residue was purified using silica gel chromatography (50-100% EtOAc/heptanes) to obtain the desired product as a vicious oil. LCMS-ESI (POS.). m/z: 417.2 (M+H)+.

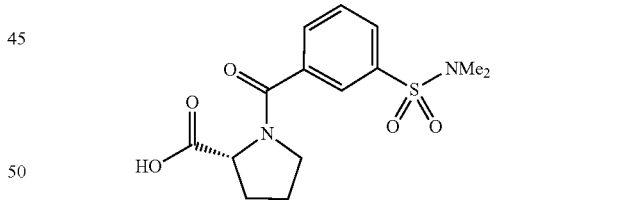

14.0

Step 2: Preparation of (3-(N,N-dimethylsulfamoyl)benzoyl)-D-proline, Intermediate 14.0

To a pressure vessel was added (3-(N,N-dimethylsulfamoyl)benzoyl)-D-prolinate (3.27 g, 7.85 mmol) and methanol (40 mL). The solution was sparged and backfilled with nitrogen. 10% Pd/C (0.084 g, 0.785 mmol) was carefully added and the vessel was charged with hydrogen (40 psi) and stirred for 12 h at rt. The solution was filtered through Celite and concentrated to give the crude product. Purification using silica gel column chromatography (0-10% MeOH:DCM) provided the desired product as a vicious oil (2.27 g). LCMS-ESI (POS.). m/z: 327.0 (M+H)+.

Intermediate 15.0: Preparation of (rac)-1-(amino(2-fluoro-4-(trifluoromethyl)phenyl)methyl)cyclopropan-1-ol hydrochloride

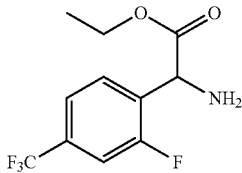 [SMILES: CCOC(=O)C(N)c1ccc(C(F)(F)F)cc1F]

Step 1: Preparation of ethyl (rac)-2-amino-2-(2-fluoro-4-(trifluoromethyl)phenyl)acetate A 250 mL round-bottom flask was charged with 2-amino-2-(2-fluoro-4-(trifluoromethyl)phenyl)acetic acid (22.1 g, 93 mmol) and ethanol (200 mL). To that solution was added thionyl chloride (20.4 mL, 280 mmol). The flask was fitted with a reflux condenser and heated to reflux. After 3 hours, the mixture was cooled and the volatiles were concentrated under reduced pressure. The oil was azeotroped with ethanol (50 mL×3). The crude material was diluted with ethyl acetate (~150 mL) and 6N HCl (200 mL) and stirred for 30 minutes then transferred into a separatory funnel. The organics were extracted with water (150 mL×5). The pH of the water was adjusted to ~8 using 6N sodium hydroxide and then extracted with chloroform (50 mL×5) to give (rac)-2-amino-2-(2-fluoro-4-(trifluoromethyl)phenyl)acetate (7.28 g, 27.5 mmol) as an off-white solid. $^1$H NMR (500 MHz, DMSO-$d_6$) δ ppm 7.74 (br t, J=7.46 Hz, 1H) 7.54-7.69 (m, 2H) 4.80 (s, 1H) 4.05-4.15 (m, 2H) 2.40 (br s, 2H) 1.12 (t, J=7.01 Hz, 3H). LCMS-ESI (POS.). m/z: 266.2 (M+H)+.

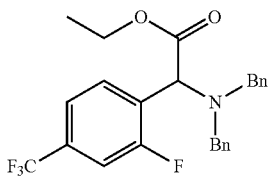

Step 2: Preparation of ethyl (rac)-2-(dibenzylamino)-2-(2-fluoro-4-(trifluoromethyl)phenyl)acetate A 100 mL round-bottom flask was charged with (rac)-2-amino-2-(2-fluoro-4-(trifluoromethyl)phenyl)acetate (7.3 g, 27.5 mmol) and suspended in acetonitrile (70 mL). To that suspension was added DIPEA (19.2 mL, 110 mmol) followed by (bromomethyl)benzene (13.1 mL, 110 mmol). The flask was fitted with a condenser and heated to reflux. After 21 hours, the contents of the flask were concentrated under reduced pressure and the resulting solids were dissolved with DCM and purified by silica gel chromatography eluting with 0-10% ethyl acetate/heptane to provide the desired product (10.98 g) as a pale yellow oil. $^1$H NMR (500 MHz, DMSO-$d_6$) δ ppm 7.56-7.82 (m, 3H) 7.19-7.43 (m, 10H) 3.26-4.26 (m, 7H) 1.11-1.30 (m, 3H). LCMS-ESI (POS.). m/z: 446.0 (M+H)+.

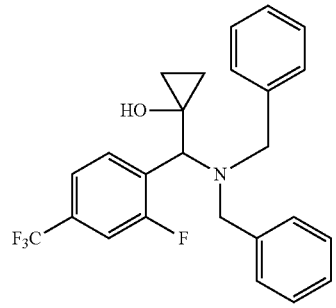 [SMILES: OC1(C(c2ccc(C(F)(F)F)cc2F)N(Cc2ccccc2)Cc2ccccc2)CC1]

Step 3: Preparation of (rac)-1-((dibenzylamino)(2-fluoro-4-(trifluoromethyl)phenyl)methyl)cyclopropan-1-ol A 250 mL round-bottom flask was charged with ethyl (rac)-2-(dibenzylamino)-2-(2-fluoro-4-(trifluoromethyl)phenyl)acetate (11 g, 24.7 mmol) and diluted with THF (82 mL). While at rt, titanium(IV) isopropoxide (3.7 mL, 12.3 mmol) was added. Ethylmagnesium bromide 3.0M in diethyl ether (30.0 mL, 90 mmol) was then added dropwise via syringe pump over the course of 1.75 hours. Immediately after addition was complete, the reaction mixture was quenched with a saturated solution of NH$_4$Cl. After stirring at rt for an additional 30 minutes, the mixture was filtered through a pad of Celite, transferred to a separatory funnel, and diluted with ethyl acetate (250 mL). The layers were separated and the aqueous was extracted with ethyl acetate (50 mL×3). The combined organic extracts were dried with magnesium sulfate, filtered, concentrated under reduced pressure and purified by silica gel chromatography eluting with 0-10% ethyl acetate/heptane to give the desired product (6.96 g) as a viscous, pale yellow oil. $^1$H NMR (500 MHz, DMSO-$d_6$) δ ppm 8.19 (br t, J=7.46 Hz, 1H) 7.58-7.66 (m, 2H) 7.25-7.35 (m, 8H) 7.17-7.24 (m, 2H) 5.46 (s, 1H) 3.93 (br d, J=14.14 Hz, 2H) 3.67 (br d, J=14.14 Hz, 2H) 3.57 (s, 1H) 0.84-0.93 (m, 1H) 0.52-0.60 (m, 1H) 0.40-0.51 (m, 1H) 0.22-0.33 (m, 1H). LCMS-ESI (POS.). m/z: 430.0 (M+H)+.

15.0

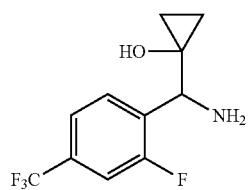

Step 4: Preparation of (rac)-1-(amino(2-fluoro-4-(trifluoromethyl)phenyl)methyl)cyclopropan-1-ol Intermediate, 15.0

A 125 mL pressure flask was charged with 10% Pd/C (0.077 g, 0.871 mmol) under an atmosphere of nitrogen. Ethanol (50 mL) was added followed by (rac)-1-((dibenzylamino)(2-fluoro-4-(trifluoromethyl)phenyl)methyl)cyclopropan-1-ol (3.74 g, 8.71 mmol). The flask was sealed charged with 25-35 psi with hydrogen. After 1 hour, Celite was added and the slurry was filtered. The filter cake was washed with ethanol (25 mL×5) to give 1.99 g of desired product as a dark green solid. The solids were then dissolved in 5 mL ethyl acetate and 4.0M HCl in dioxane (10 mL) stirred for 15 minutes at rt. The mixture was concentrated and triturated with ethyl acetate to give (rac)-1-(amino(2-fluoro-4-(trifluoromethyl)phenyl)methyl)cyclopropan-1-ol (1 g) as a gray solid. $^1$H NMR (500 MHz, DMSO-d$_6$) δ ppm 8.68 (br s, 3H) 7.91 (t, J=7.59 Hz, 1H) 7.72-7.85 (m, 2H) 6.01 (s, 1H) 4.27 (s, 1H) 0.79-0.95 (m, 2H) 0.62-0.76 (m, 2H). LCMS-ESI (POS.). m/z: 250.2 (M+H)+.

The compounds set forth in the following table were synthesized following the procedure described for Intermediate 15.0 using known starting material replacements as described.

TABLE 4

| Intermediate | Reagents | Structure, Name and Data |
|---|---|---|
| 15.1 | methyl 2-amino-2-(4-chloro-2,5-difluorophenyl)acetate (AP Bioscience) | 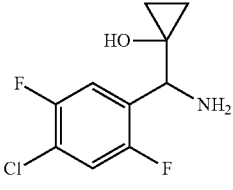 [SMILES: NC(c1cc(F)c(Cl)cc1F)C1(O)CC1] 1-(amino(4-chloro-2,5-difluorophenyl)methyl)cyclopropanol LCMS-ESI (POS.) m/z: 234.1 (M + H)+. |

Intermediate 16.0: Preparation of 3-(2-hydroxypropan-2-yl)benzoic Acid

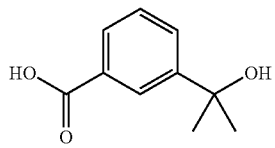

Step 1: Preparation of 3-(2-hydroxypropan-2-yl)benzoic Acid, Intermediate 16.0

3-acetylbenzoic acid (5 g, 30.5 mmol) was suspended in THF (150 mL) and cooled to −78° C. 3.4M methylmagnesium bromide solution in 2-MeTHF (22.4 mL, 76 mmol) was added dropwise over 15 min and then stirred at −78° C. for an additional 3 h. The reaction was then quenched with 1M HCl (20 mL) and extracted with EtOAc (2×100 mL). The organics were dried using Na$_2$SO$_4$, filtered, and concentrated to deliver the desired product. $^1$H NMR (500 MHz, DMSO-d$_6$) δ ppm 12.71-13.04 (m, 1H), 8.03-8.13 (m, 1H), 7.73-7.80 (m, 1H), 7.66-7.73 (m, 1H), 7.39-7.49 (m, 1H), 5.08-5.19 (m, 1H), 1.37-1.48 (m, 6H).

Intermediate 17.1: Preparation of 3-(2,2,2-trifluoro-1-hydroxyethyl)benzoic Acid

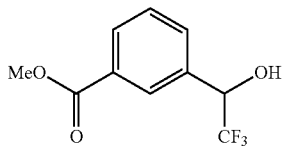

Step 1: Preparation of methyl 3-(2,2,2-trifluoro-1-hydroxyethyl)benzoate

A 100 mL round-bottom flask was charged with methyl 3-formylbenzoate (3.28 g, 20.0 mmol), (trifluoromethyl)trimethylsilane, (2.0M in THF, 15.0 mL, 30.0 mmol) in THF (40.0 mL). The reaction was cooled to 0° C. and then TBAF (1.0M solution in THF, 0.50 mL, 0.50 mmol) was added. The mixture was allowed to warm to rt and after stirring for 1 hour at that temperature another 4.0 mL of 1M TBAF in THF was added. The mixture was then concentrated, diluted with ethyl acetate, then washed with saturated aqueous NaHCO$_3$, water, brine. The organics were dried over Na$_2$SO$_4$, filtered, and concentrated to give a brown gum. The crude product was purified by silica gel chromatography (5-30% ethyl acetate/heptane) to give methyl 3-(2,2,2-trifluoro-1-hydroxyethyl)benzoate (3.69 g) as a white solid. $^1$H NMR (500 MHz, DMSO-d$_6$) δ ppm 8.12 (s, 1H), 7.98 (dd, J=7.78, 1.30 Hz, 1H), 7.77 (br d, J=7.79 Hz, 1H), 7.58 (t, J=7.79 Hz, 1H), 7.00 (d, J=5.45 Hz, 1H), 5.30-5.36 (m, 1H). LCMS-ESI (POS.) m/z: 235.2 (M+H)+.

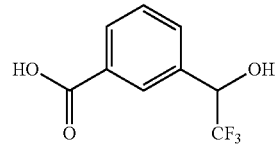

Step 2: Preparation of 3-(2,2,2-trifluoro-1-hydroxyethyl)benzoic Acid, Intermediate 17.1

A 25 mL round-bottom flask was charged with methyl 3-(2,2,2-trifluoro-1-hydroxyethyl)benzoate (500 mg, 2.14 mmol), 2M lithium hydroxide in water (1.60 mL, 3.20 mmol) in THF (8.5 mL). The reaction was stirred at 23° C. for 18 hours. The reaction was concentrated to give a white solid and used without further purification. LCMS-ESI (POS.) m/z: 221.2 (M+H)+.

The compounds set forth in the following table were synthesized following the procedure described for Intermediate 17.1 using known starting material replacements as described.

TABLE 5

| Intermediate | Reagents | Structure, Name and Data |
|---|---|---|
| 17.0 | methyl 3-acetylbenzoate (Accela) | 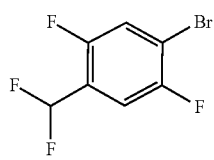<br>3-(1,1,1-trifluoro-2-hydroxypropan-2-yl)benzoic acid LCMS-ESI (POS.) m/z: 235.2 (M + H)+. |

Intermediate 18.0: Preparation of 3-((2-methoxy-2-oxoethyl)sulfonyl)benzoic Acid

Step 1: Preparation of 3-((2-methoxy-2-oxoethyl)thio)benzoic Acid

A 50 mL round-bottom flask with was charged with anhydrous potassium carbonate (610 mg, 4.41 mmol), 3-mercaptobenzoic acid (340 mg, 2.205 mmol, TCI America), chloroacetic acid methyl ester (193 μL, 2.21 mmol) and acetonitrile (4.4 mL). The reaction was stirred at rt for 2 h then diluted with water (10 mL). The pH was adjusted to 1 using 6N HCl and then extracted with DCM (3×25 mL). The combined organics were washed with brine, passed through phase separation filter, and concentrated to give a white solid that was used without further purification. LCMS-ESI (POS.) m/z: 249.0 (M+Na)+.

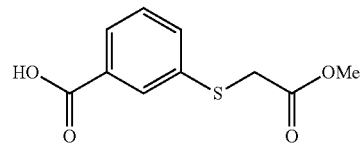 [SMILES: COC(=O)CSc1cccc(C(=O)O)c1]

18.0

Step 2: Preparation of 3-((2-methoxy-2-oxoethyl)sulfonyl)benzoic Acid, Intermediate 18.0

A 50 mL round-bottom flask was charged with 3-((2-methoxy-2-oxoethyl)thio)benzoic acid (450 mg, 2.0 mmol), MCPBA (936 mg, 4.2 mmol) in DCM (8.0 mL). The reaction was then stirred at 23° C. for 2 hours, concentrated, and purified by silica gel chromatography (0-5% 10:1 AcOH:MeOH in DCM) to afford the desired product as a white solid. ¹H NMR (500 MHz, DMSO-d₆) δ ppm 13.42-13.74 (m, 1H), 8.37-8.46 (m, 1H), 8.26-8.35 (m, 1H), 8.11-8.22 (m, 1H), 7.71-7.87 (m, 1H), 4.71-4.84 (m, 2H), 3.51-3.65 (m, 3H).

Intermediate 19.0: 4-bromo-2,5-difluorobenzaldehyde

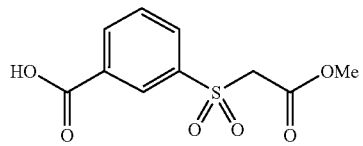

19.0

Step 1: Preparation of 4-bromo-2,5-difluorobenzaldehyde, Intermediate 19.0

A 250 mL round-bottom flask was charged with 4-bromo-2,5-difluorobenzaldehyde (5.0 g, 22.6 mmol), triethylamine trihydrofluoride (7.44 mL, 45.2 mmol) and DCM (45.2 mL). The solution was cooled to 0° C. followed by addition of (diethylamino)difluorosulfonium tetrafluoroborate (Xtalfluor-E®, 10.4 g, 45.2 mmol). The reaction was stirred for 1 h at 0° C. and then allowed to warm to rt and stirred for an additional 2 h. The solution was then cooled to 0° C. followed by dropwise addition of 1N NaOH until pH 7. The mixture was diluted with DCM, the layers were separated, the organics were passed through a phase separation column, and then concentrated to give a brown oil. ¹H NMR (500 MHz, chloroform-d) δ ppm 7.32-7.45 (m, 2H), 6.68-6.98 (m, 1H).

Intermediate 20.0: 3-((3-(Methoxycarbonyl)cyclobutyl)thio)benzoic Acid

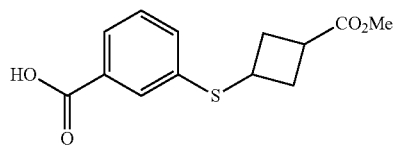

20.0

Step 1: Preparation of 3-((3-(Methoxycarbonyl)cyclobutyl)thio)benzoic acid, Intermediate 20.0

A mixture of 3-mercaptobenzoic acid (2.1 g, 13.5 mmol), methyl 3-chlorocyclobutanecarboxylate (4.0 g, 26.9 mmol; purchased as a 9:1 diastereomeric mixture (favoring trans) from Synthonix, Inc.), and potassium carbonate (7.43 g, 53.8 mmol) in DMF was stirred at 50° C. for 16 h. The reaction mixture was diluted with water and extracted with EtOAc. The combined organic layers were washed with brine, dried over MgSO₄, and concentrated under reduced pressure. The crude material was purified by MPLC using silica gel and eluting with a 0-40% EtOAc/EtOH (3:1) in heptane to provide 3-((3-(methoxycarbonyl)cyclobutyl)thio)benzoic acid (2.02 g) as white powder. ¹H NMR (400 MHz, DMSO-d₆) δ 12.91-13.22 (m, 1H), 7.74-7.77 (m, 2H), 7.44-7.49 (m, 2H), 3.96 (tt, J=7.77, 8.97 Hz, 1H), 3.56-3.61 (m, 3H), 3.11-3.23 (m, 1H), 2.67-2.73 (m, 2H), 2.10-2.21 (m, 2H). LCMS-ESI (POS.) m/z: 289.0 (M+Na)+.

Intermediate 21.0:
4-(4-(trifluoromethyl)benzoyl)pyrrolidin-2-one

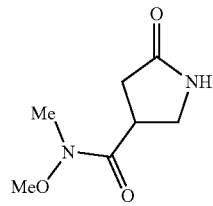

Step 1: Preparation of
N-methoxy-N-methyl-5-oxopyrrolidine-3-carboxamide

A solution of 5-oxopyrrolidine-3-carboxylic acid (1.0 g, 7.8 mmol), DIPEA (2.71 mL, 15.49 mmol) and N,O-dimethylhydroxylamine hydrochloride (0.755 g, 7.75 mmol) in DCM (20 mL) was cooled to 0° C. EDC hydrochloride (1.6 g, 8.5 mmol) was added and the reaction mixture was allowed to warm to rt and stir for additional 3 h. The mixture was diluted with saturated NaHCO₃ solution and the aqueous layer was extracted DCM (25 mL, 5×). The combined organic layers were dried over MgSO₄, filtered, and concentrated under reduced pressure. The crude material was purified by MPLC using silica gel eluting with a gradient of 10-100% EtOAc/EtOH (3:1) in heptane to provide N-methoxy-N-methyl-5-oxopyrrolidine-3-carboxamide (0.88 g) as colorless oil. ¹H NMR (400 MHz, chloroform-d) δ 6.08-6.25 (m, 1H), 3.65-3.77 (m, 4H), 3.56-3.63 (m, 2H), 2.64-2.79 (m, 1H), 2.52 (dd, J=9.48, 16.95 Hz, 1H).

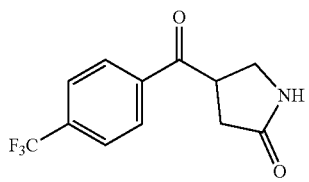 [SMILES: O=C1CC(C(=O)c2ccc(C(F)(F)F)cc2)CN1]

Step 2: Preparation of
4-(4-(trifluoromethyl)benzoyl)pyrrolidin-2-one

N-methoxy-N-methyl-5-oxopyrrolidine-3-carboxamide (0.27 g, 1.57 mmol) and 1-bromo-4-(trifluoromethyl)benzene (0.98 g, 4.39 mmol) were dissolved in THF (6.3 mL) and cooled to −78° C. A solution of n-BuLi (1.6M in hexanes, 1.69 mL, 4.23 mmol) was added dropwise and the reaction mixture was stirred at −78° C. for an additional 20 min. The reaction was diluted with EtOAc and quenched with saturated aqueous NH₄Cl solution and diluted with EtOAc. The organics were separated, dried over MgSO₄, filtered, and concentrated under reduced pressure. The residue was suspended in heptane and filtered to give 4-(4-(trifluoromethyl)benzoyl)pyrrolidin-2-one (0.20 g) as white solid. LCMS-ESI (POS.) m/z: 258.0 (M+H)+.

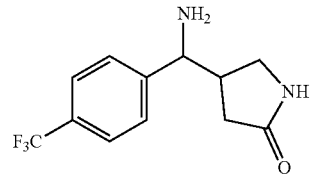 [SMILES: NC(c1ccc(C(F)(F)F)cc1F)C1CNC(=O)C1]

Step 3: Preparation of 4-(amino(4-(trifluoromethyl)phenyl)methyl)pyrrolidin-2-one, Intermediate 21.0

A solution of 4-(4-(trifluoromethyl)benzoyl)pyrrolidin-2-one (0.2 g, 0.78 mmol) in methanol (7.8 mL) was treated with ammonium acetate (0.6 g, 7.8 mmol) and sodium cyanoborohydride (0.147 g, 2.3 mmol). The reaction mixture was stirred at rt for 16 h and then concentrated and partitioned between DCM and a saturated aqueous NaHCO₃. The aqueous layer was extracted with DCM, and the combined organic extracts were dried over MgSO₄, filtered, and concentrate to afford crude 4-(amino(4-(trifluoromethyl)phenyl)methyl)pyrrolidin-2-one as light yellow oil. This product was directly used in the subsequent reaction without further purification. LCMS-ESI (POS.) m/z: 259.0 (M+H)+.

The compounds set forth in the following table were synthesized following the procedure described for Intermediate 21.0 using known starting material replacements as described.

TABLE 6

| Intermediate | Reagents | Structure, Name and Data |
|---|---|---|
| 21.1 | 1-bromo-2-fluoro-4-(trifluoromethyl)-benzene (Combi-Blocks, Inc) | ![structure] 4-(amino(2-fluoro-4-(trifluoromethyl)phenyl)methyl)pyrrolidin-2-one LCMS-ESI (POS.) m/z: 291.0 (M + H)+ |
| 21.2 | 1-bromo-2,5-difluoro-4-(trifluoromethyl)benzene (Combi-Blocks) | ![structure] 4-(amino(2,5-difluoro-4-(trifluoromethyl)phenyl)methyl)pyrrolidin-2-one LCMS-ESI (POS.) m/z: 295.1 (M + H)+ |

Intermediate 22.0: 4-(2-Fluoro-4-(trifluoromethyl)benzoyl)pyrrolidin-2-one

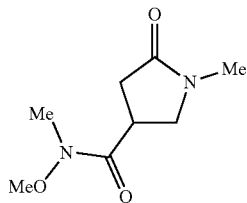 [SMILES: CON(C)C(=O)C1CC(=O)N(C)C1]

Step 1: Preparation of N-Methoxy-N,1-dimethyl-5-oxopyrrolidine-3-carboxamide This compound was prepared from 1-methyl-5-oxopyrrolidine-3-carboxylic acid (1.00 g, 6.99 mmol) in the same manner as the one described in the preparation of 21.0. $^1$H NMR (500 MHz, DMSO-$d_6$) δ 3.66-3.72 (m, 3H), 3.52-3.59 (m, 2H), 3.34-3.38 (m, 1H), 2.68-2.73 (m, 3H), 2.41-2.46 (m, 2H).

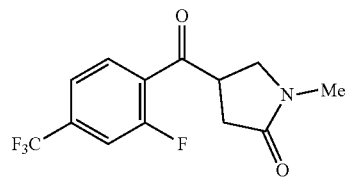 [SMILES: CN1CC(C(=O)c2ccc(C(F)(F)F)cc2F)CC1=O]

Step 2: Preparation of 4-(2-Fluoro-4-(trifluoromethyl)benzoyl)-1-methylpyrrolidin-2-one This compound was prepared from N-methoxy-N,1-dimethyl-5-oxopyrrolidine-3-carboxamide (0.98 g, 5.26 mmol) and 1-bromo-2-fluoro-4-(trifluoromethyl)benzene (1.79 g, 7.37 mmol) in the same manner as the one described in the preparation of 21.0, except that the crude product was purified by MPLC using silica gel eluting with a gradient of 0-35% mixed EtOAc/EtOH (3:1) in heptane. LCMS-ESI (POS.) m/z: 290.2 (M+H)+.

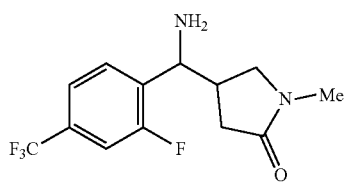

22.0

Step 3: Preparation of 4-(amino(2-fluoro-4-(trifluoromethyl)phenyl)methyl)-1-methylpyrrolidin-2-one, Intermediate 22.0

A mixture of 4-(2-fluoro-4-(trifluoromethyl)benzoyl)-1-methylpyrrolidin-2-one (0.21 g, 0.73 mmol), potassium acetate (0.106 g, 1.70 mmol) and hydroxylamine hydrochloride (0.065 g, 1.55 mmol) in DCM (4 mL) was stirred at 50° C. for 12 h. The mixture was diluted with EtOAc and washed with water. The aqueous fractions were extracted with EtOAc, and the combined organic layers were dried over MgSO$_4$, filtered, and concentrated under reduced pressure to provide crude oxime product 4-((2-fluoro-4-(trifluoromethyl)phenyl)(hydroxyimino)methyl)-1-methylpyrrolidin-2-one (0.20 g). LCMS-ESI (POS.) m/z: 305.0 (M+H)+. This product was directly used in the subsequent reaction without further purification.

To a 25-mL pressure flask was added a solution of 4-((2-fluoro-4-(trifluoromethyl)phenyl)(hydroxyimino)methyl)-1-methylpyrrolidin-2-one (0.20 g, 0.657 mmol) in AcOH (3 mL). Zinc dust (420 mg, 6.57 mmol) was added and the reaction mixture stirred at 50° C. for 12 h. The remaining solid was filtered off, the filtrate was concentrated, dissolved in DCM, and treated with a saturated aqueous NaHCO$_3$. The biphasic mixture was stirred for 10 min then extracted with DCM. The combined organic layers were dried over MgSO$_4$, filtered, and concentrated to afford crude 4-(amino(2-fluoro-4-(trifluoromethyl)phenyl)methyl)-1-methylpyrrolidin-2-one as yellow oil. This product was directly used in the subsequent reactions without further purification. LCMS-ESI (POS.) m/z: 291.2 (M+H)+.

Intermediate 23.0: (R)-1-(3-(methylthio)benzoyl)-2,3-dihydro-1H-pyrrole-2-carboxylic Acid

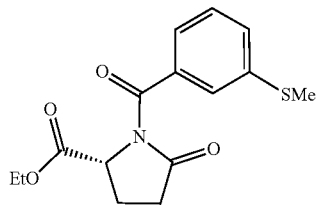 [SMILES: CCOC(=O)[C@H]1CCC(=O)N1C(=O)c1cccc(SC)c1]

Step 1: Preparation of (R)-Ethyl 1-(3-(methylthio)benzoyl)-5-oxopyrrolidine-2-carboxylate To a 25-mL vial was added 3-(methylthio)benzoic acid (0.3 g, 1.78 mmol), DCM (3.5 mL) and a few drops of DMF. Oxalyl chloride (0.19 mL, 2.14 mmol) was added dropwise, and the reaction mixture was stirred at rt for 2 h. The solvent was evaporated to afford crude acid chloride product as yellow solid which was directly used in the subsequent reaction without purification.

To a 25-mL vial was added (R)-ethyl 5-oxopyrrolidine-2-carboxylate (0.18 g, 1.13 mmol), DIPEA (0.586 mL, 4.53 mmol), DMAP (0.028 g, 0.227 mmol), and DCM (4.25 mL). The acid chloride from above (0.317 g, 1.7 mmol) was added in several portions over 5 min, and the resulting reaction mixture was stirred at rt for 12 h. The reaction was quenched with a saturated aqueous NaHCO$_3$, and the aqueous fraction was extracted with DCM. The combined organic layers were dried over MgSO$_4$, filtered, and concentrated under reduced pressure. The crude material was purified by MPLC using silica gel and eluting with 0-30% EtOAc in heptane to provide (R)-ethyl 1-(3-(methylthio)benzoyl)-5-oxopyrrolidine-2-carboxylate (0.34 g) as colorless oil. LCMS-ESI (POS.) m/z: 308.2 (M+H)+. $^1$H NMR (400 MHz, chloroform-d) δ 7.50-7.58 (m, 1H), 7.38-7.46 (m, 2H), 7.30-7.38 (m, 1H), 4.89 (dd, J=3.89, 8.86 Hz, 1H), 4.28 (dq, J=0.98, 7.14 Hz, 2H), 2.69-2.85 (m, 1H), 2.55-2.65 (m, 1H), 2.42-2.54 (m, 4H), 2.18 (dq, J=4.15, 8.91 Hz, 1H), 1.32 (t, J=7.10 Hz, 3H).

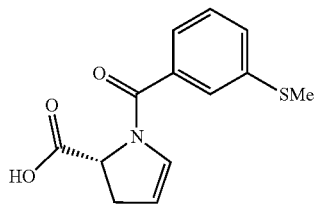

23.0

Step 2: Preparation of (R)-1-(3-(methylthio)benzoyl)-2,3-dihydro-1H-pyrrole-2-carboxylic Acid, Intermediate 23.0

A solution of (R)-ethyl 1-(3-(methylthio)benzoyl)-5-oxopyrrolidine-2-carboxylate (0.35 g, 1.14 mmol) in toluene (7.6 mL) was cooled to −78° C. and treated with Li(Et)$_3$BH (1M in THF, 1.25 mL, 1.25 mmol) dropwise. After 30 min at −78° C., DIPEA (1.03 mL, 7.97 mmol) and DMAP (0.014 g, 0.11 mmol) were added, followed by dropwise addition of TFAA (0.178 mL, 1.25 mmol). The reaction mixture was allowed to slowly warm to rt and stir for an additional 3 h. The reaction was concentrated and the crude material was purified by MPLC using silica gel and eluting with 0-30% EtOAc in heptane to provide (R)-ethyl 1-(3-(methylthio)benzoyl)-2,3-dihydro-1H-pyrrole-2-carboxylate (0.087 g) as yellow oil. LCMS-ESI (POS.) m/z: 292.2 (M+H)+. $^1$H NMR (400 MHz, chloroform-d) δ 7.32-7.46 (m, 4H), 6.52 (br s, 1H), 5.14 (br s, 1H), 5.01 (dd, J=4.87, 11.40 Hz, 1H), 4.26-4.33 (m, 2H), 3.06-3.21 (m, 1H), 2.69-2.81 (m, 1H), 2.51-2.52 (m, 3H), 1.30-1.36 (m, 3H).

(R)-ethyl 1-(3-(methylthio)benzoyl)-2,3-dihydro-1H-pyrrole-2-carboxylate (0.08 g, 0.275 mmol) was dissolved in 1,4-dioxane (1.4 mL) and treated with lithium hydroxide (0.032 g, 1.373 mmol). The solution was stirred at rt for 3 h and then diluted with water and acidified with 1N HCl to pH=3. The mixture was extracted with EtOAc, and the combined organic layers were dried over MgSO$_4$, filtered, and concentrated under reduced pressure to afford crude (R)-1-(3-(methylthio)benzoyl)-2,3-dihydro-1H-pyrrole-2-carboxylic acid as light-yellow oil. This material was directly used in subsequent reactions without further purification. LCMS-ESI (POS.) m/z: 264.2 (M+H)+.

Intermediate 24.0: (S)-3-((R)-2-((4-(trifluoromethyl)benzyl)carbamoyl)pyrrolidine-1-carbonyl)piperidine-1-sulfonyl chloride

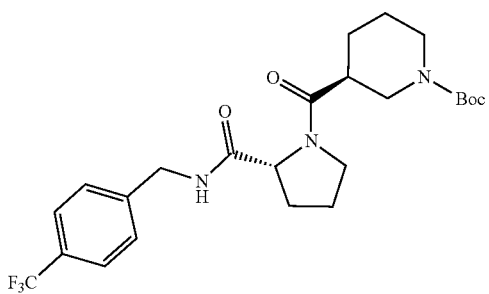 [SMILES: CC(C)(C)OC(=O)N1CCC[C@H](C(=O)N2CCC[C@@H]2C(=O)NCc2ccc(C(F)(F)F)cc2)C1]

Step 1: Preparation of (S)-tert-butyl 3-((R)-2-((4-(trifluoromethyl)benzyl)carbamoyl)pyrrolidine-1-carbonyl)piperidine-1-carboxylate To a solution of (S)-1-Boc-piperidine-3-carboxylic acid (93 mg, 0.404 mmol) and TBTU (142 mg, 0.441 mmol) in DCM (15.7 mL) is added DIPEA (0.23 mL, 1.29 mmol). The reaction mixture was stirred for 5 min and then treated with (R)—N-(4-(trifluoromethyl)benzyl)pyrrolidine-2-carboxamide (100 mg, 0.367 mmol) as a solution in DCM (2 mL). After 1 h, the solvent was evaporated, and the mixture was purified by MPLC using silica gel eluting with a gradient of 5-40% mixed EtOAc/EtOH (3:1) in heptane to provide (S)-tert-butyl 3-((R)-2-((4-(trifluoromethyl)benzyl)carbamoyl) pyrrolidine-1-carbonyl)piperidine-1-carboxylate (148 mg). $^1$H NMR (500 MHz, DMSO-d$_6$) (8.29-8.79 (m, 1H), 7.60-7.77 (m, 2H), 7.36-7.57 (m, 2H), 4.23-4.51 (m, 3H), 3.81-4.08 (m, 2H), 3.42-3.73 (m, 2H), 3.27-3.38 (m, 1H), 2.05-2.25 (m, 1H), 1.71-2.01 (m, 4H), 1.43-1.68 (m, 2H), 1.31-1.42 (m, 10H).

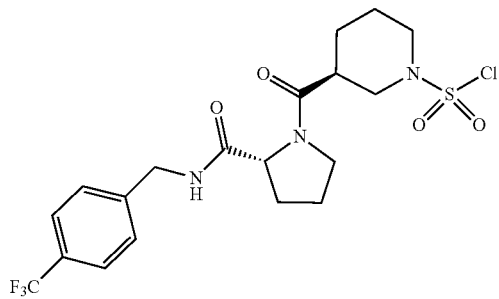

24.0

Step 2: Preparation of (S)-3-((R)-2-((4-(trifluoromethyl)benzyl)carbamoyl)pyrrolidine-1-carbonyl)piperidine-1-sulfonyl chloride, Intermediate 24.0

(S)-tert-butyl 3-((R)-2-((4-(trifluoromethyl)benzyl)carbamoyl)pyrrolidine-1-carbonyl)piperidine-1-carboxylate (4.48 g, 9.27 mmol) was dissolved in DCM (50 mL). TFA (25 mL) was added slowly, and the reaction mixture was stirred at rt for 1 h. The reaction was concentrated and the residue was dissolved in DCM and washed with 2N NaOH. The organic layers were dried over MgSO$_4$, filtered, and concentrated under reduced pressure to provide crude (R)-1-((S)-piperidine-3-carbonyl)-N-(4-(trifluoromethyl)benzyl)pyrrolidine-2-carboxamide (3.55 g). LCMS-ESI (POS.) m/z: 384.2 (M+H)+. 2.74 g (7.15 mmol) of this product was dissolved in DCM (84.0 mL) and cooled to −30° C. To this solution was added DIPEA (2.49 mL, 14.30 mmol) and sulfuryl chloride (1.74 mL, 21.5 mmol). The reaction mixture was allowed to warm to rt and stirred for an additional 1 h. The reaction was concentrated and the mixture was purified by MPLC using silica gel eluting 5-50% EtOAc/EtOH (3:1) in heptane to provide (S)-3-((R)-2-((4-(trifluoromethyl)benzyl)carbamoyl)pyrrolidine-1-carbonyl)piperidine-1-sulfonyl chloride (2.88 g). $^1$H NMR (500 MHz, chloroform-d) δ 7.58 (d, J=8.17 Hz, 2H), 7.37 (br d, J=8.04 Hz, 3H), 4.61 (dd, J=2.21, 8.04 Hz, 1H), 4.49-4.57 (m, 1H), 4.38-4.47 (m, 1H), 3.92 (br dd, J=1.88, 12.00 Hz, 2H), 3.45-3.70 (m, 2H), 3.03 (t, J=11.68 Hz, 1H), 2.82-2.89 (m, 1H), 2.76-2.81 (m, 1H), 2.44 (qdd, J=3.00, 6.34, 9.33 Hz, 1H), 2.14-2.30 (m, 1H), 2.01-2.11 (m, 1H), 1.89-1.99 (m, 3H), 1.74-1.86 (m, 1H), 1.44-1.57 (m, 1H).

The compounds set forth in the following table were synthesized following the procedure described for Intermediate 24.0 using known starting material replacements as described.

water, and brine. The organic phase was dried over MgSO₄, filtered, concentrated and purified by silica gel chromatography eluting with a gradient of 5% ethyl acetate in DCM, to provide methyl 1-(N,N-dimethylsulfamoyl)-1H-pyrazole-4-carboxylate (0.54 g), LCMS-ESI (POS.) m/z 310.0 (M+H)⁺.

TABLE 7

| Intermediate | Reagents | Structure, Name and Data |
|---|---|---|
| 24.1 | 2-fluoro-4-(trifluoromethyl)-benzylamine (Enamine, Ltd.). | 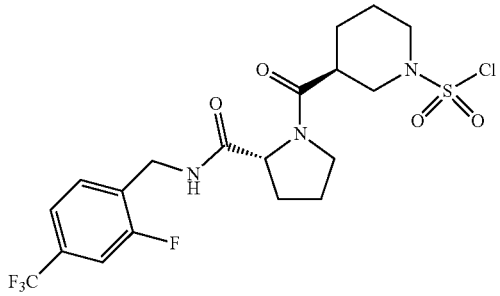 [SMILES: O=C(NCc1ccc(C(F)(F)F)cc1F)[C@H]1CCCN1C(=O)[C@H]1CCCN(S(=O)(=O)Cl)C1] (S)-3-((R)-2-((2-fluoro-4-(trifluoromethyl)benzyl)carbamoyl)pyrrolidine-1-carbonyl)piperidine-1-sulfonyl chloride. ¹H NMR (400 MHz, chloroform-d) δ ppm 7.29-7.49 (m, 4H), 4.39-4.67 (m, 3H), 3.85-4.00 (m, 2H), 3.50-3.73 (m, 2H), 2.98-3.12 (m, 1H), 2.83-2.90 (m, 1H), 2.12-2.48 (m, 2H), 1.74-2.10 (m, 5H), 1.48-1.62 (m, 1H). |
| 24.2 | (2R,4S)-1-(tert-butoxycarbonyl)-4-fluoro-pyrrolidine-2-carboxylic acid (Synthonix) | 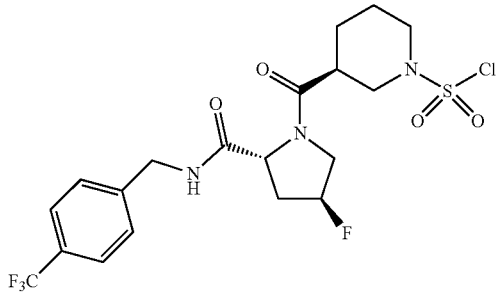 [SMILES: O=C(NCc1ccc(C(F)(F)F)cc1)[C@H]1C[C@H](F)CN1C(=O)[C@H]1CCCN(S(=O)(=O)Cl)C1] (S)-3-((2R,4S)-4-fluoro-2-((4-(trifluoromethyl)benzyl)carbamoyl)pyrrolidine-1-carbonyl)piperidine-1-sulfonyl chloride. LCMS-ESI (POS.) m/z: 402.2 (M + H)+ (penultimate amine) |

Intermediate 25.0:
1-(N,N-dimethylsulfamoyl)-1H-pyrazole-4-carboxylic Acid

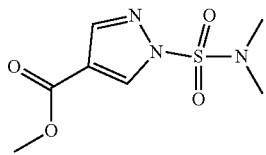

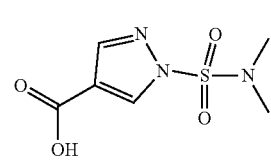

25.0

Step 1: Preparation of methyl 1-(N,N-dimethylsulfamoyl)-1H-pyrazole-4-carboxylate To a solution of methyl 1H-pyrazole-4-carboxylate (0.3 g, 2.4 mmol) and DBU (0.39 mL, 2.6 mmol) in acetonitrile (12 mL) was slowly added dimethylsulfamoyl chloride (0.27 mL, 2.51 mmol). The reaction mixture was stirred at rt for 1 h and was then concentrated under reduced pressure. The resulting residue was partitioned between water and ethyl acetate. The organic phase was washed with 10% citric acid,

Step 2: Preparation of 1-(N,N-dimethylsulfamoyl)-1H-pyrazole-4-carboxylic acid, Intermediate 25.0

To a solution of methyl 1-(N,N-dimethylsulfamoyl)-1H-pyrazole-4-carboxylate (0.54 g, 2.32 mmol) in a mixture of 1:1 THF/MeOH (5 mL) was added lithium hydroxide (0.285 g, 11.89 mmol) in water (10 mL). The reaction mixture was stirred at rt for 5 h and was then acidified with to pH=1 with 1N HCl. The solvent was concentrated under reduced pressure and the remaining aqueous phase was extracted with DCM/MeOH (10:1). The combined organic phase was dried over MgSO₄, filtered, and concentrated. The crude was used without further purification, LCMS-ESI (POS.) m/z 220.0 (M+H)+.

Intermediate 26.0: (2R)-1-(tert-butoxycarbonyl)-4-(difluoromethyl)pyrrolidine-2-carboxylic Acid

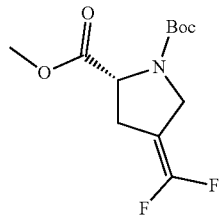 [SMILES: COC(=O)[C@H]1CC(=C(F)F)CN1C(=O)OC(C)(C)C]

Step 1: Preparation of (R)-1-tert-butyl 2-methyl 4-(difluoromethylene)pyrrolidine-1,2-dicarboxylate A solution of 1-tert-butyl 2-methyl (2R)-4-oxopyrrolidine-1,2-dicarboxylate (1.0 g, 3.99 mmol, Synthonix) in THF (40 mL) was cooled to 0° C. and then treated successively with HMPT (3.18 mL, 16.95 mmol) and dibromodifluoromethane (1.64 mL, 16.95 mmol). The mixture was then removed from the ice bath and allowed to stir at rt for 1 h. To the mixture was then added zinc dust (1.11 g, 17.0 mmol) followed by HMPT (0.19 mL, 1.04 mmol) and then heated at reflux for 3.5 h. The mixture was then cooled to rt, diluted with water and EtOAc, and then filtered through Celite washing with EtOAc. The organics were separated and the aqueous was extracted with EtOAc (2×). The combined organics were then washed with saturated aqueous CuSO₄ (1×), water (1×), brine (1×), and then dried over Na₂SO₄ and concentrated to afford 510 mg of a brown oil. The crude was purified via flash chromatography (0-10% EtOAc in heptanes) to afford 292 mg of 1-(tert-butyl) 2-methyl (R)-4-(difluoromethylene)pyrrolidine-1,2-dicarboxylate as a clear, colorless oil. ¹H NMR (400 MHz, chloroform-d) δ ppm 4.40-4.60 (m, 1H), 4.02-4.20 (m, 2H), 3.76 (s, 3H), 2.83-3.02 (m, 1H), 2.67 (br d, J=15.13 Hz, 1H), 1.41-1.53 (m, 9H).

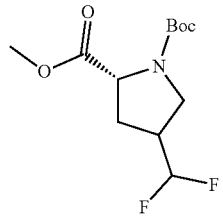 [SMILES: COC(=O)[C@H]1CC(C(F)F)CN1C(=O)OC(C)(C)C]

Step 2: Preparation of (2R)-1-tert-butyl 2-methyl 4-(difluoromethyl)pyrrolidine-1,2-dicarboxylate To a solution of (R)-1-tert-butyl 2-methyl 4-(difluoromethylene)pyrrolidine-1,2-dicarboxylate (280 mg, 1.01) in ethanol (10 mL) was added 10% Pd/C (105 mg, 0.987 mmol) and then placed under an atmosphere of H₂ (30 psi) for 24 h. The mixture was then filtered through a Celite washing with ethanol. The filtrate was concentrated under reduced pressure to afford 270.2 mg of (2R)-1-tert-butyl 2-methyl 4-(difluoromethyl)pyrrolidine-1,2-dicarboxylate as a clear colorless oil, (5:1 diastereomeric mixture). This mixture was carried forward into next step without further purification. 1H NMR (500 MHz, chloroform-d) δ ppm 5.63-5.97 (m, 1H), 4.14-4.54 (m, 1H), 3.65-3.82 (m, 4H), 3.45-3.54 (m, 1H), 2.60-2.78 (m, 1H), 2.38-2.54 (m, 1H), 1.93-2.19 (m, 1H), 1.37-1.52 (m, 9H).

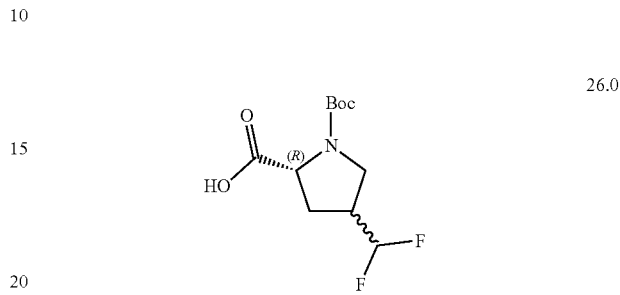

Step 3: Preparation of (2R)-1-(tert-butoxycarbonyl)-4-(difluoromethyl)pyrrolidine-2-carboxylic acid, Intermediate 26.0

To a solution of (2R)-1-tert-butyl 2-methyl 4-(difluoromethyl)pyrrolidine-1,2-dicarboxylate (270 mg, 0.967 mmol) in THF (2.5 mL) and water (1.25 mL) was added LiOH*hydrate (122 mg, 2.90 mmol). The mixture was stirred at rt for 18 h and then concentrated under reduced pressure to remove the THF. The pH of the remaining aqueous solution adjusted to pH 1-2 with addition of 1N HCl, then extracted with DCM (3×). The combined organics were dried over Na₂SO₄ and concentrated under reduced pressure to afford 269 mg of (2R)-1-(tert-butoxycarbonyl)-4-(difluoromethyl)pyrrolidine-2-carboxylic acid as a white solid. (5:1 diastereomeric mixture). This material was used without further purification.

Intermediate 27.0: (R)-1-((S)-piperidine-3-carbonyl)-N-(4-(trifluoromethyl)benzyl)pyrrolidine-2-carboxamide hydrochloride

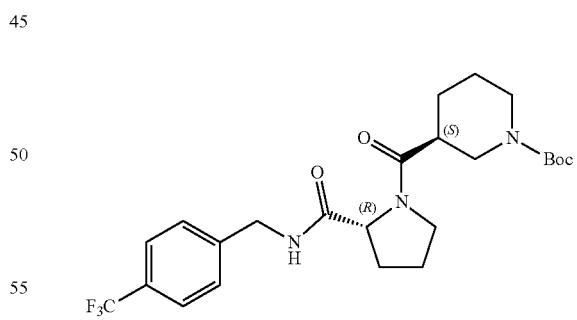

Step 1: Preparation of tert-butyl (S)-3-((R)-2-((4-(trifluoromethyl)benzyl)carbamoyl)pyrrolidine-1-carbonyl)piperidine-1-carboxylate Using the general coupling procedure outline in Route R, Intermediate 28.0 was couple with (S)-1-(tert-butoxycarbonyl)piperidine-3-carboxylic acid to provide the desired product. LCMS-APCI (POS.) m/z: 384.2 (M+H-Boc)+.

27.0

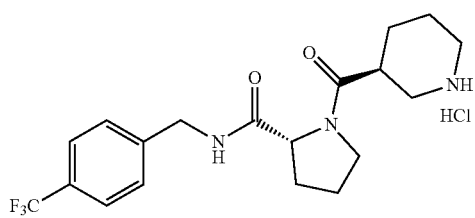

Step 2: Preparation of (R)-1-((S)-piperidine-3-carbonyl)-N-(4-(trifluoromethyl)benzyl)pyrrolidine-2-carboxamide hydrochloride To a solution of tert-butyl (S)-3-((R)-2-((4-(trifluoromethyl)benzyl)carbamoyl)pyrrolidine-1-carbonyl)piperidine-1-carboxylate (0.580 g, 1.20 mmol) in DCM (10.0 mL) at rt was added TFA (2.0 mL, 26.1 mmol). The solution was allowed to stir at rt for two hours. The solution was concentrated to dryness under reduced pressure to afford (R)-1-((S)-piperidine-3-carbonyl)-N-(4-(trifluoromethyl)benzyl)pyrrolidine-2-carboxamide (0.588 g, 1.18 mmol) as an off-white solid. LCMS-APCI (POS.) m/z: 384.2 (M+H)+.

Intermediate 28.11: (R)—N-(4-(trifluoromethyl)benzyl)piperidine-2-carboxamide

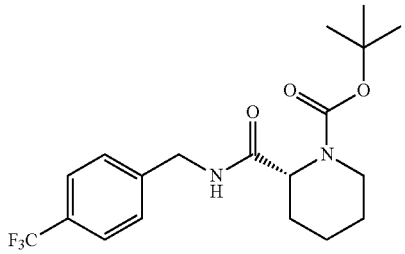 [SMILES: CC(C)(C)OC(=O)N1CCCC[C@@H]1C(=O)NCc1ccc(C(F)(F)F)cc1]

Step 1: Preparation of tert-butyl (R)-2-((4-(trifluoromethyl)benzyl)carbamoyl)piperidine-1-carboxylate A solution of (R)-1-(tert-butoxycarbonyl)piperidine-2-carboxylic acid (0.200 g, 0.872 mmol) and DIPEA (0.289 mL, 1.75 mmol) in DMF (2 mL) was cooled to 0° C. HBTU (0.496 g, 1.31 mmol) was added and the reaction allowed to stir at 0° C. for one minute. 4-(trifluoromethyl)phenyl)methanamine (0.183 g 1.05 mmol) was then added and the reaction mixture was allowed to warm to rt and stir for 20 min. The reaction was then washed with a saturated aqueous NaHCO$_3$, and the aqueous layer was extracted with DCM (5×10 mL). The combined organic layers were dried over MgSO$_4$ and concentrated under reduced pressure. The crude material was purified by MPLC using silica gel and eluted with a gradient of 10-100% EtOAc in hexane, to provide tert-butyl (R)-2-((4-(trifluoromethyl)benzyl)carbamoyl)piperidine-1-carboxylate (0.202 g, 0.523 mmol) as a white solid. LCMS-APCI (POS.) m/z: 287.1 (M+H-Boc)+.

28.11

Step 2: Preparation of (R)—N-(4-(trifluoromethyl)benzyl)piperidine-2-carboxamide To a solution of tert-butyl (R)-2-((4-(trifluoromethyl)benzyl)carbamoyl)piperidine-1-carboxylate (0.200 g, 0.518 mmol) in DCM (1.0 mL) at rt was added TFA (5.0 mL, 65.4 mmol). The solution was allowed to stir at rt for 2 h and then concentrated to dryness under reduced pressure to afford the desired product (0.207 g, 0.641 mmol) as an off-white solid. LCMS-APCI (POS.) m/z: 287.2 (M+H)+.

The compounds set forth in the following table were synthesized following the procedure described for Intermediate 28.11 using known starting material replacements as described. HCl can also be used to remove the Boc groups to give the HCl salts.

TABLE 8

| Intermediate | Amine | Boc-Amino Acid | Structure, Name and Data |
|---|---|---|---|
| 28.0 | 4-CF$_3$-benzylamine | D-N-Boc-proline | (R)-N-(4-(trifluoromethyl)benzyl) pyrrolidine-2-carboxamide hydrochloride<br>LCMS-APCI (POS.) m/z: 273.1 (M + H)+ |
| 28.1 | Intermediate 9.5 | | |

TABLE 8-continued

| Intermediate | Amine | Boc-Amino Acid | Structure, Name and Data |
|---|---|---|---|
| | | | (1R,3R,5R)-N-((R)-cyclopropyl(2-fluoro-4-(trifluoromethyl)phenyl)methyl)-2-azabicyclo[3.1.0]hexane-3-carboxamide 2,2,2-trifluoroacetate |
| 28.2 | Intermediate 9.5 | D-N-Boc-proline | (R)-N-((R)-cyclopropyl(2-fluoro-4-(trifluoromethyl)phenyl)methyl)pyrrolidine-2-carboxamide 2,2,2-trifluoroacetate |
| 28.3 | Intermediate 9.5 | | (2R,4S)-N-((R)-cyclopropyl(2-fluoro-4-(trifluoromethyl)phenyl)methyl)-4-fluoropyrrolidine-2-carboxamide 2,2,2-trifluoroacetate |
| 28.4 | Intermediate 9.2 | | (1R,3R,5R)-N-((R)-(4-chloro-2,5-difluorophenyl)(cyclopropyl)methyl)-2-azabicyclo[3.1.0]hexane-3-carboxamide hydrochloride |
| 28.X | Intermediate 8.0 | | (1R,3R,5R)-N-((R)-(-2,5-difluoro-4-trifluoromethylphenyl)(cyclopropymethyl)-2-azabicyclo[3.1.0]hexane-3-carboxamide hydrochloride |
| 28.8 | Intermediate 8.0 | | (2R,4R)-N-((R)-cyclopropyl(2,5-difluoro-4-(trifluoromethyl)phenyl)methyl)-4-hydroxypyrrolidine-2-carboxamide 2,2,2-trifluoroacetate |

TABLE 8-continued

| Intermediate | Amine | Boc-Amino Acid | Structure, Name and Data |
|---|---|---|---|
| 28.11 | 4-CF3-benzyl-amine | | (R)-N-(4-(trifluoromethyl)benzyl)piperidine-2-carboxamide hydrochloride |
| 28.12 | (S)-1-(4-chlorophenyl)-ethan-1-amine (Eurofins Lancaster Laboratories, LLC.) | | (R)-N-((S)-1-(4-chlorophenyl)ethyl) piperidine-2-carboxamide 2,2,2-trifluoroacetate<br>LCMS-APCI (POS.) m/z: 267.1 (M + H)+ |
| 28.13 | (R)-1-(4-chlorophenyl)-ethan-1-amine (Alpha Aesar) | | (R)-N-((R)-1-(4-chlorophenyl)ethyl)piperidine-2-carboxamide 2,2,2-trifluoroacetate<br>LCMS-APCI (POS.) m/z: 267.1 (M + H)+ |
| 28.14 | (S)-1-(3,4-dichlorophenyl)-ethan-1-amine (Enamine, Ltd.) | | (R)-N-((S)-1-(3,4-dichlorophenyl)ethyl)piperidine-2-carboxamide 2,2,2-trifluoroacetate<br>LCMS-APCI (POS.) m/z: 301.1 (M + H)+ |
| 28.15 | (R)-1-(3,4-dichlorophenyl)-ethan-1-amine (Enamine, Ltd.) | | (R)-N-((R)-1-(3,4-dichlorophenyl)ethyl)piperidine-2-carboxamide 2,2,2-trifluoroacetate<br>LCMS-APCI (POS.) m/z: 301.1 (M + H)+ |
| 28.17 | (1r,3r)-3-(trifluoromethyl)cyclo-butan-1-amine (Enamine, Ltd.) | | (R)-4,4-difluoro-N-((1r,3R)-3-(trifluoromethyl)cyclobutyl)pyrrolidine-2-carboxamide 2,2,2-trifluoroacetate<br>LCMS-APCI (POS.) m/z: 273.2 (M + H)+ |
| 28.18 | (4-(trifluoromethyl)phenyl)-methanamine (Chem-Implex International, Inc.) | | |

TABLE 8-continued

| Intermediate | Amine | Boc-Amino Acid | Structure, Name and Data |
|---|---|---|---|
| | | (Combi-Blocks, Inc.) | (R)-N-(4-(trifluoromethyl)benzyl)-5-azaspiro[2.4]heptane-6-carboxamide 2,2,2-trifluoroacetate<br>LCMS-APCI (POS.) m/z: 299.2 (M + H)+ |
| 28.19 | (4-(trifluoromethyl)phenyl)-methanamine (Chem-Implex International, Inc.) | (Advanced ChemBlocks, Inc.) | (R)-N-(4-(trifluoromethyl)benzyl)azetidine-2-carboxamide 2,2,2-trifluoroacetate<br>LCMS-APCI (POS.) m/z: 259.2 (M + H)+ |
| 28.20 | (4-(trifluoromethyl)phenyl)-methanamine (Chem-Implex International, Inc.) | N-(tert-butoxycarbonyl)-N-methyl-D-alanine (Combi-Blocks, Inc.) | (R)-2-(methylamino)-N-(4-(trifluoromethyl)benzyl)propenamide 2,2,2-trifluoroacetate<br>LCMS-APCI (POS.) m/z: 261.2 (M + H)+ |
| 28.21 | (4-(trifluoromethyl)phenyl)-methanamine (Chem-Implex International, Inc.) | (Watanabe Chemical Industries, Ltd.) | ((2R,4S)-4-fluoro-N-(4-(trifluoromethyl)benzyl)pyrrolidine-2-carboxamide 2,2,2-trifluoroacetate<br>LCMS-APCI (POS.) m/z: 291.1 (M + H)+ |
| 28.22 | (4-(trifluoromethyl)phenyl)-methanamine (Chem-Implex International, Inc.) | | (2R,4S)-4-fluoro-N-(4-(trifluoromethyl)benzyl)pyrrolidine-2-carboxamide 2,2,2-trifluoroacetate<br>LCMS-APCI (POS.) m/z: 309.1 (M + H)+ |
| 28.24 | (4-(trifluoromethyl)phenyl)-methanamine (Chem-Implex International, Inc.) | (PharmaBlock, Inc.) | (2R,4S)-4-fluoro-N-(4-(trifluoromethyl)benzyl)pyrrolidine-2-carboxamide 2,2,2-trifluoroacetate<br>LCMS-APCI (POS.) m/z: 301.1 (M + H)+ |
| 28.25 | (R)-1-(4-(trifluoromethyl)phenyl)-ethan-1-amine (Enamine, Ltd.) | | |

| Intermediate | Amine | Boc-Amino Acid | Structure, Name and Data |
|---|---|---|---|
| | | | (2R,4S)-4-fluoro-N-(4-(trifluoromethyl)benzyl)pyrrolidine-2-carboxamide 2,2,2-trifluoroacetate<br>LCMS-APCI (POS.) m/z: 323.2 (M + H)+ |
| 28.26 | (6-(trifluoromethyl)pyridin-3-yl)methanamine (Combi-Blocks, Inc.) | 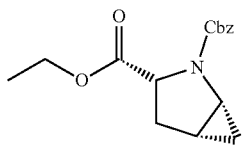 | 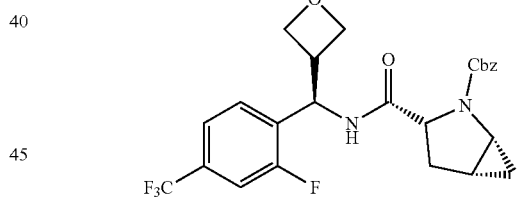<br>(2R,4S)-4-fluoro-N-(4-(trifluoromethyl)benzyl)pyrrolidine-2-carboxamide 2,2,2-trifluoroacetate<br>LCMS-APCI (POS.) m/z: 310.2 (M + H)+ |

Intermediate 28.5 Preparation of (1R,3R,5R)—N—((R)-(2-fluoro-4-(trifluoromethyl)phenyl) (oxetan-3-yl)methyl)-2-azabicyclo[3.1.0]hexane-3-carboxamide Step 1: Preparation of 2-benzyl 3-ethyl (1R,3R,5R)-2-azabicyclo[3.1.0]hexane-2,3-dicarboxylate To a 0° C. solution of ethyl ester cyclopropyl proline (10.0 g, 64.4 mmol) in dry DCM (500 mL) was added DIPEA (24.7 mL, 141.8 mmol) followed by slow addition of benzyl chloroformate (9.6 mL, 67 mmol). Both additions were monitored to ensure reaction temperature did not rise above 10° C. The mixture was allowed to slowly warm to rt and stirred for 4 h and then quenched with saturated aqueous NH₄Cl, saturated aqueous NaHCO₃, brine, dried, and concentrated under reduced pressure to give a yellow oil which was purified by silica gel chromatography (0-30% EtOAc in hexanes) to give a colorless oil (13.8 g). LCMS-APCI (POS.) m/z: 290.1 (M+H)+.

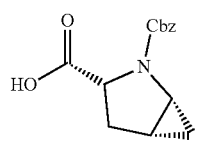

Step 2: Preparation of (1R,3R,5R)-2-((benzyloxy)carbonyl)-2-azabicyclo[3.1.0]hexane-3-carboxylic Acid To a solution of the ethyl ester (11.7 g, 45.8 mmol) in EtOH (120 mL) was added a solution of lithium hydroxide monohydrate (2.31 g, 55.0 mmol) in water (60 mL) over 5 minutes while maintaining the reaction temperature below 30 C. The reaction was stirred at room temperature overnight. The reaction mixture was concentrated under reduced pressure. The residue was partitioned between water and MTBE. The aqueous layer was collected and the organic layer discarded. The aqueous layer was then acidified to pH 1-2 by addition of 2N HCl. The aqueous layer was then extracted with DCM. The combined organic extracts were dried over sodium sulfate and the solvent concentrated to give the desired acid. Acid was used in next step without further purification. (0.8 g). LCMS-APCI (NEG.) m/z: 260.1 (M−H)+.

Step 3: Preparation of benzyl (1R,3R,5R)-3-(((R)-(2-fluoro-4-(trifluoromethyl)phenyl)(oxetan-3-yl)methyl)carbamoyl)-2-azabicyclo[3.1.0]hexane-2-carboxylate To the starting acid was combined with HBTU (3.98 g, 10.5 mmol), HOBt (1.42 g, 10.5 mmol), amine (2.18 g, 7.0 mmol), and acid (2.0 g, 7.69 mmol). To the solids were added NMP (15 mL), followed by DIEA (3.65 mL, 21 mmol). The resulting mixture was stirred at room temperature for 20 minutes. It was diluted with 125 mL ethyl acetate and washed with saturated aqueous sodium bicarbonate (125 mL), water (2×100 mL), ammonium chloride (1×100 ml) and brine. The organic phase was dried over sodium sulfate and concentrated to a viscous oil which was purified with silica gel using a gradient to 50% ethyl acetate/hexanes, providing the desired product as a white foam. (2.51 g). LCMS-APCI (POS.) m/z: 493.2 (M+H)+.

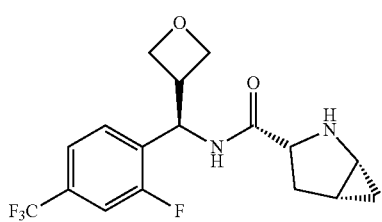

Step 4: Preparation of (1R,3R,5R)—N—((R)-(2-fluoro-4-(trifluoromethyl)phenyl)(oxetan-3-yl)methyl)-2-azabicyclo[3.1.0]hexane-3-carboxamide The starting material (2.04 g, 4.25 mmol) was combined with palladium on carbon (0.2 g) and to the solids was added MeOH (10 mL). The resulting mixture was sparged with hydrogen from a hydrogen balloon for 2 minutes and then the flask was evacuated and backfilled with hydrogen four times. The resulting mixture was stirred under balloon pressure hydrogen for 45 minutes. Observed by LC/MS was clean desired product. The reaction was filtered through Celite followed by a syringe filter and concentrated under reduced pressure, providing the pure desired product as a glassy solid/white foam (1.48 g). LCMS-APCI (POS.) m/z: 359.1 (M+H)+.

The compounds set forth in the following table were synthesized following the procedure described for Intermediate 28.5 using known starting material replacements as described.

| Intermediate | Amine | C-Amino Acid | Structure, Name and Data |
|---|---|---|---|
| 28.5 | Intermediate 29.9 | (structure) | (1R,3R,5R)-N-((R)-(2-fluoro-4-(trifluoromethyl)phenyl)(oxetan-3-yl)methyl)-2-azabicyclo[3.1.0]hexane-3-carboxamide |
| 28.6 | Intermediate 29.1 | (structure) | (1R,3R,5R)-N-((R)-(4-chloro-2,5-difluorophenyl)(oxetan-3-yl)methyl)-2-azabicyclo[3.1.0]hexane-3-carboxamide |
| 28.7 | Intermediate 29.10 | (structure) | (1R,3R,5R)-N-((R)-(2,5-difluoro-4-(trifluoromethyl)phenyl)(oxetan-3-yl)methyl)-2-azabicyclo[3.1.0]hexane-3-carboxamide |
| 28.9 | Intermediate 29.10 | (structure) | (structure) |

| Intermediate | Amine | C-Amino Acid | Structure, Name and Data |
|---|---|---|---|
| 28.10 | Intermediate 29.1 | | (2R,4R)-N-((R)-(2,5-difluoro-4-(trifluoromethyl)phenyl)(oxetan-3-yl)methyl)-4-hydroxypyrrolidine-2-carboxamide 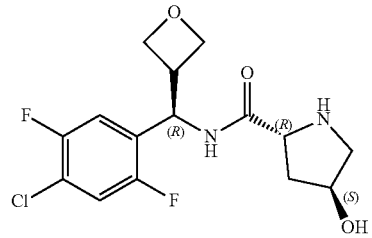 (2R,4S)-N-((R)-(4-chloro-2,5-difluorophenyl)(oxetan-3-yl)methyl)-4-hydroxypyrrolidine-2-carboxamide |

Intermediate 29.1: Preparation of (R)-(4-chloro-2,5-difluorophenyl)(oxetan-3-yl)methanamine hydrochloride

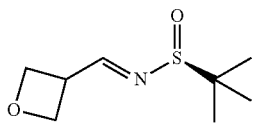

Step 1: Preparation of (S,E)-2-methyl-N-(oxetan-3-ylmethylene)propane-2-sulfinamide To a solution of oxetan-3-ylmethanol (2.0 g, 22.7 mmol) in DCM (20 mL) at 0° C. was added Dess-Martin periodinane (14.4 g, 34.0 mmol) portion wise. The ice bath was removed, and the resulting suspension was stirred at room temperature for 1.5 h. The reaction mixture was filtered through Celite, and the filtrate was partially concentrated under reduced pressure (water bath temperature 10-15° C. to prevent evaporation of aldehyde) so that approximately 10 mL of DCM remained. The resulting suspension was filtered again through Celite, and the filtered solid was rinsed with a minimum amount of DCM. To the filtrate was washed with added additional DCM (10 mL), and the resulting mixture was cooled to 0 C with an ice bath. (S)-2-methylpropane-2-sulfinamide (3.0 g, 25.0 mmol) was added portion wise, followed by titanium isopropoxide (9.7 g, 34.1 mmol). The ice bath was removed, and the reaction mixture was stirred at room temperature for 1 hour. The mixture was carefully poured into saturated aqueous NaHCO$_3$ (gas evolution) and then stirred vigorously at room temperature for 30 min. The suspension was filtered through Celite and the filter cake was washed with DCM (20 mL). The filtrate was transferred to a separatory funnel, the layers were separated, and the combined were dried over Na$_2$SO$_4$ and concentrated under reduced pressure. The remaining viscous oil was purified with silica gel (0-50% ethyl acetate in hexanes) to provide the desired product (1.2 g, 6.3 mmol) as a viscous yellow oil. $^1$H NMR (400 MHz, DMSO-d$_6$) δ 8.17 (d, J=4.3 Hz, 1H), 4.80 (ddd, J=2.7, 6.0, 8.4 Hz, 2H), 4.65 (dt, J=6.1, 14.9 Hz, 2H), 4.11 (ttd, J=4.3, 6.3, 8.4 Hz, 1H), 1.14 (s, 10H).

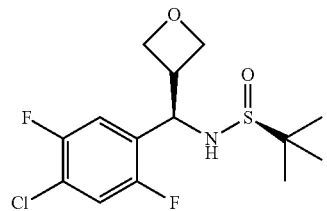 [SMILES: CC(C)(C)[S@](=O)N[C@@H](c1cc(F)c(Cl)cc1F)C1COC1]

Step 2: Preparation of (S)—N-(®-(4-chloro-2,5-difluorophenyl)(oxetan-3-yl)methyl)-2-methylpropane-2-sulfinamide To an oven-dried 500 mL round bottom flask under a nitrogen atmosphere was added 1-chloro-2,5-difluoro-4-iodobenzene (9.93 g, 36.18 mmol) in 175 mL anhydrous THF. The resulting solution was cooled to −100° C. with a diethyl ether/liquid nitrogen bath, and then n-BuLi solution (1.6M in THF, 22.6 mL, 36.2 mmol) was added dropwise so that the internal temperature remained between −90 and −100° C. The resulting yellow colored mixture was stirred between −90 and −100 C for 30 min and then (S,E)-2-methyl-N-(oxetan-3-ylmethylene)propane-2-sulfinamide (7.53 g, 39.80 mmol) in 15 mL THF was added dropwise via syringe so that the internal temperature remained between −90 and −100° C. The resulting mixture was stirred between −90 and −100° C. for 30 min and then quenched at the same temperature by dropwise addition of saturated NH$_4$Cl solution followed by warming to room temperature. The mixture was diluted with 150 mL water and 150 mL EtOAc. The layers were shaken and separated and the organic phase was washed with saturated NaCl solution, dried over Na$_2$SO$_4$, and concentrated to a viscous nearly colorless oil which was purified by MPLC using silica gel (0-100% ethyl acetate/ hexanes) to provide the desired single diastereomer (6.88 g, 20.38 mmol) as a white foam. LCMS-APCI (POS.) m/z: 338.1 (M+H)+

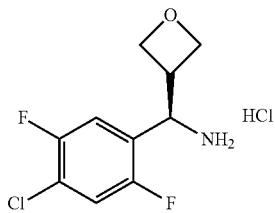

29.1

Step 3: Preparation of (R)-(4-chloro-2,5-difluorophenyl)(oxetan-3-yl)methanamine hydrochloride, Intermediate 29.1

(S)—N—((R)-(4-chloro-2,5-difluorophenyl)(oxetan-3-yl)methyl)-2-methylpropane-2-sulfinamide (6.88 g, 20.35 mmol) was dissolved in methanol and cooled to 0° C. with an ice bath. HCl (4N in 1,4-dioxane, 6.11 mL, 24.42 mmol) was added dropwise using a syringe and the resulting mixture was stirred at 0° C. for 5 minutes before the ice bath was removed. The reaction was stirred at rt for 45 minutes and then quenched with triethylamine (28 mL). The resulting mixture was concentrated under reduced pressure to provide a white solid. The solid was partitioned between saturated NaHCO$_3$ solution and DCM. The layers were separated and the aqueous phase was extracted with additional DCM. The organic extracts were combined, dried over Na$_2$SO$_4$ and concentrated under reduced pressure, providing the desired product (6.18 g, 18.28 mmol) as a viscous oil (the purity was estimated to be 70%). This material was converted to the HCl salt by the addition 1 equivalent of 4N HCl in dioxane followed by concentration under reduced pressure to give a white solid. $^1$H NMR (400 MHz, methanol-d$_4$) δ 7.30-7.41 (m, 2H), 4.85 (dd, J=6.3, 7.7 Hz, 1H), 4.68 (t, J=6.2 Hz, 1H), 4.60 (dd, J=6.4, 8.0 Hz, 1H), 4.50 (d, J=1.1, 9.8 Hz, 1H), 4.33 (td, J=1.0, 6.4 Hz, 1H), 3.33 (dh, J=1.6, 3.4 Hz, 2H).

The compounds set forth in the following table were synthesized following the procedure described for intermediate 29.1 using known starting material replacements as described

TABLE 9

| Intermediate | Aryl halide | Structure, Name and Data |
|---|---|---|
| 29.2 | 1-bromo-2,4-difluorobenzene | (R)-(2,4-difluorophenyl)(oxetan-3-yl)methanamine hydrochloride LCMS-APCI (POS.) m/z: 200.2 (M + H)+; $^1$H NMR (400 MHz, DMSO-d$_6$) δ ppm 7.46 (td, J = 6.6, 8.6 Hz, 1H), 7.22 (ddd, J = 2.6, 9.4, 10.7 Hz, 1H), 7.09 (tdd, J = 1.1, 2.6, 8.6 Hz, 1H), 5.68 (d, J = 7.1 Hz, 1H), |

TABLE 9-continued

| Intermediate | Aryl halide | Structure, Name and Data |
|---|---|---|
| | | 4.85 (dd, J = 7.0, 10.6 Hz, 1H), 4.68 (dd, J = 6.5, 7.6 Hz, 1H), 4.53 (t, J = 6.2 Hz, 1H), 4.44 (dd, J = 6.2, 7.9 Hz, 1H), 3.49 (dq, J = 7.0, 14.8 Hz, 1H), 1.03 (s, 9H). |
| 29.3 | 1-bromo-4-(trifluoromethyl)benzene | (R)-oxetan-3-yl(4-(trifluoromethyl)phenyl)methanamine hydrochloride LCMS-APCI (POS.) m/z: 232.1 (M + H)+ |
| 29.4 | 4-chloro-2-fluoro-1-iodobenzene | (R)-(4-chloro-2-fluorophenyl)(oxetan-3-yl)methanamine hydrochloride LCMS-APCI (POS.) m/z: 216.0 (M + H)+ |
| 29.5 | 4-bromo-1-chloro-2-fluorobenzene | (R)-(4-chloro-3-fluorophenyl)(oxetan-3-yl)methanamine hydrochloride LCMS-APCI (POS.) m/z: 216.0 (M + H)+ |
| 29.6 | 2-fluoro-4-iodo-1-(trifluoromethyl)benzene | (R)-(3-fluoro-4-(trifluoromethyl)phenyl)(oxetan-3-yl)methanamine hydrochloride LCMS-APCI (POS.) m/z: 250.0 (M + H)+ |

TABLE 9-continued

| Intermediate | Aryl halide | Structure, Name and Data |
|---|---|---|
| 29.7 | 1-bromo-4-chloro-benzene | 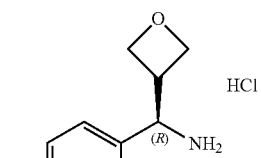<br>(R)-(4-chlorophenyl)(oxetan-3-yl)methanamine hydrochloride<br>LCMS-APCI (POS.) m/z: 198.1 (M + H)+ |
| 29.8 | (3-fluoro-oxetan-3-yl) methanol | 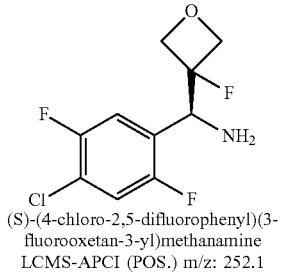<br>(S)-(4-chloro-2,5-difluorophenyl)(3-fluorooxetan-3-yl)methanamine<br>LCMS-APCI (POS.) m/z: 252.1 (M + H)+ |

Intermediate 30.0:
3-methyl-5-(methylsulfonyl)benzoic Acid

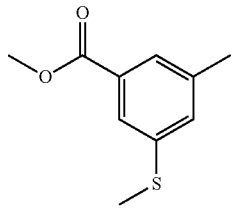

Step 1: Preparation of methyl 3-methyl-5-(methylthio)benzoate

Methyl 3-bromo-5-methylbenzoate (4.00 g, 17.5 mmol), sodium methanethiolate (1.35 g, 19.2 mmol), tris(dibenzylideneacetone)dipalladium(0) (Pd$_2$(dba)$_3$) (0.120 g, 0.131 mmol), 4,5-bis(diphenylphosphino)-9,9-dimethylxanthene (Xantphos) (0.152 g, 0.262 mmol) and DIPEA (3.74 mL, 20.9 mmol) were added to a 250 mL round-bottom flask equipped with a condenser. The flask was evacuated of air and backfilled with nitrogen three times. Dry toluene (40.0 ml) was added to the mixture, and it was stirred at 90° C. for twelve hours. To the reaction was subsequently added sodium methanethiolate (0.183 g, 2.62 mmol) followed by DIPEA (0.456 mL, 2.62 mmol) and the reaction stirred at 90° C. for two hours. The reaction mixture was cooled to room temperature and quenched with 1N aqueous hydrochloric acid solution, and extracted with EtOAc. The organic layer was washed with saturated NaCl solution and dried over MgSO$_4$. The organic layer was concentrated under reduced pressure, and the crude material was purified by MPLC using silica gel and eluted with a gradient of 0-7% EtOAc/hexanes to give methyl 3-methyl-5-(methylthio)benzoate (1.89 g, 9.63 mmol). $^1$H NMR (400 MHz, DMSO-d$_6$) δ ppm 7.56 (dtd, J=0.8, 1.5, 11.3 Hz, 2H), 7.37 (td, J=0.8, 1.7 Hz, 1H), 3.85 (s, 3H), 2.35 (q, J=0.7 Hz, 3H).

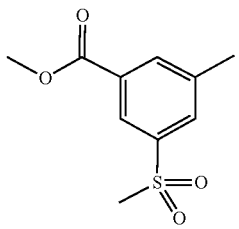

Step 2: Preparation of methyl 3-methyl-5-(methylsulfonyl)benzoate

To a solution of methyl 3-methyl-5-(methylthio)benzoate (1.00 g, 5.10 mmol) in DCM (25.0 mL) was added 3-chloroperoxybenzoic acid (2.40 g, 10.7 mmol, 77 wt %) in small portions over ten minutes. The mixture was stirred for one hour at 22° C. The reaction was quenched with saturated NaHCO$_3$ solution (40.0 mL). The reaction became clear from turbid. The aqueous phase was then extracted with DCM (60 mL), the organic layers were combined and washed with aqueous saturated NaHCO$_3$ solution (2×20 mL) and saturated NaCl solution (20 mL). The organic layer was dried over Na$_2$SO$_4$ and the solvents were removed under reduced pressure. The crude material was purified by MPLC using silica gel and eluted with a gradient of 20-60% EtOAc/hexanes to give methyl 3-methyl-5-(methylsulfonyl)benzoate (1.05 g, 4.60 mmol). $^1$H NMR (400 MHz, DMSO-d$_6$) δ ppm 8.22 (td, J=0.8, 1.8 Hz, 1H), 8.11 (dq, J=0.8, 1.7 Hz, 1H), 8.05 (td, J=0.8, 1.7 Hz, 1H), 3.91 (s, 3H), 3.27 (s, 3H).

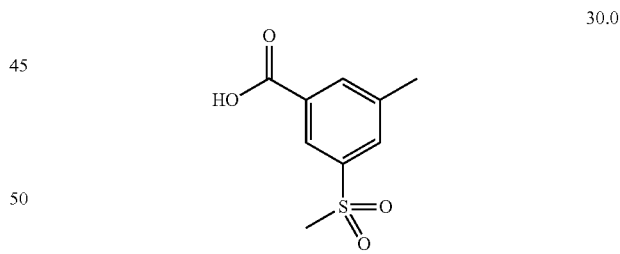

30.0

Step 3: Preparation of 3-methyl-5-(methylsulfonyl)benzoic Acid

To a solution of methyl 3-methyl-5-(methylsulfonyl)benzoate (1.03 g, 4.51 mmol) in methanol (8.0 mL) and water (8.0 mL) was added potassium hydroxide (0.633 g, 11.3 mmol) portion wise, and the mixture was heated at 60° C. for five hours. The mixture was concentrated under reduced pressure and the resulting residue was acidified to pH 2-3 with HCl (3N). The resulting white solid was filtered off and washed with water to give pure 3-methyl-5-(methylsulfonyl)benzoic acid (0.920 g, 4.29 mmol). LCMS-APCI (POS.) m/z: 215.1 (M+H)+.

The compounds set forth in the following table were synthesized following the procedure described above using known starting material replacements as described.

TABLE 10

| Intermediate | Aryl Bromide | Structure, Name and Data |
|---|---|---|
| 30.1 | methyl 3-bromo-5-fluorobenzoate | 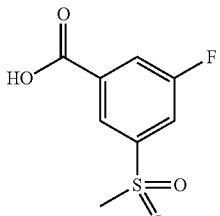<br>$^1$H NMR (400 MHz, DMSO-d$_6$) δ ppm 13.87 (s, 1H), 8.25 (t, J = 1.5 Hz, 1H), 8.06 (dddd, J = 1.5, 2.5, 8.8, 24.6 Hz, 2H), 3.35 (S, 3H).. |

Intermediate 31.1: (1R,3R,5R)-2-(2-(tert-butyl) isonicotinoyl)-2-azabicyclo[3.1.0]hexane-3-carboxylic Acid

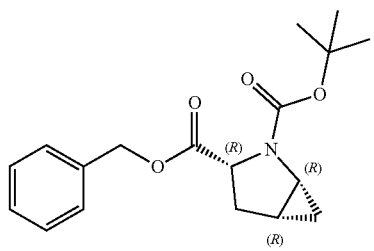

Step 1: Preparation of 3-benzyl 2-(tert-butyl) (1R, 3R,5R)-2-azabicyclo[3.1.0]hexane-2,3-dicarboxylate To a solution of (1R,3R,5R)-2-(tert-butoxycarbonyl)-2-azabicyclo[3.1.0]hexane-3-carboxylic acid (1.52 g, 6.70 mmol) in DMF (5.0 mL) was added potassium carbonate (1.03 g, 7.37 mmol). The resulting mixture was cooled to 0° C. and then benzyl bromide (0.96 mL, 8.05 mmol) was added dropwise over five minutes. The resulting mixture was allowed to warm to 22° C. and stirred overnight. It was diluted with EtOAc (70 mL) and washed 4 times with water (200 mL total volume). The organic phase was dried over Na$_2$SO$_4$ and concentrated under reduced pressure. The crude material was purified by MPLC using silica gel and eluted with a gradient of 0-15% EtOAc/hexanes to provide 3-benzyl 2-(tert-butyl) (1R,3R,5R)-2-azabicyclo[3.1.0]hexane-2,3-dicarboxylate (2.08 g, 6.56 mmol) as a colorless, viscous oil. LCMS-APCI (POS.) m/z: 218.1 (M+H-Boc)+.

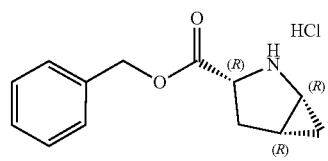

Step 2: Preparation of benzyl (1R,3R,5R)-2-azabicyclo[3.1.0]hexane-3-carboxylate hydrochloride To a solution of 3-benzyl 2-(tert-butyl) (1R,3R,5R)-2-azabicyclo[3.1.0]hexane-2,3-dicarboxylate (2.08 g, 6.56 mmol) in DCM (6.0 mL) at 22° C. was added TFA (6.0 mL, 78.4 mmol). The solution was allowed to stir at 22° C. for thirty minutes. The solution was concentrated to dryness under reduced pressure to afford benzyl (1R,3R,5R)-2-azabicyclo[3.1.0]hexane-3-carboxylate hydrochloride (2.15 g, 6.51 mmol) as an off-white solid. LCMS-APCI (POS.) m/z: 218.1 (M+H)+.

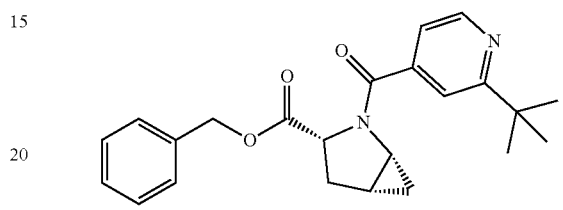

Step 3: Preparation of benzyl (1R,3R,5R)-2-(2-(tert-butyl)isonicotinoyl)-2-azabicyclo[3.1.0]hexane-3-carboxylate Benzyl (1R,3R,5R)-2-azabicyclo[3.1.0]hexane-3-carboxylate hydrochloride (0.450 g, 1.36 mmol), O-(Benzotriazol-1-yl)-N,N,N'N'-tetramethyluronium hexafluorophosphate (0.78 g, 2.04 mmol), benzotriazol-1-ol (0.28 g, 2.04 mmol) and 2-(tert-butyl)isonicotinic acid (0.269 g, 1.50 mmol) were added to a flask and NMP (5.0 mL) was added, followed by N,N-diisopropylethylamine (0.71 mL, 4.08 mmol). The resulting mixture was stirred at 22° C. for 20 minutes. The reaction was diluted with EtOAc (60 mL) and saturated NaHCO$_3$ (70 mL) solution. The layers were shaken vigorously and the organic phase was washed again with saturated NaHCO$_3$ solution, twice with water, and once with saturated sodium chloride solution. The organic phase was dried over Na$_2$SO$_4$ and concentrated under reduced pressure. The remaining viscous oil was purified by MPLC using silica gel and eluted with a gradient of 0-30% EtOAc/hexanes, providing benzyl (1R,3R,5R)-2-(2-(tert-butyl) isonicotinoyl)-2-azabicyclo[3.1.0]hexane-3-carboxylate (0.386 g, 1.02 mmol) as a colorless glassy solid. LCMS-APCI (POS.) m/z: 379.2 (M+H)+.

31.1

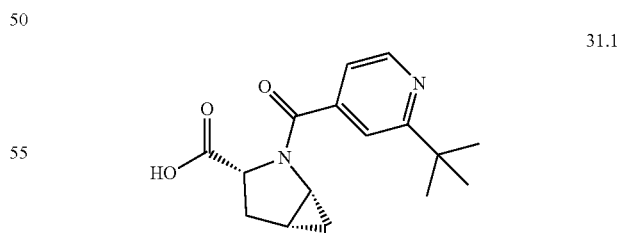

Step 4: Preparation of (1R,3R,5R)-2-(2-(tert-butyl) isonicotinoyl)-2-azabicyclo[3.1.0]hexane-3-carboxylic Acid A solution of benzyl (1R,3R,5R)-2-(2-(tert-butyl)isonicotinoyl)-2-azabicyclo[3.1.0]hexane-3-carboxylate (0.386 g, 1.02 mmol) in THF (3.0 mL) and EtOAc (3.0 mL) was prepared. The flask was evacuated and backfilled with hydrogen (balloon pressure) and stirred for eighteen hours at 22° C. The reaction was diluted with methanol (10.0 mL) and filtered through a syringe filter and then concentrated under reduced pressure, providing (1R,3R,5R)-2-(2-(tert-butyl)isonicotinoyl)-2-azabicyclo[3.1.0]hexane-3-carboxylic acid (0.285 g, 0.988 mmol) as a white foam. LCMS-APCI (POS.) m/z: 289.2 (M+H)+.

The compounds set forth in the following table were synthesized following the procedure outlined above using known starting material replacements as described.

TABLE 11

| Intermediate | Proline derivative | Aryl carboxylic acid | Structure, Name and Data |
|---|---|---|---|
| 31.0 | benzyl D-proline hydrochloride | Intermediate 13.11 | 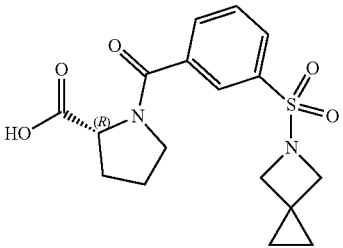<br>(3-((5-azaspiro[2.3]hexan-5-yl)sulfonyl)benzoyl)-D-proline<br>LCMS-APCI (POS.)<br>m/z: 363.1 (M − H)− |
| 31.2 | benzyl (1R,3R,5R)-2-azabicyclo[3.1.0]-hexane-3-carboxylate | 3-(tert-butyl)benzoic acid | 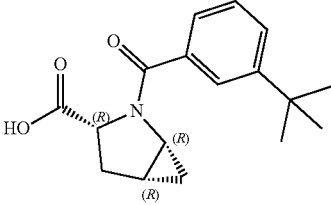<br>(1R, 3R,5R)-2-(3-(tert-butyl)benzoyl)-2-azabicyclo[3.1.0]hexane-3-carboxylic acid<br>LCMS-APCI (POS.) m/z: 288.2 (M + H)+ |
| 31.3 | benzyl (1R,3R,5R)-2-azabicyclo[3.1.0]-hexane-3-carboxylate | 2-(difluoromethyl)isonicotinic acid | 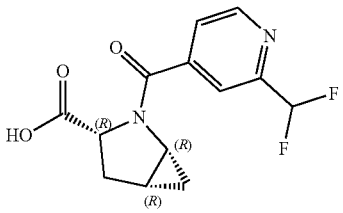<br>(1R, 3R,5R)-2-(2-(difluoromethyl)isonicotinoyl)-2-azabicyclo[3.1.0]hexane-3-carboxylic acid<br>LCMS-APCI (POS.) m/z: 283.1 (M + H)+ |
| 31.4 | benzyl (1R,3R,5R)-2-azabicyclo[3.1.0]-hexane-3-carboxylate | 3-(ethylsulfonyl)benzoic acid | 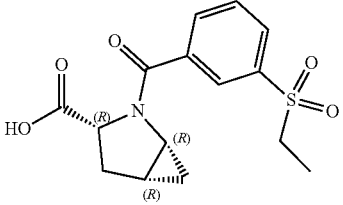<br>(1R,3R,5R)-2-(3-(ethylsulfonyl)benzoyl)-2-azabicyclo[3.1.0]hexane-3-carboxylic acid<br>LCMS-APCI (POS.) m/z: 324.1 (M + H)+ |

US 10,899,746 B2

TABLE 11-continued

| Intermediate | Proline derivative | Aryl carboxylic acid | Structure, Name and Data |
|---|---|---|---|
| 31.5 | benzyl (1R,3R,5R)-2-azabicyclo[3.1.0]-hexane-3-carboxylate | 2-methoxy-5-(methylsulfonyl)benzoic acid | 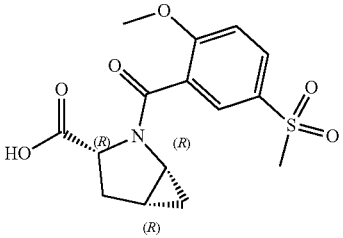<br>(1R,3R,5R)-2-(2-methoxy-5-(methylsulfonyl)benzoyl)-2-azabicyclo[3.1.0]hexane-3-carboxylic acid<br>LCMS-APCI (POS.) m/z: 340.1 (M + H)+ |
| 31.6 | 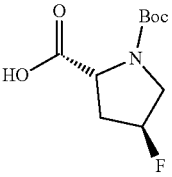 | 3-(methylsulfonyl)benzoic acid | 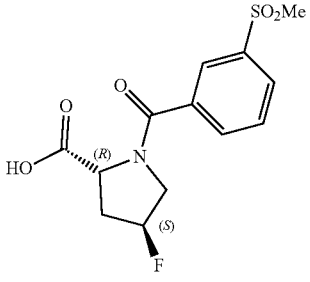<br>(2R,4S)-4-fluoro-1-(3-(methylsulfonyl)benzoyl)pyrrolidine-2-carboxylic acid<br>LCMS-APCI (POS.) m/z: 316.3 (M − H)+ |
| 31.7 | 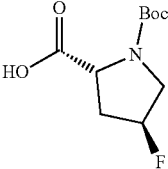 | 2-methoxy-5-(methylsulfonyl)benzoic acid | 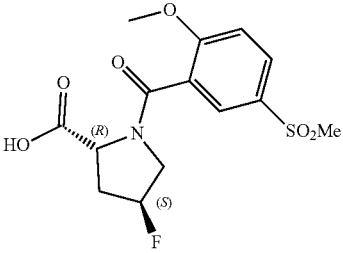<br>(2R,4S)-4-fluoro-1-(2-methoxy-5-(methylsulfonyl)benzoyl)pyrrolidine-2-carboxylic acid<br>LCMS-APCI (POS.) m/z: 346.3 (M − H)+ |
| 31.8 | benzyl (1R,3R,5R)-2-azabicyclo[3.1.0]-hexane-3-carboxylate | 2-(trifluoromethyl)isonicotinic acid | 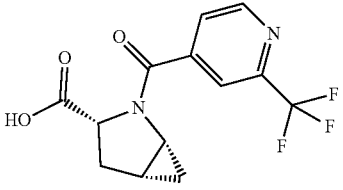 [SMILES: O=C(O)[C@H]1C[C@H]2C[C@H]2N1C(=O)c1ccnc(C(F)(F)F)c1]<br>(1R,3R,5R)-2-(2-(trifluoromethyl)isonicotinoyl)-2-azabicyclo[3.1.0]hexane-3-carboxylic acid<br>LCMS-APCI (POS.) m/z: 299.3 (M − H)+ |

Intermediate 32.0: Preparation of 3-(3-(((benzyloxy)carbonyl)amino) oxetan-3-yl)benzoic Acid

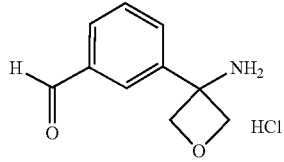 [SMILES: NC1(c2cccc(C=O)c2)COC1 ; Cl]

Step 1: Preparation of 3-(3-aminooxetan-3-yl)benzaldehyde hydrochloride

3-Bromobenzaldehyde diethyl acetal (11.65 g, 45 mmol) in dry THF (100 mL) at −78° C. was added n-butyl lithium (2.5 M in hexanes, 19 mL, 47 mmol) dropwise. The sample was stirred at −78° C. for ten minutes then added 2-methyl-N-(oxetan-3-ylidene)propane-2-sulfonamide (7.5 g, 43 mmol) dropwise. The sample was stirred at −78° C. for one hour. The mixture was diluted with 200 mL saturated ammonium chloride solution and 200 mL ethyl acetate. The layers were shaken and separated and the organic phase was dried over magnesium sulfate and concentrated under reduced pressure. The crude mixture was dissolved in ethyl acetate (250 mL). The reaction mixture was cooled to 0° C. was added 1M hydrochloric acid in ethyl acetate dropwise (24 mL, 24 mmol). The reaction mixture was stirred at 0° C. for one hour then vacuum filtered to give the desired product as a slightly off white solid (1.97 g, 9.2 mmol). $^1$H NMR (400 MHz, DMSO-$d_6$) δ 10.08 (s, 1H), 9.18 (s, 3H), 8.09 (s, 1H), 8.01 (d, J=7.9 Hz, 1H), 7.91 (d, J=7.9 Hz, 1H), 7.79-7.73 (m, 1H), 5.03-4.91 (m, 4H).

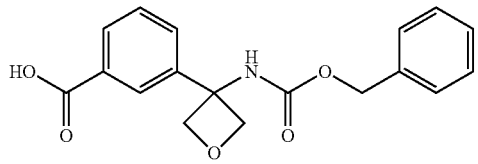 [SMILES: O=C(NC1(c2cccc(C(=O)O)c2)COC1)OCc1ccccc1]

Step 2: Preparation of benzyl (3-(3-formylphenyl)oxetan-3-yl)carbamate 3-(3-Aminooxetan-3-yl)benzaldehyde hydrochloride (1.97 g, 9.2 mmol) in dry dichloromethane (20 mL) at 0° C. was added diisopropylethylamine (4.8 mL, 28 mmol) followed by benzyl chloroformate (1.6 mL, 11 mmol) dropwise. The reaction mixture was stirred at 0° C. for thirty minutes. The mixture was diluted with 150 mL water and 150 mL dichloromethane. The layers were shaken and separated and the organic phase was washed with saturated sodium chloride solution, dried over magnesium sulfate, concentrated under reduced pressure, and purified by silica gel chromatography with a gradient to 50% ethyl acetate/hexanes to give the desired product as a clear colorless oil (2.29 g, 7.3 mmol). APCI (POS.) m/z: 312.10 (M+H)+. $^1$H NMR (400 MHz, dichloromethane-$d_2$) δ 10.04 (s, 1H), 8.04 (s, 1H), 7.92-7.82 (m, 2H), 7.67-7.57 (m, 1H), 7.49-7.26 (m, 5H), 5.80 (s, 1H), 5.12 (s, 2H), 5.05-4.84 (m, 4H).

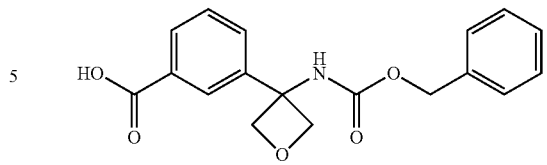

Step 3: Preparation of 3-(3-(((benzyloxy)carbonyl)amino)oxetan-3-yl)benzoic acid, Intermediate 32.0

Benzyl (3-(3-formylphenyl)oxetan-3-yl)carbamate (2.29 g, 7.3 mmol) in chloroform (24 mL), acetonitrile (24 mL), and water (36 mL) was added sodium periodate (7.86 g, 37 mmol) followed by ruthenium(III) trichloride monohydrate (0.083 g, 0.37 mmol). The reaction mixture was stirred for one hour. The mixture was diluted with 150 mL water and 150 mL 10% methanol in dichloromethane. The layers were shaken and separated and the organic phase was washed with saturated sodium chloride solution, dried over magnesium sulfate, and concentrated under reduced pressure to give the desired product as a black solid (1.872 g, 5.7 mmol). LCMS-APCI (NEG.) m/z: 326.10 (M−H)−. $^1$H NMR (400 MHz, Methanol-$d_4$) δ 8.25 (s, 1H), 7.99 (d, J=7.7 Hz, 1H), 7.87-7.74 (m, 1H), 7.58-7.47 (m, 1H), 7.44-7.11 (m, 5H), 5.10 (s, 2H), 5.05-4.80 (m, 4H).

Intermediate 33.0: Preparation of 3-(3-methyloxetan-3-yl)benzoic Acid

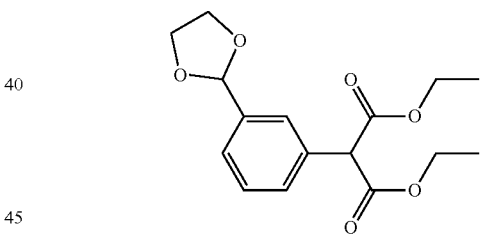

Step 1: Preparation of diethyl 2-(3-(1,3-dioxolan-2-yl)phenyl)malonate

Bis(dibenzylideneacetone)palladium(0) (0.068 g, 0.12 mmol) and potassium phosphate tribasic were combined (3.788 g, 18 mmol) under a nitrogen atmosphere. 2-(3-Bromophenyl)-1,3-dioxolane (0.900 mL, 5.9 mmol), diethyl malonate (0.993 mL, 6.5 mmol), tri-tert-butylphosphanate (0.058 mL, 0.24 mmol) and dry toluene (18 mL) were added to the reaction mixture, heated at 70 C, and stirred for 3 days. The reaction mixture was filtered through Celite, concentrated under reduced pressure, and purified by silica gel chromatography with a gradient to 30% ethyl acetate/hexanes to give the desired product as a clear yellow oil (0.324 g, 1.0 mmol). APCI (POS.) m/z: 309.10 (M+H)+. $^1$H NMR (400 MHz, dichloromethane-$d_2$) δ 7.53-7.39 (m, 4H), 5.81 (s, 1H), 4.67 (s, 1H), 4.28-4.18 (m, 4H), 4.17-4.02 (m, 4H), 1.29 (t, J=7.1 Hz, 6H).

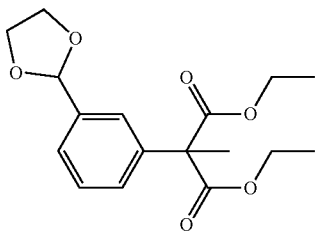 [SMILES: CCOC(=O)C(C)(C(=O)OCC)c1cccc(C2OCCO2)c1]

Step 2: Preparation of diethyl 2-(3-(1,3-dioxolan-2-yl)phenyl)-2-methylmalonate Diethyl 2-(3-(1,3-dioxolan-2-yl)phenyl)malonate (0.324 g, 1.0 mmol), methyl iodide (0.065 mL, 1.0 mmol), and 21% sodium ethoxide in ethanol (0.785 mL, 2.1 mmol) were combined, heated at 78° C., and stirred for one hour. The reaction mixture was diluted with 50 mL water and 50 mL ethyl acetate. The layers were shaken and separated and the organic phase was dried over magnesium sulfate, concentrated under reduced pressure, and purified by silica gel chromatography with a gradient to 30% ethyl acetate/hexanes to give the desired product as a clear colorless oil (0.244 g, 0.76 mmol). APCI (POS.) m/z: 323.10 (M+H)+. $^1$H NMR (400 MHz, dichloromethane-$d_2$) δ 7.50-7.48 (m, 1H), 7.46-7.38 (m, 3H), 5.80 (s, 1H), 4.30-4.19 (m, 4H), 4.17-4.00 (m, 4H), 1.87 (s, 3H), 1.28 (t, J=7.1 Hz, 6H).

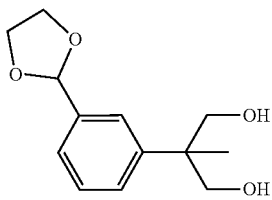 [SMILES: CC(CO)(CO)c1cccc(C2OCCO2)c1]

Step 3: Preparation of 2-(3-(1,3-dioxolan-2-yl)phenyl)-2-methylpropane-1,3-diol Diethyl 2-(3-(1,3-dioxolan-2-yl)phenyl)-2-methylmalonate (0.244 g, 0.76 mmol) in dry THF (6 mL) at 0° C. was added 2.4M lithium aluminum hydride in THF (0.63 mL, 1.5 mmol) dropwise. The reaction mixture was heated at 66° C. overnight. The reaction mixture was cooled to 0° C., added water (0.057 mL), followed by the addition of 1M sodium hydroxide in water (0.057 mL), followed by the addition of water (0.171 mL). The reaction mixture stirred for thirty minutes at room temperature, filtered through Celite, concentrated under reduced pressure, and purified by silica gel chromatography with a gradient to 100% ethyl acetate/hexanes to give the desired product as a clear colorless oil (0.116 g, 0.48 mmol). APCI (POS.) m/z: 239.10 (M+H)+. $^1$H NMR (400 MHz, dichloromethane-$d_2$) δ 7.56-7.54 (m, 1H), 7.50-7.46 (m, 1H), 7.44-7.37 (m, 2H), 5.78 (s, 1H), 4.19-4.10 (m, 2H), 4.09-4.02 (m, 2H), 3.97-3.93 (m, 2H), 3.86-3.81 (m, 2H), 1.30 (s, 3H).

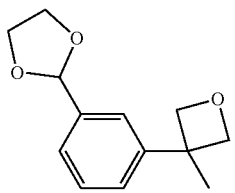 [SMILES: CC1(c2cccc(C3OCCO3)c2)COC1]

Step 4: Preparation of 2-(3-(3-Methyloxetan-3-yl)phenyl)-1,3-dioxolane 2-(3-(1,3-Dioxolan-2-yl)phenyl)-2-methylpropane-1,3-diol (0.116 g, 0.48 mmol) in dry THF (1.5 mL) at -78° C. was added 1.6M n-butyl lithium in hexanes (0.30 mL, 0.48 mmol) dropwise. The reaction mixture was stirred at -78° C. for ten minutes then added 4-toluenesulfonyl chloride (0.092 g, 0.48 mmol) in dry THF (1.5 mL) dropwise followed by 1.6M n-butyl lithium in hexanes (0.30 mL, 0.48 mmol) dropwise. The reaction mixture was heated at 70° C. overnight. The reaction mixture was cooled to 0° C., The reaction mixture was diluted with 50 mL water and 50 mL ethyl acetate. The layers were shaken and separated and the organic phase was dried over magnesium sulfate, concentrated under reduced pressure, purified by silica gel chromatography with a gradient to 50% ethyl acetate/hexanes to give the desired product as a clear colorless oil (0.040 g, 0.18 mmol). APCI (POS.) m/z: 221.15 (M+H)+. $^1$H NMR (400 MHz, dichloromethane-$d_2$) δ 7.43-7.32 (m, 3H), 7.27-7.23 (m, 1H), 5.79 (s, 1H), 4.98-4.94 (m, 2H), 4.65-4.62 (m, 2H), 4.19-3.99 (m, 4H), 1.75 (s, 3H).

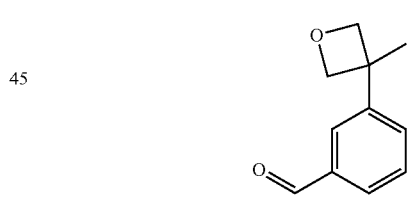

Step 5: Preparation of 3-(3-methyloxetan-3-yl)benzaldehyde 2-(3-(3-Methyloxetan-3-yl)phenyl)-1,3-dioxolane (0.040 g, 0.18 mmol) in dichloromethane (1.5 mL) was added trifluoroacetic acid (0.139 mL, 1.8 mmol). The reaction mixture was stirred for one hour, concentrated under reduced pressure, and purified by silica gel chromatography with a gradient to 50% ethyl acetate/hexanes to give the desired product as a clear colorless oil (0.030 g, 0.17 mmol). APCI (POS.) m/z: 177.10 (M+H)+. $^1$H NMR (400 MHz, dichloromethane-$d_2$) δ 10.05 (s, 1H), 7.81-7.75 (m, 2H), 7.62-7.57 (m, 1H), 7.57-7.53 (m, 1H), 5.00-4.97 (m, 2H), 4.72-4.68 (m, 2H), 1.79-1.77 (m, 3H).

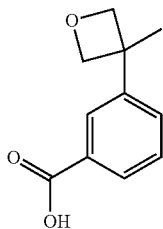

Step 6: Preparation of 3-(3-methyloxetan-3-yl)benzoic acid, Intermediate 33.0

3-(3-Methyloxetan-3-yl)benzaldehyde (0.030 g, 0.17 mmol) in chloroform (1 mL), acetonitrile (1 mL), and water (1.5 mL) was added sodium periodate (0.181 g, 0.85 mmol) followed by ruthenium(III) trichloride monohydrate (0.050 g, 0.008 mmol). The reaction mixture was stirred overnight. The reaction mixture was diluted with 50 mL water and 50 mL 10% methanol in dichloromethane. The layers were shaken and separated and the organic phase was dried over magnesium sulfate and concentrated under reduced pressure to give the desired product as a clear colorless oil (0.029 g, 0.15 mmol). APCI (NEG.) m/z: 191.1 (M–H)–. $^1$H NMR (400 MHz, Methanol-d$_4$) δ 7.83-7.79 (m, 1H), 7.79-7.77 (m, 1H), 7.39-7.37 (m, 2H), 4.89-4.86 (m, 2H), 4.60-4.57 (m, 2H), 1.63 (s, 3H).

Intermediate 34.0: Preparation of 3-(1-((benzyloxy)carbonyl)-3-fluoroazetidin-3-yl)benzoic Acid

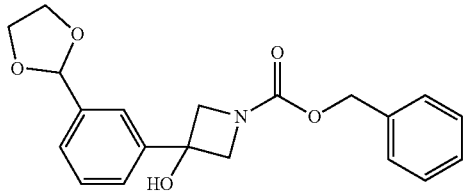 [SMILES: O=C(OCc1ccccc1)N1CC(O)(c2cccc(C3OCCO3)c2)C1]

Step 1: Preparation of benzyl 3-(3-(1,3-dioxolan-2-yl)phenyl)-3-hydroxyazetidine-1-carboxylate 2-(3-Bromophenyl)-1,3-dioxolane (1 mL, 6.6 mmol) in dry THF (10 mL) at –78° C. was added 1.6 M n-butyl lithium in hexanes (4.6 mL, 7.3 mmol) dropwise. The reaction mixture was stirred at –78° C. for 15 min then added benzyl 3-oxoazetidine-1-carboxylate (1.356 g, 6.6 mmol). The reaction mixture was allowed to warm slowly to room temperature and stirred for 3 days. The reaction mixture was diluted with 50 mL water and 50 mL ethyl acetate. The layers were shaken and separated and the organic phase was dried over magnesium sulfate, concentrated under reduced pressure, and purified by silica gel chromatography with a gradient to 100% ethyl acetate/hexanes to give the desired product as a clear colorless oil (0.798 g, 2.2 mmol). APCI (POS.) m/z: 356.10 (M+H)+. M+H=356.10, Rt=1.743 min, 3M POS. $^1$H NMR (400 MHz, dichloromethane-d$_2$) δ 7.66-7.63 (m, 1H), 7.57-7.52 (m, 1H), 7.50-7.43 (m, 2H), 7.43-7.33 (m, 5H), 5.81 (s, 1H), 5.17-5.14 (m, 2H), 4.40-4.35 (m, 2H), 4.30-4.22 (m, 2H), 4.19-4.00 (m, 4H).

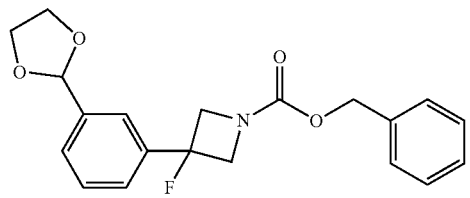 [SMILES: O=C(OCc1ccccc1)N1CC(F)(c2cccc(C3OCCO3)c2)C1]

Step 2: Preparation of benzyl 3-(3-(1,3-dioxolan-2-yl)phenyl)-3-fluoroazetidine-1-carboxylate Benzyl 3-(3-(1,3-dioxolan-2-yl)phenyl)-3-hydroxyazetidine-1-carboxylate (0.598 g, 1.7 mmol) in dry dichloromethane (16 mL) at –78° C. was added (diethylamino)sulfur trifluoride (0.267 mL, 2.0 mmol) dropwise. The reaction mixture was stirred at –78° C. for 1 hour. The reaction mixture was diluted with 50 mL 1M sodium hydroxide in water and 50 mL dichloromethane. The layers were shaken and separated and the organic phase was dried over magnesium sulfate, concentrated under reduced pressure, and purified by silica gel chromatography with a gradient to 40% ethyl acetate/hexanes to give the desired product as a clear colorless oil (0.443 g, 1.2 mmol). APCI (POS.) m/z: 358.10 (M+H)+. $^1$H NMR (400 MHz, dichloromethane-d$_2$) δ 7.62-7.59 (m, 1H), 7.54-7.46 (m, 3H), 7.44-7.33 (m, 5H), 5.82 (s, 1H), 5.19-5.15 (m, 2H), 4.55-4.45 (m, 2H), 4.45-4.35 (m, 2H), 4.19-4.10 (m, 2H), 4.10-4.01 (m, 2H).

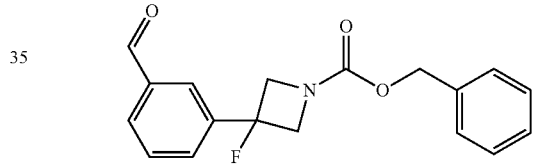

Step 3: Preparation of benzyl 3-fluoro-3-(3-formylphenyl)azetidine-1-carboxylate Benzyl 3-(3-(1,3-dioxolan-2-yl)phenyl)-3-fluoroazetidine-1-carboxylate (0.443 g, 1.2 mmol) in dichloromethane (4 mL) was added trifluoroacetic acid (0.950 mL, 12 mmol). The reaction mixture was stirred overnight. The sample was concentrated under reduced pressure and purified by silica gel chromatography with a gradient to 30% ethyl acetate/hexanes to give the desired product as a clear colorless oil (0.389 g, 1.2 mmol). APCI (POS.) m/z: 314.20 (M+H)+. $^1$H NMR (400 MHz, dichloromethane-d$_2$) δ 10.08 (s, 1H), 8.03-8.01 (m, 1H), 7.95-7.92 (m, 1H), 7.81-7.77 (m, 1H), 7.70-7.64 (m, 1H), 7.45-7.34 (m, 5H), 5.18 (s, 2H), 4.60-4.50 (m, 2H), 4.46-4.36 (m, 2H).

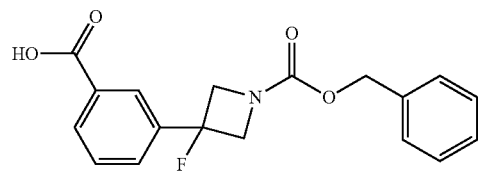

Step 4: Preparation of 3-(1-((benzyloxy)carbonyl)-3-fluoroazetidin-3-yl)benzoic Acid Benzyl 3-fluoro-3-(3-formylphenyl)azetidine-1-carboxylate (0.445 g, 1.4 mmol) and sodium periodate (1.519 g, 7.1 mmol) in chloroform (6 mL), acetonitrile (6 mL), and water (9 mL) was added ruthenium(III) trichloride monohydrate (0.015 g, 0.071 mmol). The reaction mixture was stirred overnight. The reaction mixture was diluted with 50 mL water and 50 mL 10% methanol in dichloromethane. The layers were shaken and separated and the organic phase was dried over magnesium sulfate and concentrated under reduced pressure to give the desired product as a clear red oil (0.403 g, 1.2 mmol). APCI (POS.) m/z: 330.1 (M+H)+. $^1$H NMR (400 MHz, dichloromethane-$d_2$) δ 8.28-8.22 (m, 1H), 8.18-8.12 (m, 1H), 7.84-7.75 (m, 1H), 7.65-7.58 (m, 1H), 7.45-7.34 (m, 5H), 5.19 (s, 2H), 4.60-4.49 (m, 2H), 4.48-4.38 (m, 2H).

Intermediate 35.0: Preparation of 3-(3-fluorooxetan-3-yl)benzoic Acid

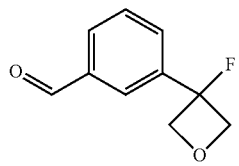

Step 1: Preparation of 3-(3-fluorooxetan-3-yl)benzaldehyde

3-Bromobenzaldehyde diethyl acetal (1 mL, 4.9 mmol) in dry THF (10 mL) at −78° C. was added 1.6M n-butyl lithium in hexanes (3.4 mL, 5.4 mmol) dropwise. The reaction mixture was stirred at −78° C. for fifteen minutes then added oxetan-3-one (0.353 g, 4.9 mmol) dropwise. The reaction mixture was stirred at −78° C. for thirty minutes. The reaction mixture was diluted with 50 mL saturated ammonium chloride solution and 50 mL ethyl acetate. The layers were shaken and separated and the organic phase was dried over magnesium sulfate, concentrated under reduced pressure to give the desired product, and purified by silica gel chromatography with a gradient to 50% ethyl acetate/hexanes. The crude mixture was dissolved in dry dichloromethane (10 mL), cooled to −78° C., and added diethylaminosulfur trifluoride (0.16 mL, 1.1 mmol) dropwise. The reaction mixture was stirred at −78° C. for thirty minutes. The reaction mixture was warmed to room temperature. The reaction mixture was diluted with 50 mL 1M sodium hydroxide and 50 mL ethyl acetate. The layers were shaken and separated and the organic phase was dried over magnesium sulfate, concentrated under reduced pressure, and purified by silica gel chromatography with a gradient to 30% ethyl acetate/hexanes to give the desired product as a clear colorless oil (0.051 g, 0.28 mmol). $^1$H NMR (400 MHz, dichloromethane-$d_2$) δ 10.10 (s, 1H), 8.13-8.10 (m, 1H), 7.96-7.92 (m, 1H), 7.92-7.88 (m, 1H), 7.72-7.66 (m, 1H), 5.20

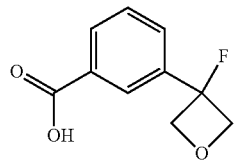

Step 2: Preparation of 3-(3-fluorooxetan-3-yl)benzoic acid, Intermediate 35.0

3-(3-Fluorooxetan-3-yl)benzaldehyde (0.051 g, 0.28 mmol) in chloroform (1 mL), acetonitrile (1 mL), and water (1.5 mL) was added sodium periodate (0.304 g, 1.4 mmol) followed by ruthenium(III) trichloride monohydrate (0.003 g, 0.014 mmol). The reaction mixture was stirred overnight. The reaction mixture was diluted with 50 mL water and 50 mL dichloromethane. The layers were shaken and separated and the organic phase was dried over magnesium sulfate and concentrated under reduced pressure to give the desired product as a white solid (0.050 g, 0.26 mmol). $^1$H NMR (400 MHz, Methanol-$d_4$) δ 8.25-8.23 (m, 1H), 8.10-8.05 (m, 1H), 7.85-7.81 (m, 1H), 7.63-7.58 (m, 1H), 5.15-5.06 (m, 2H), 5.00-4.91 (m, 2H).

Intermediate 36.0: Preparation of 3-(1-((benzyloxy)carbonyl)-3-hydroxyazetidin-3-yl)benzoic Acid

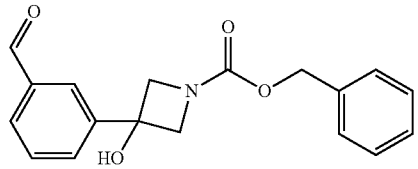 [SMILES: O=Cc1cccc(C2(F)CN(C(=O)OCc3ccccc3)C2)c1]

Step 1: Preparation of benzyl 3-(3-formylphenyl)-3-hydroxyazetidine-1-carboxylate Benzyl 3-(3-(1,3-dioxolan-2-yl)phenyl)-3-hydroxyazetidine-1-carboxylate (0.199 g, 0.56 mmol) in dichloromethane (2 mL) was added trifluoroacetic acid (0.430 mL, 5.6 mmol). The reaction mixture was stirred overnight. The sample was concentrated under reduced pressure and purified by silica gel chromatography with a gradient to 40% ethyl acetate/hexanes to give the desired product as a clear colorless oil (0.144 g, 0.46 mmol). APCI (POS.) m/z: 312.10 (M+H)+. $^1$H NMR (400 MHz, dichloromethane-$d_2$) δ 10.06 (s, 1H), 8.10-8.06 (m, 1H), 7.89-7.82 (m, 2H), 7.65-7.60 (m, 1H), 7.42-7.32 (m, 5H), 5.15 (s, 2H), 4.39-4.28 (m, 4H).

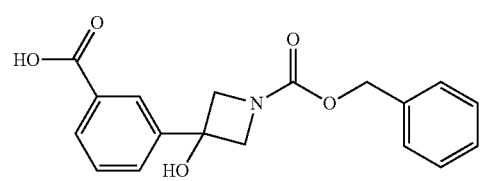 [SMILES: O=C(O)c1cccc(C2(F)CN(C(=O)OCc3ccccc3)C2)c1]

Step 2: Preparation of 3-(1-((benzyloxy)carbonyl)-3-hydroxyazetidin-3-yl)benzoic acid, Intermediate 36.0

Benzyl 3-(3-formylphenyl)-3-hydroxyazetidine-1-carboxylate (0.144 g, 0.46 mmol) and sodium periodate (0.495 g, 2.3 mmol) in chloroform (2 mL), acetonitrile (2 mL), and water (3 mL) was added ruthenium(III) trichloride monohydrate (0.005 g, 0.023 mmol). The reaction mixture was stirred overnight. The reaction mixture was diluted with 50 mL water and 50 mL 10% methanol in dichloromethane. The layers were shaken and separated and the organic phase was dried over magnesium sulfate and concentrated under reduced pressure to give the desired product was a slightly yellow solid (0.105 g, 0.32 mmol). APCI (POS.) m/z: 328.10 (M+H)+. $^1$H NMR (400 MHz, dichloromethane-$d_2$) δ 8.17-8.13 (m, 1H), 7.96-7.91 (m, 1H), 7.70-7.65 (m, 1H), 7.44-7.39 (m, 1H), 7.30-7.18 (m, 5H), 5.02 (s, 2H), 4.28-4.23 (m, 2H), 4.21-4.16 (m, 2H).

Intermediate 37.0: Preparation of (1S,3s)-3-((R)-amino(2,5-difluoro-4-(trifluoromethyl)phenyl)methyl)cyclobutan-1-ol

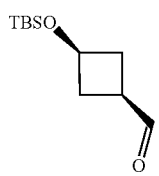 [SMILES: CC(C)(C)[Si](C)(C)O[C@H]1C[C@@H](C=O)C1]

Step 1: Preparation of (1s,3s)-3-((tert-butyldimethylsilyl)oxy)cyclobutane-1-carbaldehyde To a solution of ((1s,3s)-3-((tert-butyldimethylsilyl)oxy)cyclobutyl)methanol (2.5 g, 11.6 mmol) in DCM (30 mL) at 0 C was added Dess-Martin periodinane (7.35 g, 17.3 mmol). The reaction was stirred for 15 mins at 0 C and then the solution was warmed to rt. The reaction was monitored by TLC analysis. After the completion of the reaction, the reaction was cooled to 0 C and then quenched with 2:1 sodium thiosulfate-sodium bicabonate solution. The reaction was stirred until the phases became clear. The aq. layer was extracted once with DCM and the combined organic layer was dried, filtered, and concentrated to provide the product as a colorless oil (1.24 g, 5.78 mmol). $^1$H NMR (DMSO-$d_6$) δ: 9.55 (d, J=2.5 Hz, 1H), 4.23 (tt, J=7.9, 6.8 Hz, 1H), 2.65 (ttd, J=9.9, 7.6, 2.5 Hz, 1H), 2.37-2.29 (m, 2H), 1.99-1.92 (m, 2H), 0.82 (s, 11H), 0.00 (s, 7H).

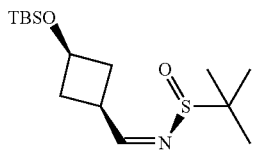

Step 2: Preparation of (S)—N—((Z)-((1s,3R)-3-((tert-butyldimethylsilyl)oxy)cyclobutyl)methylene)-2-methylpropane-2-sulfinamide A 100 mL round bottom flask was charged with (1s,3s)-3-((tert-butyldimethylsilyl)oxy)cyclobutane-1-carbaldehyde (1.85 g, 8.63 mmol) and diluted with 1,2-dichloroethane (25 mL). To that solution was added (S)-(-)-2-methyl-2-propane-sulfinamide (1.05 g, 8.63 mmol) and copper(II) sulfate, anhydrous (2 eq). The flask was fitted with a findenser and heated to 55° C. After 24 hours, LCMS showed peak containing a mass consistent with the desired product. The room temperature solution was filtered through a pad of Celite and concentrated under reduced pressure. The material was left of the high vacuum overnight to provide product as a vicious green oil (2.45 g, 7.71 mmol). APCI (POS.) m/z: 318.20 (M+H)+. $^1$H NMR (DMSO-$d_6$) δ: 7.92 (d, J=4.6 Hz, 1H), 4.24 (tt, J=8.0, 6.8 Hz, 1H), 2.95-2.77 (m, 1H), 2.47-2.41 (m, 2H), 2.05-1.74 (m, 2H), 1.08 (s, 9H), 0.82 (s, 9H), 0.00 (s, 7H).

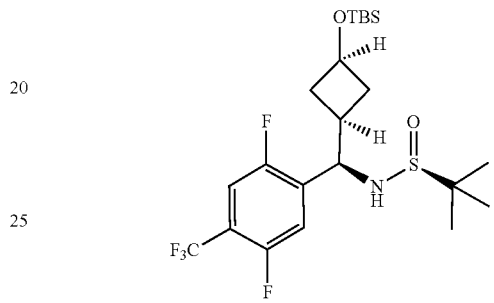

Step 3: Preparation of (S)—N—((R)-((1s,3S)-3-((tert-butyldimethylsilyl)oxy)cyclobutyl)(2,5-difluoro-4-(trifluoromethyl)phenyl)methyl)-2-methyl-propane-2-sulfinamide To a 100 mL oven-dried 3 necked round bottom flask under nitrogen was added 1-bromo-2,5-difluoro-4-(trifluoromethyl)benzene (1.09 g, 3.45 mmol) in anhydrous THF (15 mL). The resulting solution was cooled to -70 C (internal temperature) with an acetone dry-ice bath. Isopropylmagnesium chloride lithium chloride complex (2.79 mL, 3.62 mmol, 1.3 M) was then added dropwise while maintaining the internal reaction temperature between -65 C and -70 C. The resulting solution was stirred at -70 C for 30 minutes, and then (S)—N—((Z)-((1s,3R)-3-((tert-butyldimethylsilyl)oxy)cyclobutyl)methylene)-2-methylpropane-2-sulfinamide in 5 mL THF was added dropwise while maintaining the internal temperature between -65 and -70 C. The resulting solution was stirred at the same temperature for 120 minutes, and then the dry-ice was removed from the cooling bath and the reaction was allowed to warm to 0 C over 30 minutes and at rt overnight (no reaction observed at 0 C—reaction proceeded at rt). It was then quenched with 30 ml saturated ammonium chloride (aqueous) and then diluted with 40 mL ethyl acetate and 40 mL water. The layers were shaken and separated and the organic phase was washed with brine, dried over sodium sulfate and concentrated to a crude sticky solid which was purified with silica gel using a gradient from 0 to 20% ethyl acetate/hexanes, providing the desired product as a white foam (1.06 g, 1.91 mmol, 2:1 mixture of diastereomers). APCI (POS.) m/z: 500.20 (M+H)+. $^1$H NMR (DMSO-$d_6$) δ: 7.82-7.60 (m, 4H), 5.77-5.61 (m, 2H), 4.46 (t, J=8.4 Hz, 2H), 4.12-4.02 (m, 2H), 2.43 (ddt, J=12.1, 10.5, 6.1 Hz, 2H), 2.17 (ddd, J=17.1, 9.8, 7.6 Hz, 2H), 2.11-2.01 (m, 2H), 1.83-1.67 (m, 2H), 1.64-1.46 (m, 2H), 1.06 (s, 18H), 0.84 (d, J=2.1 Hz, 18H), 0.00 (s, 12H).

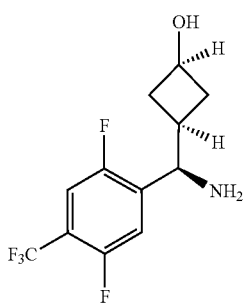 [SMILES: N[C@@H](c1cc(F)c(C(F)(F)F)cc1F)[C@H]1C[C@@H](O)C1]

Step 4: Preparation of (1S,3s)-3-((R)-amino(2,5-difluoro-4-(trifluoromethyl)phenyl)methyl)cyclobutan-1-ol, (Intermediate 37.0)

To a solution of (S)—N—((R)-((1 s,3S)-3-((tert-butyldimethylsilyl)oxy)cyclobutyl)(2,5-difluoro-4-(trifluoromethyl)phenyl)methyl)-2-methylpropane-2-sulfinamide (0.95 g, 1.90 mmol) in 15 mL of methanol at 0° C. in an ice bath under argon was added 4M HCl in dioxane (1.42 mL, 5.70 mmol) dropwise and stirred for 5 minutes. Then the reaction mixture was stirred at 0 C for 30 mins and warmed to RT and stirred for 30 minutes while continuously monitoring with TLC analysis. The reaction was deemed to be complete after 30 minutes (LCMS analysis). After the reaction was completed, the reaction was quenched by adding triethylamine (10 mL). The resulting mixture was concentrated under reduced pressure, and the remaining white solid was partitioned between saturated sodium bicarbonate (30 mL) and DCM (30 mL). The layers were separated and the aqueous phase was extracted with additional DCM (30 mL). The organic layers were combined, dried over sodium sulfate, filtered and concentrated under vacuum, providing the desired product as a viscous oil (0.51 g, 1.81 mmol). APCI (POS.) m/z: 282.20 (M+H)+. $^1$H NMR (400 MHz, DMSO-$d_6$) δ 7.70 (dt, J=9.9, 3.7 Hz, 2H), 5.08-4.87 (m, 1H), 4.11-4.00 (m, 1H), 3.86 (d, J=6.3 Hz, 1H), 2.32-2.23 (m, 1H), 2.17 (d, J=40.5 Hz, 2H), 2.04-1.93 (m, 1H), 1.91-1.78 (m, 1H), 1.61 (ddt, J=29.0, 10.0, 8.2 Hz, 2H).

The compounds set forth in the following table were synthesized following the procedure outlined above using known starting material replacements as described.

TABLE 12

| Intermediate | Reagents | Structure, Name and Data |
|---|---|---|
| Intermediate 37.0 | ((1S,3S)-3-((tert-butyldimethylsilyl)oxy)cyclobutyl)methanol | (1S,3s)-3-((R)-amino(2,5-difluoro-4-(trifluoromethyl)phenyl)methyl)cyclobutan-1-ol LCMS-ESI (POS.) m/z: 282.20 (M + H)+ |
| Intermediate 37.1 | ((1R,3R)-3-((tert-butyldimethylsilyl)oxy)cyclobutyl)methanol | (1R,3r)-3-((R)-amino(2,5-difluoro-4-(trifluoromethyl)phenyl)methyl)cyclobutan-1-ol LCMS-ESI (POS.) m/z: 282.20 (M + H)+ |

General Procedures

Route A:

General Scheme for Route A

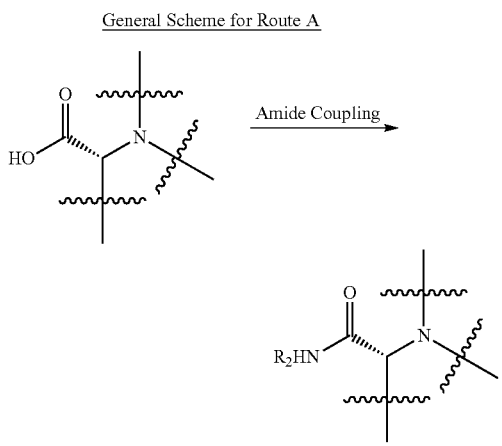

Example Route A: Example 758

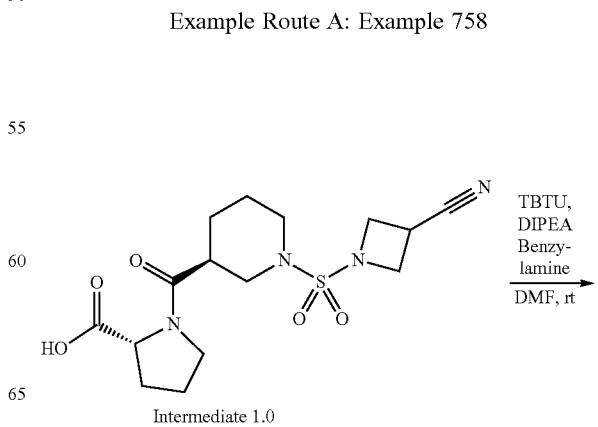

Intermediate 1.0

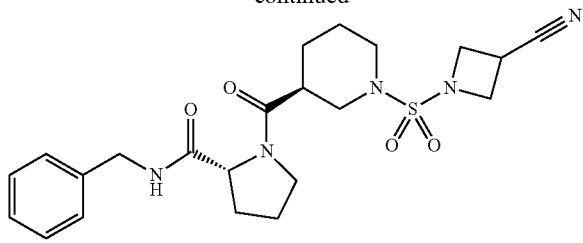

Example 758

Step 1: A 40-mL pressure release vial was charged with (R)-1-((S)-1-((3-cyanoazetidin-1-yl)sulfonyl)piperidine-3-carbonyl)pyrrolidine-2-carboxylic acid (Intermediate 1, 150 mg, 0.41 mmol) and DMF (2.0 mL). To that solution was added DIPEA (0.20 mL, 1.15 mmol), benzylamine (0.10 mL, 0.92 mmol) and TBTU (195 mg, 0.61 mmol), respectively. The vial was sealed and allowed to stir at room temperature for 30 min. The crude material was filtered through a 0.45 μm syringe tip filter and purified by preparative HPLC (XSelect CSH Prep C18 10 μm ODB 19×100 mm, A: water 0.1% formic acid B: acetonitrile 0.1% formic acid, Gradient: 25% (2 min), 25-70% (12 min), Flow Rate: 40 mL/min, monitored @ 215 nm) to give (R)—N-benzyl-1-((S)-1-((3-cyanoazetidin-1-yl)sulfonyl)piperidine-3-carbonyl)pyrrolidine-2-carboxamide (Example 758, 145 mg) as a fluffy white solid. $^1$H NMR (500 MHz, chloroform-d) δ ppm 7.18-7.38 (m, 5H), 4.62 (br d, J=5.97 Hz, 1H), 4.40-4.50 (m, 2H), 4.10-4.17 (m, 4H), 3.78 (br d, J=12.07 Hz, 2H), 3.57-3.66 (m, 2H), 3.42-3.49 (m, 1H), 2.97-3.02 (m, 1H), 2.69-2.82 (m, 2H), 2.44-2.49 (m, 1H), 2.18-2.26 (m, 1H), 1.49-2.14 (m, 7H). LCMS-ESI (POS.) m/z: 460.2 (M+H)+.

In a second illustrative example the compound of Example 403 is prepared by the process of the general scheme for Route A:

Example 402: Preparation of (2R,4S)—N—((R)-cyclopropyl(2-fluoro-4-(trifluoromethyl)phenyl)methyl)-4-fluoro-1-(3-(methylsulfonyl)benzoyl) pyrrolidine-2-carboxamide Step 1: Preparation of (2R,4S)-tert-butyl 2-(((R)-cyclopropyl(2-fluoro-4-(trifluoromethyl)phenyl)methyl)carbamoyl)-4-fluoropyrrolidine-1-carboxylate. (R)-cyclopropyl(2-fluoro-4-(trifluoromethyl)phenyl)methanamine hydrochloride (Intermediate 9.5, 1.4 g, 5.14 mmol), TBTU (1.7 g, 5.14 mmol), and (2R,4S)-1-Boc-4-fluoropyrrolidine-2-carboxylic acid (1.2 g, 5.14 mmol) were added to a 100-mL round-bottom flask. DCM (26 mL) was added and the reaction was stirred at rt as DIPEA (2.70 mL, 15.43 mmol) was introduced in a single portion. The reaction was stirred at rt for 30 min. The crude solution was then carried on directly to the subsequent step. LCMS (POS.) m/z: 471.0 (M+Na)+.

Step 2: Preparation of (2R,4S)—N—((R)-cyclopropyl(2-fluoro-4-(trifluoromethyl)phenyl)methyl)-4-fluoropyrrolidine-2-carboxamide Crude (2R,4S)-tert-butyl 2-(((R)-cyclopropyl(2-fluoro-4-(trifluoromethyl)phenyl)methyl)carbamoyl)-4-fluoropyrrolidine-1-carboxylate (2.31 g, 5.14 mmol) dissolved in DCM (25.7 mL) from the previous step was stirred at rt. TFA (7.66 mL, 103 mmol) was added dropwise and the reaction was stirred at rt for 1 h. The volatiles were removed under reduced pressure and the product was used directly without purification. LCMS (POS.) m/z: 349.2 (M+H)+.

Step 3: Preparation of (2R,4S)—N—((R)-cyclopropyl(2-fluoro-4-(trifluoromethyl)phenyl)methyl)-4-fluoro-1-(3-(methylsulfonyl)benzoyl)pyrrolidine-2-carboxamide A 50 mL round-bottom flask was charged with (2R,4S)—N—((R)-cyclopropyl(2-fluoro-4-(trifluoromethyl)phenyl)methyl)-4-fluoropyrrolidine-2-carboxamide (1.69 g, 5.00 mmol), DIPEA (2.6 mL, 15.0 mmol), 3-(methylsulfonyl)benzoic acid (1.00 g, 5.00 mmol), TBTU (1.69 g, 5.25 mmol), and DMF (10.0 mL). The reaction was stirred for 1 h and then purified directly by preparative HPLC (XSelect CSH Prep C18 10 μm ODB 19×100 mm, A: water 0.1% TFA B: acetontrile 0.1% TFA, gradient: 25% (2 min), 25-70% (12 min), flow Rate: 40 mL/min, monitored @ 215 nm) to give the title compound as a white solid (1.78 g). $^1$H NMR (500 MHz, DMSO-d$_6$) δ ppm 8.57-8.92 (m, 1H), 7.46-8.11 (m, 7H), 5.17-5.42 (m, 1H), 4.56-4.76 (m, 2H), 3.49-4.25 (m, 6H), 1.81-2.04 (m, 1H), 0.80-1.29 (m, 1H), −0.23-0.66 (m, 4H). LCMS (POS.) m/z: 531.0 (M+H)+.

In a third illustrative example the compound of Example 365 is prepared by the process of the general scheme for Route A:

Example 364: Preparation of (R)—N—((R)-cyclopropyl(2-fluoro-4-(trifluoromethyl)phenyl)methyl)-1-(3-(methylsulfonyl)benzoyl) pyrrolidine-2-carboxamide Step 1: Preparation of (R)-tert-butyl 2-(((R)-cyclopropyl(2-fluoro-4-(trifluoromethyl)phenyl)methyl)carbamoyl)pyrrolidine-1-carboxylate A 50 mL round bottom flask with magnetic stir bar was charged with (R)-cyclopropyl(2-fluoro-4-(trifluoromethyl)phenyl)methanamine hydrochloride (Intermediate 9.5, 940 mg, 3.49 mmol), DIPEA (1.82 mL, 10.5 mmol), N-(tert-butoxycarbonyl)-D-proline (750 mg, 3.49 mmol), and TBTU (1.12 g, 3.49 mmol) in DCM (7.0 mL). The reaction was stirred at rt for 4 h and then washed once with 1N HCl and then once with brine. The organics were separated, dried over sodium sulfate, and concentrated under reduced pressure. The crude product was adsorbed onto silica gel and purified by column chromatography (silica gel, 230-400 mesh) using 0-100% EtOAc/hexanes to give the title compound as a white solid (1.45 g, 3.37 mmol). $^1$H NMR (500 MHz, chloroform-d) δ ppm 7.42-7.53 (m, 1H), 7.36-7.42 (m, 1H), 7.31 (br d, J=9.86 Hz, 1H), 4.12-4.73 (m, 2H), 3.20-3.71 (m, 2H), 1.75-2.55 (m, 4H), 1.10-1.77 (m, 11H), 0.48-0.77 (m, 2H), 0.26-0.48 (m, 2H). LCMS (POS.) m/z: 453.2 (M+Na)+.

Step 2: Preparation of (R)—N—((R)-cyclopropyl(2-fluoro-4-(trifluoromethyl)phenyl)methyl)pyrrolidine-2-carboxamide hydrochloride A 100 mL round-bottom flask with magnetic stir bar was charged with (R)-tert-butyl 2-(((R)-cyclopropyl(2-fluoro-4-(trifluoromethyl)phenyl)methyl)carbamoyl)pyrrolidine-1-carboxylate (1.45 g, 3.37 mmol), DCM (15 mL) and HCl (4M in 1,4-dioxane, 12.63 mL, 50.5 mmol). The reaction was stirred at rt for 2 h. The volatiles were then removed under reduced pressure to give desired product as a white solid (1.20 g). ¹H NMR (500 MHz, DMSO-d₆) δ ppm 9.75-10.22 (m, 1H), 9.46 (br d, J=6.75 Hz, 1H), 8.47 (br d, J=2.85 Hz, 1H), 7.69-7.78 (m, 1H), 7.59-7.69 (m, 2H), 4.43-4.56 (m, 1H), 4.25 (br t, J=7.79 Hz, 1H), 3.33 (s, 1H), 3.16 (br t, J=7.14 Hz, 2H), 2.25-2.42 (m, 1H), 1.72-1.96 (m, 2H), 1.61-1.72 (m, 1H), 1.19-1.37 (m, 1H), 0.56-0.68 (m, 1H), 0.50 (tt, J=8.79, 4.57 Hz, 1H), 0.41 (dq, J=9.47, 4.80 Hz, 1H), 0.34 (dt, J=9.54, 4.70 Hz, 1H). LCMS (POS.) m/z: 331.2 (M+H)+.

Step 3: Preparation of (R)—N—((R)-cyclopropyl(2-fluoro-4-(trifluoromethyl)phenyl)methyl)-1-(3-(methylsulfonyl)benzoyl) pyrrolidine-2-carboxamide 3-(methylsulfonyl)benzoic acid (1.15 g, 5.76 mmol), TBTU (1.85 g, 5.76 mmol), and (R)—N—((R)-cyclopropyl(2-fluoro-4-(trifluoromethyl)phenyl)methyl)pyrrolidine-2-carboxamide (1.59 g, 4.8 mmol) were suspended in DCM (24 mL). DIPEA (2.5 mL, 14.40 mmol) was added dropwise and the reaction was stirred at rt for 1 h. The reaction mixture was washed once with saturated sodium bicarbonate solution, dried over sodium sulfate, filtered, and concentrated. The crude product was purified directly by preparative HPLC (XSelect CSH Prep C18 10 μm ODB 19×100 mm, A: water 0.1% TFA B: acetontrile 0.1% TFA, gradient: 25% (2 min), 25-70% (12 min), flow Rate: 40 mL/min, monitored @ 215 nm) to give the title compound as a white solid (1.58 g, 3.08 mmol). ¹H NMR (500 MHz, DMSO-d₆) δ ppm 8.49-8.78 (m, 1H), 7.51-8.07 (m, 7H), 4.18-4.65 (m, 2H), 3.38-3.69 (m, 2H), 3.25-3.31 (m, 3H), 2.13-2.29 (m, 1H), 1.64-1.92 (m, 3H), 0.88-1.29 (m, 1H), −0.06-0.66 (m, 4H). LCMS (POS.) m/z: 513.2 (M+H)+.

Route B:

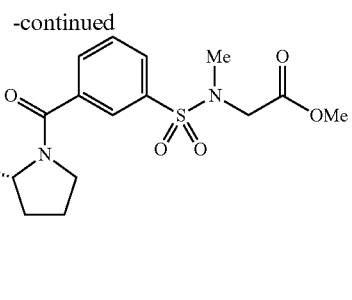

Example 346

Step 1: 3-(chlorosulfonyl)benzoyl chloride (0.091 mL, 0.379 mmol) was dissolved in DCM (1.0 mL) at 0° C. DIPEA (0.165 mL, 0.948 mmol) was added followed by (R)—N-(4-(trifluoromethyl)benzyl)pyrrolidine-2-carboxamide (Intermediate 28.0, 0.06 g, 0.190 mmol) dropwise over 15 minutes. Sarcosine methyl ester hydrochloride, DMAP (0.023 g, 0.190 mmol), and DIPEA (0.165 mL, 0.948 mmol) were then added and the reaction was warmed to rt for 60 min. The crude material was filtered through a 0.45 μm syringe tip filter and purified by preparative HPLC (XSelect CSH Prep C18 10 μm ODB 19×100 mm, A: water 0.1% formic acid B: acetonitrile 0.1% formic acid, gradient: 25% (2 min), 25-70% (12 min), flow rate: 40 mL/min, monitored @ 215 nm) to give methyl (R)-2-(N-methyl-3-(2-((4-(trifluoromethyl)benzyl)carbamoyl)pyrrolidin-1-carbonyl)phenylsulfonamido)acetate, Example 346 (13 mg) as a fluffy white solid. ¹H NMR (400 MHz, chloroform-d) δ ppm 7.27-7.92 (m, 9H), 7.24-7.25 (m, 1H), 4.62-4.76 (m, 1H), 4.38-4.54 (m, 2H), 3.92-4.01 (m, 2H), 3.45-3.59 (m, 4H), 3.30-3.43 (m, 1H), 2.74-2.90 (m, 3H), 2.35-2.47 (m, 1H), 1.98-2.12 (m, 2H), 1.96-2.13 (m, 2H), 1.73-1.89 (m, 1H). LCMS-ESI (POS.) m/z: 542.2 (M+H)+.

Route C:

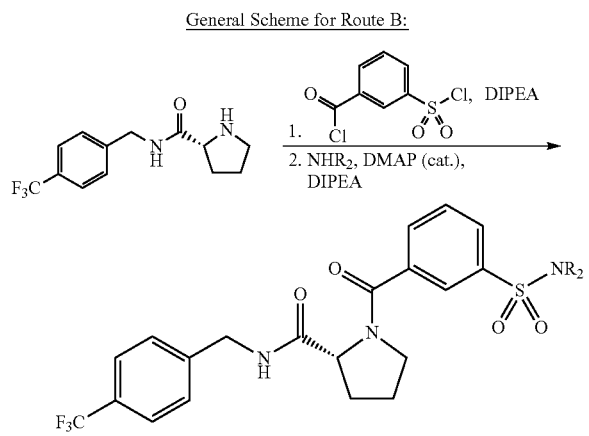

Example Route B: Example 346

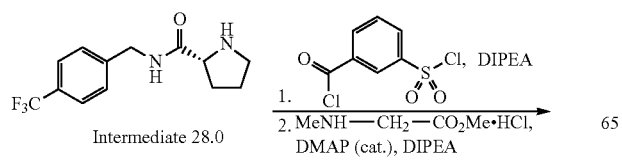

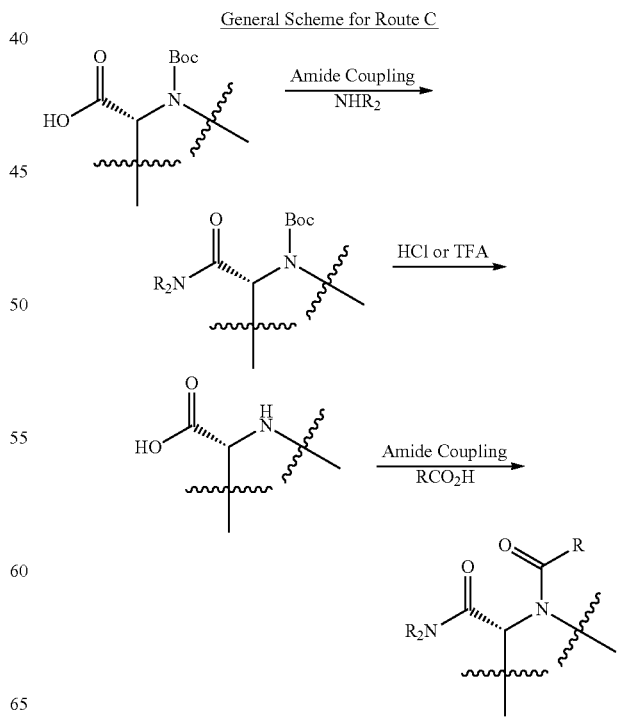

General Scheme for Route C

Example Route C: Example 19

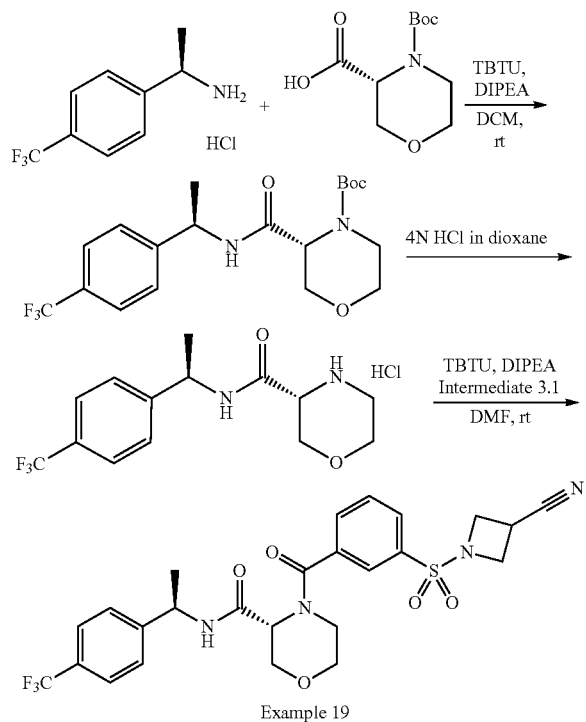

Example 19

Step 1: A 40-mL pressure release vial was charged with (R)-4-(tert-butoxycarbonyl)morpholine-3-carboxylic acid (500 mg, 2.16 mmol) and dissolved in DCM (10 mL). To that stirring solution at rt was added DIPEA (0.94 mL, 5.41 mmol), (R)-1-(4-(trifluoromethyl)phenyl)ethanamine (532 mg, 2.81 mmol) and TBTU (764 mg, 2.38 mmol). After 2 hours at rt, the crude material was loaded directly onto a silica gel column, and purified by flash chromatography (50 g Biotage eluting with 0-50% ethyl acetate:ethanol 3:1 (v/v) in heptane) to provide tert-butyl (R)-3-(((R)-1-(4-(trifluoromethyl)phenyl)ethyl)carbamyl)morpline-4-carbxyate (829 mg, 2.06 mmol) as an amorphous white foam. LCMS-ESI (POS.) m/z: 425.2 (M+Na)+.

Step 2: A 40-mL pressure release vial was charged with tert-butyl (R)-3-(((R)-1-(4-(trifluoromethyl)phenyl)ethyl)carbamoyl)morpholine-4-carboxylate (829 mg, 2.06 mmol) and dissolved in dichloromethane (10 mL). To that solution was added 4.0M HCl in dioxane (2.06 mL, 8.24 mmol). The vial was sealed and allowed to stir at rt for 19 h. The white precipitate was collected by filtration and washed with heptane to give (R)—N—((R)-1-(4-(trifluoromethyl)phenyl)ethyl) morpholine-3-carboxamide hydrochloride (635 mg) as an analytically pure white solid. LCMS-ESI (POS.) m/z: 303.2 (M+H)+.

Step 3: A 40-mL pressure release vial was charged with (R)—N—((R)-1-(4-(trifluoromethyl)phenyl)ethyl)morpholine-3-carboxamide hydrochloride (150 mg, 0.443 mmol) and DMF (2.5 mL). To that stirring solution at rt was added DIPEA (0.50 mL, 2.86 mmol), 3-((3-cyanoazetidin-1-yl)sulfonyl)benzoic acid (Intermediate 3.1, 130 mg, 0.487 mmol) and finally TBTU (213 mg, 0.664 mmol). The vial was sealed and allowed to stir for 24 h at rt. The reaction was diluted with a small amount of water and filtered through a 0.45 μm syringe tip filter and purified by preparative HPLC (XSelect CSH Prep C18 10 μm ODB 19×100 mm, A: water 0.1% TFA B: acetonitrile 0.1% TFA, gradient: 25% (2 min), 25-70% (12 min), flow Rate: 40 mL/min, monitored @215 nm) to give (R)-4-(3-((3-cyanoazetidin-1-yl)sulfonyl)benzoyl)-N—((R)-1-(4-(trifluoromethyl)phenyl)ethyl)morpholine-3-carboxamide, also referred to as (3R)-4-((3-((3-cyano-1-azetidinyl)sulfonyl)phenyl)carbonyl)-N-((1R)-1-(4-(trifluoromethyl)phenyl)ethyl)-3-morpholinecarboxamide Example 19 (221.2 mg) as an off-white solid. $^1$H NMR (500 MHz, DMSO-d$_6$) δ ppm 8.52-8.73 (m, 1H), 7.95 (br s, 1H), 7.75-7.88 (m, 3H), 7.70 (br d, J=8.04 Hz, 2H), 7.54 (br d, J=6.62 Hz, 2H), 5.05 (br s, 1H), 4.20-4.44 (m, 2H), 3.52-4.07 (m, 8H), 3.10-3.49 (m, 2H), 1.32-1.48 (m, 3H). LCMS-ESI (POS.) m/z: 551.2 (M+H)+.

Second illustrative example prepared by the general scheme for Route C:

Example 218: Preparation of (1R,3R,5R)—N—((R)-(4-chloro-2,5-difluorophenyl) (cyclopropyl)methyl)-2-(5-(methylsulfonyl)nicotinoyl)-2-azabicyclo[3.1.0]hexane-3-carboxamide (which compound is also referred to herein as (1R,3R,5R)—N—((R)-(4-chloro-2,5-difluorophenyl) (cyclopropyl)methyl)-2-((5-(methylsulfonyl)-3-pyridinyl)carbonyl)-2-azabicyclo[3.1.0]hexane-3-carboxamide)

Step 1: Preparation of (S,E)-N-(4-chloro-2,5-difluorobenzylidene)-2-methylpropane-2-sulfinamide (S)-(−)-2-methyl-2-propanesulfinamide (18.88 g, 156 mmol and copper(II) sulfate (9.42 g, 212 mmol) were suspended in 1,2-dichloroethane (283 mL at rt. 4-Chloro-2,5-difluorobenzaldehyde (25.00 g, 142 mmol) was added and the reaction was heated to 55° C. for 12 h. The turbid yellow solution was filtered through celite and silica. The filter cake was washed with 1,2-dichloroethane (250 mL) and then the filtrate was concentrated to give a pale yellow solid. $^1$H NMR (400 MHz, DMSO-d$_6$) δ ppm 8.61 (s, 1H), 8.02-7.91 (m, 2H), 1.20 (s, 9H). LCMS (POS.) m/z: 280.0 (M+H)+.

Step 2: Preparation of (S)—N—((R)-(4-chloro-2,5-difluorophenyl)(cyclopropyl)methyl)-2-methyl propane-2-sulfinamide (S,E)-N-(4-chloro-2,5-difluorobenzylidene)-2-methylpropane-2-sulfinamide (4.0 g, 14.3 mmol) was dissolved in DCM (72 mL) and cooled to −78° C. Cyclopropylmagnesium bromide (1M in 2-MeTHF, 21.5 mL, 21.5 mmol, 1.5 equiv) was then added dropwise and the reaction was allowed to slowly warm to rt and stirred an additional 2 hours. The reaction was quenched by addition of saturated aqueous ammonium chloride solution with rapid stirring. The organics were separated, and the aqueous layer was washed twice with DCM (2×50 mL). The combined organics were dried over sodium sulfate, filtered, and concentrated. The crude product was purified by column chromatography (silica gel, 230-400 mesh) using 10-70% EtOAc in hexanes to give the title compound as a viscous yellow oil. The stereochemistry was assigned based on literature precedent (Ellman, J. A.; Owens, T. D.; Tang, T. P. Acc. Chem. Res. 2002, 35, 984). $^1$H NMR (500 MHz, chloroform-d) δ ppm 7.20-7.26 (m, 1H), 7.10-7.20 (m, 1H), 3.90 (d, J=9.34

Hz, 1 H), 3.59 (br s, 1H), 1.23 (s, 8H), 0.67-0.77 (m, 1H), 0.44-0.62 (m, 3H). LCMS-ESI (POS.) m/z: 322.2 (M+H)+.

Step 3. Preparation of (R)-(4-chloro-2,5-difluorophenyl)(cyclopropyl)methanamine hydrochloride (Intermediate 9.2)

(S)—N—((R)-(4-chloro-2,5-difluorophenyl)(cyclopropyl)methyl)-2-methylpropane-2-sulfinamide (3.8 g, 12.0 mmol) was dissolved in methanol (14.0 mL) followed by addition of HCl (4M in dioxane, 6 mL, 24.0 mmol). The solution was stirred 2 h and then the volatiles were removed under reduced pressure. The crude solid was slurried in EtOAc and then the solids were collected by filtration to give (R)-(4-chloro-2,5-difluorophenyl)(cyclopropyl)methanamine hydrochloride (Intermediate 9.2, 2.6 g) as a white solid. $^1$H NMR (400 MHz, DMSO-d$_6$) δ ppm 8.88 (br s, 3H), 7.99 (dd, J=9.85, 6.32 Hz, 1H), 7.77 (dd, J=9.43, 6.22 Hz, 1H), 3.79 (br d, J=8.50 Hz, 1H), 1.35-1.44 (m, 1H), 0.64-0.72 (m, 2H), 0.48-0.57 (m, 1H), 0.28-0.35 (m, 1H). LCMS (POS.) m/z: 201.2 (M-NH$_2$)+.

Step 4. Preparation of 1R,3R,5R)-tert-butyl 3-(((R)-(4-chloro-2,5-difluorophenyl)(cyclopropyl)methyl)carbamoyl)-2-azabicyclo[3.1.0]hexane-2-carboxylate A 20 mL vial with a stir bar was charged with (1R,3R,5R)-2-(tert-butoxycarbonyl)-2-azabicyclo[3.1.0]hexane-3-carboxylic acid (100 mg, 0.440 mmol) TBTU (141 mg, 0.440 mmol) (R)-(4-chloro-2,5-difluorophenyl)(cyclopropyl)methanamine hydrochloride (Intermediate 9.2, 112 mg, 0.440 mmol), DIPEA (0.129 mL, 0.88 mmol) and DCM (1.1 mL). The reaction was stirred at 25° C. for 2 h, concentrated, and then purified by column chromatography (silica gel, 230-400 mesh) using 0-50% EtOAc in hexanes to give the title compound as a white solid (178 mg). $^1$H NMR (500 MHz, DMSO-d$_6$) δ ppm 8.22-8.72 (m, 1H), 7.25-7.70 (m, 2H), 4.06-4.56 (m, 2H), 3.36 (br d, J=3.89 Hz, 1H), 1.57-1.80 (m, 1H), 1.12-1.56 (m, 13H), 0.74-0.94 (m, 2H), 0.39-0.70 (m, 3H), 0.22-0.39 (m, 2H). LCMS (POS.) m/z: 465.2 (M+Na)+.

Step 5. Preparation of (1R,3R,5R)—N—((R)-(4-chloro-2,5-difluorophenyl)(cyclopropyl)methyl)-2-azabicyclo[3.1.0]hexane-3-carboxamide hydrochloride (Intermediate 28.4)

A 100 mL round bottom flask with magnetic stir bar was charged with (1R,3R,5R)-tert-butyl 3-(((R)-(4-chloro-2,5-difluorophenyl) (cyclopropyl)methyl)carbamoyl)-2-azabicyclo[3.1.0]hexane-2-carboxylate (1.9 g, 4.4 mmol), HCl (4M in dioxane, 2.2 mL, 8.9 mmol) and DCM (11.0 mL). After stirring at rt for 2 h, the volatiles were removed under reduced pressure to produce a white solid (Intermediate 28.4, 1.60 g). $^1$H NMR (500 MHz, DMSO-d$_6$) δ ppm 10.55 (br s, 1H) 9.33 (d, J=7.27 Hz, 1H) 8.74 (br s, 1H) 7.64 (t, J=7.56 Hz, 1H) 7.60 (t, J=7.76 Hz, 1H) 4.56 (dd, J=10.90, 3.11 Hz, 1H) 4.35-4.44 (m, 1H) 3.56 (s, 1H) 3.23-3.30 (m, 1H) 2.47-2.53 (m, 3H) 2.00 (dd, J=13.75, 3.11 Hz, 1H) 1.67-1.76 (m, 1H) 1.19-1.30 (m, 2H) 0.69-0.87 (m, 2H) 0.44-0.61 (m, 3H) 0.25-0.42 (m, 2H). LCMS (POS.) m/z: 327.2 (M+H)+.

Step 6. Preparation of (1R,3R,5R)—N—((R)-(4-chloro-2,5-difluorophenyl) (cyclopropyl)methyl)-2-(5-(methylsulfonyl)nicotinoyl)-2-azabicyclo[3.1.0]hexane-3-carboxamide (Example 218)

5-(methylsulfonyl)-3-pyridinecarboxylic acid (2.28 g, 11.32 mmol), TBTU (3.82 g, 11.89 mmol), and (1R,3R,5R)—N—((R)-(4-chloro-2,5-difluorophenyl)(cyclopropyl)methyl)-2-azabicyclo[3.1.0]hexane-3-carboxamide hydrochloride (Intermediate 28.4, 3.7 g, 11.32 mmol) were suspended in DCM (56.6 mL) at rt. DIPEA (5.92 mL, 34.0 mmol) was added and the reaction was stirred at rt for 30 minutes. The reaction was diluted with DCM and washed once with 1N HCl, dried over sodium sulfate, filtered and concentrated. The crude material was purified by preparative HPLC (XSelect CSH Prep C18 10 µm ODB 19×100 mm, A: water 0.1% TFA B: acetontrile 0.1% TFA, gradient: 25% (2 min), 25-70% (12 min), flow Rate: 40 mL/min, monitored @ 215 nm) to give (1R,3R,5R)—N—((R)-(4-chloro-2,5-difluorophenyl)(cyclopropyl)methyl)-2-(5-(methylsulfonyl)nicotinoyl)-2-azabicyclo[3.1.0]hexane-3-carboxamide as a white solid (Example 218, 2.77 g).

Third Illustrative Example Prepared by the General Scheme for Route C:

Example 314: Preparation of (1R,3R,5R)—N—((R)-(4-chloro-2,5-difluorophenyl)(cyclopropyl)methyl)-2-(2-(methylsulfonyl)isonicotinoyl)-2-azabicyclo[3.1.0]hexane-3-carboxamide, also referred to as (1R,3R,5R)—N—((R)-(4-chloro-2,5-difluorophenyl)(cyclopropyl)methyl)-2-((2-(methylsulfonyl)-4-pyridinyl)carbonyl)-2-azabicyclo[3.1.0]hexane-3-carboxamide Preparation of (1R,3R,5R)—N—((R)-(4-chloro-2,5-difluorophenyl)(cyclopropyl)methyl)-2-(2-(methylsulfonyl)isonicotinoyl)-2-azabicyclo[3.1.0]hexane-3-carboxamide. TBTU (78 mg, 0.24 mmol), (1R,3R,5R)—N—((R)-(4-chloro-2,5-difluorophenyl)(cyclopropyl)methyl)-2-azabicyclo[3.1.0]hexane-3-carboxamide (Intermediate 28.4, 72 mg, 0.22 mmol), and 2-(methylsulfonyl)isonicotinic acid (49 mg, 0.24 mmol) were dissolved in DMF (1.1 mL) at rt. DIPEA (0.12 mL, 0.660 mmol) was added and the reaction was stirred at rt for 2 h. The reaction mixture was then purified preparative HPLC (XSelect CSH Prep C18 10 µm ODB 19×100 mm, A: water 0.1% TFA B: acetontrile 0.1% TFA, gradient: 25% (2 min), 25-70% (12 min), flow Rate: 40 mL/min, monitored @ 215 nm) to give a white solid (Example 314, 48.1 mg).

In a Fourth Illustrative Example the Compound of Example 214 is Prepared by the Process of the General Scheme for Route C:

Example 214: Preparation of (1R,3R,5R)—N—((R)-cyclopropyl(2,5-difluoro-4-(trifluoromethyl)phenyl)methyl)-2-(5-(methylsulfonyl)nicotinoyl)-2-azabicyclo[3.1.0]hexane-3-carboxamide (which Compound is Also Referred to Herein as (1R,3R,5R)—N—((R)-cyclopropyl(2,5-difluoro-4-(trifluoromethyl)phenyl)methyl)-2-((5-(methylsulfonyl)-3-pyridinyl)carbonyl)-2-azabicyclo[3.1.0]hexane-3-carboxamide)

Step 1. Preparation of 2,5-difluoro-4-(trifluoromethyl)benzaldehyde. To a solution of 1-bromo-2,5-difluoro-4-(trifluoromethyl)benzene (130 g, 498 mmol, Oakwood, Inc.) in THF (1.3 L) was added isopropylmagnesium chloride (2M solution in THF, 274 mL, 548 mmol) drop-wise under nitrogen atmosphere at −45° C. The reaction mixture was stirred at −45° C. for 30 min and then DMF (174 mL, 2.24 mol) was slowly added and stirred for 20 min. The reaction mixture was allowed to warm to 0° C. and quenched with saturated aqueous NH$_4$Cl solution (500 mL), diluted with water (1.5 L), and extracted with EtOAc (3×2 L). The organic extracts were washed with brine (2.0 L) and dried over Na$_2$SO$_4$, filtered, and concentrated under reduced pressure to give 2,5-difluoro-4-(trifluoromethyl)benzaldehyde (65 g) as a colorless oil. $^1$H NMR (400 MHz, Chloroform-d): δ 10.38 (s, 1H), 7.71 (dd, J=9.2, 5.2 Hz, 1H), 7.52 (dd, J=9.2, 5.2 Hz, 1H).

Step 2: Preparation of (S,E)-N-(2,5-difluoro-4-(trifluoromethyl)benzylidene)-2-methylpropane-2-sulfinamide To a suspension of copper(II) sulfate (228 g, 1.43 mol) and (S)-(-)-2-methylpropane-2-sulfinamide (130 g, 1.07 mol) in 1,2-dichloroethane (2.2 L) was added 2,5-difluoro-4-(trifluoromethyl)benzaldehyde (150 g, 0.714 mol) at rt. The reaction was heated to 80° C. and stirred for 18 h. The mixture was then filtered through a pad of Celite and the filter cake was washed with 1,2-dichloroethane (500 mL). The filtrate was concentrated under reduced pressure and purified by column chromatography (silica gel, 60-120 mesh) eluting with 4-10% EtOAc in hexanes to provide (S,E)-N-(2,5-difluoro-4-(trifluoromethyl)benzylidene)-2-methylpropane-2-sulfinamide (195 g) as a brown viscous oil. $^1$H NMR (400 MHz, Chloroform-d): 68.88 (s, 1H), 7.85 (dd, J=9.6, 5.6 Hz, 1H), 7.47 (dd, J=9.2, 5.2 Hz, 1H), 1.31 (s, 9H).

Step 3: Preparation of (S)—N—((S)-cyclopropyl(2,5-difluoro-4-(trifluoromethyl)phenyl)methyl)-2-methylpropane-2-sulfinamide and (S)—N—((R)-cyclopropyl(2,5-difluoro-4-(trifluoromethyl)phenyl)methyl)-2-methylpropane-2-sulfinamide A solution of (S,E)-N-(2,5-difluoro-4-(trifluoromethyl)benzylidene)-2-methylpropane-2-sulfinamide (195 g, 622 mmol) in DCM (3.6 L) was cooled to -78° C. Cyclopropylmagnesium bromide (0.5M in THF, 1.87 L, 934 mmol) was then added dropwise over 1 h. The reaction mixture was stirred at -78° C. for an additional 1 h and then allowed to warm to rt over 2 h. The reaction mixture was quenched with saturated aqueous NH$_4$Cl solution (700 mL) and extracted with DCM (3×700 mL). The organic extracts were washed with water (500 mL), brine (500 mL), dried over Na$_2$SO$_4$, and concentrated under reduced pressure. The crude residue purified by column chromatography (silica gel, 230-400 mesh) using 5-15% EtOAc in hexanes. The first eluting peak (minor) was assigned as (S)—N—((S)-cyclopropyl(2,5-difluoro-4-(trifluoromethyl)phenyl)methyl)-2-methylpropane-2-sulfinamide (16 g) based on literature precedent (see Ellman, J. A.; Owens, T. D.; Tang, T. P. Acc. Chem. Res. 2002, 35, 984) and collected as a brown oil. $^1$H NMR (400 MHz, DMSO-d$_6$): δ7.78-7.65 (m, 2H), 5.95 (d, J=8.0 Hz, 1H), 3.87 (dd, J=8.0, 7.4 Hz, 1H), 1.27-1.20 (m, 1H), 1.12 (s, 9H), 0.65-0.60 (m, 1H), 0.52-0.46 (m, 2H), 0.37-0.33 (m, 1H). LCMS-ESI (POS.) m/z: 356.1 (M+H)+. The second eluting peak (major) was assigned as (R)—N—((R)-cyclopropyl(2,5-difluoro-4-(trifluoromethyl)phenyl)methyl)-2-methylpropane-2-sulfinamide (95 g) based on literature precedent (Ellman, J. A.; Owens, T. D.; Tang, T. P. Acc. Chem. Res. 2002, 35, 984) and collected as a brown oil. $^1$H NMR (400 MHz, DMSO-d$_6$): δ 7.78-7.70 (m, 2H), 5.73 (d, J=6.8 Hz, 1H), 3.87 (dd, J=8.0, 6.8 Hz, 1H), 1.32-1.27 (m, 1H), 1.08 (s, 9H), 0.65-0.61 (m, 1H), 0.52-0.46 (m, 2H), 0.37-0.33 (m, 1H). LCMS-ESI (POS.) m/z: 356.2 (M+H)+.

Step 4: Preparation of (R)-cyclopropyl(2,5-difluoro-4-(trifluoromethyl)phenyl)methanamine hydrochloride, Intermediate 8.0

To a solution of (S)—N—((R)-cyclopropyl(2,5-difluoro-4-(trifluoromethyl)phenyl)methyl)-2-methylpropane-2-sulfinamide (95 g, 268 mmol) in methanol (450 mL) was added HCl (4M in dioxane, 134 mL, 535 mmol) at 0° C. and stirred at rt for 2 h. The reaction mixture was concentrated under reduced pressure and azeotroped with DCM (500 mL). The residual solid was triturated with diethyl ether (500 mL), collected by filtration, and dried under vacuum to give (R)-cyclopropyl(2,5-difluoro-4-(trifluoromethyl)phenyl)methanamine hydrochloride (Intermediate 8.0, 73 g) as an off-white solid. $^1$H NMR (400 MHz, DMSO-d$_6$): δ 9.10 (s, 3H), 8.19 (dd, J=10.8, 5.6 Hz, 1H), 7.88 (dd, J=8.4, 6.4 Hz, 1H), 3.87 (d, J=8.8 Hz, 1H), 1.46-1.38 (m, 1H), 0.78-0.68 (m, 2H), 0.57-0.53 (m, 1H), 0.39-0.33 (m, 1H). LCMS-ESI (POS.) m/z: 252.1 (M+H)+.

Step 5: Preparation of (1R,3R,5R)-tert-butyl 3-(((R)-cyclopropyl(2,5-difluoro-4-(trifluoromethyl)phenyl)methyl)carbamoyl)-2-azabicyclo[3.1.0]hexane-2-carboxylate A 50 mL round-bottom flask was charged with TBTU (1.61 g, 5.0 mmol), DIPEA (2.6 mL, 15.0 mmol), (R)-cyclopropyl(2,5-difluoro-4-(trifluoromethyl)phenyl)methanamine hydrochloride (Intermediate 8.0, 1.44 g, 5.00 mmol), (1R,3R,5R)-2-(tert-butoxycarbonyl)-2-azabicyclo[3.1.0]hexane-3-carboxylic acid (1.14 g, 5.00 mmol), and DCM (12.5 mL). The reaction was stirred for 20 min and then diluted with DCM and then washed 1N HCl, saturated aqueous sodium bicarbonate, and brine. The organics were dried over sodium sulfate, filtered, and concentrated to give a viscous yellow oil that was purified by column chromatography (silica gel, 230-400 mesh) using 0-50% EtOAc in hexanes to give the title compound as a white solid (2.01 g). $^1$H NMR (500 MHz, DMSO-d$_6$): δ 8.52-8.76 (m, 1H) 7.66-7.78 (m, 1H) 7.56-7.66 (m, 1H) 4.55 (br dd, J=10.90, 2.85 Hz, 1H) 4.31-4.46 (m, 2H) 3.27-3.36 (m, 1H) 2.60 (td, J=12.46, 6.23 Hz, 1H) 1.80 (dd, J=13.36, 2.72 Hz, 1H) 1.40-1.52 (m, 1H) 1.37 (s, 3H) 1.19-1.32 (m, 2H) 1.10 (s, 5H) 0.94-1.07 (m, 1H) 0.79-0.94 (m, 1H) 0.19-0.64 (m, 5H). LCMS-ESI (POS.) m/z: 483.2 (M+Na)+.

Step 6: Preparation of (1R,3R,5R)—N—((R)-cyclopropyl(2,5-difluoro-4-(trifluoromethyl)phenyl)methyl)-2-azabicyclo[3.1.0]hexane-3-carboxamide methanesulfonate 500 mL round-bottom flask equipped with magnetic stir bar, reflux condenser and argon inlet was charged with (1R,3R,5R)-tert-butyl 3-(((R)-cyclopropyl(2,5-difluoro-4-(trifluoromethyl)phenyl)methyl)carbamoyl)-2-azabicyclo[3.1.0]hexane-2-carboxylate (24.3 g, 52.8 mmol) and methyl tert-butyl ether (200 mL). The flask was placed into heating block and heated to 50° C. then methanesulfonic acid (5.14 mL, 79 mmol) was added dropwise via syringe within 5 min (slow gas evolution starts after addition of ~1 mL). The mixture was stirred at 50° C. until gas evolution stopped (~2 h) at which point a white solid precipitated. The mixture was allowed to reach rt and stirred overnight at rt. The white solid was filtered off and washed with 20 mL MTBE and dried to afford (1R,3R,5R)—N—((R)-cyclopropyl(2,5-difluoro-4-(trifluoromethyl)phenyl)methyl)-2-azabicyclo[3.1.0]hexane-3-carboxamide methanesulfonate as a white solid (21.13 g, 46.3 mmol). $^1$H NMR (500 MHz, DMSO-d$_6$) δ ppm 8.46 (d, J=8.04 Hz, 1H) 7.67-7.76 (m, 1H) 4.32 (t, J=8.82 Hz, 1H) 3.73-3.84 (m, 1H) 3.22 (br s, 1H) 2.79 (td, J=6.29, 2.72 Hz, 1H) 1.92-2.06 (m, 2H) 1.35 (qd, J=8.52, 4.54 Hz, 1H) 1.18-1.29 (m, 1H) 0.51-0.61 (m, 1H) 0.46 (tt, J=8.56, 4.41 Hz, 1H) 0.25-0.38 (m, 3H) −0.35--0.24 (m, 1H). LCMS-ESI (POS.) m/z: 361.2 (M+H)+.

Step 7: Preparation of (1R,3R,5R)—N—((R)-cyclopropyl(2,5-difluoro-4-(trifluoromethyl)phenyl)methyl)-2-(5-(methylsulfonyl)nicotinoyl)-2-azabicyclo[3.1.0]hexane-3-carboxamide (Example 214)

To a suspension of (1R,3R,5R)—N—((R)-cyclopropyl(2,5-difluoro-4-(trifluoromethyl)phenyl)methyl)-2-azabicyclo[3.1.0]hexane-3-carboxamide methanesulfonate (11.19 g, 24.52 mmol) in isopropyl acetate (65.0 mL), 5-(methylsulfonyl)nicotinic acid (4.93 g, 24.52 mmol) was added followed by DIPEA (12.85 mL, 73.5 mmol). The resulting mixture was stirred for 2 min then 1-propanephosphonic acid cyclic anhydride (50 wt. % solution in EtOAc, 21.89 mL, 36.8 mmol) was added dropwise and the mixture was stirred for 1 h at rt. The reaction was treated with HCl (2N, 36.8 mL, 73.5 mmol) and stirred for 20 min at rt. The organic layer was separated and washed with water and brine, filtered through celite and concentrated to afford yellow oil. This oil was diluted with 10 mL i-PrOH and heated to 60° C. and stirred at rt for 30 min. The precipitated material was collected by filtration and washed with i-PrOH (~15 mL) and dried to afford (1R,3R,5R)—N—((R)-cyclopropyl(2,5-difluoro-4-(trifluoromethyl)phenyl)methyl)-2-(5-(methylsulfonyl)nicotinoyl)-2-azabicyclo[3.1.0]hexane-3-carboxamide (Example 214, 9.68 g) $^1$H NMR (500 MHz, DMSO-d$_6$) δ ppm 8.83-9.24 (m, 2H), 8.28-8.80 (m, 2H), 7.68-7.82 (m, 1H), 7.36-7.64 (m, 1H), 4.00-5.05 (m, 2H), 3.34-3.41 (m, 4H), 2.56-2.76 (m, 1H), 1.53-1.79 (m, 2H), −0.28-1.24 (m, 7H). LCMS-ESI (POS.) m/z: 544.2 (M+H)+.

In a fifth illustrative example the compound of Example 279 is prepared by the process of the general scheme for Route C:

Example 279: Preparation of (1R,3R,5R)—N—((R)-cyclopropyl(2,5-difluoro-4-(trifluoromethyl)phenyl)methyl)-2-(2-(methylsulfonyl)isonicotinoyl)-2-azabicyclo[3.1.0]hexane-3-carboxamide, Also Referred to Herein as (1R,3R,5R)—N—((R)-cyclopropyl(2,5-difluoro-4-(trifluoromethyl)phenyl)methyl)-2-((2-(methylsulfonyl)-4-pyridinyl)carbonyl)-2-azabicyclo[3.1.0]hexane-3-carboxamide Step 1: Preparation of (1R,3R,5R)-tert-butyl 3-(((R)-cyclopropyl(2,5-difluoro-4-(trifluoromethyl)phenyl)methyl)carbamoyl)-2-azabicyclo[3.1.0]hexane-2-carboxylate A 50 mL round-bottom flask was charged with TBTU (1.61 g, 5.0 mmol), DIPEA (2.6 mL, 15.0 mmol), (R)-cyclopropyl(2,5-difluoro-4-(trifluoromethyl)phenyl)methanamine hydrochloride (Intermediate 8.0, 1.44 g, 5.00 mmol), (1R,3R,5R)-2-(tert-butoxycarbonyl)-2-azabicyclo[3.1.0]hexane-3-carboxylic acid (1.14 g, 5.00 mmol), and DCM (12.5 mL). The reaction was stirred for 20 min and then diluted with DCM and then washed 1N HCl, saturated aqueous sodium bicarbonate, and brine. The organics were dried over sodium sulfate, filtered, and concentrated to give a viscous yellow oil that was purified by column chromatography (silica gel, 230-400 mesh) using 0-50% EtOAc in hexanes to give the title compound as a white solid (2.01 g). 8.52-8.76 (m, 1H) 7.66-7.78 (m, 1H) 7.56-7.66 (m, 1H) 4.55 (br dd, J=10.90, 2.85 Hz, 1H) 4.31-4.46 (m, 2H) 3.27-3.36 (m, 1H) 2.60 (td, J=12.46, 6.23 Hz, 1H) 1.80 (dd, J=13.36, 2.72 Hz, 1H) 1.40-1.52 (m, 1H) 1.37 (s, 3H) 1.19-1.32 (m, 2H) 1.10 (s, 5H) 0.94-1.07 (m, 1H) 0.79-0.94 (m, 1H) 0.19-0.64 (m, 5H). LCMS (POS.) m/z: 483.2 (M+Na)+.

Step 2: Preparation of (1R,3R,5R)—N—((R)-cyclopropyl(2,5-difluoro-4-(trifluoromethyl)phenyl)methyl)-2-azabicyclo[3.1.0]hexane-3-carboxamide A 50 mL round-bottom flask was charged with (1R,3R,5R)-tert-butyl 3-(((R)-cyclopropyl(2,5-difluoro-4-(trifluoromethyl)phenyl)methyl)carbamoyl)-2-azabicyclo[3.1.0]hexane-2-carboxylate (2.01 g, 4.37 mmol) and DCM (8.8 mL) followed by addition of TFA (3.4 mL, 43.7 mmol). The reaction was stirred for 2 h and then diluted with 50 mL DCM. The excess acid was quenched by drop-wise addition of saturated sodium bicarbonate solution with rapid stirring. The layers were separate and the aqueous fraction was washed twice with 50 mL DCM. The combined organics were dried over sodium sulfate, filtered, and concentrated to give the desired product as a white solid (1.51 g, 4.2 mmol). $^1$H NMR (500 MHz, DMSO-d$_6$) δ ppm 8.46 (d, J=8.04 Hz, 1H) 7.67-7.76 (m, 2H) 4.32 (t, J=8.82 Hz, 1H) 3.73-3.84 (m, 1H) 3.22 (br s, 1H) 2.79 (td, J=6.29, 2.72 Hz, 1H) 1.92-2.06 (m, 2H) 1.35 (qd, J=8.52, 4.54 Hz, 1H) 1.18-1.29 (m, 1H) 0.51-0.61 (m, 1H) 0.46 (tt, J=8.56, 4.41 Hz, 1H) 0.25-0.38 (m, 3H) −0.35--0.24 (m, 1H). LCMS (POS.) m/z: 361.2 (M+H)+.

Step 3: Preparation of (1R,3R,5R)—N—((R)-cyclopropyl(2,5-difluoro-4-(trifluoromethyl)phenyl)methyl)-2-(2-(methylsulfonyl)isonicotinoyl)-2-azabicyclo[3.1.0]hexane-3-carboxamide A 25 mL round-bottom flask was charged with (1R,3R,5R)—N—((R)-cyclopropyl(2,5-difluoro-4-(trifluoromethyl)phenyl)methyl)-2-azabicyclo[3.1.0]hexane-3-carboxamide (273 mg, 0.758 mmol), 2-(methylsulfonyl)isonicotinic acid (152 mg, 0.758 mmol), TBTU (243 mg, 0.758 mmol), DIPEA (0.377 mL, 2.17 mmol), and DMF (3.6 mL). The reaction was stirred for 2.5 h. The reaction mixture was purified directly by preparative HPLC (XSelect CSH Prep C18 10 μm ODB 19×100 mm, A: water 0.1% TFA B: acetontrile 0.1% TFA, gradient: 25% (2 min), 25-70% (12 min), flow Rate: 40 mL/min, monitored @ 215 nm) to give the title compound (237.8 mg). $^1$H NMR (500 MHz, DMSO-d$_6$) b ppm 8.94 (d, J=4.80 Hz, 1H), 8.75 (d, J=7.40 Hz, 1H), 7.83-8.27 (m, 2H), 7.69-7.81 (m, 1H), 7.59 (dd, J=11.03, 5.45 Hz, 1H), 4.11-5.04 (m, 2H), 3.19-3.37 (m, 4H), 2.54-2.76 (m, 1H), 1.53-1.83 (m, 2H), −0.22-1.30 (m, 7H). LCMS-ESI (POS.) m/z: 544.0 (M+H)+.

In a Sixth Illustrative Example the Compound of Example 270 is Prepared by the Process of the General Scheme for Route C:

Example 270: Preparation of (1R,3R,5R)—N—((R)-cyclopropyl(2-fluoro-4-(trifluoromethyl)phenyl)methyl)-2-(3-(methylsulfonyl)benzoyl)-2-azabicyclo[3.1.0]hexane-3-carboxamide Step 1: (1R,3R,5R)—N—((R)-cyclopropyl(2-fluoro-4-(trifluoromethyl)phenyl)methyl)-2-(3-(methylsulfonyl)benzoyl)-2-azabicyclo[3.1.0]hexane-3-carboxamide To a rt solution of (1R,3R,5R)-2-(3-(methylsulfonyl)benzoyl)-2-azabicyclo[3.1.0]hexane-3-carboxylic acid (Intermediate 5.0, 47 mg, 0.151 mmol), (R)-cyclopropyl(2-fluoro-4-(trifluoromethyl)phenyl)methanamine hydrochloride (Intermediate 9.5, 37 mg, 0.138 mmol), hydroxybenzotriazole (37 mg, 0.275 mmol) and 0-(benzotriazol-1-yl)-N,N,N',N'-tetramethyluronium hexafluorophosphate (104 mg, 0.275 mmol) in DMF (0.6 mL) was added DIPEA (0.24 mL, 1.38 mmol). The resulting mixture was stirred at rt for 20 min then diluted with water (0.5 mL) and extracted with EtOAc (2×1 mL). The organic phase was dried and concentrated to a viscous oil which was purified by reverse phase HPLC (10%-100% water (w/0.1% TFA)/acetontrile (w/0.1% TFA), 40 min gradient, Phenomonex Gemini 5 μm C18 column) to provide the desired product (68.0 mg, 0.130 mmol) as a white foam. $^1$H NMR (DMSO-$d_6$) δ: 8.74 (d, J=7.5 Hz, 1H), 8.18 (t, J=1.8 Hz, 1H), 8.09-7.99 (m, 2H), 7.79 (t, J=7.8 Hz, 1H), 7.74-7.59 (m, 2H), 4.96 (dd, J=11.5, 3.5 Hz, 2H), 4.58 (t, J=7.9 Hz, 2H), 3.27 (s, 3H), 1.82-1.60 (m, 3H), 1.13-1.05 (m, 1H), 0.82-0.66 (m, 2H), 0.56 (d, J=8.0 Hz, 1H), 0.47 (d, J=8.4 Hz, 1H), 0.35 (d, J=4.7 Hz, 2H). LCMS-APCI (POS.) m/z: 525.2 (M+H)+.

Preparation of Common Intermediate 5.0 (1R,3R,5R)-2-(3-(methylsulfonyl)benzoyl)-2-azabicyclo[3.1.0]hexane-3-carboxylic Acid Step 1: Preparation of (1R,3R,5R)-ethyl 2-azabicyclo[3.1.0]hexane-3-carboxylate hydrochloride A 100 mL round-bottom flask was charged with (1R,3R,5R)-2-tert-butyl 3-ethyl 2-azabicyclo[3.1.0]hexane-2,3-dicarboxylate (1.0 g, 3.92 mmol, Synthonix, Inc.) and DCM (13.0 mL). To that solution was added HCl (4.0M in dioxane, 4.90 mL, 19.6 mmol). After 2.5 h at rt, the mixture was concentrated under reduced pressure and azeotroped with methanol (2×10 mL) to give (1R,3R,5R)-ethyl 2-azabicyclo[3.1.0]hexane-3-carboxylate hydrochloride (0.751 g, 100%) as a foam. LCMS-ESI (POS.). m/z: 156.2 (M+H)+.

Step 2: Preparation of (1R,3R,5R)-ethyl 2-(3-(methylsulfonyl)benzoyl)-2-azabicyclo[3.1.0]hexane-3-carboxylate A 100 mL round-bottom flask was charged with (1R,3R,5R)-ethyl 2-azabicyclo[3.1.0]hexane-3-carboxylate hydrochloride (0.75 g, 3.9 mmol) and DCM (20 mL). To that stirring solution at rt was added 3-(methylsulfonyl)benzoic acid (1.2 g, 5.9 mmol), TBTU (1.9 g, 5.9 mmol) and DIPEA (3.4 mL, 19.6 mmol). After 24 h, the reaction mixture was concentrated under reduced pressure. The resulting oil was diluted with DCM, and purified by MPLC on silica gel, eluting with 0-50% EtOAc in heptane to provide (1R,3R,5R)-ethyl 2-(3-(methylsulfonyl)benzoyl)-2-azabicyclo[3.1.0]hexane-3-carboxylate (1.1 g, 83%). LCMS-ESI (POS.). m/z: 338.0 (M+H)+.

Step 3: Preparation of (1R,3R,5R)-2-(3-(methylsulfonyl)benzoyl)-2-azabicyclo[3.1.0]hexane-3-carboxylic acid, Intermediate 5.0

To a 50 mL round-bottom flask was added (1R,3R,5R)-ethyl 2-(3-(methylsulfonyl)benzoyl)-2-azabicyclo[3.1.0]hexane-3-carboxylate (1.0 g, 3.0 mmol), lithium hydroxide (0.14 g, 14.8 mmol) and 1,4-dioxane (10 mL) and water (10 mL). The reaction mixture was stirred at rt for 1 h, then diluted with water and acidified to pH=2 with 1N HCl. The mixture was extracted with 3:1 DCM/MeOH, and the combined organic extracts were washed with brine, dried over MgSO$_4$, filtered, and concentrated under reduced pressure to afford (1R,3R,5R)-2-(3-(methylsulfonyl)benzoyl)-2-azabicyclo[3.1.0]hexane-3-carboxylic acid (0.81 g) as white solid. LCMS-ESI (POS.). m/z: 310.0 (M+H)+.

Preparation of Common Intermediate 9.5 (R)-cyclopropyl(2-fluoro-4-(trifluoromethyl)phenyl) methanamine hydrochloride Step 1: Preparation of (S,E)-N-(2-fluoro-4-(trifluoromethyl)benzylidene)-2-methylpropane-2-sulfinamide (Common Intermediate 9.5)

Copper(II) sulfate (31.2 g, 195 mmol) and (S)-2-methylpropane-2-sulfinamide (17.35 g, 143 mmol) were suspended in 1,2-dichloroethane (260 mL). 2-fluoro-4-(trifluoromethyl)benzaldehyde (25 g, 130 mmol) was added, and the reaction was heated to 55° C. The mixture was filtered through a pad of celite and silica gel. The filter cake was washed with 1,2-dichloroethane, and the filtrate was concentrated under reduced pressure to give (S,E)-N-(2-fluoro-4-(trifluoromethyl)benzylidene)-2-methylpropane-2-sulfinamide as a viscous yellow oil (38.3 g, 130 mmol). $^1$H NMR (500 MHz, chloroform-d) δ ppm 8.14 (t, J=7.40 Hz, 1H), 7.51 (d, J=8.30 Hz, 1H), 7.45 (d, J=9.86 Hz, 1H), 1.29 (s, 9H). LCMS (POS.) m/z: 296.0 (M+H)+.

Step 2: Preparation of (S)—N—((R)-cyclopropyl(2-fluoro-4-(trifluoromethyl)phenyl)methyl)-2-methylpropane-2-sulfinamide A 1 L three-neck round-bottom flask was charged with (S,E)-N-(2-fluoro-4-(trifluoromethyl)benzylidene)-2-methylpropane-2-sulfinamide (20.1 g) and DCM (295 mL). The solution was cooled −78° C. followed by addition of cyclopropyl magnesium bromide (1 M solution in 2-MeTHF, 89 mL, 89 mmol) at a rate of 90 mL/hr. The reaction was stirred for an additional hour and then the cold bath was removed and the solution allowed to warm to 0° C. To the solution was added saturated ammonium chloride solution (150 mL) followed by water (100 mL). The layers were separated and the organic were washed once with saturated brine solution, dried over sodium sulfate, and concentrated under reduced pressure to give a yellow oil (19 g). The crude product was carried on without purification. The stereochemistry was assigned based on literature precedent (Ellman, J. A.; Owens, T. D.; Tang, T. P. Acc. Chem. Res. 2002, 35, 984).

Step 3: Preparation of (R)-cyclopropyl(2-fluoro-4-(trifluoromethyl)phenyl)methanamine hydrochloride (Common Intermediate 9.5)

(S)—N—((R)-cyclopropyl(2-fluoro-4-(trifluoromethyl)phenyl)methyl)-2-methylpropane-2-sulfinamide was dissolved in DCM (200 mL) followed by addition of HCl (4 M solution in dioxane, 50 mL, 200 mmol). After stirring 1 h the product was precipitated by addition of heptane. The precipitate was collected by filtration and the solids were washed with heptane and dried under nitrogen atmosphere overnight to give the desired product as a white solid (11.4 g, 42.3 mmol). $^1$H NMR (400 MHz, chloroform-d) b ppm 0.46 (dq, J=9.81, 5.13 Hz, 1H) 0.61-0.77 (m, 3H) 1.41-1.50 (m, 1H) 3.96 (br dd, J=9.38, 5.13 Hz, 1H) 7.37-7.47 (m, 2H) 7.87 (t, J=7.46 Hz, 1H) 9.17 (br s, 3H).

Route D:

General Scheme for Route D

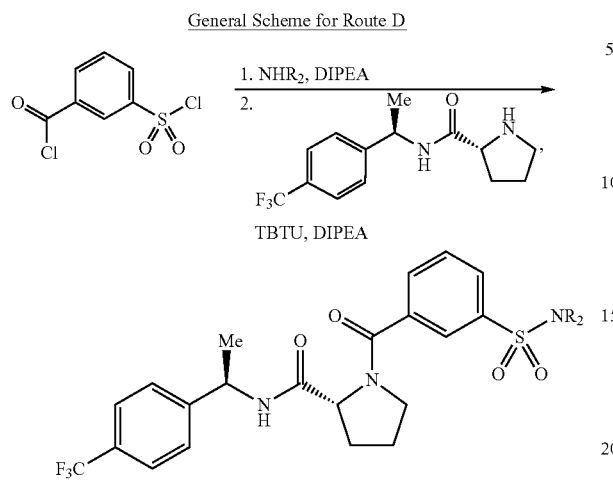

Example Route D: Example 749

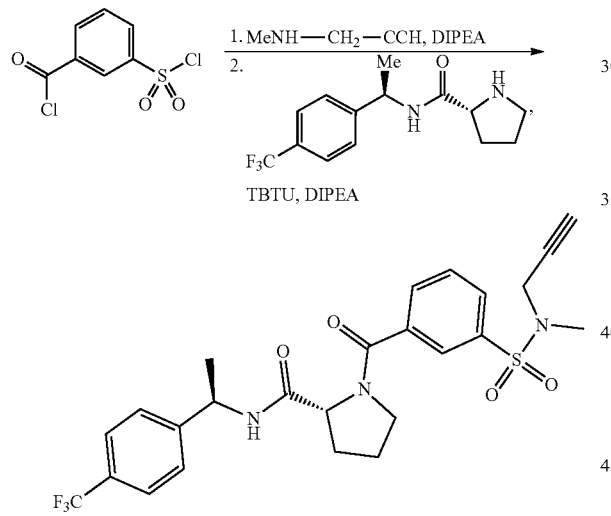

Example 749

N-methylprop-2-yn-1-amine (10.4 mg, 0.15 mmol) was added to a 4-mL vial and chilled to −30° C. To this was added a solution of 3-(chlorosulfonyl)benzoic acid (0.050 g, 0.225 mmol) and DIPEA (0.065 mL, 0.56 mmol) in DCM (0.750 mL). The reaction was allowed to slowly warm to rt and stirred for an additional 1 h. A solution of (R)—N—((R)-1-(4-(trifluoromethyl)phenyl)ethyl) pyrrolidine-2-carboxamide (0.052 g, 0.180 mmol), DIPEA (0.065 mL, 0.375 mmol, 0.56 mmol), and TBTU (0.058 g, 0.180 mmol) was then added and the coupling was stirred at rt for 12 h. The crude product was purified by preparative HPLC method (column: Xbridge or Xselect 19×100 mm, 10 μm, mobile phase: 0.1% NH$_4$OH in ACN and water) to give 1-(3-(methyl(2-propyn-1-yl)sulfamoyl)benzoyl)-N-((1R)-1-(4-(trifluoromethyl)phenyl)ethyl)-D-prolinamide Example 749 (12 mg) as a colorless film. $^1$H NMR (500 MHz, DMSO-d$_6$) δ ppm 8.49-8.91 (m, 1H), 7.50-8.04 (m, 8H), 4.84-5.27 (m, 1H), 3.99-4.48 (m, 2H), 3.59-3.68 (m, 1H), 3.39-3.54 (m, 3H), 2.69-3.15 (m, 4H), 2.69-3.19 (m, 1H), 1.68-2.06 (m, 4H), 1.31-1.46 (m, 3H). LCMS-ESI (POS.) m/z: 522.2 (M+H)+.

Route E

General Scheme for Route E

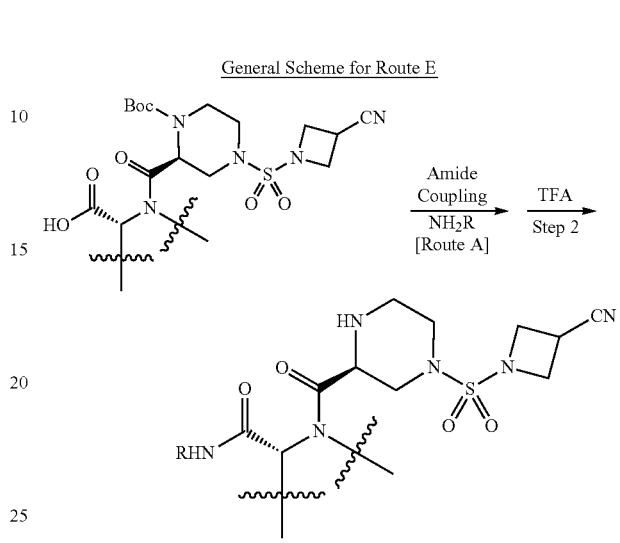

Example Route E: Example 790

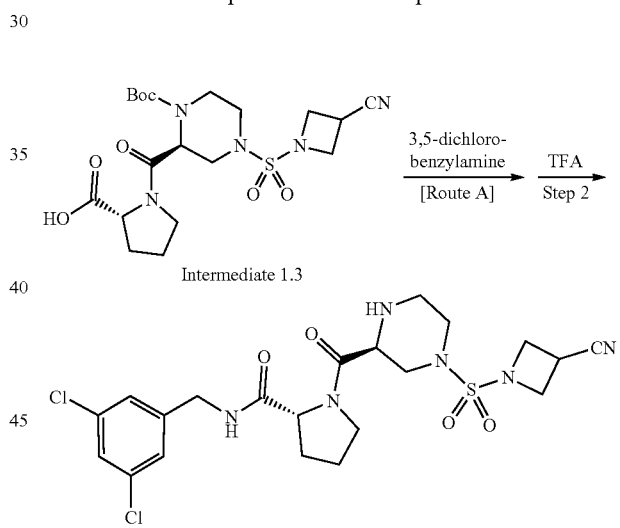

Example 790

The procedure described for Route A was performed employing 3,5-dichlorobenzylamine and Intermediate 1.3 followed by the subsequent manipulation:

Step 2: Crude tert-butyl (S)-4-((3-cyanoazetidin-1-yl)sulfonyl)-2-((R)-2-((3,5-dichlorobenzyl)carbamoyl)pyrrolidine-1-carbonyl)piperazine-1-carboxylate (200 mg, 0.318 mmol) was dissolved in DCM (3.0 mL, 0.1 M) at rt. TFA (1.5 mL) was added and the reaction was stirred for 3 h and then saturated sodium bicarbonate was added and the organics were extracted with ethyl acetate and washed with brine. The organics were concentrated to provide 1-(((2S)-4-((3-cyano-1-azetidinyl)sulfonyl)-2-piperazinyl)carbonyl)-N-(3,5-dichlorobenzyl)-D-prolinamide Example 790 (32 mg) as a white solid. 1H NMR (400 MHz, DMSO-d6) δ 8.28-8.78 (m, 1H), 8.03-8.25 (m, 1H), 7.30-7.61 (m, 1H), 7.22-7.25

(m, 1H), 4.22-4.39 (m, 3H), 4.01-4.14 (m, 2H), 3.88-3.98 (m, 2H), 3.70-3.88 (m, 2H), 3.30-3.62 (m, 6H), 2.91-3.06 (m, 1H), 2.68-2.78 (m, 2H), 1.74-2.16 (m, 4H). LCMS-ESI (POS.) m/z: 529.0 (M+H)+.
Route F
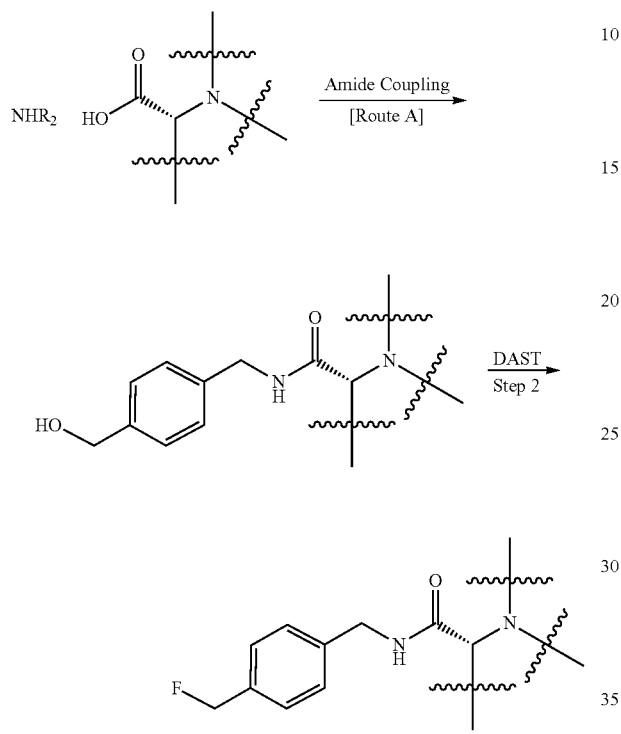
General Scheme for Route F
Example Route F: Example 157
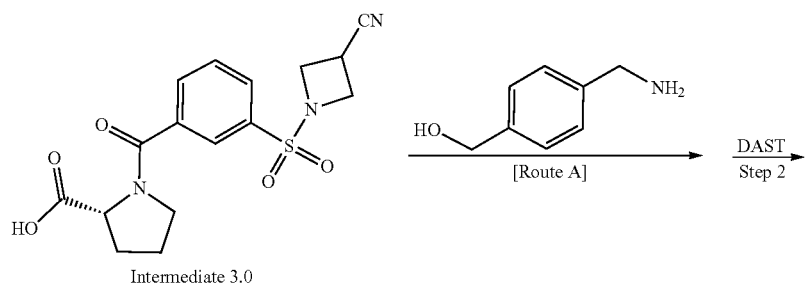
Intermediate 3.0
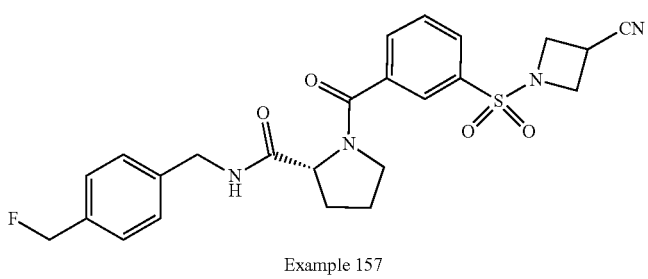
Example 157

The procedure described for Route A was performed employing (4-(aminomethyl)phenyl)methanol and Intermediate 3.0 followed by the subsequent manipulation:

Step 2: (R)-1-(3-((3-cyanoazetidin-1-yl)sulfonyl)benzoyl)-N-(4-(hydroxymethyl)benzyl)pyrrolidine-2-carboxamide (332 mg, 0.688 mmol) was dissolved in dichloromethane (3.4 mL) and cooled to −78° C. To this was added 1.0M DAST in DCM (1.0 mL, 1.03 mmol) dropwise. The reaction was stirred at −78° C. for 1 h and then allowed to warm to rt. The mixture was concentrated under reduced pressure and purified by preparative HPLC (XSelect CSH Prep C18 10 µm ODB 19×100 mm, A: water 0.1% TFA B: acetonitrile 0.1% TFA, gradient: 25% (2 min), 25-70% (12 min), flow rate: 40 mL/min, monitored @ 215 nm) to give 1-((3-((3-cyano-1-azetidinyl)sulfonyl)phenyl)carbonyl)-N-(4-(fluoromethyl)benzyl)-D-prolinamide Example 157 (8.7 mg) as a white solid. $^1$H NMR (500 MHz, DMSO-$d_6$) δ ppm 8.57 (t, J=5.97 Hz, 1H), 7.62-8.06 (m, 4H), 6.94-7.44 (m, 4H), 5.38-5.47 (m, 1H), 5.29-5.35 (m, 1H), 3.78-4.55 (m, 8H), 3.60-3.67 (m, 2H), 2.17-2.31 (m, 1H), 1.76-1.97 (m, 3H). LCMS-ESI (POS.) m/z: 485.2 (M+H)+.

Route G

General Scheme for Route G

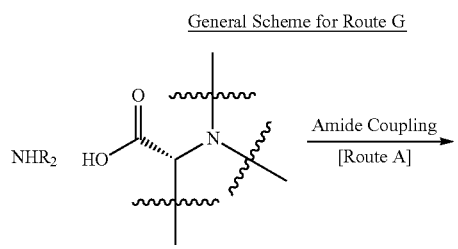

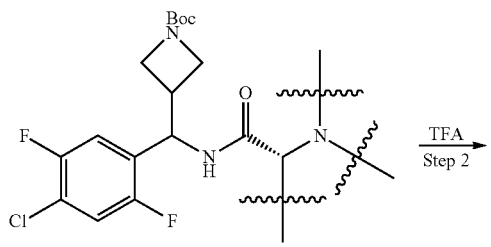

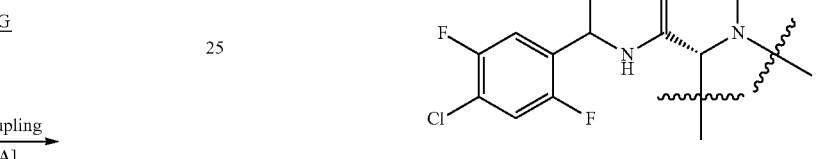

Example Route G: Example 558

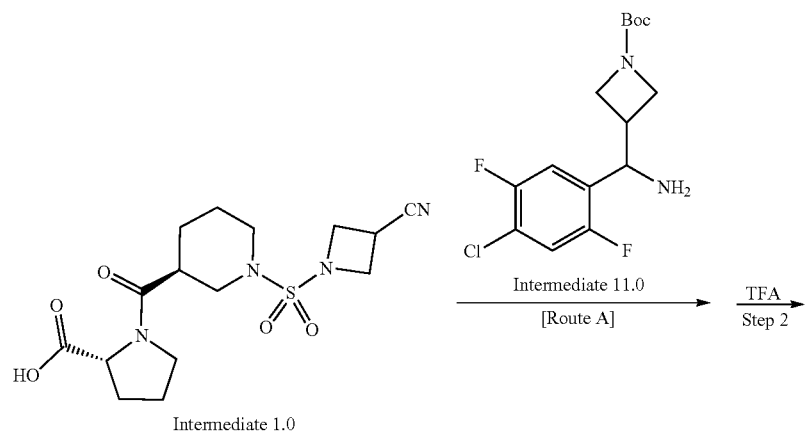

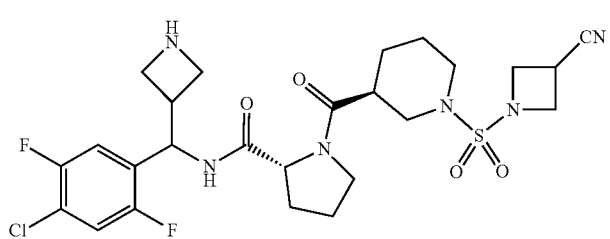

Example 558

The procedure described for Route A was performed employing Intermediate 11.0 and Intermediate 1.0 followed by the subsequent manipulation:

Step 2: tert-Butyl 3-((R)-(4-chloro-2,5-difluorophenyl)((R)-1-((S)-1-((3-cyanoazetidin-1-yl)sulfonyl) piperidine-3-carbonyl)pyrrolidine-2-carboxamido)methyl)azetidine-1-carboxylate was dissolved in DCM (2.2 mL) at rt. TFA (0.675 mL, 8.76 mmol) was added and the solution was stirred for 1 h. Saturated aqueous sodium bicarbonate was added and the organics were extracted with ethyl acetate, washed with brine, and purified by preparative HPLC (XSelect CSH Prep 018 10 µm ODB 19×100 mm, A: water 0.1% TFA B: acetonitrile 0.1% TFA, gradient: 25% (2 min), 25-70% (12 min), flow rate: 40 mL/min, monitored @ 215 nm) to give a diastereomeric mixture of (R)—N—((S)-azetidin-3-yl(4-chloro-2,5-difluorophenyl)methyl)-1-((S)-1-((3-cyanoazetidin-1-yl)sulfonyl)piperidine-3-carbonyl) pyrrolidine-2-carboxamide and (R)—N—((R)-azetidin-3-yl (4-chloro-2,5-difluorophenyl)methyl)-1-((S)-1-((3-cyanoazetidin-1-yl)sulfonyl)piperidine-3-carbonyl) pyrrolidine-2-carboxamide. The diastereomeric mixture was separated by preparative SFC method (Column: Chiralpak IC 2×15 cm, mobile phase: 55% methanol with 0.2% DEA, flowrate: 80 mL/min, 215 nm, inlet pressure: 100 bar) to deliver the both epimers. The second eluting peak was assigned as N—((R)-3-azetidinyl(4-chloro-2,5-difluorophenyl)methyl)-1-(((3S)-1-((3-cyano-1-azetidinyl)sulfonyl)-3-piperidinyl)carbonyl)-D-prolinamide Example 558 based on literature precedent (Ellman, J. A.; Owens, T. D.; Tang, T. P. *Acc. Chem. Res.* 2002, 35, 984). $^1$H NMR (500 MHz, DMSO-d$_6$) δ ppm 7.32-8.67 (m, 3H), 5.06-5.38 (m, 1H), 4.21-4.51 (m, 1H), 3.97-4.11 (m, 2H), 3.84-3.96 (m, 2H), 3.74-3.81 (m, 1H), 3.51-3.64 (m, 3H), 3.43-3.49 (m, 1H), 3.08-3.29 (m, 3H), 2.69-3.04 (m, 3H), 2.56-2.68 (m, 1H), 1.63-2.25 (m, 7H), 1.11-1.56 (m, 3H). LCMS-ESI (POS.) m/z: 585.2 (M+H)+.

Route H

General Scheme for Route H

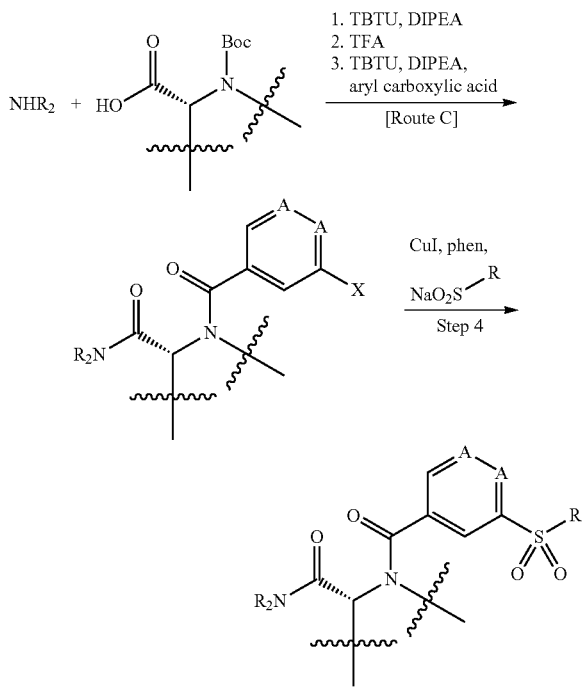

Example Route H: Example 310

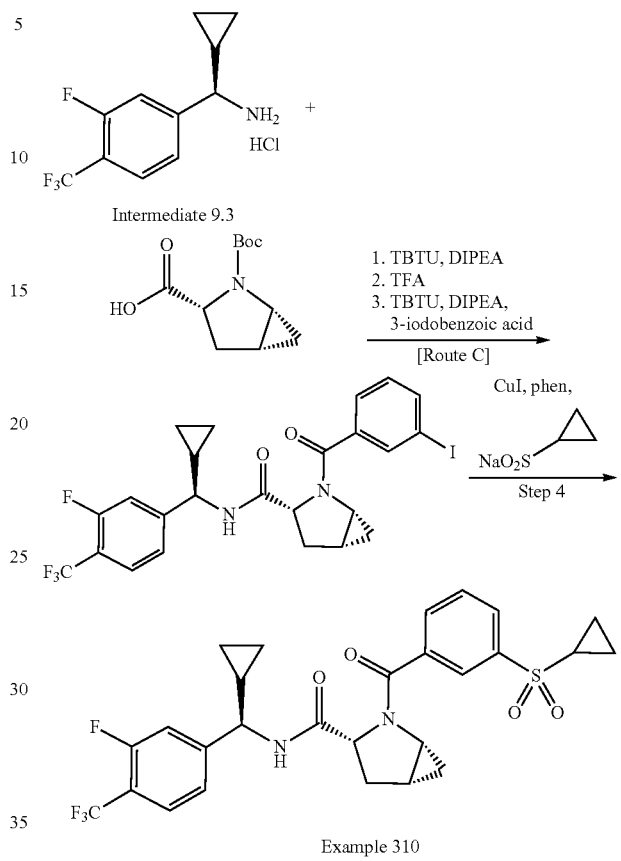

Example 310

The procedure described for Route C was performed employing Intermediate 9.3, (1R,3R,5R)-2-(tert-butoxycarbonyl)-2-azabicyclo[3.1.0]hexane-3-carboxylic acid, and 3-iodobenzoic acid followed by the subsequent manipulation:

Step 4: (1R,3R,5R)—N—((R)-cyclopropyl(3-fluoro-4-(trifluoromethyl)phenyl)methyl)-2-(3-iodobenzoyl)-2-azabicyclo[3.1.0]hexane-3-carboxamide (126 mg, 0.22 mmol), 1,10-phenanthroline (0.016 g, 0.089 mmol), copper (I) iodide (1.5 mg, 0.045 mmol), and cyclopropanesulfinic acid sodium salt (5.8 mg, 0.33 mmol) were added to a 8 mL reaction vial. Dimethyl sulfoxide (0.90 mL) was added, the vial was sealed with a Teflon cap and heated at 85° C. for 12 h. The mixture was then cooled to rt and purified by preparative HPLC (XSelect CSH Prep C18 10 µm ODB 19×100 mm, A: water 0.1% TFA B: acetonitrile 0.1% TFA, gradient: 25% (2 min), 25-70% (12 min), flow rate: 40 mL/min, monitored @ 215 nm) to give (1R,3R,5R)—N—((R)-cyclopropyl(3-fluoro-4-(trifluoromethyl)phenyl) methyl)-2-(3-(cyclopropylsulfonyl)benzoyl)-2-azabicyclo [3.1.0]hexane-3-carboxamide Example 310 (56 mg) as a white solid. $^1$H NMR (500 MHz, chloroform-d) δ ppm 8.23-8.29 (m, 1H), 7.96-8.08 (m, 2H), 7.65-7.75 (m, 1H), 7.48-7.59 (m, 2H), 7.14-7.25 (m, 2H), 5.13-5.22 (m, 1H), 4.26-4.39 (m, 1H), 3.24-3.32 (m, 1H), 2.54-2.63 (m, 1H), 2.47-2.54 (m, 1H), 2.35-2.45 (m, 1H), 1.72-1.85 (m, 1H), 1.32-1.44 (m, 2H), 1.03-1.26 (m, 4H), 0.85-0.96 (m, 1H), 0.52-0.71 (m, 2H), 0.31-0.46 (m, 2H). LCMS-ESI (POS.) m/z: 551.2 (M+H)+.

Route I

General Scheme for Route I

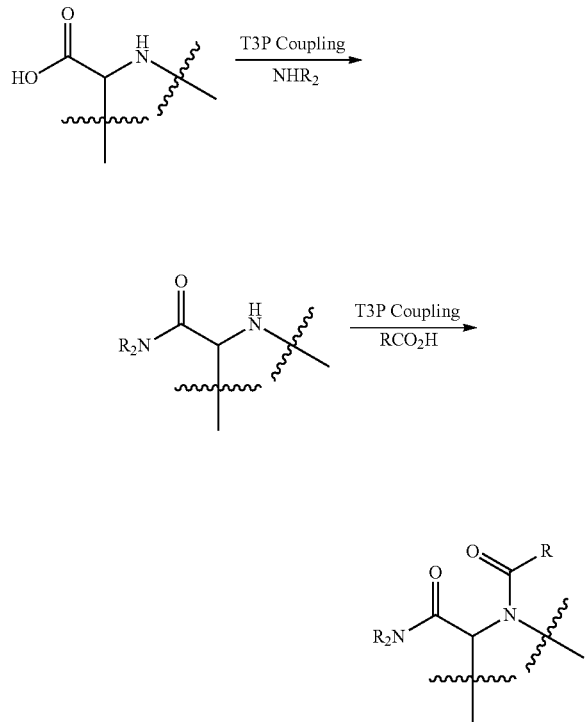

Example Route I: Example 481

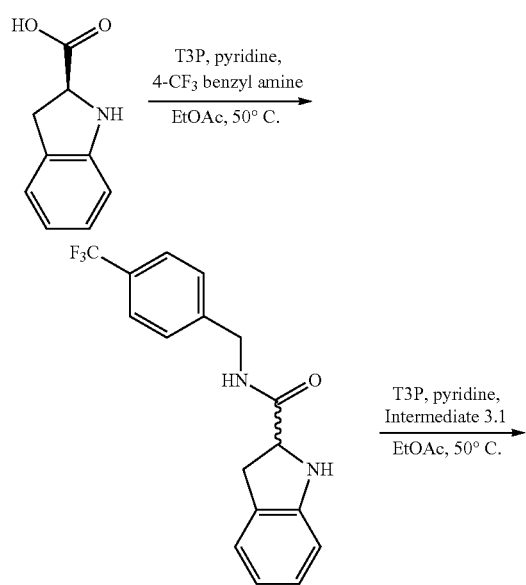

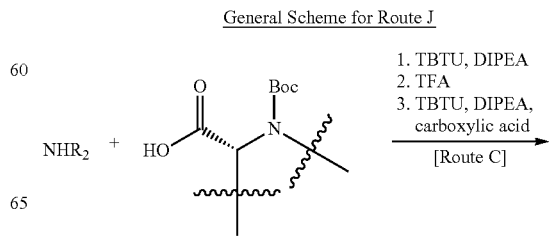

Example 481

Step 1: To a 40-mL vial was added (4-(trifluoromethyl)phenyl)methanamine (0.32 g, 1.84 mmol), (S)-(−)-indoline-2-carboxylic acid (0.30 g, 1.84 mmol), ethyl acetate (6.1 mL), pyridine (3.1 mL), and 1-propanephosphonic acid cyclic anhydride (1.84 mL, 1.84 mmol). The vial was capped and heated to 50° C. for 1 h. The reaction was concentrated and purified by silica gel chromatography using 0-50% EtOAc/heptane to give (rac)-N-(4-(trifluoromethyl)benzyl)indoline-2-carboxamide (0.336 g). LCMS-ESI (POS.) m/z: 321.2 (M+H)+.

Step 2: To a 20-mL vial was added 3-((3-cyanoazetidin-1-yl)sulfonyl)benzoic acid (Intermediate 3.1, 0.304 g, 1.143 mmol), N-(4-(trifluoromethyl)benzyl)indoline-2-carboxamide (0.366 g, 1.143 mmol), ethyl acetate (3.81 mL), pyridine (1.90 mL), and 1-propanephosphonic acid cyclic anhydride (1.5 mL, 1.485 mmol). The vial was capped and heated to 50° C. for 1 h, then cooled to rt and purified by preparative HPLC (Xselect 19×100 mm, 10 μm, mobile phase: 0.1% NH$_4$OH in ACN and water) to provide both (2R)-1-((3-((3-cyano-1-azetidinyl)sulfonyl)phenyl)carbonyl)-N-(4-(trifluoromethyl)benzyl)-2,3-dihydro-1H-indole-2-carboxamide and (2S)-1-((3-((3-cyano-1-azetidinyl)sulfonyl)phenyl)carbonyl)-N-(4-(trifluoromethyl)benzyl)-2,3-dihydro-1H-indole-2-carboxamide (Example 481) (0.021 g) as a white solid. $^1$H NMR (500 MHz, DMSO-d$_6$) δ ppm 7.87-8.09 (m, 3H), 7.87 (br s, 1H), 7.77-7.84 (m, 1H), 7.71 (br d, J=7.66 Hz, 1H), 7.60-7.67 (m, 2H), 7.56 (br d, J=7.66 Hz, 1H), 7.44 (br s, 1H), 7.36 (br d, J=7.27 Hz, 1H), 7.21-7.31 (m, 2H), 7.15-7.21 (m, 1H), 7.07-7.15 (m, 1H), 6.88-7.07 (m, 1H), 4.27 (br s, 1H), 4.08 (br d, J=5.06 Hz, 1H), 3.94-4.04 (m, 2H), 3.80-3.93 (m, 2H), 3.05 (s, 1H). LCMS-ESI (POS.) m/z: 569.2 (M+H)+.

Route J

General Scheme for Route J

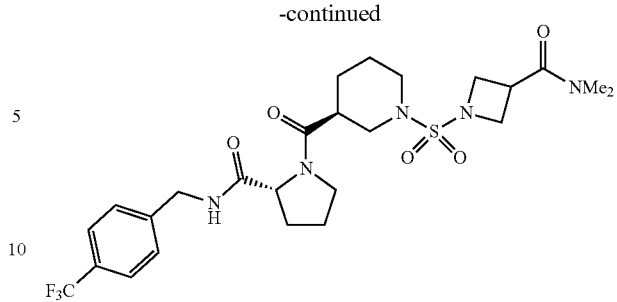

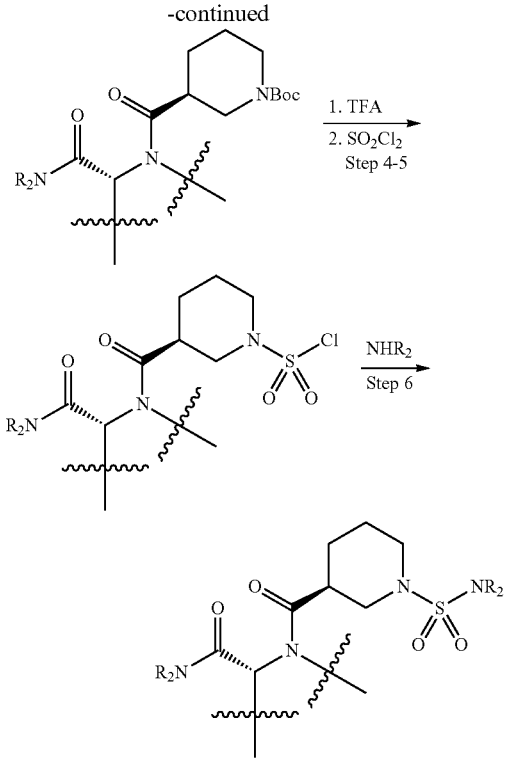

Example Route J: Example 712

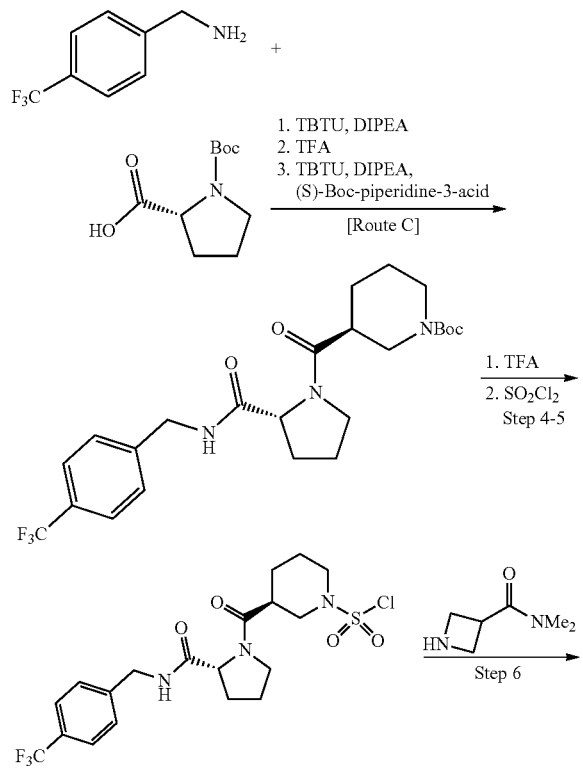

Example 712.

The procedure described for Route C was performed employing 4-trifluoromethylbenzylamine and D-Boc-proline followed by the subsequent manipulations:

Step 4: tert-Butyl (S)-3-((R)-2-((4-(trifluoromethyl)benzyl)carbamoyl)pyrrolidine-1-carbonyl)piperidine-1-carboxylate (4.48 g, 9.27 mmol) was dissolved in DCM (50 mL). While at rt, TFA (25 mL) was added slowly, and the reaction mixture was stirred at rt for 1 h. The solvent was evaporated, and the residue was dissolved in DCM and washed with 2N NaOH. The organic layers were dried over MgSO₄, filtered, and concentrated under reduced pressure to provide crude (R)-1-((S)-piperidine-3-carbonyl)-N-(4-(trifluoromethyl)benzyl)pyrrolidine-2-carboxamide (3.55 g). LCMS-ESI (POS) m/z: 384.2 (M+H)+.

Step 5: (R)-1-((S)-piperidine-3-carbonyl)-N-(4-(trifluoromethyl)benzyl)pyrrolidine-2-carboxamide (2.74 g, 7.15 mmol) was dissolved in DCM (84.0 mL) and cooled to −30° C. To this solution was added DIPEA (2.49 mL, 14.30 mmol) and sulfuryl chloride (1.74 mL, 21.45 mmol). The reaction mixture was allowed to warm to rt and stir for 1 h. The solvent was evaporated, and the mixture was purified by MPLC using silica gel (230-400 mesh) and eluted with a gradient of 5-50% 3:1 EtOAc/EtOH in heptane to provide (S)-3-((R)-2-((4-(trifluoromethyl)benzyl)carbamoyl)pyrrolidine-1-carbonyl)piperidine-1-sulfonyl chloride (Intermediate 24, 2.88 g). ¹H NMR (500 MHz, chloroform-d) δ 7.58 (d, J=8.17 Hz, 2H), 7.37 (br d, J=8.04 Hz, 3H), 4.61 (dd, J=2.21, 8.04 Hz, 1H), 4.49-4.57 (m, 1H), 4.38-4.47 (m, 1H), 3.92 (br dd, J=1.88, 12.00 Hz, 2H), 3.45-3.70 (m, 2H), 3.03 (t, J=11.68 Hz, 1H), 2.82-2.89 (m, 1H), 2.76-2.81 (m, 1H), 2.44 (qdd, J=3.00, 6.34, 9.33 Hz, 1H), 2.14-2.30 (m, 1H), 2.01-2.11 (m, 1H), 1.89-1.99 (m, 3H), 1.74-1.86 (m, 1H), 1.44-1.57 (m, 1H).

Step 6: To a solution of (S)-3-((R)-2-((4-(trifluoromethyl)benzyl)carbamoyl)pyrrolidine-1-carbonyl)piperidine-1-sulfonyl chloride (95 mg, 0.18 mmol) and 6,6-difluoro-2-azaspiro[3.3]heptane hydrochloride (100 mg, 0.59 mmol) in DMF (1.9 mL) at rt was added triethylamine (0.28 mL, 1.97 mmol). The reaction mixture was stirred for 12 h at rt and then purified by reverse-phase HPLC (25-70% MeCN/water) to afford (R)-1-((S)-1-((3-(dimethylcarbamoyl)azetidin-1-yl)sulfonyl)piperidine-3-carbonyl)-N-(4-(trifluoromethyl)benzyl)pyrrolidine-2-carboxamide Example 712 (72 mg) as a white powder. ¹H NMR (400 MHz, chloroform-d) δ 7.55-7.65 (m, 2H), 7.45-7.54 (m, 1H), 7.32-7.44 (m, 2H), 4.61 (dd, J=1.97, 7.98 Hz, 1H), 4.47-4.55 (m, 1H), 4.35-4.45 (m, 1H), 4.10-4.18 (m, 2H), 4.03 (dt, J=3.84, 8.24 Hz, 2H), 3.76-3.86 (m, 2H), 3.60 (dd, J=5.23, 8.76 Hz, 2H), 3.47-3.56 (m, 1H), 2.90-3.01 (m, 4H), 2.86-2.90 (m, 3H), 2.67-2.84 (m, 2H), 2.42-2.52 (m, 1H), 2.11-2.25 (m, 1H), 1.98-2.11

(m, 1H), 1.82-1.95 (m, 2H), 1.73-1.82 (m, 1H), 1.58-1.65 (m, 1H), 1.49-1.58 (m, 1H). LCMS-ESI (POS.) m/z: 574.2 (M+H)+.

Route K

General Scheme for Route K

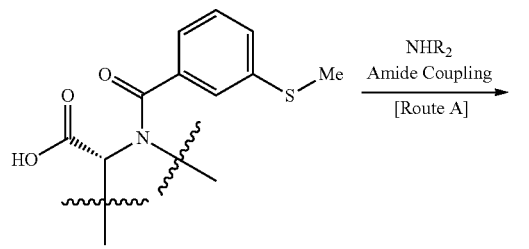

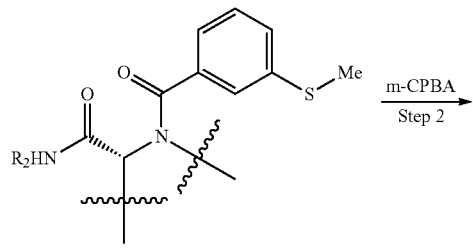

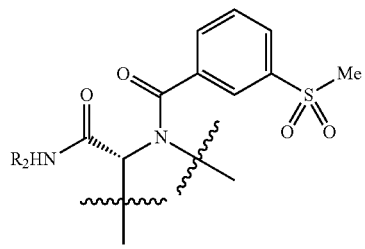

Example Route K: Example 377

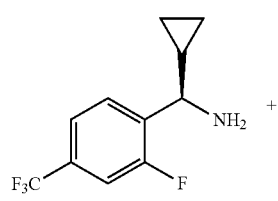

Intermediate 9.5

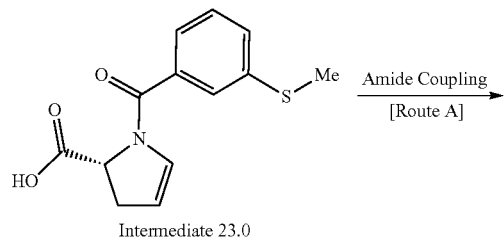

Intermediate 23.0

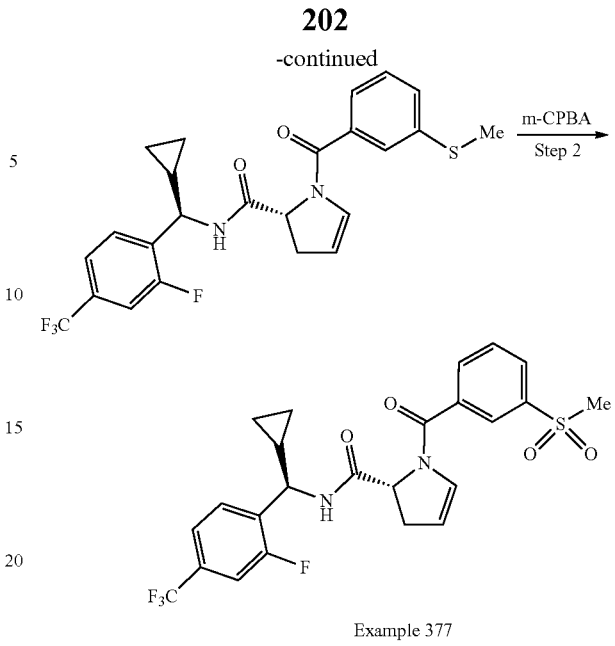

Example 377

The procedure described for Route A was performed employing Intermediate 9.5 and Intermediate 23.0 followed by the subsequent manipulation:

Step 2: To a 10-mL vial was added (R)—N—((R)-cyclopropyl(2-fluoro-4-(trifluoromethyl)phenyl)methyl)-1-(3-(methylthio)benzoyl)-2,3-dihydro-1H-pyrrole-2-carboxamide (0.06 g, 0.125 mmol) in DCM (1.2 mL). After cooling to 0° C., MCPBA (77 wt %, 0.051 g, 0.226 mmol) was added in 3 portions. The mixture was stirred at 0° C. for 30 min and then diluted with DCM and washed with a 1N NaOH solution. The aqueous fraction was extracted with DCM, and the combined organic layers were dried over MgSO₄, filtered, and concentrated. The residue was purified by Gilson reverse-phase HPLC (25-70% ACN/water) to provide (2R)—N—((R)-cyclopropyl(2-fluoro-4-(trifluoromethyl)phenyl)methyl)-1-(3-(methylsulfonyl)benzoyl)-2,3-dihydro-1H-pyrrole-2-carboxamide Example 377 (0.008 g) as white powder. $^1$H NMR (500 MHz, chloroform-d) δ ppm 8.16 (s, 1H), 8.11 (br d, J=7.79 Hz, 1H), 7.86 (d, J=7.66 Hz, 1H), 7.69-7.77 (m, 2H), 7.48-7.54 (m, 1H), 7.43 (d, J=8.04 Hz, 1H), 7.36 (d, J=10.38 Hz, 1H), 6.31-6.37 (m, 1H), 5.33-5.39 (m, 1H), 5.10 (dd, J=3.70, 10.45 Hz, 1H), 4.61 (t, J=7.98 Hz, 1H), 3.21 (br dd, J=1.43, 17.26 Hz, 1H), 3.10-3.14 (m, 3H), 2.76-2.98 (m, 1H), 1.26-1.35 (m, 1H), 0.61-0.69 (m, 1H), 0.54-0.61 (m, 1H), 0.44-0.50 (m, 1H), 0.37-0.44 (m, 1H). LCMS-ESI (POS.) m/z: 511.0 (M+H)+.

Route L

General Scheme for Route L

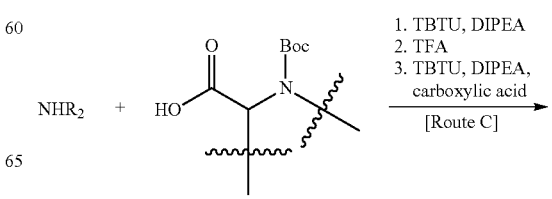

1. TBTU, DIPEA
2. TFA
3. TBTU, DIPEA, carboxylic acid

[Route C]

203
-continued

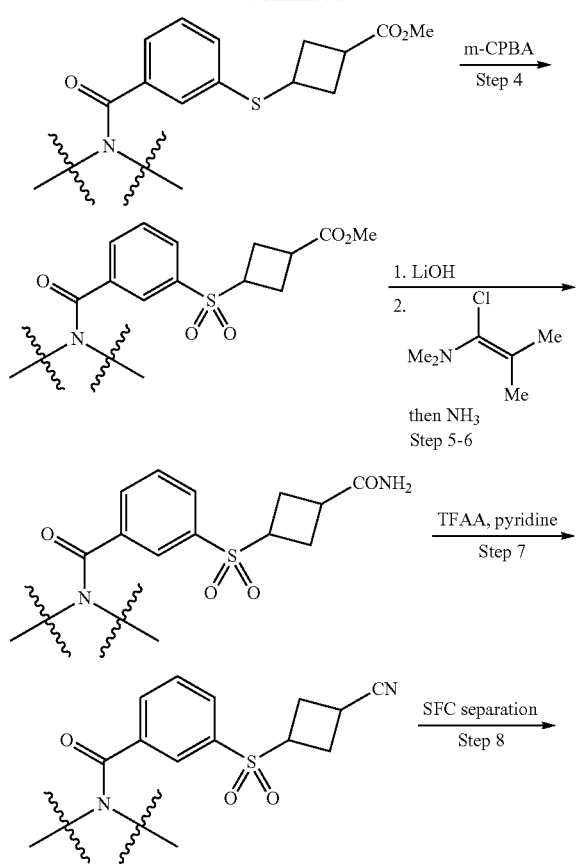

Example Route L: Example 507

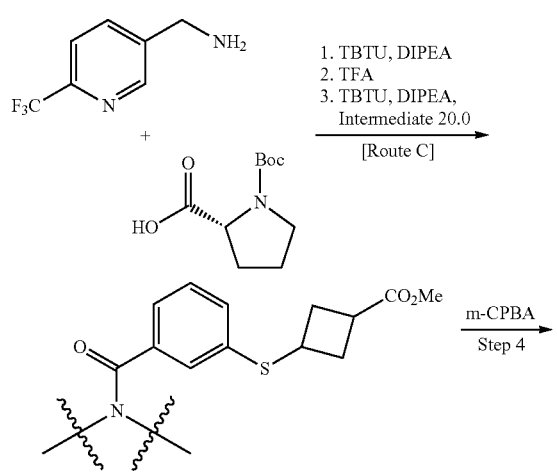

204
-continued

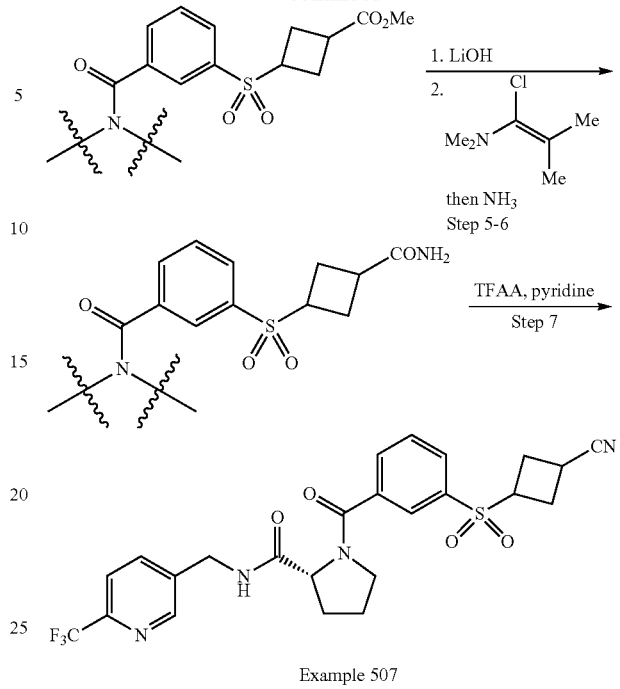

Example 507

The sequence described for Route C was performed with (6-(trifluoromethyl)pyridin-3-yl)methanamine, D-Boc-proline, and Intermediate 20.0 followed by the subsequent manipulations:

Step 4: A mixture of methyl (R)-3-((3-(2-(((6-(trifluoromethyl)pyridin-3-yl)methyl)carbamoyl)pyrrolidine-1-carbonyl)phenyl)thio)cyclobutanecarboxylate (0.15 g, 0.29 mmol) and MCPBA (77 wt %, 0.18 g, 0.81 mmol) in DCM (3 mL) was stirred at rt for 16 h. The reaction mixture was diluted with DCM and washed with 1N NaOH solution. The combined organic layers were dried over $MgSO_4$, filtered, and concentrated under reduced pressure. The crude material was then purified by MPLC using silica gel (230-400 mesh) and eluted with a gradient of 0-60% 3:1 EtOAc/EtOH in heptane, to provide methyl (R)-3-((3-(2-(((6-(trifluoromethyl)pyridin-3-yl)methyl)carbamoyl)pyrrolidine-1-carbonyl)phenyl)sulfonyl)cyclobutanecarboxylate (0.14 g) as a light-yellow oil. LCMS-ESI (POS) m/z: 554.0 (M+H)+.

Step 5: A solution of methyl (R)-3-((3-(2-(((6-(trifluoromethyl)pyridin-3-yl)methyl)carbamoyl)pyrrolidine-1-carbonyl)phenyl)sulfonyl)cyclobutanecarboxylate (0.16 g, 0.289 mmol) in THF (1.7M), methanol (0.6 mL), and water (0.6 mL) was treated with lithium hydroxide (34.6 mg, 1.45 mmol). The solution was stirred at rt for 2 h, then diluted with water and acidified with 1N HCl solution to pH=3. The mixture was extracted with EtOAc/EtOH (3:1), and the combined organic layers were dried over $MgSO_4$, filtered, and concentrated under reduced pressure. The resulting crude acid was used without purification. LCMS-ESI (POS) m/z: 540.1 (M+H)+.

Step 6: This crude acid from above was suspended in DCM (2 mL) and treated with 1-chloro-N,N,2-trimethyl-1-propenylamine (0.058 mL, 0.434 mmol). After 1 h, $NH_3$ (0.5M solution in 1,4-dioxane, 2.89 mL, 1.45 mmol) was added in one portion, and the mixture was stirred at rt for 12 h. The solvent was evaporated, and the residue was purified by MPLC using silica gel (230-400 mesh) and eluted with a gradient of 10-100% 3:1 EtOAc/EtOH in heptane, to provide (R)-1-(3-((3-carbamoylcyclobutyl)sulfonyl)benzoyl)-N-((6-(trifluoromethyl)pyridin-3-yl)methyl) pyrrolidine-2-carboxamide (0.135 g) as off-white powder. LCMS-ESI (POS) m/z: 539.2 (M+H)+.

Step 7: A solution of (R)-1-(3-((3-carbamoylcyclobutyl)sulfonyl)benzoyl)-N-((6-(trifluoromethyl)pyridin-3-yl)methyl)pyrrolidine-2-carboxamide (0.135 g, 0.251 mmol) and pyridine (0.12 mL, 1.50 mmol) in DCM (2.5 mL) was cooled to 0° C. TFAA (0.087 mL, 0.627 mmol) was added dropwise and the reaction mixture was allowed to warm to rt and stir for an additional 2 h. The solvent was evaporated under reduced pressure and the residue was purified by MPLC using silica gel (230-400 mesh) and eluted with a gradient of 0-50% 3:1 EtOAc/EtOH in heptane to provide (R)-1-(3-((3-cyanocyclobutyl)sulfonyl)benzoyl)-N-((6-(trifluoromethyl)pyridin-3-yl)methyl)pyrrolidine-2-carboxamide (Example 507, 0.063 g) as colorless oil. $^1$H NMR (500 MHz, DMSO-$d_6$) δ ppm 8.38-8.81 (m, 2H), 7.53-8.15 (m, 6H), 4.03-4.60 (m, 5H), 3.37-3.68 (m, 3H), 3.13-3.22 (m, 1H), 2.53-2.68 (m, 4H), 2.18- 2.35 (m, 1H), 1.76-2.00 (m, 3H). LCMS-ESI (POS.) m/z: 521.0 (M+H)+.

Route M

General Scheme for Route M

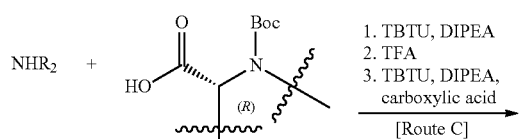

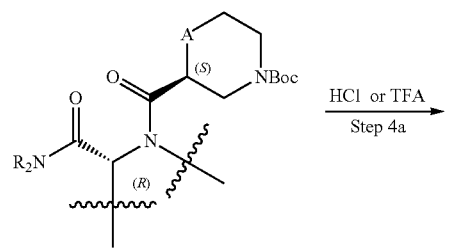

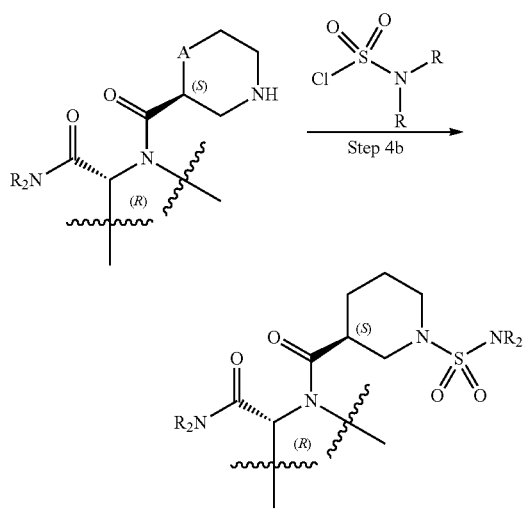

Example Route M: Example 240

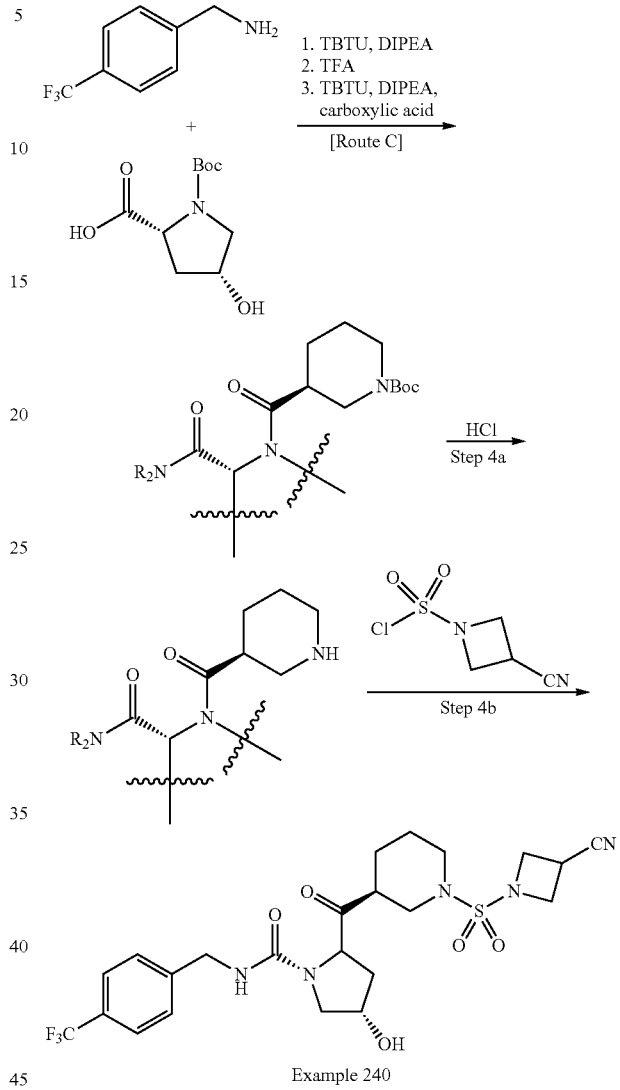

Example 240

The sequence described for Route C was performed with 4-trifluoromethylbenzylamine, Boc-cis-4-hydroxy-D-proline, (S)—N-Boc-piperidine-3-carboxylic acid followed by the subsequent manipulations:

Step 4a: A 40 mL pressure release vial was charged with (S)-tert-butyl 3-((2R,4R)-4-hydroxy-2-((4-(trifluoromethyl)benzyl)carbamoyl)pyrrolidine-1-carbonyl)piperidine-1-carboxylate (645 mg, 1.291 mmol) and dissolved in ethyl acetate (6.5 mL). To that solution was added HCl, 4.0M in dioxane (3.2 mL, 12.91 mmol). The vial was sealed and placed and stirred at room temperature. After 4 hours, LCMS showed complete consumption of the starting material to polar peak containing a mass consistent with the desired product. The reaction mixture was concentrated under reduced pressure. The resulting white film was dissolved with DCM and ethyl acetate was added until the solution became faintly turbid. After 20 minutes, the white solids were collected by filtration to give (2R,4R)-4-hydroxy-1-((S)-piperidine-3-carbonyl)-N-(4-(trifluoromethyl)

benzyl)pyrrolidine-2-carboxamide hydrochloride (390 mg, 0.895 mmol) as a white solid. LCMS-ESI (POS.) m/z: 400.2 (M+H)+.

Step 4b: A 40 mL pressure vial was charged with (2R,4R)-4-hydroxy-1-((S)-piperidine-3-carbonyl)-N-(4-(trifluoromethyl)benzyl)pyrrolidine-2-carboxamide hydrochloride (200 mg, 0.459 mmol) and dissolved in DMF (2.0 mL). To that solution was added triethylamine (0.638 mL, 4.59 mmol) followed by 3-cyanoazetidine-1-sulfonyl chloride (249 mg, 1.377 mmol). The vial was sealed and the reaction was let stir overnight. After 20 hours, LCMS showed complete consumption of the starting material to a peak containing a mass consistent with the desired product (m/z=563+H). The crude reaction was filtered through a 0.45p syringe tip filter, and purified by preparative HPLC: 50 μm Silica Gel 19×100 mm XSelect CSH Prep C18 10 μm ODB 19×100 mm, A: water 0.1% TFA B: acetonitrile 0.1% TFA, Gradient: 25% (2 min), 25-70% (12 min), Flow Rate: 40 mL/min, 3 injections monitored @215 nm. The fractions containing product were transferred into a recovery flask and the acetonitrile was removed until the solution became turbid. After which, the turbid solution was lyophilized to give (2R,4R)-1-((S)-1-((3-cyanoazetidin-1-yl)sulfonyl)piperidine-3-carbonyl)-4-hydroxy-N-(4-(trifluoromethyl)benzyl)pyrrolidine-2-carboxamide (also referred to as (4R)-1-(((3S)-1-((3-cyano-1-azetidinyl)sulfonyl)-3-piperidinyl)carbonyl)-4-hydroxy-N-(4-(trifluoromethyl)benzyl)-D-prolinamide) Example 240 (49.7 mg, 0.091 mmol) as a fluffy white solid. $^{1}$H NMR (500 MHz, chloroform-d) δ ppm 7.50-7.66 (m, 3H), 7.38 (br s, 2H), 4.69 (br d, J=7.66 Hz, 1H), 4.55-4.64 (m, 1H), 4.52 (br s, 1H), 4.41 (br d, J=14.53 Hz, 1H), 3.99-4.17 (m, 4H), 3.60-3.81 (m, 4H), 3.42 (br s, 1H), 2.93 (br t, J=11.16 Hz, 1H), 2.76 (br t, J=11.42 Hz, 1H), 2.60 (br s, 1H), 2.31-2.44 (m, 1H), 2.19 (br s, 1H), 1.23-1.98 (m, 5H). LCMS-ESI (POS.) m/z: 544.2 (M+H)+.

Route N

General Scheme for Route N

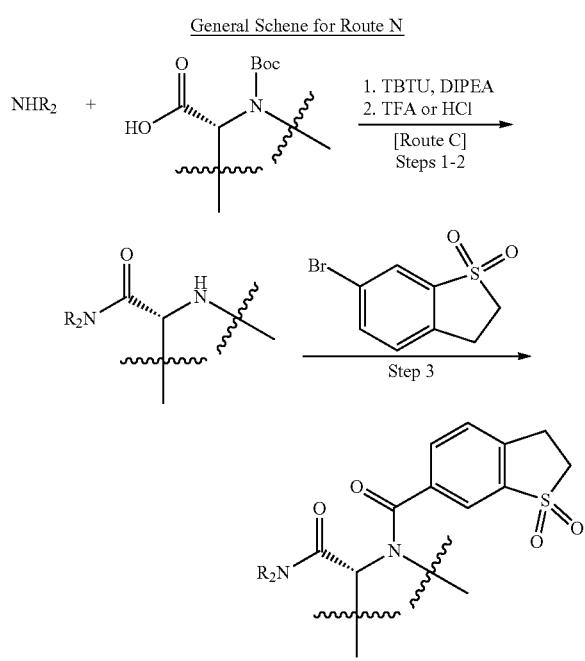

Example Route N: Example 653

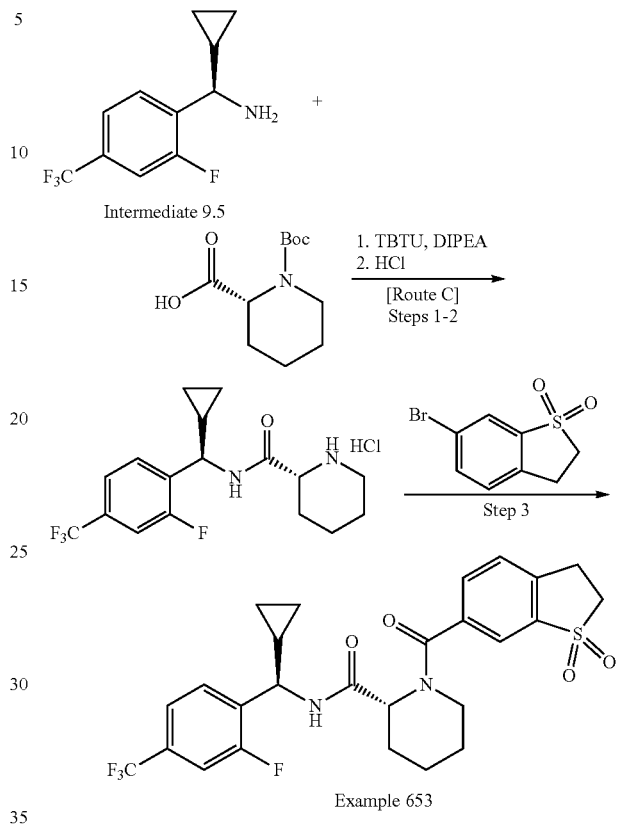

Steps 1 and 2 of Route C were conducted with Intermediate 9.5 and (R)-1-(tert-butoxycarbonyl)piperidine-2-carboxylic acid followed by the subsequent manipulation.

Step 3: Chamber A of a COware two-chamber system with stir bars was charged with potassium fluoride (14.1 mg, 0.243 mmol) and methyldiphenylsilanecarboxylic acid (58.8 mg, 0.243 mmol). Chamber B was then charged with 6-bromo-2,3-dihydrobenzo[b]thiophene-1,1-dioxide (50.0 mg, 0.202 mmol), (R)—N—((R)-cyclopropyl(2-fluoro-4-(trifluoromethyl)phenyl)methyl)piperidine-2-carboxamide hydrochloride (154 mg, 0.405 mmol), 1,4-dioxane (270 μL), methanesulfonato[9,9-dimethyl-4,5-bis(diphenylphosphino)xanthene](2 methylamino-1,1 biphenyl-2-yl)palladium(II) (9.7 mg, 10.1 μmol) and triethylamine (114 μL, 0.809 mmol). The vessel was sealed and purged with nitrogen gas followed by addition of dioxane (270 μL) to chamber A. The vessel was heated to 60° C. overnight with rapid stirring. The solution from chamber B was directly purified by silica gel chromatography using 0-50% EtOAc in heptane to give the desired product as a white solid ((2R)—N—((R)-cyclopropyl(2-fluoro-4-(trifluoromethyl)phenyl)methyl)-1-((1,1-dioxido-2,3-dihydro-1-benzothiophen-6-yl)carbonyl)-2-piperidinecarboxamide Example 653, 56.2 mg, 0.104 mmol). $^{1}$H NMR (500 MHz, chloroform-d) δ ppm 7.83 (br s, 1H), 7.70 (br d, J=7.01 Hz, 1H), 7.31-7.55 (m, 5H), 7.14 (br d, J=5.71 Hz, 1H), 5.22 (br s, 1H), 4.57 (br t, J=7.40 Hz, 1H), 3.36-3.77 (m, 6H), 2.99-3.25 (m, 1H), 2.25 (br d, J=13.75 Hz, 1H), 1.18-2.03 (m, 17H), 0.54-0.83 (m, 2H). LCMS-ESI (POS) m/z: 561.2 (M+Na)+.

Route O
General Scheme for Route O:

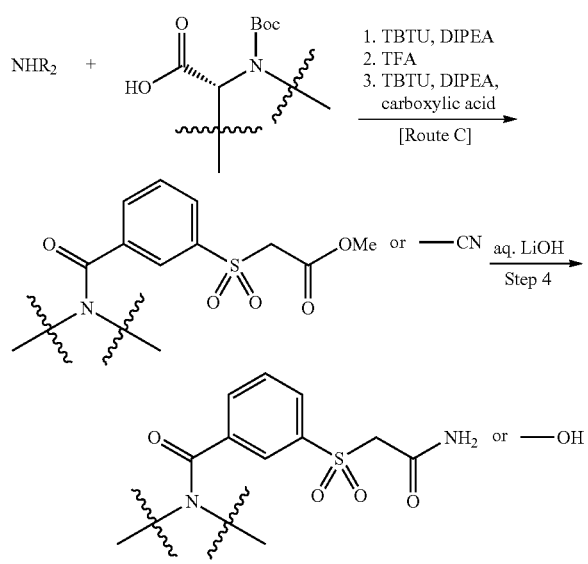

Example Route O: Example 306

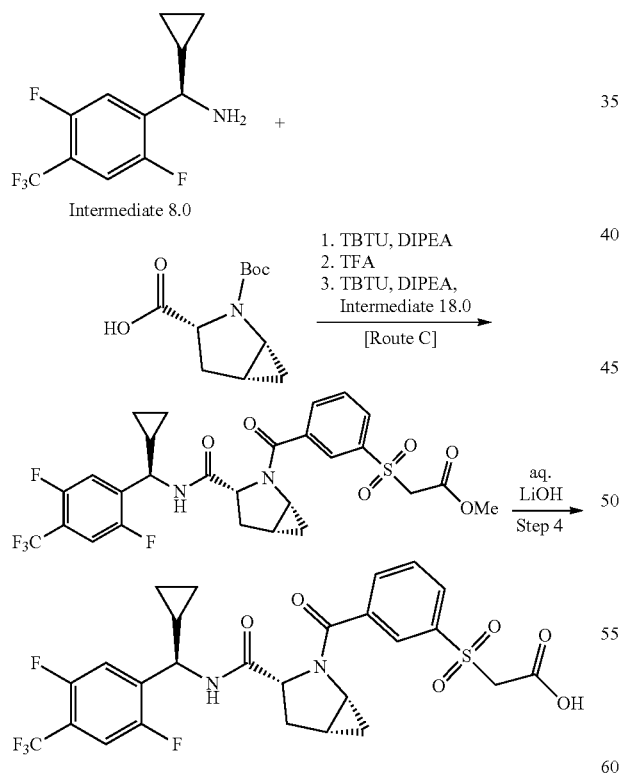

The sequence described for Route C was performed using Intermediate 8.0, (1R,3R,5R)-2-(tert-butoxycarbonyl)-2-azabicyclo[3.1.0]hexane-3-carboxylic acid, and Intermediate 18.0 followed by the subsequent manipulation:

Step 4: A 1-dram vial with stir bar was charged with methyl 2-((3-(((1R,3R,5R)-3-(((R)-cyclopropyl(2,5-difluoro-4-(trifluoromethyl)phenyl)methyl)carbamoyl)-2-azabicyclo[3.1.0]hexane-2-carbonyl)phenyl)sulfonyl)acetate (75 mg, 0.125 mmol), lithium hydroxide (15.0 mg, 0.624 mmol) and THF (416 μL) and water (83 μL). The reaction was heated at 40° C. for 72 hours and then concentrated and purified by reverse phase HPLC XSelect CSH Prep C18 10 μm ODB 19×100 mm, A: water 0.1% TFA B: acetonitrile 0.1% TFA, gradient: 25% (2 min), 25-70% (12 min), flow Rate: 40 mL/min, monitored @ 254 nm to afford ((3-(((1R,3R,5R)-3-(((R)-cyclopropyl(2,5-difluoro-4-(trifluoromethyl)phenyl)methyl)carbamoyl)-2-azabicyclo[3.1.0]hexan-2-yl)carbonyl)phenyl)sulfonyl)acetic acid Example 306 (34.5 mg) as a white solid. $^1$H NMR (500 MHz, DMSO-$d_6$) δ ppm 13.28 (br d, J=1.30 Hz, 1H), 8.71 (d, J=7.27 Hz, 1H), 8.39 (br d, J=7.01 Hz, 1H), 8.20 (s, 1H), 7.95-8.12 (m, 2H), 7.19-7.83 (m, 4H), 4.95 (dd, J=11.29, 3.50 Hz, 1H), 4.43-4.68 (m, 4H), 4.02-4.16 (m, 1H), 3.72-3.77 (m, 1H), 3.22 (td, J=6.16, 2.47 Hz, 1H), 2.52-2.77 (m, 2H), 1.62-1.79 (m, 2H), 1.51 (s, 1H), 1.12-1.32 (m, 1H), 1.00-1.12 (m, 1H), 0.66-0.80 (m, 1H), 0.23-0.64 (m, 4H). LCMS-ESI (POS.) m/z: 587.0 (M+H)+.

Route P

General Scheme for Route P

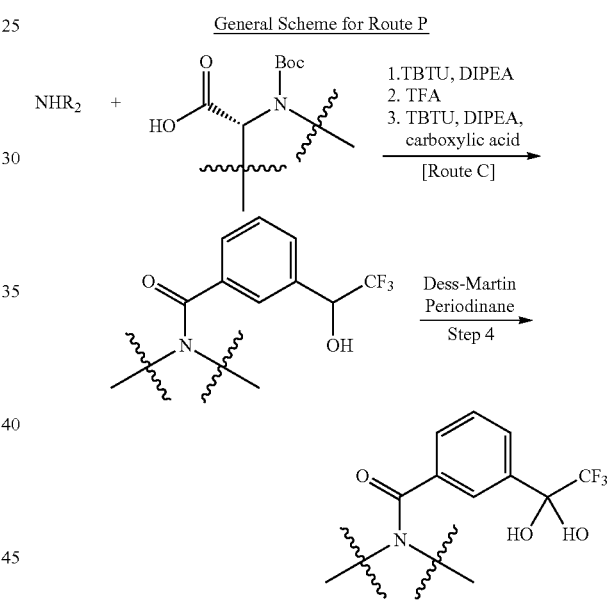

Example Route P: Example 523

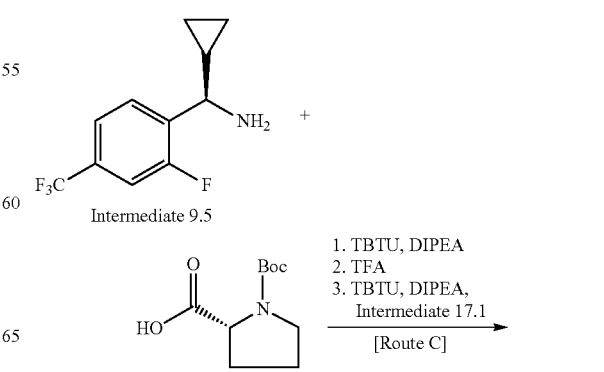

-continued

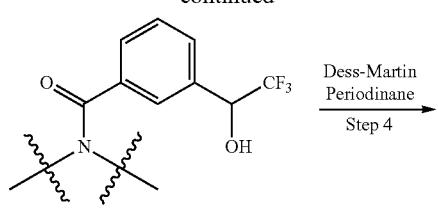

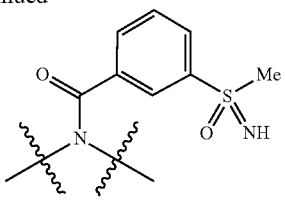

Example Route Q: Example 752

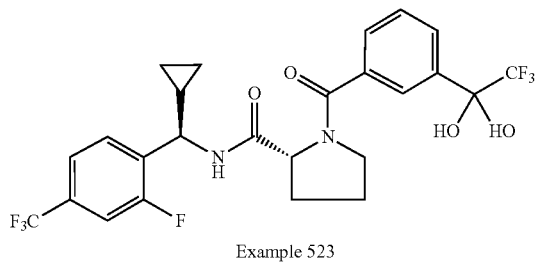

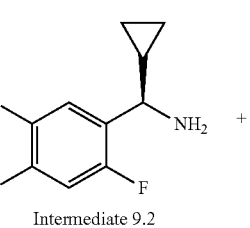

Example 523

The sequence described for Route C was performed using Intermediate 9.5, D-Boc-proline, and Intermediate 17.1 followed by the subsequent manipulation:

Step 4: A 2-dram vial with a stir bar was charged with the (2R)—N—((R)-cyclopropyl(2-fluoro-4-(trifluoromethyl)phenyl)methyl)-1-(3-(2,2,2-trifluoro-1-hydroxyethyl)benzoyl)pyrrolidine-2-carboxamide (29.6 mg, 0.056 mmol), Dess-Martin Periodinane (23.6 mg, 0.056 mmol), and dichloromethane (222 µL). The reaction stirred at rt for 16 hours and then concentrated and purified by reverse phase HPLC (XSelect CSH Prep C18 10 µm ODB 19×100 mm, A: water 0.1% TFA B: acetonitrile 0.1% TFA, gradient: 25% (2 min), 25-95% (12 min), flow Rate: 40 mL/min, monitored @254 nm to give (R)—N—((R)-cyclopropyl(2-fluoro-4-(trifluoromethyl)phenyl)methyl)-1-(3-(2,2,2-trifluoro-1,1-dihydroxyethyl)benzoyl)pyrrolidine-2-carboxamide, also referred to as N—((R)-cyclopropyl(2-fluoro-4-(trifluoromethyl)phenyl)methyl)-1-(3-(2,2,2-trifluoro-1,1-dihydroxyethyl)benzoyl)-D-prolinamide (Example 523) as a white solid (25.3 mg). $^1$H NMR (500 MHz, DMSO-d$_6$) δ ppm 8.67-8.77 (m, 1H), 7.27-8.18 (m, 9H), 4.55-4.67 (m, 1H), 4.49-4.55 (m, 1H), 4.10-4.41 (m, 1H), 3.35-3.69 (m, 3H), 3.28-3.30 (m, 1H), 2.12-2.25 (m, 1H), 1.58-1.88 (m, 4H), 1.11-1.31 (m, 2H), 0.26-0.67 (m, 4H). LCMS-ESI (POS.) m/z: 549.2 (M+H)+.

Route Q

General Scheme for Route Q

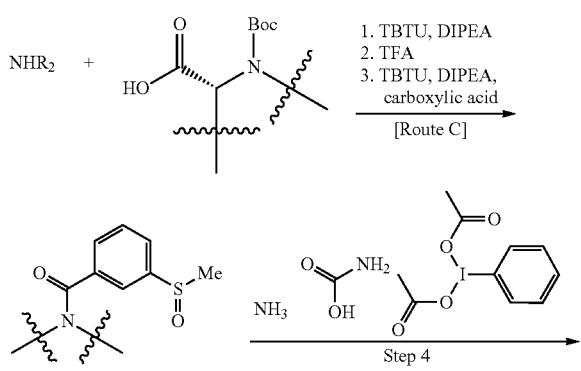

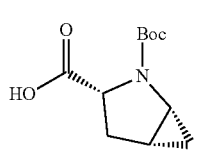

Intermediate 9.2

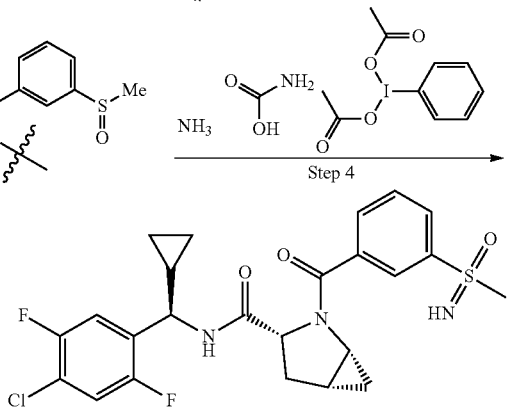

Example 752

The sequence described for Route C was performed using Intermediate 9.2, (1R,3R,5R)-2-(tert-butoxycarbonyl)-2-azabicyclo[3.1.0]hexane-3-carboxylic acid, and 3-(methylsulfinyl)benzoic acid followed by the subsequent manipulation:

Step 4: A 1-dram vial with a stir bar was charged with (1R,3R,5R)—N—((R)-cyclopropyl(2-fluoro-4-(trifluoromethyl)phenyl)methyl)-2-(3-(methylsulfinyl)benzoyl)-2-azabicyclo[3.1.0]hexane-3-carboxamide (107.4 mg, 0.211 mmol), ammonium carbamate (49.5 mg, 0.634 mmol), (diacetoxyiodo)benzene (102 mg, 0.317 mmol) and acetonitrile (422 µL). The reaction was stirred at rt for 72 hours and then concentrated. The crude mixture was purified by reverse phase HPLC XSelect CSH Prep C18 10 µm ODB 19×100 mm, A: water 0.1% TFA B: acetonitrile 0.1% TFA, gradient: 25% (2 min), 25-95% (12 min), flow Rate: 40 mL/min, monitored @ 254 nm to give (1R,3R,5R)—N—((R)-(4-chloro-2,5-difluorophenyl)(cyclopropyl)methyl)-2-(3-(S-methylsulfonimidoyl)benzoyl)-2-azabicyclo[3.1.0]hexane- 3-carboxamide Example 752 as a white solid (42.4 mg). $^1$H NMR (500 MHz, DMSO-$d_6$) δ ppm 8.62 (br d, J=7.53 Hz, 1H), 8.21-8.43 (m, 1H), 7.29-8.20 (m, 5H), 4.61-5.02 (m, 1H), 3.96-4.57 (m, 1H), 3.04-3.88 (m, 5H), 2.52-2.79 (m, 2H), 1.53-1.86 (m, 2H), 1.02-1.35 (m, 2H), −0.29-0.97 (m, 6H). LCMS-ESI (POS.) m/z: 508.0 (M+H)+.

Route R

General Scheme for Route R

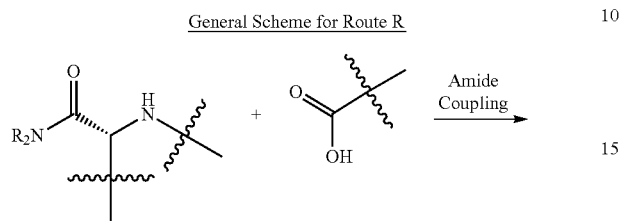

Example Route R: Example 577

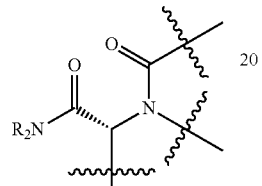

Intermediate 28.2

+

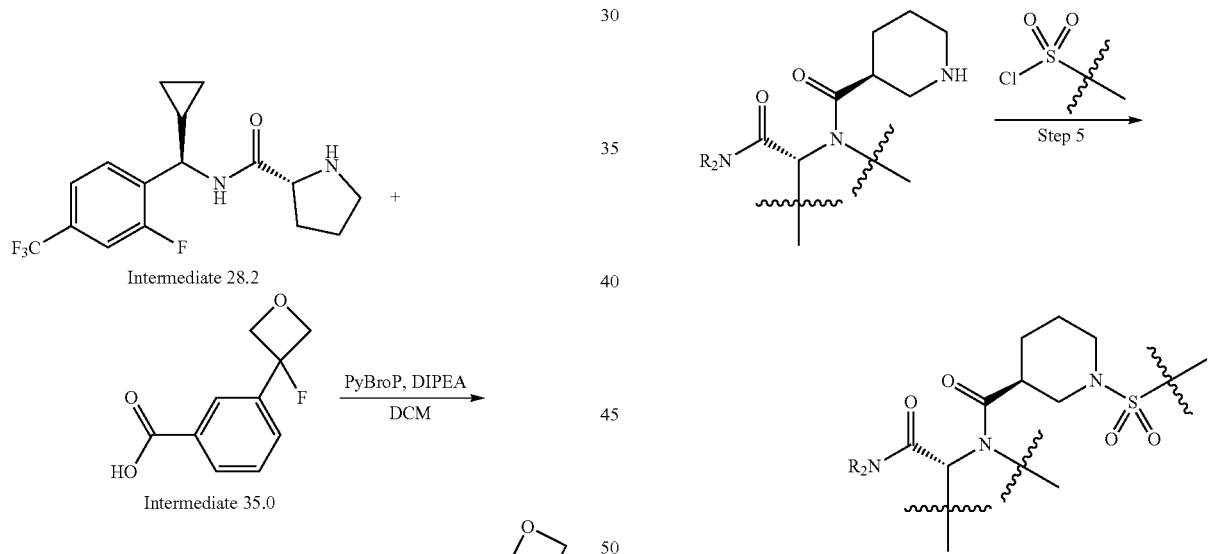

Intermediate 35.0

Example 577

Step 1: (R)—N—((R)-cyclopropyl(2-fluoro-4-(trifluoromethyl)phenyl)methyl)pyrrolidine-2-carboxamide (Intermediate 28.2, 0.020 g, 0.061 mmol), 3-(3-fluorooxetan-3-yl)benzoic acid (Intermediate 35.0, 0.012 g, 0.061 mmol), bromotripyrrolidinophosphonium hexafluorophosphate (PyBroP) (0.031 g, 0.067 mmol) in dry dichloromethane (1 mL) was added DIPEA (0.021 mL, 0.12 mmol). The reaction mixture was stirred for 30 min, concentrated under reduced pressure, and purified by reverse phase HPLC (Phenomenex, gemini 5 μm C18 150×21.2 mm, 10-80% acetonitrile in water with 0.1% formic acid in 25 minutes) to give N—((R)-cyclopropyl(2-fluoro-4-(trifluoromethyl)phenyl)methyl)-1-(3-(3-fluoro-3-oxetanyl)benzoyl)-D-prolinamide Example 577 as a clear colorless oil (0.022 g, 0.043 mmol). $^1$H NMR (400 MHz, methanol-$d_4$) δ 7.84-7.37 (m, 7H), 5.13-5.01 (m, 2H), 5.00-4.89 (m, 2H), 4.66-4.11 (m, 2H), 3.74-3.46 (m, 2H), 2.38-2.25 (m, 1H), 2.00-1.78 (m, 3H), 1.35-0.96 (m, 1H), 0.74-−0.04 (m, 4H). LCMS-APCI (POS.) m/z: 509.20 (M+H)+.

Route S

General Scheme for Route S

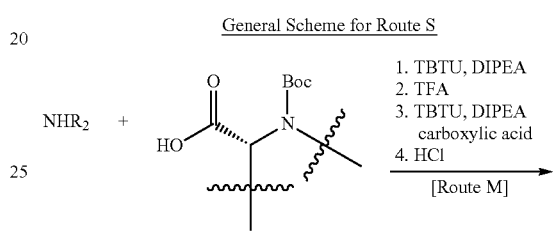

Example Route S: Example 780

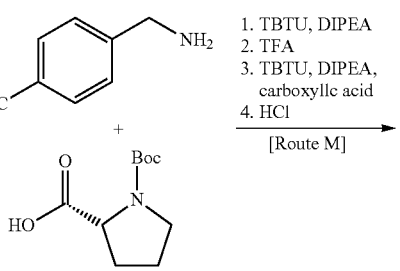

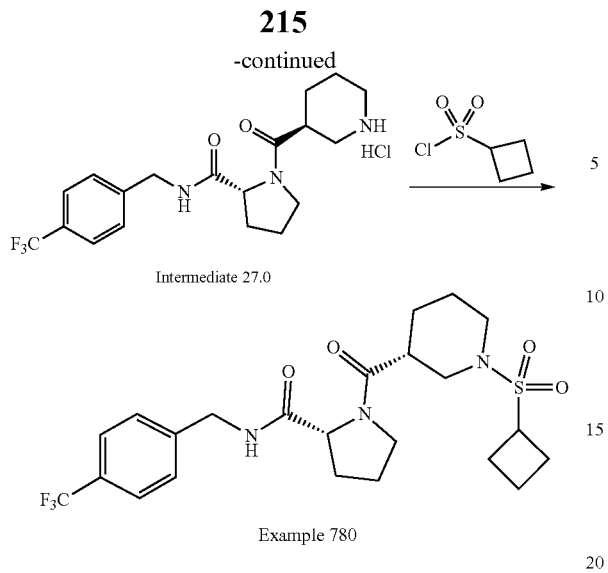

Intermediate 27.0

Example 780

The sequence described for Route M was performed using 4-(trifluoromethyl)phenyl)methanamine, D-Boc-proline, and (S)-1-(tert-butoxycarbonyl)piperidine-3-carboxylic acid followed by the subsequent manipulation:

Step 5: To a solution of (R)-1-((S)-piperidine-3-carbonyl)-N-(4-(trifluoromethyl)benzyl)pyrrolidine-2-carboxamide hydrochloride (Intermediate 27.0) (0.386 g, 0.776 mmol) in dry DCM (1.0 mL) at 0° C. was added DIPEA (0.257 mL, 1.55 mmol). The sample was stirred for 15 min at rt then cooled to 0° C. While at 0° C. cyclobutanesulfonyl chloride (248 g, 1.16 mmol) was added slowly. The mixture was stirred at 0° C. for 20 min and then quenched with methanol and concentrated under reduced pressure. The mixture was dissolved in DMF and purified by reverse phase HPLC (40 min gradient with 10-100% acetonitrile in water (0.1% formic acid modifier), Phenomonex Gemini 5 μm C18 150×21.20 mm column) to give (R)-1-((S)-1-(cyclobutylsulfonyl) piperidine-3-carbonyl)-N-(4-(trifluoromethyl) benzyl)pyrrolidine-2-carboxamide (Example 780, 0.212 g, 0.379 mmol) as a white solid. $^1$H NMR (400 MHz, methanol-$d_4$) δ ppm 7.64 (d, J=8.1 Hz, 2H), 7.50 (d, J=7.9 Hz, 2H), 4.48 (d, J=2.2 Hz, 2H), 4.44 (dd, J=4.4, 8.3 Hz, 1H), 3.93-4.03 (m, 1H), 3.70-3.77 (m, 3H), 2.73-2.83 (m, 2H), 2.43-2.53 (m, 3H), 2.24-2.37 (m, 4H), 1.94- 2.12 (m, 7H), 1.50-1.65 (m, 2H). LCMS-APCI (POS.) m/z: 502.2 (M+H)+.

Route T

General Scheme for Route T

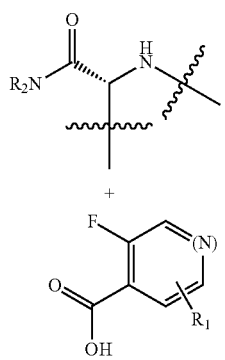

Example Route T: Example 550

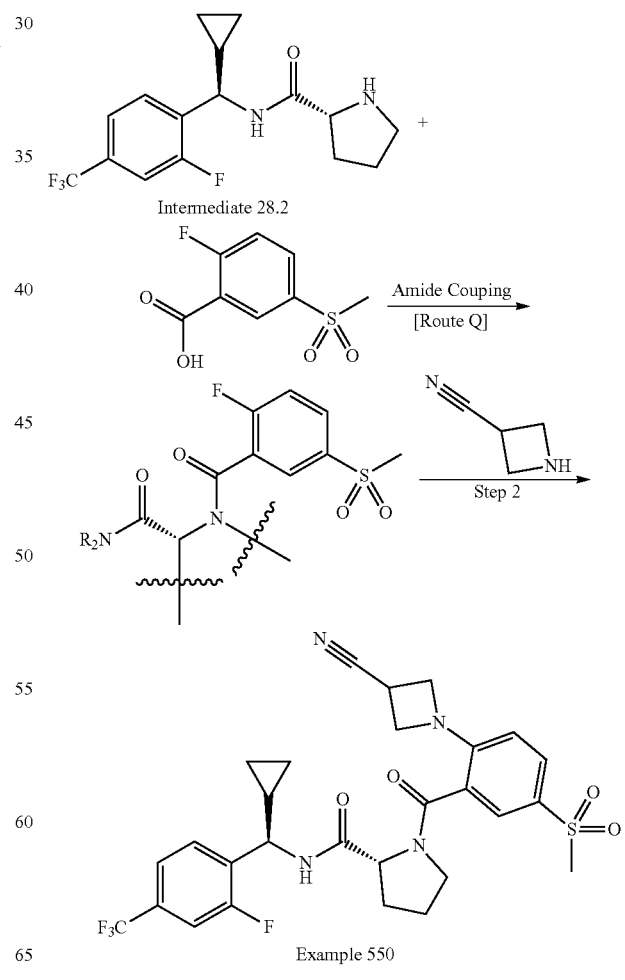

Example 550

The sequence described for Route R was performed using Intermediate 28.2 and 2-fluoro-5-(methylsulfonyl)benzoic acid followed by the subsequent manipulation:

Step 2: To a solution of (R)—N—((R)-cyclopropyl(2-fluoro-4-(trifluoromethyl)phenyl)methyl)-1-(2-fluoro-5-(methylsulfonyl)benzoyl)pyrrolidine-2-carboxamide (0.40 g, 0.075 mmol) and DIPEA (0.80 mL, 0.88 mmol) in DMSO (0.80 mL) was added azetidine-3-carbonitrile (92.86 mg, 1.13 mmol), and the solution was allowed to stir at 80° C. for 6 h. It was washed with a saturated aqueous NaHCO₃ and the aqueous layer was extracted extensively with DCM. The combined organic layers were concentrated under reduced pressure then dissolved in DMF and purified by reverse phase HPLC (40 min gradient with 10-100% acetonitrile in water (0.1% formic acid modifier), Phenomonex Gemini 5 µm C18 150×21.20 mm column) to give (R)-1-(2-(3-cyanoazetidin-1-yl)-5-(methylsulfonyl)benzoyl)-N—((R)-cyclopropyl(2-fluoro-4-(trifluoromethyl)phenyl)methyl) pyrrolidine-2-carboxamide (Example 550, 0.014 g, 0.024 mmol) as an amorphous solid. ¹H NMR (500 MHz, DMSO-d₆) δ ppm 8.71-8.81 (m, 1H), 8.46 (dd, J=7.3, 16.3 Hz, 1H), 8.09 (ddd, J=2.4, 4.6, 8.6 Hz, 1H), 7.87-7.97 (m, 1H), 7.48-7.79 (m, 5H), 4.46-4.69 (m, 3H), 4.26-4.38 (m, 2H), 4.16 (dd, J=8.9, 17.1 Hz, 2H), 3.97-4.11 (m, 1H), 3.82-3.93 (m, 1H), 3.51-3.61 (m, 1H), 3.11-3.31 (m, 4H), 2.13-2.28 (m, 2H), 1.67-1.90 (m, 4H), 1.22 (dd, J=4.6, 8.1 Hz, 1H), 0.96 (d, J=6.4 Hz, 2H), 0.85-0.93 (m, 1H), 0.58-0.64 (m, 1H), 0.47-0.51 (m, 1H), 0.38-0.47 (m, 2H), 0.27-0.36 (m, 1H), −0.02 (d, J=49.1 Hz, 2H). LCMS-APCI (POS.) m/z: 593.2 (M+H)+.

Route U

General Scheme for Route U

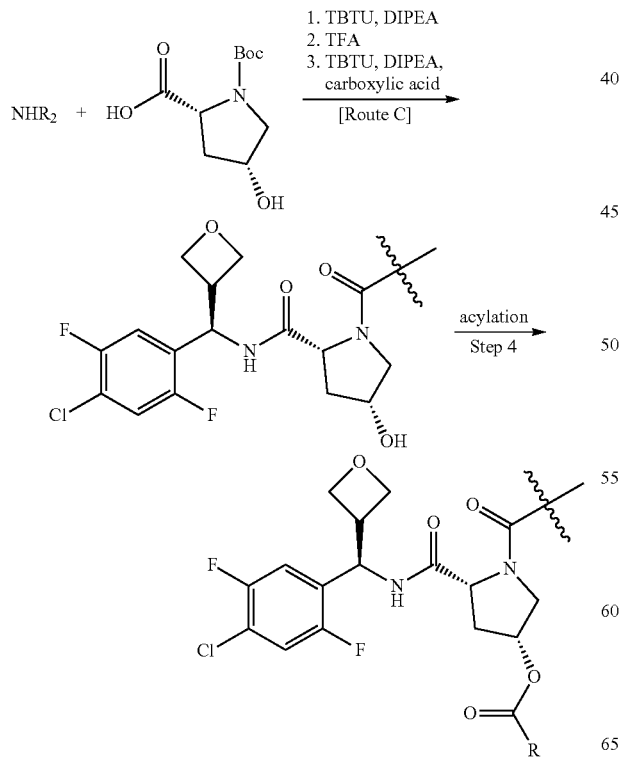

Example Route U: Example 476

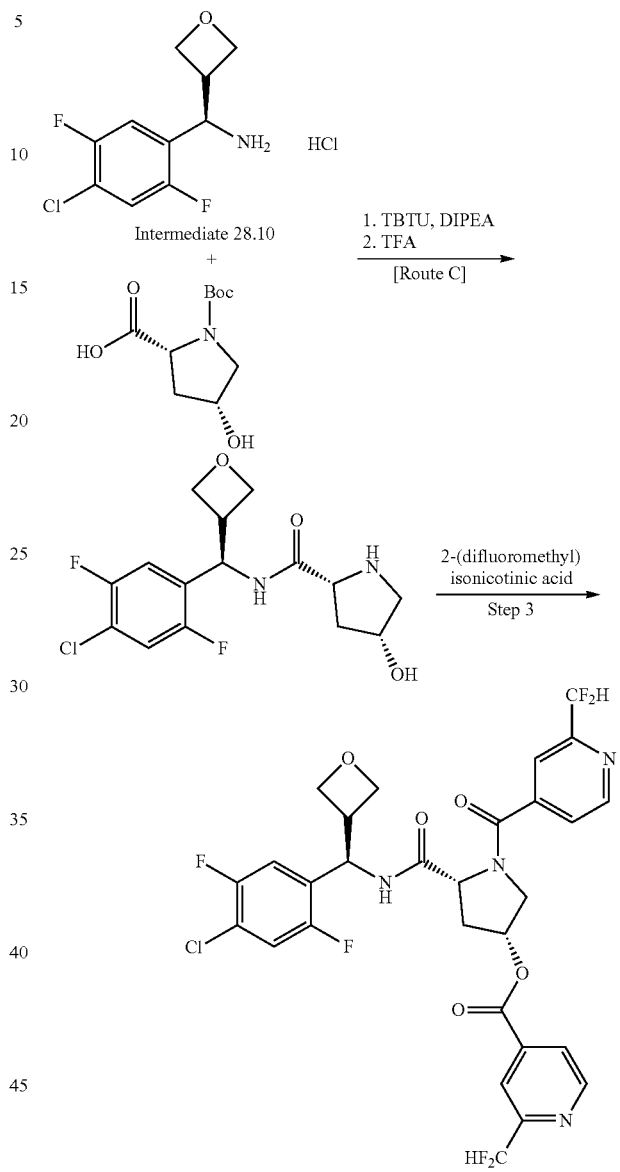

Example 476

The sequence described for Route C was performed using Intermediate 28.10 and (2R,4R)-1-(tert-butoxycarbonyl)-4-hydroxypyrrolidine-2-carboxylic acid, followed by the subsequent manipulation:

Step 3: A 8 mL vial was charged with 2-(difluoromethyl) isonicotinic acid (30 mg, 0.173 mmol), HBTU (98 mg, 0.26), (2R,4R)—N—((R)-(4-chloro-2,5-difluorophenyl)(oxetan-3-yl)methyl)-4-hydroxypyrrolidine-2-carboxamide (60 mg, 0.173 mmol) and DCM (1 mL). Triethylamine (0.241 mL, 1.73 mmol) was subsequently added dropwise. After stirring for 20 min at rt, the mixture was concentrated under reduced pressure and purified by HPLC (40 min gradient with 10-100% acetonitrile in water (0.1% formic acid modifier), Phenomonex Gemini 5 µm C18 150×21.20 mm column) to provide the di-acetylated product Example 476 (14.0 mg). ¹H NMR (400 MHz, DMSO-d₆) δ ppm 8.79

(d, J=3.2, 5.1 Hz, 1H), 8.75 (d, J=5.0 Hz, 1H), 8.49 (d, J=8.2 Hz, 1H), 7.75-7.79 (m, 2H), 7.71 (ddd, J=1.4, 5.1, 9.1 Hz, 1H), 7.61-7.66 (m, 1H), 7.27-7.35 (m, 1H), 7.15 (td, J=2.6, 6.3, 7.1 Hz, 2H), 6.86-7.11 (m, 3H), 5.50-5.57 (m, 1H), 5.17 (dd, J=8.2, 9.7 Hz, 1H), 4.53 (d, J=9.1 Hz, 1H), 4.26-4.41 (m, 3H), 3.87-3.96 (m, 3H), 3.82 (t, J=6.1 Hz, 1H), 3.00-3.12 (m, 1H), 2.81 (ddd, J=4.5, 9.3, 14.1 Hz, 1H), 2.28 (d, J=14.4 Hz, 1H). LCMS-APCI (POS.) m/z: 657.1 (M+H)+.

Route V

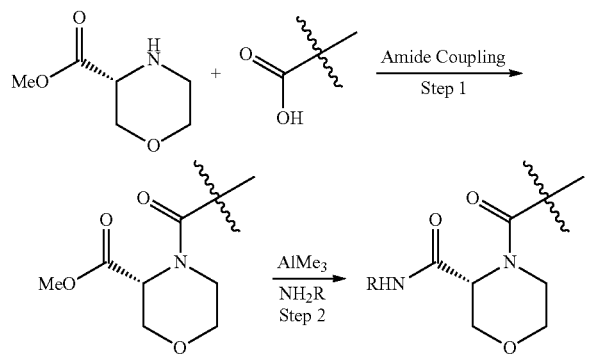

Example Route V: Example 537

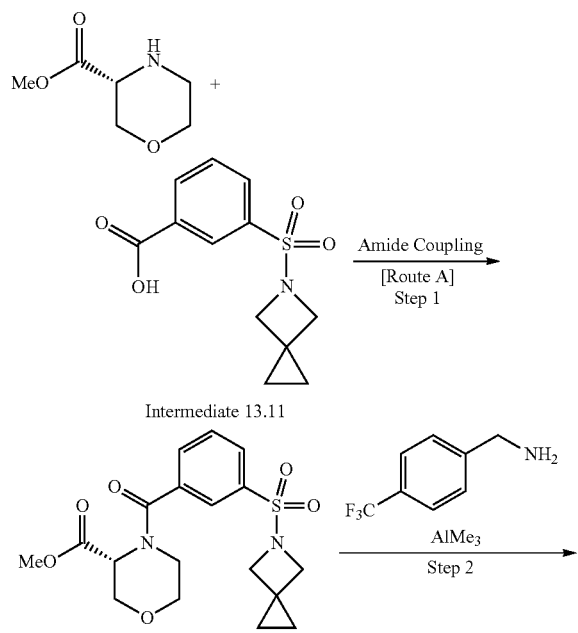

The sequence described for Route A was performed using Intermediate 13.11 and (R)-methyl morpholine-3-carboxylate followed by the subsequent manipulation:

Step 2: A solution of (4-(trifluoromethyl)phenyl)methanamine (Chem-Impex International, Inc.) (0.888 g, 0.507 mmol) in 1,4-dioxane (0.254 mL) was cooled to 0° C. and trimethylaluminum (6.0 mL, 2M in heptanes). The mixture was stirred for thirty minutes while being allowed to warm to rt. To this mixture was added methyl (R)-4-(3-((5-azaspiro[2.3]hexan-5-yl)sulfonyl)benzoyl)morpholine-3-carboxylate (0.100 g, 0.254 mmol) and the mixture was heated at 100° C. for 12 h. The mixture was cooled to 0° C. and quenched with saturated NH₄Cl solution. It was extracted with EtOAc three times, dried over MgSO₄, and concentrated under reduced pressure. The crude material was purified by reverse-phase HPLC (40 min gradient with 10-100% acetonitrile in water (0.1% formic acid modifier), Phenomonex Gemini 5 μm C18 150×21.20 mm column) to give (R)-4-(3-((5-azaspiro[2.3]hexan-5-yl)sulfonyl)benzoyl)-N-(4-(trifluoromethyl)benzyl)morpholine-3-carboxamide (Example 537, 0.048 g, 0.089 mmol). ¹H NMR (400 MHz, methanol-d₄) δ ppm 8.00 (d, J=7.9 Hz, 2H), 7.71-7.90 (m, 2H), 7.63 (d, J=8.1 Hz, 2H), 7.39-7.57 (m, 2H), 5.09 (s, 1H), 4.51 (d, J=39.6 Hz, 4H), 3.88 (s, 6H), 3.64 (d, J=39.5 Hz, 2H), 3.48 (s, 1H), 3.35 (m, 1H), 0.48 (s, 4H). LCMS-APCI (POS.) m/z: 538.1 (M+H)+.

Route W

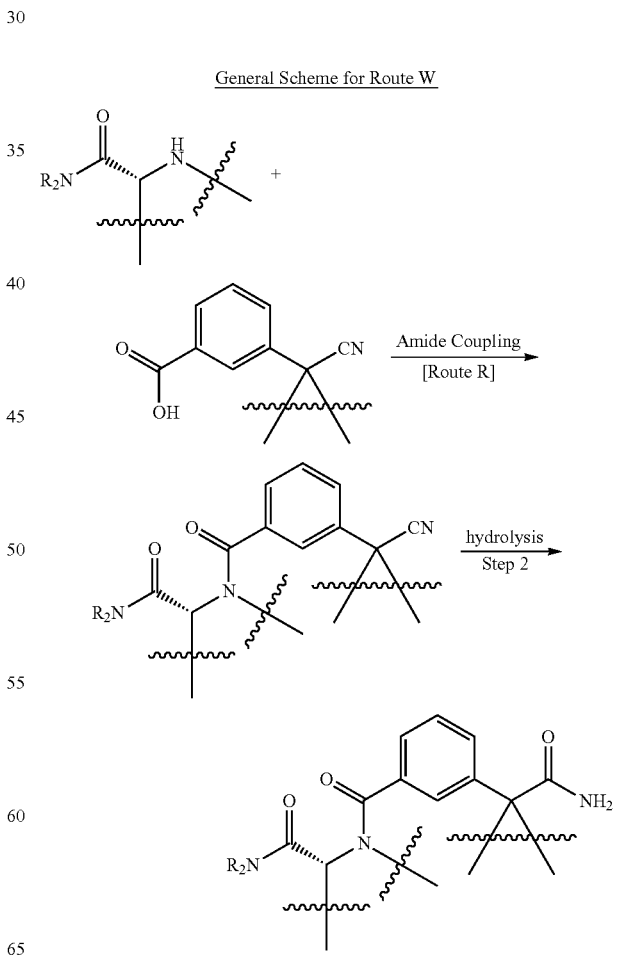

Example Route W: Example 497

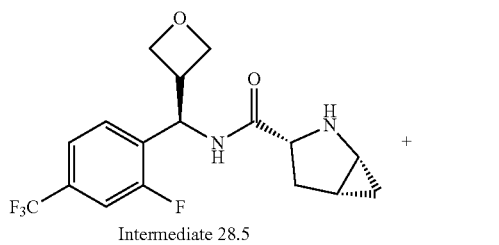

Intermediate 28.5

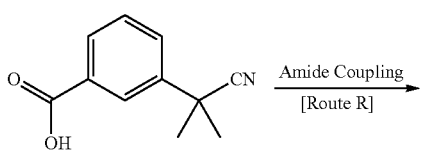

Amide Coupling
[Route R]

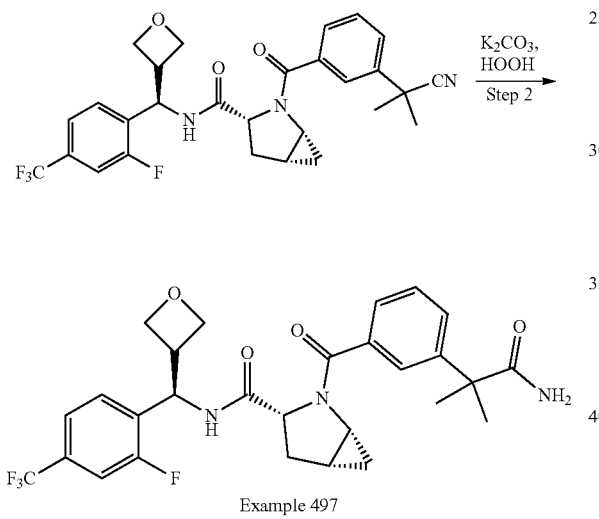

K₂CO₃, HOOH
Step 2

Example 497

The sequence described for Route R was performed using Intermediate 28.5 and 3-(2-cyanopropan-2-yl)benzoic acid followed by the subsequent manipulation:

Step 2: To a solution of (1R,3R,5R)-2-(3-(2-cyanopropan-2-yl)benzoyl)-N—((R)-(2-fluoro-4-(trifluoromethyl)phenyl)(oxetan-3-yl)methyl)-2-azabicyclo[3.1.0]hexane-3-carboxamide (0.035 g, 0.033 mmol) and potassium carbonate (0.028 g, 0.198 mmol) in DMSO (1.0 mL) was added hydrogen peroxide (0.10 mL, 30% in water). The resulting mixture was allowed to stir at rt for 1 h. The mixture was then purified by reverse phase HPLC (40 min gradient with 10-100% acetonitrile in water (0.1% formic acid modifier), Phenomonex Gemini 5 μm C18 150×21.20 mm column) to give (1R,3R,5R)-2-(3-(1-amino-2-methyl-1-oxopropan-2-yl)benzoyl)-N—((R)-(2-fluoro-4-(trifluoromethyl)phenyl)(oxetan-3-yl)methyl)-2-azabicyclo[3.1.0]hexane-3-carboxamide (Example 497, 0.022 g, 0.040 mmol) as a white solid. ¹H NMR (400 MHz, methanol-d₄) δ ppm 7.88 (t, J=1.8 Hz, 1H), 7.65 (dt, J=1.4, 7.5 Hz, 1H), 7.56-7.59 (m, 1H), 7.51-7.56 (m, 2H), 7.44-7.50 (m, 2H), 5.65 (d, J=10.2 Hz, 1H), 4.99 (dd, J=4.2, 11.4 Hz, 1H), 4.83-4.86 (m, 1H), 4.60-4.70 (m, 2H), 4.40 (t, J=0.9, 12.5 Hz, 1H), 3.51-3.61 (m, 1H), 2.57-2.68 (m, 1H), 1.91 (dd, J=4.2, 13.5 Hz, 1H), 1.72-1.80 (m, 1H), 1.60 (d, J=4.1 Hz, 7H), 1.22 (td, J=2.6, 5.3 Hz, 1H), 0.84-0.91 (m, 1H). LCMS-APCI (POS.) m/z: 548.2 (M+H)+.

Route X:

General Scheme for Route X

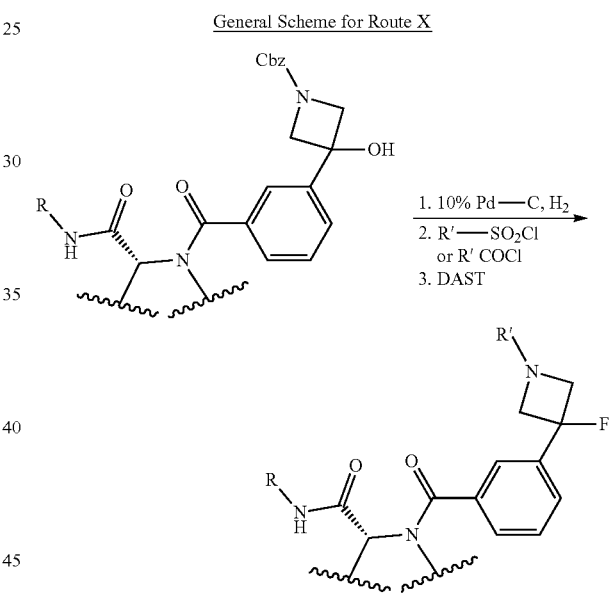

1. 10% Pd—C, H₂
2. R'—SO₂Cl or R' COCl
3. DAST

Example for Route X: Example 422

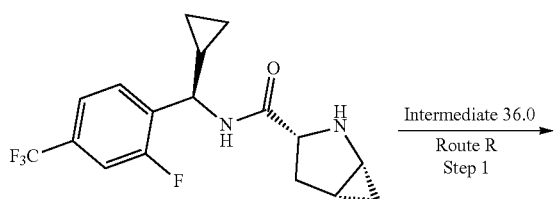

Intermediate 36.0
Route R
Step 1

Intermediate 28.1

-continued

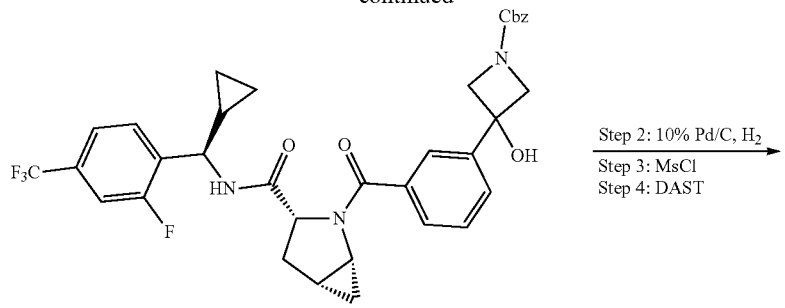

Step 2: 10% Pd/C, H₂
Step 3: MsCl
Step 4: DAST

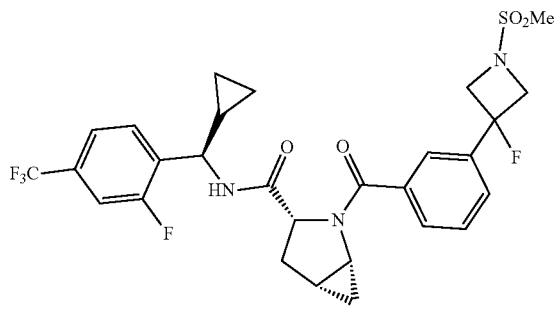

Example 422

Step 1: (1R,3R,5R)—N—((R)-cyclopropyl(2-fluoro-4-(trifluoromethyl)phenyl)methyl)-2-azabicyclo[3.1.0]hexane-3-carboxamide (0.100 g, 0.29 mmol, Intermediate 28.1), 3-(1-((benzyloxy)carbonyl)-3-hydroxyazetidin-3-yl)benzoic acid (0.096 g, 0.29 mmol, Intermediate 36.0), and bromotripyrrolidinophosphonium hexafluorophosphate (0.150 g, 0.32 mmol) in dry DCM (1 mL) was added DIPEA (0.102 mL, 0.58 mmol). The reaction mixture was stirred for 1 h and then concentrated under reduced pressure. Purification by silica gel chromatography (0-100% ethyl acetate in hexanes) to delivered the alcohol as a clear colorless oil (0.140 g, 0.22 mmol). ¹H NMR (400 MHz, dichloromethane-d₂) δ 7.91-7.31 (m, 13H), 5.15 (s, 2H), 5.14-5.09 (m, 1H), 4.66-4.60 (m, 1H), 4.37-4.25 (m, 4H), 3.35-3.27 (m, 1H), 2.57-2.46 (m, 1H), 2.37-2.25 (m, 1H), 1.76-1.67 (m, 1H), 1.24-1.17 (m, 1H), 1.02-0.95 (m, 1H), 0.85-0.77 (m, 1H), 0.61-0.47 (m, 2H), 0.45-0.32 (m, 2H). LCMS-APCI (POS.) m/z: 652.15 (M+H)+.

Step 2: Benzyl 3-(3-((1R,3R,5R)-3-(((R)-cyclopropyl(2-fluoro-4-(trifluoromethyl)phenyl)methyl) carbamoyl)-2-azabicyclo[3.1.0]hexane-2-carbonyl)phenyl)-3-hydroxyazetidine-1-carboxylate (0.140 g, 0.22 mmol) and 10% palladium on carbon (0.100 g, 0.44 mmol) were combined under an atmosphere of nitrogen followed by addition of dry methanol (5 mL). The vessel was then purged with hydrogen and stirred overnight. The reaction mixture was put under a nitrogen atmosphere, Celite was added and then the mixture was filtered through Celite, and concentrated under reduced pressure to give the desired product as a clear colorless oil (0.109 g, 0.21 mmol). ¹H NMR (400 MHz, dichloromethane-d₂) δ 7.87-7.14 (m, 8H), 5.03-4.87 (m, 1H), 4.55-4.41 (m, 1H), 4.01-3.72 (m, 1H), 3.57-3.45 (m, 1H), 3.25-3.15 (m, 1H), 3.09-2.67 (m, 2H), 2.42-2.10 (m, 2H), 1.57 (s, 1H), 1.14-1.01 (m, 1H), 0.93-0.81 (m, 1H), 0.74-0.64 (m, 1H), 0.48-0.32 (m, 2H), 0.31-0.13 (m, 2H). LCMS-APCI (POS.) m/z: 518.20 (M+H)+.

Step 3: (1R,3R,5R)—N—((R)-cyclopropyl(2-fluoro-4-(trifluoromethyl)phenyl)methyl)-2-(3-(3-hydroxyazetidin-3-yl)benzoyl)-2-azabicyclo[3.1.0]hexane-3-carboxamide (0.054 g, 0.10 mmol) in dry DCM (1 mL) was added DIPEA (0.055 mL, 0.32 mmol) followed by methanesulfonyl chloride (0.024 mL, 0.32 mmol). The reaction mixture was stirred for one hour, concentrated under reduced pressure, and purified by silica gel chromatography with a gradient to 0-10% methanol in DCM to give the desired product as a clear colorless oil (0.014 g, 0.023 mmol). LCMS-APCI (POS.) m/z: 596.10 (M+H)+.

Step 4: (1R,3R,5R)—N—((R)-cyclopropyl(2-fluoro-4-(trifluoromethyl)phenyl)methyl)-2-(3-(3-hydroxy-1-(methylsulfonyl)azetidin-3-yl)benzoyl)-2-azabicyclo[3.1.0]hexane-3-carboxamide (0.014 g, 0.024 mmol) in dry DCM (1 mL) at −78° C. was added (diethylamino)sulfur trifluoride (0.006 mL, 0.048 mmol) dropwise. The reaction mixture was stirred at −78° C. for 30 min, concentrated under reduced pressure, and purified by reverse phase HPLC (40 min gradient with 10-100% acetonitrile in water (0.1% formic acid modifier), Phenomonex Gemini 5 μm C18 150×21.20 mm column) to give the desired product as a clear colorless oil (Example 422, 0.001 g, 0.002 mmol). ¹H NMR (400 MHz, methanol-d₄) δ 8.86-8.80 (m, 1H), 8.27 (s, 1H), 8.02 (s, 1H), 7.86-7.81 (m, 1H), 7.77-7.71 (m, 1H), 7.70-7.58 (m, 2H), 7.55-7.51 (m, 1H), 7.49-7.43 (m, 1H), 4.52-4.30 (m, 6H), 3.12-3.06 (m, 3H), 2.73- 2.64 (m, 1H), 1.97-1.91 (m, 1H), 1.81-1.75 (m, 1H), 1.35-1.24 (m, 2H), 1.19-1.15 (m, 1H), 0.89-0.82 (m, 1H), 0.73-0.64 (m, 1H), 0.60-0.41 (m, 3H). LCMS-APCI (POS.) m/z: 598.20 (M+H)+.

Example for Route Y: Synthesis of (1R,3R,5R)—N—((S)-(4-Chloro-2,5-difluorophenyl)(3-fluorooxetan-3-yl)methyl)-2-(3-(methylsulfonyl)benzoyl)-2-azabicyclo[3.1.0]hexane-3-carboxamide (Example 812)

Example 812

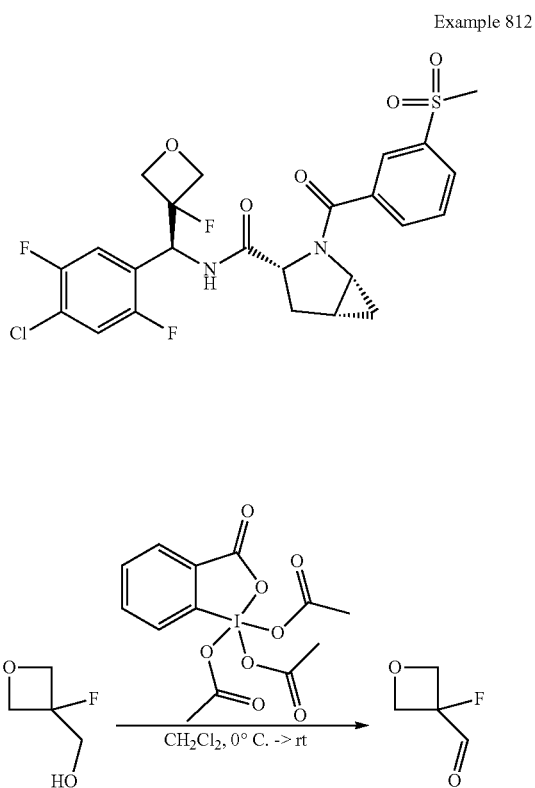

Synthesis of 3-Fluorooxetane-3-carbaldehyde (3-Fluorooxetan-3-yl)methanol (1.0 g, 9.43 mmol) was dissolved in dichloromethane (15 mL) and cooled to 0° C. with an ice bath. To the solution was added Dess-Martin periodinane (5.20 g, 12.25 mmol), portion wise. The resulting mixture was stirred overnight, during which time it was allowed to warm to room temperature. Observed by TLC, using 70% ethyl acetate/hexanes and visualized with PMA stain, was disappearance of starting material, a new non-polar spot with Rf~0.75, and DMP by-products. The mixture was filtered through celite and the filtrate was concentrated to ~¾ original volume (~5 mL of dichloromethane) was removed under reduced pressure using rotary evaporator with water bath temperature 5-10° C.). The resulting mixture was carried forward without further characterization or attempts to isolate. For the purpose of reagent equivalents added in the following step, a quantitative yield for this step was used.

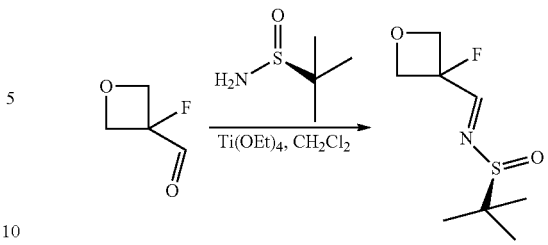

Synthesis of (S,E)-N-((3-Fluorooxetan-3-yl)methylene)-2-methylpropane-2-sulfinamide The reaction mixture from Step 1 was cooled to 0° C. with an ice bath. To the cool solution of 3-Fluorooxetane-3-carbaldehyde (9.91 g, 95.2 mmol) in dichloromethane (10 mL) was added portionwise (S)-(−)-2-methyl-2-propanesulfinamide (11.54 g, 95.2 mmol), followed by titanium tetraethoxide (19.74 mL, 95.2 mmol). The ice bath was removed and the resulting mixture was stirred at room temperature for 18 hours. It was carefully quenched with 250 mL saturated aqueous sodium bicarbonate and diluted with additional dichloromethane (300 mL). The resulting biphasic suspension was stirred at room temperature for 30 minutes and then filtered through celite. The filtered solid was washed with dichloromethane (75 mL). The organic phase (filtrate) was washed with saturated aqueous sodium chloride, dried over sodium sulfate and concentrated to a colorless, viscous oil. This oil was purified with silica gel using a gradient to 20% ethyl acetate/hexanes, providing (S,E)-N-((3-fluorooxetan-3-yl)methylene)-2-methylpropane-2-sulfinamide (5.70 g, 27.5 mmol) as a colorless oil. Care was taken to not leave the desired product under high vacuum due to potential evaporation of the desired product. 1H NMR (DMSO-d6) δ: 8.13 (d, J=9.2 Hz, 1H), 4.95-4.77 (m, 4H), 1.17 (s, 9H).

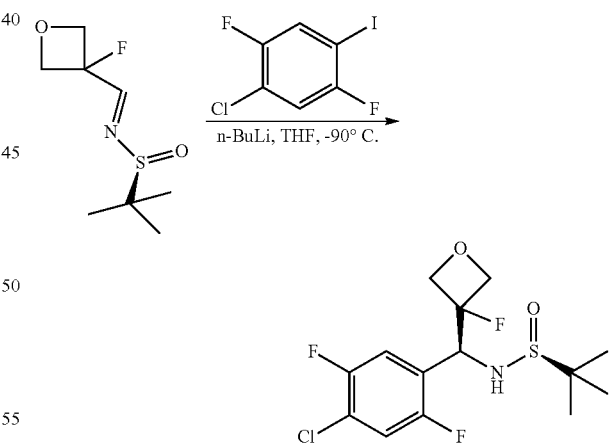

Synthesis of (S)—N—((S)-(4-Chloro-2,5-difluorophenyl)(3-fluorooxetan-3-yl)methyl)-2-methylpropane-2-sulfinamide To an oven dried, 100 mL, round bottom flask, under a nitrogen atmosphere, was added 1-chloro-2,5-difluoro-4-iodobenzene (2.41 g, 8.77 mmol) in anhydrous THF (35 mL). The resulting solution was cooled to −100° C. with an ether/liquid nitrogen bath, and then n-butyllithium (1.6M in hexanes, 5.48 mL, 8.77 mmol) was added dropwise, keeping the internal temperature between −90 and −100° C. The resulting yellow mixture was stirred between −90 and −100° C. for 30 minutes, and then (S,E)-N-((3-fluorooxetan-3-yl)methylene)-2-methylpropane-2-sulfinamide (2.0 g, 9.65 mmol) in THF (5 mL) was added dropwise via syringe, keeping the internal temperature between −90 and −100° C. The resulting mixture was stirred between −90 and −100° C. for 30 minutes and then quenched at the same temperature by dropwise addition of saturated ammonium chloride (25 mL). The mixture was diluted with water (50 mL) and ethyl acetate (50 mL). The layers were shaken and separated and the organic phase was washed with saturated aqueous sodium chloride, dried over sodium sulfate and concentrated to a viscous nearly colorless oil which was purified with silica gel using a gradient to 50% ethyl acetate/hexanes providing (S)—N—((S)-(4-chloro-2,5-difluorophenyl)(3-fluorooxetan-3-yl)methyl)-2-methylpropane-2-sulfinamide (1.64 g, 4.6 mmol) the desired single diastereomer, as a white foam. 1H NMR (400 MHz, Methanol-d4) δ 7.58-7.37 (m, 2H), 5.28 (d, J=26.1 Hz, 1H), 4.99-4.89 (m, 1H), 4.85-4.76 (m, 1H), 4.69-4.50 (m, 2H), 1.21 (s, 9H). LCMS-ESI (POS.) m/z: 356.10 (M+H)+.

sure, providing the desired product, (S)-(4-chloro-2,5-difluorophenyl)(3-fluorooxetan-3-yl)methanamine (1.08 g, 3.65 mmol) as a viscous, nearly colorless oil which solidified to a white solid while drying under high vacuum overnight. Purity was estimated to be 85%, and the product was used in the following step without additional purification. 1H NMR (Methanol-d4) δ: 7.51 (ddd, J=9.8, 6.3, 1.4 Hz, 1H), 7.38 (dd, J=9.3, 6.2 Hz, 1H), 4.87-4.75 (m, 1H), 4.76-4.66 (m, 2H), 4.65-4.53 (m, 2H).

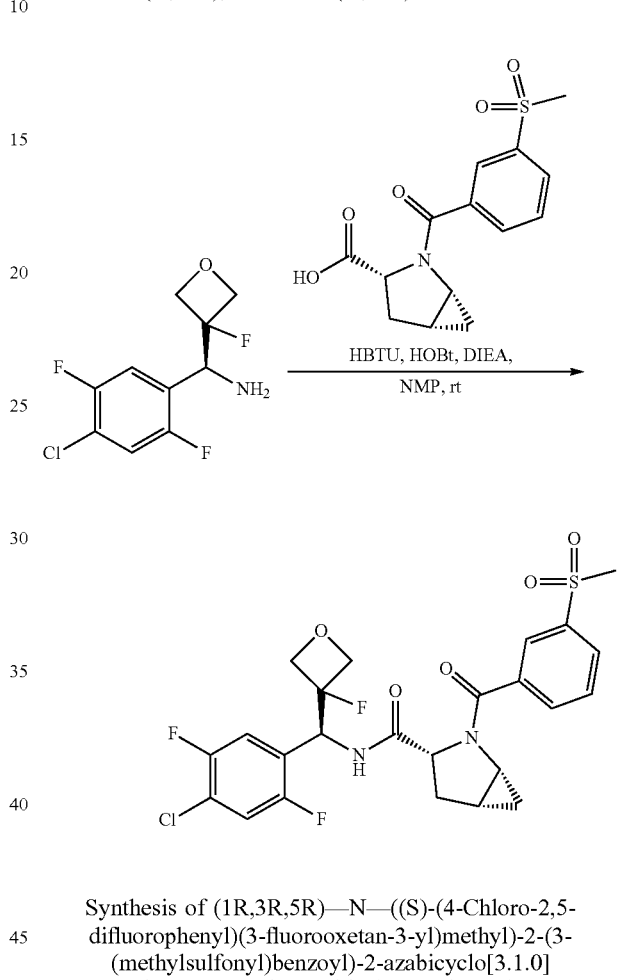

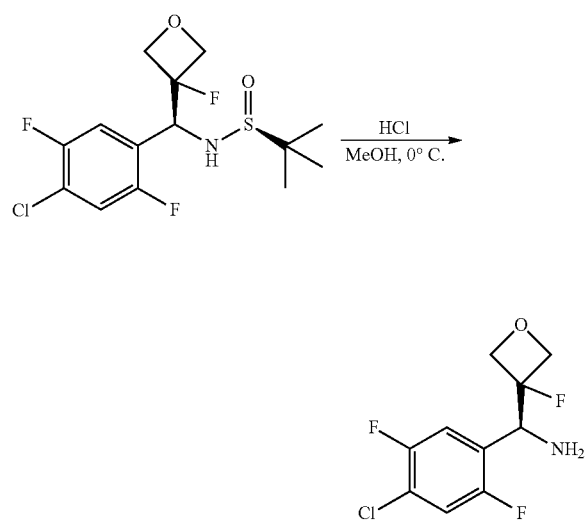

Synthesis of (S)-(4-Chloro-2,5-difluorophenyl)(3-fluorooxetan-3-yl)methanamine (S)—N—((S)-(4-Chloro-2,5-difluorophenyl)(3-fluorooxetan-3-yl)methyl)-2-methylpropane-2-sulfinamide (1.63 g, 4.57 mmol) was dissolved in methanol (15 mL) and cooled to 0° C. with an ice bath. Hydrogen chloride (4M in 1,4-dioxane, 1.5 mL, 5.94 mmol) was added dropwise using a syringe, and the resulting mixture was stirred at 0° C. for 5 minutes. After which time, the ice bath was removed. The reaction was stirred at room temperature for 45 minutes and the reaction progress was monitored with LC/MS. The reaction was quenched with trimethylamine (6.33 mL, 45.7 mmol) and the resulting mixture was concentrated in vacuo, providing a white solid. This solid was partitioned between saturated aqueous sodium bicarbonate (100 mL) and dichloromethane (100 mL). The layers were separated and the aqueous phase was extracted with additional dichloromethane (50 mL). The organic extracts were combined, dried over sodium sulfate and concentrated under reduced pres- Synthesis of (1R,3R,5R)—N—((S)-(4-Chloro-2,5-difluorophenyl)(3-fluorooxetan-3-yl)methyl)-2-(3-(methylsulfonyl)benzoyl)-2-azabicyclo[3.1.0]hexane-3-carboxamide (Example 812)

To a room temperature solution of (1R,3R,5R)-2-(3-(methylsulfonyl)benzoyl)-2-azabicyclo[3.1.0]hexane-3-carboxylic acid (92 mg, 0.30 mmol), (S)-(4-chloro-2,5-difluorophenyl)(3-fluorooxetan-3-yl)methanamine (78 mg, 0.25 mmol), hydroxybenzotriazole (50 mg, 0.37 mmol) and O-(benzotriazol-1-yl)-N,N,N',N'-tetramethyluronium hexafluorophosphate (141 mg, 0.37 mmol) in N-methyl-2-pyrrolidone (3.0 mL) was added N,N-diisopropylethylamine (0.13 mL, 0.74 mmol). The resulting mixture was stirred at room temperature for 20 minutes. It was diluted with ethyl acetate (40 mL) and washed once with saturated aqueous sodium bicarbonate (40 mL). The organic phase was dried over sodium sulfate and concentrated to an oil which was purified with reverse phase HPLC using 10-100% acetonitrile/water over 40 minutes, with formic acid present (phenomenex gemini C18 5 micron column), providing (1R,3R,5R)—N—((S)-(4-chloro-2,5-difluorophenyl)(3-fluorooxetan-3-yl)methyl)-2-(3-(methylsulfonyl)benzoyl)-2-azabicyclo[3.1.0]hexane-3-carboxamide (105 mg, 0.19 mmol) as a white amorphous solid. 1H NMR (Methanol-d4) δ: 8.39 (s, 1H), 8.16-8.10 (m, 2H), 7.79 (t, J=7.8 Hz, 1H), 7.46 (dd, J=9.3, 6.1 Hz, 1H), 7.39 (dd, J=9.7, 6.3 Hz, 1H), 5.98 (d, J=28.0 Hz, 1H), 5.05 (dd, J=11.4, 4.3 Hz, 1H), 4.82-4.74 (m, 2H), 4.65-4.55 (m, 2H), 3.33 (s, 1H), 3.19 (s, 3H), 2.77-2.63 (m, 1H), 1.95-1.86 (m, 1H), 1.86-1.77 (m, 1H), 1.34-1.27 (m, 1H), 0.97-0.88 (m, 1H) LCMS-ESI (POS.) m/z: 543.10 (M+H)+.

Example for Route Z: Preparation of (1R,3R,5R)—N—((R)-cyclopropyl(2,5-difluoro-4-(trifluoromethyl)phenyl)methyl)-2-(2-(hydroxymethyl)-5-(methylsulfonyl)benzoyl)-2-azabicyclo[3.1.0]hexane-3-carboxamide (Example 814)

Example 814

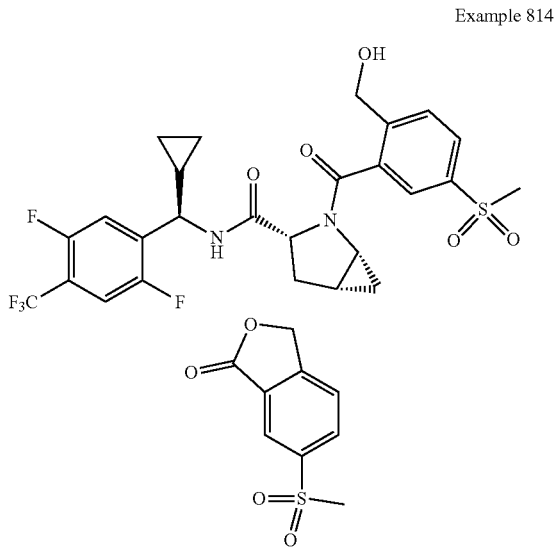

Synthesis of 6-(methylsulfonyl)isobenzofuran-1(3H)-one 3-oxo-1,3-dihydroisobenzofuran-5-sulfonyl chloride (3.5 g, 15.05 mmol), sodium bicarbonate (2.53 g, 30.1 mmol) and sodium sulfite (3.79 g, 30.1 mmol) were added to a flask with a stir bar. The flask was placed in a 50 C hot bath and water (35 mL) was added. The reaction mixture was concentrated after two hours at 50 C. The concentrated reaction mixture was allowed to dry on the high-vac overnight. The material was then redissolved in DMF (35 mL); the sides of the flask were scraped with a spatula to ensure all solids were suspended in solution. Methyl iodide (4.7 mL, 75 mmol) was then added to the reaction mixture. The reaction was allowed to stir at room temperature for three hours, at which point it was taken up in ethyl acetate (30 mL) and washed with sodium bicarbonate (30 mL). The mixture was separated and the aqueous layer washed once more with ethyl acetate (30 mL). The organics were dried over magnesium sulfate, filtered, and the filtrate concentrated. The resulting material was triturated with DCM to afford the pure product as a white solid (2.25 g). $^1$H NMR (DMSO-d$_6$) δ: 8.39-8.26 (m, 2H), 7.98 (dd, J=8.0, 0.9 Hz, 1H), 5.56 (s, 2H), 3.34 (s, 3H).

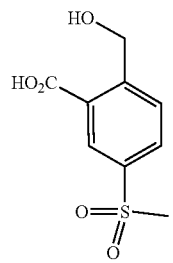

Synthesis of 2-(hydroxymethyl)-5-(methylsulfonyl)benzoic Acid 6-(methylsulfonyl)isobenzofuran-1(3H)-one (2.25 g, 10.6 mmol) was dissolved in methanol (9 mL) and aqueous sodium hydroxide (0.952 mg of KOH in 27 mL H$_2$O) was added. The solution was refluxed at 100 C. After three hours of refluxing, the reaction mixture was cooled to room temperature and concentrated in-vacuo. The oil was then redissolved in ethyl acetate and water was added. The solution was adjusted to pH 2 with 3N HCl. At this time, the layers were separated and the aqueous layer washed with ethyl acetate a total of three times. The combined organics were dried over magnesium sulfate, filtered, and concentrated to give (2.441 g) of pure fine white powder that was the desired product. LCMS-ESI (NEG.) m/z: 229.10 (M−H).

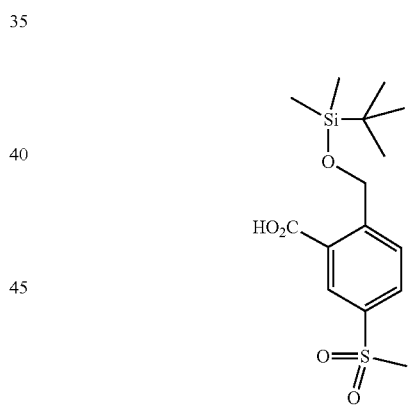

Synthesis of 2-(((tert-butyldimethylsilyl)oxy)methyl)-5-(methylsulfonyl)benzoic acid. To a solution of TBSCl (1.505 mL, 8.69 mmol) in toluene (5 mL) and dichloromethane (5 mL) in a 40 mL vial were added imidazole (296 mg, 4.34 mmol) followed by 2-(hydroxymethyl)-5-(methylsulfonyl)benzoic acid (500 mg, 2.172 mmol). The vial was sealed and stirred at 37 C overnight. In the morning, the solution was now a suspension of white solid in clear liquid. The LCMS shows that the reaction had gone about ⅔ to completion. The material was worked up with dichloromethane and 1N HCl. The combined organics were dried over magnesium sulfate, filtered, and the filtrate concentrated. The material was loaded onto a 40 g silica column and purified with a gradient to 85% EA in hexanes to provide the product (0.47 g) as a white solid set-up. R$_f$=0.15 (SiO$_2$, 75% EtOAc/hexanes). LCMS-ESI (NEG.) m/z: 343.10 (M−H).

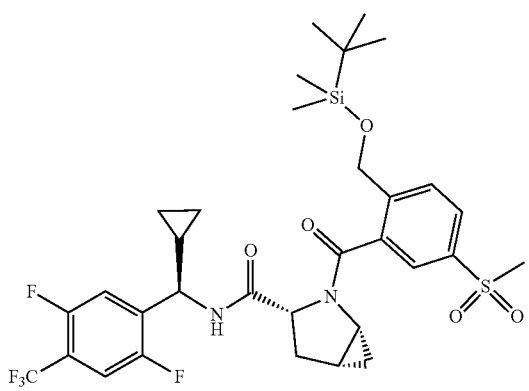 [SMILES: CC(C)(C)[Si](C)(C)OCc1ccc(S(C)(=O)=O)cc1C(=O)N1[C@@H](C(=O)N[C@@H](c2cc(F)c(C(F)(F)F)cc2F)C2CC2)C[C@H]2C[C@H]21]

Synthesis of (1R,3R,5R)-2-(2-(((tert-butyldimethyl-silyl)oxy)methyl)-5-(methylsulfonyl)benzoyl)-N—((R)-cyclopropyl(2,5-difluoro-4-(trifluoromethyl)phenyl)methyl)-2-azabicyclo[3.1.0]hexane-3-carboxamide 2-(((tert-butyldimethylsilyl)oxy)methyl)-5-(methylsulfonyl)benzoic acid (35 mg, 0.102 mmol) was dissolved in DMF (0.2 mL) and DIEA (0.035 mL, 0.203 mmol) and HBTU (43 mg, 0.112 mmol) was added. After one minute of stirring, (1R,3R,5R)—N—((R)-cyclopropyl(2,5-difluoro-4-(trifluoromethyl)phenyl)methyl)-2-azabicyclo[3.1.0]hexane-3-carboxamide (40.3 mg, 0.112 mmol) was added to the reaction mixture. After five minutes of stirring at room temperature, the desired product was observed by LCMS. The reaction mixture was filtered through a 0.45 u silica plug and purified by reverse phase HPLC using 10-100% acetonitrile/water over 40 minutes (phenomenex gemini c-18 5-micron column), providing the product (70 mg). LCMS-ESI (pos.) m/z: 687.3 (M+H)+.

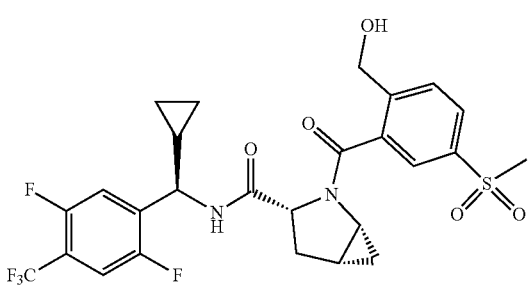 [SMILES: CS(=O)(=O)c1ccc(CO)c(C(=O)N2[C@@H](C(=O)N[C@@H](c3cc(F)c(C(F)(F)F)cc3F)C3CC3)C[C@H]3C[C@H]32)c1]

Synthesis of (1R,3R,5R)—N—((R)-cyclopropyl(2,5-difluoro-4-(trifluoromethyl)phenyl)methyl)-2-(2-(hydroxymethyl)-5-(methylsulfonyl)benzoyl)-2-azabicyclo[3.1.0]hexane-3-carboxamide, Example 814

(1R,3R,5R)-2-(2-(((tert-butyldimethylsilyl)oxy)methyl)-5-(methylsulfonyl)benzoyl)-N—((R)-cyclopropyl(2,5-difluoro-4-(trifluoromethyl)phenyl)methyl)-2-azabicyclo[3.1.0]hexane-3-carboxamide (70 mg, 0.102 mmol) was dissolved in THF (0.5 mL) and TBAF (355 mg, 1.02 mmol) was added. The reaction mixture was stirred at room temperature for one hour. The reaction mixture was then taken up in aqueous sat. ammonium chloride and extracted with dichloromethane twice. The combined organics were concentrated and the resulting oil redissolved in DMF, filtered through a 0.45 u silica plug and purified by reverse phase HPLC using 10-100% acetonitrile/water over 40 minutes (phenomenex gemini c-18 5-micron column), providing the product (23 mg). LCMS-ESI (pos.) m/z: 571.2 (M−H)+. 1H NMR (DMSO-d6) δ: 8.76 (d, J=7.4 Hz, 1H), 8.00 (dd, J=8.1, 2.0 Hz, 1H), 7.88 (d, J=1.9 Hz, 1H), 7.86-7.74 (m, 2H), 7.59 (dd, J=11.1, 5.5 Hz, 1H), 5.64 (t, J=5.7 Hz, 1H), 4.89 (dd, J=11.4, 3.2 Hz, 1H), 4.71 (qd, J=15.1, 5.8 Hz, 2H), 4.54 (t, J=8.0 Hz, 1H), 3.25 (s, 3H), 3.00 (td, J=6.2, 2.5 Hz, 1H), 1.80 (dd, J=13.5, 3.3 Hz, 1H), 1.67-1.54 (m, 1H), 1.21 (dq, J=8.2, 4.1, 3.5 Hz, 1H), 0.97 (td, J=5.2, 2.7 Hz, 1H), 0.59 (t, J=8.5 Hz, 2H), 0.55-0.45 (m, 1H), 0.40 (d, J=4.8 Hz, 2H).

Example for Route AA: Synthesis of (1R,3R,5R)—N—((R)-(2,5-Difluoro-4-(trifluoromethyl)phenyl)(oxetan-3-yl)methyl)-2-(5-methylthiophene-2-carbonyl)-2-azabicyclo[3.1.0]hexane-3-carboxamide (Example 816)

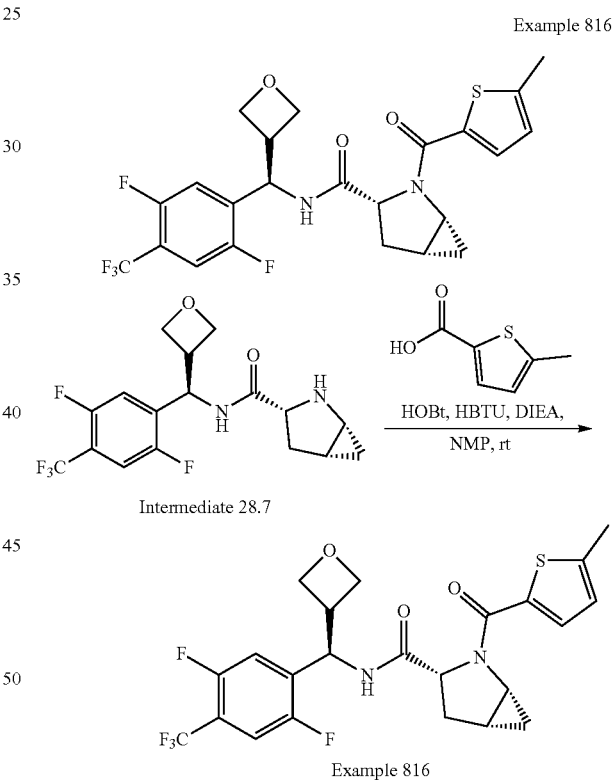

To a room temperature solution of (1R,3R,5R)—N—((R)-(2,5-difluoro-4-(trifluoromethyl)phenyl)(oxetan-3-yl)methyl)-2-azabicyclo[3.1.0]hexane-3-carboxamide (34 mg, 0.09 mmol), 5-methylthiophene-2-carboxylic acid (19 mg, 0.136 mmol), hydroxybenzotriazole (37 mg, 0.27 mmol) and O-(benzotriazol-1-yl)-N,N,N',N'-tetramethyluronium hexafluorophosphate (103 mg, 0.27 mmol) in N-methyl-2-pyrrolidone (1.0 mL) was added N,N-diisopropylethylamine (0.8 mL, 0.45 mmol). The resulting mixture was stirred at room temperature for 20 minutes. It was diluted with ethyl acetate (15 mL) and washed once with saturated aqueous sodium bicarbonate (15 mL). The organic phase was dried over sodium sulfate and concentrated to an oil which was purified with reverse phase HPLC using 10-100% acetonitrile/water over 40 minutes, without formic acid present (phenomenex gemini C18 5 micron column), providing (1R,3R,5R)—N—((R)-(2,5-difluoro-4-(trifluoromethyl)phenyl)(oxetan-3-yl)methyl)-2-(5-methylthiophene-2-carbonyl)-2-azabicyclo[3.1.0]hexane-3-carboxamide (27 mg, 0.054 mmol) as an amorphous foam. 1H NMR (Methanol-d4) δ: 7.72 (d, J=3.8 Hz, 1H), 7.54 (dd, J=9.5, 5.7 Hz, 1H), 7.36 (dd, J=10.6, 5.5 Hz, 1H), 6.91-6.84 (m, 1H), 5.57 (d, J=10.3 Hz, 1H), 4.96 (dd, J=11.2, 4.6 Hz, 1H), 4.85 (t, J=7.0 Hz, 1H), 4.70-4.59 (m, 2H), 4.39 (t, J=6.2 Hz, 1H), 3.80-3.69 (m, 1H), 3.58-3.42 (m, 1H), 2.73-2.57 (m, 1H), 2.54 (s, 3H), 1.93-1.74 (m, 2H), 1.26-1.16 (m, 1H), 1.05-0.93 (m, 1H). LCMS-ESI (POS.) m/z: 501.10 (M+H)+.

The compounds set forth in the following table were synthesized following the procedure described for Example 816 using known starting material replacements as described.

TABLE 13

| A-B Intermediate | C-Ring | Structure, Name and Data |
|---|---|---|
| 28.7 | 5-methylthiophene-2-carboxylic acid | Example 816<br>(1R,3R,5R)-N-((R)-(2,5-difluoro-4-(trifluoromethyl)phenyl)(oxetan-3-yl)methyl)-2-(5-methylthiophene-2-carbonyl)-2-azabicyclo[3.1.0]hexane-3-carboxamide<br>LCMS-ESI (POS.) m/z: 501.1 (M + H)+ |
| 28.1 | 2-amino-5-(methylsulfonyl)-benzoic acid | Example 813<br>(1R,3R,5R)-2-(2-amino-5-(methylsulfonyl)benzoyl)-N-((R)-cyclopropyl(2-fluoro-4-(trifluoromethyl)phenyl)methyl)-2-azabicyclo[3.1.0]hexane-3-carboxamide<br>LCMS-ESI (POS.) m/z: 540.2 (M + H)+ |
| 28.7 | 1,4-dimethyl-1H-pyrazole-5-carboxylic acid | Example 815<br>(1R,3R,5R)-N-((R)-(2,5-difluoro-4-(trifluoromethyl)phenyl)(oxetan-3-yl)methyl)-2-(2-methoxyisonicotinoyl)-2-azabicyclo[3.1.0]hexane-3-carboxamide<br>LCMS-APCI (POS.) m/z: 512.2 (M + H)+ |

TABLE 13-continued

| A-B Intermediate | C-Ring | Structure, Name and Data |
|---|---|---|
| 28.7 | 1,4-dimethyl-1H-pyrazole-5-carboxylic acid | 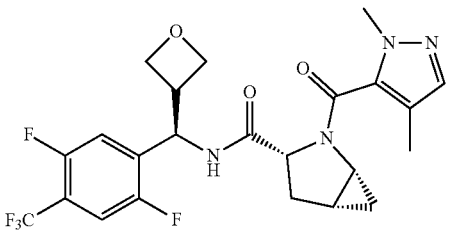 [SMILES: Cc1cnn(C)c1C(=O)N1[C@@H](C(=O)N[C@@H](c2cc(F)c(C(F)(F)F)cc2F)C2COC2)C[C@H]2C[C@H]21]<br>Example 818<br>(1R,3R,5R)-N-((R)-(2,5-difluoro-4-(trifluoromethyl)phenyl)(oxetan-3-yl)methyl)-2-(1,4-dimethyl-1H-pyrazole-5-carbonyl)-2-azabicyclo[3.1.0]hexane-3-carboxamide<br>LCMS-APCI (POS.) m/z: 499.2 (M + H)+ |
| 28.7 | 5-methyl-1H-indazole-7-carboxylic acid | 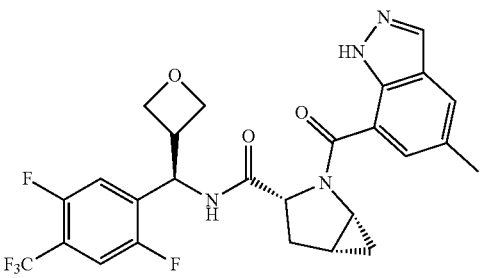 [SMILES: Cc1cc(C(=O)N2[C@@H](C(=O)N[C@@H](c3cc(F)c(C(F)(F)F)cc3F)C3COC3)C[C@H]3C[C@H]32)c2[nH]ncc2c1]<br>Example 820<br>(1R,3R,5R)-N-((R)-(2,5-difluoro-4-(trifluoromethyl)phenyl)(oxetan-3-yl)methyl)-2-(5-methyl-1H-indazole-7-carbonyl)-2-azabicyclo[3.1.0]hexane-3-carboxamide<br>LCMS-APCI (POS.) m/z: 535.2 (M + H)+ |
| 28.X | 5-chloro-1H-indazole-7-carboxylic acid | 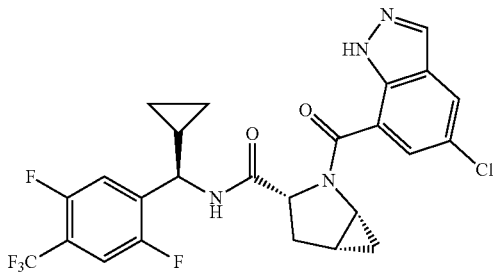 [SMILES: O=C(N[C@@H](c1cc(F)c(C(F)(F)F)cc1F)C1CC1)[C@H]1C[C@H]2C[C@H]2N1C(=O)c1cc(Cl)cc2cn[nH]c12]<br>Example 821<br>(1R,3R,5R)-2-(5-chloro-1H-indazole-7-carbonyl)-N-((R)-cyclopropyl(2,5-difluoro-4-(trifluoromethyl)phenyl)methyl)-2-azabicyclo[3.1.0]hexane-3-carboxamide<br>LCMS-APCI (POS.) m/z: 539.2 (M + H)+ |
| 28.7 | 5-(trifluoromethyl)-isoxazole-3-carboxylic acid | 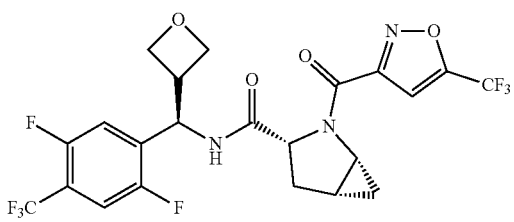 [SMILES: O=C(N[C@@H](c1cc(F)c(C(F)(F)F)cc1F)C1COC1)[C@H]1C[C@H]2C[C@H]2N1C(=O)c1cc(C(F)(F)F)on1]<br>Example 823<br>(1R,3R,5R)-N-((R)-(2,5-difluoro-4-(trifluoromethyl)phenyl)(oxetan-3-yl)methyl)-2-(5-(trifluoromethyl)isoxazole-3-carbonyl)-2-azabicyclo[3.1.0]hexane-3-carboxamide<br>LCMS-APCI (POS.) m/z: 540.2 (M + H)+ |

TABLE 13-continued

| A-B Intermediate | C-Ring | Structure, Name and Data |
|---|---|---|
| 28.7 | 3,4-dimethyl-isoxazole-5-carboxylic acid | 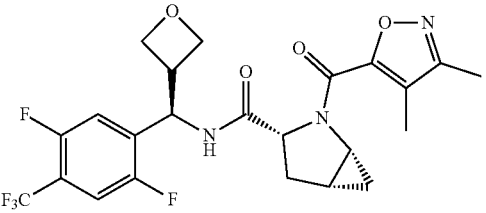 [SMILES: Cc1noc(C(=O)N2[C@@H](C(=O)N[C@@H](c3cc(F)c(C(F)(F)F)cc3F)C3COC3)C[C@H]3C[C@H]32)c1C]
Example 824
(1R,3R,5R)-N-((R)-(2,5-difluoro-4-(trifluoromethyl)phenyl)(oxetan-3-yl)methyl)-2-(3,4-dimethylisoxazole-5-carbonyl)-2-azabicyclo[3.1.0]hexane-3-carboxamide
LCMS-APCI (POS.) m/z: 500.2 (M + H)+ |
| 28.7 | 3,5-dimethyl-isoxazole-4-carboxylic acid | 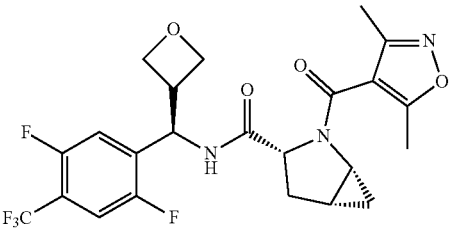
Example 825
(1R,3R,5R)-N-((R)-(2,5-difluoro-4-(trifluoromethyl)phenyl)(oxetan-3-yl)methyl)-2-(3,5-dimethylisoxazole-4-carbonyl)-2-azabicyclo[3.1.0]hexane-3-carboxamide
LCMS-APCI (POS.) m/z: 500.2 (M + H)+ |
| 28.7 | 3-(trifluoro-methyl)isoxazole-5-carboxylic acid | 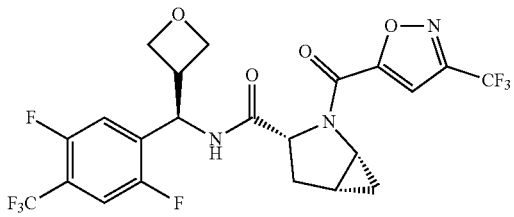
Example 826
(1R,3R,5R)-N-((R)-(2,5-difluoro-4-(trifluoromethyl)phenyl)(oxetan-3-Amethyl)-2-(3-(trifluoromethyl)isoxazole-5-carbonyl)-2-azabicyclo[3.1.0]hexane-3-carboxamide
LCMS-APCI (POS.) m/z: 540.1 (M + H)+ |

Example of Route AB: Preparation of (1R,3R,5R)—N—((S)-1-(4-chloro-2,5-difluorophenyl)-2,2-difluoroethyl)-2-(5-(methylsulfonyl)nicotinoyl)-2-azabicyclo[3.1.0]hexane-3-carboxamide (Example 817)

Example 817

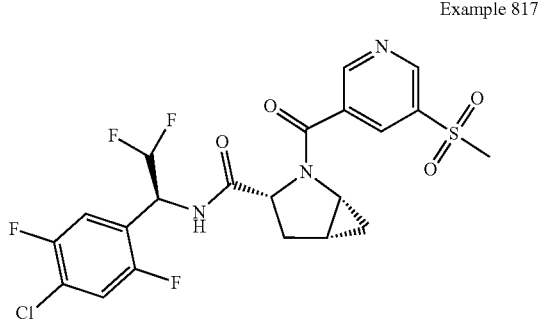

Synthesis of (R)—N—((S)-1-(4-chloro-2,5-difluorophenyl)-2,2-difluoroethyl)-2-methylpropane-2-sulfinamide KO'Bu (8 mL, 8 mmol, 1 M in THF) was added to a solution of (R,E)-N-(4-chloro-2,5-difluorobenzylidene)-2-methylpropane-2-sulfinamide (0.7 g, 2.5 mmol) and difluoromethyl trimethylsilane (0.96 g, 7.5 mmol) in 14 mL in THF at –78 C. The mixture was stirred for 5 minutes at –78 C and monitored by LCMS. Product peak observed. The reaction was subsequently quenched at this temperature with satd aq ammonium chloride. The solution was partitioned between saturated aq. ammonium chloride (20 mL) and EtOAc (20 mL). The layers were separated and the aqueous phase was extracted with additional EtOAc (20 mL). The organic layers were combined, dried over sodium sulfate, filtered and concentrated under vacuum, providing the desired crude as a viscous oil. The crude was purified by silica gel column chromatography (0% to 40% EtOAc/hexanes) to provide the product as a yellow viscous oil (5:1 ratio of diastereomers) (126 mg). LCMS-ESI (pos.) m/z: 332.1 (M+H)+.

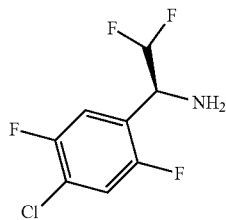 [SMILES: N[C@@H](c1cc(F)c(Cl)cc1F)C(F)F]

Preparation of (S)-1-(4-chloro-2,5-difluorophenyl)-2,2-difluoroethan-1-amine To a solution of (R)—N—((S)-1-(4-chloro-2,5-difluorophenyl)-2,2-difluoroethyl)-2-methylpropane-2-sulfinamide (0.112 g, 0.34 mmol) in methanol (2 mL) at 0° C. in an ice bath under argon was added 4M HCl in dioxane (0.2 mL, 0.81 mmol) dropwise and stirred for 5 minutes. Then the reaction mixture was stirred at 0 C for 30 mins and monitored by LCMS and TLC analysis. The reaction was deemed to be complete after 30 minutes. After the reaction was completed, the reaction was quenched by adding triethylamine (0.5 mL). The resulting mixture was concentrated under reduced pressure, and the remaining white solid was partitioned between saturated sodium bicarbonate (5 mL) and DCM (5 mL). The layers were separated and the aqueous phase was extracted with additional DCM (5 mL). The organic layers were combined, dried over sodium sulfate, filtered and concentrated under vacuum, providing the desired product as a viscous oil (5:1 ratio of diastereomers) (55 mg). LCMS-ESI (pos.) m/z: 228.0 (M+H)+.

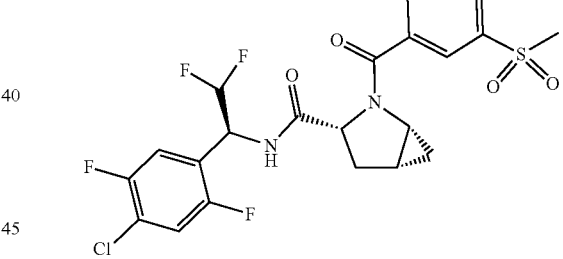

Synthesis of (1R,3R,5R)—N—((S)-1-(4-chloro-2,5-difluorophenyl)-2,2-difluoroethyl)-2-(5-(methylsulfonyl)nicotinoyl)-2-azabicyclo[3.1.0]hexane-3-carboxamide, Example 817

A 8 mL vial was charged with (1R,3R,5R)-2-(5-(methylsulfonyl)nicotinoyl)-2-azabicyclo[3.1.0]hexane-3-carboxylic acid (61 mg, 0.2 mmol), HBTU (0.112 g, 0.3 mmol), (S)-1-(4-chloro-2,5-difluorophenyl)-2,2-difluoroethan-1-amine (45 mg, 0.2 mmol, 5:1 ratio of diastereomer) and dissolved in DMF (1 ml). Triethyamine (0.276 mL, 1.98 mmol) was subsequently added DROPWISE and stirred for 20 mins and analyzed by LCMS. The reaction was filtered and purified by reverse phase HPLC using 10-100% acetonitrile/water over 40 minutes (phenomenex gemini c-18 5-micron column), providing the desired diasteromers.

Major diastereomer, Intermediate 39: (1R,3R,5R)—N—((S)-1-(4-chloro-2,5-difluorophenyl)-2,2-difluoroethyl)-2-(5-(methylsulfonyl)nicotinoyl)-2-azabicyclo[3.1.0]hexane- 3-carboxamide. LCMS-ESI (pos.) m/z: 520.1 (M+H)+. ¹H NMR (DMSO-d₆) δ: 9.22 (d, J=2.3 Hz, 1H), 9.20-9.14 (m, 2H), 8.51 (d, J=2.1 Hz, 1H), 7.78 (dd, J=9.3, 6.2 Hz, 1H), 7.59 (dd, J=9.7, 6.2 Hz, 1H), 6.31 (td, J=54.9, 3.6 Hz, 1H), 5.63-5.41 (m, 1H), 5.04 (dd, J=11.4, 3.6 Hz, 1H), 3.41 (s, 4H), 2.72-2.58 (m, 1H), 1.84-1.69 (m, 2H), 1.11 (td, J=5.2, 2.6 Hz, 1H), 0.80 (ddd, J=11.4, 7.8, 4.7 Hz, 1H).

Minor diastereomer: (1R,3R,5R)—N—((R)-1-(4-chloro-2,5-difluorophenyl)-2,2-difluoroethyl)-2-(5-(methylsulfonyl)nicotinoyl)-2-azabicyclo[3.1.0]hexane-3-carboxamide. LCMS-ESI (pos.) m/z: 520.1 (M+H)+. ¹H NMR (Methanol-d₄) δ: 9.20 (t, J=2.1 Hz, 2H), 8.68 (t, J=2.1 Hz, 1H), 7.48 (dd, J=9.5, 6.3 Hz, 1H), 7.41 (dd, J=9.3, 6.1 Hz, 1H), 6.19 (td, J=55.0, 3.0 Hz, 1H), 5.63 (ddd, J=15.6, 13.0, 3.1 Hz, 1H), 5.16 (dd, J=11.4, 4.1 Hz, 1H), 3.41 (td, J=6.2, 2.6 Hz, 1H), 3.26 (s, 3H), 2.90-2.72 (m, 1H), 2.13 (dd, J=13.6, 4.0 Hz, 1H), 1.99-1.84 (m, 1H), 1.40-1.29 (m, 1H), 0.98 (dtd, J=9.1, 5.6, 1.1 Hz, 1H).

Example of Route AC: Synthesis of (1R,3R,5R)—N—((R)-(2,5-Difluoro-4-(trifluoromethyl)phenyl)(oxetan-3-yl)methyl)-2-(3-(2-hydroxypropan-2-yl)benzoyl)-2-azabicyclo[3.1.0]hexane-3-carboxamide (Example 819)

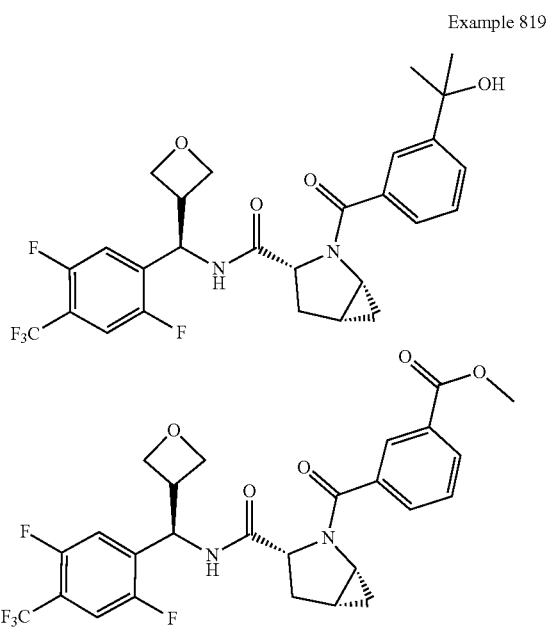

Example 819

Synthesis of Methyl 3-((1R,3R,5R)-3-(((R)-(2,5-Difluoro-4-(trifluoromethyl)phenyl)(oxetan-3-yl)methyl)carbamoyl)-2-azabicyclo[3.1.0]hexane-2-carbonyl)benzoate To a room temperature solution of (1R,3R,5R)—N—((R)-(2,5-difluoro-4-(trifluoromethyl)phenyl)(oxetan-3-yl)methyl)-2-azabicyclo[3.1.0]hexane-3-carboxamide (79 mg, 0.21 mmol), 3-(methoxycarbonyl)benzoic acid (42 mg, 0.23 mmol), hydroxybenzotriazole (57 mg, 0.42 mmol) and O-(benzotriazol-1-yl)-N,N,N',N'-tetramethyluronium hexafluorophosphate (159 mg, 0.42 mmol) in N-methyl-2-pyrrolidone (1.0 mL) was added N,N-diisopropylethylamine (0.18 mL, 1.05 mmol). The resulting mixture was stirred at room temperature for 20 minutes. It was diluted with ethyl acetate (15 mL) and washed once with saturated aqueous sodium bicarbonate (15 mL). The organic phase was dried over sodium sulfate and concentrated to an oil which was purified with silica gel using 0-60% ethyl acetate/hexanes, providing methyl 3-((1R,3R,5R)-3-(((R)-(2,5-difluoro-4-(trifluoromethyl)phenyl)(oxetan-3-yl)methyl)carbamoyl)-2-azabicyclo[3.1.0]hexane-2-carbonyl)benzoate (80 mg, 0.15 mmol) as an amorphous foam. 1H NMR (Methanol-d4) δ: 8.44 (t, J=1.8, 0.6 Hz, 1H), 8.21-8.14 (m, 1H), 8.07-7.97 (m, 1H), 7.63 (t, J=7.7, 0.6 Hz, 1H), 7.56 (dd, J=9.5, 5.7 Hz, 1H), 7.38 (dd, J=10.6, 5.5 Hz, 1H), 5.63 (d, J=10.2 Hz, 1H), 5.00 (dd, J=11.4, 4.2 Hz, 1H), 4.87-4.83 (m, 1H), 4.68 (t, J=7.8, 6.5 Hz, 1H), 4.62 (t, J=6.2 Hz, 1H), 4.43-4.38 (m, 1H), 3.96 (s, 3H), 3.64-3.46 (m, 1H), 3.32-3.28 (m, 1H), 2.75-2.58 (m, 1H), 1.91 (dd, J=13.6, 4.2 Hz, 1H), 1.86-1.73 (m, 1H), 1.29-1.19 (m, 1H), 0.94-0.82 (m, 1H). LCMS-ESI (POS.) m/z: 539.20 (M+H)+.

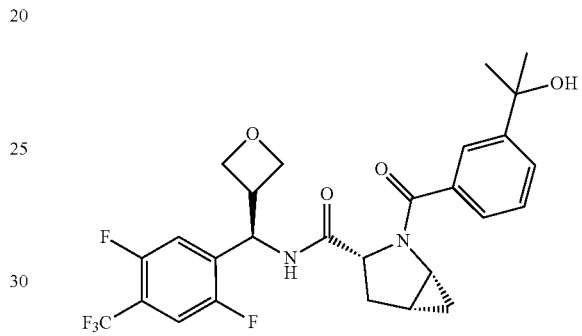

Synthesis of (1R,3R,5R)—N—((R)-(2,5-Difluoro-4-(trifluoromethyl)phenyl)(oxetan-3-yl)methyl)-2-(3-(2-hydroxypropan-2-yl)benzoyl)-2-azabicyclo[3.1.0]hexane-3-carboxamide (Example 819)

Methyl 3-((1R,3R,5R)-3-(((R)-(2,5-difluoro-4-(trifluoromethyl)phenyl)(oxetan-3-yl)methyl)carbamoyl)-2-azabicyclo[3.1.0]hexane-2-carbonyl)benzoate (74 mg, 0.137 mmol) was dissolved in THF (5 mL) and methylmagnesium bromide (3.0M in THF, 0.23 mL, 0.69 mmol) was added in one portion at room temperature. The resulting mixture was stirred at room temperature for 15 minutes and quenched with 1 mL saturated ammonium chloride. The mixture was diluted with 15 mL water and 35 mL ethyl acetate. The layers were shaken and separated and the organic phase was washed with brine, dried over sodium sulfate and concentrated to a crude residue which was purified with reverse phase HPLC using 10-100% acetonitrile/water over 40 minutes with no formic acid present (phenomenex gemini c-18 5-micron column), providing (1R,3R,5R)—N—((R)-(2,5-difluoro-4-(trifluoromethyl)phenyl)(oxetan-3-yl)methyl)-2-(3-(2-hydroxypropan-2-yl)benzoyl)-2-azabicyclo[3.1.0]hexane-3-carboxamide (9 mg, 0.017 mmol) as a white solid. 1H NMR (Methanol-d4) δ: 7.94 (s, 1H), 7.70-7.59 (m, 2H), 7.56 (dd, J=9.6, 5.7 Hz, 1H), 7.45 (t, J=7.8, 0.5 Hz, 1H), 7.38 (dd, J=10.5, 5.5 Hz, 1H), 5.62 (d, J=10.2 Hz, 1H), 4.99 (dd, J=11.4, 4.2 Hz, 1H), 4.85 (t, J=7.7, 6.6 Hz, 1H), 4.68 (t, J=7.8, 6.5 Hz, 1H), 4.62 (t, J=6.2 Hz, 1H), 4.45-4.35 (m, 1H), 3.62-3.44 (m, 1H), 2.71-2.58 (m, 1H), 1.92 (dd, J=13.5, 4.1 Hz, 1H), 1.83-1.71 (m, 1H), 1.58 (d, J=2.0 Hz, 7H), 1.28-1.16 (m, 1H), 0.93-0.80 (m, 1H). LCMS-ESI (POS.) m/z: 539.20 (M+H)+.

Example of Route AD: (1R,3R,5R)—N—((R)-cyclopropyl(2,5-difluoro-4-(trifluoromethyl)phenyl)methyl)-2-(5-(1-hydroxyethyl)-2-methylisonicotinoyl)-2-azabicyclo[3.1.0]hexane-3-carboxamide (Example 822)

Example 822

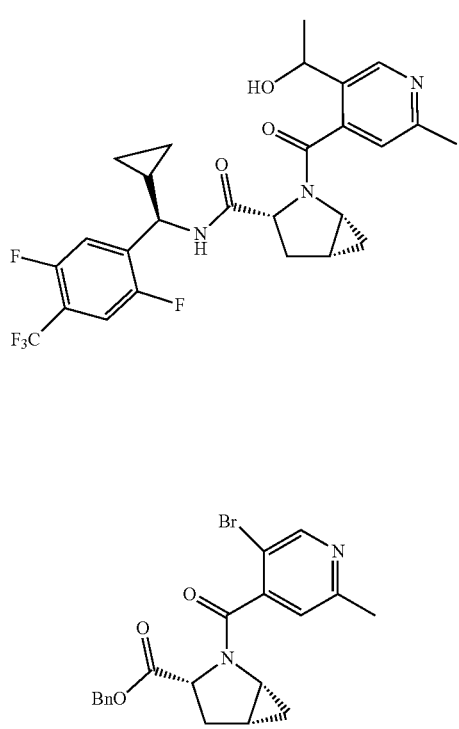

Synthesis of Benzyl (1R,3R,5R)-2-(5-bromo-2-methylisonicotinoyl)-2-azabicyclo[3.1.0]hexane-3-carboxylate A 40 mL vial was charged with 5-bromo-2-methylisonicotinic acid (1.96 g, 9.06 mmol), HBTU (5.15 g, 13.58 mmol), benzyl (1R,3R,5R)-2-azabicyclo[3.1.0]hexane-3-carboxylate 2,2,2-trifluoroacetate (3.0 g, 9.06 mmol) and dissolved in DMF (15 ml). Triethyamine (12.6 mL, 90.6 mmol) was subsequently added DROPWISE and stirred for 20 mins and analyzed by. The reaction was deemed to be complete. The reaction was subsequently quenched with satd aq ammonium chloride. The layers were separated and the organic layer was washed with satd aq sodium bicarbonate solution and brine. The organic layers were combined, dried over sodium sulfate, filtered and concentrated under vacuum, providing the desired crude as a viscous oil. The crude was purified by silica gel column chromatography (0% to 40% EtOAc/hexanes) to provide the product as a yellow viscous oil (3.76 g). $R_f$=0.38 (SiO$_2$, 50% EtOAc/hexanes). ESI (pos.) m/z: 416.2 (M+H)+. $^1$H NMR (DMSO-d$_6$) δ: 8.63 (s, 1H), 7.41-7.27 (m, 5H), 7.12 (s, 1H), 5.10 (d, J=1.7 Hz, 2H), 4.86 (dd, J=11.7, 3.3 Hz, 1H), 2.98 (td, J=6.1, 2.5 Hz, 1H), 2.74-2.59 (m, 1H), 2.40 (s, 3H), 2.03-1.88 (m, 1H), 1.63 (dq, J=8.8, 5.8 Hz, 1H), 0.80 (td, J=5.4, 2.5 Hz, 1H), 0.68-0.47 (m, 1H).

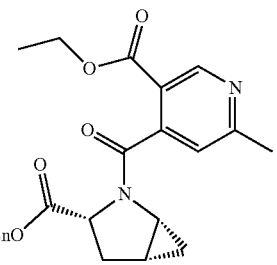

Synthesis of Benzyl (1R,3R,5R)-2-(5-(1-ethoxyvinyl)-2-methylisonicotinoyl)-2-azabicyclo[3.1.0]hexane-3-carboxylate To a solution of benzyl (1R,3R,5R)-2-(5-bromo-2-methylisonicotinoyl)-2-azabicyclo[3.1.0]hexane-3-carboxylate (0.3 g, 0.722 mmol) in dioxane (3.5 ml) was added tributyl (1-ethoxylvinyl) tin (0.287 g, 0.795 mmol) and dichlorobis(triphenylphosphine)palladium(II) (5 mg, 0.007 mmol). The mixture was stirred at 100° C. for 12 h, diluted with EtOAc (15 ml), and filtered through a thin pad of celite. The filtrate was concentrated under reduced pressure and purified by silica gel column chromatography (SiO2, 10% to 40% EtOAc/hexanes) to provide the product as a oil. (87 mg). $R_f$=0.38 (SiO$_2$, 50% EtOAc/hexanes). ESI (pos.) m/z: 407.2 (M+H)+. $^1$H NMR (Chloroform-d) δ: 8.62 (s, 1H), 7.37-7.26 (m, 5H), 7.11 (s, 1H), 5.20-5.05 (m, 2H), 5.00-4.88 (m, 1H), 4.52 (d, J=3.2 Hz, 1H), 4.28 (d, J=3.1 Hz, 1H), 3.80 (q, J=7.0 Hz, 2H), 3.02 (td, J=6.3, 2.5 Hz, 1H), 2.56 (s, 3H), 2.09 (dd, J=13.8, 3.4 Hz, 1H), 1.60 (dq, J=9.0, 6.0 Hz, 1H), 1.23 (t, J=7.0 Hz, 3H), 0.93-0.84 (m, 1H), 0.59 (dtd, J=9.1, 6.1, 1.2 Hz, 1H).

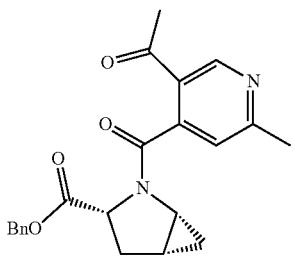 [SMILES: CC(=O)c1cnc(C)cc1C(=O)N1[C@@H](C(=O)OCc2ccccc2)C[C@H]2C[C@H]21]

Synthesis of benzyl (1R,3R,5R)-2-(5-acetyl-2-methylisonicotinoyl)-2-azabicyclo[3.1.0]hexane-3-carboxylate To a solution of benzyl (1R,3R,5R)-2-(5-(1-ethoxyvinyl)-2-methylisonicotinoyl)-2-azabicyclo[3.1.0]hexane-3-carboxylate (1.48 g, 3.64 mmol) in THF (25 mL) was added HCl (4 M in dioxan, 0.98 mL, 39.2 mmol). The reaction was stirred overnight and monitored by LCMS analysis. After the completion of the reaction, the solvent was evaporated and the crude was partitioned between EtOAc and water. The aq layer was extracted once with EtOAc and the combined organic layer was dried, filtered, and concentrated. The crude was taken through the next step without further purification. (1.28 g). ESI (pos.) m/z: 379.1 (M+H)+. $^1$H NMR (DMSO-d$_6$) δ: 9.00 (s, 1H), 7.39-7.29 (m, 5H), 7.06 (s, 1H), 5.11 (s, 2H), 4.85 (dd, J=11.6, 3.6 Hz, 1H), 2.90 (td, J=6.2, 2.5 Hz, 1H), 2.75-2.60 (m, 1H), 2.54 (s, 3H), 2.49

(s, 3H), 2.01-1.93 (m, 1H), 1.73-1.42 (m, 1H), 0.72 (td, J=5.3, 2.5 Hz, 1H), 0.62-0.48 (m, 1H).

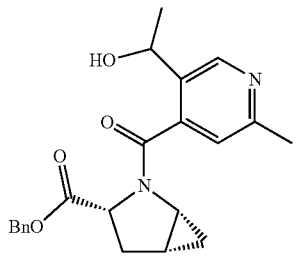 [SMILES: Cc1cc(C(=O)N2[C@@H](C(=O)OCc3ccccc3)C[C@H]3C[C@H]32)c(C(C)O)cn1]

Synthesis of benzyl (1R,3R,5R)-2-(5-(1-hydroxy-ethyl)-2-methylisonicotinoyl)-2-azabicyclo[3.1.0]hexane-3-carboxylate To a solution of benzyl (1R,3R,5R)-2-(5-acetyl-2-methylisonicotinoyl)-2-azabicyclo[3.1.0]hexane-3-carboxylate (0.35 g, 0.93 mmol) in MeOH (5.0 mL) was added SODIUM BOROHYDRIDE (70 mg, 1.85 mmol) in small portions. The reaction was stirred for 30 mins and monitored by LCMS analysis. After the completion of reaction, the solvent was evaporated and the crude was partitioned between EtOAc and water. The aq layer was extracted once with EtOAc and the combined organic layer was dried, filtered, and concentrated. The crude was taken through the next step without further purification (0.35 g; 2:1 ratio of diastereomers). R$_f$=0.36 (SiO$_2$, 100% EtOAc/hexanes). ESI (pos.) m/z: 381.2 (M+H)+.

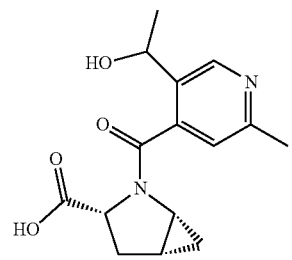 [SMILES: Cc1cc(C(=O)N2[C@@H](C(=O)O)C[C@H]3C[C@H]32)c(C(C)O)cn1]

Synthesis of (1R,3R,5R)-2-(5-(1-hydroxyethyl)-2-methylisonicotinoyl)-2-azabicyclo[3.1.0]hexane-3-carboxylic Acid To a solution of benzyl (1R,3R,5R)-2-(5-(1-hydroxy-ethyl)-2-methylisonicotinoyl)-2-azabicyclo[3.1.0]hexane-3-carboxylate (400 mg, 1.05 mmol) in EtOAc-THF (2.5 ml, 1:1) was added palladium (20 mg). The solution was purged with hydrogen for 5 mins and the mixture was stirred at rt for 12 hr while monitoring with LCMS analysis. After 12 hours LCMS analysis showed the product mass. The reaction was filtered over a pad of celite, concentrated, and dried. The crude was taken through the next step without further purification (215 mg; 2:1 ratio of diastereomers). ESI (pos.) m/z: 291.2 (M+H)+.

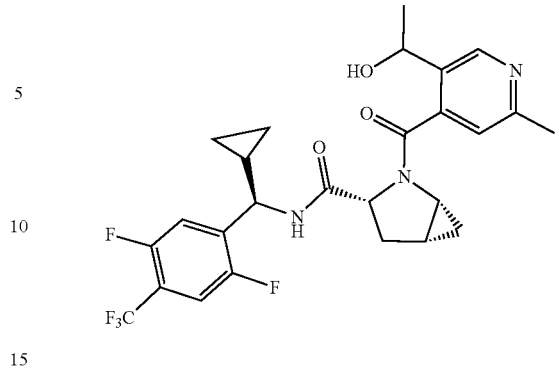

Synthesis of (1R,3R,5R)—N—((R)-cyclopropyl(2,5-difluoro-4-(trifluoromethyl)phenyl)methyl)-2-(5-(1-hydroxyethyl)-2-methylisonicotinoyl)-2-azabicy-clo[3.1.0]hexane-3-carboxamide, Example 822

A 8 mL vial was charged with (1R,3R,5R)-2-(5-(1-hydroxyethyl)-2-methylisonicotinoyl)-2-azabicyclo[3.1.0]hexane-3-carboxylic acid (113 mg, 0.39 mmol), HBTU (221 mg, 0.584 mmol), (R)-chloro(cyclopropyl(2,5-difluoro-4-(trifluoromethyl)phenyl)methyl)-15-azane (112 mg, 0.39 mmol) and dissolved in DMF (1 ml). Triethyamine (0.39 g, 3.9 mmol) was subsequently added dropwise and stirred for 20 mins and analyzed by LCMS (ac-0802-001). the reaction was deemed to be complete. The reaction was filtered and purified by reverse phase HPLC using 10-100% acetonitrile/water over 40 minutes (phenomenex gemini c-18 5-micron column), providing the desired product (major diastereomer, 17 mg). ESI (pos.) m/z: 524.2 (M+H)+. $^1$H NMR (Methanol-d$_4$) δ: 8.61 (s, 1H), 7.55-7.41 (m, 2H), 7.31 (s, 1H), 5.24-5.12 (m, 1H), 4.94 (ddd, J=11.3, 3.2, 1.5 Hz, 1H), 4.50 (d, J=9.1 Hz, 1H), 3.09 (td, J=6.3, 2.7 Hz, 1H), 2.72-2.61 (m, 1H), 2.55 (s, 3H), 2.01 (dd, J=13.5, 3.4 Hz, 1H), 1.76-1.64 (m, 1H), 1.49 (d, J=6.6 Hz, 3H), 1.26 (tdd, J=9.5, 6.4, 4.0 Hz, 1H), 1.03 (td, J=5.4, 2.5 Hz, 1H), 0.75-0.63 (m, 2H), 0.63-0.54 (m, 1H), 0.54-0.41 (m, 2H).

Example of Route AE: Synthesis of (R)—N—((R)-(2,5-difluoro-4-(trifluoromethyl)phenyl)((1s,3S)-3-hydroxycyclobutyl)methyl)-1-(3-(methylsulfonyl)benzoyl) pyrrolidine-2-carboxamide (Example 827)

Example 827

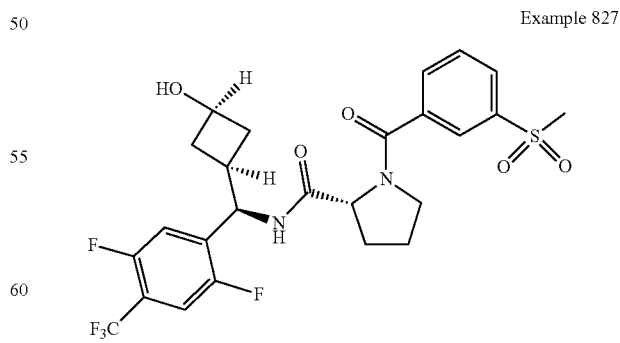

A 8 mL vial was charged with acid (53 mg, 0.18 mmol), HBTU (101 mg, 0.27 mmol), amine (50 mg, 0.18 mmol) and dissolved in dichloromethane (1 ml). Triethyamine was subsequently added DROPWISE and stirred for 20 mins and analyzed by LCMS (ac-0821-001). The reaction was concentrated under vacuo, and purified by reverse phase HPLC using 10-100% acetonitrile/water over 40 minutes (phenomenex gemini c-18 5-micron column), providing the desired product (30 mg). ESI (pos.) m/z: 561.2 (M+H)+. ¹H NMR (DMSO-d₆) δ: 8.51 (d, J=7.9 Hz, 1H), 8.10-8.01 (m, 2H), 7.91 (s, 1H), 7.74 (dd, J=9.6, 6.5 Hz, 2H), 7.53 (dd, J=11.1, 5.4 Hz, 1H), 5.04 (d, J=7.1 Hz, 2H), 4.49 (dd, J=8.3, 5.2 Hz, 1H), 3.87 (q, J=7.1 Hz, 1H), 3.63-3.49 (m, 2H), 3.28 (s, 3H), 2.35 (dd, J=11.3, 5.8 Hz, 1H), 2.23 (ddd, J=14.5, 7.7, 3.9 Hz, 1H), 2.06 (dt, J=12.2, 6.9 Hz, 2H), 1.82 (dt, J=13.5, 7.5 Hz, 3H), 1.72 (dd, J=7.4, 4.7 Hz, 1H), 1.62 (q, J=7.9 Hz, 1H).

The compounds set forth in the following table were synthesized following the procedure described for Example 827 using known starting material replacements as described.

TABLE 14

| Amine | B-C Ring Intermediate | Structure, Name and Data |
|---|---|---|
| Intermediate 37.0 | Intermediate 5.0 | 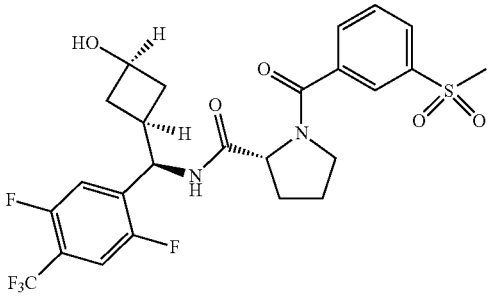<br>Example 827<br>((R)-N-((R)-(2,5-difluoro-4-(trifluoromethyl)phenyl)((1s,3S)-3-hydroxycyclobutyl)methyl)-1-(3-(methylsulfonyl)benzoyl)pyrrolidine-2-carboxamide<br>LCMS-ESI (POS.) m/z: 561.2 (M + H)+ |
| Intermediate 37.1 | Intermediate 5.0 | 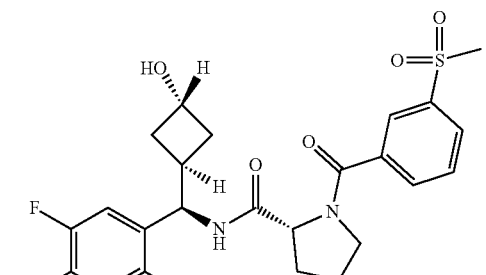<br>Example 828<br>((R)-N-((R)-(2,5-difluoro-4-(trifluoromethyl)phenyl)((1r,3R)-3-hydroxycyclobutyl)methyl)-1-(3-(methylsulfonyl)benzoyl)pyrrolidine-2-carboxamide<br>LCMS-ESI (POS.) m/z: 561.2 (M + H)+ |
| Intermediate 37.0 | Intermediate 31.3 | 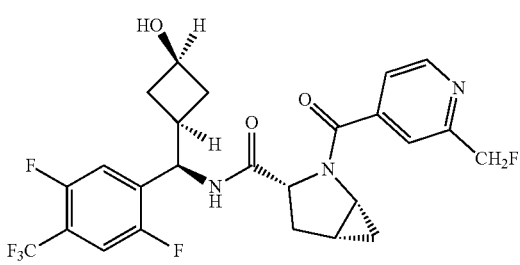<br>Example 830<br>(1R,3R,5R)-N-((R)-(2,5-difluoro-4-(trifluoromethyl)phenyl)((1s,3S)-3-hydroxycyclobutyl)methyl)-2-(2-(fluoromethyl)isonicotinoyl)-2-azabicyclo[3.1.0]hexane-3-carboxamide<br>LCMS-ESI (POS.) m/z: 546.2 (M + H)+ |

US 10,899,746 B2

TABLE 14-continued

| Amine | B-C Ring Intermediate | Structure, Name and Data |
|---|---|---|
| Intermediate 37.1 | Intermediate 31.3 | 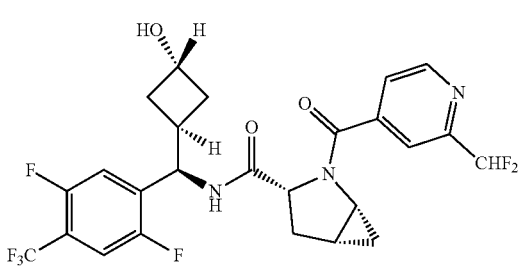<br>Example 831<br>(1R,3R,5R)-N-((R)-(2,5-difluoro-4-(trifluoromethyl)phenyl)((1r,3R)-3-hydroxycyclobutyl)methyl)-2-(2-(difluoromethyl)isonicotinoyl)-2-azabicyclo[3.1.0]hexane-3-carboxamide<br>LCMS-ESI (POS.) m/z: 546.2 (M + H)+ |
| Intermediate 21.2 | Intermediate 31.8 | 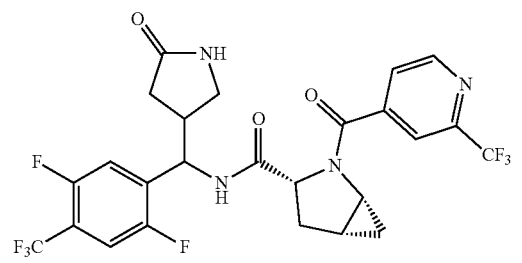<br>Example 832<br>(1R,3R,5R)-N-((2,5-difluoro-4-(trifluoromethyl)phenyl)(5-oxopyrrolidin-3-yl)methyl)-2-(2-(trifluoromethyl)isonicotinoyl)-2-azabicyclo[3.1.0]hexane-3-carboxamide<br>LCMS-ESI (POS.) m/z: 577.2 (M + H)+ |

Example of Route AF: (1R,3R,5R)—N—((R)-(2,5-difluoro-4-(trifluoromethyl)phenyl)3-hydroxy-3-methylcyclobutyl)methyl)-2-(3-(methylsulfonyl)benzoyl)-2-azabicyclo[3.1.0]hexane-3-carboxamide (Example 829)

Example 829

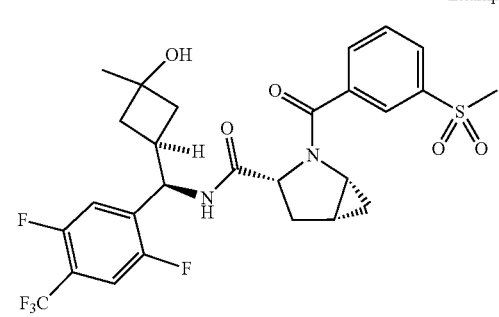

-continued

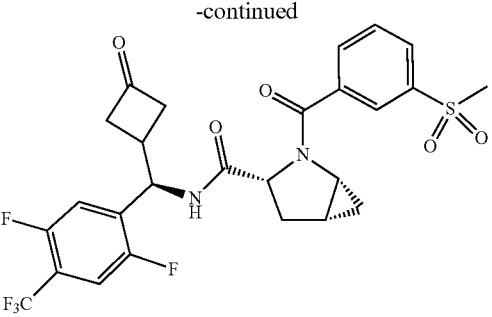

Synthesis of (1R,3R,5R)—N—((R)-(2,5-difluoro-4-(trifluoromethyl)phenyl)(3-oxocyclobutyl)methyl)-2-(3-(methylsulfonyl)benzoyl)-2-azabicyclo[3.1.0]hexane-3-carboxamide To a solution of (1R,3R,5R)—N—((R)-(2,5-difluoro-4-(trifluoromethyl)phenyl)((1s,3S)-3-hydroxycyclobutyl)methyl)-2-(3-(methylsulfonyl)benzoyl)-2-azabicyclo[3.1.0]hexane-3-carboxamide (0.32 g, 0.56 mmol) in DCM (4 mL) at 0 C was added Dess-Martin periodinane (0.356 g, 0.84 mmol). The reaction was stirred for 15 mins at 0 C and then the solution was warmed to rt. The reaction was monitored by TLC analysis. After the completion of the reaction, the reaction was cooled to 0 C and then quenched with 2:1 sodium thiosulfate-sodium bicabonate solution. The reaction was stirred until the phases became clear. The aq layer was extracted once with DCM and the combined organic layer was dried, filtered, and concentrated and taken through the next step without further purification (245 mg). ESI (pos.) m/z: 571.2 (M+H)$^+$. $^1$H NMR (DMSO-d$_6$) δ: 8.82 (d, J=8.3 Hz, 1H), 8.18 (t, J=1.8 Hz, 1H), 8.05 (ddt, J=21.7, 7.8, 1.4 Hz, 2H), 7.87-7.75 (m, 2H), 7.65 (dd, J=10.9, 5.7 Hz, 1H), 5.27 (t, J=8.4 Hz, 1H), 4.92 (dd, J=11.4, 3.8 Hz, 1H), 3.31-3.22 (m, 4H), 3.16-3.06 (m, 1H), 3.06-2.93 (m, 2H), 2.93-2.79 (m, 2H), 2.64-2.54 (m, 1H), 1.73 (ddd, J=15.3, 11.3, 5.1 Hz, 2H), 1.17 (td, J=5.0, 2.6 Hz, 1H), 0.77 (ddt, J=14.4, 8.6, 5.7 Hz, 1H).

Synthesis of (1R,3R,5R)—N—((R)-(2,5-difluoro-4-(trifluoromethyl)phenyl)(3-hydroxy-3-methylcyclobutyl)methyl)-2-(3-(methylsulfonyl)benzoyl)-2-azabicyclo[3.1.0]hexane-3-carboxamide (Example 829)

A 8 mL vial was charged with (1R,3R,5R)—N—((R)-(2,5-difluoro-4-(trifluoromethyl)phenyl)(3-oxocyclobutyl)methyl)-2-(3-(methylsulfonyl)benzoyl)-2-azabicyclo[3.1.0]hexane-3-carboxamide (200 mg, 0.35 mmol) and dissolved in THF (3 mL). The solution was cooled to 0 C and methyl magnesium bromide (0.23 mL, 0.701 mmol, 3M in ether) was subsequently added DROPWISE and stirred for 20 mins and analyzed by LCMS. The reaction was quenched with satd aq ammonium chloride and extracted with ethyl acetate. The combined organic layer were washed with brine, dried, and concentrated under vacuo. The crude was purified by reverse phase HPLC using 10-100% acetonitrile/water over 40 minutes (phenomenex gemini c-18 5-micron column), providing the desired product (10 mg). ESI (pos.) m/z: 587.2 (M+H)+. $^1$H NMR (Methanol-d$_4$) δ: 8.39 (t, J=1.8 Hz, 1H), 8.12 (ddd, J=8.0, 3.1, 1.3 Hz, 2H), 7.78 (t, J=7.8 Hz, 1H), 7.52 (dd, J=9.5, 5.7 Hz, 1H), 7.35 (dd, J=10.7, 5.4 Hz, 1H), 5.06 (dd, J=11.3, 4.0 Hz, 1H), 3.37 (s, 1H), 3.19 (s, 3H), 2.69 (ddd, J=13.7, 11.5, 6.4 Hz, 1H), 2.29 (dq, J=10.0, 4.3, 3.8 Hz, 2H), 2.03 (dd, J=14.2, 2.2 Hz, 1H), 1.99-1.86 (m, 3H), 1.81 (dq, J=9.0, 6.1 Hz, 1H), 1.31 (s, 3H), 1.23 (td, J=5.4, 2.6 Hz, 1H), 0.90 (dt, J=8.8, 5.7 Hz, 1H).

All compounds shown in the below table were prepared using a synthetic route as indicated, and their LCMS and NMR characterization are as shown.

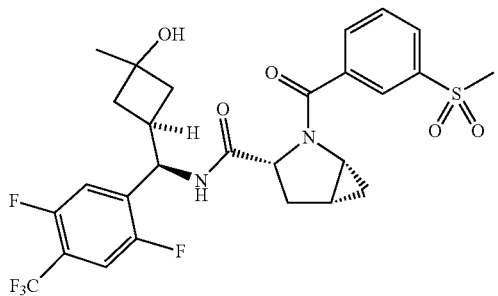

| Ex. # | Structure | Name | LCMS-ESI (POS/NEG) m/z: (M + H)+ | NMR Data | Syn. Rte. |
|---|---|---|---|---|---|
| 1 | | 1-(3-((3-cyano-1-azetidinyl)sulfonyl)benzoyl)-N-((1R)-2-cyclopropyl-1-(4-(trifluoromethyl)phenyl)ethyl)-D-prolinamide | LCMS-ESI (POS.) m/z: 575.2 (M + H)$^+$ | 1H NMR (500 MHz, DMSO-d6) δ ppm 8.28-8.55 (m, 1 H), 7.39-8.00 (m, 8 H), 4.59-5.01 (m, 1 H), 4.34-4.56 (m, 1 H), 4.02 (br dd, J = 8.69, 3.76 Hz, 2 H), 3.82-3.89 (m, 2 H), 3.41-3.64 (m, 3 H), 2.19-2.32 (m, 1 H), 1.69-1.93 (m, 4 H), 1.16-1.51 (m, 1 H), −0.15-0.78 (m, 5 H) | A |

| Ex. # | Structure Name | LCMS-ESI (POS/NEG) m/z: (M + H)+ | NMR Data | Syn. Rte. |
|---|---|---|---|---|
| 2 | 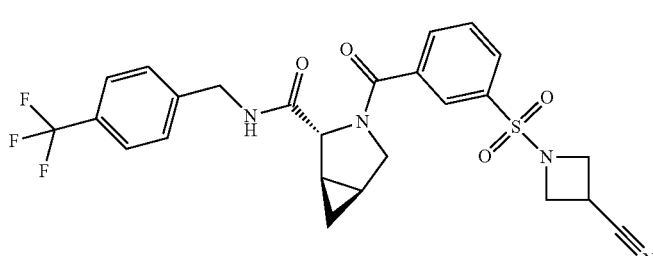<br>N-((R)-(4-chloro-2-fluorophenyl)(cyclopropyl)methyl)-1-(((3S)-1-((3-cyano-1-azetidinyl)sulfonyl)-3-piperidinyl)carbonyl)-D-prolinamide | LCMS-ESI (POS.) m/z: 552.2 (M + H)+ | 1H NMR (500 MHz, DMSO-d6) δ ppm 8.35-8.86 (m, 1 H), 7.40-7.47 (m, 1 H), 7.34-7.40 (m, 1 H), 7.25-7.31 (m, 1 H), 4.45-4.51 (m, 1 H), 4.29-4.43 (m, 1 H), 4.03-4.10 (m, 2 H), 3.90-3.98 (m, 2 H), 3.79 (qt, J = 9.01, 6.08 Hz, 1 H), 3.34-3.59 (m, 4 H), 2.67-2.88 (m, 2 H), 2.13-2.33 (m, 1 H), 1.97-2.06 (m, 1 H), 1.57-1.93 (m, 5 H), 1.33-1.56 (m, 2 H), 1.06-1.22 (m, 1 H), 0.49-0.58 (m, 1 H), 0.22-0.48 (m, 3 H) | A |
| 3 | 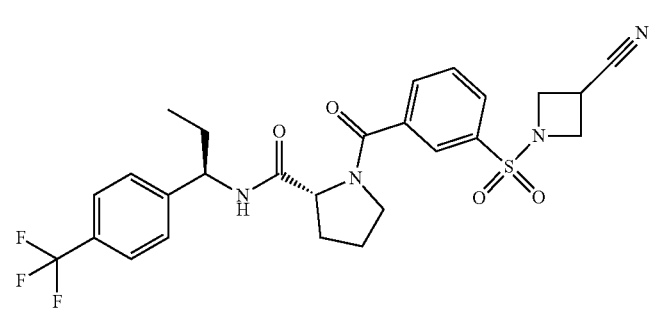 [SMILES: CC[C@@H](NC(=O)[C@H]1CCCN1C(=O)c1cccc(S(=O)(=O)N2CC(C#N)C2)c1)c1ccc(C(F)(F)F)cc1]<br>1-(3-((3-cyano-1-azetidinyl)sulfonyl)benzoyl)-N-((1R)-1-(4-(trifluoromethyl)phenyl)propyl)-D-prolinamide | LCMS-ESI (POS.) m/z: 549.2 (M + H)+ | 1H NMR (500 MHz, DMSO-d6) δ ppm 8.25-8.53 (m, 1 H), 7.37-7.99 (m, 8 H), 4.31-4.86 (m, 2 H), 3.93-4.13 (m, 2 H), 3.81-3.93 (m, 2 H), 3.44-3.69 (m, 3 H), 2.17-2.32 (m, 1 H), 1.40-1.93 (m, 5 H), 0.45-0.97 (m, 3 H) | A |
| 4 | 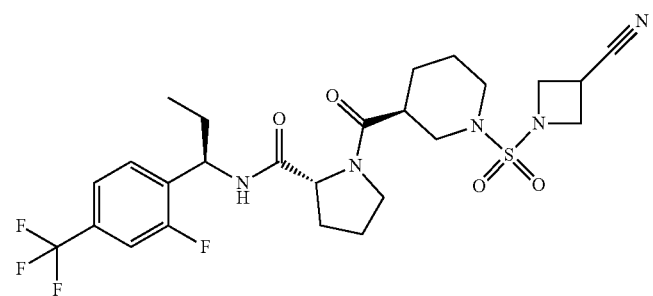 [SMILES: CC[C@@H](NC(=O)[C@H]1CCCN1C(=O)[C@H]1CCCN(S(=O)(=O)N2CC(C#N)C2)C1)c1ccc(C(F)(F)F)cc1F]<br>1-(((3S)-1-((3-cyano-1-azetidinyl)sulfonyl)-3-piperidinyl)carbonyl)-N-((1R)-1-(2-fluoro-4-(trifluoromethyl)phenyl)propyl)-D-prolinamide | LCMS-ESI (POS.) m/z: 574.2 (M + H)+ | 1H NMR (500 MHz, DMSO-d6) δ ppm 8.30-8.82 (m, 1 H), 7.55 (br d, J = 15.57 Hz, 3 H), 4.84-5.07 (m, 1 H), 4.31-4.55 (m, 1 H), 4.05-4.12 (m, 2 H), 3.91-3.98 (m, 2 H), 3.76-3.84 (m, 1 H), 3.31-3.62 (m, 4 H), 2.70-2.88 (m, 2 H), 2.60-2.68 (m, 1 H), 2.01-2.22 (m, 1 H), 1.61-1.92 (m, 7 H), 1.34-1.52 (m, 2 H), 0.80-0.97 (m, 3 H) | A |
| 5 | 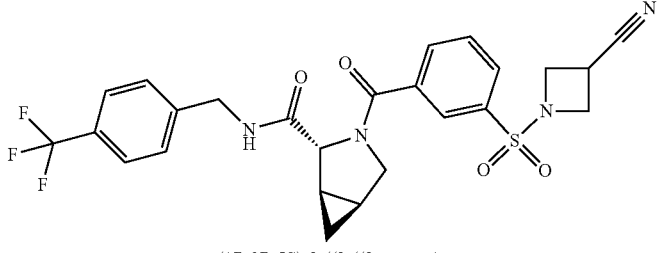<br>(1R,2R,5S)-3-((3-((3-cyano-1-azetidinyl)sulfonyl)phenyl)carbonyl)-N-(4-(trifluoromethyl)benzyl)-3-azabicyclo[3.1.0]hexane-2-carboxamide | LCMS-ESI (POS.) m/z: 533.2 (M + H)+ | 1H NMR (500 MHz, CHLOROFORM-d) δ ppm 7.23-7.95 (m, 8 H), 6.15-7.17 (m, 1 H), 4.82-4.95 (m, 1 H), 4.39-4.60 (m, 2 H), 3.77-4.15 (m, 5 H), 3.36-3.45 (m, 1 H), 3.26-3.36 (m, 1 H), 1.86-1.95 (m, 1 H), 1.57-1.80 (m, 1 H), 0.70-0.95 (m, 1 H), 0.06-0.31 (m, 1 H) | C |

| Ex. # | Structure Name | LCMS-ESI (POS/NEG) m/z: (M + H)+ | NMR Data | Syn. Rte. |
|---|---|---|---|---|
| 6 | 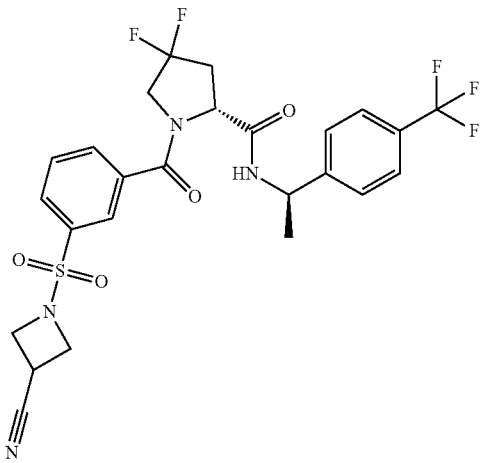 [SMILES: C[C@@H](NC(=O)[C@H]1CC(F)(F)CN1C(=O)c1cccc(S(=O)(=O)N2CC(C#N)C2)c1)c1ccc(C(F)(F)F)cc1]<br>1-((3-((3-cyano-1-azetidinyl)sulfonyl)phenyl)carbonyl)-4,4-difluoro-N-((1R)-1-(4-(trifluoromethyl)phenyl)ethyl)-D-prolinamide | LCMS-APCI (NEG.) m/z: 569.2 (M − H) | $^1$H NMR (400 MHz, Methanol-$d_4$) δ ppm 8.12 (s, 1 H), 8.01 (dd, J = 7.8, 14.8 Hz, 2 H), 7.81 (t, J = 7.7 Hz, 1 H), 7.59-7.69 (m, 2 H), 7.52 (d, J = 8.0 Hz, 2 H), 5.12 (q, J = 7.1 Hz, 1 H), 4.12 (td, J = 2.9, 8.7 Hz, 3 H), 3.94 (dd, J = 6.0, 8.5 Hz, 3 H), 3.45-3.61 (m, 1 H), 2.82 (td, J = 7.9, 14.4, 14.9 Hz, 1 H), 2.32-2.54 (m, 1 H), 1.53 (d, J = 7.0 Hz, 3 H). | Q |
| 7 | 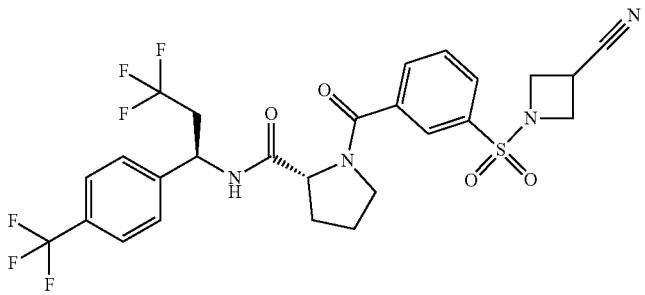 [SMILES: N#CC1CN(S(=O)(=O)c2cccc(C(=O)N3CCC[C@@H]3C(=O)N[C@H](CC(F)(F)F)c3ccc(C(F)(F)F)cc3)c2)C1]<br>1-(3-((3-cyano-1-azetidinyl)sulfonyl)benzoyl)-N-((1R)-3,3,3-trifluoro-1-(4-(trifluoromethyl)phenyl)propyl)-D-prolinamide | LCMS-ESI (POS.) m/z: 603.0 (M + H)$^+$ | 1H NMR (500 MHz, DMSO-d6) δ ppm 8.55-8.69 (m, 1 H), 7.52-8.01 (m, 8 H), 5.03-5.36 (m, 1 H), 4.44-4.55 (m, 1 H), 3.94-4.08 (m, 2 H), 3.81-3.90 (m, 2 H), 3.43-3.66 (m, 3 H), 2.62-2.95 (m, 2 H), 2.18-2.32 (m, 1 H), 1.71-1.95 (m, 3 H) | A |
| 8 | 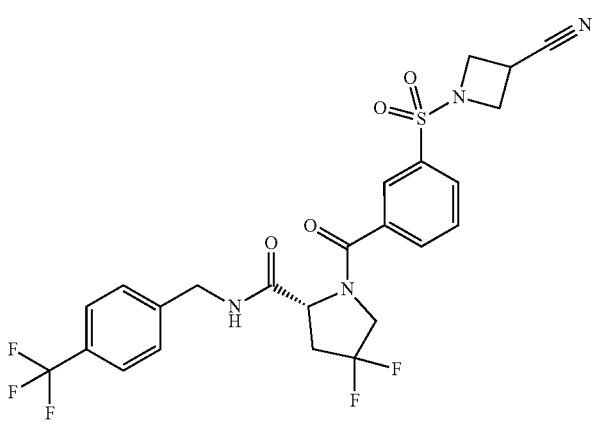 [SMILES: N#CC1CN(S(=O)(=O)c2cccc(C(=O)N3CC(F)(F)C[C@@H]3C(=O)NCc3ccc(C(F)(F)F)cc3)c2)C1]<br>1-((3-((3-cyano-1-azetidinyl)sulfonyl)phenyl)carbonyl)-4,4-difluoro-N-(4-(trifluoromethyl)benzyl)-D-prolinamide | LCMS-APCI (POS.) m/z: 557.2 (M + H)$^+$ | $^1$H NMR (400 MHz, Methanol-$d_4$) δ ppm 7.19-8.20 (m, 8 H), 3.86-4.99 (m, 9 H), 3.44-3.58 (m, 1 H), 2.79-3.05 (m, 1 H), 2.47-2.69 (m, 1 H). | Q |

| Ex. # | Structure Name | LCMS-ESI (POS/NEG) m/z: (M + H)+ | NMR Data | Syn. Rte. |
|---|---|---|---|---|
| 9 | 1-(((3S)-1-((3-cyano-1-azetidinyl)sulfonyl)-3-piperidinyl)carbonyl)-N-((1R)-1-(2-fluoro-4-(trifluoromethyl)phenyl)-2-methylpropyl)-D-prolinamide | LCMS-ESI (POS.) m/z: 588.2 (M + H)+ | 1H NMR (500 MHz, DMSO-d6) δ ppm 8.25-8.75 (m, 1 H), 7.52-7.65 (m, 3 H), 4.80-4.89 (m, 1 H), 4.59-4.60 (m, 1 H), 4.35 (dd, J = 8.50, 3.83 Hz, 1 H), 4.04-4.08 (m, 2 H), 3.91-3.98 (m, 2 H), 3.75-3.85 (m, 1 H), 3.30-3.61 (m, 4 H), 2.69-2.88 (m, 2 H), 2.60-2.67 (m, 1 H), 1.31-2.03 (m, 9 H), 0.66-1.03 (m, 6 H) | A |
| 10 | 1-(3-((3-cyano-1-azetidinyl)sulfonyl)benzoyl)-N-((1R)-1-(2-fluoro-4-(trifluoromethyl)phenyl)-2-methylpropyl)-D-prolinamide | LCMS-ESI (POS.) m/z: 581.0 (M + H)+ | 1H NMR (400 MHz, DMSO-d6) δ ppm 8.52 (br J = 8.29 Hz, 1 H), 7.55-7.94 (m, 7 H), 6.46-6.48 (m, 1 H), 4.82-4.95 (m, 1 H), 4.51-4.57 (m, 1 H), 4.02 (br dd, J = 8.76, 2.75 Hz, 3 H), 3.42-3.63 (m, 4 H), 1.96-2.15 (m, 1 H), 1.62-1.86 (m, 4 H), 0.47-1.02 (m, 6 H) | A |
| 11 | 1-(((3S)-1-((3-cyano-1-azetidinyl)sulfonyl)-3-piperidinyl)carbonyl)-N-((R)-cyclopropyl(4-(trifluoromethyl)phenyl)methyl)-D-prolinamide | LCMS-ESI (POS.) m/z: 568.2 (M + H)+ | 1H NMR (500 MHz, DMSO-d6) δ ppm 8.32-8.97 (m, 1 H), 7.63-7.73 (m, 2 H), 7.49-7.60 (m, 2 H), 4.49 (br dd, J = 8.43, 2.98 Hz, 1 H), 4.27 (br d, J = 8.17 Hz, 1 H), 4.06 (t, J = 7.79 Hz, 2 H), 3.92-3.97 (m, 2 H), 3.75-3.85 (m, 1 H), 3.25-3.58 (m, 4 H), 2.69-2.87 (m, 2 H), 2.55-2.67 (m, 1 H), 1.63-2.09 (m, 6 H), 1.36-1.54 (m, 2 H), 1.04-1.16 (m, 1 H) 0.30-0.58 (m, 4 H) | A |
| 12 | 1-(3-((3-cyano-1-azetidinyl)sulfonyl)benzoyl)-N-((1R)-1-(2-fluoro-4-(trifluoromethyl)phenyl)propyl)-D-prolinamide | LCMS-ESI (POS.) m/z: 567.0 (M + H)+ | 1H NMR (500 MHz, DMSO-d6) δ ppm 8.57 (d, J = 7.79 Hz, 1 H), 7.42-8.02 (m, 7 H), 4.65-5.10 (m, 1 H), 4.33-4.58 (m, 1 H), 3.98-4.05 (m, 2 H), 3.85-3.92 (m, 2 H), 3.46-3.69 (m, 3 H), 2.18-2.30 (m, 1 H), 1.43-1.92 (m, 5 H), 0.54-0.96 (m, 3 H) | A |

| Ex. # | Structure Name | LCMS-ESI (POS/NEG) m/z: (M + H)+ | NMR Data | Syn. Rte. |
|---|---|---|---|---|
| 13 | 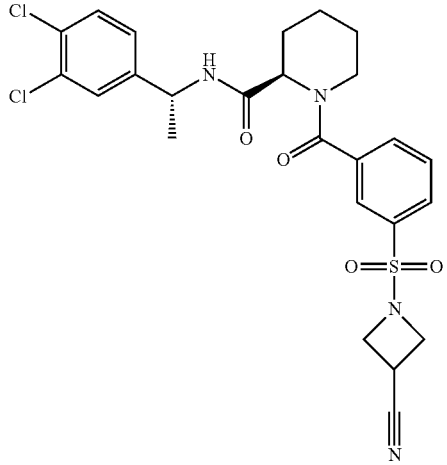 [SMILES: C[C@@H](NC(=O)[C@H]1CCCCN1C(=O)c1cccc(S(=O)(=O)N2CC(C#N)C2)c1)c1ccc(Cl)c(Cl)c1]<br>(2R)-1-((3-((3-cyano-1-azetidinyl)sulfonyl)phenyl)carbonyl)-N-((1R)-1-(3,4-dichlorophenyl)ethyl)-2-piperidinecarboxamide | LCMS-APCI (NEG.) m/z: 547.1 (M − H) | $^1$H NMR (400 MHz, Methanol-$d_4$) δ ppm 7.05 (s, 0 H), 6.41-6.57 (m, 2 H), 6.21-6.41 (m, 2 H), 6.00 (dd, J = 2.0, 8.5 Hz, 2 H), 5.79 (s, 1 H), 3.78 (s, 1 H), 3.54 (s, 1 H), 2.63 (td, J = 2.2, 8.7 Hz, 2 H), 2.33-2.49 (m, 2 H), 1.90-2.13 (m, 2 H), 0.57-0.88 (m, 1 H), 0.19-0.51 (m, 2 H), − 0.20-0.15 (m, 6 H). | Q |
| 14 | 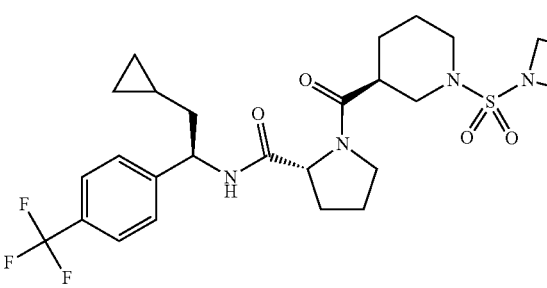<br>1-(((3S)-1-((3-cyano-1-azetidinyl)sulfonyl)-3-piperidinyl)carbonyl)-N-((1R)-2-cyclopropyl-1-(4-(trifluoromethyl)phenyl)ethyl)-D-prolinamide | LCMS-ESI (POS.) m/z: 582.2 (M + H)+ | 1H NMR (500 MHz, DMSO-d6) δ ppm 8.19-8.72 (m, 1 H), 7.60-7.74 (m, 2 H), 7.41-7.58 (m, 2 H), 4.81-5.03 (m, 1 H), 4.32-4.49 (m, 1 H), 4.02-4.08 (m, 2 H), 3.90-3.97 (m, 2 H), 3.70-3.82 (m, 1 H), 3.26-3.44 (m, 1 H), 3.26-3.66 (m, 3 H), 2.69-2.90 (m, 2 H), 2.58-2.67 (m, 1 H), 1.62-2.11 (m, 7 H), 1.28-1.58 (m, 3 H), 0.56-0.78 (m, 1 H), 0.28-0.48 (m, 2 H), − 0.08-0.20 (m, 2H) | A |
| 15 | 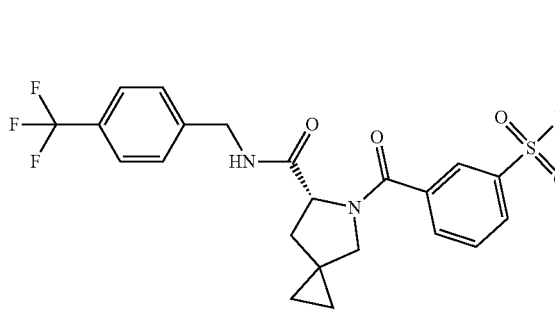<br>(6R)-5-((3-((3-cyano-1-azetidinyl)sulfonyl)phenyl)carbonyl)-N-(4-(trifluoromethyl)benzyl)-5-azaspiro[2.4]heptane-6-carboxamide | LCMS-APCI (POS.) m/z: 547.1 (M + H)+ | $^1$H NMR (400 MHz, Methanol-$d_4$) δ ppm 8.16 (s, 1 H), 8.00 (ddd, J = 1.6, 6.8, 8.8 Hz, 2 H), 7.79 (t, J = 7.7 Hz, 1 H), 7.62 (d, J = 8.4 Hz, 2 H), 7.54 (d, J = 8.1 Hz, 2 H), 4.79 (t, J = 7.6 Hz, 1 H), 4.61 (dd, J = 5.0, 15.8 Hz, 1 H), 4.42-4.56 (m, 1 H), 4.12 (td, J = 2.9, 8.8 Hz, 2 H), 3.88-3.94 (m, 2 H), 3.77 (d, J = 10.1 Hz, 1 H), 3.46-3.58 (m, 1 H), 2.15 (qd, J = 7.5, 12.6 Hz, 2 H), 0.50-0.68 (m, 4 H). | Q |

| Ex. # | Structure Name | LCMS-ESI (POS/NEG) m/z: (M + H)+ | NMR Data | Syn. Rte. |
|---|---|---|---|---|
| 16 | 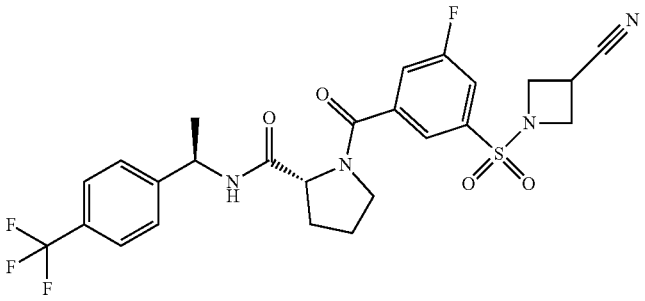 [SMILES: C[C@@H](NC(=O)[C@H]1CCCN1C(=O)c1cc(F)cc(S(=O)(=O)N2CC(C#N)C2)c1)c1ccc(C(F)(F)F)cc1]<br>1-((3-((3-cyano-1-azetidinyl)sulfonyl)-5-fluorophenyl)carbonyl)-N-((1R)-1-(4-(trifluoromethyl)phenyl)ethyl)-D-prolinamide | LCMS-ESI (POS.) m/z: 553.2 (M + H)+ | 1H NMR (500 MHz, DMSO-d6) δ ppm 8.53 (d, J = 7.53 Hz, 1 H), 7.57-7.89 (m, 5 H), 7.39-7.55 (m, 2 H), 5.00 (t, J = 7.01 Hz, 1 H), 4.49 (dd, J = 8.37, 5.26 Hz, 1 H), 3.91-4.11 (m, 5 H), 3.47-3.69 (m, 2 H), 2.19-2.28 (m, 1 H), 1.74-1.89 (m, 3 H), 1.10-1.43 (m, 3 H) | C |
| 17 | 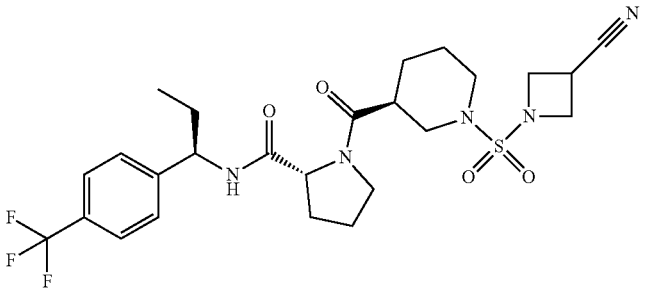 [SMILES: CC[C@@H](NC(=O)[C@H]1CCCN1C(=O)[C@H]1CCCN(S(=O)(=O)N2CC(C#N)C2)C1)c1ccc(C(F)(F)F)cc1]<br>1-(((3S)-1-((3-cyano-1-azetidinyl)sulfonyl)-3-piperidinyl)carbonyl)-N-((1R)-1-(4-(trifluoromethyl)phenyl)propyl)-D-prolinamide | LCMS-ESI (POS.) m/z: 556.2 (M + H)+ | 1H NMR (500 MHz, DMSO-d6) δ ppm 8.17-8.72 (m, 1 H), 7.63-7.76 (m, 2 H), 7.44-7.54 (m, 2 H), 4.68-4.81 (m, 1 H), 4.33-4.41 (m, 1 H), 4.03-4.10 (m, 2 H), 3.90-3.99 (m, 2 H), 3.76-3.85 (m, 1 H), 3.29-3.63 (m, 4 H), 2.70-2.88 (m, 2 H), 2.60-2.68 (m, 1 H), 1.61-2.16 (m, 8 H), 1.30-1.57 (m, 2 H), 0.76-0.95 (m, 3 H) | A |
| 18 | 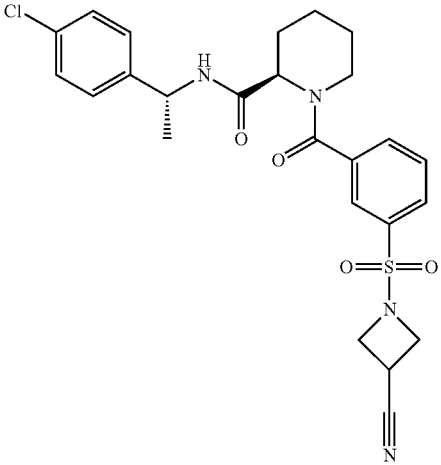 [SMILES: C[C@@H](NC(=O)[C@H]1CCCCN1C(=O)c1cccc(S(=O)(=O)N2CC(C#N)C2)c1)c1ccc(Cl)cc1]<br>(2R)-N-((1R)-1-(4-chlorophenyl)ethyl)-1-((3-((3-cyano-1-azetidinyl)sulfonyl)phenyl)carbonyl)-2-piperidinecarboxamide | LCMS-APCI (NEG.) m/z: 513.2 (M − H) | 1H NMR (400 MHz, Methanol-d4) δ ppm 8.47 (s, 1 H), 7.84-8.02 (m, 4 H), 7.69-7.84 (m, 2 H), 7.33 (d, J = 4.6 Hz, 7 H), 5.23 (s, 1 H), 5.06 (d, J = 7.3 Hz, 2 H), 4.10 (td, J = 2.8, 8.9 Hz, 4 H), 3.78-3.98 (m, 4 H), 3.49 (s, 4 H), 2.12-2.34 (m, 2 H), 1.82-2.00 (m, 1H), 1.61-1.82 (m, 4 H), 1.40-1.61 (m, 9 H). | Q |

-continued

| Ex. # | Structure Name | LCMS-ESI (POS/NEG) m/z: (M + H)+ | NMR Data | Syn. Rte. |
|---|---|---|---|---|
| 19 | (3R)-4-((3-((3-cyano-1-azetidinyl)sulfonyl)phenyl)carbonyl)-N-((1R)-1-(4-(trifluoromethyl)phenyl)ethyl)-3-morpholinecarboxamide | LCMS-ESI (POS.) m/z: 551.2 (M + H)+ | 1H NMR (500 MHz, DMSO-d6) δ ppm 8.52-8.73 (m, 1 H), 7.95 (br s, 1 H), 7.75-7.88 (m, 3 H), 7.70 (br d, J = 8.04 Hz, 2 H), 7.54 (br d, J = 6.62 Hz, 2 H), 5.05 (br s, 1 H), 4.20-4.44 (m, 2 H), 3.52-4.07 (m, 8 H), 3.10-3.49 (m, 2 H), 1.32-1.48 (m, 3 H) | C |
| 20 | N-(4-chloro-2,5-difluorobenzyl)-1-(((3S)-1-((3-cyano-1-azetidinyl)sulfonyl)-3-piperidinyl)carbonyl)-D-prolinamide | LCMS-ESI (POS.) m/z: 530.2 (M + H)+ | 1H NMR (500 MHz, DMSO-d6) δ ppm 8.32-8.69 (m, 1 H), 7.60 (dd, J = 9.28, 6.29 Hz, 1 H), 7.24-7.37 (m, 1 H), 4.18-4.54 (m, 3 H), 3.99-4.09 (m, 2 H), 3.86-3.98 (m, 2 H), 3.75-3.83 (m, 1 H), 3.40-3.71 (m, 4 H), 2.62-2.87 (m, 3 H), 1.86-2.33 (m, 4 H), 1.37-1.81 (m, 4 H) | A |
| 21 | 1-((3-((3-cyano-1-azetidinyl)sulfonyl)phenyl)carbonyl)-N-(4-(trifluoromethyl)benzyl)-D-prolinamide | LCMS-APCI (NEG.) m/z: 519.1 (M − H) | $^1$H NMR (400 MHz, Methanol-d$_4$) δ ppm 8.14 (t, J = 1.8 Hz, 1 H), 8.00 (dt, J = 2.3, 8.2 Hz, 2 H), 7.80 (dd, J = 6.7, 9.0 Hz, 1 H), 7.56-7.68 (m, 3 H), 7.52-7.58 (m, 2 H), 4.52-4.68 (m, 2 H), 4.46 (d, J = 15.8 Hz, 1 H), 4.11 (td, J = 2.5, 8.9 Hz, 2 H), 3.87-3.99 (m, 3 H), 3.69 (dt, J = 6.8, 10.4 Hz, 1 H), 3.54 (dddd, J = 5.2, 7.9, 15.3, 18.1 Hz, 2 H), 2.33-2.44 (m, 1 H), 1.91-2.05 (m, 3 H). | Q |

| Ex. # | Structure Name | LCMS-ESI (POS/NEG) m/z: (M + H)+ | NMR Data | Syn. Rte. |
|---|---|---|---|---|
| 22 | 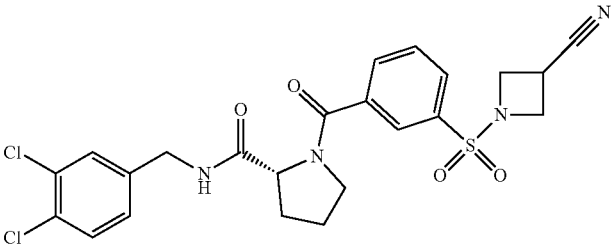 [SMILES: N#CC1CN(S(=O)(=O)c2cccc(C(=O)N3CCC[C@@H]3C(=O)NCc3ccc(Cl)c(Cl)c3)c2)C1]<br>1-((3-((3-cyano-1-azetidinyl)sulfonyl)phenyl)carbonyl)-N-(3,4-dichlorobenzyl)-D-prolinamide | LCMS-ESI (POS.) m/z: 521.0 (M + H)+ | 1H NMR (400 MHz, CHLOROFORM-d) δ ppm 7.98-8.03 (m, 1 H), 7.91-7.95 (m, 1 H), 7.80-7.85 (m, 1 H), 7.66-7.72 (m, 1 H), 7.36-7.44 (m, 2 H), 7.26-7.31 (m, 1 H), 7.14 (dd, J = 8.21, 1.94 Hz, 1 H), 4.75 (dd, J = 7.57, 5.03 Hz, 1 H), 4.38-4.48 (m, 2 H), 4.11-4.17 (m, 2 H), 4.02 (dd, J = 8.01, 6.71 Hz, 2 H), 3.57-3.67 (m, 1 H), 3.44-3.52 (m, 1 H), 3.31-3.42 (m, 1 H), 2.44-2.54 (m, 1 H), 2.06-2.20 (m, 2 H), 1.84-1.98 (m, 1 H) | A |
| 23 | 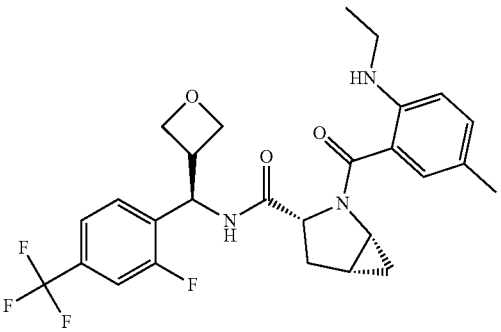 [SMILES: CCNc1ccc(C)cc1C(=O)N1[C@@H](C(=O)N[C@@H](c2ccc(C(F)(F)F)cc2F)C2COC2)C[C@H]2C[C@H]21]<br>(1R,3R,5R)-2-(2-(ethylamino)-5-methylbenzoyl)-N-((R)-(2-fluoro-4-(trifluoromethyl)phenyl)(3-oxetanyl)methyl)-2-azabicyclo[3.1.0]hexane-3-carboxamide | LCMS-APCI (POS.) m/z: 520.2 (M + H)+ | $^1$H NMR (400 MHz, DMSO-$d_6$) δ ppm 8.76 (d, J = 7.9 Hz, 1 H), 7.70 (d, J = 10.2 Hz, 1 H), 7.54-7.65 (m, 2 H), 7.00-7.12 (m, 2 H), 6.57 (d, J = 8.4 Hz, 1 H), 5.49 (t, J = 8.7 Hz, 1 H), 4.91 (d, J = 10.5 Hz, 1 H), 4.66 (t, J = 7.0 Hz, 1 H), 4.52 (t, J = 7.1 Hz, 1 H), 4.42 (t, J = 6.0 Hz, 1 H), 4.23 (t, J = 6.0 Hz, 1 H), 3.00-3.14 (m, 3 H), 2.19 (s, 3 H), 1.72 (dd, J = 13.2 Hz, 1 H), 1.56 (h, 1 H), 1.15 (t, J = 7.1 Hz, 2 H), 0.93 (s, 1 H), 0.63 (q, J = 5.9 Hz, 1 H). | Q |
| 24 | 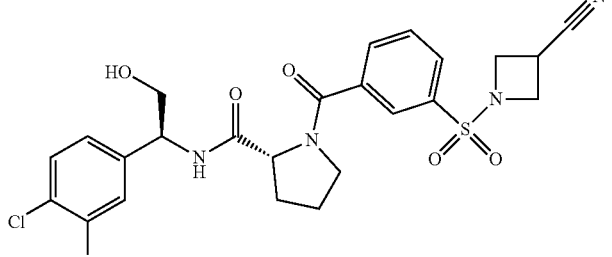 | LCMS-ESI (POS.) m/z: 535.2 (M + H)+ | 1H NMR (500 MHz, DMSO-d6) δ ppm 8.21-8.57 (m, 1 H), 7.70-8.03 (m, 4 H), 7.23-7.44 (m, 3 H), 5.05-5.14 (m, 1 H), 4.52-4.60 (m, 1 H), 3.29-4.10 (m, 10 H), 2.16-2.31 (m, 1 H), 1.69-1.96 (m, 3 H) | A |

| Ex. # | Structure Name | LCMS-ESI (POS/NEG) m/z: (M + H)+ | NMR Data | Syn. Rte. |
|---|---|---|---|---|
|  | N-((1S)-1-(4-chloro-3-fluorophenyl)-2-hydroxyethyl)-1-(3-((3-cyano-1-azetidinyl)sulfonyl)benzoyl)-D-prolinamide |  |  |  |
| 25 | 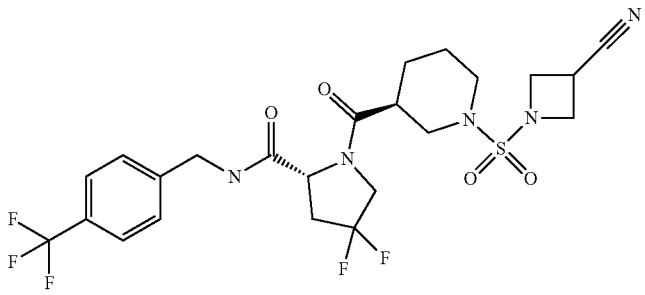 [SMILES: N#CC1CN(S(=O)(=O)N2CCC[C@H](C(=O)N3CC(F)(F)C[C@@H]3C(=O)NCc3ccc(C(F)(F)F)cc3)C2)C1]<br>1-(((3S)-1-((3-cyano-1-azetidinyl)sulfonyl)-3-piperidinyl)carbonyl)-4,4-difluoro-N-(4-(trifluoromethyl)benzyl)-D-prolinamide | LCMS-ESI (NEG.) m/z: 562.2 (M − H)− | 1H NMR (500 MHz, DMSO-d6) δ ppm 8.54-8.92 (m, 1 H), 7.65-7.71 (m, 2 H), 7.46 (br d, J = 8.17 Hz, 2 H), 4.53-4.88 (m, 1 H), 4.31-4.49 (m, 2 H), 3.51-4.24 (m, 9 H), 2.74-3.03 (m, 3 H), 2.55-2.67 (m, 1 H), 2.32-2.43 (m, 1 H), 1.85-1.97 (m, 1 H), 1.71 (br dd, J = 13.69, 3.18 Hz, 1 H), 1.31-1.55 (m, 2 H) | M |
| 26 | 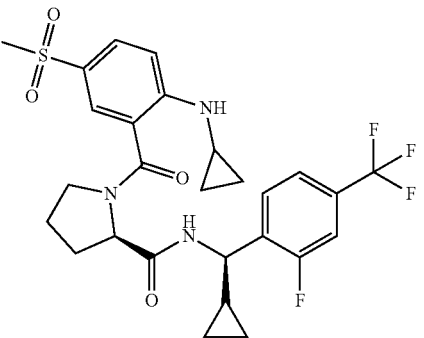 [SMILES: CS(=O)(=O)c1ccc(NC2CC2)c(C(=O)N2CCC[C@@H]2C(=O)N[C@@H](c2ccc(C(F)(F)F)cc2F)C2CC2)c1]<br>1-(2-(cyclopropylamino)-5-(methylsulfonyl)benzoyl)-N-((R)-cyclopropyl(2-fluoro-4-(trifluoromethyl)phenyl)methyl)-D-prolinamide | LCMS-APCI (POS.) m/z: 568.2 (M + H)+ | $^1$H NMR (400 MHz, DMSO-d$_6$) δ ppm 8.95 (d, J = 7.2 Hz, 1 H), 7.62-7.77 (m, 3 H), 7.52 (d, J = 2.2 Hz, 1 H), 7.08 (d, J = 8.8 Hz, 1 H), 7.03 (s, 1 H), 4.55-4.64 (m, 2 H), 3.16-3.26 (m, 2 H), 3.11 (s, 2 H), 2.17-2.29 (m, 2 H), 1.63-1.81 (m, 4 H), 1.17-1.28 (m, 2 H), 0.73-0.84 (m, 2 H), 0.57-0.64 (m, 1 H), 0.29-0.52 (m, 5 H). | S |
| 27 | 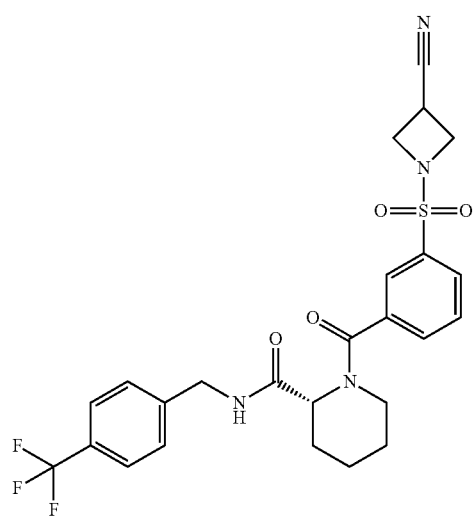 [SMILES: N#CC1CN(S(=O)(=O)c2cccc(C(=O)N3CCCC[C@@H]3C(=O)NCc3ccc(C(F)(F)F)cc3)c2)C1]<br>(2R)-1-((3-((3-cyano-1-azetidinyl)sulfonyl)phenyl)carbonyl)-N-(4-(trifluoromethyl)benzyl)-2-piperidinecarboxamide, (2S)-1-((3-((3-cyano-1-azetidinyl)sulfonyl)phenyl)carbonyl)-N-(4-(trifluoromethyl)benzyl)-2-piperidinecarboxamide | LCMS-APCI (NEG.) m/z: 533.2 (M − H) | $^1$H NMR (400 MHz, DMSO-d$_6$) δ 8.12 (s, 1 H), 7.92 (d, J = 6.0 Hz, 1 H), 7.85 (s, 1 H), 7.76 (s, 2 H), 7.76 (d, J = 10.5 Hz, 1 H), 7.66 (d, J = 7.9 Hz, 2 H), 7.51 (d, J = 8.0 Hz, 2 H), 4.84 (s, 1 H), 4.46 (d, J = 5.8 Hz, 2 H), 4.13 (t, J = 8.6 Hz, 2 H), 3.93 (ddd, J = 8.7, 6.1, 3.1 Hz, 2 H), 3.83 (d, J = 13.8 Hz, 1 H), 3.75-3.60 (m, 1 H), 3.37-3.16 (m, 1 H), 2.22 (d, J = 13.9 Hz, 1 H), 1.71 (d, J = 39.4 Hz, 3 H), 1.53 (d, J = 3.6 Hz, 0 H), 1.58-1.45 (m, 2 H). | Q |

| Ex. # | Structure Name | LCMS-ESI (POS/NEG) m/z: (M + H)+ | NMR Data | Syn. Rte. |
|---|---|---|---|---|
| 28 | 1-(((3S)-1-((3-cyano-1-azetidinyl)sulfonyl)-3-piperidinyl)carbonyl)-N-((1R)-3,3,3-trifluoro-1-(4-(trifluoromethyl)phenyl)propyl)-D-prolinamide | LCMS-ESI (POS.) m/z: 610.2 (M + H)+ | 1H NMR (500 MHz, DMSO-d6) δ ppm 8.24-8.98 (m, 1 H), 7.66-7.81 (m, 2 H), 7.48-7.63 (m, 2 H), 5.16-5.31 (m, 1 H), 4.21-4.43 (m, 1 H), 4.03-4.14 (m, 2 H), 3.91-3.97 (m, 2 H), 3.78-3.83 (m, 2 H), 3.30-3.63 (m, 4 H), 2.78-2.96 (m, 3 H), 2.59-2.68 (m, 1 H), 2.07-2.24 (m, 1 H), 1.58-1.97 (m, 5 H), 1.25-1.56 (m, 2 H) | A |
| 29 | 1-(((3S)-1-((3-cyano-1-azetidinyl)sulfonyl)-3-piperidinyl)carbonyl)-N-((1R)-1-(2-fluoro-4-(trifluoromethyl)phenyl)ethyl)-D-prolinamide | LCMS-ESI (POS.) m/z: 560.2 (M + H)+ | 1H NMR (500 MHz, DMSO-d6) δ ppm 8.39-8.81 (m, 1 H), 7.49-7.67 (m, 3 H), 5.04-5.22 (m, 1 H), 4.27-4.53 (m, 1 H), 4.02-4.11 (m, 2 H), 3.90-3.98 (m, 2 H), 3.74-3.86 (m, 1 H), 3.51-3.61 (m, 3 H), 3.32-3.41 (m, 1 H), 2.70-2.87 (m, 2 H), 2.15-2.35 (m, 1 H), 1.95-2.14 (m, 1 H), 1.63-1.93 (m, 5 H), 1.34-1.56 (m, 5 H) | C |
| 30 | 1-(3-((3-cyano-1-azetidinyl)sulfonyl)benzoyl)-N-((R)-cyclopropyl(4-(trifluoromethyl)phenyl)methyl)-D-prolinamide | LCMS-ESI (POS.) m/z: 561.2 (M + H)+ | 1H NMR (500 MHz, DMSO-d6) δ ppm 8.45-8.68 (m, 1 H), 7.37-8.03 (m, 8 H), 4.26-4.60 (m, 2 H), 3.95-4.07 (m, 2 H), 3.79-3.91 (m, 2 H), 3.43-3.71 (m, 3 H), 2.15-2.35 (m, 1 H), 1.65-1.95 (m, 3 H), −0.07-1.24 (m, 5 H) | A |
| 31 | 1-(3-((3-cyano-1-azetidinyl)sulfonyl)benzoyl)-N-((1S)-2-hydroxy-1-(4-(trifluoromethyl)phenyl)ethyl)-D-prolinamide | LCMS-ESI (POS.) m/z: 551.0 (M + H)+ | 1H NMR (500 MHz, DMSO-d6) δ ppm 8.26-8.57 (m, 1 H), 7.42-8.02 (m, 8 H), 4.92 (q, J = 6.31 Hz, 1 H), 4.57 (br dd, J = 8.17, 4.80 Hz, 1 H), 3.26-4.07 (m, 10H), 2.16-2.29 (m, 1 H), 1.64-1.96 (m, 3 H) | A |

-continued

| Ex. # | Structure Name | LCMS-ESI (POS/NEG) m/z: (M + H)+ | NMR Data | Syn. Rte. |
|---|---|---|---|---|
| 32 | 1-(((3S)-1-((3-cyano-1-azetidinyl)sulfonyl)-3-piperidinyl)carbonyl)-N-(3-fluoro-4-(trifluoromethyl)benzyl)-D-prolinamide | LCMS-ESI (POS.) m/z: 546.2 (M + H)+ | 1H NMR (500 MHz, DMSO-d6) δ ppm 8.39-8.79 (m, 1 H), 7.68-7.79 (m, 1 H), 7.35 (br d, J = 12.07 Hz, 1 H), 7.24-7.31 (m, 1 H), 4.25-4.55 (m, 3 H), 4.00-4.10 (m, 2 H), 3.88-3.98 (m, 2 H), 3.74-3.83 (m, 1 H), 3.35-3.70 (m, 4 H), 2.63-2.87 (m, 3 H), 1.36-2.16 (m, 8 H) | A |
| 33 | (1R,3R,5R)-2-(((3S)-1-((3-cyano-1-azetidinyl)sulfonyl)-3-piperidinyl)carbonyl)-N-(2-fluoro-4-(trifluoromethyl)benzyl)-2-azabicyclo[3.1.0]hexane-3-carboxamide | LCMS-ESI (POS.) m/z: 558.2 (M + H)+ | 1H NMR (500 MHz, DMSO-d6) δ ppm 8.22-8.97 (m, 1 H), 7.31-7.74 (m, 3 H), 4.59-4.96 (m, 1 H), 4.19-4.59 (m, 2 H), 3.29-4.15 (m, 10 H), 2.57-3.00 (m, 3 H), 1.95-2.29 (m, 1 H), 1.00-1.95 (m, 5 H), 0.58-0.87 (m, 1 H) | C |
| 34 | (4R)-N-((R)-(4-chloro-2,5-difluorophenyl)(3-oxetanyl)methyl)-1-(2-(ethylamino)-5-methylbenzoyl)-4-hydroxy-D-prolinamide | LCMS-APCI (POS.) m/z: 508.1 (M + H)+ | 1H NMR (400 MHz, DMSO-d6) δ ppm 8.70 (s, 1 H), 7.60-7.72 (m, 1 H), 7.48 (dd, J = 6.3, 9.8 Hz, 1 H), 7.03 (d, J = 8.1 Hz, 1 H), 6.89 (s, 1 H), 6.55 (d, J = 8.3 Hz, 1 H), 5.45 (d, J = 26.1 Hz, 2 H), 5.13 (s, 1 H), 4.65 (s, 1 H), 4.32-4.55 (m, 3 H), 4.05-4.29 (m, 2 H), 3.42 (s, 2 H), 3.15-3.27 (m, 1 H), 3.05 (q, J = 6.8 Hz, 2 H), 2.42 (q, J = 7.2 Hz, 2 H), 2.18 (s, 3 H), 1.58 (s, 1 H), 1.14 (t, J = 7.1 Hz, 3 H). | Q |
| 35 | 1-(((3S)-1-((3-cyano-1-azetidinyl)sulfonyl)-3-piperidinyl)carbonyl)-N-((R)-cyclopropyl(2,5-difluoro-4-(trifluoromethyl)phenyl)methyl)-D-prolinamide | LCMS-ESI (POS.) m/z: 604.2 (M + H)+ | 1H NMR (500 MHz, DMSO-d6) δ ppm 8.34-8.94 (m, 1 H), 7.48-7.80 (m, 2 H), 4.31-4.57 (m, 2 H), 4.27-4.32 (m, 1 H), 4.01-4.07 (m, 2 H), 3.87-3.93 (m, 1 H), 3.73-3.82 (m, 1 H), 3.50-3.62 (m, 3 H), 3.26-3.46 (m, 1 H), 2.57-2.87 (m, 3 H), 2.00-2.29 (m, 1 H), 1.62-1.98 (m, 5 H), 1.35-1.58 (m, 2 H), 1.09-1.24 (m, 1 H), 0.27-0.62 (m, 4 H) | A |

| Ex. # | Structure Name | LCMS-ESI (POS/NEG) m/z: (M + H)+ | NMR Data | Syn. Rte. |
|---|---|---|---|---|
| 36 | 1-(((3S)-1-((3-cyano-1-azetidinyl)sulfonyl)-3-piperidinyl)carbonyl)-N-((1R)-3-hydroxy-1-(4-(trifluoromethyl)phenyl)propyl)-D-prolinamide | LCMS-ESI (POS.) m/z: 572.2 (M + H)+ | 1H NMR (400 MHz, CHLOROFORM-d) δ ppm 7.58-7.68 (m, 2 H), 7.43 (d, J = 8.19 Hz, 2 H), 7.35-7.40 (m, 1 H), 5.17-5.25 (m, 1 H), 4.47 (dd, J = 7.93, 2.85 Hz, 1 H), 4.06-4.18 (m, 4 H), 3.57-3.83 (m, 6 H), 3.44 (tt, J = 8.71, 6.53 Hz, 1 H), 3.00 (dd, J = 12.70, 11.04 Hz, 1 H), 2.67-2.85 (m, 2 H), 2.14-2.32 (m, 2 H), 1.93-2.14 (m, 4 H), 1.77-1.89 (m, 2 H), 1.53-1.75 (m, 3 H) | A |
| 37 | 1-(3-((3-cyano-1-azetidinyl)sulfonyl)benzoyl)-N-((S)-cyclopropyl(4-(trifluoromethyl)phenyl)methyl)-D-prolinamide | LCMS-ESI (POS.) m/z: 561.2 (M + H)+ | 1H NMR (500 MHz, DMSO-d6) δ ppm 8.59 (d, J = 8.04 Hz, 1 H), 7.20-8.00 (m, 8 H), 4.08-4.60 (m, 2 H), 3.98-4.04 (m, 1 H), 3.82-3.94 (m, 2 H), 3.77-4.05 (m, 1 H), 3.44-3.71 (m, 3 H), 2.23-2.37 (m, 1 H), 1.79-2.00 (m, 3 H), 1.07-1.23 (m, 1 H), 0.22-0.62 (m, 4 H) | A |
| 38 | N-(3-chloro-4-(trifluoromethyl)benzyl)-1-(((3S)-1-((3-cyano-1-azetidinyl)sulfonyl)-3-piperidinyl)carbonyl)-D-prolinamide | LCMS-ESI (POS.) m/z: 562.2 (M + H)+ | 1H NMR (400 MHz, CHLOROFORM-d) δ ppm 7.61-7.66 (m, 1 H), 7.56 (br t, J = 5.86 Hz, 1 H), 7.37 (s, 1 H), 7.24 (d, J = 7.98 Hz, 1 H), 4.60-4.65 (m, 1 H), 4.56 (dd, J = 15.70, 6.89 Hz, 1 H), 4.33 (dd, J = 15.76, 5.29 Hz, 1 H), 4.06-4.17 (m, 4 H), 3.72-3.83 (m, 2 H), 3.53-3.66 (m, 2 H), 3.43 (tt, J = 8.69, 6.54 Hz, 1 H), 2.98 (dd, J = 12.75, 10.99 Hz, 1 H), 2.65-2.83 (m, 2 H), 2.40-2.51 (m, 1 H), 2.12-2.28 (m, 1 H), 2.01-2.12 (m, 1 H), 1.77-1.99 (m, 3 H), 1.63-1.73 (m, 1 H), 1.48-1.59 (m, 1 H) | A |
| 39 | N-((R)-(4-chloro-2,5-difluorophenyl)(cyclopropyl)methyl)-1-(((3S)-1-((3-cyano-1-azetidinyl)sulfonyl)-3-piperidinyl)carbonyl)-D-prolinamide | LCMS-ESI (POS.) m/z: 570.0 (M + H)+ | 1H NMR (500 MHz, DMSO-d6) δ ppm 8.27-8.88 (m, 1 H), 7.34-7.65 (m, 2 H), 5.57-5.58 (m, 1 H), 4.43-4.50 (m, 1 H), 4.27-4.31 (m, 1 H), 4.01-4.06 (m, 2 H), 3.88-3.95 (m, 2 H), 3.72-3.81 (m, 1 H), 3.23-3.58 (m, 4 H), 2.77-2.84 (m, 1 H), 2.68 (s, 1 H), 2.18-2.34 (m, 1 H), 1.99-2.17 (m, 1 H), 1.64-1.93 (m, 5 H), 1.32-1.54 (m, 2 H), 1.06-1.19 (m, 1 H), 0.26-0.61 (m, 4 H) | A |

| Ex. # | Structure Name | LCMS-ESI (POS/NEG) m/z: (M + H)+ | NMR Data | Syn. Rte. |
|---|---|---|---|---|
| 40 | 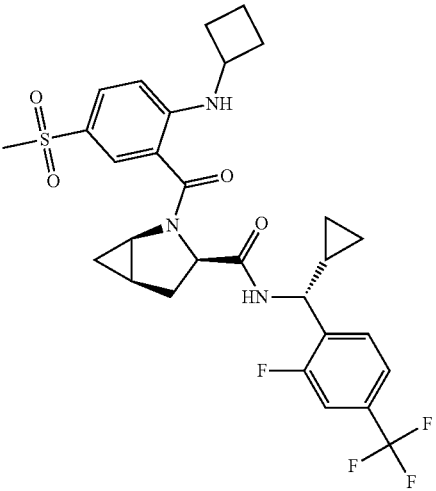 [SMILES: CS(=O)(=O)c1ccc(NC2CCC2)c(C(=O)N2[C@@H](C(=O)N[C@@H](c3ccc(C(F)(F)F)cc3F)C3CC3)C[C@H]3C[C@H]32)c1]<br>(1R,3R,5R)-2-(2-(cyclobutylamino)-5-(methylsulfonyl)benzoyl)-N-((R)-cyclopropyl(2-fluoro-4-(trifluoromethyl)phenyl)methyl)-2-azabicyclo[3.1.0]hexane-3-carboxamide | LCMS-APCI (POS.) m/z: 594.2 (M + H)+ | 1H NMR (400 MHz, DMSO-d6) δ ppm 8.97 (d, J = 6.7 Hz, 1 H), 7.61-7.72 (m, 3 H), 7.01 (d, J = 6.0 Hz, 1 H), 6.65 (d, J = 8.7 Hz, 1 H), 4.94-5.03 (m, 1 H), 4.43-4.52 (m, 1 H), 3.89-4.01 (m, 2 H), 3.09 (s, 3 H), 1.80-1.90 (m, 2 H), 1.69 (dt, J = 8.9, 16.9 Hz, 3 H), 1.52-1.62 (m, 2 H), 1.17-1.29 (m, 2 H), 0.67-0.76 (m, 1 H), 0.53-0.67 (m, 2 H), 0.24-0.53 (m, 4 H). | S |
| 41 | 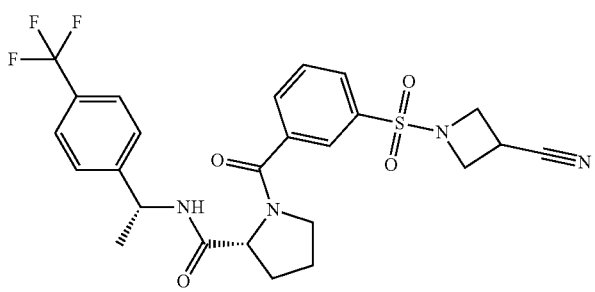 [SMILES: C[C@@H](NC(=O)[C@H]1CCCN1C(=O)c1cccc(S(=O)(=O)N2CC(C#N)C2)c1)c1ccc(C(F)(F)F)cc1]<br>1-((3-((3-cyano-1-azetidinyl)sulfonyl)phenyl)carbonyl)-N-((1R)-1-(4-(trifluoromethyl)phenyl)ethyl)-D-prolinamide | LCMS-APCI (NEG.) m/z: 533.2 (M − H) | 1H NMR (400 MHz, Methanol-d4) δ ppm 8.11 (t, J = 1.8 Hz, 1 H), 7.94-8.05 (m, 2 H), 7.78 (q, J = 6.7, 7.3 Hz, 2 H), 7.63 (d, J =8.1 Hz, 1 H), 7.52 (d, J = 8.1 Hz, 2 H), 5.10 (td, J = 4.9, 7.2 Hz, 1 H), 4.61 (dd, J = 5.9, 8.2 Hz, 1 H), 4.11 (dd, J = 7.8, 9.6 Hz, 3 H), 3.88-3.99 (m, 3 H), 3.63 (dt, J =6.8, 10.5 Hz, 1 H), 3.52 (dtd, J = 3.2, 6.4, 11.6 Hz, 2 H), 2.33 (tdt, J = 6.7, 11.9, 14.2 Hz, 1 H), 1.86-1.98 (m, 3 H), 1.52 (dd, J = 2.0, 7.1 Hz, 3 H). | A |
| 42 | 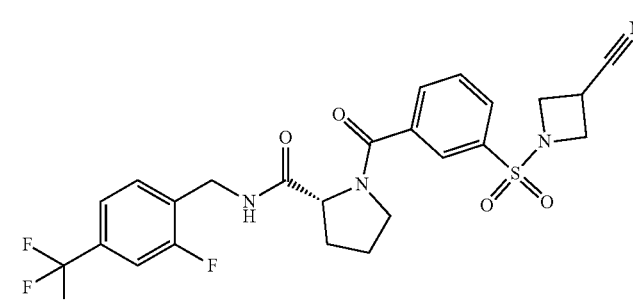<br>1-((3-((3-cyano-1-azetidinyl)sulfonyl)phenyl)carbonyl)-N-(2-fluoro-4-(trifluoromethyl)benzyl)-D-prolinamide | LCMS-ESI (POS.) m/z: 539.0 (M + H)+ | 1H NMR (500 MHz, CHLOROFORM-d) δ ppm 7.99-8.05 (m, 1 H), 7.92-7.98 (m, 1 H), 7.81-7.86 (m, 1 H), 7.68-7.76 (m, 1 H), 7.49-7.56 (m, 1 H), 7.37-7.45 (m, 1 H), 7.30-7.36 (m, 1 H), 7.26-7.27 (m, 1 H), 4.72-4.80 (m, 1 H), 4.51-4.63 (m, 2 H), 4.10-4.18 (m, 2 H), 3.99-4.07 (m, 2 H), 3.58-3.68 (m, 1 H), 3.44-3.54 (m, 1 H), 3.31-3.42 (m, 1 H), 2.38-2.49 (m, 1 H), 2.09-2.19 (m, 2 H), 1.86-1.99 (m, 1 H) | A |

| Ex. # | Structure Name | LCMS-ESI (POS/NEG) m/z: (M + H)+ | NMR Data | Syn. Rte. |
|---|---|---|---|---|
| 43 | 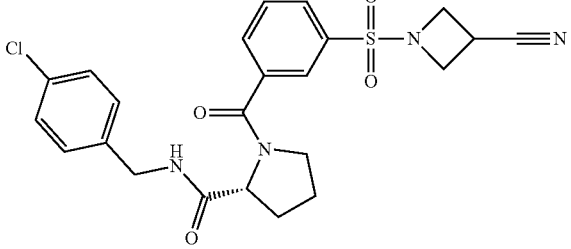<br>N-(4-chlorobenzyl)-1-((3-((3-cyano-1-azetidinyl)sulfonyl)phenyl)carbonyl)-D-prolinamide | LCMS-APCI (NEG.) m/z: 485.1 (M − H) | 1H NMR (400 MHz, Methanol-d4) δ ppm 8.13 (t, J = 1.8 Hz, 1 H), 7.99 (dd, J = 1.8, 7.8 Hz, 2 H), 7.80 (t, J = 7.8 Hz, 1 H), 7.27-7.36 (m, 4 H), 4.55-4.67 (m, 1 H), 4.49 (d, J = 15.4 Hz, 1 H), 4.32-4.43 (m, 1 H), 4.11 (t, J = 8.6 Hz, 2 H), 3.93 (dt, J = 5.8, 8.6 Hz, 3 H), 3.53 (dddt, J = 4.5, 6.4, 10.9, 13.5 Hz, 2 H), 2.31-2.46 (m, 1 H), 1.99-2.06 (m, 2 H), 1.85-1.96 (m, 1 H). | A |
| 44 | 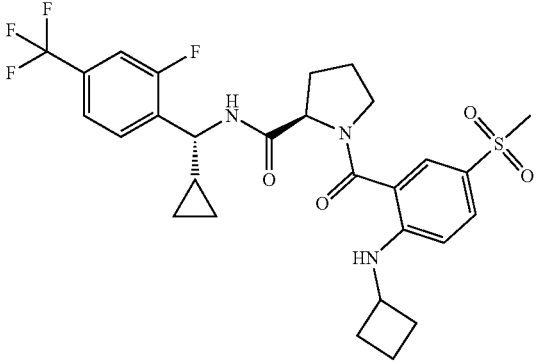 [SMILES: CS(=O)(=O)c1ccc(NC2CCC2)c(C(=O)N2CCC[C@@H]2C(=O)N[C@@H](c2ccc(C(F)(F)F)cc2F)C2CC2)c1]<br>1-(2-(cyclobutylamino)-5-(methylsulfonyl)benzoyl)-N-((R)-cyclopropyl(2-fluoro-4-(trifluoromethyl)phenyl)methyl)-D-prolinamide | LCMS-APCI (POS.) m/z: 582.2 (M + H)+ | 1H NMR (400 MHz, DMSO-d6) δ ppm 8.98 (d, J = 7.1 Hz, 1 H), 7.59-7.75 (m, 4 H), 7.50 (d, J = 2.3 Hz, 1 H), 6.99 (d, J = 6.0 Hz, 1 H), 6.66 (d, J = 8.9 Hz, 1 H), 4.53-4.66 (m, 3 H), 3.90-4.01 (m, 2 H), 3.10 (s, 2 H), 1.63-1.91 (m, 8 H), 1.19-1.29 (m, 2 H), 0.56-0.66 (m, 2 H), 0.40-0.54 (m, 3 H), 0.30-0.40 (m, 2 H). | S |
| 45 | 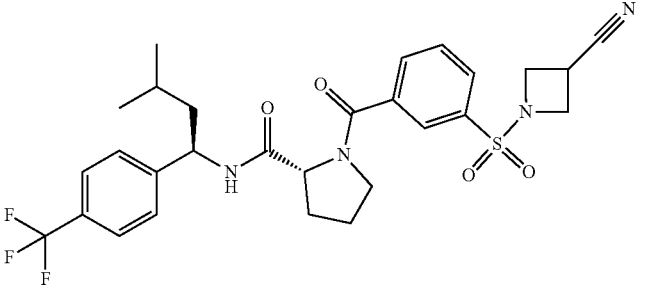 [SMILES: CC(C)C[C@@H](NC(=O)[C@H]1CCCN1C(=O)c1cccc(S(=O)(=O)N2CC(C#N)C2)c1)c1ccc(C(F)(F)F)cc1]<br>1-(3-((3-cyano-1-azetidinyl)sulfonyl)benzoyl)-N-((1R)-3-methyl-1-(4-(trifluoromethyl)phenyl)butyl)-D-prolinamide | LCMS-ESI (POS.) m/z: 577.2 (M + H)+ | 1H NMR (500 MHz, DMSO-d6) δ ppm 8.24-8.55 (m, 1 H), 7.35-8.02 (m, 8 H), 4.83-5.00 (m, 1 H), 4.35-4.50 (m, 1 H), 3.92-4.07 (m, 2 H), 3.78-3.90 (m, 2 H), 3.42-3.67 (m, 3 H), 1.04-2.26 (m, 7 H), 0.63-0.97 (m, 6 H) | A |
| 46 | 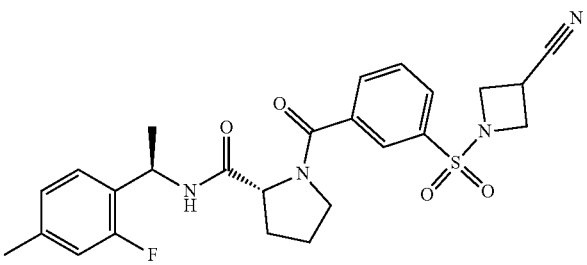 [SMILES: Cc1ccc([C@@H](C)NC(=O)[C@H]2CCCN2C(=O)c2cccc(S(=O)(=O)N3CC(C#N)C3)c2)c(F)c1]<br>1-((3-((3-cyano-1-azetidinyl)sulfonyl)phenyl)carbonyl)-N-((1R)-1-(2-fluoro-4-methylphenyl)ethyl)-D-prolinamide | LCMS-ESI (POS.) m/z: 499.2 (M + H)+ | 1H NMR (500 MHz, DMSO-d6) δ ppm 8.14-8.53 (m, 1 H), 7.69-8.01 (m, 4 H), 6.89-7.31 (m, 3 H), 4.80-5.18 (m, 1 H), 4.22-4.56 (m, 1 H), 3.94-4.10 (m, 2 H), 3.81-3.94 (m, 2 H), 3.41-3.70 (m, 3 H), 2.15-2.32 (m, 4 H), 1.70-1.91 (m, 3 H), 0.99-1.45 (m, 3 H) | A |

| Ex. # | Structure Name | LCMS-ESI (POS/NEG) m/z: (M + H)+ | NMR Data | Syn. Rte. |
|---|---|---|---|---|
| 47 | 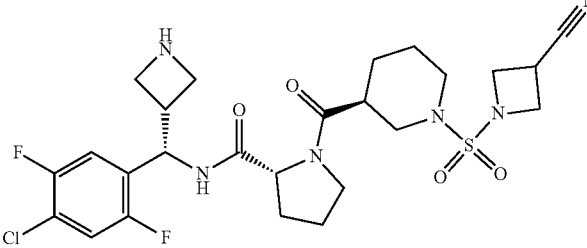<br>N-((S)-3-azetidinyl(4-chloro-2,5-difluorophenyl)methyl)-1-(((3S)-1-((3-cyano-1-azetidinyl)sulfonyl)-3-piperidinyl)carbonyl)-D-prolinamide | LCMS-ESI (POS.) m/z: 585.2 (M + H)+ | 1H NMR (500 MHz, DMSO-d6) δ ppm 7.07-8.78 (m, 3 H), 5.21 (br t, J = 8.43 Hz, 1 H), 4.16-4.50 (m, 1 H), 4.00-4.12 (m, 2 H), 3.88-4.00 (m, 2 H), 3.75-3.86 (m, 1 H), 3.50-3.68 (m, 4 H), 3.12-3.28 (m, 2 H), 2.73-3.01 (m, 3 H), 2.58-2.68 (m, 1 H), 1.58-2.24 (m, 7 H), 0.70-1.55 (m, 4 H) | G |
| 48 | 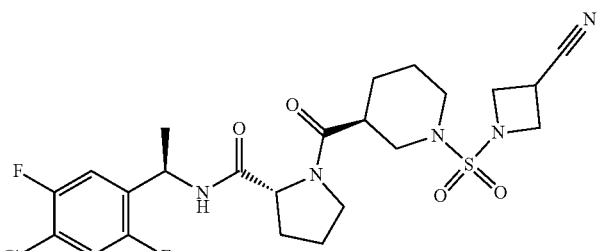<br>N-((1R)-1-(4-chloro-2,5-difluorophenyl)ethyl)-1-(((3S)-1-((3-cyano-1-azetidinyl)sulfonyl)-3-piperidinyl)carbonyl)-D-prolinamide | LCMS-ESI (POS.) m/z: 544.0 (M + H)+ | 1H NMR (500 MHz, DMSO-d6) δ ppm 8.23-8.76 (m, 1 H), 7.24-7.67 (m, 2 H), 4.97-5.16 (m, 1 H), 4.21-4.57 (m, 1 H), 4.01-4.12 (m, 2 H), 3.88-3.99 (m, 2 H), 3.75-3.86 (m, 1 H), 3.49-3.69 (m, 3 H), 3.21-3.44 (m, 3 H), 2.70-2.90 (m, 2 H), 2.60-2.69 (m, 1 H), 2.03-2.38 (m, 1 H), 1.60-1.96 (m, 5 H), 1.27-1.59 (m, 5 H) | A |
| 49 | 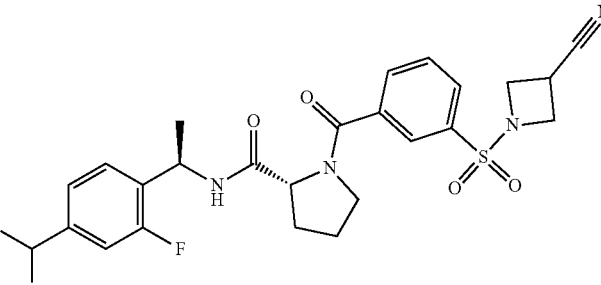<br>1-((3-((3-cyano-1-azetidinyl)sulfonyl)phenyl)carbonyl)-N-((1R)-1-(4-(difluoromethyl)-2-fluorophenyl)ethyl)-D-prolinamide | LCMS-ESI (POS.) m/z: 535.2 (M + H)+ | 1H NMR (500 MHz, CHLOROFORM-d) δ ppm 7.36-8.09 (m, 5 H), 7.30-7.35 (m, 1 H), 7.16-7.28 (m, 1 H), 7.13-7.28 (m, 1 H), 6.76-6.78 (m, 1 H), 6.50-6.77 (m, 1 H), 5.27-5.37 (m, 1 H), 4.67-4.77 (m, 1 H), 4.01-4.22 (m, 4 H), 3.60-3.72 (m, 1 H), 3.44-3.55 (m, 1 H), 3.33-3.44 (m, 1 H), 2.26-2.40 (m, 1 H), 2.07-2.23 (m, 2 H), 1.86-1.99 (m, 1 H), 1.50-1.60 (m, 1 H), 1.34-1.42 (m, 1 H), 1.56 (d, J = 7.01 Hz, 2 H) | A |
| 50 | 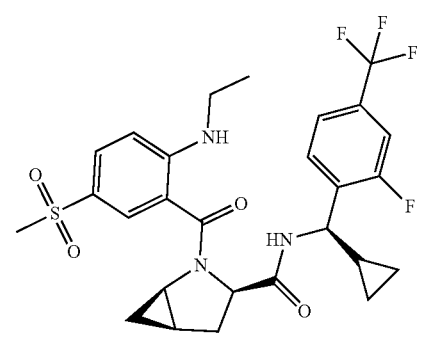 [SMILES: CCNc1ccc(S(C)(=O)=O)cc1C(=O)N1[C@@H](C(=O)N[C@@H](c2ccc(C(F)(F)F)cc2F)C2CC2)C[C@H]2C[C@H]21]<br>(1R,3R,5R)-N-((R)-cyclopropyl(2-fluoro-4-(trifluoromethyl)phenyl)methyl)-2-(2-(ethylamino)-5-(methylsulfonyl)benzoyl)-2-azabicyclo[3.1.0]hexane-3-carboxamide | LCMS-APCI (POS.) m/z: 568.2 (M + H)+ | 1H NMR (400 MHz, DMSO-d6) δ ppm 8.88 (d, J = 7.2 Hz, 1 H), 7.60-7.74 (m, 3 H), 6.79 (d, J = 8.9 Hz, 1 H), 6.66 (t, J = 5.0 Hz, 1 H), 4.93-5.02 (m, 1 H), 4.54 (t, J = 7.8 Hz, 1 H), 3.19 (dd, J = 5.3, 7.3 Hz, 2 H), 3.09 (s, 2 H), 1.79 (d, J = 13.9 Hz, 1 H), 1.53-1.63 (m, 1 H), 1.16-1.25 (m, 1 H), 1.13 (t, J = 7.2 Hz, 2 H), 0.73-0.82 (m, 1 H), 0.53-0.65 (m, 2 H), 0.29-0.53 (m, 3 H). | S |

| Ex. # | Structure Name | LCMS-ESI (POS/NEG) m/z: (M + H)+ | NMR Data | Syn. Rte. |
|---|---|---|---|---|
| 51 | 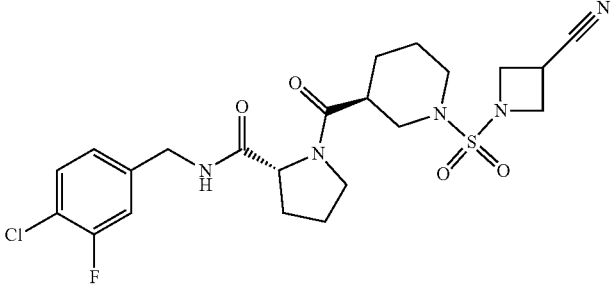 [SMILES: N#CC1CN(S(=O)(=O)N2CCC[C@H](C(=O)N3CCC[C@@H]3C(=O)NCc3ccc(Cl)c(F)c3)C2)C1]<br>N-(4-chloro-3-fluorobenzyl)-1-(((3S)-1-((3-cyano-1-azetidinyl)sulfonyl)-3-piperidinyl)carbonyl)-D-prolinamide | LCMS-ESI (POS.) m/z: 512.2 (M + H)+ | 1H NMR (500 MHz, DMSO-d6) δ ppm 8.29-8.77 (m, 1 H), 7.46-7.58 (m, 1 H), 7.20-7.33 (m, 1 H), 7.06-7.15 (m, 1 H), 4.17-4.53 (m, 3 H), 3.99-4.12 (m, 2 H), 3.86-3.99 (m, 2 H), 3.72-3.85 (m, 1 H), 3.24-3.70 (m, 4 H), 2.71-2.87 (m, 2 H), 2.58-2.70 (m, 1 H), 2.03-2.25 (m, 1 H), 1.66-1.99 (m, 5 H), 1.34-1.55 (m, 2 H) | A |
| 52 | 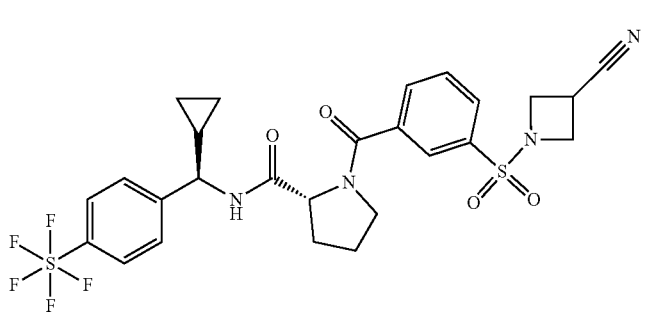 [SMILES: N#CC1CN(S(=O)(=O)c2cccc(C(=O)N3CCC[C@@H]3C(=O)N[C@@H](c3ccc(S(F)(F)(F)(F)F)cc3)C3CC3)c2)C1]<br>1-(3-((3-cyano-1-azetidinyl)sulfonyl)benzoyl)-N-((R)-cyclopropyl(4-(pentafluoro-lambda~6~-sulfanyl)phenyl)methyl)-D-prolinamide | LCMS-ESI (POS.) m/z: 619.0 (M + H)+ | 1H NMR (500 MHz, DMSO-d6) δ ppm 8.46-8.79 (m, 1 H), 7.69-8.00 (m, 6 H), 7.42-7.62 (m, 2 H), 4.25-4.57 (m, 2 H), 3.96-4.05 (m, 2 H), 3.86-3.94 (m, 2 H), 3.57 (br dd, J = 6.94, 5.77 Hz, 1 H), 3.42-3.54 (m, 2 H), 2.18-2.29 (m, 1 H), 1.67-1.87 (m, 3 H), 0.86-1.18 (m, 1 H), −0.10-0.55 (m, 4 H) | A |
| 53 | 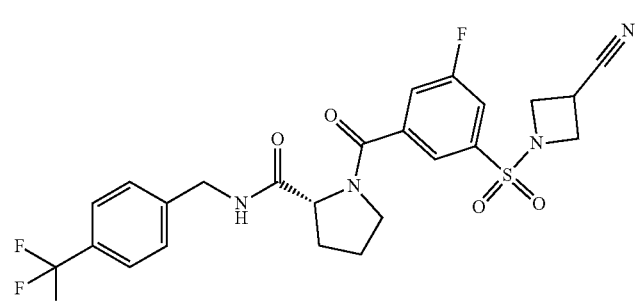<br>1-((3-((3-cyano-1-azetidinyl)sulfonyl)-5-fluorophenyl)carbonyl)-N-(4-(trifluoromethyl)benzyl)-D-prolinamide | LCMS-ESI (POS.) m/z: 539.2 (M + H)+ | 1H NMR (500 MHz, DMSO-d6) δ ppm 8.50-8.68 (m, 1 H), 7.56-7.94 (m, 4 H), 7.17-7.53 (m, 2 H), 4.32-4.55 (m, 3 H), 3.88-4.29 (m, 6 H), 3.45-3.72 (m, 2 H), 2.20-2.32 (m, 1 H), 1.77-1.98 (m, 3 H) | C |
| 54 | 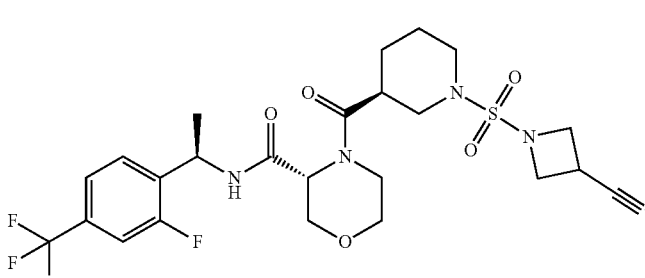<br>(3R)-4-(((3S)-1-((3-cyano-1-azetidinyl)sulfonyl)-3-piperidinyl)carbonyl)-N-((1R)-1-(2-fluoro-4-(trifluoromethyl)phenyl)ethyl)-3-morpholinecarboxamide | LCMS-ESI (POS.) m/z: 598.2 (M + Na)+ | 1H NMR (500 MHz, DMSO-d6) δ ppm 8.52-8.72 (m, 1 H), 7.51-7.68 (m, 3 H), 5.06-5.28 (m, 1 H), 4.51-4.77 (m, 1 H), 4.24-4.47 (m, 1 H), 3.24-4.10 (m, 11 H), 2.68-2.98 (m, 3 H), 2.51-2.58 (m, 1 H), 1.76-1.92 (m, 1 H), 1.28-1.75 (m, 6 H) | C |

| Ex. # | Structure Name | LCMS-ESI (POS/NEG) m/z: (M + H)+ | NMR Data | Syn. Rte. |
|---|---|---|---|---|
| 55 | 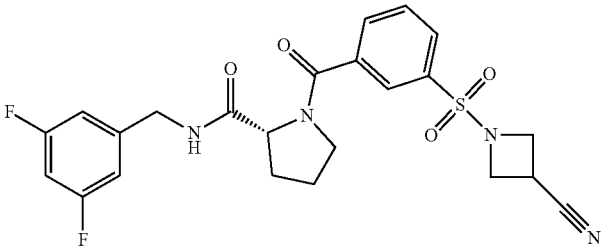 [SMILES: N#CC1CN(S(=O)(=O)c2cccc(C(=O)N3CCC[C@@H]3C(=O)NCc3cc(F)cc(F)c3)c2)C1]<br>1-(3-((3-cyano-1-azetidinyl)sulfonyl)benzoyl)-N-(3,5-difluorobenzyl)-D-prolinamide | LCMS-ESI (POS.) m/z: 489.2 (M + H)+ | 1H NMR (500 MHz, DMSO-d6) δ ppm 8.45-8.68 (m, 1 H), 7.63-8.05 (m, 4 H), 6.70-7.13 (m, 3 H), 4.10-4.56 (m, 3 H), 3.81-4.08 (m, 4 H), 3.44-3.69 (m, 3 H), 2.19-2.33 (m, 1 H), 1.77-1.97 (m, 3 H) | A |
| 56 | 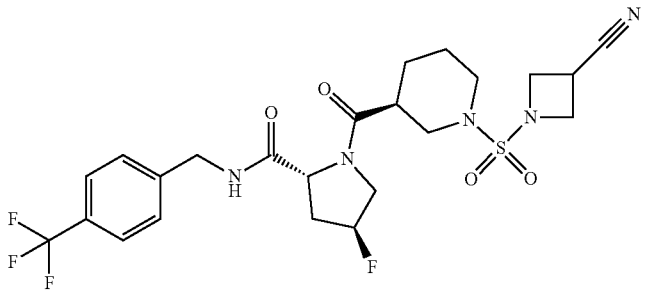 [SMILES: N#CC1CN(S(=O)(=O)N2CCC[C@H](C(=O)N3C[C@@H](F)C[C@@H]3C(=O)NCc3ccc(C(F)(F)F)cc3)C2)C1]<br>(4S)-1-(((3S)-1-((3-cyano-1-azetidinyl)sulfonyl)-3-piperidinyl)carbonyl)-4-fluoro-N-(4-(trifluoromethyl)benzyl)-D-prolinamide | LCMS-ESI (POS.) m/z: 546.2 (M + H)+ | 1H NMR (500 MHz, CHLOROFORM-d) δ ppm 7.59 (s, 1 H), 7.57 (s, 1 H), 7.38 (s, 1 H), 7.37 (s, 1 H), 5.26-5.43 (m, 1 H), 4.73 (t, J = 7.79 Hz, 1 H), 4.52-4.59 (m, 1 H), 4.39-4.46 (m, 1 H), 4.07-4.15 (m, 4 H), 4.00 (br dd, J = 18.94, 12.98 Hz, 1 H), 3.78 (br t, J = 12.85 Hz, 2 H), 3.57-3.72 (m, 1 H), 3.39-3.50 (m, 1 H), 2.88-2.97 (m, 1 H), 2.66-2.83 (m, 3 H), 2.34-2.44 (m, 1 H), 1.88 (br d, J = 12.85 Hz, 1 H), 1.80 (br d, J = 13.10 Hz, 1 H), 1.58-1.70 (m, 1 H), 1.50-1.58 (m, 1 H), 1.37-1.48 (m, 1 H) | M |
| 57 | 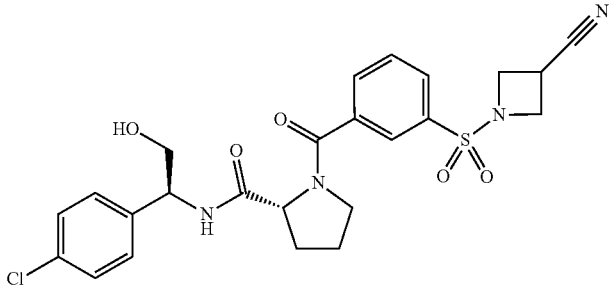 [SMILES: N#CC1CN(S(=O)(=O)c2cccc(C(=O)N3CCC[C@@H]3C(=O)N[C@H](CO)c3ccc(Cl)cc3)c2)C1]<br>N-((1S)-1-(4-chlorophenyl)-2-hydroxyethyl)-1-(3-((3-cyano-1-azetidinyl)sulfonyl)benzoyl)-D-prolinamide | LCMS-ESI (POS.) m/z: 517.2 (M + H)+ | 1H NMR (500 MHz, DMSO-d6) δ ppm 8.20-8.48 (m, 1 H), 7.20-8.03 (m, 8 H), 4.82-4.87 (m, 1 H), 4.56 (br d, J = 5.19 Hz, 1 H), 4.30-4.36 (m, 1 H), 3.85-4.07 (m, 4 H), 3.31-3.72 (m, 5 H), 2.18-2.29 (m, 1 H), 1.62-1.92 (m, 3 H) | A |
| 58 | 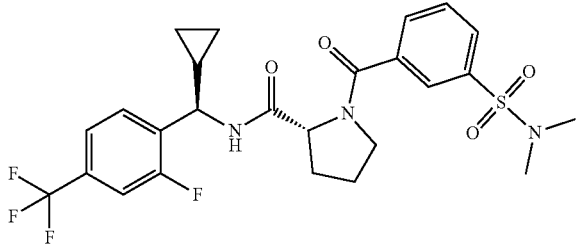 [SMILES: CN(C)S(=O)(=O)c1cccc(C(=O)N2CCC[C@@H]2C(=O)N[C@@H](c2ccc(C(F)(F)F)cc2F)C2CC2)c1]<br>N-((R)-cyclopropyl(2-fluoro-4-(trifluoromethyl)phenyl)methyl)-1-(3-(dimethylsulfamoyl)benzoyl)-D-prolinamide | LCMS-ESI (POS.) m/z: 542.2 (M + H)+ | 1H NMR (500 MHz, DMSO-d6) δ ppm 8.46-8.82 (m, 1 H), 7.43-7.97 (m, 7 H), 4.13-4.67 (m, 2 H), 3.41-3.65 (m, 2 H), 2.56-2.69 (m, 6 H), 2.16-2.33 (m, 1 H), 1.58-1.94 (m, 3 H), 1.14-1.30 (m, 1 H), −0.06-0.64 (m, 4 H) | A |

| Ex. # | Structure Name | LCMS-ESI (POS/NEG) m/z: (M + H)+ | NMR Data | Syn. Rte. |
|---|---|---|---|---|
| 59 | 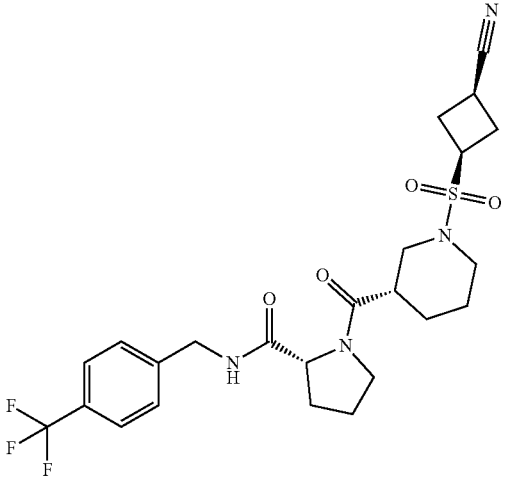 [SMILES: N#C[C@H]1C[C@@H](S(=O)(=O)N2CCC[C@H](C(=O)N3CCC[C@@H]3C(=O)NCc3ccc(C(F)(F)F)cc3)C2)C1]<br>1-(((3S)-1-((cis-3-cyanocyclobutyl)sulfonyl)-3-piperidinyl)carbonyl)-N-(4-(trifluoromethyl)benzyl)-D-prolinamide | LCMS-APCI (POS.) m/z: 527.2 (M + H)+ | $^1$H NMR (Methanol-d$_4$) δ: 7.74-7.59 (m, 2 H), 7.59-7.42 (m, 2 H), 4.70-4.52 (m, 1 H), 4.52-4.40 (m, 2 H), 4.12-3.89 (m, 1 H), 3.89-3.68 (m, 3 H), 3.39-3.31 (m, 3 H), 2.96-2.65 (m, 7 H), 2.34-2.22 (m, 1 H), 2.19-1.88 (m, 4 H), 1.90-1.76 (m, 1 H), 1.72-1.49 (m, 2 H) | R |
| 60 | 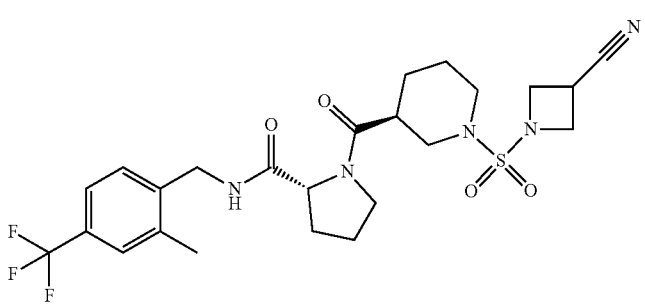<br>1-(((3S)-1-((3-cyano-1-azetidinyl)sulfonyl)-3-piperidinyl)carbonyl)-N-(2-methyl-4-(trifluoromethyl)benzyl)-D-prolinamide | LCMS-ESI (POS.) m/z: 542.2 (M + H)+ | 1H NMR (500 MHz, DMSO-d6) δ ppm 8.28 (br t, J = 5.77 Hz, 1 H), 7.27-7.60 (m, 3 H), 4.20-4.56 (m, 3 H), 4.00-4.15 (m, 2 H), 3.87-3.98 (m, 2 H), 3.74-3.86 (m, 1 H), 3.42-3.73 (m, 4 H), 2.72-2.91 (m, 2 H), 2.59-2.71 (m, 1 H), 2.30-2.38 (m, 3 H), 2.04-2.23 (m, 1 H), 1.64-2.01 (m, 5 H), 1.33-1.56 (m, 2 H) | A |
| 61 | 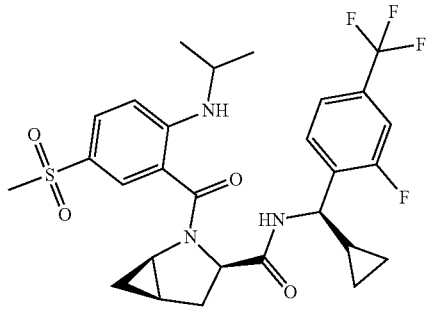<br>(1R,3R,5R)-N-((R)-cyclopropyl(2-fluoro-4-(trifluoromethyl)phenyl)methyl)-2-(5-(methylsulfonyl-2-(2-propanylamino)benzoyl)-2-azabicyclo[3.1.0]hexane-3-carboxamide | LCMS-APCI (POS.) m/z: 582.2 (M + H)+ | $^1$H NMR (400 MHz, DMSO-d$_6$) δ ppm 8.91 (d, J = 6.8 Hz, 1 H), 7.55-7.74 (m, 4 H), 6.80 (d, J = 9.6 Hz, 1 H), 6.58 (d, J = 7.5 Hz, 1 H), 4.93-5.02 (m, 1 H), 4.50 (t, J = 7.8 Hz, 1 H), 3.74 (q, J = 6.5 Hz, 2 H), 3.09 (s, 3 H), 1.83 (d, J = 14.1 Hz, 2 H), 1.50-1.62 (m, 2 H), 1.17-1.29 (m, 2 H), 1.11 (dd, J = 6.3, 14.4 Hz, 4 H), 0.69-0.77 (m, 1 H), 0.25-0.65 (m, 6 H). | S |

| Ex. # | Structure Name | LCMS-ESI (POS/NEG) m/z: (M + H)+ | NMR Data | Syn. Rte. |
|---|---|---|---|---|
| 62 | 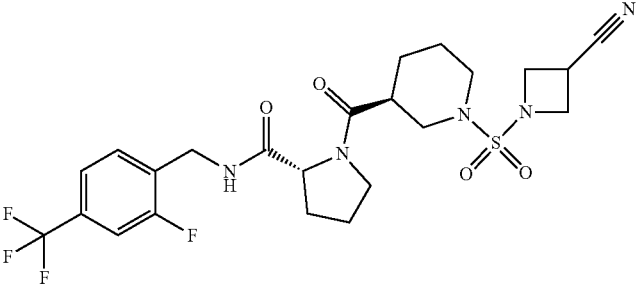<br>1-(((3S)-1-((3-cyano-1-azetidinyl)sulfonyl)-3-piperidinyl)carbonyl)-N-(2-fluoro-4-(trifluoromethyl)benzyl)-D-prolinamide | LCMS-ESI (POS.) m/z: 546.2 (M + H)+ | 1H NMR (500 MHz, CHLOROFORM-d) δ ppm 7.36-7.45 (m, 2 H), 7.29-7.34 (m, 1 H), 4.43-4.62 (m, 3 H), 4.04-4.15 (m, 4 H), 3.77 (br d, J = 12.20 Hz, 2 H), 3.50-3.70 (m, 2 H), 3.37-3.48 (m, 1 H), 2.87-3.03 (m, 1 H), 2.64-2.84 (m, 2 H), 2.41 (ddd, J = 9.44, 6.52, 3.37 Hz, 1 H), 2.12-2.23 (m, 2 H), 2.04 (dddd, J = 12.91, 9.76, 6.46, 6.29 Hz, 1 H), 1.78-1.97 (m, 3 H), 1.50-1.71 (m, 2 H) | C |
| 63 | 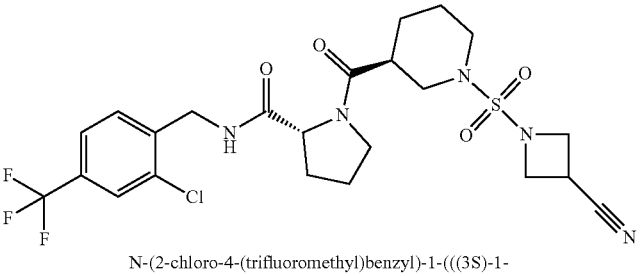<br>N-(2-chloro-4-(trifluoromethyl)benzyl)-1-(((3S)-1-((3-cyano-1-azetidinyl)sulfonyl)-3-piperidinyl)carbonyl)-D-prolinamide | LCMS-ESI (POS.) m/z: 562.2 (M + H)+ | 1H NMR (400 MHz, CHLOROFORM-d) δ ppm 7.60-7.68 (m, 1 H), 7.43-7.58 (m, 3 H), 4.43-4.65 (m, 3 H), 4.06-4.18 (m, 4 H), 3.72-3.82 (m, H), 3.52-3.64 (m, 2 H), 3.43 (tt, J = 8.71, 6.53 Hz, 1 H), 2.98 (dd, J = 12.70, 11.04 Hz, 1 H), 2.65-2.83 (m, 2 H), 2.44 (ddt, J = 12.21, 6.19, 3.03, 3.03 Hz, 1 H), 2.10-2.23 (m, 1 H), 1.99-2.10 (m, 1 H), 1.78-1.97 (m, 3 H), 1.62-1.75 (m, 1 H), 1.49-1.59 (m, 1 H) | A |
| 64 | 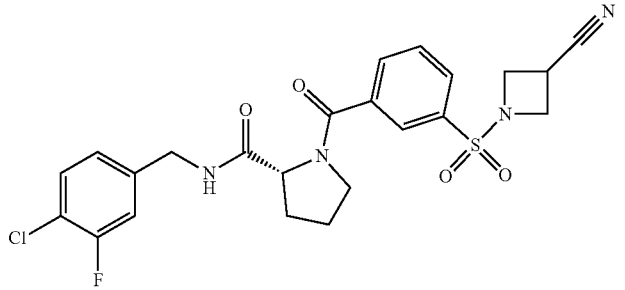 [SMILES: N#CC1CN(S(=O)(=O)c2cccc(C(=O)N3CCC[C@@H]3C(=O)NCc3ccc(Cl)c(F)c3)c2)C1]<br>N-(4-chloro-3-fluorobenzyl)-1-((3-((3-cyano-1-azetidinyl)sulfonyl)phenyl)carbonyl)-D-prolinamide | LCMS-ESI (POS.) m/z: 505.2 (M + H)+ | 1H NMR (500 MHz, DMSO-d6) δ ppm 8.63 (t, J = 6.03 Hz, 1 H), 7.66-8.04 (m, 4 H), 7.51 (d, J = 8.04 Hz, 1 H), 7.17 (s, 2 H), 4.28-4.54 (m, 3 H), 4.11 (br dd, J = 17.00, 5.71 Hz, 1 H), 3.84-3.94 (m, 3 H), 3.57-3.71 (m, 2 H), 3.40-3.52 (m, 1 H), 2.18-2.34 (m, 1 H), 1.73-1.97 (m, 3 H) | A |
| 65 | 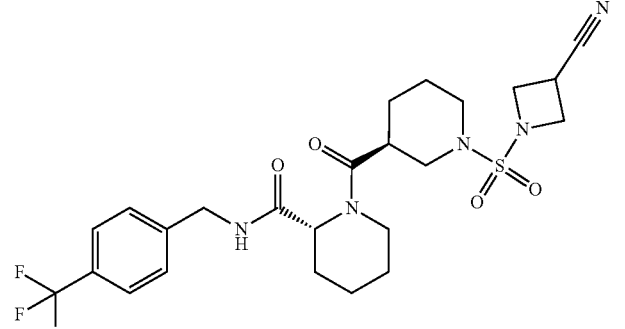<br>(2R)-1-(((3S)-1-((3-cyano-1-azetidinyl)sulfonyl)-3-piperidinyl)carbonyl)-N-(4-(trifluoromethyl)benzyl)-2-piperidinecarboxamide | LCMS-ESI (POS.) m/z: 564.0 (M + Na)+ | 1H NMR (500 MHz, DMSO-d6) δ ppm 8.65-8.70* (m, 1 H), 8.38 (br t, J = 6.23 Hz, 1 H), 7.69 (br d, J = 8.17 Hz, 2 H), 7.42-7.49 (m, 2 H), 5.05 (br d, J = 4.93 Hz, 1 H), 4.69-4.74* (m, 1 H), 4.29-4.42 (m, 2 H), 4.02-4.08 (m, 2 H), 3.89-3.95 (m, 2 H), 3.72-3.87 (m, 2 H), 3.50-3.65 (m, 2 H), 3.25-3.30 (m, 1 H), 2.60-2.96 (m, 3 H), 2.25-2.32* (m, 1 H), 2.14 (br dd, J = 13.56, 2.66 Hz, 1 H), 1.48-1.89 (m, 6 H), 1.17-1.46 (m, 3 H). Spectrum appears as 2:1 mixture of rotamers, *denotes resolved minor rotamer peaks. | M |

| Ex. # | Structure Name | LCMS-ESI (POS/NEG) m/z: (M + H)+ | NMR Data | Syn. Rte. |
|---|---|---|---|---|
| 66 | 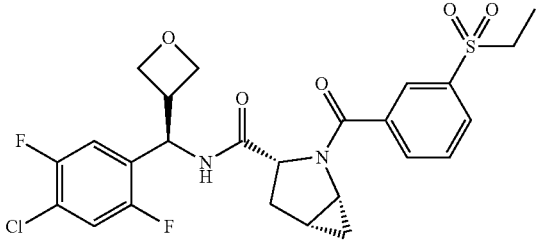 [SMILES: CCS(=O)(=O)c1cccc(C(=O)N2[C@@H](C(=O)N[C@@H](c3cc(F)c(Cl)cc3F)C3COC3)C[C@H]3C[C@H]32)c1]<br>(1R,3R,5R)-N-((R)-(4-chloro-2,5-difluorophenyl)(3-oxetanyl)methyl)-2-(3-(ethylsulfonyl)benzoyl)-2-azabicyclo[3.1.0]hexane-3-carboxamide | LCMS-APCI (POS.) m/z: 539.1 (M + H)+ | $^1$H NMR (400 MHz, Methanol-$d_4$) δ ppm 8.34 (t, J = 1.7 Hz, 1 H), 8.13 (dt, J = 1.3, 7.7 Hz, 1 H), 8.07 (ddd, J = 1.1, 1.9, 7.9 Hz, 1 H), 7.79 (t, J = 7.8 Hz, 1 H), 7.39 (dd, J = 6.1, 9.4 Hz, 1 H), 7.27 (dd, J = 6.3, 9.4 Hz, 1 H), 5.57 (d, J = 10.2 Hz, 1 H), 4.99 (dd, J = 4.3, 11.4 Hz, 1 H), 4.84 (dd, J = 6.5, 7.6 Hz, 1 H), 4.67 (dd, J = 6.4, 7.8 Hz, 1 H), 4.60 (t, J = 6.2 Hz, 1 H), 4.38 (t, J = 0.8, 12.5 Hz, 1 H), 3.51 (dddd, J = 5.0, 6.3, 7.8, 16.6 Hz, 1 H), 3.37 (s, 2 H), 3.24-3.32 (m, 3 H), 2.67 (dddd, J = 1.1, 6.5, 11.7, 13.3 Hz, 1 H), 1.90 (dd, J = 4.2, 13.5 Hz, 1 H), 1.76-1.85 (m, 1 H), 1.22-1.31 (m, 4 H), 0.90 (dtd, J = 1.1, 5.7, 9.0 Hz, 1 H). | A |
| 67 | 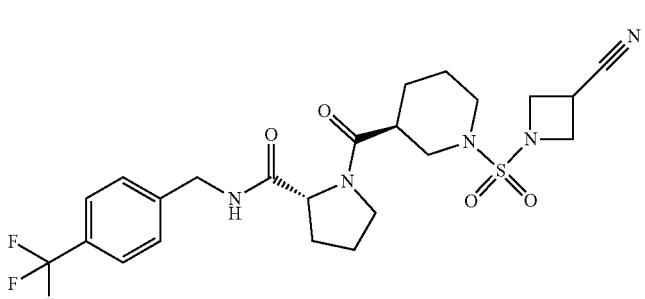<br>1-(((3S)-1-((3-cyano-1-azetidinyl)sulfonyl)-3-piperidinyl)carbonyl)-N-(4-(trifluoromethyl)benzyl)-D-prolinamide | LCMS-ESI (POS.) m/z: 528.2 (M + H)+ | 1H NMR (500 MHz, DMSO-$d_6$) δ ppm 8.72* (t, J = 5.81 Hz, 1 H), 8.36 (t, J = 6.07 Hz, 1 H), 7.65-7.71 (m, 2 H), 7.45 (br d, J = 7.85 Hz, 2 H), 4.28-4.50 (m, 3 H), 4.03-4.10 (m, 2 H), 3.90-3.98 (m, 2 H), 3.75-3.83 (m, 1 H), 3.34-3.68 (m, 4 H), 2.73-2.87 (m, 2 H), 2.64-2.70 (m, 1 H), 2.28-2.35* (m, 1 H), 2.18-2.26* (m, 1 H), 2.05-2.15 (m, 1 H), 1.68-1.98 (m, 5 H), 1.37-1.54 (m, 2 H). Spectrum appears as 2:1 mixture of rotamers, *denotes resolved minor rotamer peaks. | M |
| 68 | 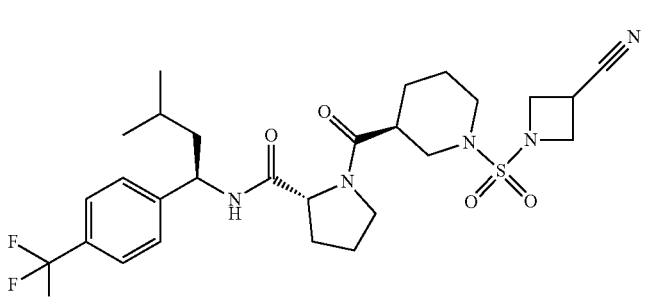<br>1-(((3S)-1-((3-cyano-1-azetidinyl)sulfonyl)-3-piperidinyl)carbonyl)-N-((1R)-3-methyl-1-(4-(trifluoromethyl)phenyl)butyl)-D-prolinamide | LCMS-ESI (POS.) m/z: 584.2 (M + H)+ | 1H NMR (500 MHz, DMSO-$d_6$) δ ppm 8.12-8.75 (m, 1 H), 7.60-7.75 (m, 2 H), 7.42-7.56 (m, 2 H), 4.82-4.97 (m, 1 H), 4.30-4.43 (m, 1 H), 4.02-4.10 (m, 2 H), 3.91-3.98 (m, 2 H), 3.75-3.84 (m, 1 H), 3.32-3.63 (m, 4 H), 2.87 (s, 2 H), 2.02-2.22 (m, 1 H), 1.30-1.92 (m, 11 H), 0.80-0.95 (m, 6 H) | A |

| Ex. # | Structure Name | LCMS-ESI (POS/NEG) m/z: (M + H)+ | NMR Data | Syn. Rte. |
|---|---|---|---|---|
| 69 | N-((1R)-1-(4-chloro-3-fluorophenyl)ethyl)-1-(((3S)-1-((3-cyano-1-azetidinyl)sulfonyl)-3-piperidinyl)carbonyl)-D-prolinamide | LCMS-ESI (POS.) m/z: 526.2 (M + H)+ | 1H NMR (500 MHz, DMSO-d6) δ ppm 8.64* (d, J = 7.66 Hz, 1 H), 8.19-8.27 (m, 1 H), 7.48-7.56 (m, 1 H), 7.29 (br d, J = 11.16 Hz, 1 H), 7.11-7.16 (m, 1 H), 4.83-4.94 (m, 1 H), 4.41-4.49* (m, 1 H), 4.19-4.28 (m, 1 H), 4.02-4.09 (m, 2 H), 3.90-3.98 (m, 2 H), 3.76-3.84 (m, 1 H), 3.29-3.64 (m, 4 H), 2.74-2.84 (m, 2 H), 2.61-2.68 (m, 1 H), 2.26-2.35* (m, 1 H), 2.16-2.26* (m, 1 H), 2.02-2.15 (m, 1 H), 1.64-1.91 (m, 5 H), 1.37-1.54 (m, 2 H), 1.34-1.37* (m, 3 H), 1.30-1.34 (m, 3 H). Spectrum appears as 3:1 mixture of rotamers, *denotes resolved minor rotamer peaks. | C |
| 70 | N-(4-chloro-2-fluorobenzyl)-1-(((3S)-1-((3-cyano-1-azetidinyl)sulfonyl)-3-piperidinyl)carbonyl)-D-prolinamide | LCMS-ESI (POS.) m/z: 512.2 (M + H)+ | 1H NMR (500 MHz, CHLOROFORM-d) δ ppm 7.28-7.38 (m, 1 H), 7.20-7.26 (m, 1 H), 7.04-7.13 (m, 2 H), 4.56 (dd, J = 8.04, 1.95 Hz, 1 H), 4.35-4.46 (m, 2 H), 4.06-4.14 (m, 4 H), 3.69-3.79 (m, 2 H), 3.51-3.62 (m, 2 H), 3.39-3.47 (m, 1 H), 2.89-3.01 (m, 1 H), 2.65-2.80 (m, 2 H), 2.35-2.46 (m, 1 H), 2.09-2.27 (m, 1 H), 1.98-2.07 (m, 1 H), 1.77-1.95 (m, 3 H), 1.49-1.71 (m, 2 H) | A |
| 71 | N-((1R)-1-(4-chlorophenyl)ethyl)-1-((3-((3-cyano-1-azetidinyl)sulfonyl)phenyl)carbonyl)-D-prolinamide | LCMS-APCI (NEG.) m/z: 499.1 (M − H) | ¹H NMR (400 MHz, Methanol-d₄) δ ppm 8.05-8.18 (m, 1 H), 7.92-8.04 (m, 2 H), 7.74-7.80 (m, 1 H), 7.32 (s, 4 H), 5.02 (td, J = 5.9, 8.3, 9.4 Hz, 1 H), 4.58 (dd, J = 5.8, 8.3 Hz, 1 H), 4.07-4.13 (m, 2 H), 3.90-3.96 (m, 2 H), 3.47-3.58 (m, 2 H), 2.26-2.37 (m, 1 H), 1.85-1.99 (m, 3 H), 1.49 (d, J = 7.1 Hz, 3 H). | A |
| 72 | 1-(((3S)-1-((3-(methylsulfonyl)-1-azetidinyl)sulfonyl)-3-piperidinyl)carbonyl)-N-(4-(trifluoromethyl)benzyl)-D-prolinamide | LCMS-ESI (POS.) m/z: 581.2 (M + H)+ | 1H NMR (500 MHz, CHLOROFORM-d) δ ppm 7.57 (br d, J = 8.04 Hz, 2 H), 7.44 (br s, 1 H), 7.35 (d, J = 8.04 Hz, 2 H), 4.60 (br d, J = 6.49 Hz, 1 H), 4.37-4.55 (m, 2 H), 4.12-4.26 (m, 5 H), 3.89-3.98 (m, H), 3.78 (br d, J = 12.46 Hz, 3 H), 3.54-3.64 (m, 2 H), 2.91-3.05 (m, 4 H), 2.66-2.89 (m, 2 H), 2.45 (ddd, J = 9.28, 6.29, 3.37 Hz, 2 H), 2.09-2.27 (m, 1 H), 1.99-2.09 (m, 1 H), 1.74-1.96 (m, 3 H), 1.45-1.72 (m, 4 H) | M |

-continued

| Ex. # | Structure Name | LCMS-ESI (POS/NEG) m/z: (M + H)+ | NMR Data | Syn. Rte. |
|---|---|---|---|---|
| 73 | 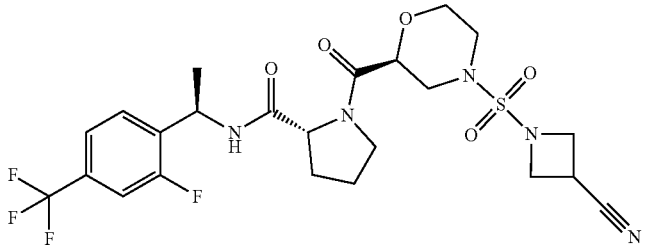 [SMILES: C[C@@H](NC(=O)[C@H]1CCCN1C(=O)[C@@H]1CN(S(=O)(=O)N2CC(C#N)C2)CCO1)c1ccc(C(F)(F)F)cc1F]<br>1-(((2S)-4-((3-cyano-1-azetidinyl)sulfonyl)-2-morpholinyl)carbonyl)-N-((1R)-1-(2-fluoro-4-(trifluoromethyl)phenyl)ethyl)-D-prolinamide | LCMS-ESI (POS.) m/z: 562.2 (M + H)+ | 1H NMR (500 MHz, DMSO-d6) δ ppm 8.54-8.80 (m, 1 H), 7.51-7.66 (m, 3 H), 5.03-5.23 (m, 1 H), 4.22-4.37 (m, 1 H), 4.08-4.16 (m, 2 H), 3.99 (td, J = 8.14, 6.16 Hz, 2 H), 3.88-3.95 (m, 1 H), 3.77-3.86 (m, 1 H), 3.25-3.64 (m, 5 H), 2.89-3.11 (m, 2 H), 2.03-2.28 (m, 2 H), 1.58-1.90 (m, 3 H), 1.34-1.43 (m, 3 H) | C |
| 74 | 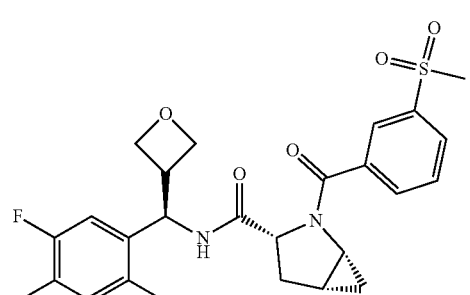<br>(1R,3R,5R)-N-((R)-(4-chloro-2,5-difluorophenyl)(3-oxetanyl)methyl)-2-(3-(methylsulfonyl)benzoyl)-2-azabicyclo[3.1.0]hexane-3-carboxamide | LCMS-APCI (POS.) m/z: 525.1 (M + H)+ | ¹H NMR (400 MHz, Methanol-d₄) δ ppm 8.39 (t, J = 1.6 Hz, 1 H), 8.09-8.15 (m, 2 H), 7.79 (t, 1 H), 7.39 (dd, J = 6.1, 9.4 Hz, 1 H), 7.27 (dd, J = 6.3, 9.4 Hz, 1 H), 5.57 (d, J = 10.2 Hz, 1 H), 4.99 (dd, J = 4.2, 11.4 Hz, 1 H), 4.84 (dd, J = 6.5, 7.6 Hz, 1 H), 4.67 (dd, J = 6.5, 7.8 Hz, 1 H), 4.60 (t, J = 6.2 Hz, 1 H), 4.38 (t, J = 6.2 Hz, 1 H), 3.46-3.56 (m, 1 H), 3.37 (s, 1 H), 3.19 (s, 3 H), 2.67 (dddd, J = 1.1, 6.5, 11.7, 13.5 Hz, 1 H), 1.91 (dd, 1 H), 1.76-1.85 (m, 1 H), 1.27 (td, J = 2.6, 5.3 Hz, 1 H), 0.91 (dtd, J = 1.1, 5.7, 9.0 Hz, 1 H). | A |
| 75 | 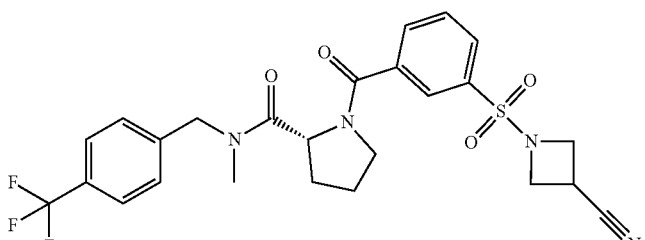<br>1-((3-((3-cyano-1-azetidinyl)sulfonyl)phenyl)carbonyl)-N-methyl-N-(4-(trifluoromethyl)benzyl)-D-prolinamide | LCMS-ESI (POS.) m/z: 535.2 (M + Na)+ | 1H NMR (400 MHz, CHLOROFORM-d) δ ppm 7.36-8.24 (m, 8 H), 4.77-5.12 (m, 2 H), 4.46-4.73 (m, 1 H), 3.98-4.17 (m, 4 H), 3.70-3.85 (m, 1 H), 3.45-3.64 (m, 1 H), 3.26-3.42 (m, 1 H), 3.15 (s, 2 H), 3.03 (s, 1 H), 1.76-2.49 (m, 4 H) | C |
| 76 | 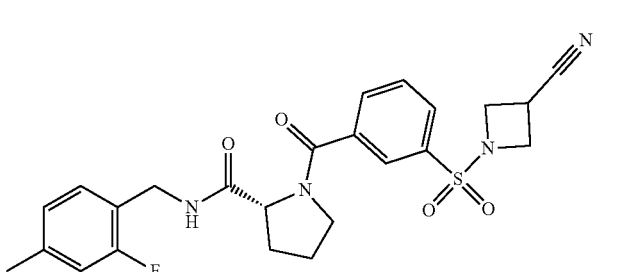<br>1-((3-((3-cyano-1-azetidinyl)sulfonyl)phenyl)carbonyl)-N-(2-fluoro-4-methylbenzyl)-D-prolinamide | LCMS-ESI (POS.) m/z: 485.2 (M + H)+ | 1H NMR (500 MHz, CHLOROFORM-d) δ ppm 8.03-8.09 (m, 1 H), 8.00-8.09 (m, 1 H), 7.96-8.03 (m, 1 H), 7.95-8.00 (m, 1 H), 7.84-7.93 (m, 1 H), 7.68-7.79 (m, 1 H), 7.21-7.29 (m, 1 H), 7.03-7.12 (m, 1 H), 6.88-7.01 (m, 2 H), 4.69-4.82 (m, 1 H), 4.47-4.61 (m, 2 H), 4.12-4.22 (m, 2 H), 4.03-4.11 (m, 2 H), 3.58-3.73 (m, 1 H), 3.45-3.56 (m, 1 H), 3.31-3.45 (m, 1 H), 2.32-2.50 (m, 4 H), 2.11-2.24 (m, 2 H), 1.87-2.00 (m, 1 H) | A |

-continued

| Ex. # | Structure Name | LCMS-ESI (POS/NEG) m/z: (M + H)+ | NMR Data | Syn. Rte. |
|---|---|---|---|---|
| 77 | 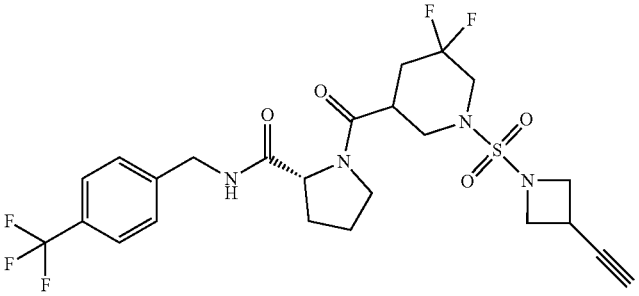 [SMILES: C#CC1CN(S(=O)(=O)N2CC(C(=O)N3CCC[C@@H]3C(=O)NCc3ccc(C(F)(F)F)cc3)CC(F)(F)C2)C1]<br>1-((-1-((3-cyano-1-azetidinyl)sulfonyl)-5,5-difluoro-3-piperidinyl)carbonyl)-N-(4-(trifluoromethyl)benzyl)-D-prolinamide | LCMS-ESI (POS.) m/z: 564.2 (M + H)+ | 1H NMR (500 MHz, CHLOROFORM-d) δ ppm 7.60 (t, J = 7.27 Hz, 2 H), 7.28-7.42 (m, 2 H), 7.09 (br d, J = 5.71 Hz, 1 H), 4.40-4.56 (m, 3 H), 4.00-4.19 (m, 6 H), 3.83 (br d, J = 12.98 Hz, 1 H), 3.55-3.76 (m, 3 H), 3.31-3.50 (m, 1 H), 2.94-3.14 (m, 3 H), 2.82-2.94 (m, 1 H), 1.89-2.54 (m, 6 H) | M |
| 78 | 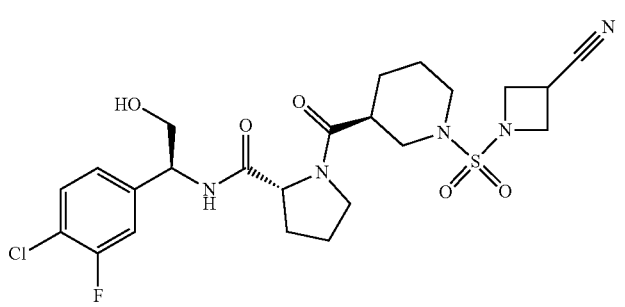 [SMILES: N#CC1CN(S(=O)(=O)N2CCC[C@H](C(=O)N3CCC[C@@H]3C(=O)N[C@H](CO)c3ccc(Cl)c(F)c3)C2)C1]<br>N-((1S)-1-(4-chloro-3-fluorophenyl)-2-hydroxyethyl)-1-(((3S)-1-((3-cyano-1-azetidinyl)sulfonyl)-3-piperidinyl)carbonyl)-D-prolinamide | LCMS-ESI (POS.) m/z: 542.2 (M + H)+ | 1H NMR (500 MHz, DMSO-d6) δ ppm 8.14-8.67 (m, 1 H), 7.17-7.53 (m, 3 H), 4.97-5.10 (m, 1 H), 4.24-4.56 (m, 1 H), 3.98-4.12 (m, 2 H), 3.89-3.98 (m, 2 H), 3.74-3.86 (m, 1 H), 3.27-3.67 (m, 6 H), 2.55-2.89 (m, 3 H), 1.21-2.33 (m, 9 H) | A |
| 79 | 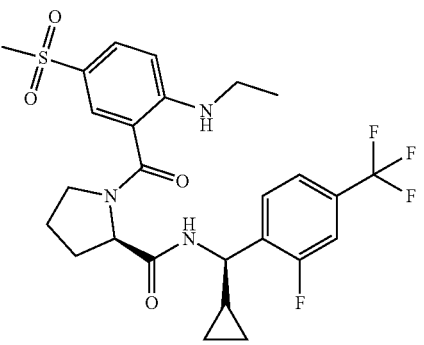 [SMILES: CCNc1ccc(S(C)(=O)=O)cc1C(=O)N1CCC[C@@H]1C(=O)N[C@@H](c1ccc(C(F)(F)F)cc1F)C1CC1]<br>N-((R)-cyclopropyl(2-fluoro-4-(trifluoromethyl)phenyl)methyl)-1-(2-(ethylamino)-5-(methylsulfonyl)benzoyl)-D-prolinamide | LCMS-APCI (POS.) m/z: 556.2 (M + H)+ | 1H NMR (400 MHz, DMSO-d6) δ ppm 8.92 (d, J = 7.5 Hz, 1 H), 7.61-7.75 (m, 3 H), 7.53 (s, 1 H), 6.78 (d, J = 8.9 Hz, 1 H), 6.61 (t, 1 H), 4.56-4.64 (m, 2 H), 3.13-3.31 (m, 5 H), 3.10 (s, 2 H), 2.19-2.30 (m, 2 H), 1.73 (s, 3 H), 1.19-1.28 (m, 1 H), 1.14 (t, J = 7.1 Hz, 3 H), 0.56-0.65 (m, 1 H), 0.44-0.52 (m, 1 H), 0.32-0.43 (m, 2 H). | S |
| 80 | 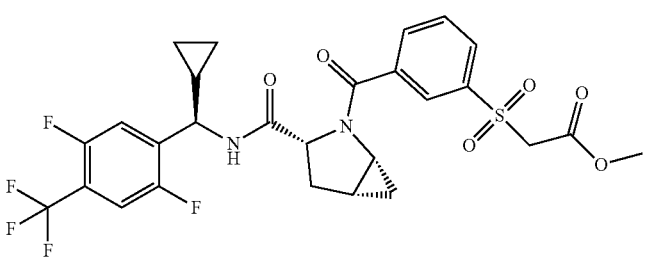 [SMILES: COC(=O)CS(=O)(=O)c1cccc(C(=O)N2[C@@H](C(=O)N[C@@H](c3cc(F)c(C(F)(F)F)cc3F)C3CC3)C[C@H]3C[C@H]32)c1]<br>methyl ((3-(((1R,3R,5R)-3-(((R)-cyclopropyl(2,5-difluoro-4-(trifluoromethyl)phenyl)methyl)carbamoyl)-2-azabicyclo[3.1.0]hexan-2-yl)carbonyl)phenyl)sulfonyl)acetate | LCMS-ESI (POS.) m/z: 601.2 (M + H)+ | 1H NMR (500 MHz, DMSO-d6) δ ppm 8.35-8.79 (m, 1 H), 8.18 (s, 1 H), 7.94-8.10 (m, 2 H), 7.65-7.87 (m, 2 H), 7.36-7.64 (m, 1 H), 4.47-5.06 (m, 4 H), 3.52-4.19 (m, 3 H), 3.23 (td, J = 6.16, 2.47 Hz, 1 H), 2.52-2.76 (m, 1 H), 1.51-1.83 (m, 2 H), 1.06-1.40 (m, 6 H), −0.24-0.98 (m, 7 H) | C |

-continued

| Ex. # | Structure Name | LCMS-ESI (POS/NEG) m/z: (M + H)+ | NMR Data | Syn. Rte. |
|---|---|---|---|---|
| 81 | 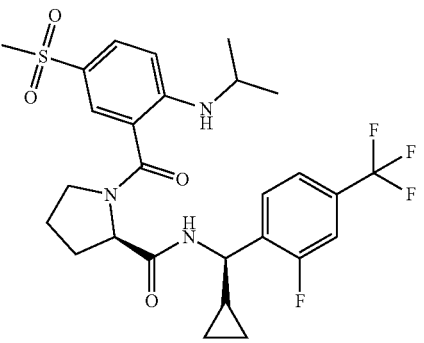 [SMILES: CC(C)Nc1ccc(S(C)(=O)=O)cc1C(=O)N1CCC[C@@H]1C(=O)N[C@@H](c1ccc(C(F)(F)F)cc1F)C1CC1]<br>N-((R)-cyclopropyl(2-fluoro-4-(trifluoromethyl)phenyl)methyl)-1-(5-(methylsulfonyl)-2-(2-propanylamino)benzoyl)-D-prolinamide | LCMS-APCI (POS.) m/z: 570.2 (M + H)+ | $^1$H NMR (400 MHz, Methanol-$d_4$) δ ppm 7.76 (dd, J = 2.4, 8.9 Hz, 1 H), 7.68 (dd, J = 2.2 Hz, 2 H), 7.52 (d, J = 8.3 Hz, 1 H), 7.45 (d, J = 10.6 Hz, 1 H), 6.85 (d, J = 8.9 Hz, 1 H), 4.68-4.73 (m, 1 H), 4.60 (d, J = 6.9 Hz, 1 H), 3.80 (p, J = 6.4 Hz, 1 H), 3.39-3.56 (m, 2 H), 3.07 (s, 3 H), 2.37 (q, J = 7.2 Hz, 1 H), 1.88 (s, 3 H), 1.31 (s, 3 H), 1.23 (dd, J = 6.3, 11.6 Hz, 5 H), 0.84-0.96 (m, 1 H), 0.67-0.75 (m, 1 H), 0.51-0.62 (m, 2 H), 0.41-0.49 (m, 1 H). | S |
| 82 | 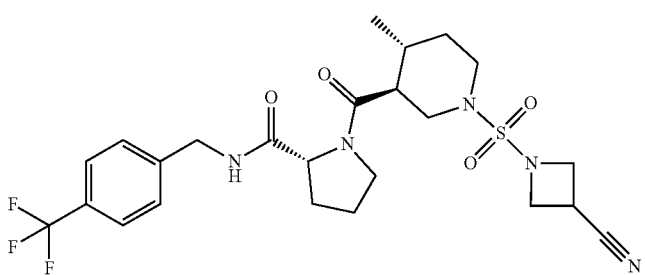 [SMILES: C[C@@H]1CCN(S(=O)(=O)N2CC(C#N)C2)C[C@H]1C(=O)N1CCC[C@@H]1C(=O)NCc1ccc(C(F)(F)F)cc1]<br>1-(((3S,4R)-1-((3-cyano-1-azetidinyl)sulfonyl)-4-methyl-3-piperidinyl)carbonyl)-N-(4-(trifluoromethyl)benzyl)-D-prolinamide | LCMS-ESI (POS.) m/z: 542.2 (M + H)+ | 1H NMR (400 MHz, CHLOROFORM-d) δ 7.51-7.65 (m, 2 H), 7.32-7.47 (m, 3 H), 4.55-4.69 (m, 1 H), 4.36-4.55 (m, 2 H), 4.02-4.19 (m, 4 H), 3.53-3.63 (m, 2 H), 3.35-3.53 (m, 3 H), 3.23-3.35 (m, 1 H), 3.00-3.14 (m, 1 H), 2.79-2.93 (m, 1 H), 2.37-2.51 (m, 1 H), 2.12-2.30 (m, 2 H), 1.63-2.10 (m, 4 H), 0.70-0.98 (m, 3 H) | |
| 83 | 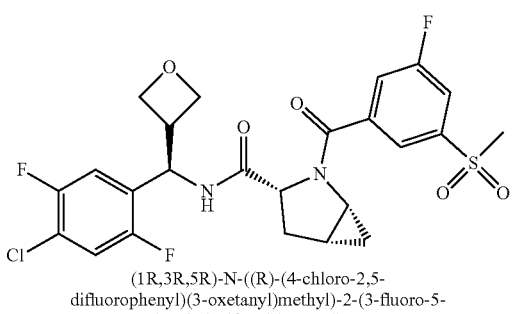<br>(1R,3R,5R)-N-((R)-(4-chloro-2,5-difluorophenyl)(3-oxetanyl)methyl)-2-(3-fluoro-5-(methylsulfonyl)benzoyl)-2-azabicyclo[3.1.0]hexane-3-carboxamide | LCMS-APCI (POS.) m/z: 543.1 (M + H)+ | $^1$H NMR (400 MHz, DMSO-$d_6$) δ ppm 8.67 (d, J = 8.1 Hz, 1 H), 8.04 (t, J = 1.5 Hz, 1 H), 7.98 (ddd, J = 1.5, 2.5, 8.0 Hz, 1 H), 7.77-7.85 (m, 1 H), 7.67 (dd, J = 6.2, 9.5 Hz, 1 H), 7.44 (dd, J = 6.3, 9.7 Hz, 1 H), 5.41 (t, J = 9.0 Hz, 1 H), 4.87 (dd, J = 3.7, 11.4 Hz, 1 H), 4.63 (dd, J = 6.3, 7.7 Hz, 1 H), 4.51 (dd, J = 6.3, 7.8 Hz, 1 H), 4.37 (t, J = 6.2 Hz, 1 H), 4.20 (t, J = 6.2 Hz, 1 H), 3.34 (s, 3 H), 3.31(d, J = 1.8 Hz, 1 H), 2.57 (dt, J = 6.0, 11.8 Hz, 1 H), 1.65-1.82 (m, 2 H), 1.16 (td, J = 2.6, 5.1 Hz, 1 H), 0.68-0.85 (m, 1 H). | Q |

| Ex. # | Structure Name | LCMS-ESI (POS/NEG) m/z: (M + H)+ | NMR Data | Syn. Rte. |
|---|---|---|---|---|
| 84 | 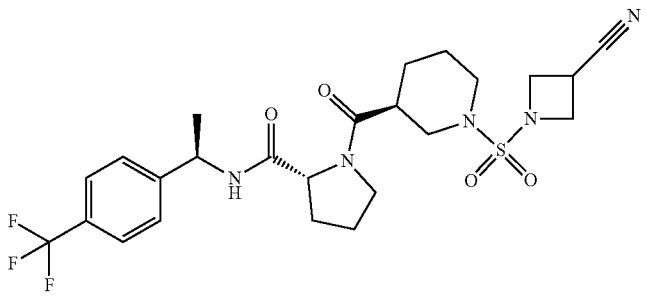 [SMILES: C[C@@H](NC(=O)[C@H]1CCCN1C(=O)[C@H]1CCCN(S(=O)(=O)N2CC(C#N)C2)C1)c1ccc(C(F)(F)F)cc1]<br>1-(((3S)-1-((3-cyano-1-azetidinyl)sulfonyl)-3-piperidinyl)carbonyl)-N-((1R)-1-(4-(trifluoromethyl)phenyl)ethyl)-D-prolinamide | LCMS-ESI (POS.) m/z: 542.2 (M + H)+ | 1H NMR (500 MHz, DMSO-d6) δ ppm 8.71* (d, J = 7.01 Hz, 1 H), 8.34 (d, J = 7.91 Hz, 1 H), 7.65-7.72 (m, 2 H), 7.49 (t, J = 7.22 Hz, 2 H), 4.89-5.01 (m, 1 H), 4.42-4.50* (m, 1 H), 4.23-4.33 (m, 1 H), 4.02-4.09 (m, 2 H), 3.90-3.96 (m, 2 H), 3.75-3.85 (m 1 H), 3.50-3.62 (m, 3 H), 3.28-3.42 (m, 1 H), 2.73-2.86 (m, 2 H), 2.61-2.67 (m, 1 H), 2.26-2.35* (m, 1 H), 2.16-2.26* (m, 1 H), 2.03-2.14 (m, 1 H), 1.65-1.91 (m, 5 H), 1.39-1.54 (m, 2 H), 1.33-1.39 (m, 3 H). Spectrum appears as 2:1 mixture of rotamers, *denotes resolved minor rotamer peaks. | C |
| 85 | 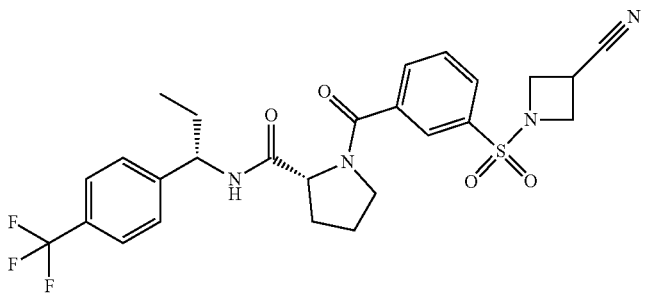 [SMILES: CC[C@H](NC(=O)[C@H]1CCCN1C(=O)c1cccc(S(=O)(=O)N2CC(C#N)C2)c1)c1ccc(C(F)(F)F)cc1]<br>1-(3-((3-cyano-1-azetidinyl)sulfonyl)benzoyl)-N-((1S)-1-(4-(trifluoromethyl)phenyl)propyl)-D-prolinamide | LCMS-ESI (POS.) m/z: 549.2 (M + H)+ | 1H NMR (500 MHz, DMSO-d6) δ ppm 8.25-8.49 (m, 1 H), 7.15-8.00 (m, 8 H), 4.57-4.85 (m, 1 H), 4.42 (s, 1 H), 3.80-4.05 (m, 4 H), 3.57-3.68 (m, 2 H), 3.45-3.54 (m, 1 H), 2.21-2.34 (m, 1 H), 1.59-1.96 (m, 5 H), 0.74-0.95 (m, 3 H) | A |
| 86 | 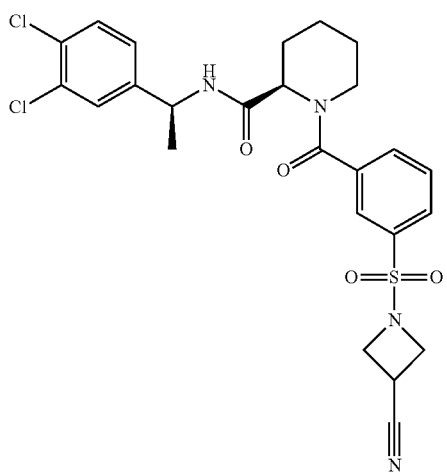 [SMILES: C[C@H](NC(=O)[C@H]1CCCCN1C(=O)c1cccc(S(=O)(=O)N2CC(C#N)C2)c1)c1ccc(Cl)c(Cl)c1]<br>(2R)-1-((3-((3-cyano-1-azetidinyl)sulfonyl)phenyl)carbonyl)-N-((1S)-1-(3,4-dichlorophenyl)ethyl)-2-piperidinecarboxamide | LCMS-APCI (NEG.) m/z: 547.1 (M − H) | 1H NMR (400 MHz, Methanol-d4) δ ppm 7.85-8.01 (m, 2 H), 7.73-7.83 (m, 0 H), 7.41-7.59 (m, 2 H), 7.28 (s, 1 H), 5.21 (s, 1 H), 5.01 (qd, J = 2.1, 7.2 Hz, 1 H), 4.01-4.17 (m, 2 H), 3.82-3.97 (m, 2 H), 3.39-3.62 (m, 2 H), 3.34 (s, 1 H), 2.21 (s, 1 H), 1.90 (s, 1 H), 1.61-1.81 (m, 2 H), 1.52-1.61 (m, 1 H), 1.47 (d, J = 7.1 Hz, 3 H). | Q |

| Ex. # | Structure Name | LCMS-ESI (POS/NEG) m/z: (M + H)+ | NMR Data | Syn. Rte. |
|---|---|---|---|---|
| 87 | 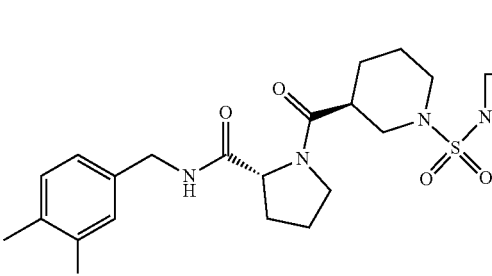<br>1-(((3S)-1-((3-cyano-1-azetidinyl)sulfonyl)-3-piperidinyl)carbonyl)-N-(3-fluoro-4-methylbenzyl)-D-prolinamide | LCMS-ESI (POS.) m/z: 504.2 (M + H)+ | 1H NMR (500 MHz, DMSO-d6) δ ppm 8.19-8.67 (m, 1 H), 7.15-7.27 (m, 1 H), 6.89-7.04 (m, 2 H), 4.16-4.51 (m, 3 H), 3.99-4.12 (m, 2 H), 3.85-3.98 (m, 2 H), 3.73-3.83 (m, 1 H), 3.41-3.71 (m, 4 H), 2.61-2.89 (m, 3 H), 2.04-2.34 (m, 4 H), 1.65-1.99 (m, 5 H), 1.34-1.56 (m, 2 H) | A |
| 88 | 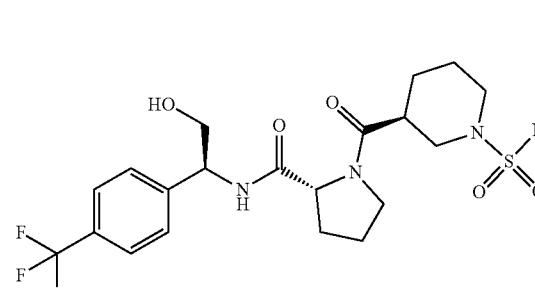<br>1-(((3S)-1-((3-cyano-1-azetidinyl)sulfonyl)-3-piperidinyl)carbonyl)-N-((1S)-2-hydroxy-1-(4-(trifluoromethyl)phenyl)ethyl)-D-prolinamide | LCMS-ESI (POS.) m/z: 558.2 (M + H)+ | 1H NMR (500 MHz, DMSO-d6) δ ppm 8.15-8.71 (m, 1 H), 7.44-7.74 (m, 4 H), 4.83-4.92 (m, 1 H), 4.35 (br dd, J = 8.56, 4.02 Hz, 1 H), 4.03-4.11 (m, 2 H), 3.90-3.98 (m, 2 H), 3.76-3.86 (m, 1 H), 3.31-3.68 (m, 6 H), 2.73-2.89 (m, 2 H), 2.61-2.68 (m, 1 H), 1.62-2.37 (m, 7 H), 1.34-1.56 (m, 2 H) | A |
| 89 | 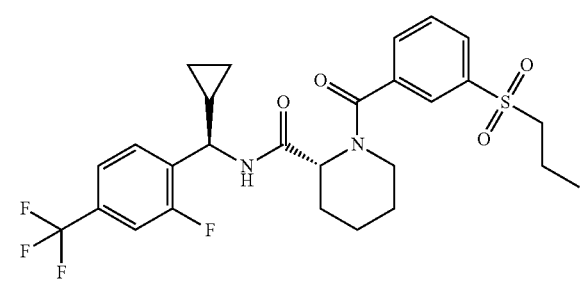 [SMILES: CCCS(=O)(=O)c1cccc(C(=O)N2CCCC[C@@H]2C(=O)N[C@@H](c2ccc(C(F)(F)F)cc2F)C2CC2)c1]<br>(2R)-N-((R)-cyclopropyl(2-fluoro-4-(trifluoromethyl)phenyl)methyl)-1-(3-(propylsulfonyl)benzoyl)-2-piperidinecarboxamide | LCMS-ESI (POS.) m/z: 577.2 (M + Na)+ | 1H NMR (500 MHz, CHLOROFORM-d) δ ppm 7.30-8.08 (m, 9 H), 7.13 (br d, J = 7.01 Hz, 1 H), 5.19-5.32 (m, 1 H), 4.57 (br t, J = 8.04 Hz, 1 H), 3.59 (br d, J = 12.98 Hz, 1 H), 3.11-3.34 (m, 2 H), 2.06-2.49 (m, 6 H), 1.50-1.95 (m, 6 H), 1.18-1.43 (m, 9 H), 0.35-0.74 (m, 5 H) | C |
| 90 | 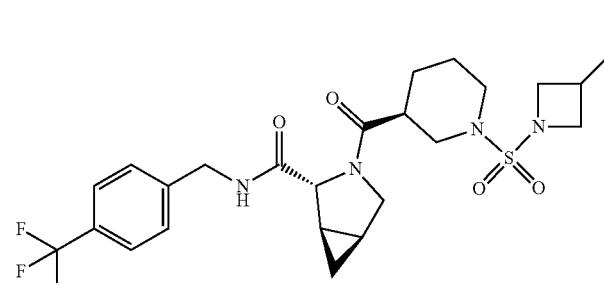<br>(1R,2R,5S)-3-(((3S)-1-((3-cyano-1-azetidinyl)sulfonyl)-3-piperidinyl)carbonyl)-N-(4-(trifluoromethyl)benzyl)-3-azabicyclo[3.1.0]hexane-2-carboxamide | LCMS-ESI (POS.) m/z: 540.2 (M + H)+ | 1H NMR (500 MHz, CHLOROFORM-d) δ ppm 7.54-7.69 (m, 2 H), 7.32-7.47 (m, 2 H), 7.00-7.19 (m, 1 H), 4.57-4.65 (m, 1 H), 4.48-4.60 (m, 1 H), 4.34-4.46 (m, 1 H), 4.33-4.68 (m, 1 H), 4.01-4.19 (m, 4 H), 3.64-3.80 (m, 4 H), 3.35-3.46 (m, 1 H), 2.87-2.97 (m, 1 H), 2.70-2.82 (m, 1 H), 2.54-2.66 (m, 1 H), 1.71-1.97 (m, 4 H), 1.53-1.63 (m, 1 H), 1.32-1.46 (m, 1 H), 0.75-0.92 (m, 1 H), 0.09-0.25 (m, 1 H) | C |

-continued

| Ex. # | Structure Name | LCMS-ESI (POS/NEG) m/z: (M + H)+ | NMR Data | Syn. Rte. |
|---|---|---|---|---|
| 91 | 1-(((3S)-1-((3-cyano-1-azetidinyl)sulfonyl)-3-piperidinyl)carbonyl)-N-(3,4-dichlorobenzyl)-D-prolinamide | LCMS-ESI (POS.) m/z: 528.2 (M + H)+ | 1H NMR (500 MHz, CHLOROFORM-d) δ ppm 7.28-7.48 (m, 3 H), 7.06-7.12 (m, 1 H), 4.54-4.63 (m, 1 H), 4.23-4.50 (m, 2 H), 4.04-4.17 (m, 4 H), 3.71-3.81 (m, 2 H), 3.51-3.70 (m, 2 H), 3.39-3.48 (m, 1 H), 2.91-3.01 (m, 1 H), 2.67-2.85 (m, 3 H), 2.38-2.46 (m, 1 H), 2.16-2.26 (m, 1 H), 1.98-2.12 (m, 1 H), 1.80-1.98 (m, 3 H), 1.50-1.73 (m, 2 H) | C |
| 92 | (1R,3R,5R)-N-((R)-(4-chloro-2,5-difluorophenyl)(cyclopropyl)methyl)-2-(3-(cyclopropylsulfonyl)benzoyl)-2-azabicyclo[3.1.0]hexane-3-carboxamide | LCMS-ESI (POS.) m/z: 535.0 (M + H)+ | 1H NMR (500 MHz, DMSO-d6) δ ppm 8.28-8.67 (m, 1 H), 7.22-8.20 (m, 6 H), 4.93 (dd, J = 11.29, 3.50 Hz, 1 H), 4.04-4.56 (m, 1 H), 3.15-3.80 (m, 1 H), 2.85-2.99 (m, 1 H), 2.52-2.59 (m, 1 H), 1.62-1.80 (m, 1 H), 1.56 (br dd, J = 8.56, 5.45 Hz, 1 H), 1.00-1.27 (m, 6 H), −0.24-0.96 (m, 5 H) | H |
| 93 | 2-((3-((3-cyano-1-azetidinyl)sulfonyl)phenyl)carbonyl)-N-(4-(trifluoromethyl)benzyl)-2,3-dihydro-1H-isoindole-1-carboxamide | LCMS-ESI (POS.) m/z: 569.2 (M + H)+ | 1H NMR (500 MHz, DMSO-d6) δ ppm 8.97 (t, J = 6.77 Hz, 1 H), 8.11 (br s, 1 H), 8.01 (br d, J = 7.66 Hz, 1 H), 7.83-7.96 (m, 2 H), 7.72 (br s, 1 H), 7.53-7.68 (m, 2 H), 7.41-7.51 (m, 2 H), 7.22-7.41 (m, 3 H), 5.77 (br s, 1 H), 5.02 (br d, J = 14.01 Hz, 1 H), 4.74 (br d, J = 13.62 Hz, 1 H), 4.45-4.52 (m, 1 H), 4.41 (br d, J = 5.71 Hz, 1 H), 3.96-4.12 (m, 2 H), 3.84-3.96 (m, 2 H), 3.17 (s, 1 H) | I |
| 94 | (1R,3R,5R)-N-((R)-(4-chloro-2,5-difluorophenyl)(3-oxetanyl)methyl)-2-(3-((2-hydroxyethyl)sulfonyl)benzoyl)-2-azabicyclo[3.1.0]hexane-3-carboxamide | LCMS-APCI (POS.) m/z: 555.1 (M + H)+ | $^1$H NMR (400 MHz, DMSO-$d_6$) δ ppm 8.67 (d, J = 8.2 Hz, 1 H), 8.16 (t, J = 1.7 Hz, 1 H), 7.96-8.05 (m, 2 H), 7.77 (t, J = 7.8 Hz, 1 H), 7.67 (dd, J = 6.3, 9.4 Hz, 1 H), 7.45 (dd, J = 6.3, 9.7 Hz, 1 H), 5.41 (t, J = 8.9 Hz, 1 H), 4.83-4.93 (m, 2 H), 4.63 (dd, J = 6.3, 7.7 Hz, 1 H), 4.46-4.54 (m, 1 H), 4.33-4.41 (m, 2 H), 4.20 (t, J = 6.2 Hz, 1 H), 3.71 (q, J = 5.9 Hz, 2 H), 3.51 (t, J = 6.2 Hz, 2 H), 3.20-3.30 (m, 1 H), 1.72 (dd, J = 3.6, 13.3 Hz, 2 H), 1.17 (dd, J = 2.6, 5.1 Hz, 3 H), 0.72-0.86 (m, 2 H). | Q |

| Ex. # | Structure Name | LCMS-ESI (POS/NEG) m/z: (M + H)+ | NMR Data | Syn. Rte. |
|---|---|---|---|---|
| 95 | 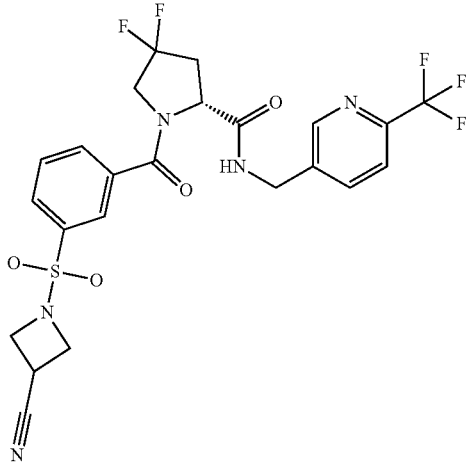 [SMILES: N#CC1CN(S(O)(O)c2cccc(C(=O)N3CC(F)(F)C[C@@H]3C(=O)NCc3ccc(C(F)(F)F)nc3)c2)C1]<br>1-((3-((3-cyano-1-azetidinyl)sulfonyl)phenyl)carbonyl)-4,4-difluoro-N-((6-(trifluoromethyl)-3-pyridinyl)methyl)-D-prolinamide | LCMS-APCI (NEG.) m/z: 556.1 (M − H) | ¹H NMR (400 MHz, Methanol-d₄) δ ppm 8.70 (s, 1 H), 8.14 (s, 1 H), 7.96-8.07 (m, 4 H), 7.75-7.84 (m, 2 H), 4.69 (d, J = 15.9 Hz, 1 H), 4.50 (d, J = 15.8 Hz, 1 H), 4.13 (td, J = 3.0, 8.3 Hz, 3 H), 3.95 (dd, J = 6.0, 8.5 Hz, 3 H), 3.52 (tt, J = 6.1, 8.8 Hz, 1 H), 2.78-2.96 (m, 1 H), 2.48-2.65 (m, 1 H). | Q |
| 96 | 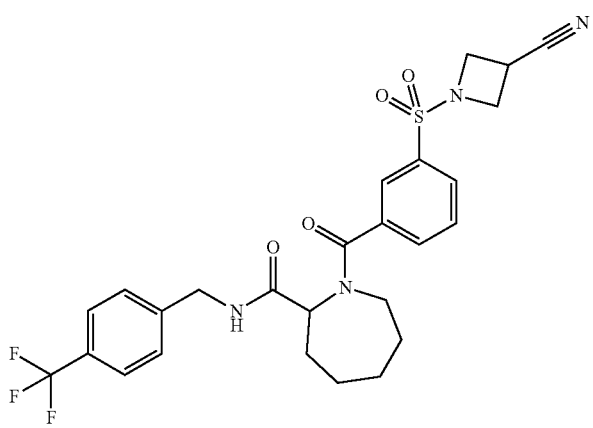 [SMILES: N#CC1CN(S(=O)(=O)c2cccc(C(=O)N3CCCCCC3C(=O)NCc3ccc(C(F)(F)F)cc3)c2)C1]<br>(2)-1-((3-((3-cyano-1-azetidinyl)sulfonyl)phenyl)carbonyl)-N-(4-(trifluoromethyl)benzyl)-2-azepanecarboxamide | LCMS-APCI (NEG.) m/z: 547.2 (M − H) | ¹H NMR (400 MHz, Methanol-d₄) ppm 7.40-8.03 (m, 8 H), 4.36-4.84 (m, 3 H), 4.05-4.16 (m, 2 H), 3.88-3.98 (m, 2 H), 3.11-3.68 (m, 3 H), 2.25-2.44 (m, 1 H), 1.26-2.10 (m, 7 H). | Q |
| 97 | 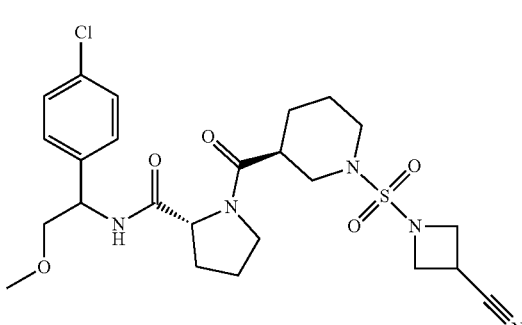<br>N-(-1-(4-chlorophenyl)-2-methoxyethyl)-1-(((3S)-1-((3-cyano-1-azetidinyl)sulfonyl)-3-piperidinyl)carbonyl)-D-prolinamide | LCMS-ESI (POS.) m/z: 538.2 (M + H)⁺ | 1H NMR (500 MHz, DMSO-d6) δ ppm 8.12-8.71 (m, 1 H), 7.23-7.60 (m, 4 H), 4.88-5.09 (m, 1 H), 4.32-4.54 (m, 1 H), 4.01-4.12 (m, 2 H), 3.88-4.00 (m, 2 H), 3.71-3.87 (m, 1 H), 3.43-3.68 (m, 6 H), 3.15-3.27 (m, 3 H), 2.59-2.90 (m, 3 H), 2.01-2.31 (m, 1 H), 1.64-1.99 (m, 5 H), 1.29-1.58 (m, 2 H) | A |

-continued

| Ex. # | Structure Name | LCMS-ESI (POS/NEG) m/z: (M + H)+ | NMR Data | Syn. Rte. |
|---|---|---|---|---|
| 98 | 1-(((3S)-1-((3-cyano-1-azetidinyl)sulfonyl)-3-piperidinyl)carbonyl)-N-((1R)-1-(2-fluoro-4-methylphenyl)ethyl)-D-prolinamide | LCMS-ESI (POS.) m/z: 506.2 (M + H)+ | 1H NMR (500 MHz, DMSO-d6) δ ppm 8.24 (d, J = 7.79 Hz, 1 H), 7.12-7.29 (m, 1 H), 6.89-7.06 (m, 2 H), 5.79-5.80 (m, 1 H), 4.96-5.22 (m, 1 H), 4.26-4.51 (m, 1 H), 4.01-4.13 (m, 2 H), 3.89-3.98 (m, 2 H), 3.74-3.85 (m, 1 H), 3.48-3.61 (m, 3 H), 3.28-3.42 (m, 1 H), 2.69-2.87 (m, 2 H), 2.57-2.69 (m, 1 H), 2.24-2.31 (m, 3 H), 1.98-2.22 (m, 1 H), 1.60-1.93 (m, 5 H), 1.37-1.57 (m, 2 H), 1.23-1.37 (m, 3 H) | A |
| 99 | 1-(((3S)-1-((3-cyano-1-azetidinyl)sulfonyl)-3-piperidinyl)carbonyl)-N-(2,4-dichlorobenzyl)-D-prolinamide | LCMS-ESI (POS.) m/z: 528.0 (M + H)+ | additional 1H count due to H$_2$O overlap 1H NMR (400 MHz, CHLOROFORM-d) δ ppm 7.44 (br t, J = 5.75 Hz, 1 H), 7.39 (dd, J = 7.93, 1.61 Hz, 1 H), 7.26 (dd, J = 7.67, 1.55 Hz, 1 H), 7.15-7.20 (m, 1 H), 4.53-4.64 (m, 2 H), 4.42-4.50 (m, 1 H), 4.07-4.14 (m, 4 H), 3.73-3.80 (m, 2 H), 3.53-3.60 (m, 2 H), 3.38-3.48 (m, 1 H), 2.98 (dd, J = 12.70, 11.04 Hz, 1 H), 2.64-2.82 (m, 2 H), 2.40-2.48 (m, 1 H), 2.08-2.22 (m, 1 H), 1.99-2.08 (m, 1 H), 1.78-1.96 (m, 3 H), 1.45-1.72 (m, 3 H) | A |
| 100 | 1-(3-((3-cyano-1-azetidinyl)sulfonyl)benzoyl)-N-(2,3,5-trifluorobenzyl)-D-prolinamide | LCMS-ESI (POS.) m/z: 507.2 (M + H)+ | 1H NMR (500 MHz, DMSO-d6) δ ppm 8.47-8.70 (m, 1 H), 7.60-8.04 (m, 4 H), 7.36-7.46 (m, 1 H), 6.64-7.12 (m, 1 H), 4.15-4.54 (m, 3 H), 3.83-4.07 (m, 4 H), 3.45-3.69 (m, 3 H), 2.21-2.31 (m, 1 H), 1.75-1.98 (m, 3 H) | A |
| 101 | (1R,3R,5R)-N-((R)-cyclopropyl(2-fluoro-4-(trifluoromethyl)phenyl)methyl)-2-(2-((2-methyl-2-propanyl)amino)-5-(methylsulfonyl)benzoyl)-2-azabicyclo[3.1.0]hexane-3-carboxamide | LCMS-APCI (POS.) m/z: 596.2 (M + H)+ | $^1$H NMR (400 MHz, DMSO-d$_6$) δ ppm 8.87 (d, J = 6.9 Hz, 1 H), 7.52-7.72 (m, 3 H), 7.04 (d, J = 9.0 Hz, 1 H), 6.49 (s, 1 H), 4.96 (dd, J = 3.1, 11.3 Hz, 1 H), 4.49 (t, J = 7.8 Hz, 1 H), 3.09 (s, 2 H), 1.80 (dd, J = 16.1 Hz, 1 H), 1.52-1.62 (m, 1 H), 1.33 (s, 4 H), 1.15-1.25 (m, 1 H), 0.69-0.80 (m, 1 H), 0.57-0.69 (m, 1 H), 0.26-0.49 (m, 2 H). | S |

| Ex. # | Structure Name | LCMS-ESI (POS/NEG) m/z: (M + H)+ | NMR Data | Syn. Rte. |
|---|---|---|---|---|
| 102 | 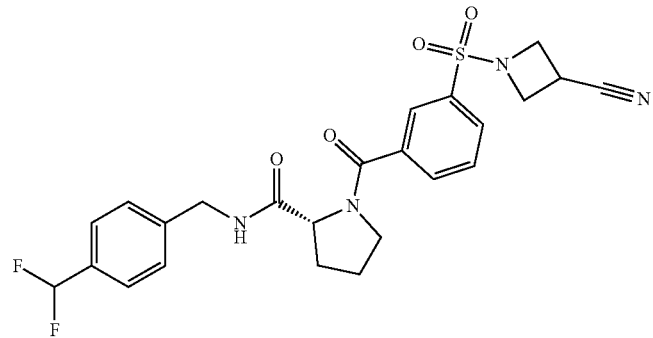 [SMILES: N#CC1CN(S(=O)(=O)c2cccc(C(=O)N3CCC[C@@H]3C(=O)NCc3ccc(C(F)F)cc3)c2)C1]<br>1-((3-((3-cyano-1-azetidinyl)sulfonyl)phenyl)carbonyl)-N-(4-(difluoromethyl)benzyl)-D-prolinamide | LCMS-APCI (POS.) m/z: 503.2 (M + H)+ | 1H NMR (400 MHz, Methanol-d4) δ ppm 7.12-8.30 (m, 8 H), 6.56-6.90 (m, 1 H), 3.88-4.67 (m, 7 H), 3.39-3.84 (m, 3 H), 2.30-2.46 (m, 1 H), 1.86-2.13 (m, 3 H). | A |
| 103 | 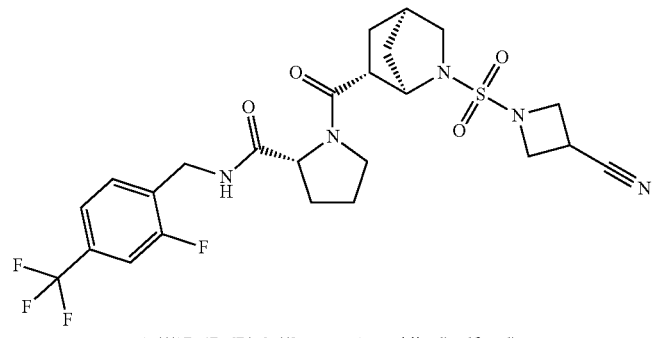<br>1-(((1R,4R,6R)-2-((3-cyano-1-azetidinyl)sulfonyl)-2-azabicyclo[2.2.1]hept-6-yl)carbonyl)-N-(2-fluoro-4-(trifluoromethyl)benzyl)-D-prolinamide | LCMS-ESI (POS.) m/z: 558.0 (M + H)+ | 1H NMR (400 MHz, CHLOROFORM-d) δ 7.28-7.48 (m, 4 H), 4.42-4.58 (m, 3H), 4.10-4.20 (m, 3 H), 4.03-4.10 (m, 2 H), 3.54-3.68 (m, 2 H), 3.41 (tt, J = 6.32, 8.81 Hz, 1 H), 3.27 (td, J = 3.03, 8.66 Hz, 1 H), 3.12 (dd, J = 5.29, 8.71 Hz, 1 H), 3.07 (d, J = 8.71 Hz, 1 H), 2.67 (br s, 1 H), 2.40 (tdd, J = 3.11, 6.39, 12.37 Hz, 1 H), 2.10-2.23 (m, 1 H), 1.98-2.08 (m, 1 H), 1.77-1.97 (m, 4 H), 1.67 (br d, J = 10.26 Hz, 1 H) | M |
| 104 | 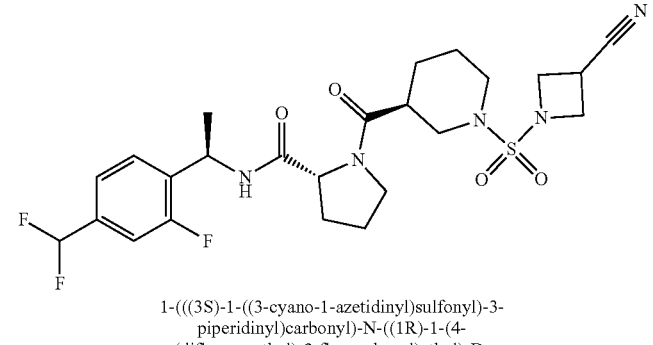<br>1-(((3S)-1-((3-cyano-1-azetidinyl)sulfonyl)-3-piperidinyl)carbonyl)-N-((1R)-1-(4-(difluoromethyl)-2-fluorophenyl)ethyl)-D-prolinamide | LCMS-ESI (POS.) m/z: 542.2 (M + H)+ | 1H NMR (500 MHz, CHLOROFORM-d) δ ppm 7.28-7.45 (m, 2 H), 7.13-7.25 (m, 1 H), 7.11-7.30 (m, 2 H), 6.46-6.76 (m, 1 H), 5.15-5.26 (m, 1 H), 4.48-4.58 (m, 1 H), 4.01-4.19 (m, 4 H), 3.70-3.84 (m, 2 H), 3.52-3.67 (m, 2 H), 3.37-3.49 (m, 1 H), 2.91-3.06 (m, 1 H), 2.67-2.86 (m, 2 H), 2.25-2.34 (m, 1 H), 2.08-2.21 (m, 1 H), 1.96-2.08 (m, 2 H), 1.80-1.96 (m, 2 H), 1.56-1.76 (m, 2 H), 1.51-1.56 (m, 1 H), 1.37-1.50 (m, 2 H), 1.37-1.55 (m, 3 H) | A |
| 105 | 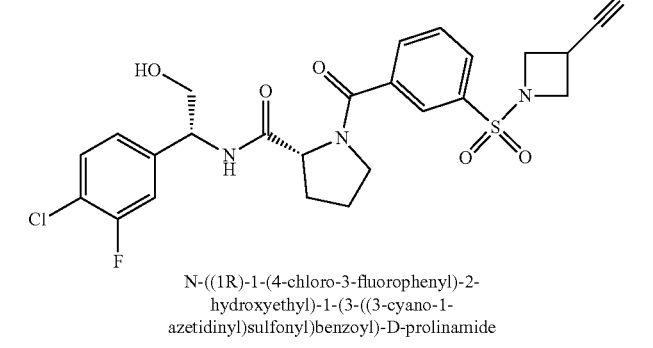<br>N-((1R)-1-(4-chloro-3-fluorophenyl)-2-hydroxyethyl)-1-(3-((3-cyano-1-azetidinyl)sulfonyl)benzoyl)-D-prolinamide | LCMS-ESI (POS.) m/z: 535.2 (M + H)+ | 1H NMR (500 MHz, DMSO-d6) δ ppm 8.18-8.51 (m, 1 H), 6.98-8.02 (m, 7 H), 4.84-4.91 (m, 1 H), 4.52-4.59 (m, 1 H), 3.36-4.15 (m, 10 H), 2.16-2.34 (m, 1 H), 1.73-2.02 (m, 3 H) | A |

| Ex. # | Structure Name | LCMS-ESI (POS/NEG) m/z: (M + H)+ | NMR Data | Syn. Rte. |
|---|---|---|---|---|
| 106 | 1-((3-((3-cyano-1-azetidinyl)sulfonyl)phenyl)carbonyl)-N-(4-methylbenzyl)-D-prolinamide | LCMS-ESI (POS.) m/z: 467.2 (M + H)+ | 1H NMR (400 MHz, CHLOROFORM-d) δ ppm 7.99-8.04 (m, 1 H), 7.91-7.97 (m, 1 H), 7.82-7.88 (m, 1 H), 7.66-7.74 (m, 1 H), 7.13-7.24 (m, 4 H), 6.98 (br t, J = 5.18 Hz, 1 H), 4.69-4.74 (m, 1 H), 4.45 (dd, J = 8.58, 5.83 Hz, 2 H), 4.09-4.16 (m, 2 H), 4.03 (d, J = 6.84 Hz, 2 H), 4.01 (s, 1 H), 3.60-3.69 (m, 1 H), 3.43-3.53 (m, 1 H), 3.35 (tt, J = 8.75, 6.54 Hz, 1 H), 2.38-2.47 (m, 1 H), 2.11-2.24 (m, 2 H), 1.87-1.97 (m, 1 H), 1.84-2.26 (m, 1 H) | A |
| 107 | 1-(((3S)-1-((3-cyano-1-azetidinyl)sulfonyl)-3-piperidinyl)carbonyl)-N-((S)-cyclopropyl(4-(trifluoromethyl)phenyl)methyl)-D-prolinamide | LCMS-ESI (POS.) m/z: 568.2 (M + H)+ | 1H NMR (500 MHz, DMSO-d6) δ ppm 8.25-8.79 (m, 1 H), 7.55-7.77 (m, 4 H), 4.29-4.46 (m, 2 H), 4.05-4.09 (m, 2 H), 3.87-3.94 (m, 2 H), 3.74-3.83 (m, 1 H), 3.44-3.65 (m, 4 H), 3.16-3.17 (m, 1 H), 2.70-2.91 (m, 2 H), 2.57-2.67 (m, 1 H), 2.08-2.26 (m, 1 H), 1.66-1.94 (m, 5 H), 1.12-1.53 (m, 3 H), 0.29-0.65 (m, 4 H) | A |
| 108 | N-((R)-cyclopropyl(2-fluoro-4-(trifluoromethyl)phenyl)methyl)-1-(2-(ethylamino)-5-methylbenzoyl)-D-prolinamide | LCMS-APCI (POS.) m/z: 492.2 (M + H)+ | 1H NMR (400 MHz, DMSO-d6) δ ppm 8.80 (d, J = 7.3 Hz, 1 H), 7.57-7.76 (m, 3 H), 7.01 (dd, J = 2.1, 8.5 Hz, 1 H), 6.88 (s, 1 H), 6.54 (d, J = 8.5 Hz, 1 H), 5.49 (s, 1 H), 4.51-4.66 (m, 2 H), 3.15-3.27 (m, 1 H), 2.99-3.11 (m, 2 H), 2.17 (s, 4 H), 1.61-1.78 (m, 3 H), 1.17-1.27 (m, 1 H), 1.12 (t, J = 7.1 Hz, 3 H), 0.59 (s, 1 H), 0.32-0.53 (m, 3 H). | Q |
| 109 | | LCMS-ESI (POS.) m/z: 544.2 (M + H)+ | 1H NMR (500 MHz, CHLOROFORM-d) δ ppm 7.56-7.66 (m, 2 H), 7.34-7.44 (m, 2 H), 6.23-6.69 (m, 1 H), 4.93 (d, J = 3.37 Hz, 1 H), 4.41-4.68 (m, 3 H), 4.05-4.17 (m, 4 H), 3.94-4.01 (m, 1 H), 3.72-3.88 (m, 2 H), 3.47-3.72 (m, 4 H), 3.36-3.47 (m, 1 H), 2.91-3.11 (m, 1 H), 2.72-2.90 (m, 2 H), 1.37-1.94 (m, 4 H) | M |

-continued

| Ex. # | Structure Name | LCMS-ESI (POS/NEG) m/z: (M + H)+ | NMR Data | Syn. Rte. |
|---|---|---|---|---|
| | (3R)-4-(((3S)-1-((3-cyano-1-azetidinyl)sulfonyl)-3-piperidinyl)carbonyl)-N-(4-(trifluoromethyl)benzyl)-3-morpholinecarboxamide | | | |
| 110 | (4S)-N-((R)-(4-chloro-2,5-difluorophenyl)(3-oxetanyl)methyl)-1-(2-(ethylamino)-5-methylbenzoyl)-4-hydroxy-D-prolinamide | LCMS-APCI (POS.) m/z: 508.2 (M + H)+ | 1H NMR (400 MHz, DMSO-d6) δ ppm 8.73 (d, J = 8.3 Hz, 1 H), 7.66 (dd, J = 6.2, 9.4 Hz, 1 H), 7.47 (dd, J = 6.2, 9.8 Hz, 1 H), 7.04 (d, J = 8.3 Hz, 1 H), 6.91 (s, 1 H), 6.56 (d, J = 8.4 Hz, 1 H), 5.38-5.57 (m, 2 H), 5.03 (d, J = 3.1 Hz, 1 H), 4.65 (t, J = 7.0 Hz, 1 H), 4.48-4.61 (m, 2 H), 4.43 (t, J = 6.1 Hz, 1 H), 4.22 (d, J = 6.1 Hz, 2 H), 3.57 (dd, J = 3.7, 10.9 Hz, 1 H), 3.41 (dt, J = 6.5, 14.0 Hz, 1 H), 2.98-3.18 (m, 3 H), 2.18 (s, 3 H), 2.02-2.12 (m, 1 H), 1.15 (t, J = 7.1 Hz, 3 H). | Q |
| 111 | N-((R)-(4-chloro-2,5-difluorophenyl)(3-oxetanyl)methyl)-1-(3-(methylsulfonyl)benzoyl)-D-prolinamide | LCMS-APCI (POS.) m/z: 513.1 (M + H)+ | 1H NMR (400 MHz, Methanol-d4) δ ppm 8.22 (t, J = 1.6 Hz, 1 H), 8.10 (ddd, J = 1.1, 1.9, 7.9 Hz, 1 H), 7.96 (dt, J = 1.3, 7.9 Hz, 1 H), 7.75 (t, J = 7.7 Hz, 1 H), 7.39 (dd, J = 6.1, 9.5 Hz, 1 H), 7.31 (dd, J = 6.3, 9.4 Hz, 1 H), 5.64 (d, J = 10.4 Hz, 1 H), 4.64-4.72 (m, 2 H), 4.50-4.58 (m, 2 H), 4.41 (t, 1 H), 3.75 (dp, J = 4.8, 9.5 Hz, 1 H), 3.65 (dt, J = 7.2, 10.2 Hz, 1 H), 3.48-3.58 (m, 2 H), 2.27-2.40 (m, 1 H), 1.95-2.05 (m, 1 H), 1.82-1.95 (m, 3 H). | A |
| 112 | (1R,3R,5R)-N-((R)-(4-chloro-2,5-difluorophenyl)(cyclopropyl)methyl)-2-(3-((2-hydroxyethyl)sulfonyl)benzoyl)-2-azabicyclo[3.1.0]hexane-3-carboxamide | LCMS-APCI (POS.) m/z: 539.1 (M + H)+ | 1H NMR (400 MHz, DMSO-d6) δ ppm 8.63 (d, J = 7.7 Hz, 1 H), 8.14-8.17 (m, 1 H), 8.02 (ddt, J = 1.3, 7.8, 14.0 Hz, 2 H), 7.77 (t, J = 7.8 Hz, 1 H), 7.60-7.69 (m, 1 H), 7.50 (dd, J = 6.3, 9.8 Hz, 1 H), 4.90-4.98 (m, 1 H), 4.87 (t, J = 5.4 Hz, 1 H), 4.51 (t, J = 7.9 Hz, 1 H), 4.36 (t, J = 5.1 Hz, 1 H), 3.70 (q, J = 5.9 Hz, 2 H), 3.50 (t, J = 6.1 Hz, 2 H), 3.23 (dt, J = 3.2, 6.3 Hz, 1 H), 1.71 (td, J = 5.4, 13.8 Hz, 3 H), 1.14-1.21 (m, 1 H), 1.09-1.14 (m, 1 H), 0.74 (dt, J = 5.2, 10.4 Hz, 2 H), 0.54 (d, J = 8.2 Hz, 1 H), 0.46 (d, J = 8.6 Hz, 2 H), 0.34 (d, J = 3.7 Hz, 2 H). | Q |

-continued

| Ex. # | Structure Name | LCMS-ESI (POS/NEG) m/z: (M + H)+ | NMR Data | Syn. Rte. |
|---|---|---|---|---|
| 113 | (2R)-N-((R)-(4-chloro-2,5-difluorophenyl)(cyclopropyl)methyl)-1-(3-(methylsulfonyl)benzoyl)-2-piperidinecarboxamide | LCMS-ESI (POS.) m/z: 533.0 (M + Na)+ | 1H NMR (500 MHz, DMSO-d6) δ ppm 8.62 (br s, 1 H), 7.44-8.09 (m, 6 H), 4.35-5.26 (m, 2 H), 4.12 (br s, 1 H), 3.32-3.45 (m, 1 H), 3.27 (br s, 3 H), 2.03-2.22(m, 1 H), 1.12-1.77 (m, 6 H), 0.25-0.66 (m, 4 H) | C |
| 114 | N-((R)-(4-chloro-3-fluorophenyl)(cyclopropyl)methyl)-1-(3-(dimethylsulfamoyl)benzoyl)-D-prolinamide | LCMS-ESI (POS.) m/z: 508.2 (M + H)+ | 1H NMR (500 MHz, DMSO-d6) δ ppm 8.54 (br d, J = 8.04 Hz, 1 H), 7.06-7.96 (m, 7 H), 3.82-4.53 (m, 2 H), 3.40-3.68 (m, 2 H), 2.58-2.69 (m, 6 H), 2.20-2.37 (m, 1 H), 1.67-1.98 (m, 3 H), 1.11-1.22 (m, 1 H), −0.19-0.67 (m, 4 H) | A |
| 115 | (1R,3R,5R)-N-((R)-cyclopropyl(2,5-difluoro-4-(trifluoromethyl)phenyl)methyl)-2-(3-(trifluoromethyl)benzoyl)-2-azabicyclo[3.1.0]hexane-3-carboxamide | LCMS-APCI (POS.) m/z: 533.1 (M + H)+ | 1H NMR (400 MHz, DMSO-d6) δ ppm 8.71 (d, J = 7.5 Hz, 1 H), 7.99 (d, J = 7.7 Hz, 1 H), 7.95 (s, 1 H), 7.90 (d, J = 8.0 Hz, 1 H), 7.72-7.81 (m, 2 H), 7.60 (dd, J = 5.6, 11.0 Hz, 1 H), 4.95 (dd, J = 3.6, 11.4 Hz, 1 H), 4.53 (t, J = 7.9 Hz, 1 H), 3.24 (td, J = 2.5, 6.2 Hz, 1 H), 2.58 (dt, J = 6.4, 12.0 Hz, 1 H), 1.74 (dd, J = 3.6, 13.6 Hz, 1 H), 1.64-1.71 (m, 1 H), 1.16-1.25 (m, 1 H), 1.04-1.12 (m, 1 H), 0.74 (dt, J = 5.3, 9.8 Hz, 1 H), 0.53-0.62 (m, 1 H), 0.41-0.50 (m, 1 H), 0.37 (s, 2 H). | Q |
| 116 | 1-(((2S)-4-((3-cyano-1-azetidinyl)sulfonyl)-2-morpholinyl)carbonyl)-N-(2-fluoro-4-(trifluoromethyl)benzyl)-D-prolinamide | LCMS-ESI (POS.) m/z: 548.2 (M + H)+ | 1H NMR (400 MHz, CHLOROFORM-d) δ 7.41-7.52 (m, 1 H), 7.35-7.40 (m, 1 H), 7.31 (d, J = 9.85 Hz, 1 H), 7.20 (br t, J = 5.75 Hz, 1 H), 4.60-4.80 (m, 1 H), 4.45-4.59 (m, 2 H), 4.13-4.21 (m, 5 H), 4.00 (td, J = 2.80, 11.30 Hz, 1 H), 3.82 (ddd, J = 4.04, 8.06, 10.50 Hz, 1 H), 3.64-3.75 (m, 2 H), 3.42-3.57 (m, 3 H), 3.18 (dd, J = 9.64, 12.75 Hz, 1 H), 3.04 (ddd, J = 3.32, 10.88, 12.44 Hz, 1 H), 2.36-2.45 (m, 1 H), 2.07-2.21 (m, 1 H), 1.88-2.05 (m, 2 H) | C |

| Ex. # | Structure Name | LCMS-ESI (POS/NEG) m/z: (M + H)+ | NMR Data | Syn. Rte. |
|---|---|---|---|---|
| 117 | 1-(((3S)-1-((3-cyano-1-azetidinyl)sulfonyl)-3-piperidinyl)carbonyl)-N-((R)-cyclopropyl(4-(pentafluoro-lambda-6~-sulfanyl)phenyl)methyl)-D-prolinamide | LCMS-ESI (POS.) m/z : 626.0 (M + H)+ | 1H NMR (500 MHz, DMSO-d6) δ ppm 8.33-8.96 (m, 1 H), 7.43-7.95 (m, 4 H), 4.40-4.53 (m, 1 H), 4.24 (br t, J = 8.17 Hz, 1 H), 4.02-4.11 (m, 2 H), 3.89-3.99 (m, 2 H), 3.74-3.85 (m, 1 H), 3.33-3.61 (m, 4 H), 2.64-2.83 (m, 1 H), 2.07-2.28 (m, 2 H), 1.63-1.94 (m, 6 H), 1.35-1.52 (m, 2 H), 1.07-1.17 (m, 1 H), 0.29-0.61 (m, 4 H) | A |
| 118 | (1R,3R,5R)-N-((R)-cyclopropyl(2-fluoro-4-(trifluoromethyl)phenyl)methyl)-2-(2-((2-hydroxyethyl)amino)-5-(methylsulfonyl)benzoyl)-2-azabicyclo[3.1.0]hexane-3-carboxamide | LCMS-APCI (POS.) m/z: 584.2 (M + H)+ | 1H NMR (400 MHz, DMSO-d6) δ ppm 8.82 (d, J = 7.6 Hz, 1 H), 7.87 (d, J = 2.3 Hz, 1 H), 7.59-7.74 (m, 3 H), 6.78-6.91 (m, 2 H), 4.93-5.01 (m, 1 H), 4.80 (t, J = 5.3 Hz, 1 H), 4.59 (t, J = 8.0 Hz, 1 H), 3.58 (p, J = 5.5 Hz, 2 H), 3.20-3.30 (m, 2 H), 3.18 (s, 1 H), 3.09 (s, 2 H), 1.73 (dd, J = 3.3, 13.6 Hz, 2 H), 1.54-1.65 (m, 1 H), 1.13-1.27 (m, 2 H), 0.87-0.99 (m, 1 H), 0.62-0.69 (m, 1 H), 0.54-0.62 (m, 1 H), 0.41-0.54 (m, 1 H), 0.29-0.41 (m, 2 H). | S |
| 119 | N-(4-chloro-2-methylbenzyl)-1-(((3S)-1-((3-cyano-1-azetidinyl)sulfonyl)-3-piperidinyl)carbonyl)-D-prolinamide | LCMS-ESI (POS.) m/z: 508.2 (M + H)+ | 1H NMR (500 MHz, DMSO-d6) δ ppm 8.10-8.60 (m, 1 H), 7.03-7.35 (m, 3 H), 4.12-4.51 (m, 3 H), 4.01-4.12 (m, 2 H), 3.89-3.99 (m, 2 H), 3.73-3.87 (m, 1 H), 3.39-3.69 (m, 4 H), 2.60-2.84 (m, 3 H), 2.07-2.36 (m, 4 H), 1.66-2.01 (m, 5 H), 1.26-1.57 (m, 2 H) | A |
| 120 |  | LCMS-ESI (POS.) m/z: 517.2 (M + H)+ | 1H NMR (500 MHz, DMSO-d6) δ ppm 8.24-8.58 (m, 1 H), 7.72-8.01 (m, 4 H), 7.31-7.56 (m, 4 H), 6.85-7.12 (m, 1 H), 4.69-5.02 (m, 1 H), 4.56 (s, 1 H), 3.99-4.07 (m, 2 H), 3.87-3.90 (m, 2 H), 3.48-3.65 (m, 3 H), 2.19-2.29 (m, 1 H), 1.74-1.94 (m, 3 H), 1.09-1.43 (m, 3 H) | A |

| Ex. # | Structure Name | LCMS-ESI (POS/NEG) m/z: (M + H)+ | NMR Data | Syn. Rte. |
|---|---|---|---|---|
| 121 | 1-((3-((3-cyano-1-azetidinyl)sulfonyl)phenyl)carbonyl)-N-((1R)-1-(4-(difluoromethyl)phenyl)ethyl)-D-prolinamide | | | |
| | 3-((3-cyano-1-azetidinyl)sulfonyl)-N-methyl-N-((1R)-1-methyl-2-oxo-2-(((1R)-1-(4-(trifluoromethyl)phenyl)ethyl)amino)ethyl)benzamide | LCMS-ESI (POS.) m/z: 523.1 (M + H)+ | 1H NMR (500 MHz, DMSO-d6) δ ppm 8.38-8.66 (m, 1 H), 7.75-7.97 (m, 4 H), 7.47-7.74 (m, 4 H), 5.01 (br s, 1 H), 3.56-4.25 (m, 6 H), 2.80-2.96 (m, 3 H), 1.29-1.46 (m, 6 H) | C |
| 122 | (4R)-1-((3-((3-cyano-1-azetidinyl)sulfonyl)phenyl)carbonyl)-4-fluoro-N-(4-(trifluoromethyl)benzyl)-D-prolinamide | LCMS-APCI (POS.) m/z: 539.2 (M + H)+ | 1H NMR (400 MHz, Methanol-d4) δ ppm 6.87-7.52 (m, 1 H), 6.63-6.78 (m, 2 H), 6.49-6.57 (m, 1 H), 5.99-6.45 (m, 4 H), 3.90-4.18 (m, 1 H), 3.53-3.65 (m, 1 H), 2.45-3.34 (m, 8 H), 2.14-2.30 (m, 1 H), 1.11-1.45 (m, 2 H). | Q |
| 123 | 1-((1-((3-cyano-1-azetidinyl)sulfonyl)-1H-pyrazol-4-yl)carbonyl)-N-(4-(trifluoromethyl)benzyl)-D-prolinamide | LCMS-ESI (POS) m/z: 511.0 (M + H)+ | 1H NMR (400 MHz, CHLOROFORM-d) δ 8.31-8.45 (m, 1 H), 8.18-8.26 (m, 1 H), 7.55-7.64 (m, 2 H), 7.38-7.45 (m, 2 H), 7.30-7.38 (m, 1 H), 4.75-4.85 (m, 1 H), 4.51-4.64 (m, 1 H), 4.38-4.51 (m, 5 H), 3.82-3.92 (m, 1 H), 3.71-3.82 (m, 1 H), 3.47-3.58 (m, 1 H), 2.43-2.55 (m, 1 H), 2.22-2.36 (m, 1 H), 1.97-2.16 (m, 2 H) | M |
| 124 | 1-(3-((3-cyano-1-azetidinyl)sulfonyl)benzoyl)-N-((1R)-1-(3,5-difluorophenyl)propyl)-D-prolinamide | LCMS-ESI (Pos.) m/z: 517.2 (M + H)+ | 1H NMR (500 MHz, DMSO-d6) δ ppm 8.38 (d, J = 8.30 Hz, 1 H), 7.58-8.04 (m, 4 H), 6.78-7.16 (m, 3 H), 4.32-4.82 (m, 2 H), 3.99-4.09 (m, 2 H), 3.86-3.90 (m, 2 H), 3.41-3.68 (m, 3 H), 3.29-3.30 (m, 1 H), 2.19-2.32 (m, 1 H), 1.74 (br dd, J = 5.71, 2.72 Hz, 5 H), 0.39-0.97 (m, 3 H) | A |

-continued

| Ex. # | Structure Name | LCMS-ESI (POS/NEG) m/z: (M + H)+ | NMR Data | Syn. Rte. |
|---|---|---|---|---|
| 125 | 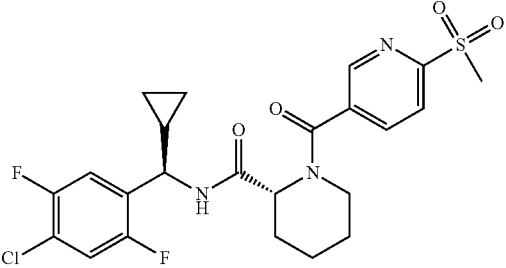 [SMILES: CS(=O)(=O)c1ccc(C(=O)N2CCCC[C@@H]2C(=O)N[C@@H](c2cc(F)c(Cl)cc2F)C2CC2)cn1]<br>(2R)-N-((R)-(4-chloro-2,5-difluorophenyl)(cyclopropyl)methyl)-1-((6-(methylsulfonyl)-3-pyridinyl)carbonyl)-2-piperidinecarboxamide | LCMS-ESI (POS.) m/z: 512.0 (M + H)+ | 1H NMR (500 MHz, DMSO-d6) δ ppm 8.80-8.99 (m, 1 H), 8.43-8.67 (m, 1 H), 7.95-8.10 (m, 2 H), 7.47-7.70 (m, 2 H), 4.45 (br s, 2 H), 3.32-3.55 (m, 4 H), 3.01-3.15 (m, 1 H), 1.97-2.25 (m, 1 H), 1.10-1.81 (m, 6 H), 0.26-0.65 (m, 4 H) | C |
| 126 | 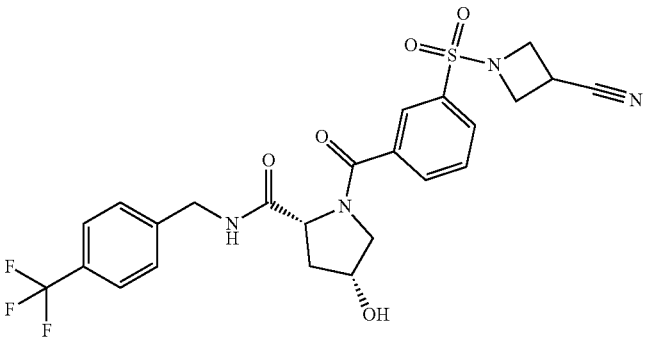 [SMILES: N#CC1CN(S(=O)(=O)c2cccc(C(=O)N3C[C@H](O)C[C@@H]3C(=O)NCc3ccc(C(F)(F)F)cc3)c2)C1]<br>(4R)-1-((3-((3-cyano-1-azetidinyl)sulfonyl)phenyl)carbonyl)-4-hydroxy-N-(4-(trifluoromethyl)benzyl)-D-prolinamide | LCMS-APCI (POS.) m/z: 537.2 (M + H)+ | 1H NMR (400 MHz, Methanol-d4) δ ppm 7.28-8.19 (m, 8 H), 3.90-4.74 (m, 8 H), 3.46-3.78 (m, 3 H), 2.49-2.62 (m, 1 H), 2.00-2.18 (m, 1 H). | C |
| 127 | 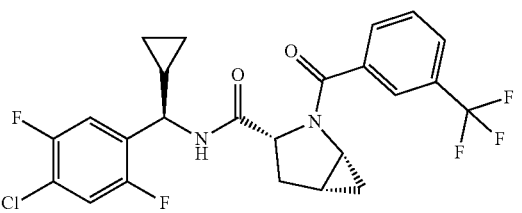 [SMILES: O=C(N[C@@H](c1cc(F)c(Cl)cc1F)C1CC1)[C@H]1C[C@H]2C[C@H]2N1C(=O)c1cccc(C(F)(F)F)c1]<br>(1R,3R,5R)-N-((R)-(4-chloro-2,5-difluorophenyl)(cyclopropyl)methyl)-2-(3-(trifluoromethyl)benzoyl)-2-azabicyclo[3.1.0]hexane-3-carboxamide | LCMS-APCI (POS.) m/z: 499.1 (M + H)+ | 1H NMR (400 MHz, Methylene Chloride-d2) δ ppm 8.02 (s, 1 H), 7.96 (d, J = 7.8 Hz, 1 H), 7.81 (d, J = 8.0 Hz, 1 H), 7.67 (t, J = 7.7 Hz, 1 H), 7.58-7.64 (m, 1 H), 7.20 (ddd, J = 3.7, 6.3, 9.4 Hz, 1 H), 5.10-5.16 (m, 1 H), 4.53 (t, J = 7.8 Hz, 1 H), 3.30 (dt, J = 3.3, 6.3 Hz, 1 H), 2.54-2.61 (m, 1 H), 2.25-2.35 (m, 1 H), 1.30 (s, 1 H), 1.09-1.22 (m, 1 H), 0.99-1.06 (m, 1 H), 0.82-0.89 (m, 1 H), 0.50-0.57 (m, 1 H), 0.32-0.39 (m, 1 H). | Q |

| Ex. # | Structure Name | LCMS-ESI (POS/NEG) m/z: (M + H)+ | NMR Data | Syn. Rte. |
|---|---|---|---|---|
| 128 | 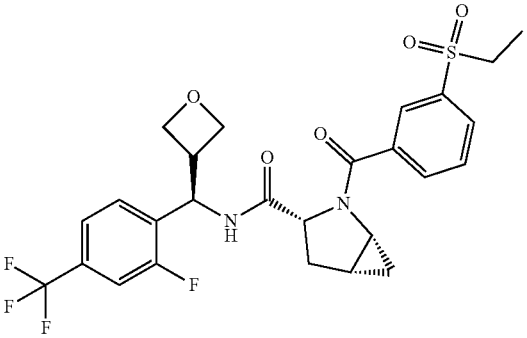 [SMILES: CCS(=O)(=O)c1cccc(C(=O)N2[C@@H](C(=O)N[C@@H](c3ccc(C(F)(F)F)cc3F)C3COC3)C[C@H]3C[C@H]32)c1]<br>(1R,3R,5R)-2-(3-(ethylsulfonyl)benzoyl)-N-((R)-(2-fluoro-4-(trifluoromethyl)phenyl)(3-oxetanyl)methyl)-2-azabicyclo[3.1.0]hexane-3-carboxamide | LCMS-APCI (POS.) m/z: 555.2 (M + H)+ | 1H NMR (400 MHz, Methanol-d4) δ ppm 8.35 (t, J = 1.7 Hz, 1 H), 8.13 (dt, J = 1.3, 7.7 Hz, 1 H), 8.07 (ddd, J = 1.1, 1.9, 7.9 Hz, 1 H), 7.79 (t, J = 7.8 Hz, 1 H), 7.48-7.60 (m, 3 H), 5.63-5.69 (m, 1 H), 5.01 (dd, J = 4.2, 11.4 Hz, 1 H), 4.62-4.70 (m, 2 H), 4.40 (t, J = 6.3 Hz, 1 H), 3.51-3.62 (m, 1 H), 3.37 (s, 4 H), 3.24-3.31 (m, 3 H), 2.62-2.71 (m, 1 H), 1.91 (dd, J = 4.2, 13.5 Hz, 1 H), 1.81 (dq, J = 6.2, 9.1 Hz, 1 H), 1.26 (t, J = 7.4 Hz, 4 H), 0.85-0.92 (m, 1 H). | A |
| 129 | 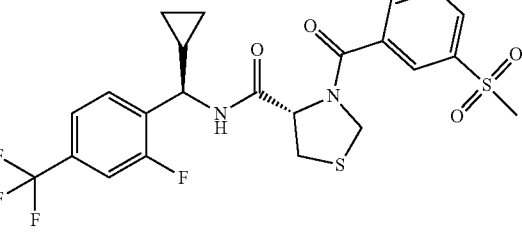<br>(4S)-N-((R)-cyclopropyl(2-fluoro-4-(trifluoromethyl)phenyl)methyl)-3-(3-(methylsulfonyl)benzoyl)-1,3-thiazolidine-4-carboxamide | LCMS-ESI (POS.) m/z: 531.0 (M + H)+ | 1H NMR (500 MHz, CHLOROFORM-d) δ ppm 8.07-8.18 (m, 2 H), 7.79-7.87 (m, 1 H), 7.67-7.76 (m, 1 H), 7.41-7.50 (m, 2 H), 7.37 (d, J = 10.51 Hz, 1 H), 5.03-5.15 (m, 1 H), 4.44-4.64 (m, 3 H), 3.54-3.68 (m, 1 H), 3.27 (dd, J = 11.94, 7.40 Hz, 1 H), 3.02-3.18 (m, 3 H), 1.23-1.33 (m, 1 H), 0.60-0.68 (m, 1 H), 0.52-0.60 (m, 1 H), 0.36-0.48 (m, 2 H), (1H obscured by CDCl3) | C |
| 130 | 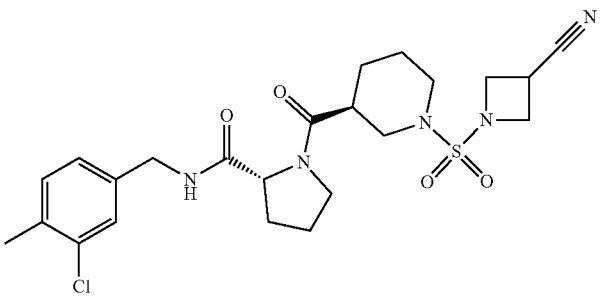 [SMILES: Cc1ccc(CNC(=O)[C@H]2CCCN2C(=O)[C@H]2CCCN(S(=O)(=O)N3CC(C#N)C3)C2)cc1Cl]<br>N-(3-chloro-4-methylbenzyl)-1-(((3S)-1-((3-cyano-1-azetidinyl)sulfonyl)-3-piperidinyl)carbonyl)-D-prolinamide | LCMS-ESI (POS.) m/z: 508.2 (M + H)+ | 1H NMR (500 MHz, DMSO-d6) δ ppm 8.26 (br t, J = 5.97 Hz, 1 H), 7.01-7.36 (m, 3 H), 4.15-4.52 (m, 3 H), 3.99-4.11 (m, 2 H), 3.86-3.99 (m, 2 H), 3.73-3.84 (m, 1 H), 3.62-3.70 (m, 1 H), 3.50-3.61 (m, 3 H), 3.35-3.50 (m, 3 H), 2.71-2.87 (m, 2 H), 2.60-2.70 (m, 1 H), 2.04-2.23 (m, 1 H), 1.66-1.97 (m, 5 H), 1.29-1.57 (m, 2 H) | A |
| 131 | 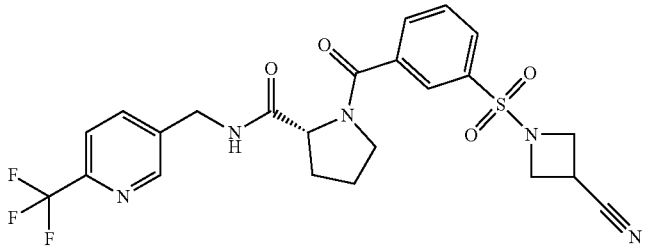 [SMILES: N#CC1CN(S(=O)(=O)c2cccc(C(=O)N3CCC[C@@H]3C(=O)NCc3ccc(C(F)(F)F)nc3)c2)C1]<br>1-((3-((3-cyano-1-azetidinyl)sulfonyl)phenyl)carbonyl)-N-((6-(trifluoromethyl)-3-pyridinyl)methyl)-D-prolinamide | LCMS-APCI (NEG.) m/z: 520.1 (M − H) | 1H NMR (400 MHz, Methanol-d4) δ ppm 8.69 (d, J = 2.3 Hz, 1 H), 8.13 (q, J = 2.0 Hz, 1 H), 7.95-8.08 (m, 3 H), 7.73-7.83 (m, 2 H), 4.55-4.71 (m, 2 H), 4.49 (d, J = 15.8 Hz, 1 H), 4.08-4.16 (m, 2 H), 3.93 (ddd, J = 4.5, 6.2, 8.5 Hz, 2 H), 3.69 (dt, J = 6.8, 10.3 Hz, 1 H), 3.45-3.64 (m, 2 H), 2.32-2.43 (m, 1 H), 1.90-2.07 (m, 3 H). | A |

-continued

| Ex. # | Structure Name | LCMS-ESI (POS/NEG) m/z: (M + H)+ | NMR Data | Syn. Rte. |
|---|---|---|---|---|
| 132 | 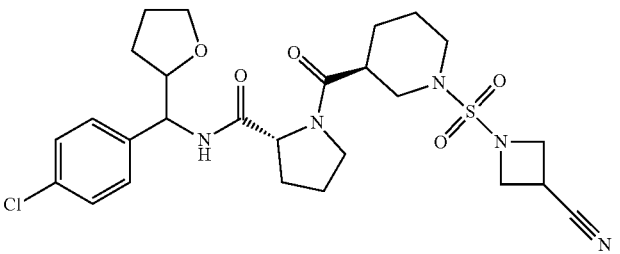 [SMILES: N#CC1CN(S(=O)(=O)N2CCC[C@H](C(=O)N3CCC[C@@H]3C(=O)NC(c3ccc(Cl)cc3)C3CCCO3)C2)C1]<br>N-(-(4-chlorophenyl)(-tetrahydro-2-furanyl)methyl)-1-(((3S)-1-((3-cyano-1-azetidinyl)sulfonyl)-3-piperidinyl)carbonyl)-D-prolinamide | LCMS-ESI (POS.) m/z: 564.2 (M + H)+ | 1H NMR (500 MHz, DMSO-d6) δ ppm 8.06-8.77 (m, 1 H), 7.26-7.41 (m, 4 H), 4.62-4.93 (m, 1 H), 4.28-4.60 (m, 1 H), 3.86-4.18 (m, 5 H), 3.34-3.85 (m, 7 H), 2.58-2.88 (m, 2 H), 1.26-2.31 (m, 13 H) | A |
| 133 | 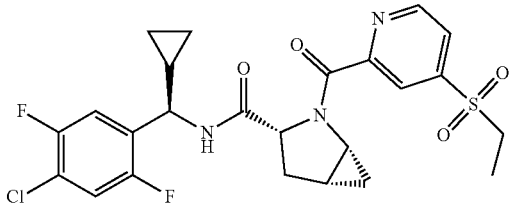 [SMILES: CCS(=O)(=O)c1ccnc(C(=O)N2[C@@H](C(=O)N[C@@H](c3cc(F)c(Cl)cc3F)C3CC3)C[C@H]3C[C@H]32)c1]<br>(1R,3R,5R)-N-((R)-(4-chloro-2,5-difluorophenyl)(cyclopropyl)methyl)-2-((4-(ethylsulfonyl)-2-pyridinyl)carbonyl)-2-azabicyclo[3.1.0]hexane-3-carboxamide | LCMS-ESI (POS.) m/z: 524.0 (M + H)+ | 1H NMR (500 MHz, DMSO-d6) δ ppm 8.41-9.08 (m, 2 H), 7.93-8.21 (m, 2 H), 7.30-7.70 (m, 2 H), 4.85-5.53 (m, 2 H), 4.03-4.61 (m, 2 H), 3.71-3.95 (m, 1 H), 3.34-3.61 (m, 2 H), 2.53-2.84 (m, 1 H), 1.47-1.92 (m, 2 H), 0.94-1.30 (m, 4 H), 0.24-0.84 (m, 4 H), −0.21-0.03 (m, 1 H) | H |
| 134 | 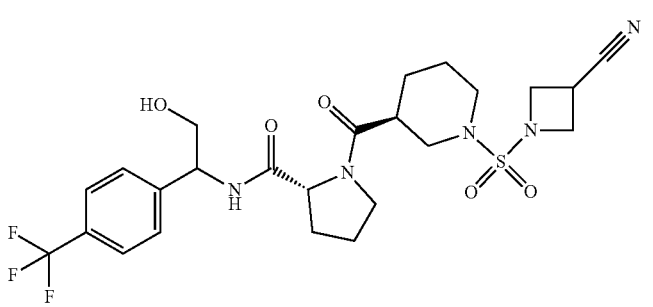 [SMILES: N#CC1CN(S(=O)(=O)N2CCC[C@H](C(=O)N3CCC[C@@H]3C(=O)NC(CO)c3ccc(C(F)(F)F)cc3)C2)C1]<br>1-(((3S)-1-((3-cyano-1-azetidinyl)sulfonyl)-piperidinyl)carbonyl)-N-(-2-hydroxy-1-(4-(trifluoromethyl)phenyl)ethyl)-D-prolinamide | LCMS-ESI (POS.) m/z: 558.2 (M + H)+ | 1H NMR (500 MHz, DMSO-d6) δ ppm 8.12-8.67 (m, 1 H), 7.66 (br d, J = 7.79 Hz, 2 H), 7.45-7.59 (m, 2 H), 4.79-5.04 (m, 2 H), 4.30-4.59 (m, 1 H), 4.01-4.16 (m, 2 H), 3.89-4.00 (m, 2 H), 3.42-3.84 (m, 7 H), 2.59-2.94 (m, 3 H), 2.01-2.32 (m, 1 H), 1.61-2.00 (m, 5 H), 1.27-1.57 (m, 2 H) | A |
| 135 | 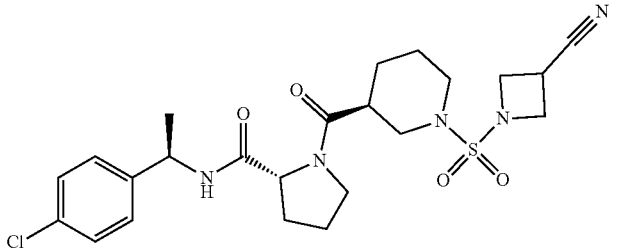 [SMILES: C[C@@H](NC(=O)[C@H]1CCCN1C(=O)[C@H]1CCCN(S(=O)(=O)N2CC(C#N)C2)C1)c1ccc(Cl)cc1]<br>N-((1R)-1-(4-chlorophenyl)ethyl)-1-(((3S)-1-((3-cyano-1-azetidinyl)sulfonyl)-3-piperidinyl)carbonyl)-D-prolinamide | LCMS-ESI (POS.) m/z: 508.2 (M + H)+ | 1H NMR (500 MHz, CHLOROFORM-d) δ ppm 7.28-7.31 (m, 2 H), 7.21-7.25 (m, 2 H), 4.96 (quin, J = 7.07 Hz, 1 H), 4.54 (br d, J = 6.88 Hz, 1 H), 4.06-4.15 (m, 4 H), 3.77 (br d, J = 12.46 Hz, 2 H), 3.52-3.63 (m, 2 H), 3.38-3.47 (m, 1 H), 3.00 (t, J = 11.87 Hz, 1 H), 2.67-2.82 (m, 2 H), 2.31-2.43 (m, 1 H), 2.08-2.24 (m, 1 H), 1.94-2.06 (m, 2 H), 1.77-1.89 (m, 2 H), 1.56-1.73 (m, 3 H), 1.40 (d, J = 6.88 Hz, 3 H) | C |

-continued

| Ex. # | Structure Name | LCMS-ESI (POS/NEG) m/z: (M + H)+ | NMR Data | Syn. Rte. |
|---|---|---|---|---|
| 136 | 1-((3-((3-cyano-1-azetidinyl)sulfonyl)phenyl)carbonyl)-N-((2-(trifluoromethyl)-5-pyrimidinyl)methyl)-D-prolinamide | LCMS-APCI (POS.) m/z: 523.1 (M + H)+ | 1H NMR (400 MHz, Methanol-d4) δ ppm 8.66-9.02 (m, 2 H), 8.11-8.27 (m, 1 H), 7.88-8.05 (m, 2 H), 7.60-7.85 (m, 1 H), 4.30-4.73 (m, 3 H), 4.06-4.17 (m, 2 H), 3.91-3.99 (m, 2 H), 3.47-3.83 (m, 3 H), 2.34-2.47 (m, 1 H), 1.90-2.13 (m, 3 H). | A |
| 137 | N-(4-chloro-3-methylbenzyl)-1-(((3S)-1-((3-cyano-1-azetidinyl)sulfonyl)-3-piperidinyl)carbonyl)-D-prolinamide | LCMS-ESI (POS.) m/z: 508.2 (M + H)+ | 1H NMR (500 MHz, DMSO-d6) δ ppm 8.26 (s, 1 H), 6.98-7.41 (m, 3 H), 4.10-4.52 (m, 3 H), 4.01-4.10 (m, 2 H), 3.85-3.99 (m, 2 H), 3.73-3.83 (m, 1 H), 3.41-3.72 (m, 4 H), 2.61-2.90 (m, 3 H), 2.26-2.41 (m, 3 H), 2.04-2.28 (m, 1 H), 1.66-1.97 (m, 5 H), 1.22-1.60 (m, 2 H) | A |
| 138 | (1R,3R,5R)-N-((R)-(4-chloro-2,5-difluorophenyl)(cyclopropyl)methyl)-2-((4-(cyclopropylsulfonyl)-2-pyridinyl)carbonyl)-2-azabicyclo[3.1.0]hexane-3-carboxamide | LCMS-ESI (POS.) m/z: 536.0 (M + H)+ | 1H NMR (500 MHz, DMSO-d6) δ ppm 8.77-9.04 (m, 1 H), 8.45-8.66 (m, 1 H), 8.12 (dd, J = 14.01, 1.04 Hz, 1 H), 7.92-8.06 (m, 1 H), 7.37-7.67 (m, 2 H), 4.84-5.57 (m, 1 H), 3.67-4.62 (m, 2 H), 2.52-3.21 (m, 2 H), 1.48-1.92 (m, 2 H), 1.10-1.30 (m, 4 H), 0.90-1.07 (m, 1 H), −0.25-0.85 (m, 6 H) | H |
| 139 | (1R,3R,5R)-N-((R)-(4-chloro-2,5-difluorophenyl)(cyclopropyl)methyl)-2-(3-sulfamoylbenzoyl)-2-azabicyclo[3.1.0]hexane-3-carboxamide | LCMS-ESI (POS.) m/z: 510.0 (M + H)+ | 1H NMR (400 MHz, CHLOROFORM-d) δ ppm 8.28-8.35 (m, 1 H), 8.06 (d, J = 7.88 Hz, 1 H), 7.96 (d, J = 7.77 Hz, 1 H), 7.63 (t, J = 7.77 Hz, 1 H), 7.49 (br d, J = 7.15 Hz, 1 H), 7.14 (ddd, J = 9.30, 5.99, 3.47 Hz, 2 H), 5.34 (br s, 2 H), 5.13 (dd, J = 10.31, 3.27 Hz, 1 H), 4.48 (t, J = 7.93 Hz, 1 H), 3.28 (td, J = 6.19, 2.64 Hz, 1 H), 2.32-2.50 (m, 2 H), 1.66-1.82 (m, 1 H), 1.11-1.29 (m, 2 H), 0.89 (dt, J = 8.73, 6.21 Hz, 1 H), 0.45-0.62 (m, 2 H), 0.26-0.42 (m, 2 H) | C |

| Ex. # | Structure Name | LCMS-ESI (POS/NEG) m/z: (M + H)+ | NMR Data | Syn. Rte. |
|---|---|---|---|---|
| 140 | (1R,3R,5R)-N-((R)-(4-chloro-2,5-difluorophenyl)(3-oxetanyl)methyl)-2-(3-methyl-5-(methylsulfonyl)benzoyl)-2-azabicyclo[3.1.0]hexane-3-carboxamide | LCMS-APCI (POS.) m/z: 539.2 (M + H)+ | 1H NMR (400 MHz, DMSO-d6) δ ppm 8.66 (d, J = 8.3 Hz, 1 H), 7.99 (t, J = 1.8 Hz, 1 H), 7.90 (s, 1 H), 7.80 (s, 1 H), 7.62-7.71 (m, 1 H), 7.44 (dd, J = 6.3, 9.8 Hz, 1 H), 5.34-5.47 (m, 1 H), 4.87 (dd, J = 3.7, 11.4 Hz, 1 H), 4.63 (dd, J = 6.4, 7.7 Hz, 1 H), 4.51 (dd, J = 6.3, 7.8 Hz, 1 H), 4.37 (t, J = 6.1 Hz, 1 H), 4.20 (t, J = 6.3 Hz, 1 H), 3.25 (s, 3 H), 2.49 (s, 3 H), 1.64-1.78 (m, 2 H), 1.16 (td, J = 2.6, 5.1 Hz, 1 H), 0.77 (dt, J = 5.3, 10.1 Hz, 1 H). | Q |
| 141 | (4S)-N-((R)-(4-chloro-2,5-difluorophenyl)(3-oxetanyl)methyl)-4-fluoro-1-(3-(methylsulfonyl)benzoyl)-D-prolinamide | LCMS-APCI (POS.) m/z: 531.1 (M + H)+ | 1H NMR (400 MHz, DMSO-d6) δ ppm 8.77 (d, J = 8.3 Hz, 1 H), 8.09 (ddd, J = 1.1, 1.9, 7.8 Hz, 1 H), 7.86-8.05 (m, 2 H), 7.68-7.83 (m, 1 H), 7.57-7.68 (m, 1 H), 7.47 (dd, J = 6.2, 9.8 Hz, 1 H), 5.48 (t, J = 9.1 Hz, 1 H), 5.20-5.42 (m, 1 H), 4.59-5.02 (m, 2 H), 4.38-4.57 (m, 1 H), 4.20-4.37 (m, 1 H), 4.10 (q, J = 5.2 Hz, 1 H), 3.87-4.04 (m, 1 H), 3.54-3.73 (m, 1 H), 3.42 (h, J = 6.5 Hz, 1 H), 3.28 (s, 2 H), 3.18 (d, J = 5.3 Hz, 1 H), 1.82-2.09 (m, 1 H). | A |
| 142 | 1-((2-((3-cyano-1-azetidinyl)sulfonyl)-4-pyridinyl)carbonyl)-N-(2-fluoro-4-(trifluoromethyl)benzyl)-D-prolinamide | LCMS-ESI (POS.) m/z: 540.2 (M + H)+ | 1H NMR (400 MHz, CHLOROFORM-d) δ ppm 8.59-8.95 (m, 1 H), 7.91-8.11 (m, 1 H), 7.67 (dd, J = 4.87, 1.45 Hz, 1 H), 7.48-7.56 (m, 1 H), 7.42 (d, J = 7.88 Hz, 1 H), 7.31-7.37 (m, 1 H), 7.10 (br t, J = 5.80 Hz, 1 H), 4.72 (dd, J = 7.67, 4.66 Hz, 1 H), 4.59 (d, J = 6.01 Hz, 2 H), 4.35-4.52 (m, 4 H), 3.38-3.65 (m, 3 H), 2.38-2.52 (m, 1 H), 2.09-2.26 (m, 2 H), 1.88-2.07 (m, 1 H) | C |
| 143 | 1-(((3S)-1-((3-cyano-1-azetidinyl)sulfonyl)-4,4-difluoro-3-piperidinyl)carbonyl)-N-(4-(trifluoromethyl)benzyl)-D-prolinamide | LCMS-ESI (POS.) m/z: 564.2 (M + H)+ | 1H NMR (500 MHz, CHLOROFORM-d) δ ppm 7.55 (d, J = 8.30 Hz, 2 H), 7.28-7.43 (m, 2 H), 4.74 (br d, J = 6.23 Hz, 1 H), 4.59 (dd, J = 15.70, 6.62 Hz, 1 H), 4.38 (dd, J = 15.70, 5.32 Hz, 1 H), 4.05-4.21 (m, 4 H), 3.64-3.83 (m, 3 H), 3.40-3.59 (m, 3 H), 3.12-3.31 (m, 3 H), 2.40-2.59 (m, 1 H), 2.22-2.39 (m, 1 H), 2.00-2.20 (m, 3 H), 1.93 (tt, J = 11.74, 7.59 Hz, 1 H), 1.68 (br s, 1 H), 1.25-1.43 (m, 3 H) | M |

-continued

| Ex. # | Structure Name | LCMS-ESI (POS/NEG) m/z: (M + H)+ | NMR Data | Syn. Rte. |
|---|---|---|---|---|
| 144 | 1-(((2S)-4-((3-cyano-1-azetidinyl)sulfonyl)-2-piperazinyl)carbonyl)-N-((1R)-1-(2-fluoro-4-(trifluoromethyl)phenyl)ethyl)-D-prolinamide | LCMS-ESI (POS.) m/z: 561.2 (M + H)+ | 1H NMR (400 MHz, CHLOROFORM-d) δ 7.29-7.47 (m, 4 H), 5.12-5.30 (m, 1 H), 4.53 (dd, J = 1.92, 8.14 Hz, 1 H), 4.08-4.23 (m, 4 H), 3.82-3.90 (m, 1 H), 3.79 (dd, J = 3.21, 10.47 Hz, 1 H), 3.69-3.75 (m, 1 H), 3.60-3.67 (m, 1 H), 3.42-3.56 (m, 2 H), 3.14-3.22 (m, 1 H), 2.92-3.02 (m, 1 H), 2.74-2.87 (m, 3 H), 2.33-2.41 (m, 1 H), 2.00-2.20 (m, 2 H), 1.86-1.99 (m, 1 H), 1.47 (d, J = 6.95 Hz, 3 H) | E |
| 145 | 1-(((3S)-1-((3-cyano-1-azetidinyl)sulfonyl)-3-piperidinyl)carbonyl)-N-(2-methyl-3-(trifluoromethyl)benzyl)-D-prolinamide | LCMS-ESI (POS.) m/z: 542.0 (M + H)+ | 1H NMR (500 MHz, DMSO-d6) δ ppm 8.16-8.65 (m, 1 H), 7.30-7.63 (m, 3 H), 4.26-4.54 (m, 3 H), 4.04-4.10 (m, 2 H), 3.93 (br d, J = 2.85 Hz, 2 H), 3.73-3.79 (m, 1 H), 3.28-3.63 (m, 4 H), 2.71-2.86 (m, 2 H), 2.58-2.71 (m, 1 H), 2.30-2.39 (m, 3 H), 1.66-2.16 (m, 6 H), 1.32-1.56 (m, 2 H) | A |
| 146 | 1-(3-(dimethylsulfamoyl)benzoyl)-N-((1R)-1-(2-fluoro-4-(trifluoromethyl)phenyl)propyl)-D-prolinamide | LCMS-ESI (POS.) m/z: 530.2 (M + H)+ | 1H NMR (500 MHz, DMSO-d6) δ ppm 8.29-8.62 (m, 1 H), 7.40-7.89 (m, 7 H), 4.45-5.04 (m, 2 H), 3.39-3.66 (m, 2 H), 2.57-2.71 (m, 6 H), 2.16-2.32 (m, 1 H), 1.40-1.97 (m, 5 H), 0.52-1.03 (m, 3 H) | A |
| 147 | N-((R)-cyclopropyl(2,5-difluoro-4-(trifluoromethyl)phenyl)methyl)-1-(3-(methylsulfonyl)benzoyl)-D-prolinamide | LCMS-ESI (POS.) m/z: 531.0 (M + H)+ | 1H NMR (500 MHz, DMSO-d6) δ ppm 8.70 (d, J = 7.53 Hz, 1 H), 7.63-8.09 (m, 5 H), 7.59 (dd, J = 10.96, 5.38 Hz, 1 H), 4.50-4.57 (m, 1 H), 4.11-4.25 (m, 1 H), 3.40-3.63 (m, 2 H), 3.20-3.33 (m, 3 H), 2.15-2.32 (m, 1 H), 1.67-1.91 (m, 3 H), 0.90-1.26 (m, 1 H), −0.07-0.67 (m, 4 H) | A |

| Ex. # | Structure Name | LCMS-ESI (POS/NEG) m/z: (M + H)+ | NMR Data | Syn. Rte. |
|---|---|---|---|---|
| 148 | (1R,3R,5R)-N-((R)-cyclopropyl(2-fluoro-4-(trifluoromethyl)phenyl)methyl)-2-(2-(methylamino)-5-(methylsulfonyl)benzoyl)-2-azabicyclo[3.1.0]hexane-3-carboxamide | LCMS-APCI (POS.) m/z: 554.2 (M + H)+ | 1H NMR (400 MHz, DMSO-d6) δ ppm 8.82 (d, J = 7.5 Hz, 1 H), 7.60-7.79 (m, 4 H), 6.69-6.80 (m, 2 H), 4.97 (dd, J = 3.3, 11.7 Hz, 1 H), 4.62 (t, J = 8.0 Hz, 1 H), 3.09 (s, 3 H), 2.83 (d, J = 4.9 Hz, 2 H), 1.54-1.78 (m, 3 H), 1.11-1.23 (m, 2 H), 0.83-0.91 (m, 1 H), 0.53-0.69 (m, 2 H), 0.42-0.53 (m, 1 H), 0.36 (d, J = 4.4 Hz, 2 H). | S |
| 149 | 1-(((2S)-4-((3-cyano-1-azetidinyl)sulfonyl)-2-morpholinyl)carbonyl)-N-(4-(trifluoromethyl)benzyl)-D-prolinamide | LCMS-ESI (POS.) m/z: 530.2 (M + H)+ | 1H NMR (500 MHz, DMSO-d6) δ ppm 8.50 (t, J = 5.97 Hz, 1 H), 7.65-7.71 (m, 2 H), 7.44-7.49 (m, 2 H), 4.25-4.40 (m, 3 H), 4.07-4.15 (m, 2 H), 3.91-4.01 (m, 3 H), 3.77-3.89 (m, 2 H), 3.56-3.69 (m, 2 H), 3.36-3.48 (m, 2 H), 2.89-3.08 (m, 2 H), 2.05-2.14 (m, 1 H), 1.90-2.00 (m, 1 H), 1.72-1.87 (m, 2 H) | M |
| 150 | N-((1R)-1-(4-chlorophenyl)ethyl)-1-(((3S)-1-((3-(methylsulfonyl)-1-azetidinyl)sulfonyl)-3-piperidinyl)carbonyl)-D-prolinamide | LCMS-ESI (POS.) m/z: 561.2 (M + H)+ | 1H NMR (400 MHz, CHLOROFORM-d) δ 7.25-7.38 (m, 5 H), 4.97 (quin, J = 7.13 Hz, 1 H), 4.54 (dd, J = 2.13, 8.03 Hz, 1 H), 4.15-4.29 (m, 4 H), 3.90-4.02 (m, 1 H), 3.80 (br d, J = 12.54 Hz, 2 H), 3.48-3.65 (m, 2 H), 3.04 (dd, J = 11.04, 12.70 Hz, 1 H), 2.95 (s, 3 H), 2.68-2.89 (m, 2 H), 2.32-2.42 (m, 1 H), 2.09-2.22 (m, 1 H), 1.95-2.09 (m, 2 H), 1.80-1.90 (m, 2 H), 1.67-1.72 (m, 1 H), 1.57-1.64 (m, 1 H), 1.41 (d, J = 6.95 Hz, 3 H) | A |
| 151 | N-(2-fluoro-4-(trifluoromethyl)benzyl)-1-(((3S)-1-((3-(1H-1,2,3-triazol-1-yl)-1-azetidinyl)sulfonyl)-3-piperidinyl)carbonyl)-D-prolinamide | LCMS-ESI (POS.) m/z: 588.2 (M + H)+ | 1H NMR (400 MHz, CHLOROFORM-d) δ 7.78-7.90 (m, 2 H), 7.29-7.51 (m, 4 H), 5.36-5.52 (m, 1 H), 4.60 (dd, J = 2.07, 8.09 Hz, 1 H), 4.39-4.58 (m, 4 H), 4.31 (dd, J = 5.91, 8.91 Hz, 2 H), 3.79-3.88 (m, 2 H), 3.51-3.63 (m, 2 H), 2.99-3.14 (m, 1 H), 2.84 (dt, J = 2.80, 12.44 Hz, 1 H), 2.75 (tt, J = 3.52, 11.30 Hz, 1 H), 2.44 (tdd, J = 2.85, 6.47, 12.40 Hz, 1 H), 2.10-2.23 (m, 1 H), 2.00-2.10 (m, 1 H), 1.79-1.91 (m, 2 H), 1.62-1.76 (m, 2 H), 1.50-1.62 (m, 1 H) | J |

| Ex. # | Structure Name | LCMS-ESI (POS/NEG) m/z: (M + H)+ | NMR Data | Syn. Rte. |
|---|---|---|---|---|
| 152 | 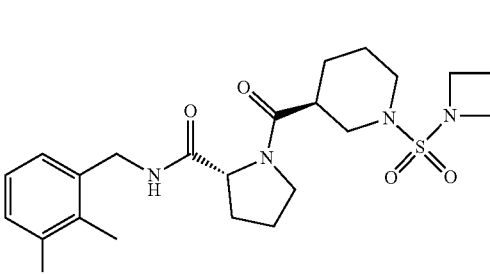<br>N-(3-chloro-2-methylbenzyl)-1-(((3S)-1-((3-cyano-1-azetidinyl)sulfonyl)-3-piperidinyl)carbonyl)-D-prolinamide | LCMS-ESI (POS.) m/z: 508.2 (M + H)+ | 1H NMR (500 MHz, DMSO-d6) δ ppm 8.20 (s, 1 H), 7.08-7.47 (m, 3 H), 4.16-4.54 (m, 3 H), 3.99-4.13 (m, 2 H), 3.86-3.99 (m, 2 H), 3.73-3.85 (m, 1 H), 3.42-3.69 (m, 4 H), 2.57-2.89 (m, 3 H), 2.26-2.37 (m, 3 H), 2.07-2.16 (m, 1 H), 1.65-1.98 (m, 5 H), 1.28-1.57 (m, 2 H) | A |
| 153 | 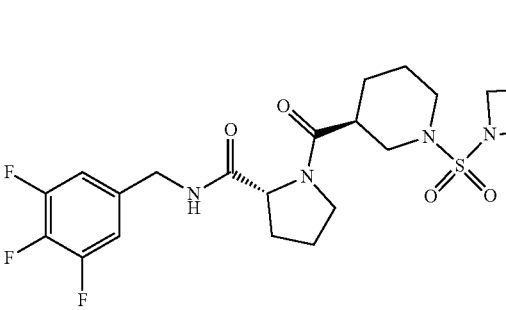<br>1-(((3S)-1-((3-cyano-1-azetidinyl)sulfonyl)-3-piperidinyl)carbonyl)-N-(3,4,5-trifluorobenzyl)-D-prolinamide | LCMS-ESI (POS.) m/z: 514.2 (M + H)+ | 1H NMR (500 MHz, DMSO-d6) δ ppm 8.67-8.72* (m, 1 H), 8.39 (t, J = 6.10 Hz, 1 H), 7.14-7.21 (m, 2 H), 4.17-4.35 (m, 3 H), 3.99-4.09 (m, 2 H), 3.89-3.98 (m, 2 H), 3.75-3.82 (m, 1 H), 3.30-3.71 (m, 4 H), 2.70-2.86 (m, 2 H), 2.64-2.69 (m, 1 H), 2.27-2.35* (m, 1 H), 2.18-2.27* (m, 1 H), 2.04-2.17 (m, 1 H), 1.67-1.97 (m, 5 H), 1.35-1.56 (m, 2 H). Spectrum appears as 3:1 mixture of rotamers, *denotes resolved minor rotamer peaks. | A |
| 154 | 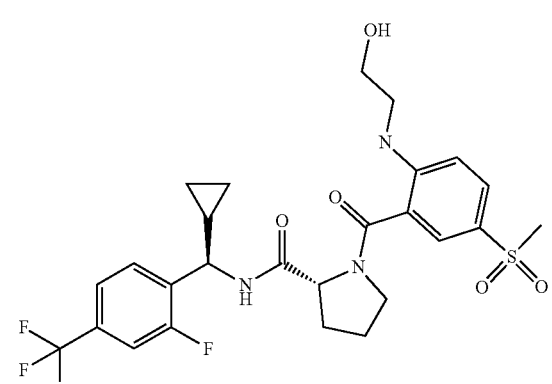<br>N-((R)-cyclopropyl(2-fluoro-4-(trifluoromethyl)phenyl)methyl)-1-(2-((2-hydroxyethyl)amino)-5-(methylsulfonyl)benzoyl)-D-prolinamide | LCMS-APCI (POS.) m/z: 572.2 (M + H)+ | 1H NMR (400 MHz, DMSO-d6) δ ppm 8.89 (d, J = 7.6 Hz, 1 H), 7.69 (ddd, J = 8.4, 18.2, 20.8 Hz, 3 H), 7.57 (s, 1 H), 6.85 (d, J = 9.0 Hz, 1 H), 6.68 (t, 1 H), 4.54-4.81 (m, 3 H), 4.35 (t, J = 5.1 Hz, 1 H), 3.57 (q, J = 5.3 Hz, 2 H), 3.21-3.36 (m, 9 H), 3.11 (s, 2 H), 2.14-2.30 (m, 2 H), 1.60-1.82 (m, 3 H), 1.13-1.28 (m, 1 H), 0.54-0.65 (m, 1 H), 0.46-0.54 (m, 1 H), 0.39 (s, 2 H). | S |
| 155 | 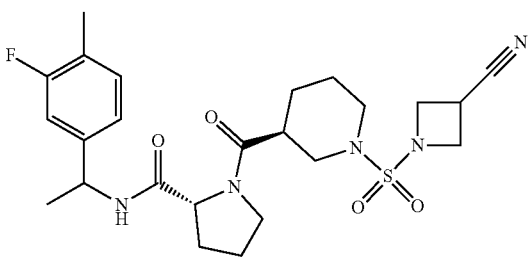 [SMILES: Cc1ccc(C(C)NC(=O)[C@H]2CCCN2C(=O)[C@H]2CCCN(S(=O)(=O)N3CC(C#N)C3)C2)cc1F]<br>1-(((3S)-1-((3-cyano-1-azetidinyl)sulfonyl)-3-piperidinyl)carbonyl)-N-(-1-(3-fluoro-4-methylphenyl)ethyl)-D-prolinamide, | LCMS-ESI (POS.) m/z: 506.2 (M + H)+ | 1H NMR (500 MHz, DMSO-d6) δ ppm 8.06-8.62 (m, 1 H), 7.14-7.29 (m, 1 H), 6.93-7.13 (m, 2 H), 4.74-4.99 (m, 1 H), 4.23-4.48 (m, 1 H), 3.73-4.12 (m, 5 H), 3.47-3.66 (m, 4 H), 2.63-2.89 (m, 3 H), 2.12-2.35 (m, 4 H), 1.61-2.11 (m, 6 H), 1.31-1.57 (m, 4 H) | A |

| Ex. # | Structure Name | LCMS-ESI (POS/NEG) m/z: (M + H)+ | NMR Data | Syn. Rte. |
|---|---|---|---|---|
| 156 | 1-(((3S)-1-((3-cyano-3-methyl-1-azetidinyl)sulfonyl)-3-piperidinyl)carbonyl)-N-(4-(trifluoromethyl)benzyl)-D-prolinamide | LCMS-ESI (POS.) m/z: 542.2 (M + H)+ | 1H NMR (500 MHz, CHLOROFORM-d) δ ppm 7.57 (d, J = 8.04 Hz, 2 H), 7.38-7.46 (m, 1 H), 7.35 (d, J = 7.78 Hz, 2 H), 4.60 (dd, J = 8.04, 1.82 Hz, 1 H), 4.49-4.55 (m, 1 H), 4.37-4.46 (m, 1 H), 4.18 (d, J = 8.04 Hz, 2 H), 3.73-3.81 (m, 4 H), 2.95 (dd, J = 12.72, 10.90 Hz, 1 H), 2.63-2.82 (m, 2 H), 2.41-2.51 (m, 1 H), 2.12-2.25 (m, 1 H), 2.01-2.11 (m, 1 H), 1.58-1.96 (m, 8 H), 1.45-1.56 (m, 1 H), 1.21-1.35 (m, 2 H) | M |
| 157 | 1-((3-((3-cyano-1-azetidinyl)sulfonyl)phenyl)carbonyl)-N-(4-(fluoromethyl)benzyl)-D-prolinamide | LCMS-ESI (POS.) m/z: 485.2 (M + H)+ | 1H NMR (500 MHz, DMSO-d6) δ ppm 8.57 (t, J = 5.97 Hz, 1 H), 7.62-8.06 (m, 4 H), 6.94-7.44 (m, 4 H), 5.38-5.47 (m, 1 H), 5.29-5.35 (m, 1 H), 3.78-4.55 (m, 8 H), 3.60-3.67 (m, 2 H), 2.17-2.31 (m, 1 H), 1.76-1.97 (m, 3 H) | F |
| 158 | 1-(3-((3-cyano-1-azetidinyl)sulfonyl)benzoyl)-N-((1S)-2-hydroxy-1-(3-(trifluoromethyl)phenyl)ethyl)-D-prolinamide | LCMS-ESI (POS.) m/z: 551.0 (M + H)+ | 1H NMR (500 MHz, DMSO-d6) δ ppm 8.30-8.60 (m, 1 H), 7.44-8.04 (m, 8 H), 4.66-5.05 (m, 2 H), 4.32-4.60 (m, 1 H), 3.83-4.08 (m, 4 H), 3.34-3.72 (m, 5 H), 2.21-2.32 (m, 1 H), 1.72-1.90 (m, 3 H) | A |
| 159 | (2R)-N-((R)-(4-chloro-2,5-difluorophenyl)(cyclopropyl)methyl)-1-((4-(methylsulfonyl)-2-pyridinyl)carbonyl)-2-piperidinecarboxamide | LCMS-ESI (POS.) m/z: 512.2 (M + H)+ | 1H NMR (500 MHz, DMSO-d6) δ ppm 8.79-9.01 (m, 1 H), 8.44-8.70 (m, 1 H), 7.95-8.09 (m, 2 H), 7.45-7.67 (m, 2 H), 4.42-5.20 (m, 2 H), 3.39 (d, J = 13.23 Hz, 4 H), 3.00-3.13 (m, 1 H), 2.16 (br s, 1 H), 1.11-1.75 (m, 6 H), 0.29-0.62 (m, 4 H) | C |

-continued

| Ex. # | Structure Name | LCMS-ESI (POS/NEG) m/z: (M + H)+ | NMR Data | Syn. Rte. |
|---|---|---|---|---|
| 160 | (1R,3R,5R)-N-((R)-(4-chloro-2,5-difluorophenyl)(cyclopropyl)methyl)-2-((5-(ethylsulfonyl)-3-pyridinyl)carbonyl)-2-azabicyclo[3.1.0]hexane-3-carboxamide | LCMS-ESI (POS.) m/z: 524.0 (M + H)+ | 1H NMR (500 MHz, DMSO-d6) δ ppm 8.85-9.20 (m, 2 H), 8.19-8.73 (m, 2 H), 7.55-7.69 (m, 1 H), 7.30-7.53 (m, 1 H), 4.62-5.00 (m, 1 H), 3.97-4.56 (m, 1 H), 3.28-3.79 (m, 3 H), 2.54-2.81 (m, 1 H), 1.54-1.88 (m, 2 H), 1.04-1.26 (m, 5 H), 0.40-0.85 (m, 3 H), −0.31-0.39 (m, 3 H) | H |
| 161 | (1R,3R,5R)-N-((R)-cyclobutyl(2-fluoro-4-(trifluoromethyl)phenyl)methyl)-2-(3-(methylsulfonyl)benzoyl)-2-azabicyclo[3.1.0]hexane-3-carboxamide | LCMS-ESI (POS.) m/z: 539.0 (M + H)+ | 1H NMR (500 MHz, DMSO-d6) δ ppm 8.54 (d, J = 7.79 Hz, 1 H) 7.35-8.24 (m, 7 H) 4.62-5.11 (m, 2 H) 3.21-3.28 (m, 4 H) 2.52-2.59 (m, 1 H) 1.13-2.35(m, 9 H) 0.62-1.13 (m, 2 H) | A |
| 162 | N-(4-chlorobenzyl)-1-((3-((3-cyano-1-azetidinyl)sulfonyl)phenyl)carbonyl)-N-methyl-prolinamide | LCMS-APCI (POS.) m/z: 501.2 (M + H)+ | 1H NMR (400 MHz, Methanol-d4) δ ppm 8.13 (t, J = 2.1 Hz, 1 H), 8.00 (dt, J = 1.6, 7.4 Hz, 2 H), 7.81 (td, J = 1.3, 7.9 Hz, 1 H), 7.49 (d, J = 8.5 Hz, 1 H), 7.38-7.42 (m, 1 H), 7.32 (dd, J = 2.2, 8.2 Hz, 2 H), 5.08 (dt, J = 5.6, 8.2 Hz, 1 H), 4.42 (d, J = 15.2 Hz, 1 H), 4.00-4.22 (m, 3 H), 3.91-3.97 (m, 2 H), 3.70 (dq, J = 6.1, 6.7, 13.5 Hz, 1 H), 3.55-3.62 (m, 1 H), 3.52 (ddt, J = 2.4, 6.2, 12.4 Hz, 1 H), 3.04 (s, 3 H), 2.39-2.54 (m, 1 H), 2.02-2.12 (m, 1 H), 1.89-2.02 (m, 2 H). | A |
| 163 | (1R,3R,5R)-N-((R)-(4-chloro-2,5-difluorophenyl)(cyclopropyl)methyl)-2-((5-(cyclopropylsulfonyl)-3-pyridinyl)carbonyl)-2-azabicyclo[3.1.0]hexane-3-carboxamide | LCMS-ESI (POS.) m/z: 536.0 (M + H)+ | 1H NMR (500 MHz, DMSO-d6) δ ppm 8.84-9.29 (m, 2 H), 8.17-8.75 (m, 2 H), 7.25-7.72 (m, 2 H), 4.65-5.02 (m, 1 H), 4.01-4.58 (m, 1 H), 3.28-3.86 (m, 1 H), 2.96-3.20 (m, 1 H), 2.54-2.83 (m, 1 H), 1.52-1.85 (m, 2 H), 1.04-1.33 (m, 6 H), −0.32-0.98 (m, 6 H) | H |

-continued

| Ex. # | Structure Name | LCMS-ESI (POS/NEG) m/z: (M + H)+ | NMR Data | Syn. Rte. |
|---|---|---|---|---|
| 164 | N-(4-chlorobenzyl)-1-(((3S)-1-((3-cyano-1-azetidinyl)sulfonyl)-3-piperidinyl)carbonyl)-D-prolinamide | LCMS-ESI (POS.) m/z: 494.2 (M + H)+ | 1H NMR (500 MHz, DMSO-d6) δ ppm 8.67* (t, J = 5.84 Hz, 1 H), 8.31 (t, J = 6.03 Hz, 1 H), 7.34-7.41 (m, 2 H), 7.23-7.29 (m, 2 H), 4.19-4.50 (m, 3 H), 4.01-4.10 (m, 2 H), 3.90-3.98 (m, 2 H), 3.75-3.83 (m, 1 H), 3.30-3.68 (m, 4 H), 2.72-2.86 (m, 2 H), 2.64 (tdd, J = 11.09, 11.09, 3.44, 3.31 Hz, 1 H), 2.25-2.33* (m, 1 H), 2.16-2.25* (m, 1 H), 2.04-2.13 (m, 1 H), 1.67-1.98 (m, 5 H), 1.35-1.54 (m, 2 H). Spectrum appears as 2:1 mixture of rotamers, *denotes resolved minor rotamer peaks. | C |
| 165 | 1-(3-((3-cyano-1-azetidinyl)sulfonyl)benzoyl)-N-((1S)-1-(3,5-difluorophenyl)propyl)-D-prolinamide | LCMS-ESI (POS.) m/z: 517.2 (M + H)+ | 1H NMR (500 MHz, DMSO-d6) δ ppm 8.17-8.48 (m, 1 H), 6.63-8.02 (m, 7 H), 4.50-4.74 (m, 2 H), 3.75-4.09 (m, 4 H), 3.44-3.70 (m, 3 H), 2.21-2.38 (m, 1 H), 1.46-2.05 (m, 5 H), 0.67-0.97 (m, 3 H) | A |
| 166 | 1-(((3S)-1-((-2-(3-fluorophenyl)-1-azetidinyl)sulfonyl)-3-piperidinyl)carbonyl)-N-(4-(trifluoromethyl)benzyl)-D-prolinamide | LCMS-ESI (NEG.) m/z: 595.2 (M − H)+ | 1H NMR (500 MHz, DMSO-d6) δ 8.24-8.75 (m, 1 H), 7.60-7.74 (m, 2 H), 7.06-7.51 (m, 6 H), 5.06-5.21 (m, 1 H), 4.21-4.47 (m, 3 H), 3.79-3.95 (m, 1 H), 3.35-3.73 (m, 6 H), 2.57-2.73 (m, 2 H), 2.02-2.39 (m, 3 H), 1.51-2.02 (m, 5 H), 1.11-1.41 (m, 2 H) | J |
| 167 | 3-((3-cyano-1-azetidinyl)sulfonyl)-N-methyl-N-((1R)-1-methyl-2-oxo-2-(((1S)-1-(4-(trifluoromethyl)phenyl)ethyl)amino)ethyl)benzamide | LCMS-ESI (POS.) m/z: 543.0 (M + Na)+ | 1H NMR (500 MHz, CHLOROFORM-d) δ ppm 7.89-8.01 (m, 2 H), 7.58-7.84 (m, 4 H), 7.40-7.52 (m, 2 H), 6.81-6.97 (m, 1 H), 5.08-5.24 (m, 2 H), 4.12-4.22 (m, 2 H), 3.99-4.10 (m, 2 H), 3.34-3.44 (m, 1 H), 2.88-3.19 (m, 3 H), 1.46-1.56 (m, 6 H) | C |

| Ex. # | Structure Name | LCMS-ESI (POS/NEG) m/z: (M + H)+ | NMR Data | Syn. Rte. |
|---|---|---|---|---|
| 168 | 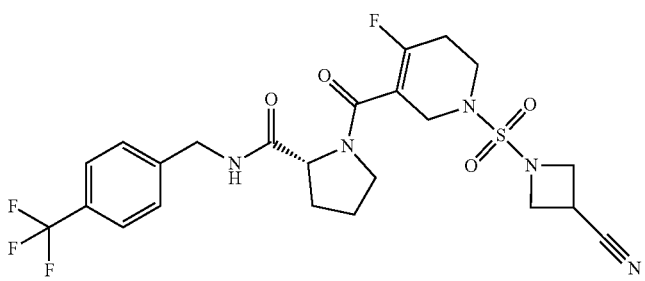 [SMILES: N#CC1CN(S(=O)(=O)N2CCC(F)=C(C(=O)N3CCC[C@@H]3C(=O)NCc3ccc(C(F)(F)F)cc3)C2)C1]<br>1-((1-((3-cyano-1-azetidinyl)sulfonyl)-4-fluoro-1,2,5,6-tetrahydro-3-pyridinyl)carbonyl)-N-(4-(trifluoromethyl)benzyl)-D-prolinamide | LCMS-ESI (POS.) m/z: 544.2 (M + H)+ | 1H NMR (500 MHz, CHLOROFORM-d) δ ppm 7.58 (m, J = 8.04 Hz, 2 H), 7.28-7.45 (m, 2 H), 7.16-7.26 (m, 1 H), 4.67 (dd, J = 7.66, 4.02 Hz, 1 H), 4.51-4.61 (m, 1 H), 4.29-4.51 (m, 1 H), 4.02-4.18 (m, 5 H), 3.83-4.01 (m, 1 H), 3.55-3.64 (m, 3 H), 3.38-3.53 (m, 2 H), 2.51-2.62 (m, 1 H), 2.40-2.51 (m, 2 H), 2.01-2.20 (m, 2 H), 1.88-2.01 (m, 1 H) | M |
| 169 | 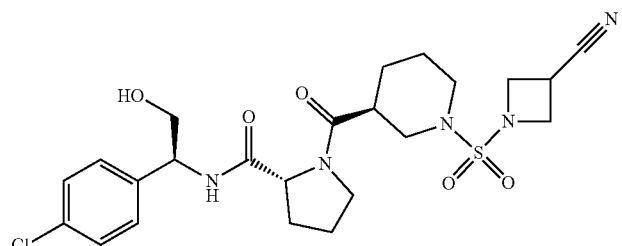<br>N-((1S)-1-(4-chlorophenyl)-2-hydroxyethyl)-1-(((3S)-1-((3-cyano-1-azetidinyl)sulfonyl)-3-piperidinyl)carbonyl)-D-prolinamide | LCMS-ESI (POS.) m/z: 524.2 (M + H)+ | 1H NMR (500 MHz, DMSO-d6) δ ppm 8.12 (d, J = 8.04 Hz, 1 H), 7.19-7.45 (m, 4 H), 4.77-4.87 (m, 1 H), 4.49-4.54 (m, 1 H), 4.33 (br d, J = 4.41 Hz, 1 H), 3.98-4.11 (m, 2 H), 3.89-3.95 (m, 1 H), 3.96 (s, 1 H), 3.70-3.84 (m, 1 H), 3.27-3.61 (m, 6 H), 2.70-2.90 (m, 2 H), 2.60-2.66 (m, 1 H), 2.00-2.22 (m, 1 H), 1.59-1.91 (m, 5 H), 1.30-1.56 (m, 2 H) | A |
| 170 | 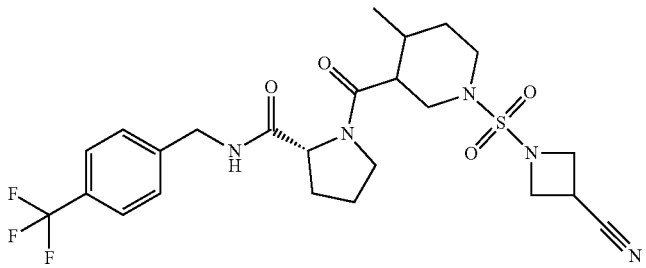<br>1-((-1-((3-cyano-1-azetidinyl)sulfonyl)-4-methyl-3-piperidinyl)carbonyl)-N-(4-(trifluoromethyl)benzyl)-D-prolinamide | LCMS-ESI (POS.) m/z: 565.2 (M + Na)+ | 1H NMR (400 MHz, CHLOROFORM-d) δ ppm 7.58 (t, J = 8.19 Hz, 2 H), 7.28-7.45 (m, 3 H), 4.38-4.65 (m, 3 H), 4.00-4.19 (m, 4 H), 3.00-3.78 (m, 8 H), 2.85 (br dd, J = 9.12, 4.56 Hz, 1 H), 2.31-2.52 (m, 1 H), 2.10-2.28 (m, 2 H), 1.56-2.08 (m, 4 H), 1.05 (d, J = 7.26 Hz, 1 H), 0.75-0.87 (m, 1 H) | M |
| 171 | 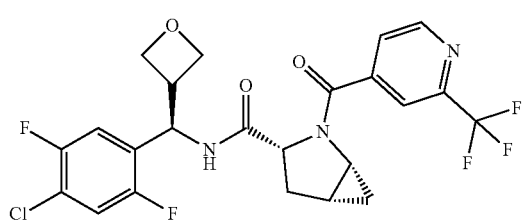 [SMILES: O=C(N[C@@H](c1cc(F)c(Cl)cc1F)C1COC1)[C@H]1C[C@H]2C[C@H]2N1C(=O)c1ccnc(C(F)(F)F)c1]<br>(1R,3R,5R)-N-((R)-(4-chloro-2,5-difluorophenyl)(3-oxetanyl)methyl)-2-((2-(trifluoromethyl)-4-pyridinyl)carbonyl)-2-azabicyclo[3.1.0]hexane-3-carboxamide | LCMS-APCI (POS.) m/z: 516.1 (M + H)+ | 1H NMR (400 MHz, DMSO-d6) δ ppm 8.94 (d, J = 5.1 Hz, 1 H), 8.69 (d, J = 8.1 Hz, 1 H), 7.88-8.02 (m, 1 H), 7.61-7.73 (m, 1 H), 7.44 (dd, J = 6.3, 9.7 Hz, 1 H), 5.41 (t, J = 9.0 Hz, 1 H), 4.87 (dd, J = 3.6, 11.3 Hz, 1 H), 4.63 (dd, J = 6.3, 7.7 Hz, 1 H), 4.46-4.54 (m, 1 H), 4.37 (t, J = 6.2 Hz, 1 H), 4.16-4.26 (m, 1 H), 3.36-3.47 (m, 1 H), 1.67-1.78 (m, 1 H), 1.08-1.19 (m, 1 H), 0.66-0.81 (m, 1 H). | Q |

| Ex. # | Structure Name | LCMS-ESI (POS/NEG) m/z: (M + H)+ | NMR Data | Syn. Rte. |
|---|---|---|---|---|
| 172 | 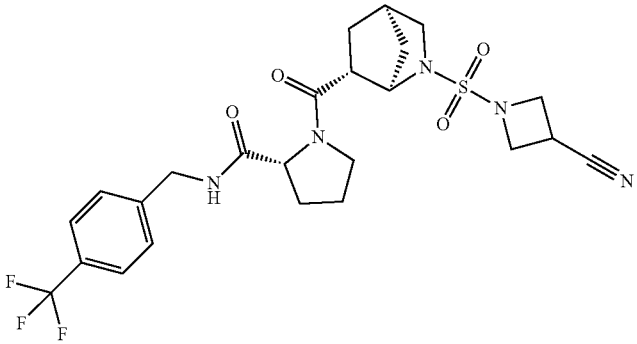 [SMILES: N#CC1CN(S(=O)(=O)N2C[C@H]3C[C@@H]2[C@H](C(=O)N2CCC[C@@H]2C(=O)NCc2ccc(C(F)(F)F)cc2)C3)C1]<br>1-(((1R,4R,6R)-2-((3-cyano-1-azetidinyl)sulfonyl)-2-azabicyclo[2.2.1]hept-6-yl)carbonyl)-N-(4-(trifluoromethyl)benzyl)-D-prolinamide | LCMS-ESI (POS.) m/z: 540.2 (M + H)+ | 1H NMR (400 MHz, CHLOROFORM-d) δ 7.50-7.65 (m, 2 H), 7.31-7.44 (m, 3 H), 4.56 (dd, J = 2.33, 8.03 Hz, 1 H), 4.46-4.53 (m, 1 H), 4.38-4.45 (m, 1 H), 4.01-4.19 (m, 5 H), 3.54-3.70 (m, 2 H), 3.41 (tt, J = 6.32, 8.76 Hz, 1 H), 3.21-3.30 (m, 1 H), 3.11 (dd, J = 5.29, 8.50 Hz, 1 H), 3.06 (d, J = 8.81 Hz, 1 H), 2.65 (br s, 1 H), 2.41 (tdd, J = 3.01, 6.44, 12.32 Hz, 1 H), 2.14-2.23 (m, 1 H), 2.00-2.09 (m, 1 H), 1.86-1.98 (m, 2 H), 1.76-1.86 (m, 2 H), 1.58-1.69 (m, 1 H) | M |
| 173 | 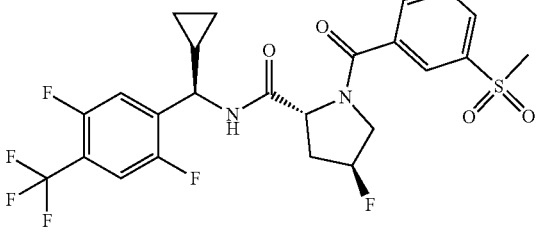<br>(4S)-N-((R)-cyclopropyl(2,5-difluoro-4-(trifluoromethyl)phenyl)methyl)-4-fluoro-1-(3-(methylsulfonyl)benzoyl)-D-prolinamide | LCMS-ESI (POS.) m/z: 549.0 (M + H)+ | 1H NMR (500 MHz, DMSO-d6) δ ppm 8.88 (d, J = 7.27 Hz, 1 H), 7.66-8.15 (m, 5 H), 7.38-7.62 (m, 1 H), 5.19-5.42 (m, 1 H), 4.52-4.73 (m, 2 H), 3.83-3.99 (m, 1 H), 3.49-3.67 (m, 1 H), 3.23-3.34 (m, 3 H), 2.52-2.59 (m, 1 H), 1.83-2.07 (m, 1 H), 0.84-1.32 (m, 1 H), −0.25-0.63 (m, 4 H) | C |
| 174 | 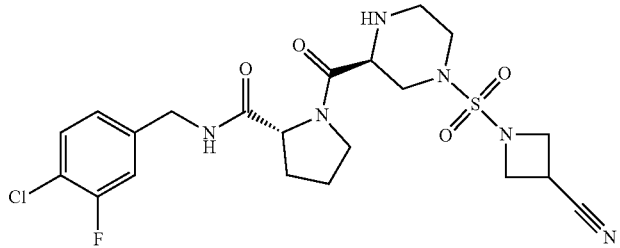 [SMILES: N#CC1CN(S(=O)(=O)N2CCN[C@H](C(=O)N3CCC[C@@H]3C(=O)NCc3ccc(Cl)c(F)c3)C2)C1]<br>N-(4-chloro-3-fluorobenzyl)-1-(((2S)-4-((3-cyano-1-azetidinyl)sulfonyl)-2-piperazinyl)carbonyl)-D-prolinamide | LCMS-ESI (POS.) m/z: 513.0 (M + H)+ | 1H NMR (400 MHz, CHLOROFORM-d) δ 7.30-7.45 (m, 2 H), 6.93-7.14 (m, 2 H), 4.53-4.73 (m, 1 H), 4.26-4.50 (m, 2 H), 4.06-4.25 (m, 4 H), 3.80-3.90 (m, 1 H), 3.68-3.80 (m, 2 H), 3.59-3.68 (m, 1 H), 3.41-3.59 (m, 2 H), 3.15 (br d, J = 13.37 Hz, 1 H), 2.80-3.00 (m, 4 H), 2.37-2.51 (m, 1 H), 1.90-2.23 (m, 3 H) | E |
| 175 | 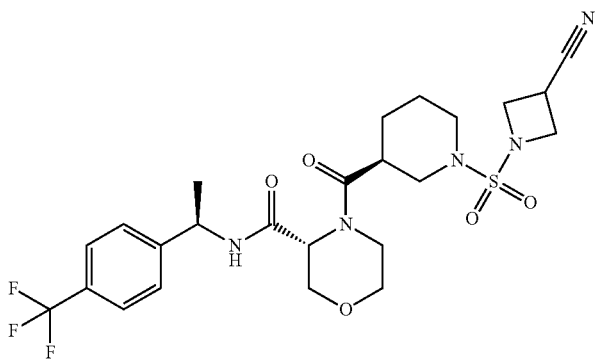 [SMILES: C[C@@H](NC(=O)[C@H]1COCCN1C(=O)[C@H]1CCCN(S(=O)(=O)N2CC(C#N)C2)C1)c1ccc(C(F)(F)F)cc1]<br>(3R)-4-(((3S)-1-((3-cyano-1-azetidinyl)sulfonyl)-3-piperidinyl)carbonyl)-N-((1R)-1-(4-(trifluoromethyl)phenyl)ethyl)-3-morpholinecarboxamide | LCMS-ESI (POS.) m/z: 558.2 (M + H)+ | 1H NMR (500 MHz, DMSO-d6) δ ppm 8.41-8.63 (m, 1 H), 7.68 (br d, J = 8.17 Hz, 2 H), 7.44-7.58 (m, 3 H), 4.92-5.10 (m, 1 H), 4.49-4.77 (m, 1 H), 4.44 (br d, J = 11.81 Hz, 1 H), 4.23-4.48 (m, 1 H), 3.89-4.14 (m, 5 H), 3.27-3.84 (m, 5 H), 2.71-2.97 (m, 3 H), 1.76-1.92 (m, 1 H), 1.63-1.76 (m, 1 H), 1.22-1.58 (m, 5 H) | B |

| Ex. # | Structure Name | LCMS-ESI (POS/NEG) m/z: (M + H)+ | NMR Data | Syn. Rte. |
|---|---|---|---|---|
| 176 | 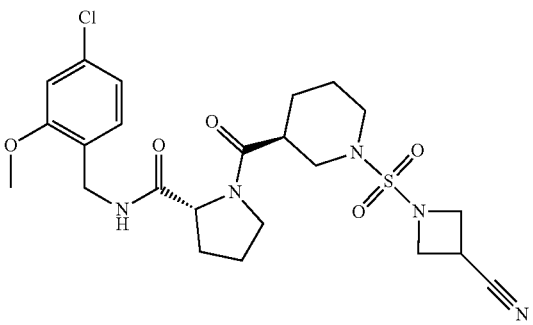 [SMILES: COc1cc(Cl)ccc1CNC(=O)[C@H]1CCCN1C(=O)[C@H]1CCCN(S(=O)(=O)N2CC(C#N)C2)C1]<br>N-(4-chloro-2-methoxybenzyl)-1-(((3S)-1-((3-cyano-1-azetidinyl)sulfonyl)-3-piperidinyl)carbonyl)-D-prolinamide | LCMS-ESI (POS.) m/z: 524.2 (M + H)+ | 1H NMR (500 MHz, DMSO-d6) δ ppm 8.05-8.50 (m, 1 H), 6.87-7.21 (m, 3 H), 4.29-4.51 (m, 1 H), 4.11-4.27 (m, 2 H), 3.72-4.12 (m, 8 H), 3.43-3.70 (m, 4 H), 2.59-2.91 (m, 3 H), 1.69-2.34 (m, 6 H), 1.32-1.58 (m, 2 H) | A |
| 177 | 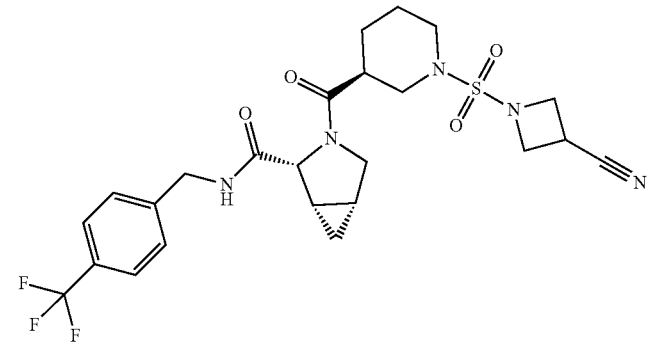 [SMILES: N#CC1CN(S(=O)(=O)N2CCC[C@H](C(=O)N3C[C@@H]4C[C@@H]4[C@@H]3C(=O)NCc3ccc(C(F)(F)F)cc3)C2)C1]<br>(1S,2R,5R)-3-(((3S)-1-((3-cyano-1-azetidinyl)sulfonyl)-3-piperidinyl)carbonyl)-N-(4-(trifluoromethyl)benzyl)-3-azabicyclo[3.1.0]hexane-2-carboxamide | LCMS-ESI (POS.) m/z: 540.2 (M + H)+ | 1H NMR (500 MHz, CHLOROFORM-d) δ ppm 7.38-7.74 (m, 1 H), 5.96-6.20 (m, 1 H), 5.92-6.47 (m, 1 H), 4.40-4.69 (m, 3 H), 4.01-4.16 (m, 4 H), 3.60-3.92 (m, 4 H), 3.39-3.49 (m, 1 H), 3.02 (s, 3 H), 1.57-2.02 (m, 6 H), 0.77-1.00 (m, 2 H) | C |
| 178 | 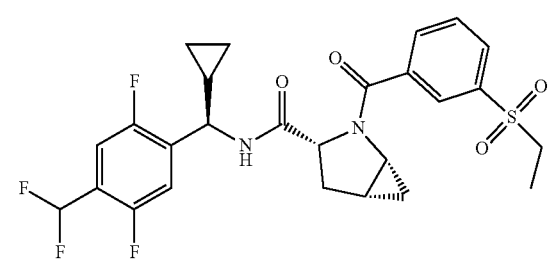 [SMILES: CCS(=O)(=O)c1cccc(C(=O)N2[C@@H](C(=O)N[C@@H](c3cc(F)c(C(F)F)cc3F)C3CC3)C[C@H]3C[C@H]32)c1]<br>(1R,3R,5R)-N-((R)-cyclopropyl(4-(difluoromethyl)-2,5-difluorophenyl)methyl)-2-(3-(ethylsulfonyl)benzoyl)-2-azabicyclo[3.1.0]hexane-3-carboxamide | LCMS-ESI (POS.) m/z: 539.2 (M + H)+ | 1H NMR (500 MHz, DMSO-d6) δ ppm 8.33-8.74 (m, 1 H), 7.03-8.19 (m, 6 H), 4.94 (dd, J = 11.42, 3.63 Hz, 2 H), 4.53 (br t, J = 7.91 Hz, 1 H), 3.18-3.44 (m, 2 H), 2.56 (td, J = 12.59, 6.23 Hz, 1 H), 1.51-1.80 (m, 2 H), 1.03-1.26 (m, 4 H), −0.27-0.95 (m, 5 H) | C |

| Ex. # | Structure Name | LCMS-ESI (POS/NEG) m/z: (M + H)+ | NMR Data | Syn. Rte. |
|---|---|---|---|---|
| 179 | 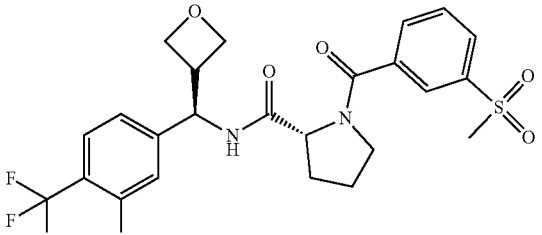<br>N-((R)-(3-fluoro-4-(trifluoromethyl)phenyl)(3-oxetanyl)methyl)-1-(3-(methylsulfonyl)benzoyl)-D-prolinamide | LCMS-APCI (POS.) m/z: 529.1 (M + H)+ | 1H NMR (400 MHz, Methanol-d4) δ ppm 8.23 (t, J = 1.7 Hz, 1 H), 8.05-8.13 (m, 2 H), 7.96 (dt, J = 1.4, 7.7 Hz, 1 H), 7.63-7.81 (m, 3 H), 7.31-7.38 (m, 2 H), 7.20 (dd, J = 5.2, 9.2 Hz, 1 H), 5.45-5.52 (m, 1 H), 4.88 (d, J = 14.2 Hz, 5 H), 4.64-4.72 (m, 2 H), 4.55-4.62 (m, 1 H), 4.44-4.54 (m, 2 H), 3.71-3.78 (m, 1 H), 3.66 (dt, J = 7.2, 10.2 Hz, 1 H), 3.53 (dddd, J = 5.4, 7.0, 10.2, 13.7 Hz, 2 H), 3.37 (s, 1 H), 3.19 (s, 4 H), 2.36 (tdd, J = 5.6, 8.9, 11.8 Hz, 1 H), 1.96-2.06 (m, 1 H), 1.81-1.96 (m, 3 H). | A |
| 180 | 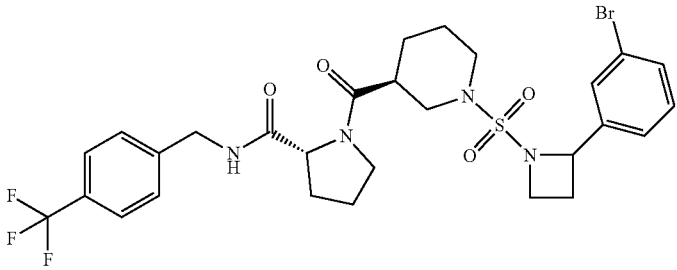 [SMILES: O=C(NCc1ccc(C(F)(F)F)cc1)[C@H]1CCCN1C(=O)[C@H]1CCCN(S(=O)(=O)N2CCC2c2cccc(Br)c2)C1]<br>1-(((3S)-1-((-2-(3-bromophenyl)-1-azetidinyl)sulfonyl)-3-piperidinyl)carbonyl)-N-(4-(trifluoromethyl)benzyl)-D-prolinamide, | LCMS-ESI (POS.) m/z: 657.2 (M + H)+ | 1H NMR (500 MHz, DMSO-d6) δ 8.26-8.76 (m, 1 H), 7.58-7.83 (m, 3 H), 7.24-7.58 (m, 5 H), 5.05-5.19 (m, 1 H), 4.23-4.47 (m, 3 H), 3.80-3.96 (m, 1 H), 3.42-3.78 (m, 6 H), 2.60-2.75 (m, 2 H), 2.01-2.37 (m, 3 H), 1.55-2.01 (m, 5 H), 1.10-1.45 (m, 2H) | J |
| 181 | 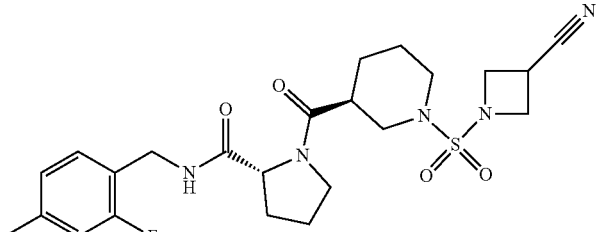<br>1-(((3S)-1-((3-cyano-1-azetidinyl)sulfonyl)-3-piperidinyl)carbonyl)-N-(2-fluoro-4-methylbenzyl)-D-prolinamide | LCMS-ESI (POS.) m/z: 492.2 (M + H)+ | 1H NMR (500 MHz, CHLOROFORM-d) δ ppm 7.09-7.24 (m, 2 H), 6.80-6.96 (m, 2 H), 4.50-4.60 (m, 1 H), 4.35-4.47 (m, 2 H), 4.04-4.16 (m, 4 H), 3.69-3.79 (m, 2 H), 3.52-3.63 (m, 2 H), 3.37-3.47 (m, 1 H), 2.91-3.03 (m, 1 H), 2.64-2.82 (m, 2 H), 2.27-2.40 (m, 4 H), 2.10-2.24 (m, 1 H), 1.97-2.08 (m, 1 H), 1.86-1.97 (m, 2 H), 1.75-1.83 (m, 1 H), 1.49-1.71 (m, 2 H) | A |
| 182 | 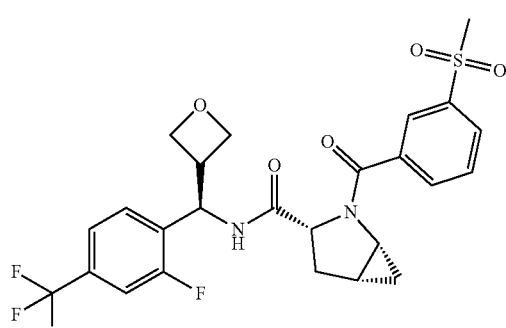<br>(1R,3R,5R)-N-((R)-(2-fluoro-4-(trifluoromethyl)phenyl)(3-oxetanyl)methyl)-2-(3-(methylsulfonyl)benzoyl)-2-azabicyclo[3.1.0]hexane-3-carboxamide | LCMS-APCI (POS.) m/z: 541.1 (M + H)+ | 1H NMR (400 MHz, Methanol-d4) δ ppm 8.39 (t, J = 1.7 Hz, 1 H), 8.10-8.15 (m, 2 H), 7.79 (t, J = 7.8 Hz, 1 H), 7.48-7.58 (m, 3 H), 5.66 (d, J = 10.2 Hz, 1 H), 5.01 (dd, J = 4.2, 11.4 Hz, 1 H), 4.61-4.70 (m, 2 H), 4.37-4.42 (m, 1 H), 3.52-3.62 (m, 1 H), 3.19 (s, 3 H), 2.67 (dddd, J = 1.1, 6.5, 11.5, 13.3 Hz, 1 H), 1.91 (dd, J = 4.2, 13.6 Hz, 1 H), 1.77-1.84 (m, 1 H), 1.25 (td, J = 2.7, 5.3 Hz, 1 H), 0.90 (dtd, J = 1.1, 5.7, 9.0 Hz, 1 H). | A |

| Ex. # | Structure Name | LCMS-ESI (POS/NEG) m/z: (M + H)+ | NMR Data | Syn. Rte. |
|---|---|---|---|---|
| 183 | 1-((-1-((3-cyano-1-azetidinyl)sulfonyl)-3-fluoro-3-piperidinyl)carbonyl)-N-(4-(trifluoromethyl)benzyl)-D-prolinamide | LCMS-ESI (POS.) m/z: 546.2 (M + H)+ | 1H NMR (500 MHz, DMSO-d6) δ ppm 8.46-8.56 (m, 1 H), 7.68 (d, J = 8.17 Hz, 2 H), 7.44-7.48 (m, 2 H), 4.29-4.74 (m, 3 H), 4.02-4.09 (m, 2 H), 3.88-3.98 (m, 2 H), 3.68-3.88 (m, 3 H), 3.33-3.63 (m, 3 H), 2.90-2.99 (m, 1 H), 2.03-2.23 (m, 2 H), 1.59-2.01 (m, 6 H) | M |
| 184 | (1R,3R,5R)-2-(3-(1-carbamoylcyclopropyl)benzoyl)-N-((R)-(4-chloro-2,5-difluorophenyl)(3-oxetanyl)methyl)-2-azabicyclo[3.1.0]hexane-3-carboxamide | LCMS-APCI (POS.) m/z: 530.2 (M + H)+ | 1H NMR (Methanol-d4) δ: 7.88-7.81 (m, 1 H), 7.72 (d, J = 7.6, 1.5 Hz, 1 H), 7.59 (d, J = 7.7, 1.5 Hz, 1 H), 7.51 (t, J = 7.7 Hz, 1 H), 7.39 (dd, J = 9.4, 6.1 Hz, 1 H), 7.28 (dd, J = 9.4, 6.3 Hz, 1 H), 5.57 (d, J = 10.2 Hz, 1 H), 4.98 (dd, J = 11.4, 4.2 Hz, 1 H), 4.83 (t, J = 7.6, 6.5 Hz, 1 H), 4.67 (t, J = 7.8, 6.4 Hz, 1 H), 4.60 (t, J = 6.2 Hz, 1 H), 4.38 (t, J = 6.2 Hz, 1 H), 3.59-3.45 (m, 1 H), 3.42-3.35 (m, 1 H), 3.35-3.30 (m, 2 H), 2.73-2.55 (m, 1 H), 1.91 (dd, J = 13.5, 4.2 Hz, 1 H), 1.83-1.73 (m, 1 H), 1.61-1.48 (m, 2 H), 1.29-1.21 (m, 1 H), 1.21-1.09 (m, 2 H), 0.90-0.82 (m, 1 H) | V |
| 185 | 1-(3-(dimethylsulfamoyl)benzoyl)-N-((1R)-1-(2-fluoro-4-(trifluoromethyl)phenyl)-2-methylpropyl)-D-prolinamide | LCMS-ESI (POS.) m/z: 544.2 (M + H)+ | 1H NMR (500 MHz, DMSO-d6) δ ppm 8.26-8.56 (m, 1 H), 7.40-7.91 (m, 7 H), 4.45-4.93 (m, 2 H), 3.41-3.63 (m, 2 H), 2.53-2.75 (m, 6 H), 2.12-2.36 (m, 1 H), 1.59-2.06 (m, 4 H), 0.47-1.07 (m, 6 H) | A |
| 186 | N-((R)-cyclopropyl(2-fluoro-4-(trifluoromethyl)phenyl)methyl)-1-(2-((2-methyl-2-propanyl)amino)-5-(methylsulfonyl)benzoyl)-D-prolinamide | LCMS-APCI (POS.) m/z: 584.2 (M + H)+ | 1H NMR (400 MHz, Methanol-d4) δ ppm 7.73 (dd, 1 H), 7.69 (d, J = 2.4 Hz, 1 H), 7.66 (d, J = 7.5 Hz, 1 H), 7.48 (dd, J = 9.5, 29.4 Hz, 2 H), 7.11 (d, J = 9.0 Hz, 1 H), 4.64-4.69 (m, 1 H), 4.59 (d, J = 9.1 Hz, 2 H), 3.45-3.54 (m, 1 H), 3.39-3.46 (m, 1 H), 3.07 (s, 3 H), 2.33-2.43 (m, 1 H), 1.84-1.95 (m, 3 H), 1.43 (s, 8 H), 1.31 (s, 3 H), 0.85-0.96 (m, 1 H), 0.67-0.75 (m, 1 H), 0.50-0.62 (m, 2 H), 0.41-0.49 (m, 1 H). | S |

| Ex. # | Structure Name | LCMS-ESI (POS/NEG) m/z: (M + H)+ | NMR Data | Syn. Rte. |
|---|---|---|---|---|
| 187 | 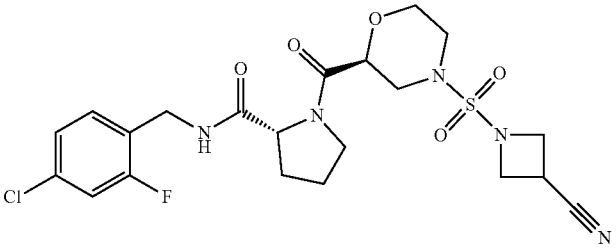 [SMILES: N#CC1CN(S(=O)(=O)N2CCO[C@H](C(=O)N3CCC[C@@H]3C(=O)NCc3ccc(Cl)cc3F)C2)C1]<br>N-(4-chloro-2-fluorobenzyl)-1-(((2S)-4-((3-cyano-1-azetidinyl)sulfonyl)-2-morpholinyl)carbonyl)-D-prolinamide | LCMS-ESI (POS.) m/z: 514.0 (M + H)+ | 1H NMR (400 MHz, CHLOROFORM-d) δ 7.22-7.27 (m, 1 H), 7.05-7.17 (m, 3 H), 4.56-4.78 (m, 1 H), 4.37-4.52 (m, 2 H), 4.12-4.22 (m, 5 H), 3.91-4.02 (m, 1 H), 3.81 (ddd, J = 4.04, 8.09, 10.47 Hz, 1 H), 3.61-3.74 (m, 2 H), 3.42-3.56 (m, 3 H), 3.19 (dd, J = 9.48, 12.70 Hz, 1 H), 3.05 (ddd, J = 3.27, 10.70, 12.47 Hz, 1 H), 2.35-2.43 (m, 1 H), 2.08-2.20 (m, 1 H), 1.86-2.04 (m, 2 H) | C |
| 188 | 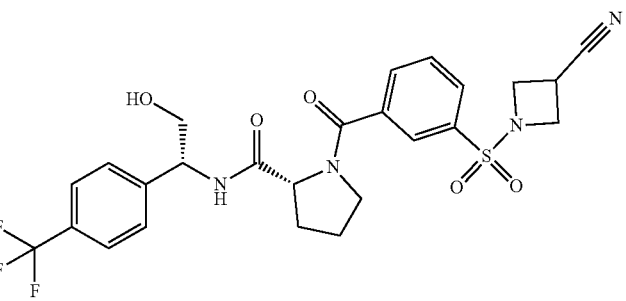<br>1-(3-((3-cyano-1-azetidinyl)sulfonyl)benzoyl)-N-((1R)-2-hydroxy-1-(4-(trifluoromethyl)phenyl)ethyl)-D-prolinamide | LCMS-ESI (POS.) m/z: 551.0 (M + H)+ | 1H NMR (500 MHz, DMSO-d6) δ ppm 8.48 (d, J = 7.92 Hz, 1 H), 7.18-8.03 (m, 8 H), 4.87-4.96 (m, 1 H), 4.60 (br dd, J = 7.91, 5.06 Hz, 1 H), 3.78-4.03 (m, 4 H), 3.41-3.70 (m, 5 H), 3.38-4.07 (m, 1 H), 2.19-2.34 (m, 1 H), 1.70-2.02 (m, 3 H) | A |
| 189 | 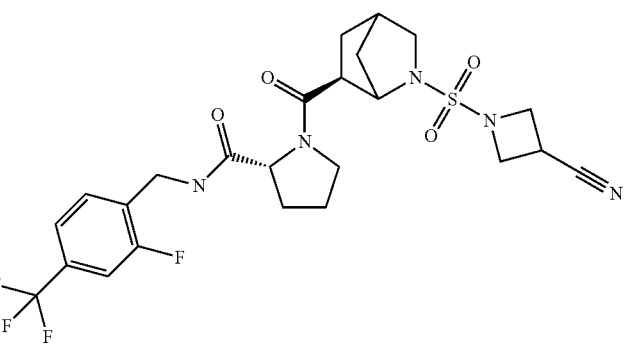<br>1-((2-((3-cyano-1-azetidinyl)sulfonyl)-2-azabicyclo[2.2.1]hept-6-yl)carbonyl)-N-(2-fluoro-4-(trifluoromethyl)benzyl)-D-prolinamide | LCMS-ESI (POS.) m/z: 558.2 (M + H)+ | 1H NMR (400 MHz, CHLOROFORM-d) δ 7.41-7.54 (m, 2 H), 7.34-7.41 (m, 2 H), 7.28-7.34 (m, 1 H), 4.40-4.61 (m, 3 H), 4.02-4.19 (m, 5 H), 3.48-3.82 (m, 2 H), 3.35-3.47 (m, 1 H), 3.22-3.30 (m, 1 H), 3.04-3.19 (m, 2 H), 2.62-2.72 (m, 1 H), 2.35-2.48 (m, 1 H), 2.13-2.24 (m, 1 H), 1.97-2.09 (m, 1 H), 1.74-1.97 (m, 3 H), 1.63-1.73 (m, 1 H) | M |
| 190 | 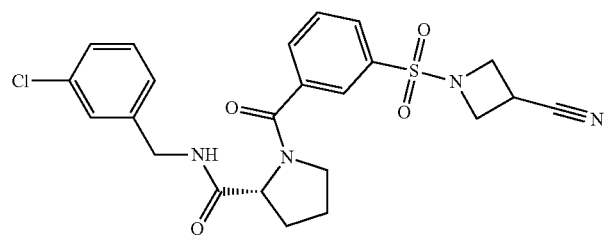 [SMILES: N#CC1CN(S(=O)(=O)c2cccc(C(=O)N3CCC[C@@H]3C(=O)NCc3cccc(Cl)c3)c2)C1]<br>N-(3-chlorobenzyl)-1-((3-((3-cyano-1-azetidinyl)sulfonyl)phenyl)carbonyl)-D-prolinamide | LCMS-APCI (NEG.) m/z: 485.1 (M – H) | 1H NMR (400 MHz, MeOD) δ ppm 8.14 (d, J = 1.7 Hz, 1 H), 7.94-8.04 (m, 2 H), 7.79 (t, J = 7.8 Hz, 1 H), 7.36 (t, J = 2.0 Hz, 1 H), 7.19-7.34 (m, 3 H), 4.60 (dd, J = 5.9, 8.1 Hz, 1 H), 4.44 (q, J = 15.4 Hz, 2 H), 4.11 (td, J = 1.1, 8.7 Hz, 2 H), 3.93 (ddd, J = 4.8, 6.2, 8.5 Hz, 2 H), 3.54 (dddd, J = 5.3, 7.7, 15.0, 17.7 Hz, 2 H), 2.32-2.41 (m, 1 H), 1.99-2.06 (m, 2 H), 1.86-1.96 (m, 1 H). | A |

| Ex. # | Structure Name | LCMS-ESI (POS/NEG) m/z: (M + H)+ | NMR Data | Syn. Rte. |
|---|---|---|---|---|
| 191 | 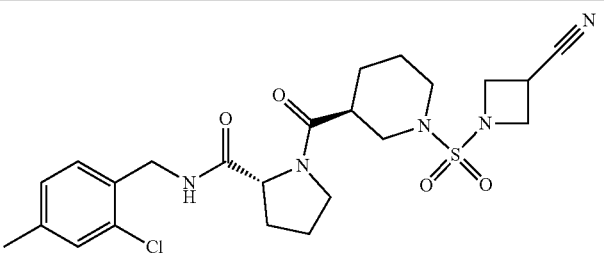 [SMILES: Cc1ccc(CNC(=O)[C@H]2CCCN2C(=O)[C@H]2CCCN(S(=O)(=O)N3CC(C#N)C3)C2)c(Cl)c1]<br>N-(2-chloro-4-methylbenzyl)-1-(((3S)-1-((3-cyano-1-azetidinyl)sulfonyl)-3-piperidinyl)carbonyl)-D-prolinamide | LCMS-ESI (POS.) m/z: 508.2 (M + H)+ | 1H NMR (500 MHz, DMSO-d6) δ ppm 8.25 (s, 1 H), 7.05-7.31 (m, 3 H), 4.16-4.53 (m, 3 H), 4.01-4.10 (m, 2 H), 3.89-3.99 (m, 2 H), 3.73-3.82 (m, 1 H), 3.42-3.72 (m, 4 H), 3.31-3.38 (m, 3 H), 2.71-2.89 (m, 2 H), 2.61-2.70 (m, 1 H), 2.48-2.52 (m, 5 H), 2.02-2.24 (m, 1 H), 1.62-2.00 (m, 5 H), 1.31-1.60 (m, 2 H) | A |
| 192 | 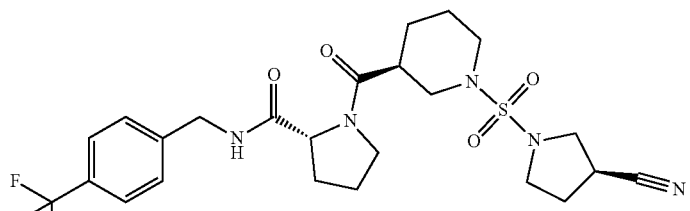<br>1-(((3S)-1-(((3S)-3-cyano-1-pyrrolidinyl)sulfonyl)-3-piperidinyl)carbonyl)-N-(4-(trifluoromethyl)benzyl)-D-prolinamide | LCMS-ESI (POS.) m/z: 542.2 (M + Na)+ | 1H NMR (400 MHz, CHLOROFORM-d) δ ppm 7.57 (br d, J = 7.88 Hz, 2 H), 7.31-7.45 (m, 3 H), 4.34-4.66 (m, 3 H), 3.80 (br d, J = 12.44 Hz, 2 H), 3.56-3.70 (m, 3 H), 3.42-3.56 (m, 3 H), 3.17 (quin, J = 6.38 Hz, 1 H), 2.93-3.10 (m, 1 H), 2.69-2.93 (m, 2 H), 2.14-2.43 (m, 4 H), 1.45-2.12 (m, 6 H) | M |
| 193 | 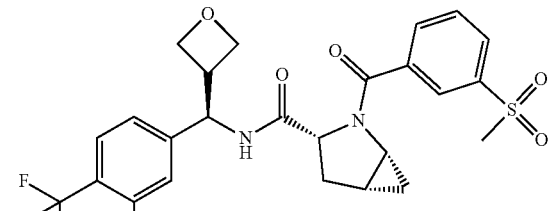<br>(1R,3R,5R)-N-((R)-(3-fluoro-4-(trifluoromethyl)phenyl)(3-oxetanyl)methyl)-2-(3-(methylsulfonyl)benzoyl)-2-azabicyclo'3.1.0'hexane-3-carboxamide | LCMS-APCI (POS.) m/z: 541.1 (M + H)+ | 1H NMR (400 MHz, Methanol-d4) δ ppm 8.39 (t, 1 H), 8.09-8.15 (m, 2 H), 7.79 (t, 1 H), 7.71 (t, 1 H), 7.29-7.35 (m, 2 H), 5.40 (d, J = 10.1 Hz, 1 H), 5.02 (dd, J = 4.3, 11.4 Hz, 1 H), 4.84 (dd, J = 6.5, 7.7 Hz, 1 H), 4.67 (dd, J = 6.4, 7.9 Hz, 1 H), 4.61 (t, J = 6.3 Hz, 1 H), 4.46 (t, J = 6.3 Hz, 1 H), 3.50 (dtt, J = 6.1, 7.8, 10.2 Hz, 1 H), 3.37 (s, 2 H), 3.19 (s, 3 H), 2.69 (dddd, J = 1.1, 6.5, 11.4, 13.5 Hz, 1 H), 1.93 (dd, 1 H), 1.78-1.86 (m, 1 H), 1.28 (td, J = 2.7, 5.3 Hz, 1 H), 0.91 (dtd, J = 1.0, 5.7, 8.9 Hz, 1 H). | A |
| 194 | 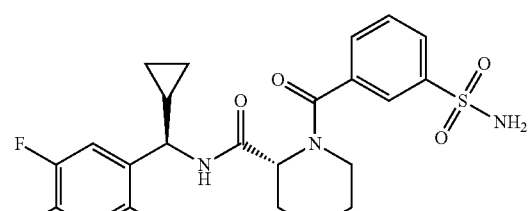<br>(2R)-N-((R)-(4-chloro-2,5-difluorophenyl)(cyclopropyl)methyl)-1-(3-sulfamoylbenzoyl)-2-piperidinecarboxamide | LCMS-ESI (NEG.) m/z: 510.0 (M − H)− | 1H NMR (400 MHz, CHLOROFORM-d) δ ppm 8.05-8.16 (m, 1 H), 7.92-8.04 (m, 1 H), 7.66-7.78 (m, 1 H), 7.59 (t, J = 7.77 Hz, 1 H), 7.40-7.48 (m, 1 H), 7.04-7.20 (m, 2 H), 5.32-5.84 (m, 2 H), 4.72 (t, J = 6.84 Hz, 1 H), 4.48 (dd, J = 8.55, 7.20 Hz, 1 H), 3.57-3.88 (m, 1 H), 3.40-3.54 (m, 1 H), 1.94-2.28 (m, 3 H), 1.80-1.93 (m, 1 H), 1.06 (br d, J = 3.11 Hz, 1 H), 0.48-0.65 (m, 2 H), 0.17-0.47 (m, 2 H) | C |

| Ex. # | Structure Name | LCMS-ESI (POS/NEG) m/z: (M + H)+ | NMR Data | Syn. Rte. |
|---|---|---|---|---|
| 195 | 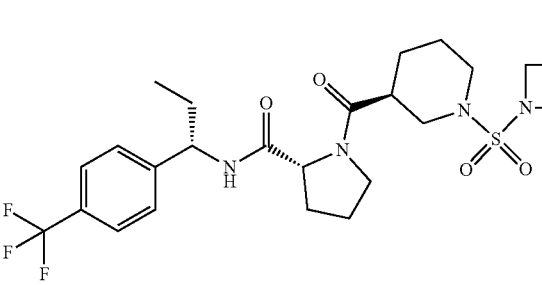<br>1-(((3S)-1-((3-cyano-1-azetidinyl)sulfonyl)-3-piperidinyl)carbonyl)-N-((1S)-1-(4-(trifluoromethyl)phenyl)propyl)-D-prolinamide | LCMS-ESI (POS.) m/z: 556.2 (M + H)+ | 1H NMR (500 MHz, DMSO-d6) δ ppm 8.15 (d, J = 8.30 Hz, 1 H), 7.50-7.75 (m, 4 H), 4.68-4.84 (m, 1 H), 4.29-4.48 (m, 1 H), 3.88-4.10 (m, 4 H), 3.74-3.83 (m, 1 H), 3.28-3.48 (m, 2 H), 2.68-2.88 (m, 2 H), 2.58-2.66 (m, 1 H), 1.18-2.26 (m, 12 H), 0.79-0.91 (m, 3 H) | A |
| 196 | 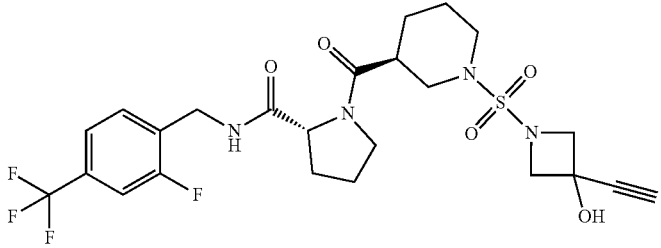 [SMILES: C#CC1(O)CN(S(=O)(=O)N2CCC[C@H](C(=O)N3CCC[C@@H]3C(=O)NCc3ccc(C(F)(F)F)cc3F)C2)C1]<br>1-(((3S)-1-((3-ethynyl-3-hydroxy-1-azetidinyl)sulfonyl)-3-piperidinyl)carbonyl)-N-(2-fluoro-4-(trifluoromethyl)benzyl)-D-prolinamide | LCMS-ESI (POS.) m/z: 561.0 (M + H)+ | 1H NMR (400 MHz, CHLOROFORM-d) δ 7.29-7.47 (m, 4 H), 4.56-4.63 (m, 1 H), 4.42-4.56 (m, 2 H), 4.09-4.15 (m, 2 H), 4.02 (dd, J = 3.63, 8.29 Hz, 2 H), 3.73-3.85 (m, 2 H), 3.53-3.65 (m, 2 H), 2.93-3.05 (m, 2 H), 2.76-2.86 (m, 1 H), 2.71-2.76 (m, 1 H), 2.37-2.47 (m, 1 H), 2.09-2.24 (m, 1 H), 1.99-2.09 (m, 1 H), 1.77-1.96 (m, 3 H), 1.53-1.72 (m, 3 H) | J |
| 197 | 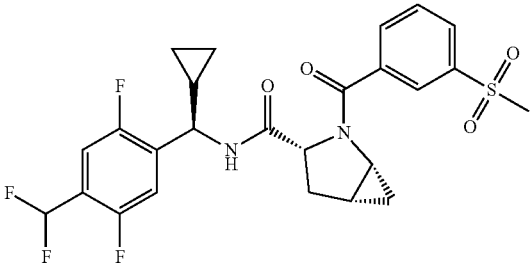 [SMILES: CS(=O)(=O)c1cccc(C(=O)N2[C@@H](C(=O)N[C@@H](c3cc(F)c(C(F)F)cc3F)C3CC3)C[C@H]3C[C@H]32)c1]<br>(1R,3R,5R)-N-((R)-cyclopropyl(4-(difluoromethyl)-2,5-difluorophenyl)methyl)-2-(3-(methylsulfonyl)benzoyl)-2-azabicyclo[3.1.0]hexane-3-carboxamide | LCMS-ESI (POS.) m/z: 525.0 (M + H)+ | 1H NMR (500 MHz, DMSO-d6) δ ppm 8.34-8.73 (m, 1 H), 7.62-8.22 (m, 4 H), 6.99-7.58 (m, 2 H), 6.98-7.37 (m, 1 H), 4.03-5.05 (m, 3 H), 1.50-1.81 (m, 2 H), 1.02-1.25 (m, 2 H), −0.27-0.97 (m, 5 H) | C |
| 198 | 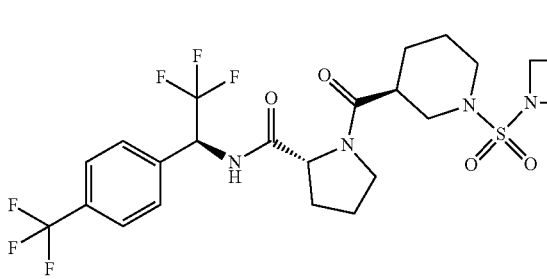<br>1-(((3S)-1-((3-cyano-1-azetidinyl)sulfonyl)-3-piperidinyl)carbonyl)-N-((1S)-2,2,2-trifluoro-1-(4-(trifluoromethyl)phenyl)ethyl)-D-prolinamide | LCMS-ESI (POS.) m/z: 596.2 (M + H)+ | 1H NMR (500 MHz, DMSO-d6) δ ppm 9.22 (d, J = 9.34 Hz, 1 H), 7.64-7.94 (m, 4 H), 5.89 (s, 1 H), 4.44 (dd, J = 8.56, 4.15 Hz, 1 H), 4.01-4.14 (m, 2 H), 3.89-4.01 (m, 2 H), 3.74-3.85 (m, 1 H), 3.27-3.64 (m, 4 H), 2.72-2.91 (m, 2 H), 2.56-2.69 (m, 1 H), 2.01-2.22 (m, 1 H), 1.30-1.92 (m, 7 H) | A |

| Ex. # | Structure Name | LCMS-ESI (POS/NEG) m/z: (M + H)+ | NMR Data | Syn. Rte. |
|---|---|---|---|---|
| 199 | 1-(((3S)-1((3-cyclopropyl-3-hydroxy-1-azetidinyl)sulfonyl)-3-piperidinyl)carbonyl)-N-(2-fluoro-4-(trifluoromethyl)benzyl)-D-prolinamide | LCMS-ESI (POS.) m/z: 577.1 (M + H)+ | 1H NMR (400 MHz, CHLOROFORM-d) δ 7.40-7.51 (m, 2 H), 7.34-7.40 (m, 1 H), 7.29-7.34 (m, 1 H), 4.59 (dd, J = 2.18, 7.98 Hz, 1 H), 4.43-4.57 (m, 2 H), 3.73-3.83 (m, 4 H), 3.51-3.69 (m, 4 H), 2.96 (dd, J = 10.88, 12.65 Hz, 1 H), 2.67-2.82 (m, 2 H), 2.37-2.46 (m, 1 H), 2.09-2.23 (m, 1 H), 1.98-2.09 (m, 1 H), 1.76-1.95 (m, 3 H), 1.50-1.72 (m, 3 H), 1.24 (tt, J = 5.21, 8.32 Hz, 1 H), 0.53-0.64 (m, 2 H), 0.42-0.49 (m, 2 H) | J |
| 200 | 1-(((2S)-4-((3-cyano-1-azetidinyl)sulfonyl)-2-piperazinyl)carbonyl)-N-(2-fluoro-4-(trifluoromethyl)benzyl)-D-prolinamide | LCMS-ESI (POS.) m/z: 547.2 (M + Na)+ | 1H NMR (400 MHz, CHLOROFORM-d) δ ppm 7.42-7.50 (m, 1 H), 7.34-7.42 (m, 2 H), 7.31 (d, J = 9.95 Hz, 1 H), 4.43-4.62 (m, 3 H), 4.09-4.19 (m, 4 H), 3.76-3.95 (m, 1 H), 3.66-3.73 (m, 2 H), 3.41-3.63 (m, 3 H), 3.14 (br d, J = 13.68 Hz, 1 H), 2.74-2.97 (m, 3 H), 2.36-2.53 (m, 1 H), 2.01-2.20 (m, 2 H), 1.78-1.99 (m, 2 H) | M |
| 201 | (4S)-N-((R)-(4-chloro-2,5-difluorophenyl)(cyclopropyl)methyl)-4-fluoro-1-(3-(methylsulfonyl)benzoyl)-D-prolinamide | LCMS-ESI (POS.) m/z: 515.0 (M + H)+ | 1H NMR (500 MHz, DMSO-d6) δ ppm 8.46-8.85 (m, 1 H), 7.26-8.13 (m, 6 H), 5.21-5.45 (m, 1 H), 3.88-4.76 (m, 3 H), 3.58-3.68 (m, 2 H), 3.26-3.30 (m, 3 H), 1.82-2.05 (m, 1 H), 0.80-1.32 (m, 1 H), −0.28-0.63 (m, 4 H) | C |
| 202 | (1R,3R,5R)-N-((R)-(4-chloro-2,5-difluorophenyl)(cyclopropyl)methyl)-2-((4-(methylsulfonyl)-2-pyridinyl)carbonyl)-2-azabicyclo[3.1.0]hexane-3-carboxamide | LCMS-ESI (POS.) m/z: 510.0 (M + H)+ | 1H NMR (500 MHz, DMSO-d6) δ ppm 8.78-9.05 (m, 1 H), 8.42-8.67 (m, 1 H), 8.13-8.26 (m, 1 H), 7.99-8.08 (m, 1 H), 7.53-7.70 (m, 1 H), 7.36-7.53 (m, 1 H), 4.86-5.51 (m, 1 H), 4.11-4.56 (m, 1 H), 3.84-3.97 (m, 1 H), 3.39 (d, J = 8.82 Hz, 3 H), 2.54-2.79 (m, 1 H), 1.70-1.90 (m, 1 H), 1.53-1.68 (m, 1 H), 0.45-1.22 (m, 4 H), 0.25-0.37 (m, 2 H), −0.20-0.02 (m, 1 H) | C |

| Ex. # | Structure Name | LCMS-ESI (POS/NEG) m/z: (M + H)+ | NMR Data | Syn. Rte. |
|---|---|---|---|---|
| 203 | 1-(((3S)-1-((3-(1H-1,2,3-triazol-1-yl)-1-azetidinyl)sulfonyl)-3-piperidinyl)carbonyl)-N-(4-(trifluoromethyl)benzyl)-D-prolinamide | LCMS-ESI (POS.) m/z: 570.2 (M + Na)+ | 1H NMR (500 MHz, DMSO-d6) δ ppm 7.38-8.82 (m, 7 H), 5.54 (br d, J = 7.78 Hz, 1 H), 4.13-4.46 (m, 7 H), 3.49-3.81 (m, 4 H), 2.59-2.97 (m, 3 H), 1.34-2.26 (m, 8 H) | M |
| 204 | 1-(3-((3-cyano-1-azetidinyl)sulfonyl)benzoyl)-N-((1S)-1-(2-fluoro-4-(trifluoromethyl)phenyl)propyl)-D-prolinamide | LCMS-ESI (POS.) m/z: 567.0 (M + H)+ | 1H NMR (500 MHz, DMSO-d6) δ ppm 8.54 (d, J = 7.91 Hz, 1 H), 7.12-8.03 (m, 7 H), 4.78-5.03 (m, 1 H), 4.41-4.56 (m, 1 H), 3.82-4.05 (m, 4 H), 3.43-3.71 (m, 3 H), 3.03-3.04 (m, 1 H), 2.23-2.38 (m, 1 H), 1.79-2.00 (m, 3 H), 1.57-1.74 (m, 2 H), 0.70-0.96 (m, 3 H) | A |
| 205 | 1-(3-((3-cyano-1-azetidinyl)sulfonyl)benzoyl)-N-((1R)-1-(3,5-difluorophenyl)ethyl)-D-prolinamide | LCMS-ESI (POS.) m/z: 503.2 (M + H)+ | 1H NMR (500 MHz, DMSO-d6) δ ppm 8.23-8.51 (m, 1 H), 7.68-8.00 (m, 4 H), 6.87-7.18 (m, 3 H), 4.62-5.01 (m, 1 H), 4.24-4.52 (m, 1 H), 3.95-4.07 (m, 2 H), 3.82-3.92 (m, 2 H), 3.43-3.70 (m, 3 H), 2.20-2.30 (m, 1 H), 1.72-1.92 (m, 3 H), 1.05-1.42 (m, 3 H) | A |
| 206 | 1-(((3S)-1-((3-cyano-1-azetidinyl)sulfonyl)-3-piperidinyl)carbonyl)-N-(2,3-dichlorobenzyl)-D-prolinamide | LCMS-ESI (POS.) m/z: 528.1 (M + H)+ | 1H NMR (400 MHz, CHLOROFORM-d) δ ppm 7.44 (br t, J = 5.75 Hz, 1 H), 7.39 (dd, J = 7.93, 1.61 Hz, 1 H), 7.26 (dd, J = 7.67, 1.55 Hz, 1 H), 7.15-7.20 (m, 1 H), 4.53-4.64 (m, 2 H), 4.42-4.50 (m, 1 H), 4.07-4.14 (m, 4 H), 3.73-3.80 (m, 2 H), 3.53-3.60 (m, 2 H), 3.38-3.48 (m, 1 H), 2.98 (dd, J = 12.70, 11.04 Hz, 1 H), 2.64-2.82 (m, 2 H), 2.40-2.48 (m, 1 H), 2.08-2.22 (m, 1 H), 1.99-2.08 (m, 1 H), 1.78-1.96 (m, 3 H), 1.45-1.72 (m, 3 H) | A |

-continued

| Ex. # | Structure Name | LCMS-ESI (POS/NEG) m/z: (M + H)+ | NMR Data | Syn. Rte. |
|---|---|---|---|---|
| 207 | 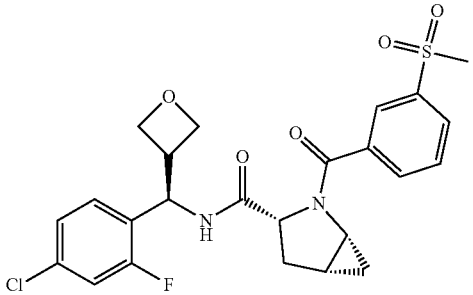 [SMILES: CS(=O)(=O)c1cccc(C(=O)N2[C@@H](C(=O)N[C@@H](c3ccc(Cl)cc3F)C3COC3)C[C@H]3C[C@H]32)c1]<br>(1R,3R,5R)-N-((R)-(4-chloro-2-fluorophenyl)(3-oxetanyl)methyl)-2-(3-(methylsulfonyl)benzoyl)-2-azabicyclo[3.1.0]hexane-3-carboxamide | LCMS-APCI (POS.) m/z: 507.1 (M + H)+ | 1H NMR (400 MHz, Methanol-d4) δ ppm 8.39 (t, J = 1.7 Hz, 1 H), 8.09-8.15 (m, 2 H), 7.78 (t, J = 7.8 Hz, 1 H), 7.34 (t, J = 8.2 Hz, 1 H), 7.25 (ddt, J = 2.2, 4.4, 8.1 Hz, 2 H), 5.58 (d, J = 10.2 Hz, 1 H), 4.99 (dd, J = 4.2, 11.4 Hz, 1 H), 4.84 (dd, J = 6.5, 7.7 Hz, 1 H), 4.59-4.69 (m, 2 H), 4.37 (t, J = 6.2 Hz, 1 H), 3.47-3.58 (m, 1 H), 3.19 (s, 3 H), 2.66 (dddd, J = 1.1, 6.5, 11.6, 13.3 Hz, 1 H), 1.91 (dd, J = 4.2, 13.5 Hz, 1 H), 1.76-1.84 (m, 1 H), 1.24-1.29 (m, 1 H), 0.90 (dtd, J = 1.0, 5.7, 9.1 Hz, 1 H). | A |
| 208 | 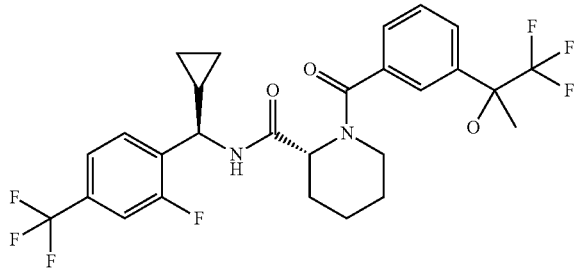 [SMILES: CC(O)(c1cccc(C(=O)N2CCCC[C@@H]2C(=O)N[C@@H](c2ccc(C(F)(F)F)cc2F)C2CC2)c1)C(F)(F)F]<br>(2R)-N-((R)-cyclopropyl(2-fluoro-4-(trifluoromethyl)phenyl)methyl)-1-(3-(-1,1,1-trifluoro-2-hydroxy-2-propanyl)benzoyl)-2-piperidinecarboxamide | LCMS-ESI (POS.) m/z: 583.2 (M + Na)+ | 1H NMR (500 MHz, CHLOROFORM-d) δ ppm 7.29-7.81 (m, 9 H), 5.26 (br d, J = 3.11 Hz, 1 H), 4.25-4.91 (m, 2 H), 3.70 (br d, J = 13.75 Hz, 1 H), 3.10 (br t, J = 12.59 Hz, 1 H), 1.15-2.47 (m, 19 H), 0.26-0.83 (m, 5 H) | C |
| 209 | 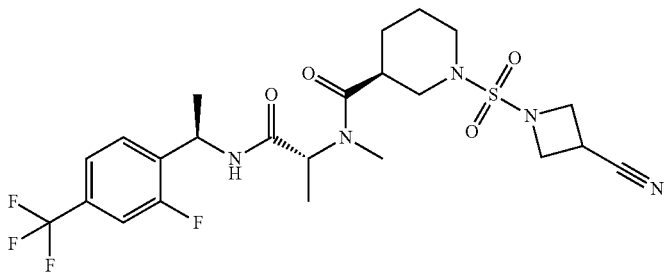<br>(3S)-1-((3-cyano-1-azetidinyl)sulfonyl)-N-((2R)-1-(((1R)-1-(2-fluoro-4-(trifluoromethyl)phenyl)ethyl)amino)-1-oxo-2-propanyl)-N-methyl-3-piperidinecarboxamide | LCMS-ESI (POS.) m/z: 570.2 (M + Na)+ | 1H NMR (500 MHz, DMSO-d6) δ ppm 8.34-8.64 (m, 1 H), 7.53-7.67 (m, 3 H), 5.06-5.24 (m, 1 H), 4.59-4.92 (m, 1 H), 4.02-4.13 (m, 2 H), 3.90-4.00 (m, 2 H), 3.73-3.84 (m, 1 H), 3.51-3.67 (m, 2 H), 2.94 (s, 2 H), 2.72-2.92 (m, 3 H), 1.67-1.88 (m, 2 H), 1.47-1.62 (m, 1 H), 1.32-1.42 (m, 4 H), 1.19-1.30 (m, 4 H) | C |

-continued

| Ex. # | Structure Name | LCMS-ESI (POS/NEG) m/z: (M + H)+ | NMR Data | Syn. Rte. |
|---|---|---|---|---|
| 210 | 1-(((3S)-1-((3-((4-chlorobenzyl)oxy)-1-azetidinyl)sulfonyl)-3-piperidinyl)carbonyl)-N-(4-(trifluoromethyl)benzyl)-D-prolinamide | LCMS-ESI (POS.) m/z: 643.2 (M + H)+ | 1H NMR (500 MHz, CHLOROFORM-d) δ ppm 7.57 (d, J = 8.04 Hz, 2 H), 7.28-7.48 (m, 5 H), 7.25 (br s, 2 H), 4.59 (br d, J = 6.49 Hz, 1 H), 4.47-4.56 (m, 1 H), 4.39-4.45 (m, 3 H), 4.29 (quin, J = 5.90 Hz, 1 H), 3.89-3.96 (m, 2 H), 3.85 (dd, J = 8.30, 5.45 Hz, 2 H), 3.73-3.81 (m, 2 H), 3.54-3.62 (m, 2 H), 2.91 (t, J = 11.81 Hz, 1 H), 2.64-2.76 (m, 2 H), 2.44 (ddd, J = 9.15, 6.29, 3.50 Hz, 1 H), 2.12-2.32 (m, 1 H), 1.97-2.08 (m, 1 H), 1.83-1.95 (m, 2 H), 1.77 (br d, J = 13.23 Hz, 1 H), 1.59-1.69 (m, 1 H), 1.45-1.54 (m, 1 H) | M |
| 211 | (1R,3R,5R)-N-((R)-cyclopropyl(2-fluoro-4-(trifluoromethyl)phenyl)methyl)-2-(3-(cyclopropylsulfonyl)benzoyl)-2-azabicyclo[3.1.0]hexane-3-carboxamide | LCMS-ESI (POS.) m/z: 551.2 (M + H)+ | 1H NMR (500 MHz, DMSO-d6) δ ppm 8.40-8.78 (m, 1 H), 7.47-8.19 (m, 7 H), 4.10-5.00 (m, 2 H), 3.17-3.79 (m, 1 H), 2.86-2.98 (m, 1 H), 2.54 (s, 2 H), 1.51-1.77 (m, 2 H), −0.23-1.28 (m, 11 H) | H |
| 212 | N+190R)-cyclopropyl(2-fluoro-4-(trifluoromethyl)phenyl)methyl)-1-(3-(ethylsulfonyl)benzoyl)-D-prolinamide | LCMS-ESI (POS.) m/z: 527.2 (M + H)+ | 1H NMR (500 MHz, DMSO-d6) δ ppm 8.41-8.80 (m, 1H), 7.47-8.02 (m, 7 H), 4.47-4.66 (m, 1 H), 4.07-4.39 (m, 1H), 3.12-3.64 (m, 6 H), 2.69 (s, 1 H), 2.11-2.32 (m, 1 H), 1.62-1.96 (m, 3 H), 1.16-1.29 (m, 1 H), 1.12 (q, J = 7.35 Hz, 3 H), 0.95 (dt, J = 8.24, 4.31 Hz, 1 H), 0.52-0.66 (m, 1 H), 0.42-0.43 (m, 1 H), 0.42-0.52 (m, 1 H), 0.32-0.44 (m, 1 H), −0.07-0.15 (m, 1 H) | C |
| 213 | (1R,3R,5R)-N-((R)-(2-fluoro-4-(trifluoromethyl)phenyl)(3-oxetanyl)methyl)-2-(3-(2-methyl-2-propanyl)benzoyl)-2-azabicyclo[3.1.0]hexane-3-carboxamide | LCMS-APCI (POS.) m/z: 519.2 (M + H)+ | 1H NMR (400 MHz, Methanol-d4) δ ppm 7.88 (t, 1 H), 7.54-7.60 (m, 4 H), 7.48-7.53 (m, 1H), 7.42 (t, J = 0.5, 7.8 Hz, 1 H), 5.66 (d, J = 10.1 Hz, 1 H), 5.00 (dd, J = 4.1, 11.3 Hz, 1 H), 4.83-4.86 (m, 1 H), 4.61-4.69 (m, 2 H), 4.41 (t, J = 1 H), 3.49-3.60 (m, 1 H), 3.30 (dt, J = 3.2, 6.3 Hz, 1 H), 2.58-2.68 (m, 1 H), 1.91 (dd, J = 4.2, 13.5 Hz, 1 H), 1.72-1.80 (m, 1 H), 1.38 (s, 10 H), 1.23 (td, J = 2.6, 5.2 Hz, 1 H), 0.82-0.88 (m, 1 H). | A |

-continued

| Ex. # | Structure Name | LCMS-ESI (POS/NEG) m/z: (M + H)+ | NMR Data | Syn. Rte. |
|---|---|---|---|---|
| 214 | 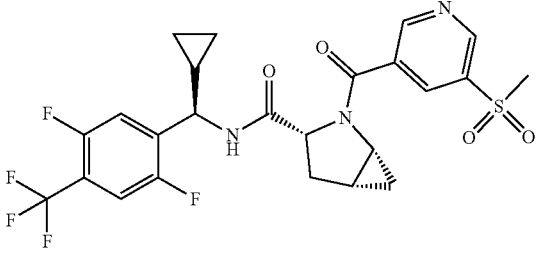<br>(1R,3R,5R)-N-((R)-cyclopropyl(2,5-difluoro-4-(trifluoromethyl)phenyl)methyl)-2-((5-(methylsulfonyl)-3-pyridinyl)carbonyl)-2-azabicyclo[3.1.0]hexane-3-carboxamide | LCMS-ESI (POS.) m/z: 498.2 (M + H)+ | 1H NMR (500 MHz, DMSO-d6) δ ppm 8.83-9.24 (m, 2 H), 8.28-8.80 (m, 2 H), 7.68-7.82 (m, 1 H), 7.36-7.64 (m, 1 H), 4.00-5.05 (m, 2 H), 3.34-3.41 (m, 4 H), 2.56-2.76 (m, 1 H), 1.53-1.79 (m, 2 H), −0.28-1.24 (m, 7 H) | C |
| 215 | 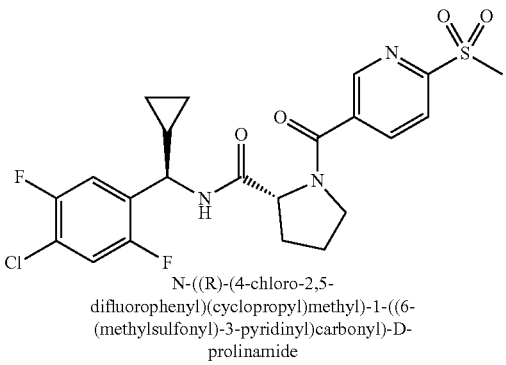<br>N-((R)-(4-chloro-2,5-difluorophenyl)(cyclopropyl)methyl)-1-((6-(methylsulfonyl)-3-pyridinyl)carbonyl)-D-prolinamide | LCMS-ESI (POS.) m/z: 498.2 (M + H)+ | 1H NMR (500 MHz, DMSO-d6) δ ppm 8.76-9.02 (m, 1 H), 8.46-8.67 (m, 1 H), 7.98-8.23 (m, 2 H), 7.40-7.66 (m, 2 H), 4.16-5.06 (m, 2 H), 3.63-3.82 (m, 2 H), 3.38 (br s, 3 H), 2.12-2.28 (m, 1 H), 1.67-1.92 (m, 3 H), 1.00-1.33 (m, 1 H), −0.04-0.57 (m, 4 H) | C |
| 216 | 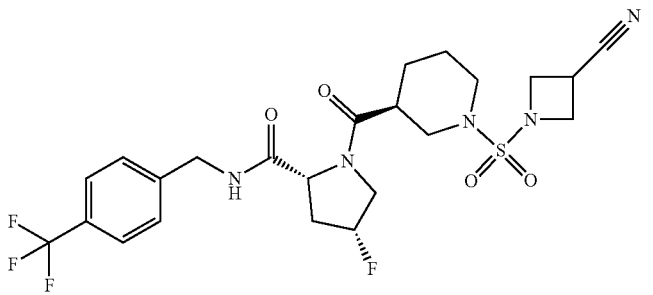 [SMILES: N#CC1CN(S(=O)(=O)N2CCC[C@H](C(=O)N3C[C@H](F)C[C@@H]3C(=O)NCc3ccc(C(F)(F)F)cc3)C2)C1]<br>(4R)-1-(((3S)-1-((3-cyano-1-azetidinyl)sulfonyl)-3-piperidinyl)carbonyl)-4-fluoro-N-(4-(trifluoromethyl)benzyl)-D-prolinamide | LCMS-ESI (POS.) m/z: 546.2 (M + H)+ | 1H NMR (500 MHz, CHLOROFORM-d) δ ppm 7.47-7.56 (m, 2 H), 7.25-7.35 (m, 2 H), 6.24-6.89 (m, 1 H), 5.16-5.36 (m, 1 H), 4.67-4.74 (m, 1 H), 4.38-4.50 (m, 2 H), 3.98-4.07 (m, 4 H), 3.58-3.90 (m, 4 H), 3.31-3.40 (m, 1 H), 2.86-2.98 (m, 2 H), 2.55-2.74 (m, 2 H), 2.09-2.23 (m, 1 H), 1.79-1.89 (m, 1 H), 1.73 (br d, J = 13.49 Hz, 1 H), 1.45-1.66 (m, 2 H) | M |
| 217 | 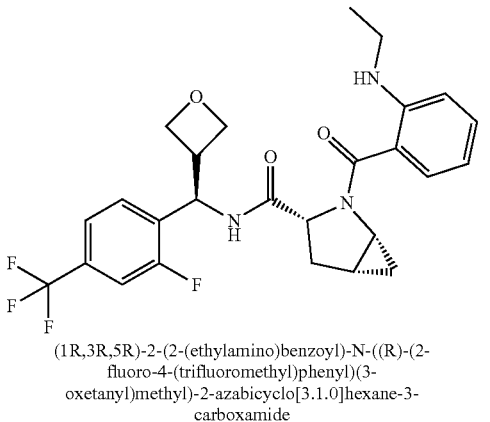<br>(1R,3R,5R)-2-(2-(ethylamino)benzoyl)-N-((R)-(2-fluoro-4-(trifluoromethyl)phenyl)(3-oxetanyl)methyl)-2-azabicyclo[3.1.0]hexane-3-carboxamide | LCMS-APCI (POS.) m/z: 506.2 (M + H)+ | 1H NMR (400 MHz, DMSO-d6) δ ppm 8.77 (d, J = 8.0 Hz, 1 H), 7.70 (d, J = 10.3 Hz, 1 H), 7.55-7.66 (m, 2 H), 7.17-7.31 (m, 2 H), 6.55-6.68 (m, 2 H), 5.72 (t, 1 H), 5.50 (t, J = 8.8 Hz, 1 H), 4.92 (dd, J = 11.2 Hz, 1 H), 4.66 (t, J+32 7.0 Hz, 1 H), 4.52 (t, J+32 7.0 Hz, 1 H), 4.43 (t, J+32 6.2 Hz, 1 H), 4.23 (t, J+32 6.1 Hz, 1 H), 3.10 (q, J+32 4.0, 5.3 Hz, 3 H), 1.73 (dd, J = 13.4 Hz, 1 H), 1.57 (p, 1 H), 1.17 (t, J = 7.1 Hz, 2 H), 0.93 (s, 1 H), 0.64 (dd, J = 5.7, 13.9 Hz, 1 H). | Q |

| Ex. # | Structure Name | LCMS-ESI (POS/NEG) m/z: (M + H)+ | NMR Data | Syn. Rte. |
|---|---|---|---|---|
| 218 | 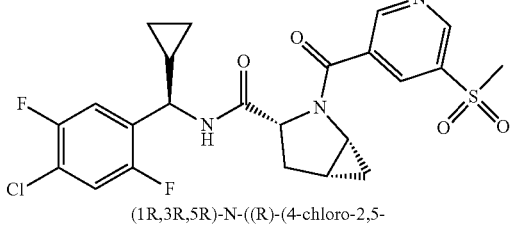 (1R,3R,5R)-N-((R)-(4-chloro-2,5-difluorophenyl)(cyclopropyl)methyl)-2-((5-(methylsulfonyl)-3-pyridinyl)carbonyl)-2-azabicyclo[3.1.0]hexane-3-carboxamide | LCMS-ESI (POS.) m/z: 510.0 (M + H)+ | 1H NMR (500 MHz, DMSO-d6) δ ppm 8.83-9.25 (m, 2 H), 8.25-8.72 (m, 2 H), 7.54-7.68 (m, 1 H), 7.29-7.54 (m, 1 H), 4.65-4.99 (m, 1 H), 4.01-4.56 (m, 1 H), 3.33-3.40 (m, 4 H), 2.54-2.76 (m, 1 H), 1.56-1.78 (m, 2 H), 0.68-1.19 (m, 3 H), −0.32-0.60 (m, 3 H) | C |
| 219 | 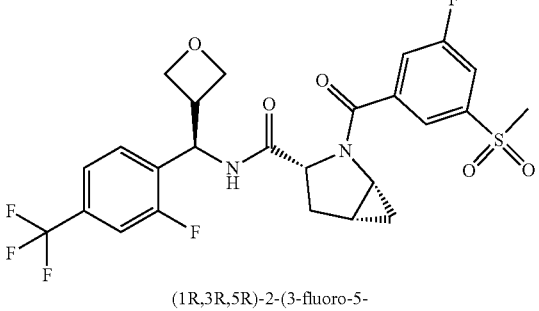 (1R,3R,5R)-2-(3-fluoro-5-(methylsulfonyl)benzoyl)-N-((R)-(2-fluoro-4-(trifluoromethyl)phenyl)(3-oxetanyl)methyl)-2-azabicyclo[3.1.0]hexane-3-carboxamide | LCMS-APCI (POS.) m/z: 559.1 (M + H)+ | 1H NMR (400 MHz, DMSO-d6) δ ppm 8.76 (d, J = 8.1 Hz, 1 H), 7.96-8.01 (m, 1 H), 7.90 (q, J = 1.6 Hz, 1 H), 7.80 (td, J = 0.8, 1.6 Hz, 1 H), 7.70 (d, J = 9.9 Hz, 1 H), 7.55-7.66 (m, 2 H), 5.44-5.55 (m, 1 H), 4.90 (dd, J = 3.6, 11.4 Hz, 1 H), 4.65 (dd, J = 6.3, 7.7 Hz, 1 H), 4.52 (dd, J = 6.2, 7.8 Hz, 1 H), 4.41 (t, J = 6.1 Hz, 1 H), 4.23 (t, J+32 6.2 Hz, 1 H), 3.25 (s, 3 H), 2.46-2.50 (m, 3 H), 1.63-1.78 (m, 2 H), 1.15 (td, J = 2.5, 5.0 Hz, 1 H), 0.68-0.82 (m, 1 H). | Q |
| 220 | 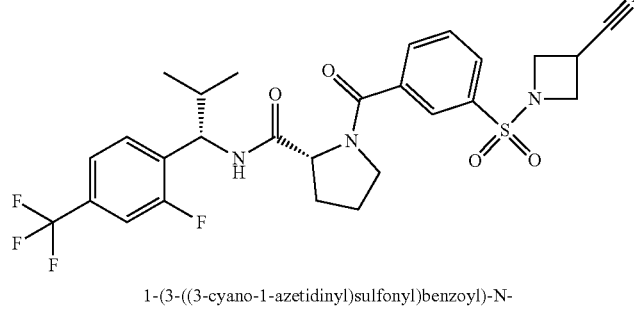 1-(3-((3-cyano-1-azetidinyl)sulfonyl)benzoyl)-N-((1S)-1-(2-fluoro-4-(trifluoromethyl)phenyl)-2-methylpropyl)-D-prolinamide | LCMS-ESI (POS.) m/z: 581.2 (M + H)+ | 1H NMR (500 MHz, DMSO-d6) δ ppm 8.47 (br d, J = 8.56 Hz, 1 H), 7.46-7.97 (m, 7 H), 4.89 (br t, J = 8.37 Hz, 1 H), 4.55 (br dd, J = 7.72, 5.77 Hz, 1 H), 4.29-4.37 (m, 1 H), 3.82-4.06 (m, 4 H), 3.45-3.69 (m, 4 H), 2.13-2.33 (m, 1 H), 1.80-1.90 (m, 3 H), 0.58-1.01 (m, 6 H) | A |
| 221 | 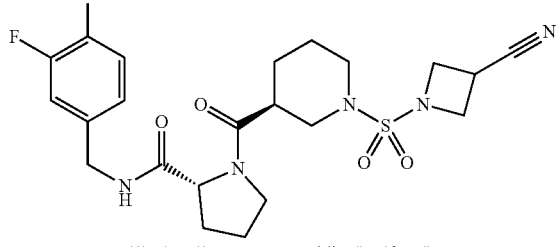 1-(((3S)-1-((3-cyano-1-azetidinyl)sulfonyl)-3-piperidinyl)carbonyl)-N-(3,4-difluorobenzyl)-D-prolinamide | LCMS-ESI (POS.) m/z: 496.2 (M + H)+ | 1H NMR (500 MHz, DMSO-d6) δ ppm 8.25-8.70 (m, 1 H), 7.22-7.40 (m, 2 H), 7.02-7.11 (m, 1 H), 4.16-4.52 (m, 3 H), 4.00-4.12 (m, 2 H), 3.87-3.97 (m, 2 H), 3.73-3.84 (m, 1 H), 3.37-3.69 (m, 4 H), 2.67-2.92 (m, 2 H), 2.02-2.33 (m, 2 H), 1.86-1.99 (m, 3 H), 1.72-1.85 (m, 2 H), 1.38-1.55 (m, 2 H) | A |

| Ex. # | Structure Name | LCMS-ESI (POS/NEG) m/z: (M + H)+ | NMR Data | Syn. Rte. |
|---|---|---|---|---|
| 222 | N-((R)-(4-chloro-2,5-difluorophenyl)(cyclopropyl)methyl)-1-((4-(methylsulfonyl)-2-pyridinyl)carbonyl)-D-prolinamide | LCMS-ESI (POS.) m/z: 498.2 (M + H)+ | 1H NMR (500 MHz, DMSO-d6) δ ppm 8.80 (br d, J = 5.06 Hz, 1 H), 8.47-8.68 (m, 1 H), 7.96-8.23 (m, 2 H), 7.37-7.62 (m, 2 H), 4.15-5.04 (m, 2 H), 3.62-3.85 (m, 2 H), 3.39 (br s, 3 H), 2.09-2.29 (m, 1 H), 1.65-1.92 (m, 3 H), 1.03-1.25 (m, 1 H), −0.03-0.63 (m, 4 H) | C |
| 223 | N-((R)-cyclopropyl(2-fluoro-4-(trifluoromethyl)phenyl)methyl)-1-(3-(cyclopropylsulfonyl)benzoyl)-D-prolinamide | LCMS-ESI (POS.) m/z: 539.2 (M + H)+ | 1H NMR (500 MHz, DMSO-d6) δ ppm 8.46-8.79 (m, 1 H), 7.50-8.06 (m, 7 H), 4.17-4.64 (m, 2 H), 2.83-3.66 (m, 3 H), 2.14-2.31 (m, 1 H), 1.62-1.95 (m, 3 H), −0.05-1.28 (m, 10 H) | H |
| 224 | N-((R)-(4-chloro-2,5-difluorophenyl)(cyclopropyl)methyl)-1-(3-sulfamoylbenzoyl)-D-prolinamide | LCMS-ESI (POS.) m/z: 498.0 (M + H)+ | 1H NMR (400 MHz, CHLOROFORM-d) δ ppm 8.05-8.15 (m, 1 H), 8.01 (s, 1 H), 7.94-8.05 (m, 1 H), 7.73 (s, 1 H), 7.66-7.77 (m, 1 H), 7.54-7.64 (m, 1 H), 7.40-7.50 (m, 1 H), 7.05-7.19 (m, 2 H), 5.34-5.79 (m, 2 H), 4.65-4.79 (m, 1 H), 4.41-4.57 (m, 1 H), 3.93-4.39 (m, 2 H), 3.59-3.87 (m, 1 H), 3.38-3.54 (m, 1 H), 1.94-2.29 (m, 1 H), 1.80-1.92 (m, 1 H), 1.05-1.28 (m, 1 H), 0.48-0.65 (m, 2 H), 0.18-0.48 (m, 2 H) | C |
| 225 | (1R,3R,5R)-N-((R)-cyclopropyl(2,5-difluoro-4-(trifluoromethyl)phenyl)methyl)-2-((2-(trifluoromethyl)-4-pyridinyl)carbonyl)-2-azabicyclo[3.1.0]hexane-3-carboxamide | LCMS-APCI (POS.) m/z: 534.2 (M + H)+ | 1H NMR (DMSO-d6) δ: 9.15 (d, J = 4.9 Hz, 1H), 8.96 (d, J = 7.4 Hz, 1H), 8.20 (s, 1H), 8.03-7.95 (m, 1H), 7.81 (dd, J = 11.1, 5.6 Hz, 1H), 5.14 (dd, J = 11.4, 3.5 Hz, 1H), 4.73 (t, J = 7.9 Hz, 1H), 2.05-1.88 (m, 3H), 1.51-1.35 (m, 2H), 1.29 (td, J = 5.1, 2.6 Hz, 1H), 1.02-0.87 (m, 2H), 0.79 (t, J = 8.8 Hz, 1H), 0.68 (t, J = 9.1 Hz, 1H), 0.58 (s, 2H) | Q |

| Ex. # | Structure Name | LCMS-ESI (POS/NEG) m/z: (M + H)+ | NMR Data | Syn. Rte. |
|---|---|---|---|---|
| 226 | 3-((3-cyano-1-azetidinyl)sulfonyl)-N-methyl-N-((1R)-1-methyl-2-oxo-2-((4-(trifluoromethyl)benzyl)amino)ethyl)benzamide | LCMS-APCI (NEG.) m/z: 507.1 (M − H) | 1H NMR (400 MHz, Methanol-d4) δ ppm 7.94-8.03 (m, 2 H), 7.73-7.91 (m, 2 H), 7.61-7.67 (m, 2 H), 7.41-7.56 (m, 2 H), 5.05-5.17 (m, 1 H), 4.30-4.62 (m, 3 H), 4.03-4.17 (m, 2 H), 3.84-3.99 (m, 2 H), 3.43-3.61 (m, 1 H), 2.95-3.09 (m, 3 H), 1.43-1.62 (m, 3 H). | Q |
| 227 | 1-(((3S)-1-((3-(1,2-oxazol-3-yl)-1-azetidinyl)sulfonyl)-3-piperidinyl)carbonyl)-N-(4-(trifluoromethyl)benzyl)-D-prolinamide | LCMS-ESI (POS.) m/z: 570.2 (M + H)+ | 1H NMR (500 MHz, DMSO-d6) δ 8.83-9.04 (m, 1H), 8.31-8.77 (m, 1H), 7.60-7.77 (m, 2H), 7.38-7.53 (m, 2H), 6.56-6.74 (m, 1H), 4.26-4.51 (m, 3H), 4.10-4.24 (m, 2H), 3.86-4.04 (m, 3H), 3.51-3.72 (m, 4H), 2.71-2.92 (m, 2H), 2.60-2.71 (m, 1H), 2.06-2.38 (m, 1H), 1.63-1.99 (m, 5H), 1.35-1.55 (m, 2H) | J |
| 228 | N-((R)-cyclopropyl(2-fluoro-4-(trifluoromethyl)phenyl)methyl)-1-(2-(methylamino)-5-(methylsulfonyl)benzoyl)-D-prolinamide | LCMS-APCI (POS.) m/z: 542.2 (M + H)+ | 1H NMR (400 MHz, DMSO-d6) δ ppm 8.90 (d, J = 7.6 Hz, 1 H), 7.60-7.77 (m, 4 H), 7.54 (s, 2 H), 6.76 (d, J = 8.8 Hz, 2 H), 6.63 (d, J = 5.2 Hz, 1 H), 4.55-4.70 (m, 3 H), 3.10 (s, 3 H), 2.82 (d, J = 4.8 Hz, 3 H), 2.19-2.30 (m, 2 H), 1.62-1.80 (m, 4 H), 1.15-1.31 (m, 2 H), 0.96 (d, J = 6.5 Hz, 2 H), 0.59 (d, J = 8.8 Hz, 1 H), 0.39 (s, 3 H). | S |
| 229 | 1-(((3S)-1-((3-cyano-1-azetidinyl)sulfonyl)-3-piperidinyl)carbonyl)-N-((1S)-1-(2-fluoro-4-(trifluoromethyl)phenyl)-2-methylpropyl)-D-prolinamide | LCMS-ESI (POS.) m/z: 588.2 (M + H)+ | 1H NMR (500 MHz, DMSO-d6) δ ppm 8.22 (d, J = 8.69 Hz, 1 H), 7.52-7.70 (m, 3 H), 4.85 (br t, J = 8.50 Hz, 1 H), 4.35-4.51 (m, 1 H), 3.73-4.10 (m, 5 H), 3.30-3.66 (m, 4 H), 2.70-2.86 (m, 2 H), 2.58-2.67 (m, 1 H), 1.66-2.12 (m, 7 H), 1.28-1.58 (m, 2 H), 0.70-0.99 (m, 6 H) | A |

-continued

| Ex. # | Structure Name | LCMS-ESI (POS/NEG) m/z: (M + H)+ | NMR Data | Syn. Rte. |
|---|---|---|---|---|
| 230 | 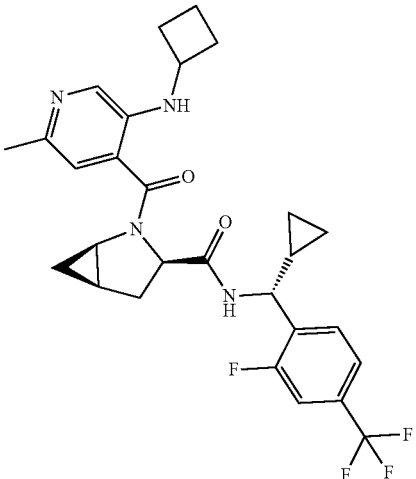 [SMILES: Cc1cc(C(=O)N2[C@@H](C(=O)N[C@@H](c3ccc(C(F)(F)F)cc3F)C3CC3)C[C@H]3C[C@H]32)c(NC2CCC2)cn1]<br>(1R,3R,5R)-2((5-(cyclobutylamino)-2-methyl-4-pyridinyl)carbonyl)-N-((R)-cyclopropyl(2-fluoro-4-(trifluoromethyl)phenyl)methyl)-2-azabicyclo[3.1.0]hexane-3-carboxamide | LCMS-APCI (POS.) m/z: 531.2 (M + H)+ | 1H NMR (400 MHz, Methylene Chloride-d2) δ ppm 8.00 (s, 1 H), 7.44-7.54 (m, 2 H), 7.36-7.43 (m, 2 H), 6.65 (d, J = 6.7 Hz, 1 H), 5.05 (dd, J = 2.8, 11.2 Hz, 1 H), 4.49 (dd, J = 6.6, 9.3 Hz, 1 H), 3.94 (q, J = 7.6 Hz, 1 H), 3.11 (td, J = 2.6, 6.2 Hz, 1 H), 2.59-2.66 (m, 1 H), 2.47 (ddd, J = 3.4, 7.2, 12.9 Hz, 2 H), 2.16 (dd, J = 2.7, 13.4 Hz, 1 H), 1.80-2.03 (m, 4 H), 1.74 (dt, J = 5.9, 9.1 Hz, 1 H), 1.26-1.35 (m, 1 H), 0.97 (ddd, J = 2.7, 5.1, 6.2 Hz, 1 H), 0.67-0.77 (m, 2 H), 0.56-0.64 (m, 1 H), 0.47 (ddt, J = 4.7, 9.5, 22.4 Hz, 2 H). | S |
| 231 | 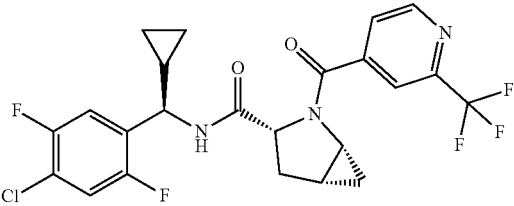<br>(1R,3R,5R)-N-((R)-(4-chloro-2,5-difluorophenyl)(cyclopropyl)methyl)-2-((2-(trifluoromethyl)-4-pyridinyl)carbonyl)-2-azabicyclo[3.1.0]hexane-3-carboxamide | LCMS-APCI (POS.) m/z: 500.1 (M + H)+ | 1H NMR (DMSO-d6) δ: 9.18 (d, J = 4.9 Hz, 1H), 8.90 (d, J = 7.6 Hz, 1H), 8.23(s, 1H), 7.92-7.85 (m, 1H), 7.73 (dd, J = 9.8, 6.3 Hz, 1H), 5.15 (dd, J = 11.4, 3.5 Hz, 1H), 4.74 (t, J = 8.0 Hz, 1H), 3.52 (td, J = 6.1, 2.6 Hz, 1H), 2.03-1.90 (m, 3H), 1.51-1.38 (m, 1H), 1.37-1.28 (m, 1H), 1.03-0.93 (m, 2H), 0.85-0.74 (m, 1H), 0.74-0.66 (m, 1H), 0.62-0.51 (m, 2H) | Q |
| 232 | 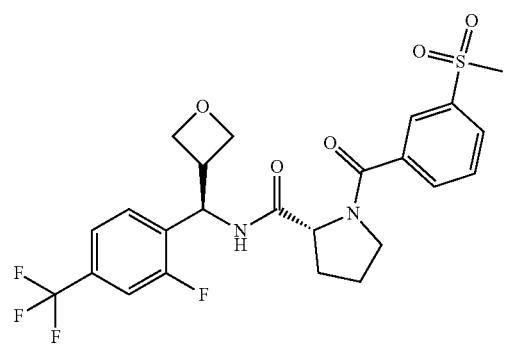 [SMILES: CS(=O)(=O)c1cccc(C(=O)N2CCC[C@@H]2C(=O)N[C@@H](c2ccc(C(F)(F)F)cc2F)C2COC2)c1]<br>N-((R)-(2-fluoro-4-(trifluoromethyl)phenyl)(3-oxetanyl)methyl)-1-(3-(methylsulfonyl)benzoyl)-D-prolinamide | LCMS-APCI (POS.) m/z: 529.1 (M + H)+ | 1 H NMR (400 MHz, Methanol-d4) δ ppm 8.23 (t, 1 H), 8.07-8.14 (m, 1 H), 7.96 (dt, J = 1.3, 7.7 Hz, 1 H), 7.72-7.81 (m, 2 5.25-5.76 (m, 1 H), 4.88-4.94 (m, 1 H), 4.65-4.72 (m, 2 H), 4.53-4.61 (m, 1 H), 4.43 (t, J = 6.2 Hz, 1 H), 4.07 (dt, J = 6.2, 34.7 Hz, 1 H), 3.68-3.78 (m, 1 H), 3.49-3.67 (m, 3 H), 2.33 (dtd, J = 5.8, 9.7, 10.4, 12.4 Hz, 1 H), 1.94-2.06 (m, 1H), 1.80-1.94 (m, 3 H). | A |

| Ex. # | Structure Name | LCMS-ESI (POS/NEG) m/z: (M + H)+ | NMR Data | Syn. Rte. |
|---|---|---|---|---|
| 233 | (1R,3R,5R)-N-((R)-(4-chloro-2,5-difluorophenyl)(3-oxetanyl)methyl)-2-((4-(trifluoromethyl)-2-pyridinyl)carbonyl)-2-azabicyclo[3.1.0]hexane-3-carboxamide | LCMS-APCI (POS.) m/z: 516.1 (M + H)+ | 1H NMR (400 MHz, DMSO-d6) δ ppm 8.97 (d, J = 5.1 Hz, 1 H), 8.72 (d, J = 5.1 Hz, 1 H), 8.64 (d, J = 8.3 Hz, 1 H), 8.45 (d, J = 8.3 Hz, 1 H), 8.00-8.06 (m, 1 H), 7.95-8.00 (m, 1 H), 7.85-7.91 (m, 1 H), 7.65 (ddd, J = 6.3, 9.5, 18.0 Hz, 2 H), 7.46 (dd, J = 6.2, 9.7 Hz, 1 H), 7.28 (dd, J = 6.4, 9.8 Hz, 1 H), 5.36-5.53 (m, 2 H), 5.12 (t, J = 9.1 Hz, 1 H), 4.88 (dd, J = 3.3, 11.3 Hz, 1 H), 4.65 (dd, J = 6.3, 7.7 Hz, 1 H), 4.52 (dd, J = 1 H), 4.33-4.44 (m, 2 H), 4.22 (t, J = 6.1 Hz, 1 H), 3.92 (td, J = 3.2, 6.3 Hz, 1 H), 3.84 (td, J = 3.2, 6.1 Hz, 3 H), 3.58-3.65 (m, 2 H), 3.37-3.46 (m, 1 H), 3.19-3.29 (m, 1 H), 2.64-2.82 (m, 2 H), 1.82 (dd, J = 2.9, 13.4 Hz, 1 H), 1.75-1.79 (m, 1 H), 1.72 (dd, J = 3.4, 13.3 Hz, 1 H), 1.51-1.69 (m, 2 H), 1.02-1.11 (m, 1 H), 0.73-0.81 (m, 1 H), 0.64-0.70 (m, 1 H). | Q |
| 234 | 1-((3-((3,3-dimethyl-1-azetidinyl)sulfonyl)phenyl)carbonyl)-N-(4-(trifluoromethyl)benzyl)-D-prolinamide | LCMS-APCI (NEG.) m/z: 522.2 (M − H) | 1H NMR (400 MHz, Methanol-d4) δ ppm 8.10 (t, J = 1.7 Hz, 1 H), 7.96 (dd, J = 1.6, 7.7 Hz, 2 H), 7.73-7.82 (m, 1 H), 7.62 (d, J = 8.1 Hz, 2 H), 7.55 (t, J = 9.2 Hz, 2 H), 4.55-4.64 (m, 2 H), 4.47 (d, J = 15.9 Hz, 1 H), 3.68 (dt, J = 6.9, 10.2 Hz, 1 H), 3.54 (ddd, J = 4.5, 7.0, 10.2 Hz, 1 H), 3.47 (s, 4 H), 2.31-2.48 (m, 1 H), 1.99-2.09 (m, 2 H), 1.92 (ddd, J = 3.5, 7.0, 14.2 Hz, 1 H), 1.04 (s, 6 H). | Q |
| 235 | N-((R)-cyclobutyl(2-fluoro-4-(trifluoromethyl)phenyl)methyl)-1-(3-(methylsulfonyl)benzoyl)-D-prolinamide | LCMS-ESI (POS.) m/z: 527.2 (M + H)+ | 1H NMR (500 MHz, DMSO-d6) δ ppm 8.23-8.50 (m, 1 H), 7.70-8.06 (m, 3 H), 7.41-7.67 (m, 4 H), 4.74-5.14 (m, 1 H), 4.33-4.55 (m, 1 H), 3.39-3.61 (m, 2 H), 3.22-3.29 (m, 3 H), 2.50 (d, J = 28.16 Hz, 1 H), 2.12-2.30 (m, 1 H), 1.31-2.10 (m, 9 H) | A |

| Ex. # | Structure Name | LCMS-ESI (POS/NEG) m/z: (M + H)+ | NMR Data | Syn. Rte. |
|---|---|---|---|---|
| 236 | 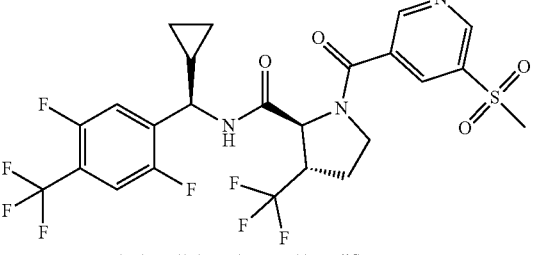<br>(3S)-N-((R)-cyclopropyl(2,5-difluoro-4-(trifluoromethyl)phenyl)methyl)-1-((5-(methylsulfonyl)-3-pyridinyl)carbonyl)-3-(trifluoromethyl)-L-prolinamide | LCMS-ESI (POS.) m/z: 600.0 (M + H)+ | 1H NMR (500 MHz, CHLOROFORM-d) δ ppm 9.27 (s, 1 H), 9.05 (s, 1 H), 8.41 (s, 1 H), 7.43 (br d, J = 6.23 Hz, 1 H), 7.35 (dd, J = 9.41, 5.64 Hz, 1 H), 7.20 (dd, J = 9.93, 5.51 Hz, 1 H), 4.93 (d, J = 5.06 Hz, 1 H), 4.48 (dd, J = 8.76, 6.68 Hz, 1 H), 3.71-3.79 (m, 1 H), 3.64-3.71 (m, 1 H), 3.48-3.61 (m, 1 H), 3.18 (s, 3 H), 2.35-2.45 (m, 1 H), 2.12-2.22 (m, 1 H), 1.19-1.29 (m, 1 H), 0.65-0.72 (m, 1 H), 0.58-0.65 (m, 1 H), 0.41-0.50 (m, 2 H) | C |
| 237 | <br>1-(((3S)-1-((3-(2-fluoroethoxy)-1-azetidinyl)sulfonyl)-3-piperidinyl)carbonyl)-N-(2-fluoro-4-(trifluoromethyl)benzyl)-D-prolinamide | LCMS-ESI (POS.) m/z: 583.0 (M + H)+ | 1H NMR (400 MHz, CHLOROFORM-d) δ 7.49 (br t, J = 5.96 Hz, 1H), 7.35-7.46 (m, 2H), 7.31 (d, J = 9.95 Hz, 1H), 4.58-4.64 (m, 2H), 4.42-4.58 (m, 3H), 4.25-4.36 (m, 1H), 3.96-4.04 (m, 2H), 3.88 (dd, J = 5.18, 8.40 Hz, 2H), 3.75-3.84 (m, 2H), 3.68-3.73 (m, 1H), 3.55-3.66 (m, 3H), 2.94 (dd, J = 11.14, 12.70 Hz, 1 H), 2.64-2.82 (m, 2H), 2.38-2.50 (m, 1H), 2.08-2.22 (m, 1H), 1.98-2.08 (m, 1H), 1.74-1.96 (m, 3H), 1.48-1.74 (m, 3H) | J |
| 238 | 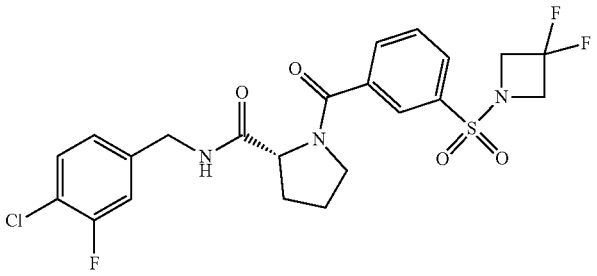 [SMILES: O=C(NCc1ccc(Cl)c(F)c1)[C@H]1CCCN1C(=O)c1cccc(S(=O)(=O)N2CC(F)(F)C2)c1]<br>N-(4-chloro-3-fluorobenzyl)-1-(3-((3,3-difluoro-1-azetidinyl)sulfonyl)benzoyl)-D-prolinamide | LCMS-ESI (POS.) m/z: 516.0 (M + H)+ | 1H NMR (500 MHz, DMSO-d6) δ ppm 8.43-8.69 (m, 1 H), 6.98-8.11 (m, 7 H), 4.08-4.54 (m, 7 H), 3.39-3.71 (m, 2 H), 2.17-2.34 (m, 1 H), 1.73-2.01 (m, 3 H) | C |
| 239 | 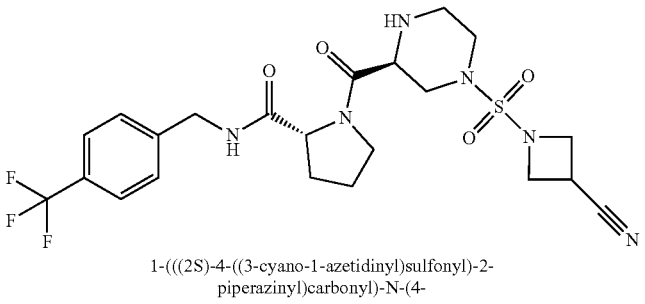<br>1-(((2S)-4-((3-cyano-1-azetidinyl)sulfonyl)-2-piperazinyl)carbonyl)-N-(4-(trifluoromethyl)benzyl)-D-prolinamide | LCMS-ESI (POS.) m/z: 529.2 (M + H)+ | 1H NMR (400 MHz, CHLOROFORM-d) δ ppm 7.49-7.65 (m, 3 H), 7.28-7.47 (m, 2 H), 6.77 (s, 1 5.31 (s, 1 H), 4.36-4.60 (m, 4 H), 3.93-4.19 (m, 6 H), 3.69-3.89 (m, 3 3.41-3.66 (m, 4 H), 3.12-3.24 (m, 1 H), 2.84-3.00 (m, 3 H), 2.37-2.65 (m, 1 H), 1.95-2.20 (m, 5 H) | M |

| Ex. # | Structure Name | LCMS-ESI (POS/NEG) m/z: (M + H)+ | NMR Data | Syn. Rte. |
|---|---|---|---|---|
| 240 | (4R)-1-(((3S)-1-((3-cyano-1-azetidinyl)sulfonyl)-3-piperidinyl)carbonyl)-4-hydroxy-N-(4-(trifluoromethyl)benzyl)-D-prolinamide | LCMS-ESI (POS.) m/z: 544.2 (M + H)+ | 1H NMR (500 MHz, CHLOROFORM-d) δ ppm 7.50-7.66 (m, 3 H), 7.38 (br s, 2 H), 4.69 (br d, J = 7.66 Hz, 1 H), 4.55-4.64 (m, 1 H), 4.52 (br s, 1 H), 4.41 (br d, J = 14.53 Hz, 1 H), 3.99-4.17 (m, 4 H), 3.60-3.81 (m, 4 H), 3.42 (br s, 1 H), 2.93 (br t, J = 11.16 Hz, 1 H), 2.76 (br t, J = 11.42 Hz, 1 H), 2.60 (br s, 1 H), 2.31-2.44 (m, 1 H), 2.19 (br s, 1 H), 1.23-1.98 (m, 5 H) | M |
| 241 | N-((R)-cyclopropyl(2,5-difluoro-4-(trifluoromethyl)phenyl)methyl)-1-(5-(methylsulfonyl)nicotinoyl)-3-(trifluoromethyl)pyrrolidine-2-carboxamide | LCMS-ESI (POS.) m/z: 600.0 (M + H)+ | 1H NMR (500 MHz, CHLOROFORM-d) δ ppm 9.27 (t, J = 2.08 Hz, 1 H), 9.03 (dd, J = 17.00, 1.95 Hz, 1 H), 8.26-8.46 (m, 1 H), 7.38-7.59 (m, 1 H), 7.29-7.38 (m, 1 H), 7.09-7.23 (m, 1 H), 4.91-5.05 (m, 1 H), 4.40-4.55 (m, 1 H), 3.47-3.82 (m, 3 H), 3.18 (d, J = 5.06 Hz, 3 H), 2.32-2.47 (m, 1 H), 2.06-2.23 (m, 1 H), 1.14-1.31 (m, 1 H), 0.55-0.79 (m, 2 H), 0.37-0.53 (m, 2 H) | C |
| 242 | (2R)-1-((S)-1-((3-cyanoazetidin-1-yl)sulfonyl)piperidine-3-carbonyl)-N-(4-methoxy-2,3-dihydro-1H-inden-1-yl)pyrrolidine-2-carboxamide | LCMS-ESI (POS.) m/z: 516.2 (M + H)+ | 1H NMR (500 MHz, DMSO-d6) δ ppm 7.94-8.53 (m, 1 H), 6.68-7.30 (m, 3 H), 5.18-5.37 (m, 1 H), 4.22-4.46 (m, 1 H), 4.03-4.12 (m, 2 H), 3.88-3.97 (m, 2 H), 3.77 (br d, J = 3.24 Hz, 4 H), 3.49-3.70 (m, 4 H), 2.59-2.96 (m, 5 H), 1.64-2.41 (m, 8 H), 1.32-1.57 (m, 2 H) | A |
| 243 | 1-(((3S)-1-((3-cyano-1-azetidinyl)sulfonyl)-3-piperidinyl)carbonyl)-N-(4-methylbenzyl)-D-prolinamide | LCMS-ESI (POS.) m/z: 474.2 (M + H)+ | 1H NMR (500 MHz, CHLOROFORM-d) δ ppm 7.12 (s, 4 H), 4.57 (dd, J = 8.04, 1.82 Hz, 1 H), 4.31-4.44 (m, 2 H), 4.04-4.16 (m, 4 H), 3.75 (br d, J = 12.72 Hz, 2 H), 3.50-3.67 (m, 2 H), 3.37-3.50 (m, 1 H), 2.96 (dd, J = 12.46, 11.16 Hz, 1 H), 2.65-2.84 (m, 2 H), 2.43 (ddd, J = 12.20, 6.49, 3.11 Hz, 1 H), 2.30-2.36 (m, 3 H), 2.12-2.30 (m, 2 H), 1.97-2.10 (m, 2 H), 1.76-1.97 (m, 4 H), 1.46-1.72 (m, 5 H) | C |

| Ex. # | Structure Name | LCMS-ESI (POS/NEG) m/z: (M + H)+ | NMR Data | Syn. Rte. |
|---|---|---|---|---|
| 244 | Diastereomer #1-(1R,3R,5R)-N-((2-fluoro-4-(trifluoromethyl)phenyl)(5-oxopyrrolidin-3-yl)methyl)-2-(3-(methylsulfonyl)benzoyl)-2-azabicyclo[3.1.0]hexane-3-carboxamide | LCMS-ESI (POS.) m/z: 568.2 (M + H)+ | 1H NMR (500 MHz, CHLOROFORM-d) δ ppm 8.55-8.76 (m, 1H), 8.17-8.38 (m, 1H), 8.00-8.16 (m, 2H), 7.64-7.94 (m, 1H), 7.33-7.53 (m, 3H), 6.74-7.00 (m, 1H), 5.45-5.86 (m, 1H), 5.17-5.40 (m, 1H), 3.40-3.57 (m, 1H), 3.29-3.40 (m, 1H), 3.21-3.29 (m, 1H), 3.14 (s, 3H), 3.06-3.12 (m, 1H), 2.43-2.53 (m, 1H), 2.31-2.43 (m, 2H), 2.09-2.22 (m, 1H), 1.73-1.83 (m, 1H), 1.38-1.45 (m, 1H), 0.89-0.99 (m, 1H) | C |
| 245 | 1-(((3S)-1-((3-cyano-1-azetidinyl)sulfonyl)-3-piperidinyl)carbonyl)-N-((1R)-1-(3,5-difluorophenyl)propyl)-D-prolinamide | LCMS-ESI (POS.) m/z: 524.2 (M + H)+ | 1H NMR (500 MHz, DMSO-d6) δ ppm 8.10 (d, J = 8.30 Hz, 1 H), 6.78-7.19 (m, 3 H), 4.61-4.77 (m, 1 H), 4.26-4.52 (m, 1 H), 3.99-4.12 (m, 2 H), 3.91-3.97 (m, 2 H), 3.82 (br d, J = 7.40 Hz, 2 H), 3.28-3.63 (m, 4 H), 2.58-2.91 (m, 3 H), 1.43-2.09 (m, 9 H), 0.80-0.94 (m, 3 H) | A |
| 246 | (1R,3R,5R)-N-((R)-cyclopropyl(2-fluoro-4-(trifluoromethyl)phenyl)methyl)-2-(3-(ethylsulfonyl)benzoyl)-2-azabicyclo[3.1.0]hexane-3-carboxamide | LCMS-ESI (POS.) m/z: 539.0 (M + H)+ | 1H NMR (500 MHz, DMSO-d6) δ ppm 8.73 (br d, J = 7.40 Hz, 1 H), 7.49-8.14 (m, 7 H), 4.10-5.03 (m, 2 H), 3.55-3.67 (m, 1 H), 3.17-3.35 (m, 3 H), 2.53-2.60 (m, 1 H), 1.48-1.78 (m, 2 H), 1.17-1.30 (m, 1 H), 1.03-1.12 (m, 3 H), −0.22-0.76 (m, 5 H) | C |
| 247 | | LCMS-APCI (POS.) m/z: 612.2 (M + H)+ | 1H NMR (400 MHz, Methanol-d4) δ ppm 7.18-7.66 (m, 7 H), 3.92-4.47 (m, 6 H), 3.27-3.57 (m, 2 H), 2.47-2.56 (m, 1 H), 2.06-2.19 (m, 1H), 1.61-1.82 (m, 3 H), 1.05-1.17 (m, 1 H), 0.79-0.98 (m, 4 H),−0.21-0.55 (m, 4 H). | W |

| Ex. # | Structure Name | LCMS-ESI (POS/NEG) m/z: (M + H)+ | NMR Data | Syn. Rte. |
|---|---|---|---|---|
| | N-((R)-cyclopropyl(2-fluoro-4-(trifluoromethyl)phenyl)methyl)-1-(3-(1-(cyclopropylsulfonyl)-3-fluoro-3-azetidinyl)benzoyl)-D-prolinamide | | | |
| 248 | 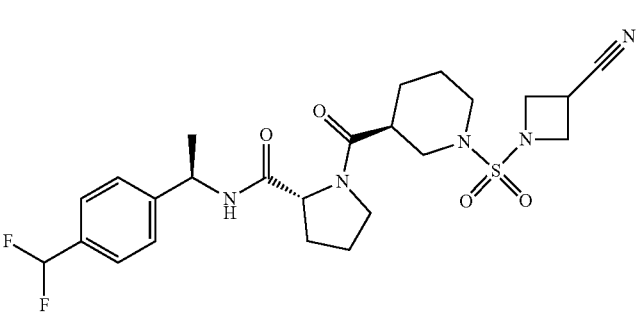 [SMILES: C[C@@H](NC(=O)[C@H]1CCCN1C(=O)[C@H]1CCCN(S(=O)(=O)N2CC(C#N)C2)C1)c1ccc(C(F)F)cc1]<br>1-(((3S)-1-((3-cyano-1-azetidinyl)sulfonyl)-3-piperidinyl)carbonyl)-N-((1R)-1-(4-(difluoromethyl)phenyl)ethyl)-D-prolinamide | LCMS-ESI (POS.) m/z: 524.2 (M + H)+ | 1H NMR (500 MHz, DMSO-d6) δ ppm 8.15-8.71 (m, 1 H), 7.48-7.59 (m, 2 H), 7.33-7.44 (m, 2 H), 6.76-7.16 (m, 1 H), 4.86-5.01 (m, 1 H), 4.30-4.49 (m, 1 H), 4.05-4.14 (m, 2 H), 3.93-4.00 (m, 2 H), 3.75-3.87 (m, 1 H), 3.52-3.60 (m, 3 H), 3.29-3.42 (m, 1 H), 2.70-2.88 (m, 2 H), 2.60-2.67 (m, 1 H), 2.01-2.32 (m, 1 H), 1.65-1.92 (m, 5 H), 1.39-1.55 (m, 2 H), 1.29-1.39 (m, 3 H) | A |
| 249 | 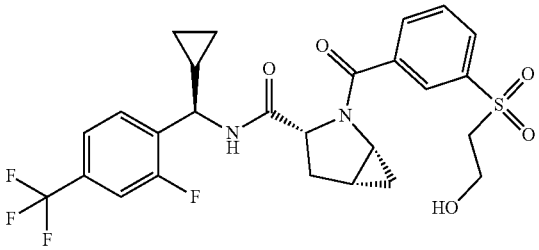 [SMILES: O=C(N[C@@H](c1ccc(C(F)(F)F)cc1F)C1CC1)[C@H]1C[C@H]2C[C@H]2N1C(=O)c1cccc(S(=O)(=O)CCO)c1]<br>(1R,3R,5R)-N-((R)-cyclopropyl(2-fluoro-4-(trifluoromethyl)phenyl)methyl)-2-(3-((2-hydroxyethyl)sulfonyl)benzoyl)-2-azabicyclo[3.1.0]hexane-3-carboxamide | LCMS-APCI (POS.) m/z: 555.2 (M + H)+ | 1H NMR (400 MHz, DMSO-d6) δ ppm 8.74 (d, J = 7.5 Hz, 1 H), 8.15 (t, J = 1.7 Hz, 1 H), 7.96-8.06 (m, 2 H), 7.77 (t, J = 7.8 Hz, 1 H), 7.66 (dd, J = 7.3, 15.5 Hz, 3 H), 4.96 (dd, J = 3.4, 11.5 Hz, 1 H), 4.87 (t, J = 5.4 Hz, 1 H), 4.58 (t, J = 7.8 Hz, 1 H), 4.35 (t, J = 5.1 Hz, 1 H), 3.70 (q, J = 6.2 Hz, 2 H), 3.50 (t, J = 6.2 Hz, 2 H), 3.20-3.26 (m, 1 H), 1.63-1.75 (m, 2 H), 1.14-1.22 (m, 2 H), 0.67-0.77 (m, 2 H), 0.56 (d, 1 H), 0.47 (d, J = 8.4 Hz, 1 H), 0.35 (d, J = 4.6 Hz, 2 H). | Q |
| 250 | 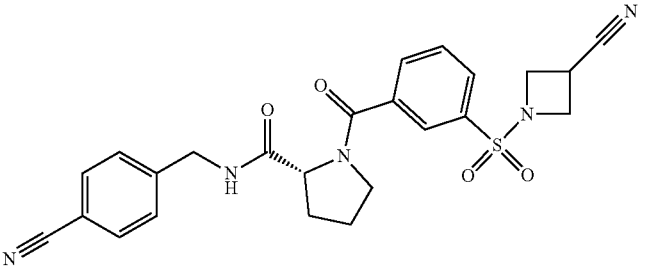 [SMILES: N#Cc1ccc(CNC(=O)[C@H]2CCCN2C(=O)c2cccc(S(=O)(=O)N3CC(C#N)C3)c2)cc1]<br>1-((3-((3-cyano-1-azetidinyl)sulfonyl)phenyl)carbonyl)-N-(4-cyanobenzyl)-D-prolinamide | LCMS-ESI (POS.) m/z: 478.2 (M + H)+ | 1H NMR (500 MHz, CHLOROFORM-d) δ ppm 7.96-8.02 (m, 1 H), 7.90-7.96 (m, 1 H), 7.78-7.82 (m, 1 H), 7.66-7.72 (m, 1 H), 7.57-7.64 (m, 2 H), 7.36-7.44 (m, 2 H), 7.26-7.31 (m, 1 H), 4.71-4.79 (m, 1 H), 4.48-4.58 (m, 2 H), 4.11-4.19 (m, 2 H), 3.96-4.05 (m, 2 H), 3.55-3.65 (m, 1 H), 3.43-3.51 (m, 1 H), 3.32-3.42 (m, 1 H), 2.43-2.54 (m, 1 H), 2.05-2.20 (m, 2 H), 1.83-1.95 (m, 1 H) | A |

| Ex. # | Structure Name | LCMS-ESI (POS/NEG) m/z: (M + H)+ | NMR Data | Syn. Rte. |
|---|---|---|---|---|
| 251 | (4S)-1-((3-((3-cyano-1-azetidinyl)sulfonyl)phenyl)carbonyl)-4-hydroxy-N-(4-(trifluoromethyl)benzyl)-D-prolinamide | LCMS-APCI (POS.) m/z: 537.2 (M + H)+ | 1H NMR (400 MHz, Methanol-d4) δ ppm 7.75-9.01 (m, 4 H), 7.10-7.66 (m, 4 H), 4.80 (dd, J = 7.6, 9.8 Hz, 1 H), 4.59-4.69 (m, 1 H), 3.74-4.54 (m, 7 H), 3.46-3.58 (m, 1 H), 3.41-3.46 (m, 1 H), 2.32-2.44 (m, 1 H), 2.08-2.19 (m, 1 H). | C |
| 252 | N-((R)-cyclopropyl(2-fluoro-4-(trifluoromethyl)phenyl)methyl)-1-(3-(trifluoromethyl)benzoyl)-D-prolinamide | LCMS-APCI (POS.) m/z: 503.2 (M + H)+ | 1H NMR (400 MHz, DMSO-d6) δ ppm 8.62 (dd, J = 7.6, 65.3 Hz, 1 H), 7.76-7.90 (m, 1 H), 7.55-7.76 (m, 2 H), 4.49-4.62 (m, 1 H), 4.14-4.37 (m, 1 H), 3.39-3.63 (m, 2 H), 2.14-2.27 (m, 1 H), 1.65-1.88 (m, 2 H), 0.91-1.27 (m, 2 H), 0.54 (dd, J = 8.5, 35.9 Hz, 1 H), 0.33-0.41 (m, 1 H), -0.08-0.11 (m, 1 H). | A |
| 253 | (2R)-N-((R)-cyclopropyl(2-fluoro-4-(trifluoromethyl)phenyl)methyl)-1-(3-(methylsulfonyl)benzoyl)-2-piperidinecarboxamide | LCMS-ESI (POS.) m/z: 527.0 (M + H)+ | 1H NMR (400 MHz, CHLOROFORM-d) δ ppm 7.96-8.11 (m, 2 H), 7.56-7.80 (m, 2 H), 7.41-7.52 (m, 2 H), 7.37 (d, J = 10.47 Hz, 1 H), 7.03-7.19 (m, 1 H), 5.14-5.34 (m, 1 H), 4.47-4.64 (m, 1 H), 3.51-3.73 (m, 1 H), 3.14-3.28 (m, 1 H), 2.98-3.13 (m, 3 H), 2.21-2.32 (m, 1 H), 1.63-1.92 (m, 4 H), 1.47-1.58 (m, 1 H), 1.20-1.36 (m, 1 H), 0.64-0.73 (m, 1 H), 0.54-0.64 (m, 1 H), 0.34-0.52 (m, 2 H) | C |
| 254 | N-((1R)-1-(4-chloro-2-fluorophenyl)ethyl)-1-(((2S)-4-((3-cyano-1-azetidinyl)sulfonyl)-2-piperazinyl)carbonyl)-D-prolinamide | LCMS-ESI (POS.) m/z: 527.2 (M + Na)+ | 1H NMR (400 MHz, CHLOROFORM-d) δ ppm 7.34 (br d, J = 7.26 Hz, 1 H), 7.19-7.26 (m, 1 H), 7.04-7.15 (m, 2 H), 5.13 (quin, J = 7.10 Hz, 1 H), 4.45-4.55 (m, 1 H), 4.08-4.18 (m, 5 H), 3.76-3.94 (m, 1 H), 3.65-3.74 (m, 2 H), 3.41-3.63 (m, 4 H), 3.15 (br d, J = 13.48 Hz, 1 H), 2.75-2.98 (m, 3 H), 2.27-2.42 (m, 1 H), 2.06-2.20 (m, 1 H), 1.95-2.04 (m, 1 H), 1.72-1.95 (m, 2 H), 1.43 (d, J = 7.05 Hz, 3 H) | M |

| Ex. # | Structure Name | LCMS-ESI (POS/NEG) m/z: (M + H)+ | NMR Data | Syn. Rte. |
|---|---|---|---|---|
| 255 | 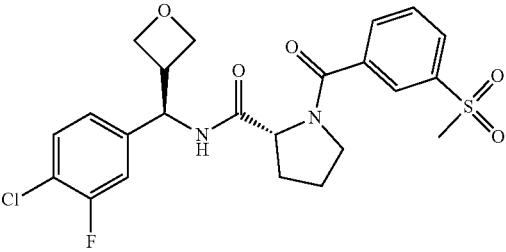 [SMILES: CS(=O)(=O)c1cccc(C(=O)N2CCC[C@@H]2C(=O)N[C@@H](c2ccc(Cl)c(F)c2)C2COC2)c1]<br>N-((R)-(4-chloro-3-fluorophenyl)(3-oxetanyl)methyl)-1-(3-(methylsulfonyl)benzoyl)-D-prolinamide | LCMS-APCI (POS.) m/z: 495.1 (M + H)+ | 1H NMR (400 MHz, Methanol-d4) δ ppm 8.23 (t, J = 1.6 Hz, 1 H), 8.05-8.12 (m, 2 H), 7.96 (dt, J = 1.3, 7.7 Hz, 1 H), 7.73-7.79 (m, 1 H), 7.48 (t, 1 H), 7.25 (dd, J = 2.0, 10.2 Hz, 1 H), 7.17 (dt, J = 1.3, 8.2 Hz, 1 H), 5.41 (d, J = 10.3 Hz, 1 H), 4.63-4.70 (m, 2 H), 4.53-4.58 (m, 1 H), 4.46 (t, J = 6.3 Hz, 1 H), 3.62-3.70 (m, 1 H), 3.47-3.58 (m, 2 H), 3.19 (s, 4 H), 2.27-2.38 (m, 1 H), 1.96-2.05 (m, 1 H), 1.79-1.95 (m, 3 H). | A |
| 256 | 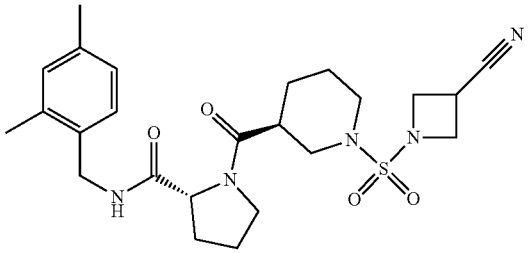 [SMILES: Cc1ccc(CNC(=O)[C@H]2CCCN2C(=O)[C@H]2CCCN(S(=O)(=O)N3CC(C#N)C3)C2)c(C)c1]<br>1-(((3S)-1-((3-cyano-1-azetidinyl)sulfonyl)-3-piperidinyl)carbonyl)-N-(2,4-dimethylbenzyl)-D-prolinamide | LCMS-ESI (POS.) m/z: 488.2 (M + H)+ | 1H NMR (500 MHz, DMSO-d6) δ ppm 8.04-8.44 (m, 1 H), 7.03-7.09 (m, 1 H), 6.90-6.98 (m, 2 H), 4.27-4.52 (m, 1 H), 4.10-4.26 (m, 2 H), 4.01-4.09 (m, 2 H), 3.88-3.97 (m, 2 H), 3.74-3.83 (m, 1 H), 3.34-3.69 (m, 4 H), 2.70-2.87 (m, 2 H), 2.19-2.25 (m, 6 H), 2.01-2.12 (m, 1 H), 1.69-1.99 (m, 6 H), 1.33-1.57 (m, 2 H) | A |
| 257 | 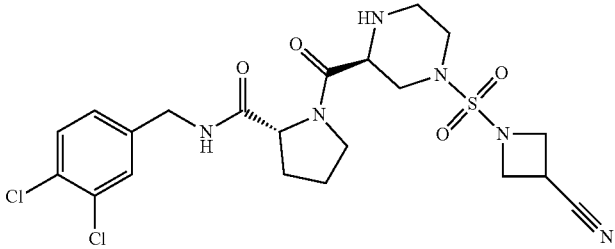 [SMILES: N#CC1CN(S(=O)(=O)N2CCN[C@H](C(=O)N3CCC[C@@H]3C(=O)NCc3ccc(Cl)c(Cl)c3)C2)C1]<br>1-(((2S)-4-((3-cyano-1-azetidinyl)sulfonyl)-2-piperazinyl)carbonyl)-N-(3,4-dichlorobenzyl)-D-prolinamide | LCMS-ESI (POS.) m/z: 529.0 (M + H)+ | 1H NMR (400 MHz, CHLOROFORM-d) δ 7.32-7.46 (m, 3H), 7.06-7.19 (m, 1H), 4.55-4.67 (m, 1H), 4.30-4.47 (m, 2H), 4.01-4.24 (m, 5H), 3.78-3.90 (m, 1H), 3.66-3.78 (m, 2H), 3.39-3.66 (m, 3H), 3.10-3.22 (m, 1H), 2.75-3.02 (m, 3H), 2.39-2.55 (m, 1H), 2.12-2.25 (m, 1H), 1.86-2.01 (m, 2H) | E |
| 258 | 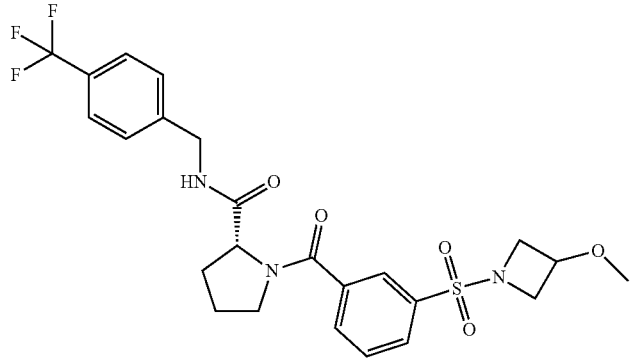 [SMILES: COC1CN(S(=O)(=O)c2cccc(C(=O)N3CCC[C@@H]3C(=O)NCc3ccc(C(F)(F)F)cc3)c2)C1]<br>1-((3-((3-methoxy-1-azetidinyl)sulfonyl)phenyl)carbonyl)-N-(4-(trifluoromethyl)benzyl)-D-prolinamide | LCMS-ESI (POS.) m/z: 526.2 (M + H)+ | 1H NMR (500 MHz, DMSO-d6) δ ppm 8.47-8.72 (m, 1 H), 7.60-8.04 (m, 6 H), 7.14-7.55 (m, 2 H), 3.85-4.55 (m, 6 H), 3.59 (br s, 1 H), 3.39-3.51 (m, 3 H), 2.98-3.09 (m, 3 H), 2.19-2.34 (m, 1 H), 1.77-2.02 (m, 3 H) | C |

-continued

| Ex. # | Structure Name | LCMS-ESI (POS/NEG) m/z: (M + H)+ | NMR Data | Syn. Rte. |
|---|---|---|---|---|
| 259 | 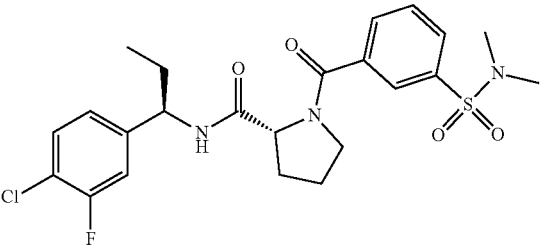 [SMILES: CC[C@@H](NC(=O)[C@H]1CCCN1C(=O)c1cccc(S(=O)(=O)N(C)C)c1)c1ccc(Cl)c(F)c1]<br>N-((1R)-1-(4-chloro-3-fluorophenyl)propyl)-1-(3-(dimethylsulfamoyl)benzoyl)-D-prolinamide | LCMS-ESI (POS.) m/z: 496.2 (M + H)+ | 1H NMR (500 MHz, DMSO-d6) δ ppm 8.13-8.48 (m, 1 H), 6.88-7.98 (m, 7 H), 4.33-4.77 (m, 2 H), 3.40-3.67 (m, 2 H), 2.56-2.75 (m, 6 H), 2.15-2.34 (m, 1 H), 1.32-1.95 (m, 5 H), 0.43-0.94 (m, 3 H) | A |
| 260 | 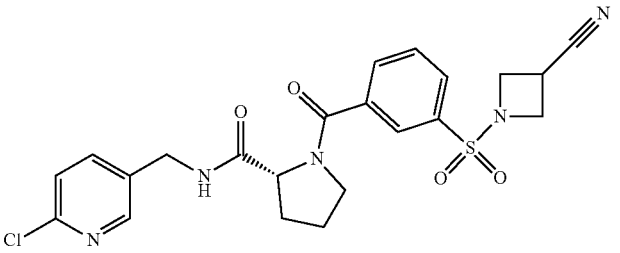 [SMILES: N#CC1CN(S(=O)(=O)c2cccc(C(=O)N3CCC[C@@H]3C(=O)NCc3ccc(Cl)nc3)c2)C1]<br>N-((6-chloro-3-pyridinyl)methyl)-1-((3-((3-cyano-1-azetidinyl)sulfonyl)phenyl)carbonyl)-D-prolinamide | LCMS-ESI (POS.) m/z: 488.2 (M + H)+ | 1H NMR (500 MHz, CHLOROFORM-d) δ ppm 8.29-8.34 (m, 1 H), 7.98-8.05 (m, 1 H), 7.93-7.96 (m, 1 H), 7.81-7.87 (m, 1 H), 7.68-7.75 (m, 1 H), 7.62-7.68 (m, 1 H), 7.33-7.41 (m, 1 H), 7.29 (d, J = 8.17 Hz, 1 H), 4.71-4.80 (m, 1 H), 4.40-4.57 (m, 2 H), 4.14-4.23 (m, 2 H), 4.04 (t, J = 7.33 Hz, 2 H), 3.60-3.68 (m, 1 H), 3.45-3.52 (m, 1 H), 3.34-3.43 (m, 1 H), 2.42-2.55 (m, 1 H), 2.10-2.19 (m, 2 H), 1.88-1.95 (m, 1 H) | A |
| 261 | 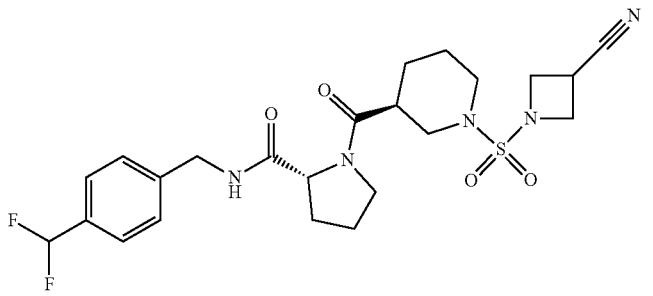 [SMILES: N#CC1CN(S(=O)(=O)N2CCC[C@H](C(=O)N3CCC[C@@H]3C(=O)NCc3ccc(C(F)F)cc3)C2)C1]<br>1-(((3S)-1-((3-cyano-1-azetidinyl)sulfonyl)-3-piperidinyl)carbonyl)-N-(4-(difluoromethyl)benzyl)-D-prolinamide | LCMS-ESI (POS.) m/z: 510.2 (M + H)+ | 1H NMR (500 MHz, CHLOROFORM-d) δ ppm 7.45 (br d, J = 7.79 Hz, 2 H), 7.36 (br s, 1 H), 7.32 (br d, J = 7.78 Hz, 2 H), 6.62 (t, J = 56.44 Hz, 1 H), 4.59 (br d, J = 6.88 Hz, 1 H), 4.49 (br dd, J = 15.25, 6.16 Hz, 1 H), 4.40 (br dd, J = 15.18, 5.32 Hz, 1 H), 4.02-4.16 (m, 4 H), 3.75 (br d, J = 12.46 Hz, 2 H), 3.51-3.63 (m, 2 H), 3.37-3.47 (m, 1 H), 2.85-3.03 (m, 1 H), 2.64-2.80 (m, 2 H), 2.37-2.49 (m, 1 H), 2.11-2.23 (m, 1 H), 1.99-2.08 (m, 1 H), 1.86-1.95 (m, 2 H), 1.79 (br d, J = 13.49 Hz, 1 H), 1.57-1.68 (m, 1 H), 1.42-1.56 (m, 1 H). | C |
| 262 | 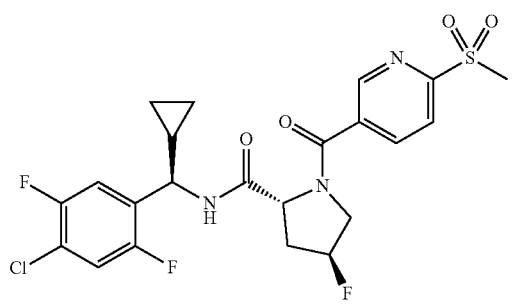 [SMILES: CS(=O)(=O)c1ccc(C(=O)N2C[C@@H](F)C[C@@H]2C(=O)N[C@@H](c2cc(F)c(Cl)cc2F)C2CC2)cn1]<br>(4S)-N-((R)-(4-chloro-2,5-difluorophenyl)(cyclopropyl)methyl)-4-fluoro-1-((6-(methylsulfonyl)-3-pyridinyl)carbonyl)-D-prolinamide | LCMS-ESI (POS.) m/z: 516.0 (M + H)+ | 1H NMR (500 MHz, DMSO-d6) δ ppm 8.60-9.03 (m, 2 H), 8.15-8.28 (m, 1 H), 7.99-8.10 (m, 1 H), 7.33-7.67 (m, 2 H), 5.28-5.39 (m, 1 H), 4.49-4.78 (m, 1 H), 3.98-4.18 (m, 2 H), 3.65 (br dd, J = 14.01, 2.72 Hz, 1 H), 3.35-3.46 (m, 3 H), 2.52-2.69 (m, 1 H), 1.81-2.03 (m, 1 H), 0.89-1.34 (m, 1 H), − 0.16-0.68 (m, 4 H) | C |

| Ex. # | Structure Name | LCMS-ESI (POS/NEG) m/z: (M + H)+ | NMR Data | Syn. Rte. |
|---|---|---|---|---|
| 263 | 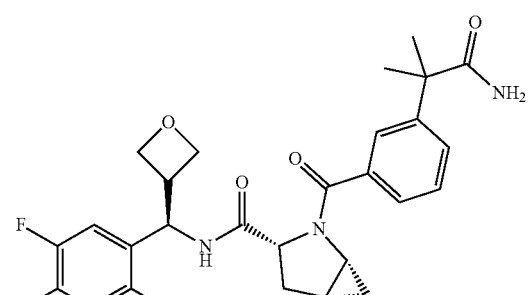<br>(1R,3R,5R)-2-(3-(1-amino-2-methyl-1-oxo-2-propanyl)benzoyl)-N-((R)-(4-chloro-2,5-difluorophenyl)(3-oxetanyl)methyl)-2-azabicyclo[3.1.0]hexane-3-carboxamide | LCMS-APCI (POS.) m/z: 532.2 (M + H)+ | 1H NMR (400 MHz, Methanol-d4) δ ppm 7.87 (t, 1 H), 7.65 (dt, J = 1.2, 7.6 Hz, 1 H), 7.57 (ddd, J = 1.2, 2.0, 7.9 Hz, 1 H), 7.48 (t, 1 H), 7.39 (dd, J = 6.1, 9.5 Hz, 1 H), 7.28 (dd, J = 6.3, 9.4 Hz, 1 H), 5.56 (d, J = 10.2 Hz, 1 H), 4.97 (dd, J = 4.2, 11.4 Hz, 1 H), 4.83 (dd, J = 6.5, 7.6 Hz, 1 H), 4.67 (dd, J = 6.4, 7.8 Hz, 1 H), 4.60 (t, J = 6.2 Hz, 1 H), 4.38 (t, J = 0.9, 12.4 Hz, 1 H), 3.46-3.55 (m, 1 H), 3.37 (s, 3 H), 2.59-2.68 (m, 1 H), 1.91 (dd, J = 4.2, 13.5 Hz, 1 H), 1.77 (dq, J = 5.9, 9.0 Hz, 1 H), 1.60 (d, J = 4.2 Hz, 6 H), 1.23 (td, J = 2.6, 5.3 Hz, 1 H), 0.89 (dt, J = 5.8, 8.1 Hz, 1 H). | V |
| 264 | 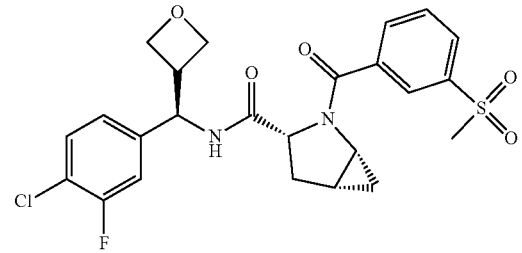 [SMILES: CS(=O)(=O)c1cccc(C(=O)N2[C@@H](C(=O)N[C@@H](c3ccc(Cl)c(F)c3)C3COC3)C[C@H]3C[C@H]32)c1]<br>(1R,3R,5R)-N-((R)-(4-chloro-3-fluorophenyl)(3-oxetanyl)methyl)-2-(3-(methylsulfonyl)benzoyl)-2-azabicyclo[3.1.0]hexane-3-carboxamide | LCMS-APCI (POS.) m/z: 507.1 (M + H)+ | 1H NMR (400 MHz, Methanol-d4) δ ppm 8.39 (t, J = 1.6 Hz, 1 H), 8.09-8.15 (m, 2 H), 7.79 (t, 1 H), 7.48 (t, J = 7.6, 8.2 Hz, 1 H), 7.23 (dd, J = 2.0, 10.2 Hz, 1 H), 7.13-7.17 (m, 1 H), 5.30-5.36 (m, 1 H), 5.00 (dd, J = 4.2, 11.4 Hz, 1 H), 4.83 (dd, J = 6.5, 7.7 Hz, 1 H), 4.66 (dd, J = 6.4, 7.9 Hz, 1 H), 4.60 (t, J = 6.2 Hz, 1 H), 4.42 (t, J = 6.3 Hz, 1 H), 3.47 (dddd, J = 1.7, 6.0, 7.8, 10.1 Hz, 1 H), 3.19 (s, 3 H), 2.61-2.73 (m, 1 H), 1.91 (dd, 1 H), 1.77-1.86 (m, 1 H), 1.29 (td, J = 2.7, 5.3 Hz, 1 H), 0.91 (dtd, J = 1.0, 5.7, 9.0 Hz, 1 H). | A |
| 265 | 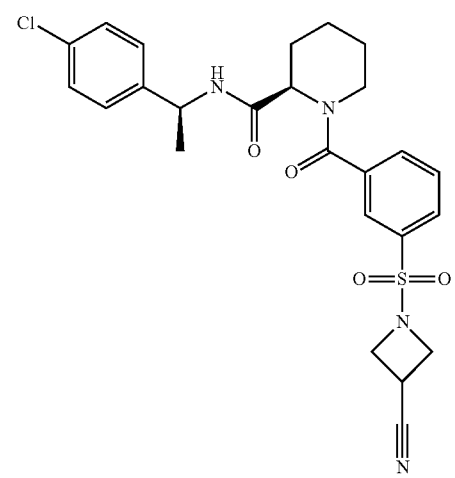 [SMILES: C[C@H](NC(=O)[C@H]1CCCCN1C(=O)c1cccc(S(=O)(=O)N2CC(C#N)C2)c1)c1ccc(Cl)cc1]<br>(2R)-N-((1S)-1-(4-chlorophenyl)ethyl)-1-((3-((3-cyano-1-azetidinyl)sulfonyl)phenyl)carbonyl)-2-piperidinecarboxamide | LCMS-APCI (NEG.) m/z: 513.2 (M − H) | 1H NMR (400 MHz, Methanol-d4) δ ppm 8.47 (s, 1 H), 7.84-8.02 (m, 4 H), 7.69-7.84 (m, 2 H), 7.33 (d, J = 4.6 Hz, 7 H), 5.23 (s, 1 H), 5.06 (d, J = 7.3 Hz, 2 H), 4.10 (td, J = 2.8, 8.9 Hz, 4 H), 3.78-3.98 (m, 4 H), 3.49 (s, 4 H), 2.12-2.34 (m, 2 H), 1.82-2.00 (m, 1H), 1.61-1.82 (m, 4 H), 1.40-1.61 (m, 9 H). | Q |

| Ex. # | Structure Name | LCMS-ESI (POS/NEG) m/z: (M + H)+ | NMR Data | Syn. Rte. |
|---|---|---|---|---|
| 266 | (1R,3R,5R)-N-((R)-(4-chloro-2,5-difluorophenyl)(cyclopropyl)methyl)-2-((4-(trifluoromethyl)-2-pyridinyl)carbonyl)-2-azabicyclo[3.1.0]hexane-3-carboxamide | LCMS-APCI (POS.) m/z: 500.1(M + H)+ | 1H NMR (DMSO-d6) δ: 9.14 (d, J = 5.1 Hz, 1H), 8.96 (d, J = 5.1 Hz, 1H), 8.78 (d, J = 7.7 Hz, 1H), 8.66 (d, J = 8.0 Hz, 1H), 8.20-8.16 (m, 1H), 8.14 (d, J = 5.2 Hz, 1H), 8.09 (d, J = 4.8 Hz, 1H), 7.81 (dd, J = 9.5, 6.2 Hz, 1H), 7.76 (dd, J = 9.4, 6.3 Hz, 1H), 7.69 (dd, J = 9.9, 6.3 Hz, 1H), 7.60 (dd, J = 9.9, 6.3 Hz, 1H), 5.62 (dd, J = 11.5, 2.8 Hz, 1H), 5.10 (dd, J = 11.4, 3.3 Hz, 1H), 4.69 (t, J = 7.9 Hz, 2H), 4.29 (t, J = 8.5 Hz, 2H), 4.15-4.06 (m, 1H), 4.00 (td, J = 6.3, 2.5 Hz, 1H), 2.01 (dd, J = 13.4, 2.9 Hz, 2H), 1.91 (dd, J = 13.3, 3.2 Hz, 1H), 1.83 (s, 1H), 1.75 (s, 1H), 1.43-1.32 (m, 2H), 0.99-0.87 (m, 2H), 0.86-0.79 (m, 1H), 0.72 (d, J = 9.0 Hz, 1H), 0.64 (t, J = 8.6 Hz, 1H), 0.53 (s, 1H), 0.49 (d, J = 8.1 Hz, 2H) | Q |
| 267 | (1R,3R,5R)-N-((R)-(4-chloro-2,5-difluorophenyl)(3-oxetanyl)methyl)-2-((2-(difluoromethyl)-4-pyridinyl)carbonyl)-2-azabicyclo[3.1.0]hexane-3-carboxamide | LCMS-APCI (POS.) m/z: 598.1 (M + H)+ | 1H NMR (400 MHz, Methanol-d4) δ ppm 8.81 (d, J = 0.7, 5.0 Hz, 1 H), 8.01 (s, 1 H), 7.87 (ddt, J = 0.9, 1.7, 5.1 Hz, 1 H), 7.39 (dd, J = 6.1, 9.5 Hz, 1 H), 7.27 (dd, J = 6.3, 9.4 Hz, 1 H), 6.82 (t, J = 55.1 Hz, 1 H), 5.57 (d, J = 10.2 Hz, 1 H), 4.96 (dd, J = 4.1, 11.4 Hz, 1 H), 4.84 (dd, J = 6.5, 7.7 Hz, 1 H), 4.67 (dd, J = 6.5, 7.8 Hz, 1 H), 4.61 (t, J = 6.2 Hz, 1 H), 4.38 (t, 1 H), 3.46-3.56 (m, 1 H), 3.29 (ddd, J = 2.6, 5.9, 6.6 Hz, 1 H), 2.68 (td, J = 6.3, 12.4 Hz, 1 H), 1.90 (dd, J = 4.1, 13.5 Hz, 1 H), 1.77-1.84 (m, 1 H), 1.26 (td, J = 2.6, 5.3 Hz, 1 H), 0.88 (ddd, J = 5.0, 6.1, 8.3 Hz, 1 H). | A |
| 268 | (2R)-N-((4-chlorophenyl)(phenyl)methyl)-1-((S)-1-((3-cyanoazetidin-1-yl)sulfonyl)piperidine-3-carbonyl)pyrrolidine-2-carboxamide | LCMS-ESI (POS.) m/z: 570.2 (M + H)+ | 1H NMR (500 MHz, DMSO-d6) δ ppm 8.65-9.10 (m, 1 H), 7.17-7.46 (m, 9 H), 6.02-6.14 (m, 1 H), 4.38-4.55 (m, 1 H), 3.87-4.11 (m, 4 H), 3.72-3.83 (m, 1 H), 3.33-3.65 (m, 4 H), 2.59-2.88 (m, 3 H), 2.03-2.30 (m, 1 H), 1.68-1.95 (m, 5 H), 1.32-1.55 (m, 2 H) | A |

| Ex. # | Structure Name | LCMS-ESI (POS/NEG) m/z: (M + H)+ | NMR Data | Syn. Rte. |
|---|---|---|---|---|
| 269 | (4S)-N-((R)-(4-chloro-2,5-difluorophenyl)(cyclopropyl)methyl)-4-fluoro-1-((4-(methylsulfonyl)-2-pyridinyl)carbonyl)-D-prolinamide | LCMS-ESI (POS.) m/z: 516.2 (M + H)+ | 1H NMR (500 MHz, DMSO-d6) δ ppm 8.85-9.03 (m, 1 H), 8.67-8.81 (m, 1 H), 8.16-8.28 (m, 1 H), 8.02-8.11 (m, 1 H), 7.36-7.66 (m, 2 H), 4.55-5.42 (m, 2 H), 3.90-4.21 (m, 2 H), 3.61-3.76 (m, 1 H), 3.38-3.39 (m, 3 H), 2.56-2.67 (m, 1 H), 1.82-2.05 (m, 1 H), 1.00-1.25 (m, 1 H), 0.31-0.62 (m, 3 H), −0.17-0.11 (m, 1 H) | C |
| 270 | (1R,3R,5R)-N-((R)-cyclopropyl(2-fluoro-4-(trifluoromethyl)phenyl)methyl)-2-(3-(methylsulfonyl)benzoyl)-2-azabicyclo[3.1.0]hexane-3-carboxamide | LCMS-ESI (POS.) m/z: 525.0 (M + H)+ | 1H NMR (400 MHz, CHLOROFORM-d) δ ppm 8.33 (s, 1 H), 8.09 (d, J = 7.88 Hz, 1 H), 8.01 (d, J = 7.67 Hz, 1 H), 7.71 (t, J = 7.77 Hz, 1 H), 7.62 (br d, J = 7.46 Hz, 1 H), 7.28-7.48 (m, 3 H), 5.11 (br d, J = 9.12 Hz, 1 H), 4.60 (t, J = 7.98 Hz, 1 H), 3.22-3.29 (m, 1 H), 3.11 (s, 3 H), 2.61 (br d, J = 13.27 Hz, 1 H), 2.29 (td, J = 11.82, 6.22 Hz, 1 H), 1.66-1.78 (m, 1 H), 1.10-1.33 (m, 3 H), 0.83-0.89 (m, 1 H), 0.46-0.61 (m, 2 H), 0.33-0.43 (m, 2 H) | C |
| 271 | 1-(((2S,3S)-1-((3-cyano-1-azetidinyl)sulfonyl)-2-methyl-3-piperidinyl)carbonyl)-N-(4-(trifluoromethyl)benzyl)-D-prolinamide | LCMS-ESI (POS.) m/z: 542.2 (M + H)+ | 1H NMR (500 MHz, CHLOROFORM-d) δ ppm 7.56 (d, J = 8.04 Hz, 2 H), 7.43 (br t, J = 5.58 Hz, 1 H), 7.35 (d, J = 8.04 Hz, 2 H), 4.40-4.56 (m, 3 H), 4.24 (quin, J = 6.10 Hz, 1 H), 3.98-4.16 (m, 4 H), 3.60-3.75 (m, 3 H), 3.34-3.43 (m, 1 H), 2.99-3.08 (m, 1 H), 2.88-2.96 (m, 1 H), 2.41 (ddd, J = 9.02, 6.42, 3.24 Hz, 1 H), 2.12-2.28 (m, 1 H), 1.88-2.09 (m, 3 H), 1.75 (br d, J = 13.49 Hz, 1 H), 1.49-1.68 (m, 2 H), 1.19-1.29 (m, 3 H) | M |
| 272 | N-(3-chloro-4-fluorobenzyl)-1-(((3S)-1-((3-cyano-1-azetidinyl)sulfonyl)-3-piperidinyl)carbonyl)-D-prolinamide | LCMS-ESI (POS.) m/z: 512.2 (M + H)+ | 1H NMR (500 MHz, DMSO-d6) δ ppm 8.32 (s, 1 H), 7.18-7.51 (m, 3 H), 5.85-5.85 (m, 1 H), 4.17-4.49 (m, 3 H), 4.00-4.14 (m, 2 H), 3.87-4.00 (m, 2 H), 3.73-3.86 (m, 1 H), 3.50-3.73 (m, 3 H), 3.33-3.49 (m, 1 H), 2.61-2.91 (m, 3 H), 2.04-2.33 (m, 1 H), 1.65-1.98 (m, 5 H), 1.34-1.59 (m, 2 H) | A |

| Ex. # | Structure Name | LCMS-ESI (POS/NEG) m/z: (M + H)+ | NMR Data | Syn. Rte. |
|---|---|---|---|---|
| 273 | (4S)-4-fluoro-N-((R)-(3-fluoro-4-(trifluoromethyl)phenyl)(3-oxetanyl)methyl)-1-(3-(methylsulfonyl)benzoyl)-D-prolinamide | LCMS-APCI (POS.) m/z: 547.1 (M + H)+ | 1H NMR (400 MHz, Methanol-d4) δ ppm 8.25 (t, J = 1.8 Hz, 1 H), 8.11-8.16 (m, 1 H), 7.98 (dt, J = 1.3, 7.7 Hz, 1 H), 7.79 (t, J = 7.8 Hz, 1 H), 7.70 (t, J = 7.7 Hz, 1 H), 7.35 (d, J = 10.6 Hz, 2 H), 5.47-5.52 (m, 1 H), 5.33-5.41 (m, 1 H), 5.18-5.28 (m, 1 H), 4.77 (dd, J = 7.5, 10.2 Hz, 1 H), 4.65-4.71 (m, 2 H), 4.49 (t, J = 6.3 Hz, 1 H), 3.91-4.07 (m, 1 H), 3.72 (ddd, J = 2.2, 12.7, 19.9 Hz, 1 H), 3.54 (dddd, J = 1.7, 6.0, 7.7, 10.1 Hz, 1 H), 3.37 (s, 2 H), 3.19 (s, 4 H), 2.53-2.67 (m, 1 H), 2.04-2.23 (m, 1 H). | A |
| 274 | 1-(((3S)-1-( (3-(difluoromethyl)-1-azetidinyl)sulfonyl)-3-piperidinyl)carbonyl)-N-(4-(trifluoromethyl)benzyl)-D-prolinamide | LCMS-ESI (POS.) m/z: 553.2 (M + Na)+ | 1H NMR (500 MHz, DMSO-d6) δ ppm 8.22-8.80 (m, 1 H), 7.57-7.82 (m, 2 H), 7.45 (br d, J = 7.79 Hz, 2 H), 6.06-6.46 (m, 1 H), 4.26-4.56 (m, 3 H), 3.37-3.99 (m, 8 H), 3.03-3.24 (m, 1 H), 2.59-2.93 (m, 3 H), 1.67-2.40 (m, 6 H), 1.32-1.58 (m, 2 H) | |
| 275 | (1R,3R,5R)-2-(3-(ethylsulfonyl)benzoyl)-N-((R)-3-oxetanyl(4-(trifluoromethyl)phenyl)methyl)-2-azabicyclo[3.1.0]hexane-3-carboxamide | LCMS-APCI (POS.) m/z: 537.2 (M + H)+ | 1H NMR (Methanol-d4) δ: 8.76 (d, J = 8.2 Hz, 1H), 8.35 (t, J = 1.7 Hz, 1H), 8.13 (d, J = 7.7, 1.4 Hz, 1H), 8.08 (d, J = 7.9, 1.9, 1.2 Hz, 1H), 7.79 (t, J = 8.1, 7.6 Hz, 1H), 7.73-7.66 (m, 2H), 7.52 (d, J = 8.1 Hz, 2H), 5.47-5.37 (m, 1H), 5.01 (dd, J = 11.4, 4.2 Hz, 1H), 4.86-4.82 (m, 1H), 4.72-4.57 (m, 2H), 4.44 (t, J = 6.3 Hz, 1H), 3.59-3.41 (m, 1H), 3.31-3.24 (m, 3H), 2.68 (td, J = 12.7, 6.6 Hz, 2H), 1.92 (dd, J = 13.5, 4.2 Hz, 2H), 1.87-1.73 (m, 2H), 0.97-0.83 (m, 2H) | C |
| 276 | (2R)-1-((S)-1-( (3-cyanoazetidin-1-yl)sulfonyl)piperidine-3-carbonyl)-N-(3-(hydroxymethyl)-2,3-dihydro-1H-inden-1-yl)pyrrolidine-2-carboxamide | LCMS-ESI (POS.) m/z: 516.2 (M + H)+ | 1H NMR (500 MHz, DMSO-d6) δ ppm 7.93-8.51 (m, 1 H), 6.98-7.46 (m, 4 H), 5.14-5.35 (m, 1 H), 4.67-4.88 (m, 1 H), 4.20-4.51 (m, 1 H), 3.85-4.13 (m, 4 H), 3.69-3.84 (m, 2 H), 3.41-3.70 (m, 5 H), 3.10-3.21 (m, 1 H), 2.60-2.97 (m, 4 H), 1.33-2.30 (m, 9 H) | A |

| Ex. # | Structure Name | LCMS-ESI (POS/NEG) m/z: (M + H)+ | NMR Data | Syn. Rte. |
|---|---|---|---|---|
| 277 | (1R,3R,5R)-N-((R)-(4-chloro-2,5-difluorophenyl)(cyclopropyl)methyl)-2-(((3S)-1-(methylsulfonyl)-3-piperidinyl)carbonyl)-2-azabicyclo[3.1.0]hexane-3-carboxamide | LCMS-ESI (POS.) m/z: 516.2 (M + H)+ | 1H NMR (500 MHz, CHLOROFORM-d) δ ppm 7.69 (br d, J = 6.62 Hz, 1 H), 7.05-7.18 (m, 2 H), 4.85 (br d, J = 10.12 Hz, 1 H), 4.42-4.51 (m, 1 H), 3.97 (br d, J = 11.42 Hz, 1 H), 3.89 (br d, J = 11.29 Hz, 1 H), 3.41-3.55 (m, 1 H), 2.99-3.17 (m, 1 H), 2.88-2.98 (m, 1 H), 2.77-2.87 (m, 3 H), 2.69 (br t, J = 11.35 Hz, 1 H), 2.48-2.63 (m, 1 H), 2.12-2.30 (m, 2 H), 1.93 (br d, J = 13.49 Hz, 1 H), 1.77-1.86 (m, 1 H), 1.70-1.77 (m, 1 H), 1.60-1.69 (m, 1 H), 1.14 (br dd, J = 7.66, 3.95 Hz, 1 H), 0.89-0.97 (m, 1 H), 0.83 (br d, J = 7.79 Hz, 1 H), 0.48-0.68 (m, 2 H), 0.34 (br d, J = 3.24 Hz, 1 H), 0.26-0.43 (m, 1 H) | M |
| 278 | (1R,3R,5R)-N-((R)-(4-chloro-3,5-difluorophenyl)(cyclopropyl)methyl)-2-(3-(methylsulfonyl)benzoyl)-2-azabicyclo[3.1.0]hexane-3-carboxamide | LCMS-ESI (POS.) m/z: 509.2 (M + H)+ | 1H NMR (500 MHz, DMSO-d6) δ ppm 8.37-8.70 (m, 1 H) 7.90-8.21 (m, 3 H) 7.68-7.81 (m, 1 H) 7.14-7.33 (m, 2 H) 4.65-4.99 (m, 1 H) 3.79-4.27 (m, 1 H) 3.24-3.28 (m, 4 H) 2.54-2.62 (m, 1 H) 1.55-1.82 (m, 2 H) 0.69-1.17 (m, 3 H) 0.09-0.56 (m, 4 H) | C |
| 279 | (1R,3R,5R)-N-((R)-cyclopropyl(2,5-difluoro-4-(trifluoromethyl)phenyl)methyl)-2-((2-(methylsulfonyl)-4-pyridinyl)carbonyl)-2-azabicyclo[3.1.0]hexane-3-carboxamide | LCMS-ESI (POS.) m/z: 544.0 (M + H)+ | 1H NMR (500 MHz, DMSO-d6) δ ppm 8.94 (d, J = 4.80 Hz, 1 H), 8.75 (d, J = 7.40 Hz, 1 H), 7.83-8.27 (m, 2 H), 7.69-7.81 (m, 1 H), 7.59 (dd, J = 11.03, 5.45 Hz, 1 H), 4.11-5.04 (m, 2 H), 3.19-3.37 (m, 4 H), 2.54-2.76 (m, 1 H), 1.53-1.83 (m, 2 H), −0.22-1.30 (m, 7 H) | C |
| 280 | (4S)-N-((R)-(4-chloro-2,5-difluorophenyl)(cyclopropyl)methyl)-4-fluoro-1-(3-sulfamoylbenzoyl)-D-prolinamide | LCMS-ESI (POS.) m/z: 516.0 (M + H)+ | 1H NMR (400 MHz, CHLOROFORM-d) δ ppm 8.16 (s, 1 H), 8.06 (d, J = 7.98 Hz, 1 H), 7.76 (d, J = 7.77 Hz, 1 H), 7.50-7.66 (m, 2 H), 7.03-7.20 (m, 2 H), 5.42-6.13 (m, 2 H), 5.12-5.31 (m, 1 H), 4.92 (t, J = 8.40 Hz, 1 H), 4.42-4.53 (m, 1 H), 3.68-3.94 (m, 2 H), 2.41-2.62 (m, 2 H), 0.88-1.27 (m, 1 H), −0.11-0.63 (m, 4 H) | C |

-continued

| Ex. # | Structure Name | LCMS-ESI (POS/NEG) m/z: (M + H)+ | NMR Data | Syn. Rte. |
|---|---|---|---|---|
| 281 | N-((R)-cyclopropyl(2-fluoro-4-(trifluoromethyl)phenyl)methyl)-1-(3-((2,2,2-trifluoroethyl)sulfonyl)benzoyl)-D-prolinamide | LCMS-ESI (POS.) m/z: 581.1 (M + H)+ | 1H NMR (500 MHz, DMSO-d6) δ ppm 8.43-8.79 (m, 1 H), 7.50-8.21 (m, 7 H), 4.87-5.24 (m, 2 H), 4.12-4.70 (m, 2 H), 3.33-3.70 (m, 2 H), 2.14-2.31 (m, 1 H), 1.57-2.01 (m, 3 H), 0.76-1.37 (m, 1 H),-0.16-0.76 (m, 4 H) | C |
| 282 | (1R,3R,5R)-N-((R)-(4-chloro-2,5-difluorophenyl)(3-oxetanyl)methyl)-2-((5-(trifluoromethyl)-3-pyridinyl)carbonyl)-2-azabicyclo[3.1.0]hexane-3-carboxamide | LCMS-APCI (POS.) m/z: 516.1 (M + H)+ | 1H NMR (400 MHz, DMSO-d6) δ ppm 9.12-9.18 (m, 1 H), 8.53 (dd, J = 8.0, 113.7 Hz, 1 H), 8.24-8.37 (m, 1 H), 7.65 (ddd, J = 6.2, 9.4, 18.7 Hz, 1 H), 7.44 (dd, J = 6.3, 9.7 Hz, 1 H), 5.41 (t, J = 8.9 Hz, 1 H), 4.90 (dd, J = 3.8, 11.4 Hz, 1 H), 4.63 (dd, 1 H), 4.51 (dd, 1 H), 4.37 (t, J = 6.1 Hz, 1 H), 4.20 (t, J = 6.1 Hz, 1 H), 3.37 (td, J = 2.7, 6.3 Hz, 1 H), 2.54-2.64 (m, 1 H), 1.66-1.78 (m, 1 H), 1.11-1.20 (m, 1 H), 0.80 (dt, J = 5.6, 9.9 Hz, 1 H). | Q |
| 283 | 1-((3-((3-cyano-1-azetidinyl)sulfonyl)phenyl)carbonyl)-N-(4-cyclopropylbenzyl)-D-prolinamide | LCMS-ESI (POS.) m/z: 493.0 (M + H)+ | 1H NMR (400 MHz, CHLOROFORM-d) δ ppm 7.98-8.06 (m, 1 H), 7.91-7.97 (m, 1 H), 7.81-7.88 (m, 1 H), 7.66-7.72 (m, 1 H), 7.15-7.22 (m, 2 H), 7.05 (s, 2 H), 6.96 (br t, J = 5.05 Hz, 1 H), 4.66-4.76 (m, 1 H), 4.39-4.52 (m, 2 H), 4.10-4.20 (m, 2 H), 4.01-4.08 (m, 2 H), 3.60-3.68 (m, 1 H), 3.44-3.52 (m, 1 H), 3.35-3.38 (m, 1 H), 2.35-2.49 (m, 1 H), 2.12-2.23 (m, 2 H), 1.85-1.97 (m, 2 H), 0.94-1.03 (m, 2 H), 0.66-0.75 (m, 2 H) | A |
| 284 | N-(2-chloro-4-fluorobenzyl)-1-(((3S)-1-((3-cyano-1-azetidinyl)sulfonyl)-3-piperidinyl)carbonyl)-D-prolinamide | LCMS-ESI (POS.) m/z: 512.2 (M + H)+ | 1H NMR (500 MHz, DMSO-d6) δ ppm 8.18-8.70 (m, 1 H), 7.16-7.45 (m, 3 H), 4.18-4.54 (m, 3 H), 4.00-4.11 (m, 2 H), 3.89-3.98 (m, 2 H), 3.75-3.85 (m, 2 H), 3.41-3.59 (m, 3 H), 2.70-2.91 (m, 2 H), 2.58-2.68 (m, 1 H), 2.04-2.33 (m, 1 H), 1.62-2.00 (m, 5 H), 1.31-1.55 (m, 2 H) | A |

| Ex. # | Structure Name | LCMS-ESI (POS/NEG) m/z: (M + H)+ | NMR Data | Syn. Rte. |
|---|---|---|---|---|
| 285 | <br>1-(((3S)-1-((3-cyano-1-azetidinyl)sulfonyl)-3-piperidinyl)carbonyl)-N-((1R)-1-(4-methylphenyl)ethyl)-D-prolinamide | LCMS-ESI (POS.) m/z: 488.2 (M + H)+ | 1H NMR (500 MHz, CHLOROFORM-d) δ ppm 7.15-7.25 (m, 4 H), 7.04-7.14 (m, 1 H), 5.02 (s, 1 H), 4.53 (dd, J = 7.98, 2.79 Hz, 1 H), 4.08-4.20 (m, 4 H), 3.74-3.85 (m, 2 H), 3.59-3.71 (m, 2 H), 3.42-3.50 (m, 1 H), 2.97-3.08 (m, 1 H), 2.71-2.86 (m, 2 H), 2.34-2.41 (m, 3 H), 2.17-2.33 (m, 2 H), 1.82-2.12 (m, 4 H), 1.59-1.77 (m, 2 H), 1.39-1.51 (m, 3 H) | A |
| 286 | <br>N-((R)-cyclopropyl(2-fluoro-4-(trifluoromethyl)phenyl)methyl)-1-(3-(3-fluoro-1-(methylsulfonyl)-3-azetidinyl)benzoyl)-D-prolinamide | LCMS-APCI (POS.) m/z: 586.2 (M + H)+ | 1H NMR (400 MHz, Methanol-d4) δ ppm 7.18-7.63 (m, 7 H), 4.12-4.47 (m, 6 H), 3.28-3.56 (m, 2 H), 2.87-2.91 (m, 3 H), 2.06-2.20 (m, 1 H), 1.60-1.82 (m, 3 H), 0.79-1.17 (m, 1 H), -0.22-0.57 (m, 4 H). | W |
| 287 | 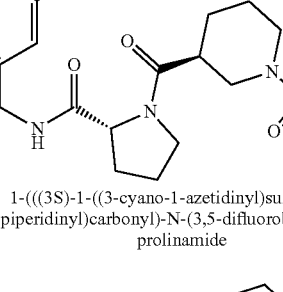<br>1-(((3S)-1-((3-cyano-1-azetidinyl)sulfonyl)-3-piperidinyl)carbonyl)-N-(3,5-difluorobenzyl)-D-prolinamide | LCMS-ESI (POS.) m/z: 496.2 (M + H)+ | 1H NMR (500 MHz, DMSO-d6) δ ppm 8.31-8.72 (m, 1 H), 7.02-7.19 (m, 1 H), 6.90-6.99 (m, 2 H), 4.22-4.54 (m, 3 H), 3.98-4.12 (m, 2 H), 3.86-3.97 (m, 2 H), 3.74-3.83 (m, 1 H), 3.42-3.72 (m, 4 H), 2.81 (q, J = 11.16 Hz, 2 H), 2.61-2.75 (m, 1 H), 2.06-2.34 (m, 1 H), 1.67-2.01 (m, 5 H), 1.36-1.58 (m, 2 H) | A |
| 288 | 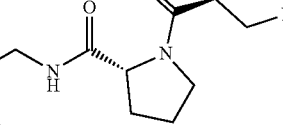<br>1-(((3S)-1-((3-cyano-1-azetidinyl)sulfonyl)-3-piperidinyl)carbonyl)-N-(3-fluoro-2-methylbenzyl)-D-prolinamide | LCMS-ESI (POS.) m/z: 492.2 (M + H)+ | 1H NMR (500 MHz, DMSO-d6) δ ppm 8.15-8.56 (m, 1 H), 7.13-7.24 (m, 1 H), 6.99-7.10 (m, 2 H), 4.17-4.50 (m, 3 H), 4.01-4.10 (m, 2 H), 3.88-3.97 (m, 2 H), 3.74-3.83 (m, 1 H), 3.33-3.68 (m, 4 H), 2.70-2.87 (m, 2 H), 2.59-2.69 (m, 1 H), 2.04-2.34 (m, 4 H), 1.66-2.00 (m, 5 H), 1.34-1.56 (m, 2 H) | A |

| Ex. # | Structure Name | LCMS-ESI (POS/NEG) m/z: (M + H)+ | NMR Data | Syn. Rte. |
|---|---|---|---|---|
| 289 | 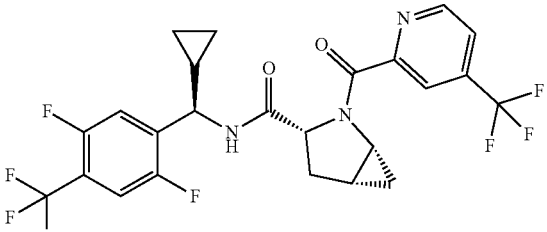<br>(1R,3R,5R)-N-((R)-cyclopropyl(2,5-difluoro-4-(trifluoromethyl)phenyl)methyl)-2-((4-(trifluoromethyl)-2-pyridinyl)carbonyl)-2-azabicyclo[3.1.0]hexane-3-carboxamide | LCMS-APCI (POS.) m/z: 534.1 (M + H)+ | 1H NMR (Methanol-d4) δ: 8.88 (d, J = 5.1 Hz, 1H), 8.75 (d, J = 5.1 Hz, 1H), 8.12 (d, 2H), 7.80 (d, J = 5.0 Hz, 1H), 7.75 (d, 1H), 7.51-7.36 (m, 3H), 7.30 (dd, J = 10.7, 5.6 Hz, 1H), 5.64 (dd, J = 11.7, 3.1 Hz, 1H), 5.01 (dd, J = 11.4, 3.7 Hz, 1H), 4.48 (d, J = 9.1 Hz, 1H), 4.09 (d, J = 9.4 Hz, 1H), 4.00-3.85 (m, 2H), 2.91-2.73 (m, 1H), 2.73-2.58 (m, 1H), 2.03-1.83 (m, 2H), 1.81-1.69 (m, 1H), 1.69-1.58 (m, 1H), 1.31-1.16 (m, 2H), 1.16-1.00 (m, 2H), 0.93-0.79 (m, 2H), 0.79-0.61 (m, 2H), 0.61-0.51 (m, 1H), 0.51-0.40 (m, 3H), 0.19-0.06 (m, 1H), 0.04--0.07 (m, 1H) | Q |
| 290 | 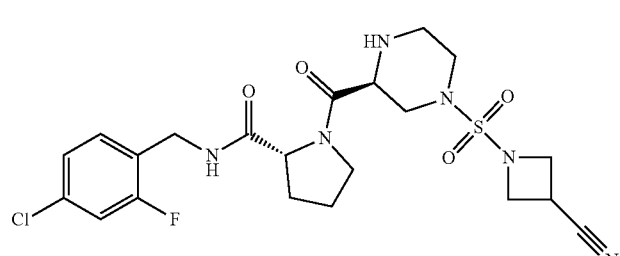<br>N-(4-chloro-2-fluorobenzyl)-1-(((2S)-4-((3-cyano-1-azetidinyl)sulfonyl)-2-piperazinyl)carbonyl)-D-prolinamide | LCMS-ESI 1 (POS.) m/z: 513.2 (M + Na)+ | 1H NMR (400 MHz, CHLOROFORM-d) δ ppm 7.22-7.30 (m, 2 H), 7.05-7.16 (m, 2 H), 4.33-4.57 (m, 3 H), 4.09-4.17 (m, 4 H), 3.75-3.84 (m, 1 H), 3.64-3.70 (m, 2 H), 3.40 3.61 (m, 3 H), 3.08-3.15 (m, 1 H), 2.73-2.95 (m, 3 H), 2.38-2.45 (m, 1 H), 2.00-2.21 (m, 2 H), 1.80-1.96 (m, 3 H) | M |
| 291 | 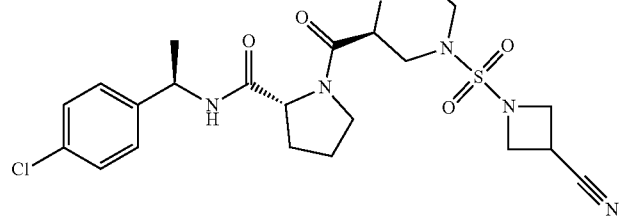<br>N-((1R)-1-(4-chlorophenyl)ethyl)-1-(((2S)-4-((3-cyano-1-azetidinyl)sulfonyl)-2-morpholinyl)carbonyl)-D-prolinamide | LCMS-ESI (POS.) m/z: 510.2 (M + H)+ | 1H NMR (400 MHz, CHLOROFORM-d) δ 7.29-7.34 (m, 2H), 7.21-7.27 (m, 2H), 6.93-7.05 (m, 1H), 4.91-5.16 (m, 1H), 4.49-4.76 (m, 1H), 4.11-4.25 (m, 5H), 3.91-4.05 (m, 1H), 3.77-3.89 (m, 1H), 3.63-3.75 (m, 2H), 3.42-3.57 (m, 3H), 3.21 (br dd, J = 9.69, 12.28 Hz, 1H), 3.00-3.10 (m, 1H), 2.29-2.39 (m, 1H), 2.07-2.21 (m, 1H), 1.85-2.03 (m, 2H), 1.44 (br d, J = 6.84 Hz, 3H) | C |
| 292 | 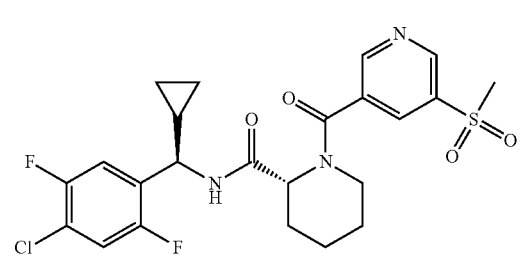 [SMILES: CS(=O)(=O)c1cncc(C(=O)N2CCCC[C@@H]2C(=O)N[C@@H](c2cc(F)c(Cl)cc2F)C2CC2)c1]<br>(2R)-N-((R)-(4-chloro-2,5-difluorophenyl)(cyclopropyl)methyl)-1-((5-(methylsulfonyl)-3-pyridinyl)carbonyl)-2-piperidinecarboxamide | LCMS-ESI (POS.) m/z: 512.0 (M + H)+ | 1H NMR (500 MHz, DMSO-d6) δ ppm 9.08-9.23 (m, 1 H), 8.80-9.00 (m, 1 H), 8.56-8.73 (m, 1 H), 8.16-8.40 (m, 1 H), 7.42-7.72 (m, 2 H), 4.23-5.23 (m, 2 H), 3.26-3.41 (m, 4 H), 2.17 (br s, 1 H), 1.66-1.80 (m, 1 H), 1.12-1.64 (m, 6 H), 0.23-0.59 (m, 4 H) | C |

-continued

| Ex. # | Structure Name | LCMS-ESI (POS/NEG) m/z: (M + H)+ | NMR Data | Syn. Rte. |
|---|---|---|---|---|
| 293 | 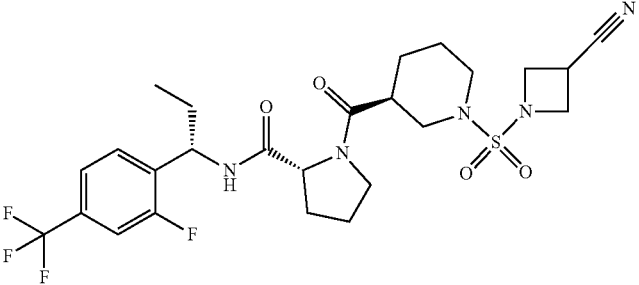 [SMILES: CC[C@H](NC(=O)[C@H]1CCCN1C(=O)[C@H]1CCCN(S(=O)(=O)N2CC(C#N)C2)C1)c1ccc(C(F)(F)F)cc1F]<br>1-(((3S)-1-((3-cyano-1-azetidinyl)sulfonyl)-3-piperidinyl)carbonyl)-N-((1S)-1-(2-fluoro-4-(trifluoromethyl)phenyl)propyl)-D-prolinamide | LCMS-ESI (POS.) m/z: 574.2 (M + H)+ | 1H NMR (500 MHz, DMSO-d6) δ ppm 8.27 (d, J = 8.04 Hz, 1 H), 7.53-7.69 (m, 3 H), 4.86-5.04 (m, 1 H), 4.31-4.49 (m, 1 H), 4.01-4.11 (m, 2 H), 3.90-3.96 (m, 2 H), 3.74-3.82 (m, 1 H), 3.36-3.66 (m, 4 H), 2.69-2.86 (m, 2 H), 2.63 (tt, J = 11.24, 3.49 Hz, 1 H), 2.07-2.21 (m, 1 H), 1.82-1.97 (m, 3 H), 1.61-1.79 (m, 4 H), 1.25-1.52 (m, 2 H), 0.81-0.92 (m, 3 H) | A |
| 294 | 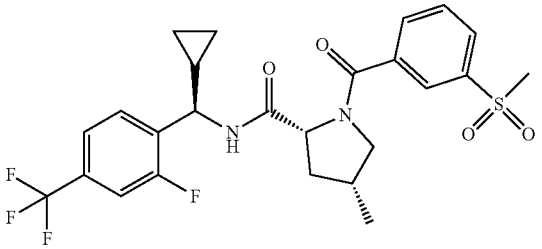<br>(4R)-N-((R)-cyclopropyl(2-fluoro-4-(trifluoromethyl)phenyl)methyl)-4-methyl-1-(3-(methylsulfonyl)benzoyl)-D-prolinamide | LCMS-ESI (POS.) m/z: 527.0 (M + H)+ | 1H NMR (500 MHz, DMSO-d6) δ ppm 8.73 (d, J = 7.53 Hz, 1 H), 7.45-8.10 (m, 7 H), 4.01-4.67 (m, 2 H), 3.42-3.52 (m, 1 H), 3.23-3.33 (m, 3 H), 2.83-3.19 (m, 1 H), 2.09-2.40 (m, 2 H), 1.16-1.36 (m, 2 H), 0.80-1.04 (m, 3 H), -0.26-0.63 (m, 4 H) | C |
| 295 | 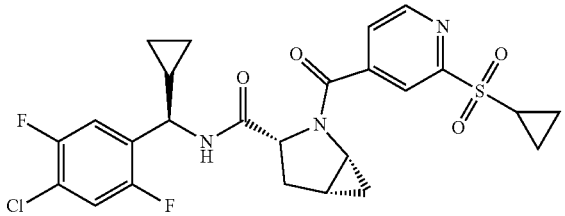 [SMILES: O=C(N[C@@H](c1cc(F)c(Cl)cc1F)C1CC1)[C@H]1C[C@H]2C[C@H]2N1C(=O)c1ccnc(S(=O)(=O)C2CC2)c1]<br>(1R,3R,5R)-N-((R)-(4-chloro-2,5-difluorophenyl)(cyclopropyl)methyl)-2-((2-(cyclopropylsulfonyl)-4-pyridinyl)carbonyl)-2-azabicyclo[3.1.0]hexane-3-carboxamide | LCMS-ESI (POS.) m/z: 536.0 (M + H)+ | 1H NMR (500 MHz, DMSO-d6) δ ppm 8.38-9.05 (m, 2 H), 7.69-8.23 (m, 2 H), 7.28-7.68 (m, 2 H), 4.60-4.99 (m, 1 H), 4.04-4.57 (m, 1 H), 3.23-3.88 (m, 1 H), 2.91-3.12 H (m, 1 H), 2.53-2.79 (m, 1 H), 1.53-1.83 (m, 2 H), 1.04-1.31 (m, 5 H), -0.23-0.97 (m, 5 H) | H |
| 296 | 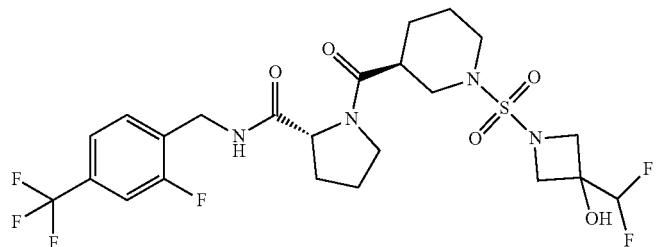 [SMILES: O=C(NCc1ccc(C(F)(F)F)cc1F)[C@H]1CCCN1C(=O)[C@H]1CCCN(S(=O)(=O)N2CC(O)(C(F)F)C2)C1]<br>1-(((3S)-1-((3-(difluoromethyl)-3-hydroxy-1-azetidinyl)sulfonyl)-3-piperidinyl)carbonyl)-N-(2-fluoro-4-(trifluoromethyl)benzyl)-D-prolinamide | LCMS-ESI (POS.) m/z: 587.2 (M + H)+ | 1H NMR (400 MHz, CHLOROFORM-d) δ ppm 7.41-7.47 (m, 1 H), 7.28-7.41 (m, 3 H), 5.72-6.04 (m, 1 H), 4.42-4.61 (m, 3 H), 3.99-4.05 (m, 2 H), 3.90-3.98 (m, 2 H), 3.69-3.80 (m, 2 H), 3.53-3.66 (m, 2 H), 3.34 (s, 1 H), 3.01 (dd, J = 12.75, 10.57 Hz, 1 H), 2.78-2.87 (m, 1 H), 2.67-2.77 (m, 1 H), 2.41 (ddt, J = 12.50, 6.34, 2.97, 2.97 Hz, 1 H), 2.11-2.24 (m, 1 H), 1.98-2.09 (m, 1 H), 1.78-1.97 (m, 3 H), 1.63-1.73 (m, 1 H), 1.50-1.58 (m, 1 H) | J |

-continued

| Ex. # | Structure Name | LCMS-ESI (POS/NEG) m/z: (M + H)+ | NMR Data | Syn. Rte. |
|---|---|---|---|---|
| 297 | 1-(((3S)-1-((3-cyano-1-azetidinyl)sulfonyl)-3-piperidinyl)carbonyl)-N-(4-fluoro-3-(trifluoromethyl)benzyl)-D-prolinamide | LCMS-ESI (POS.) m/z: 546.2 (M + H)+ | 1H NMR (500 MHz, DMSO-d6) δ ppm 8.34-8.77 (m, 1 H), 7.41-7.68 (m, 3 H), 4.21-4.52 (m, 3 H), 4.00-4.10 (m, 2 H), 3.87-3.97 (m, 2 H), 3.74-3.83 (m, 1 H), 3.35-3.69 (m, 4 H), 2.67-2.91 (m, 2 H), 1.62-2.33 (m, 7 H), 1.31-1.56 (m, 2 H) | A |
| 298 | N-((2R)-1-((1-(4-chlorophenyl)ethyl)amino)-1-oxopropan-2-)-3-((3-cyanoazetidin-1-yl)sulfonyl)-N-methylbenzamide | LCMS-ESI (POS.) m/z: 511.0 (M + Na)+ | 1H NMR (500 MHz, CHLOROFORM-d) δ ppm 7.58-7.99 (m, 4 H), 7.23-7.37 (m, 4 H), 6.75-6.99 (m, 1 H), 5.02-5.25 (m, 2 H), 4.12 4.24 2 H), 3.97-4.08 (m, 2 H), 3.32-3.43 (m, 1 H), 2.92-3.01 (m, 2 H), 2.75-3.01 (m, 1 H), 1.44-1.55 (m, 6 H) | C |
| 299 | (2S)-4-((3-cyano-1-azetidinyl)sulfonyl)-N-((2R)-1-(((1R)-1-(2-fluoro-4-(trifluoromethyl)phenyl)ethyl)amino)-1-oxo-2-propanyl)-N-methyl-2-morpholinecarboxamide | LCMS-ESI (POS.) m/z: 550.2 (M + H)+ | 1H NMR (500 MHz, DMSO-d6) δ ppm 8.45-8.62 (m, 1 H), 7.54-7.70 (m, 3 H), 5.07-5.22 (m, 1 H), 4.62-4.90 (m, 1 H), 4.26-4.41 (m, 1 H), 4.08-4.19 (m, 2 H), 3.97-4.07 (m, 2 H), 3.78-3.96 (m, 2 H), 3.58-3.76 (m, 1 H), 3.35-3.55 (m, 2 H), 3.04 (ddd, J = 19.11, 12.16, 9.99 Hz, 1 H), 2.65-2.99 (m, 4 H), 1.33-1.43 (m, 3 H), 1.25 (dd, J = 14.34, 6.94 Hz, 3H) | C |
| 300 | (2R)-N-((R)-cyclopropyl(3-fluoro-4-(trifluoromethyl)phenyl)methyl)-1-(3-(methylsulfonyl)benzoyl)-2-piperidinecarboxamide | LCMS-ESI (POS.) m/z: 527.2 (M + H)+ | 1H NMR (500 MHz, DMSO-d6) δ ppm 8.71 (br d, J = 2.85 Hz, 1 H), 7.98-8.04 (m, 1 H), 7.90 (s, 1 H), 7.64-7.81 (m, 3 H), 7.48 (br d, J = 10.64 Hz, 1 H), 7.36-7.44 (m, 1 H), 2.94-5.28 (m, 7 H), 2.04-2.27 (m, 1 H), 1.46-1.81 (m, 3 H), 1.33-1.45 (m, 1 H), 1.08-1.25 (m, 2 H), 0.46-0.65 (m, 3 H), 0.31-0.43 (m, 1 H) | C |

| Ex. # | Structure Name | LCMS-ESI (POS/NEG) m/z: (M + H)+ | NMR Data | Syn. Rte. |
|---|---|---|---|---|
| 301 | 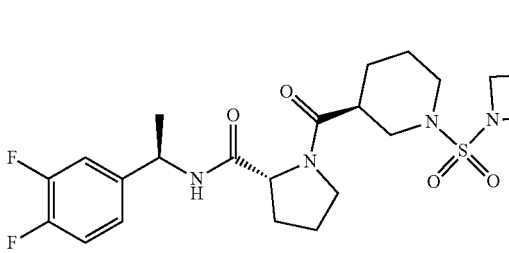<br>1-(((3S)-1-((3-cyano-1-azetidinyl)sulfonyl)-3-piperidinyl)carbonyl)-N-((1R)-1-(3,4-difluorophenyl)ethyl)-D-prolinamide | LCMS-ESI (POS.) m/z: 510.2 (M + H)+ | 1H NMR (500 MHz, DMSO-d6) δ ppm 8.58* (d, J = 7.66 Hz, 1 H), 8.18 (d, J = 7.91 Hz, 1 H), 7.27-7.40 (m, 2 H), 7.08-7.14 (m, 1 H), 4.82-4.95 (m, 1 H), 4.46* (dd, J = 8.30, 2.72 Hz, 1 H), 4.27 (dd, J = 8.50, 4.09 Hz, 1 H), 4.02-4.09 (m, 2 H), 3.89-3.97 (m, 2 H), 3.74-3.84 (m, 1 H), 3.51-3.64 (m, 3 H), 3.27-3.43 (m, 1 H), 2.71-2.85 (m, 2 H), 2.60-2.68 (m, 1 H), 2.30* (br t, J = 10.70 Hz, 1 H), 2.17-2.26* (m, 1 H), 2.03-2.12 (m, 1 H), 1.64-1.93 (m, 5 H), 1.38-1.55 (m, 2 H), 1.36* (d, J = 7.01 Hz, 3 H), 1.33 (d, J = 7.01 Hz, 3 H). Spectrum appears as 2:1 mixture of rotamers, *denotes resolved minor rotamer peaks. | C |
| 302 | 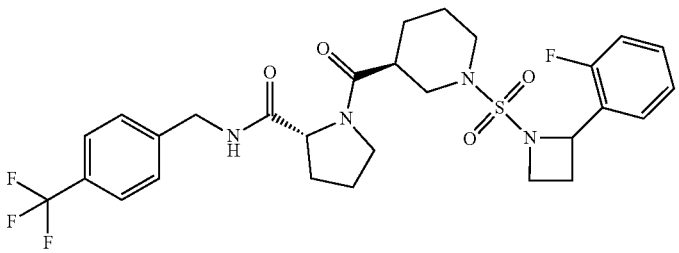 [SMILES: O=C(NCc1ccc(C(F)(F)F)cc1)[C@H]1CCCN1C(=O)[C@H]1CCCN(S(=O)(=O)N2CCC2c2ccccc2F)C1]<br>(2R)-1-((3S)-1-((2-(2-fluorophenyl)azetidin-1-yl)sulfonyl)piperidine-3-carbonyl)-N-(4-(trifluoromethyl)benzyl)pyrrolidine-2-carboxamide | LCMS-ESI (NEG.) m/z: 595.2 (M − H)+ | 1H NMR (500 MHz, DMSO-d6) δ 8.27-8.76 (m, 1H), 7.61-7.77 (m, 3H), 7.12-7.51 (m, 5H), 5.25-5.42 (m, 1H), 4.22-4.47 (m, 3H), 3.83-3.98 (m, 1H), 3.33-3.78 (m, 7H), 2.61-2.70 (m, 1H), 2.01-2.38 (m, 3H), 1.52-2.01 (m, 5H), 1.06-1.45 (m, 2H) | J |
| 303 | 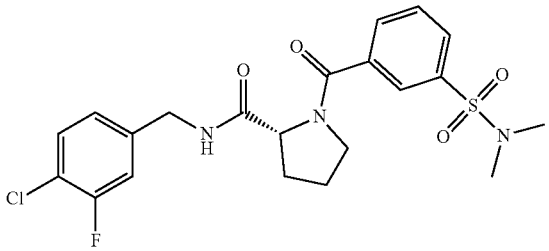 [SMILES: CN(C)S(=O)(=O)c1cccc(C(=O)N2CCC[C@@H]2C(=O)NCc2ccc(Cl)c(F)c2)c1]<br>N-(4-chloro-3-fluorobenzyl)-1-(3-(dimethylsulfamoyl)benzoyl)-D-prolinamide | LCMS-ESI (POS.) m/z: 468.0 (M + H)+ | 1H NMR (500 MHz, DMSO-d6) δ ppm 8.61 (t, J = 5.97 Hz, 1 H), 7.11-7.96 (m, 7 H), 4.01-4.52 (m, 3 H), 3.42-3.68 (m, 2 H), 3.25-3.39 (m, 3 H), 2.54-2.67 (m, 6 H), 2.18-2.33 (m, 1 H), 1.75-1.99 (m, 3 H) | C |
| 304 | 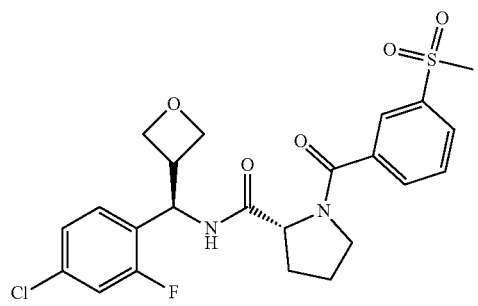<br>N-((R)-(4-chloro-2-fluorophenyl)(3-oxetanyl)methyl)-1-(3-(methylsulfonyl)benzoyl)-D-prolinamide | LCMS-APCI (POS.) m/z: 595.1 (M + H)+ | 1H NMR (400 MHz, Methanol-d4) δ ppm 8.22 (t, 1 H), 8.04-8.12 (m, 2 H), 7.96 (dt, J = 1.3, 7.8 Hz, 1 H), 7.73-7.79 (m, 1 H), 7.37 (t, J = 8.2 Hz, 1 H), 7.18-7.27 (m, 3 H), 5.65 (d, J = 10.4 Hz, 1 H), 5.51 (s, 1 H), 4.68 (td, 2 H), 4.44-4.59 (m, 2 H), 4.40 (t, J = 6.2 Hz, 1 H), 3.70-3.78 (m, 1 H), 3.65 (dt, J = 7.2, 10.2 Hz, 1 H), 3.49-3.60 (m, 2 H), 2.26-2.38 (m, 1 H), 1.94-2.05 (m, 1 H), 1.80-1.93 (m, 3 H). | A |

-continued

| Ex. # | Structure Name | LCMS-ESI (POS/NEG) m/z: (M + H)+ | NMR Data | Syn. Rte. |
|---|---|---|---|---|
| 305 | N-((1R)-1-(4-chlorophenyl)-2-hydroxyethyl)-1-(3-((3-cyano-1-azetidinyl)sulfonyl)benzoyl)-D-prolinamide | LCMS-ESI (POS.) m/z: 517.2 (M + H)+ | 1H NMR (500 MHz, DMSO-d6) δ ppm 8.16-8.47 (m, 1 H), 6.99-8.08 (m, 8 H), 4.82-4.89 (m, 1 H), 4.56-4.58 (m, 1 H), 4.35-4.41 (m, 1 H), 3.79-4.03 (m, 4 H), 3.42-3.72 (m, 5 H), 2.24 (br d, J = 2.59 Hz, 1 H), 1.73-2.00 (m, 3 H) | A |
| 306 | ((3-(((1R,3R,5R)-3-(((R)-cyclopropyl(2,5-difluoro-4-(trifluoromethyl)phenyl)methyl)carbamo)-2-azabicyclo[3.1.0]hexan-2-yl)carbonyl)phenyl)sulfonyl)acetic acid | LCMS-ESI (POS.) m/z: 587.0 (M + H)+ | 1H NMR (500 MHz, DMSO-d6) δ ppm 13.28 (br d, J = 1.30 Hz, 1 H), 8.71 (d, J = 7.27 Hz, 1 H), 8.39 (br d, J = 7.01 Hz, 1 H), 8.20 (s, 1 H), 7.95-8.12 (m, 2 H), 7.19-7.83 (m, 4 H), 4.95 (dd, J = 11.29, 3.50 Hz, 1 H), 4.43-4.68 (m, 4 H), 4.02-4.16 (m, 1 H), 3.72-3.77 (m, 1 H), 3.22 (td, J = 6.16, 2.47 Hz, 1 H), 2.52-2.77 (m, 2 H), 1.62-1.79 (m, 2 H), 1.51 (s, 1 H), 1.12-1.32 (m, 1 H), 1.00-1.12 (m, 1 H), 0.66-0.80 (m, 1 H), 0.23-0.64 (m, 4 H) | O |
| 307 | (1R,3R,5R)-N-((R)-cyclopropyl(3-fluoro-4-(trifluoromethyl)phenyl)methyl)-2-(3-(methylsulfonyl)benzoyl)-2-azabicyclo[3.1.0]hexane-3-carboxamide | LCMS-ESI (POS.) m/z: 525.0 (M + H)+ | 1H NMR (500 MHz, DMSO-d6) δ ppm 8.42-8.73 (m, 1 H) 7.89-8.22 (m, 3 H) 7.20-7.82 (m, 4 H) 4.66-5.02 (m, 1 H) 3.82-4.34 (m, 1 H) 3.23-3.28 (m, 4 H) 2.55 (s, 1 H) 1.79 (dd, J = 13.30, 3.70 Hz, 1 H) 1.52-1.73 (m, 1 H) 0.67-1.18 (m, 3 H)-0.30-0.58 (m, 4 H) | A |
| 308 | N-((1S)-1-(4-chlorophenyl)-2,2,2-trifluoroethyl)-1-(((3S)-1-((3-cyano-1-azetidinyl)sulfonyl)-3-piperidinyl)carbonyl)-D-prolinamide | LCMS-ESI (POS.) m/z: 562.2 (M + H)+ | 1H NMR (500 MHz, DMSO-d6) δ ppm 8.97-9.58 (m, 1 H), 7.41-7.63 (m, 4 H), 5.72-5.86 (m, 1 H), 4.36-4.64 (m, 1 H), 4.01-4.11 (m, 2 H), 3.88-4.01 (m, 2 H), 3.74-3.83 (m, 1 H), 3.31-3.65 (m, 4 H), 2.72-2.92 (m, 2 H), 2.59-2.70 (m, 1 H), 2.02-2.21 (m, 1 H), 1.57-1.97 (m, 5 H), 1.31-1.56 (m, 2 H) | A |

-continued

| Ex. # | Structure Name | LCMS-ESI (POS/NEG) m/z: (M + H)+ | NMR Data | Syn. Rte. |
|---|---|---|---|---|
| 309 | (1R,3R,5R)-N-((R)-cyclopropyl(2-methoxy-4-(trifluoromethyl)phenyl)methyl)-2-(3-(methylsulfonyl)benzoyl)-2-azabicyclo[3.1.0]hexane-3-carboxamide | LCMS-ESI (POS.) m/z: 537.2 (M + H)+ | 1H NMR (500 MHz, CHLOROFORM-d) δ ppm 8.25-8.43 (m, 1 H), 8.10 (br d, J = 7.78 Hz, 1 H), 8.04 (br d, J = 7.66 Hz, 1 H), 7.66-7.81 (m, 2 H), 7.32 (br d, J = 7.78 Hz, 1 H), 7.21 (br d, J = 7.53 Hz, 1 H), 7.03-7.13 (m, 1 H), 5.10 (dd, J = 10.38, 1.95 Hz, 1 H), 4.64 (br t, J = 8.50 Hz, 1 H), 3.78-4.01 (m, 3 H), 3.25 (td, J = 6.07, 2.40 Hz, 1 H), 3.13 (s, 3 H), 2.63 (dd, J = 13.17, 2.01 Hz, 1 H), 2.20-2.36 (m, 1 H), 1.68-1.83 (m, 1 H), 1.22-1.35 (m, 1 H), 1.09-1.21 (m, 1 H), 0.72-0.93 (m, 1 H), 0.36-0.60 (m, 3 H), 0.23-0.36 (m, 1 H) | A |
| 310 | (1R,3R,5R)-N-((R)-cyclopropyl(3-fluoro-4-(trifluoromethyl)phenyl)methyl)-2-(3-(cyclopropylsulfonyl)benzoyl)-2-azabicyclo[3.1.0]hexane-3-carboxamide | LCMS-ESI (POS.) m/z: 551.2 (M + H)+ | 1H NMR (500 MHz, CHLOROFORM-d) δ ppm 8.23-8.29 (m, 1 H), 7.96-8.08 (m, 2 H), 7.65-7.75 (m, 1 H), 7.48-7.59 (m, 2 H), 7.14-7.25 (m, 2 H), 5.13-5.22 (m, 1 H), 4.26-4.39 (m, 1 H), 3.24-3.32 (m, 1 H), 2.54-2.63 (m, 1 H), 2.47-2.54 (m, 1 H), 2.35-2.45 (m, 1 H), 1.72-1.85 (m, 1 H), 1.32-1.44 (m, 2 H), 1.03-1.26 (m, 4 H), 0.85-0.96 (m, 1 H), 0.52-0.71 (m, 2 H), 0.31-0.46 (m, 2 H) | H |
| 311 | 1-(((3S)-1-((3-(2,2-difluoroethoxy)-1-azetidinyl)sulfonyl)-3-piperidinyl)carbonyl)-N-(4-(trifluoromethyl)benzyl)-D-prolinamide | LCMS-ESI (POS.) m/z: 583.2 (M + Na)+ | 1H NMR (500 MHz, DMSO-d6) δ ppm 8.22-8.86 (m, 1 H), 7.56-7.83 (m, 2 H), 7.45 (br d, J = 7.79 Hz, 2 H), 5.95-6.33 (m, 1 H), 4.25-4.53 (m, 5 H), 3.91-4.07 (m, 2 H), 3.51-3.84 (m, 9 H), 2.60-2.93 (m, 3 H), 1.30-2.42 (m, 10 H) | M |
| 312 | | LCMS-APCI (POS.) m/z: 548.2 (M + H)+ | 1H NMR (400 MHz, Methanol-d4) δ ppm 8.16 (t, J = 1.7 Hz, 1 H), 7.97-8.00 (m, 2 H), 7.73-7.80 (m, 1 H), 7.60-7.67 (m, 2 H), 7.54 (d, J = 8.2 Hz, 2 H), 4.80 (t, J = 7.5 Hz, 1 H), 4.61 (dd, J = 4.6, 15.7 Hz, 1 H), 4.44-4.55 (m, 1 H), 3.88 (s, 4 H), 3.78 (d, J = 9.9 Hz, 1 H), 2.06-2.26 (m, 2 H), 0.60 (dddd, J = 3.1, 6.1, 14.3, 25.3 Hz, 4 H), 0.47 (s, 4 H). | Q |

| Ex. # | Structure Name | LCMS-ESI (POS/NEG) m/z: (M + H)+ | NMR Data | Syn. Rte. |
|---|---|---|---|---|
| | (6R)-5-(((3-(5-azaspiro[2.3]hex-5-ylsulfonyl)phenyl)carbonyl)-N-(4-(trifluoromethyl)benzyl)-5-azaspiro[2.4]heptane-6-carboxamide | | | |
| 313 | 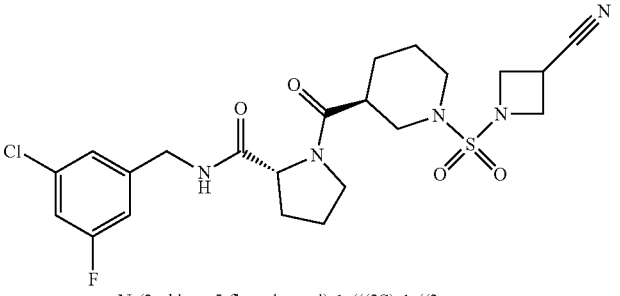<br>N-(3-chloro-5-fluorobenzyl)-1-(((3S)-1-((3-cyano-1-azetidinyl)sulfonyl)-3-piperidinyl)carbonyl)-D-prolinamide | LCMS-ESI (Pos.) m/z: 512.2 (M + H)+ | 1H NMR (500 MHz, DMSO-d6) δ ppm 8.35 (br t, J = 5.97 Hz, 1 H), 6.99-7.35 (m, 3 H), 4.32-4.36 (m, 1 H), 4.24-4.29 (m, 2 H), 3.98-4.12 (m, 2 H), 3.85-3.97 (m, 2 H), 3.78 (tt, J = 8.69, 6.16 Hz, 1 H), 3.28-3.69 (m, 4 H), 2.71-2.88 (m, 2 H), 2.60-2.70 (m, 1 H), 2.06-2.31 (m, 1 H), 1.63-1.98 (m, 5 H), 1.35-1.56 (m, 2 H) | A |
| 314 | 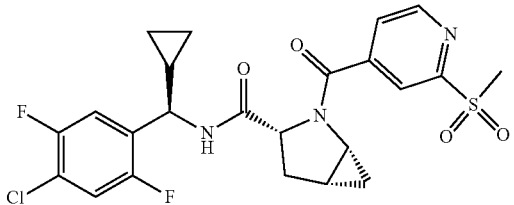 [SMILES: CS(=O)(=O)c1cc(C(=O)N2[C@@H](C(=O)N[C@@H](c3cc(F)c(Cl)cc3F)C3CC3)C[C@H]3C[C@H]32)ccn1]<br>(1R,3R,5R)-N-((R)-(4-chloro-2,5-difluorophenyl)(cyclopropyl)methyl)-2-((2-(methylsulfonyl)-4-pyridinyl)carbonyl)-2-azabicyclo[3.1.0]hexane-3-carboxamide | LCMS-ESI (POS.) m/z: 510.0 (M + H)+ | 1H NMR (500 MHz, DMSO-d6) δ ppm 8.79-8.99 (m, 1 H), 8.39-8.71 (m, 1 H), 7.70-8.24 (m, 2 H), 7.55-7.67 (m, 1 H), 7.30-7.53 (m, 1 H), 4.58-4.97 (m, 1 H), 4.08-4.54 (m, 1 H), 3.26-3.34 (m, 4 H), 2.54-2.72 (m, 1 H), 1.55-1.79 (m, 2 H), -0.24-1.25 (m, 7 H) | C |
| 315 | 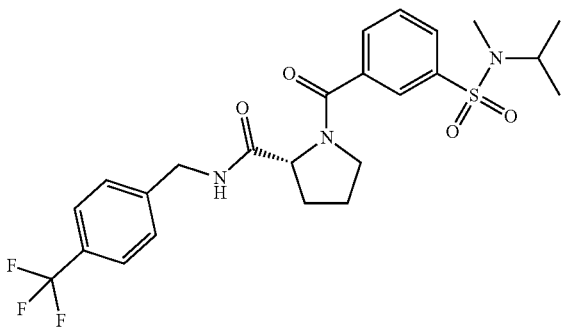 [SMILES: CC(C)N(C)S(=O)(=O)c1cccc(C(=O)N2CCC[C@@H]2C(=O)NCc2ccc(C(F)(F)F)cc2)c1]<br>1-(3-(methyl(2-propanyl)sulfamoyl)benzoyl)-N-(4-(trifluoromethyl)benzyl)-D-prolinamide | LCMS-ESI (POS.) m/z: 512.2 (M + H)+ | 1H NMR (500 MHz, DMSO-d6) δ ppm 8.62 (s, 1 H), 7.14-7.96 (m, 8 H), 4.13-4.53 (m, 3 H), 3.99-4.10 (m, 1 H), 3.54-3.64 (m, 1 H), 2.58-2.71 (m, 3 H), 2.14-2.36 (m, 1 H), 1.67-1.99 (m, 3 H), 0.85-1.01 (m, 7 H) | C |
| 316 | 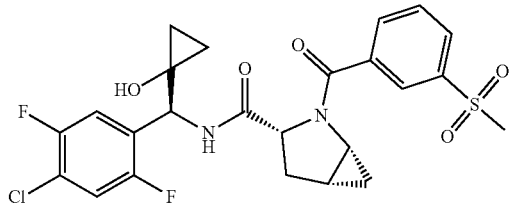 [SMILES: CS(=O)(=O)c1cccc(C(=O)N2[C@@H](C(=O)N[C@@H](c3cc(F)c(Cl)cc3F)C3(O)CC3)C[C@H]3C[C@H]32)c1]<br>(1R,3R,5R)-N-((S)-(4-chloro-2,5-difluorophenyl)(1-hydroxycyclopropyl)methyl)-2-(3-(methylsulfonyl)benzoyl)-2-azabicyclo[3.1.0]hexane-3-carboxamide | LCMS-ESI (POS.) m/z: 525.0 (M + H)+ | 1H NMR (500 MHz, DMSO-d6) δ ppm 8.54 (d, J = 8.29 Hz, 1 H), 8.15-8.19 (m, 1 H), 7.99-8.09 (m, 2 H), 7.75-7.82 (m, 1 H), 7.60-7.66 (m, 1 H), 7.44-7.52 (m, 1 H), 5.53 (s, 1 H), 4.97 (dd, J = 11.30, 3.63 Hz, 1 H), 4.88 (d, J = 8.19 Hz, 1 H), 3.23-3.28 (m, 4 H), 2.52-2.62 (m, 1 H), 1.65-1.75 (m, 2 H), 1.10-1.15 (m, 1 H), 0.62-0.79 (m, 4 H), 0.51-0.58 (m, 1 H) | A |

| Ex. # | Structure Name | LCMS-ESI (POS/NEG) m/z: (M + H)+ | NMR Data | Syn. Rte. |
|---|---|---|---|---|
| 317 | 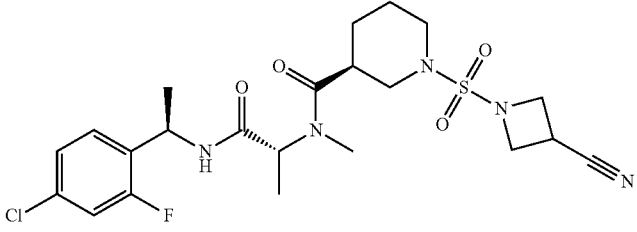 [SMILES: C[C@H](C(=O)N[C@H](C)c1ccc(Cl)cc1F)N(C)C(=O)[C@H]1CCCN(S(=O)(=O)N2CC(C#N)C2)C1]<br>(3S)-N-((2R)-1-(((1R)-1-(4-chloro-2-fluorophenyl)ethyl)amino)-1-oxo-2-propanyl)-1-((3-cyano-1-azetidinyl)sulfonyl)-N-methyl-3-piperidinecarboxamide | LCMS-ESI (POS.) m/z: 514.2 (M + H)+ | 1H NMR (500 MHz, DMSO-d6) δ ppm 8.24-8.53 (m, 1 H), 7.33-7.44 (m, 2 H), 7.24-7.30 (m, 1 H), 5.00-5.17 (m, 1 H), 4.57-4.92 (m, 1 H), 4.02-4.12 (m, 2 H), 3.90-3.99 (m, 2 H), 3.74-3.84 (m, 1 H), 3.51-3.66 (m, 2 H), 2.67-2.97 (m, 6 H), 1.66-1.89 (m, 2 H), 1.39-1.61 (m, 2 H), 1.29-1.38 (m, 4 H), 1.22 (d, J = 7.14 Hz, 2 H) | B |
| 318 | 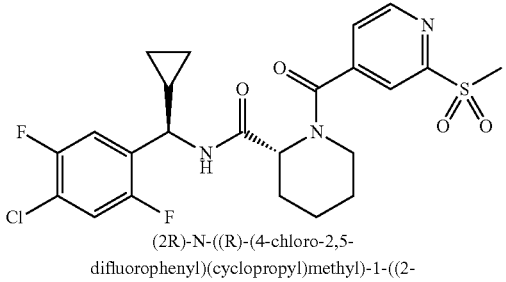<br>(2R)-N-((R)-(4-chloro-2,5-difluorophenyl)(cyclopropyl)methyl)-1-((2-(methylsulfonyl)-4-pyridinyl)carbonyl)-2-piperidinecarboxamide | LCMS-ESI (POS.) m/z: 534.0 (M + Na)+ | 1H NMR (500 MHz, DMSO-d6) δ ppm 8.82-8.94 (m, 1 H), 8.53-8.76 (m, 1 H), 7.95 (br d, J = 6.49 Hz, 1 H), 7.43-7.81 (m, 3 H), 5.14 (br J = 4.54 Hz, H), 4.33-4.47 (m, 1 H), 3.28-3.37 (m, 4 H), 2.05 (br d, J = 12.46 Hz, 1 H), 1.06-1.78 (m, 7 H), 0.25-0.66 (m, 4 H) | C |
| 319 | 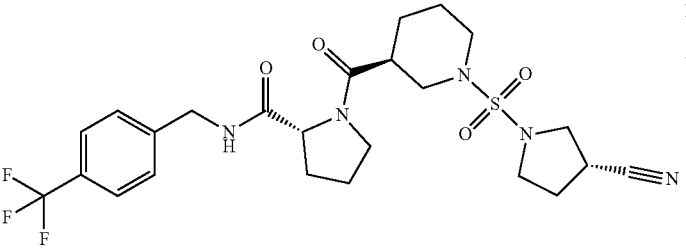 [SMILES: N#C[C@@H]1CCN(S(=O)(=O)N2CCC[C@H](C(=O)N3CCC[C@@H]3C(=O)NCc3ccc(C(F)(F)F)cc3)C2)C1]<br>1-(((3S)-1-(((3R)-3-cyano-1-pyrrolidinyl)sulfonyl)-3-piperidinyl)carbonyl)-N-(4-(trifluoromethyl)benzyl)-D-prolinamide | LCMS-ESI (POS.) m/z: 542.2 (M + Na)+ | 1H NMR (400 MHz, CHLOROFORM-d) δ ppm 7.57 (m, J = 8.09 Hz, 2 H), 7.42 (t, J = 6.07 Hz, 1 H), 7.35 (m, J = 8.09 Hz, 2 H), 4.47-4.63 (m, 2 H), 4.38-4.46 (m, 1 H), 3.79 (br d, J = 12.85 Hz, 2 H), 3.43-3.67 (m, 6 H), 3.11-3.20 (m, 1 H), 3.01 (dd, J = 12.75, 11.09 Hz, 1 H), 2.70-2.86 (m, 2 H), 2.15-2.43 (m, 4 H), 1.88-2.09 (m, 3 H), 1.62-1.84 (m, 2 H), 1.46-1.57 (m, 1 H) | M |
| 320 | 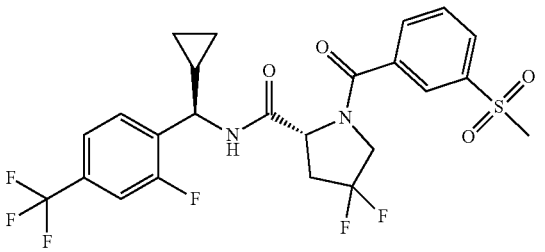 [SMILES: CS(=O)(=O)c1cccc(C(=O)N2CC(F)(F)C[C@@H]2C(=O)N[C@@H](c2ccc(C(F)(F)F)cc2F)C2CC2)c1]<br>N-((R)-cyclopropyl(2-fluoro-4-(trifluoromethyl)phenyl)methyl)-4,4-difluoro-1-(3-(methylsulfonyl)benzoyl)-D-prolinamide | LCMS-ESI (POS.) m/z: 549.0 (M + H)+ | 1H NMR (400 MHz, CHLOROFORM-d) δ ppm 8.06-8.16 (m, 2 H), 7.78-7.86 (m, 1 H), 7.69-7.78 (m, 1 H), 7.40-7.54 (m, 3 H), 7.36 (d, J = 10.26 Hz, 1 H), 5.01 (br t, J = 8.14 Hz, 1 H), 4.57 (br t, J = 8.03 Hz, 1 H), 3.88-4.04 (m, 1 H), 3.74-3.84 (m, 1 H), 2.94-3.20 (m, 4 H), 2.48-2.66 (m, 1 H), 1.20-1.34 (m, 1 H), 0.50-0.67 (m, 2 H), 0.33-0.49 (m, 2 H) | C |

-continued

| Ex. # | Structure Name | LCMS-ESI (POS/NEG) m/z: (M + H)+ | NMR Data | Syn. Rte. |
|---|---|---|---|---|
| 321 | 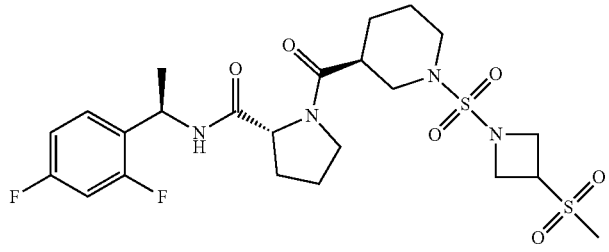 [SMILES: C[C@@H](NC(=O)[C@H]1CCCN1C(=O)[C@H]1CCCN(S(=O)(=O)N2CC(S(C)(=O)=O)C2)C1)c1ccc(F)cc1F]<br>N-((1R)-1-(2,4-difluorophenyl)ethyl)-1-(((3S)-1-((3-(methylsulfonyl)-1-azetidinyl)sulfonyl)-3-piperidinyl)carbonyl)-D-prolinamide | LCMS-ESI (POS.) m/z: 563.1 (M + H)+ | 1H NMR (400 MHz, CHLOROFORM-d) δ 7.22-7.28 (m, 2H), 6.75-6.89 (m, 2H), 5.08-5.23 (m, 1H), 4.56-4.79 (m, 2H), 4.47-4.56 (m, 1H), 4.16-4.28 (m, 4H), 3.90-4.00 (m, 1H), 3.76-3.84 (m, 2H), 3.58-3.67 (m, 2H), 2.99-3.09 (m, 1H), 2.93-2.97 (m, 3H), 2.81-2.91 (m, 1H), 2.71-2.81 (m, 1H), 2.22-2.32 (m, 1H), 2.09-2.21 (m, 1H), 1.94-2.06 (m, 2H), 1.58-1.72 (m, 2H), 1.39-1.48 (m, 3H) | A |
| 322 | 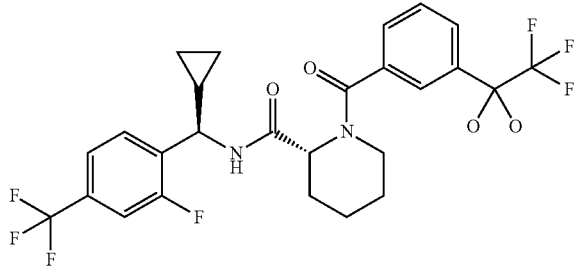<br>(2R)-N-((R)-cyclopropyl(2-fluoro-4-(trifluoromethyl)phenyl)methyl)-1-(3-(2,2,2-trifluoro-1,1-dihydroxyethyl)benzoyl)-2-piperidinecarboxamide | LCMS-ESI (POS.) m/z: 585.2 (M + Na)+ | 1H NMR (500 MHz, DMSO-d6) δ ppm 8.62-8.92 (m, 1 H), 7.30-8.14 (m, 9 H), 4.36-5.27 (m, 2 H), 3.33-3.43 (m, 1 H), 1.94-2.26 (m, 1 H), 1.07-1.84 (m, 7 H), 0.24-0.74 (m, 4 H) | P |
| 323 | 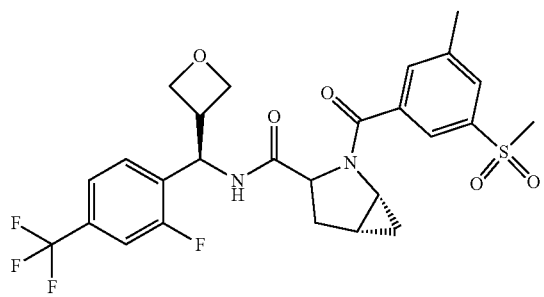 [SMILES: Cc1cc(C(=O)N2C(C(=O)N[C@@H](c3ccc(C(F)(F)F)cc3F)C3COC3)C[C@H]3C[C@H]32)cc(S(C)(=O)=O)c1]<br>(1R,3R,5R)-N-((R)-(2-fluoro-4-(trifluoromethyl)phenyl)(3-oxetanyl)methyl)-2-(3-methyl-5-(methylsulfonyl)benzoyl)-2-azabicyclo[3.1.0]hexane-3-carboxamide | LCMS-APCI (POS.) m/z: 555.2 (M + H)+ | 1H NMR (400 MHz, DMSO-d6) δ ppm 8.76 (d, J = 8.1 Hz, 1 H), 7.95-8.03 (m, 1 H), 7.90 (d, J = 1.6 Hz, 1 H), 7.81 (d, J = 1.7 Hz, 1 H), 7.68-7.75 (m, 1 H), 7.55-7.65 (m, 2 H), 5.49 (dd, J = 8.1, 9.6 Hz, 1 H), 4.90 (dd, J = 3.7, 11.3 Hz, 1 H), 4.65 (dd, J = 6.3, 7.8 Hz, 1 H), 4.52 (dd, J = 6.1, 7.9 Hz, 1 H), 4.41 (t, J = 6.1 Hz, 1 H), 4.23 (t, J = 6.2 Hz, 1 H), 3.41 (q, J = 7.2, 7.7 Hz, 1 H), 3.22-3.27 (m, 4 H), 2.57 (dd, J = 6.2, 12.5 Hz, 1 H), 1.61-1.78 (m, 3 H), 1.15 (td, J = 2.6, 5.1 Hz, 1 H), 0.76 (dt, J = 5.3, 10.0 Hz, 1 H). | Q |

| Ex. # | Structure Name | LCMS-ESI (POS/NEG) m/z: (M + H)+ | NMR Data | Syn. Rte. |
|---|---|---|---|---|
| 324 | 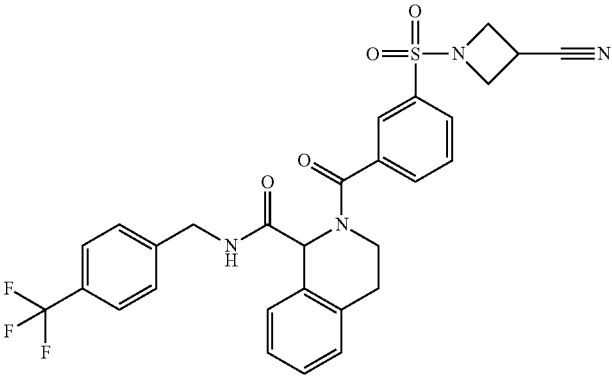 [SMILES: N#CC1CN(S(=O)(=O)c2cccc(C(=O)N3CCc4ccccc4C3C(=O)NCc3ccc(C(F)(F)F)cc3)c2)C1]<br>2-(3-((3-cyanoazetidin-1-yesulfonyl)benzoyl)-N-(4-(trifluoromethyl)benzyl)-1,2,3,4-tetrahydroisoquinoline-1-carboxamide | LCMS-ESI (POS.) m/z: 583.2 (M + H)+ | 1H NMR (500 MHz, DMSO-d6) δ ppm 9.10 (br s, 1 H), 7.98 (br d, J = 7.01 Hz, 1 H), 7.90-7.95 (m, 1 H), 7.78-7.89 (m, 1 H), 7.71 (br d, J = 7.79 Hz, 1 H), 7.65 (br d, J = 7.79 Hz, 2 H), 7.59 (br d, J = 4.80 Hz, 1 H), 7.46 (br d, J = 7.27 Hz, 1 H), 7.25-7.30 (m, 2 H), 7.10-7.25 (m, 2 H), 5.83 (s, 1 H), 4.42 (br d, J = 5.32 Hz, 1 H), 3.97-4.10 (m, 2 H), 3.77-3.94 (m, 2 H), 3.63-3.76 (m, 1 H), 3.53-3.63 (m, 1 H), 3.08-3.23 (m, 2 H), 2.93-3.06 (m, 1 H), 2.71-2.93 (m, 1 H) | I |
| 325 | 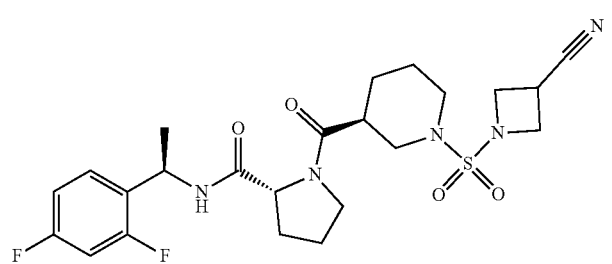 [SMILES: C[C@@H](NC(=O)[C@H]1CCCN1C(=O)[C@H]1CCCN(S(=O)(=O)N2CC(C#N)C2)C1)c1ccc(F)cc1F]<br>1-(((3S)-1-((3-cyano-1-azetidinyl)sulfonyl)-3-piperidinyl)carbonyl)-N-((1R)-1-(2,4-difluorophenyl)ethyl)-D-prolinamide | LCMS-ESI (POS.) m/z: 510.2 (M + H)+ | 1H NMR (500 MHz, DMSO-d6) δ ppm 8.65* (d, J = 7.40 Hz, 1 H), 8.30 (d, J = 7.53 Hz, 1 H), 7.32-7.39 (m, 1 H), 7.14-7.21 (m, 1 H), 7.02-7.10 (m, 1 H), 5.11* (quin, J = 7.04 Hz, 1 H), 5.03 (quin, J = 7.20 Hz, 1 H), 4.46* (dd, J = 8.43, 2.72 Hz, 1 H), 4.29 (dd, J = 8.56, 4.02 Hz, 1 H), 4.00-4.09 (m, 2 H), 3.91-3.97 (m, 2 H), 3.79 (dtt, J = 9.23, 9.12, 9.12, 6.11, 6.11 Hz, 1 H), 3.28-3.61 (m, 4 H), 2.71-2.85 (m, 2 H), 2.63 (tt, J = 11.13, 3.34 Hz, 1 H), 2.28-2.35* (m, 1 H), 2.15-2.23* (m, 1 H), 2.02-2.10 (m, 1 H), 1.63-1.92 (m, 5 H), 1.37-1.54 (m, 2 H), 1.36* (d, J = 7.01 Hz, 3 H), 1.32 (d, J = 7.01 Hz, 3 H). Spectrum appears as 2:1 mixture of rotamers, *denotes resolved minor rotamer peaks | C |
| 326 | 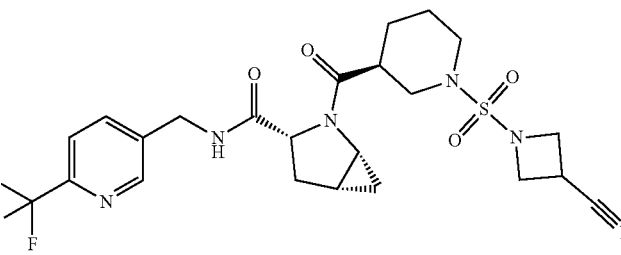<br>(1R,3R,5R)-2-(((3S)-1-((3-cyano-1-azetidinyl)sulfonyl)-3-piperidinyl)carbonyl)-N-((6-(trifluoromethyl)-3-pyridinyl)methyl)-2-azabicyclo[3.1.0]hexane-3-carboxamide | LCMS-ESI (POS.) m/z: 541.2 (M + H)+ | 1H NMR (500 MHz, DMSO-d6) δ ppm 8.60-8.83 (m, 1 H), 8.54 (t, J = 5.97 Hz, 1 H), 7.80-7.98 (m, 2 H), 4.27-4.83 (m, 4 H), 4.00-4.13 (m, 2 H), 3.85-4.00 (m, 2H), H), 3.72-3.85 (m, 1 H), 3.42-3.72 (m, 3 H), 2.57-3.03 (m, 3 H), 1.97-2.19 (m, 1 H), 1.06-1.88 (m, 6 H), 0.55-0.83 (m, 1 H) | C |

| Ex. # | Structure Name | LCMS-ESI (POS/NEG) m/z: (M + H)+ | NMR Data | Syn. Rte. |
|---|---|---|---|---|
| 327 | 1-(((3S)-1-((3-cyano-3-fluoro-1-azetidinyl)sulfonyl)-3-piperidinyl)carbonyl)-N-(2-fluoro-4-(trifluoromethyl)benzyl)-D-prolinamide | LCMS-ESI (POS.) m/z: 564.0 (M + H)+ | 1H NMR (400 MHz, CHLOROFORM-d) δ 7.36-7.48 (m, 3H), 7.29-7.34 (m, 1H), 4.58-4.62 (m, 1H), 4.42-4.58 (m, 2H), 4.24-4.38 (m, 4H), 3.74-3.84 (m, 2H), 3.52-3.64 (m, 2H), 3.00 (dd, J = 10.99, 12.75 Hz, 1H), 2.80 (dt, J = 2.85, 12.41 Hz, 1H), 2.71 (tt, J = 3.58, 11.20 Hz, 1H), 2.36-2.49 (m, 1H), 2.11-2.25 (m, 1H), 1.99-2.10 (m, 1H), 1.79-1.97 (m, 3H), 1.63-1.74 (m, 1H), 1.49-1.56 (m, 1H) | J |
| 328 | (3R)-N-((R)-(4-chloro-2,5-difluorophenyl)(cyclopropyl)methyl)-4-(3-(methylsulfonyl)benzoyl)-3-morpholinecarboxamide | LCMS-ESI (POS.) m/z: 513.0 (M + H)+ | 1H NMR (500 MHz, DMSO-d6) δ ppm 8.58-8.80 (m, 1 H), 8.03 (dd, J = 8.82, 1.82 Hz, 1 H), 7.82-7.92 (m, 1 H), 7.56-7.79 (m, 3 H), 7.43-7.55 (m, 1 H), 3.35-5.01 (m, 7 H), 3.18-3.28 (m, 4 H), 1.09-1.29 (m, 1 H), 0.41-0.66 (m, 2 H), 0.22-0.40 (m, 2 H) | C |
| 329 | 1-((3-(2-oxa-6-azaspiro[3.3]hept-6-ylsulfonyl)phenyl)carbonyl)-N-(4-(trifluoromethyl)benzyl)-D-prolinamide | LCMS-ESI (POS.) m/z: 538.2 (M + H)+ | 1H NMR (500 MHz, DMSO-d6) δ ppm 8.50-8.72 (m, 1 H), 7.60-8.03 (m, 6 H), 7.11-7.55 (m, 2 H), 4.13-4.54 (m, 7 H), 3.81-4.02 (m, 4 H), 3.50-3.67 (m, 2 H), 2.22-2.35 (m, 1 H), 1.74-2.01 (m, 3 H) | C |
| 330 | N-((1S)-1-(4-chlorophenyl)ethyl)-1-((3-((3-cyano-1-azetidinyl)sulfonyl)phenyl)carbonyl)-D-prolinamide | LCMS-APCI (NEG.) m/z: 499.1 (M − H) | 1H NMR (400 MHz, Methanol-d4) δ ppm 8.09 (t, J = 1.7 Hz, 1 H), 7.95-7.99 (m, 1 H), 7.78 (t, J = 7.8 Hz, 1 H), 7.37-7.46 (m, 2 H), 7.26-7.33 (m, 2 H), 5.03 (q, J = 7.3 Hz, 1 H), 4.60 (dd, J = 6.1, 8.0 Hz, 1 H), 4.09 (t, J = 8.7 Hz, 2 H), 3.92 (dt, J = 6.2, 8.5 Hz, 2 H), 3.64 (dt, J = 6.9, 10.3 Hz, 1 H), 3.46-3.59 (m, 2 H), 2.31-2.42 (m, 1 H), 1.96-2.07 (m, 2 H), 1.83-1.94 (m, 1 H), 1.47 (d, J = 7.0 Hz, 3 H). | A |

| Ex. # | Structure Name | LCMS-ESI (POS/NEG) m/z: (M + H)+ | NMR Data | Syn. Rte. |
|---|---|---|---|---|
| 331 | 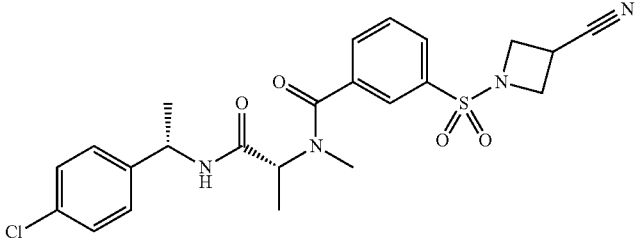 [SMILES: C[C@H](NC(=O)[C@@H](C)N(C)C(=O)c1cccc(S(=O)(=O)N2CC(C#N)C2)c1)c1ccc(Cl)cc1]<br>N-((1R)-2-(((1S)-1-(4-chlorophenyl)ethyl)amino)-1-methyl-2-oxoethyl)-3-((3-cyano-1-azetidinyl)sulfonyl)-N-methylbenzamide | LCMS-ESI (POS.) m/z: 511.2 (M + Na)+ | 1H NMR (500 MHz, CHLOROFORM-d) δ ppm 7.88-8.01 (m, 2 H), 7.63-7.85 (m, 2 H), 7.26-7.39 (m, 4 H), 6.70-6.91 (m, 1 H), 5.11-5.21 (m, 1 H), 5.03-5.11 (m, 1 H), 4.14-4.23 (m, 1 H), 4.11-4.29 (m, 1 H), 3.96-4.08 (m, 2 H), 3.33-3.46 (m, 1 H), 2.89-3.13 (m, 3 H), 1.41-1.53 (m, 6 H) | C |
| 332 | 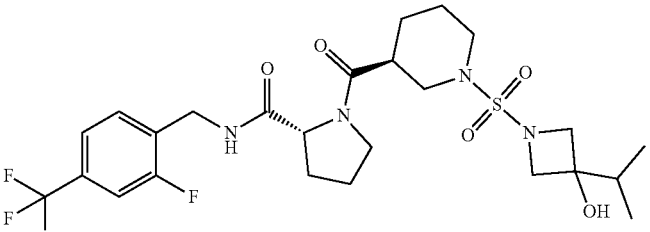<br>N-(2-fluoro-4-(trifluoromethyl)benzyl)-1-(((3S)-1-((3-hydroxy-3-(2-propanyl)-1-azetidinyl)sulfonyl)-3-piperidinyl)carbonyl)-D-prolinamide | LCMS-ESI (POS.) m/z: 579.2 (M + H)+ | 1H NMR (400 MHz, CHLOROFORM-d) δ 7.44 (br t, J = 7.62 Hz, 2H), 7.35-7.40 (m, 1H), 7.31 (d, J = 9.85 Hz, 1H), 4.59 (dd, J = 2.13, 8.03 Hz, 1H), 4.43-4.56 (m, 2H), 3.72-3.88 (m, 6H), 3.55-3.63 (m, 2H), 2.92-3.15 (m, 1H), 2.68-2.84 (m, 2H), 2.39-2.48 (m, 1H), 2.09-2.24 (m, 2H), 1.62-2.06 (m, 7H), 0.96 (d, J = 6.84 Hz, 6H) | J |
| 333 | 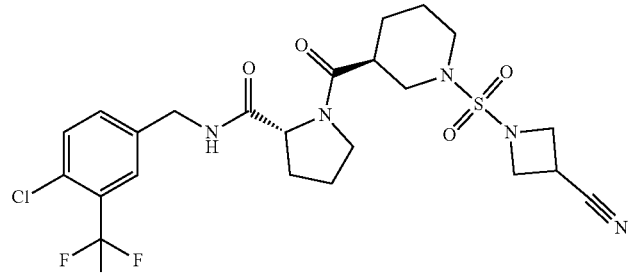<br>N-(4-chloro-3-(trifluoromethyl)benzyl)-1-(((3S)-1-((3-cyano-1-azetidinyl)sulfonyl)-3-piperidinyl)carbonyl)-D-prolinamide | LCMS-ESI (POS.) m/z: 562.0 (M + H)+ | 1H NMR (400 MHz, CHLOROFORM-d) δ ppm 7.53-7.56 (m, 1 H), 7.50 (br t, J = 5.44 Hz, 1 H), 7.44-7.48 (m, 1 H), 7.35-7.40 (m, 1 H), 4.60 (dd, J = 7.98, 2.07 Hz, 1 H), 4.54 (dd, J = 15.50, 6.79 Hz, 1 H), 4.32 (dd, J = 15.50, 5.44 Hz, 1 H), 4.07-4.16 (m, 4 H), 3.73-3.80 (m, 2 H), 3.54-3.63 (m, 2 H), 3.43 (tt, J = 8.68, 6.56 Hz, 1 H), 2.90-3.03 (m, 1 H), 2.65-2.81 (m, 2 H), 2.42-2.51 (m, 1 H), 2.12-2.26 (m, 1 H), 2.01-2.11 (m, 1 H), 1.85-1.96 (m, 2 H), 1.77-1.85 (m, 1 H), 1.61-1.73 (m, 1 H), 1.42-1.55 (m, 1 H) | A |
| 334 | 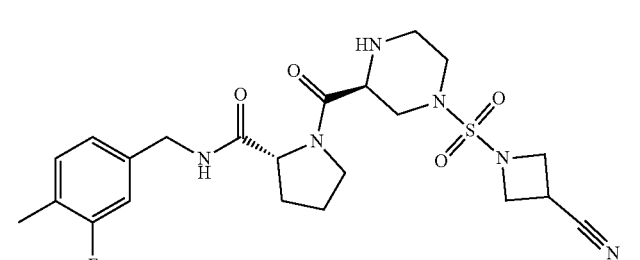<br>1-(((2S)-4-((3-cyano-1-azetidinyl)sulfonyl)-2-piperazinyl)carbonyl)-N-(3-fluoro-4-methylbenzyl)-D-prolinamide | LCMS-ESI (POS.) m/z: 493.2 (M + Na)+ | 1H NMR (400 MHz, CHLOROFORM-d) δ ppm 7.10-7.23 (m, 2 H), 6.89-6.97 (m, 2 H), 4.58 (dd, J = 8.09, 1.87 Hz, 1 H), 4.30-4.49 (m, 2 H), 4.10-4.18 (m, 4 H), 3.77-3.96 (m, 1 H), 3.65-3.71 (m, 2 H), 3.41-3.63 (m, 3 H), 3.13 (br d, J = 13.48 Hz, 1 H), 2.73-2.95 (m, 3 H), 2.39-2.49 (m, 1 H), 2.12-2.28 (m, 3 H), 2.01-2.09 (m, 2 H), 1.80-1.97 (m, 2 H) | M |

| Ex. # | Structure Name | LCMS-ESI (POS/NEG) m/z: (M + H)+ | NMR Data | Syn. Rte. |
|---|---|---|---|---|
| 335 | 1-(((3S)-1-((3-cyano-1-azetidinyl)sulfonyl)-3-piperidinyl)carbonyl)-N-(2-fluoro-3-(trifluoromethyl)benzyl)-D-prolinamide | LCMS-ESI (POS.) m/z: 546.2 (M + H)+ | 1H NMR (500 MHz, DMSO-d6) δ ppm 8.38 (br s, 1 H), 7.31-7.75 (m, 3 H), 4.25-4.44 (m, 3 H), 3.89-4.12 (m, 4 H), 3.74-3.84 (m, 1 H), 3.50-3.70 (m, 1 H), 3.26-3.48 (m, 3 H), 2.62-2.89 (m, 3 H), 2.17-2.32 (m, 1 H), 1.67-1.97 (m, 5 H), 1.35-1.57 (m, 2 H) | A |
| 336 | 1-(((3S)-1-((3-cyano-1-azetidinyl)sulfonyl)-3-piperidinyl)carbonyl)-N-(3,4-dimethylbenzyl)-D-prolinamide | LCMS-ESI (POS.) m/z: 488.2 (M + H)+ | 1H NMR (500 MHz, DMSO-d6) δ 8.11-8.56 (m, 1 H), 7.02-7.10 (m, 1 H), 7.00 (s, 1 H), 6.89-6.97 (m, 1 H), 4.11-4.47 (m, 3 H), 3.99-4.10 (m, 2 H), 3.86-3.97 (m, 2 H), 3.74-3.82 (m, 1 H), 3.34-3.68 (m, 4 H), 2.66-2.85 (m, 2 H), 1.71-2.32 (m, 13 H), 1.36-1.55 (m, 2 H) | A |
| 337 | N-((1R)-2-((4-chlorobenzyl)amino)-1-methyl-2-oxoethyl)-3-((3-cyano-1-azetidinyl)sulfonyl)-N-methylbenzamide | LCMS-ESI (POS.) m/z: 475.0 (M + H)+ | 1H NMR (500 MHz, CHLOROFORM-d) δ ppm 8.06 (br d, J = 12.33 Hz, 1 H), 7.86-7.96 (m, 2 H), 7.61-7.73 (m, 2 H), 7.32 (d, J = 8.30 Hz, 2 H), 7.22 (d, J = 8.24 Hz, 2 H), 6.90 (br s, 1 H), 5.31 (s, 1 H), 5.20 (br d, J = 6.23 Hz, 1 H), 4.49 (br dd, J = 14.69, 5.81 Hz, 1 H), 4.39 (dd, J = 14.86, 5.64 Hz, 1 H), 4.05-4.23 (m, 3 H), 3.97-4.05 (m, 2 H), 3.29-3.42 (m, 1 H), 3.06 (br s, 1 H), 2.92 (br s, 1 H), 2.83-3.10 (m, 1 H), 2.01 (s, 1 H), 1.60 (s, 2 H), 1.51 (br d, J = 6.94 Hz, 3 H), 1.32 (br dd, J = 14.69, 6.58 Hz, 1 H), 0.96-0.96 (m, 1 H) | C |
| 338 | 1-(((3S)-1-((3-cyano-1-azetidinyl)sulfonyl)-3-piperidinyl)carbonyl)-N-(pentafluorobenzyl)-D-prolinamide | LCMS-ESI (POS.) m/z: 550.2 (M + H)+ | 1H NMR (500 MHz, DMSO-d6) δ ppm 8.29-8.80 (m, 1 H), 4.16-4.47 (m, 3 H), 3.98-4.10 (m, 2 H), 3.86-3.96 (m, 2 H), 3.78 (tq, J = 8.80, 5.90 Hz, 1 H), 3.45-3.64 (m, 3 H), 3.36-3.44 (m, 1 H), 2.58-2.83 (m, 3 H), 1.63-2.18 (m, 6 H), 1.29-1.56 (m, 2 H) | A |

-continued

| Ex. # | Structure Name | LCMS-ESI (POS/NEG) m/z: (M + H)+ | NMR Data | Syn. Rte. |
|---|---|---|---|---|
| 339 | 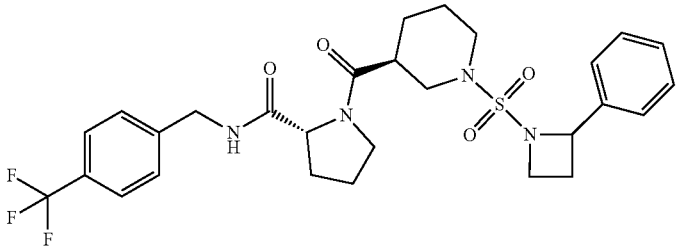 [SMILES: O=C(NCc1ccc(C(F)(F)F)cc1)[C@H]1CCCN1C(=O)[C@H]1CCCN(S(=O)(=O)N2CCC2c2ccccc2)C1]<br>1-(((3S)-1-(((2R)-2-phenyl-1-azetidinyl)sulfonyl)-3-piperidinyl)carbonyl)-N-(4-(trifluoromethyl)benzyl)-D-prolinamide, 1-(((3S)-1-(((2S)-2-phenyl-1-azetidinyl)sulfonyl)-3-piperidinyl)carbonyl)-N-(4-(trifluoromethyl)benzyl)-D-prolinamide | LCMS-ESI (POS.) m/z: 579.2 (M + Na)+ | 1H NMR (500 MHz, DMSO-d6) δ ppm 8.25-8.77 (m, 1 H), 7.58-7.87 (m, 2 H), 7.06-7.55 (m, 7 H), 4.93-5.29 (m, 1 H), 4.19-4.53 (m, 3 H), 3.89 (q, J = 8.56 Hz, 1 H), 3.37-3.79 (m, 4 H), 2.52-2.82 (m, 2 H), 0.91-2.45 (m, 11 H) | M |
| 340 | 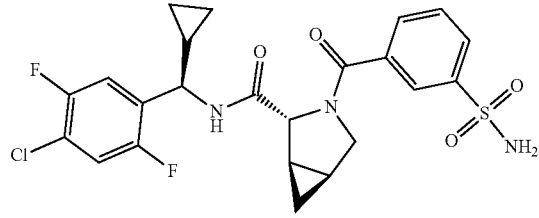 [SMILES: NS(=O)(=O)c1cccc(C(=O)N2C[C@H]3C[C@H]3[C@@H]2C(=O)N[C@@H](c2cc(F)c(Cl)cc2F)C2CC2)c1]<br>(1R,2R,5S)-N-((R)-(4-chloro-2,5-difluorophenyl)(cyclopropyl)methyl)-3-(3-sulfamoylbenzoyl)-3-azabicyclo[3.1.0]hexane-2-carboxamide | LCMS-ESI (POS.) m/z: 510.0 (M + H)+ | 1H NMR (400 MHz, CHLOROFORM-d) δ ppm 8.09 (t, J = 1.45 Hz, 1 H), 8.02 (dt, J = 7.77, 1.50 Hz, 1 H), 7.62-7.69 (m, 1 H), 7.55-7.62 (m, 1 H), 7.40-7.48 (m, 1 H), 7.08-7.22 (m, 2 H), 5.41-5.69 (m, 2 H), 4.29-4.55 (m, 1 H), 3.89-4.27 (m, 1 H), 3.46-3.82 (m, 2 H), 1.70-1.79 (m, 1 H), 1.66 (dquin, J = 7.28, 3.86, 3.86, 3.86, 3.86 Hz, 1 H), 1.21-1.33 (m, 1 H), 0.78-0.87 (m, 1 H), 0.52-0.72 (m, 2 H), 0.29-0.49 (m, 2 H), 0.11-0.29 (m, 1 H) | C |
| 341 | 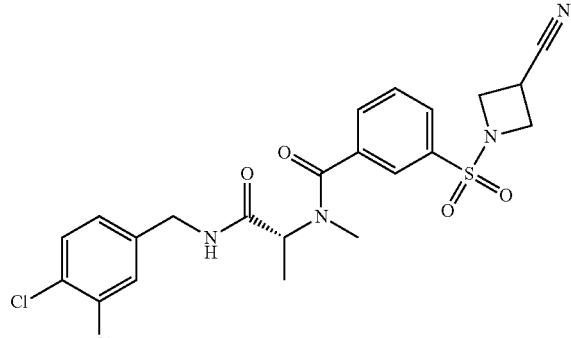<br>3-((3-cyano-1-azetidinyl)sulfonyl)-N-((1R)-2-((3,4-dichlorobenzyl)amino)-1-methyl-2-oxoethyl)-N-methylbenzamide | LCMS-ESI (POS.) m/z: 509.0 (M + H)+ | 1H NMR (500 MHz, CHLOROFORM-d) δ ppm 7.89-7.97 (m, 2 H), 7.70 (br s, 2 H), 7.58-7.66 (m, 1 H), 7.42 (d, J = 8.24 Hz, 1 H), 7.28-7.36 (m, 1 H), 7.09-7.26 (m, 1 H), 7.03 (br s, 1 H), 5.31 (s, 1 H), 5.19 (br d, J = 6.49 Hz, 1 H), 4.48 (br dd, J = 15.02, 6.00 Hz, 1 H), 4.36 (dd, J = 15.18, 5.71 Hz, 1 H), 4.15 (t, J = 8.43 Hz, 2 H), 4.02 (br s, 2 H), 3.31-3.43 (m, 1 H), 3.08 (br s, 1 H), 2.94 (br s, 3 H), 2.01 (s, 1 H), 1.62 (br s, 1 H), 1.52 (br d, J = 6.88 Hz, 4 H) | C |
| 342 | 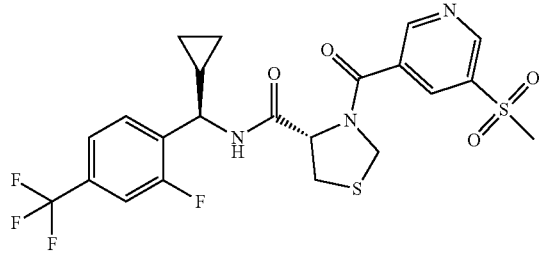 [SMILES: CS(=O)(=O)c1cncc(C(=O)N2CSC[C@@H]2C(=O)N[C@@H](c2ccc(C(F)(F)F)cc2F)C2CC2)c1]<br>(4S)-N-((R)-cyclopropyl(2-fluoro-4-(trifluoromethyl)phenyl)methyl)-3-((5-(methylsulfonyl)-3-pyridinyl)carbonyl)-1,3-thiazolidine-4-carboxamide | LCMS-ESI (POS.) m/z: 532.0 (M + H)+ | 1H NMR (500 MHz, CHLOROFORM-d) δ ppm 9.19-9.36 (m, 1 H), 8.97-9.14 (m, 1 H), 8.34-8.48 (m, 1 H), 7.40-7.50 (m, 2 H), 7.33-7.40 (m, 1 H), 7.08-7.18 (m, 1 H), 4.97-5.23 (m, 1 H), 4.62-4.73 (m, 1 H), 4.41-4.60 (m, 2 H), 3.48-3.74 (m, 1 H), 3.27-3.38 (m, 1 H), 3.06-3.25 (m, 3 H), 1.27-1.37 (m, 1 H), 0.53-0.77 (m, 2 H), 0.33-0.51 (m, 2 H) | C |

| Ex. # | Structure Name | LCMS-ESI (POS/NEG) m/z: (M + H)+ | NMR Data | Syn. Rte. |
|---|---|---|---|---|
| 343 | 1-(((3S)-1-((3-(difluoromethoxy)-1-azetidinyl)sulfonyl)-3-piperidinyl)carbonyl)-N-(4-(trifluoromethyl)benzyl)-D-prolinamide | LCMS-ESI (POS.) m/z: 569.2 (M + H)+ | 1H NMR (500 MHz, DMSO-d6) δ 8.28-8.77 (m, 1H), 7.39-7.79 (m, 4H), 6.49-6.95 (m, 1H), 4.86-5.02 (m, 1H), 4.26-4.52 (m, 3H), 4.01-4.17 (m, 2H), 3.75-3.85 (m, 2H), 3.51-3.70 (m, 4H), 2.69-2.90 (m, 2H), 2.60-2.69 (m, 1H), 2.03-2.38 (m, 1H), 1.65-2.03 (m, 5H), 1.34-1.57 (m, 2H) | J |
| 344 | (1R,3R,5R)-N-((R)-(4-chloro-2-fluorophenyl)(cyclopropyl)methyl)-2-(3-(methylsulfonyl)benzoyl)-2-azabicyclo[3.1.0]hexane-3-carboxamide | LCMS-ESI (POS.) m/z: 491.0 (M + H)+ | 1H NMR (500 MHz, DMSO-d6) δ ppm 8.29-8.68 (m, 1 H) 7.87-8.20 (m, 3 H) 7.23-7.81 (m, 4 H) 4.59-4.99 (m, 1 H) 4.06-4.58 (m, 1 H) 3.20-3.27 (m, 4 H) 2.51-2.59 (m, 1 H) 1.51-1.74 (m, 2 H) 0.77-1.19 (m, 2 H) 0.67-0.76 (m, 1 H) 0.48-0.56 (m, 1 H) 0.38-0.46 (m, 1 H) 0.19-0.37 (m, 2 H) | A |
| 345 | 1-(2-amino-5-(methylsulfonyl)benzoyl)-N-((R)-cyclopropyl(2-fluoro-4-(trifluoromethyl)phenyl)methyl)-D-prolinamide | LCMS-ESI (POS.) m/z: 528.0 (M + H)+ | 1H NMR (500 MHz, DMSO-d6) δ ppm 8.90 (s, 1 H), 7.41-7.78 (m, 5 H), 6.79 (d, J = 8.69 Hz, 1 H), 6.04-6.66 (m, 2 H), 4.18-4.67 (m, 2 H), 3.53-3.60 (m, 1 H), 3.23-3.30 (m, 1 H), 2.97-3.15 (m, 3 H), 2.17-2.30 (m, 1 H), 1.60-1.90 (m, 3 H), 0.86-1.29 (m, 1 H), 0.00-0.69 (m, 4 H) | C |
| 346 | methyl N-methyl-N-((3-(((2R)-2-((4-(trifluoromethyl)benzyl)carbamo)-1-pyrrolidinyl)carbonyl)phenyl)sulfonyl)glycinate | LCMS-ESI (POS.) m/z: 542.2 (M + H)+ | 1H NMR (400 MHz, CHLOROFORM-d) δ ppm 7.27-7.92 (m, 9 H), 7.24-7.25 (m, 1 H), 4.62-4.76 (m, 1 H), 4.38-4.54 (m, 2 H), 3.92-4.01 (m, 2 H), 3.45-3.59 (m, 4 H), 3.30-3.43 (m, 1 H), 2.74-2.90 (m, 3 H), 2.35-2.47 (m, 1 H), 1.98-2.12 (m, 2 H), 1.96-2.13 (m, 2 H), 1.73-1.89 (m, 1 H) | B |

| Ex. # | Structure Name | LCMS-ESI (POS/NEG) m/z: (M+H)+ | NMR Data | Syn. Rte. |
|---|---|---|---|---|
| 347 | 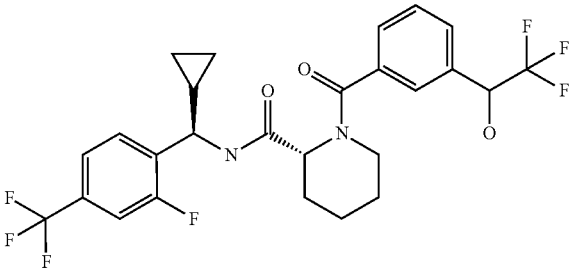 [SMILES: O=C(N[C@@H](c1ccc(C(F)(F)F)cc1F)C1CC1)[C@H]1CCCCN1C(=O)c1cccc(C(O)C(F)(F)F)c1]<br>(2R)-N-((R)-cyclopropyl(2-fluoro-4-(trifluoromethyl)phenyl)methyl)-1-(3-(2,2,2-trifluoro-1-hydroxyethyl)benzoyl)piperidine-2-carboxamide | LCMS-ESI (POS.) m/z: 569.2 (M + Na)+ | 1H NMR (500 MHz, CHLOROFORM-d) δ ppm 7.32-7.67 (m, 9 H), 7.24 (br s, 1 H), 4.20-5.36 (m, 3 H), 3.69 (br d, J = 13.23 Hz, 1 H), 3.13 (br t, J = 12.85 Hz, 1 H), 2.35-2.77 (m, 6 H), 2.25 (br d, J = 13.49 Hz, 1 H), 1.10-1.97 (m, 8 H), 0.32-0.75 (m, 5 H) | C |
| 348 | 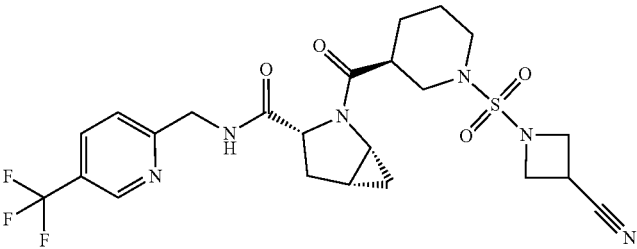 [SMILES: N#CC1CN(S(=O)(=O)N2CCC[C@H](C(=O)N3[C@@H](C(=O)NCc4ccc(C(F)(F)F)cn4)C[C@H]4C[C@H]43)C2)C1]<br>(1R,3R,5R)-2-(((3S)-1-((3-cyano-1-azetidinyl)sulfonyl)-3-piperidinyl)carbonyl)-N-((5-(trifluoromethyl)-2-pyridinyl)methyl)-2-azabicyclo[3.1.0]hexane-3-carboxamide | LCMS-ESI (POS.) m/z: 541.3 (M + H)+ | 1H NMR (500 MHz, DMSO-d6) δ ppm 8.88 (s, 1 H), 8.51-8.81 (m, 1 H), 8.11-8.21 (m, 1 H), 7.42-7.58 (m, 1 H), 4.62-4.90 (m, 2 H), 4.36-4.52 (m, 3 H), 4.00-4.14 (m, 2 H), 3.86-4.00 (m, 2 H), 3.79 (tt, J = 8.89, 6.03 Hz, 1 H), 3.46-3.72 (m, 3 H), 2.64-2.98 (m, 3 H), 2.02-2.18 (m, 1 H), 1.86 (dd, J = 13.49, 3.37 Hz, 1 H), 1.60-1.82 (m, 2 H), 1.26-1.60 (m, 2 H), 0.98-1.17 (m, 1 H), 0.57-0.85 (m, 1 H) | C |
| 349 | 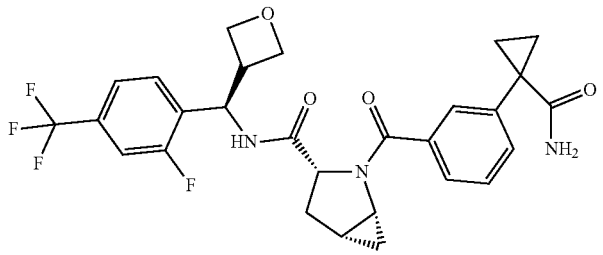 [SMILES: NC(=O)C1(c2cccc(C(=O)N3[C@@H](C(=O)N[C@@H](c4ccc(C(F)(F)F)cc4F)C4COC4)C[C@H]4C[C@H]43)c2)CC1]<br>(1R,3R,5R)-2-(3-(1-carbamoylcyclopropyl)benzoyl)-N+190R)-(2-fluoro-4-(trifluoromethyl)phenyl)(3-oxetanyl)methyl)-2-azabicyclo[3.1.0]hexane-3-carboxamide | LCMS-APCI (POS.) m/z: 546.2 (M + H)+ | 1H NMR (400 MHz, Methanol-d4) δ ppm 7.85 (t, J = 1.7 Hz, 1 H), 7.72 (dt, J = 1.5, 7.6 Hz, 1 H), 7.59 (dt, J = 1.4, 7.8 Hz, 1 H), 7.54-7.57 (m, 2 H), 7.48-7.53 (m, 2 H), 5.65 (d, J = 10.1 Hz, 1 H), 5.00 (dd, J = 4.1, 11.4 Hz, 1 H), 4.83-4.86 (m, 1 H), 4.61-4.70 (m, 2 H), 4.40 (t, J = 6.2 Hz, 1 H), 3.52-3.61 (m, 1 H), 3.35-3.40 (m, 2 H), 2.59-2.69 (m, 1 H), 1.92 (dd, J = 4.2, 13.5 Hz, 1 H), 1.73-1.80 (m, 1 H), 1.56 (td, J = 2.0, 3.0, 3.5 Hz, 2 H), 1.22 (td, J = 2.6, 5.3 Hz, 1 H), 1.10-1.20 (m, 2 H), 0.85 (dt, J = 5.9, 9.1 Hz, 1 H). | V |

| Ex. # | Structure Name | LCMS-ESI (POS/NEG) m/z: (M + H)+ | NMR Data | Syn. Rte. |
|---|---|---|---|---|
| 350 | 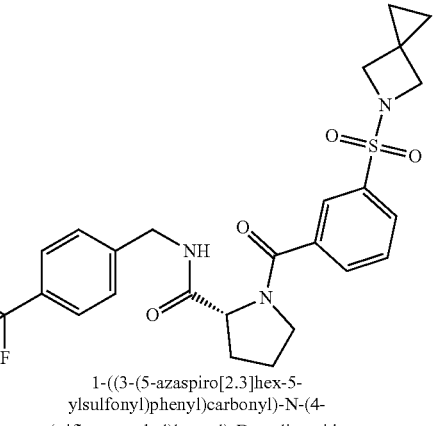<br>1-((3-(5-azaspiro[2.3]hex-5-ylsulfonyl)phenyl)carbonyl)-N-(4-(trifluoromethyl)benzyl)-D-prolinamide | LCMS-APCI (POS.) m/z: 522.2 (M + H)+ | 1H NMR (400 MHz, Methanol-d4) δ ppm 8.15 (q, J = 1.5 Hz, 1 H), 7.92-8.06 (m, 2 H), 7.71-7.83 (m, 1 H), 7.58-7.66 (m, 2 H), 7.54 (d, J = 8.1 Hz, 2 H), 4.55-4.67 (m, 2 H), 4.47 (dd, J = 5.1, 15.9 Hz, 1 H), 3.88 (s, 4 H), 3.69 (dt, J = 6.9, 10.3 Hz, 1 H), 3.55 (ddd, J = 4.4, 6.8, 10.4 Hz, 1 H), 2.38 (ddd, J = 5.5, 8.2, 11.9 Hz, 1 H), 2.04 (ddq, J = 5.9, 6.4, 12.5, 18.8 Hz, 2 H), 1.93 (ddt, J = 5.6, 7.6, 10.8 Hz, 1 H), 0.47 (d, J = 1.1 Hz, 4 H). | Q |
| 351 | 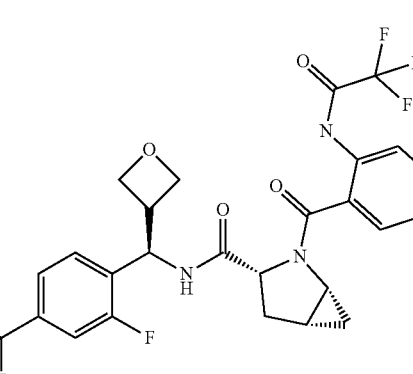<br>(1R,3R,5R)-N-((R)-(2-fluoro-4-(trifluoromethyl)phenyl)(3-oxetanyl)methyl)-2-(2-(2,2,2-trifluoroacetamido)benzoyl)-2-azabicyclo[3.1.0]hexane-3-carboxamide | LCMS-APCI (POS.) m/z: 574.1 (M + H)+ | 1H NMR (400 MHz, DMSO-d6) δ ppm 11.18 (s, 1 H), 8.76 (d, J = 8.0 Hz, 1 H), 7.64-7.75 (m, 2 H), 7.49-7.64 (m, 2 H), 7.35-7.49 (m, 1 H), 5.49 (t, J = 8.9 Hz, 1 H), 4.87 (dd, J = 9.0 Hz, 1 H), 4.64 (t, 1 H), 4.51 (t, 1 H), 4.40 (t, J = 6.2 Hz, 1 H), 4.22 (t, J = 6.2 Hz, 1 H), 3.15-3.23 (m, 1 H), 1.73 (dd, J = 14.4 Hz, 1 H), 1.59-1.70 (m, 1 H), 0.62-0.74 (m, 1 H). | Q |
| 352 | 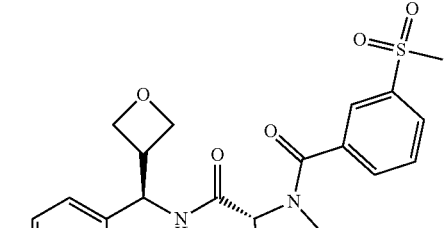<br>(4S)-N-((R)-(4-chloro-2-fluorophenyl)(3-oxetanyl)methyl)-4-fluoro-1-(3-(methylsulfonyl)benzoyl)-D-prolinamide | LCMS-APCI (POS.) m/z: 513.1 (M + H)+ | 1H NMR (400 MHz, Methanol-d4) δ ppm 8.25 (t, 1 H), 8.13 (ddd, J = 1.1, 1.9, 7.9 Hz, 1 H), 7.95-7.99 (m, 1 H), 7.79 (td, J = 0.5, 7.8 Hz, 1 H), 7.37 (t, J = 8.2 Hz, 1 H), 7.22-7.27 (m, 2 H), 5.67 (d, J = 10.4 Hz, 1 H), 5.27 (d, J = 52.0 Hz, 1 H), 4.72-4.78 (m, 1 H), 4.68 (td, J = 0.9, 6.7 Hz, 2 H), 4.39 (t, J = 6.2 Hz, 1 H), 3.98 (ddd, J = 2.8, 12.6, 37.4 Hz, 1 H), 3.52-3.75 (m, 2 H), 3.37 (s, 3 H), 3.20 (d, J = 4.1 Hz, 4 H), 2.57 (td, J = 7.6, 15.9, 16.4 Hz, 1 H), 2.01-2.20 (m, 1 H). | A |

| Ex. # | Structure Name | LCMS-ESI (POS/NEG) m/z: (M + H)+ | NMR Data | Syn. Rte. |
|---|---|---|---|---|
| 353 | 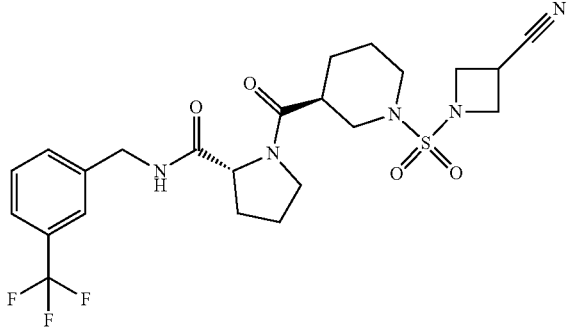 [SMILES: N#CC1CN(S(=O)(=O)N2CCC[C@H](C(=O)N3CCC[C@@H]3C(=O)NCc3cccc(C(F)(F)F)c3)C2)C1]<br>1-(((3S)-1-((3-cyano-1-azetidinyl)sulfonyl)-3-piperidinyl)carbonyl)-N-(3-(trifluoromethyl)benzyl)-D-prolinamide | LCMS-ESI (POS.) m/z: 528.2 (M + H)⁺ | 1H NMR (500 MHz, CHLOROFORM-d) δ ppm 7.41-7.53 (m, 4 H), 4.53-4.63 (m, 2 H), 4.37 (dd, J = 15.44, 5.45 Hz, 1 H), 4.05-4.14 (m, 4 H), 3.69-3.79 (m, 2 H), 3.51-3.64 (m, 2 H), 3.42 (tt, J = 8.68, 6.57 Hz, 1 H), 2.95 (dd, J = 12.59, 11.16 Hz, 1 H), 2.65-2.79 (m, 2 H), 2.44-2.44 (m, 1 H), 2.39-2.49 (m, 1 H), 2.12-2.30 (m, 1 H), 2.00-2.08 (m, 1 H), 1.83-1.94 (m, 2 H), 1.74-1.82 (m, 1 H), 1.58-1.74 (m, 1 H), 1.42-1.55 (m, 1 H), 1.36-1.97 (m, 1 H) | A |
| 354 | 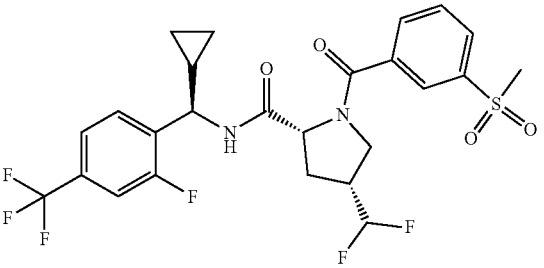 [SMILES: CS(=O)(=O)c1cccc(C(=O)N2C[C@H](C(F)F)C[C@@H]2C(=O)N[C@@H](c2ccc(C(F)(F)F)cc2F)C2CC2)c1]<br>(4R)-N-((R)-cyclopropyl(2-fluoro-4-(trifluoromethyl)phenyl)methyl)-4-(difluoromethyl)-1-(3-(methylsulfonyl)benzoyl)-D-prolinamide | LCMS-ESI (POS.) m/z: 563.0 (M + H)⁺ | Note: cyclopropyl methyne obscured by non-specific grease<br>1H NMR (500 MHz, CHLOROFORM-d) δ ppm 8.12-8.19 (m, 1 H), 8.10 (br d, J = 7.79 Hz, 1 H), 7.82 (br d, J = 7.66 Hz, 1 H), 7.65-7.75 (m, 1 H), 7.45-7.51 (m, 1 H), 7.42 (br d, J = 7.79 Hz, 2 H), 7.35 (br d, J = 10.25 Hz, 1 H), 5.66-5.98 (m, 1 H), 4.85 (t, J = 7.59 Hz, 1 H), 4.57 (br t, J = 7.98 Hz, 1 H), 3.53-3.70 (m, 2 H), 3.12 (s, 3 H), 2.63-2.78 (m, 1 H), 2.43-2.54 (m, 1 H), 2.31 (dt, J = 13.56, 8.34 Hz, 1 H), 1.02-1.17 (m, 1 H), 0.59-0.66 (m, 1 H), 0.51-0.58 (m, 1 H), 0.34-0.48 (m, 2 H) | C |
| 355 | 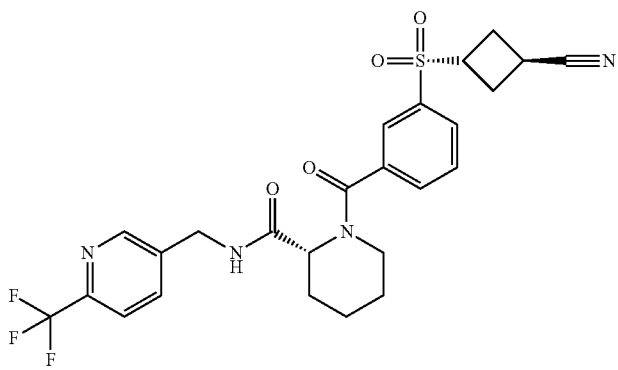<br>(2R)-1-((3-((trans-3-cyanocyclobutyl)sulfonyl)phenyl)carbonyl)-N-((6-(trifluoromethyl)-3-pyridinyl)methyl)-2-piperidinecarboxamide | LCMS-ESI (POS.) m/z: 535.2 (M + H)⁺ | 1H NMR (500 MHz, DMSO-d6) δ ppm 8.51-8.93 (m, 2H), 7.56-8.08 (m, 6H), 3.88-5.31 (m, 5H), 3.35-3.42 (m, 1H), 3.17-3.29 (m, 1H), 2.56-2.65 (m, 4H), 2.06-2.28 (m, 1H), 1.26-1.78 (m, 5H) | L |

| Ex. # | Structure Name | LCMS-ESI (POS/NEG) m/z: (M + H)+ | NMR Data | Syn. Rte. |
|---|---|---|---|---|
| 356 | 1-(((3S)-1-((3-cyano-1-azetidinyl)sulfonyl)-3-piperidinyl)carbonyl)-N-(2,3,5-trifluorobenzyl)-D-prolinamide | LCMS-ESI (POS.) m/z: 514.2 (M + H)+ | 1H NMR (500 MHz, DMSO-d6) δ ppm 8.34-8.74 (m, 1 H), 7.34-7.47 (m, 1 H), 6.91-7.04 (m, 1 H), 4.25-4.55 (m, 3 H), 3.99-4.11 (m, 2 H), 3.86-3.98 (m, 2 H), 3.74-3.83 (m, 1 H), 3.40-3.72 (m, 4 H), 2.75-2.87 (m, 2 H), 2.61-2.71 (m, 1 H), 2.11 (dq, J = 12.25, 8.11 Hz, 1 H), 1.87-2.33 (m, 3 H), 1.69-1.85 (m, 2 H), 1.35-1.57 (m, 2 H) | A |
| 357 | (2R)-1-((S)-1-((3-cyanoazetidin-1-yl)sulfonyl)piperidine-3-carbonyl)-N-(4,6-difluoro-2,3-dihydrobenzofuran-3-yl)pyrrolidine-2-carboxamide | LCMS-ESI (POS.) m/z: 524.2 (M + H)+ | 1H NMR (500 MHz, DMSO-d6) δ ppm 8.38-8.97 (m, 1 H), 6.61-6.82 (m, 2 H), 5.51-5.70 (m, 1 H), 4.69-4.86 (m, 1 H), 4.16-4.45 (m, 2 H), 4.00-4.12 (m, 2 H), 3.87-3.99 (m, 2 H), 3.73-3.84 (m, 1 H), 3.41-3.66 (m, 4 H), 2.59-2.89 (m, 3 H), 2.01-2.30 (m, 1 H), 1.64-1.99 (m, 5 H), 1.30-1.58 (m, 2 H) | A |
| 358 | 1-(((3S)-1-((3-cyano-1-azetidinyl)sulfonyl)-3-piperidinyl)carbonyl)-N-(3-methyl-5-(trifluoromethyl)benzyl)-D-prolinamide | LCMS-ESI (POS.) m/z: 542.0 (M + H)+ | 1H NMR (500 MHz, DMSO-d6) δ ppm 8.28-8.75 (m, 1 H), 7.30-7.51 (m, 3 H), 4.27-4.52 (m, 3 H), 4.08 (br d, J = 2.08 Hz, 2 H), 3.91-3.96 (m, 2 H), 3.73-3.81 (m, 1 H), 3.29-3.68 (m, 4 H), 2.73-2.89 (m, 2 H), 2.61-2.73 (m, 1 H), 2.31-2.42 (m, 3 H), 1.64-2.17 (m, 6 H), 1.31-1.57 (m, 2 H) | A |
| 359 | (2R)-N-((R)-cyclopropyl(2-fluoro-4-(trifluoromethyl)phenyl)methyl)-1-(3-sulfamoylbenzoyl)-2-piperidinecarboxamide | LCMS-ESI (NEG.) m/z: 526.2 (M+ 31 H)− | 1H NMR (400 MHz, CHLOROFORM-d) δ ppm 7.91-8.08 (m, 2 H), 7.55-7.68 (m, 2 H), 7.45-7.53 (m, 1 H), 7.39-7.45 (m, 1 H), 7.35 (d, J = 10.47 Hz, 1 H), 7.01-7.17 (m, 1 H), 4.63-5.30 (m, 3 H), 4.35-4.62 (m, 1 H), 3.53-3.68 (m, 1 H), 3.13-3.31 (m, 1 H), 2.17-2.33 (m, 1 H), 1.64-1.91 (m, 4 H), 1.42-1.59 (m, 1 H), 1.19-1.37 (m, 1 H), 0.52-0.76 (m, 2 H), 0.34-0.49 (m, 2 H) | C |

-continued

| Ex. # | Structure Name | LCMS-ESI (POS/NEG) m/z: (M + H)+ | NMR Data | Syn. Rte. |
|---|---|---|---|---|
| 360 | 1-(((3S)-1-((3-cyano-1-azetidinyl)sulfonyl)-3-piperidinyl)carbonyl)-N-(2,4-difluorobenzyl)-D-prolinamide | LCMS-ESI (POS.) m/z: 496.2 (M + H)+ | 1H NMR (500 MHz, DMSO-d6) δ ppm 8.25-8.66 (m, 1 H), 7.26-7.37 (m, 1 H), 7.14-7.24 (m, 1 H), 7.04 (td, J = 8.30, 2.98 Hz, 1 H), 4.17-4.54 (m, 3 H), 4.00-4.11 (m, 2 H), 3.88-3.97 (m, 2 H), 3.79 (tq, J = 8.81, 5.94 Hz, 1 H), 3.34-3.68 (m, 4 H), 2.71-2.87 (m, 2 H), 1.85-2.32 (m, 4 H), 1.31-1.84 (m, 5 H) | A |
| 361 | (1R,3R,5R)-N-((R)-cyclopropyl(2,5-difluoro-4-(trifluoromethyl)phenyl)methyl)-2-((5-(trifluoromethyl)-3-pyridinyl)carbonyl)-2-azabicyclo[3.1.0]hexane-3-carboxamide | LCMS-APCI (POS.) m/z: 534.1 (M + H)+ | 1H NMR (DMSO-d6) δ: 9.20-9.14 (m, 2H), 8.78 (d, J = 7.4 Hz, 1H), 8.42-8.35 (m, 1H), 7.81 (dd, J = 9.5, 5.8 Hz, 1H), 7.63 (dd, J = 11.0, 5.6 Hz, 1H), 4.99 (dd, J = 11.4, 3.6 Hz, 1H), 4.56 (t, J = 7.9 Hz, 1H), 1.88-1.69 (m, 3H), 1.33-1.18 (m, 2H), 1.18-1.10 (m, 1H), 0.88-0.74 (m, 2H), 0.68-0.58 (m, 1H), 0.58-0.48 (m, 1H), 0.41 (s, 1H) | Q |
| 362 | N-((R)-(4-chloro-2,5-difluorophenyl)(cyclopropyl)methyl)-1-((5-(methylsulfonyl)-3-pyridinyl)carbonyl)-D-prolinamide | LCMS-ESI (POS.) m/z: 498.2 (M + H)+ | 1H NMR (500 MHz, DMSO-d6) δ ppm 9.11-9.22 (m, 1 H), 8.79-9.09 (m, 1 H), 8.46-8.65 (m, 1 H), 8.26-8.46 (m, 1 H), 7.31-7.63 (m, 2 H), 4.29 (s, 2 H), 3.51-3.61 (m, 2 H), 3.33-3.36 (m, 3 H), 2.14-2.31 (m, 1 H), 1.65-1.90 (m, 3 H), 0.84-1.24 (m, 1 H), −0.18-0.62 (m, 4 H) | C |
| 363 | 1-(((3S)-1-((3-cyano-1-azetidinyl)sulfonyl)-3-piperidinyl)carbonyl)-N-methyl-N-(4-(trifluoromethyl)benzyl)-D-prolinamide | LCMS-ESI (POS.) m/z: 542.2 (M + H)+ | 1H NMR (400 MHz, CHLOROFORM-d) δ ppm 7.58-7.69 (m, 3 H), 7.46 (d, J = 7.88 Hz, 1 H), 7.35 (d, J = 7.78 Hz, 2 H), 4.87 (dd, J = 7.88, 4.56 Hz, 1 H), 4.68-4.78 (m, 2 H), 4.53-4.66 (m, 1 H), 4.05-4.15 (m, 6 H), 3.63-3.86 (m, 6 H), 3.38-3.49 (m, 1 H), 2.88-3.13 (m, 6 H), 2.69-2.83 (m, 3 H), 2.18-2.30 (m, 2 H), 1.91-2.16 (m, 5 H), 1.77-1.88 (m, 2 H), 1.55-1.74 (m, 3 H) | M |

| Ex. # | Structure Name | LCMS-ESI (POS/NEG) m/z: (M + H)+ | NMR Data | Syn. Rte. |
|---|---|---|---|---|
| 364 | 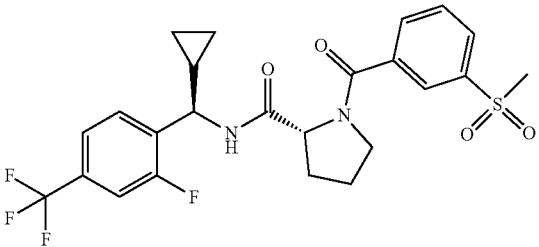 [SMILES: CS(=O)(=O)c1cccc(C(=O)N2CCC[C@@H]2C(=O)N[C@@H](c2ccc(C(F)(F)F)cc2F)C2CC2)c1]<br>(R)-N-((R)-cyclopropyl(2-fluoro-4-(trifluoromethyl)phenyl)methyl)-1-(3-(methylsulfonyl)benzoyl)pyrrolidine-2-carboxamide | LCMS-ESI (POS.) m/z: 513.2 (M + H)+ | 1H NMR (500 MHz, DMSO-d6) δ ppm 8.49-8.76 (m, 1 H), 7.51-8.10 (m, 7 H), 4.17-4.67 (m, 2 H), 3.35-3.64 (m, 3 H), 3.24-3.30 (m, 3 H), 2.13-2.31 (m, 1 H), 1.62-1.94 (m, 3 H), 0.86-1.31 (m, 1 H), −0.06-0.65 (m, 4 H) | C |
| 365 | 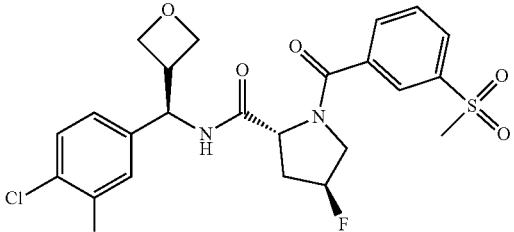<br>(4S)-N-((R)-(4-chloro-3-fluorophenyl)(3-oxetanyl)methyl)-4-fluoro-1-(3-(methylsulfonyl)benzoyl)-D-prolinamide | LCMS-APCI (POS.) m/z: 513.1 (M + H)+ | 1H NMR (400 MHz, Methanol-d4) δ ppm 8.13 (t, J = 1.7 Hz, 1 H), 8.01 (ddd, J = 1.1, 1.9, 7.9 Hz, 1 H), 7.86 (dt, J = 1.4, 7.7 Hz, 1 H), 7.67 (t, J = 7.8 Hz, 1 H), 7.36 (t, J = 7.9 Hz, 1 H), 7.13 (dd, J = 2.0, 10.1 Hz, 1 H), 7.05 (dd, J = 2.0, 8.2 Hz, 1 H), 5.30 (d, J = 10.4 Hz, 1 H), 5.07-5.24 (m, 1 H), 4.62 (dt, J = 6.7, 8.7 Hz, 1 H), 4.51-4.58 (m, 2 H), 4.33 (t, J = 6.2 Hz, 1 H), 3.93 (dt, J = 2.9, 12.5 Hz, 1 H), 3.59 (ddd, J = 2.3, 12.7, 19.9 Hz, 1 H), 3.34-3.43 (m, 1 H), 3.25 (s, 2 H), 3.07 (s, 3 H), 2.42-2.53 (m, 1 H), 1.93-2.11 (m, 1 H). | A |
| 366 | 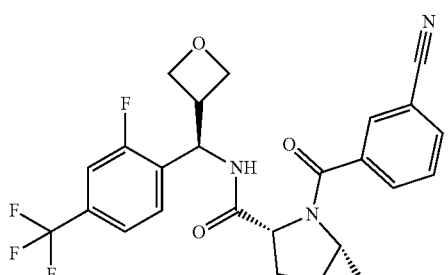<br>(1R,3R,5R)-2-(3-cyanobenzoyl)-N-((R)-(2-fluoro-4-(trifluoromethyl)phenyl)(3-oxetanyl)methyl)-2-azabicyclo[3.1.0]hexane-3-carboxamide | LCMS-APCI (POS.) m/z: 488.2 (M + H)+ | 1H NMR (400 MHz, Methanol-d4) δ ppm 8.06-8.12 (m, 2 H), 7.89 (dt, 1 H), 7.70 (td, J = 0.7, 7.8 Hz, 1 H), 7.48-7.58 (m, 3 H), 5.65 (d, J = 10.2 Hz, 1 H), 4.99 (dd, J = 4.1, 11.4 Hz, 1 H), 4.83-4.87 (m, 1 H), 4.60-4.70 (m, 2 H), 4.40 (t, 1 H), 3.51-3.61 (m, 1 H), 3.37 (s, 2 H), 3.30 (td, J = 3.1, 6.2 Hz, 1 H), 2.60-2.71 (m, 1 H), 1.90 (dd, J = 4.1, 13.5 Hz, 1 H), 1.74-1.83 (m, 1 H), 1.23 (td, J = 2.6, 5.3 Hz, 1 H), 0.88 (ddd, J = 5.4, 7.3, 8.8 Hz, 1 H). | Q |

| Ex. # | Structure Name | LCMS-ESI (POS/NEG) m/z: (M + H)+ | NMR Data | Syn. Rte. |
|---|---|---|---|---|
| 367 | 1-(((3S)-1-((3-(1H-pyrrol-1-)-1-azetidinyl)sulfonyl)-3-piperidinyl)carbonyl)-N-(4-(trifluoromethyl)benzyl)-D-prolinamide | LCMS-ESI (POS.) m/z: 568.2 (M + H)⁺ | 1H NMR (500 MHz, CHLOROFORM-d) δ ppm 7.57 (d, J = 8.04 Hz, 2 H), 7.34-7.49 (m, 3 H), 6.87 (t, J = 1.95 Hz, 2 H), 6.22 (t, J = 1.95 Hz, 2 H), 4.82 (quin, J = 7.07 Hz, 1 H), 4.60 (dd, J = 8.04, 1.56 Hz, 1 H), 4.39-4.54 (m, 2 H), 4.21-4.28 (m, 2 H), 4.10-4.19 (m, 2 H), 3.83 (br d, J = 12.46 Hz, 2 H), 3.55-3.63 (m, 2 H), 2.92-2.99 (m, 1 H), 2.69-2.82 (m, 2 H), 2.44 (ddd, J = 9.28, 6.42, 3.50 Hz, 1 H), 2.13-2.31 (m, 1 H), 2.01-2.08 (m, 1 H), 1.76-1.95 (m, 3 H), 1.43-1.72 (m, 2 H), 1.19-1.34 (m, 2 H) | M |
| 368 | N-(2-fluoro-4-(trifluoromethyl)benzyl)-1-(3-((3-hydroxy-3-methyl-1-azetidinyl)sulfonyl)benzoyl)-D-prolinamide | LCMS-ESI (POS.) m/z: 544.2 (M + H)⁺ | 1H NMR (400 MHz, CHLOROFORM-d) δ 8.00 (s, 1H), 7.94 (d, J = 7.88 Hz, 1H), 7.79 (br d, J = 7.77 Hz, 1H), 7.63-7.70 (m, 1H), 7.49-7.56 (m, 1H), 7.40 (br d, J = 8.09 Hz, 1H), 7.29-7.35 (m, 2H), 4.75 (dd, J = 5.18, 7.05 Hz, 1H), 4.58 (br d, J = 5.91 Hz, 2H), 3.57-3.76 (m, 5H), 3.40-3.51 (m, 1H), 2.37-2.49 (m, 1H), 2.02-2.19 (m, 3H), 1.86-1.97 (m, 1H), 1.42-1.48 (m, 3H) | C |
| 369 | 1-(3-cyclopropylbenzoyl)-N-((R)-cyclopropyl(2-fluoro-4-(trifluoromethyl)phenyl)methyl)-D-prolinamide | LCMS-ESI (POS.) m/z: 475.2 (M + H)⁺ | 1H NMR (600 MHz, DMSO-d6) δ ppm 8.46-8.80 (m, 1 H), 7.53-7.74 (m, 3 H), 6.96-7.40 (m, 4 H), 4.23-4.66 (m, 2 H), 3.42-3.65 (m, 2 H), 2.08-2.23 (m, 1 H), 1.15-2.05 (m, 5 H), 0.06-1.09 (m, 9 H) | C |
| 370 | 1-(3-(methylsulfonyl)benzoyl)-N-((R)-3-oxetanyl(4-(trifluoromethyl)phenyl)methyl)-D-prolinamide | LCMS-APCI (POS.) m/z: 511.1 (M + H)⁺ | 1H NMR (400 MHz, Methanol-d4) δ ppm 8.20 (s, 1 H), 8.09 (d, J = 7.9 Hz, 2 H), 7.94 (d, J = 7.7 Hz, 1 H), 7.75 (t, J = 7.7 Hz, 1 H), 7.67 (d, J = 8.1 Hz, 2 H), 7.53 (d, J = 8.1 Hz, 2 H), 7.39 (d, 1 H), 5.48 (d, J = 10.2 Hz, 1 H), 4.88 (t, J = 7.1 Hz, 1 H), 4.47 (t, J = 6.2 Hz, 1H), 3.97-4.17 (m, 1 H), 3.76 (s, 1 H), 3.60-3.69 (m, 1 H), 3.49-3.60 (m, 2 H), 2.25-2.39 (m, 2 H), 1.78-2.07 (m, 5 H). | A |

| Ex. # | Structure Name | LCMS-ESI (POS/NEG) m/z: (M + H)+ | NMR Data | Syn. Rte. |
|---|---|---|---|---|
| 371 | 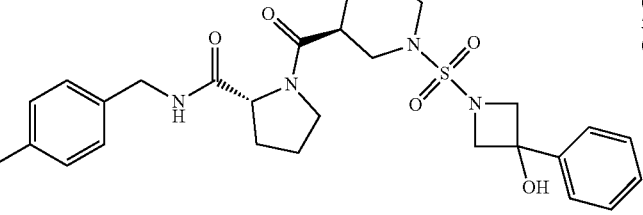<br>1-(((3S)-1-((3-hydroxy-3-phenyl-1-azetidinyl)sulfonyl)-3-piperidinyl)carbonyl)-N-(4-(trifluoromethyl)benzyl)-D-prolinamide | LCMS-ESI (POS.) m/z: 595.2 (M + H)+ | 1H NMR (500 MHz, CHLOROFORM-d) δ ppm 7.52-7.66 (m, 4 H), 7.34-7.45 (m, 5 H), 4.47-4.64 (m, 2 H), 4.36-4.47 (m, 1 H), 4.10-4.30 (m, 4 H), 3.81 (br t, J = 14.92 Hz, 2 H), 3.55-3.68 (m, 2 H), 2.94-3.14 (m, 2 H), 2.80-2.92 (m, 1 H), 2.74 (br t, J = 10.90 Hz, 1 H), 2.31-2.45 (m, 1 H), 2.12-2.31 (m, 1 H), 2.00-2.09 (m, 1 H), 1.86-1.98 (m, 2 H), 1.82 (br d, J = 13.49 Hz, 1 H), 1.67 (q, J = 12.46 Hz, 1 H), 1.42-1.61 (m, 1 H) | M |
| 372 | 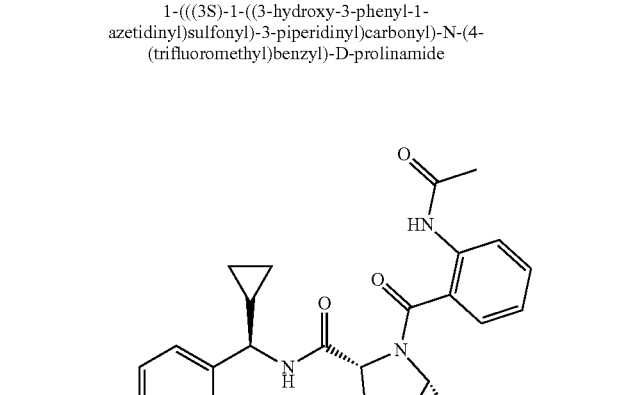<br>(1R,3R,5R)-2-(2-acetamidobenzoyl)-N-((R)-cyclopropyl(2-fluoro-4-(trifluoromethyl)phenyl)methyl)-2-azabicyclo[3.1.0]hexane-3-carboxamide | LCMS-APCI (POS.) m/z: 504.1 (M + H)+ | 1H NMR (400 MHz, DMSO-d6) δ ppm 9.58 (s, 1 H), 9.02 (d, J = 6.9 Hz, 1 H), 8.18 (d, J = 8.3 Hz, 1 H), 7.60-7.72 (m, 2 H), 7.32-7.42 (m, 2 H), 7.15 (td, J = 1.1, 7.4 Hz, 1 H), 4.98 (dd, J = 2.9, 11.4 Hz, 1 H), 4.46-4.54 (m, 1 H), 4.36 (t, J = 5.1 Hz, 1 H), 3.40-3.46 (m, 1 H), 3.00 (td, J = 2.6, 6.2 Hz, 1 H), 2.56-2.65 (m, 1 H), 1.94 (s, 2 H), 1.86 (dd, J = 3.0, 13.7 Hz, 1 H), 1.48-1.61 (m, 1 H), 1.18-1.29 (m, 1 H), 1.06 (t, J = 7.0 Hz, 1 H), 0.57-0.67 (m, 2 H), 0.46-0.57 (m, 2 H), 0.30-0.46 (m, 2 H). | Q |
| 373 | 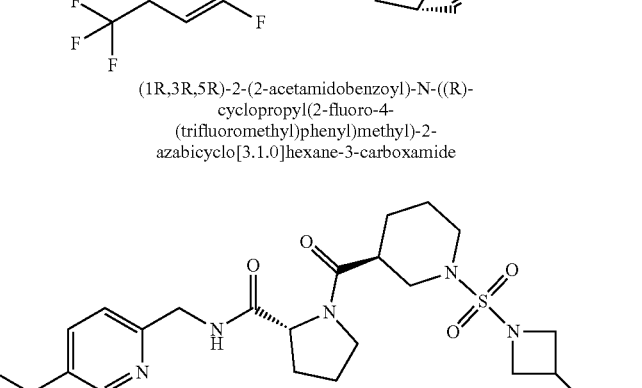<br>1-(((3S)-1-((3-cyano-1-azetidinyl)sulfonyl)-3-piperidinyl)carbonyl)-N-((5-(trifluoromethyl)-2-pyridinyl)methyl)-D-prolinamide | LCMS-ESI (POS.) m/z: 529.2 (M + H)+ | 1H NMR (400 MHz, CHLOROFORM-d) δ 8.72-8.88 (m, 1H), 7.84-8.01 (m, 1H), 7.50-7.64 (m, 1H), 7.36-7.46 (m, 1H), 4.60-4.75 (m, 3H), 4.05-4.19 (m, 4H), 3.74-3.85 (m, 2H), 3.57-3.69 (m, 2H), 3.36-3.50 (m, 1H), 2.94-3.06 (m, 1H), 2.68-2.84 (m, 2H), 2.34-2.45 (m, 1H), 2.10-2.23 (m, 1H), 1.92-2.03 (m, 2H), 1.56-1.88 (m, 4H) | A |
| 374 | 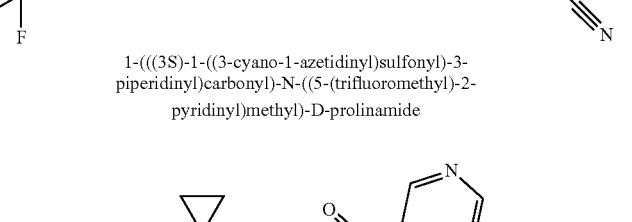<br>(1R,3R,5R)-N-((R)-(4-chloro-2,5-difluorophenyl)(cyclopropyl)methyl)-2-((5-(trifluoromethyl)-3-pyridinyl)carbonyl)-2-azabicyclo[3.1.0]hexane-3-carboxamide | LCMS-APCI (POS.) m/z: 500.1 (M + H)+ | 1H NMR (DMSO-d6) δ: 9.17-9.11 (m, 2H), 8.65 (d, J = 7.7 Hz, 1H), 8.34 (s, 1H), 7.64 (dd, 1H), 7.50 (dd, J = 9.8, 6.4 Hz, 1H), 4.94 (dd, J = 11.4, 3.6 Hz, 2H), 4.50 (t, J = 7.9 Hz, 1H), 4.04 (q, J = 7.2 Hz, 2H), 1.81-1.64 (m, 3H), 1.28-1.06 (m, 5H), 0.82-0.67 (m, 2H), 0.59-0.49 (m, 1H), 0.45 (t, J = 9.1 Hz, 2H), 0.38-0.27 (m, 2H) | Q |

| Ex. # | Structure Name | LCMS-ESI (POS/NEG) m/z: (M + H)+ | NMR Data | Syn. Rte. |
|---|---|---|---|---|
| 375 | (1R,3R,5R)-2-(3-(methylsulfonyl)benzoyl)-N-((R)-3-oxetanyl(4-(trifluoromethyl)phenyl)methyl)-2-azabicyclo[3.1.0]hexane-3-carboxamide | LCMS-APCI (POS.) m/z: 523.1 (M + H)+ | 1H NMR (400 MHz, Methanol-d4) δ ppm 8.40 (td, J = 0.5, 1.8 Hz, 1 H), 8.13 (dddd, J = 1.1, 1.8, 4.1, 7.9 Hz, 2 H), 7.76-7.81 (m, 1 H), 7.69 (d, 2 H), 7.52 (d, 2 H), 5.41 (d, J = 10.1 Hz, 1 H), 5.02 (dd, J = 4.2, 11.4 Hz, 1 H), 4.85 (dd, J = 6.5, 7.7 Hz, 1 H), 4.60-4.69 (m, 2 H), 4.44 (t, J = 6.3 Hz, 1 H), 3.46-3.55 (m, 1 H), 3.19 (s, 3 H), 2.63-2.72 (m, 1 H), 1.92 (dd, J = 4.2, 13.5 Hz, 1 H), 1.76-1.85(m, 1 H), 1.29 (td, J = 2.6, 5.3 Hz, 1 H), 0.87-0.95 (m, 1 H). | A |
| 376 | N-((5-chloro-1,3-thiazol-2-yl)methyl)-1-((3-((3-cyano-1-azetidinyl)sulfonyl)phenyl)carbonyl)-D-prolinamide | LCMS-APCI (NEG.) m/z: 492.1 (M − H) | 1H NMR (400 MHz, Methanol-d4) δ ppm 8.12 (d, J = 1.7 Hz, 1 H), 7.94-8.03 (m, 2 H), 7.80 (t, J = 7.8 Hz, 1 H), 7.50 (d, J = 1.1 Hz, 1 H), 4.55 (t, J = 2.6 Hz, 3 H), 4.07-4.17 (m, 2 H), 3.93 (dt, J = 5.8, 8.6 Hz, 2 H), 3.68 (dt, J = 6.9, 10.4 Hz, 1 H), 3.45-3.60 (m, 2 H), 2.28-2.40 (m, 1 H), 1.88-2.07 (m, 3 H). | A |
| 377 | (2R)-N-((R)-cyclopropyl(2-fluoro-4-(trifluoromethyl)phenyl)methyl)-1-(3-(methylsulfonyl)benzoyl)-2,3-dihydro-1H-pyrrole-2-carboxamide | LCMS-ESI (POS.) m/z: 511.0 (M + H)+ | 1H NMR (500 MHz, CHLOROFORM-d) δ ppm 8.16 (s, 1H), 8.11 (br d, J = 7.79 Hz, 1H), 7.86 (d, J = 7.66 Hz, 1H), 7.69-7.77 (m, 2H), 7.48-7.54 (m, 1H), 7.43 (d, J = 8.04 Hz, 1H), 7.36 (d, J = 10.38 Hz, 1H), 6.31-6.37 (m, 1H), 5.33-5.39 (m, 1H), 5.10 (dd, J = 3.70, 10.45 Hz, 1H), 4.61 (t, J = 7.98 Hz, 1H), 3.21 (br dd, J = 1.43, 17.26 Hz, 1H), 3.10-3.14 (m, 3H), 2.76-2.98 (m, 1H), 1.26-1.35 (m, 1H), 0.61-0.69 (m, 1H), 0.54-0.61 (m, 1H), 0.44-0.50 (m, 1H), 0.37-0.44 (m, 1H) | K |
| 378 | 1-(3-chlorobenzoyl)-N-((R)-cyclopropyl(2-fluoro-4-(trifluoromethyl)phenyl)methyl)-D-prolinamide | LCMS-ESI (POS.) m/z: 469.0 (M + H)+ | 1H NMR (500 MHz, DMSO-d6) δ ppm 8.52-8.72 (m, 1 H), 7.27-7.74 (m, 7 H), 4.23-4.64 (m, 2 H), 3.50-3.62 (m, 1 H), 3.45-3.49 (m, 1 H), 2.13-2.22 (m, 1 H), 1.66-1.92 (m, 3 H), 0.96-1.29 (m, 1 H), 0.03-0.64 (m, 4 H) | C |

| Ex. # | Structure Name | LCMS-ESI (POS/NEG) m/z: (M + H)+ | NMR Data | Syn. Rte. |
|---|---|---|---|---|
| 379 | 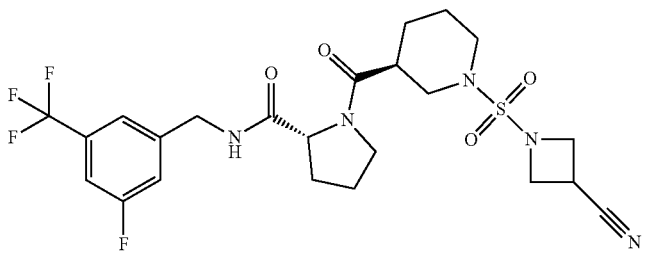<br>1-(((3S)-1-((3-cyano-1-azetidinyl)sulfonyl)-3-piperidinyl)carbonyl)-N-(3-fluoro-5-(trifluoromethyl)benzyl)-D-prolinamide | LCMS-ESI (POS.) m/z: 546.2 (M + H)+ | 1H NMR (500 MHz, DMSO-d6) δ ppm 8.38-8.80 (m, 1 H), 7.46-7.56 (m, 2 H), 7.41 (br d, J = 9.73 Hz, 1 H), 4.32-4.55 (m, 2 H), 4.28 (dd, J = 8.50, 4.22 Hz, 1 H), 3.99-4.09 (m, 2 H), 3.87-3.96 (m, 2 H), 3.75-3.83 (m, 1 H), 3.61-3.71 (m, 1 H), 3.33-3.61 (m, 3 H), 2.73-2.85 (m, 2 H), 2.62-2.69 (m, 1 H), 2.06-2.28 (m, 1 H), 1.63-1.97 (m, 5 H), 1.35-1.57 (m, 2 H) | A |
| 380 | 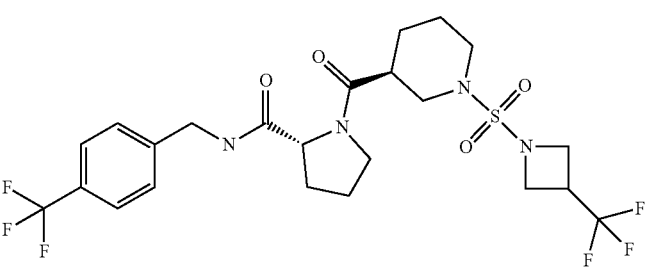 [SMILES: O=C(NCc1ccc(C(F)(F)F)cc1)[C@H]1CCCN1C(=O)[C@H]1CCCN(S(=O)(=O)N2CC(C(F)(F)F)C2)C1]<br>1-(((3S)-1-((3-(trifluoromethyl)-1-azetidinyl)sulfonyl)-3-piperidinyl)carbonyl)-N-(4-(trifluoromethyl)benzyl)-D-prolinamide | LCMS-ESI (POS.) m/z: 571.2 (M + H)+ | 1H NMR (500 MHz, CHLOROFORM-d) δ ppm 7.57 (m, J = 8.04 Hz, 2 H), 7.41 (br s, 1 H), 7.28-7.37 (m, 2 H), 4.47-4.66 (m, 2 H), 4.37-4.47 (m, 1 H), 4.22 (quin, J = 7.01 Hz, 1 H), 3.75-3.85 (m, 6 H), 3.56-3.65 (m, 2 H), 2.89 (t, J = 11.81 Hz, 1 H), 2.67-2.78 (m, 2 H), 2.57 (ddd, J = 10.06, 6.94, 2.98 Hz, 2 H), 2.38-2.46 (m, 1 H), 2.02-2.24 (m, 4 H), 1.85-1.98 (m, 2 H), 1.78 (br d, J = 13.75 Hz, 1 H), 1.57-1.70 (m, 1 H), 1.36-1.57 (m, 2 H) | M |
| 381 | 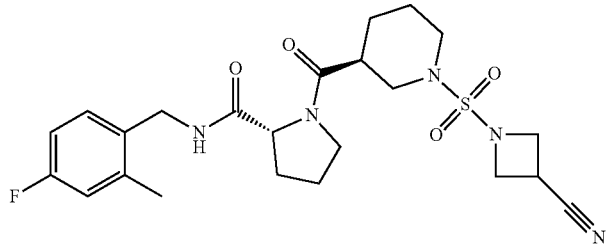 [SMILES: Cc1cc(F)ccc1CNC(=O)[C@H]1CCCN1C(=O)[C@H]1CCCN(S(=O)(=O)N2CC(C#N)C2)C1]<br>1-(((3S)-1-((3-cyano-1-azetidinyl)sulfonyl)-3-piperidinyl)carbonyl)-N-(4-fluoro-2-methylbenzyl)-D-prolinamide | LCMS-ESI (POS.) m/z: 492.2 (M + H)+ | 1H NMR (500 MHz, DMSO-d6) δ ppm 8.10-8.50 (m, 1 H), 7.16-7.24 (m, 1 H), 6.99-7.05 (m, 1 H), 6.91-6.99 (m, 1 H), 4.11-4.49 (m, 3 H), 4.01-4.10 (m, 2 H), 3.88-3.97 (m, 2 H), 3.74-3.84 (m, 1 H), 3.37-3.68 (m, 4 H), 2.71-2.87 (m, 2 H), 2.59-2.69 (m, 1 H), 2.16-2.33 (m, 3 H), 1.66-2.13 (m, 6 H), 1.32-1.56 (m, 2 H) | A |
| 382 | 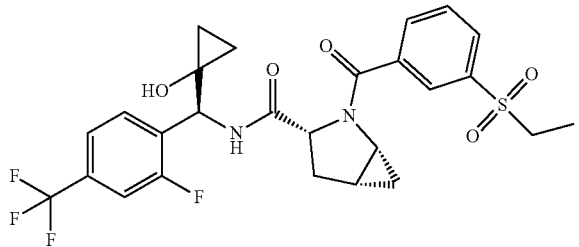 [SMILES: CCS(=O)(=O)c1cccc(C(=O)N2[C@@H](C(=O)N[C@@H](c3ccc(C(F)(F)F)cc3F)C3(O)CC3)C[C@H]3C[C@H]32)c1]<br>(1R,3R,5R)-2-(3-(ethylsulfonyl)benzoyl)-N-((S)-(2-fluoro-4-(trifluoromethyl)phenyl)(1-hydroxycyclopropyl)methyl)-2-azabicyclo[3.1.0]hexane-3-carboxamide | LCMS-ESI (POS.) m/z: 555.0 (M + H)+ | 1H NMR (500 MHz, DMSO-d6) δ ppm 8.61 (br d, J = 8.04 Hz, 1 H) 8.10-8.14 (m, 1 H) 8.02 (dd, J = 7.72, 1.62 Hz, 2 H) 7.79 (t, J = 7.79 Hz, 1 H) 7.51-7.75 (m, 4 H) 5.27-5.55 (m, 1 H) 5.00 (dd, J = 11.35, 3.57 Hz, 1 H) 4.96 (d, J = 7.91 Hz, 1 H) 3.32-3.38 (m, 2 H) 3.23 (td, J = 6.16, 2.47 Hz, 1 H) 1.07-1.16 (m, 5 H) 0.52-0.78 (m, 6 H) | C |

-continued

| Ex. # | Structure Name | LCMS-ESI (POS/NEG) m/z: (M + H)+ | NMR Data | Syn. Rte. |
|---|---|---|---|---|
| 383 | (1R,3R,5R)-N-((R)-cyclopropyl(2-fluoro-4-(trifluoromethyl)phenyl)methyl)-2-((5-(ethylamino)-2-methyl-4-pyridinyl)carbonyl)-2-azabicyclo[3.1.0]hexane-3-carboxamide | LCMS-APCI (POS.) m/z: 505.2 (M + H)+ | 1H NMR (400 MHz, Methylene Chloride-d2) δ ppm 8.07 (s, 1 H), 7.43-7.56 (m, 2 H), 7.38 (d, J = 10.8 Hz, 2 H), 7.17 (s, 1 H), 5.09 (dd, J = 10.4 Hz, 1 H), 4.58 (t, J = 8.0 Hz, 1 H), 3.19-3.35 (m, 3 H), 2.49 (s, 3 H), 2.29-2.40 (m, 1 H), 1.67-1.75 (m, 1 H), 1.39-1.56 (m, 3 H), 1.30 (t, J = 7.1 Hz, 3 H), 1.17-1.27 (m, 2 H), 0.92-1.00 (m, 1 H), 0.77-0.84 (m, 1 H), 0.51-0.66 (m, 2 H), 0.36-0.46 (m, 2 H). | S |
| 384 | N-(4-(trifluoromethyl)benzyl)-1-(((3S)-1-(((3S)-3-(trifluoromethyl)-1-pyrrolidinyl)sulfonyl)-3-piperidinyl)carbonyl)-D-prolinamide | LCMS-ESI (POS.) m/z: 585.2 (M + H)+ | 1H NMR (500 MHz, CHLOROFORM-d) δ ppm 7.57 (d, J = 8.04 Hz, 2 H), 7.42 (br s, 1 H), 7.35 (d, J = 7.50 Hz, 2 H), 4.57-4.67 (m, 1 H), 4.53 (dd, J = 15.31, 6.49 Hz, 1 H), 4.41 (dd, J = 15.31, 5.71 Hz, 1 H), 3.72-3.89 (m, 2 H), 3.52-3.66 (m, 3 H), 3.33-3.45 (m, 3 H), 2.87-3.09 (m, 2 H), 2.62-2.84 (m, 3 H), 2.44 (ddd, J = 9.34, 6.36, 3.50 Hz, 1 H), 2.01-2.24 (m, 4 H), 1.85-1.98 (m, 2 H), 1.76-1.83 (m, 1 H), 1.62-1.75 (m, 1 H), 1.39-1.60 (m, 1 H) | M |
| 385 | 1-(3-((3-hydroxy-3-methyl-1-azetidinyl)sulfonyl)benzoyl)-N-(4-(trifluoromethyl)benzyl)-D-prolinamide | LCMS-ESI (POS.) m/z: 562.2 (M + H)+ | 1H NMR (400 MHz, CHLOROFORM-d) δ 7.33-8.07 (m, 8H), 7.16-7.26 (m, 1H), 4.54-4.78 (m, 2H), 4.06-4.20 (m, 2H), 3.72-3.77 (m, 2H), 3.57-3.69 (m, 3H), 3.47-3.55 (m, 1H), 2.38-2.50 (m, 1H), 2.12-2.26 (m, 2H), 1.58-1.99 (m, 1H), 1.43-1.53 (m, 3H) | C |
| 386 | 1-(3-((3-cyano-1-azetidinyl)sulfonyl)benzoyl)-N-((1R)-2-hydroxy-1-(3-(trifluoromethyl)phenyl)ethyl)-D-prolinamide | LCMS-ESI (POS.) m/z: 551.0 (M + H)+ | 1H NMR (500 MHz, DMSO-d6) δ ppm 8.48 (s, 1 H), 7.20-8.02 (m, 8 H), 4.74-5.06 (m, 2 H), 4.25-4.67 (m, 1 H), 3.78-4.10 (m, 4 H), 3.43-3.71 (m, 5 H), 2.16-2.31 (m, 1 H), 1.73-2.01 (m, 3 H) | A |

| Ex. # | Structure Name | LCMS-ESI (POS/NEG) m/z: (M + H)+ | NMR Data | Syn. Rte. |
|---|---|---|---|---|
| 387 | 1-(((3S)-1-((3-cyano-1-azetidinyl)sulfonyl)-3-piperidinyl)carbonyl)-N-(3-methoxy-4-methylbenzyl)-D-prolinamide | LCMS-ESI (POS.) m/z: 504.2 (M + H)+ | 1H NMR (500 MHz, DMSO-d6) δ ppm 8.18-8.60 (m, 1 H), 7.00-7.12 (m, 1 H), 6.77-6.88 (m, 1 H), 6.66-6.75 (m, 1 H), 4.19-4.50 (m, 3 H), 3.99-4.13 (m, 2 H), 3.85-3.98 (m, 2 H), 3.71-3.84 (m, 4 H), 3.46-3.69 (m, 4 H), 2.60-2.83 (m, 3 H), 2.02-2.38 (m, 4 H), 1.66-2.01 (m, 5 H), 1.31-1.56 (m, 2 H) | A |
| 388 | 1-(((3S)-1-((3-cyano-1-azetidinyl)sulfonyl)-3-piperidinyl)carbonyl)-N-((1R)-2-methoxy-1-(3-(trifluoromethyl)phenyl)ethyl)-D-prolinamide, 1-(((3S)-1-((3-cyano-1-azetidinyl)sulfonyl)-3-piperidinyl)carbonyl)-N-((1S)-2-methoxy-1-(3-(trifluoromethyl)phenyl)ethyl)-D-prolinamide | LCMS-ESI (POS.) m/z: 572.2 (M + H)+ | 1H NMR (500 MHz, DMSO-d6) δ ppm 8.23-8.81 (m, 1 H), 7.49-7.82 (m, 4 H), 5.00-5.22 (m, 1 H), 4.32-4.59 (m, 1 H), 4.06 (br t, J = 8.24 Hz, 2 H), 3.88-3.99 (m, 2 H), 3.74-3.86 (m, 1 H), 3.47-3.67 (m, 6 H), 3.21-3.27 (m, 3 H), 2.59-2.90 (m, 3 H), 2.02-2.34 (m, 1 H), 1.62-2.00 (m, 5 H), 1.30-1.57 (m, 2 H) | A |
| 389 | (1R,3R,5R)-N-((R)-(4-chloro-2,5-difluorophenyl)(cyclopropyl)methyl)-2-((2-(ethylsulfonyl)-4-pyridinyl)carbonyl)-2-azabicyclo[3.1.0]hexane-3-carboxamide | LCMS-ESI (POS.) m/z: 524.1 (M + H)+ | 1H NMR (500 MHz, DMSO-d6) δ ppm 8.83-8.99 (m, 1 H), 8.39-8.74 (m, 1 H), 8.17 (s, 1 H), 7.95 (dd, J = 4.80, 1.43 Hz, 1 H), 7.31-7.79 (m, 2 H), 4.56-5.03 (m, 2 H), 4.02-4.54 (m, 2 H), 3.76 (td, J = 6.23, 2.34 Hz, 1 H), 3.40-3.54 (m, 2 H), 3.29 (td, J = 6.16, 2.47 Hz, 1 H), 2.53-2.77 (m, 1 H), 1.54-1.81 (m, 2 H), 1.05-1.31 (m, 5 H), 0.41-0.99 (m, 3 H), −0.25-0.40 (m, 3 H) | H |
| 390 | 1-(((3S)-1-((3-cyano-1-azetidinyl)sulfonyl)-3-piperidinyl)carbonyl)-N-(3,5-dichlorobenzyl)-D-prolinamide | LCMS-ESI (POS.) m/z: 528.0 (M + H)+ | 1H NMR (400 MHz, CHLOROFORM-d) δ ppm 7.54 (br t, J = 5.86 Hz, 1 H), 7.25 (t, J = 1.87 Hz, 1 H), 7.11 (d, J = 1.87 Hz, 2 H), 4.63 (dd, J = 7.98, 2.07 Hz, 1 H), 4.52 (dd, J = 15.65, 7.05 Hz, 1 H), 4.23 (dd, J = 15.65, 5.18 Hz, 1 H), 4.06-4.16 (m, 4 H), 3.73-3.82 (m, 2 H), 3.54-3.64 (m, 2 H), 3.43 (tt, J = 8.68, 6.56 Hz, 1 H), 2.99 (dd, J = 12.75, 10.99 Hz, 1 H), 2.66-2.83 (m, 2 H), 2.48 (ddt, J = 12.44, 6.63, 2.75, 2.75 Hz, 1 H), 2.13-2.27 (m, 1 H), 2.01-2.12 (m, 1 H), 1.98 (br d, J = 12.96 Hz, 1 H), 1.79-1.94 (m, 2 H), 1.62-1.74 (m, 1 H), 1.51-1.61 (m, 1 H) | A |

| Ex. # | Structure Name | LCMS-ESI (POS/NEG) m/z: (M + H)+ | NMR Data | Syn. Rte. |
|---|---|---|---|---|
| 391 | 1-(((3S)-1-((3-cyano-1-azetidinyl)sulfonyl)-3-piperidinyl)carbonyl)-N-((1R)-1-(3,5-difluorophenyl)ethyl)-D-prolinamide | LCMS-ESI (POS.) m/z: 510.2 (M + H)+ | 1H NMR (500 MHz, DMSO-d6) δ ppm 8.16-8.65 (m, 1 H), 6.94-7.18 (m, 3 H), 4.84-4.98 (m, 1 H), 4.24-4.51 (m, 1 H), 4.01-4.09 (m, 2 H), 3.88-3.97 (m, 2 H), 3.74-3.85 (m, 1 H), 3.52-3.65 (m, 3 H), 3.32-3.51 (m, 1 H), 2.65-2.86 (m, 2 H), 2.19-2.35 (m, 1 H), 2.04-2.15 (m, 1 H), 1.62-1.96 (m, 5 H), 1.38-1.56 (m, 2 H), 1.08-1.36 (m, 3 H) | A |
| 392 | (1R,3R,5R)-N-((R)-(2-fluoro-4-(trifluoromethyl)phenyl)(3-oxetanyl)methyl)-2-((2-(trifluoromethyl)-4-pyridinyl)carbonyl)-2-azabicyclo[3.1.0]hexane-3-carboxamide | LCMS-APCI (POS.) m/z: 532.1 (M + H)+ | 1H NMR (400 MHz, DMSO-d6) δ ppm 8.91 (d, 1 H), 8.63 (d, J = 8.0, 125.8 Hz, 1 H), 7.85-8.04 (m, 2 H), 7.58-7.74 (m, 3 H), 7.37-7.58 (m, 1 H), 5.49 (t, 2 H), 4.90 (dd, J = 3.6, 11.3 Hz, 1 H), 4.65 (dd, J = 6.3, 7.7 Hz, 1 H), 4.52 (dd, J = 6.2, 7.9 Hz, 1 H), 4.41 (t, J = 6.1 Hz, 1 H), 4.20-4.38 (m, 1 H), 3.59-3.88 (m, 1 H), 3.37-3.47 (m, 1 H), 3.29 (dd, J = 2.6, 6.2 Hz, 1 H), 2.56-2.76 (m, 1 H), 1.57-1.76 (m, 2 H), 1.14 (td, J = 2.5, 5.1 Hz, 1 H), 0.66-0.80 (m, 1 H). | Q |
| 393 | (1R,2R,5S)-N-((R)-(4-chloro-2,5-difluorophenyl)(cyclopropyl)methyl)-3-((2-(methylsulfonyl)-4-pyridinyl)carbonyl)-3-azabicyclo[3.1.0]hexane-2-carboxamide | LCMS-ESI (POS.) m/z: 510.0 (M + H)+ | 1H NMR (400 MHz, CHLOROFORM-d) δ ppm 8.74-8.89 (m, 1 H), 8.01-8.14 (m, 1 H), 7.49-7.63 (m, 1 H), 7.10-7.22 (m, 2 H), 7.06 (br d, J = 6.95 Hz, 1 H), 4.79-5.35 (m, 1 H), 4.21-4.52 (m, 1 H), 3.82-4.19 (m, 1 H), 3.39 (d, J = 10.26 Hz, 1 H), 3.21-3.32 (m, 3 H), 1.85 (td, J = 7.44, 4.09 Hz, 1 H), 1.66-1.74 (m, 1 H), 1.11-1.29 (m, 1 H), 0.87 (td, J = 7.67, 6.01 Hz, 1 H), 0.51-0.70 (m, 2 H), 0.33-0.49 (m, 2 H), 0.19-0.33 (m, 1 H) | C |
| 394 | 1-(((3S)-1-((3-cyano-1-azetidinyl)sulfonyl)-3-piperidinyl)carbonyl)-N-(2,5-difluorobenzyl)-D-prolinamide | LCMS-ESI (POS.) m/z: 496.2 (M + H)+ | 1H NMR (500 MHz, DMSO-d6) δ ppm 8.28-8.70 (m, 1 H), 7.17-7.28 (m, 1 H), 7.01-7.17 (m, 2 H), 4.19-4.56 (m, 3 H), 4.00-4.11 (m, 2 H), 3.87-3.98 (m, 2 H), 3.74-3.83 (m, 1 H), 3.38-3.70 (m, 4 H), 2.68-2.91 (m, 2 H), 1.88-2.33 (m, 4 H), 1.33-1.87 (m, 5 H) | A |

| Ex. # | Structure Name | LCMS-ESI (POS/NEG) m/z: (M + H)+ | NMR Data | Syn. Rte. |
|---|---|---|---|---|
| 395 | 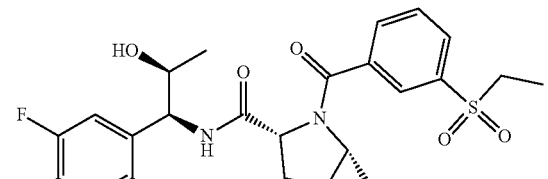<br>(1R,3R,5R)-N-((1S,2S)-1-(4-chloro-2,5-difluorophenyl)-2-hydroxypropyl)-2-(3-(ethylsulfonyl)benzoyl)-2-azabicyclo[3.1.0]hexane-3-carboxamide | LCMS-ESI (POS.) m/z: 527.2 (M + H)+ | 1H NMR (500 MHz, DMSO-d6) δ ppm 8.45 (d, J = 8.43 Hz, 1 H) 8.13 (s, 1 H) 8.00-8.06 (m, 2 H) 7.80 (t, J = 7.79 Hz, 1 H) 7.62 (dd, J = 9.41, 6.16 Hz, 1 H) 7.41 (dd, J = 9.99, 6.10 Hz, 1 H) 5.09 (dd, J = 11.29, 3.50 Hz, 1 H) 4.93-4.99 (m, 2 H) 3.79-3.86 (m, 1 H) 3.33-3.37 (m, 2 H) 3.25 (td, J = 6.07, 2.40 Hz, 1 H) 2.54-2.62 (m, 1 H) 1.74-1.79 (m, 1 H) 1.65-1.72 (m, 1 H) 1.07-1.13 (m, 7 H) 0.71-0.78 (m, 1 H) | C |
| 396 | 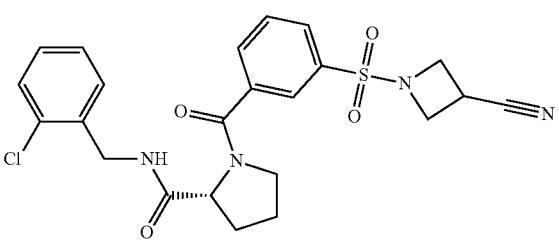 [SMILES: N#CC1CN(S(=O)(=O)c2cccc(C(=O)N3CCC[C@@H]3C(=O)NCc3ccccc3Cl)c2)C1]<br>N-(2-chlorobenzyl)-1-((3-((3-cyano-1-azetidinyl)sulfonyl)phenyl)carbonyl)-D-prolinamide | LCMS-APCI (NEG.) m/z: 485.1 (M − H) | 1H NMR (400 MHz, Methanol-d4) δ ppm 8.13 (q, J = 2.0 Hz, 1 H), 7.99 (ddd, J = 1.6, 3.1, 8.2 Hz, 2 H), 7.79 (dd, J = 6.5, 9.1 Hz, 1 H), 7.50 (d, J = 7.6 Hz, 1 H), 7.34-7.41 (m, 1 H), 7.17-7.33 (m, 3 H), 4.64 (ddd, J = 2.4, 6.1, 8.4 Hz, 1 H), 4.53 (d, J = 2.3 Hz, 2 H), 4.11 (td, J = 2.3, 8.8 Hz, 2 H), 3.92 (dtd, J = 2.5, 5.6, 8.2 Hz, 3 H), 3.68 (dt, J = 7.0, 9.7 Hz, 1 H), 3.48-3.61 (m, 2 H), 2.28-2.46 (m, 1 H), 2.00-2.07 (m, 2 H), 1.83-1.95 (m, 1 H). | A |
| 397 | 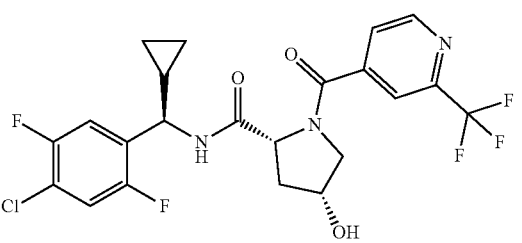 [SMILES: O=C(N[C@@H](c1cc(F)c(Cl)cc1F)C1CC1)[C@H]1C[C@@H](O)CN1C(=O)c1ccnc(C(F)(F)F)c1]<br>(4R)-N-((R)-(4-chloro-2,5-difluorophenyl)(cyclopropyl)methyl)-4-hydroxy-1-((2-(trifluoromethyl)-4-pyridinyl)carbonyl)-D-prolinamide | LCMS-APCI (POS.) m/z: 504.1 (M + H)+ | 1H NMR (400 MHz, DMSO-d6) δ ppm 9.01 (dd, J = 4.9, 33.8 Hz, 1 H), 8.71 (dd, J = 7.6, 67.9 Hz, 1 H), 8.04 (dt, J = 1.2, 32.3 Hz, 1 H), 7.91 (ddd, J = 1.1, 4.4, 61.1 Hz, 1 H), 7.74 (ddd, J = 6.2, 9.4, 12.0 Hz, 1 H), 7.52-7.68 (m, 1 H), 5.28 (dd, J = 5.4, 83.6 Hz, 1 H), 4.57-4.68 (m, 1 H), 4.16-4.40 (m, 1 H), 3.85 (ddd, J = 5.9, 11.0, 103.4 Hz, 1 H), 3.37-3.46 (m, 1 H), 2.56 (ddd, J = 5.9, 9.1, 14.7 Hz, 1 H), 1.77-1.87(m, 1 H), 1.35 (dq, J = 3.6, 4.5, 8.2 Hz, 1 H), 0.58-0.75 (m, 1 H), 0.52 (s, 1 H), 0.40-0.49 (m, 1 H). | Q |

| Ex. # | Structure Name | LCMS-ESI (POS/NEG) m/z: (M + H)+ | NMR Data | Syn. Rte. |
|---|---|---|---|---|
| 398 | 1-(((3S)-1-((3-(3-chlorophenyl)-1-azetidinyl)sulfonyl)-3-piperidinyl)carbonyl)-N-(4-(trifluoromethyl)benzyl)-D-prolinamide | LCMS-ESI (POS.) m/z: 613.2 (M + H)+ | 1H NMR (500 MHz, CHLOROFORM-d) δ ppm 7.57 (d, J = 8.04 Hz, 2 H), 7.43 (t, J = 6.76 Hz, 1 H), 7.24-7.36 (m, 5 H), 4.60 (br d, J = 6.49 Hz, 1 H), 4.39-4.55 (m, 3 H), 4.17-4.23 (m, 3 H), 3.97 (t, J = 7.40 Hz, 3 H), 3.84 (br d, J = 12.20 Hz, 3 H), 3.75 (quin, J = 7.72 Hz, 1 H), 3.56-3.65 (m, 3 H), 2.96 (t, J = 11.94 Hz, 1 H), 2.68-2.84 (m, 3 H), 2.44 (ddd, J = 9.21, 6.36, 3.37 Hz, 1 H), 2.14-2.31 (m, 1 H), 2.00-2.09 (m, 1 H), 1.85-1.95 (m, 3 H), 1.76-1.84 (m, 1 H), 1.61-1.74 (m, 1 H), 1.53 (qd, J = 12.72, 3.63 Hz, 1H) | M |
| 399 | (4R)-N-((R)-(4-chloro-2,5-difluorophenyl)(3-oxetanyl)methyl)-4-hydroxy-1-((2-(trifluoromethyl)-4-pyridinyl)carbonyl)-D-prolinamide | LCMS-APCI (POS.) m/z: 520.1 (M + H)+ | 1H NMR (400 MHz, Methanol-d4) δ ppm 8.88 (d, J = 4.9 Hz, 1 H), 8.02 (s, 1 H), 7.84 (ddd, J = 1.5, 4.3, 6.3 Hz, 1 H), 7.35 (ddd, J = 6.2, 9.5, 26.1 Hz, 2 H), 5.64 (dd, J = 5.2, 10.2 Hz, 1 H), 4.70 (dd, J = 6.4, 7.8 Hz, 1 H), 4.58-4.66 (m, 2 H), 4.39-4.50 (m, 1 H), 4.31-4.39 (m, 1 H), 3.68 (dd, J = 5.3, 10.6 Hz, 1 H), 3.52-3.59 (m, 1 H), 3.47 (dd, J = 4.6, 10.5 Hz, 1 H), 2.43-2.59 (m, 1 H), 1.85-1.99 (m, 1 H). | Q |
| 400 | 1-(((3S)-1-((3-cyano-1-azetidinyl)sulfonyl)-3-piperidinyl)carbonyl)-N-((2-(trifluoromethyl)-5-pyrimidinyl)methyl)-D-prolinamide | LCMS-ESI (POS.) m/z: 530.2 (M + H)+ | 1H NMR (500 MHz, DMSO-d6) δ ppm 8.86-8.98 (m, 2 H), 8.48-8.81 (m, 1 H), 4.33-4.58 (m, 2 H), 4.19-4.28 (m, 1 H), 4.01-4.11 (m, 2 H), 3.88-3.98 2 H), 3.74 3.83 (m, 1 H), 3.31-3.70 (m, 4 H), 2.72-2.89 (m, 2 H), 2.58-2.70 (m, 1 H), 1.62-2.40 (m, 6 H), 1.33-1.56 (m, 2 H) | A |
| 401 | (2R)-N-((R)-cyclopropyl(2-fluoro-4-(trifluoromethyl)phenyl)methyl)-1-(3-(methylsulfonyl)benzoyl)-2,5-dihydro-1H-pyrrole-2-carboxamide | LCMS-ESI (POS.) m/z: 511.2 (M + H)+ | 1H NMR (500 MHz, CHLOROFORM-d) δ ppm 8.12-8.24 (m, 1 H), 7.96-8.12 (m, 1 H), 7.76-7.91 (m, 1 H), 7.67-7.76 (m, 1 H), 7.40-7.61 (m, 3 H), 7.32-7.39 (m, 1 H), 5.89-6.18 (m, 2 H), 5.44-5.61 (m, 1 H), 4.54-4.66 (m, 1 H), 4.34-4.53 (m, 1 H), 4.05-4.19 (m, 1 H), 3.06-3.17 (m, 3 H), 1.07-1.36 (m, 1 H), 0.59-0.73 (m, 1 H), 0.52-0.59 (m, 1 H), 0.11-0.50 (m, 2 H) | C |

| Ex. # | Structure Name | LCMS-ESI (POS/NEG) m/z: (M + H)+ | NMR Data | Syn. Rte. |
|---|---|---|---|---|
| 402 | (2R,4S)-N-((R)-cyclopropyl(2-fluoro-4-(trifluoromethyl)phenyl)methyl)-4-fluoro-1-(3-(methylsulfonyl)benzoyl)pyrrolidine-2-carboxamide | LCMS-ESI (POS.) m/z: 531.2 (M + H)+ | 1H NMR (500 MHz, DMSO-d6) δ ppm 8.55-8.94 (m, 1 H), 7.44-8.13 (m, 7 H), 5.16-5.46 (m, 1 H), 4.56-4.80 (m, 2 H), 3.48-4.15 (m, 3 H), 3.26-3.31 (m, 3 H), 1.81-2.05 (m, 1 H), 0.80-1.27 (m, 1 H),-0.28-0.68 (m, 4 H) | C |
| 403 | (1R,3R,5R)-N-((R)-(4-chlorophenyl)(3-oxetanyl)methyl)-2-(3-(ethylsulfonyl)benzoyl)-2-azabicyclo[3.1.0]hexane-3-carboxamide | LCMS-APCI (POS.) m/z: 503.1 (M + H)+ | 1H NMR (400 MHz, Methanol-d4) δ ppm 8.35 (t, J = 1.7 Hz, 1 H), 8.13 (dt, J = 1.3, 7.7 Hz, 1 H), 8.07 (ddd, J = 1.1, 1.9, 7.9 Hz, 1 H), 7.79 (t, J = 7.8 Hz, 1 H), 7.35-7.41 (m, 2 H), 7.28-7.34 (m, 2 H), 5.33 (d, J = 10.2 Hz, 1 H), 4.99 (dd, J = 4.2, 11.4 Hz, 1 H), 4.83 (dd, J = 6.4, 7.7 Hz, 1 H), 4.58-4.67 (m, 2 H), 4.40 (t, J = 6.3 Hz, 1 H), 3.42-3.52 (m, 1 H), 3.23-3.38 (m, 7 H), 2.66 (dddd, J = 1.1, 6.5, 11.4, 12.4 Hz, 1 H), 1.91 (dd, 1 H), 1.75-1.84 (m, 1 H), 1.23-1.31 (m, 4 H), 0.90 (dtd, J = 1.1, 5.6, 9.0 Hz, 1 H). | A |
| 404 | 1-(((3S)-1-((3-cyano-1-azetidinyl)sulfonyl)-3-piperidinyl)carbonyl)-N-((1S)-2-hydroxy-1-(3-(trifluoromethyl)phenyl)ethyl)-D-prolinamide | LCMS-ESI (POS.) m/z: 558.0 (M + H)+ | 1H NMR (500 MHz, DMSO-d6) δ ppm 8.13-8.81 (m, 1 H), 7.46-7.70 (m, 4 H), 4.82-5.00 (m, 2 H), 4.32-4.60 (m, 1 H), 4.01-4.15 (m, 2 H), 3.89-4.00 (m, 2 H), 3.75-3.85 (m, 1 H), 3.46-3.70 (m, 5 H), 3.35-3.42 (m, 1 H), 2.70-2.89 (m, 2 H), 2.62-2.70 (m, 1 H), 2.07-2.39 (m, 1 H), 1.60-1.98 (m, 5 H), 1.31-1.58 (m, 2 H) | A |
| 405 | (1R,3R,5R)-N-((1S,2S)-1-(4-chloro-2,5-difluorophenyl)-2-hydroxypropyl)-2-(3-(methylsulfonyl)benzoyl)-2-azabicyclo[3.1.0]hexane-3-carboxamide | LCMS-ESI (POS.) m/z: 513.0 (M + H)+ | 1H NMR (500 MHz, DMSO-d6) δ ppm 8.21-8.49 (m, 1 H) 7.19-8.20 (m, 6 H) 4.64-5.12 (m, 3 H) 3.68-3.88 (m, 1 H) 3.22-3.28 (m, 4 H) 2.57 (td, J = 12.52, 6.23 Hz, 1 H) 1.53-1.81 (m, 2 H) 0.41-1.16 (m, 5 H) | A |

| Ex. # | Structure Name | LCMS-ESI (POS/NEG) m/z: (M + H)+ | NMR Data | Syn. Rte. |
|---|---|---|---|---|
| 406 | 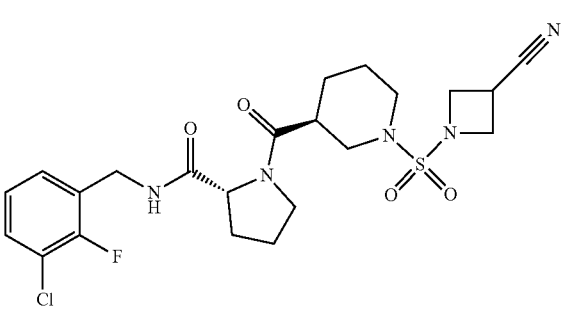<br>N-(3-chloro-2-fluorobenzyl)-1-(((3S)-1-((3-cyano-1-azetidinyl)sulfonyl)-3-piperidinyl)carbonyl)-D-prolinamide | LCMS-ESI (POS.) m/z: 512.2 (M + H)+ | 1H NMR (500 MHz, DMSO-d6) δ ppm 8.23-8.79 (m, 1 H), 7.09-7.55 (m, 3 H), 4.21-4.51 (m, 3 H), 3.99-4.14 (m, 2 H), 3.88-3.99 (m, 2 H), 3.73-3.85 (m, 1 H), 3.34-3.69 (m, 4 H), 2.71-2.88 (m, 2 H), 2.61-2.71 (m, 1 H), 1.63-2.30 (m, 6 H), 1.32-1.55 (m, 2 H) | A |
| 407 | 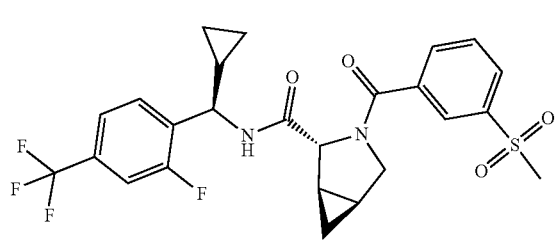 [SMILES: CS(=O)(=O)c1cccc(C(=O)N2C[C@H]3C[C@H]3[C@@H]2C(=O)N[C@@H](c2ccc(C(F)(F)F)cc2F)C2CC2)c1]<br>(1R,2R,5S)-N-((R)-cyclopropyl(2-fluoro-4-(trifluoromethyl)phenyl)methyl)-3-(3-(methylsulfonyl)benzoyl)-3-azabicyclo[3.1.0]hexane-2-carboxamide | LCMS-ESI (POS.) m/z: 525.0 (M + H)+ | 1H NMR (400 MHz, CHLOROFORM-d) δ ppm 7.97-8.10 (m, 2 H), 7.72-7.80 (m, 1 H), 7.65-7.72 (m, 1 H), 7.46-7.53 (m, 1 H), 7.39-7.46 (m, 1 H), 7.30-7.39 (m, 1 H), 7.22-7.27 (m, 1 H), 4.85-4.97 (m, 1 H), 4.53-4.65 (m, 1 H), 3.87 (dd, J = 10.31, 4.09 Hz, 1 H), 3.45 (d, J = 10.37 Hz, 1 H), 3.10 (s, 2 H), 3.00-3.13 (m, 1 H), 1.83-1.91 (m, 1 H), 1.62-1.71 (m, 1 H), 1.21-1.34 (m, 1 H), 0.78-0.89 (m, 1 H), 0.50-0.69 (m, 2 H), 0.29-0.49 (m, 2 H), 0.19-0.27 (m, 1 H) | C |
| 408 | 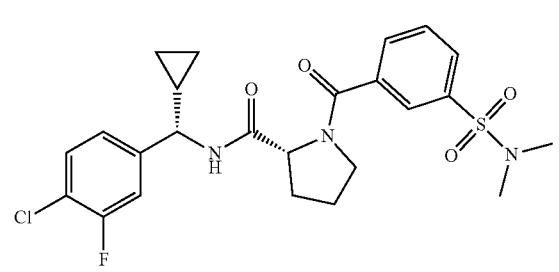 [SMILES: CN(C)S(=O)(=O)c1cccc(C(=O)N2CCC[C@@H]2C(=O)N[C@H](c2ccc(Cl)c(F)c2)C2CC2)c1]<br>N-((S)-(4-chloro-3-fluorophenyl)(cyclopropyl)methyl)-1-(3-(dimethylsulfamoyl)benzoyl)-D-prolinamide | LCMS-ESI (POS.) m/z: 508.2 (M + H)+ | 1H NMR (500 MHz, DMSO-d6) δ ppm 8.56 (br d, J = 8.04 Hz, 1 H), 6.65-7.92 (m, 7 H), 4.01-4.58 (m, 2 H), 3.43-3.72 (m, 2 H), 2.63 (s, 6 H), 2.25 (br s, 1 H), 1.71-2.01 (m, 3 H), 1.00-1.14 (m, 1 H), 0.18-0.62 (m, 4 H) | A |

| Ex. # | Structure Name | LCMS-ESI (POS/NEG) m/z: (M + H)+ | NMR Data | Syn. Rte. |
|---|---|---|---|---|
| 409 | 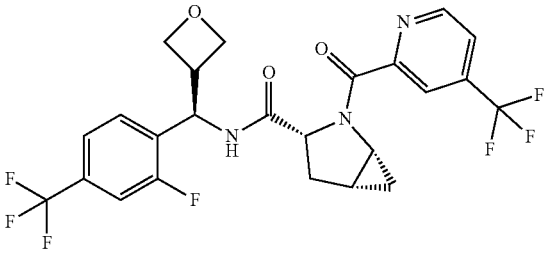 [SMILES: O=C(N[C@@H](c1ccc(C(F)(F)F)cc1F)C1COC1)[C@H]1C[C@H]2C[C@H]2N1C(=O)c1cc(C(F)(F)F)ccn1]<br>(1R,3R,5R)-N-((R)-(2-fluoro-4-(trifluoromethyl)phenyl)(3-oxetanyl)methyl)-2-((4-(trifluoromethyl)-2-pyridinyl)carbonyl)-2-azabicyclo[3.1.0]hexane-3-carboxamide | LCMS-APCI (POS.) m/z: 532.1 (M + H)+ | 1H NMR (Methanol-d4) δ: 8.93 (d, J = 5.1 Hz, 1H), 8.74 (d, J = 5.1 Hz, 1H), 8.23-8.13 (m, 2H), 7.85 (d, J = 5.1 Hz, 1H), 7.77 (d, J = 5.1 Hz, 1H), 7.62-7.36 (m, 5H), 5.72 (dd, J = 11.7, 3.0 Hz, 1H), 5.67 (d, J = 10.2 Hz, 1H), 5.32 (d, J = 9.6 Hz, 1H), 5.00 (dd, J = 11.5, 3.8 Hz, 1H), 4.72-4.61 (m, 2H), 4.57-4.50 (m, 1H), 4.42 (t, J = 6.2 Hz, 1H), 4.16 (t, J = 6.1 Hz, 1H), 4.04 (t, J = 6.3 Hz, 1H), 3.97 (td, J = 6.3, 2.6 Hz, 1H), 3.57 (d, J = 15.6 Hz, 1H), 2.90-2.77 (m, 1H), 2.72-2.58 (m, 1H), 1.99 (dd, J = 13.4, 3.0 Hz, 1H), 1.92 (dd, J = 13.5, 3.8 Hz, 1H), 1.82-1.72 (m, 1H), 1.71-1.60 (m, 1H), 1.31 (s, 3H), 1.18-1.11 (m, 1H), 0.99-0.72 (m, 5H) | Q |
| 410 | 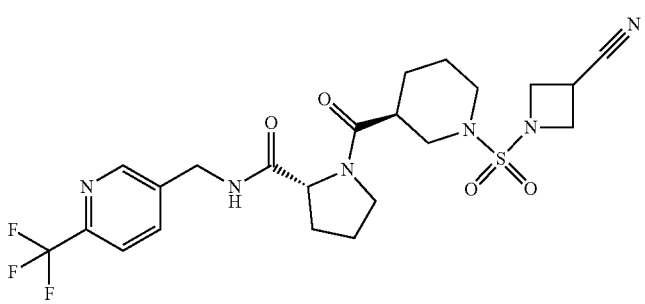<br>1-(((3S)-1-((3-cyano-1-azetidinyl)sulfonyl)-3-piperidinyl)carbonyl)-N-((6-(trifluoromethyl)-3-pyridinyl)methyl)-D-prolinamide | LCMS-ESI (POS.) m/z: 529.2 (M + H)+ | 1H NMR (500 MHz, DMSO-d6) δ ppm 8.78* (t, J = 5.77 Hz, 1 H), 8.62-8.68 (m, 1 H), 8.45 (t, J = 5.97 Hz, 1 H), 7.90 (t, J = 6.81 Hz, 1 H), 7.83-7.88 (m, 1 H), 4.24-4.52 (m, 3 H), 4.01-4.10 (m, 2 H), 3.90-3.97 (m, 2 H), 3.79 (tq, J = 8.85, 6.00 Hz, 1 H), 3.31-3.69 (m, 4 H), 2.73-2.89 (m, 2 H), 2.65 (tt, J = 11.14, 3.39 Hz, 1 H), 2.26-2.34* (m, 1 H), 2.17-2.26* (m, 1 H), 2.07-2.15 (m, 1 H), 1.66-1.99 (m, 5 H), 1.36-1.55 (m, 2 H). Spectrum appears as 3:1 mixture of rotamers, *denotes resolved minor rotamer peaks. | C |
| 411 | 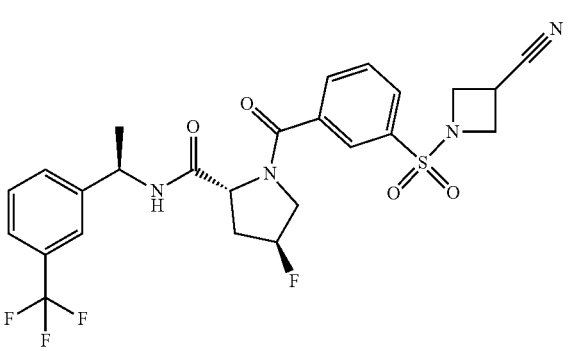<br>(4S)-1-((3-((3-cyano-1-azetidinyl)sulfonyl)phenyl)carbonyl)-4-fluoro-N-((1R)-1-(3-(trifluoromethyl)phenyl)ethyl)-D-prolinamide | LCMS-ESI (POS.) m/z: 530.2 (M + H)+ | 1H NMR (500 MHz, DMSO-d6) δ ppm 8.38-8.76 (m, 1 H), 7.72-8.04 (m, 4 H), 7.43-7.67 (m, 4 H), 5.21-5.47 (m, 1 H), 4.56-5.09 (m, 2 H), 3.60-4.07 (m, 7 H), 2.53-2.61 (m, 1 H), 1.90-2.08 (m, 1 H), 0.96-1.48 (m, 3 H) | C |

| Ex. # | Structure Name | LCMS-ESI (POS/NEG) m/z: (M + H)+ | NMR Data | Syn. Rte. |
|---|---|---|---|---|
| 412 | 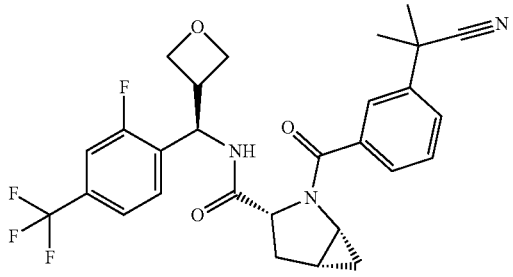 [SMILES: CC(C)(C#N)c1cccc(C(=O)N2[C@@H](C(=O)N[C@@H](c3ccc(C(F)(F)F)cc3F)C3COC3)C[C@H]3C[C@H]32)c1]<br>(1R,3R,5R)-2-(3-(2-cyano-2-propanyl)benzoyl)-N-((R)-(2-fluoro-4-(trifluoromethyl)phenyl)(3-oxetanyl)methyl)-2-azabicyclo[3.1.0]hexane-3-carboxamide | LCMS-APCI (POS.) m/z: 530.2 (M + H)+ | 1H NMR (400 MHz, Methanol-d4) δ ppm 8.00 (t, J = 1.8 Hz, 1 H), 7.75 (dt, J = 1.4, 7.6 Hz, 1 H), 7.71 (ddd, J = 1.1, 2.1, 8.0 Hz, 1 H), 7.54-7.59 (m, 3 H), 7.49-7.54 (m, 1 H), 5.66 (d, J = 10.1 Hz, 1 H), 5.00 (dd, J = 4.2, 11.4 Hz, 1 H), 4.83-4.86 (m, 1 H), 4.62-4.70 (m, 2 H), 4.40 (t, J = 6.2 Hz, 1 H), 3.30 (dd, J = 2.7, 6.3 Hz, 1 H), 2.60-2.70 (m, 1 H), 1.91 (dd, J = 4.2, 13.6 Hz, 1 H), 1.78 (s, 8 H), 1.24 (td, J = 2.6, 5.3 Hz, 1 H), 0.89 (dt, J = 5.7, 8.6 Hz, 1 H). | Q |
| 413 | 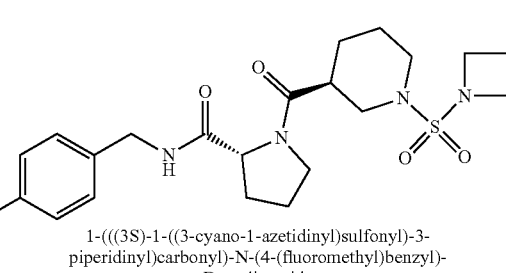<br>1-(((3S)-1-((3-cyano-1-azetidinyl)sulfonyl)-3-piperidinyl)carbonyl)-N-(4-(fluoromethyl)benzyl)-D-prolinamide | LCMS-ESI (POS.) m/z: 492.2 (M + H)+ | 1H NMR (500 MHz, DMSO-d6) δ ppm 8.28 (s, 1 H), 7.25-7.42 (m, 4 H), 5.40-5.44 (m, 1 H), 5.32-5.35 (m, 1 H), 4.25-4.50 (m, 3 H), 4.03-4.11 (m, 2 H), 3.90-3.97 (m, 2 H), 3.76-3.83 (m, 1 H), 3.34-3.69 (m, 4 H), 2.73-2.86 (m, 2 H), 2.61-2.70 (m, 1 H), 2.03-2.23 (m, 1 H), 1.66-1.96 (m, 5 H), 1.34-1.55 (m, 2 H) | F |
| 414 | 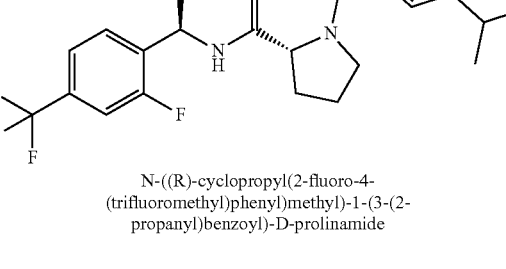<br>N-((R)-cyclopropyl(2-fluoro-4-(trifluoromethyl)phenyl)methyl)-1-(3-(2-propanyl)benzoyl)-D-prolinamide | LCMS-ESI (POS.) m/z: 477.2 (M + H)+ | 1H NMR (500 MHz, CHLOROFORM-d) δ ppm 7.93 (br d, J = 6.75 Hz, 1 H), 7.45-7.57 (m, 1 H), 7.29-7.44 (m, 7 H), 4.83 (dd, J = 7.66, 4.80 Hz, 1 H), 4.65 (t, J = 7.79 Hz, 1 H), 3.37-3.61 (m, 2 H), 2.97 (dt, J = 13.75, 6.88 Hz, 1 H), 2.41-2.54 (m, 1 H), 1.93-2.19 (m, 2 H), 1.76-1.93 (m, 1 H), 1.29 (d, J = 6.75 Hz, 7 H), 0.48-0.71 (m, 2 H), 0.33-0.48 (m, 2 H) | C |
| 415 | 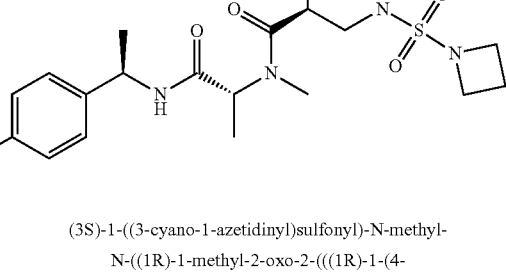<br>(3S)-1-((3-cyano-1-azetidinyl)sulfonyl)-N-methyl-N-((1R)-1-methyl-2-oxo-2-(((1R)-1-(4-(trifluoromethyl)phenyl)ethyl)amino)ethyl)-3-piperidinecarboxamide | LCMS-ESI (POS.) m/z: 530.2 (M + H)+ | 1H NMR (500 MHz, DMSO-d6) δ ppm 8.23-8.56 (m, 1 H), 7.68 (d, J = 8.04 Hz, 2 H), 7.47-7.57 (m, 2 H), 4.85-5.04 (m, 2 H), 4.01-4.12 (m, 2 H), 3.90-3.99 (m, 2 H), 3.48-3.84 (m, 3 H), 2.69-2.97 (m, 6 H), 1.65-1.91 (m, 2 H), 1.33-1.61 (m, 6 H), 1.23 (dd, J = 9.34, 7.27 Hz, 2 H) | B |

| Ex. # | Structure Name | LCMS-ESI (POS/NEG) m/z: (M + H)+ | NMR Data | Syn. Rte. |
|---|---|---|---|---|
| 416 | 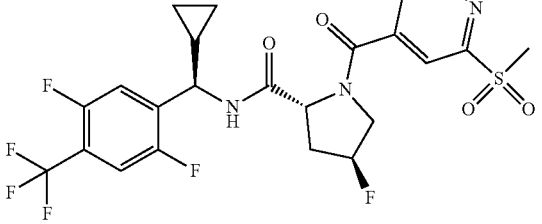<br>(4S)-N-((R)-cyclopropyl(2,5-difluoro-4-(trifluoromethyl)phenyl)methyl)-4-fluoro-1-((2-(methylsulfonyl)-4-pyridinyl)carbonyl)-D-prolinamide | LCMS-ESI (POS.) m/z: 550.0 (M + H)+ | 1H NMR (500 MHz, DMSO-d6) δ ppm 8.67-8.99 (m, 2 H), 7.68-8.08 (m, 3 H), 7.37-7.60 (m, 1 H), 5.21-5.39 (m, 1 H), 4.52-4.68 (m, 2 H), 3.84-4.01 (m, 1 H), 3.55-3.71 (m, 1 H), 3.26-3.41 (m, 3 H), 2.53-2.63 (m, 1 H), 1.90-2.11 (m, 1 H), 0.86-1.31 (m, 1 H), −0.26-0.69 (m, 4 H) | C |
| 417 | 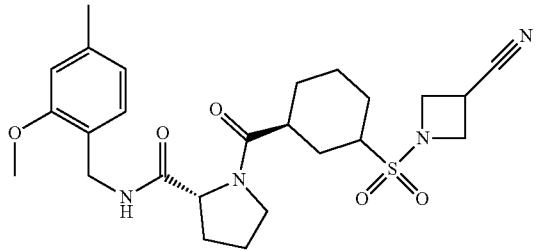 [SMILES: COc1cc(C)ccc1CNC(=O)[C@H]1CCCN1C(=O)[C@H]1CCCC(S(=O)(=O)N2CC(C#N)C2)C1]<br>1-(((3S)-1-((3-cyano-1-azetidinyl)sulfonyl)-3-piperidinyl)carbonyl)-N-(2-methoxy-4-methylbenzyl)-D-prolinamide | LCMS-ESI (POS.) m/z: 504.2 (M + H)+ | 1H NMR (500 MHz, DMSO-d6) δ ppm 7.93-8.43 (m, 1 H), 6.92-7.15 (m, 1 H), 6.62-6.89 (m, 2 H), 4.11-4.53 (m, 3 H), 3.87-4.09 (m, 4 H), 3.71-3.82 (m, 4 H), 3.42-3.70 (m, 4 H), 2.61-2.90 (m, 3 H), 2.28 (s, 3 H), 1.68-2.22 (m, 6 H), 1.33-1.56 (m, 1 H) | A |
| 418 | 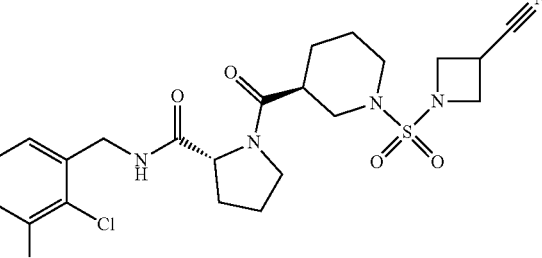<br>N-(2-chloro-3-fluorobenzyl)-1-(((3S)-1-((3-cyano-1-azetidinyl)sulfonyl)-3-piperidinyl)carbonyl)-D-prolinamide | LCMS-ESI (POS.) m/z: 512.2 (M + H)+ | 1H NMR (500 MHz, DMSO-d6) δ ppm 8.28-8.76 (m, 1 H), 7.00-7.48 (m, 3 H), 4.24-4.38 (m, 3 H), 3.98-4.06 (m, 1 H), 3.85-3.97 (m, 2 H), 3.71-3.83 (m, 1 H), 3.31-3.67 (m, 4 H), 2.72-2.86 (m, 2 H), 2.62-2.70 (m, 1 H), 2.06-2.28 (m, 1 H), 1.67-1.98 (m, 5 H), 1.30-1.52 (m, 2 H), 1.20-2.03 (m, 1 H) | A |
| 419 | 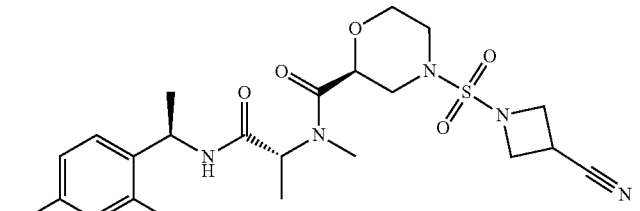<br>(2S)-N-((2R)-1-(((1R)-1-(4-chloro-2-fluorophenyl)ethyl)amino)-1-oxo-2-propanyl)-4-((3-cyano-1-azetidinyl)sulfonyl)-N-methyl-2-morpholinecarboxamide | LCMS-ESI (POS.) m/z: 516.2 (M + H)+ | 1H NMR (500 MHz, DMSO-d6) δ ppm 8.34-8.53 (m, 1 H), 7.34-7.48 (m, 2 H), 7.25-7.31 (m, 1 H), 5.00-5.17 (m, 1 H), 4.59-4.88 (m, 1 H), 4.26-4.41 (m, 1 H), 4.08-4.18 (m, 2 H), 3.97-4.07 (m, 2 H), 3.79-3.96 (m, 2 H), 3.57-3.75 (m, 1 H), 3.34-3.54 (m, 2 H), 3.04 (ddd, J = 16.84, 12.36, 9.99 Hz, 1 H), 2.64-2.99 (m, 4 H), 1.29-1.39 (m, 3 H), 1.24 (dd, J = 17.19, 6.94 Hz, 3 H) | C |

| Ex. # | Structure Name | LCMS-ESI (POS/NEG) m/z: (M + H)+ | NMR Data | Syn. Rte. |
|---|---|---|---|---|
| 420 | 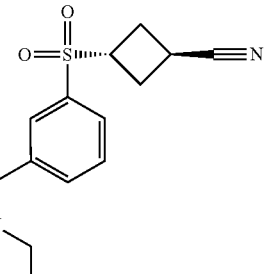<br>(2R)-N-((6-chloro-3-pyridinyl)methyl)-1-((3-((trans-3-cyanocyclobutyl)sulfonyl)phenyl)carbonyl)-2-piperidinecarboxamide | LCMS-ESI (POS.) m/z: 501.0 (M + H)+ | 1H NMR (400 MHz, DMSO-d6) δ ppm 8.21-8.76 (m, 2H), 7.61-8.04 (m, 5H), 7.38-7.55 (m, 1H), 4.01-5.25 (m, 4H), 3.34-3.44 (m, 1H), 3.14-3.28 (m, 1H), 2.55-2.66 (m, 4H), 2.04-2.28 (m, 1H), 1.20-1.77 (m, 5H) | L |
| 421 | 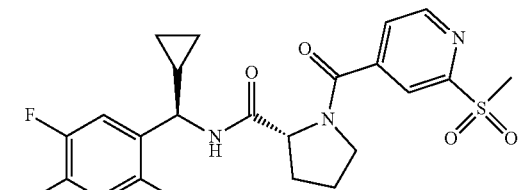<br>N-((R)-(4-chloro-2,5-difluorophenyl)(cyclopropyl)methyl)-1-((2-(methylsulfonyl)-4-pyridinyl)carbonyl)-D-prolinamide | LCMS-ESI (POS.) m/z: 498.0 (M + H)+ | 1H NMR (500 MHz, DMSO-d6) δ ppm 8.83-8.96 (m, 1 H), 8.64 (br d, J = 7.66 Hz, 1 H), 7.76-8.12 (m, 2 H), 7.39-7.69 (m, 2 H), 4.09-4.55 (m, 2 H), 3.49-3.64 (m, 2 H), 3.32 (br d, J = 15.05 Hz, 3 H), 2.10-2.32 (m, 1 H), 1.64-1.94 (m, 3 H), 0.86-1.24 (m, 1 H), 0.37 (br s, 4 H) | C |
| 422 | 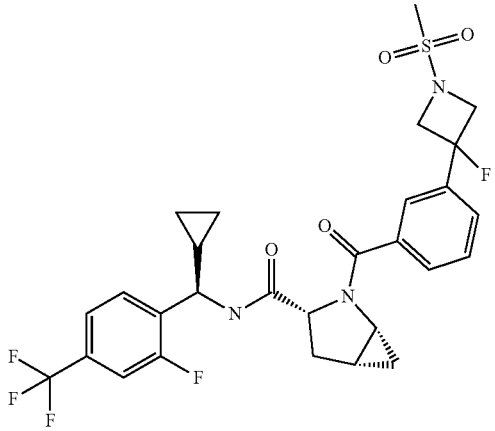 [SMILES: CS(=O)(=O)N1CC(F)(c2cccc(C(=O)N3[C@@H](C(=O)N[C@@H](c4ccc(C(F)(F)F)cc4F)C4CC4)C[C@H]4C[C@H]43)c2)C1]<br>(1R,3R,5R)-N-((R)-cyclopropyl(2-fluoro-4-(trifluoromethyl)phenyl)methyl)-2-(3-(3-fluoro-1-(methylsulfonyl)-3-azetidinyl)benzoyl)-2-azabicyclo[3.1.0]hexane-3-carboxamide | LCMS-APCI (POS.) m/z: 598.2 (M + H)+ | 1H NMR (400 MHz, Methanol-d4) δ ppm 8.80-8.86 (m, 1 H), 8.27 (s, 1 H), 8.02 (s, 1 H), 7.81-7.86 (m, 1 H), 7.71-7.77 (m, 1 H), 7.58-7.70 (m, 2 H), 7.51-7.55 (m, 1 H), 7.43-7.49 (m, 1 H), 4.30-4.52 (m, 6 H), 3.06-3.12 (m, 3 H), 2.64-2.73 (m, 1 H), 1.91-1.97 (m, 1 H), 1.75-1.81 (m, 1 H), 1.24-1.35 (m, 2 H), 1.15-1.19 (m, 1 H), 0.82-0.89 (m, 1 H), 0.64-0.73 (m, 1 H), 0.41-0.60 (m, 3 H). | W |
| 423 | 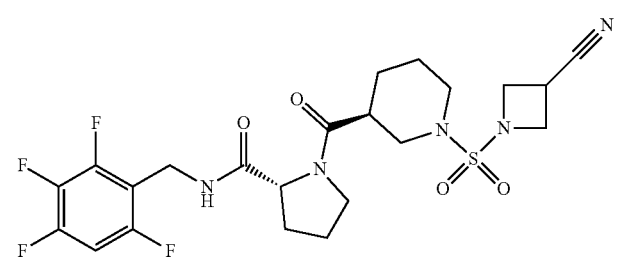 [SMILES: N#CC1CN(S(=O)(=O)N2CCC[C@H](C(=O)N3CCC[C@@H]3C(=O)NCc3c(F)cc(F)c(F)c3F)C2)C1]<br>1-(((3S)-1-((3-cyano-1-azetidinyl)sulfonyl)-3-piperidinyl)carbonyl)-N-(2,3,4,6-tetrafluorobenzyl)-D-prolinamide | LCMS-ESI (POS.) m/z: 532.2 (M + H)+ | 1H NMR (500 MHz, DMSO-d6) δ ppm 8.21-8.67 (m, 1 H), 7.36-7.55 (m, 1 H), 4.15-4.44 (m, 3 H), 4.01-4.08 (m, 2 H), 3.86-3.97 (m, 2 H), 3.74-3.83 (m, 1 H), 3.36-3.62 (m, 4 H), 2.57-2.83 (m, 3 H), 1.81-2.25 (m, 4 H), 1.63-1.77 (m, 2 H), 1.32-1.57 (m, 2 H) | A |

| Ex. # | Structure Name | LCMS-ESI (POS/NEG) m/z: (M + H)+ | NMR Data | Syn. Rte. |
|---|---|---|---|---|
| 424 | 1-(((3S)-1-((3-(4-chlorophenoxy)-1-azetidinyl)sulfonyl)-3-piperidinyl)carbonyl)-N-(4-(trifluoromethyl)benzyl)-D-prolinamide | LCMS-ESI (POS.) m/z: 629.2 (M + H)+ | 1H NMR (500 MHz, CHLOROFORM-d) δ ppm 7.57 (d, J = 8.04 Hz, 2 H), 7.44 (br s, 1 H), 7.28-7.40 (m, 2 H), 7.23-7.26 (m, 2 H), 6.64-6.70 (m, 2 H), 4.83-4.90 (m, 1 H), 4.56-4.68 (m, 1 H), 4.36-4.56 (m, 2 H), 4.11-4.29 (m, 2 H), 4.00 (dt, J = 8.63, 4.12 Hz, 2 H), 3.81 (br d, J = 12.72 Hz, 2 H), 3.52-3.65 (m, 2 H), 2.89-2.99 (m, 1 H), 2.67-2.81 (m, 2 H), 2.42-2.62 (m, 1 H), 2.11-2.33 (m, 2 H), 1.97-2.09 (m, 1 H), 1.59-1.94 (m, 5 H), 1.44-1.59 (m, 2 H) | M |
| 425 | 1-(((3S)-1-((cis-3-carbamoylcyclobutyl)sulfonyl)-3-piperidinyl)carbonyl)-N-(4-(trifluoromethyl)benzyl)-D-prolinamide | LCMS-APCI (POS.) m/z: 545.2 (M + H)+ | 1H NMR (Methanol-d4) δ: 7.65 (dd, J = 18.5, 7.9 Hz, 2H), 7.50 (d, J = 7.8 Hz, 2H), 4.66-4.38 (m, 3H), 3.94-3.68 (m, 4H), 3.69-3.39 (m, 1H), 3.11 (p, J = 9.1 Hz, 1H), 2.91 (q, J = 11.7, 11.0 Hz, 1H), 2.85-2.75 (m, 2H), 2.62 (q, J = 10.1 Hz, 2H), 2.54-2.41 (m, 2H), 2.41-2.21 (m, 1H), 2.16-1.89 (m, 4H), 1.89-1.77 (m, 1H), 1.69-1.50 (m, 2H) | R |
| 426 | N-((R)-(4-chloro-3-fluorophenyl)(cyclopropyl)methyl)-1-(3-(methylsulfonyl)benzoyl)-D-prolinamide | LCMS-ESI (POS.) m/z: 479.2 (M + H)+ | 1H NMR (500 MHz, DMSO-d6) δ ppm 8.37-8.60 (m, 1 H), 7.04-8.09 (m, 7 H), 3.82-4.56 (m, 2 H), 3.39-3.67 (m, 2 H), 3.21-3.31 (m, 3 H), 2.15-2.34 (m, 1 H), 1.68-1.93 (m, 3 H),-0.19-1.23 (m, 5 H) | C |
| 427 | (4S)-1-(((3S)-1-((3-cyano-1-azetidinyl)sulfonyl)-3-piperidinyl)carbonyl)-4-fluoro-N-(3-(trifluoromethyl)benzyl)-D-prolinamide | LCMS-ESI (POS.) m/z: 546.2 (M + H)+ | 1H NMR (500 MHz, DMSO-d6) δ ppm 8.55-8.87 (m, 1 H), 7.61-7.67 (m, 1 H), 7.52-7.61 (m, 3 H), 5.23-5.49 (m, 1 H), 4.32-4.68 (m, 3 H), 4.02-4.09 2 H), 3.89 4.02 (m, 3 H), 3.70-3.88 (m, 2 H), 3.55 (br d, J = 11.55 Hz, 2 H), 2.72-2.90 (m, 2 H), 2.61-2.72 (m, 1 H), 2.39-2.47 (m, 1 H), 1.94-2.21 (m, 1 H), 1.78-1.93 (m, 1 H), 1.72 (br d, J = 13.36 Hz, 1 H), 1.45-1.57 (m, 1 H), 1.31-1.45 (m, 1 H) | C |

-continued

| Ex. # | Structure Name | LCMS-ESI (POS/NEG) m/z: (M + H)+ | NMR Data | Syn. Rte. |
|---|---|---|---|---|
| 428 | 1-(((2S)-4-((3-cyano-1-azetidinyl)sulfonyl)-2-piperazinyl)carbonyl)-N-((1R)-1-(4-(trifluoromethyl)phenyl)ethyl)-D-prolinamide | LCMS-ESI (POS.) m/z: 543.2 (M + Na)+ | 1H NMR (400 MHz, CHLOROFORM-d) δ ppm 7.53-7.65 (m, 2 H), 7.28-7.45 (m, 3 H), 5.03 (t, J = 6.95 Hz, 1 H), 4.53 (br d, J = 6.84 Hz, 1 H), 4.03-4.25 (m, 4 H), 3.83 (br t, J = 7.46 Hz, 1 H), 3.66-3.78 (m, 2 H), 3.41-3.63 (m, 3 H), 3.15 (br d, J = 13.68 Hz, 1 H), 2.76-2.99 (m, 3 H), 1.77-2.47 (m, 5 H), 1.40 (s, 3 H) | M |
| 429 | N-(3,5-difluorobenzyl)-1-(((3S)-1-((3-(methylsulfonyl)-1-azetidinyl)sulfonyl)-3-piperidinyl)carbonyl)-D-prolinamide | LCMS-ESI (POS.) m/z: 549.0 (M + H)+ | 1H NMR (400 MHz, CHLOROFORM-d) δ 7.40-7.57 (m, 1H), 6.64-6.80 (m, 3H), 4.62 (dd, J = 2.02, 8.03 Hz, 1H), 4.51 (dd, J = 6.89, 15.70 Hz, 1H), 4.16-4.33 (m, 5H), 3.90-4.00 (m, 1H), 3.74-3.84 (m, 2H), 3.52-3.64 (m, 2H), 2.93-3.06 (m, 4H), 2.78-2.87 (m, 1H), 2.69-2.78 (m, 1H), 2.42-2.51 (m, 1H), 2.13-2.26 (m, 1H), 2.03-2.11 (m, 1H), 1.79-2.00 (m, 3H), 1.65-1.73 (m, 1H), 1.53-1.61 (m, 1H) | A |
| 430 | (4S)-N-((R)-cyclopropyl(2,5-difluoro-4-(trifluoromethyl)phenyl)methyl)-4-fluoro-1-((5-(methylsulfonyl)-3-pyridinyl)carbonyl)-D-prolinamide | LCMS-ESI (POS.) m/z: 550.0 (M + H)+ | 1H NMR (500 MHz, DMSO-d6) δ ppm 8.65-9.25 (m, 3 H), 8.27-8.45 (m, 1 H), 7.65-7.81 (m, 1 H), 7.37-7.62 (m, 1 H), 5.29-5.46 (m, 1 H), 4.49-4.72 (m, 2 H), 3.60-4.09 (m, 2 H), 3.34-3.48 (m, 3 H), 2.53-2.64 (m, 1 H), 1.86-2.09 (m, 1 H), 0.82-1.30 (m, 1 H), −0.31-0.67 (m, 4 H) | C |
| 431 | 1-(((3S)-1-((3-cyano-1-azetidinyl)sulfonyl)-3-piperidinyl)carbonyl)-N-((1S)-1-(4-(trifluoromethyl)phenyl)ethyl)-D-prolinamide | LCMS-ESI (POS.) m/z: 542.2 (M + H)+ | 1H NMR (500 MHz, DMSO-d6) δ ppm 8.22-8.69 (m, 1 H), 7.62-7.77 (m, 2 H), 7.48-7.60 (m, 2 H), 4.86-5.04 (m, 1 H), 4.28-4.45 (m, 1 H), 4.00-4.09 (m, 2 H), 3.88-3.98 (m, 2 H), 3.74-3.83 (m, 1 H), 3.46-3.64 (m, 4 H), 2.73-2.91 (m, 2 H), 2.57-2.67 (m, 1 H), 2.02-2.23 (m, 1 H), 1.67-1.95 (m, 5 H), 1.33-1.56 (m, 5 H) | A |

| Ex. # | Structure Name | LCMS-ESI (POS/NEG) m/z: (M + H)+ | NMR Data | Syn. Rte. |
|---|---|---|---|---|
| 432 | 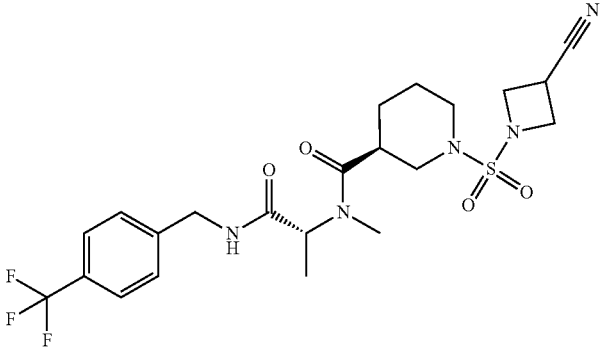 [SMILES: C[C@H](C(=O)NCc1ccc(C(F)(F)F)cc1)N(C)C(=O)[C@H]1CCCN(S(=O)(=O)N2CC(C#N)C2)C1]<br>(3S)-1-((3-cyano-1-azetidinyl)sulfonyl)-N-methyl-N-((1R)-1-methyl-2-oxo-2-((4-(trifluoromethyl)benzyl)amino)ethyl)-3-piperidinecarboxamide | LCMS-ESI (NEG.) m/z: 515.2 (M − H)⁻ | 1H NMR (500 MHz, DMSO-d6) δ ppm 8.30-8.73 (m, 1 H), 7.68 (br t, J = 6.62 Hz, 2 H), 7.38-7.51 (m, 2 H), 4.62-5.02 (m, 1 H), 4.27-4.43 (m, 2 H), 3.46-4.11 (m, 6 H), 2.66-2.98 (m, 6 H), 1.60-1.90 (m, 2 H), 1.29-1.59 (m, 3 H), 1.14-1.29 (m, 3 H) | C |
| 433 | 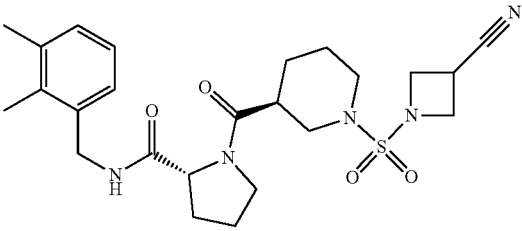 [SMILES: Cc1cccc(CNC(=O)[C@H]2CCCN2C(=O)[C@H]2CCCN(S(=O)(=O)N3CC(C#N)C3)C2)c1C]<br>1-(((3S)-1-((3-cyano-1-azetidinyl)sulfonyl)-3-piperidinyl)carbonyl)-N-(2,3-dimethylbenzyl)-D-prolinamide | LCMS-ESI (POS.) m/z: 487.2 (M + H)+ | 1H NMR (500 MHz, DMSO-d6) δ ppm 8.04-8.46 (m, 1 H), 6.98-7.10 (m, 3 H), 4.14-4.49 (m, 3 H), 4.01-4.10 (m, 2 H), 3.88-3.97 (m, 2 H), 3.74-3.84 (m, 1 H), 3.34-3.68 (m, 4 H), 2.67-2.89 (m, 2 H), 2.17-2.34 (m, 4 H), 2.09-2.15 (m, 3 H), 1.68-2.10 (m, 6 H), 1.31-1.54 (m, 2 H) | A |
| 434 | 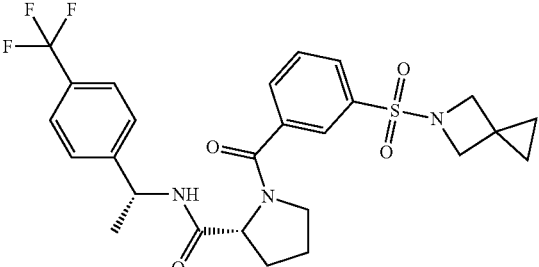<br>1-((3-(5-azaspiro[2.3]hex-5-ylsulfonyl)phenyl)carbonyl)-N-((1R)-1-(4-(trifluoromethyl)phenyl)ethyl)-D-prolinamide | LCMS-APCI (NEG.) m/z: 534.2 (M − H) | 1H NMR (400 MHz, Methanol-d4) δ ppm 8.12 (t, J = 1.8 Hz, 1 H), 7.97 (ddt, J = 1.5, 7.8, 16.0 Hz, 2 H), 7.75-7.79 (m, 1 H), 7.63 (d, J = 8.1 Hz, 2 H), 7.52 (d, J = 8.1 Hz, 2 H), 4.98-5.16 (m, 1 H), 4.61 (dd, J = 5.9, 8.2 Hz, 1 H), 3.88 (s, 4 H), 3.63 (dt, J = 7.0, 10.8 Hz, 1 H), 3.46-3.57 (m, 1 H), 2.27-2.39 (m, 1 H), 1.87-1.98 (m, 3 H), 1.53 (d, J = 7.0 Hz, 3 H), 0.47 (s, 4 H). | A |
| 435 | 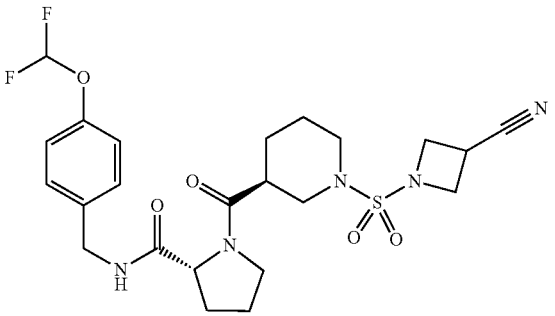 [SMILES: N#CC1CN(S(=O)(=O)N2CCC[C@H](C(=O)N3CCC[C@@H]3C(=O)NCc3ccc(OC(F)F)cc3)C2)C1]<br>1-(((3S)-1-((3-cyano-1-azetidinyl)sulfonyl)-3-piperidinyl)carbonyl)-N-(4-(difluoromethoxy)benzyl)-D-prolinamide | LCMS-ESI (POS.) m/z: 526.2 (M + H)+ | 1H NMR (500 MHz, DMSO-d6) δ ppm 8.18-8.68 (m, 1 H), 6.98-7.48 (m, 5 H), 4.19-4.50 (m, 3 H), 3.90-4.12 (m, 4 H), 3.74-3.85 (m, 1 H), 3.44-3.70 (m, 4 H), 2.62-2.90 (m, 3 H), 1.67-2.34 (m, 6 H), 1.34-1.56 (m, 2 H) | A |

| Ex. # | Structure Name | LCMS-ESI (POS/NEG) m/z: (M + H)+ | NMR Data | Syn. Rte. |
|---|---|---|---|---|
| 436 | 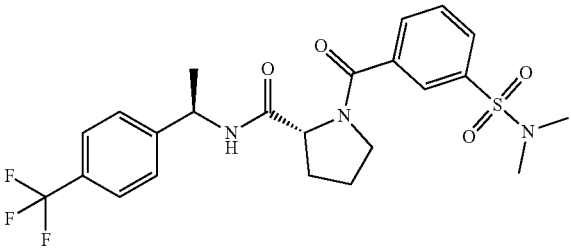 [SMILES: C[C@@H](NC(=O)[C@H]1CCCN1C(=O)c1cccc(S(=O)(=O)N(C)C)c1)c1ccc(C(F)(F)F)cc1]<br>1-(3-(dimethylsulfamoyl)benzoyl)-N-((1R)-1-(4-(trifluoromethyl)phenyl)ethyl)-D-prolinamide | LCMS-ESI (POS.) m/z: 498.2 (M + H)+ | 1H NMR (500 MHz, DMSO-d6) δ ppm 8.26-8.60 (m, 1 H), 7.78-7.91 (m, 1 H), 7.71-7.93 (m, 1 H), 7.36-7.98 (m, 1 H), 4.66-5.06 (m, 1 H), 4.25-4.55 (m, 1 H), 3.41-3.65 (m, 2 H), 3.32 (s, 4 H), 2.71-2.72 (m, 1 H), 2.57-2.70 (m, 6 H), 2.15-2.31 (m, 1 H), 1.71-1.96 (m, 3 H), 1.06-1.47 (m, 3 H) | D |
| 437 | 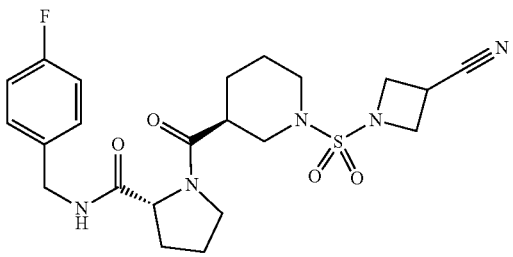 [SMILES: N#CC1CN(S(=O)(=O)N2CCC[C@H](C(=O)N3CCC[C@@H]3C(=O)NCc3ccc(F)cc3)C2)C1]<br>1-(((3S)-1-((3-cyano-1-azetidinyl)sulfonyl)-3-piperidinyl)carbonyl)-N-(4-fluorobenzyl)-D-prolinamide | LCMS-ESI (POS.) m/z: 478.2 (M + H)+ | 1H NMR (500 MHz, DMSO-d6) δ ppm 8.22-8.66 (m, 1 H), 7.22-7.30 (m, 2 H), 7.08-7.18 (m, 2 H), 4.17-4.48 (m, 3 H), 4.01-4.11 (m, 2 H), 3.88-3.99 (m, 2 H), 3.74-3.83 (m, 1 H), 3.34-3.70 (m, 4 H), 2.59-2.89 (m, 3 H), 2.03-2.32 (m, 1 H), 1.64-1.98 (m, 5 H), 1.34-1.56 (m, 2 H) | A |
| 438 | 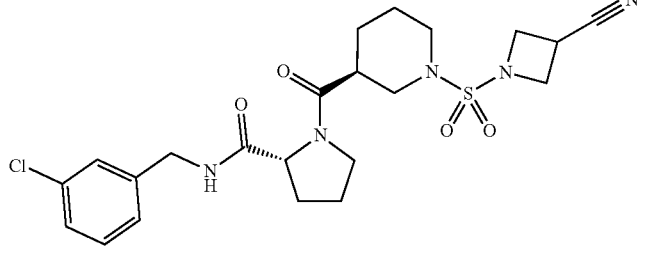<br>N-(3-chlorobenzyl)-1-(((3S)-1-((3-cyano-1-azetidinyl)sulfonyl)-3-piperidinyl)carbonyl)-D-prolinamide | LCMS-ESI (POS.) m/z: 494.2 (M + H)+ | 1H NMR (500 MHz, DMSO-d6) δ ppm 8.24-8.79 (m, 1 H), 7.20-7.38 (m, 3 H), 7.15 (br d, J = 7.40 Hz, 1 H), 4.13-4.35 (m, 3 H), 3.94-4.08 (m, 2 H), 3.81-3.93 (m, 2 H), 3.69-3.80 (m, 1 H), 3.22-3.64 (m, 4 H), 2.67-2.84 (m, 2 H), 2.51-2.66 (m, 1 H), 2.03-2.31 (m, 1 H), 1.60-1.96 (m, 5 H), 1.26-1.54 (m, 2 H) | A |
| 439 | 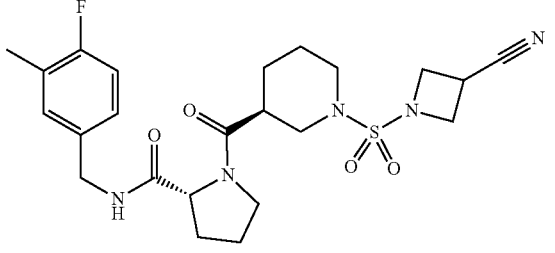 [SMILES: Cc1cc(CNC(=O)[C@H]2CCCN2C(=O)[C@H]2CCCN(S(=O)(=O)N3CC(C#N)C3)C2)ccc1F]<br>1-(((3S)-1-((3-cyano-1-azetidinyl)sulfonyl)-3-piperidinyl)carbonyl)-N-(4-fluoro-3-methylbenzyl)-D-prolinamide | LCMS-ESI (POS.) m/z: 492.2 (M + H)+ | 1H NMR (500 MHz, DMSO-d6) δ ppm 8.17-8.61 (m, 1 H), 6.96-7.25 (m, 3 H), 4.18-4.51 (m, 3 H), 4.00-4.11 (m, 2 H), 3.86-4.00 (m, 2 H), 3.72-3.83 (m, 1 H), 3.41-3.70 (m, 4 H), 2.60-2.90 (m, 3 H), 2.16-2.34 (m, 3 H), 2.03-2.14 (m, 1 H), 1.65-2.03 (m, 5 H), 1.32-1.59 (m, 2 H) | A |
| 440 | 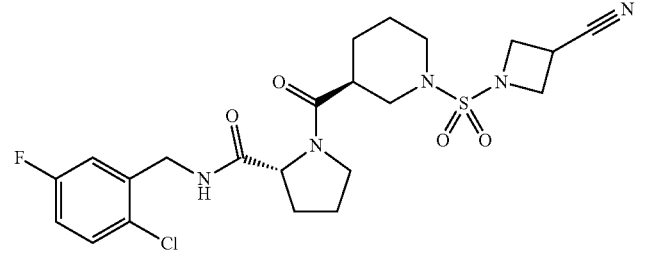 [SMILES: N#CC1CN(S(=O)(=O)N2CCC[C@H](C(=O)N3CCC[C@@H]3C(=O)NCc3cc(F)ccc3Cl)C2)C1] | LCMS-ESI (POS.) m/z: 512.2 (M + H)+ | 1H NMR (500 MHz, DMSO-d6) δ ppm 8.39 (br t, J = 5.97 Hz, 1 H), 7.05-7.59 (m, 3 H), 4.21-4.59 (m, 3 H), 4.00-4.14 (m, 2 H), 3.85-4.00 (m, 2 H), 3.74-3.85 (m, 1 H), 3.37-3.73 (m, 4 H), 2.73-2.87 (m, 2 H), 2.61-2.71 (m, 1 H), 1.63-2.29 (m, 6 H), 1.32-1.56 (m, 2 H) | A |

-continued

| Ex. # | Structure Name | LCMS-ESI (POS/NEG) m/z: (M + H)+ | NMR Data | Syn. Rte. |
|---|---|---|---|---|
| | N-(2-chloro-5-fluorobenzyl)-1-(((3S)-1-((3-cyano-1-azetidinyl)sulfonyl)-3-piperidinyl)carbonyl)-D-prolinamide | | | |
| 441 | 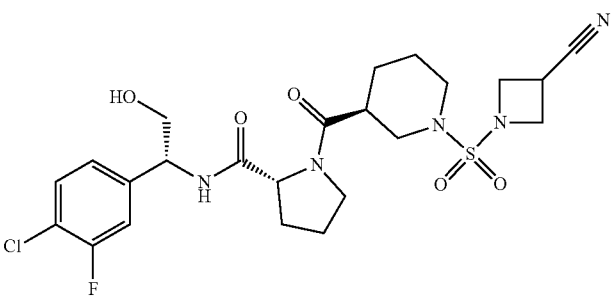 [SMILES: N#CC1CN(S(=O)(=O)N2CCC[C@H](C(=O)N3CCC[C@@H]3C(=O)N[C@@H](CO)c3ccc(Cl)c(F)c3)C2)C1]<br>N-((1R)-1-(4-chloro-3-fluorophenyl)-2-hydroxyethyl)-1-(((3S)-1-((3-cyano-1-azetidinyl)sulfonyl)-3-piperidinyl)carbonyl)-D-prolinamide | LCMS-ESI (POS.) m/z: 542.2 (M + H)+ | 1H NMR (500 MHz, DMSO-d6) δ ppm 8.19 (d, J = 8.17 Hz, 1 H), 7.07-7.57 (m, 3 H), 5.23-5.24 (m, 1 H), 4.78 (br d, J = 7.66 Hz, 1 H), 4.39 (dd, J = 8.17, 3.50 Hz, 1 H), 3.70-4.11 (m, 5 H), 3.30-3.63 (m, 6 H), 3.24-4.17 (m, 1 H), 2.57-2.88 (m, 3 H), 1.72-2.27 (m, 6 H), 1.32-1.58 (m, 2 H) | A |
| 442 | 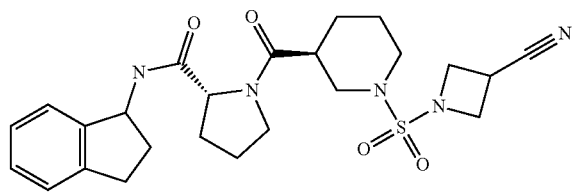 [SMILES: N#CC1CN(S(=O)(=O)N2CCC[C@H](C(=O)N3CCC[C@@H]3C(=O)NC3CCc4ccccc43)C2)C1]<br>(2R)-1-((S)-1-((3-cyanoazetidin-1-yl)sulfonyl)piperidine-3-carbonyl)-N-(2,3-dihydro-1H-inden-1-yl)pyrrolidine-2-carboxamide | LCMS-ESI (POS.) m/z: 486.2 (M + H)+ | 1H NMR (500 MHz, DMSO-d6) δ ppm 7.96-8.58 (m, 1 H), 7.03-7.32 (m, 4 H), 5.20-5.40 (m, 1 H), 4.20-4.48 (m, 1 H), 3.87-4.14 (m, 4 H), 3.42-3.85 (m, 5 H), 2.60-2.97 (m, 5 H), 1.67-2.44 (m, 8 H), 1.31-1.58 (m, 2 H) | A |
| 443 | 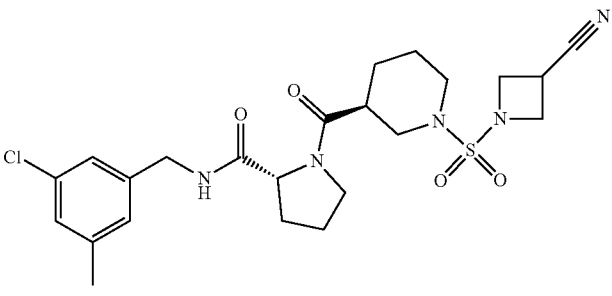 [SMILES: Cc1cc(Cl)cc(CNC(=O)[C@H]2CCCN2C(=O)[C@H]2CCCN(S(=O)(=O)N3CC(C#N)C3)C2)c1]<br>N-(3-chloro-5-methylbenzyl)-1-(((3S)-1-((3-cyano-1-azetidinyl)sulfonyl)-3-piperidinyl)carbonyl)-D-prolinamide | LCMS-ESI (POS.) m/z: 508.2 (M + H)+ | 1H NMR (500 MHz, DMSO-d6) δ ppm 8.23-8.66 (m, 1 H), 6.94-7.19 (m, 3 H), 5.50-5.51 (m, 1 H), 4.14-4.54 (m, 3 H), 3.99-4.09 (m, 2 H), 3.86-3.97 (m, 2 H), 3.74-3.84 (m, 1 H), 3.40-3.71 (m, 4 H), 3.32-3.39 (m, 1 H), 2.71-2.90 (m, 2 H), 2.60-2.71 (m, 1 H), 2.02-2.25 (m, 1 H), 1.63-1.99 (m, 5 H), 1.33-1.59 (m, 2 H) | A |
| 444 | 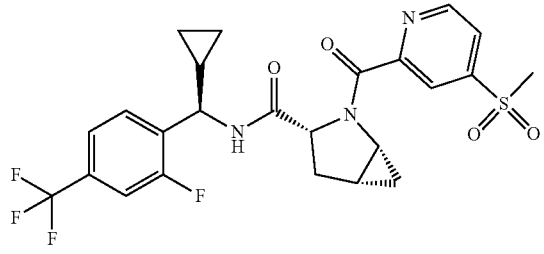 [SMILES: CS(=O)(=O)c1ccnc(C(=O)N2[C@@H](C(=O)N[C@@H](c3ccc(C(F)(F)F)cc3F)C3CC3)C[C@H]3C[C@H]32)c1]<br>(1R,3R,5R)-N-((R)-cyclopropyl(2-fluoro-4-(trifluoromethyl)phenyl)methyl)-2-(4-(methylsulfonyl)picolino)-2-azabicyclo[3.1.0]hexane-3-carboxamide | LCMS-ESI (POS.) m/z: 526.0 (M + H)+ | 1H NMR (500 MHz, DMSO-d6) δ ppm 8.77-9.05 (m, 1 H), 8.52-8.74 (m, 1 H), 8.12-8.25 (m, 1 H), 8.03 (ddd, J = 13.88, 5.06, 1.82 Hz, 1 H), 7.55-7.75 (m, 3 H), 4.88-5.53 (m, 1 H), 4.14-4.65 (m, 1 H), 3.76-3.95 (m, 1 H), 3.40 (d, J = 5.97 Hz, 4 H), 2.52-2.78 (m, 2 H), 1.50-1.92 (m, 2 H), 0.43-1.25 (m, 4 H), -0.19-0.42 (m, 3 H) | C |

-continued

| Ex. # | Structure Name | LCMS-ESI (POS/NEG) m/z: (M + H)+ | NMR Data | Syn. Rte. |
|---|---|---|---|---|
| 445 | 1-(((3S)-1-((3-cyano-1-azetidinyl)sulfonyl)-3-piperidinyl)carbonyl)-N-(4-fluoro-3,5-dimethylbenzyl)-D-prolinamide | LCMS-ESI (POS.) m/z: 506.2 (M + H)+ | 1H NMR (500 MHz, DMSO-d6) δ ppm 8.15-8.56 (m, 1 H), 3.99-4.49 (m, 5 H), 3.86-3.97 (m, 2 H), 3.73-3.82 (m, 1 H), 3.40-3.72 (m, 4 H), 2.62-2.87 (m, 3 H), 2.18 (s, 7 H), 2.02-2.12 (m, 1 H), 1.85-1.98 (m, 3 H), 1.67-1.84 (m, 3 H), 1.35-1.54 (m, 2 H) | A |
| 446 | N-((R)-cyclopropyl(2-fluoro-4-(trifluoromethyl)phenyl)methyl)-4,4-difluoro-1-(3-sulfamoylbenzoyl)-D-prolinamide | LCMS-ESI (POS.) m/z: 550.0 (M + H)+ | 1H NMR (400 MHz, CHLOROFORM-d) δ ppm 8.04-8.14 (m, 2 H), 7.69-7.76 (m, 1 H), 7.61-7.69 (m, 1 H), 7.54 (br d, J = 6.12 Hz, 1 H), 7.38-7.50 (m, 2 H), 7.35 (br d, J = 10.47 Hz, 1 H), 5.32-5.67 (m, 2 H), 5.00 (br t, J = 8.19 Hz, 1 H), 4.56 (br t, J = 7.93 Hz, 1 H), 3.93-4.08 (m, 1 H), 3.72-3.85 (m, 1 H), 2.83-3.01 (m, 1 H), 2.51-2.68 (m, 1 H), 1.21-1.33 (m, 1 H), 0.49-0.66 (m, 2 H), 0.31-0.49 (m, 2 H) | C |
| 447 | 1-(((3S)-1-((3-cyano-1-azetidinyl)sulfonyl)-3-piperidinyl)carbonyl)-N-(4-cyclopropylbenzyl)-D-prolinamide | LCMS-ESI (POS.) m/z: 500.2 (M + H)+ | 1H NMR (500 MHz, CHLOROFORM-d) δ ppm 7.08-7.15 (m, 2 H), 6.99-7.06 (m, 2 H), 4.56 (br dd, J = 7.79, 2.60 Hz, 1 H), 4.29-4.45 (m, 2 H), 3.99-4.14 (m, 4 H), 3.69-3.78 (m, 2 H), 3.50-3.65 (m, 2 H), 3.39-3.47 (m, 1 H), 2.83-3.02 (m, 1 H), 2.65-2.83 (m, 2 H), 2.37-2.43 (m, 1 H), 2.16-2.22 (m, 1 H), 2.00-2.07 (m, 1 H), 1.86-1.95 (m, 3 H), 1.77-1.84 (m, 1 H), 1.40-1.71 (m, 3 H), 0.91-0.99 (m, 2 H), 0.62-0.72 (m, 2 H) | C |
| 448 | (3R)-4-(((3S)-1-((3-cyano-1-azetidinyl)sulfonyl)-3-piperidinyl)carbonyl)-N-(4-(difluoromethyl)benzyl)-3-morpholinecarboxamide | LCMS-ESI (POS.) m/z: 526.2 (M + H)+ | 1H NMR (500 MHz, DMSO-d6) δ ppm 8.40-8.75 (m, 1 H), 7.52 (br d, J = 7.79 Hz, 2 H), 7.33-7.43 (m, 2 H), 6.87-7.16 (m, 1 H), 4.55-4.80 (m, 1 H), 4.30-4.45 (m, 3 H), 4.00-4.14 (m, 3 H), 3.87-3.98 (m, 2 H), 3.71-3.86 (m, 3 H), 3.50-3.68 (m, 1 H), 3.24-3.50 (m, 2 H), 2.69-2.98 (m, 3 H), 1.78-1.95 (m, 1 H), 1.64-1.76 (m, 1 H), 1.46-1.62 (m, 1 H), 1.31-1.46 (m, 1 H), 1.31-1.46 (m, 1 H) | B |

-continued

| Ex. # | Structure Name | LCMS-ESI (POS/NEG) m/z: (M + H)+ | NMR Data | Syn. Rte. |
|---|---|---|---|---|
| 449 | 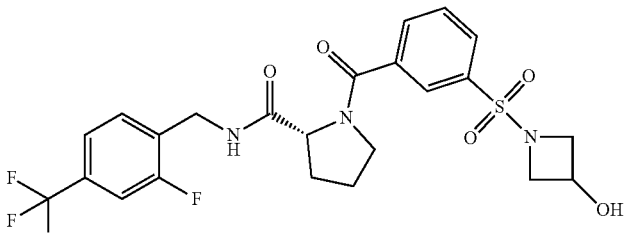<br>N-(2-fluoro-4-(trifluoromethyl)benzyl)-1-(3-((3-hydroxy-1-azetidinyl)sulfonyl)benzoyl)-D-prolinamide | LCMS-ESI (POS.) m/z: 530.0 (M + H)⁺ | 1H NMR (400 MHz, CHLOROFORM-d) δ 7.90-8.03 (m, 2H), 7.75-7.86 (m, H), 7.64-7.72 (m, 1H), 7.48-7.63 (m, 1H), 7.36-7.45 (m, 1H), 7.33 (br d, J = 9.95 Hz, 1H), 7.22 (br t, J = 5.60 Hz, 1H), 4.74 (dd, J = 5.34, 7.20 Hz, 1H), 4.55-4.66 (m, 2H), 4.50 (quin, J = 5.96 Hz, 1H), 4.31-4.38 (m, 1H), 4.00-4.12 (m, 2H), 3.57-3.68 (m, 2H), 3.45-3.54 (m, 2H), 2.35-2.47 (m, 1H), 2.03-2.22 (m, 2H), 1.86-1.99 (m, 1H) | B |
| 450 | 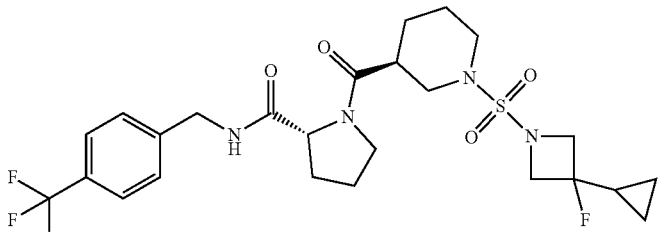<br>Chiral<br>1-(((3S)-1-((3-cyclopropyl-3-fluoro-1-azetidinyl)sulfonyl)-3-piperidinyl)carbonyl)-N-(4-(trifluoromethyl)benzyl)-D-prolinamide | LCMS-ESI (POS.) m/z: 561.2 (M + H)⁺ | 1H NMR (500 MHz, DMSO-d6) δ 8.29-8.76 (m, 1H), 7.60-7.75 (m, 2H), 7.38-7.53 (m, 2H), 4.26-4.51 (m, 3H), 3.49-3.93 (m, 8H), 2.60-2.87 (m, 3H), 2.05-2.36 (m, 1H), 1.66-2.03 (m, 5H), 1.29-1.57 (m, 3H), 0.55-0.71 (m, 2H), 0.36-0.55 (m, 2H) | J |
| 451 | 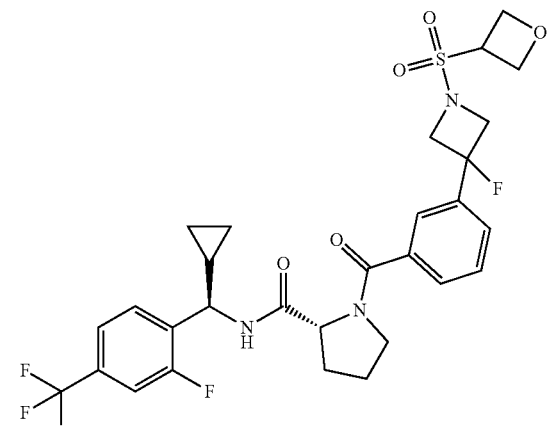<br>N-((R)-cyclopropyl(2-fluoro-4-(trifluoromethyl)phenyl)methyl)-1-(3-(3-fluoro-1-(3-oxetanylsulfonyl)-3-azetidinyl)benzoyl)-D-prolinamide | LCMS-ESI APCI (POS.) m/z: 628.2 (M + H)⁺ | 1H NMR (400 MHz, Methanol-d4) δ ppm 7.36-7.80 (m, 7 H), 4.69-4.97 (m, 4 H), 4.09-4.65 (m, 6 H), 3.45-3.74 (m, 2 H), 2.24-2.38 (m, 1 H), 1.78-2.00 (m, 3 H), 1.21-1.36 (m, 1 H), 0.37-0.73 (m, 4 H). | W |
| 452 | 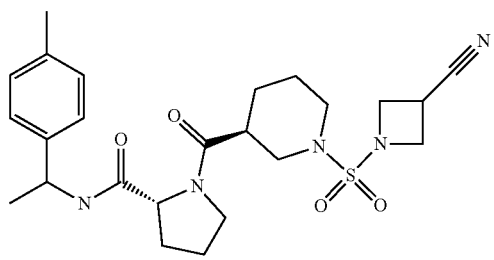 [SMILES: Cc1ccc(C(C)NC(=O)[C@H]2CCCN2C(=O)[C@H]2CCCN(S(=O)(=O)N3CC(C#N)C3)C2)cc1]<br>(2R)-1-((S)-1-( (3-cyanoazetidin-1-yl)sulfonyl)piperidine-3-carbonyl)-N-(1-(p-tolyl)ethyl)pyrrolidine-2-carboxamide | LCMS-ESI (POS.) m/z: 488.2 (M + H)⁺ | 1H NMR (500 MHz, DMSO-d6) δ ppm 7.99-8.53 (m, 1 H), 7.03-7.24 (m, 4 H), 4.78-4.97 (m, 1 H), 4.25-4.47 (m, 1 H), 4.01-4.13 (m, 2 H), 3.71-4.00 (m, 4 H), 3.47-3.66 (m, 4 H), 2.62-2.90 (m, 3 H), 2.02-2.39 (m, 4 H), 1.63-1.98 (m, 6 H), 1.34-1.55 (m, 3 H) | A |

-continued

| Ex. # | Structure Name | LCMS-ESI (POS/NEG) m/z: (M + H)+ | NMR Data | Syn. Rte. |
|---|---|---|---|---|
| 453 | 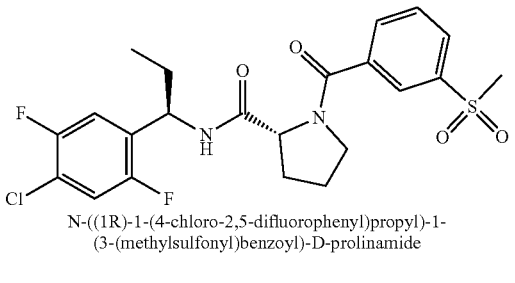<br>N-((1R)-1-(4-chloro-2,5-difluorophenyl)propyl)-1-(3-(methylsulfonyl)benzoyl)-D-prolinamide | LCMS-ESI (POS.) m/z: 485.2 (M + H)+ | 1H NMR (500 MHz, DMSO-d6) δ ppm 8.20-8.50 (m, 1 H), 7.59-8.11 (m, 1 H), 7.51-8.12 (m, 4 H), 7.19-7.48 (m, 1 H), 4.56-5.02 (m, 1 H), 4.29-4.54 (m, 1 H), 3.41-3.64 (m, 2 H), 3.20-3.36 (m, 3 H), 2.15-2.33 (m, 1 H), 1.32-1.96 (m, 5 H), 0.44-0.96 (m, 3 H) | A |
| 454 | 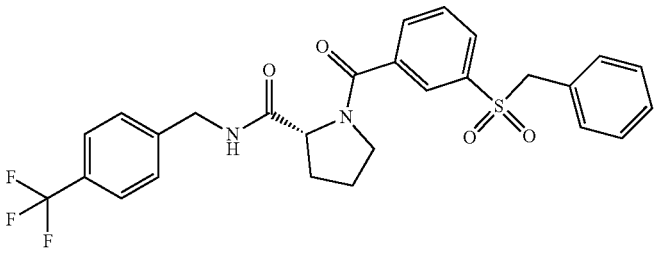 [SMILES: O=C(NCc1ccc(C(F)(F)F)cc1)[C@H]1CCCN1C(=O)c1cccc(S(=O)(=O)Cc2ccccc2)c1]<br>1-(3-(benzylsulfonyl)benzoyl)-N-(4-(trifluoromethyl)benzyl)-D-prolinamide | LCMS-ESI (POS.) m/z: 531.2 (M + H)+ | 1H NMR (500 MHz, DMSO-d6) δ ppm 8.42-8.73 (m, 1 H), 7.09-7.91 (m, 13 H), 4.56-4.79 (m, 2 H), 4.10-4.51 (m, 3 H), 3.35-3.68 (m, 1 H), 3.09-3.30 (m, 1 H), 2.16-2.35 (m, 1 H), 1.71-1.99 (m, 3 H) | C |
| 455 | 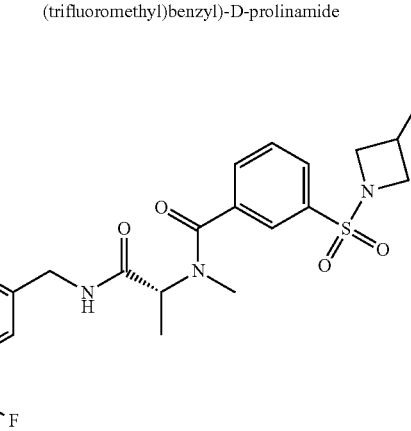<br>3-((3-cyano-1-azetidinyl)sulfonyl)-N-methyl-N-((1R)-1-methyl-2-oxo-2-((3-(trifluoromethyl)benzyl)amino)ethyl)benzamide | LCMS-ESI (POS.) m/z: 509.2 (M + H)+ | 1H NMR (500 MHz, CHLOROFORM-d) δ ppm 7.87-7.95 (m, 2 H), 7.52-7.72 (m, 3 H), 7.44-7.51 (m, 3 H), 7.09 (br s, 1 H), 5.21 (br d, J = 6.55 Hz, 1 H), 4.60 (br dd, J = 15.02, 5.94 Hz, 1 H), 4.45 (dd, J = 15.18, 5.71 Hz, 1 H), 4.13 (t, J = 8.47 Hz, 2 H), 4.01 (br s, 2 H), 3.28-3.43 (m, 1 H), 2.89-3.07 (m, 3 H), 2.00 (s, 1 H), 1.71-1.94 (m, 1 H), 1.51 (br d, J = 6.81 Hz, 3 H) | C |
| 456 | 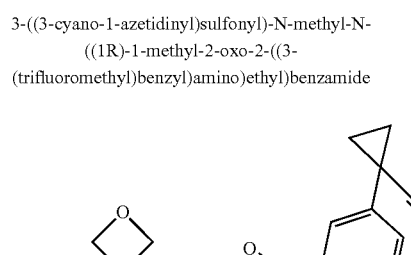<br>(1R,3R,5R)-2-(3-(1-cyanocyclopropyl)benzoyl)-N-((R)-(2-fluoro-4-(trifluoromethyl)phenyl)(3-oxetanyl)methyl)-2-azabicyclo[3.1.0]hexane-3-carboxamide | LCMS-ESI APCI (POS.) m/z: 528.2 (M + H)+ | 1H NMR (400 MHz, Methanol-d4) δ ppm 7.77 (q, J = 1.6 Hz, 1 H), 7.69-7.74 (m, 1 H), 7.48-7.59 (m, 5 H), 5.65 (d, J = 10.1 Hz, 1 H), 4.99 (dd, J = 4.2, 11.4 Hz, 1 H), 4.61-4.70 (m, 2 H), 4.40 (t, J = 0.9, 12.5 Hz, 1 H), 3.50-3.61 (m, 1 H), 3.29 (dd, J = 2.7, 6.3 Hz, 1 H), 2.60-2.69 (m, 1 H), 2.05 (s, 1 H), 1.91 (dd, J = 4.2, 13.6 Hz, 1 H), 1.75-1.82 (m, 3 H), 1.51-1.63 (m, 2 H), 1.23 (td, J = 2.6, 5.3 Hz, 1 H), 0.84-0.91 (m, 1 H). | Q |

| Ex. # | Structure Name | LCMS-ESI (POS/NEG) m/z: (M + H)+ | NMR Data | Syn. Rte. |
|---|---|---|---|---|
| 457 | 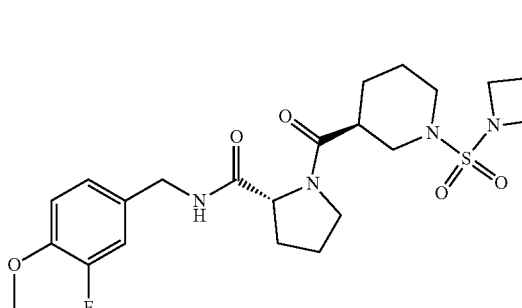<br>1-(((3S)-1-((3-cyano-1-azetidinyl)sulfonyl)-3-piperidinyl)carbonyl)-N-(3-fluoro-4-methoxybenzyl)-D-prolinamide | LCMS-ESI (POS.) m/z: 508.2 (M + H)+ | 1H NMR (500 MHz, CHLOROFORM-d) δ ppm 6.88-7.02 (m, 3 H), 4.59 (dd, J = 8.04, 1.82 Hz, 1 H), 4.41 (dd, J = 15.05, 6.49 Hz, 1 H), 4.27 (dd, J = 15.05, 5.45 Hz, 1 H), 4.08-4.16 (m, 4 H), 3.88-3.91 (m, 3 H), 3.70-3.81 (m, 2 H), 3.54-3.64 (m, 2 H), 3.40-3.48 (m, 1 H), 2.97 (dd, J = 12.46, 11.16 Hz, 1 H), 2.67-2.81 (m, 2 H), 2.42-2.49 (m, 1 H), 2.15-2.31 (m, 1 H), 2.02-2.09 (m, 1 H), 1.79-1.98 (m, 3 H), 1.51-1.70 (m, 4 H) | C |
| 458 | 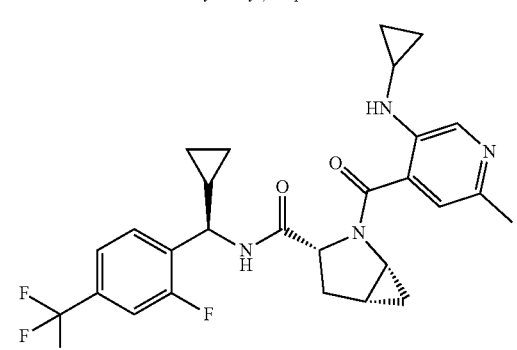<br>(1R,3R,5R)-2((5-(cyclopropylamino)-2-methyl-4-pyridinyl)carbonyl)-N-((R)-cyclopropyl(2-fluoro-4-(trifluoromethyl)phenyl)methyl)-2-azabicyclo3.1.0lhexane-3-carboxamide | LCMS-ESI APCI (POS.) m/z: 517.2 (M + H)+ | 1H NMR (400 MHz, Methylene Chloride-d2) δ ppm 8.49 (s, 1 H), 7.46-7.56 (m, 2 H), 7.40 (d, J = 15.5 Hz, 2 H), 6.80 (d, J = 7.0 Hz, 1 H), 6.50 (s, 1 H), 5.03 (dd, J = 2.8, 11.2 Hz, 1 H), 4.53 (dd, J = 7.0, 9.0 Hz, 1 H), 3.12 (td, J = 2.6, 6.2 Hz, 1 H), 2.69 (s, 3 H), 2.48-2.61 (m, 2 H), 2.19 (dd, J = 2.8, 13.4 Hz, 1 H), 1.68-1.78 (m, 1 H), 1.25-1.35 (m, 1 H), 0.93-0.98 (m, 1 H), 0.85-0.93 (m, 2 H), 0.63-0.76 (m, 2 H), 0.59 (dddd, J = 3.1, 4.6, 6.4, 9.9 Hz, 3 H), 0.36-0.51 (m, 2 H). | S |
| 459 | 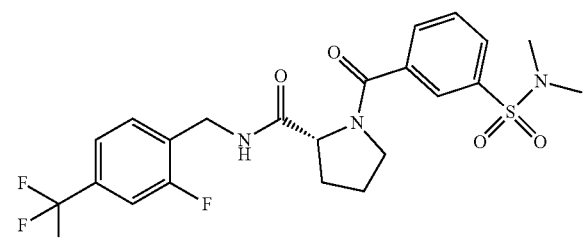<br>1-(3-(dimethylsulfamoyl)benzoyl)-N-(2-fluoro-4-(trifluoromethyl)benzyl)-D-prolinamide | LCMS-ESI (POS.) m/z: 502.2 (M + H)+ | 1H NMR (500 MHz, DMSO-d6) δ ppm 8.46-8.73 (m, 1 H), 7.90 (d, J = 1.30 Hz, 7 H), 4.18-4.54 (m, 3 H), 3.44-3.65 (m, 2 H), 2.55-2.68 (m, 6 H), 2.21-2.33 (m, 1 H), 1.74-1.99 (m, 3 H) | A |
| 460 | 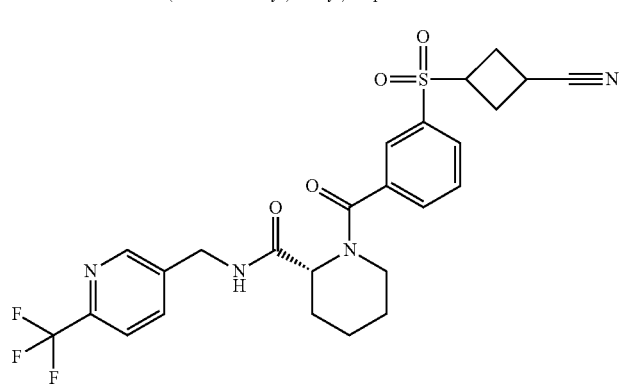<br>(R)-1-(3-((3-cyanocyclobutyl)sulfonyl)benzoyl)-N-((6-(trifluoromethyl)pyridin-3-yl)methyl)piperidine-2-carboxamide | LCMS-ESI (POS.) m/z: 535.0 (M + H)+ | 1H NMR (500 MHz, DMSO-d6) δ ppm 8.58-8.79 (m, 2H), 7.66-8.01 (m, 6H), 4.10-4.58 (m, 5H), 3.20-3.47 (m, 2H), 2.56-2.68 (m, 4H), 2.02-2.29 (m, 1H), 1.22-1.79 (m, 5H) | L |

| Ex. # | Structure Name | LCMS-ESI (POS/NEG) m/z: (M + H)+ | NMR Data | Syn. Rte. |
|---|---|---|---|---|
| 461 | 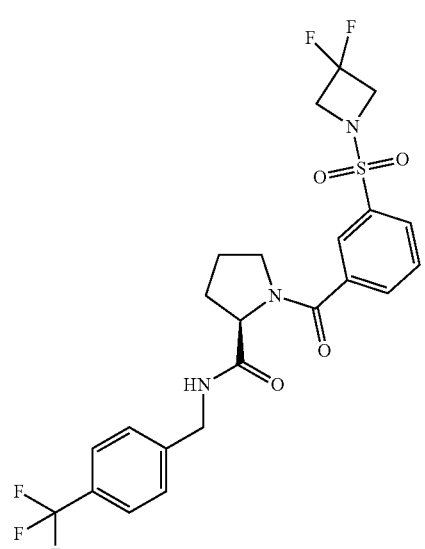<br>1-((3-((3,3-difluoro-1-azetidinyl)sulfonyl)phenyl)carbonyl)-N-(4-(trifluoromethyl)benzyl)-D-prolinamide | LCMS-APCI (NEG.) m/z: 530.1 (M − H) | 1H NMR (400 MHz, Methanol-d4) δ ppm 8.17 (d, J = 1.7 Hz, 1 H), 8.01 (ddt, J = 1.3, 7.7, 15.0 Hz, 2 H), 7.79 (t, J = 7.8 Hz, 1 H), 7.44-7.68 (m, 5 H), 4.56-4.73 (m, 2 H), 4.46 (d, J = 15.7 Hz, 1 H), 4.18-4.29 (m, 6 H), 3.67 (dt, J = 6.9, 10.3 Hz, 1 H), 3.53 (ddd, J = 4.4, 7.1, 10.1 Hz, 1 H), 2.30-2.48 (m, 1 H), 2.00-2.08 (m, 2 H), 1.32 (dd, J = 6.6, 8.6 Hz, 1 H). | Q |
| 462 | 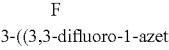<br>N-((1S)-1-(4-chloro-3-fluorophenyl)ethyl)-1-(((3S)-1-((3-cyano-1-azetidinyl)sulfonyl)-3-piperidinyl)carbonyl)-D-prolinamide | LCMS-ESI (POS.) m/z: 526.2 (M + H)+ | 1H NMR (500 MHz, DMSO-d6) δ ppm 8.51-8.56* (m, 1 H), 8.28 (d, J = 8.04 Hz, 1 H), 7.51 (t, J = 8.04 Hz, 1 H), 7.33-7.41 (m, 1 H), 7.14-7.21 (m, 1 H), 4.81-4.96 (m, 1 H), 4.42* (br d, J = 8.69 Hz, 1 H), 4.25-4.32 (m, 1 H), 4.00-4.08 (m, 2 H), 3.89-3.96 (m, 2 H), 3.79 (ddd, J = 14.89, 8.79, 6.42 Hz, 1 H), 3.49-3.64 (m, 3 H), 3.43 (m, 1 H), 2.72-2.87 (m, 2 H), 2.59-2.68 (m, 1 H), 2.14-2.28* (m, 1 H), 2.02-2.10* (m, 1 H), 1.92-1.99 (m, 1 H), 1.65-1.92 (m, 5 H), 1.37-1.53 (m, 2 H), 1.29-1.37 (m, 3 H). Spectrum appears as 2:1 mixture of rotamers, *denotes resolved minor rotamer peaks. | C |
| 463 | 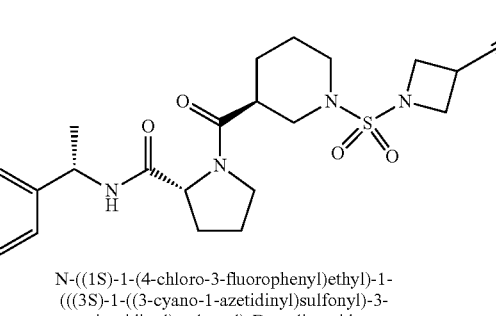<br>1-(((3S)-1-((3-fluoro-3-phenyl-1-azetidinyl)sulfonyl)-3-piperidinyl)carbonyl)-N-(4-(trifluoromethyl)benzyl)-D-prolinamide | LCMS-ESI (POS.) m/z: 597.4 (M + H)+ | 1H NMR (500 MHz, DMSO-d6) δ 8.31-8.78 (m, 1H), 7.33-7.80 (m, 9H), 4.18-4.52 (m, 7H), 3.51-3.74 (m, 4H), 2.76-2.97 (m, 2H), 2.60-2.73 (m, 1H), 2.02-2.39 (m, 1H), 1.67-2.02 (m, 5H), 1.37-1.58 (m, 2H) | J |

| Ex. # | Structure Name | LCMS-ESI (POS/NEG) m/z: (M + H)+ | NMR Data | Syn. Rte. |
|---|---|---|---|---|
| 464 | 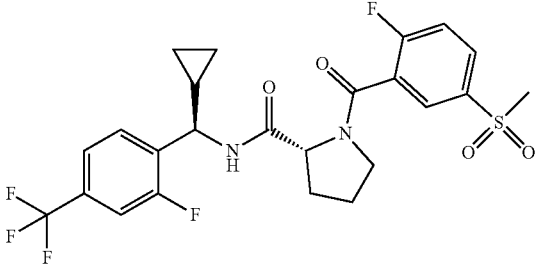 [SMILES: CS(=O)(=O)c1ccc(F)c(C(=O)N2CCC[C@@H]2C(=O)N[C@@H](c2ccc(C(F)(F)F)cc2F)C2CC2)c1]<br>N-((R)-((R)-fluoro-4-(trifluoromethyl)phenyl)methyl)-1-(2-fluoro-5-(methylsulfonyl)benzoyl)-D-prolinamide | LCMS-ESI (POS.) m/z: 531.0 (M + H)+ | 1H NMR (500 MHz, DMSO-d6) δ ppm 8.74 (d, J = 7.40 Hz, 1 H), 7.46-8.16 (m, 6 H), 4.52-4.67 (m, 1 H), 4.12-4.32 (m, 1 H), 3.50-3.64 (m, 1 H), 3.24-3.38 (m, 4 H), 2.15-2.28 (m, 1 H), 1.66-1.88 (m, 3 H), 0.84-1.24 (m, 1 H), -0.11-0.64 (m, 4 H) | C |
| 465 | 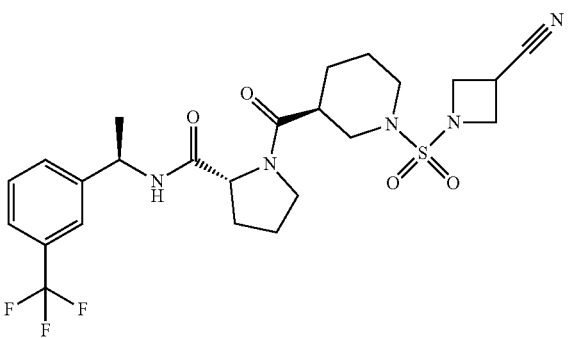 [SMILES: C[C@@H](NC(=O)[C@H]1CCCN1C(=O)[C@H]1CCCN(S(=O)(=O)N2CC(C#N)C2)C1)c1cccc(C(F)(F)F)c1]<br>1-(((3S)-1-((3-cyano-1-azetidinyl)sulfonyl)-3-piperidinyl)carbonyl)-N-((1R)-1-(3-(trifluoromethyl)phenyl)ethyl)-D-prolinamide | LCMS-ESI (POS.) m/z: 542.2 (M + H)+ | 1H NMR (500 MHz, CHLOROFORM-d) δ ppm 7.34-7.55 (m, 5 H), 5.03 (quin, J = 7.07 Hz, 1 H), 4.56 (dd, J = 8.04, 2.08 Hz, 1 H), 4.06-4.15 (m, 4 H), 3.74-3.80 (m, 2 H), 3.71 (br d, J = 12.85 Hz, 1 H), 3.53-3.64 (m, 2 H), 3.43 (tt, J = 8.68, 6.50 Hz, 1 H), 3.00 (dd, J = 12.59, 11.16 Hz, 1 H), 2.67-2.83 (m, 2 H), 2.28-2.41 (m, 1 H), 2.09-2.22 (m, 1 H), 1.96-2.06 (m, 2 H), 1.75-1.92 (m, 2 H), 1.57-1.71 (m, 2 H), 1.44 (d, J = 7.01 Hz, 3 H) | A |
| 466 | 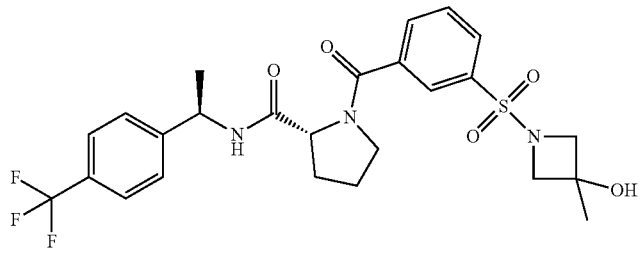 [SMILES: C[C@@H](NC(=O)[C@H]1CCCN1C(=O)c1cccc(S(=O)(=O)N2CC(C)(O)C2)c1)c1ccc(C(F)(F)F)cc1]<br>1-(3-((3-hydroxy-3-methyl-1-azetidinyl)sulfonyl)benzoyl)-N-((1R)-1-(4-(trifluoromethyl)phenyl)ethyl)-D-prolinamide | LCMS-ESI (POS.) m/z: 540.2 (M + H)+ | 1H NMR (400 MHz, CHLOROFORM-d) δ 7.39-8.06 (m, 8H), 7.04-7.18 (m, 1H), 4.84-5.21 (m, 1H), 4.33-4.76 (m, 1H), 3.95-4.26 (m, 3H), 3.72-3.80 (m, 2H), 3.36-3.72 (m, 4H), 2.25-2.42 (m, 1H), 2.08-2.19 (m, 2H), 1.83-1.97 (m, 1H), 1.51-1.56 (m, 3H), 1.24-1.34 (m, 1H) | C |
| 467 | 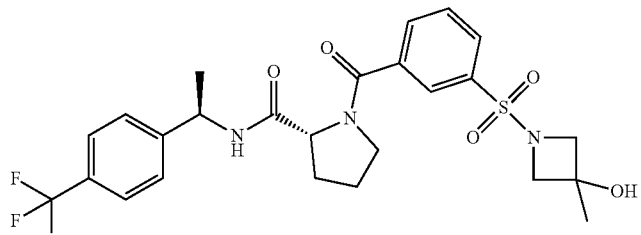<br>1-(((3S)-1-((3-hydroxy-3-(trifluoromethyl)-1-azetidinyl)sulfonyl)-3-piperidinyl)carbonyl)-N-(4-(trifluoromethyl)benzyl)-D-prolinamide | LCMS-ESI (POS.) m/z: 587.2 (M + H)+ | 1H NMR (500 MHz, CHLOROFORM-d) δ ppm 7.57 (d, J = 8.04 Hz, 2 H), 7.28-7.43 (m, 2 H), 7.14-7.26 (m, 1 H), 4.37-4.58 (m, 3 H), 3.94-4.20 (m, 4 H), 3.50-3.76 (m, 4 H), 3.02 (dd, J = 12.46, 10.12 Hz, 1 H), 2.79-2.92 (m, 1 H), 2.71 (qd, J = 6.79, 3.76 Hz, 1 H), 2.30-2.45 (m, 1 H), 2.13-2.27 (m, 1 H), 1.74-2.10 (m, 5 H), 1.47-1.71 (m, 5 H), 1.19-1.36 (m, 2 H) | M |

| Ex. # | Structure Name | LCMS-ESI (POS/NEG) m/z: (M + H)+ | NMR Data | Syn. Rte. |
|---|---|---|---|---|
| 468 | 1-(((3S)-1-((3-cyano-1-azetidinyl)sulfonyl)-3-piperidinyl)carbonyl)-N-((1S)-1-(3,5-difluorophenyl)propyl)-D-prolinamide | LCMS-ESI (POS.) m/z: 524.2 (M + H)+ | 1H NMR (500 MHz, DMSO-d6) δ ppm 8.13 (d, J = 8.30 Hz, 1 H), 6.96-7.11 (m, 3 H), 4.62-4.80 (m, 1 H), 4.29-4.48 (m, 1 H), 3.89-4.09 (m, 4 H), 3.74-3.85 (m, 2 H), 3.57 (br d, J = 6.88 Hz, 2 H), 2.80 (br d, J = 11.55 Hz, 3 H), 1.21-2.15 (m, 11 H), 0.75-0.91 (m, 3 H) | A |
| 469 | 1-(((3S)-1-((3-((4-fluorophenyl)amino)-1-azetidinyl)sulfonyl)-3-piperidinyl)carbonyl)-N-(4-(trifluoromethyl)benzyl)-D-prolinamide | LCMS-ESI (POS.) m/z: 612.2 (M + H)+ | 1H NMR (500 MHz, DMSO-d6) δ 8.27-8.76 (m, 1H), 7.61-7.73 (m, 2H), 7.38-7.50 (m, 2H), 6.87-7.00 (m, 2H), 6.45-6.58 (m, 2H), 6.17-6.28 (m, 1H), 4.25-4.52 (m, 3H), 4.04-4.20 (m, 3H), 3.50-3.71 (m, 6H), 2.71-2.90 (m, 2H), 2.60-2.71 (m, 1H), 2.03-2.38 (m, 1H), 1.67-2.00 (m, 5H), 1.36-1.57 (m, 2H) | J |
| 470 | 1-(((3S)-1-((3-cyano-1-azetidinyl)sulfonyl)-3-pyrrolidinyl)carbonyl)-N-(2-fluoro-4-(trifluoromethyl)benzyl)-D-prolinamide | LCMS-ESI (POS.) m/z: 532.2 (M + H)+ | 1H NMR (400 MHz, CHLOROFORM-d) δ 7.42-7.52 (m, 1H), 7.29-7.42 (m, 3H), 4.59 (dd, J = 2.33, 8.14 Hz, 1H), 4.45-4.55 (m, 2H), 4.10-4.23 (m, 4H), 3.38-3.67 (m, 7H), 3.23 (quin, J = 6.92 Hz, 1H), 2.35-2.45 (m, 1H), 2.14-2.25 (m, 2H), 2.00-2.12 (m, 2H), 1.85-1.99 (m, 1H) | M |
| 471 | (1R,3R,5R)-N-((R)-(4-chloro-2,5-difluorophenyl)(3-oxetanyl)methyl)-2-((4-cyclopropyl-2-pyridinyl)carbonyl)-2-azabicyclo[3.1.0]hexane-3-carboxamide | LCMS-APCI (POS.) m/z: 488.1 (M + H)+ | 1H NMR (400 MHz, Methanol-d4) δ ppm 8.50 (dd, J = 0.9, 5.1 Hz, 1 H), 7.50 (dd, 1 H), 7.36-7.47 (m, 2 H), 7.27 (dd, J = 6.3, 9.4 Hz, 1 H), 5.57 (d, J = 10.3 Hz, 1 H), 4.91-5.00 (m, 1 H), 4.84 (dd, J = 6.5, 7.7 Hz, 1 H), 4.67 (dd, J = 6.4, 7.8 Hz, 1 H), 4.60 (t, J = 6.2 Hz, 1 H), 4.38 (t, J = 6.2 Hz, 1 H), 3.45-3.56 (m, 1 H), 3.27 (td, J = 2.6, 6.2 Hz, 1 H), 2.66 (td, J = 6.6, 12.7 Hz, 1 H), 2.12-2.22 (m, 1 H), 1.89 (dd, J = 4.1, 13.6 Hz, 1 H), 1.72-1.85 (m, 1 H), 1.23 (td, J = 2.6, 5.3 Hz, 1 H), 0.97-1.13 (m, 4 H), 0.85 (dt, J = 5.8, 8.7 Hz, 1 H). | Q |

| Ex. # | Structure Name | LCMS-ESI (POS/NEG) m/z: (M + H)+ | NMR Data | Syn. Rte. |
|---|---|---|---|---|
| 472 | 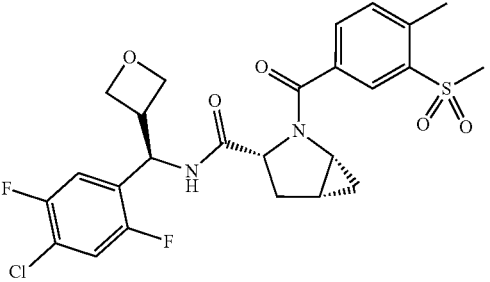 [SMILES: Cc1ccc(C(=O)N2[C@@H](C(=O)N[C@@H](c3cc(F)c(Cl)cc3F)C3COC3)C[C@H]3C[C@H]32)cc1S(C)(=O)=O]<br>(1R,3R,5R)-N-((R)-(4-chloro-2,5-difluorophenyl)(3-oxetanyl)methyl)-2-(4-methyl-3-(methylsulfonyl)benzoyl)-2-azabicyclo[3.1.0]hexane-3-carboxamide | LCMS-APCI (POS.) m/z: 539.1 (M + H)+ | 1H NMR (400 MHz, DMSO-d6) δ ppm 8.65 (d, J = 8.2 Hz, 1 H), 8.28 (d, J = 1.8 Hz, 1 H), 7.89-7.95 (m, 1 H), 7.66 (dd, J = 6.2, 9.4 Hz, 1 H), 7.59 (d, J = 8.0 Hz, 1 H), 7.44 (dd, J = 6.2, 9.7 Hz, 1 H), 5.41 (t, J = 9.0 Hz, 1 H), 4.88 (dd, J = 3.8, 11.4 Hz, 1 H), 4.62 (dd, J = 6.4, 7.7 Hz, 1 H), 4.51 (dd, J = 6.2, 7.8 Hz, 1 H), 4.36 (t, J = 6.1 Hz, 1 H), 4.19 (t, J = 6.1 Hz, 1 H), 3.27 (s, 4 H), 2.70 (s, 3 H), 2.52-2.58 (m, 1 H), 1.70 (dd, J = 3.9, 13.4 Hz, 2 H), 1.16 (ddd, J = 2.0, 4.7, 7.5 Hz, 1 H), 0.79 (dt, J = 5.3, 9.6 Hz, 1 H). | Q |
| 473 | 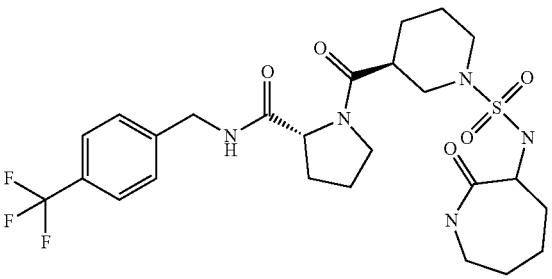 [SMILES: O=C1NCCCCC1NS(=O)(=O)N1CCC[C@H](C(=O)N2CCC[C@@H]2C(=O)NCc2ccc(C(F)(F)F)cc2)C1]<br>(2R)-1-((3S)-1-(N-(2-oxoazepan-3-yl)sulfamoyl)piperidine-3-carbonyl)-N-(4-(trifluoromethyl)benzyl)pyrrolidine-2-carboxamide | LCMS-ESI (POS.) m/z: 574.4 (M + H)+ | 1H NMR (500 MHz, DMSO-d6) δ 8.29-8.77 (m, 1H), 7.61-7.98 (m, 3H), 7.37-7.55 (m, 2H), 6.73-7.06 (m, 1H), 4.24-4.50 (m, 3H), 3.83-4.01 (m, 1H), 3.42-3.72 (m, 4H), 3.01-3.19 (m, 2H), 2.55-2.78 (m, 3H), 1.11-2.36 (m, 14H) | J |
| 474 | 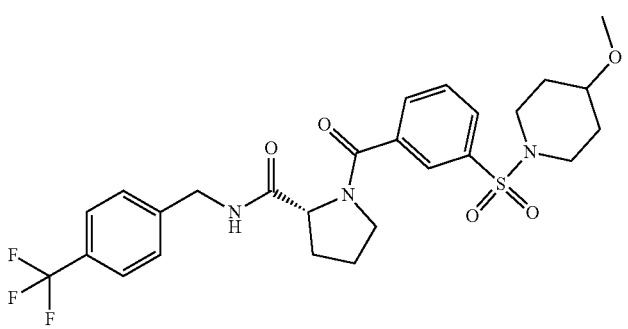 [SMILES: COC1CCN(S(=O)(=O)c2cccc(C(=O)N3CCC[C@@H]3C(=O)NCc3ccc(C(F)(F)F)cc3)c2)CC1]<br>1-((3-((4-methoxy-1-piperidinyl)sulfonyl)phenyl)carbonyl)-N-(4-(trifluoromethyl)benzyl)-D-prolinamide | LCMS-ESI (POS.) m/z: 554.2 (M + H)+ | 1H NMR (400 MHz, CHLOROFORM-d) δ ppm 7.91 (s, 1 H), 7.85 (br d, J = 7.93 Hz, 1 H), 7.73 (d, J = 7.72 Hz, 1 H), 7.54-7.66 (m, 3 H), 7.42 (d, J = 8.03 Hz, 2 H), 7.28-7.35 (m, 1 H), 4.76 (dd, J = 7.31, 5.08 Hz, 1 H), 4.55 (d, J = 5.96 Hz, 2 H), 3.60 (dt, J = 10.33, 6.68 Hz, 1 H), 3.46 (dt, J = 10.06, 6.40 Hz, 1 H), 3.38 (s, 1 H), 3.24-3.32 (m, 4 H), 3.10-3.21 (m, 2 H), 2.96-3.09 (m, 2 H), 2.33-2.57 (m, 1 H), 2.14 (br d, J = 5.23 Hz, 2 H), 2.00-2.01 (m, 1 H), 1.85-1.91 (m, 3 H), 1.66-1.82 (m, 2 H) | B |

| Ex. # | Structure Name | LCMS-ESI (POS/NEG) m/z: (M + H)+ | NMR Data | Syn. Rte. |
|---|---|---|---|---|
| 475 | (1R)-N-((R)-cyclopropyl(2-fluoro-4-(trifluoromethyl)phenyl)methyl)-2-(3-(methylsulfonyl)benzoyl)-2-azaspiro[3.3]heptane-1-carboxamide | LCMS-ESI (POS.) m/z: 539.2 (M + H)+ | 1H NMR (400 MHz, CHLOROFORM-d) δ ppm 8.17-8.37 (m, 1 H), 7.91-8.17 (m, 2 H), 7.60-7.83 (m, 1 H), 7.44-7.57 (m, 1 H), 7.36-7.44 (m, 1 H), 7.29-7.36 (m, 1 H), 7.01-7.24 (m, 1 H), 4.72-4.79 (m, 1 H), 4.48-4.71 (m, 1 H), 4.28-4.48 (m, 1 H), 4.10-4.28 (m, 1 H), 2.91-3.25 (m, 3 H), 2.27-2.60 (m, 2 H), 2.09-2.25 (m, 1 H), 1.98-2.08 (m, 1 H), 1.89-1.97 (m, 1 H), 1.76-1.89 (m, 1 H), 1.20-1.34 (m, 1 H), 0.61-0.74 (m, 1 H), 0.53-0.61 (m, 1 H), 0.26-0.52 (m, 2 H) | C |
| 476 | (3R,5R)-5-(((R)-(4-chloro-2,5-difluorophenyl)(3-oxetanyl)methyl)carbamoyl)-1-((2-(difluoromethyl)-4-pyridinyl)carbonyl)-3-pyrrolidinyl 2-(difluoromethyl)-4-pyridinecarboxylate | LCMS-APCI (POS.) m/z: 657.1 (M + H)+ | 1H NMR (400 MHz, DMSO-d6) δ ppm 8.79 (d, J = 3.2, 5.1 Hz, 1 H), 8.75 (d, J = 5.0 Hz, 1 H), 8.49 (d, J = 8.2 Hz, 1 H), 7.75-7.79 (m, 2 H), 7.71 (ddd, J = 1.4, 5.1, 9.1 Hz, 1 H), 7.61-7.66 (m, 1 H), 7.27-7.35 (m, 1 H), 7.15 (td, J = 2.6, 6.3, 7.1 Hz, 2 H), 6.86-7.11 (m, 3 H), 5.50-5.57 (m, 1 H), 5.17 (dd, J = 8.2, 9.7 Hz, 1 H), 4.53 (d, J = 9.1 Hz, 1 H), 4.26-4.41 (m, 3 H), 3.87-3.96 (m, 3 H), 3.82 (t, J = 6.1 Hz, 1 H), 3.00-3.12 (m, 1 H), 2.81 (ddd, J = 4.5, 9.3, 14.1 Hz, 1 H), 2.28 (d, J = 14.4 Hz, 1 H). | U |
| 477 | 1-(((3S)-1-((3-(4-fluorophenyl)-1-azetidinyl)sulfonyl)-3-piperidinyl)carbonyl)-N-(4-(trifluoromethyl)benzyl)-D-prolinamide | LCMS-ESI (POS.) m/z: 597.2 (M + H)+ | 1H NMR (500 MHz, DMSO-d6) δ 8.26-8.76 (m, 1H), 7.60-7.73 (m, 2H), 7.34-7.51 (m, 4H), 7.11-7.26 (m, 2H), 4.22-4.52 (m, 3H), 4.08-4.22 (m, 2H), 3.76-3.92 (m, 3H), 3.41-3.71 (m, 4H), 2.70-2.90 (m, 2H), 2.59-2.70 (m, 1H), 2.02-2.40 (m, 1H), 1.65-2.02 (m, 5H), 1.33-1.59 (m, 2H) | J |

| Ex. # | Structure Name | LCMS-ESI (POS/NEG) m/z: (M + H)+ | NMR Data | Syn. Rte. |
|---|---|---|---|---|
| 478 | 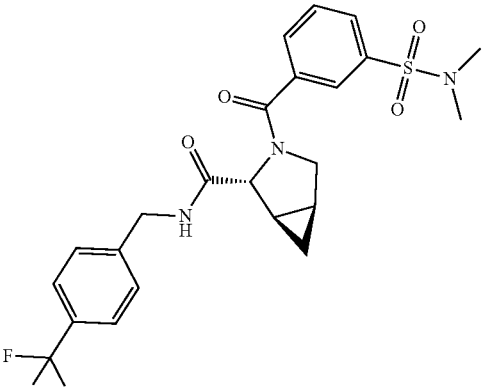<br>(1R,2R,5S)-3-(3-(dimethylsulfamoyl)benzoyl)-N-(4-(trifluoromethyl)benzyl)-3-azabicyclo[3.1.0]hexane-2-carboxamide | LCMS-ESI (POS.) m/z: 496.2 (M + H)+ | 1H NMR (500 MHz, DMSO-d6) δ ppm 8.55-8.88 (m, 1 H), 7.22-7.92 (m, 8 H), 4.70-4.75 (m, 1 H), 4.67-4.79 (m, 1 H), 4.19-4.53 (m, 2 H), 3.81-3.95 (m, 1 H), 3.31-3.64 (m, 1 H), 2.56-2.69 (m, 6 H), 1.57-1.76 (m, 2 H), 0.22-0.87 (m, 2 H) | C |
| 479 | 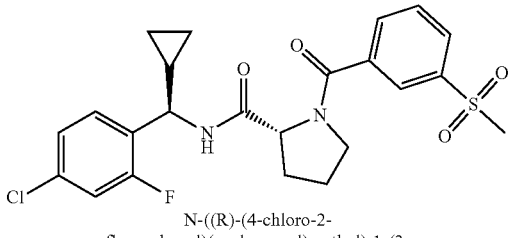<br>N-((R)-(4-chloro-2-fluorophenyl)(cyclopropyl)methyl)-1-(3-(methylsulfonyl)benzoyl)-D-prolinamide | LCMS-ESI (POS.) m/z: 479.2 (M + H)+ | 1H NMR (500 MHz, DMSO-d6) δ ppm 8.40-8.65 (m, 1 H), 7.63-8.08 (m, 4 H), 7.24-7.52 (m, 3 H), 4.14-4.59 (m, 2 H), 3.39-3.62 (m, 2 H), 3.24-3.29 (m, 3 H), 2.13-2.26 (m, 1 H), 1.65-1.89 (m, 3 H), 0.85-1.23 (m, 1 H), −0.08-0.58 (m, 4 H) | A |
| 480 | 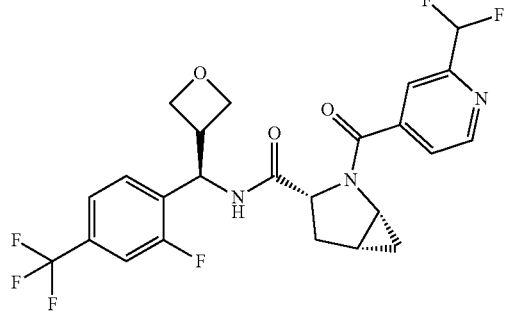<br>(1R,3R,5R)-2((2-(difluoromethyl)-4-pyridinyl)carbonyl)-N-((R)-(2-fluoro-4-(trifluoromethyl)phenyl)(3-oxetanyl)methyl)-2-azabicyclo[3.1.0]hexane-3-carboxamide | LCMS-APCI (POS.) m/z: 514.1 (M + H)+ | 1H NMR (400 MHz, Methanol-d4) δ ppm 8.69 (d, J = 0.7, 5.0 Hz, 1 H), 7.89 (s, 1 H), 7.75 (d, J = 0.9, 1.7, 5.0 Hz, 1 H), 7.35-7.47 (m, 3 H), 6.70 (t, J = 55.1 Hz, 1 H), 5.54 (d, J = 10.1 Hz, 1 H), 4.87 (dd, J = 4.1, 11.4 Hz, 1 H), 4.71-4.78 (m, 6 H), 4.50-4.58 (m, 2 H), 4.28 (t, 1 H), 3.40-3.50 (m, 1 H), 3.17 (ddd, J = 2.6, 5.9, 6.6 Hz, 1 H), 2.50-2.60 (m, 1 H), 1.79 (dd, 1 H), 1.65-1.72 (m, 1 H), 1.13 (tt, J = 2.6, 5.4 Hz, 1 H), 0.75 (ddd, J = 4.8, 5.9, 8.5 Hz, 1 H). | A |
| 481 | 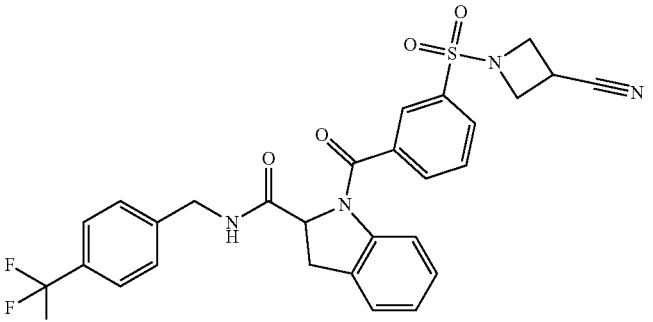<br>(2R)-1-((3-((3-cyano-1-azetidinyl)sulfonyl)phenyl)carbonyl)-N-(4- | LCMS-ESI (POS.) m/z: 569.2 (M + H)+ | 1H NMR (500 MHz, DMSO-d6) δ ppm 7.87-8.09 (m, 3 H), 7.87 (br s, 1 H), 7.77-7.84 (m, 1 H), 7.71 (br d, J = 7.66 Hz, 1 H), 7.60-7.67 (m, 2 H), 7.56 (br d, J = 7.66 Hz, 1 H), 7.44 (br s, 1 H), 7.36 (br d, J = 7.27 Hz, 1 H), 7.21-7.31 (m, 2 H), 7.15-7.21 (m, 1 H), 7.07-7.15 (m, 1 H), 6.88-7.07 (m, 1 H), 4.27 (br s, 1 H), 4.08 (br d, J = 5.06 Hz, 1 H), 3.94-4.04 (m, 2 H), 3.80-3.93 (m, 2 H), 3.05 (s, 1 H) | I |

| Ex. # | Structure Name | LCMS-ESI (POS/NEG) m/z: (M + H)+ | NMR Data | Syn. Rte. |
|---|---|---|---|---|
| | (trifluoromethyl)benzyl)-2,3-dihydro-1H-indole-2-carboxamide, (2S)-1-((3-((3-cyano-1-azetidinyl)sulfonyl)phenyl)carbonyl)-N-(4-(trifluoromethyl)benzyl)-2,3-dihydro-1H-indole-2-carboxamide | | | |
| 482 | Diastereomer #2-(1R,3R,5R)-N-((2-fluoro-4-(trifluoromethyl)phenyl)(5-oxopyrrolidin-3-yl)methyl)-2-(3-(methylsulfonyl)benzoyl)-2-azabicyclo[3.1.0]hexane-3-carboxamide | LCMS-ESI (POS.) m/z: 538.2 (M + H)+ | 1H NMR (400 MHz, DMSO-d6) δ ppm 8.32-8.72 (m, 1H), 7.37-8.12 (m, 9H), 4.56-5.05 (m, 1H), 4.31-4.56 (m, 1H), 3.41-3.65 (m, 2H), 3.23-3.30 (m, 3H), 2.93-3.01 (m, 1H), 2.73-2.93 (m, 1H), 2.53-2.69 (m, 1H), 2.11-2.27 (m, 2H), 1.55-1.92 (m, 4H) | A |
| 483 | 1-(((3S)-1-((3-cyclobutyl-1-azetidinyl)sulfonyl)-3-piperidinyl)carbonyl)-N-(4-(trifluoromethyl)benzyl)-D-prolinamide | LCMS-ESI (POS.) m/z: 557.2 (M + H)+ | 1H NMR (500 MHz, DMSO-d6) δ 8.28-8.81 (m, 1H), 7.61-7.74 (m, 2H), 7.37-7.52 (m, 2H), 4.24-4.52 (m, 3H), 3.71-3.87 (m, 2H), 3.42-3.71 (m, 7H), 2.58-2.83 (m, 4H), 2.06-2.35 (m, 1H), 1.59-2.04 (m, 11H), 1.30-1.54 (m, 2H) | J |
| 484 | (1S,2R,5R)-N-((R)-cyclopropyl(2-fluoro-4-(trifluoromethyl)phenyl)methyl)-3-(3-(methylsulfonyl)benzoyl)-3-azabicyclo[3.1.0]hexane-2-carboxamide | LCMS-ESI (POS.) m/z: 525.0 (M + H)+ | 1H NMR (400 MHz, CHLOROFORM-d) δ ppm 7.89-8.14 (m, 2 H), 7.73-7.85 (m, 1 H), 7.56-7.71 (m, 1 H), 7.29-7.52 (m, 3 H), 5.93-6.60 (m, 1 H), 4.69 (d, J = 5.60 Hz, 1 H), 4.50-4.63 (m, 1 H), 3.49-4.13 (m, 2 H), 2.97-3.18 (m, 3 H), 1.92-2.09 (m, 1 H), 1.68-1.80 (m, 1 H), 1.14-1.32 (m, 1 H), 0.35-1.02 (m, 6 H) | C |
| 485 | (1R,3R,5R)-N-((R)-(4-chloro-3-fluorophenyl)(cyclopropyl)methyl)-2-(3-(methylsulfonyl)benzoyl)-2-azabicyclo[3.1.0]hexane-3-carboxamide | LCMS-ESI (POS.) m/z: 491.0 (M + H)+ | 1H NMR (500 MHz, DMSO-d6) δ ppm 8.30-8.68 (m, 1 H), 7.86-8.21 (m, 3 H), 7.64-7.83 (m, 1 H), 7.48-7.59 (m, 1 H), 7.33-7.43 (m, 1 H), 7.17-7.30 (m, 1 H), 4.63-4.97 (m, 1 H), 4.17-4.28 (m, 1 H), 3.20-3.30 (m, 4 H), 2.55-2.69 (m, 1 H), 1.65-1.97 (m, 2 H), 1.02-1.29 (m, 2 H), 0.68-0.81 (m, 1 H),-0.36-0.53 (m, 4 H) | C |

| Ex. # | Structure Name | LCMS-ESI (POS/NEG) m/z: (M + H)+ | NMR Data | Syn. Rte. |
|---|---|---|---|---|
| 486 | 1-(3-(1-azetidinylsulfonyl)benzoyl)-N-(4-(trifluoromethyl)benzyl)-D-prolinamide | LCMS-ESI (POS.) m/z: 496.2 (M + H)+ | 1H NMR (500 MHz, DMSO-d6) δ ppm 8.44-8.75 (m, 1 H), 7.07-7.98 (m, 8 H), 4.17-4.55 (m, 3 H), 3.69 (br t, J = 7.79 Hz, 4 H), 3.17 (br d, J = 6.36 Hz, 1 H), 2.62-2.68 (m, 1 H), 2.24-2.32 (m, 1 H), 2.01-2.02 (m, 1 H), 1.81-2.04 (m, 5 H), 0.94-1.07 (m, 10 H) | C |
| 487 | (1R,3R,5R)-N-((R)-(4-chloro-2,5-difluorophenyl)(3-oxetanyl)methyl)-2-((6-(trifluoromethyl)-4-pyrimidinyl)carbonyl)-2-azabicyclo[3.1.0]hexane-3-carboxamide | LCMS-APCI (POS.) m/z: 517.1 (M + H)+ | 1H NMR (400 MHz, DMSO-d6) δ ppm 9.51 (d, J = 1.3, 80.7 Hz, 1 H), 8.61 (d, J = 8.3, 55.4 Hz, 1 H), 8.20 (d, J = 1.3, 17.1 Hz, 1 H), 7.65 (ddd, J = 6.2, 9.5, 15.8 Hz, 1 H), 7.37 (dd, J = 6.4, 9.8, 62.4 Hz, 1 H), 5.37-5.47 (m, 1 H), 4.83-5.18 (m, 1 H), 4.58 (dt, J = 7.3, 49.2 Hz, 1 H), 4.18-4.45 (m, 2 H), 3.78-3.88 (m, 1 H), 1.58-1.89 (m, 2 H), 1.08-1.14 (m, 1 H), 0.60-0.84 (m, 1 H). | Q |
| 488 | (4S)-N-((R)-(4-chloro-2,5-difluorophenyl)(cyclopropyl)methyl)-4-fluoro-1-((5-(methylsulfonyl)-3-pyridinyl)carbonyl)-D-prolinamide | LCMS-ESI (POS.) m/z: 516.0 (M + H)+ | 1H NMR (500 MHz, DMSO-d6) δ ppm 9.20 (d, J = 2.08 Hz, 1 H), 9.06 (d, J = 1.82 Hz, 1 H), 8.59-8.83 (m, 1 H), 8.41 (t, J = 1.95 Hz, 1 H), 7.30-7.67 (m, 2 H), 5.20-5.46 (m, 1 H), 3.95-4.74 (m, 3 H), 3.74 (br s, 2 H), 3.37-3.45 (m, 3 H), 1.82-2.16 (m, 1 H), 0.81-1.32 (m, 1 H), -0.35-0.73 (m, 4 H) | C |
| 489 | 1-(((3S)-1-((3-((trifluoroacetyl)amino)-1-azetidinyl)sulfonyl)-3-piperidinyl)carbonyl)-N-(4-(trifluoromethyl)benzyl)-D-prolinamide | LCMS-ESI (POS.) m/z: 614.2 (M + H)+ | 1H NMR (500 MHz, DMSO-d6) δ 8.29-8.79 (m, 1H), 7.62-7.76 (m, 2H), 7.40-7.51 (m, 2H), 4.27-4.60 (m, 4H), 3.82-4.06 (m, 4H), 3.51-3.75 (m, 5H), 2.70-2.91 (m, 2H), 2.60-2.70 (m, 1H), 2.02-2.37 (m, 1H), 1.68-2.02 (m, 5H), 1.33-1.58 (m, 2H) | J |

| Ex. # | Structure Name | LCMS-ESI (POS/NEG) m/z: (M + H)+ | NMR Data | Syn. Rte. |
|---|---|---|---|---|
| 490 | 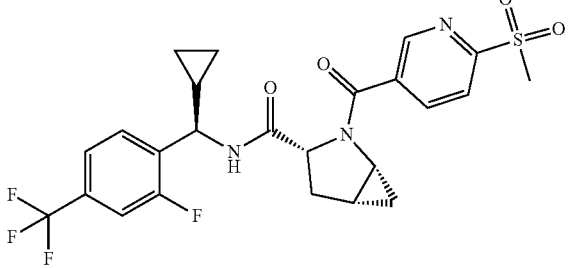<br>(1R,3R,5R)-N-((R)-cyclopropyl(2-fluoro-4-(trifluoromethyl)phenyl)methyl)-2-((6-(methylsulfonyl)-3-pyridinyl)carbonyl)-2-azabicyclo[3.1.0]hexane-3-carboxamide | LCMS-ESI (POS.) m/z: 526.0 (M + H)+ | 1H NMR (500 MHz, DMSO-d6) δ ppm 8.50-9.03 (m, 2 H), 8.11-8.25 (m, 1 H), 7.98-8.10 (m, 1 H), 7.53-7.75 (m, 3 H), 4.90-5.53 (m, 1 H), 4.14-4.68 (m, 1 H), 3.78-3.99 (m, 1 H), 3.40 (br d, J = 5.71 Hz, 3 H), 2.54-2.80 (m, 1 H), 1.50-1.90 (m, 2 H), −0.17-1.24 (m, 7 H) | C |
| 491 | 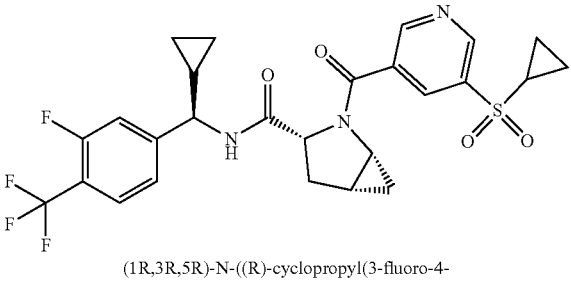<br>(1R,3R,5R)-N-((R)-cyclopropyl(3-fluoro-4-(trifluoromethyl)phenyl)methyl)-2-((5-(cyclopropylsulfonyl)-3-pyridinyl)carbonyl)-2-azabicyclo[3.1.0]hexane-3-carboxamide | LCMS-ESI (POS.) m/z: 552.2 (M + H)+ | 1H NMR (500 MHz, CHLOROFORM-d) δ ppm 9.19-9.32 (m, 2 H), 8.55-8.65 (m, 1 H), 7.57-7.66 (m, 1 H), 7.33-7.41 (m, 1 H), 7.18-7.28 (m, 2 H), 5.11-5.24 (m, 1 H), 4.31-4.45 (m, 1 H), 3.27-3.35 (m, 1 H), 2.53-2.66 (m, 2 H), 2.37-2.50 (m, 1 H), 1.82-1.90 (m, 1 H), 1.42-1.54 (m, 2 H), 1.10-1.30 (m, 4 H), 0.95-1.02 (m, 1 H), 0.56-0.72 (m, 2 H), 0.38-0.50 (m, 2 H) | H |
| 492 | 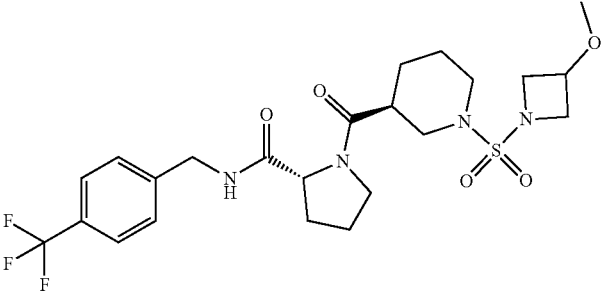 [SMILES: COC1CN(S(=O)(=O)N2CCC[C@H](C(=O)N3CCC[C@@H]3C(=O)NCc3ccc(C(F)(F)F)cc3)C2)C1]<br>1-(((3S)-1-((3-methoxy-1-azetidinyl)sulfonyl)-3-piperidinyl)carbonyl)-N-(4-(trifluoromethyl)benzyl)-D-prolinamide | LCMS-ESI (POS.) m/z: 533.2 (M + H)+ | 1H NMR (500 MHz, DMSO-d6) δ ppm 8.72* (t, J = 5.77 Hz, 1 H), 8.36 (t, J = 5.97 Hz, 1 H), 7.65-7.71 (m, 2 H), 7.45 (d, J = 7.98 Hz, 2 H), 4.28-4.49 (m, 3 H), 4.16 (quin, J = 5.61 Hz, 1 H), 3.90-3.97 (m, 2 H), 3.33-3.67 (m, 6 H), 3.19 (s, 3 H), 2.69-2.84 (m, 2 H), 2.62-2.69 (m, 1 H), 2.27-2.35* (m, 1 H), 2.18-2.26* (m, 1 H), 2.06-2.14 (m, 1 H), 1.67-2.00 (m, 5 H), 1.33-1.55 (m, 2 H). Spectrum appears as 2:1 mixture of rotamers, *denotes resolved minor rotamer peaks. | M |
| 493 | 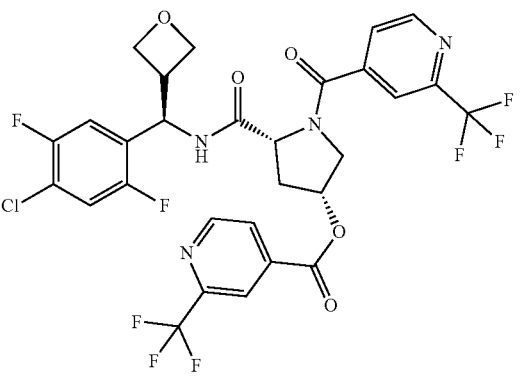 [SMILES: O=C(O[C@@H]1C[C@H](C(=O)N[C@@H](c2cc(F)c(Cl)cc2F)C2COC2)N(C(=O)c2ccnc(C(F)(F)F)c2)C1)c1ccnc(C(F)(F)F)c1] | LCMS-APCI (POS.) m/z: 693.2 (M + H)+ | 1H NMR (400 MHz, DMSO-d6) δ ppm 8.90 (q, J = 5.1 Hz, 2 H), 8.52 (d, J = 8.1 Hz, 1 H), 7.98-8.04 (m, 1 H), 7.86-7.89 (m, 1 H), 7.77 (ddd, J = 1.4, 4.9, 10.5 Hz, 2 H), 7.06-7.15 (m, 2 H), 5.57 (d, J = 3.9 Hz, 1 H), 5.09-5.20 (m, 1 H), 4.57 (d, J = 9.2 Hz, 1 H), 4.31 (ddd, J = 6.1, 7.7, 14.1 Hz, 2 H), 3.87-3.96 (m, 3 H), 3.77 (t, J = 6.1 Hz, 1 H), 3.06 (p, J = 7.1 Hz, 1 H), 2.81 (ddd, J = 4.4, 9.4, 14.3 Hz, 1 H), 2.27-2.36 (m, 1H). | T |

| Ex. # | Structure Name | LCMS-ESI (POS/NEG) m/z: (M + H)+ | NMR Data | Syn. Rte. |
|---|---|---|---|---|
| | (3R,5R)-5-(((R)-(4-chloro-2,5-difluorophenyl)(3-oxetanyl)methyl)carbamo)-1-((2-(trifluoromethyl)-4-pyridinyl)carbonyl)-3-pyrrolidinyl 2-(trifluoromethyl)-4-pyridinecarboxylate | | | |
| 494 | (2R,4S)-1-((S)-1-((3-cyanoazetidin-1-yl)sulfonyl)piperidine-3-carbonyl)-4-fluoro-N-((R)-1-(3-(trifluoromethyl)phenyl)ethyl)pyrrolidine-2-carboxamide | LCMS-ESI (POS.) m/z: 560.2 (M + H)+ | 1H NMR (500 MHz, DMSO-d6) δ ppm 8.44-8.90 (m, 1 H), 7.51-7.65 (m, 4 H), 5.17-5.45 (m, 1 H), 4.89-5.08 (m, 1 H), 4.36-4.68 (m, 1 H), 4.03-4.12 (m, 2 H), 3.85-4.00 (m, 3 H), 3.65-3.85 (m, 2 H), 3.54 (br d, J = 8.82 Hz, 2 H), 2.72-2.89 (m, 2 H), 2.57-2.71 (m, 1 H), 2.34-2.46 (m, 1 H), 1.67-2.09 (m, 3 H), 1.30-1.56 (m, 5 H) | C |
| 495 | (1R,3R,5R)-N-((R)-cyclopropyl(2-fluoro-4-(trifluoromethyl)phenyl)methyl)-2-((2-(trifluoromethyl)-4-pyridinyl)carbonyl)-2-azabicyclo[3.1.0]hexane-3-carboxamide | LCMS-APCI (POS.) m/z: 516.2 (M + H)+ | 1H NMR (400 MHz, DMSO-d6) δ ppm 8.94 (d, J = 4.9 Hz, 2 H), 8.65 (d, J = 7.5, 94.9 Hz, 2 H), 7.99 (t, J = 1.2 Hz, 1 H), 7.93 (d, 1 H), 7.54-7.77 (m, 5 H), 4.94 (dd, J = 3.5, 11.4 Hz, 1 H), 4.53-4.69 (m, 2 H), 4.35 (t, J = 5.1 Hz, 1 H), 4.12 (t, J = 8.3 Hz, 1 H), 3.71-3.81 (m, 1 H), 3.28 (td, J = 2.8, 6.2 Hz, 1 H), 2.56-2.64 (m, 1 H), 1.57-1.78 (m, 3 H), 1.19 (dt, J = 4.9, 8.9 Hz, 2 H), 0.85-0.95 (m, 1 H), 0.66-0.78 (m, 2 H), 0.52-0.62 (m, 1 H), 0.46 (t, J = 9.1 Hz, 1 H), 0.21-0.39 (m, 3 H), −0.29-0.00 (m, 2 H). | Q |
| 496 | 1-(((3S)-1-((3-cyano-1-azetidinyl)sulfonyl)-3-piperidinyl)carbonyl)-N-(3-fluorobenzyl)-D-prolinamide | LCMS-ESI (POS.) m/z: 478.2 (M + H)+ | 1H NMR (500 MHz, DMSO-d6) δ ppm 8.25-8.69 (m, 1 H), 7.30-7.42 (m, 1 H), 6.96-7.14 (m, 3 H), 3.87-4.50 (m, 6 H), 3.75-3.82 (m, 1 H), 3.42-3.69 (m, 5 H), 2.60-2.89 (m, 3 H), 2.06-2.34 (m, 1 H), 1.66-2.02 (m, 5 H), 1.35-1.60 (m, 2 H) | A |

-continued

| Ex. # | Structure Name | LCMS-ESI (POS/NEG) m/z: (M + H)+ | NMR Data | Syn. Rte. |
|---|---|---|---|---|
| 497 | 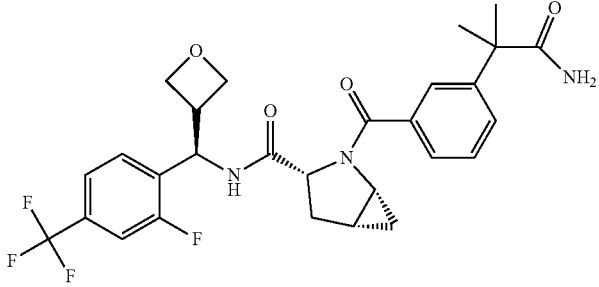 [SMILES: CC(C)(C(N)=O)c1cccc(C(=O)N2[C@@H](C(=O)N[C@@H](c3ccc(C(F)(F)F)cc3F)C3COC3)C[C@H]3C[C@H]32)c1]<br>(1R,3R,5R)-2-(3-(1-amino-2-methyl-1-oxo-2-propanyl)benzoyl)-N-((R)-(2-fluoro-4-(trifluoromethyl)phenyl)(3-oxetanyl)methyl)-2-azabicyclo[3.1.0]hexane-3-carboxamide | LCMS-APCI (POS.) m/z: 548.2 (M + H)+ | 1H NMR (400 MHz, Methanol-d4) δ ppm 7.88 (t, J = 1.8 Hz, 1 H), 7.65 (dt, J = 1.4, 7.5 Hz, 1 H), 7.56-7.59 (m, 1 H), 7.51-7.56 (m, 2 H), 7.44-7.50 (m, 2 H), 5.65 (d, J = 10.2 Hz, 1 H), 4.99 (dd, J = 4.2, 11.4 Hz, 1 H), 4.83-4.86 (m, 1 H), 4.60-4.70 (m, 2 H), 4.40 (t, J = 0.9, 12.5 Hz, 1 H), 3.51-3.61 (m, 1 H), 2.57-2.68 (m, 1 H), 1.91 (dd, J = 4.2, 13.5 Hz, 1 H), 1.72-1.80 (m, 1 H), 1.60 (d, J = 4.1 Hz, 7 H), 1.22 (td, J = 2.6, 5.3 Hz, 1 H), 0.84-0.91 (m, 1 H). | V |
| 498 | 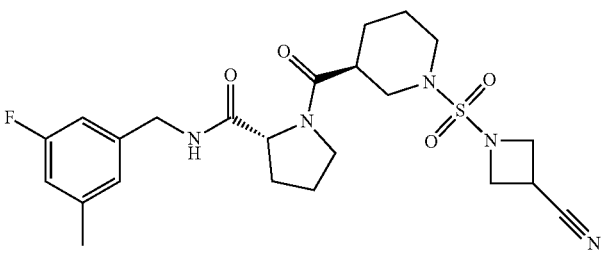 [SMILES: Cc1cc(F)cc(CNC(=O)[C@H]2CCCN2C(=O)[C@H]2CCCN(S(=O)(=O)N3CC(C#N)C3)C2)c1]<br>1-(((3S)-1-((3-cyano-1-azetidinyl)sulfonyl)-3-piperidinyl)carbonyl)-N-(3-fluoro-5-methylbenzyl)-D-prolinamide | LCMS-ESI (POS.) m/z: 492.2 (M + H)+ | 1H NMR (500 MHz, DMSO-d6) δ ppm 8.22-8.65 (m, 1 H), 6.79-6.93 (m, 3 H), 4.16-4.52 (m, 3 H), 3.98-4.09 (m, 2 H), 3.86-3.97 (m, 2 H), 3.73-3.83 (m, 1 H), 3.36-3.70 (m, 4 H), 2.70-2.87 (m, 2 H), 2.61-2.69 (m, 1 H), 2.05-2.33 (m, 4 H), 1.67-2.00 (m, 5 H), 1.35-1.55 (m, 2 H) | A |
| 499 | 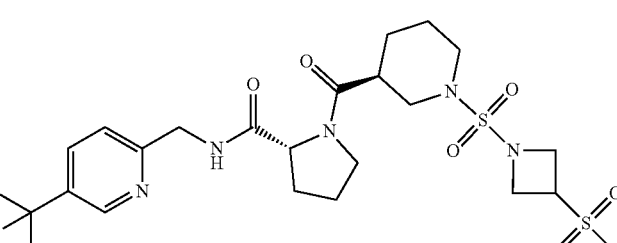<br>1-(((3S)-1-((3-(methylsulfonyl)-1-azetidinyl)sulfonyl)-3-piperidinyl)carbonyl)-N-((5-(trifluoromethyl)-2-pyridinyl)methyl)-D-prolinamide | LCMS-ESI (POS.) m/z: 582.0 (M + H)+ | 1H NMR (500 MHz, METHANOL-d4) δ ppm 8.75-8.90 (m, 1 H), 8.11 (br d, J = 6.49 Hz, 1 H), 7.47-7.69 (m, 1 H), 4.43-4.77 (m, 3 H), 4.09-4.35 (m, 5 H), 3.44-3.84 (m, 4 H), 2.78-3.11 (m, 6 H), 1.46-2.66 (m, 9 H) | A |

-continued

| Ex. # | Structure Name | LCMS-ESI (POS/NEG) m/z: (M + H)+ | NMR Data | Syn. Rte. |
|---|---|---|---|---|
| 500 | (1R,3R,5R)-N-((R)-(4-chloro-2,5-difluorophenyl)(3-oxetanyl)methyl)-2-((2-(trifluoromethyl)-4-pyrimidinyl)carbonyl)-2-azabicyclo[3.1.0]hexane-3-carboxamide | LCMS-APCI (POS.) m/z: 517.1 (M + H)+ | 1H NMR (400 MHz, DMSO-d6) δ ppm 9.28 (d, J = 5.1 Hz, 1 H), 9.24 (d, J = 5.2 Hz, 1 H), 8.69 (d, J = 8.2 Hz, 1 H), 8.53 (d, J = 8.0 Hz, 1 H), 8.08 (t, J = 4.6 Hz, 2 H), 7.64 (ddd, J = 6.2, 9.4, 21.9 Hz, 2 H), 7.45 (dd, J = 6.3, 9.8 Hz, 1 H), 7.29 (dd, J = 6.3, 9.7 Hz, 1 H), 5.38-5.46 (m, 2 H), 5.03-5.10 (m, 1 H), 4.87 (dd, J = 3.5, 11.4 Hz, 1 H), 4.65 (t, 1 H), 4.52 (t, 1 H), 4.32-4.42 (m, 3 H), 4.30 (t, 1 H), 4.21 (t, J = 6.1 Hz, 2 H), 3.85 (t, J = 6.1 Hz, 1 H), 3.70-3.80 (m, 2 H), 3.65 (t, J = 5.9 Hz, 1 H), 3.41-3.48 (m, 2 H), 3.15-3.26 (m, 2 H), 2.74-2.85 (m, 2 H), 1.87 (dd, J = 2.7, 13.6 Hz, 1 H), 1.71 (dd, J = 3.8, 13.5 Hz, 2H), 1.57-1.66 (m, 2 H), 1.11 (dd, J = 5.1, 7.7 Hz, 1 H), 1.06 (t, J = 7.0 Hz, 2 H), 0.80 (q, J = 7.6 Hz, 2 H), 0.64-0.71 (m, 1 H), 0.38-0.49 (m, 1 H). | Q |
| 501 | (4R)-N-((R)-(4-chloro-2,5-difluorophenyl)(3-oxetanyl)methyl)-1-((2-(difluoromethyl)-4-pyridinyl)carbonyl)-4-hydroxy-D-prolinamide | LCMS-APCI (POS.) m/z: 502.2 (M + H)+ | 1H NMR (400 MHz, Methanol-d4) δ ppm 8.80 (d, J = 4.9 Hz, 1 H), 7.88 (t, J = 1.1 Hz, 1 H), 7.67-7.76 (m, 1 H), 7.27-7.43 (m, 2 H), 6.81 (t, J = 55.1 Hz, 1 H), 5.63 (d, J = 10.2 Hz, 1 H), 4.70 (dd, J = 6.4, 7.8 Hz, 1 H), 4.55-4.68 (m, 3 H), 4.43 (q, J = 5.6, 6.1 Hz, 1 H), 4.34 (p, J = 5.2 Hz, 1 H), 3.62-3.74 (m, 1 H), 3.49-3.60 (m, 1 H), 3.47 (dd, J = 4.7, 10.5 Hz, 1 H), 2.44-2.58 (m, 1 H), 1.84-1.97(m, 1 H). | Q |
| 502 | (2R)-N-(chroman-4-)-1-((S)-1-((3-cyanoazetidin-1-yl)sulfonyl)piperidine-3-carbonyl)pyrrolidine-2-carboxamide | LCMS-ESI (POS.) m/z: 502.2 (M + H)+ | 1H NMR (500 MHz, DMSO-d6) δ ppm 7.98-8.76 (m, 1 H), 7.02-7.22 (m, 2 H), 6.82-6.95 (m, 1 H), 6.70-6.81 (m, 1 H), 4.89-5.07 (m, 1 H), 4.23-4.48 (m, 1 H), 4.11-4.22 (m, 2 H), 4.07 (br t, J = 8.43 Hz, 2 H), 3.89-4.00 (m, 2 H), 3.74-3.84 (m, 1 H), 3.42-3.72 (m, 4 H), 2.60-2.91 (m, 3 H), 2.17-2.40 (m, 1 H), 1.63-2.14 (m, 7 H), 1.32-1.56 (m, 2 H) | A |

| Ex. # | Structure Name | LCMS-ESI (POS/NEG) m/z: (M + H)+ | NMR Data | Syn. Rte. |
|---|---|---|---|---|
| 503 | 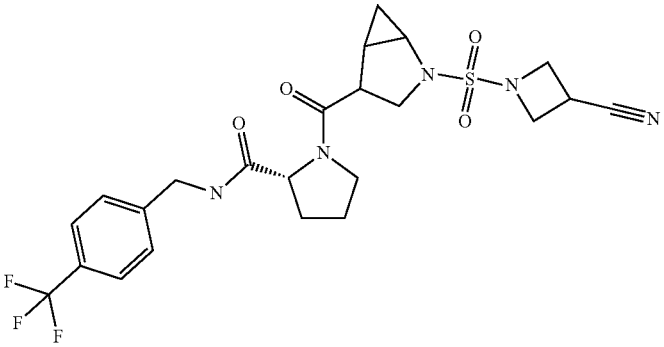 [SMILES: N#CC1CN(S(=O)(=O)N2CC(C(=O)N3CCC[C@@H]3C(=O)NCc3ccc(C(F)(F)F)cc3)C3CC32)C1]<br>(2R)-1-(2-((3-cyanoazetidin-1-yl)sulfonyl)-2-azabicyclo[3.1.0]hexane-4-carbonyl)-N-(4-(trifluoromethyl)benzyl)pyrrolidine-2-carboxamide | LCMS-ESI (POS.) m/z: 526.2 (M + H)+ | 1H NMR (400 MHz, CHLOROFORM-d) δ 7.54-7.64 (m, 2H), 7.45-7.52 (m, 1H), 7.33-7.44 (m, 2H), 7.28-7.32 (m, 1H), 4.35-4.70 (m, 3H), 4.12-4.27 (m, 3H), 3.13-3.79 (m, 6H), 2.41-2.57 (m, 1H), 2.15-2.33 (m, 1H), 2.00-2.15 (m, 1H), 1.56-1.99 (m, 2H), 0.92-1.38 (m, 1H), 0.36-0.90 (m, 1H) | M |
| 504 | 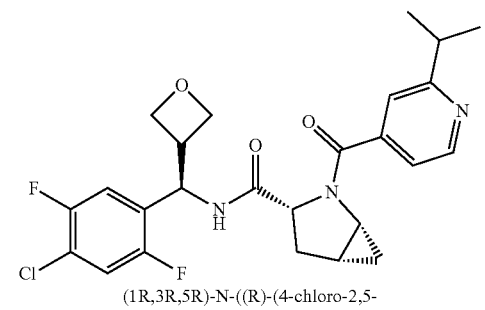<br>(1R,3R,5R)-N-((R)-(4-chloro-2,5-difluorophenyl)(3-oxetanyl)methyl)-2-((2-(2-propanyl)-4-pyridinyl)carbonyl)-2-azabicyclo[3.1.0]hexane-3-carboxamide | LCMS-APCI (POS.) m/z: 490.2 (M + H)+ | 1H NMR (400 MHz, Methanol-d4) δ ppm 8.60 (dd, J = 0.9, 5.1 Hz, 1 H), 7.65 (t, J = 1.1 Hz, 1 H), 7.55 (dd, J = 1.6, 5.1 Hz, 1 H), 7.39 (dd, J = 6.1, 9.5 Hz, 1 H), 7.27 (dd, J = 6.3, 9.4 Hz, 1 H), 5.57 (d, J = 10.2 Hz, 1 H), 4.95 (dd, J = 4.1, 11.4 Hz, 1 H), 4.84 (dd, J = 6.5, 7.6 Hz, 1 H), 4.67 (dd, J = 6.4, 7.9 Hz, 1 H), 4.61 (t, J = 6.2 Hz, 1 H), 4.38 (t, J = 0.8, 12.4 Hz, 1 H), 3.45-3.56 (m, 1 H), 3.27 (td, J = 2.6, 6.2 Hz, 1 H), 3.16 (dt, J = 6.9, 13.9 Hz, 1 H), 2.61-2.71 (m, 1 H), 1.90 (dd, J = 4.1, 13.5 Hz, 1 H), 1.76-1.84 (m, 1 H), 1.35 (dd, J = 2.2, 6.9 Hz, 7 H), 1.24 (td, J = 2.6, 5.3 Hz, 1 H), 0.85 (dtd, J = 1.1, 5.7, 9.0 Hz, 1 H). | Q |
| 505 | 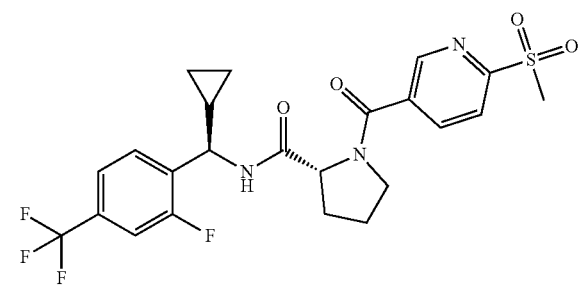 [SMILES: CS(=O)(=O)c1ccc(C(=O)N2CCC[C@@H]2C(=O)N[C@@H](c2ccc(C(F)(F)F)cc2F)C2CC2)cn1]<br>N-((R)-cyclopropyl(2-fluoro-4-(trifluoromethyl)phenyl)methyl)-1-((6-(methylsulfonyl)-3-pyridinyl)carbonyl)-D-prolinamidev | LCMS-ESI (POS.) m/z: 514.2 (M + H)+ | 1H NMR (500 MHz, DMSO-d6) δ ppm 8.78-9.03 (m, 1 H), 8.60 (br d, J = 7.53 Hz, 1 H), 7.97-8.25 (m, 2 H), 7.52-7.78 (m, 3 H), 4.18-5.11 (m, 2 H), 3.61-3.82 (m, 2 H), 3.39 (br s, 3 H), 2.09-2.29 (m, 1 H), 1.65-1.92 (m, 3 H), 1.03-1.24 (m, 1 H), −0.06-0.65 (m, 4 H) | C |
| 506 | 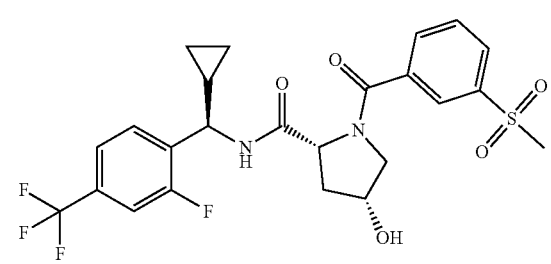 [SMILES: CS(=O)(=O)c1cccc(C(=O)N2C[C@H](O)C[C@@H]2C(=O)N[C@@H](c2ccc(C(F)(F)F)cc2F)C2CC2)c1] | LCMS-ESI (POS.) m/z: 529.2 (M + H)+ | 1H NMR (500 MHz, DMSO-d6) δ ppm 8.79 (d, J = 7.40 Hz, 1 H), 7.36-8.08 (m, 9 H), 4.25-4.65 (m, 2 H), 4.09-4.22 (m, 1 H), 3.55-3.89 (m, 1 H), 3.20-3.29 (m, 3 H), 2.36-2.45 (m, 1 H), 1.55-1.70 (m, 1 H), 0.86-1.29 (m, 1 H),−0.12-0.62 (m, 4 H) | C |

-continued

| Ex. # | Structure Name | LCMS-ESI (POS/NEG) m/z: (M + H)+ | NMR Data | Syn. Rte. |
|---|---|---|---|---|
| | (4R)-N-((R)-cyclopropyl(2-fluoro-4-(trifluoromethyl)phenyl)methyl)-4-hydroxy-1-(3-(methylsulfonyl)benzoyl)-D-prolinamide | | | |
| 507 | (R)-1-(3-((3-cyanocyclobutyl)sulfonyl)benzoyl)-N-((6-(trifluoromethyl)pyridin-3-yl)methyl)pyrrolidine-2-carboxamide | LCMS-ESI (POS.) m/z: 521.0 (M + H)+ | 1H NMR (500 MHz, DMSO-d6) δ ppm 8.38-8.81 (m, 2H), 7.53-8.15 (m, 6H), 4.03-4.60 (m, 5H), 3.37-3.68 (m, 3H), 3.13-3.22 (m, 1H), 2.53-2.68 (m, 4H), 2.18-2.35 (m, 1H), 1.76-2.00 (m, 3H) | L |
| 508 | 1-(((3S)-1-((3-cyano-1-azetidinyl)sulfonyl)-3-piperidinyl)carbonyl)-N-(5-fluoro-2-methylbenzyl)-D-prolinamide | LCMS-ESI (POS.) m/z: 492.2 (M + H)+ | 1H NMR (500 MHz, DMSO-d6) δ ppm 8.19-8.57 (m, 1 H), 7.12-7.22 (m, 1 H), 6.91-7.04 (m, 2 H), 4.29-4.53 (m, 1 H), 4.12-4.29 (m, 2 H), 3.99-4.10 (m, 2 H), 3.86-3.97 (m, 2 H), 3.75-3.83 (m, 1 H), 3.40-3.70 (m, 4 H), 2.66-2.86 (m, 2 H), 2.04-2.34 (m, 5 H), 1.68-2.00 (m, 5 H), 1.36-1.55 (m, 2 H) | A |
| 509 | 1-(((3S)-1-((3-ethyl-3-hydroxy-1-azetidinyl)sulfonyl)-3-piperidinyl)carbonyl)-N-(2-fluoro-4-(trifluoromethyl)benzyl)-D-prolinamide | LCMS-ESI (POS.) m/z: 565.2 (M + H)+ | 1H NMR (400 MHz, CHLOROFORM-d) δ ppm 7.40-7.50 (m, 2 H), 7.35-7.40 (m, 1 H), 7.29-7.35 (m, 1 H), 4.59 (dd, J = 7.98, 2.18 Hz, 1 H), 4.42-4.57 (m, 2 H), 3.73-3.84 (m, 6 H), 3.53-3.65 (m, 2 H), 2.98 (dd, J = 12.65, 10.78 Hz, 1 H), 2.67-2.84 (m, 2 H), 2.30-2.47 (m, 2 H), 2.09-2.24 (m, 1 H), 1.97-2.09 (m, 1 H), 1.86-1.95 (m, 2 H), 1.77-1.85 (m, 3 H), 1.64-1.74 (m, 1 H), 1.49-1.59 (m, 1 H), 0.99 (t, J = 7.41 Hz, 3 H) | J |
| 510 | (4S)-N-((R)-(4-chloro-2,5-difluorophenyl)(cyclopropyl)methyl)-4-fluoro-1-((2-(methylsulfonyl)-4-pyridinyl)carbonyl)-D-prolinamide | LCMS-ESI (POS.) m/z: 516.0 (M + H)+ | 1H NMR (500 MHz, DMSO-d6) δ ppm 8.85-8.97 (m, 1 H), 8.57-8.83 (m, 1 H), 7.24-8.11 (m, 4 H), 5.18-5.48 (m, 1 H), 3.84-4.69 (m, 3 H), 3.61-3.73 (m, 2 H), 3.29-3.34 (m, 3 H), 1.86-2.11 (m, 1 H), 0.84-1.29 (m, 1 H), -0.26-0.63 (m, 4 H) | C |

| Ex. # | Structure Name | LCMS-ESI (POS/NEG) m/z: (M + H)+ | NMR Data | Syn. Rte. |
|---|---|---|---|---|
| 511 | N-((1R)-1-(4-chlorophenyl)ethyl)-1-(((2S)-4-((3-cyano-1-azetidinyl)sulfonyl)-2-piperazinyl)carbonyl)-D-prolinamide | LCMS-ESI (POS.) m/z: 509.2 (M + H)+ | 1H NMR (400 MHz, CHLOROFORM-d) δ ppm 7.28-7.36 (m, 2 H), 7.17-7.26 (m, 3 H), 4.96 (br t, J = 6.84 Hz, 1 H), 4.50 (br d, J = 7.88 Hz, 1 H), 4.04-4.23 (m, 5 H), 3.81 (br t, J = 7.05 Hz, 1 H), 3.63-3.74 (m, 2 H), 3.40-3.63 (m, 4 H), 3.14 (br d, J = 12.85 Hz, 1 H), 2.72-2.97 (m, 3 H), 2.38 (br s, 1 H), 2.06-2.25 (m, 2 H), 2.02 (br s, 2 H), 1.73-1.97 (m, 3 H), 1.36-1.57 (m, 3 H) | M |
| 512 | (1R,2R,5S)-N-((R)-(4-chloro-2,5-difluorophenyl)(cyclopropyl)methyl)-3-((5-(methylsulfonyl)-3-pyridinyl)carbonyl)-3-azabicyclo[3.1.0]hexane-2-carboxamide | LCMS-ESI (POS.) m/z: 510.0 (M + H)+ | 1H NMR (400 MHz, CHLOROFORM-d) δ ppm 9.16-9.27 (m, 1 H), 8.90-9.02 (m, 1 H), 8.18-8.38 (m, 1 H), 7.10-7.21 (m, 2 H), 6.97-7.10 (m, 1 H), 4.82-4.97 (m, 1 H), 4.21-4.54 (m, 1 H), 3.75-4.01 (m, 1 H), 3.43-3.50 (m, 1 H), 3.09-3.20 (m, 3 H), 1.78-1.90 (m, 1 H), 1.68-1.76 (m, 1 H), 1.10-1.31 (m, 1 H), 0.80-0.95 (m, 1 H), 0.51-0.70 (m, 2 H), 0.34-0.47 (m, 2 H), 0.22-0.33 (m, 1 H) | C |
| 513 | (1R,3R,5R)-N-((1R)-1-(4-chloro-2,5-difluorophenyl)ethyl)-2-(3-(ethylsulfonyl)benzoyl)-2-azabicyclo[3.1.0]hexane-3-carboxamide | LCMS-ESI (POS.) m/z: 497.0 (M + H)+ | 1H NMR (500 MHz, DMSO-d6) δ ppm 7.66-8.67 (m, 5 H), 7.62 (dd, J = 9.54, 6.16 Hz, 1 H), 7.37 (br d, J = 3.24 Hz, 1 H), 4.49-5.07 (m, 2 H), 3.33-3.38 (m, 2 H), 3.20-3.27 (m, 1 H), 2.54-2.69 (m, 1 H), 1.55-1.81 (m, 2 H), 0.68-1.41 (m, 8 H) | C |
| 514 | (2R)-1-(1-(((3-cyanoazetidin-1-yl)sulfonyl)-3-fluoropiperidine-3-carbonyl)-N-(4-(trifluoromethyl)benzyl)pyrrolidine-2-carboxamide | LCMS-ESI (POS.) m/z: 546.2 (M + H)+ | 1H NMR (500 MHz, DMSO-d6) δ ppm 8.50-8.61 (m, 1 H), 7.67 (d, J = 8.17 Hz, 2 H), 7.46 (br d, J = 7.79 Hz, 2 H), 4.28-4.74 (m, 3 H), 3.99-4.09 (m, 2 H), 3.88-3.96 (m, 2 H), 3.70-3.85 (m, 3 H), 3.23-3.63 (m, 3 H), 2.81-3.00 (m, 1 H), 2.04-2.29 (m, 2 H), 1.81-1.98 (m, 3 H), 1.58-1.79 (m, 3 H) | M |

-continued

| Ex. # | Structure Name | LCMS-ESI (POS/NEG) m/z: (M + H)+ | NMR Data | Syn. Rte. |
|---|---|---|---|---|
| 515 | 1-(((3S)-1-((3-cyano-1-azetidinyl)sulfonyl)-3-piperidinyl)carbonyl)-N-((3-fluoro-5-(trifluoromethyl)-2-pyridinyl)methyl)-D-prolinamide | LCMS-ESI (POS.) m/z: 547.2 (M + H)+ | 1H NMR (400 MHz, CHLOROFORM-d) δ ppm 8.58-8.70 (m, 1 H), 7.65-7.71 (m, 1 H), 7.60-7.64 (m, 1 H), 4.61-4.81 (m, 3 H), 3.96-4.17 (m, 4 H), 3.73-3.83 (m, 2 H), 3.55-3.73 (m, 2 H), 3.36-3.48 (m, 1 H), 2.93-3.05 (m, 1 H), 2.68-2.84 (m, 2 H), 2.28-2.56 (m, 2 H), 2.27-2.46 (m, 1 H), 2.10-2.23 (m, 1 H), 1.92-2.09 (m, 3 H), 1.75 (br s, 2 H), 1.50-1.63 (m, 1 H) | A |
| 516 | 1-(((3S)-1-((3-cyano-1-azetidinyl)sulfonyl)-3-piperidinyl)carbonyl)-N-(2,3-difluorobenzyl)-D-prolinamide | LCMS-ESI (POS.) m/z: 496.2 (M + H)+ | 1H NMR (500 MHz, DMSO-d6) δ ppm 8.30-8.72 (m, 1 H), 7.26-7.37 (m, 1 H), 7.05-7.23 (m, 2 H), 4.24-4.51 (m, 3 H), 4.01-4.11 (m, 2 H), 3.89-3.98 (m, 2 H), 3.74-3.84 (m, 1 H), 3.35-3.66 (m, 4 H), 2.71-2.88 (m, 2 H), 1.87-2.33 (m, 4 H), 1.34-1.85 (m, 5 H) | A |
| 517 | 1-(((2S)-4-((3-cyano-1-azetidinyl)sulfonyl)-2-morpholinyl)carbonyl)-N-(3,5-difluorobenzyl)-D-prolinamide | LCMS-ESI (POS.) m/z: 498.0 (M + H)+ | 1H NMR (400 MHz, CHLOROFORM-d) δ 7.23 (br t, J = 5.34 Hz, 1H), 6.74-6.82 (m, 2H), 6.67-6.73 (m, 1H), 4.62-4.87 (m, 1H), 4.42-4.54 (m, 1H), 4.30-4.40 (m, 1H), 4.12-4.23 (m, 5H), 3.97-4.06 (m, 1H), 3.84 (ddd, J = 4.20, 8.11, 10.50 Hz, 1H), 3.66-3.75 (m, 2H), 3.42-3.58 (m, 3H), 3.19 (dd, J = 9.69, 12.70 Hz, 1H), 3.03 (ddd, J = 3.32, 11.04, 12.39 Hz, 1H), 2.41-2.50 (m, 1H), 2.09-2.23 (m, 1H), 1.88-2.06 (m, 2H) | C |
| 518 | methyl 3-(((S)-3-((R)-2-((4-(trifluoromethyl)benzyl)carbamoyl)pyrrolidine-1-carbonyl)piperidin-1-yl)sulfonyl)cyclobutanecarboxylate | LCMS-APCI (POS.) m/z: 560.2 (M + H)+ | 1H NMR (Methanol-d4) δ: 7.78-7.59 (m, 1H), 7.58-7.43 (m, 1H), 4.68-4.38 (m, 4H), 3.83 (d, J = 11.9 Hz, 2H), 3.77-3.70 (m, 6H), 3.01-2.73 (m, 2H), 2.64 (ddd, J = 20.9, 14.6, 8.6 Hz, 4H), 2.26 (dt, J = 14.8, 7.8 Hz, 2H), 2.18-1.89 (m, 2H), 1.90-1.72 (m, 2H), 1.72-1.46 (m, 4H) | R |

-continued

| Ex. # | Structure Name | LCMS-ESI (POS/NEG) m/z: (M + H)+ | NMR Data | Syn. Rte. |
|---|---|---|---|---|
| 519 | Diasteromer #1-(1R,3R,5R)-N-((2-fluoro-4-(trifluoromethyl)phenyl)(1-methyl-5-oxopyrrolidin-3-yl)methyl)-2-(3-(methylsulfonyl)benzoyl)-2-azabicyclo[3.1.0]hexane-3-carboxamide | LCMS-ESI (POS.) m/z: 582.0 (M + H)+ | 1H NMR (500 MHz, CHLOROFORM-d) δ ppm 8.22-8.34 (m, 1H), 8.00-8.14 (m, 3H), 7.68-7.78 (m, 1H), 7.42-7.51 (m, 2H), 7.33-7.41 (m, 1H), 5.24 (t, J = 9.02 Hz, 1H), 5.14 (dd, J = 2.14, 10.57 Hz, 1H), 3.32 (dt, J = 2.66, 6.26 Hz, 1H), 3.15-3.21 (m, 4H), 3.09 (dd, J = 6.94, 9.93 Hz, 1H), 2.89 (sxt, J = 8.25 Hz, 1H), 2.77-2.80 (m, 3H), 2.73 (dd, J = 2.21, 13.23 Hz, 1H), 2.34-2.45 (m, 1H), 2.18-2.32 (m, 2H), 1.73-1.81 (m, 1H), 1.00-1.06 (m, 1H), 0.89-0.98 (m, 1H) | C |
| 520 | 1-(3-((3-cyano-1-azetidinyl)sulfonyl)benzoyl)-N-((5-methyl-2-pyridinyl)methyl)-D-prolinamide | LCMS-ESI (POS.) m/z: 468.2 (M + H)+ | 1H NMR (500 MHz, METHANOL-d4) δ ppm 8.27-8.36 (m, 1 H), 8.16 (s, 1 H), 7.89-8.06 (m, 2 H), 7.77-7.86 (m, 1 H), 7.38-7.71 (m, 2 H), 4.19-4.70 (m, 3 H), 4.03-4.17 (m, 2 H), 3.90-4.01 (m, 2 H), 3.42-3.87 (m, 4 H), 2.37-2.48 (m, 1 H), 2.34 (s, 3 H), 1.85-2.16 (m, 1 H), 1.30 (br s, 1 H) | A |
| 521 | N-((R)-cyclopropyl(2-fluoro-4-(trifluoromethyl)phenyl)methyl)-1-(2-(ethylamino)benzoyl)-D-prolinamide | LCMS-APCI (POS.) m/z: 478.2 (M + H)+ | 1H NMR (400 MHz, DMSO-d6) δ ppm 8.81 (d, 1 H), 7.58-7.78 (m, 3 H), 7.16-7.25 (m, 1 H), 7.06 (d, 1 H), 6.53-6.66 (m, 2 H), 5.73 (s, 1 H), 4.60 (d, J = 25.1 Hz, 2 H), 3.18-3.28 (m, 1 H), 3.02-3.17 (m, 2 H), 2.12-2.25 (m, 2 H), 1.63-1.79 (m, 3 H), 1.17-1.28 (m, 1 H), 1.13 (t, J = 7.1 Hz, 3 H), 0.52-0.63 (m, 1 H), 0.31-0.52 (m, 3 H). | Q |
| 522 | (1R,3R,5R)-2-(3-(ethylsulfonyl)benzoyl)-N-((S)-(1-hydroxycyclobutyl)(4-(trifluoromethyl)phenyl)methyl)-2-azabicyclo[3.1.0]hexane-3-carboxamide | LCMS-ESI (POS.) m/z: 551.2 (M + H)+ | 1H NMR (500 MHz, DMSO-d6) δ ppm 8.42-8.47 (m, 1 H) 8.13 (s, 1 H) 7.99-8.04 (m, 2 H) 7.77-7.82 (m, 1 H) 7.64-7.69 (m, 2 H) 7.56-7.60 (m, 2 H) 5.37 (s, 1 H) 5.05-5.13 (m, 1 H) 4.92-4.99 (m, 1 H) 3.20-3.26 (m, 1 H) 1.69-2.19 (m, 6 H) 1.44-1.69 (m, 4 H) 1.06-1.17 (m, 5 H) 0.68-0.76 (m, 1 H) | C |

| Ex. # | Structure Name | LCMS-ESI (POS/NEG) m/z: (M + H)+ | NMR Data | Syn. Rte. |
|---|---|---|---|---|
| 523 | N-((R)-cyclopropyl(2-fluoro-4-(trifluoromethyl)phenyl)methyl)-1-(3-(2,2,2-trifluoro-1,1-dihydroxyethyl)benzoyl)-D-prolinamide | LCMS-ESI (POS.) m/z: 549.2 (M + H)+ | 1H NMR (500 MHz, DMSO-d6) δ ppm 8.67-8.77 (m, 1 H), 7.27-8.18 (m, 9 H), 4.55-4.67 (m, 1 H), 4.49-4.55 (m, 1 H), 4.10-4.41 (m, 1 H), 3.35-3.69 (m, 3 H), 3.28-3.30 (m, 1 H), 2.12-2.25 (m, 1 H), 1.58-1.88 (m, 4 H), 1.11-1.31 (m, 2 H), 0.26-0.67 (m, 4 H) | P |
| 524 | (2R)-1-((S)-1-((3-cyanoazetidin-1-yl)sulfonyl)piperidine-3-carbonyl)-N-(1-(2,5-difluorophenyl)-2,2-difluoroethyl)pyrrolidine-2-carboxamide | LCMS-ESI (POS.) m/z: 546.2 (M + H)+ | 1H NMR (500 MHz, DMSO-d6) δ ppm 8.70-9.25 (m, 1 H), 7.17-7.56 (m, 3 H), 5.44-6.48 (m, 2 H), 4.33-4.66 (m, 1 H), 3.86-4.15 (m, 4 H), 3.73-3.85 (m, 1 H), 3.45-3.70 (m, 4 H), 2.58-2.87 (m, 3 H), 2.03-2.32 (m, 1 H), 1.24-2.00 (m, 7 H) | A |
| 525 | N-((R)-cyclopropyl(2-fluoro-4-(trifluoromethyl)phenyl)methyl)-4,4-difluoro-1-(3-(methylsulfonyl)benzoyl)piperidine-2-carboxamide | LCMS-ESI (POS.) m/z: 563.2 (M + H)+ | 1H NMR (500 MHz, DMSO-d6) δ ppm 8.67-8.86 (m, 1 H), 7.99-8.09 (m, 1 H), 7.91-7.97 (m, 1 H), 7.53-7.86 (m, 5 H), 4.22-5.46 (m, 2 H), 3.40-3.66 (m, 1 H), 3.25 (br s, 3 H), 2.26-2.84 (m, 3 H), 1.89-2.21 (m, 2 H), 1.19-1.31 (m, 1 H), 0.55-0.65 (m, 1 H), 0.45-0.53 (m, 1 H), 0.27-0.41 (m, 2 H) | C |
| 526 | N-((R)-cyclopropyl(2-fluoro-4-(trifluoromethyl)phenyl)methyl)-1-((4-(methylsulfonyl)-2-pyridinyl)carbonyl)-D-prolinamide | LCMS-APCI (POS.) m/z: 514.1 (M + H)+ | 1H NMR (400 MHz, DMSO-d6) δ ppm 8.86 (dd, J = 5.1, 55.2 Hz, 1 H), 8.63 (dd, J = 7.6, 50.4 Hz, 1 H), 7.97-8.18 (m, 2 H), 7.51-7.71 (m, 2 H), 4.52-5.05 (m, 3 H), 4.22 (t, J = 8.3 Hz, 1 H), 3.66-3.84 (m, 1 H), 3.61 (t, J = 6.6 Hz, 1 H), 1.61-1.84 (m, 2 H), 0.99-1.21 (m, 2 H), 0.30-0.59 (m, 2 H), −0.04-0.12 (m, 1 H). | Q |

| Ex. # | Structure Name | LCMS-ESI (POS/NEG) m/z: (M + H)+ | NMR Data | Syn. Rte. |
|---|---|---|---|---|
| 527 | 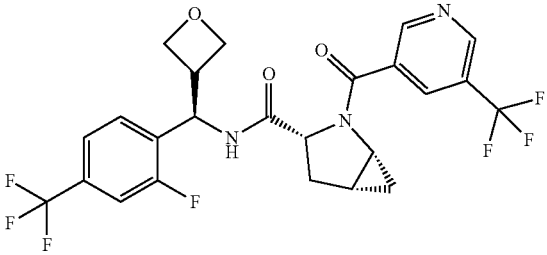 [SMILES: O=C(N[C@@H](c1ccc(C(F)(F)F)cc1F)C1COC1)[C@H]1C[C@H]2C[C@H]2N1C(=O)c1cncc(C(F)(F)F)c1]<br>(1R,3R,5R)-N-((R)-(2-fluoro-4-(trifluoromethyl)phenyl)(3-oxetanyl)methyl)-2-((5-(trifluoromethyl)-3-pyridinyl)carbonyl)-2-azabicyclo[3.1.0]hexane-3-carboxamide | LCMS-APCI (POS.) m/z: 532.2 (M + H)+ | 1H NMR (DMSO-d6) δ: 9.15 (s, 1H), 8.78 (d, J = 8.1 Hz, 1H), 8.40-8.31 (m, 1H), 7.77-7.66 (m, 1H), 7.66-7.53 (m, 2H), 5.49 (t, 1H), 4.93 (dd, J = 11.4, 3.7 Hz, 1H), 4.66 (t, J = 7.7, 6.3 Hz, 1H), 4.52 (dd, J = 7.8, 6.2 Hz, 1H), 4.41 (t, J = 6.1 Hz, 1H), 4.23 (t, J = 6.2 Hz, 1H), 3.50-3.35 (m, 2H), 1.80-1.65 (m, 2H), 1.28-1.08 (m, 2H), 0.85-0.67 (m, 2H) | Q |
| 528 | 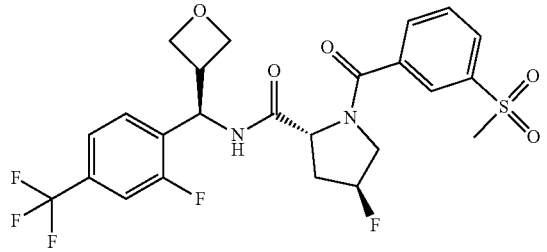 [SMILES: CS(=O)(=O)c1cccc(C(=O)N2C[C@@H](F)C[C@@H]2C(=O)N[C@@H](c2ccc(C(F)(F)F)cc2F)C2COC2)c1]<br>(4S)-4-fluoro-N-((R)-(2-fluoro-4-(trifluoromethyl)phenyl)(3-oxetanyl)methyl)-1-(3-(methylsulfonyl)benzoyl)-D-prolinamide | LCMS-APCI (POS.) m/z: 547.1 (M + H)+ | 1H NMR (400 MHz, Chloroform-d) δ ppm 7.97 -8.10 (m, 2 H), 7.94 (s, 1 H), 7.86 (d, J = 8.5 Hz, 1 H), 7.75 (dt, J = 1.4, 7.7 Hz, 1 H), 7.62 (td, J = 0.5, 7.7 Hz, 1 H), 7.33-7.43 (m, 2 H), 7.28 (dd, J = 1.6, 10.4 Hz, 1 H), 5.58 (t, J = 8.4 Hz, 1 H), 5.06-5.27 (m, 1 H), 4.93 (t, J = 8.3 Hz, 1 H), 4.64 (ddd, J = 6.6, 7.8, 12.7 Hz, 2 H), 4.48 (t, J = 6.3 Hz, 1 H), 4.33 (t, J = 6.2 Hz, 1 H), 3.71-3.77 (m, 1 H), 3.62-3.70 (m, 2 H), 3.36-3.46 (m, 1 H), 3.03 (s, 3 H), 2.68 (dddd, J = 4.0, 8.5, 14.9, 41.4 Hz, 1 H), 2.40 (ddd, J = 8.1, 14.8, 22.0 Hz, 1 H), 0.71-0.85 (m, 3 H). | A |
| 529 | 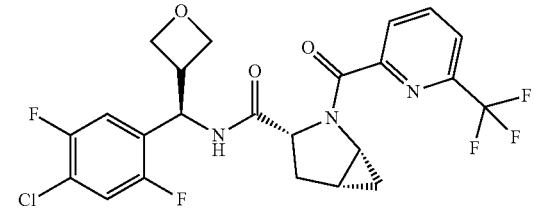 [SMILES: O=C(N[C@@H](c1cc(F)c(Cl)cc1F)C1COC1)[C@H]1C[C@H]2C[C@H]2N1C(=O)c1cccc(C(F)(F)F)n1]<br>(1R,3R,5R)-N-((R)-(4-chloro-2,5-difluorophenyl)(3-oxetanyl)methyl)-2-((6-(trifluoromethyl)-2-pyridinyl)carbonyl)-2-azabicyclo[3.1.0]hexane-3-carboxamide | LCMS-APCI (POS.) m/z: 516.1 (M + H)+ | 1H NMR (400 MHz, Methanol-d4) δ ppm 8.08-8.27 (m, 2 H), 7.89-8.02 (m, 1 H), 7.03-7.43 (m, 2 H), 5.54-5.81 (m, 2 H), 4.94-5.21 (m, 2 H), 4.61-4.71 (m, 1 H), 4.45-4.56 (m, 1 H), 4.40 (t, J = 6.2 Hz, 1 H), 3.97-4.05 (m, 1 H), 3.79-3.91 (m, 1 H), 2.82-2.95 (m, 1 H), 2.66 (td, J = 6.4, 12.7 Hz, 1 H), 1.94 (ddd, J = 3.4, 13.5, 37.5 Hz, 1 H), 1.63-1.83 (m, 1 H), 1.20-1.59 (m, 2 H), 1.18 (td, J = 2.6, 5.4 Hz, 1 H), 0.81-0.94 (m, 1 H), 0.72-0.82 (m, 1 H), 0.62-0.72 (m, 1 H). | Q |

| Ex. # | Structure Name | LCMS-ESI (POS/NEG) m/z: (M + H)+ | NMR Data | Syn. Rte. |
|---|---|---|---|---|
| 530 | 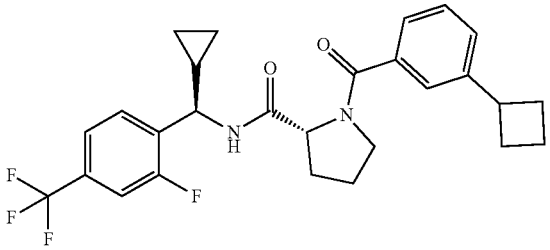 [SMILES: O=C(N[C@@H](c1ccc(C(F)(F)F)cc1F)C1CC1)[C@H]1CCCN1C(=O)c1cccc(C2CCC2)c1]<br>1-(3-cyclobutylbenzoyl)-N-((R)-cyclopropyl(2-fluoro-4-(trifluoromethyl)phenyl)methyl)-D-prolinamide | LCMS-ESI (POS.) m/z: 489.2 (M + H)+ | 1H NMR (600 MHz, DMSO-d6) δ ppm 8.72 (br d, J = 7.16 Hz, 1 H), 7.58-7.73 (m, 3 H), 7.11-7.43 (m, 3 H), 4.24-4.62 (m, 2 H), 3.41-3.64 (m, 3 H), 1.60-2.39 (m, 7 H), − 0.09-1.36 (m, 2 H) | C |
| 531 | 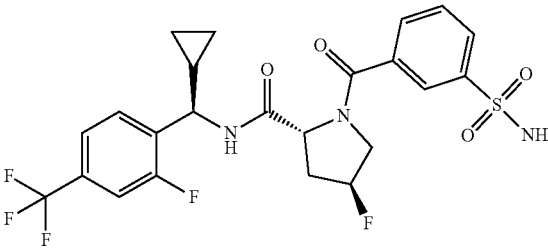<br>(4S)-N-((R)-cyclopropyl(2-fluoro-4-(trifluoromethyl)phenyl)methyl)-4-fluoro-1-(3-sulfamoylbenzoyl)-D-prolinamide | LCMS-ESI (POS.) m/z: 532.0 (M + H)+ | 1H NMR (400 MHz, CHLOROFORM-d) δ ppm 8.15 (d, J = 1.45 Hz, 1 H), 7.95-8.09 (m, 1 H), 7.72-7.80 (m, 1 H), 7.56-7.73 (m, 2 H), 7.44-7.55 (m, 1 H), 7.38-7.44 (m, 1 H), 7.30-7.38 (m, 1 H), 5.46-6.01 (m, 2 H), 5.09-5.30 (m, 1 H), 4.88-5.01 (m, 1 H), 4.53-4.73 (m, 1 H), 3.67-3.90 (m, 2 H), 2.34-2.66 (m, 2 H), 1.18-1.32 (m, 1 H), 0.46-0.66 (m, 2 H), 0.28-0.46 (m, 2 H) | C |
| 532 | 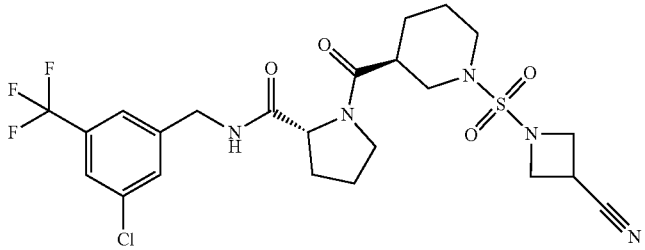 [SMILES: N#CC1CN(S(=O)(=O)N2CCC[C@H](C(=O)N3CCC[C@@H]3C(=O)NCc3cc(Cl)cc(C(F)(F)F)c3)C2)C1]<br>N-(3-chloro-5-(trifluoromethyl)benzyl)-1-(((3S)-1-((3-cyano-1-azetidinyl)sulfonyl)-3-piperidinyl)carbonyl)-D-prolinamide | LCMS-ESI (POS.) m/z: 562.2 (M + H)+ | 1H NMR (400 MHz, CHLOROFORM-d) δ ppm 7.59 (br t, J = 5.96 Hz, 1 H), 7.50 (s, 1 H), 7.41 (s, 1 H), 7.38 (s, 1 H), 4.56-4.65 (m, 2 H), 4.31 (dd, J = 15.65, 5.29 Hz, 1 H), 4.06-4.16 (m, 4 H), 3.73-3.82 (m, 2 H), 3.54-3.64 (m, 2 H), 3.43 (tt, J = 8.66, 6.58 Hz, 1 H), 2.98 (dd, J = 12.80, 11.04 Hz, 1 H), 2.66-2.81 (m, 2 H), 2.43-2.52 (m, 1 H), 2.13-2.27 (m, 1 H), 2.00-2.12 (m, 1 H), 1.86-2.00 (m, 2 H), 1.78-1.86 (m, 1 H), 1.63-1.73 (m, 1 H), 1.47-1.60 (m, 1 H) | A |

| Ex. # | Structure Name | LCMS-ESI (POS/NEG) m/z: (M + H)+ | NMR Data | Syn. Rte. |
|---|---|---|---|---|
| 533 | 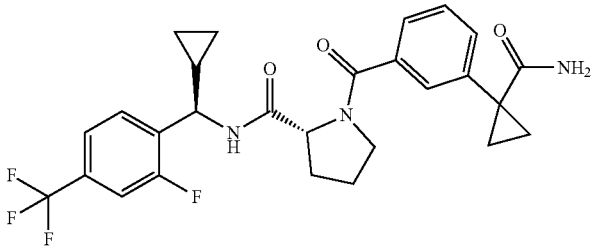 [SMILES: NC(=O)C1(c2cccc(C(=O)N3CCC[C@@H]3C(=O)N[C@@H](c3ccc(C(F)(F)F)cc3F)C3CC3)c2)CC1]<br>1-(3-(1-carbamoylcyclopropyl)benzoyl)-N-((R)-cyclopropyl(2-fluoro-4-(trifluoromethyl)phenyl)methyl)-D-prolinamide | LCMS-ESI (POS.) m/z: 518.0 (M + H)+ | 1H NMR (400 MHz, CHLOROFORM-d) δ ppm 7.60-7.64 (m, 1 H), 7.55-7.60 (m, 1 H), 7.46-7.55 (m, 4 H), 7.40-7.45 (m, 1 H), 7.32-7.38 (m, 1 H), 6.72-6.86 (m, 1 H), 5.50-5.65 (m, 1 H), 4.70-4.83 (m, 1 H), 4.50-4.65 (m, 1 H), 3.54-3.64 (m, 1 H), 3.43-3.54 (m, 1 H), 2.28-2.44 (m, 1 H), 2.02-2.19 (m, 2 H), 1.81-2.00 (m, 1 H), 1.69-1.79 (m, 2 H), 1.16-1.32 (m, 3 H), 0.51-0.69 (m, 2 H), 0.29-0.51 (m, 2 H) | O |
| 534 | 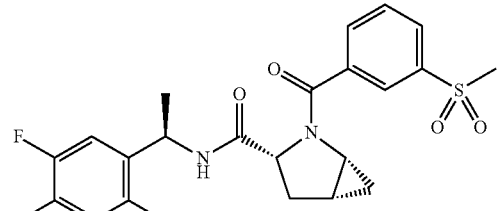<br>(1R,3R,5R)-N-((1R)-1-(4-chloro-2,5-difluorophenyl)ethyl)-2-(3-(methylsulfonyl)benzoyl)-2-azabicyclo[3.1.0]hexane-3-carboxamide | LCMS-ESI (POS.) m/z: 483.0 (M + H)+ | 1H NMR (500 MHz, DMSO-d6) δ ppm 7.66-8.67 (m, 5 H), 7.50-7.66 (m, 1 H), 7.11-7.43 (m, 1 H), 4.44-5.08 (m, 2 H), 3.17-3.29 (m, 4 H), 2.54-2.68 (m, 1 H), 1.55-1.81 (m, 2 H), 0.64-1.42 (m, 5 H) | C |
| 535 | 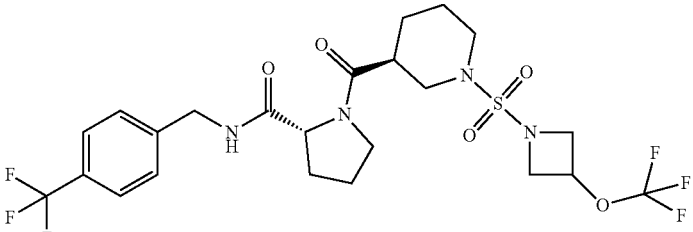<br>1-(((3S)-1-((3-(trifluoromethoxy)-1-azetidinyl)sulfonyl)-3-piperidinyl)carbonyl)-N-(4-(trifluoromethyl)benzyl)-D-prolinamide | LCMS-ESI (POS.) m/z: 587.2 (M + H)+ | 1H NMR (400 MHz, CHLOROFORM-d) δ ppm 7.57 (d, J = 8.29 Hz, 2 H), 7.39-7.46 (m, 1 H), 7.35 (d, J = 8.09 Hz, 2 H), 4.89 (quin, J = 5.96 Hz, 1 H), 4.47-4.65 (m, 2 H), 4.37-4.46 (m, 1 H), 4.01-4.13 (m, 4 H), 3.78 (br d, J = 12.65 Hz, 2 H), 3.53-3.64 (m, 2 H), 2.93 (dd, J = 12.65, 11.20 Hz, 1 H), 2.64-2.80 (m, 2 H), 2.34-2.53 (m, 1 H), 2.12-2.33 (m, 2 H), 2.00-2.09 (m, 1 H), 1.76-1.95 (m, 3 H), 1.44-1.71 (m, 2 H) | M |

| Ex. # | Structure Name | LCMS-ESI (POS/NEG) m/z: (M + H)+ | NMR Data | Syn. Rte. |
|---|---|---|---|---|
| 536 | 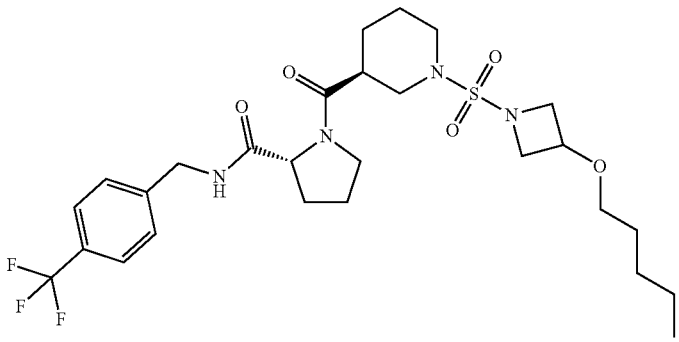 [SMILES: CCCCCOC1CN(S(=O)(=O)N2CCC[C@H](C(=O)N3CCC[C@@H]3C(=O)NCc3ccc(C(F)(F)F)cc3)C2)C1]<br>1-(((3S)-1-((3-(pentyloxy)-1-azetidinyl)sulfonyl)-3-piperidinyl)carbonyl)-N-(4-(trifluoromethyl)benzyl)-D-prolinamide | LCMS-ESI (POS.) m/z: 589.2 (M + H)+ | 1H NMR (500 MHz, DMSO-d6) δ ppm 8.04-9.09 (m, 1 H), 7.61-7.74 (m, 2 H), 7.45 (br d, J = 7.79 Hz, 2 H), 4.17-4.58 (m, 4 H), 3.94 (br t, J = 5.97 Hz, 2 H), 3.50-3.74 (m, 6 H), 2.60-2.86 (m, 3 H), 1.65-2.39 (m, 7 H), 1.21-1.59 (m, 8 H), 0.78-0.97 (m, 3 H) | M |
| 537 | 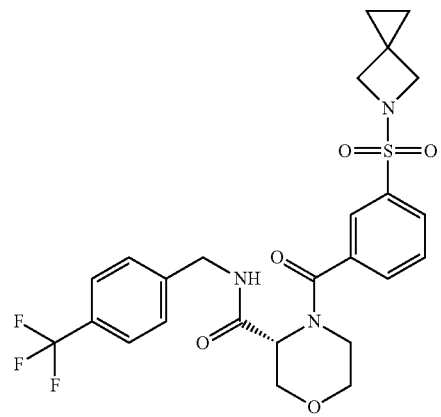 [SMILES: O=C(NCc1ccc(C(F)(F)F)cc1)[C@H]1COCCN1C(=O)c1cccc(S(=O)(=O)N2CC3(CC3)C2)c1]<br>(3R)-4-((3-(5-azaspiro[2.3]hex-5-ylsulfonyl)phenyl)carbonyl)-N-(4-(trifluoromethyl)benzyl)-3-morpholinecarboxamide | LCMS-APCI (POS.) m/z: 538.1 (M + H)+ | 1H NMR (400 MHz, Methanol-d4) δ ppm 8.00 (d, J = 7.9 Hz, 2 H), 7.71-7.90 (m, 2 H), 7.63 (d, J = 8.1 Hz, 2 H), 7.39-7.57 (m, 2 H), 5.09 (s, 1 H), 4.51 (d, J = 39.6 Hz, 4 H), 3.88 (s, 6 H), 3.64 (d, J = 39.5 Hz, 2 H), 3.48 (s, 1 H), 3.35 (m, 1 H), 0.48 (s, 4 H). | V |
| 538 | 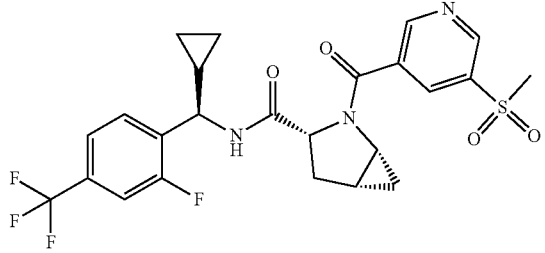 [SMILES: CS(=O)(=O)c1cncc(C(=O)N2[C@@H](C(=O)N[C@@H](c3ccc(C(F)(F)F)cc3F)C3CC3)C[C@H]3C[C@H]32)c1]<br>(1R,3R,5R)-N-((R)-cyclopropyl(2-fluoro-4-(trifluoromethyl)phenyl)methyl)-2-((5-(methylsulfonyl)-3-pyridinyl)carbonyl)-2-azabicyclo[3.1.0]hexane-3-carboxamide | LCMS-ESI (POS.) m/z: 526.0 (M + H)+ | 1H NMR (500 MHz, DMSO-d6) δ ppm 8.82-9.23 (m, 2 H), 8.51-8.80 (m, 1 H), 8.25-8.51 (m, 1 H), 7.76 (d, J = 6.49 Hz, 3 H), 4.66-5.03 (m, 1 H), 4.08-4.62 (m, 1 H), 3.58-3.74 (m, 1 H), 3.37-3.40 (m, 3 H), 2.55-2.73 (m, 1 H), 1.55-1.78 (m, 2 H), −0.28-1.25 (m, 7 H) | C |

-continued

| Ex. # | Structure Name | LCMS-ESI (POS/NEG) m/z: (M + H)+ | NMR Data | Syn. Rte. |
|---|---|---|---|---|
| 539 | 1-(((3R)-1-((3-cyano-1-azetidinyl)sulfonyl)-3-piperidinyl)carbonyl)-N-(2-fluoro-4-(trifluoromethyl)benzyl)-D-prolinamide | LCMS-ESI (POS.) m/z: 546.2 (M + H)+ | 1H NMR (500 MHz, DMSO-d6) δ ppm 8.39-8.88 (m, 1 H), 7.48-7.73 (m, 3 H), 4.22-4.49 (m, 3 H), 3.91-4.09 (m, 4 H), 3.76-3.84 (m, 1 H), 3.36-3.73 (m, 4 H), 2.70-2.91 (m, 2 H), 2.61-2.69 (m, 1 H), 2.10-2.31 (m, 1 H), 1.28-1.97 (m, 7 H) | C |
| 540 | 1-(((3S)-1-((3-cyano-1-azetidinyl)sulfonyl)-3-piperidinyl)carbonyl)-N-((1R)-1-(4-cyanophenyl)ethyl)-D-prolinamide | LCMS-ESI (POS.) m/z: 499.2 (M + H)+ | 1H NMR (500 MHz, DMSO-d6) δ ppm 8.71* (d, J = 7.14 Hz, 1 H), 8.34 (d, J = 7.66 Hz, 1 H), 7.76-7.81 (m, 2 H), 7.43-7.49 (m, 2 H), 4.86-4.99 (m, 1 H), 4.45-4.50* (m, 1 H), 4.29 (dd, J = 8.43, 4.15 Hz, 1 H), 4.03-4.09 (m, 2 H), 3.90-3.97 (m, 2 H), 3.75-3.84 (m, 1 H), 3.29-3.61 (m, 4 H), 2.71-2.87 (m, 2 H), 2.60-2.68 (m, 1 H), 2.26-2.35* (m, 1 H), 2.16-2.26* (m, 1 H), 2.02-2.14 (m, 1 H), 1.63-1.93 (m, 5 H), 1.39-1.57 (m, 2 H), 1.37* (d, J = 7.01 Hz, 3 H), 1.34 (d, J = 7.01 Hz, 3 H) Spectrum appears as 3:1 mixture of rotamers, *denotes resolved minor rotamer peaks | A |
| 541 | (1R,3R,5R)-N-((R)-(2-fluoro-4-(trifluoromethyl)phenyl)(3-oxetanyl)methyl)-2-((5-((2-hydroxyethyl)amino)-2-methyl-4-pyridinyl)carbonyl)-2-azabicyclo[3.1.0]hexane-3-carboxamide | LCMS-APCI (POS.) m/z: 537.2 (M + H)+ | 1H NMR (400 MHz, DMSO-d6) δ ppm 8.80 (d, J = 8.1 Hz, 1 H), 8.02 (s, 1 H), 7.71 (d, J = 10.5 Hz, 1 H), 7.60 (dt, J = 8.3, 15.1 Hz, 2 H), 7.10 (s, 1 H), 5.52-5.58 (m, 1 H), 5.50 (t, J = 8.8 Hz, 1 H), 4.86-4.92 (m, 1 H), 4.73 (t, J = 5.3 Hz, 1 H), 4.61-4.69 (m, 1 H), 4.52 (t, J = 7.0 Hz, 1 H), 4.42 (t, J = 6.2 Hz, 1 H), 4.35 (t, J = 5.1 Hz, 1 H), 4.22 (q, J = 4.6, 5.3 Hz, 2 H), 3.59 (p, J = 5.9 Hz, 2 H), 3.18-3.24 (m, 1 H), 3.09-3.15 (m, 1 H), 1.57-1.75 (m, 3 H), 0.96-1.03 (m, 1 H), 0.57-0.70 (m, 1 H). | S |

| Ex. # | Structure Name | LCMS-ESI (POS/NEG) m/z: (M + H)+ | NMR Data | Syn. Rte. |
|---|---|---|---|---|
| 542 | 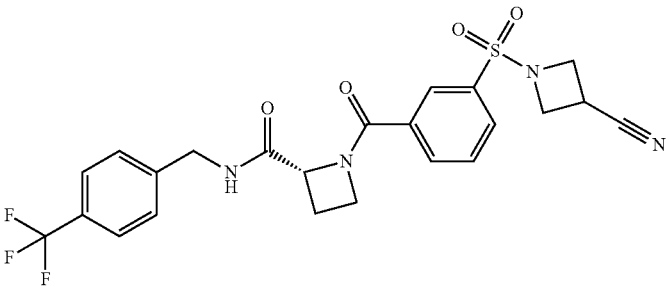 [SMILES: N#CC1CN(S(=O)(=O)c2cccc(C(=O)N3CC[C@@H]3C(=O)NCc3ccc(C(F)(F)F)cc3)c2)C1]<br>(2R)-1-((3-((3-cyano-1-azetidinyl)sulfonyl)phenyl)carbonyl)-N-(4-(trifluoromethyl)benzyl)-2-azetidinecarboxamide | LCMS-APCI (POS.) m/z: 507.2 (M + H)⁺ | 1H NMR (400 MHz, Methanol-d4) δ ppm 7.09-8.34 (m, 8 H), 4.95-5.20 (m, 1 H), 3.86-4.64 (m, 8 H), 3.38-3.59 (m, 1 H), 2.60-2.86 (m, 1 H), 2.14-2.46 (m, 1 H). | Q |
| 543 | 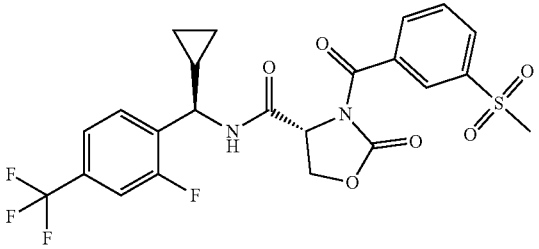 [SMILES: CS(=O)(=O)c1cccc(C(=O)N2C(=O)OC[C@@H]2C(=O)N[C@@H](c2ccc(C(F)(F)F)cc2F)C2CC2)c1]<br>(4R)-N-((R)-cyclopropyl(2-fluoro-4-(trifluoromethyl)phenyl)methyl)-3-(3-(methylsulfonyl)benzoyl)-2-oxo-1,3-oxazolidine-4-carboxamide | LCMS-ESI (NEG.) m/z: 527.0 (M − H)⁻ | 1H NMR (400 MHz, DMSO-d6) δ ppm 9.17 (d, J = 7.26 Hz, 1 H), 8.08-8.17 (m, 2 H), 7.94 (d, J = 7.67 Hz, 1 H), 7.73-7.79 (m, 1 H), 7.64-7.73 (m, 2 H), 7.59-7.64 (m, 1 H), 5.08 (dd, J = 8.71, 3.73 Hz, 1 H), 4.67 (t, J = 8.91 Hz, 1 H), 4.59 (t, J = 7.88 Hz, 1 H), 4.14 (dd, J = 8.86, 3.68 Hz, 1 H), 3.26 (s, 3 H), 1.19-1.31 (m, 1 H), 0.58-0.67 (m, 1 H), 0.45-0.56 (m, 1 H), 0.38 (dtt, J = 12.80, 8.76, 8.76, 4.48, 4.48 Hz, 2 H) | C |
| 544 | 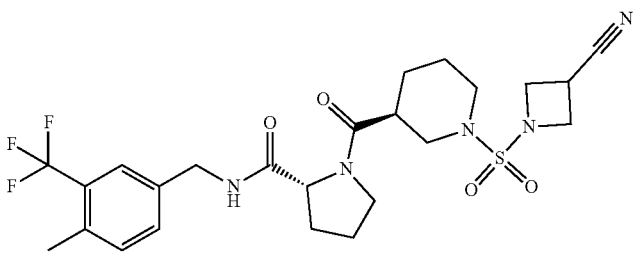 [SMILES: Cc1ccc(CNC(=O)[C@H]2CCCN2C(=O)[C@H]2CCCN(S(=O)(=O)N3CC(C#N)C3)C2)cc1C(F)(F)F]<br>1-(((3S)-1-((3-cyano-1-azetidinyl)sulfonyl)-3-piperidinyl)carbonyl)-N-(4-methyl-3-(trifluoromethyl)benzyl)-D-prolinamide | LCMS-ESI (POS.) m/z: 542.2 (M + H)⁺ | 1H NMR (500 MHz, DMSO-d6) δ ppm 8.32 (s, 1 H), 7.33-7.59 (m, 3 H), 4.23-4.52 (m, 3 H), 4.03-4.09 (m, 2 H), 3.92-3.97 (m, 2 H), 3.76-3.81 (m, 1 H), 3.30-3.70 (m, 4 H), 2.72-2.88 (m, 2 H), 2.61-2.69 (m, 1 H), 2.35-2.43 (m, 3 H), 1.63-2.23 (m, 6 H), 1.31-1.56 (m, 2 H) | A |

| Ex. # | Structure Name | LCMS-ESI (POS/NEG) m/z: (M + H)+ | NMR Data | Syn. Rte. |
|---|---|---|---|---|
| 545 | 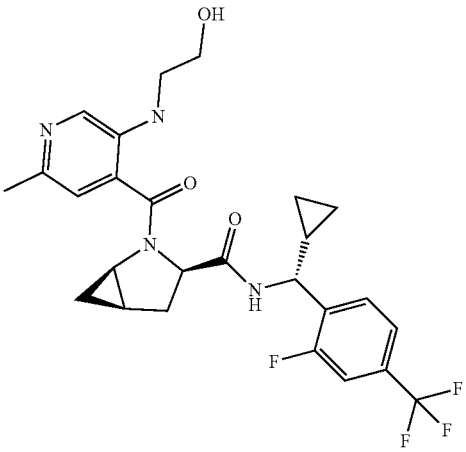 [SMILES: Cc1cc(C(=O)N2[C@@H](C(=O)N[C@@H](c3ccc(C(F)(F)F)cc3F)C3CC3)C[C@H]3C[C@H]32)c(NCCO)cn1]<br>(1R,3R,5R)-N-((R)-cyclopropyl(2-fluoro-4-(trifluoromethyl)phenyl)methyl)-2-((5-((2-hydroxyethyl)amino)-2-methyl-4-pyridinyl)carbonyl)-2-azabicyclo[3.1.0]hexane-3-carboxamide | LCMS-APCI (POS.) m/z: 521.2 (M + H)+ | 1H NMR (400 MHz, DMSO-d6) δ ppm 8.85 (d, J = 7.4 Hz, 1 H), 8.05 (s, 1 H), 7.62-7.73 (m, 2 H), 7.26 (s, 1 H), 4.94 (dd, J = 3.1, 11.5 Hz, 1 H), 4.68-4.80(m, 1 H), 4.59 (t, J = 8.0 Hz, 1 H), 3.52-3.62 (m, 2 H), 3.23 (s, 2 H), 3.11-3.16 (m, 1 H), 2.41 (s, 2 H), 1.75 (dd, J = 3.2, 13.6 Hz, 1 H), 1.56-1.65 (m, 1 H), 1.15-1.29 (m, 2 H), 0.87-0.93 (m, 1 H), 0.54-0.65 (m, 2 H), 0.43-0.51 (m, 1 H), 0.29-0.42 (m, 2 H). | S |
| 546 | 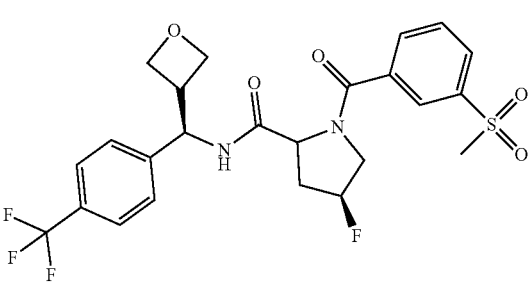 [SMILES: CS(=O)(=O)c1cccc(C(=O)N2C[C@@H](F)CC2C(=O)N[C@@H](c2ccc(C(F)(F)F)cc2)C2COC2)c1]<br>(4S)-4-fluoro-1-(3-(methylsulfonyl)benzoyl)-N-((R)-3-oxetanyl(4-(trifluoromethyl)phenyl)methyl)-D-prolinamide | LCMS-APCI (POS.) m/z: 529.1 (M + H)+ | 1H NMR (400 MHz, Chloroform-d) δ ppm 8.08-8.14 (m, 2 H), 7.78-7.86 (m, 2 H), 7.69-7.75 (m, 1 H), 7.64 (d, J = 8.1 Hz, 2 H), 7.41 (d, J = 8.0 Hz, 2 H), 5.45 (t, J = 8.2 Hz, 1 H), 5.04 (t, J = 8.3 Hz, 1 H), 4.68-4.76 (m, 2 H), 4.54 (t, J = 6.3 Hz, 1 H), 4.41 (t, J = 6.3 Hz, 1 H), 3.70-3.83 (m, 4 H), 3.45 (dt, J = 6.9, 14.0 Hz, 2 H), 3.12 (s, 3 H), 2.80-2.99 (m, 3 H), 2.41-2.54 (m, 2 H), 1.28 (d, J = 7.0 Hz, 5 H), 0.81-0.95 (m, 2 H). | A |
| 547 | 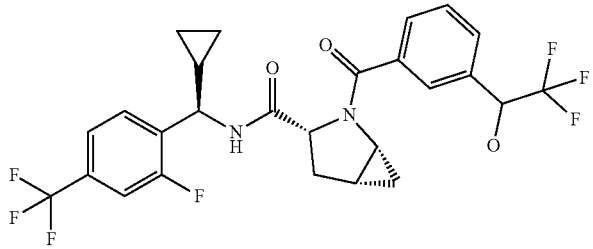 [SMILES: O=C(N[C@@H](c1ccc(C(F)(F)F)cc1F)C1CC1)[C@H]1C[C@H]2C[C@H]2N1C(=O)c1cccc(C(O)C(F)(F)F)c1]<br>(1R,3R,5R)-N-((R)-cyclopropyl(2-fluoro-4-(trifluoromethyl)phenyl)methyl)-2-(3-(2,2,2-trifluoro-1-hydroxyethyl)benzoyl)-2-azabicyclo[3.1.0]hexane-3-carboxamide | LCMS-ESI (POS.) m/z: 545.2 (M + H)+ | 1H NMR (500 MHz, CHLOROFORM-d) δ ppm 7.97-8.16 (m, 1 H), 7.58-7.82 (m, 1 H), 7.29-7.56 (m, 2 H), 5.33-7.15 (m, 1 H), 4.35-4.65 (m, 1 H), 2.89-4.08 (m, 4 H), 2.72-2.89 (m, 3 H), 1.52-2.64 (m, 2 H), 1.13-1.47 (m, 2 H), 0.29-0.73 (m, 2 H) | C |

| Ex. # | Structure Name | LCMS-ESI (POS/NEG) m/z: (M + H)+ | NMR Data | Syn. Rte. |
|---|---|---|---|---|
| 548 | 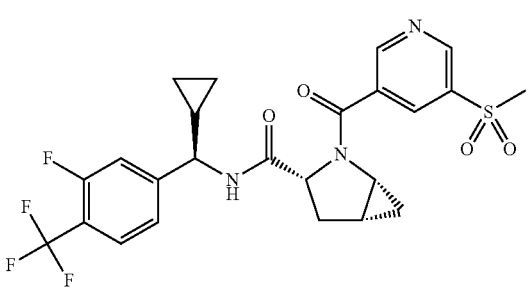 [SMILES: CS(=O)(=O)c1cncc(C(=O)N2[C@@H](C(=O)N[C@@H](c3ccc(C(F)(F)F)c(F)c3)C3CC3)C[C@H]3C[C@H]32)c1]<br>(1R,3R,5R)-N-((R)-cyclopropyl(3-fluoro-4-(trifluoromethyl)phenyl)methyl)-2-((5-(methylsulfonyl)-3-pyridinyl)carbonyl)-2-azabicyclo[3.1.0]hexane-3-carboxamide | LCMS-ESI (POS.) m/z: 526.0 (M + H)+ | 1H NMR (500 MHz, DMSO-d6) δ ppm 8.80-9.26 (m, 2 H), 8.53-8.75 (m, 1 H), 8.26-8.51 (m, 1 H), 7.69-7.83 (m, 1 H), 7.16-7.52 (m, 2 H), 4.67-5.03 (m, 1 H), 4.21-4.31 (m, 1 H), 3.31-3.42 (m, 4 H), 2.58-2.79 (m, 1 H), 1.59-1.85 (m, 2 H), − 0.07 (s, 7 H) | C |
| 549 | 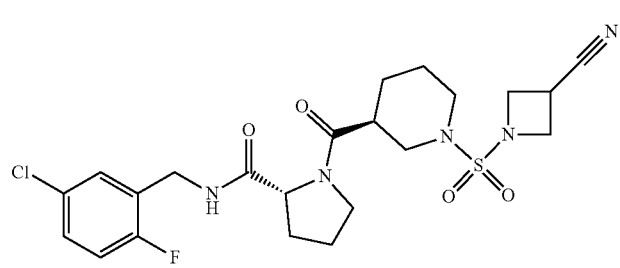 [SMILES: N#CC1CN(S(=O)(=O)N2CCC[C@H](C(=O)N3CCC[C@@H]3C(=O)NCc3cc(Cl)ccc3F)C2)C1]<br>N-(5-chloro-2-fluorobenzyl)-1-(((3S)-1-((3-cyano-1-azetidinyl)sulfonyl)-3-piperidinyl)carbonyl)-D-prolinamide | LCMS-ESI (POS.) m/z: 512.2 (M + H)+ | 1H NMR (500 MHz, DMSO-d6) δ ppm 8.23-8.74 (m, 1 H), 7.13-7.44 (m, 3 H), 4.27-4.36 (m, 3 H), 3.97-4.09 (m, 2 H), 3.85-3.95 (m, 2 H), 3.73-3.83 (m, 1 H), 3.36-3.71 (m, 4 H), 2.71-2.88 (m, 2 H), 2.62-2.71 (m, 1 H), 1.65-2.30 (m, 7 H), 1.29-1.51 (m, 2 H) | A |
| 550 | 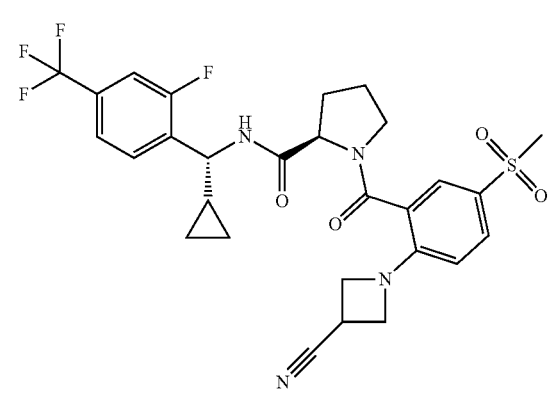 [SMILES: CS(=O)(=O)c1ccc(N2CC(C#N)C2)c(C(=O)N2CCC[C@@H]2C(=O)N[C@@H](c2ccc(C(F)(F)F)cc2F)C2CC2)c1]<br>1-(2-(3-cyano-1-azetidinyl)-5-(methylsulfonyl)benzoyl)-N-((R)-cyclopropyl(2-fluoro-4-(trifluoromethyl)phenyl)methyl)-D-prolinamide | LCMS-APCI (POS.) m/z: 593.2 (M + H)+ | 1H NMR (400 MHz, DMSO-d6) δ ppm 8.71-8.81 (m, 1 H), 8.46 (dd, J = 7.3, 16.3 Hz, 1 H), 8.09 (ddd, J = 2.4, 4.6, 8.6 Hz, 1 H), 7.87-7.97 (m, 1 H), 7.48-7.79 (m, 5 H), 4.46-4.69 (m, 3 H), 4.26-4.38 (m, 2 H), 4.16 (dd, J = 8.9, 17.1 Hz, 2 H), 3.97-4.11 (m, 1 H), 3.82-3.93 (m, 1 H), 3.51-3.61 (m, 1 H), 3.11-3.31 (m, 4 H), 2.13-2.28 (m, 2 H), 1.67-1.90 (m, 4 H), 1.22 (dd, J = 4.6, 8.1 Hz, 1 H), 0.96 (d, J = 6.4 Hz, 2 H), 0.85-0.93 (m, 1 H), 0.58-0.64 (m, 1 H), 0.47-0.51 (m, 1 H), 0.38-0.47 (m, 2 H), 0.27-0.36 (m, 1 H), -0.02 (d, J = 49.1 Hz, 2 H). | T |

| Ex. # | Structure Name | LCMS-ESI (POS/NEG) m/z: (M + H)+ | NMR Data | Syn. Rte. |
|---|---|---|---|---|
| 551 | 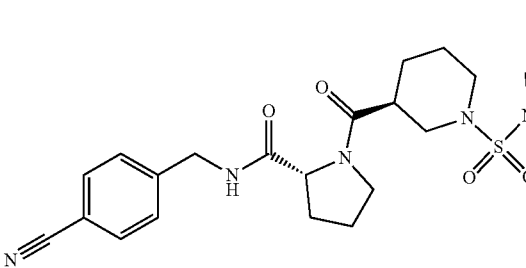<br>1-(((3S)-1-((3-cyano-1-azetidinyl)sulfonyl)-3-piperidinyl)carbonyl)-N-(4-cyanobenzyl)-D-prolinamide | LCMS-ESI (POS.) m/z: 485.2 (M + H)+ | 1H NMR (500 MHz, CHLOROFORM-d) δ ppm 7.60 (d, J = 8.30 Hz, 2 H), 7.41-7.53 (m, 1 H), 7.28-7.41 (m, 2 H), 4.60 (dd, J = 7.91, 1.95 Hz, 1 H), 4.39-4.54 (m, 3 H), 4.04-4.17 (m, 5 H), 3.77 (br d, J = 12.72 Hz, 2 H), 3.52-3.66 (m, 2 H), 3.38-3.50 (m, 1 H), 2.65-2.84 (m, 3 H), 2.44 (ddd, J = 9.34, 6.36, 3.24 Hz, 2 H), 2.11-2.33 (m, 2 H), 1.98-2.10 (m, 2 H), 1.79-1.98 (m, 4 H), 1.66 (qt, J = 13.02, 3.96 Hz, 1 H), 1.50-1.60 (m, 1 H) | C |
| 552 | 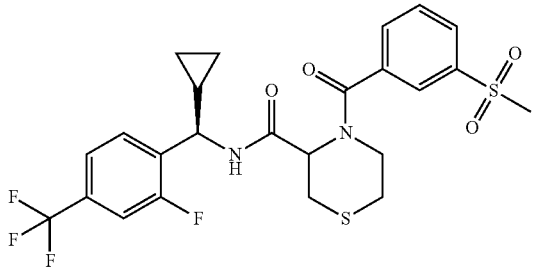 [SMILES: CS(=O)(=O)c1cccc(C(=O)N2CCSCC2C(=O)N[C@@H](c2ccc(C(F)(F)F)cc2F)C2CC2)c1]<br>N-((R)-cyclopropyl(2-fluoro-4-(trifluoromethyl)phenyl)methyl)-4-(3-(methylsulfonyl)benzoyl)thiomorpholine-3-carboxamide | LCMS-ESI (POS.) m/z: 545.2 (M + H)+ | 1H NMR (500 MHz, DMSO-d6) δ ppm 8.58-8.99 (m, 1 H), 7.56-8.08 (m, 6 H), 4.29-5.53 (m, 2 H), 3.43-3.74 (m, 1 H), 2.90-3.19 (m, 2 H), 1.18-1.35 (m, 1 H), 0.17-0.68 (m, 4 H) | C |
| 553 | 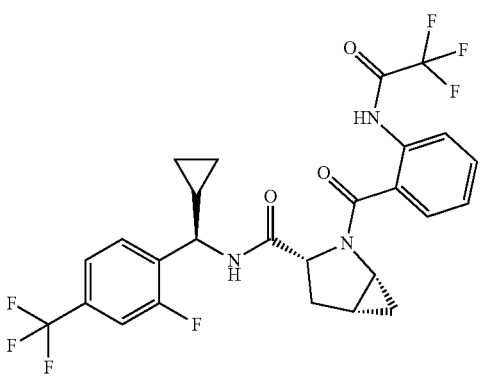 [SMILES: O=C(N[C@@H](c1ccc(C(F)(F)F)cc1F)C1CC1)[C@H]1C[C@H]2C[C@H]2N1C(=O)c1ccccc1NC(=O)C(F)(F)F]<br>(1R,3R,5R)-N-((R)-cyclopropyl(2-fluoro-4-(trifluoromethyl)phenyl)methyl)-2-(2-(2,2,2-trifluoroacetamido)benzoyl)-2-azabicyclo[3.1.0]hexane-3-carboxamide | LCMS-APCI (POS.) m/z: 558.1 (M + H)+ | 1H NMR (400 MHz, DMSO-d6) δ ppm 11.18 (s, 1 H), 8.77 (d, J = 7.3 Hz, 1 H), 7.59-7.74 (m, 4 H), 7.51-7.59 (m, 1 H), 7.36-7.45 (m, 1 H), 4.93 (dd, J = 3.5, Hz, H), (t, J = 8.0 Hz, 1 H), 3.18 (td, J = 2.5, 6.2 Hz, 1 H), 1.75 (dd, J = 3.4, 13.5 Hz, 1 H), 1.60-1.70 (m, 1 H), 1.13-1.27 (m, 1 H), 0.91-0.99 (m, 1 H), 0.62-0.70 (m, 1 H), 0.52-0.62 (m, 1 H), 0.43-0.52 (m, 1 H), 0.29-0.43 (m, 2 H). | Q |

| Ex. # | Structure Name | LCMS-ESI (POS/NEG) m/z: (M + H)+ | NMR Data | Syn. Rte. |
|---|---|---|---|---|
| 554 | 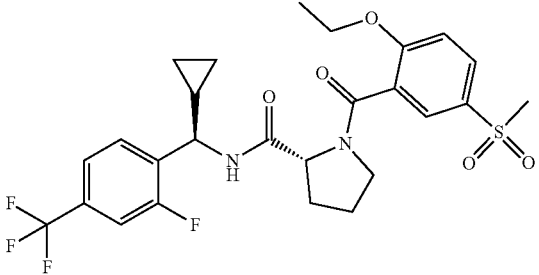 [SMILES: CCOc1ccc(S(C)(=O)=O)cc1C(=O)N1CCC[C@@H]1C(=O)N[C@@H](c1ccc(C(F)(F)F)cc1F)C1CC1]<br>N-((R)-cyclopropyl(2-fluoro-4-(trifluoromethyl)phenyl)methyl)-1-(2-ethoxy-5-(methylsulfonyl)benzoyl)-D-prolinamide | LCMS-APCI (POS.) m/z: 557.2 (M + H)+ | 1H NMR (400 MHz, DMSO-d6) δ ppm 8.30-8.64 (m, 2 H), 7.94 (ddd, J = 2.4, 4.3, 8.9 Hz, 1 H), 7.45-7.82 (m, 4 H), 7.30-7.39 (m, 1 H), 4.61 (t, J = 7.9 Hz, 1 H), 4.49-4.54 (m, 1 H), 4.11-4.37 (m, 3 H), 3.48-3.62 (m, 1 H), 3.13-3.27 (m, 3 H), 2.09-2.25 (m, 2 H), 1.66-1.82 (m, 2 H), 1.35 (dt, J = 6.9, 9.2 Hz, 2 H), 1.16-1.31 (m, 2 H), 0.86-0.99 (m, 1 H), 0.26-0.65 (m, 4 H), −0.09-0.09 (m, 1 H). | S |
| 555 | 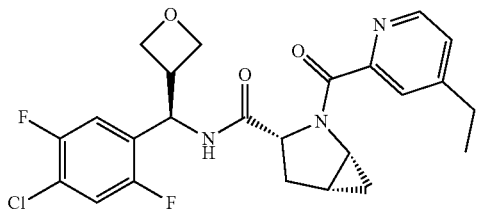 [SMILES: CCc1ccnc(C(=O)N2[C@@H](C(=O)N[C@@H](c3cc(F)c(Cl)cc3F)C3COC3)C[C@H]3C[C@H]32)c1]<br>(1R,3R,5R)-N-((R)-(4-chloro-2,5-difluorophenyl)(3-oxetanyl)methyl)-2-((4-ethyl-2-pyridinyl)carbonyl)-2-azabicyclo[3.1.0]hexane-3-carboxamide | LCMS-APCI (POS.) m/z: 476.1 (M + H)+ | 1H NMR (400 MHz, Methanol-d4) δ ppm 8.53 (dd, J = 0.8, 5.1 Hz, 1 H), 7.70-7.76 (m, 1 H), 7.31-7.47 (m, 2 H), 7.28 (dd, J = 6.3, 9.4 Hz, 1 H), 5.19-5.63 (m, 2 H), 4.61-4.71 (m, 1 H), 4.54 (ddd, J = 4.5, 6.4, 7.9 Hz, 1 H), 4.39 (t, J = 6.1 Hz, 1 H), 4.04 (dt, J = 6.1, 22.8 Hz, 1 H), 3.82 (dtd, J = 2.9, 6.0, 86.6 Hz, 1 H), 3.46-3.57 (m, 1 H), 2.59-2.85 (m, 2 H), 1.93 (dd, J = 3.6, 13.5 Hz, 1 H), 1.60-1.78 (m, 1 H), 1.22-1.40 (m, 3 H), 1.09-1.17 (m, 1 H), 0.83-0.92 (m, 1 H), 0.70-0.79 (m, 1 H). | Q |
| 556 | 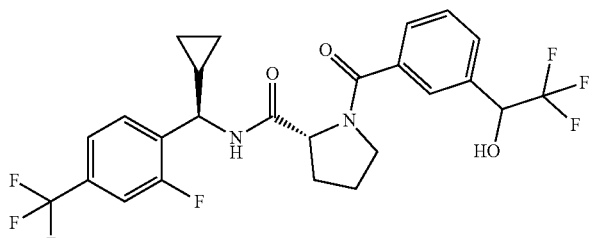<br>(2R)-N-((R)-cyclopropyl(2-fluoro-4-(trifluoromethyl)phenyl)methyl)-1-(3-(2,2,2-trifluoro-1-hydroxyethyl)benzoyl)pyrrolidine-2-carboxamide | LCMS-ESI (POS.) m/z: 533.2 (M + H)+ | 1H NMR (500 MHz, CHLOROFORM-d) δ ppm 7.53-7.68 (m, 4 H), 7.49 (br t, J = 7.40 Hz, 2 H), 7.41 (br d, J = 8.04 Hz, 1 H), 7.34 (d, J = 10.38 Hz, 1 H), 5.03 (quin, J = 6.88 Hz, 1 H), 4.69-4.81 (m, 1 H), 4.59 (t, J = 7.91 Hz, 1 H), 3.53-3.67 (m, 1 H), 3.39-3.53 (m, 1 H), 2.30-2.52 (m, 1 H), 1.93-2.30 (m, 10 H), 1.76-1.93 (m, 1 H), 1.15-1.33 (m, 1 H), 0.50-0.72 (m, 2 H), 0.34-0.50 (m, 2 H) | C |

| Ex. # | Structure Name | LCMS-ESI (POS/NEG) m/z: (M + H)+ | NMR Data | Syn. Rte. |
|---|---|---|---|---|
| 557 | 1-(((3S)-1-((3-cyano-1-azetidinyl)sulfonyl)-3-piperidinyl)carbonyl)-N-(2-fluoro-4-methoxybenzyl)-D-prolinamide | LCMS-ESI (POS.) m/z: 508.2 (M + H)+ | 1H NMR (500 MHz, DMSO-d6) δ ppm 8.14-8.61 (m, 1 H), 7.12-7.28 (m, 1 H), 6.69-6.86 (m, 2 H), 4.11-4.44 (m, 3 H), 3.86-4.10 (m, 4 H), 3.69-3.84 (m, 4 H), 3.41-3.67 (m, 4 H), 2.60-2.88 (m, 3 H), 1.65-2.32 (m, 6 H), 1.31-1.57 (m, 2 H) | A |
| 558 | N-((R)-3-azetidinyl(4-chloro-2,5-difluorophenyl)methyl)-1-(((3S)-1-((3-cyano-1-azetidinyl)sulfonyl)-3-piperidinyl)carbonyl)-D-prolinamide | LCMS-ESI (POS.) m/z: 585.2 (M + H)+ | 1H NMR (500 MHz, DMSO-d6) δ ppm 7.32-8.67 (m, 3 H), 5.06-5.38 (m, 1 H), 4.21-4.51 (m, 1 H), 3.97-4.11 (m, 2 H), 3.84-3.96 (m, 2 H), 3.74-3.81 (m, 1 H), 3.51-3.64 (m, 3 H), 3.43-3.49 (m, 1 H), 3.08-3.29 (m, 3 H), 2.69-3.04 (m, 3 H), 2.56-2.68 (m, 1 H), 1.63-2.25 (m, 7 H), 1.11-1.56 (m, 3 H) | G |
| 559 | (1R,3R,5R)-N-((S)-(2-fluoro-4-(trifluoromethyl)phenyl)(1-hydroxycyclopropyl)methyl)-2-(3-(methylsulfonyl)benzoyl)-2-azabicyclo[3.1.0]hexane-3-carboxamide | LCMS-ESI (POS.) m/z: 541.2 (M + H)+ | 1H NMR (500 MHz, DMSO-d6) δ ppm 8.38-8.62 1 H), 7.50-8.20 (m, 7 H), 5.21-5.77 (m, 1 H), 4.46-5.20 (m, 2 H), 3.21-3.29 (m, 4 H), 2.52-2.76 (m, 1 H), 1.51-1.79 (m, 2 H), 0.83-1.13 (m, 1 H), 0.05-0.79 (m, 5 H) | C |
| 560 | 1-((3-(((3R)-3-hydroxy-1-pyrrolidinyl)sulfonyl)phenyl)carbonyl)-N-(4-(trifluoromethyl)benzyl)-D-prolinamide, 1-((3-(((3S)-3-hydroxy-1-pyrrolidinyl)sulfonyl)phenyl)carbonyl)-N-(4-(trifluoromethyl)benzyl)-D-prolinamide | LCMS-ESI (POS.) m/z: 526.2 (M + H)+ | 1H NMR (400 MHz, CHLOROFORM-d) δ ppm 7.96-8.03 (m, 1 H), 7.88-7.94 (m, 1 H), 7.69-7.76 (m, 1 H), 7.57-7.62 (m, 2 H), 7.19-7.45 (m, 4 H), 4.66-4.79 (m, 1 H), 4.47-4.61 (m, 2 H), 4.18-4.39 (m, 2 H), 3.54-3.67 (m, 1 H), 3.18-3.53 (m, 6 H), 2.35-2.45 (m, 1 H), 1.78-2.02 (m, 4 H) | B |

| Ex. # | Structure Name | LCMS-ESI (POS/NEG) m/z: (M + H)+ | NMR Data | Syn. Rte. |
|---|---|---|---|---|
| 561 | 1-(((3S)-1-((3-cyano-1-azetidinyl)sulfonyl)-3-piperidinyl)carbonyl)-N-((1R)-2-hydroxy-1-(4-(trifluoromethyl)phenyl)ethyl)-D-prolinamide | LCMS-ESI (POS.) m/z: 558.2 (M + H)+ | 1H NMR (500 MHz, DMSO-d6) δ ppm 8.11-8.63 (m, 1 H), 7.47-7.79 (m, 4 H), 4.82-4.89 (m, 1 H), 4.39-4.54 (m, 1 H), 3.74-4.13 (m, 5 H), 3.61-3.72 (m, 1 H), 3.49-3.60 (m, 4 H), 3.31-3.48 (m, 1 H), 2.58-2.90 (m, 3 H), 1.31-2.30 (m, 9 H) | A |
| 562 | 1-(((3S)-1-((3-(1H-imidazol-1-)-1-azetidinyl)sulfonyl)-3-piperidinyl)carbonyl)-N-(4-(trifluoromethyl)benzyl)-D-prolinamide | LCMS-ESI (POS.) m/z: 569.2 (M + H)+ | 1H NMR (500 MHz, CHLOROFORM-d) δ ppm 7.60-7.68 (m, 1 H), 7.42-7.57 (m, 3 H), 7.34 (d, J = 7.79 Hz, 2 H), 7.19-7.26 (m, 1 H), 7.14 (s, 1 H), 4.92 (quin, J = 6.81 Hz, 1 H), 4.59 (br d, J = 6.75 Hz, 1 H), 4.38-4.53 (m, 2 H), 4.27-4.34 (m, 2 H), 4.08-4.15 (m, 2 H), 3.81 (br d, J = 12.20 Hz, 2 H), 3.53-3.64 (m, 2 H), 2.97 (t, J = 11.94 Hz, 1 H), 2.67-2.81 (m, 2 H), 2.42 (ddd, J = 9.15, 6.42, 3.11 Hz, 1 H), 2.10-2.33 (m, 1 H), 2.00-2.08 (m, 2 H), 1.77-1.95 (m, 3 H), 1.57-1.72 (m, 1 H), 1.50 (qd, J = 12.67, 3.50 Hz, 1 H), 1.23-1.31 (m, 2 H) | M |
| 563 | N-((R)-cyclopropyl(2-fluoro-4-(trifluoromethyl)phenyl)methyl)-1-(2,6-difluoro-3-(methylsulfonyl)benzoyl)-D-prolinamide | LCMS-ESI (POS.) m/z: 549.0 (M + H)+ | 1H NMR (500 MHz, DMSO-d6) δ ppm 8.46-8.84 (m, 1 H), 7.38-8.10 (m, 5 H), 4.53-4.61 (m, 1 H), 4.27 (ddd, J = 13.07, 8.27, 4.35 Hz, 1 H), 3.50-3.65 (m, 1 H), 3.28-3.42 (m, 4 H), 2.16-2.28 (m, 1 H), 1.67-1.84 (m, 3 H), 0.88-1.21 (m, 1 H), −0.23-0.58 (m, 4 H) | C |

| Ex. # | Structure Name | LCMS-ESI (POS/NEG) m/z: (M + H)+ | NMR Data | Syn. Rte. |
|---|---|---|---|---|
| 564 | 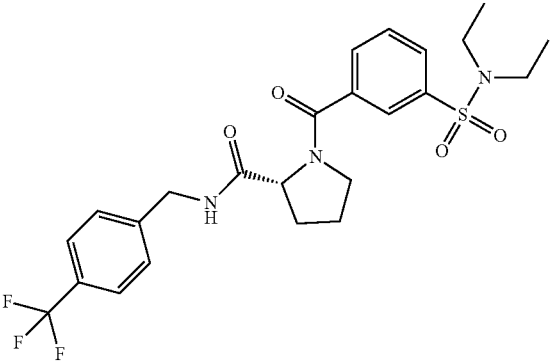 [SMILES: CCN(CC)S(=O)(=O)c1cccc(C(=O)N2CCC[C@@H]2C(=O)NCc2ccc(C(F)(F)F)cc2)c1]<br>1-(3-(diethylsulfamoyl)benzoyl)-N-(4-(trifluoromethyl)benzyl)-D-prolinamide | LCMS-ESI (POS.) m/z: 512.2 (M + H)+ | 1H NMR (500 MHz, DMSO-d6) δ ppm 8.65 (br t, J = 5.84 Hz, 1 H), 7.10-8.03 (m, 8 H), 4.02-4.53 (m, 3 H), 3.57-3.64 (m, 5 H), 3.39-3.51 (m, 1 H), 3.04-3.26 (m, 9 H), 2.20-2.32 (m, 1 H), 1.75-2.01 (m, 3 H), 0.98-1.10 (m, 6 H) | C |
| 565 | 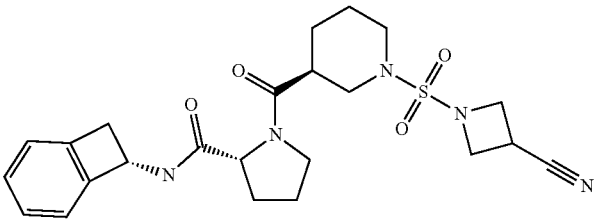 [SMILES: N#CC1CN(S(=O)(=O)N2CCC[C@H](C(=O)N3CCC[C@@H]3C(=O)N[C@H]3Cc4ccccc43)C2)C1]<br>N-((7S)-bicyclo[4.2.0]octa-1,3,5-trien-7-)-1-(((3S)-1-((3-cyano-1-azetidinyl)sulfonyl)-3-piperidinyl)carbonyl)-D-prolinamide | LCMS-ESI (POS.) m/z: 472.2 (M + H)+ | 1H NMR (400 MHz, CHLOROFORM-d) δ ppm 7.28-7.37 (m, 2 H), 7.21-7.27 (m, 1 H), 7.17 (d, J = 7.26 Hz, 1 H), 7.12 (d, J = 7.05 Hz, 1 H), 5.47 (ddd, J = 7.96, 5.16, 2.33 Hz, 1 H), 4.55 (dd, J = 8.03, 2.33 Hz, 1 H), 4.06-4.14 (m, 4 H), 3.75 (dt, J = 12.41, 1.52 Hz, 2 H), 3.69 (dd, J = 14.31, 4.98 Hz, 1 H), 3.53-3.66 (m, 2 H), 3.36-3.49 (m, 1 H), 2.88-3.09 (m, 2 H), 2.65-2.83 (m, 2 H), 2.38-2.57 (m, 1 H), 2.15-2.33 (m, 1 H), 2.01-2.12 (m, 1 H), 1.87-2.01 (m, 2 H), 1.77-1.87 (m, 1 H), 1.64-1.73 (m, 1 H), 1.50-1.60 (m, 1 H) | A |
| 566 | 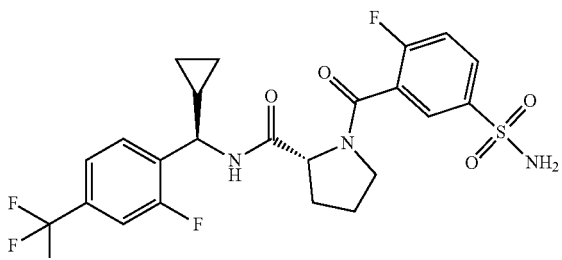<br>N-((R)-cyclopropyl(2-fluoro-4-(trifluoromethyl)phenyl)methyl)-1-(2-fluoro-5-sulfamoylbenzoyl)-D-prolinamide | LCMS-ESI (POS.) m/z: 532.2 (M + H)+ | 1H NMR (500 MHz, DMSO-d6) δ ppm 8.42-8.79 (m, 1 H), 7.89-7.96 (m, 1 H), 7.73-7.89 (m, 1 H), 7.41-7.73 (m, 6 H), 4.12-4.63 (m, 2 H), 3.48-3.63 (m, 1 H), 3.23-3.31 (m, 1 H), 2.12-2.30 (m, 1 H), 1.64-1.88 (m, 3 H), 0.79-1.31 (m, 1 H), −0.11-0.65 (m, 4 H) | C |
| 567 | 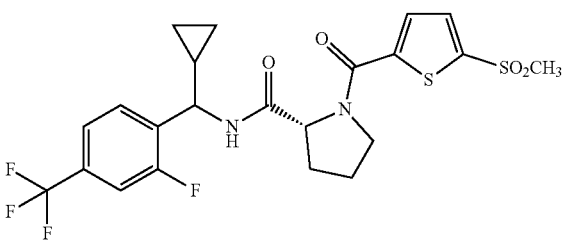 [SMILES: CS(=O)(=O)c1ccc(C(=O)N2CCC[C@@H]2C(=O)NC(c2ccc(C(F)(F)F)cc2F)C2CC2)s1] | LCMS-ESI (POS.) m/z: 519.0 (M + H)+ | 1H NMR (500 MHz, DMSO-d6) δ ppm 8.62-8.96 (m, 1 H), 7.35-7.87 (m, 5 H), 4.26-4.82 (m, 2 H), 3.79-3.88 (m, 1 H), 3.57 (br d, J = 7.40 Hz, 2 H), 3.33-3.41 (m, 3 H), 1.59-2.35 (m, 5 H), 1.10-1.29 (m, 1 H), 0.15-0.65 (m, 4 H) | C |

| Ex. # | Structure Name | LCMS-ESI (POS/NEG) m/z: (M + H)+ | NMR Data | Syn. Rte. |
|---|---|---|---|---|
| | (2R)-N-(cyclopropyl(2-fluoro-4-(trifluoromethyl)phenyl)methyl)-1-(5 (methylsulfonyl)thiophene-2-carbonyl)pyrrolidine-2-carboxamide | - | | |
| 568 | 1((3-(dimethylsulfamoyl)phenyl)carbonyl)-N-(4-(trifluoromethyl)benzyl)-D-prolinamide | LCMS-APCI (NEG.) m/z: 582.2 (M − H) | 1H NMR (400 MHz, Methanol-d4) δ ppm 8.05 (t, J = 1.8 Hz, 1 H), 7.90 (dt, J = 1.5, 7.9 Hz, 2 H), 7.72 (t, J = 7.8 Hz, 1 H), 7.49-7.65 (m, 5 H), 4.52-4.66 (m, 2 H), 4.46 (dd, J = 5.1, 15.8 Hz, 1 H), 3.67 (dt, J = 6.9, 10.4 Hz, 1 H), 3.54 (ddd, J = 4.5, 7.1, 10.3 Hz, 1 H), 2.71 (d, J = 2.2 Hz, 6 H), 2.38 (ddd, J = 5.3, 8.1, 11.3 Hz, 1 H), 1.96-2.10 (m, 3 H). | Q |
| 569 | (2R)-N-(cyclopropyl(2-fluoro-4-(trifluoromethyl)phenyl)methyl)-1-(6-(methylsulfonyl)nicotinoyl)pyrrolidine-2-carboxamide | LCMS-ESI (POS.) m/z: 514.0 (M + H)+ | 1H NMR (500 MHz, DMSO-d6) δ ppm 8.52-9.06 (m, 2 H), 7.35-8.30 (m, 5 H), 4.22-5.23 (m, 2 H), 3.59-3.70 (m, 2 H), 3.20-3.45 (m, 3 H), 2.09-2.39 (m, 1 H), 1.67-1.97 (m, 3 H), 1.01-1.30 (m, 1 H),-0.09-0.68 (m, 4 H) | C |
| 570 | (1R,3R,5R)-N-((R)-(4-cyano-2,5-difluorophenyl)(cyclopropyl)methyl)-2-(3-(methylsulfonyl)benzoyl)-2-azabicyclo[3.1.0]hexane-3-carboxamide | LCMS-ESI (POS.) m/z: 500.0 (M + H)+ | 1H NMR (500 MHz, DMSO-d6) δ ppm 8.42-8.75 (m, 1 H) 8.17 (s, 1 H) 8.06 (d, J = 7.78 Hz, 1 H) 7.66-8.03 (m, 4 H) 7.41-7.63 (m, 1 H) 4.94 (dd, J = 11.35, 3.44 Hz, 1 H) 4.49 (t, J = 7.85 Hz, 1 H) 3.24-3.28 (m, 4 H) 1.64-1.76 (m, 2 H) 1.13-1.22 (m, 1 H) 1.08 (td, J = 4.96, 2.66 Hz, 1 H) 0.67-0.78 (m, 1 H) 0.42-0.61 (m, 2 H) 0.36 (br d, J = 2.08 Hz, 2 H) | C |
| 571 | 1-(((3S)-1-((3-cyano-1-azetidinyl)sulfonyl)-3-piperidinyl)carbonyl)-N-(2-methylbenzyl)-D-prolinamide | LCMS-ESI (POS.) m/z: 474.2 (M + H)+ | 1H NMR (500 MHz, DMSO-d6) δ ppm 8.07-8.51 (m, 1 H), 7.10-7.22 (m, 4 H), 4.14-4.50 (m, 3 H), 4.00-4.10 (m, 2 H), 3.89-3.97 (m, 2 H), 3.73-3.83 (m, 1 H), 3.35-3.69 (m, 4 H), 2.60-2.87 (m, 3 H), 2.04-2.34 (m, 4 H), 1.68-2.00 (m, 5 H), 1.35-1.56 (m, 2 H) | A |

-continued

| Ex. # | Structure Name | LCMS-ESI (POS/NEG) m/z: (M + H)+ | NMR Data | Syn. Rte. |
|---|---|---|---|---|
| 572 | 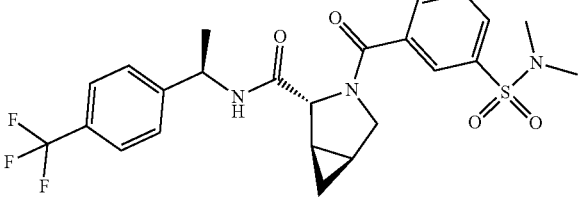<br>(1R,2R,5S)-3-(3-(dimethylsulfamoyl)benzoyl)-N-((1R)-1-(4-(trifluoromethyl)phenyl)ethyl)-3-azabicyclo[3.1.0]hexane-2-carboxamide | LCMS-ESI (POS.) m/z: 510.0 (M + H)+ | 1H NMR (500 MHz, DMSO-d6) δ ppm 8.44-8.92 (m, 1 H), 7.43-7.91 (m, 8 H), 4.82-5.05 (m, 1 H), 4.08-4.76 (m, 1 H), 3.69-3.85 (m, 1 H), 3.23-3.57 (m, 1 H), 2.57-2.70 (m, 6 H), 1.48-1.65 (m, 2 H), 1.09-1.47 (m, 3 H), 0.24-0.80 (m, 2 H) | C |
| 573 | 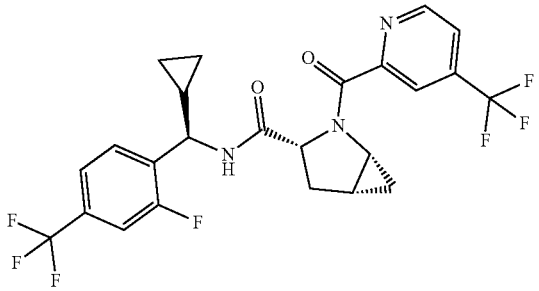 [SMILES: O=C(N[C@@H](c1ccc(C(F)(F)F)cc1F)C1CC1)[C@H]1C[C@H]2C[C@H]2N1C(=O)c1cc(C(F)(F)F)ccn1]<br>(1R,3R,5R)-N-((R)-cyclopropyl(2-fluoro-4-(trifluoromethyl)phenyl)methyl)-2-((4-(trifluoromethyl)-2-pyridinyl)carbonyl)-2-azabicyclo[3.1.0]hexane-3-carboxamide | LCMS-APCI (POS.) m/z: 516.1 (M + H)+ | 1H NMR (400 MHz, DMSO-d6) δ ppm 8.89-9.25 (m, 2 H), 8.71 (dd, J = 7.6, 86.8 Hz, 1 H), 8.22-8.43 (m, 1 H), 7.56-7.84 (m, 2 H), 5.03 (dd, J = 3.5, 11.4 Hz, 1 H), 4.59-4.83 (m, 1 H), 3.74-4.20 (m, 1 H), 3.41 (dt, J = 3.1, 6.3 Hz, 4 H), 2.62-2.82 (m, 1 H), 1.60-1.84 (m, 2 H), 1.08-1.39 (m, 2 H), 0.72-1.04 (m, 2 H), 0.25-0.69 (m, 3 H),-0.28-0.07 (m, 1 H). | Q |
| 574 | 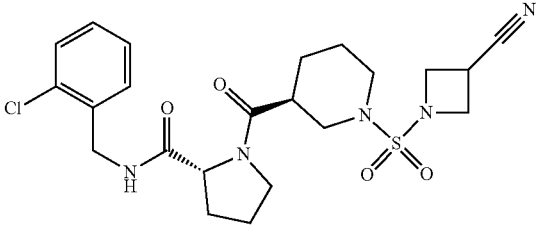 [SMILES: N#CC1CN(S(=O)(=O)N2CCC[C@H](C(=O)N3CCC[C@@H]3C(=O)NCc3ccccc3Cl)C2)C1]<br>N-(2-chlorobenzyl)-1-(((3S)-1-((3-cyano-1-azetidinyl)sulfonyl)-3-piperidinyl)carbonyl)-D-prolinamide | LCMS-ESI (POS.) m/z: 494.2 (M + H)+ | 1H NMR (500 MHz, DMSO-d6) δ ppm 8.20-8.70 (m, 1 H), 7.39-7.49 (m, 1 H), 7.24-7.37 (m, 3 H), 4.22-4.53 (m, 3 H), 4.00-4.10 (m, 2 H), 3.88-3.98 (m, 2 H), 3.75-3.84 (m, 1 H), 3.36-3.70 (m, 4 H), 2.65-2.89 (m, 2 H), 1.36-2.34 (m, 9 H) | A |
| 575 | 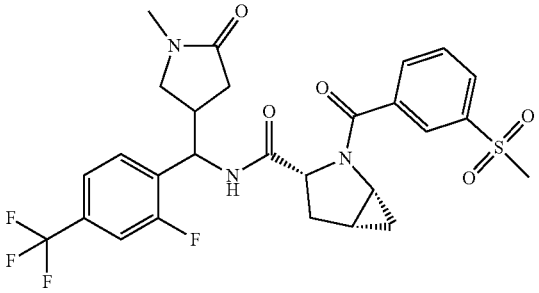 [SMILES: CN1CC(C(NC(=O)[C@H]2C[C@H]3C[C@H]3N2C(=O)c2cccc(S(C)(=O)=O)c2)c2ccc(C(F)(F)F)cc2F)CC1=O]<br>Diastereomer #2-(1R,3R,5R)-N-((2-fluoro-4-(trifluoromethyl)phenyl)(1-methyl-5-oxopyrrolidin-3-yl)methyl)-2-(3-(methylsulfonyl)benzoyl)-2-azabicyclo[3.1.0]hexane-3-carboxamide | LCMS-ESI (POS.) m/z: 582.0 (M + H)+ | 1H NMR (500 MHz, CHLOROFORM-d) Shift 8.33-8.38 (m, 1H), 8.10-8.15 (m, 1H), 7.95-8.08 (m, 2H), 7.70-7.79 (m, 1H), 7.43-7.50 (m, 2H), 7.34-7.41 (m, 1H), 5.36 (dd, J = 7.85, 9.15 Hz, 1H), 5.16 (dd, J = 2.40, 10.57 Hz, 1H), 3.68-3.81 (m, 1H), 3.25-3.38 (m, 2H), 3.18-3.21 (m, 3H), 2.87-2.96 (m, 1H), 2.72 (dd, J = 2.34, 13.23 Hz, 1H), 2.49-2.58 (m, 3H), 2.40 (dd, J = 9.41, 17.06 Hz, 1H), 2.24-2.34 (m, 1H), 2.12 (dd, J = 6.88, 17.13 Hz, 1H), 1.72-1.82 (m, 1H), 1.03-1.10 (m, 1H), 0.93-1.01 (m, 1H) | C |

| Ex. # | Structure Name | LCMS-ESI (POS/NEG) m/z: (M + H)+ | NMR Data | Syn. Rte. |
|---|---|---|---|---|
| 576 | 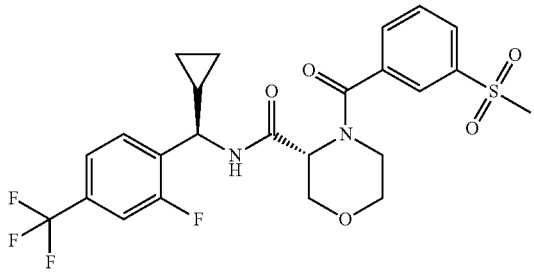<br>(3R)-N-((R)-cyclopropyl(2-fluoro-4-(trifluoromethyl)phenyl)methyl)-4-(3 (methylsulfonyl)benzoyl)-3-morpholinecarboxamide | LCMS-ESI (POS.) m/z: 529.0 (M + H)+ | 1H NMR (400 MHz, CHLOROFORM-d) δ ppm 7.99-8.15 (m, 2 H), 7.74-7.82 (m, 1 H), 7.53-7.74 (m, 1 H), 7.40-7.51 (m, 2 H), 7.33-7.40 (m, 1 H), 6.80-7.08 (m, 1 H), 4.51 (br s, 3 H), 3.32-4.21 (m, 5 H), 2.97-3.18 (m, 3 H), 1.20-1.41 (m, 1 H), 0.55-0.75 (m, 2 H), 0.36-0.53 (m, 2 H) | C |
| 577 | 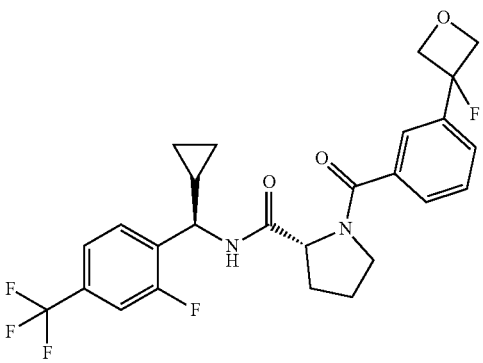 [SMILES: O=C(N[C@@H](c1ccc(C(F)(F)F)cc1F)C1CC1)[C@H]1CCCN1C(=O)c1cccc(C2(F)COC2)c1]<br>N-((R)-cyclopropyl(2-fluoro-4-(trifluoromethyl)phenyl)methyl)-1-(3-(3-fluoro-3-oxetanyl)benzoyl)-D-prolinamide | LCMS-APCI (POS.) m/z: 509.2 (M + H)+ | 1H NMR (400 MHz, Methanol-d4) δ ppm 7.37-7.84 (m, 7 H), 5.01-5.13 (m, 2 H), 4.89-5.00 (m, 2 H), 4.11-4.66 (m, 2 H), 3.46-3.74 (m, 2 H), 2.25-2.38 (m, 1 H), 1.78-2.00 (m, 3 H), 0.96-1.35 (m, 1 H), -0.04-0.74 (m, 4 H). | R |
| 578 | 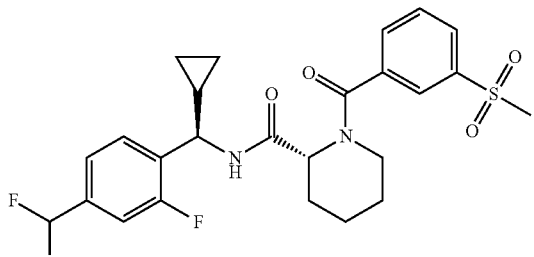<br>(2R)-N-((R)-cyclopropyl(4-(difluoromethyl)-2-fluorophenyl)methyl)-1-(3-(methylsulfonyl)benzoyl)-2-piperidinecarboxamide | LCMS-ESI (POS.) m/z: 531.2 (M + H)+ | 1H NMR (500 MHz, DMSO-d6) δ ppm 8.69 (d, J = 7.27 Hz, 1 H), 8.01 (dd, J = 8.69, 1.69 Hz, 1 H), 7.89 (br s, 1 H), 7.55-7.81 (m, 3 H), 7.30-7.48 (m, 2 H), 6.88-7.17 (m, 1 H), 4.03- (m, 3 H), 3.31-3.48 (m, 1 H), 2.00-2.25 (m, 1 H), 1.03-1.88 (m, 6 H), 0.23-0.71 (m, 4 H) | C |
| 579 | 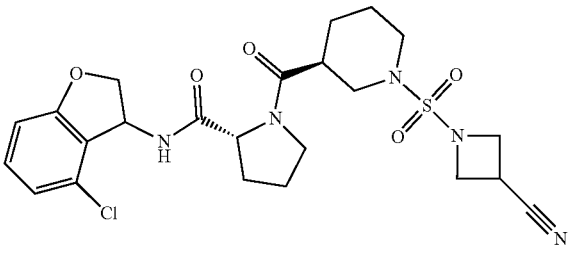 [SMILES: N#CC1CN(S(=O)(=O)N2CCC[C@H](C(=O)N3CCC[C@@H]3C(=O)NC3COc4cccc(Cl)c43)C2)C1]<br>(2R)-N-(4-chloro-2,3-dihydrobenzofuran-3-)-1-((S)-1-((3-cyanoazetidin-1-yl)sulfonyl)piperidine-3-carbonyl)pyrrolidine-2-carboxamide | LCMS-ESI (POS.) m/z: 522.2 (M + H)+ | 1H NMR (500 MHz, DMSO-d6) δ ppm 8.30-8.87 (m, 1 H), 7.21-7.31 (m, 1 H), 6.91-6.99 (m, 1 H), 6.80-6.88 (m, 1 H), 5.50-5.71 (m, 1 H), 4.65-4.74 (m, 1 H), 4.02-4.42 (m, 4 H), 3.90-3.97 (m, 2 H), 3.74-3.84 (m, 1 H), 3.33-3.69 (m, 4 H), 2.63-2.89 (m, 2 H), 2.14-2.33 (m, 1 H), 1.66-2.10 (m, 6 H), 1.31-1.56 (m, 2 H) | A |

-continued

| Ex. # | Structure Name | LCMS-ESI (POS/NEG) m/z: (M + H)+ | NMR Data | Syn. Rte. |
|---|---|---|---|---|
| 580 | 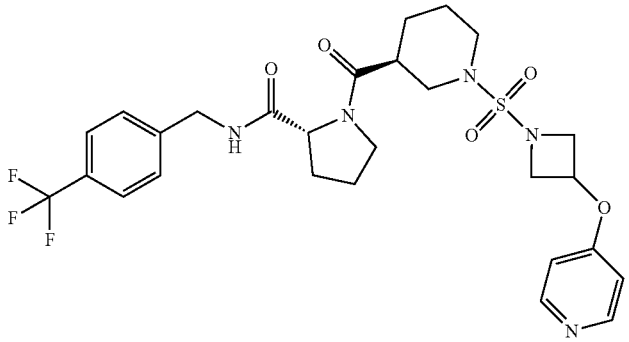 [SMILES: O=C(NCc1ccc(C(F)(F)F)cc1)[C@H]1CCCN1C(=O)[C@H]1CCCN(S(=O)(=O)N2CC(Oc3ccncc3)C2)C1]<br>1-(((3S)-1-((3-(4-pyridinyloxy)-1-azetidinyl)sulfonyl)-3-piperidinyl)carbonyl)-N-(4-(trifluoromethyl)benzyl)-D-prolinamide | LCMS-ESI (POS.) m/z: 596.4 (M + H)+ | 1H NMR (500 MHz, DMSO-d6) δ 8.24-8.85 (m, 3H), 7.57-7.75 (m, 2H), 7.34-7.55 (m, 2H), 6.87-6.97 (m, 1H), 5.07-5.18 (m, 1H), 4.22-4.53 (m, 5H), 3.76-3.94 (m, 2H), 3.51-3.70 (m, 4H), 2.59-2.90 (m, 4H), 2.02-2.42 (m, 1H), 1.66-2.02 (m, 5H), 1.36-1.57 (m, 2H) | J |
| 581 | 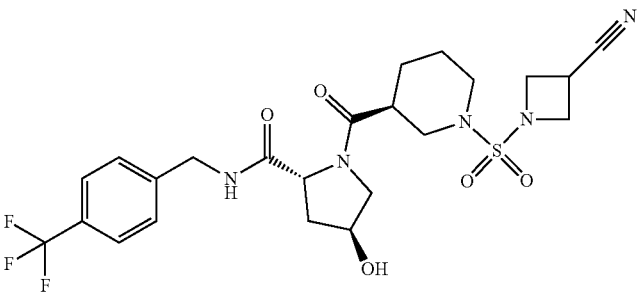 [SMILES: N#CC1CN(S(=O)(=O)N2CCC[C@H](C(=O)N3C[C@@H](O)C[C@@H]3C(=O)NCc3ccc(C(F)(F)F)cc3)C2)C1]<br>(4S)-1-(((3S)-1-((3-cyano-1-azetidinyl)sulfonyl)-3-piperidinyl)carbonyl)-4-hydroxy-N-(4-(trifluoromethyl)benzyl)-D-prolinamide | LCMS-ESI (POS.) m/z: 544.2 (M + H)+ | 1H NMR (500 MHz, CHLOROFORM-d) δ ppm 7.57 (d, J = 8.04 Hz, 2 H), 7.36 (d, J = 7.92 Hz, 2 H), 7.33 (br t, J = 5.84 Hz, 1 H), 4.65-4.73 (m, 2 H), 4.49-4.57 (m, 1 H), 4.40-4.46 (m, 1 H), 4.06-4.16 (m, 4 H), 3.81 (br d, J = 11.03 Hz, 1 H), 3.75 (br d, J = 12.72 Hz, 1 H), 3.60-3.70 (m, 2 H), 3.38-3.46 (m, 1 H), 2.93 (dd, J = 12.72, 11.03 Hz, 1 H), 2.78 (td, J = 12.36, 2.66 Hz, 1 H), 2.62-2.73 (m, 2 H), 2.05 (ddd, J = 13.04, 8.50, 4.02 Hz, 1 H), 1.89 (br d, J = 13.36 Hz, 1 H), 1.78-1.84 (m, 1 H), 1.59-1.70 (m, 2 H), 1.49-1.58 (m, 1 H) | M |
| 582 | 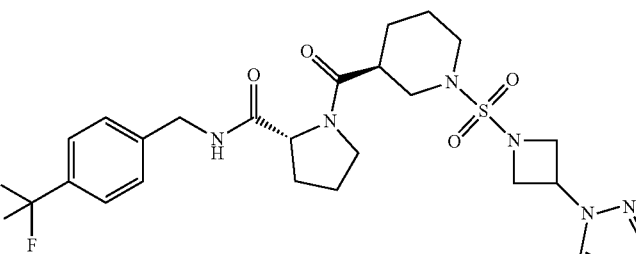<br>1-(((3S)-1-((3-(1H-pyrazol-1-)-1-azetidinyl)sulfonyl)-3-piperidinyl)carbonyl)-N-(4-(trifluoromethyl)benzyl)-D-prolinamide | LCMS-ESI (POS.) m/z: 569.2 (M + H)+ | 1H NMR (500 MHz, DMSO-d6) δ ppm 8.30-8.79 (m, 1 H), 7.84 (br s, 1 H), 7.62-7.72 (m, 2 H), 7.59 (s, 1 H), 7.37-7.52 (m, 2 H), 6.30 (s, 1 H), 5.19-5.36 (m, 1 H), 4.26-4.55 (m, 4 H), 4.08-4.26 (m, 5 H), 3.42-3.81 (m, 6 H), 2.63-2.97 (m, 3 H), 1.34-2.41 (m, 9 H) | M |
| 583 | 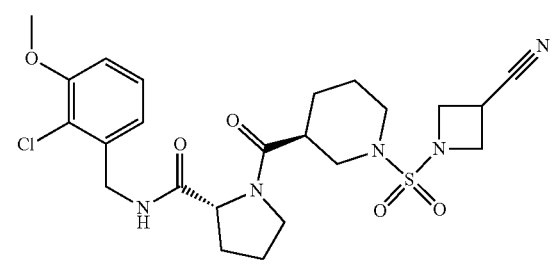 [SMILES: COc1cccc(CNC(=O)[C@H]2CCCN2C(=O)[C@H]2CCCN(S(=O)(=O)N3CC(C#N)C3)C2)c1Cl] | LCMS-ESI (POS.) m/z: 524.2 (M + H)+ | 1H NMR (500 MHz, DMSO-d6) δ ppm 8.23-8.64 (m, 1 H), 7.19-7.36 (m, 1 H), 7.03-7.12 (m, 1 H), 6.82-7.00 (m, 1 H), 3.43-4.54 (m, 16 H), 2.60-2.94 (m, 3 H), 2.05-2.36 (m, 1 H), 1.35-2.04 (m, 6 H) | A |

-continued

| Ex. # | Structure Name | LCMS-ESI (POS/NEG) m/z: (M + H)+ | NMR Data | Syn. Rte. |
|---|---|---|---|---|
| | N-(2-chloro-3-methoxybenzyl)-1-(((3S)-1-((3-cyano-1-azetidinyl)sulfonyl)-3-piperidinyl)carbonyl)-D-prolinamide | | | |
| 584 | N-((R)-cyclopropyl(2-fluoro-4-(trifluoromethyl)phenyl)methyl)-1-(3-(dimethylamino)benzoyl)-D-prolinamide | LCMS-ESI (POS.) m/z: 478.2 (M + H)+ | 1H NMR (500 MHz, DMSO-d6) δ ppm 8.46-8.70 (m, 1 H), 7.56-7.75 (m, 3 H), 7.14-7.32 (m, 1 H), 6.55-6.92 (m, 3 H), 4.56-4.61 (m, 1 H), 4.30 (br dd, J = 19.40, 7.85 Hz, 1 H), 3.36-3.60 (m, 2 H), 2.82-2.97 (m, 6 H), 2.06-2.22 (m, 1 H), 1.64-1.82 (m, 3 H), 1.00-1.25 (m, 1 H), 0.10-0.62 (m, 4 H) | |
| 585 | 1-(((3S)-1-((3-cyano-1-azetidinyl)sulfonyl)-3-piperidinyl)carbonyl)-N-((1R)-1-(3-fluoro-4-methoxyphenyl)ethyl)-D-prolinamide, 1-(((3S)-1-((3-cyano-1-azetidinyl)sulfonyl)-3-piperidinyl)carbonyl)-N-((1S)-1-(3-fluoro-4-methoxyphenyl)ethyl)-D-prolinamide | LCMS-ESI (POS.) m/z: 522.2 (M + H)+ | 1H NMR (500 MHz, DMSO-d6) δ ppm 8.04-8.56 (m, 1 H), 6.98 7.23 (m, 3 H), 4.76-4.98 (m, 1 H), 4.25-4.49 (m, 1 H), 4.01-4.12 (m, 2 H), 3.88-3.99 (m, 2 H), 3.74-3.86 (m, 4 H), 3.47-3.68 (m, 4 H), 2.60-2.90 (m, 3 H), 2.01-2.35 (m, 1 H), 1.63-1.98 (m, 5 H), 1.23-1.56 (m, 5 H) | A |
| 586 | (5R)-N-((R)-cyclopropyl(2-fluoro-4-(trifluoromethyl)phenyl)methyl)-5-methyl-1-(3-(methylsulfonyl)benzoyl)-D-prolinamide | LCMS-ESI (POS.) m/z: 527.2 (M + H)+ | 1H NMR (400 MHz, CHLOROFORM-d) δ ppm 7.95-8.14 (m, 2 H), 7.60-7.93 (m, 3 H), 7.46-7.58 (m, 1 H), 7.39-7.45 (m, 1 H), 7.31-7.39 (m, 1 H), 3.79-4.93 (m, 3 H), 2.88-3.19 (m, 3 H), 2.50-2.73 (m, 1 H), 1.95-2.27 (m, 2 H), 1.65-1.86 (m, 1 H), 1.00-1.62 (m, 4 H), 0.53-0.73 (m, 2 H), 0.29-0.53 (m, 2 H) | C |
| 587 | 1-(((3S)-1-((trans-3-cyanocyclobutyl)sulfonyl)-3-piperidinyl)carbonyl)-N-(4-(trifluoromethyl)benzyl)-D-prolinamide | LCMS-APCI (POS.) m/z: 527.2 (M + H)+ | 1H NMR (Methanol-d4) δ: 7.75-7.59 (m, 2H), 7.58-7.41 (m, 2H), 4.69-4.51 (m, 1H), 4.51-4.46 (m, 1H), 4.46-4.40 (m, 1H), 4.20-4.06 (m, 1H), 3.88-3.80 (m, 1H), 3.79-3.69 (m, 2H), 3.57-3.41 (m, 1H), 3.37 (s, 1H), 3.03-2.67 (m, 7H), 2.31-2.19 (m, 1H), 2.18-1.88 (m, 4H), 1.88-1.74 (m, 1H), 1.71-1.46 (m, 2H) | R |

| Ex. # | Structure Name | LCMS-ESI (POS/NEG) m/z: (M + H)+ | NMR Data | Syn. Rte. |
|---|---|---|---|---|
| 588 | 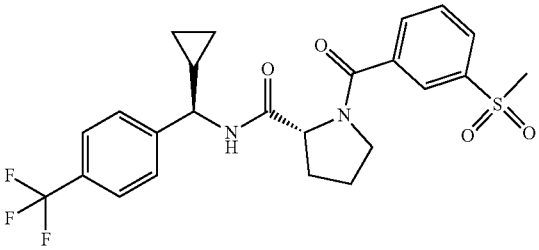 [SMILES: CS(=O)(=O)c1cccc(C(=O)N2CCC[C@@H]2C(=O)N[C@@H](c2ccc(C(F)(F)F)cc2)C2CC2)c1]<br>N-((R)-cyclopropyl(4-(trifluoromethyl)phenyl)methyl)-1-(3-(methylsulfonyl)benzoyl)-D-prolinamide | LCMS-ESI (POS.) m/z: 495.2 (M + H)+ | 1H NMR (500 MHz, DMSO-d6) δ ppm 8.44-8.72 (m, 1 H), 6.51-8.11 (m, 8 H), 3.89-4.58 (m, 2 H), 3.40-3.66 (m, 2 H), 3.24-3.30 (m, 3 H), 2.16-2.33 (m, 1 H), 1.69-1.96 (m, 3 H), 0.82-1.25 (m, 1 H),-0.14-0.64 (m, 4 H) | A |
| 589 | 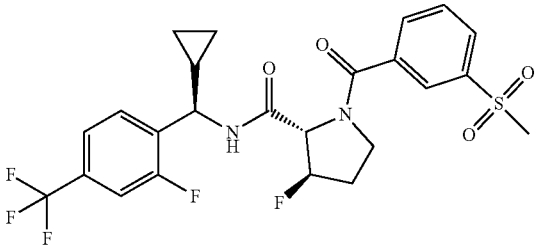 [SMILES: CS(=O)(=O)c1cccc(C(=O)N2CC[C@@H](F)[C@@H]2C(=O)N[C@@H](c2ccc(C(F)(F)F)cc2F)C2CC2)c1]<br>(3R)-N-((R)-cyclopropyl(2-fluoro-4-(trifluoromethyl)phenyl)methyl)-3-fluoro-1-(3-(methylsulfonyl)benzoyl)-D-prolinamide | LCMS-ESI (POS.) m/z: 531.0 (M + H)+ | 1H NMR (500 MHz, CHLOROFORM-d) δ ppm 8.14 (s, 1 H), 8.06-8.11 (m, 1 H), 7.84 (d, J = 7.66 Hz, 1 H), 7.70-7.75 (m, 1 H), 7.64-7.70 (m, 1 H), 7.47-7.52 (m, 1 H), 7.41-7.46 (m, 1 H), 7.37 (d, J = 9.99 Hz, 1 H), 5.27-5.65 (m, 1 H), 4.87-5.12 (m, 1 H), 4.37-4.65 (m, 1 H), 3.52-3.78 (m, 2 H), 3.06-3.19 (m, 3 H), 2.22-2.57 (m, 2 H), 1.13-1.36 (m, 1 H), 0.63-0.75 (m, 1 H), 0.53-0.63 (m, 1 H), 0.22-0.52 (m, 2 H) | C |
| 590 | 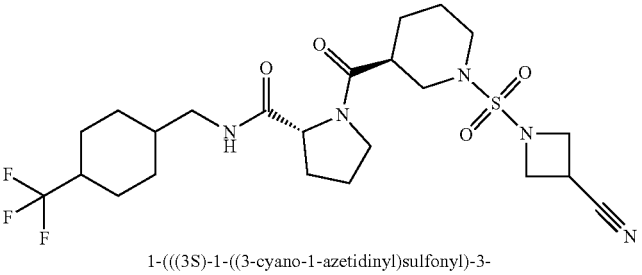<br>1-(((3S)-1-((3-cyano-1-azetidinyl)sulfonyl)-3-piperidinyl)carbonyl)-N-((cis-4-(trifluoromethyl)cyclohexyl)methyl)-D-prolinamide, 1-(((3S)-1-((3-cyano-1-azetidinyl)sulfonyl)-3-piperidinyl)carbonyl)-N-((4-(trifluoromethyl)cyclohexyl)methyl)-D-prolinamide | LCMS-ESI (POS.) m/z: 534.2 (M + H)+ | 1H NMR (400 MHz, DMSO-d6) δ ppm 8.04-8.20 (m, 1 H), 7.64-7.77 (m, 1 H), 7.70 (br d, J = 4.25 Hz, 1 H), 4.17-4.38 (m, 1 H), 3.98-4.12 (m, 2 H), 3.85-3.97 (m, 2 H), 3.73-3.84 (m, 1 H), 3.29-3.67 (m, 4 H), 3.02-3.19 (m, 1 H), 2.60-2.99 (m, 3 H), 1.99-2.30 (m, 2 H), 1.80-1.93 (m, 3 H), 0.83-1.37 (m, 3 H) | A |
| 591 | 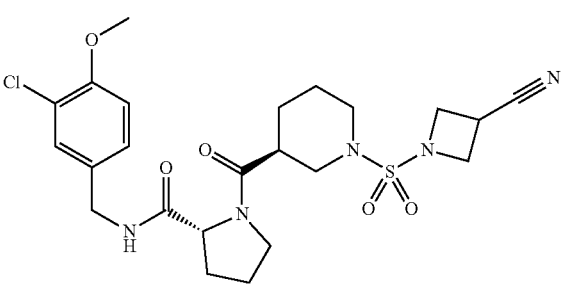 [SMILES: COc1ccc(CNC(=O)[C@H]2CCCN2C(=O)[C@H]2CCCN(S(=O)(=O)N3CC(C#N)C3)C2)cc1Cl]<br>N-(3-chloro-4-methoxybenzyl)-1-(((3S)-1-((3-cyano-1-azetidinyl)sulfonyl)-3-piperidinyl)carbonyl)-D-prolinamide | LCMS-ESI (POS.) m/z: 524.2 (M + H)+ | 1H NMR (500 MHz, DMSO-d6) δ ppm 8.20-8.62 (m, 1 H), 7.26-7.32 (m, 1 H), 7.14-7.19 (m, 1 H), 7.05-7.13 (m, 1 H), 4.12-4.49 (m, 3 H), 4.01-4.09 (m, 2 H), 3.89-3.98 (m, 2 H), 3.77-3.87 (m, 4 H), 3.36-3.71 (m, 4 H), 2.60-2.87 (m, 3 H), 2.03-2.29 (m, 1 H), 1.66-1.96 (m, 5 H), 1.35-1.55 (m, 2 H) | A |

| Ex. # | Structure Name | LCMS-ESI (POS/NEG) m/z: (M + H)+ | NMR Data | Syn. Rte. |
|---|---|---|---|---|
| 592 | 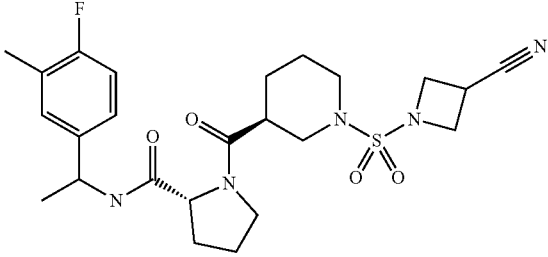 [SMILES: Cc1cc(C(C)NC(=O)[C@H]2CCCN2C(=O)[C@H]2CCCN(S(=O)(=O)N3CC(C#N)C3)C2)ccc1F]<br>(2R)-1-((S)-1-((3-cyanoazetidin-1-yl)sulfonyl)piperidine-3-carbonyl)-N-(1-(4-fluoro-3-methylphenyl)ethyl)pyrrolidine-2-carboxamide | LCMS-ESI (POS.) m/z: 506.2 (M + H)+ | 1H NMR (500 MHz, DMSO-d6) δ ppm 8.01-8.60 (m, 1 H), 6.92-7.37 (m, 3 H), 4.76-4.98 (m, 1 H), 4.23-4.52 (m, 1 H), 3.42-4.13 (m, 10 H), 2.61-2.92 (m, 3 H), 1.64-2.40 (m, 8 H), 1.21-1.60 (m, 5 H) | A |
| 593 | 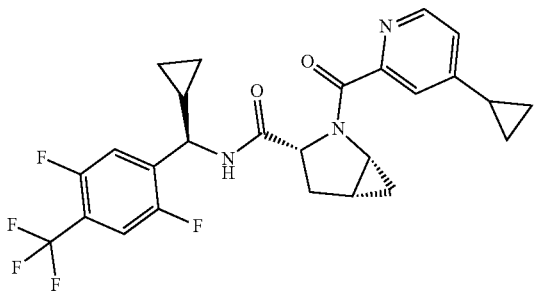 [SMILES: O=C(N[C@@H](c1cc(F)c(C(F)(F)F)cc1F)C1CC1)[C@H]1C[C@H]2C[C@H]2N1C(=O)c1cc(C2CC2)ccn1]<br>(1R,3R,5R)-N-((R)-cyclopropyl(2,5-difluoro-4-(trifluoromethyl)phenyl)methyl)-2-((4-cyclopropyl-2-pyridinyl)carbonyl)-2-azabicyclo[3.1.0]hexane-3-carboxamide | LCMS-APCI (POS.) m/z: 506.2 (M + H)+ | 1H NMR (Methanol-d4) δ: 8.69 (d, J = 6.8 Hz, 1H), 8.33 (dd, J = 5.2, 0.9 Hz, 1H), 7.38-7.31 (m, 2H), 7.30-7.23 (m, 2H), 4.83 (dd, J = 11.4, 3.9 Hz, 1H), 4.33 (dd, J = 8.9, 6.9 Hz, 1H), 3.09 (td, J = 6.3, 2.6 Hz, 1H), 2.52 (td, J = 12.4, 6.3 Hz, 1H), 2.09-1.93 (m, 1H), 1.75 (dd, J = 13.6, 3.9 Hz, 1H), 1.66-1.55 (m, 1H), 1.18-1.02 (m, 1H), 1.00-0.95 (m, 1H), 0.95-0.88 (m, 2H), 0.88-0.80 (m, 2H), 0.69-0.59 (m, 1H), 0.57-0.47 (m, 1H), 0.46-0.39 (m, 1H), 0.39-0.23 (m, 2H) | Q |
| 594 | 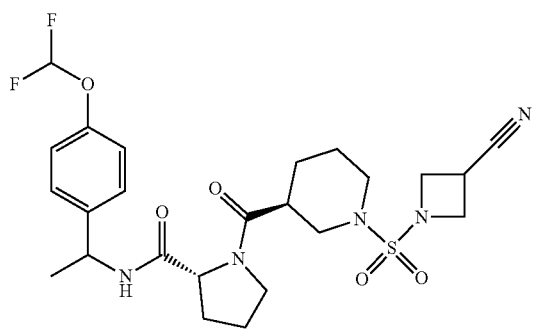 [SMILES: CC(NC(=O)[C@H]1CCCN1C(=O)[C@H]1CCCN(S(=O)(=O)N2CC(C#N)C2)C1)c1ccc(OC(F)F)cc1]<br>(2R)-1-((S)-1-((3-cyanoazetidin-1-yl)sulfonyl)piperidine-3-carbonyl)-N-(1-(4-(difluoromethoxy)phenyl)ethyl)pyrrolidine-2-carboxamide | LCMS-ESI (POS.) m/z: 540.2 (M + H)+ | 1H NMR (500 MHz, DMSO-d6) δ ppm 8.06-8.59 (m, 1 H), 6.98-7.45 (m, 5 H), 4.24-5.05 (m, 2 H), 4.01-4.13 (m, 2 H), 3.86-3.98 (m, 2 H), 3.71-3.84 (m, 1 H), 3.46-3.67 (m, 4 H), 2.60-2.92 (m, 3 H), 1.34-2.33 (m, 11 H) | A |

-continued

| Ex. # | Structure Name | LCMS-ESI (POS/NEG) m/z: (M + H)+ | NMR Data | Syn. Rte. |
|---|---|---|---|---|
| 595 | 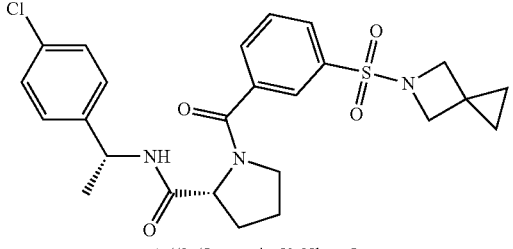<br>1-((3-(5-azaspiro[2.3]hex-5-ylsulfonyl)phenyl)carbonyl)-N-((1R)-1-(4-chlorophenyl)ethyl)-D-prolinamide | LCMS-APCI (NEG.) m/z: 500.2 (M − H) | 1H NMR (400 MHz, Methanol-d4) δ ppm 8.12 (s, 1 H), 7.91-8.02 (m, 2 H), 7.76 (q, J = 6.8, 7.3 Hz, 2 H), 7.32 (d, J = 0.8 Hz, 4 H), 4.97-5.10 (m, 1 H), 4.59 (dd, J = 6.0, 8.3 Hz, 1 H), 3.89 (s, 4 H), 3.57-3.69 (m, 1 H), 3.52 (dt, J = 6.0, 10.6 Hz, 1 H), 2.28-2.37 (m, 1 H), 1.87-1.97 (m, 3 H), 1.49 (d, J = 7.0 Hz, 3 H), 0.47 (s, 4 H). | A |
| 596 | 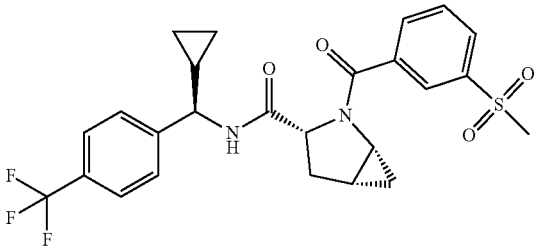 [SMILES: CS(=O)(=O)c1cccc(C(=O)N2[C@@H](C(=O)N[C@@H](c3ccc(C(F)(F)F)cc3)C3CC3)C[C@H]3C[C@H]32)c1]<br>(1R,3R,5R)-N-((R)-cyclopropyl(4-(trifluoromethyl)phenyl)methyl)-2-(3-(methylsulfonyl)benzoyl)-2-azabicyclo[3.1.0]hexane-3-carboxamide | LCMS-ESI (POS.) m/z: 507.0 (M + H)+ | 1H NMR (500 MHz, DMSO-d6) δ ppm 8.40-8.72 (m, 1 H) 7.89-8.21 (m, 3 H) 7.38-7.82 (m, 5 H) 3.70-5.07 (m, 2 H) 3.23-3.28 (m, 4 H) 2.53-2.61 (m, 1 H) 1.78 (dd, J = 13.56, 3.57 Hz, 1 H) 1.54-1.73 (m, 1 H) 0.65-1.19 (m, 3 H)-0.30-0.60 (m, 4 H) | A |
| 597 | 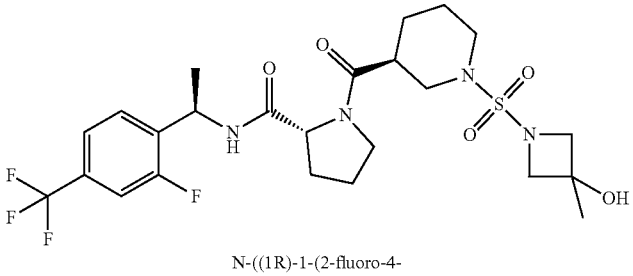<br>N-((1R)-1-(2-fluoro-4-(trifluoromethyl)phenyl)ethyl)-1-(((3S)-1-((3-hydroxy-3-methyl-1-azetidinyl)sulfonyl)-3-piperidinyl)carbonyl)-D-prolinamide | LCMS-ESI (POS.) m/z: 565.2 (M + H)+ | 1H NMR (400 MHz, CHLOROFORM-d) δ 7.50 (br d, J = 7.46 Hz, 1H), 7.37-7.46 (m, 2H), 7.31 (d, J = 10.37 Hz, 1H), 5.22 (quin, J = 7.18 Hz, 1H), 4.57 (dd, J = 2.12, 8.03 Hz, 1H), 3.90 (dd, J = 5.39, 8.09 Hz, 2H), 3.75-3.85 (m, 2H), 3.70-3.75 (m, 2H), 3.53-3.66 (m, 2H), 3.04 (dd, J = 10.73, 12.49 Hz, 1H), 2.70-2.88 (m, 2H), 2.30-2.39 (m, 1H), 2.08-2.20 (m, 1H), 1.96-2.08 (m, 2H), 1.81-1.90 (m, 2H), 1.62-1.73 (m, 3H), 1.56 (s, 3H), 1.45 (d, J = 6.95 Hz, 3H) | A |
| 598 | 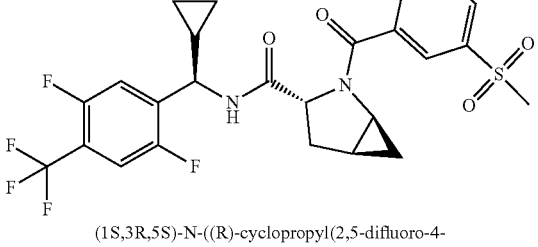<br>(1S,3R,5S)-N-((R)-cyclopropyl(2,5-difluoro-4-(trifluoromethyl)phenyl)methyl)-2-((5-(methylsulfonyl)-3-pyridinyl)carbonyl)-2-azabicyclo[3.1.0]hexane-3-carboxamide | LCMS-ESI (POS.) m/z: 544.2 (M + H)+ | 1H NMR (400 MHz, CHLOROFORM-d) δ ppm 9.14-9.43 (m, 2 H), 8.56-8.72 (m, 1 H), 7.41 (br d, J = 6.12 Hz, 1 H), 7.33 (dd, J = 9.48, 5.65 Hz, 1 H), 7.21 (dd, J = 10.06, 5.49 Hz, 1 H), 4.76 (dd, J = 8.40, 2.80 Hz, 1 H), 4.49 (dd, J = 8.55, 6.89 Hz, 1 H), 3.22-3.30 (m, 1 H), 3.18 (s, 3 H), 2.76 (ddd, J = 13.61, 7.44, 2.70 Hz, 1 H), 2.01-2.17 (m, 2 H), 1.20-1.33 (m, 1 H), 1.11-1.20 (m, 1 H), 0.82 (td, J = 5.08, 2.80 Hz, 1 H), 0.66-0.77 (m, 1 H), 0.56-0.66 (m, 1 H), 0.40-0.52 (m, 2 H) | C |

| Ex. # | Structure Name | LCMS-ESI (POS/NEG) m/z: (M + H)+ | NMR Data | Syn. Rte. |
|---|---|---|---|---|
| 599 | 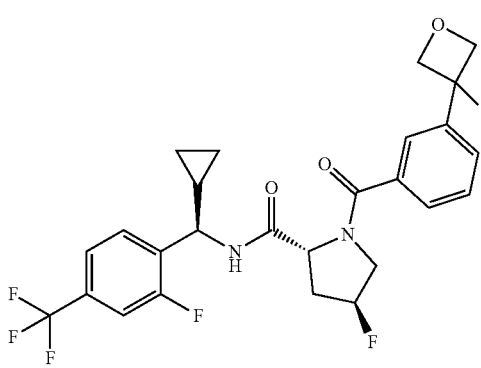<br>(4S)-N-((R)-cyclopropyl(2-fluoro-4-(trifluoromethyl)phenyl)methyl)-4-fluoro-1-(3-(3-fluoro-3-oxetanyl)benzoyl)-D-prolinamide | LCMS-APCI (POS.) m/z: 527.1 (M + H)$^+$ | 1H NMR (400 MHz, Methanol-d4) δ ppm 7.46-8.01 (m, 7 H), 5.26-5.51 (m, 1 H), 4.84-5.25 (m, 4 H), 4.73-4.76 (m, 1 H), 3.73-4.30 (m, 3 H), 2.66-2.82 (m, 1 H), 2.02-2.29 (m, 1 H), 1.03-1.50 (m, 1 H), − 0.05-0.89 (m, 4 H). | Q |
| 600 | 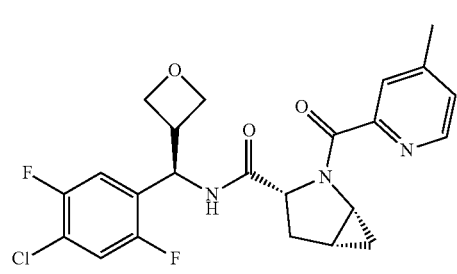 [SMILES: Cc1ccnc(C(=O)N2[C@@H](C(=O)N[C@@H](c3cc(F)c(Cl)cc3F)C3COC3)C[C@H]3C[C@H]32)c1]<br>(1R,3R,5R)-N-((R)-(4-chloro-2,5-difluorophenyl)(3-oxetanyl)methyl)-2-((4-methyl-2-pyridinyl)carbonyl)-2-azabicyclo[3.1.0]hexane-3-carboxamide | LCMS-APCI (POS.) m/z: 462.1 (M + H)$^+$ | 1H NMR (400 MHz, Methanol-d4) δ ppm 8.41 (d, J = 0.8, 5.0, 75.4 Hz, 1 H), 7.68 (dt, J = 0.8, 1.7, 13.4 Hz, 1 H), 7.31-7.42 (m, 2 H), 7.07-7.32 (m, 2 H), 5.20-5.62 (m, 2 H), 4.95 (dd, J = 3.7, 11.4 Hz, 1 H), 4.82-4.86 (m, 1 H), 4.60-4.71 (m, 2 H), 4.50-4.60 (m, 1 H), 4.40 (t, 1 H), 4.06 (dt, J = 6.1, 14.7 Hz, 1 H), 3.82 (dtd, J = 3.0, 6.1, 86.9 Hz, 2 H), 3.46-3.57 (m, 1 H), 3.37 (s, 1 H), 2.72-2.83 (m, 1 H), 2.58-2.70 (m, 1 H), 2.46 (d, J = 16.8 Hz, 5 H), 1.89-1.99 (m, 2 H), 1.69-1.78 (m, 1 H), 1.59-1.68 (m, 1 H), 1.13 (td, J = 2.6, 5.4 Hz, 1 H), 0.83-0.92 (m, 1 H), 0.68-0.79 (m, 1 H). | Q |
| 601 | 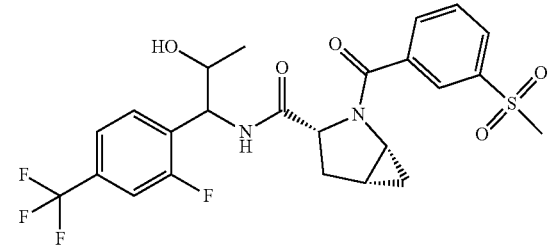 [SMILES: CC(O)C(NC(=O)[C@H]1C[C@H]2C[C@H]2N1C(=O)c1cccc(S(C)(=O)=O)c1)c1ccc(C(F)(F)F)cc1F]<br>(1R,3R,5R)-N-(1-(2-fluoro-4-(trifluoromethyl)phenyl)-2-hydroxypropyl)-2-(3-(methylsulfonyl)benzoyl)-2-azabicyclo[3.1.0]hexane-3-carboxamide | LCMS-ESI (POS.) m/z: 529.0 (M + H)$^+$ | 1H NMR (500 MHz, DMSO-d6) δ ppm 8.27-8.57 (m, 1 H) 7.39-8.22 (m, 7 H) 4.71-5.15 (m, 3 H) 3.59-3.91 (m, 1 H) 3.23-3.28 (m, 4 H) 2.53-2.60 (m, 1 H) 1.54-1.83 (m, 2 H) 0.47-1.13 (m, 5 H) | A |

| Ex. # | Structure Name | LCMS-ESI (POS/NEG) m/z: (M + H)+ | NMR Data | Syn. Rte. |
|---|---|---|---|---|
| 602 | 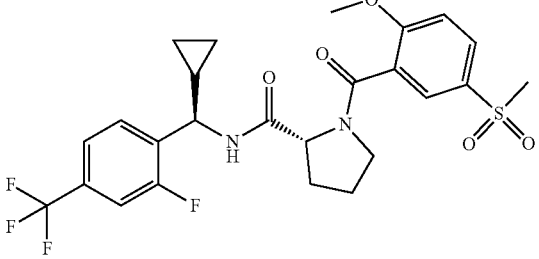<br>N-((R)-cyclopropyl(2-fluoro-4-(trifluoromethyl)phenyl)methyl)-1-(2-methoxy-5-(methylsulfonyl)benzoyl)-D-prolinamide | LCMS-ESI (POS.) m/z: 543.0 (M + H)+ | 1H NMR (500 MHz, DMSO-d6) δ ppm 8.30-8.67 (m, 1 H), 7.96 (ddd, J = 8.79, 6.58, 2.40 Hz, 1 H), 7.46-7.72 (m, 4 H), 7.29-7.39 (m, 1 H), 4.13-4.63 (m, 2 H), 3.88-3.95 (m, 3 H), 3.42-3.53 (m, 1 H), 3.13-3.25 (m, 4 H), 2.10-2.23 (m, 1 H), 1.76-1.86 (m, 1 H), 1.64-1.83 (m, 3 H), 0.86-1.26 (m, 1 H), −0.07-0.65 (m, 4 H) | C |
| 603 | 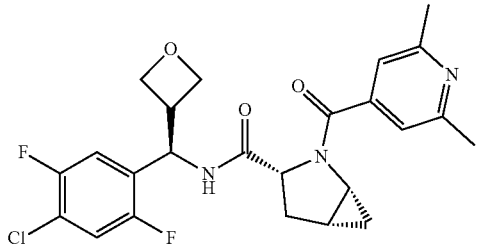 [SMILES: Cc1cc(C(=O)N2[C@@H](C(=O)N[C@@H](c3cc(F)c(Cl)cc3F)C3COC3)C[C@H]3C[C@H]32)cc(C)n1]<br>(1R,3R,5R)-N-((R)-(4-chloro-2,5-difluorophenyl)(3-oxetanyl)methyl)-2-((2,6-dimethyl-4-pyridinyl)carbonyl)-2-azabicyclo[3.1.0]hexane-3-carboxamide | LCMS-APCI (POS.) m/z: 476.1 (M + H)+ | 1H NMR (400 MHz, Methanol-d4) δ ppm 7.35-7.43 (m, 3 H), 7.27 (dd, J = 6.3, 9.4 Hz, 1 H), 5.54-5.60 (m, 1 H), 4.92 (dd, J = 4.0, 11.4 Hz, 1 H), 4.84 (dd, J = 6.5, 7.7 Hz, 1 H), 4.67 (dd, J = 6.4, 7.8 Hz, 1 H), 4.60 (t, J = 6.2 Hz, 1 H), 4.38 (t, 1 H), 3.46-3.56 (m, 1 H), 3.27 (td, J = 2.6, 6.2 Hz, 1 H), 2.61-2.70 (m, 1 H), 2.54 (s, 1 H), 1.90 (dd, J = 4.0, 13.6 Hz, 1 H), 1.74-1.82 (m, 1 H), 1.22 (td, J = 2.6, 5.4 Hz, 1 H), 0.80-0.88 (m, 1 H). | Q |
| 604 | 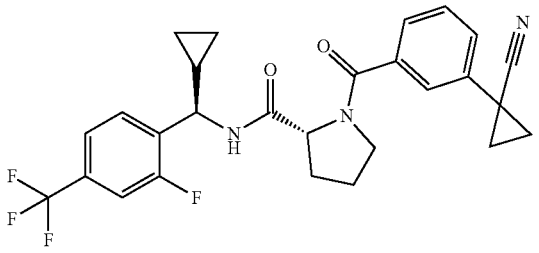 [SMILES: N#CC1(c2cccc(C(=O)N3CCC[C@@H]3C(=O)N[C@@H](c3ccc(C(F)(F)F)cc3F)C3CC3)c2)CC1]<br>1-(3-(1-cyanocyclopropyl)benzoyl)-N-((R)-cyclopropyl(2-fluoro-4-(trifluoromethyl)phenyl)methyl)-D-prolinamide | LCMS-ESI (POS.) m/z: 500.0 (M + H)+ | 1H NMR (400 MHz, CHLOROFORM-d) δ ppm 7.30-7.83 (m, 8 H), 4.41-5.03 (m, 2 H), 3.22 3.77 (m, 2 H), 2.32-2.60 (m, 1 H), 1.97-2.21 (m, 2 H), 1.74-1.96 (m, 3 H), 1.39-1.54 (m, 2 H), 1.16-1.27 (m, 1 H), 0.19-0.78 (m, 4 H) | C |
| 605 | 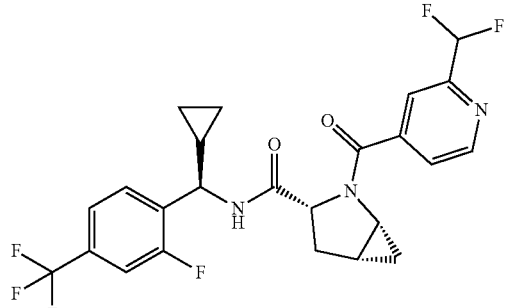<br>(1R,3R,5R)-N-((R)-cyclopropyl(2-fluoro-4-(trifluoromethyl)phenyl)methyl)-2-((2-(difluoromethyl)-4-pyridinyl)carbonyl)-2-azabicyclo[3.1.0]hexane-3-carboxamide | LCMS-APCI (POS.) m/z: 498.1 (M + H)+ | 1H NMR (400 MHz, Methanol-d4) δ ppm 8.55-9.02 (m, 2 H), 8.02-8.13 (m, 1 H), 7.87-7.98 (m, 1 H), 7.71-7.84 (m, 1 H), 7.48-7.69 (m, 2 H), 6.71-7.07 (m, 1 H), 5.10-5.17 (m, 1 H), 4.63-4.70 (m, 1 H), 3.34-3.39 (m, 1 H), 2.73-2.95 (m, 1 H), 1.94-2.06 (m, 1 H), 1.72-1.93 (m, 1 H), 1.32-1.43 (m, 1 H), 1.22-1.30 (m, 1 H), −0.05-1.14 (m, 5 H). | Q |

| Ex. # | Structure Name | LCMS-ESI (POS/NEG) m/z: (M + H)+ | NMR Data | Syn. Rte. |
|---|---|---|---|---|
| 606 | 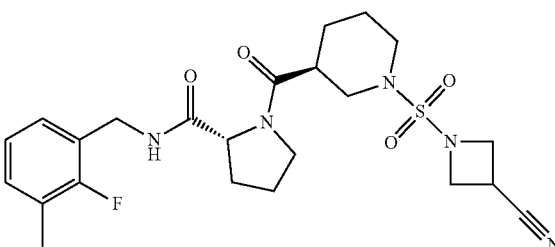<br>1-(((3S)-1-((3-cyano-1-azetidinyl)sulfonyl)-3-piperidinyl)carbonyl)-N-(2-fluoro-3-methylbenzyl)-D-prolinamide | LCMS-ESI (POS.) m/z: 492.2 (M + H)+ | 1H NMR (500 MHz, DMSO-d6) δ ppm 8.18-8.62 (m, 1 H), 7.00-7.20 (m, 3 H), 4.18-4.50 (m, 3 H), 4.00-4.10 (m, 2 H), 3.88-3.98 (m, 2 H), 3.74-3.83 (m, 1 H), 3.34-3.68 (m, 4 H), 2.61-2.86 (m, 3 H), 2.01-2.33 (m, 4 H), 1.66-1.99 (m, 5 H), 1.35-1.56 (m, 2 H) | A |
| 607 | 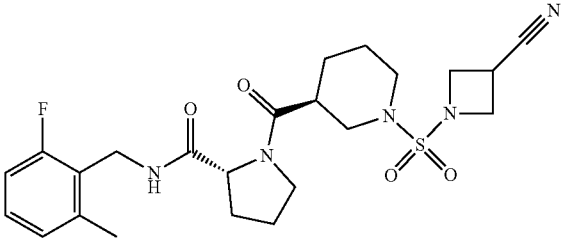 [SMILES: Cc1cccc(F)c1CNC(=O)[C@H]1CCCN1C(=O)[C@H]1CCCN(S(=O)(=O)N2CC(C#N)C2)C1]<br>1-(((3S)-1-((3-cyano-1-azetidinyl)sulfonyl)-3-piperidinyl)carbonyl)-N-(2-fluoro-6-methylbenzyl)-D-prolinamide | LCMS-ESI (POS.) m/z: 492.2 (M + H)+ | 1H NMR (500 MHz, DMSO-d6) δ ppm 7.88-8.41 (m, 1 H), 7.14-7.27 (m, 1 H), 6.92-7.10 (m, 2 H), 4.17-4.47 (m, 3 H), 3.99-4.10 (m, 2 H), 3.86-3.96 (m, 2 H), 3.71-3.85 (m, 1 H), 3.40-3.66 (m, 4 H), 2.60-2.88 (m, 3 H), 2.11-2.35 (m, 3 H), 1.33-2.02 (m, 8 H) | A |
| 608 | 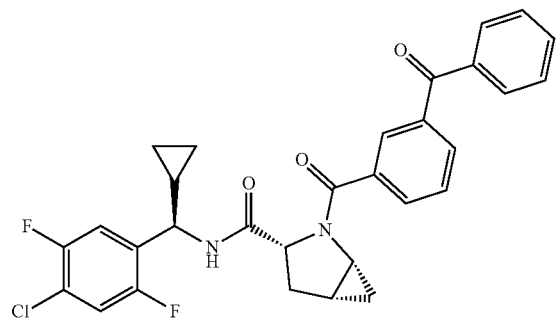 [SMILES: O=C(c1ccccc1)c1cccc(C(=O)N2[C@@H](C(=O)N[C@@H](c3cc(F)c(Cl)cc3F)C3CC3)C[C@H]3C[C@H]32)c1]<br>(1R,3R,5R)-2-(3-benzoylbenzoyl)-N-((R)-(4-chloro-2,5-difluorophenyl)(cyclopropyl)methyl)-2-azabicyclo[3.1.0]hexane-3-carboxamide | LCMS-+APCI (POS.) m/z: 535.1 (M + H)+ | 1H NMR (400 MHz, DMSO-d6) δ ppm 8.59 (d, J = 7.7 Hz, 1 H), 8.01 (t, J = 1.7 Hz, 1 H), 7.96 (dt, J = 1.5, 7.7 Hz, 1 H), 7.91 (dt, J = 1.4, 7.8 Hz, 1 H), 7.72-7.82 (m, 2 H), 7.67-7.75 (m, 2 H), 7.60 (q, J = 6.8, 7.6 Hz, 3 H), 7.48 (dd, J = 6.3, 9.8 Hz, 1 H), 4.93 (dd, J = 3.5, 11.3 Hz, 1 H), 4.48 (t, J = 8.0 Hz, 1 H), 4.35 (t, J = 5.1 Hz, 1 H), 1.70 (dd, J = 3.6, 13.6 Hz, 2 H), 1.10-1.21 (m, 1 H), 0.98-1.03 (m, 1 H), 0.70 (dd, J = 5.3, 9.2 Hz, 1 H), 0.48-0.57 (m, 1 H), 0.43 (t, J = 8.8 Hz, 1 H). | Q |
| 609 | 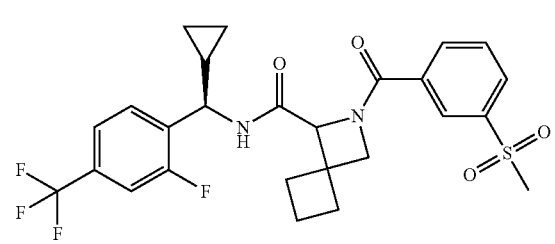 [SMILES: CS(=O)(=O)c1cccc(C(=O)N2CC3(CCC3)C2C(=O)N[C@@H](c2ccc(C(F)(F)F)cc2F)C2CC2)c1]<br>N-((R)-cyclopropyl(2-fluoro-4-(trifluoromethyl)phenyl)methyl)-2-(3-(methylsulfonyl)benzoyl)-2-azaspiro[3.3]heptane-1-carboxamide | LCMS-ESI (POS.) m/z: 539.2 (M + H)+ | 1H NMR (400 MHz, CHLOROFORM-d) δ ppm 7.82-8.38 (m, 3 H), 7.29-7.79 (m, 4 H), 6.54-7.22 (m, 1 H), 4.48-4.86 (m, 2 H), 4.08-4.46 (m, 2 H), 2.94-3.23 (m, 3 H), 1.73-2.60 (m, 6 H), 1.17-1.37 (m, 1 H), 0.24-0.79 (m, 4 H) | C |

-continued

| Ex. # | Structure Name | LCMS-ESI (POS/NEG) m/z: (M + H)+ | NMR Data | Syn. Rte. |
|---|---|---|---|---|
| 610 | N-(2-fluoro-4-(trifluoromethyl)benzyl)-1-(((3S)-1-((3-hydroxy-1-azetidinyl)sulfonyl)-3-piperidinyl)carbonyl)-D-prolinamide | LCMS-ESI (POS.) m/z: 559.0 (M + H)+ | 1H NMR (400 MHz, CHLOROFORM-d) δ 7.29-7.50 (m, 4H), 4.54-4.61 (m, 2H), 4.43-4.54 (m, 2H), 3.99-4.06 (m, 2H), 3.72-3.86 (m, 4H), 3.55-3.63 (m, 2H) 2.96 (dd J = 10.83, 12.59 Hz, 1H), 2.66-2.83 (m, 2H), 2.36-2.45 (m, 1H), 2.09-2.22 (m, 1H), 1.98-2.09 (m, 1H), 1.85-1.95 (m, 2H), 1.77-1.85 (m, 1H), 1.59-1.72 (m, 2H), 1.48-1.59 (m, 1H) | J |
| 611 | (1R,3R,5R)-2((5-cyclopropyl-3-pyridinyl)carbonyl)-N-((R)-(2-fluoro-4-(trifluoromethyl)phenyl)(3-oxetanyl)methyl)-2-azabicyclo[3.1.0]hexane-3-carboxamide | LCMS-APCI (POS.) m/z: 504.2 (M + H)+ | 1H NMR (400 MHz, Methanol-d4) δ ppm 8.70 (d, J = 1.9 Hz, 1 H), 8.52 (d, J = 2.2 Hz, 1 H), 7.82 (t, J = 2.1 Hz, 1 H), 7.45-7.59 (m, 2 H), 5.65 (d, J = 10.1 Hz, 1 H), 4.99 (dd, J = 4.2, 11.4 Hz, 1 H), 4.61-4.70 (m, 2 H), 4.40 (t, J = 6.1 Hz, 1 H), 3.54 (dd, J = 7.4, 14.5 Hz, 1 H), 2.66 (td, J = 6.4, 12.7 Hz, 1 H), 2.08 (ddd, J = 5.0, 8.5, 13.4 Hz, 1 H), 1.86-1.93 (m, 1 H), 1.74-1.86(m, 1 H), 1.09-1.18 (m, 1 H), 0.78-0.92 (m, 3 H). | Q |
| 612 | (1R,3R,5R)-N-((R)-cyclopropyl(2-fluoro-4-(trifluoromethyl)phenyl)methyl)-2-(2-methoxy-5-(methylsulfonyl)benzoyl)-2-azabicyclo[3.1.0]hexane-3-carboxamide | LCMS-APCI (POS.) m/z: 555.1 (M + H)+ | 1H NMR (400 MHz, DMSO-d6) δ ppm 8.54 (s, 1 H), 7.96 (dd, J = 2.5, 8.8, 15.9 Hz, 1 H), 7.53-7.71 (m, 2 H), 7.32-7.48 (m, 1 H), 4.84 (dd, J = 3.1, 11.3 Hz, 1 H), 4.58 (t, J = 7.9 Hz, 1 H), 4.34 (t, J = 5.1 Hz, 2 H), 3.94 (s, 2 H), 3.18 (s, 2 H), 2.98 (td, J = 2.5, 6.2 Hz, 1 H), 1.74 (dd, J = 13.8, 33.6 Hz, 1 H), 1.54 (dt, J = 5.8, 11.5 Hz, 1 H), 1.12-1.23 (m, 1 H), 0.93 (td, J = 2.5, 5.1 Hz, 1 H), 0.42-0.62 (m, 2 H), 0.21-0.41 (m, 2 H). | Q |
| 613 | N-((6-chloro-3-pyridinyl)methyl)-1-(((3S)-1-((3-cyano-1-azetidinyl)sulfonyl)-3-piperidinyl)carbonyl)-D-prolinamide | LCMS-ESI (POS.) m/z: 495.2 (M + H)+ | 1H NMR (500 MHz, DMSO-d6) δ ppm 8.71* (t, J = 5.77 Hz, 1 H), 8.38 (t, J = 6.03 Hz, 1 H), 8.25-8.33 (m, 1 H), 7.69 (dd, J = 8.24, 2.40 Hz, 1 H), 7.47 (d, J = 8.17 Hz, 1 H), 4.20-4.51 (m, 3 H), 4.02-4.10 (m, 2 H), 3.90-3.98 (m, 2 H), 3.76-3.83 (m, 1 H), 3.29-3.69 (m, 4 H), 2.70-2.90 (m, 2 H), 2.64 (tt, J = 11.09, 3.50 Hz, 1 H), 2.23-2.30* (m, 1 H), 2.15-2.23* (m, 1 H), 2.05-2.13 (m, 1 H), 1.63-1.96 (m, 5 H), 1.34-1.54 (m, 2 H). Spectrum appears as 2:1 mixture of rotamers, *denotes resolved minor rotamer peaks. | C |

| Ex. # | Structure Name | LCMS-ESI (POS/NEG) m/z: (M + H)+ | NMR Data | Syn. Rte. |
|---|---|---|---|---|
| 614 | 1-(((3S)-1-((3-cyano-1-azetidinyl)sulfonyl)-3-piperidinyl)carbonyl)-N-(4-methoxy-2-methylbenzyl)-D-prolinamide | LCMS-ESI (POS.) m/z: 504.2 (M + H)+ | 1H NMR (500 MHz, DMSO-d6) δ ppm 7.98-8.42 (m, 1 H), 7.04-7.17 (m, 1 H), 6.64-6.79 (m, 2 H), 4.01-4.50 (m, 5 H), 3.40-3.99 (m, 10 H), 2.56-2.90 (m, 3 H), 2.01-2.34 (m, 4 H), 1.32-1.99 (m, 7 H) | A |
| 615 | (1R,3R,5R)-N-((R)-cyclopropyl(2,5-difluoro-4-(trifluoromethyl)phenyl)methyl)-2-((6-(trifluoromethyl)-2-pyridinyl)carbonyl)-2-azabicyclo[3.1.0]hexane-3-carboxamide | LCMS-APCI (POS.) m/z: 534.1 (M + H)+ | 1H NMR (DMSO-d6) δ: 8.94 (d, J = 7.4 Hz, 1H), 8.75 (d, J = 8.0 Hz, 1H), 8.50 (t, 1H), 8.44 (t, J = 7.8 Hz, 1H), 8.34-8.19 (m, 4H), 7.99 (dd, J = 9.4, 5.8 Hz, 1H), 7.92 (dd, J = 9.4, 5.8 Hz, 1H), 7.82 (dd, J = 11.1, 5.5 Hz, 1H), 7.72 (dd, J = 11.1, 5.6 Hz, 1H), 5.71 (dd, J = 11.5, 2.8 Hz, 1H), 5.15 (dd, J = 11.4, 3.3 Hz, 1H), 4.76 (t, J = 7.9 Hz, 1H), 4.30 (t, J = 8.5 Hz, 2H), 4.05 (td, J = 6.3, 2.5 Hz, 1H), 3.99 (td, J = 6.3, 2.3 Hz, 1H), 3.03 (td, J = 12.6, 6.0 Hz, 1H), 2.11 (dd, J = 13.6, 2.9 Hz, 1H), 1.95 (dd, J = 13.5, 3.4 Hz, 1H), 1.92-1.84 (m, 1H), 1.85-1.73 (m, 1H), 1.50-1.39 (m, 1H), 1.31-1.14 (m, 2H), 1.02-0.91 (m, 1H), 0.89-0.78 (m, 2H), 0.78-0.67 (m, 2H), 0.67-0.58 (m, 2H), 0.57-0.47 (m, 2H), 0.25-0.12 (m, 1H), 0.04--0.05 (m, 1H) | Q |
| 616 | (5R)-N-((R)-cyclopropyl(2-fluoro-4-(trifluoromethyl)phenyl)methyl)-5-methyl-1-(3-(methylsulfonyl)benzoyl)-L-prolinamide | LCMS-ESI (POS.) m/z: 527.2 (M + H)+ | 1H NMR (400 MHz, CHLOROFORM-d) δ ppm 7.83-8.15 (m, 3 H), 7.58-7.81 (m, 2 H), 7.46-7.57 (m, 1 H), 7.39-7.46 (m, 1 H), 7.31-7.39 (m, 1 H), 3.85-4.86 (m, 3 H), 2.91-3.19 (m, 3 H), 2.49-2.71 (m, 1 H), 1.98-2.28 (m, 2 H), 1.70-1.87 (m, 1 H), 0.89-1.41 (m, 4 H), 0.53-0.73 (m, 2 H), 0.30-0.52 (m, 2 H) | C |

| Ex. # | Structure Name | LCMS-ESI (POS/NEG) m/z: (M + H)+ | NMR Data | Syn. Rte. |
|---|---|---|---|---|
| 617 | (1R,3R,5R)-N-(4-chloro-2,5-difluorobenzyl)-2-(3-(ethylsulfonyl)benzoyl)-2-azabicyclo[3.1.0]hexane-3-carboxamide | LCMS-ESI (POS.) m/z: 483.0 (M + H)+ | 1H NMR (500 MHz, DMSO-d6) δ ppm 8.28-8.68 (m, 1 H), 7.31-8.21 (m, 6 H), 4.53-4.99 (m, 1 H), 4.21-4.40 (m, 2 H), 3.24-3.38 (m, 3 H), 2.56 2.67 (m, 1 H), 1.63-2.00 (m, 2 H), 0.75-1.27 (m, 5 H) | C |
| 618 | N-(5-chloro-2-methylbenzyl)-1-(((3S)-1-((3-cyano-1-azetidinyl)sulfonyl)-3-piperidinyl)carbonyl)-D-prolinamide | LCMS-ESI (POS.) m/z: 508.2 (M + H)+ | 1H NMR (500 MHz, DMSO-d6) δ ppm 8.22 (br t, J = 5.84 Hz, 1 H), 6.92-7.32 (m, 3 H), 4.11-4.55 (m, 3 H), 3.98-4.09 (m, 2 H), 3.85-3.98 (m, 2 H), 3.73 3.85 (m, 1 H), 3.41 3.72 (m, 4 H), 3.31-3.41 (m, 3 H), 2.62-2.93 (m, 3 H), 2.05-2.16 (m, 1 H), 1.61-2.00 (m, 5 H), 1.23-1.59 (m, 2 H) | A |
| 619 | (4R)-N-((R)-cyclopropyl(2-fluoro-4-(trifluoromethyl)phenyl)methyl)-4-fluoro-1-(3-(methylsulfonyl)benzoyl)-D-prolinamide | LCMS-ESI (POS.) m/z: 531.2 (M + H)+ | 1H NMR (500 MHz, DMSO-d6) δ ppm 8.54-8.68 (m, 1 H), 7.21-8.18 (m, 7 H), 5.12-5.42 (m, 1 H), 4.25-4.78 (m, 2 H), 3.57-4.10 (m, 2 H), 3.18-3.29 (m, 3 H), 2.53-2.61 (m, 1 H), 2.04-2.30 (m, 1 H), 1.05-1.33 (m, 1 H), 0.45-0.67 (m, 1 H), 0.03-0.44 (m, 3 H) | C |
| 620 | (2R)-N-((6-chloro-3-pyridinyl)methyl)-1-((3-((cis-3-cyanocyclobutyl)sulfonyl)phenyl)carbonyl)-2-piperidinecarboxamide, (2R)-N-((6-chloro-3-pyridinyl)methyl)-1-((3-((trans-3-cyanocyclobutyl)sulfonyl)phenyl)carbonyl)-2-piperidinecarboxamide | LCMS-ESI (POS.) m/z: 501.0 (M + H)+ | 1H NMR (500 MHz, DMSO-d6) δ ppm 8.22-8.75 (m, 2H), 7.65-8.04 (m, 5H), 7.44-7.55 (m, 1H), 5.05-5.20 (m, 1H), 3.98-4.53 (m, 5H), 3.13-3.44 (m, 2H), 2.54-2.67 (m, 4H), 2.17-2.28 (m, 1H), 1.22-1.74 (m, 5H) | L |

| Ex. # | Structure Name | LCMS-ESI (POS/NEG) m/z: (M + H)+ | NMR Data | Syn. Rte. |
|---|---|---|---|---|
| 621 | (1R,3R,5R)-N-((R)-(4-chloro-2,5-difluorophenyl)(3-oxetanyl)methyl)-2-((2-methyl-4-pyridinyl)carbonyl)-2-azabicyclo[3.1.0]hexane-3-carboxamide | LCMS-APCI (POS.) m/z: 462.2 (M + H)+ | 1H NMR (400 MHz, Methanol-d4) δ ppm 8.57 (dd, J = 0.8, 5.2 Hz, 1 H), 7.60 (s, 1 H), 7.54 (dd, J = 0.7, 1.6, 5.2 Hz, 1 H), 7.39 (dd, J = 6.1, 9.5 Hz, 1 H), 7.27 (dd, J = 6.3, 9.4 Hz, 1 H), 5.57 (d, J = 10.2 Hz, 1 H), 4.94 (dd, J = 4.0, 11.4 Hz, 1 H), 4.84 (dd, J = 6.5, 7.7 Hz, 1 H), 4.67 (dd, J = 6.4, 7.8 Hz, 1 H), 4.60 (t, J = 6.2 Hz, 1 H), 4.38 (t, 1 H), 3.46-3.56 (m, 1 H), 3.37 (s, 2 H), 3.28 (td, J = 2.6, 6.2 Hz, 1 H), 2.63-2.71 (m, 1 H), 2.62 (s, 3 H), 1.90 (dd, J = 4.0, 13.5 Hz, 1 H), 1.74-1.82 (m, 1 H), 1.23 (td, J = 2.6, 5.3 Hz, 1 H), 0.85 (dtd, J = 1.1, 5.7, 9.1 Hz, 1 H). | Q |
| 622 | (2R)-1-((S)-1-((3-cyanoazetidin-1-yl)sulfonyl)piperidine-3-carbonyl)-N-(5-fluoro-6-methoxy-2,3-dihydro-1H-inden-1-yl)pyrrolidine-2-carboxamide | LCMS-ESI (POS.) m/z: 534.2 (M + H)+ | 1H NMR (500 MHz, DMSO-d6) δ ppm 7.96-8.53 (m, 1 H), 6.81-7.17 (m, 2 H), 5.15-5.32 (m, 1 H), 4.18-4.51 (m, 1 H), 4.00-4.13 (m, 2 H), 3.88-3.99 (m, 2 H), 3.74-3.87 (m, 4 H), 3.44-3.72 (m, 4 H), 2.58-2.94 (m, 5 H), 2.08-2.43 (m, 2 H), 1.63-2.06 (m, 6 H), 1.30-1.57 (m, 2 H) | A |
| 623 | 1-(((3S)-1-((3-cyano-1-azetidinyl)sulfonyl)-3-piperidinyl)carbonyl)-N-(2,3,5,6-tetrafluorobenzyl)-D-prolinamide | LCMS-ESI (POS.) m/z: 532.2 (M + H)+ | 1H NMR (500 MHz, DMSO-d6) δ ppm 8.25-8.74 (m, 1 H), 7.70-7.90 (m, 1 H), 4.18-4.51 (m, 3 H), 4.00-4.10 (m, 2 H), 3.88-3.97 (m, 2 H), 3.72-3.84 (m, 1 H), 3.36-3.65 (m, 4 H), 2.57-2.86 (m, 3 H), 1.80-2.27 (m, 4 H), 1.63-1.79 (m, 2 H), 1.30-1.57 (m, 2 H) | A |
| 624 | | LCMS-ESI (POS.) m/z: 527.0 (M + H)+ | 1H NMR (500 MHz, DMSO-d6) δ ppm 8.47-8.77 (m, 1 H), 7.52-8.09 (m, 7 H), 4.22-4.65 (m, 2 H), 3.53-3.76 (m, 1 H), 3.22-3.30 (m, 3 H), 3.01-3.14 (m, 1 H), 2.11-2.35 (m, 1 H), 1.76-1.99 (m, 2 H), 0.83-1.30 (m, 4 H), −0.07-0.63 (m, 4 H) | C |

-continued

| Ex. # | Structure Name | LCMS-ESI (POS/NEG) m/z: (M + H)+ | NMR Data | Syn. Rte. |
|---|---|---|---|---|
| | (4S)-N-((R)-cyclopropyl(2-fluoro-4-(trifluoromethyl)phenyl)methyl)-4-methyl-1-(3-(methylsulfonyl)benzoyl)-D-prolinamide | | | |
| 625 | (2R)-1-((S)-1-((3-cyanoazetidin-1-yl)sulfonyl)piperidine-3-carbonyl)-N-(1-(4-methoxyphenyl)propyl)pyrrolidine-2-carboxamide | LCMS-ESI (POS.) m/z: 518.2 (M + H)+ | 1H NMR (500 MHz, DMSO-d6) δ ppm 7.87-8.52 (m, 1 H), 6.77-7.31 (m, 4 H), 4.55-4.71 (m, 1 H), 4.25-4.49 (m, 1 H), 3.89-4.13 (m, 4 H), 3.72 (br d, J = 2.60 Hz, 5 H), 3.43-3.66 (m, 4 H), 2.59-3.01 (m, 3 H), 1.99-2.33 (m, 1 H), 1.29-1.96 (m, 8 H), 0.74-1.11 (m, 3 H) | A |
| 626 | 1-(((3S)-1-((trans-3-carbamoylcyclobutyl)sulfonyl)-3-piperidinyl)carbonyl)-N-(4-(trifluoromethyl)benzyl)-D-prolinamide | LCMS-APCI (POS.) m/z: 545.2 (M + H)+ | 1H NMR (Methanol-d4) δ: 7.74-7.59 (m, 2H), 7.51 (t, J = 7.7 Hz, 2H), 4.63-4.37 (m, 3H), 4.06-3.68 (m, 5H), 3.27-3.21 (m, 1H), 3.00-2.73 (m, 3H), 2.71-2.54 (m, 4H), 2.51-2.18 (m, 2H), 2.19-1.87 (m, 4H), 1.88-1.79 (m, 1H), 1.72-1.41 (m, 2H) | R |
| 627 | 1-(3-((3-cyano-1-azetidinyl)sulfonyl)benzoyl)-N-((1R)-2,2-dimethyl-1-(4-(trifluoromethyl)phenyl)propyl)-D-prolinamide | LCMS-ESI (POS.) m/z: 577.2 (M + H)+ | 1H NMR (500 MHz, DMSO-d6) δ ppm 8.06-8.48 (m, 1 H), 7.35-8.01 (m, 8 H), 4.67-4.83 (m, 1 H), 4.41-4.58 (m, 1 H), 4.02 (br d, J = 4.41 Hz, 2 H), 3.82-3.89 (m, 2 H), 3.43-3.65 (m, 3 H), 2.08-2.36 (m, 1 H), 1.54-1.89 (m, 3 H), 0.51-0.96 (m, 8 H) | A |
| 628 | (1R,3R,5R)-N-((R)-(4-chloro-3-fluorophenyl)(cyclopropyl)methyl)-2-((5-(methylsulfonyl)-3-pyridinyl)carbonyl)-2-azabicyclo[3.1.0]hexane-3-carboxamide | LCMS-ESI (POS.) m/z: 492.0 (M + H)+ | 1H NMR (500 MHz, DMSO-d6) δ ppm 8.83-9.24 (m, 2 H), 8.25-8.67 (m, 2 H), 7.00-7.65 (m, 3 H), 4.96 (dd, J = 11.42, 3.63 Hz, 1 H), 4.15-4.29 (m, 1 H), 3.32-3.40 (m, 4 H), 2.57-2.79 (m, 1 H), 1.56-1.88 (m, 2 H), 0.70-1.21 (m, 3 H), -0.11 (s, 4 H) | C |

| Ex. # | Structure Name | LCMS-ESI (POS/NEG) m/z: (M + H)+ | NMR Data | Syn. Rte. |
|---|---|---|---|---|
| 629 | N-((1S)-1-(4-chloro-3-fluorophenyl)propyl)-1-(3-(dimethylsulfamoyl)benzoyl)-D-prolinamide | LCMS-ESI (POS.) m/z: 496.2 (M + H)+ | 1H NMR (500 MHz, DMSO-d6) δ ppm 8.37 (br d, J = 8.17 Hz, 1 H), 6.78-7.93 (m, 7 H), 4.35-4.78 (m, 2 H), 3.40-3.68 (m, 2 H), 2.50-2.67 (m, 6 H), 2.20-2.40 (m, 1 H), 1.44-2.04 (m, 5 H), 0.68-0.95 (m, 3 H) | A |
| 630 | N-((1R)-1-(2-fluoro-4-(trifluoromethyl)phenyl)propyl)-1-(3-(methylsulfonyl)benzoyl)-D-prolinamide | LCMS-ESI (POS.) m/z: 501.2 (M + H)+ | 1H NMR (500 MHz, DMSO-d6) δ ppm 8.29-8.63 (m, 1 H), 7.41-8.13 (m, 7 H), 4.64-5.09 (m, 1 H), 4.35-4.60 (m, 1 H), 3.41-3.66 (m, 2 H), 3.19-3.32 (m, 3 H), 2.14-2.33 (m, 1 H), 1.89-1.96 (m, 1 H), 1.65-2.00 (m, 3 H), 1.38-1.49 (m, 1 H), 0.45-1.02 (m, 3 H) | C |
| 631 | 1-(((3S)-1-((3-hydroxy-1-azetidinyl)sulfonyl)-3-piperidinyl)carbonyl)-N-(4-(trifluoromethyl)benzyl)-D-prolinamide | LCMS-ESI (POS.) m/z: 519.2 (M + H)+ | 1H NMR (500 MHz, CHLOROFORM-d) δ ppm 7.53-7.66 (m, 2 H), 7.31-7.45 (m, 3 H), 4.48-4.64 (m, 3 H), 4.37-4.47 (m, 1 H), 3.99-4.08 (m, 2 H), 3.71-3.86 (m, 4 H), 3.53-3.64 (m, 2 H), 2.89-3.04 (m, 1 H), 2.64-2.83 (m, 2 H), 2.44 (ddd, J = 9.28, 6.29, 3.37 Hz, 1 H), 2.10-2.33 (m, 2 H), 1.99-2.09 (m, 2 H), 1.46-1.96 (m, 8 H), 1.22-1.35 (m, 1 H) | M |
| 632 | (2R)-1-((S)-1-((3-cyanoazetidin-1-yl)sulfonyl)piperidine-3-carbonyl)-N-(1-(4-(difluoromethoxy)-3-methoxyphenyl)ethyl)pyrrolidine-2-carboxamide | LCMS-ESI (POS.) m/z: 570.2 (M + H)+ | 1H NMR (500 MHz, DMSO-d6) δ ppm 8.05-8.62 (m, 1 H), 6.75-7.21 (m, 4 H), 4.76-5.04 (m, 1 H), 4.21-4.52 (m, 1 H), 3.72-4.15 (m, 8 H), 3.48-3.67 (m, 3 H), 3.17 (br d, J = 4.28 Hz, 1 H), 2.59-2.92 (m, 3 H), 2.14-2.39 (m, 1 H), 1.96-2.14 (m, 1 H), 1.64-1.93 (m, 4 H), 1.29-1.59 (m, 5 H) | A |

| Ex. # | Structure Name | LCMS-ESI (POS/NEG) m/z: (M + H)+ | NMR Data | Syn. Rte. |
|---|---|---|---|---|
| 633 | (2R)-1-((S)-1-((3-cyanoazetidin-1-yl)sulfonyl)piperidine-3-carbonyl)-N-(1-(5-fluoro-2-methoxyphenyl)ethyl)pyrrolidine-2-carboxamide | LCMS-ESI (POS.) m/z: 522.2 (M + H)+ | 1H NMR (500 MHz, DMSO-d6) δ ppm 8.09-8.55 (m, 1 H), 6.86-7.23 (m, 3 H), 4.97-5.28 (m, 1 H), 4.26-4.54 (m, 1 H), 3.88-4.13 (m, 4 H), 3.73-3.87 (m, 4 H), 3.44-3.67 (m, 4 H), 2.59-2.92 (m, 3 H), 1.23-2.35 (m, 11 H) | A |
| 634 | N-((1S)-1-(4-chloro-3-fluorophenyl)-2-hydroxyethyl)-1-(3-(dimethylsulfamoyl)benzoyl)-D-prolinamide | LCMS-ESI (POS.) m/z: 498.2 (M + H)+ | 1H NMR (500 MHz, DMSO-d6) δ ppm 8.46 (br d, J = 7.66 Hz, 1 H), 7.16-7.97 (m, 7 H), 5.15-5.28 (m, 1 H), 4.82 (br d, J = 7.27 Hz, 1 H), 4.28-4.55 (m, 1 H), 3.60 (br d, J = 6.10 Hz, 2 H), 3.24-3.52 (m, 2 H), 2.57-2.71 (m, 6 H), 2.16-2.29 (m, 1 H), 1.67-1.97 (m, 3 H) | A |
| 635 | 1-((3-(5-azaspiro[2.3]hex-5-ylsulfonyl)phenyl)carbonyl)-N-((1R)-1-(3,4-dichlorophenyl)ethyl)-D-prolinamide | LCMS-APCI (NEG.) m/z: 534.1 (M − H) | 1H NMR (400 MHz, Methanol-d4) δ ppm 8.12 (t, J = 1.7 Hz, 1 H), 7.95-8.02 (m, 2 H), 7.69-7.81 (m, 2 H), 7.45-7.52 (m, 2 H), 5.00 (p, J = 6.7 Hz, 1 H), 4.59 (dd, J = 6.2, 8.2 Hz, 1 H), 3.89 (s, 4 H), 3.64 (dt, J = 7.3, 10.3 Hz, 1 H), 3.45-3.56 (m, 1 H), 2.26-2.43 (m, 1 H), 1.86-2.00 (m, 3 H), 1.50 (d, J = 7.0 Hz, 3 H), 0.47 (s, 4 H). | A |
| 636 | N-((1R)-1-(4-chloro-2,5-difluorophenyl)ethyl)-1-(3-(methylsulfonyl)benzoyl)-D-prolinamide | LCMS-ESI (POS.) m/z: 471.0 (M + H)+ | 1H NMR (500 MHz, DMSO-d6) δ ppm 8.23-8.59 (m, 1 H), 7.18-8.13 (m, 6 H), 4.76-5.20 (m, 1 H), 4.25-4.61 (m, 1 H), 3.38-3.68 (m, 2 H), 3.22-3.35 (m, 3 H), 2.14-2.33 (m, 1 H), 1.69-2.02 (m, 3 H), 0.95-1.50 (m, 3 H) | A |

-continued

| Ex. # | Structure Name | LCMS-ESI (POS/NEG) m/z: (M + H)+ | NMR Data | Syn. Rte. |
|---|---|---|---|---|
| 637 | 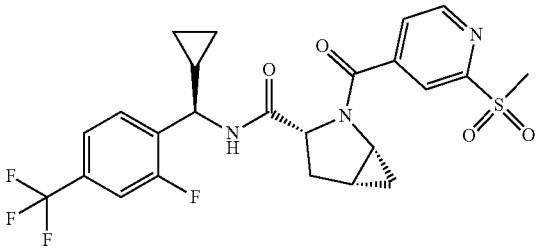 [SMILES: CS(=O)(=O)c1cc(C(=O)N2[C@@H](C(=O)N[C@@H](c3ccc(C(F)(F)F)cc3F)C3CC3)C[C@H]3C[C@H]32)ccn1]<br>(1R,3R,5R)-N-((R)-cyclopropyl(2-fluoro-4-(trifluoromethyl)phenyl)methyl)-2-((2-(methylsulfonyl)-4-pyridinyl)carbonyl)-2-azabicyclo[3.1.0]hexane-3-carboxamide | LCMS-ESI (POS.) m/z: 526.0 (M + H)+ | 1H NMR (500 MHz, DMSO-d6) δ ppm 8.94 (br d, J = 4.67 Hz, 1 H), 8.76 (br d, J = 7.40 Hz, 1 H), 7.85-8.23 (m, 2 H), 7.52-7.77 (m, 3 H), 4.94 (br dd, J = 11.42, 2.34 Hz, 1 H), 4.57 (br t, J = 7.72 Hz, 1 H), 3.29-3.34 (m, 3 H), 3.28 (br s, 1 H), 2.55-2.72 (m, 1 H), 1.57-1.80 (m, 2 H), −0.21-1.28 (m, 7 H) | C |
| 638 | 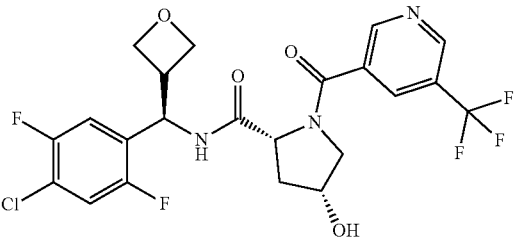 [SMILES: O=C(N[C@@H](c1cc(F)c(Cl)cc1F)C1COC1)[C@H]1C[C@@H](O)CN1C(=O)c1cncc(C(F)(F)F)c1]<br>(4R)-N-((R)-(4-chloro-2,5-difluorophenyl)(3-oxetanyl)methyl)-4-hydroxy-1-((5-(trifluoromethyl)-3-pyridinyl)carbonyl)-D-prolinamide | LCMS-APCI (POS.) m/z: 520.1 (M + H)+ | 1H NMR (400 MHz, Methanol-d4) δ ppm 8.99-9.13 (m, 2 H), 8.42 (d, J = 2.2 Hz, 1 H), 7.25-7.45 (m, 2 H), 5.63 (d, J = 10.3 Hz, 1 H), 4.57-4.77 (m, 3 H), 4.41-4.50 (m, 1 H), 4.36 (p, J = 5.3 Hz, 1 H), 3.75 (dd, J = 5.4, 10.4 Hz, 1 H), 3.55 (td, J = 5.3, 10.4 Hz, 2 H), 2.45-2.62 (m, 1 H), 1.93 (dt, J = 5.6, 12.9 Hz, 1 H). | Q |
| 639 | 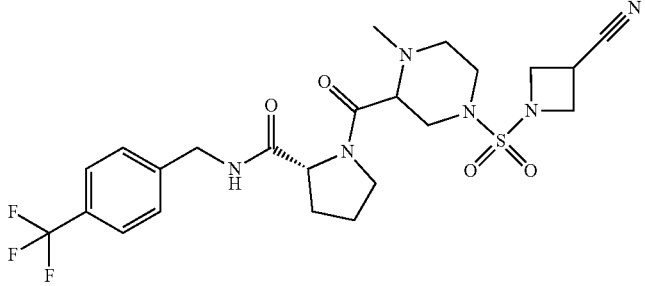 [SMILES: CN1CCN(S(=O)(=O)N2CC(C#N)C2)CC1C(=O)N1CCC[C@@H]1C(=O)NCc1ccc(C(F)(F)F)cc1]<br>(2R)-1-(4-((3-cyanoazetidin-1-yl)sulfonyl)-1-methylpiperazine-2-carbonyl)-N-(4-(trifluoromethyl)benzyl)pyrrolidine-2-carboxamide | LCMS-ESI (POS.) m/z: 543.2 (M + H)+ | 1H NMR (500 MHz, DMSO-d6) δ ppm 8.48 (br d, J = 5.19 Hz, 1 H), 7.58-7.76 (m, 2 H), 7.47 (br dd, J = 12.13, 8.11 Hz, 2 H), 4.24-4.56 (m, 3 H), 4.02-4.16 (m, 2 H), 3.89-4.00 (m, 2 H), 3.68-3.84 (m, 2 H), 3.55-3.67 (m, 1 H), 3.46-3.54 (m, 1 H), 3.35-3.46 (m, 2 H), 2.81-3.12 (m, 4 H), 2.62-3.21 (m, 5 H), 2.36-2.37 (m, 1 H), 2.22-2.33 (m, 1 H), 2.07-2.14 (m, 1 H), 1.88-2.05 (m, 2 H), 1.70-1.83 (m, 1 H) | M |

-continued

| Ex. # | Structure Name | LCMS-ESI (POS/NEG) m/z: (M + H)+ | NMR Data | Syn. Rte. |
|---|---|---|---|---|
| 640 | 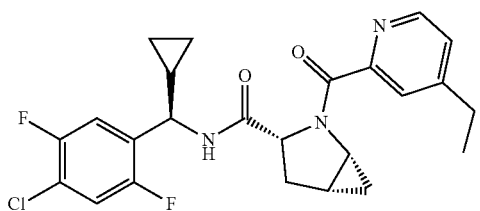 [SMILES: CCc1ccnc(C(=O)N2[C@@H](C(=O)N[C@@H](c3cc(F)c(Cl)cc3F)C3CC3)C[C@H]3C[C@H]32)c1]<br>(1R,3R,5R)-N-((R)-(4-chloro-2,5-difluorophenyl)(cyclopropyl)methyl)-2-((4-ethyl-2-pyridinyl)carbonyl)-2-azabicyclo[3.1.0]hexane-3-carboxamide | LCMS-APCI (POS.) m/z: 460.2 (M + H)+ | 1H NMR (DMSO-d6) δ: 8.67 (d, J = 7.7 Hz, 1H), 8.63 (d, J = 5.0, 0.8 Hz, 1H), 8.51 (d, J = 8.1 Hz, 1H), 8.47 (d, J = 5.0, 0.8 Hz, 1H), 7.75 (dd, J = 9.5, 6.2 Hz, 1H), 7.72-7.66 (m, 3H), 7.61 (dd, J = 9.8, 6.3 Hz, 1H), 7.56-7.47 (m, 2H), 7.44 (dd, J = 5.0, 1.8 Hz, 1H), 5.58 (dd, J = 11.6, 2.8 Hz, 1H), 4.99 (dd, J = 11.4, 3.1 Hz, 1H), 4.63 (t, J = 8.0 Hz, 1H), 4.26 (t, J = 8.4 Hz, 2H), 4.08 (td, J = 6.3, 2.6 Hz, 1H), 3.92 (td, J = 6.2, 2.5 Hz, 1H), 2.91-2.70 (m, 4H), 2.00-1.78 (m, 3H), 1.76-1.57 (m, 2H), 1.44-1.24 (m, 6H), 1.20-1.04 (m, 2H), 0.95-0.77 (m, 2H), 0.74-0.63 (m, 2H), 0.61-0.52 (m, 1H), 0.52-0.36 (m, 3H), 0.15--0.05 (m, 2H) | Q |
| 641 | 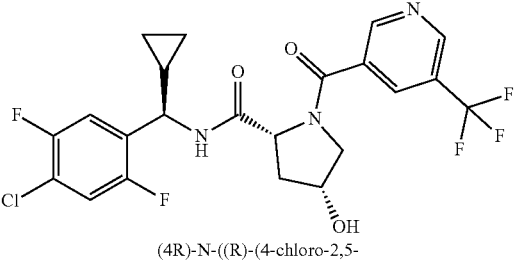<br>(4R)-N-((R)-(4-chloro-2,5-difluorophenyl)(cyclopropyl)methyl)-4-hydroxy-1-((5-(trifluoromethyl)-3-pyridinyl)carbonyl)-D-prolinamide | LCMS-APCI (POS.) m/z: 504.1 (M + H)+ | 1H NMR (400 MHz, DMSO-d6) δ ppm 9.27 (dd, 1 H), 9.12 (dd, J = 1.9, 70.9 Hz, 1 H), 8.74 (dd, J = 7.7, 45.9 Hz, 1 H), 8.44 (d, J = 44.7 Hz, 1 H), 7.77 (ddd, J = 6.2, 9.4, 12.8 Hz, 1 H), 7.62 (ddd, J = 6.3, 9.9, 44.8 Hz, 1 H), 5.33 (dd, J = 5.4, 84.1 Hz, 1 H), 4.59-4.71 (m, 1 H), 4.44 (dq, J = 5.8, 33.1 Hz, 1 H), 3.98-4.24 (m, 1 H), 3.70 (ddd, J = 6.0, 10.0, 101.4 Hz, 1 H), 1.86 (dt, J = 6.4, 12.7 Hz, 1 H), 1.31-1.44 (m, 1 H), 1.04-1.16(m, 1 H),0.70 (dt, J = 8.7, 36.1 Hz, 1 H), 0.55 (s, 1 H), 0.44-0.52 (m, 1 H), − 0.05-0.24 (m, 1 H). | Q |
| 642 | 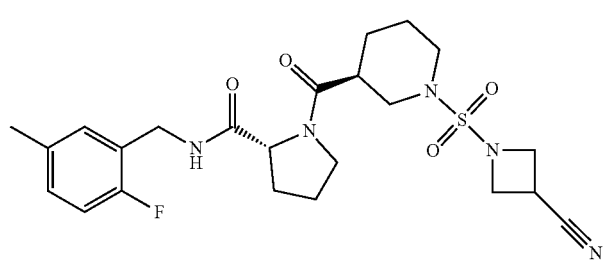 [SMILES: Cc1ccc(F)c(CNC(=O)[C@H]2CCCN2C(=O)[C@H]2CCCN(S(=O)(=O)N3CC(C#N)C3)C2)c1]<br>1-(((3S)-1-((3-cyano-1-azetidinyl)sulfonyl)-3-piperidinyl)carbonyl)-N-(2-fluoro-5-methylbenzyl)-D-prolinamide | LCMS-ESI (POS.) m/z: 492.2 (M + H)+ | 1H NMR (500 MHz, DMSO-d6) δ ppm 8.19-8.59 (m, 1 H), 6.99-7.16 (m, 3 H), 4.15-4.51 (m, 3 H), 3.99-4.09 (m, 2 H), 3.87-3.97 (m, 2 H), 3.74-3.83 (m, 1 H), 3.33-3.70 (m, 4 H), 2.62-2.86 (m, 3 H), 2.03-2.34 (m, 4 H), 1.67-1.99 (m, 5 H), 1.36-1.56 (m, 2 H) | Q |

| Ex. # | Structure Name | LCMS-ESI (POS/NEG) m/z: (M + H)+ | NMR Data | Syn. Rte. |
|---|---|---|---|---|
| 643 | 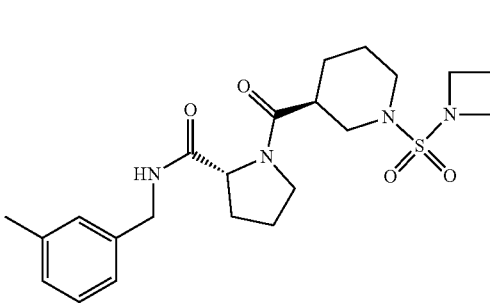<br>1-(((3S)-1-((3-cyano-1-azetidinyl)sulfonyl)-3-piperidinyl)carbonyl)-N-(3-methylbenzyl)-D-prolinamide | LCMS-ESI (POS.) m/z: 474.2 (M + H)+ | 1H NMR (500 MHz, DMSO-d6) δ ppm 8.18-8.63 (m, 1 H), 6.96-7.25 (m, 4 H), 4.14-4.50 (m, 3 H), 3.97-4.09 (m, 2 H), 3.86-3.96 (m, 2 H), 3.74-3.83 (m, 1 H), 3.33-3.71 (m, 4 H), 2.62-2.92 (m, 2 H), 2.26-2.29 (m, 3 H), 1.86-2.12 (m, 4 H), 1.66-1.84 (m, 3 H), 1.36-1.53 (m, 2 H) | A |
| 644 | <br>1-((3-((3-cyano-1-azetidinyl)sulfonyl)phenyl)carbonyl)-N-((5-(trifluoromethyl)-2-pyridinyl)methyl)-D-prolinamide | LCMS-APCI (NEG.) m/z: 520.1 (M − H) | 1H NMR (400 MHz, Methanol-d4) δ ppm 8.74 (d, J = 5.3 Hz, 1 H), 8.14 (t, J = 1.8 Hz, 1 H), 8.00 (ddt, J = 1.3, 3.2, 7.9 Hz, 2 H), 7.73-7.85 (m, 2 H), 7.53-7.62 (m, 1 H), 4.57-4.71 (m, 3 H), 4.11 (td, J = 1.2, 8.6 Hz, 2 H), 3.92 (ddq, J = 3.3, 6.4, 9.6 Hz, 2 H), 3.69 (dt, J = 6.9, 10.2 Hz, 1 H), 3.56-3.64 (m, 1 H), 3.44-3.56 (m, 1 H), 2.36-2.44 (m, 1 H), 2.01-2.09 (m, 2 H), 1.89-2.00 (m, OH). | A |
| 645 | 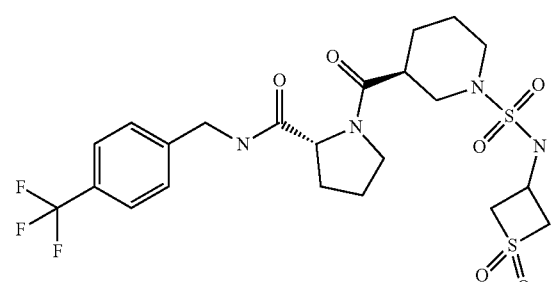<br>1-(((3S)-1-((1,1-dioxido-3-thietanyl)sulfamo)-3-piperidinyl)carbonyl)-N-(4-(trifluoromethyl)benzyl)-D-prolinamide | LCMS-ESI (POS.) m/z: 567.2 (M + H)+ | 1H NMR (500 MHz, DMSO-d6) δ 8.29-8.79 (m, 1H), 7.22-8.12 (m, 5H), 4.00-4.58 (m, 7H), 3.37-3.72 (m, 6H), 2.61-2.79 (m, 2H), 1.63-2.43 (m, 6H), 1.29-1.60 (m, 2H) | J |
| 646 | 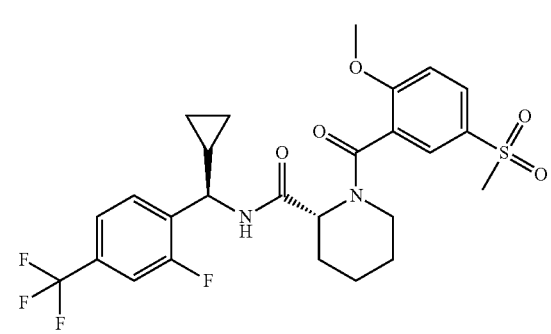 [SMILES: COc1ccc(S(C)(=O)=O)cc1C(=O)N1CCCC[C@@H]1C(=O)N[C@@H](c1ccc(C(F)(F)F)cc1F)C1CC1]<br>(2R)-N-((R)-cyclopropyl(2-fluoro-4-(trifluoromethyl)phenyl)methyl)-1-(2-methoxy-5-(methylsulfonyl)benzoyl)-2-piperidinecarboxamide | LCMS-APCI (POS.) m/z: 557.2 (M + H)+ | 1H NMR (400 MHz, DMSO-d6) δ ppm 8.76 (dd, J = 7.2, 18.8 Hz, 1 H), 7.93-7.99 (m, 1 H), 7.55-7.78 (m, 4 H), 7.30-7.39 (m, 1 H), 5.21 (dd, 1 H), 4.47-4.57 (m, 1 H), 4.35-4.48 (m, 1 H), 3.92 (s, 4 H), 3.11-3.25 (m, 4 H), 2.81-3.11 (m, 2 H), 2.18 (t, J = 13.4 Hz, 2 H), 1.41-1.72 (m, 4 H), 1.01-1.40 (m, 5 H), 0.24-0.68 (m, 6 H). | C |

-continued

| Ex. # | Structure Name | LCMS-ESI (POS/NEG) m/z: (M + H)+ | NMR Data | Syn. Rte. |
|---|---|---|---|---|
| 647 | 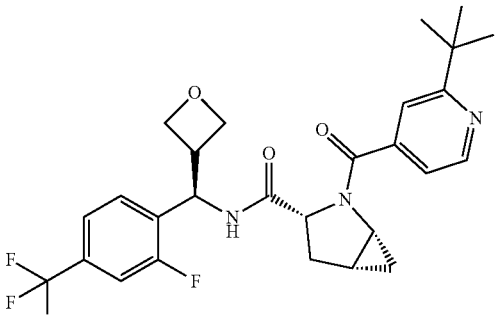<br>(1R,3R,5R)-N-((R)-(2-fluoro-4-(trifluoromethyl)phenyl)(3-oxetanyl)methyl)-2-((2-(2-methyl-2-propanyl)-4-pyridinyl)carbonyl)-2-azabicyclo[3.1.0]hexane-3-carboxamide | LCMS-APCI (POS.) m/z: 520.2 (M + H)+ | 1H NMR (400 MHz, Methanol-d4) δ ppm 8.64 (dd, J = 0.9, 5.0 Hz, 1 H), 7.82 (dd, J = 0.9, 1.5 Hz, 1 H), 7.54-7.59 (m, 2 H), 7.49-7.54 (m, 2 H), 5.66 (d, J = 10.1 Hz, 1 H), 4.97 (dd, J = 4.1, 11.4 Hz, 1 H), 4.86-4.89 (m, 5 H), 4.62-4.70 (m, 2 H), 4.37-4.43 (m, 1 H), 3.52-3.62 (m, 1 H), 3.27 (td, J = 2.6, 6.2 Hz, 1 H), 2.61-2.71 (m, 1 H), 1.86-1.94 (m, 1 H), 1.74-1.83 (m, 1 H), 1.24 (td, J = 2.6, 5.3 Hz, 1 H), 0.81-0.89 (m, 1 H). | A |
| 648 | 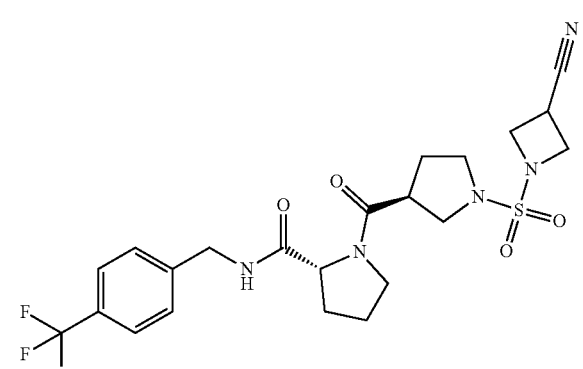<br>1-(((3S)-1-((3-cyano-1-azetidinyl)sulfonyl)-3-pyrrolidinyl)carbonyl)-N-(4-(trifluoromethyl)benzyl)-D-prolinamide | LCMS-ESI (POS.) m/z: 514.2 (M + H)+ | 1H NMR (400 MHz, DMSO-d6) δ ppm 8.75* (t, J = 5.96 Hz, 1 H), 8.43 (t, J = 6.04 Hz, 1 H), 7.60-7.73 (m, 2 H), 7.46 (br d, J = 7.98 Hz, 2 H), 4.53* (dd, J = 8.45, 2.64 Hz, 1 H), 4.26-4.44 (m, 3 H), 4.04-4.14 (m, 2 H), 3.92-4.01 (m, 2 H), 3.72-3.86 (m, 1 H), 3.19-3.68 (m, 7 H), 2.94* (quin, J = 7.54 Hz, 1 H), 2.06-2.26 (m, 2 H), 1.72-2.04 (m, 4 H) Spectrum appears as 3:1 mxiture of rotamers, *denotes resolved minor rotamer peaks | M |
| 649 | 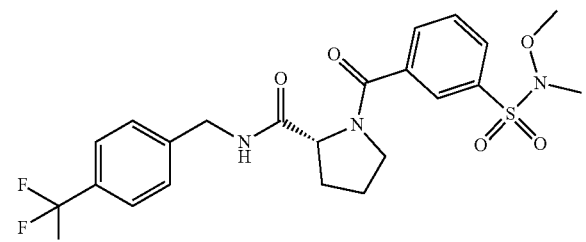<br>1-(3-(methoxy(methyl)sulfamoyl)benzoyl)-N-(4-(trifluoromethyl)benzyl)-D-prolinamide | LCMS-ESI (POS.) m/z: 500.2 (M + H)+ | 1H NMR (500 MHz, DMSO-d6) δ ppm 8.69-8.72 (m, 1 H), 7.11-8.05 (m, 8 H), 4.09-4.56 (m, 3 H), 3.69-3.80 (m, 3 H), 3.44-3.68 (m, 6 H), 3.43-3.66 (m, 6 H), 3.13 (br d, J = 3.63 Hz, 2 H), 2.68-2.85 (m, 3 H), 2.17-2.37 (m, 1 H), 1.76-2.02 (m, 3 H), 1.23 (br s, 6 H) | C |
| 650 | 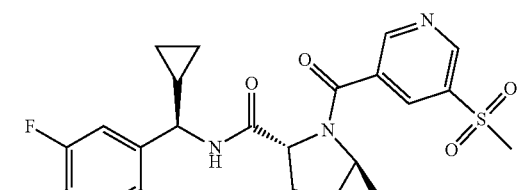<br>(1S,3R,5S)-N-((R)-(4-chloro-2,5-difluorophenyl)(cyclopropyl)methyl)-2-((5-(methylsulfonyl)-3-pyridinyl)carbonyl)-2-azabicyclo[3.1.0]hexane-3-carboxamide | LCMS-ESI (POS.) m/z: 510.0 (M + H)+ | 1H NMR (400 MHz, CHLOROFORM-d) δ ppm 9.18-9.39 (m, 2 H), 8.56-8.68 (m, 1 H), 7.29-7.37 (m, 1 H), 7.11-7.20 (m, 2 H), 4.74 (dd, J = 8.40, 2.80 Hz, 1 H), 4.48 (t, J = 7.83 Hz, 1 H), 3.21-3.29 (m, 1 H), 3.14-3.20 (m, 3 H), 2.75 (ddd, J = 13.53, 7.46, 2.44 Hz, 1 H), 2.00-2.15 (m, 2 H), 1.19-1.31 (m, 1 H), 1.10-1.19 (m, 1 H), 0.80 (td, J = 5.00, 2.64 Hz, 1 H), 0.63-0.73 (m, 1 H), 0.54-0.63 (m, 1 H), 0.35-0.51 (m, 2 H) | C |

| Ex. # | Structure Name | LCMS-ESI (POS/NEG) m/z: (M + H)+ | NMR Data | Syn. Rte. |
|---|---|---|---|---|
| 651 | 1-(((3S)-1-((3-cyano-1-azetidinyl)sulfonyl)-3-piperidinyl)carbonyl)-N-(2,5-dichlorobenzyl)-D-prolinamide | LCMS-ESI (POS.) m/z: 528.2 (M + H)+ | additional 1H count due to H2O overlap 1H NMR (400 MHz, CHLOROFORM-d) δ ppm 7.50 (br t, J = 5.96 Hz, 1 H), 7.30 (s, 1 H), 7.26 (d, J = 2.38 Hz, 1 H), 7.16-7.21 (m, 1 H), 4.64 (dd, J = 7.98, 1.97 Hz, 1 H), 4.58 (dd, J = 15.86, 6.84 Hz, 1 H), 4.37 (dd, J = 15.86, 5.49 Hz, 1 H), 4.06-4.16 (m, 4 H), 3.78 (ddt, J = 12.63, 3.90, 2.05, 2.05 Hz, 2 H), 3.53-3.65 (m, 2 H), 3.43 (tt, J = 8.66, 6.58 Hz, 1 H), 3.00 (dd, J = 12.75, 10.99 Hz, 1 H), 2.67-2.82 (m, 2 H), 2.43-2.52 (m, 1 H), 2.12-2.26 (m, 1 H), 1.95-2.11 (m, 2 H), 1.79-1.95 (m, 2 H), 1.53-1.73 (m, 3 H) | A |
| 652 | 1-(((3S)-1-((3-cyano-1-azetidinyl)sulfonyl)-3-piperidinyl)carbonyl)-N-(4-fluoro-2-(trifluoromethyl)benzyl)-D-prolinamide | LCMS-ESI (POS.) m/z: 546.2 (M + H)+ | 1H NMR (500 MHz, DMSO-d6) δ ppm 8.32-8.77 (m, 1 H), 7.33-7.65 (m, 3 H), 4.29-4.55 (m, 3 H), 4.00-4.11 (m, 2 H), 3.89-3.99 (m, 2 H), 3.75-3.84 (m, 1 H), 3.35-3.70 (m, 4 H), 2.65-2.90 (m, 2 H), 2.05-2.34 (m, 2 H), 1.68-2.02 (m, 5 H), 1.36-1.55 (m, 2 H) | A |
| 653 | (2R)-N-((R)-cyclopropyl(2-fluoro-4-(trifluoromethyl)phenyl)methyl)-1-((1,1-dioxido-2,3-dihydro-1-benzothiophen-6-yl)carbonyl)-2-piperidinecarboxamide | LCMS-ESI (POS.) m/z: 561.2 (M + H)+ | 1H NMR (500 MHz, CHLOROFORM-d) δ ppm 7.83 (br s, 1 H), 7.70 (br d, J = 7.01 Hz, 1 H), 7.31-7.55 (m, 5 H), 7.14 (br d, J = 5.71 Hz, 1 H), 5.22 (br s, 1 H), 4.57 (br t, J = 7.40 Hz, 1 H), 3.36-3.77 (m, 6 H), 2.99-3.25 (m, 1 H), 2.25 (br d, J = 13.75 Hz, 1 H), 1.18-2.03 (m, 17 H), 0.54 -0.83 (m, 2 H) | N |
| 654 | (R)-1-((S)-1-(1-oxa-6-azaspiro[3.3]heptan-6-ylsulfonyl)piperidine-3-carbonyl)-N-(4-(trifluoromethyl)benzyl)pyrrolidine-2-carboxamide | LCMS-ESI (POS.) m/z: 545.2 (M + H)+ | 1H NMR (400 MHz, CHLOROFORM-d) δ 7.57 (d, J = 8.09 Hz, 2H), 7.42-7.51 (m, 1H), 7.36 (d, J = 7.98 Hz, 2H), 4.61 (dd, J = 2.02, 8.03 Hz, 1H), 4.38-4.56 (m, 4H), 4.07-4.12 (m, 2H), 3.96-4.03 (m, 2H), 3.75-3.83 (m, 2H), 3.56-3.62 (m, 2H), 2.83-2.96 (m, 3H), 2.66-2.78 (m, 2H), 2.41-2.50 (m, 1H), 2.12-2.24 (m, 1H), 2.00-2.10 (m, 1H), 1.83-1.94 (m, 2H), 1.75-1.82 (m, 1H), 1.59-1.66 (m, 1H), 1.44-1.56 (m, 1H) | J |

| Ex. # | Structure Name | LCMS-ESI (POS/NEG) m/z: (M + H)+ | NMR Data | Syn. Rte. |
|---|---|---|---|---|
| 655 | 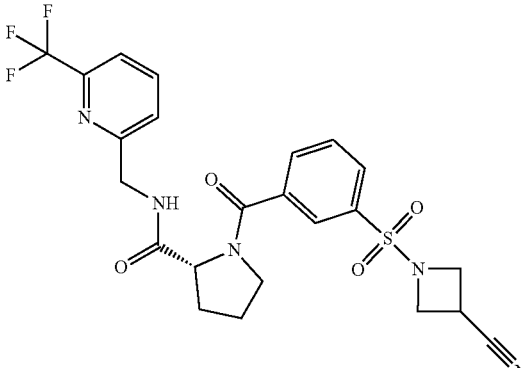<br>1-((3-((3-cyano-1-azetidinyl)sulfonyl)phenyl)carbonyl)-N-((6-(trifluoromethyl)-2-pyridinyl)methyl)-D-prolinamide | LCMS-APCI (NEG.) m/z: 520.1 (M − H) | 1H NMR (400 MHz, Methanol-d4) δ ppm 6.86 (t, J = 1.8 Hz, 1 H), 6.68-6.76 (m, 3 H), 6.49-6.57 (m, 1 H), 6.46 (d, J = 8.1 Hz, 1 H), 6.38 (d, J = 7.7 Hz, 1 H), 3.33-3.45 (m, 2 H), 3.28 (d, J = 16.6 Hz, 1 H), 2.83 (t, J = 8.6 Hz, 2 H), 2.65 (ddd, J = 4.1, 6.3, 8.7 Hz, 2 H), 2.37-2.46 (m, 1 H), 2.19-2.34 (m, 2 H), 1.04-1.16 (m, 1 H), 0.74-0.86 (m, 2 H), 0.58-0.71 (m, 1 H). | A |
| 656 | 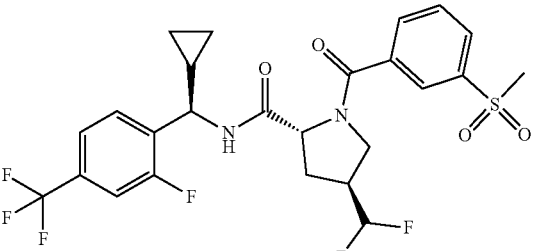<br>(4S)-N-((R)-cyclopropyl(2-fluoro-4-(trifluoromethyl)phenyl)methyl)-4-(difluoromethyl)-1-(3-(methylsulfonyl)benzoyl)-D-prolinamide | LCMS-ESI (POS.) m/z: 563.2 (M + H)+ | Note: cyclopropyl methyne obscured by non-specific grease<br>1H NMR (500 MHz, CHLOROFORM-d) δ ppm 8.11 (s, 1 H), 8.09 (br d, J = 7.91 Hz, 1 H), 7.81 (d, J = 7.79 Hz, 1 H), 7.68-7.76 (m, 1 H), 7.55 (br d, J = 7.01 Hz, 1 H), 7.45-7.51 (m, 1 H), 7.41-7.44 (m, 1 H), 7.36 (br d, J = 9.99 Hz, 1 H), 5.59-5.96 (m, 1 H), 4.90 (dd, J = 8.37, 3.57 Hz, 1 H), 4.57 (t, J = 7.98 Hz, 1 H), 3.72 (dd, J = 10.96, 7.98 Hz, 1 H), 3.52 (dd, J = 11.09, 6.16 Hz, 1 H), 3.06-3.15 (m, 3 H), 2.91-3.04 (m, 1 H), 2.52-2.69 (m, 1 H), 2.08 (dt, J = 13.36, 8.17 Hz, 1 H), 1.06-1.12 (m, 1 H), 0.61-0.69 (m, 1 H), 0.51-0.61 (m, 1 H), 0.36-0.50 (m, 2 H) | C |
| 657 | 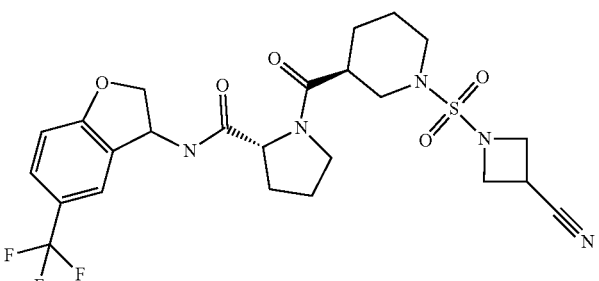<br>(2R)-1-((S)-1-((3-cyanoazetidin-1-yl)sulfonyl)piperidine-3-carbonyl)-N-(5-(trifluoromethyl)-2,3-dihydrobenzofuran-3-yl)pyrrolidine-2-carboxamide | LCMS-ESI (POS.) m/z: 556.2 (M + H)+ | 1H NMR (500 MHz, DMSO-d6) δ ppm 8.39-8.91 (m, 1 H), 7.49-7.71 (m, 2 H), 7.00-7.08 (m, 1 H), 5.49-5.65 (m, 1 H), 4.75-4.83 (m, 1 H), 4.17-4.49 (m, 2 H), 4.00-4.09 (m, 2 H), 3.88-3.97 (m, 2 H), 3.74-3.83 (m, 1 H), 3.33-3.68 (m, 4 H), 2.64-2.85 (m, 2 H), 2.13-2.42 (m, 1 H), 1.64-2.12 (m, 6 H), 1.30-1.56 (m, 2 H) | A |

| Ex. # | Structure Name | LCMS-ESI (POS/NEG) m/z: (M + H)+ | NMR Data | Syn. Rte. |
|---|---|---|---|---|
| 658 | 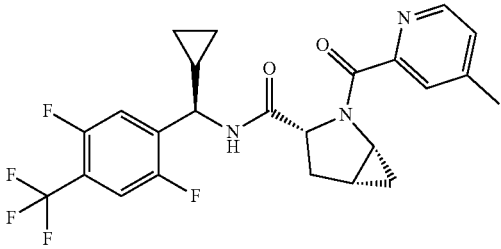 [SMILES: Cc1ccnc(C(=O)N2[C@@H](C(=O)N[C@@H](c3cc(F)c(C(F)(F)F)cc3F)C3CC3)C[C@H]3C[C@H]32)c1]<br>(1R,3R,5R)-N-((R)-cyclopropyl(2,5-difluoro-4-(trifluoromethyl)phenyl)methyl)-2-((4-methyl-2-pyridinyl)carbonyl)-2-azabicyclo[3.1.0]hexane-3-carboxamide | LCMS-APCI (POS.) m/z: 480.2 (M + H)+ | 1H NMR (DMSO-d6) δ: 8.70 (d, J = 7.5 Hz, 1H), 8.59-8.51 (m, 2H), 8.38 (d, J = 5.0, 0.7 Hz, 1H), 7.80 (ddd, J = 21.6, 9.4, 5.9 Hz, 2H), 7.71-7.62 (m, 2H), 7.62-7.53 (m, 2H), 7.41 (d, J = 5.0, 1.8, 0.9 Hz, 1H), 7.35 (d, J = 5.0, 1.7, 0.9 Hz, 1H), 5.54 (dd, J = 11.5, 2.8 Hz, 1H), 4.95 (dd, J = 11.4, 3.2 Hz, 1H), 4.60 (t, J = 7.9 Hz, 1H), 4.24 (t, J = 8.4 Hz, 1H), 4.02 (td, J = 6.3, 2.5 Hz, 1H), 3.94-3.81 (m, 1H), 2.84-2.66 (m, 1H), 2.44 (d, J = 12.9 Hz, 6H), 1.89 (dd, J = 13.4, 2.8 Hz, 1H), 1.79 (dd, J = 13.4, 3.2 Hz, 1H), 1.73-1.63 (m, 1H), 1.63-1.53 (m, 1H), 1.33-1.20 (m, 2H), 1.17-1.07 (m, 1H), 1.07-0.96 (m, 1H), 0.83-0.74 (m, 2H), 0.69-0.59 (m, 2H), 0.59-0.52 (m, 1H), 0.50-0.36 (m, 4H), 0.19-0.06 (m, 1H), 0.03-− 0.05 (m, 1H) | Q |
| 659 | 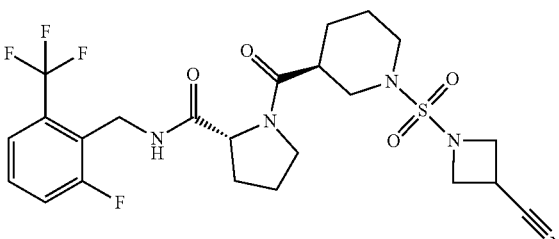<br>1-(((3S)-1-((3-cyano-1-azetidinyl)sulfonyl)-3-piperidinyl)carbonyl)-N-(2-fluoro-6-(trifluoromethyl)benzyl)-D-prolinamide | LCMS-ESI (POS.) m/z: 546.2 (M + H)+ | 1H NMR (500 MHz, DMSO-d6) δ ppm 8.02-8.44 (m, 1 H), 7.54-7.65 (m, 3 H), 4.47-4.57 (m, 1 H), 4.22-4.45 (m, 2 H), 4.01-4.10 (m, 2 H), 3.88-3.97 (m, 2 H), 3.74-3.84 (m, 1 H), 3.38-3.63 (m, 4 H), 2.70-2.85 (m, 2 H), 1.93-2.31 (m, 2 H), 1.66-1.93 (m, 5 H), 1.32-1.57 (m, 2 H) | A |
| 660 | 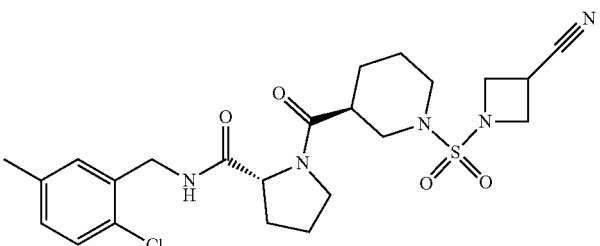<br>N-(2-chloro-5-methylbenzyl)-1-(((3S)-1-((3-cyano-1-azetidinyl)sulfonyl)-3-piperidinyl)carbonyl)-D-prolinamide | LCMS-ESI (POS.) m/z: 508.0 (M + H)+ | 1H NMR (500 MHz, DMSO-d6) δ ppm 8.17-8.66 (m, 1 H), 7.02-7.36 (m, 3 H), 4.14-4.43 (m, 3 H), 4.00-4.09 (m, 2 H), 3.86-3.99 (m, 2 H), 3.75-3.87 (m, 1 H), 3.25-3.71 (m, 4 H), 2.72-2.91 (m, 2 H), 2.62-2.72 (m, 1 H), 2.28-2.37 (m, 1 H), 2.23-2.31 (m, 3 H), 1.66-2.16 (m, 6 H), 1.33-1.58 (m, 2 H) | A |

| Ex. # | Structure Name | LCMS-ESI (POS/NEG) m/z: (M + H)+ | NMR Data | Syn. Rte. |
|---|---|---|---|---|
| 661 | 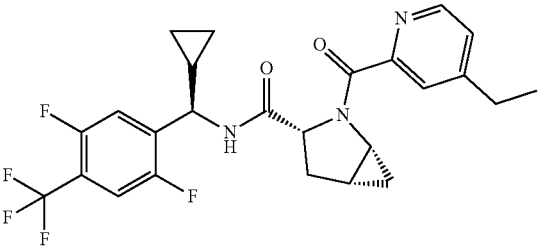 [SMILES: CCc1ccnc(C(=O)N2[C@@H](C(=O)N[C@@H](c3cc(F)c(C(F)(F)F)cc3F)C3CC3)C[C@H]3C[C@H]32)c1]<br>(1R,3R,5R)-N-((R)-cyclopropyl(2,5-difluoro-4-(trifluoromethyl)phenyl)methyl)-2-((4-ethyl-2-pyridinyl)carbonyl)-2-azabicyclo[3.1.0]hexane-3-carboxamide | LCMS-APCI (POS.) m/z: 494.2 (M + H)+ | 1H NMR (DMSO-d6) δ: 8.72 (d, J = 7.4 Hz, 1H), 8.59 (d, J = 5.0, 0.8 Hz, 1H), 8.56 (d, J = 7.9 Hz, 1H), 8.43 (d, J = 5.0, 0.8 Hz, 1H), 7.87-7.75 (m, 2H), 7.71-7.62 (m, 3H), 7.58 (dd, J = 11.0, 5.5 Hz, 1H), 7.46 (dd, J = 5.0, 1.8 Hz, 1H), 7.41 (dd, J = 5.1, 1.8 Hz, 1H), 5.55 (dd, J = 11.5, 2.7 Hz, 1H), 4.96 (dd, J = 11.4, 3.2 Hz, 1H), 4.61 (t, J = 8.0 Hz, 1H), 4.25 (t, J = 8.4 Hz, 1H), 4.05 (td, J = 6.3, 2.5 Hz, 1H), 3.89 (td, J = 6.1, 2.8 Hz, 1H), 2.87-2.69 (m, 4H), 1.90 (dd, J = 13.4, 2.9 Hz, 1H), 1.86-1.77 (m, 2H), 1.76-1.64 (m, 1H), 1.64-1.55 (m, 1H), 1.28 (q, J = 8.3, 7.6 Hz, 6H), 1.17-1.08 (m, 1H), 1.08-1.02 (m, 1H), 0.86-0.75 (m, 2H), 0.71-0.62 (m, 2H), 0.62-0.53 (m, 1H), 0.52-0.35 (m, 4H), 0.17-0.08 (m, 1H), 0.06-- 0.08 (m, 1H) | C |
| 662 | 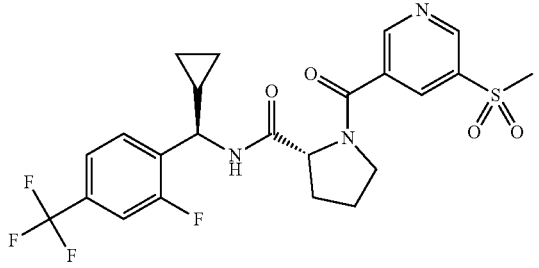 [SMILES: CS(=O)(=O)c1cncc(C(=O)N2CCC[C@@H]2C(=O)N[C@@H](c2ccc(C(F)(F)F)cc2F)C2CC2)c1]<br>N-((R)-cyclopropyl(2-fluoro-4-(trifluoromethyl)phenyl)methyl)-1-((5-(methylsulfonyl)-3-pyridinyl)carbonyl)-D-prolinamide | LCMS-ESI (POS.) m/z: 514.2 (M + H)+ | 1H NMR (500 MHz, DMSO-d6) δ ppm 8.22-9.20 (m, 4 H), 7.48-7.77 (m, 3 H), 4.12-4.63 (m, 2 H), 3.53 (br dd, J = 14.99, 7.20 Hz, 2 H), 3.39 (br d, J = 10.51 Hz, 3 H), 2.12-2.32 (m, 1 H), 1.67-1.92 (m, 3 H), 0.86-1.29 (m, 1 H),-0.14-0.64 (m, 4 H) | C |
| 663 | 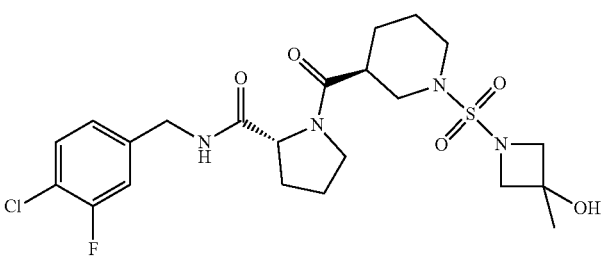 [SMILES: CC1(O)CN(S(=O)(=O)N2CCC[C@H](C(=O)N3CCC[C@@H]3C(=O)NCc3ccc(Cl)c(F)c3)C2)C1]<br>N-(4-chloro-3-fluorobenzyl)-1-(((3S)-1-((3-hydroxy-3-methyl-1-azetidinyl)sulfonyl)-3-piperidinyl)carbonyl)-D-prolinamide | LCMS-ESI (POS.) m/z: 517.2 (M + H)+ | 1H NMR (400 MHz, CHLOROFORM-d) δ 7.38-7.46 (m, 1H), 7.33 (t, J = 7.83 Hz, 1H), 7.03 (dd, J = 1.87, 9.85 Hz, 1H), 6.94-7.00 (m, 1H), 4.59 (dd, J = 2.18, 7.98 Hz, 1H), 4.43-4.52 (m, 1H), 4.30 (dd, J = 5.49, 15.45 Hz, 1H), 3.88 (dd, J = 2.33, 8.14 Hz, 2H), 3.67-3.84 (m, 4H), 3.56-3.65 (m, 2H), 2.99 (dd, J = 10.68, 12.65 Hz, 1H), 2.68-2.85 (m, 2H), 2.40-2.48 (m, 1H), 2.13-2.25 (m, 1H), 2.01-2.10 (m, 1H), 1.79-1.96 (m, 3H), 1.63-1.71 (m, 2H), 1.55 (s, 3H) | A |

-continued

| Ex. # | Structure Name | LCMS-ESI (POS/NEG) m/z: (M + H)+ | NMR Data | Syn. Rte. |
|---|---|---|---|---|
| 664 | 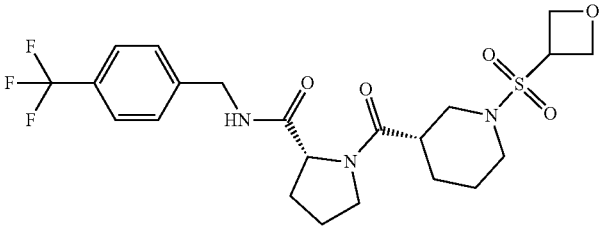 [SMILES: O=C(NCc1ccc(C(F)(F)F)cc1)[C@H]1CCCN1C(=O)[C@H]1CCCN(S(=O)(=O)C2COC2)C1]{br}1-(((3S)-1-(3-oxetanylsulfonyl)-3-piperidinyl)carbonyl)-N-(4-(trifluoromethyl)benzyl)-D-prolinamide | LCMS-APCI (POS.) m/z: 504.1 (M + H)+ | 1H NMR (400 MHz, Methanol-d4) δ ppm 7.63 (d, J = 8.0 Hz, 2 H), 7.50 (d, J = 7.9 Hz, 2 H), 4.90-4.95 (m, 2 H), 4.83-4.88 (m, 2 H), 4.63-4.74 (m, 1 H), 4.38-4.52 (m, 3 H), 3.73-3.87 (m, 4 H), 2.73-2.85 (m, 2 H), 2.19-2.33 (m, 1 H), 1.91-2.16 (m, 5 H), 1.79-1.86 (m, 1 H), 1.54-1.66 (m, 2 H). | R |
| 665 | 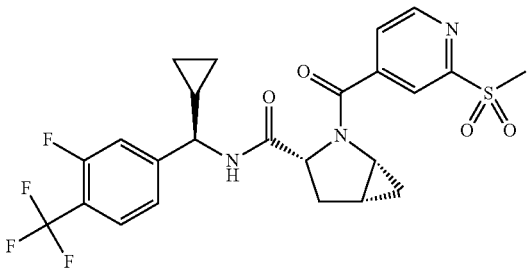 [SMILES: CS(=O)(=O)c1cc(C(=O)N2[C@@H](C(=O)N[C@@H](c3ccc(C(F)(F)F)c(F)c3)C3CC3)C[C@H]3C[C@H]32)ccn1]{br}(1R,3R,5R)-N-((R)-cyclopropyl(3-fluoro-4-(trifluoromethyl)phenyl)methyl)-2-((2-(methylsulfonyl)-4-pyridinyl)carbonyl)-2-azabicyclo[3.1.0]hexane-3-carboxamide | LCMS-ESI (POS.) m/z: 526.2 (M + H)+ | 1H NMR (500 MHz, DMSO-d6) δ ppm 8.80-8.99 (m, 1 H), 8.51-8.79 (m, 1 H), 7.67-8.18 (m, 2 H), 7.62-8.26 (m, 3 H), 7.20-7.54 (m, 2 H), 4.71-5.03 (m, 1 H), 3.87-4.30 (m, 1 H), 3.14-3.38 (m, 4 H), 2.57-2.82 (m, 1 H), 1.57-1.88 (m, 2 H), − 0.31-1.19 (m, 7 H) | C |
| 666 | 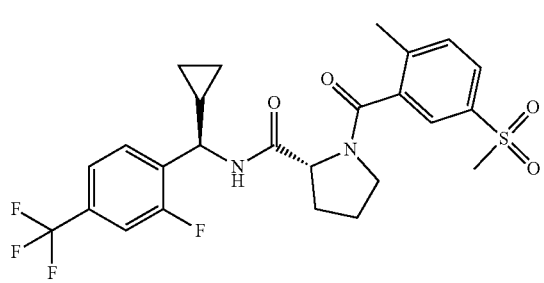 [SMILES: Cc1ccc(S(C)(=O)=O)cc1C(=O)N1CCC[C@@H]1C(=O)N[C@@H](c1ccc(C(F)(F)F)cc1F)C1CC1]{br}N-((R)-cyclopropyl(2-fluoro-4-(trifluoromethyl)phenyl)methyl)-1-(2-methyl-5-(methylsulfonyl)benzoyl)-D-prolinamide | LCMS-APCI (POS.) m/z: 527.2 (M + H)+ | 1H NMR (400 MHz, DMSO-d6) δ ppm 8.78 (d, J = 7.5 Hz, 1 H), 7.86 (dd, J = 2.1, 8.0 Hz, 1 H), 7.49-7.74 (m, 6 H), 4.55-4.65 (m, 2 H), 4.35 (t, J = 5.1 Hz, 1 H), 4.09-4.29 (m, 3 H), 3.50-3.64 (m, 2 H), 3.23 (d, J = 1.5 Hz, 3 H), 3.13 (t, J = 6.5 Hz, 2 H), 2.37 (s, 2 H), 2.31 (s, 1 H), 1.65-1.80 (m, 4 H), 1.18-1.26 (m, 1 H), 0.43-0.51 (m, 1 H), 0.40 (d, J = 4.9 Hz, 1 H), 0.31 (d, J = 8.2 Hz, 1 H). | Q |

| Ex. # | Structure Name | LCMS-ESI (POS/NEG) m/z: (M + H)+ | NMR Data | Syn. Rte. |
|---|---|---|---|---|
| 667 | 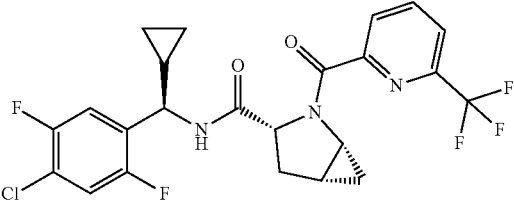 [SMILES: O=C(N[C@@H](c1cc(F)c(Cl)cc1F)C1CC1)[C@H]1C[C@H]2C[C@H]2N1C(=O)c1cccc(C(F)(F)F)n1]<br>(1R,3R,5R)-N-((R)-(4-chloro-2,5-difluorophenyl)(cyclopropyl)methyl)-2-((6-(trifluoromethyl)-2-pyridinyl)carbonyl)-2-azabicyclo[3.1.0]hexane-3-carboxamide | LCMS-APCI (POS.) m/z: 500.1 (M + H)+ | 1H NMR (DMSO-d6) δ: 8.63 (d, J = 7.7 Hz, 1H), 8.44 (d, J = 8.1 Hz, 1H), 8.28 (t, J = 7.9, 0.7 Hz, 1H), 8.21 (t, J = 7.9, 0.7 Hz, 1H), 8.09-8.02 (m, 2H), 8.01-7.97 (m, 2H), 7.63 (dd, J = 9.4, 6.2 Hz, 1H), 7.57 (dd, J = 9.4, 6.2 Hz, 1H), 7.50 (dd, J = 9.9, 6.3 Hz, 1H), 7.41 (dd, J = 9.9, 6.4 Hz, 1H), 5.47 (dd, J = 11.6, 2.8 Hz, 1H), 4.91 (dd, J = 11.4, 3.3 Hz, 1H), 4.51 (t, J = 7.9 Hz, 1H), 4.04 (t, J = 8.5 Hz, 1H), 3.81 (td, J = 6.3, 2.5 Hz, 1H), 3.74 (td, J = 6.3, 2.3 Hz, 1H), 2.80 (td, J = 12.6, 5.8 Hz, 1H), 1.86 (dd, J = 13.6, 2.9 Hz, 1H), 1.74-1.63 (m, 2H), 1.62-1.53 (m, 1H), 1.29-1.13 (m, 3H), 1.08-0.99 (m, 1H), 0.99-0.89 (m, 1H), 0.65-0.58 (m, 1H), 0.57-0.51 (m, 2H), 0.49-0.40 (m, 1H), 0.39-0.32 (m, 2H), 0.31-0.19 (m, 2H), − 0.06 -- 0.17 (m, 1H), − 0.22-− 0.34 (m, 1H) | Q |
| 668 | 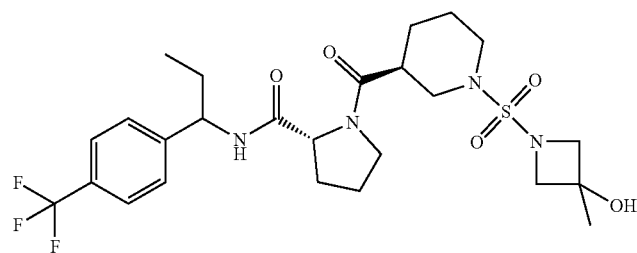 [SMILES: CCC(NC(=O)[C@H]1CCCN1C(=O)[C@H]1CCCN(S(=O)(=O)N2CC(C)(O)C2)C1)c1ccc(C(F)(F)F)cc1]<br>(2R)-1-((S)-1-((3-hydroxy-3-methylazetidin-1-yl)sulfonyl)piperidine-3-carbonyl)-N-(1-(4-(trifluoromethyl)phenyl)propyl)pyrrolidine-2-carboxamide | LCMS-ESI (POS.) m/z: 561.2 (M + H)+ | 1H NMR (400 MHz, CHLOROFORM-d) δ 7.50-7.70 (m, 3H), 7.30-7.45 (m, 2H), 4.75-4.90 (m, 1H), 4.54-4.72 (m, 1H), 3.68-3.97 (m, 6H), 3.47-3.67 (m, 2H), 2.95-3.09 (m, 1H), 2.63-2.87 (m, 2H), 2.33-2.52 (m, 1H), 2.08-2.23 (m, 1H), 1.93-2.07 (m, 2H), 1.62-1.88 (m, 7H), 1.53-1.60 (m, 3H), 0.83-0.98 (m, 3H) | A |
| 669 | 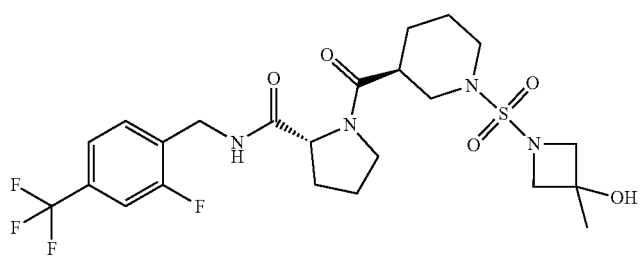 [SMILES: CC1(O)CN(S(=O)(=O)N2CCC[C@H](C(=O)N3CCC[C@@H]3C(=O)NCc3ccc(C(F)(F)F)cc3F)C2)C1]<br>N-(2-fluoro-4-(trifluoromethyl)benzyl)-1-(((3S)-1-((3-hydroxy-3-methyl-1-azetidinyl)sulfonyl)-3-piperidinyl)carbonyl)-D-prolinamide | LCMS-ESI (POS.) m/z: 573.1 (M + H)+ | 1H NMR (400 MHz, CHLOROFORM-d) δ 7.30-7.68 (m, 4H), 4.30-4.83 (m, 3H), 3.41-4.07 (m, 8H), 2.92-3.08 (m, 1H), 2.65-2.92 (m, 2H), 2.31-2.65 (m, 2H), 2.01-2.26 (m, 2H), 1.75-1.95 (m, 3H), 1.47-1.67 (m, 5H) | J |

| Ex. # | Structure Name | LCMS-ESI (POS/NEG) m/z: (M + H)+ | NMR Data | Syn. Rte. |
|---|---|---|---|---|
| 670 | 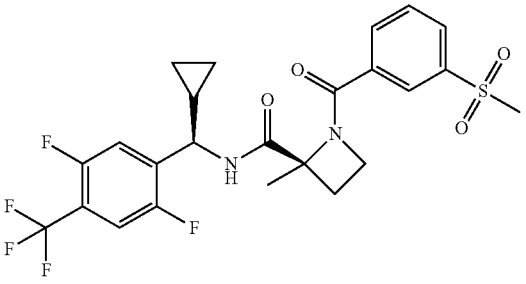 [SMILES: C[C@@]1(C(=O)N[C@@H](c2cc(F)c(C(F)(F)F)cc2F)C2CC2)CCN1C(=O)c1cccc(S(C)(=O)=O)c1]<br>(2S)-N-((R)-cyclopropyl(2,5-difluoro-4-(trifluoromethyl)phenyl)methyl)-2-methyl-1-(3-(methylsulfonyl)benzoyl)-2-azetidinecarboxamide | LCMS-ESI (POS.) m/z: 531.2 (M + H)+ | 1H NMR (500 MHz, CHLOROFORM-d) δ ppm 8.97 (br d, J = 7.01 Hz, 1 H), 8.17-8.32 (m, 1 H), 8.11 (d, J = 7.78 Hz, 1 H), 7.93 (d, J = 7.66 Hz, 1 H), 7.72 (t, J = 7.85 Hz, 1 H), 7.33 (dd, J = 9.28, 5.64 Hz, 1 H), 7.24 (dd, J = 10.12, 5.45 Hz, 1 H), 4.54-4.60 (m, 1 H), 4.24 (td, J = 9.28, 5.58 Hz, 1 H), 4.16 (td, J = 8.95, 7.01 Hz, 1 H), 3.12 (s, 3 H), 2.96-3.04 (m, 1 H), 2.12 (ddd, J = 11.94, 9.28, 5.51 Hz, 1 H), 1.87 (s, 3 H), 1.16-1.31 (m, 1 H), 0.62-0.69 (m, 1 H), 0.53-0.62 (m, 1 H), 0.39-0.48 (m, 2 H) | C |
| 671 | 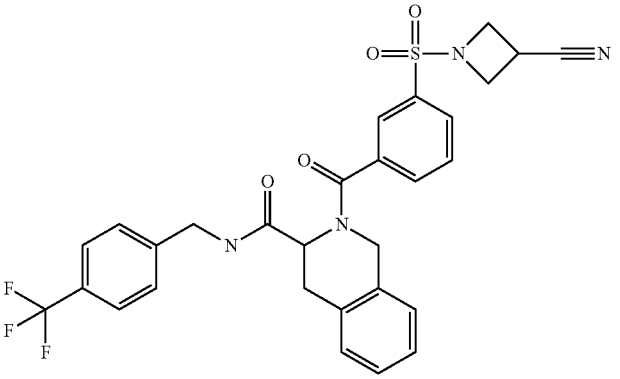 [SMILES: N#CC1CN(S(=O)(=O)c2cccc(C(=O)N3Cc4ccccc4CC3C(=O)NCc3ccc(C(F)(F)F)cc3)c2)C1]<br>2-(3-((3-cyanoazetidin-1-yesulfonyl)benzoyl)-N-(4-(trifluoromethyl)benzyl)-1,2,3,4-tetrahydroisoquinoline-3-carboxamide | LCMS-ESI (POS.) m/z: 583.2 (M + H)+ | 1H NMR (500 MHz, DMSO-d6) δ ppm 8.58 (br s, 1 H), 7.94-8.06 (m, 2 H), 7.89-7.94 (m, 1 H), 7.78-7.89 (m, 1 H), 7.53 (br d, J = 7.75 Hz, 1 H), 7.46 (br d, J = 6.62 Hz, 1 H), 7.28-7.37 (m, 1 H), 7.25 (br s, 1 H), 7.19 (br d, J = 9.60 Hz, 1 H), 7.01-7.15 (m, 2 H), 6.83-7.00 (m, 1 H), 5.02 (br s, 1 H), 4.56 (br s, 1 H), 4.34-4.48 (m, 1 H), 4.23-4.33 (m, 1 H), 4.14-4.23 (m, 1 H), 4.05-4.13 (m, 1 H), 4.02 (br s, 1 H), 3.81-3.95 (m, 2 H), 3.57-3.78 (m, 1 H), 3.21-3.28 (m, 1 H), 3.17 (s, 1 H) | I |
| 672 | 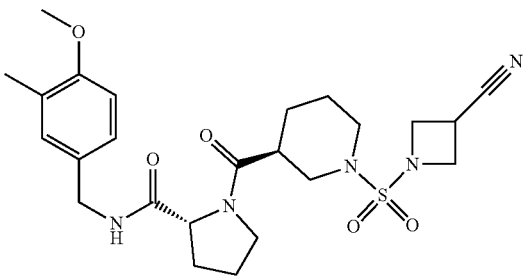<br>1-(((3S)-1-((3-cyano-1-azetidinyl)sulfonyl)-3-piperidinyl)carbonyl)-N-(4-methoxy-3-methylbenzyl)-D-prolinamide | LCMS-ESI (POS.) m/z: 504.2 (M + H)+ | 1H NMR (500 MHz, DMSO-d6) δ ppm 8.02-8.55 (m, 1 H), 6.75-7.21 (m, 3 H), 3.88-4.50 (m, 7 H), 3.70-3.85 (m, 4 H), 3.40-3.68 (m, 4 H), 2.60-2.92 (m, 3 H), 2.10-2.33 (m, 4 H), 1.66-2.08 (m, 5 H), 1.32-1.57 (m, 2 H) | A |
| 673 | 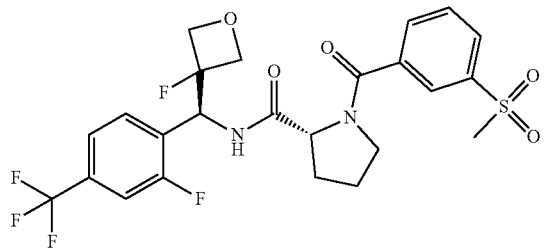 [SMILES: CS(=O)(=O)c1cccc(C(=O)N2CCC[C@@H]2C(=O)N[C@@H](c2ccc(C(F)(F)F)cc2F)C2(F)COC2)c1]<br>N-((S)-(3-fluoro-3-oxetanyl)(2-fluoro-4-(trifluoromethyl)phenyl)methyl)-1-(3-(methylsulfonyl)benzoyl)-D-prolinamide | LCMS-APCI (POS.) m/z: 547.1 (M + H)+ | 1H NMR (DMSO-d6) δ: 9.18 (d, J = 9.0 Hz, 1H), 8.09-7.99 (m, 2H), 7.80-7.66 (m, 3H), 5.93 (dd, J = 25.9, 9.0 Hz, 1H), 4.84-4.65 (m, 2H), 4.65-4.54 (m, 2H), 3.59 (t, J = 6.6 Hz, 1H), 3.56-3.40 (m, 3H), 3.28 (d, J = 10.7 Hz, 2H), 1.96-1.66 (m, 4H), 1.06 (t, J = 7.0 Hz, 2H) | A |

-continued

| Ex. # | Structure Name | LCMS-ESI (POS/NEG) m/z: (M + H)+ | NMR Data | Syn. Rte. |
|---|---|---|---|---|
| 674 | 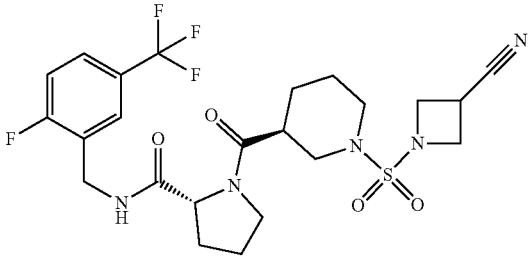 [SMILES: N#CC1CN(S(=O)(=O)N2CCC[C@H](C(=O)N3CCC[C@@H]3C(=O)NCc3cc(C(F)(F)F)ccc3F)C2)C1]<br>1-(((3S)-1-((3-cyano-1-azetidinyl)sulfonyl)-3-piperidinyl)carbonyl)-N-(2-fluoro-5-(trifluoromethyl)benzyl)-D-prolinamide | LCMS-ESI (POS.) m/z: 546.2 (M + H)+ | 1H NMR (500 MHz, DMSO-d6) δ ppm 8.38-8.76 (m, 1 H), 7.60-7.75 (m, 2 H), 7.37-7.46 (m, 1 H), 4.26-4.55 (m, 3 H), 3.98-4.10 (m, 2 H), 3.87-3.97 (m, 2 H), 3.74-3.84 (m, 1 H), 3.40-3.69 (m, 4 H), 2.59-2.90 (m, 3 H), 2.05-2.33 (m, 1 H), 1.65-1.99 (m, 5 H), 1.33-1.56 (m, 2 H) | A |
| 675 | 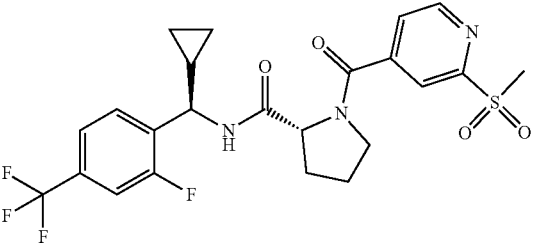 [SMILES: CS(=O)(=O)c1cc(C(=O)N2CCC[C@@H]2C(=O)N[C@@H](c2ccc(C(F)(F)F)cc2F)C2CC2)ccn1]<br>N-((R)-cyclopropyl(2-fluoro-4-(trifluoromethyl)phenyl)methyl)-1-((2-(methylsulfonyl)-4-pyridinyl)carbonyl)-D-prolinamide | LCMS-ESI (POS.) m/z: 514.2 (M + H)+ | 1H NMR (500 MHz, DMSO-d6) δ ppm 8.44-9.01 (m, 2 H), 7.42-8.10 (m, 5 H), 4.12-4.65 (m, 2 H), 3.51-3.61 (m, 2 H), 3.32 (br d, J = 11.68 Hz, 3 H), 2.12-2.30 (m, 1 H), 1.61-1.95 (m, 3 H), 0.87-1.32 (m, 1 H), − 0.11-0.68 (m, 4 H) | C |
| 676 | 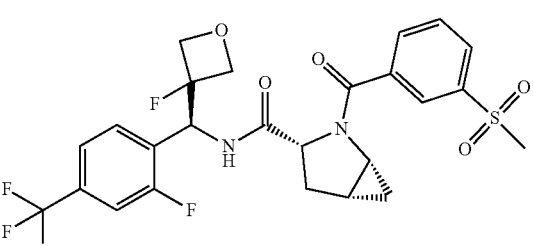<br>(1R,3R,5R)-N-((S)-(3-fluoro-3-oxetanyl)(2-fluoro-4-(trifluoromethyl)phenyl)methyl)-2-(3-(methylsulfonyl)benzoyl)-2-azabicyclo[3.1.0]hexane-3-carboxamide | LCMS-APCI (POS.) m/z: 559.1 (M + H)+ | 1H NMR (400 MHz, DMSO-d6) δ ppm 9.21 (d, J = 8.9 Hz, 1 H), 8.20 (t, J = 1.8 Hz, 1 H), 7.99-8.10 (m, 2 H), 7.74-7.83 (m, 2 H), 7.70 (s, 2 H), 5.87 (dd, J = 8.9, 25.5 Hz, 1 H), 5.02 (dd, J = 3.9, 11.4 Hz, 1 H), 4.53-4.74 (m, 3 H), 4.35 (t, J = 5.1 Hz, 1 H), 3.28 (s, 3 H), 1.73 (dd, J = 4.2, 13.6 Hz, 2 H), 1.17-1.23 (m, 1 H), 0.76-0.83 (m, 1 H). | A |
| 677 | 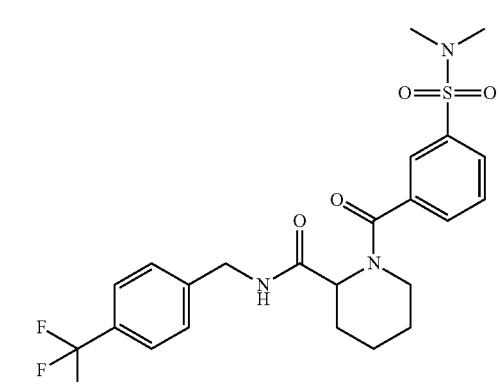<br>1-(3-(N,N-dimethylsulfamoyl)benzoyl)-N-(4-(trifluoromethyl)benzyl)piperidine-2-carboxamide | LCMS-APCI (NEG.) m/z: 496.2 (M − H) | 1H NMR (400 MHz, DMSO-d6) δ ppm 8.25 (s, 1 H), 7.79-7.87 (m, 1 H), 7.74-7.79 (m, 1 H), 7.62-7.74 (m, 4 H), 7.50 (d, J = 8.1 Hz, 2 H), 4.80 (s, 1 H), 4.44 (d, J = 5.2 Hz, 2 H), 3.82 (s, 1 H), 3.24 (s, 1 H), 2.70 (s, 5 H), 2.21 (d, J = 13.8 Hz, 1 H), 1.62-1.78 (m, 3 H), 1.47 (t, J = 10.1 Hz, 2 H). | Q |

| Ex. # | Structure Name | LCMS-ESI (POS/NEG) m/z: (M + H)+ | NMR Data | Syn. Rte. |
|---|---|---|---|---|
| 678 | 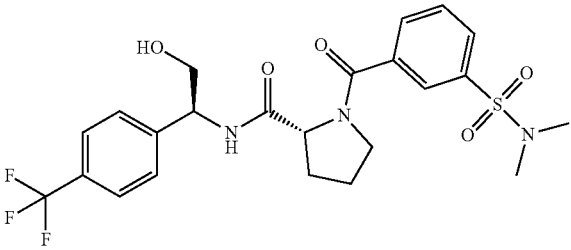 [SMILES: CN(C)S(=O)(=O)c1cccc(C(=O)N2CCC[C@@H]2C(=O)N[C@H](CO)c2ccc(C(F)(F)F)cc2)c1]<br>1-(3-(dimethylsulfamoyl)benzoyl)-N-((1S)-2-hydroxy-1-(4-(trifluoromethyl)phenyl)ethyl)-D-prolinamide | LCMS-ESI (POS.) m/z: 514.2 (M + H)+ | 1H NMR (500 MHz, DMSO-d6) δ ppm 8.48 (d, J = 7.66 Hz, 1 H), 7.38-7.96 (m, 8 H), 4.63-4.97 (m, 1 H), 4.35-4.60 (m, 1 H), 3.52-3.75 (m, 4 H), 3.27-3.51 (m, 2 H), 2.59-2.70 (m, 6 H), 2.15-2.31 (m, 1 H), 1.64-1.90 (m, 3 H) | A |
| 679 | 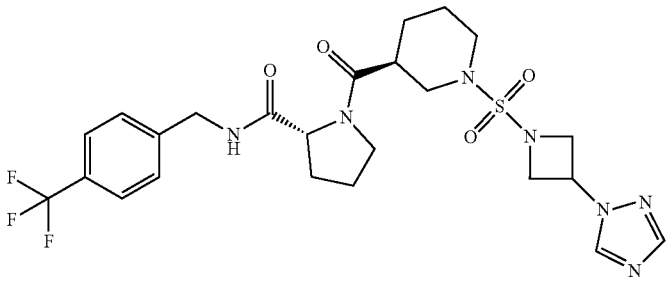 [SMILES: O=C(NCc1ccc(C(F)(F)F)cc1)[C@H]1CCCN1C(=O)[C@H]1CCCN(S(=O)(=O)N2CC(n3cncn3)C2)C1]<br>1-(((3S)-1-((3-(1H-1,2,4-triazol-1-)-1-azetidinyl)sulfonyl)-3-piperidinyl)carbonyl)-N-(4-(trifluoromethyl)benzyl)-D-prolinamide | LCMS-ESI (POS.) m/z: 570.2 (M + H)+ | 1H NMR (500 MHz, DMSO-d6) δ ppm 8.00-8.78 (m, 3 H), 7.56-7.78 (m, 2 H), 7.35-7.56 (m, 2 H), 5.41 (br d, J = 6.75 Hz, 1 H), 3.96-4.66 (m, 8 H), 3.51-3.79 (m, 4 H), 2.61-3.02 (m, 3 H), 1.30-2.42 (m, 9 H) | M |
| 680 | 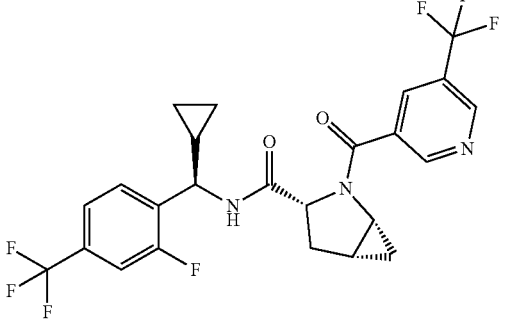<br>(1R,3R,5R)-N-((R)-cyclopropyl(2-fluoro-4-(trifluoromethyl)phenyl)methyl)-2-((5-(trifluoromethyl)-3-pyridinyl)carbonyl)-2-azabicyclo[3.1.0]hexane-3-carboxamide | LCMS-APCI (POS.) m/z: 516.2 (M + H)+ | 1H NMR (400 MHz, Methanol-d4) δ ppm 8.98-9.39 (m, 2 H), 8.33-8.73 (m, 1 H), 7.49-7.88 (m, 3 H), 5.17-5.25 (m, 1 H), 4.65-4.76 (m, 1 H), 3.44-3.52 (m, 1 H), 2.77-3.03 (m, 1 H), 2.00-2.10 (m, 1 H), 1.78-1.99 (m, 1 H), 1.37-1.48 (m, 1 H), 1.28-1.35 (m, 1 H), 0.93-1.18 (m, 1 H),-0.06-0.87 (m, 4 H). | Q |
| 681 | 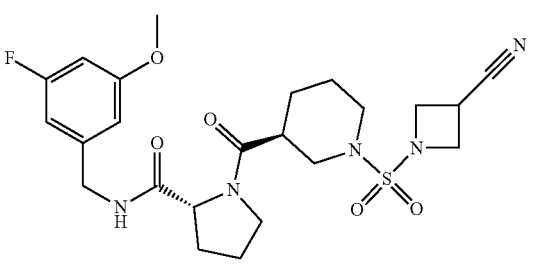 [SMILES: COc1cc(F)cc(CNC(=O)[C@H]2CCCN2C(=O)[C@H]2CCCN(S(=O)(=O)N3CC(C#N)C3)C2)c1]<br>1-(((3S)-1-((3-cyano-1-azetidinyl)sulfonyl)-3-piperidinyl)carbonyl)-N-(3-fluoro-5-methoxybenzyl)-D-prolinamide | LCMS-ESI (POS.) m/z: 508.2 (M + H)+ | 1H NMR (500 MHz, DMSO-d6) δ ppm 8.24-8.72 (m, 1 H), 6.54-6.85 (m, 3 H), 3.91-4.56 (m, 7 H), 3.71-3.85 (m, 4 H), 3.43-3.70 (m, 4 H), 2.61-2.95 (m, 3 H), 1.66-2.33 (m, 6 H), 1.28-1.62 (m, 2 H) | A |

-continued

| Ex. # | Structure Name | LCMS-ESI (POS/NEG) m/z: (M + H)+ | NMR Data | Syn. Rte. |
|---|---|---|---|---|
| 682 | 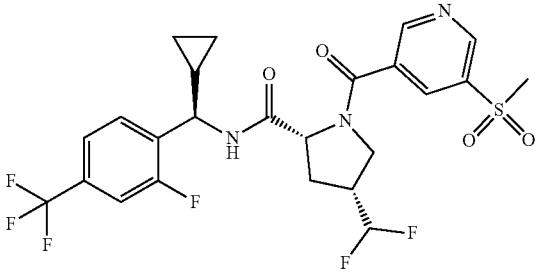 [SMILES: CS(=O)(=O)c1cncc(C(=O)N2C[C@H](C(F)F)C[C@@H]2C(=O)N[C@@H](c2ccc(C(F)(F)F)cc2F)C2CC2)c1]<br>(4R)-N-((R)-cyclopropyl(2-fluoro-4-(trifluoromethyl)phenyl)methyl)-4-(difluoromethyl)-1-((5-(methylsulfonyl)-3-pyridinyl)carbonyl)-D-prolinamide | LCMS-ESI (POS.) m/z: 564.0 (M + H)+ | Note: cyclopropyl methyne obscured by non-specific grease 1H NMR (500 MHz, CHLOROFORM-d) δ ppm 9.24-9.30 (m, 1 H), 9.05 (d, J = 1.69 Hz, 1 H), 8.41 (t, J = 1.95 Hz, 1 H), 7.45-7.52 (m, 1 H), 7.40-7.45 (m, 1 H), 7.31-7.39 (m, 2 H), 5.63-5.98 (m, 1 H), 4.88 (dd, J = 8.37, 3.70 Hz, 1 H), 4.41-4.65 (m, 1 H), 3.78 (dd, J = 10.77, 7.91 Hz, 1 H), 3.51-3.63 (m, 1 H), 3.17-3.21 (m, 3 H), 2.94-3.08 (m, 1 H), 2.50-2.59 (m, 1 H), 2.08-2.19 (m, 1 H), 1.28-1.34 (m, 1 H), 0.62-0.70 (m, 1 H), 0.54-0.62 (m, 1 H), 0.46 (dq, J = 9.55, 4.73 Hz, 1 H), 0.36-0.43 (m, 1 H) | C |
| 683 | 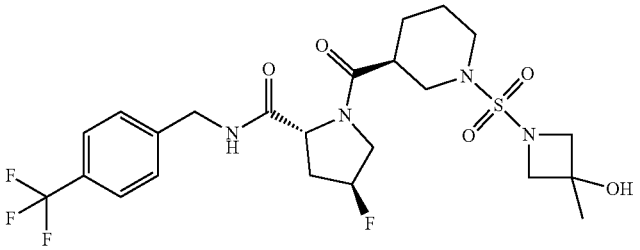 [SMILES: CC1(O)CN(S(=O)(=O)N2CCC[C@H](C(=O)N3C[C@@H](F)C[C@@H]3C(=O)NCc3ccc(C(F)(F)F)cc3)C2)C1]<br>(4S)-4-fluoro-1-(((3S)-1-((3-hydroxy-3-methyl-1-azetidinyl)sulfonyl)-3-piperidinyl)carbonyl)-N-(4-(trifluoromethyl)benzyl)-D-prolinamide | LCMS-ESI (POS.) m/z: 551.0 (M + H)+ | 1H NMR (400 MHz, CHLOROFORM-d) δ 7.54-7.66 (m, 2H), 7.35-7.45 (m, 2H), 7.29-7.35 (m, 1H), 5.18-5.48 (m, 1H), 4.72 (t, J = 7.83 Hz, 1H), 4.37-4.60 (m, 2H), 4.01 (dd, J = 12.49, 19.44 Hz, 1H), 3.84-3.91 (m, 2H), 3.59-3.84 (m, 5H), 2.95 (dd, J = 10.63, 12.80 Hz, 1H), 2.60-2.85 (m, 4H), 2.30-2.50 (m, 1H), 1.76-1.91 (m, 2H), 1.50-1.75 (m, 6H) | J |
| 684 | 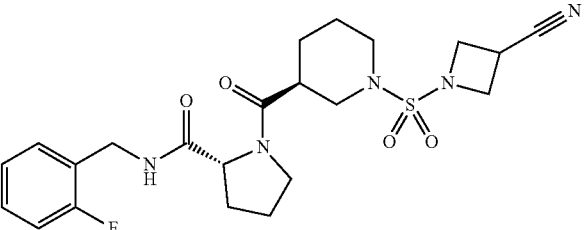<br>1-(((3S)-1-((3-cyano-1-azetidinyl)sulfonyl)-3-piperidinyl)carbonyl)-N-(2-fluorobenzyl)-D-prolinamide | LCMS-ESI (POS.) m/z: 478.2 (M + H)+ | 1H NMR (500 MHz, CHLOROFORM-d) δ ppm 7.23-7.34 (m, 4 H), 7.09-7.15 (m, 1 H), 7.03-7.09 (m, 1 H), 4.61 (br d, J = 7.53 Hz, 1 H), 4.42-4.55 (m, 2 H), 4.10-4.17 (m, 4 H), 3.78 (br d, J = 12.33 Hz, 2 H), 3.53-3.66 (m, 2 H), 3.41-3.51 (m, 1 H), 3.00 (br t, J = 11.74 Hz, 1 H), 2.69-2.83 (m, 2 H), 2.44 (br s, 1 H), 2.15-2.25 (m, 1 H), 1.51-2.12 (m, 5 H) | A |
| 685 | 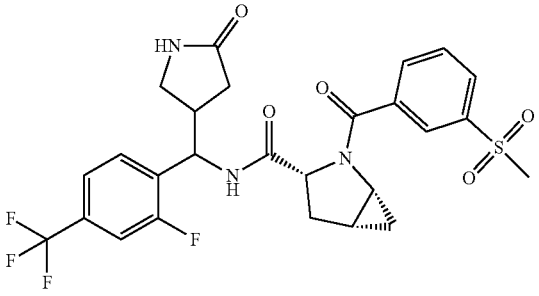 [SMILES: CS(=O)(=O)c1cccc(C(=O)N2[C@@H](C(=O)NC(c3ccc(C(F)(F)F)cc3F)C3CNC(=O)C3)C[C@H]3C[C@H]32)c1]<br>Diastereomer #3 (1R,3R,5R)-N-((2-fluoro-4-(trifluoromethyl)phenyl)(5-oxopyrrolidin-3-yl)methyl)-2-(3-(methylsulfonyl)benzoyl)-2-azabicyclo[3.1.0]hexane-3-carboxamide | LCMS-ESI (POS.) m/z: 568.2 (M + H)+ | 1H NMR (500 MHz, CHLOROFORM-d) δ ppm 8.30-8.43 (m, 1H), 8.12 (br d, J = 7.92 Hz, 1H), 8.07 (d, J = 7.79 Hz, 1H), 7.87 (br d, J = 8.95 Hz, 1H), 7.75 (t, J = 7.85 Hz, 1H), 7.43-7.50 (m, 2H), 7.38 (d, J = 10.38 Hz, 1H), 5.29-5.42 (m, 2H), 5.13 (dd, J = 2.21, 10.64 Hz, 1H), 3.38 (t, J = 9.15 Hz, 1H), 3.28-3.34 (m, 1H), 3.20-3.24 (m, 1H), 3.19 (s, 3H), 2.98-3.08 (m, 1H), 2.69 (br d, J = 12.72 Hz, 1H), 2.28-2.39 (m, 2H), 2.09 (dd, J = 6.68, 17.19 Hz, 1H), 1.70-1.82 (m, 1H), 1.04-1.11 (m, 1H), 0.93-1.00 (m, 1H) | C |

| Ex. # | Structure Name | LCMS-ESI (POS/NEG) m/z: (M + H)+ | NMR Data | Syn. Rte. |
|---|---|---|---|---|
| 686 | 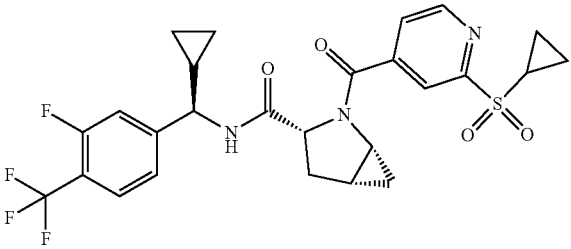 [SMILES: O=C(N[C@@H](c1ccc(C(F)(F)F)c(F)c1)C1CC1)[C@H]1C[C@H]2C[C@H]2N1C(=O)c1ccnc(S(=O)(=O)C2CC2)c1]<br>(1R,3R,5R)-N-((R)-cyclopropyl(3-fluoro-4-(trifluoromethyl)phenyl)methyl)-2-((2-(cyclopropylsulfonyl)-4-pyridinyl)carbonyl)-2-azabicyclo[3.1.0]hexane-3-carboxamide | LCMS-ESI (POS.) m/z: 552.2 (M + H)+ | 1H NMR (500 MHz, CHLOROFORM-d) δ ppm 8.95 (d, J = 4.93 Hz, 1 H), 8.26-8.37 (m, 1 H), 7.78-7.91 (m, 1 H), 7.64-7.68 (m, 1 H), 7.56-7.68 (m, 1 H), 7.37-7.49 (m, 1 H), 7.18-7.28 (m, 2 H), 5.10-5.15 (m, 1 H), 4.33-4.47 (m, 1 H), 3.20-3.28 (m, 1 H), 2.87-2.92 (m, 1 H), 2.62-2.70 (m, 1 H), 2.33-2.47 (m, 1 H), 1.77-1.90 (m, 1 H), 1.39-1.50 (m, 2 H), 1.10-1.26 (m, 4 H), 0.91-1.00 (m, 1 H), 0.58-0.74 (m, 2 H), 0.35-0.51 (m, 2 H) | H |
| 687 | 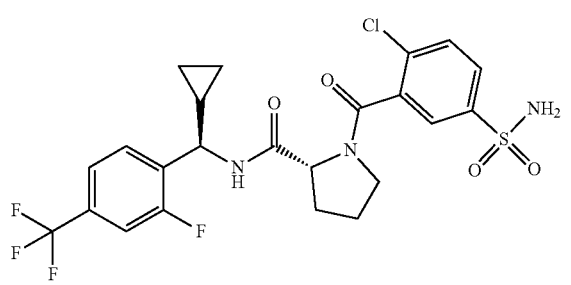 [SMILES: NS(=O)(=O)c1ccc(Cl)c(C(=O)N2CCC[C@@H]2C(=O)N[C@@H](c2ccc(C(F)(F)F)cc2F)C2CC2)c1]<br>1-(2-chloro-5-sulfamoylbenzoyl)-N-((R)-cyclopropyl(2-fluoro-4-(trifluoromethyl)phenyl)methyl)-D-prolinamide | LCMS-ESI (POS.) m/z: 548.2 (M + H)+ | 1H NMR (500 MHz, DMSO-d6) δ ppm 8.40-8.88 (m, 1 H), 7.42-7.91 (m, 8 H), 4.09-4.64 (m, 2 H), 3.48-3.66 (m, 1 H), 3.09-3.24 (m, 1 H), 2.11-2.28 (m, 1 H), 1.62-1.89 (m, 3 H), 0.85-1.28 (m, 1 H), 0.00-0.65 (m, 4 H) | C |
| 688 | 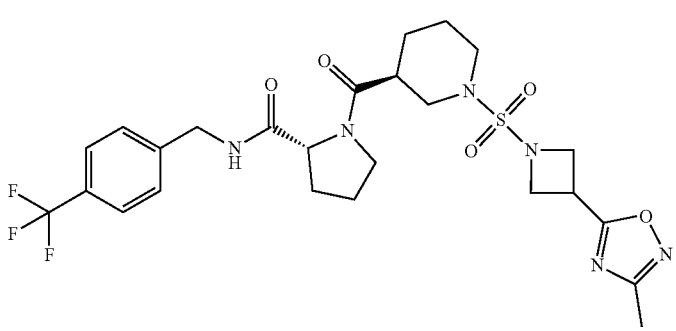 [SMILES: Cc1noc(C2CN(S(=O)(=O)N3CCC[C@H](C(=O)N4CCC[C@@H]4C(=O)NCc4ccc(C(F)(F)F)cc4)C3)C2)n1]<br>1-(((3S)-1-((3-(3-methyl-1,2,4-oxadiazol-5-)-1-azetidinyl)sulfonyl)-3-piperidinyl)carbonyl)-N-(4-(trifluoromethyl)benzyl)-D-prolinamide | LCMS-ESI (POS.) m/z: 585.2 (M + H)+ | 1H NMR (500 MHz, DMSO-d6) δ ppm 8.30-8.77 (m, 1 H), 7.59-7.75 (m, 2 H), 7.45 (br d, J = 7.01 Hz, 2 H), 4.27-4.57 (m, 3 H), 4.14-4.27 (m, 3 H), 4.03 (br d, J = 3.63 Hz, 2 H), 3.50-3.79 (m, 4 H), 2.60-2.91 (m, 3 H), 2.31-2.44 (m, 3 H), 1.69-2.17 (m, 6 H), 1.36-1.63 (m, 2 H) | M |
| 689 | 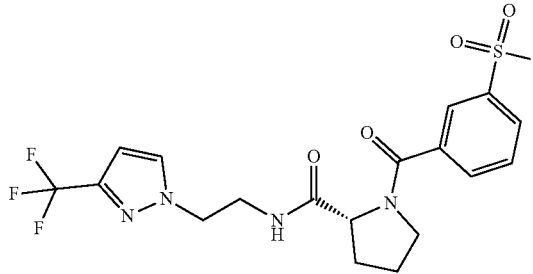<br>1-((3-((3-cyano-1-azetidinyl)sulfonyl)phenyl)carbonyl)-N-(2-(3-(trifluoromethyl)-1H-pyrazol-1-yl)ethyl)-D-prolinamide | LCMS-APCI (POS.) m/z: 525.2 (M + H)+ | 1H NMR (400 MHz, Methanol-d4) δ ppm 7.63-8.15 (m, 6 H), 6.56-6.60 (m, 1 H), 3.49-4.53 (m, 12 H), 1.83-2.34 (m, 4 H). | A |

| Ex. # | Structure Name | LCMS-ESI (POS/NEG) m/z: (M + H)+ | NMR Data | Syn. Rte. |
|---|---|---|---|---|
| 690 | 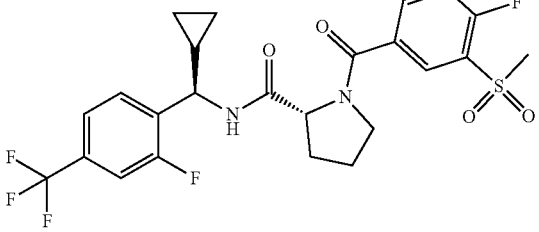<br>N-((R)-cyclopropyl(2-fluoro-4-(trifluoromethyl)phenyl)methyl)-1-(4-fluoro-3-(methylsulfonyl)benzoyl)-D-prolinamide | LCMS-ESI (POS.) m/z: 531.0 (M + H)+ | 1H NMR (500 MHz, DMSO-d6) δ ppm 8.47-8.80 (m, 1 H), 7.49-8.03 (m, 6 H), 4.30-4.32 (m, 1 H), 4.25-4.62 (m, 1 H), 3.44-3.61 (m, 2 H), 3.33-3.41 (m, 3 H), 2.14-2.30 (m, 1 H), 1.65-1.88 (m, 3 H), 0.93-1.26 (m, 1 H), −0.08-0.64 (m, 4 H) | C |
| 691 | 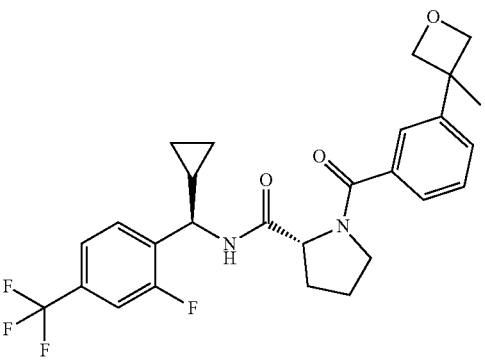 [SMILES: CC1(c2cccc(C(=O)N3CCC[C@@H]3C(=O)N[C@@H](c3ccc(C(F)(F)F)cc3F)C3CC3)c2)COC1]<br>N-((R)-cyclopropyl(2-fluoro-4-(trifluoromethyl)phenyl)methyl)-1-(3-(3-methyl-3-oxetanyl)benzoyl)-D-prolinamide | LCMS-APCI (POS.) m/z: 505.2 (M + H)+ | 1H NMR (400 MHz, Methanol-d4) δ ppm 7.18-8.95 (m, 7 H), 4.90-4.95 (m, 2 H), 4.06-4.63 (m, 4 H), 3.39-3.68 (m, 2 H), 2.17-2.32 (m, 1 H), 1.73-1.94 (m, 3 H), 1.66 (s, 3 H), 0.93-1.29 (m, 1 H), −0.06-0.67 (m, 4 H). | Q |
| 692 | 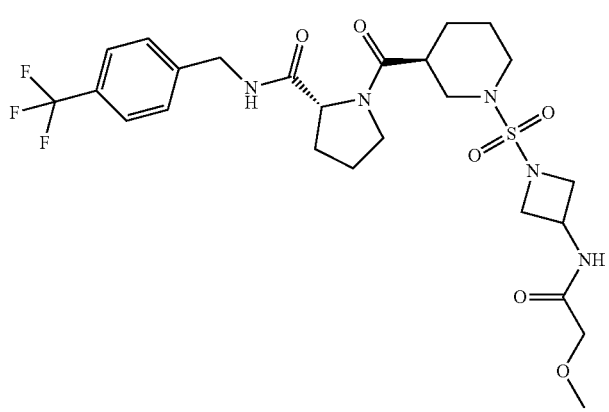 [SMILES: COCC(=O)NC1CN(S(=O)(=O)N2CCC[C@H](C(=O)N3CCC[C@@H]3C(=O)NCc3ccc(C(F)(F)F)cc3)C2)C1]<br>1-(((3S)-1-((3-((methoxyacetyl)amino)-1-azetidinyl)sulfonyl)-3-piperidinyl)carbonyl)-N-(4-(trifluoromethyl)benzyl)-D-prolinamide | LCMS-ESI (POS.) m/z: 590.2 (M + H)+ | 1H NMR (500 MHz, DMSO-d6) δ ppm 8.25-8.86 (m, 2 H), 7.45 (br d, J = 7.79 Hz, 2 H), 7.36-7.77 (m, 2 H), 6.97-7.30 (m, 1 H), 4.25-4.61 (m, 4 H), 3.88-4.09 (m, 10 H), 3.83-3.88 (m, 2 H), 3.41-3.69 (m, 4 H), 3.17 (s, 1 H), 2.58-2.91 (m, 3 H), 1.58-2.41 (m, 7 H), 1.31-1.57 (m, 2 H) | M |

| Ex. # | Structure Name | LCMS-ESI (POS/NEG) m/z: (M + H)+ | NMR Data | Syn. Rte. |
|---|---|---|---|---|
| 693 | 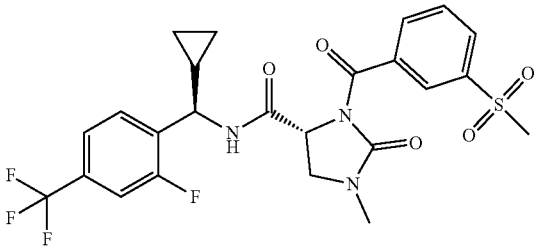 [SMILES: CN1C[C@H](C(=O)N[C@@H](c2ccc(C(F)(F)F)cc2F)C2CC2)N(C(=O)c2cccc(S(C)(=O)=O)c2)C1=O]<br>(4R)-N-((R)-cyclopropyl(2-fluoro-4-(trifluoromethyl)phenyl)methyl)-1-methyl-3-(3-(methylsulfonyl)benzoyl)-2-oxo-4-imidazolidinecarboxamide | LCMS-ESI (POS.) m/z: 542.0 (M + H)+ | 1H NMR (500 MHz, CHLOROFORM-d) δ ppm 8.19 (s, 1 H), 8.10 (d, J = 7.91 Hz, 1 H), 7.89 (d, J = 7.78 Hz, 1 H), 7.65 (t, J = 7.79 Hz, 1 H), 7.39-7.51 (m, 2 H), 7.36 (d, J = 10.38 Hz, 1 H), 7.29 (br s, 1 H), 4.97 (dd, J = 9.34, 4.02 Hz, 1 H), 4.53 (t, J = 8.17 Hz, 1 H), 3.83 (dd, J = 9.47, 4.02 Hz, 1 H), 3.62 (t, J = 9.41 Hz, 1 H), 3.10 (s, 3 H), 2.87 (s, 3 H), 1.21-1.35 (m, 1 H), 0.61-0.73 (m, 1 H), 0.52-0.60 (m, 1 H), 0.46 (dq, J = 9.70, 4.90 Hz, 1 H), 0.36-0.42 (m, 1 H) | C |
| 694 | 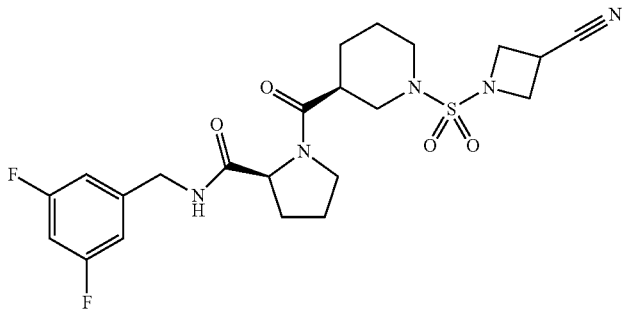 [SMILES: N#CC1CN(S(=O)(=O)N2CCC[C@H](C(=O)N3CCC[C@H]3C(=O)NCc3cc(F)cc(F)c3)C2)C1]<br>1-(((3S)-1-((3-cyano-1-azetidinyl)sulfonyl)-3-piperidinyl)carbonyl)-N-(3,5-difluorobenzyl)-L-prolinamide | LCMS-ESI (POS.) m/z: 496.2 (M + H)+ | 1H NMR (500 MHz, DMSO-d6) δ ppm 8.37-8.81 (m, 1 H), 7.02-7.16 (m, 1 H), 6.96 (br d, J = 7.40 Hz, 2 H), 4.19-4.48 (m, 3 H), 3.99-4.10 (m, 2 H), 3.89-3.97 (m, 2 H), 3.75-3.84 (m, 1 H), 3.35-3.72 (m, 4 H), 2.71-2.86 (m, 2 H), 2.60-2.69 (m, 1 H), 2.07-2.33 (m, 1 H), 1.69-1.98 (m, 5 H), 1.32-1.59 (m, 2 H) | M |
| 695 | 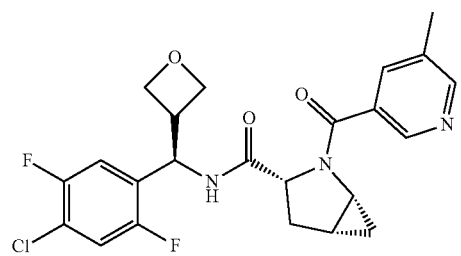 [SMILES: Cc1cncc(C(=O)N2[C@@H](C(=O)N[C@@H](c3cc(F)c(Cl)cc3F)C3COC3)C[C@H]3C[C@H]32)c1]<br>(1R,3R,5R)-N-((R)-(4-chloro-2,5-difluorophenyl)(3-oxetanyl)methyl)-2-((5-methyl-3-pyridinyl)carbonyl)-2-azabicyclo[3.1.0]hexane-3-carboxamide | LCMS-APCI (POS.) m/z: 462.1 (M + H)+ | 1H NMR (400 MHz, Methanol-d4) δ ppm 8.75 (d, J = 2.0 Hz, 1 H), 8.53 (d, 1 H), 8.03 (td, J = 0.9, 2.0 Hz, 1 H), 7.39 (dd, J = 6.1, 9.5 Hz, 1 H), 7.27 (dd, J = 6.3, 9.4 Hz, 1 H), 5.57 (d, J = 10.2 Hz, 1 H), 4.98 (dd, J = 4.2, 11.4 Hz, 1 H), 4.84 (dd, J = 6.5, 7.7 Hz, 1 H), 4.67 (dd, J = 6.4, 7.9 Hz, 1 H), 4.60 (t, J = 6.2 Hz, 1 H), 4.37 (t, J = 6.2 Hz, 1 H), 4.12 (q, J = 7.1 Hz, 1 H), 3.45-3.56 (m, 1 H), 2.67 (dddd, J = 1.1, 6.4, 11.6, 13.3 Hz, 1 H), 2.45 (s, 3 H), 2.03 (s, 1 H), 1.90 (dd, J = 4.2, 13.5 Hz, 1 H), 1.75-1.85 (m, 1 H), 1.21-1.29 (m, 2 H), 0.89 (dtd, J = 1.1, 5.7, 9.2 Hz, 1 H). | Q |

-continued

| Ex. # | Structure Name | LCMS-ESI (POS/NEG) m/z: (M + H)+ | NMR Data | Syn. Rte. |
|---|---|---|---|---|
| 696 | N-((R)-cyclopropyl(2-fluoro-4-(trifluoromethyl)phenyl)methyl)-1-methyl-3-(3-(methylsulfonyl)benzoyl)-2-oxoimidazolidine-4-carboxamide | LCMS-ESI (POS.) m/z: 542.2 (M + H)+ | Note: Amide 1H obscured by solevent 1H NMR (400 MHz, CHLOROFORM-d) δ ppm 8.19 (s, 1 H), 8.07-8.14 (m, 1 H), 7.76-7.93 (m, 1 H), 7.61-7.70 (m, 1 H), 7.40-7.52 (m, 2 H), 7.31-7.40 (m, 2 H), 4.93-5.13 (m, 1 H), 4.44-4.58 (m, 1 H), 3.81-4.02 (m, 1 H), 3.57-3.68 (m, 1 H), 3.06-3.15 (m, 3 H), 2.83-2.90 (m, 3 H), 1.22-1.35 (m, 1 H), 0.53-0.72 (m, 2 H), 0.33-0.51 (m, 2 H) | C |
| 697 | (2R)-1-((3S)-1-((2-(4-chlorophenyl)azetidin-1-yl)sulfonyl)piperidine-3-carbonyl)-N-(4-(trifluoromethyl)benzyl)pyrrolidine-2-carboxamide | LCMS-ESI (POS.) m/z: 613.2 (M + H)+ | 1H NMR (500 MHz, DMSO-d6) δ 8.27-8.76 (m, 1H), 7.58-7.75 (m, 2H), 7.27-7.57 (m, 6H), 5.00-5.20 (m, 1H), 4.19-4.48 (m, 3H), 3.77-3.93 (m, 1H), 3.34-3.75 (m, 6H), 2.53-2.73 (m, 2H), 2.02-2.34 (m, 3H), 1.53-2.02 (m, 5H), 1.13-1.44 (m, 2H) | J |
| 698 | 1-(((3S)-1-((3-cyano-1-azetidinyl)sulfonyl)-3-piperidinyl)carbonyl)-N-((1R)-1-(2-(difluoromethoxy)-4-fluorophenyl)ethyl)-D-prolinamide | LCMS-ESI (POS.) m/z: 558.2 (M + H)+ | 1H NMR (500 MHz, DMSO-d6) δ ppm 8.21 _ 8.64 (m, 1 H), 7.01-7.51 (m, 4 H), 5.01-5.19 (m, 1 H), 4.25-4.49 (m, 1 H), 4.01-4.14 (m, 2 H), 3.88-4.00 (m, 2 H), 3.74-3.85 (m, 1 H), 3.47-3.66 (m, 4 H), 2.59-2.91 (m, 3 H), 1.99-2.36 (m, 1 H), 1.61-1.97 (m, 5 H), 1.23-1.58 (m, 5 H) | A |
| 699 | 1-(((3S)-1-((3-(4-chlorobenzyl)-1-azetidinyl)sulfonyl)-3-piperidinyl)carbonyl)-N-(4-(trifluoromethyl)benzyl)-D-prolinamide | LCMS-ESI (POS.) m/z: 627.2 (M + H)+ | 1H NMR (500 MHz, CHLOROFORM-d) δ ppm 7.56 (d, J = 8.04 Hz, 2 H), 7.47 (br s, 1 H), 7.35 (d, J = 8.04 Hz, 2 H), 7.25-7.28 (m, 2 H), 7.07 (d, J = 8.56 Hz, 2 H), 4.60 (dd, J = 7.91, 1.69 Hz, 1 H), 4.38-4.55 (m, 2 H), 3.88 (t, J = 7.66 Hz, 2 H), 3.73-3.82 (m, 2 H), 3.54-3.66 (m, 4 H), 2.78-2.93 (m, 4 H), 2.62-2.78 (m, 2 H), 2.42-2.56 (m, 1 H), 2.10-2.32 (m, 1 H), 2.00-2.09 (m, 1 H), 1.81-1.98 (m, 3 H), 1.73-1.81 (m, 1 H), 1.58-1.69 (m, 3 H), 1.44-1.58 (m, 2 H) | M |

| Ex. # | Structure Name | LCMS-ESI (POS/NEG) m/z: (M + H)+ | NMR Data | Syn. Rte. |
|---|---|---|---|---|
| 700 | 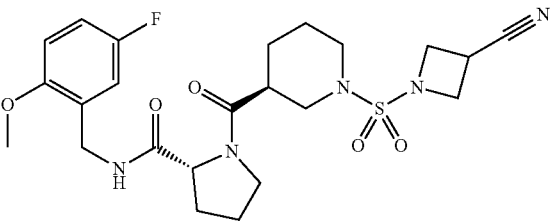 [SMILES: COc1ccc(F)cc1CNC(=O)[C@H]1CCCN1C(=O)[C@H]1CCCN(S(=O)(=O)N2CC(C#N)C2)C1]<br>1-(((3S)-1-((3-cyano-1-azetidinyl)sulfonyl)-3-piperidinyl)carbonyl)-N-(5-fluoro-2-methoxybenzyl)-D-prolinamide | LCMS-ESI (POS.) m/z: 508.2 (M + H)+ | 1H NMR (500 MHz, DMSO-d6) δ ppm 8.12-8.56 (m, 1 H), 6.82-7.17 (m, 3 H), 4.29-4.59 (m, 1 H), 4.12-4.29 (m, 2 H), 3.87-4.11 (m, 4 H), 3.74-3.84 (m, 4 H), 3.49-3.71 (m, 4 H), 2.62-2.89 (m, 3 H), 2.03-2.26 (m, 1 H), 1.63-1.99 (m, 5 H), 1.32-1.57 (m, 2 H) | A |
| 701 | 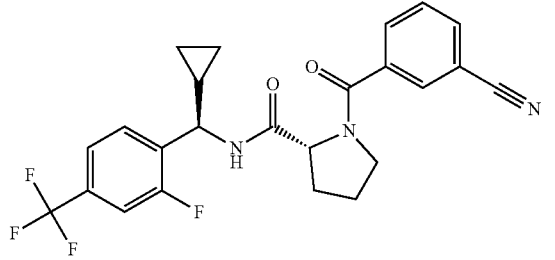 [SMILES: N#Cc1cccc(C(=O)N2CCC[C@@H]2C(=O)N[C@@H](c2ccc(C(F)(F)F)cc2F)C2CC2)c1]<br>1-(3-cyanobenzoyl)-N-((R)-cyclopropyl(2-fluoro-4-(trifluoromethyl)phenyl)methyl)-D-prolinamide | LCMS-ESI (POS.) m/z: 460.0 (M + H)+ | 1H NMR (400 MHz, CHLOROFORM-d) δ ppm 7.82-7.88 (m, 1 H), 7.74-7.81 (m, 2 H), 7.56-7.64 (m, 1 H), 7.49 (br dd, J = 16.53, 7.83 Hz, 2 H), 7.39-7.44 (m, 1 H), 7.34 (br d, J = 10.37 Hz, 1 H), 4.70-4.80 (m, 1 H), 4.60 (t, J = 7.88 Hz, 1 H), 3.52-3.63 (m, 1 H), 3.38-3.49 (m, 1 H), 2.34-2.47 (m, 1 H), 2.00-2.18 (m, 2 H), 1.83-1.97 (m, 1 H), 1.20-1.34 (m, 1 H), 0.50-0.69 (m, 2 H), 0.31-0.50 (m, 2 H) | C |
| 702 | 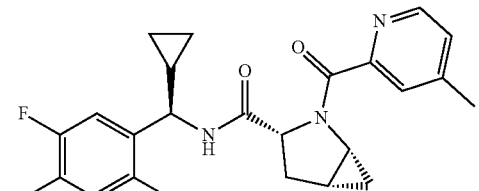<br>(1R,3R,5R)-N-((R)-(4-chloro-2,5-difluorophenyl)(cyclopropyl)methyl)-2-((4-methyl-2-pyridinyl)carbonyl)-2-azabicyclo[3.1.0]hexane-3-carboxamide | LCMS-APCI (POS.) m/z: 446.1 (M + H)+ | 1H NMR (DMSO-d6) δ: 8.66 (d, J = 7.8 Hz, 1H), 8.59 (d, J = 5.0 Hz, 1H), 8.50 (d, J = 8.1 Hz, 1H), 8.43 (d, J = 5.1 Hz, 1H), 7.78-7.63 (m, 2H), 7.60 (dd, J = 9.8, 6.3 Hz, 1H), 7.52 (dd, J = 9.9, 6.4 Hz, 1H), 7.46 (d, 1H), 7.40 (d, J = 4.9 Hz, 1H), 5.57 (dd, J = 11.5, 2.7 Hz, 1H), 4.97 (dd, J = 11.4, 3.2 Hz, 1H), 4.62 (t, J = 8.0 Hz, 1H), 4.25 (t, J = 8.4 Hz, 2H), 4.05 (td, J = 6.3, 2.5 Hz, 1H), 3.90 (td, J = 6.1, 2.7 Hz, 1H), 3.79-3.65 (m, 2H), 2.48 (d, J = 13.3 Hz, 5H), 2.01-1.76 (m, 4H), 1.75-1.67 (m, 1H), 1.66-1.57 (m, 1H), 1.38-1.20 (m, 3H), 1.16-1.04 (m, 2H), 0.89-0.77 (m, 2H), 0.73-0.60 (m, 2H), 0.60-0.51 (m, 1H), 0.50-0.39 (m, 3H), 0.16-0.05 (m, 1H) | Q |

-continued

| Ex. # | Structure Name | LCMS-ESI (POS/NEG) m/z: (M + H)+ | NMR Data | Syn. Rte. |
|---|---|---|---|---|
| 703 | 1-(((3S)-1-((3,3-difluoro-1-azetidinyl)sulfonyl)-3-piperidinyl)carbonyl)-N-(4-(trifluoromethyl)benzyl)-D-prolinamide | LCMS-ESI (POS.) m/z: 539.2 (M + H)+ | 1H NMR (500 MHz, CHLOROFORM-d) δ ppm 7.57 (d, J = 8.04 Hz, 1 H), 7.35 (d, J = 8.04 Hz, 3 H), 4.37-4.64 (m, 3 H), 3.80 (br d, J = 12.46 Hz, 2 H), 3.53-3.65 (m, 2 H), 2.96 (dd, J = 12.33, 11.29 Hz, 1 H), 2.67-2.81 (m, 2 H), 2.45 (ddd, J = 12.26, 6.16, 3.11 Hz, 1 H), 2.13-2.26 (m, 1 H), 2.00-2.11 (m, 1 H), 1.77-1.95 (m, 3 H), 1.66 (qt, J = 13.04, 3.80 Hz, 1 H), 1.50 (qd, J = 12.72, 3.89 Hz, 1 H), 1.19-1.38 (m, 2 H) | M |
| 704 | N-((R)-cyclopropyl(2-fluoro-4-(trifluoromethyl)phenyl)methyl)-1-(3-(1-(methylsulfonyl)-3-azetidinyl)benzoyl)-D-prolinamide | LCMS-APCI (POS.) m/z: 568.2 (M + H)+ | 1H NMR (400 MHz, Methanol-d4) δ ppm 7.09-7.50 (m, 7 H), 4.24-4.45 (m, 2 H), 4.11 (dd, J = 7.0, 9.4 Hz, 2 H), 3.68-3.87 (m, 3 H), 3.27-3.54 (m, 2 H), 2.79-2.83 (m, 3 H), 2.06-2.17 (m, 1H), 1.60-1.78 (m, 3 H), 0.79-1.16 (m, 1 H), -0.22-0.56 (m, 4 H). | Q |
| 705 | (2R)-N-(bicyclo[4.2.0]octa-1(6),2,4-trien-7-yl)-1-((S)-1-((3-cyanoazetidin-1-yl)sulfonyl)piperidine-3-carbonyl)pyrrolidine-2-carboxamide | LCMS-ESI (POS.) m/z: 472.2 (M + H)+ | 1H NMR (500 MHz, DMSO-d6) δ ppm 8.38-8.94 (m, 1 H), 7.05-7.36 (m, 4 H), 5.13-5.44 (m, 1 H), 4.20-4.45 (m, 1 H), 3.72-4.16 (m, 5 H), 3.49-3.71 (m, 4 H), 2.90-3.07 (m, 1 H), 2.59-2.89 (m, 3 H), 2.16-2.38 (m, 1 H), 1.66-2.12 (m, 6 H), 1.33-1.57 (m, 2 H) | A |

| Ex. # | Structure Name | LCMS-ESI (POS/NEG) m/z: (M + H)+ | NMR Data | Syn. Rte. |
|---|---|---|---|---|
| 706 | 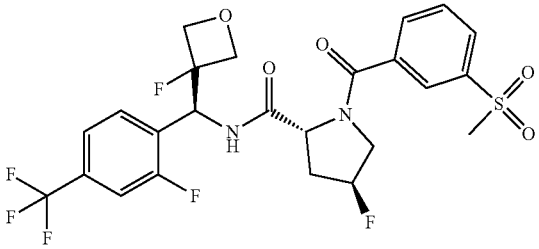 [SMILES: CS(=O)(=O)c1cccc(C(=O)N2C[C@@H](F)C[C@@H]2C(=O)N[C@@H](c2ccc(C(F)(F)F)cc2F)C2(F)COC2)c1]<br>(4S)-4-fluoro-N-((S)-(3-fluoro-3-oxetanyl)(2-fluoro-4-(trifluoromethyl)phenyl)methyl)-1-(3-(methylsulfonyl)benzoyl)-D-prolinamide | LCMS-APCI (POS.) m/z: 565.1 (M + H)+ | 1H NMR (DMSO-d6) δ: 9.33 (d, J = 8.9 Hz, 1H), 8.05-8.01 (m, 1H), 7.96-7.87 (m, 1H), 7.84-7.65 (m, 4H), 5.94 (dd, J = 26.1, 9.0 Hz, 1H), 5.38 (s, 1H), 5.25 (s, 1H), 4.86-4.51 (m, 4H), 4.07-3.86 (m, 2H), 3.62 (dd, J = 19.6, 12.5 Hz, 1H), 3.45 (qd, J = 7.0, 5.1 Hz, 2H), 1.11-1.00 (m, 3H) | C |
| 707 | 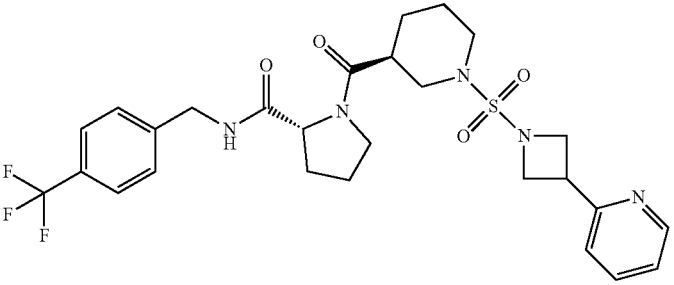 [SMILES: O=C(NCc1ccc(C(F)(F)F)cc1)[C@H]1CCCN1C(=O)[C@H]1CCCN(S(=O)(=O)N2CC(c3ccccn3)C2)C1]<br>1-(((3S)-1-((3-(2-pyridinyl)-1-azetidinyl)sulfonyl)-3-piperidinyl)carbonyl)-N-(4-(trifluoromethyl)benzyl)-D-prolinamide | LCMS-ESI (POS.) m/z: 580.2 (M + H)+ | 1H NMR (500 MHz, DMSO-d6) δ ppm 8.30-8.78 (m, 2 H), 7.60-7.85 (m, 3 H), 7.24-7.51 (m, 4 H), 4.24-4.55 (m, 4 H), 3.93-4.19 (m, 6 H), 3.42-3.77 (m, 5 H), 2.60-2.99 (m, 3 H), 1.67-2.41 (m, 7 H), 1.34-1.62 (m, 2 H) | M |
| 708 | 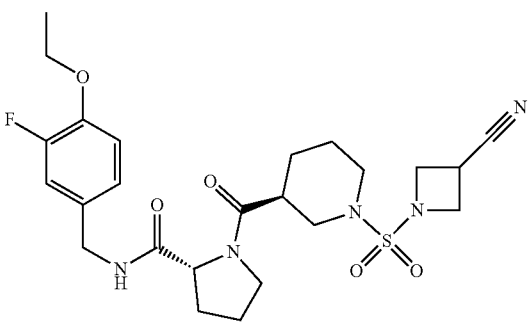 [SMILES: CCOc1ccc(CNC(=O)[C@H]2CCCN2C(=O)[C@H]2CCCN(S(=O)(=O)N3CC(C#N)C3)C2)cc1F]<br>1-(((3S)-1-((3-cyano-1-azetidinyl)sulfonyl)-3-piperidinyl)carbonyl)-N-(4-ethoxy-3-fluorobenzyl)-D-prolinamide | LCMS-ESI (POS.) m/z: 522.2 (M + H)+ | 1H NMR (500 MHz, DMSO-d6) δ ppm 8.15-8.63 (m, 1 H), 6.83-7.25 (m, 3 H), 4.16-4.51 (m, 3 H), 3.99-4.11 (m, 4 H), 3.86-3.98 (m, 2 H), 3.71-3.83 (m, 1 H), 3.40-3.65 (m, 4 H), 2.63-2.90 (m, 3 H), 2.01-2.34 (m, 1 H), 1.64-1.98 (m, 5 H), 1.38-1.57 (m, 2 H), 1.32 (br t, J = 6.94 Hz, 3 H) | A |
| 709 | 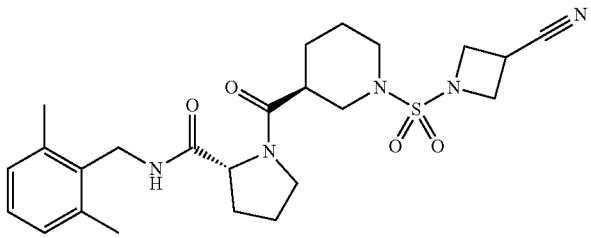 [SMILES: Cc1cccc(C)c1CNC(=O)[C@H]1CCCN1C(=O)[C@H]1CCCN(S(=O)(=O)N2CC(C#N)C2)C1]<br>1-(((3S)-1-((3-cyano-1-azetidinyl)sulfonyl)-3-piperidinyl)carbonyl)-N-(2,6-dimethylbenzyl)-D-prolinamide | LCMS-ESI (POS.) m/z: 487.2 (M + H)+ | 1H NMR (500 MHz, DMSO-d6) δ ppm 7.78-8.19 (m, 1 H), 6.98-7.11 (m, 3 H), 4.17-4.45 (m, 3 H), 4.01-4.10 (m, 2 H), 3.88-3.98 (m, 2 H), 3.73-3.85 (m, 1 H), 3.33-3.63 (m, 4 H), 2.62-2.85 (m, 2 H), 2.12-2.33 (m, 7 H), 1.67-2.05 (m, 6 H), 1.30-1.57 (m, 2 H) | A |

| Ex. # | Structure Name | LCMS-ESI (POS/NEG) m/z: (M + H)+ | NMR Data | Syn. Rte. |
|---|---|---|---|---|
| 710 | 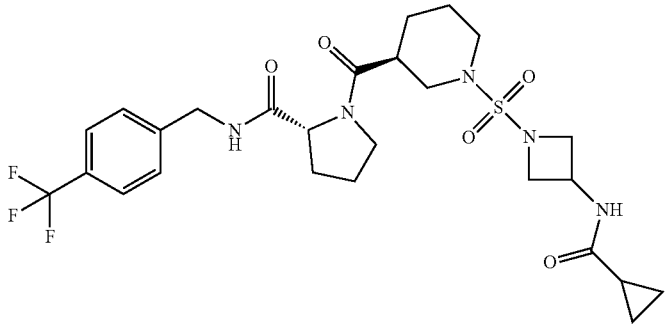 [SMILES: O=C(NC1CN(S(=O)(=O)N2CCC[C@H](C(=O)N3CCC[C@@H]3C(=O)NCc3ccc(C(F)(F)F)cc3)C2)C1)C1CC1]<br>1-(((3S)-1-((3-((cyclopropylcarbonyl)amino)-1-azetidinyl)sulfonyl)-3-piperidinyl)carbonyl)-N-(4-(trifluoromethyl)benzyl)-D-prolinamide | LCMS-ESI (POS.) m/z: 586.2 (M + H)+ | 1H NMR (500 MHz, DMSO-d6) δ ppm 8.62-8.85 (m, 1 H), 8.26-8.47 (m, 1 H), 7.35-7.76 (m, 4 H), 4.21-4.58 (m, 4 H), 3.88-4.01 (m, 2 H), 3.51-3.80 (m, 6 H), 2.61-2.98 (m, 3 H), 1.24-2.28 (m, 9 H), 0.67 (br d, J = 5.97 Hz, 4 H) | M |
| 711 | 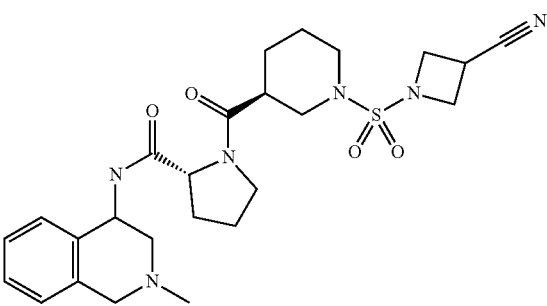 [SMILES: CN1Cc2ccccc2C(NC(=O)[C@H]2CCCN2C(=O)[C@H]2CCCN(S(=O)(=O)N3CC(C#N)C3)C2)C1]<br>(2R)-1-((S)-1-((3-cyanoazetidin-1-yl)sulfonyl)piperidine-3-carbonyl)-N-(2-methyl-1,2,3,4-tetrahydroisoquinolin-4-yl)pyrrolidine-2-carboxamide | LCMS-ESI (POS.) m/z: 514.2 (M + H)+ | 1H NMR (500 MHz, DMSO-d6) δ ppm 7.91-8.57 (m, 1 H), 6.95-7.27 (m, 4 H), 4.97-5.13 (m, 1 H), 4.23-4.51 (m, 1 H), 4.06 (br t, J = 8.24 Hz, 2 H), 3.87-4.00 (m, 2 H), 3.73-3.85 (m, 1 H), 3.41-3.66 (m, 5 H), 2.58-2.91 (m, 5 H), 2.25-2.41 (m, 4 H), 1.66-2.23 (m, 6 H), 1.31-1.57 (m, 2 H) | A |
| 712 | 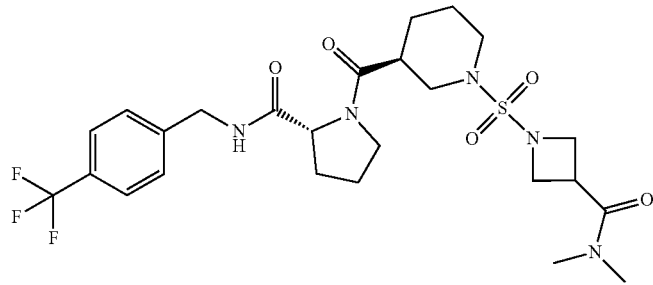 [SMILES: CN(C)C(=O)C1CN(S(=O)(=O)N2CCC[C@H](C(=O)N3CCC[C@@H]3C(=O)NCc3ccc(C(F)(F)F)cc3)C2)C1]<br>1-(((3S)-1-((3-(dimethylcarbamo)-1-azetidinyl)sulfonyl)-3-piperidinyl)carbonyl)-N-(4-(trifluoromethyl)benzyl)-D-prolinamide | LCMS-ESI (POS.) m/z: 574.2 (M + H)+ | 1H NMR (400 MHz, CHLOROFORM-d) δ 7.55-7.65 (m, 2H), 7.45-7.54 (m, 1H), 7.32-7.44 (m, 2H), 4.61 (dd, J = 1.97, 7.98 Hz, 1H), 4.47-4.55 (m, 1H), 4.35-4.45 (m, 1H), 4.10-4.18 (m, 2H), 4.03 (dt, J = 3.84, 8.24 Hz, 2H), 3.76-3.86 (m, 2H), 3.60 (dd, J = 5.23, 8.76 Hz, 2H), 3.47-3.56 (m, 1H), 2.90-3.01 (m, 4H), 2.86-2.90 (m, 3H), 2.67-2.84 (m, 2H), 2.42-2.52 (m, 1H), 2.11-2.25 (m, 1H), 1.98-2.11 (m, 1H), 1.82-1.95 (m, 2H), 1.73-1.82 (m, 1H), 1.58-1.65 (m, 1H), 1.49-1.58 (m, 1H) | J |

-continued

| Ex. # | Structure Name | LCMS-ESI (POS/NEG) m/z: (M + H)+ | NMR Data | Syn. Rte. |
|---|---|---|---|---|
| 713 | (1R,3R,5R)-N-((R)-(4-chloro-2,5-difluorophenyl)(cyclopropyl)methyl)-2-((4-cyclopropyl-2-pyridinyl)carbonyl)-2-azabicyclo[3.1.0]hexane-3-carboxamide | LCMS-APCI (POS.) m/z: 472.2 (M + H)+ | 1H NMR (DMSO-d6) δ: 8.62 (d, J = 7.6 Hz, 1H), 8.53 (d, J = 5.0, 0.8 Hz, 1H), 7.65 (dd, J = 9.4, 6.1 Hz, 1H), 7.50 (dd, J = 9.8, 6.3 Hz, 1H), 7.46 (s, 1H), 7.31 (dd, J = 5.0, 1.5 Hz, 1H), 4.89 (dd, J = 11.3, 3.4 Hz, 1H), 4.51 (t, J = 7.9 Hz, 1H), 3.68-3.56 (m, 1H), 3.22 (td, J = 6.2, 2.5 Hz, 1H), 2.27-2.15 (m, 1H), 1.82-1.75 (m, 1H), 1.72 (dd, J = 13.5, 3.6 Hz, 1H), 1.22-1.14 (m, 2H), 1.08 (td, J = 5.1, 2.6 Hz, 1H), 1.05-0.89 (m, 4H), 0.61-0.50 (m, 1H), 0.50-0.41 (m, 1H), 0.40-0.30 (m, 2H) | Q |
| 714 | 1-(((3S)-1-((3-cyano-1-azetidinyl)sulfonyl)-3-piperidinyl)carbonyl)-N-(2-methyl-5-(trifluoromethyl)benzyl)-D-prolinamide | LCMS-ESI (POS.) m/z: 542.0 (M + H)+ | 1H NMR (500 MHz, DMSO-d6) δ ppm 8.27-8.70 (m, 1 H), 7.15-7.65 (m, 3 H), 4.47-4.57 (m, 1 H), 4.31-4.38 (m, 2 H), 3.97-4.10 (m, 2 H), 3.85-3.97 (m, 2 H), 3.74-3.83 (m, 1 H), 3.30-3.71 (m, 4 H), 2.72-2.91 (m, 2 H), 2.62-2.72 (m, 1 H), 2.32-2.41 (m, 3 H), 1.64-2.27 (m, 6 H), 1.37-1.55 (m, 2 H) | A |
| 715 | N-((R)-cyclopropyl(2-fluoro-4-(trifluoromethyl)phenyl)methyl)-1-(3-methylbenzoyl)-D-prolinamide | LCMS-ESI (POS.) m/z: 449.2 (M + H)+ | 1H NMR (500 MHz, DMSO-d6) δ ppm 8.65 (br d, J = 7.40 Hz, 1 H), 7.90-8.22 (m, 1 H), 7.52-7.67 (m, 3 H), 7.22-7.33 (m, 3 H), 4.50-4.66 (m, 1 H), 4.27-4.35 (m, 1 H), 3.37-3.60 (m, 2 H), 2.29-2.40 (m, 3 H), 2.05-2.21 (m, 1 H), 1.64-1.89 (m, 3 H), 1.01-1.26 (m, 1 H), 0.09-0.65 (m, 4 H) | C |
| 716 | N-((R)-cyclopropyl(2-fluoro-4-(trifluoromethyl)phenyl)methyl)-1-(2-methyl-5-sulfamoylbenzoyl)-D-prolinamide | LCMS-ESI (POS.) m/z: 528.2 (M + H)+ | 1H NMR (500 MHz, DMSO-d6) δ ppm 8.76 (br d, J = 7.27 Hz, 1 H), 7.16-7.79 (m, 8 H), 4.09-4.66 (m, 2 H), 3.47-3.69 (m, 1 H), 3.03-3.16 (m, 1 H), 2.23-2.37 (m, 3 H), 2.13-2.23 (m, 1 H), 1.64-1.94 (m, 3 H), 0.76-1.26 (m, 1 H), −0.13-0.64 (m, 4 H) | C |

| Ex. # | Structure Name | LCMS-ESI (POS/NEG) m/z: (M + H)+ | NMR Data | Syn. Rte. |
|---|---|---|---|---|
| 717 | (1R,3R,5R)-N-((R)-cyclopropyl(2,5-difluoro-4-(trifluoromethyl)phenyl)methyl)-2-((2-methyl-4-pyridinyl)carbonyl)-2-azabicyclo[3.1.0]hexane-3-carboxamide | LCMS-APCI (POS.) m/z: 480.2 (M + H)+ | 1H NMR (400 MHz, Methanol-d4) δ ppm 8.52-8.94 (m, 2 H), 7.37-7.61 (m, 3 H), 5.02 (dd, J = 3.9, 11.4 Hz, 1 H), 4.45-4.57 (m, 1 H), 3.69-3.90 (m, 1 H), 3.28 (td, J = 2.6, 6.3 Hz, 1 H), 2.70 (td, J = 6.0, 12.4 Hz, 1 H), 2.61 (s, 2 H), 1.71-1.99 (m, 3 H), 1.28 (qd, J = 4.0, 8.2 Hz, 1 H), 1.16 (td, J = 2.6, 5.3 Hz, 1 H), 0.77-0.88 (m, 1 H), 0.70 (tt, J = 4.5, 8.3 Hz, 1 H), 0.53-0.63 (m, 1 H), 0.40-0.53 (m, 2 H). | Q |
| 718 | (1R,3R,5R)-2((4-cyclopropyl-2-pyridinyl)carbonyl)-N-((R)-(2-fluoro-4-(trifluoromethyl)phenyl)(3-oxetanyl)methyl)-2-azabicyclo[3.1.0]hexane-3-carboxamide | LCMS-APCI (POS.) m/z: 504.2 (M + H)+ | 1H NMR (DMSO-d6) δ: 8.74 (d, J = 8.1 Hz, 1H), 8.52 (d, J = 4.9, 0.8 Hz, 1H), 7.70 (d, J = 10.4 Hz, 1H), 7.63-7.56 (m, 1H), 7.48-7.39 (m, 1H), 7.31 (dd, J = 5.0, 1.5 Hz, 1H), 5.48 (t, 1H), 4.86 (dd, J = 11.3, 3.6 Hz, 1H), 4.65 (t, J = 7.8, 6.4 Hz, 1H), 4.52 (t, 1H), 4.41 (t, J = 6.2 Hz, 1H), 4.23 (t, J = 6.1 Hz, 1H), 3.79-3.68 (m, 1H), 3.47-3.37 (m, 1H), 3.22 (td, J = 6.1, 2.5 Hz, 1H), 2.28-2.14 (m, 1H), 1.71-1.62 (m, 2H), 1.16-1.06 (m, 1H), 1.03-0.87 (m, 4H), 0.81-0.65 (m, 2H) | Q |
| 719 | N-(2-chloro-6-fluorobenzyl)-1-(((3S)-1-((3-cyano-1-azetidinyl)sulfonyl)-3-piperidinyl)carbonyl)-D-prolinamide | LCMS-ESI (POS.) m/z: 512.2 (M + H)+ | 1H NMR (500 MHz, DMSO-d6) δ ppm 8.43* (t, J = 4.87 Hz, 1 H), 8.07 (t, J = 5.00 Hz, 1 H), 7.31-7.41 (m, 2 H), 7.23 (t, J = 8.89 Hz, 1 H), 4.43-4.51 (m, 1 H), 4.36-4.43* (m, 2 H), 4.23-4.30 (m, 2 H), 3.99-4.10 (m, 2 H), 3.90-3.99 (m, 2 H), 3.72-3.86 (m, 1 H), 3.27-3.63 (m, 4 H), 2.70-2.84 (m, 2 H), 2.55-2.66 (m, 1 H), 2.23-2.35* (m, 1 H), 2.11-2.21* (m, 1 H), 1.96-2.04 (m, 1 H), 1.65-1.91 (m, 5 H), 1.33-1.54 (m, 2 H) Spectrum appears as 2:1 mixture of rotamers, *denotes resolved minor rotamer peaks | A |
| 720 | (2R)-1-((3S)-1-((2-benzylazetidin-1-yl)sulfonyl)piperidine-3-carbonyl)-N-(4-(trifluoromethyl)benzyl)pyrrolidine-2-carboxamide | LCMS-ESI (POS.) m/z: 593.4 (M + H)+ | 1H NMR (500 MHz, DMSO-d6) δ 8.28-8.76 (m, 1H), 7.60-7.74 (m, 2H), 7.37-7.49 (m, 2H), 7.11-7.34 (m, 5H), 4.24-4.51 (m, 4H), 3.43-3.80 (m, 6H), 2.94-3.07 (m, 1H), 2.61-2.94 (m, 4H), 1.67-2.29 (m, 8H), 1.34-1.57 (m, 2H) | J |

| Ex. # | Structure Name | LCMS-ESI (POS/NEG) m/z: (M + H)+ | NMR Data | Syn. Rte. |
|---|---|---|---|---|
| 721 | 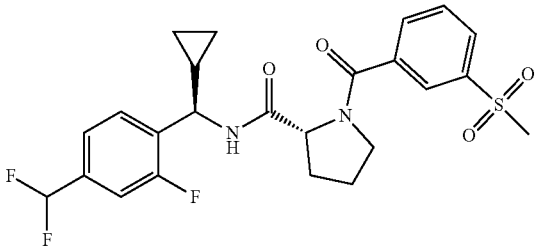 [SMILES: CS(=O)(=O)c1cccc(C(=O)N2CCC[C@@H]2C(=O)N[C@@H](c2ccc(C(F)F)cc2F)C2CC2)c1]<br>N-((R)-cyclopropyl(4-(difluoromethyl)-2-fluorophenyl)methyl)-1-(3-(methylsulfonyl)benzoyl)-D-prolinamide | LCMS-ESI (POS.) m/z: 495.2 (M + H)+ | 1H NMR (500 MHz, DMSO-d6) δ ppm 8.46-8.72 (m, 1 H), 7.30-8.07 (m, 7 H), 6.78-7.22 (m, 1 H), 4.10-4.66 (m, 2 H), 3.38-3.64 (m, 2 H), 3.25-3.26 (m, 1 H), 2.10-2.27 (m, 1 H), 1.64-1.90 (m, 3 H), 0.83-1.27 (m, 1 H), 0.26-0.63 (m, 3 H), −0.11-0.15 (m, 1 H) | C |
| 722 | 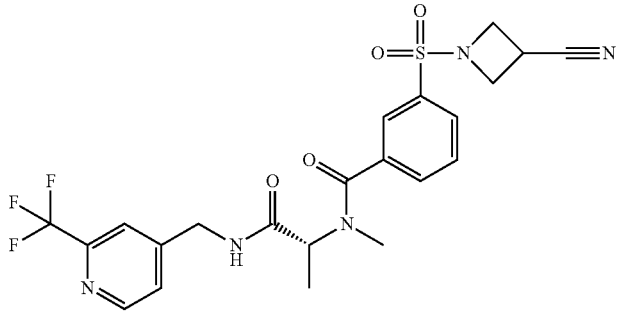 [SMILES: C[C@H](C(=O)NCc1ccnc(C(F)(F)F)c1)N(C)C(=O)c1cccc(S(=O)(=O)N2CC(C#N)C2)c1]<br>3-((3-cyano-1-azetidinyl)sulfonyl)-N-methyl-N-((1R)-1-methyl-2-oxo-2-(((2-(trifluoromethyl)-4-pyridinyl)methyl)amino)ethyl)benzamide | LCMS-ESI (POS.) m/z: 510.2 (M + H)+ | 1H NMR (400 MHz, CHLOROFORM-d) δ ppm 8.65 (d, J = 1.35 Hz, 1 H), 7.91-7.99 (m, 2 H), 7.80-7.86 (m, 1 H), 7.66-7.75 (m, 3 H), 7.12-7.25 (m, 1 H), 5.14-5.24 (m, 1 H), 4.50-4.64 (m, 2 H), 4.18 (td, J = 8.50, 1.76 Hz, 2 H), 4.00-4.07 (m, 2 H), 3.34-3.43 (m, 1 H), 2.89-3.05 (m, 3 H), 1.53 (d, J = 7.05 Hz, 3 H) | C |
| 723 | 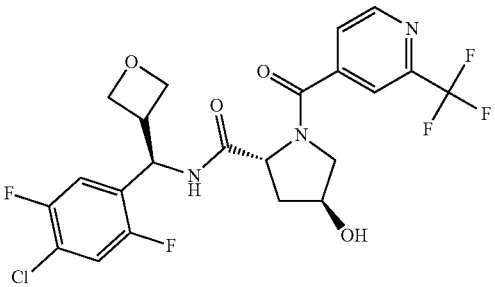 [SMILES: O=C(N[C@@H](c1cc(F)c(Cl)cc1F)C1COC1)[C@H]1C[C@H](O)CN1C(=O)c1ccnc(C(F)(F)F)c1]<br>(4S)-N-((R)-(4-chloro-2,5-difluorophenyl)(3-oxetanyl)methyl)-4-hydroxy-1-((2-(trifluoromethyl)-4-pyridinyl)carbonyl)-D-prolinamide | LCMS-APCI (POS.) m/z: 520.0 (M + H)+ | 1H NMR (400 MHz, DMSO-d6) δ ppm 8.92 (d, J = 4.9 Hz, 1 H), 8.66 (d, J = 8.3 Hz, 1 H), 7.91 (t, J = 1.1 Hz, 1 H), 7.76-7.88 (m, 1 H), 7.57-7.73 (m, 2 H), 7.46 (dd, J = 6.3, 9.8 Hz, 1 H), 7.29 (dd, J = 6.3, 9.7 Hz, 1 H), 5.47 (t, J = 9.1 Hz, 1 H), 5.22 (d, J = 4.9 Hz, 1 H), 5.10 (d, J = 3.1 Hz, 1 H), 4.92-5.04 (m, 1 H), 4.66 (dd, J = 6.4, 7.7 Hz, 1 H), 4.54 (q, J = 6.8, 7.6 Hz, 2 H), 4.38 (dt, J = 6.6, 24.6 Hz, 2 H), 4.19-4.33 (m, 2 H), 3.88 (t, J = 6.1 Hz, 1 H), 3.71 (dd, J = 3.9, 10.8 Hz, 1 H), 3.63 (t, J = 6.1 Hz, 1 H), 3.56 (d, J = 3.4 Hz, 1 H), 3.41 (s, 1 H), 3.23 (d, J = 10.9 Hz, 1 H), 3.11 (s, 1 H), 2.04-2.29 (m, 2 H), 1.69-1.93 (m, 2 H). | Q |

| Ex. # | Structure Name | LCMS-ESI (POS/NEG) m/z: (M + H)+ | NMR Data | Syn. Rte. |
|---|---|---|---|---|
| 724 | (1R,3R,5R)-N-((R)-(4-chloro-2,5-difluorophenyl)(cyclopropyl)methyl)-2-(((2S)-4-(methylsulfonyl)-2-piperazinyl)carbonyl)-2-azabicyclo[3.1.0]hexane-3-carboxamide | LCMS-ESI (POS.) m/z: 517.2 (M + H)+ | 1H NMR (500 MHz, CHLOROFORM-d) δ ppm 7.57 (br d, J = 6.75 Hz, 1 H), 7.11 (ddd, J = 12.13, 9.15, 6.23 Hz, 2 H), 4.81 (br d, J = 9.47 Hz, 1 H), 4.45 (t, J = 7.85 Hz, 1 H), 4.04 (dd, J = 10.25, 2.85 Hz, 1 H), 3.90 (br d, J = 11.42 Hz, 1 H), 3.71 (br d, J = 11.42 Hz, 1 H), 3.47-3.56 (m, 1 H), 3.25 (br d, J = 13.23 Hz, 1 H), 3.00-3.11 (m, 1 H), 2.83 (s, 3 H), 2.70-2.81 (m, 2 H), 2.57 (br d, J = 13.23 Hz, 1 H), 2.17-2.35 (m, 2 H), 1.56-1.80 (m, 1 H), 1.09-1.20 (m, 1 H), 0.92-0.98 (m, 1 H), 0.88-0.92 (m, 1 H), 0.56-0.65 (m, 1 H), 0.48-0.56 (m, 1 H), 0.36 (tq, J = 13.35, 4.60 Hz, 2 H) | M |
| 725 | 1-((3-((3-cyano-1-azetidinyl)sulfonyl)phenyl)carbonyl)-N-((5-(trifluoromethyl)-2-pyrimidinyl)methyl)-D-prolinamide | LCMS-APCI (POS.) m/z: 523.1 (M + H)+ | 1H NMR (400 MHz, Methanol-d4) δ ppm 9.02-9.13 (m, 2 H), 7.96-8.17 (m, 2 H), 7.69-7.96 (m, 2 H), 4.40-4.82 (m, 3 H), 4.03-4.16 (m, 2 H), 3.88-3.97 (m, 2 H), 3.46-3.85 (m, 3 H), 2.30-2.47 (m, 1 H), 1.88-2.25 (m, 3 H). | A |
| 726 | N-((R)-cyclopropyl(2-fluoro-4-(trifluoromethyl)phenyl)methyl)-1-(3-(3-thiophenyl)benzoyl)-D-prolinamide | LCMS-ESI (POS.) m/z: 517.0 (M + H)+ | 1H NMR (500 MHz, DMSO-d6) δ ppm 8.48-8.73 (m, 1 H), 7.21-8.02 (m, 10 H), 4.49-4.63 (m, 1 H), 4.19-4.39 (m, 1 H), 3.45-3.64 (m, 2 H), 2.12-2.28 (m, 1 H), 1.63-1.94 (m, 3 H), 0.83-1.28 (m, 1 H), − 0.17-0.76 (m, 4 H) | C |

-continued

| Ex. # | Structure Name | LCMS-ESI (POS/NEG) m/z: (M + H)+ | NMR Data | Syn. Rte. |
|---|---|---|---|---|
| 727 | (1R,3R,5R)-N-((R)-(2-fluoro-4-(trifluoromethyl)phenyl)(3-oxetanyl)methyl)-2-(4-methyl-3-(methylsulfonyl)benzoyl)-2-azabicyclo[3.1.0]hexane-3-carboxamide | LCMS-APCI (POS.) m/z: 555.2 (M + H)+ | 1H NMR (400 MHz, DMSO-d6) δ ppm 8.75 (d, J = 8.1 Hz, 1 H), 8.28 (d, J = 1.8 Hz, 1 H), 7.92 (dd, J = 1.9, 7.8 Hz, 1 H), 7.70 (d, J = 10.3 Hz, 1 H), 7.60 (p, J = 6.9, 7.9 Hz, 3 H), 5.48 (t, J = 8.9 Hz, 1 H), 4.91 (dd, J = 3.7, 11.3 Hz, 1 H), 4.65 (t, J = 7.0 Hz, 1 H), 4.51 (t, J = 7.1 Hz, 1 H), 4.41 (t, J = 6.2 Hz, 1 H), 4.22 (t, J = 6.2 Hz, 1 H), 3.38-3.47 (m, 1 H), 3.27 (s, 4 H), 2.70 (s, 3 H), 2.56 (dd, J = 6.2, 12.5 Hz, 1 H), 1.60-1.77 (m, 2 H), 1.14 (d, J = 2.7 Hz, 1 H), 0.78 (dt, J = 5.2, 10.2 Hz, 1 H). | Q |
| 728 | (1R,3R,5R)-N-((R)-(2,4-difluorophenyl)(3-oxetanyl)methyl)-2-(3-(methylsulfonyl)benzoyl)-2-azabicyclo[3.1.0]hexane-3-carboxamide | LCMS-APCI (POS.) m/z: 491.1 (M + H)+ | 1H NMR (400 MHz, Methanol-d4) δ ppm 8.39 (t, J = 1.7 Hz, 1 H), 8.09-8.20 (m, 2 H), 7.78 (t, J = 7.8 Hz, 1 H), 7.37 (td, J = 6.3, 8.7 Hz, 1 H), 6.96-7.09 (m, 2 H), 5.59 (d, J = 10.2 Hz, 1 H), 4.99 (dd, J = 4.1, 11.4 Hz, 1 H), 4.79-4.86 (m, 1 H), 4.56-4.71 (m, 2 H), 4.36 (t, J = 6.2 Hz, 1 H), 3.46-3.63 (m, 1 H), 3.19 (s, 3 H), 2.55-2.73 (m, 1 H), 1.90 (dd, J = 4.3, 13.5 Hz, 1 H), 1.75-1.84 (m, 1 H), 1.27 (td, J = 2.7, 5.3 Hz, 1 H), 0.90 (dtd, J = 1.1, 5.7, 9.0 Hz, 1 H). | A |
| 729 | 1-(((3S)-1-((3-cyano-1-azetidinyl)sulfonyl)-3-piperidinyl)carbonyl)-N-((1R)-1-(4-fluorophenyl)ethyl)-D-prolinamide, 1-(((3S)-1-((3-cyano-1-azetidinyl)sulfonyl)-3-piperidinyl)carbonyl)-N-((1S)-1-(4-fluorophenyl)ethyl)-D-prolinamide | LCMS-ESI (POS.) m/z: 492.2 (M + H)+ | 1H NMR (500 MHz, DMSO-d6) δ ppm 8.06-8.59 (m, 1 H), 7.26-7.41 (m, 2 H), 7.06-7.19 (m, 2 H), 4.80-5.01 (m, 1 H), 4.25-4.49 (m, 1 H), 4.01-4.14 (m, 2 H), 3.88-3.99 (m, 2 H), 3.72-3.83 (m, 1 H), 3.48-3.70 (m, 4 H), 2.59-2.91 (m, 3 H), 1.62-2.30 (m, 6 H), 1.24-1.59 (m, 5 H) | A |
| 730 | 1-(((3S)-1-((3-hydroxy-3-methyl-1-azetidinyl)sulfonyl)-3-piperidinyl)carbonyl)-N-(4-(trifluoromethyl)benzyl)-D-prolinamide | LCMS-ESI (POS.) m/z: 533.2 (M + H)+ | 1H NMR (500 MHz, CHLOROFORM-d) δ ppm 7.53-7.65 (m, 2 H), 7.30-7.45 (m, 3 H), 4.59 (dd, J = 7.91, 1.69 Hz, 1 H), 4.51 (dd, J = 15.44, 6.36 Hz, 1 H), 4.34-4.48 (m, 1 H), 3.67-3.92 (m, 6 H), 3.53-3.65 (m, 2 H), 2.89-3.05 (m, 1 H), 2.67-2.82 (m, 3 H), 2.43 (ddd, J = 9.41, 6.55, 3.24 Hz, 1 H), 2.13-2.36 (m, 2 H), 1.99-2.10 (m, 1 H), 1.74-1.96 (m, 4 H), 1.46-1.71 (m, 4 H) | M |

| Ex. # | Structure Name | LCMS-ESI (POS/NEG) m/z: (M + H)+ | NMR Data | Syn. Rte. |
|---|---|---|---|---|
| 731 | 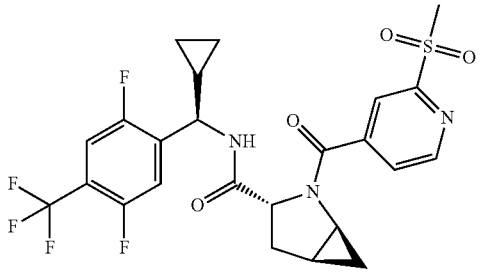 [SMILES: CS(=O)(=O)c1cc(C(=O)N2[C@@H](C(=O)N[C@@H](c3cc(F)c(C(F)(F)F)cc3F)C3CC3)C[C@@H]3C[C@@H]32)ccn1]<br>(1S,3R,5S)-N-((R)-cyclopropyl(2,5-difluoro-4-(trifluoromethyl)phenyl)methyl)-2-((2-(methylsulfonyl)-4-pyridinyl)carbonyl)-2-azabicyclo[3.1.0]hexane-3-carboxamide | LCMS-ESI (POS.) m/z: 544.2 (M + H)+ | 1H NMR (400 MHz, CHLOROFORM-d) δ ppm 8.83-8.95 (m, 1 H), 8.38-8.46 (m, 1 H), 7.75-7.89 (m, 1 H), 7.39 (br d, J = 6.53 Hz, 1 H), 7.33 (dd, J = 9.43, 5.60 Hz, 1 H), 7.20 (dd, J = 10.00, 5.55 Hz, 1 H), 4.70-4.87 (m, 1 H), 4.42-4.53 (m, 1 H), 3.29 (s, 3 H), 3.16-3.23 (m, 1 H), 2.76 (ddd, J = 13.48, 7.31, 2.95 Hz, 1 H), 1.95-2.17 (m, 2 H), 1.04-1.33 (m, 2 H), 0.66-0.80 (m, 2 H), 0.57-0.65 (m, 1 H), 0.34-0.52 (m, 2 H) | C |
| 732 | 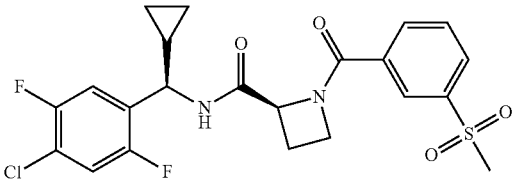 [SMILES: CS(=O)(=O)c1cccc(C(=O)N2CC[C@H]2C(=O)N[C@@H](c2cc(F)c(Cl)cc2F)C2CC2)c1]<br>(2S)-N-((R)-(4-chloro-2,5-difluorophenyl)(cyclopropyl)methyl)-1-(3-(methylsulfonyl)benzoyl)-2-azetidinecarboxamide | LCMS-ESI (POS.) m/z: 483.0 (M + H)+ | 1H NMR (500 MHz, CHLOROFORM-d) δ ppm 8.26 (br s, 1 H), 8.05-8.19 (m, 2 H), 7.98 (br d, J = 7.53 Hz, 1 H), 7.74 (br t, J = 7.66 Hz, 1 H), 7.10-7.23 (m, 2 H), 5.11 (br dd, J = 8.89, 6.94 Hz, 1 H), 4.33-4.62 (m, 2 H), 4.17-4.25 (m, 1 H), 3.12 (s, 3 H), 2.78-2.91 (m, 1 H), 2.44-2.59 (m, 1 H), 1.12-1.32 (m, 1 H), 0.59-0.68 (m, 1 H), 0.50-0.59 (m, 1 H), 0.33-0.50 (m, 2 H) | C |
| 733 | 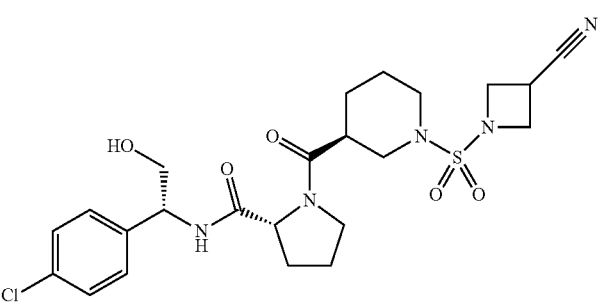 [SMILES: N#CC1CN(S(=O)(=O)N2CCC[C@H](C(=O)N3CCC[C@@H]3C(=O)N[C@@H](CO)c3ccc(Cl)cc3)C2)C1]<br>N-((1R)-1-(4-chlorophenyl)-2-hydroxyethyl)-1-(((3S)-1-((3-cyano-1-azetidinyl)sulfonyl)-3-piperidinyl)carbonyl)-D-prolinamide | LCMS-ESI (POS.) m/z: 524.2 (M + H)+ | 1H NMR (500 MHz, DMSO-d6) δ ppm 8.06-8.53 (m, 1 H), 7.27-7.44 (m, 1 H), 7.20-7.55 (m, 3 H), 5.81-5.96 (m, 1 H), 4.73-4.90 (m, 1 H), 4.32-4.52 (m, 1 H), 3.98-4.10 (m, 2 H), 3.86-3.98 (m, 2 H), 3.69-3.84 (m, 1 H), 3.30-3.68 (m, 6 H), 2.67-2.91 (m, 2 H), 2.54-2.66 (m, 1 H), 2.01-2.30 (m, 1 H), 1.67-1.99 (m, 5 H), 1.21-1.53 (m, 2 H) | A |
| 734 | 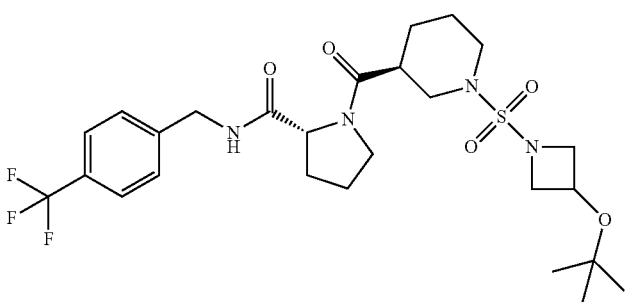 [SMILES: CC(C)(C)OC1CN(S(=O)(=O)N2CCC[C@H](C(=O)N3CCC[C@@H]3C(=O)NCc3ccc(C(F)(F)F)cc3)C2)C1]<br>1-(((3S)-1-((3-tert-butoxy-1-azetidinyl)sulfonyl)-3-piperidinyl)carbonyl)-N-(4-(trifluoromethyl)benzyl)-D-prolinamide | LCMS-ESI (POS.) m/z: 575.3 (M + H)+ | 1H NMR (500 MHz, DMSO-d6) δ ppm 8.18-8.93 (m, 1 H), 7.58-7.77 (m, 2 H), 7.45 (br d, J = 7.79 Hz, 2 H), 4.42-4.57 (m, 2 H), 4.23-4.42 (m, 3 H), 3.77-3.98 (m, 2 H), 3.52-3.71 (m, 6 H), 2.61-2.83 (m, 3 H), 1.31-2.28 (m, 10 H), 1.08-1.14 (m, 9 H) | M |

-continued

| Ex. # | Structure Name | LCMS-ESI (POS/NEG) m/z: (M + H)+ | NMR Data | Syn. Rte. |
|---|---|---|---|---|
| 735 | 1-(((3S)-1-((3-pent-1-azetidinyl)sulfonyl)-3-piperidinyl)carbonyl)-N-(4-(trifluoromethyl)benzyl)-D-prolinamide | LCMS-ESI (POS.) m/z: 573.2 (M + H)+ | 1H NMR (500 MHz, DMSO-d6) δ 8.28-8.75 (m, 1H), 7.61-7.74 (m, 2H), 7.34-7.53 (m, 2H), 4.25-4.53 (m, 3H), 3.75-3.89 (m, 2H), 3.40-3.70 (m, 6H), 2.59-2.84 (m, 3H), 2.04-2.34 (m, 1H), 1.67-2.00 (m, 5H), 1.14-1.58 (m, 11H), 0.77-0.92 (m, 3H) | J |
| 736 | (1R,3R,5R)-N-((R)-(4-chloro-2,5-difluorophenyl)(cyclopropyl)methyl)-2-((2-methyl-4-pyridinyl)carbonyl)-2-azabicyclo[3.1.0]hexane-3-carboxamide | LCMS-APCI (POS.) m/z: 446.2 (M + H)+ | 1H NMR (400 MHz, Methanol-d4) δ ppm 8.52-8.82 (m, 1 H), 7.52-7.66 (m, 1 H), 7.35 (dd, J = 6.1, 9.5 Hz, 2 H), 5.00 (dd, J = 3.8, 11.4 Hz, 1 H), 4.45-4.56 (m, 1 H), 3.69-3.80 (m, 1 H), 3.13-3.30 (m, 1 H), 2.57-2.76 (m, 3 H), 1.71-1.93 (m, 2 H), 1.12-1.40 (m, 2 H), 0.37-0.89 (m, 4 H). | Q |
| 737 | N-((R)-cyclopropyl(2-fluoro-4-(trifluoromethyl)phenyl)methyl)-1-(3-(1H-pyrazol-4-yl)benzoyl)-D-prolinamide | LCMS-ESI (POS.) m/z: 501.2 (M + H)+ | 1H NMR (600 MHz, DMSO-d6) δ ppm 12.83-13.24 (m, 1 H), 8.53-8.79 (m, 1 H), 8.12-8.37 (m, 1 H), 7.89-8.07 (m, 1 H), 7.11-7.75 (m, 6 H), 4.50-4.65 (m, 1 H), 4.19-4.40 (m, 1 H), 3.45-3.64 (m, 2 H), 3.39-3.41 (m, 1 H), 2.11-2.29 (m, 1 H), 1.63-1.92 (m, 3 H), 0.90-1.30 (m, 1 H), −0.13-0.64 (m, 4 H) | C |
| 738 | (1R,3R,5R)-N-((R)-(4-chloro-2-fluorophenyl)(3-oxetanyl)methyl)-2-((2-(2-methyl-2-propanyl)-4-pyridinyl)carbonyl)-2-azabicyclo[3.1.0]hexane-3-carboxamide | LCMS-APCI (POS.) m/z: 486.2 (M + H)+ | 1H NMR (400 MHz, Methanol-d4) δ ppm 8.64 (dd, J = 0.9, 5.0 Hz, 1 H), 7.82 (dd, J = 0.9, 1.5 Hz, 1 H), 7.51 (dd, J = 1.5, 5.0 Hz, 1 H), 7.33 (t, J = 8.2 Hz, 1 H), 7.22-7.27 (m, 2 H), 5.58 (d, J = 10.2 Hz, 1 H), 4.95 (dd, J = 4.1, 11.4 Hz, 1 H), 4.84 (dd, J = 6.5, 7.6 Hz, 1 H), 4.60-4.69 (m, 2 H), 4.37 (t, J = 0.8, 12.5 Hz, 1 H), 3.48-3.58 (m, 1 H), 3.37 (s, 1 H), 3.26 (td, J = 2.6, 6.2 Hz, 1 H), 2.60-2.69 (m, 1 H), 1.90 (dd, J = 4.1, 13.5 Hz, 1 H), 1.75-1.82 (m, 1 H), 1.42 (s, 10 H), 1.25 (dt, J = 2.7, 5.3 Hz, 1 H), 0.81-0.89 (m, 1 H). | A |

| Ex. # | Structure Name | LCMS-ESI (POS/NEG) m/z: (M + H)+ | NMR Data | Syn. Rte. |
|---|---|---|---|---|
| 739 | (2R)-1-((3S)-1-((3-(tetrahydrofuran-3-yl)azetidin-1-yl)sulfonyl)piperidine-3-carbonyl)-N-(4-(trifluoromethyl)benzyl)pyrrolidine-2-carboxamide | LCMS-ESI (POS.) m/z: 573.2 (M + H)+ | 1H NMR (500 MHz, DMSO-d6) δ 8.24-8.79 (m, 1H), 7.58-7.76 (m, 2H), 7.36-7.52 (m, 2H), 4.19-4.52 (m, 3H), 3.41-3.92 (m, 12H), 2.59-2.86 (m, 3H), 2.37-2.46 (m, 1H), 2.05-2.37 (m, 2H), 1.63-2.05 (m, 6H), 1.32-1.56 (m, 3H) | J |
| 740 | 1-(((3S)-1-((3-cyano-1-azetidinyl)sulfonyl)-3-piperidinyl)carbonyl)-N-((1R)-2,2-dimethyl-1-(4-(trifluoromethyl)phenyl)propyl)-D-prolinamide | LCMS-ESI (POS.) m/z: 584.2 (M + H)+ | 1H NMR (500 MHz, DMSO-d6) δ ppm 8.14-8.60 (m, 1 H), 7.61-7.76 (m, 2 H), 7.40-7.55 (m, 2 H), 4.68-4.78 (m, 1 H), 4.46-4.64 (m, 1 H), 4.02-4.13 (m, 2 H), 3.90-3.99 (m, 2 H), 3.74-3.84 (m, 1 H), 3.31-3.63 (m, 4 H), 2.79-2.92 (m, 1 H), 2.58-2.74 (m, 1 H), 2.15-2.34 (m, 1 H), 1.58-2.06 (m, 6 H), 1.32-1.54 (m, 2 H), 0.76-0.95 (m, 9 H) | A |
| 741 | 1-(((3S)-1-((3-cyano-1-azetidinyl)sulfonyl)-3-piperidinyl)carbonyl)-N-(5-methyl-2-(trifluoromethyl)benzyl)-D-prolinamide | LCMS-ESI (POS.) m/z: 542.0 (M + H)+ | 1H NMR (500 MHz, DMSO-d6) δ ppm 8.24-8.70 (m, 1 H), 7.32-7.58 (m, 3 H), 5.07-5.09 (m, 1 H), 4.19-4.56 (m, 3 H), 4.00-4.15 (m, 2 H), 3.85-4.00 (m, 2 H), 3.74-3.86 (m, 1 H), 3.29-3.71 (m, 4 H), 2.70-2.87 (m, 2 H), 2.60-2.70 (m, 1 H), 2.28-2.37 (m, 3 H), 1.62-2.16 (m, 6 H), 1.28-1.55 (m, 2 H) | A |
| 742 | 1-(3-(methylsulfonyl)benzoyl)-N-((1R)-5-(trifluoromethyl)-2,3-dihydro-1H-inden-1-)-D-prolinamide | LCMS-ESI (POS.) m/z: 481.2 (M + H)+ | 1H NMR (500 MHz, DMSO-d6) δ ppm 8.20-8.44 (m, 1 H), 7.21-8.09 (m, 7 H), 5.01-5.44 (m, 1 H), 4.23-4.51 (m, 1 H), 3.43-3.70 (m, 2 H), 3.22-3.28 (m, 3 H), 2.72-3.07 (m, 2 H), 2.10-2.46 (m, 2 H), 1.32-2.01 (m, 4 H) | A |

| Ex. # | Structure Name | LCMS-ESI (POS/NEG) m/z: (M + H)+ | NMR Data | Syn. Rte. |
|---|---|---|---|---|
| 743 | 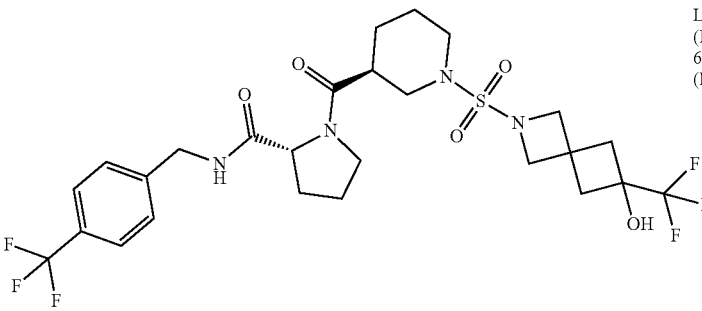<br>1-(((3S)-1-(((6-hydroxy-6-(trifluoromethyl)-2-azaspiro[3.3]hept-2-yl)sulfonyl)-3-piperidinyl)carbonyl)-N-(4-(trifluoromethyl)benzyl)-D-prolinamide | LCMS-ESI (POS.) m/z: 627.4 (M + H)+ | 1H NMR (500 MHz, DMSO-d6) δ 8.16-8.81 (m, 1H), 7.62-7.75 (m, 2H), 7.37-7.53 (m, 2H), 6.42-6.58 (m, 1H), 4.22-4.51 (m, 3H), 3.73-3.88 (m, 4H), 3.42-3.69 (m, 4H), 2.69-2.86 (m, 2H), 2.56-2.69 (m, 3H), 2.29-2.42 (m, 2H), 2.03-2.27 (m, 1H), 1.65-2.03 (m, 5H), 1.32-1.53 (m, 2H) | J |
| 744 | 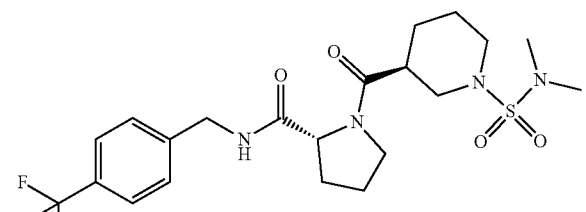<br>1-(((3S)-1-(dimethylsulfamo)-3-piperidinyl)carbonyl)-N-(4-(trifluoromethyl)benzyl)-D-prolinamide | LCMS-ESI (POS.) m/z: 491.2 (M + H)+ | 1H NMR (500 MHz, DMSO-d6) δ ppm 8.72* (t, J = 6.00 Hz, 1 H), 8.36 (t, J = 6.03 Hz, 1 H), 7.64-7.71 (m, 2 H), 7.45 (d, J = 7.98 Hz, 2 H), 4.28-4.49 (m, 3 H), 3.33-3.68 (m, 4 H), 2.76-2.89 (m, 2 H), 2.74 (s, 6 H), 2.72* (s, 6 H), 2.64-2.68 (m, 1 H), 2.28-2.36* (m, 1 H), 2.17-2.26* (m, 1 H), 2.06-2.14 (m, 1 H), 1.67-1.99 (m, 5 H), 1.37-1.55 (m, 2 H). Spectrum appears as 2:1 mixture of rotamers, *denotes resolved minor rotamer peaks. | M |
| 745 | 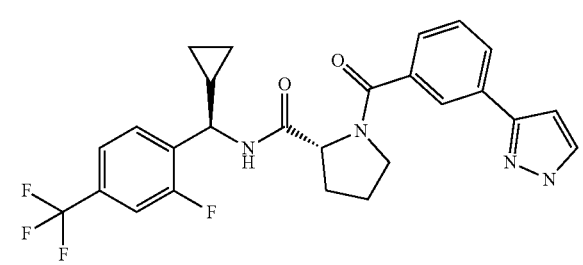 [SMILES: O=C(N[C@@H](c1ccc(C(F)(F)F)cc1F)C1CC1)[C@H]1CCCN1C(=O)c1cccc(-c2cc[nH]n2)c1]<br>N-((R)-cyclopropyl(2-fluoro-4-(trifluoromethyl)phenyl)methyl)-1-(3-(1H-pyrazol-3-yl)benzoyl)-D-prolinamide | LCMS-ESI (POS.) m/z: 501.0 (M + H)+ | 1H NMR (500 MHz, DMSO-d6) δ ppm 8.32-8.85 (m, 1 H), 7.12-8.03 (m, 9 H), 6.66-6.83 (m, 1 H), 4.54-4.63 (m, 1 H), 4.24-4.34 (m, 1 H), 3.48-3.61 (m, 2 H), 2.11-2.26 (m, 1 H), 1.70-1.92 (m, 3 H), 0.92-1.28 (m, 1 H), −0.11-0.69 (m, 4 H) | C |
| 746 | 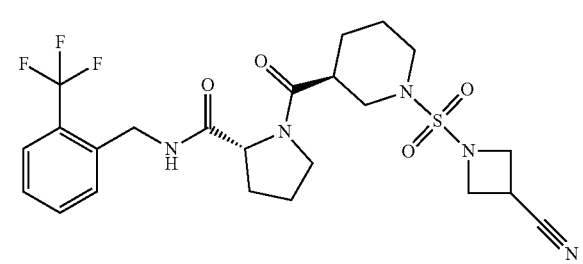 [SMILES: N#CC1CN(S(=O)(=O)N2CCC[C@H](C(=O)N3CCC[C@@H]3C(=O)NCc3ccccc3C(F)(F)F)C2)C1]<br>1-(((3S)-1-((3-cyano-1-azetidinyl)sulfonyl)-3-piperidinyl)carbonyl)-N-(2-(trifluoromethyl)benzyl)-D-prolinamide | LCMS-ESI (POS.) m/z: 528.2 (M + H)+ | 1H NMR (500 MHz, DMSO-d6) δ ppm 8.33-8.74 (m, 1 H), 7.60-7.74 (m, 2 H), 7.40-7.55 (m, 2 H), 4.31-4.56 (m, 3 H), 3.99-4.10 (m, 2 H), 3.87-3.98 (m, 2 H), 3.73-3.83 (m, 1 H), 3.35-3.70 (m, 4 H), 2.65-2.88 (m, 2 H), 1.69-2.35 (m, 7 H), 1.35-1.57 (m, 2 H) | A |

| Ex. # | Structure Name | LCMS-ESI (POS/NEG) m/z: (M + H)+ | NMR Data | Syn. Rte. |
|---|---|---|---|---|
| 747 | (1R,3R,5R)-N-((R)-cyclopropyl(2,5-difluoro-4-methoxyphenyl)methyl)-2-(3-(methylsulfonyl)benzoyl)-2-azabicyclo[3.1.0]hexane-3-carboxamide | LCMS-ESI (POS.) m/z: 505.2 (M + H)⁺ | 1H NMR (500 MHz, DMSO-d6) δ ppm 8.20-8.53 (m, 1 H) 7.88-8.20 (m, 3 H) 7.64-7.82 (m, 1 H) 7.02-7.32 (m, 2 H) 4.59-4.96 (m, 1 H) 4.08-4.58 (m, 1 H) 3.79-3.88 (m, 3 H) 3.21-3.28 (m, 4 H) 2.52-2.59 (m, 1 H) 1.53-1.74 (m, 2 H) 0.79-1.18 (m, 2 H) 0.67-0.77 (m, 1 H)-0.26-0.54 (m, 4 H) | C |
| 748 | (1R,3R,5R)-N-((R)-(2-fluoro-4-(trifluoromethyl)phenyl)(3-oxetanyl)methyl)-2-((2-(2-propanyl)-4-pyridinyl)carbonyl)-2-azabicyclo[3.1.0]hexane-3-carboxamide | LCMS-APCI (POS.) m/z: 506.2 (M + H)⁺ | 1H NMR (400 MHz, Methanol-d4) δ ppm 8.79 (d, J = 8.0 Hz, 1 H), 8.60 (dd, J = 0.9, 5.1 Hz, 1 H), 7.66 (t, J = 1.2 Hz, 1 H), 7.46-7.60 (m, 4 H), 5.63-5.70 (m, 1 H), 4.97 (dd, J = 4.0, 11.4 Hz, 1 H), 4.83-4.87 (m, 1 H), 4.59-4.70 (m, 2 H), 4.40 (t, 1 H), 3.50-3.61 (m, 1 H), 3.27 (td, J = 2.6, 6.2 Hz, 1 H), 3.16 (dt, J = 6.9, 13.9 Hz, 1 H), 2.66 (dddd, J = 1.1, 6.4, 11.6, 13.3 Hz, 1 H), 1.90 (dd, J = 4.1, 13.5 Hz, 1 H), 1.74-1.83 (m, 1 H), 1.35 (dd, J = 2.1, 7.0 Hz, 7 H), 1.23 (td, J = 2.6, 5.3 Hz, 1 H), 0.80-0.88 (m, 1 H). | Q |
| 749 | 1-(3-(methyl(2-propyn-1-)sulfamoyl)benzoyl)-N-((1R)-1-(4-(trifluoromethyl)phenyl)ethyl)-D-prolinamide | LCMS-ESI (POS.) m/z: 522.2 (M + H)⁺ | 1H NMR (500 MHz, DMSO-d6) δ ppm 8.49-8.91 (m, 1 H), 7.50-8.04 (m, 8 H), 4.84-5.27 (m, 1 H), 3.99-4.48 (m, 2 H), 3.59-3.68 (m, 1 H), 3.39-3.54 (m, 3 H), 2.69-3.15 (m, 4 H), 2.69-3.19 (m, 1 H), 1.68-2.06 (m, 4 H), 1.31-1.46 (m, 3 H) | D |
| 750 | 1-(((3S)-1-(((6R)-6-hydroxy-2-azaspiro[3.4]oct-2-yl)sulfonyl)-3-piperidinyl)carbonyl)-N-(4-(trifluoromethyl)benzyl)-D-prolinamide, 1-(((3S)-1-(((6S)-6-hydroxy-2-azaspiro[3.4]oct-2-yl)sulfonyl)-3-piperidinyl)carbonyl)-N-(4-(trifluoromethyl)benzyl)-D-prolinamide | LCMS-ESI (POS.) m/z: 629.2 (M + H)⁺ | 1H NMR (500 MHz, CHLOROFORM-d) δ ppm 7.57 (d, J = 8.04 Hz, 2 H), 7.43 (br s, 1 H), 7.28-7.39 (m, 2 H), 4.59 (br d, J = 6.75 Hz, 1 H), 4.47-4.56 (m, 1 H), 4.30-4.47 (m, 2 H), 3.89 (dd, J = 7.53, 3.63 Hz, 1 H), 3.70-3.83 (m, 5 H), 3.53-3.66 (m, 2 H), 2.81-3.02 (m, 3 H), 2.60-2.81 (m, 3 H), 2.30-2.46 (m, 1 H), 1.98-2.21 (m, 4 H), 1.75-1.96 (m, 6 H), 1.58-1.71 (m, 2 H), 1.45-1.58 (m, 1 H), 1.42 (br s, 1 H), 1.02 (br s, 1 H), 0.37 (br s, 1H) | M |

| Ex. # | Structure Name | LCMS-ESI (POS/NEG) m/z: (M + H)+ | NMR Data | Syn. Rte. |
|---|---|---|---|---|
| 751 | 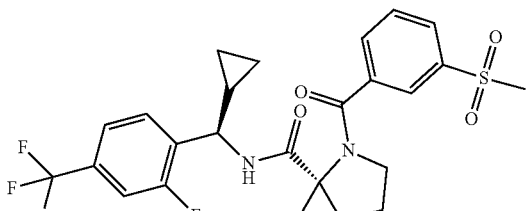<br>(1R,5R)-N-((R)-cyclopropyl(2-fluoro-4-(trifluoromethyl)phenyl)methyl)-2-(3-(methylsulfonyl)benzoyl)-2-azabicyclo[3.1.0]hexane-1-carboxamide | LCMS-ESI (POS.) m/z: 525.3 (M + H)+ | 1H NMR (500 MHz, DMSO-d6) δ ppm 7.18-8.62 (m, 8 H), 3.54-4.69 (m, 3 H), 3.04 (br s, 2 H), 3.29 (br s, 1 H), 1.76-2.34 (m, 4 H), 0.86-1.62 (m, 2 H),-0.09-0.73 (m, 4 H) | C |
| 752 | 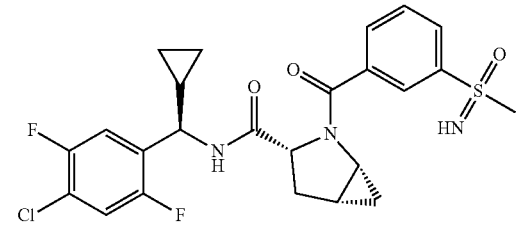 [SMILES: CS(=N)(=O)c1cccc(C(=O)N2[C@@H](C(=O)N[C@@H](c3cc(F)c(Cl)cc3F)C3CC3)C[C@H]3C[C@H]32)c1]<br>(1R,3R,5R)-N-((R)-(4-chloro-2,5-difluorophenyl)(cyclopropyl)methyl)-2-(3-(S-methylsulfonimidoyl)benzoyl)-2-azabicyclo[3.1.0]hexane-3-carboxamide | LCMS-ESI (POS.) m/z: 508.0 (M + H)+ | 1H NMR (500 MHz, DMSO-d6) δ ppm 8.62 (br d, J = 7.53 Hz, 1 H), 8.21-8.43 (m, 1 H), 7.29-8.20 (m, 5 H), 4.61-5.02 (m, 1 H), 3.96-4.57 (m, 1 H), 3.04-3.88 (m, 5 H), 2.52-2.79 (m, 2 H), 1.53-1.86 (m, 2 H), 1.02-1.35 (m, 2 H),-0.29-0.97 (m, 6 H) | Q |
| 753 | 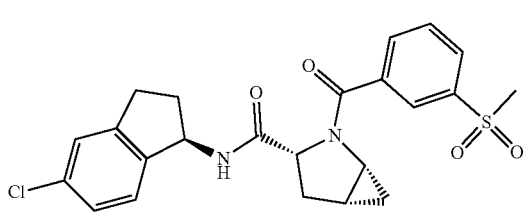 [SMILES: CS(=O)(=O)c1cccc(C(=O)N2[C@@H](C(=O)N[C@@H]3CCc4cc(Cl)ccc43)C[C@H]3C[C@H]32)c1]<br>(1R,3R,5R)-N-((1R)-5-chloro-2,3-dihydro-1H-inden-1-)-2-(3-(methylsulfonyl)benzoyl)-2-azabicyclo[3.1.0]hexane-3-carboxamide | LCMS-APCI (POS.) m/z: 459.2 (M + H)+ | 1H NMR (400 MHz, DMSO-d6) δ ppm 8.43 (d, J = 8.1 Hz, 1 H), 8.22 (t, J = 1.8 Hz, 1 H), 8.06 (ddt, J = 1.4, 7.8, 10.6 Hz, 2 H), 7.75-7.85 (m, 1 H), 7.23-7.38 (m, 2 H), 7.16 (d, J = 8.1 Hz, 1 H), 5.23 (q, J = 8.0 Hz, 1 H), 4.90 (dd, J = 3.7, 11.4 Hz, 1 H), 3.28 (s, 4 H), 2.94 (ddd, J = 3.3, 8.9, 16.4 Hz, 1 H), 2.77-2.88 (m, 1 H), 2.57-2.68 (m, 1 H), 2.39 (dtd, J = 3.3, 7.9, 11.5 Hz, 1 H), 1.81-1.99 (m, 2 H), 1.74 (dq, J = 6.0, 8.7 Hz, 1 H), 1.34 (td, J = 2.6, 5.1 Hz, 1 H), 0.77-0.95 (m, 1 H). | A |
| 754 | 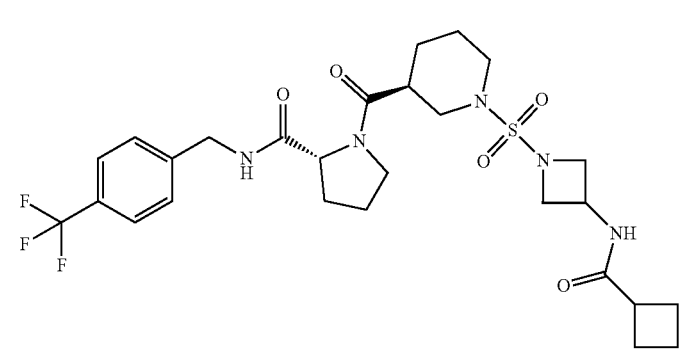 [SMILES: O=C(NC1CN(S(=O)(=O)N2CCC[C@H](C(=O)N3CCC[C@@H]3C(=O)NCc3ccc(C(F)(F)F)cc3)C2)C1)C1CCC1]<br>1-(((3S)-1-((3-((cyclobutylcarbonyl)amino)-1-azetidinyl)sulfonyl)-3-piperidinyl)carbonyl)-N-(4-(trifluoromethyl)benzyl)-D-prolinamide | LCMS-ESI (POS.) m/z: 600.4 (M + H)+ | 1H NMR (500 MHz, DMSO-d6) δ ppm 8.25-8.76 (m, 2 H), 7.59-7.77 (m, 2 H), 7.45 (br d, J = 7.79 Hz, 2 H), 4.25-4.57 (m, 4 H), 3.85-4.01 (m, 2 H), 3.51-3.75 (m, 6 H), 2.92-3.06 (m, 1 H), 2.57-2.89 (m, 3 H), 1.68-2.18 (m, 12 H), 1.33-1.58 (m, 2 H) | M |

| Ex. # | Structure Name | LCMS-ESI (POS/NEG) m/z: (M + H)+ | NMR Data | Syn. Rte. |
|---|---|---|---|---|
| 755 | 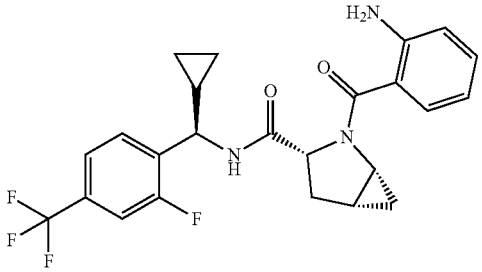 [SMILES: Nc1ccccc1C(=O)N1[C@@H](C(=O)N[C@@H](c2ccc(C(F)(F)F)cc2F)C2CC2)C[C@H]2C[C@H]21]<br>(1R,3R,5R)-2-(2-aminobenzoyl)-N-((R)-cyclopropyl(2-fluoro-4-(trifluoromethyl)phenyl)methyl)-2-azabicyclo[3.1.0]hexane-3-carboxamide | LCMS-APCI (POS.) m/z: 462.2 (M + H)+ | 1H NMR (400 MHz, DMSO-d6) δ ppm 10.91 (s, 1 H), 8.73 (d, J = 7.5 Hz, 1 H), 7.69 (q, J = 10.0, 10.8 Hz, 3 H), 7.54 (d, J = 7.5 Hz, 1 H), 7.36 (s, 1 H), 7.09 (t, J = 7.5 Hz, 1 H), 6.50 (s, 1 H), 5.09 (d, J = 12.3 Hz, 1 H), 4.63 (t, J = 7.8 Hz, 1 H), 1.72-1.81 (m, 1 H), 1.54-1.71 (m, 1 H), 1.12-1.26 (m, 1 H), 0.66-0.77 (m, 1 H), 0.52-0.63 (m, 1 H), 0.39-0.52 (m, 1 H), 0.37 (s, 2 H). | Q |
| 756 | 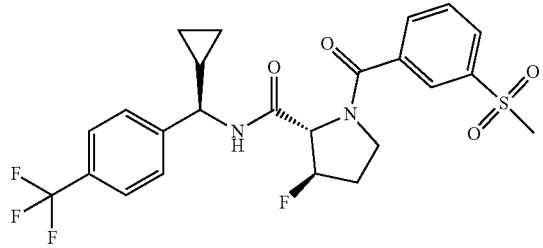 [SMILES: CS(=O)(=O)c1cccc(C(=O)N2CC[C@@H](F)[C@@H]2C(=O)N[C@@H](c2ccc(C(F)(F)F)cc2)C2CC2)c1]<br>(3R)-N-((R)-cyclopropyl(4-(trifluoromethyl)phenyl)methyl)-3-fluoro-1-(3-(methylsulfonyl)benzoyl)-D-prolinamide | LCMS-ESI (POS.) m/z: 513.2 (M + H)+ | 1H NMR (500 MHz, CHLOROFORM-d) δ ppm 8.13 (s, 1 H), 8.04-8.11 (m, 1 H), 7.84 (d, J = 7.66 Hz, 1 H), 7.67-7.75 (m, 1 H), 7.57-7.66 (m, 3 H), 7.47-7.53 (m, 2 H), 5.34-5.57 (m, 1 H), 4.83-5.10 (m, 1 H), 4.41 (t, J = 7.85 Hz, 1 H), 3.57-3.78 (m, 2 H), 3.04-3.17 (m, 3 H), 2.22-2.60 (m, 2 H), 1.11-1.31 (m, 1 H), 0.54-0.74 (m, 2 H), 0.30-0.52 (m, 2 H) | C |
| 757 | 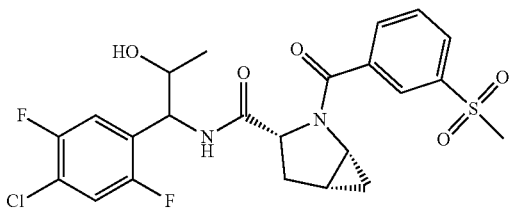 [SMILES: CC(O)C(NC(=O)[C@H]1C[C@H]2C[C@H]2N1C(=O)c1cccc(S(C)(=O)=O)c1)c1cc(F)c(Cl)cc1F]<br>(1R,3R,5R)-N-(1-(4-chloro-2,5-difluorophenyl)-2-hydroxypropyl)-2-(3-(methylsulfonyl)benzoyl)-2-azabicyclo[3.1.0]hexane-3-carboxamide | LCMS-ESI (POS.) m/z: 513.0 (M + H)+ | 1H NMR (500 MHz, DMSO-d6) δ ppm 8.52 (d, J = 8.56 Hz, 1 H) 7.18-8.19 (m, 6 H) 4.46-4.97 (m, 3 H) 3.67-3.89 (m, 1 H) 3.23-3.28 (m, 4 H) 2.52-2.58 (m, 1 H) 1.50-1.75 (m, 2 H) 0.91-1.16 (m, 4 H) 0.68-0.83 (m, 1 H) | A |
| 758 | 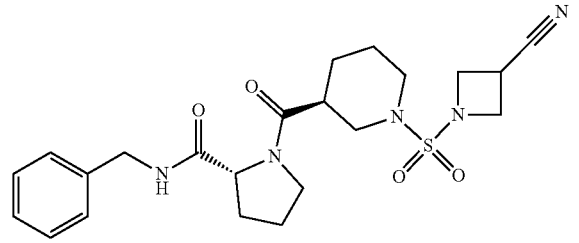 [SMILES: N#CC1CN(S(=O)(=O)N2CCC[C@H](C(=O)N3CCC[C@@H]3C(=O)NCc3ccccc3)C2)C1]<br>N-benzyl-1-(((3S)-1-((3-cyano-1-azetidinyl)sulfonyl)-3-piperidinyl)carbonyl)-D-prolinamide | LCMS-ESI (POS.) m/z: 460.2 (M + H)+ | 1H NMR (500 MHz, CHLOROFORM-d) δ ppm 7.18-7.38 (m, 5 H), 4.62 (br d, J = 5.97 Hz, 1 H), 4.40-4.50 (m, 2 H), 4.10-4.17 (m, 4 H), 3.78 (br d, J = 12.07 Hz, 2 H), 3.57-3.66 (m, 2 H), 3.42-3.49 (m, 1 H), 2.97-3.02 (m, 1 H), 2.69-2.82 (m, 2 H), 2.44-2.49 (m, 1 H), 2.18-2.26 (m, 1 H), 1.49-2.14 (m, 7 H) | A |

| Ex. # | Structure Name | LCMS-ESI (POS/NEG) m/z: (M + H)+ | NMR Data | Syn. Rte. |
|---|---|---|---|---|
| 759 | 1-((3-((3-cyano-1-azetidinyl)sulfonyl)phenyl)carbonyl)-N-(cis-3-(trifluoromethyl)cyclobut)-D-prolinamide, 1-((3-((3-cyano-1-azetidinyl)sulfonyl)phenyl)carbonyl)-N-(trans-3-(trifluoromethyl)cyclobut)-D-prolinamide | LCMS-APCI (NEG.) m/z: 483.1 (M − H) | 1H NMR (400 MHz, Methanol-d4) δ ppm 8.11 (d, J = 1.9 Hz, 1 H), 7.92-8.02 (m, 2 H), 7.76-7.82 (m, 1 H), 4.39-4.54 (m, 2 H), 4.07-4.13 (m, 2 H), 3.90-3.95 (m, 2 H), 3.66 (dt, J = 7.0, 10.1 Hz, 1 H), 3.53 (tdd, J = 3.7, 6.5, 8.8 Hz, 2 H), 3.00 (dtt, J = 5.3, 10.4, 15.8 Hz, 1 H), 2.53 (tt, J = 4.3, 9.0 Hz, 2 H), 2.26-2.46 (m, 4 H), 1.86-2.07 (m, 4 H). | A |
| 760 | 1-(((3S)-1-((3-fluoro-3-(trifluoromethyl)-1-azetidinyl)sulfonyl)-3-piperidinyl)carbonyl)-N-(4-(trifluoromethyl)benzyl)-D-prolinamide | LCMS-ESI (POS.) m/z: 589.2 (M + H)+ | 1H NMR (500 MHz, DMSO-d6) δ ppm 8.21-8.82 (m, 1 H), 7.60-7.79 (m, 2 H), 7.46 (br d, J = 7.53 Hz, 2 H), 4.08-4.56 (m, 7 H), 3.40-3.75 (m, 4 H), 2.55-2.98 (m, 3 H), 1.66-2.43 (m, 6 H), 1.32-1.60 (m, 2 H) | M |
| 761 | (2R)-N-(cyclopropyl(2-fluoro-4-(trifluoromethyl)phenyl)methyl)-1-(2-(methylsulfonyl)isonicotinoyl)pyrrolidine-2-carboxamide | LCMS-ESI (POS.) m/z: 514.0 (M + H)+ | 1H NMR (500 MHz, DMSO-d6) δ ppm 8.39-8.98 (m, 2 H), 7.26-8.14 (m, 5 H), 4.13-4.67 (m, 2 H), 3.37-3.60 (m, 2 H), 3.17-3.35 (m, 3 H), 2.17-2.37 (m, 1 H), 1.64-2.03 (m, 3 H), 0.87-1.29 (m, 1 H), -0.13-0.68 (m, 3 H), −0.19-0.70 (m, 1 H) | C |
| 762 | (1S,3R,5S)-N-((R)-cyclopropyl(2-fluoro-4-(trifluoromethyl)phenyl)methyl)-2-(3-(methylsulfonyl)benzoyl)-2-azabicyclo[3.1.0]hexane-3-carboxamide | LCMS-ESI (POS.) m/z: 525.0 (M + H)+ | 1H NMR (500 MHz, CHLOROFORM-d) δ ppm 8.31-8.42 (m, 1 H), 8.08 (br d, J = 7.78 Hz, 1 H), 8.03 (br d, J = 7.78 Hz, 1 H), 7.71 (t, J = 7.72 Hz, 1 H), 7.57 (br d, J = 7.14 Hz, 1 H), 7.45-7.52 (m, 1 H), 7.39-7.45 (m, 1 H), 7.35 (d, J = 10.38 Hz, 1 H), 4.76 (dd, J = 8.24, 2.66 Hz, 1 H), 4.59 (br t, J = 7.91 Hz, 1 H), 3.22 (br t, J = 4.87 Hz, 1 H), 3.11 (s, 3 H), 2.77 (ddd, J = 13.27, 7.30, 2.40 Hz, 1 H), 2.06 (br dd, J = 12.91, 9.28 Hz, 1 H), 1.95-2.03 (m, 1 H), 1.29-1.36 (m, 1 H), 1.08 (dt, J = 8.50, 5.48 Hz, 1 H), 0.71-0.80 (m, 1 H), 0.63-0.71 (m, 1 H), 0.53-0.63 (m, 1 H), 0.48 (dq, J = 9.59, 4.76 Hz, 1 H), 0.35-0.45 (m, 1 H) | C |

| Ex. # | Structure Name | LCMS-ESI (POS/NEG) m/z: (M + H)+ | NMR Data | Syn. Rte. |
|---|---|---|---|---|
| 763 | (2R)-1-((S)-1-((3-cyanoazetidin-1-yl)sulfonyl)piperidine-3-carbonyl)-N-(1-(2,3-difluorophenyl)ethyl)pyrrolidine-2-carboxamide | LCMS-ESI (POS.) m/z: 510.2 (M + H)+ | 1H NMR (500 MHz, DMSO-d6) δ ppm 8.21-8.85 (m, 1 H), 7.05-7.42 (m, 3 H), 5.00-5.22 (m, 1 H), 4.26-4.52 (m, 1 H), 3.70-4.12 (m, 6 H), 3.42-3.65 (m, 4 H), 2.59-2.92 (m, 3 H), 2.12-2.38 (m, 1 H), 1.38-2.12 (m, 9 H) | A |
| 764 | methyl N-((3-(((2R)-2-((4-(trifluoromethyl)benzyl)carbamo)-1-pyrrolidinyl)carbonyl)phenyl)sulfonyl)glycinate | LCMS-ESI (POS.) m/z: 528.2 (M + H)+ | 1H NMR (400 MHz, CHLOROFORM-d) δ ppm 8.05 (s, 1 H), 7.95 (br d, J = 7.98 Hz, 1 H), 7.72 (d, J = 7.72 Hz, 1 H), 7.52-7.63 (m, 3 H), 7.28-7.44 (m, 3 H), 5.50-5.70 (m, 1 H), 4.77 (dd, J = 7.28, 5.36 Hz, 1 H), 4.53 (d, J = 5.96 Hz, 2 H), 3.80 (d, J = 5.55 Hz, 2 H), 3.57-3.68 (m, 4 H), 3.41-3.53 (m, 1 H), 2.38-2.51 (m, 1 H), 2.01-2.25 (m, 3 H), 1.81-2.01 (m, 1 H), 1.70 (br s, 2 H) | B |
| 765 | 1-(((3S)-1-((3-cyano-1-azetidinyl)sulfonyl)-3-piperidinyl)carbonyl)-N-(2,5-dimethylbenzyl)-D-prolinamide | LCMS-ESI (POS.) m/z: 488.2 (M + H)+ | 1H NMR (500 MHz, DMSO-d6) δ ppm 8.05-8.43 (m, 1 H), 6.91-7.09 (m, 3 H), 4.32-4.51 (m, 1 H), 4.13-4.32 (m, 2 H), 4.00-4.12 (m, 2 H), 3.86-3.99 (m, 2 H), 3.73-3.81 (m, 1 H), 3.43-3.71 (m, 5 H), 2.62-2.89 (m, 3 H), 2.14-2.33 (m, 6 H), 1.69-2.11 (m, 5 H), 1.36-1.57 (m, 2 H) | A |
| 766 | (2R)-1-((3S)-1-((tetrahydrofuran-3-yl)sulfonyl)piperidine-3-carbonyl)-N-(4-(trifluoromethyl)benzyl)pyrrolidine-2-carboxamide | LCMS-APCI (POS.) m/z: 518.2 (M + H)+ | 1H NMR (Methanol-d4) δ: 7.78-7.59 (m, 1H), 7.58-7.43 (m, 1H), 4.68-4.38 (m, 4H), 3.83 (d, J = 11.9 Hz, 2H), 3.77-3.70 (m, 6H), 3.01-2.73 (m, 2H), 2.64 (ddd, J = 20.9, 14.6, 8.6 Hz, 4H), 2.26 (dt, J = 14.8, 7.8 Hz, 2H), 2.18-1.89 (m, 2H), 1.90-1.72 (m, 2H), 1.72-1.46 (m, 4H) | R |

| Ex. # | Structure Name | LCMS-ESI (POS/NEG) m/z: (M + H)+ | NMR Data | Syn. Rte. |
|---|---|---|---|---|
| 767 | 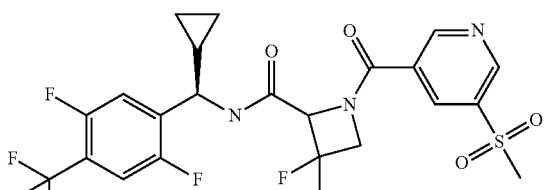<br>N-((R)-cyclopropyl(2,5-difluoro-4-(trifluoromethyl)phenyl)methyl)-3,3-difluoro-1-(5-(methylsulfonyl)nicotinoyl)azetidine-2-carboxamide | LCMS-ESI (POS.) m/z: 554.0 (M + H)+ | 1H NMR (500 MHz, CHLOROFORM-d) δ ppm 9.03-9.37 (m, 2 H), 8.34-8.67 (m, 1 H), 7.30-7.41 (m, 1 H), 7.06-7.27 (m, 1 H), 6.65-7.04 (m, 1 H), 5.13-5.41 (m, 1 H), 4.65-4.89 (m, 1 H), 4.49-4.64 (m, 1 H), 4.25-4.48 (m, 1 H), 3.08-3.25 (m, 3 H), 1.11-1.47 (m, 1 H), 0.27-0.86 (m, 4 H) | C |
| 768 | 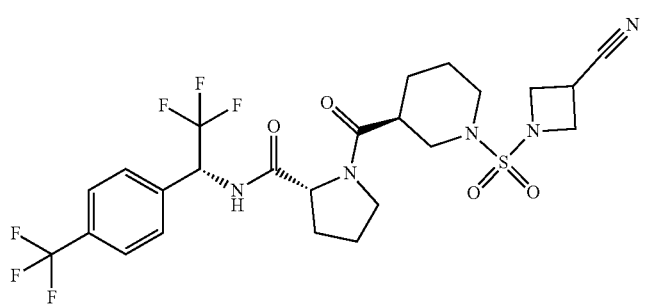 [SMILES: N#CC1CN(S(=O)(=O)N2CCC[C@H](C(=O)N3CCC[C@@H]3C(=O)N[C@H](c3ccc(C(F)(F)F)cc3)C(F)(F)F)C2)C1]<br>1-(((3S)-1-((3-cyano-1-azetidinyl)sulfonyl)-3-piperidinyl)carbonyl)-N-((1R)-2,2,2-trifluoro-1-(4-(trifluoromethyl)phenyl)ethyl)-D-prolinamide | LCMS-ESI (POS.) m/z: 596.2 (M + H)+ | 1H NMR (500 MHz, DMSO-d6) δ ppm 9.19-9.50 (m, 1 H), 7.74-7.89 (m, 4 H), 5.85-6.05 (m, 1 H), 4.46 (dd, J = 8.43, 4.15 Hz, 1 H), 3.97-4.08 (m, 2 H), 3.84-3.95 (m, 2 H), 3.71-3.80 (m, 1 H), 3.50-3.61 (m, 3 H), 2.69-2.81 (m, 2 H), 2.57-2.66 (m, 1 H), 2.12-2.23 (m, 1 H), 1.86-1.99 (m, 2 H), 1.73-1.84 (m, 2 H), 1.62-1.70 (m, 1 H), 1.48 (qt, J = 12.82, 3.60 Hz, 1 H), 1.24-1.37 (m, 1 H) | A |
| 769 | 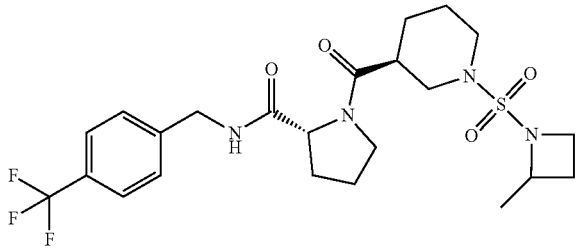 [SMILES: CC1CCN1S(=O)(=O)N1CCC[C@H](C(=O)N2CCC[C@@H]2C(=O)NCc2ccc(C(F)(F)F)cc2)C1]<br>(2R)-1-((3S)-1-((2-methylazetidin-1-yl)sulfonyl)piperidine-3-carbonyl)-N-(4-(trifluoromethyl)benzyl)pyrrolidine-2-carboxamide | LCMS-ESI (POS.) m/z: 517.2 (M + H)+ | 1H NMR (500 MHz, DMSO-d6) δ ppm 8.27-8.82 (m, 1 H), 7.58-7.83 (m, 2 H), 7.45 (br d, J = 7.79 Hz, 2 H), 4.12-4.50 (m, 4 H), 3.43-3.84 (m, 7 H), 2.59-2.87 (m, 3 H), 2.03-2.40 (m, 3 H), 1.65-2.01 (m, 7 H), 1.33-1.61 (m, 2 H), 1.22-1.31 (m, 3 H) | M |
| 770 | 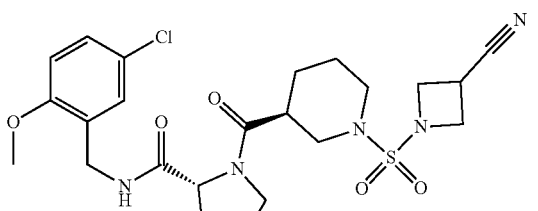<br>N-(5-chloro-2-methoxybenzyl)-1-(((3S)-1-((3-cyano-1-azetidinyl)sulfonyl)-3-piperidinyl)carbonyl)-D-prolinamide | LCMS-ESI (POS.) m/z: 524.2 (M + H)+ | 1H NMR (500 MHz, DMSO-d6) δ ppm 8.06-8.53 (m, 1 H), 7.07-7.33 (m, 2 H), 6.92-7.05 (m, 1 H), 4.11-4.54 (m, 3 H), 3.90-4.10 (m, 4 H), 3.74-3.85 (m, 4 H), 3.45-3.72 (m, 4 H), 2.62-2.89 (m, 3 H), 2.06-2.35 (m, 1 H), 1.66-2.35 (m, 5 H), 1.36-1.58 (m, 2 H) | A |

| Ex. # | Structure Name | LCMS-ESI (POS/NEG) m/z: (M + H)+ | NMR Data | Syn. Rte. |
|---|---|---|---|---|
| 771 | 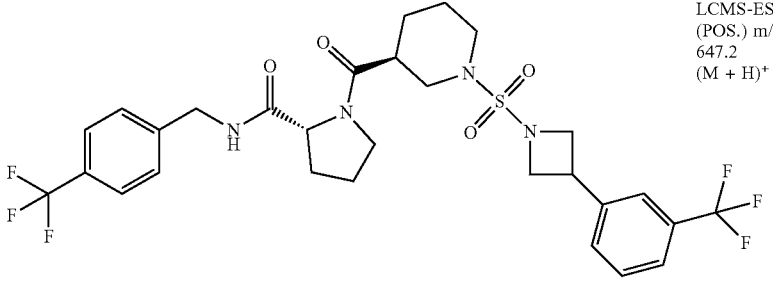<br>N-(4-(trifluoromethyl)benzyl)-1-(((3S)-1-((3-(3-(trifluoromethyl)phenyl)-1-azetidinyl)sulfonyl)-3-piperidinyl)carbonyl)-D-prolinamide | LCMS-ESI (POS.) m/z: 647.2 (M + H)+ | 1H NMR (500 MHz, DMSO-d6) δ 8.27-8.74 (m, 1H), 7.54-7.79 (m, 6H), 7.36-7.51 (m, 2H), 4.26-4.45 (m, 3H), 4.10-4.26 (m, 2H), 3.83-4.05 (m, 3H), 3.46-3.73 (m, 5H), 2.62-2.90 (m, 3H), 2.05-2.42 (m, 1H), 1.37-2.05 (m, 6H) | J |
| 772 | 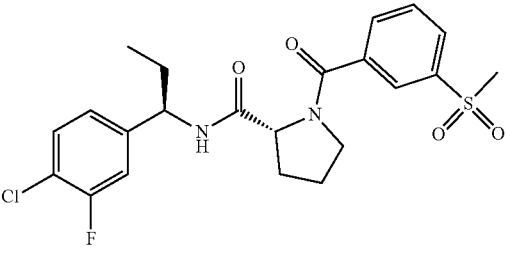 [SMILES: CC[C@@H](NC(=O)[C@H]1CCCN1C(=O)c1cccc(S(C)(=O)=O)c1)c1ccc(Cl)c(F)c1]<br>N-((1R)-1-(4-chloro-3-fluorophenyl)propyl)-1-(3-(methylsulfonyl)benzoyl)-D-prolinamide | LCMS-ESI (POS.) m/z: 467.0 (M + H)+ | 1H NMR (500 MHz, DMSO-d6) δ ppm 8.15-8.45 (m, 1 H), 6.97-8.10 (m, 7 H), 4.32-4.81 (m, 2 H), 3.42-3.61 (m, 2 H), 3.20-3.32 (m, 3 H), 2.12-2.31 (m, 1 H), 1.28-1.97 (m, 5 H), 0.36-1.01 (m, 3 H) | C |
| 773 | 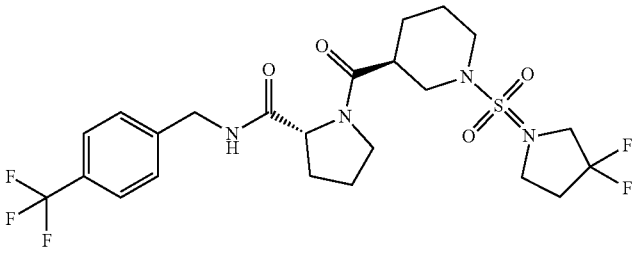<br>1-(((3S)-1-((3,3-difluoro-1-pyrrolidinyl)sulfonyl)-3-piperidinyl)carbonyl)-N-(4-(trifluoromethyl)benzyl)-D-prolinamide | LCMS-ESI (POS.) m/z: 553.2 (M + H)+ | 1H NMR (500 MHz, DMSO-d6) δ 8.30-8.83 (m, 1 H), 7.58-7.75 (m, 2 H), 7.45 (br d, J = 7.79 Hz, 2 H), 4.24-4.55 (m, 3 H), 3.56-3.70 (m, 5 H), 3.34-3.49 (m, 3 H), 2.78-2.93 (m, 2 H), 2.58-2.71 (m, 1 H), 2.37-2.48 (m, 2 H), 1.35-2.20 (m, 8 H) | M |
| 774 | 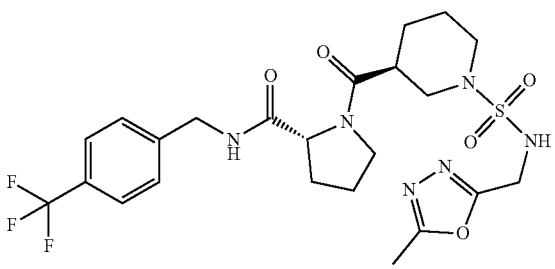 [SMILES: Cc1nnc(CNS(=O)(=O)N2CCC[C@H](C(=O)N3CCC[C@@H]3C(=O)NCc3ccc(C(F)(F)F)cc3)C2)o1]<br>1-(((3S)-1-(((5-methyl-1,3,4-oxadiazol-2-yl)methyl)sulfamo)-3-piperidinyl)carbonyl)-N-(4-(trifluoromethyl)benzyl)-D-prolinamide | LCMS-ESI (POS.) m/z: 559.2 (M + H)+ | 1H NMR (500 MHz, DMSO-d6) δ 8.30-8.79 (m, 1H), 7.90-8.15 (m, 1H), 7.60-7.76 (m, 2H), 7.36-7.54 (m, 2H), 4.21-4.52 (m, 5H), 3.38-3.72 (m, 5H), 2.53-2.75 (m, 4H), 1.64-2.37 (m, 7H), 1.27-1.49 (m, 2H) | J |

| Ex. # | Structure Name | LCMS-ESI (POS/NEG) m/z: (M + H)+ | NMR Data | Syn. Rte. |
|---|---|---|---|---|
| 775 | 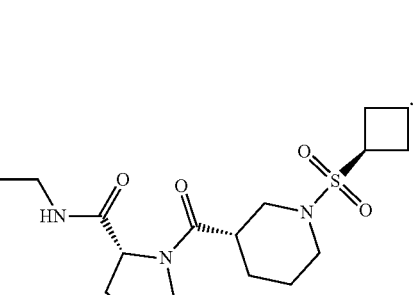<br>methyl trans-3-(((3S)-3-(((2R)-2-((4-(trifluoromethyl)benzyl)carbamo)-1-pyrrolidinyl)carbonyl)-1-piperidinyl)sulfonyl)cyclobutanecarboxylate | LCMS-APCI (POS.) m/z: 560.2 (M + H)+ | 1H NMR (Methanol-d4) δ: 7.78-7.59 (m, 1H), 7.58-7.43 (m, 1H), 4.68-4.38 (m, 4H), 3.83 (d, J = 11.9 Hz, 2H), 3.77-3.70 (m, 6H), 3.01-2.73 (m, 2H), 2.64 (ddd, J = 20.9, 14.6, 8.6 Hz, 4H), 2.26 (dt, J = 14.8, 7.8 Hz, 2H), 2.18-1.89 (m, 2H), 1.90-1.72 (m, 2H), 1.72-1.46 (m, 4H) | R |
| 776 | 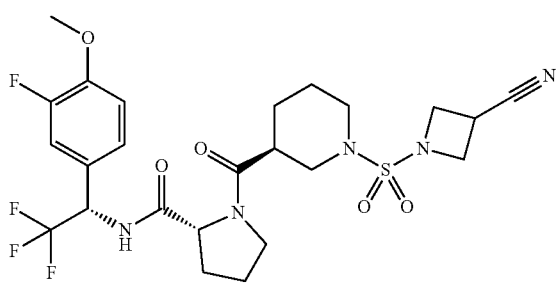 [SMILES: COc1ccc([C@H](NC(=O)[C@H]2CCCN2C(=O)[C@H]2CCCN(S(=O)(=O)N3CC(C#N)C3)C2)C(F)(F)F)cc1F]<br>1-(((3S)-1-((3-cyano-1-azetidinyl)sulfonyl)-3-piperidinyl)carbonyl)-N-((1S)-2,2,2-trifluoro-1-(3-fluoro-4-methoxyphenyl)ethyl)-D-prolinamide | LCMS-ESI (POS.) m/z: 576.2 (M + H)+ | 1H NMR (500 MHz, DMSO-d6) δ ppm 8.88-9.45 (m, 1 H), 7.09-7.50 (m, 3 H), 5.59-5.85 (m, 1 H), 4.35-4.61 (m, 1 H), 4.00-4.14 (m, 2 H), 3.89-3.97 (m, 2 H), 3.74-3.89 (m, 4 H), 3.41-3.67 (m, 4 H), 2.60-2.91 (m, 3 H), 2.02-2.33 (m, 1 H), 1.68-1.97 (m, 4 H), 1.58-1.68 (m, 1 H), 1.46-1.57 (m, 1 H), 1.32-1.45 (m, 1 H) | A |
| 777 | 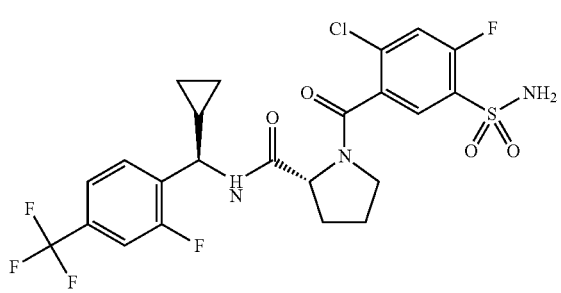 [SMILES: NS(=O)(=O)c1cc(C(=O)N2CCC[C@@H]2C(=O)N[C@@H](c2ccc(C(F)(F)F)cc2F)C2CC2)c(Cl)cc1F]<br>1-(2-chloro-4-fluoro-5-sulfamoylbenzoyl)-N-((R)-cyclopropyl(2-fluoro-4-(trifluoromethyl)phenyl)methyl)-D-prolinamide | LCMS-ESI (POS.) m/z: 566.2 (M + H)+ | 1H NMR (500 MHz, DMSO-d6) δ ppm 8.72 (br s, 1 H), 7.42-7.94 (m, 7 H), 4.46-4.65 (m, 1 H), 4.06-4.26 (m, 1 H), 3.12-3.67 (m, 2 H), 2.10-2.29 (m, 1 H), 1.65-1.91 (m, 3 H), 0.90-1.22 (m, 1 H), 0.03-0.69 (m, 4 H) | C |
| 778 | 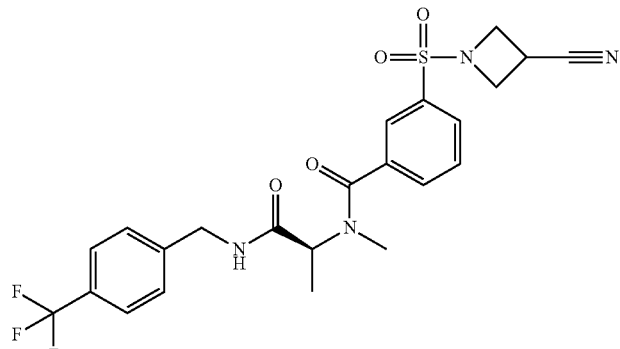<br>3-((3-cyano-1-azetidinyl)sulfonyl)-N-methyl-N-((1S)-1-methyl-2-oxo-2-((4-(trifluoromethyl)benzyl)amino)ethyl)benzamide | LCMS-APCI (NEG.) m/z: 507.1 (M − H) | 1H NMR (400 MHz, Methanol-d4) δ ppm 7.93-8.07 (m, 2 H), 7.72-7.91 (m, 2 H), 7.60-7.67 (m, 2 H), 7.42-7.58 (m, 2 H), 5.05-5.17 (m, 1 H), 4.43-4.60 (m, 2 H), 4.04-4.17 (m, 2 H), 3.85-3.98 (m, 2 H), 3.43-3.60 (m, 1 H), 2.96-3.09 (m, 3 H), 1.42-1.63 (m, 3 H). | Q |

-continued

| Ex. # | Structure Name | LCMS-ESI (POS/NEG) m/z: (M + H)+ | NMR Data | Syn. Rte. |
|---|---|---|---|---|
| 779 | (1S,3R,5S)-N-((R)-(4-chloro-2,5-difluorophenyl)(cyclopropyl)methyl)-2-((2-(methylsulfonyl)-4-pyridinyl)carbonyl)-2-azabicyclo[3.1.0]hexane-3-carboxamide | LCMS-ESI (POS.) m/z: 510.0 (M + H)+ | 1H NMR (400 MHz, CHLOROFORM-d) δ ppm 8.84-8.93 (m, 1 H), 8.36-8.48 (m, 1 H), 7.74-7.87 (m, 1 H), 7.28-7.35 (m, 1 H), 7.10-7.20 (m, 2 H), 4.73 (dd, J = 8.55, 3.06 Hz, 1 H), 4.47 (t, J = 7.83 Hz, 1 H), 3.29 (s, 3 H), 3.15-3.23 (m, 1 H), 2.76 (ddd, J = 13.48, 7.26, 2.90 Hz, 1 H), 1.99-2.15 (m, 2 H), 1.18-1.30 (m, 1 H), 1.11 (dt, J = 8.86, 5.52 Hz, 1 H), 0.76 (td, J = 5.11, 2.54 Hz, 1 H), 0.63-0.73 (m, 1 H), 0.59 (tt, J = 8.60, 4.41 Hz, 1 H), 0.33-0.52 (m, 2 H) | C |
| 780 | 1-(((3S)4-(cyclobutylsulfonyl)-3-piperidinyl)carbonyl)-N-(4-(trifluoromethyl)benzyl)-D-prolinamide | LCMS-APCI (POS.) m/z: 502.2 (M + H)+ | 1H NMR (400 MHz, Methanol-d4) δ ppm 7.64 (d, J = 8.1 Hz, 2 H), 7.50 (d, J = 7.9 Hz, 2 H), 4.48 (d, J = 2.2 Hz, 2 H), 4.44 (dd, J = 4.4, 8.3 Hz, 1 H), 3.93-4.03 (m, 1 H), 3.70-3.77 (m, 3 H), 2.73-2.83 (m, 2 H), 2.43-2.53 (m, 3 H), 2.24-2.37 (m, 4 H), 1.94-2.12 (m, 7 H), 1.50-1.65 (m, 2 H). | R |
| 781 | 1-(((3S)-1-((3-cyano-1-azetidinyl)sulfonyl)-3-piperidinyl)carbonyl)-N-(3-(difluoromethoxy)benzyl)-D-prolinamide | LCMS-ESI (POS.) m/z: 526.2 (M + H)+ | 1H NMR (500 MHz, DMSO-d6) δ ppm 8.29-8.71 (m, 1 H), 6.96-7.43 (m, 4 H), 4.24-4.55 (m, 3 H), 3.88-4.13 (m, 4 H), 3.41-3.84 (m, 6 H), 2.61-2.87 (m, 3 H), 2.06-2.34 (m, 1 H), 1.34-2.00 (m, 7 H) | A |
| 782 | 1-(((3S)-1-((3-(acetylamino)-1-azetidinyl)sulfonyl)-3-piperidinyl)carbonyl)-N-(4-(trifluoromethyl)benzyl)-D-prolinamide | LCMS-ESI (POS.) m/z: 560.2 (M + H)+ | 1H NMR (500 MHz, DMSO-d6) δ ppm 7.82-8.91 (m, 2 H), 7.35-7.81 (m, 1 H), 6.86-7.35 (m, 1 H), 4.38-4.59 (m, 1 H), 4.26-4.37 (m, 2 H), 4.04-4.26 (m, 5 H), 3.86-4.04 (m, 2 H), 3.59-3.73 (m, 2 H), 3.53-3.59 (m, 1 H), 3.27-3.49 (m, 1 H), 2.62-2.84 (m, 2 H), 2.00-2.15 (m, 1 H), 1.67-1.99 (m, 4 H), 1.30-1.63 (m, 1 H) | M |

| Ex. # | Structure Name | LCMS-ESI (POS/NEG) m/z: (M + H)+ | NMR Data | Syn. Rte. |
|---|---|---|---|---|
| 783 | 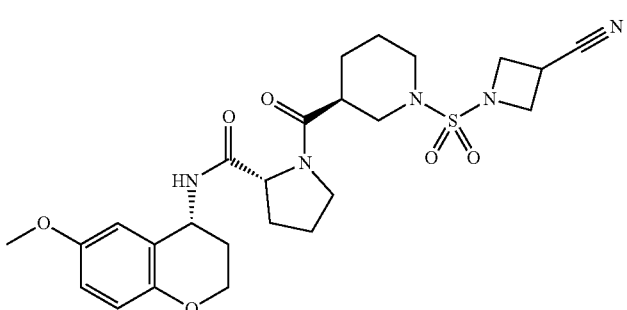<br>1-(((3S)-1-((3-cyano-1-azetidinyl)sulfonyl)-3-piperidinyl)carbonyl)-N-((4R)-6-methoxy-3,4-dihydro-2H-chromen-4-yl)-D-prolinamide | LCMS-ESI (POS.) m/z: 532.2 (M + H)+ | 1H NMR (500 MHz, DMSO-d6) δ ppm 8.04-8.74 (m, 1 H), 6.53-6.84 (m, 3 H), 4.81-5.04 (m, 1 H), 4.21-4.46 (m, 1 H), 3.41-4.19 (m, 13 H), 2.59-2.87 (m, 3 H), 1.65-2.33 (m, 9 H), 1.31-1.57 (m, 2 H) | A |
| 784 | 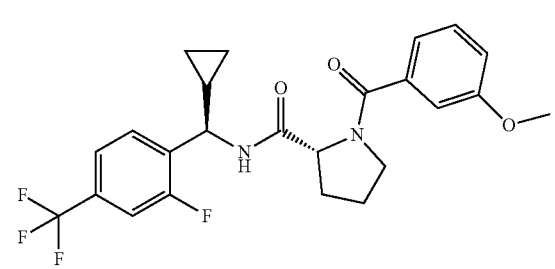 [SMILES: COc1cccc(C(=O)N2CCC[C@@H]2C(=O)N[C@@H](c2ccc(C(F)(F)F)cc2F)C2CC2)c1]<br>N-((R)-cyclopropyl(2-fluoro-4-(trifluoromethyl)phenyl)methyl)-1-(3-methoxybenzoyl)-D-prolinamide | LCMS-ESI (POS.) m/z: 465.2 (M + H)+ | 1H NMR (500 MHz, DMSO-d6) δ ppm 8.42-8.65 (m, 1 H), 6.66-7.71 (m, 8 H), 4.18-4.57 (m, 2 H), 3.66-3.76 (m, 3 H), 3.42-3.56 (m, 1 H), 2.00-2.16 (m, 1 H), 1.55-1.81 (m, 3 H), 0.89-1.17 (m, 1 H), 0.00-0.56 (m, 4 H) | C |
| 785 | 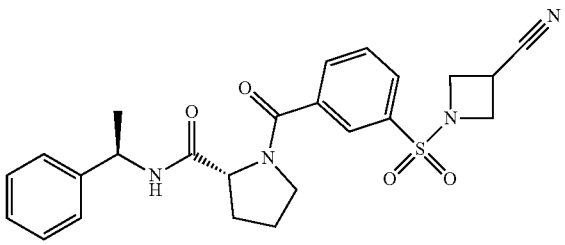 [SMILES: C[C@@H](NC(=O)[C@H]1CCCN1C(=O)c1cccc(S(=O)(=O)N2CC(C#N)C2)c1)c1ccccc1]<br>1-((3-((3-cyano-1-azetidinyl)sulfonyl)phenyl)carbonyl)-N-((1R)-1-phenylethyl)-D-prolinamide | LCMS-ESI (POS.) m/z: 467.2 (M + H)+ | 1H NMR (400 MHz, CHLOROFORM-d) δ ppm 7.77-7.99 (m, 2 H), 7.60-7.77 (m, 2 H), 7.29-7.41 (m, 4 H), 7.14-7.27 (m, 2 H), 5.11 (quin, J = 7.23 Hz, 1 H), 4.75-4.87 (m, 1 H), 4.73-6.10 (m, 1 H), 3.97-4.22 (m, 4 H), 3.27-3.94 (m, 3 H), 1.80-2.59 (m, 4 H), 1.41-1.57 (m, 3 H) | A |

| Ex. # | Structure Name | LCMS-ESI (POS/NEG) m/z: (M + H)+ | NMR Data | Syn. Rte. |
|---|---|---|---|---|
| 786 | 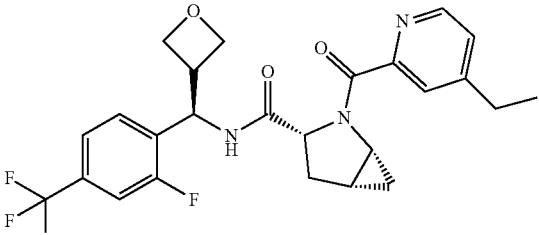<br>(1R,3R,5R)-2((4-ethyl-2-pyridinyl)carbonyl)-N-((R)-(2-fluoro-4-(trifluoromethyl)phenyl)(3-oxetanyl)methyl)-2-azabicyclo[3.1.0]hexane-3-carboxamide | LCMS-APCI (POS.) m/z: 492.2 (M + H)+ | 1H NMR (DMSO-d6) δ: 8.71 (d, J = 8.1 Hz, 1H), 8.52 (dd, J = 5.0, 0.8 Hz, 1H), 8.46 (d, J = 8.3 Hz, 1H), 8.33 (dd, J = 5.0, 0.8 Hz, 1H), 7.74-7.53 (m, 5H), 7.45 (t, J = 7.6 Hz, 1H), 7.39 (dd, J = 5.0, 1.8 Hz, 1H), 7.33 (dd, J = 5.0, 1.8 Hz, 1H), 5.56-5.44 (m, 2H), 5.19 (t, J = 9.0 Hz, 1H), 4.86 (d, J = 11.4, 3.4 Hz, 1H), 4.75-4.62 (m, 1H), 4.58-4.50 (m, 1H), 4.45 (t, J = 6.1 Hz, 1H), 4.38 (dd, J = 7.8, 6.2 Hz, 2H), 4.26 (t, J = 6.1 Hz, 1H), 3.97 (td, J = 6.3, 2.6 Hz, 1H), 3.90 (t, J = 6.2 Hz, 1H), 3.85 (t, J = 6.1 Hz, 1H), 3.81-3.75 (m, 1H), 3.49-3.38 (m, 1H), 3.29-3.17 (m, 1H), 2.69 (dq, J = 15.0, 7.6 Hz, 4H), 1.77 (dd, J = 13.4, 2.8 Hz, 1H), 1.69 (dd, J = 13.5, 3.2 Hz, 1H), 1.60 (d, J = 8.7 Hz, 1H), 1.51 (p, J = 6.2 Hz, 1H), 1.21 (dt, J = 9.7, 7.6 Hz, 6H), 1.08-1.01 (m, 1H), 0.71 (dd, J = 6.4, 4.1 Hz, 2H), 0.65-0.51 (m, 1H) | Q |
| 787 | 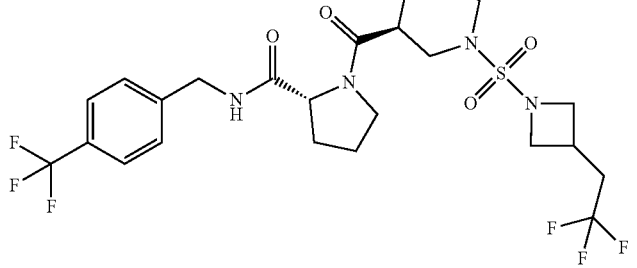<br>1-(((3S)-1-((3-(2,2,2-trifluoroethyl)-1-azetidinyl)sulfonyl)-3-piperidinyl)carbonyl)-N-(4-(trifluoromethyl)benzyl)-D-prolinamide | LCMS-ESI (POS.) m/z: 585.2 (M + Na)+ | 1H NMR (500 MHz, DMSO-d6) δ ppm 8.28-8.75 (m, 1 H), 7.61-7.74 (m, 2 H), 7.45 (br d, J = 7.27 Hz, 2 H), 4.26-4.53 (m, 3 H), 3.84-3.96 (m, 2 H), 3.51-3.67 (m, 6 H), 2.70-2.90 (m, 3 H), 2.53-2.68 (m, 3 H), 1.33-2.39 (m, 9 H) | M |
| 788 | 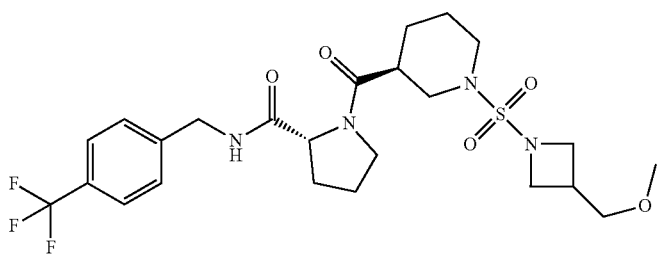 [SMILES: COCC1CN(S(=O)(=O)N2CCC[C@H](C(=O)N3CCC[C@@H]3C(=O)NCc3ccc(C(F)(F)F)cc3)C2)C1]<br>1-(((3S)-1((3-(methoxymethyl)-1-azetidinyl)sulfonyl)-3-piperidinyl)carbonyl)-N-(4-(trifluoromethyl)benzyl)-D-prolinamide | LCMS-ESI (POS.) m/z: 547.2 (M + H)+ | 1H NMR (500 MHz, CHLOROFORM-d) δ ppm 7.57 (d, J = 8.04 Hz, 2 H), 7.49 (br t, J = 5.06 Hz, 1 H), 7.33-7.42 (m, 3 H), 4.61 (dd, J = 7.79, 1.56 Hz, 1 H), 4.38-4.54 (m, 2 H), 3.93 (t, J = 8.04 Hz, 2 H), 3.73-3.84 (m, 2 H), 3.67 (ddd, J = 7.91, 5.71, 2.72 Hz, 2 H), 3.55-3.62 (m, 2 H), 3.52 (d, J = 6.75 Hz, 2 H), 3.37 (s, 3 H), 2.92 (dd, J = 12.33, 11.29 Hz, 1 H), 2.65-2.86 (m, 3 H), 2.41-2.61 (m, 1 H), 2.11-2.24 (m, 1 H), 1.99-2.10 (m, 1 H), 1.81-1.94 (m, 3 H), 1.74-1.81 (m, 1 H), 1.46-1.72 (m, 4 H) | M |

| Ex. # | Structure Name | LCMS-ESI (POS/NEG) m/z: (M + H)+ | NMR Data | Syn. Rte. |
|---|---|---|---|---|
| 789 | (1R,3R,5R)-N-((R)-(2-fluoro-4-(trifluoromethyl)phenyl)(3-oxetanyl)methyl)-2-((6-(trifluoromethyl)-2-pyridinyl)carbonyl)-2-azabicyclo[3.1.0]hexane-3-carboxamide | LCMS-APCI (POS.) m/z: 532.1 (M + H)+ | 1H NMR (Methanol-d4) δ: 8.27-8.16 (m, 2H), 8.13 (t, J = 7.4 Hz, 1H), 7.97 (d, 1H), 7.91 (dd, J = 7.6, 1.3 Hz, 1H), 7.61-7.51 (m, 3H), 7.51-7.43 (m, 2H), 7.37 (t, J = 7.7 Hz, 1H), 5.78 (dd, J = 11.7, 2.9 Hz, 1H), 5.66 (d, J = 10.2 Hz, 1H), 5.26 (d, J = 10.4 Hz, 1H), 4.99 (dd, J = 11.3, 3.8 Hz, 1H), 4.74-4.62 (m, 2H), 4.59-4.46 (m, 1H), 4.47-4.37 (m, 1H), 4.07-3.96 (m, 2H), 3.95-3.82 (m, 2H), 3.66-3.52 (m, 1H), 2.96-2.82 (m, 1H), 2.66 (td, J = 12.6, 6.5 Hz, 1H), 2.09-1.95 (m, 1H), 1.95-1.86 (m, 2H), 1.86-1.73 (m, 1H), 1.71-1.62 (m, 1H), 1.57 (d, J = 6.8 Hz, 1H), 1.37-1.21 (m, 3H), 1.16 (td, J = 5.4, 2.6 Hz, 1H), 0.98-0.81 (m, 2H), 0.81-0.72 (m, 1H), 0.71-0.61 (m, 1H) | Q |
| 790 | 1-(((2S)-4-((3-cyano-1-azetidinyl)sulfonyl)-2-piperazinyl)carbonyl)-N-(3,5-dichlorobenzyl)-D-prolinamide | LCMS-ESI (POS.) m/z: 529.0 (M + H)+ | 1H NMR (400 MHz, DMSO-d6) δ 8.28-8.78 (m, 1H), 8.03-8.25 (m, 1H), 7.30-7.61 (m, 1H), 7.22-7.25 (m, 1H), 4.22-4.39 (m, 3H), 4.01-4.14 (m, 2H), 3.88-3.98 (m, 2H), 3.70-3.88 (m, 2H), 3.30-3.62 (m, 6H), 2.91-3.06 (m, 1H), 2.68-2.78 (m, 2H), 1.74-2.16 (m, 4H) | E |
| 791 | (5S)-N-((R)-cyclopropyl(2-fluoro-4-(trifluoromethyl)phenyl)methyl)-5-methyl-1-(3-(methylsulfonyl)benzoyl)-D-prolinamide | LCMS-ESI (POS.) m/z: 527.2 (M + H)+ | 1H NMR (400 MHz, CHLOROFORM-d) δ ppm 7.98 (br s, 2 H), 7.54-7.85 (m, 2 H), 7.29-7.49 (m, 3 H), 7.22-7.27 (m, 1 H), 4.31-4.84 (m, 2 H), 4.02-4.25 (m, 1 H), 3.00-3.15 (m, 3 H), 2.33-2.49 (m, 1 H), 1.84-2.29 (m, 2 H), 1.63-1.71 (m, 1 H), 0.82-1.42 (m, 4 H), −0.05-0.63 (m, 4 H) | C |

| Ex. # | Structure Name | LCMS-ESI (POS/NEG) m/z: (M + H)+ | NMR Data | Syn. Rte. |
|---|---|---|---|---|
| 792 | 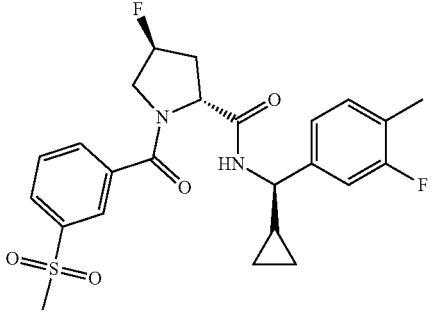 [SMILES: Cc1ccc([C@H](NC(=O)[C@H]2C[C@H](F)CN2C(=O)c2cccc(S(C)(=O)=O)c2)C2CC2)cc1F]<br>(4S)-N-((R)-cyclopropyl(3-fluoro-4-methylphenyl)methyl)-4-fluoro-1-(3-(methylsulfonyl)benzoyl)-D-prolinamide | LCMS-APCI (NEG.) m/z: 475.1 (M − H) | 1H NMR (400 MHz, DMSO-d6) δ ppm 8.66 (d, J = 8.3 Hz, 1 H), 7.88-8.12 (m, 1 H), 7.69-7.82 (m, 1 H), 6.87-7.25 (m, 2 H), 5.33 (dd, J = 18.5, 52.7 Hz, 1 H), 4.26-4.74 (m, 2 H), 3.95 (dd, J = 13.2, 37.8 Hz, 1 H), 3.60 (dd, J = 12.7, 20.1 Hz, 1 H), 3.29 (d, J = 5.1 Hz, 1 H), 2.19 (d, 1 H), 1.86-2.09 (m, 1 H), 0.47-0.80 (m, 1 H), 0.33-0.46 (m, 1 H), −0.34-0.06 (m, 1 H). | A |
| 793 | 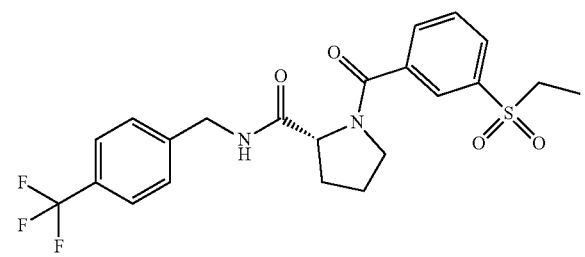 [SMILES: CCS(=O)(=O)c1cccc(C(=O)N2CCC[C@@H]2C(=O)NCc2ccc(C(F)(F)F)cc2)c1]<br>1-(3-(ethylsulfonyl)benzoyl)-N-(4-(trifluoromethyl)benzyl)-D-prolinamide | LCMS-ESI (POS.) m/z: 469.0 (M + H)+ | 1H NMR (500 MHz, DMSO-d6) δ ppm 8.41-8.71 (m, 1 H), 7.13-8.14 (m, 8 H), 4.38-4.40 (m, 1 H), 4.07-4.52 (m, 2 H), 3.41-3.71 (m, 2 H), 3.34-3.39 (m, 1 H), 3.19-3.28 (m, 1 H), 2.17-2.35 (m, 1 H), 1.73-1.99 (m, 3 H), 0.93-1.17 (m, 3 H) | C |
| 794 | 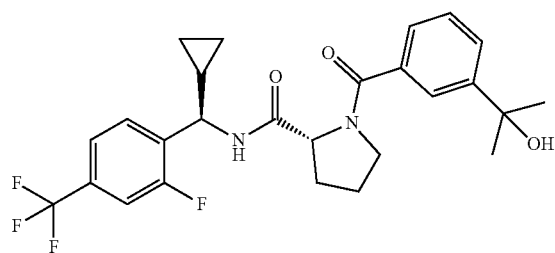 [SMILES: CC(C)(O)c1cccc(C(=O)N2CCC[C@@H]2C(=O)N[C@@H](c2ccc(C(F)(F)F)cc2F)C2CC2)c1]<br>N-((R)-cyclopropyl(2-fluoro-4-(trifluoromethyl)phenyl)methyl)-1-(3-(2-hydroxy-2-propanyl)benzoyl)-D-prolinamide | LCMS-ESI (POS.) m/z: 493.0 (M + H)+ | 1H NMR (500 MHz, DMSO-d6) δ ppm 8.40-8.74 (m, 1 H), 7.41-7.74 (m, 5 H), 6.53-7.40 (m, 2 H), 5.02-5.12 (m, 1 H), 4.25-4.63 (m, 2 H), 3.37-3.64 (m, 2 H), 2.11-2.22 (m, 1 H), 1.64-1.88 (m, 3 H), 1.37-1.47 (m, 6 H), 0.98-1.25 (m, 1 H), 0.05-0.62 (m, 4 H) | C |
| 795 | 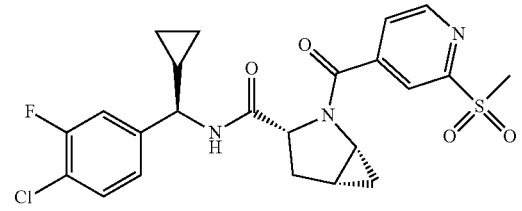 [SMILES: CS(=O)(=O)c1cc(C(=O)N2[C@@H](C(=O)N[C@@H](c3ccc(Cl)c(F)c3)C3CC3)C[C@H]3C[C@H]32)ccn1]<br>(1R,3R,5R)-N-((R)-(4-chloro-3-fluorophenyl)(cyclopropyl)methyl)-2-((2-(methylsulfonyl)-4-pyridinyl)carbonyl)-2-azabicyclo[3.1.0]hexane-3-carboxamide | LCMS-ESI (POS.) m/z: 492.2 (M + H)+ | 1H NMR (500 MHz, DMSO-d6) δ ppm 8.28-9.00 (m, 2 H), 7.69-8.22 (m, 2 H), 7.49-7.62 (m, 1 H), 7.01-7.46 (m, 2 H), 4.59-5.02 (m, 1 H), 3.80-4.31 (m, 1 H), 3.26-3.34 (m, 4 H), 2.57-2.70 (m, 1 H), 1.56 (s, 2 H), 0.69-1.29 (m, 3 H), − 0.32-0.56 (m, 4 H) | C |

| Ex. # | Structure Name | LCMS-ESI (POS/NEG) m/z: (M + H)+ | NMR Data | Syn. Rte. |
|---|---|---|---|---|
| 796 | 1-(3-(1-acet-3-fluoro-3-azetidinyl)benzoyl)-N-((R)-cyclopropyl(2-fluoro-4-(trifluoromethyl)phenyl)methyl)-D-prolinamide | LCMS-APCI (POS.) m/z: 550.2 (M + H)+ | 1H NMR (400 MHz, Methanol-d4) δ ppm 7.17-7.61 (m, 7 H), 3.91-4.54 (m, 6 H), 3.27-3.55 (m, 2 H), 1.61-2.19 (m, 7 H), 1.05-1.17(m, 1 H), 0.20-0.56(m,4 H). | W |
| 797 | (1R,3R,5R)-N-((R)-cyclopropyl(2,5-difluoro-4-(trifluoromethyl)phenyl)methyl)-2-((5-methyl-3-pyridinyl)carbonyl)-2-azabicyclo[3.1.0]hexane-3-carboxamide | LCMS-APCI (POS.) m/z: 480.2 (M + H)+ | 1H NMR (Methanol-d4) δ: 8.64 (s, 1H), 8.42 (s, 1H), 7.91 (s, 1H), 7.40 (dd, J = 9.5, 5.7 Hz, 1H), 7.32 (dd, J = 10.8, 5.6 Hz, 1H), 4.93 (dd, J = 11.4, 4.0 Hz, 1H), 4.39 (d, J = 9.0 Hz, 1H), 2.66-2.51 (m, 1H), 2.33 (s, 3H), 1.82 (dd, J = 13.5, 4.0 Hz, 1H), 1.74-1.62 (m, 1H), 1.19-1.11 (m, 1H), 1.06 (td, J = 5.3, 2.6 Hz, 1H), 0.75 (dt, J = 9.1, 5.8 Hz, 2H), 0.64-0.54 (m, 1H), 0.53-0.44 (m, 1H), 0.44-0.31 (m, 2H) | Q |
| 798 | (2R)-1-((3-((3,3-difluoro-1-azetidinyl)sulfonyl)phenyl)carbonyl)-N-((6-(trifluoromethyl)-3-pyridinyl)methyl)-2-piperidinecarboxamide | LCMS-ESI (POS.) m/z: 547.2 (M + H)+ | 1H NMR (400 MHz, DMSO-d6) δ ppm 8.68 (br s, 2 H), 7.67-8.04 (m, 6 H), 5.18* (br s, 1 H), 4.02-4.56 (m, 7 H), 3.17-3.39 (m, 2 H), 2.75-2.91* (m, 2 H), 2.25 (br d, J = 10.11 Hz, 1 H), 1.21-1.80 (m, 5 H). Spectrum appears as 2:1 mixture of rotamers, *denotes resolved minor rotamer peaks. | C |
| 799 | (2R)-1-((S)-1-((3-cyanoazetidin-1-yl)sulfonyl)piperidine-3-carbonyl)-N-(2-(trifluoromethyl)cyclobutyl)pyrrolidine-2-carboxamide | LCMS-ESI (POS.) m/z: 492.2 (M + H)+ | 1H NMR (600 MHz, DMSO-d6) δ ppm 7.98-8.62 (m, 1 H), 4.35-4.45 (m, 1 H), 4.24-4.34 (m, 1 H), 4.01-4.19 (m, 1 H), 3.99-4.46 (m, 2 H), 3.86-3.96 (m, 2 H), 3.74-3.84 (m, 1 H), 3.49-3.68 (m, 3 H), 3.27-3.34 (m, 1 H), 2.96-3.17 (m, 1 H), 2.56-2.92 (m, 3 H), 1.92-2.23 (m, 3 H), 1.83-1.91 (m, 4 H), 1.58-1.75 (m, 3 H), 1.28-1.53 (m, 2 H) | A |

| Ex. # | Structure Name | LCMS-ESI (POS/NEG) m/z: (M + H)+ | NMR Data | Syn. Rte. |
|---|---|---|---|---|
| 800 | 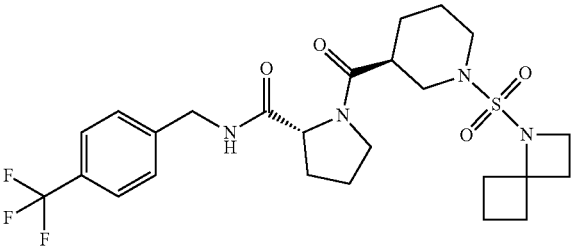 [SMILES: O=C(NCc1ccc(C(F)(F)F)cc1)[C@H]1CCCN1C(=O)[C@H]1CCCN(S(=O)(=O)N2CCC23CCC3)C1]<br>1-(((3S)-1-(1-azaspiro[3.3]hept-1-ylsulfonyl)-3-piperidinyl)carbonyl)-N-(4-(trifluoromethyl)benzyl)-D-prolinamide | LCMS-ESI (POS.) m/z: 543.2 (M + H)+ | 1H NMR (500 MHz, DMSO-d6) δ ppm 8.31-8.80 (m, 1 H), 7.57-7.76 (m, 2 H), 7.45 (br d, J = 8.04 Hz, 2 H), 4.21-4.56 (m, 3 H), 3.52-3.70 (m, 6 H), 2.61-2.84 (m, 3 H), 1.29-2.41 (m, 16 H) | M |
| 801 | 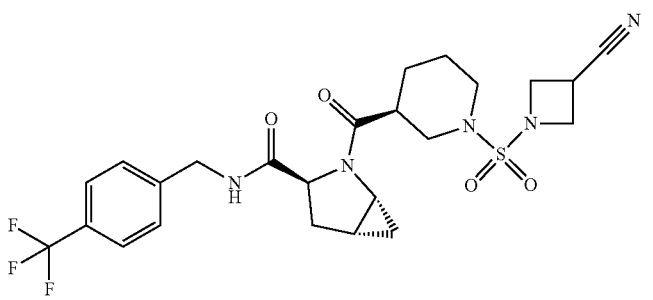 [SMILES: N#CC1CN(S(=O)(=O)N2CCC[C@H](C(=O)N3[C@@H]4C[C@@H]4C[C@H]3C(=O)NCc3ccc(C(F)(F)F)cc3)C2)C1]<br>(1R,3S,5R)-2-(((3S)-1-((3-cyano-1-azetidinyl)sulfonyl)-3-piperidinyl)carbonyl)-N-(4-(trifluoromethyl)benzyl)-2-azabicyclo[3.1.0]hexane-3-carboxamide | LCMS-ESI (POS.) m/z: 540.2 (M + H)+ | 1H NMR (500 MHz, CHLOROFORM-d) δ ppm 7.33-7.76 (m, 4 H), 7.22-7.29 (m, 1 H), 4.39-4.66 (m, 3 H), 4.03-4.18 (m, 4 H), 3.70-3.88 (m, 2 H), 3.24-3.53 (m, 2 H), 3.01-3.13 (m, 1 H), 2.90-3.01 (m, 1 H), 2.74-2.90 (m, 2 H), 1.50-2.17 (m, 5 H), 1.32-2.23 (m, 1 H), 0.52-1.26 (m, 2 H) | C |
| 802 | 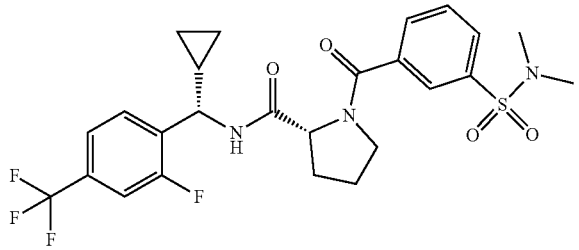 [SMILES: CN(C)S(=O)(=O)c1cccc(C(=O)N2CCC[C@@H]2C(=O)N[C@H](c2ccc(C(F)(F)F)cc2F)C2CC2)c1]<br>N-((S)-cyclopropyl(2-fluoro-4-(trifluoromethyl)phenyl)methyl)-1-(3-(dimethylsulfamoyl)benzoyl)-D-prolinamide | LCMS-ESI (POS.) m/z: 542.2 (M + H)+ | 1H NMR (500 MHz, DMSO-d6) δ ppm 8.51-8.71 (m, 1 H), 7.31-7.88 (m, 7 H), 4.28-4.65 (m, 2 H), 3.41-3.73 (m, 2 H), 2.51-2.70 (m, 6 H), 2.19-2.34 (m, 1 H), 1.73-1.99 (m, 3 H), 1.15-1.23 (m, 1 H), 0.15-0.61 (m, 4 H) | A |
| 803 | 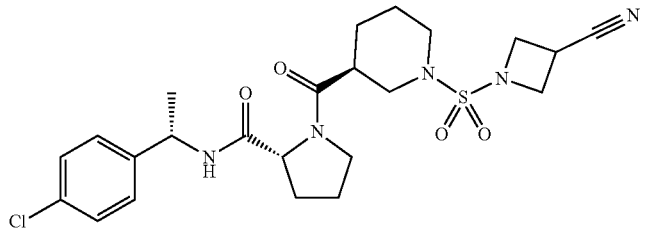 [SMILES: C[C@H](NC(=O)[C@H]1CCCN1C(=O)[C@H]1CCCN(S(=O)(=O)N2CC(C#N)C2)C1)c1ccc(Cl)cc1]<br>N-((1S)-1-(4-chlorophenyl)ethyl)-1-(((3S)-1-((3-cyano-1-azetidinyl)sulfonyl)-3-piperidinyl)carbonyl)-D-prolinamide | LCMS-ESI (POS.) m/z: 508.2 (M + H)+ | 1H NMR (500 MHz, CHLOROFORM-d) δ ppm 7.28-7.50 (m, 2 H), 7.15-7.19 (m, 2 H), 4.95-5.04 (m, 1 H), 4.60 (br d, J = 6.36 Hz, 1 H), 4.06-4.16 (m, 4 H), 3.77 (br d, J = 12.46 Hz, 2 H), 3.40-3.66 (m, 3 H), 2.93-3.02 (m, 1 H), 2.63-2.85 (m, 1 H), 2.39-2.45 (m, 1 H), 2.11-2.21 (m, 1 H), 1.97-2.05 (m, 1 H), 1.79-1.95 (m, 3 H), 1.48-1.69 (m, 2 H), 1.45 (d, J = 6.88 Hz, 3 H) | C |

| Ex. # | Structure Name | LCMS-ESI (POS/NEG) m/z: (M + H)+ | NMR Data | Syn. Rte. |
|---|---|---|---|---|
| 804 | 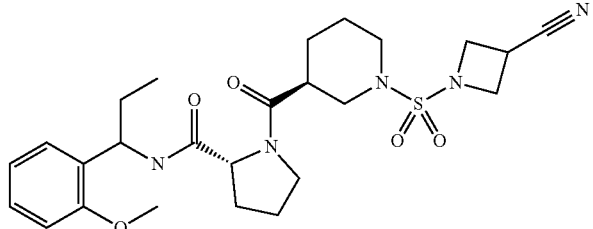<br>(2R)-1-((S)-1-( (3-cyanoazetidin-1-yl)sulfonyl)piperidine-3-carbonyl)-N-(1-(2-methoxyphenyl)propyl)pyrrolidine-2-carboxamide | LCMS-ESI (POS.) m/z: 518.2 (M + H)+ | 1H NMR (500 MHz, DMSO-d6) δ ppm 7.85-8.45 (m, 1 H), 7.11-7.31 (m, 2 H), 6.81-7.04 (m, 2 H), 4.93-5.08 (m, 1 H), 4.31-4.52 (m, 1 H), 3.89-4.14 (m, 4 H), 3.74-3.88 (m, 4 H), 3.44-3.69 (m, 4 H), 2.59-2.91 (m, 3 H), 2.00-2.37 (m, 1 H), 1.19-1.97 (m, 9 H), 0.71-0.94 (m, 3 H) | A |
| 805 | 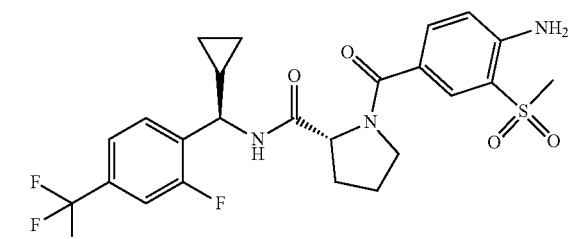<br>1-(4-amino-3-(methylsulfonyl)benzoyl)-N-((R)-cyclopropyl(2-fluoro-4-(trifluoromethyl)phenyl)methyl)-D-prolinamide | LCMS-ESI (POS.) m/z: 528.0 (M + H)+ | 1H NMR (500 MHz, DMSO-d6) δ ppm 8.63 (br d, J = 5.97 Hz, 1 H), 7.24-7.89 (m, 5 H), 6.89 (br d, J = 7.66 Hz, 1 H), 6.27-6.62 (m, 2 H), 4.19-4.66 (m, 2 H), 3.54-3.65 (m, 2 H), 3.09-3.20 (m, 3 H), 2.07-2.25 (m, 1 H), 1.56-1.95 (m, 3 H), 0.94-1.30 (m, 1 H), -0.02-0.62 (m, 4 H) | C |
| 806 | 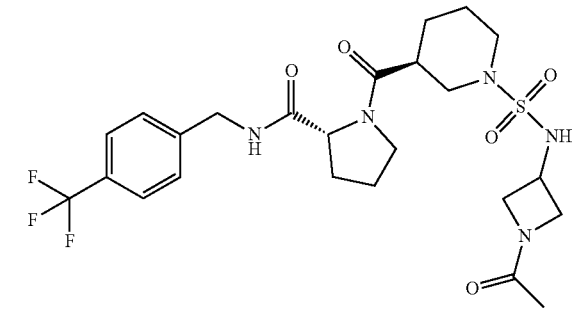 [SMILES: CC(=O)N1CC(NS(=O)(=O)N2CCC[C@H](C(=O)N3CCC[C@@H]3C(=O)NCc3ccc(C(F)(F)F)cc3)C2)C1]<br>1-(((3S)-1-((1-acet-3-azetidinyl)sulfamo)-3-piperidinyl)carbonyl)-N-(4-(trifluoromethyl)benzyl)-D-prolinamide | LCMS-ESI (POS.) m/z: 560.2 (M + H)+ | 1H NMR (500 MHz, DMSO-d6) δ 8.28-8.80 (m, 1H), 7.59-8.03 (m, 3H), 7.34-7.55 (m, 2H), 4.21-4.53 (m, 4H), 3.87-4.12 (m, 3H), 3.41-3.75 (m, 6H), 2.55-2.73 (m, 3H), 1.74-2.35 (m, 8H), 1.26-1.59 (m, 2H) | J |
| 807 | 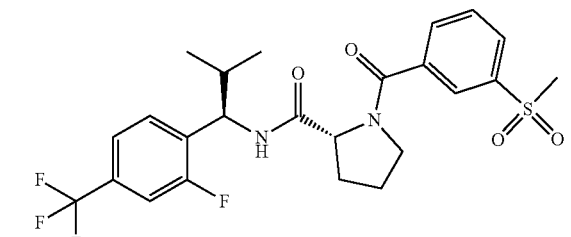<br>N-((1R)-1-(2-fluoro-4-(trifluoromethyl)phenyl)-2-methylpropyl)-1-(3-(methylsulfonyl)benzoyl)-D-prolinamide | LCMS-ESI (POS.) m/z: 512.2 (M + H)+ | 1H NMR (500 MHz, DMSO-d6) δ ppm 8.27-8.62 (m, 1 H), 7.42-8.11 (m, 7 H), 4.38-4.97 (m, 2 H), 3.39-3.65 (m, 2 H), 3.21-3.29 (m, 3 H), 2.11-2.29 (m, 1 H), 1.57-2.07 (m, 4 H), 0.48-1.08 (m, 6 H) | C |

| Ex. # | Structure Name | LCMS-ESI (POS/NEG) m/z: (M + H)+ | NMR Data | Syn. Rte. |
|---|---|---|---|---|
| 808 | 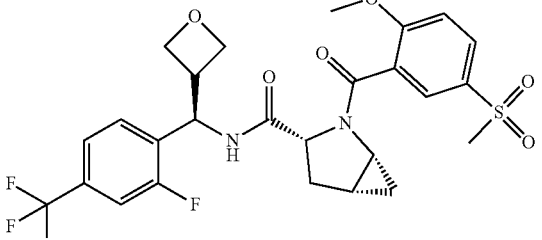<br>(1R,3R,5R)-2-(2-methoxy-5-(methylsulfonyl)benzoyl)-N-((R)-3-oxetanyl(4-(trifluoromethyl)phenyl)methyl)-2-azabicyclo[3.1.0]hexane-3-carboxamide | LCMS-APCI (POS.) m/z: 553.1 (M + H)+ | 1H NMR (400 MHz, Chloroform-d) δ ppm 8.01-8.07 (m, 3 H), 7.71 (s, 1 H), 7.61 (d, 2 H), 7.39 (d, J = 7.8 Hz, 2 H), 7.16 (d, 1 H), 5.42 (t, J = 8.3 Hz, 1 H), 5.12 (d, J = 10.5 Hz, 1 H), 4.66-4.76 (m, 2 H), 4.60 (t, J = 6.4 Hz, 1 H), 4.45 (t, J = 6.4 Hz, 1 H), 4.14 (q, J = 7.1 Hz, 1 H), 3.99 (s, 3 H), 3.45 (tdd, J = 1.7, 6.2, 8.0 Hz, 1 H), 3.09 (s, 5 H), 2.80 (dd, J = 2.0, 13.2 Hz, 1 H), 2.27-2.36 (m, 1 H), 2.07 (s, 1 H), 1.68 (dd, J = 5.3, 9.2 Hz, 1 H), 1.28 (t, J = 7.1 Hz, 1 H), 0.85-0.95 (m, 1 H), 0.72-0.80 (m, 1 H). | S |
| 809 | 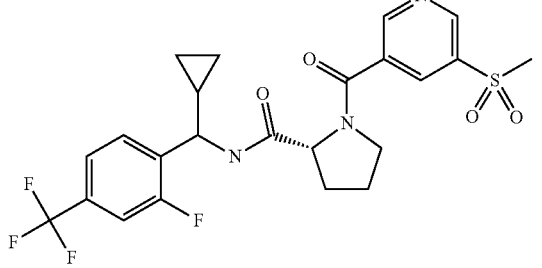<br>(2R)-N-(cyclopropyl(2-fluoro-4-(trifluoromethyl)phenyl)methyl)-1-(5-(methylsulfonyl)nicotinoyl)pyrrolidine-2-carboxamide | LCMS-ESI (POS.) m/z: 514.0 (M + H)+ | 1H NMR (500 MHz, DMSO-d6) δ ppm 8.19-9.25 (m, 4 H), 7.21-7.91 (m, 3 H), 4.26-4.67 (m, 2 H), 3.46-3.67 (m, 2 H), 3.25-3.45 (m, 3 H), 2.10-2.31 (m, 1 H), 1.65-2.00 (m, 3 H), 0.98-0.99 (m, 1 H), 0.87-1.32 (m, 1 H), −0.15-0.65 (m, 4 H) | C |
| 810 | 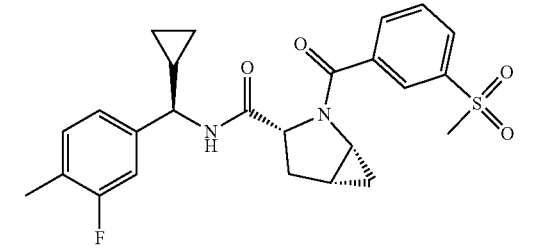 [SMILES: Cc1ccc([C@H](NC(=O)[C@H]2C[C@H]3C[C@H]3N2C(=O)c2cccc(S(C)(=O)=O)c2)C2CC2)cc1F]<br>(1R,3R,5R)-N-((R)-cyclopropyl(3-fluoro-4-methylphenyl)methyl)-2-(3-(methylsulfonyl)benzoyl)-2-azabicyclo[3.1.0]hexane-3-carboxamide | LCMS-APCI (POS.) m/z: 471.2 (M + H)+ | 1H NMR (400 MHz, DMSO-d6) δ ppm 8.53 (d, J = 8.2 Hz, 1 H), 8.19 (t, J = 1.7 Hz, 1 H), 7.98-8.10 (m, 2 H), 7.79 (t, J = 7.8 Hz, 1 H), 7.24 (t, J = 8.0 Hz, 1 H), 7.04-7.13 (m, 1 H), 4.95 (dd, J = 3.6, 11.4 Hz, 1 H), 4.35 (t, J = 5.1 Hz, 1 H), 4.26 (t, J = 8.1 Hz, 1 H), 3.26 (d, J = 6.1 Hz, 2 H), 2.14-2.24 (m, 2 H), 1.63-1.81 (m, 2 H), 1.11 (dd, J = 4.8, 8.3 Hz, 1 H), 0.71-0.80 (m, 1 H), 0.36-0.51 (m, 2 H), 0.23-0.34 (m, 1 H). | C |
| 811 | 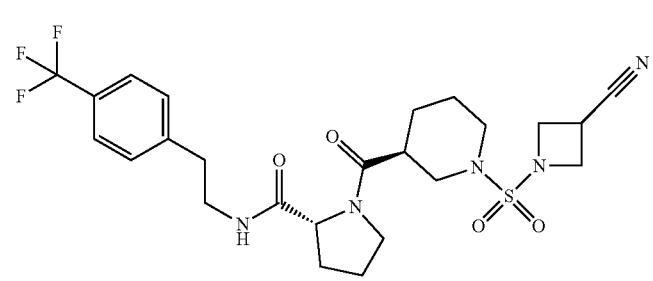 [SMILES: N#CC1CN(S(=O)(=O)N2CCC[C@H](C(=O)N3CCC[C@@H]3C(=O)NCCc3ccc(C(F)(F)F)cc3)C2)C1]<br>1-(((3S)-1-((3-cyano-1-azetidinyl)sulfonyl)-3-piperidinyl)carbonyl)-N-(2-(4-(trifluoromethyl)phenyl)ethyl)-D-prolinamide | LCMS-ESI (POS.) m/z: 542.1 (M + H)+ | 1H NMR (500 MHz, DMSO-d6) δ ppm 7.38-8.23 (m, 5 H), 4.15-4.38 (m, 1 H), 3.99-4.11 (m, 2 H), 3.86-3.99 (m, 2 H), 3.74-3.84 (m, 1 H), 3.14-3.67 (m, 6 H), 2.63-2.92 (m, 1 H), 2.51-2.96 (m, 3 H), 2.50-2.99 (m, 1 H), 1.97-2.30 (m, 1 H), 1.59-1.91 (m, 5 H), 1.28-1.57 (m, 2 H) | A |

| Ex. # | Structure Name | LCMS-ESI (POS/NEG) m/z: (M + H)+ | NMR Data | Syn. Rte. |
|---|---|---|---|---|
| 812 | 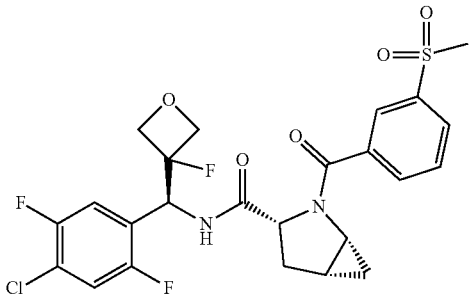 [SMILES: CS(=O)(=O)c1cccc(C(=O)N2[C@@H](C(=O)N[C@@H](c3cc(F)c(Cl)cc3F)C3(F)COC3)C[C@H]3C[C@H]32)c1]<br>(1R,3R,5R)-N-((S)-(4-Chloro-2,5-difluorophenyl)(3-fluorooxetan-3-yl)methyl)-2-(3-(methylsulfonyl)benzoyl)-2-azabicyclo[3.1.0]hexane-3-carboxamide | LCMS-ESI (POS.) m/z: 543.1 (M + H)+ | 1H NMR (Methanol-d4) δ: 8.39 (s, 1H), 8.16-8.10 (m, 2H), 7.79 (t, J = 7.8 Hz, 1H), 7.46 (dd, J = 9.3, 6.1 Hz, 1H), 7.39 (dd, J = 9.7, 6.3 Hz, 1H), 5.98 (d, J = 28.0 Hz, 1H), 5.05 (dd, J = 11.4, 4.3 Hz, 1H), 4.82-4.74 (m, 2H), 4.65-4.55 (m, 2H), 3.33 (s, 1H), 3.19 (s, 3H), 2.77-2.63 (m, 1H), 1.95-1.86 (m, 1H), 1.86-1.77 (m, 1H), 1.34-1.27 (m, 1H), 0.97-0.88 (m, 1H) | Y |
| 813 | 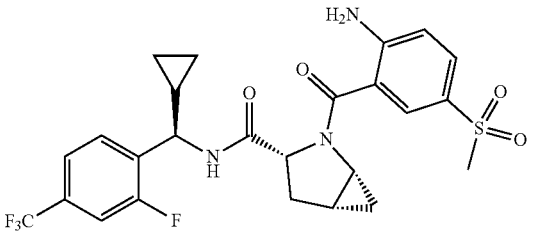 [SMILES: CS(=O)(=O)c1ccc(N)c(C(=O)N2[C@@H](C(=O)N[C@@H](c3ccc(C(F)(F)F)cc3F)C3CC3)C[C@H]3C[C@H]32)c1]<br>(1R,3R,5R)-2-(2-amino-5-(methylsulfonyl)benzoyl)-N-((R)-cyclopropyl(2-fluoro-4-(trifluoromethyl)phenypmethyl)-2-azabicyclo[3.1.0]hexane-3-carboxamide | LCMS-ESI (POS.) m/z: 540.2 | $^1$H NMR (Methanol-d$_4$) δ: 7.85 (s, 1H), 7.57 (dd, J = 8.7, 2.3 Hz, 2H), 7.47-7.32 (m, 2H), 6.77 (d, J = 8.8 Hz, 1H), 5.00 (dd, J = 11.5, 3.5 Hz, 1H), 4.47 (d, J = 8.9 Hz, 1H), 3.21-3.15 (m, 1H), 2.97 (s, 3H), 2.67-2.57 (m, 1H), 1.85 (dd, J = 13.6, 3.5 Hz, 1H), 1.65-1.55 (m, 1H), 1.25-1.14 (m, 1H), 0.97-0.90 (m, 1H), 0.71-0.63 (m, 1H), 0.63-0.54 (m, 1H), 0.52-0.45 (m, 1H), 0.45-0.38 (m, 1H), 0.38-0.26 (m, 1H) | AA |
| 814 | 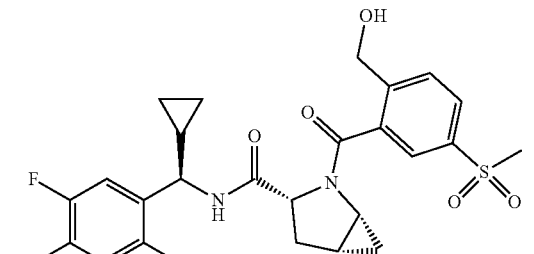<br>(1R,3R,5R)-N-((R)-cyclopropyl(2,5-difluoro-4-(trifluoromethyl)phenypmethyl)-2-(2-(hydroxymethyl)-5-(methylsulfonyl)benzoyl)-2-azabicyclo[3.1.0]hexane-3-carboxamide | LCMS-ESI (POS.) m/z: 571.2 (M − H)+ | $^1$H NMR (DMSO-d$_6$) δ: 8.76 (d, J = 7.4 Hz, 1H), 8.00 (dd, J = 8.1, 2.0 Hz, 1H), 7.88 (d, J = 1.9 Hz, 1H), 7.86-7.74 (m, 2H), 7.59 (dd, J = 11.1, 5.5 Hz, 1H), 5.64 (t, J = 5.7 Hz, 1H), 4.89 (dd, J = 11.4, 3.2 Hz, 1H), 4.71 (qd, J = 15.1, 5.8 Hz, 2H), 4.54 (t, J = 8.0 Hz, 1H), 3.25 (s, 3H), 3.00 (td, J = 6.2, 2.5 Hz, 1H), 1.80 (dd, J = 13.5, 3.3 Hz, 1H), 1.67-1.54 (m, 1H), 1.21 (dq, J = 8.2, 4.1, 3.5 Hz, 1H), 0.97 (td, J = 5.2, 2.7 Hz, 1H), 0.59 (t, J = 8.5 Hz, 2H), 0.55-0.45 (m, 1H), 0.40 (d, J = 4.8 Hz, 2H) | Z |

| Ex. # | Structure Name | LCMS-ESI (POS/NEG) m/z: (M + H)+ | NMR Data | Syn. Rte. |
|---|---|---|---|---|
| 815 | 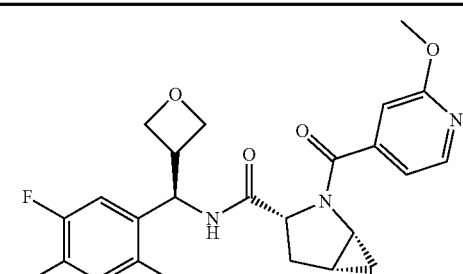<br>(1R,3R,5R)-N-((R)-(2,5-difluoro-4-(trifluoromethyl)phenyl)(oxetan-3-yl)methyl)-2-(2-methoxyisonicotinoyl)-2-azabicyclo[3.1.0]hexane-3-carboxamide | LCMS-ESI (POS.) m/z: 512.2 | $^1$H NMR (Methanol-$d_4$) δ: 8.27 (dd, J = 5.2, 0.8 Hz, 1H), 7.56 (dd, J = 9.5, 5.7 Hz, 1H), 7.37 (dd, J = 10.6, 5.5 Hz, 1H), 7.24 (dd, J = 5.2, 1.3 Hz, 1H), 7.09 (s, 1H), 5.62 (d, J = 10.2 Hz, 1H), 4.94 (dd, J = 11.4, 4.0 Hz, 1H), 4.85 (dd, J = 7.6, 6.5 Hz, 1H), 4.68 (t, J = 7.8, 6.5 Hz, 1H), 4.61 (t, J = 6.2 Hz, 1H), 4.40 (t, 1H), 3.97 (s, 3H), 3.62-3.46 (m, 1H), 3.31-3.26 (m, 1H), 2.74-2.58 (m, 1H), 1.90 (dd, J = 13.5, 4.0 Hz, 1H), 1.85-1.72 (m, 1H), 1.24-1.16 (m, 1H), 0.90-0.78 (m, 1H) | AA |
| 816 | 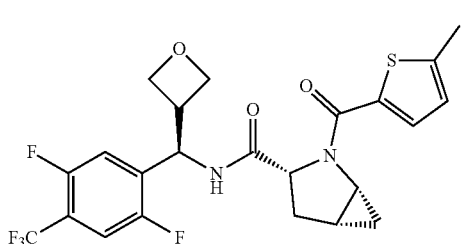<br>(1R,3R,5R)-N-((R)-(2,5-difluoro-4-(trifluoromethyl)phenyl)(oxetan-3-yl)methyl)-2-(5-methylthiophene-2-carbonyl)-2-azabicyclo[3.1.0]hexane-3-carboxamide | LCMS-ESI (POS.) m/z: 501.1 | $^1$H NMR (Methanol-$d_4$) δ: 7.72 (d, J = 3.8 Hz, 1H), 7.54 (dd, J = 9.5, 5.7 Hz, 1H), 7.36 (dd, J = 10.6, 5.5 Hz, 1H), 6.91-6.84 (m, 1H), 5.57 (d, J = 10.3 Hz, 1H), 4.96 (dd, J = 11.2, 4.6 Hz, 1H), 4.85 (t, J = 7.0 Hz, 1H), 4.70-4.59 (m, 2H), 4.39 (t, J = 6.2 Hz, 1H), 3.80-3.69 (m, 1H), 3.58-3.42 (m, 1H), 2.73-2.57 (m, 1H), 2.54 (s, 3H), 1.93-1.74 (m, 2H), 1.26-1.16 (m, 1H), 1.05-0.93 (m, 1H) | AA |
| 817 | 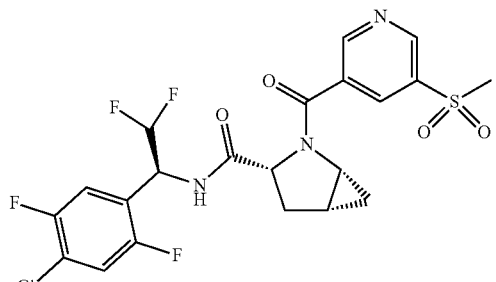<br>(1R,3R,5R)-N-((S)-1-(4-chloro-2,5-difluorophenyl)-2,2-difluoroethyl)-2-(5-(methylsulfonyl)nicotinoyl)-2-azabicyclo[3.1.0]hexane-3-carboxamide | LCMS-ESI (POS.) m/z: 520.1 | $^1$H NMR (DMSO-$d_6$) δ: 9.22 (d, J = 2.3 Hz, 1H), 9.20-9.14 (m, 2H), 8.51 (d, J = 2.1 Hz, 1H), 7.78 (dd, J = 9.3, 6.2 Hz, 1H), 7.59 (dd, J = 9.7, 6.2 Hz, 1H), 6.31 (td, J = 54.9, 3.6 Hz, 1H), 5.63-5.41 (m, 1H), 5.04 (dd, J = 11.4, 3.6 Hz, 1H), 3.41 (s, 4H), 2.72-2.58 (m, 1H), 1.84-1.69 (m, 2H), 1.11 (td, J = 5.2, 2.6 Hz, 1H), 0.80 (ddd, J = 11.4, 7.8, 4.7 Hz, 1H) | AB |
| 818 | 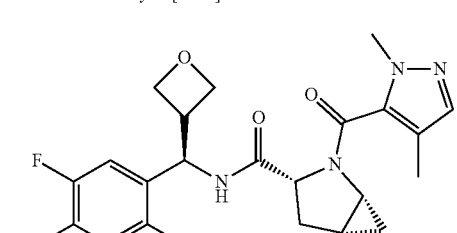<br>(1R,3R,5R)-N-((R)-(2,5-difluoro-4-(trifluoromethyl)phenyl)(oxetan-3-yl)methyl)-2-(1,4-dimethyl-1H-pyrazole-5-carbonyl)-2-azabicyclo[3.1.0]hexane-3-carboxamide | LCMS-ESI (POS.) m/z: 499.2 | $^1$H NMR (Methanol-$d_4$) δ: 7.44 (dd, J = 9.6, 5.7 Hz, 1H), 7.26 (dd, J = 10.6, 5.5 Hz, 1H), 7.23 (s, 1H), 5.59-5.44 (m, 1H), 4.87 (dd, J = 11.5, 3.6 Hz, 1H), 4.74-4.71 (m, 1H), 4.57 (t, J = 7.8, 6.5 Hz, 1H), 4.50 (t, J = 6.2 Hz, 1H), 4.31-4.26 (m, 1H), 3.79 (s, 3H), 3.51-3.31 (m, 1H), 3.12 (td, J = 6.3, 2.6 Hz, 1H), 2.63-2.47 (m, 1H), 2.07 (s, 3H), 1.98 (s, 1H), 1.80 (dd, J = 13.5, 3.6 Hz, 1H), 1.67-1.54 (m, 1H), 1.14-1.04 (m, 1H), 0.74-0.62 (m, 1H) | AA |

| Ex. # | Structure Name | LCMS-ESI (POS/NEG) m/z: (M + H)+ | NMR Data | Syn. Rte. |
|---|---|---|---|---|
| 819 | 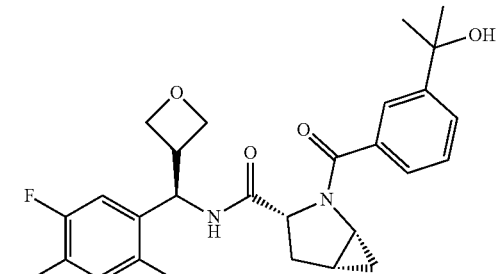 (1R,3R,5R)-N-((R)-(2,5-difluoro-4-(trifluoromethyl)phenyl)(oxetan-3-yl)methyl)-2-(3-(2-hydroxypropan-2-yl)benzoyl)-2-azabicyclo[3.1.0]hexane-3-carboxamide | LCMS-ESI (POS.) m/z: 539.2 | $^1$H NMR (Methanol-d$_4$) δ: 7.94 (s, 1H), 7.70-7.59 (m, 2H), 7.56 (dd, J = 9.6, 5.7 Hz, 1H), 7.45 (t, J = 7.8, 0.5 Hz, 1H), 7.38 (dd, J = 10.5, 5.5 Hz, 1H), 5.62 (d, J = 10.2 Hz, 1H), 4.99 (dd, J = 11.4, 4.2 Hz, 1H), 4.85 (t, J = 7.7, 6.6 Hz, 1H), 4.68 (t, J = 7.8, 6.5 Hz, 1H), 4.62 (t, J = 6.2 Hz, 1H), 4.45-4.35 (m, 1H), 3.62-3.44 (m, 1H), 2.71-2.58 (m, 1H), 1.92 (dd, J = 13.5, 4.1 Hz, 1H), 1.83-1.71 (m, 1H), 1.58 (d, J = 2.0 Hz, 7H), 1.28-1.16 (m, 1H), 0.93-0.80 (m, 1H) | AC |
| 820 | 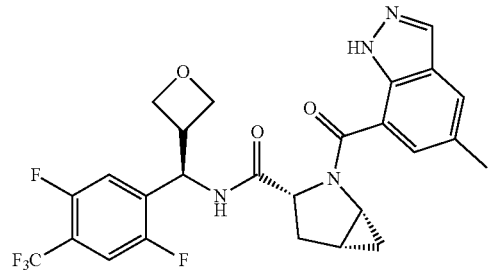 [SMILES: Cc1cc(C(=O)N2[C@@H](C(=O)N[C@@H](c3cc(F)c(C(F)(F)F)cc3F)C3COC3)C[C@H]3C[C@H]32)c2[nH]ncc2c1] (1R,3R,5R)-N-((R)-(2,5-difluoro-4-(trifluoromethyl)phenyl)(oxetan-3-yl)methyl)-2-(5-methyl-1H-indazole-7-carbonyl)-2-azabicyclo[3.1.0]hexane-3-carboxamide | LCMS-ESI (POS.) m/z: 535.2 (M + H)$^+$ | 1H NMR (400 MHz, DMSO-d6) δ 12.92 (s, 1H), 8.74 (d, J = 7.9 Hz, 1H), 8.05 (s, 1H), 7.81 (t, J = 7.6 Hz, 1H), 7.75-7.50 (m, 3H), 5.49 (t, J = 8.8 Hz, 1H), 5.00 (d, J = 11.4 Hz, 1H), 4.66 (s, 1H), 4.53 (s, 1H), 4.41 (s, 1H), 4.25 (s, 1H), 3.44 (s, 1H), 2.61 (s, 1H), 2.46 (s, 3H), 2.37 (s, 1H), 1.88-1.61 (m, 2H), 1.13 (s, 1H), 0.78 (s, 1H). | AA |
| 821 | 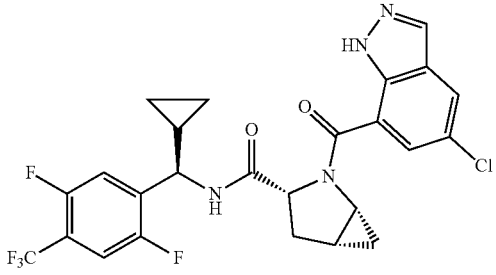 [SMILES: O=C(N[C@@H](c1cc(F)c(C(F)(F)F)cc1F)C1CC1)[C@H]1C[C@H]2C[C@H]2N1C(=O)c1cc(Cl)cc2cn[nH]c12] (1R,3R,5R)-2-(5-chloro-1H-indazole-7-carbonyl)-N-((R)-cyclopropyl(2,5-difluoro-4-(trifluoromethyl)phenyl)methyl)-2-azabicyclo[3.1.0]hexane-3-carboxamide | LCMS-ESI (POS.) m/z: 539.2 (M + H)$^+$ | 1H NMR (400 MHz, DMSO-d6) δ 13.31 (s, 1H), 8.76 (d, J = 7.4 Hz, 1H), 8.26-7.97 (m, 2H), 7.86-7.57 (m, 3H), 5.04 (dd, J = 3.5, 11.4 Hz, 1H), 4.55 (t, J = 7.9 Hz, 1H), 2.77-2.56 (m, 1H), 1.74 (ddd, J = 4.6, 11.1, 31.9 Hz, 2H), 1.33-1.12 (m, 1H), 1.07 (dt, J = 3.4, 7.2 Hz, 1H), 1.00-0.68 (m, 2H), 0.67-0.55 (m, 1H), 0.47 (t, J = 9.0 Hz, 1H), 0.38 (d, J = 4.0 Hz, 2H). | AA |
| 822 | 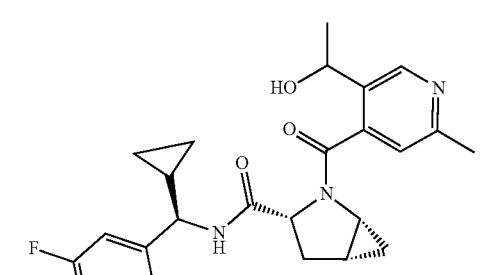 (1R,3R,5R)-N-((R)-cyclopropyl(2,5-difluoro-4-(trifluoromethyl)phenyl)methyl)-2-(5-(1-hydroxyethyl)-2-methylisonicotino)-2-azabicyclo[3.1.0]hexane-3-carboxamide | LCMS-ESI (POS.) m/z: 524.2 | $^1$H NMR (Methanol-d$_4$) δ: 8.61 (s, 1H), 7.55-7.41 (m, 2H), 7.31 (s, 1H), 5.24-5.12 (m, 1H), 4.94 (ddd, J = 11.3, 3.2, 1.5 Hz, 1H), 4.50 (d, J = 9.1 Hz, 1H), 3.09 (td, J = 6.3, 2.7 Hz, 1H), 2.72-2.61 (m, 1H), 2.55 (s, 3H), 2.01 (dd, J = 13.5, 3.4 Hz, 1H), 1.76-1.64 (m, 1H), 1.49 (d, J = 6.6 Hz, 3H), 1.26 (tdd, J = 9.5, 6.4, 4.0 Hz, 1H), 1.03 (td, J = 5.4, 2.5 Hz, 1H), 0.75-0.63 (m, 2H), 0.63-0.54 (m, 1H), 0.54-0.41 (m, 2H) | AD |

-continued

| Ex. # | Structure Name | LCMS-ESI (POS/NEG) m/z: (M + H)+ | NMR Data | Syn. Rte. |
|---|---|---|---|---|
| 823 | 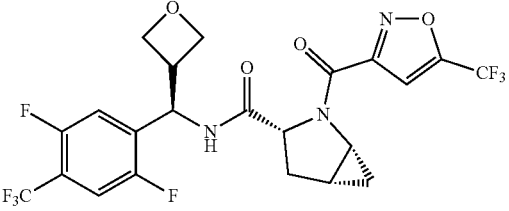 [SMILES: O=C(N[C@@H](c1cc(F)c(C(F)(F)F)cc1F)C1COC1)[C@H]1C[C@H]2C[C@H]2N1C(=O)c1cc(C(F)(F)F)on1]<br>(1R,3R,5R)-N-((R)-(2,5-difluoro-4-(trifluoromethyl)phenyl)(oxetan-3-yl)methyl)-2-(5-(trifluoromethyl)isoxazole-3-carbonyl)-2-azabicyclo[3.1.0]hexane-3-carboxamide | LCMS-ESI (POS.) m/z: 540.2 [M + H] | 1H NMR (Methanol-d4) δ: 7.61-7.50 (m, 1H), 7.46-7.40 (m, 1H), 7.40-7.26 (m, 1H), 5.61 (d, J = 10.2 Hz, 1H), 5.49 (d, 1H), 5.02-4.92 (m, 1H), 4.73-4.55 (m, 2H), 4.41 (t, J = 6.2 Hz, 1H), 4.10 (td, J = 6.3, 2.6 Hz, 1H), 3.61-3.42 (m, 1H), 3.37 (s, 2H), 2.75-2.60 (m, 1H), 1.96-1.75 (m, 1H), 1.17 (td, J = 5.5, 2.6 Hz, 1H), 0.96-0.79 (m, 1H) | AA |
| 824 | 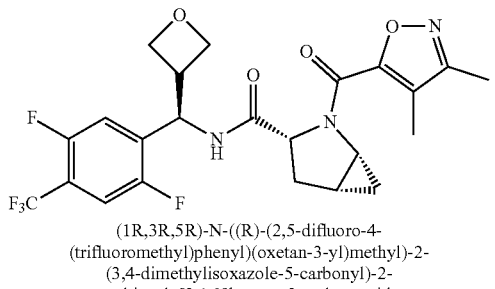<br>(1R,3R,5R)-N-((R)-(2,5-difluoro-4-(trifluoromethyl)phenyl)(oxetan-3-yl)methyl)-2-(3,4-dimethylisoxazole-5-carbonyl)-2-azabicyclo[3.1.0]hexane-3-carboxamide | LCMS-ESI (POS.) m/z: 500.20 [M + H] | 1H NMR (DMSO-d6) δ: 8.70 (d, J = 8.2 Hz, 1H), 7.80 (t, J = 7.6 Hz, 1H), 7.55 (t, J = 8.3 Hz, 1H), 5.47 (t, J = 8.9 Hz, 1H), 4.89 (dd, J = 11.5, 3.3 Hz, 1H), 4.64 (t, J = 7.7, 6.3 Hz, 1H), 4.52 (t, J = 7.8, 6.3 Hz, 1H), 4.37 (t, J = 6.2 Hz, 1H), 4.22 (t, J = 6.2 Hz, 1H), 3.33 (s, 3H), 3.32-3.26 (m, 1H), 2.25 (s, 3H), 1.73 (dd, J = 13.5, 3.4 Hz, 1H), 1.66-1.54 (m, 1H), 1.06-0.94 (m, 2H), 0.84-0.68 (m, 2H) | AA |
| 825 | 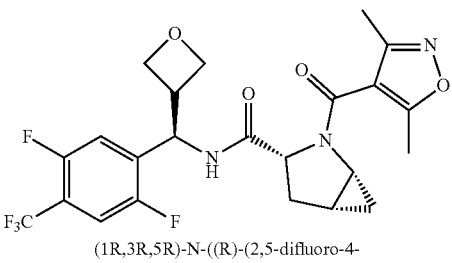<br>(1R,3R,5R)-N-((R)-(2,5-difluoro-4-(trifluoromethyl)phenyl)(oxetan-3-yl)methyl)-2-(3,5-dimethylisoxazole-4-carbonyl)-2-azabicyclo[3.1.0]hexane-3-carboxamide | LCMS-ESI (POS.) m/z: 500.2 [M + H] | 1H NMR (DMSO-d6) δ: 8.70 (d, J = 8.1 Hz, 1H), 7.80 (t, J = 7.7 Hz, 1H), 7.55 (t, J = 8.2 Hz, 1H), 5.50-5.43 (m, 1H), 4.89 (dd, J = 11.5, 3.3 Hz, 1H), 4.64 (t, J = 7.7, 6.4 Hz, 1H), 4.52 (t, J = 7.8, 6.3 Hz, 1H), 4.37 (t, J = 6.2 Hz, 1H), 4.22 (t, J = 6.2 Hz, 1H), 3.34 (s, 3H), 3.30-3.26 (m, 1H), 2.25 (s, 3H), 1.73 (dd, J = 13.6, 3.4 Hz, 1H), 1.67-1.52 (m, 2H), 1.04-0.96 (m, 1H), 0.85-0.71 (m, 2H) | AA |
| 826 | 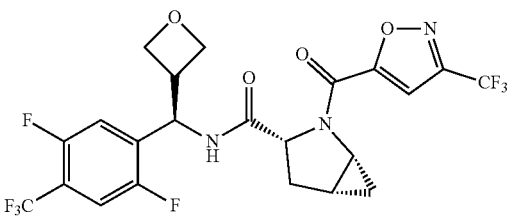<br>(1R,3R,5R)-N-((R)-(2,5-difluoro-4-(trifluoromethyl)phenyl)(oxetan-3-yl)methyl)-2-(3-(trifluoromethyl)isoxazole-5-carbonyl)-2-azabicyclo[3.1.0]hexane-3-carboxamide | LCMS-ESI (POS.) m/z: 540.10 [M + H] | 1H NMR (DMSO-d6) δ: 8.77 (t, J = 8.0 Hz, 1H), 7.83-7.72 (m, 2H), 7.57-7.51 (m, 1H), 5.45 (t, 1H), 4.88 (dd, J = 11.4, 3.8 Hz, 1H), 4.66 (t, J = 7.7, 6.3 Hz, 1H), 4.61-4.52 (m, 1H), 4.39 (t, J = 6.1 Hz, 1H), 4.23 (t, J = 6.1 Hz, 1H), 3.91-3.82 (m, 1H), 3.51-3.36 (m, 2H), 1.82-1.69 (m, 2H), 1.14-1.05 (m, 1H), 0.99-0.90 (m, 1H) | AA |

| Ex. # | Structure Name | LCMS-ESI (POS/NEG) m/z: (M + H)+ | NMR Data | Syn. Rte. |
|---|---|---|---|---|
| 827 | 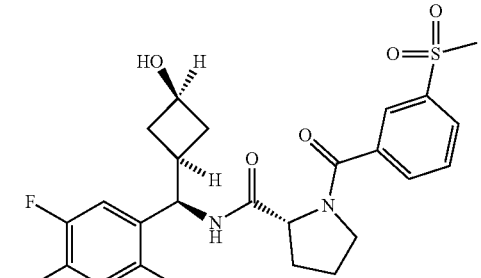(R)-N-((R)-(2,5-difluoro-4-(trifluoromethyl)phenyl)((1s,3S)-3-hydroxycyclobutyl)methyl)-1-(3-(methylsulfonyl)benzoyl)pyrrolidine-2-carboxamide | LCMS-ESI (POS.) m/z: 561.2 (M + H)+ | $^1$H NMR (DMSO-d$_6$) δ: 8.51 (d, J = 7.9 Hz, 1H), 8.04 (d, J = 1.5 Hz, 2H), 7.93-7.88 (m, 1H), 7.81-7.68 (m, 2H), 7.64 (d, J = 2.4 Hz, 1H), 7.53 (dd, J = 11.1, 5.4 Hz, 1H), 5.05 (s, 1H), 4.49 (dd, J = 8.3, 5.2 Hz, 1H), 3.87 (q, J = 7.1 Hz, 1H), 3.61-3.52 (m, 1H), 3.49-3.44 (m, 1H), 3.28 (s, 3H), 2.35 (dt, J = 12.1, 6.2 Hz, 1H), 2.23 (ddd, J = 14.5, 7.4, 4.2 Hz, 1H), 2.11-2.04 (m, 1H), 1.84 (dq, J = 20.4, 8.0, 6.8 Hz, 3H), 1.72 (ddt, J = 11.9, 8.4, 4.2 Hz, 2H), 1.65-1.56 (m, 1H) | AE |
| 828 | 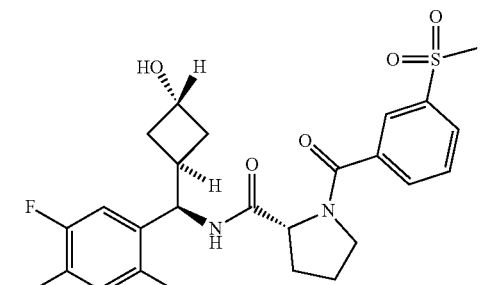(R)-N-((R)-(2,5-difluoro-4-(trifluoromethyl)phenyl)((1r,3R)-3-hydroxycyclobutyl)methyl)-1-(3-(methylsulfonyl)benzoyl)pyrrolidine-2-carboxamide | LCMS-ESI (POS.) m/z: 561.2 (M + H)+ | 1H NMR (Methanol-d4) δ: 8.22 (t, J = 1.8 Hz, 1H), 8.10 (dt, J = 7.8, 1.5 Hz, 1H), 7.96 (dt, J = 7.6, 1.4 Hz, 1H), 7.77 (d, J = 7.9 Hz, 1H), 7.53 (dd, J = 9.5, 5.7 Hz, 1H), 7.38 (dd, J = 10.7, 5.4 Hz, 1H), 5.21 (d, J = 10.9 Hz, 1H), 4.67-4.54 (m, 1H), 4.44 (dd, J = 9.0, 4.5 Hz, 1H), 3.64 (dt, J = 10.0, 6.8 Hz, 1H), 3.54 (ddd, J = 10.4, 6.8, 5.1 Hz, 1H), 2.72 (ddq, J = 13.8, 9.1, 4.2 Hz, 1H), 2.44 (ddt, J = 11.4, 7.6, 4.1 Hz, 1H), 2.32 (ddd, J = 11.8, 8.2, 5.9 Hz, 1H), 2.18 (ddd, J = 12.4, 8.3, 6.1 Hz, 1H), 2.06 (ddd, J = 11.8, 7.8, 4.0 Hz, 1H), 2.02-1.94 (m, 2H), 1.90-1.82 (m, 2H) | AE |
| 829 | 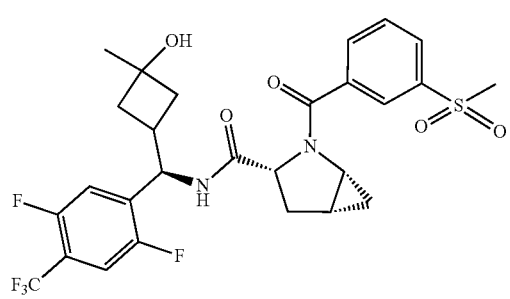 [SMILES: CC1(O)CC([C@@H](NC(=O)[C@H]2C[C@H]3C[C@H]3N2C(=O)c2cccc(S(C)(=O)=O)c2)c2cc(F)c(C(F)(F)F)cc2F)C1](1R,3R,5R)-N-((R)-(2,5-difluoro-4-(trifluoromethyl)phenyl)( 3-hydroxy-3-methylcyclobutyl)methyl)-2-(3-(methylsulfonyl)benzoyl)-2-azabicyclo[3.1.0]hexane-3-carboxamide | LCMS-ESI (POS.) m/z: 587.2 | $^1$H NMR (Methanol-d$_4$) δ: 8.39 (t, J = 1.8 Hz, 1H), 8.12 (ddd, J = 8.0, 3.1, 1.3 Hz, 2H), 7.78 (t, J = 7.8 Hz, 1H), 7.52 (dd, J = 9.5, 5.7 Hz, 1H), 7.35 (dd, J = 10.7, 5.4 Hz, 1H), 5.06 (dd, J = 11.3, 4.0 Hz, 1H), 3.37 (s, 1H), 3.19 (s, 3H), 2.69 (ddd, J = 13.7, 11.5, 6.4 Hz, 1H), 2.29 (dq, J = 10.0, 4.3, 3.8 Hz, 2H), 2.03 (dd, J = 14.2, 2.2 Hz, 1H), 1.99-1.86 (m, 3H), 1.81 (dq, J = 9.0, 6.1 Hz, 1H), 1.31 (s, 3H), 1.23 (td, J = 5.4, 2.6 Hz, 1H), 0.90 (dt, J = 8.8, 5.7 Hz, 1H) | AF |

-continued

| Ex. # | Structure Name | LCMS-ESI (POS/NEG) m/z: (M + H)+ | NMR Data | Syn. Rte. |
|---|---|---|---|---|
| 830 | (1R,3R,5R)-N-((R)-(2,5-difluoro-4-(trifluoromethyl)phenyl)((1s,3S)-3-hydroxycyclobutyl)methyl)-2-(2-(difluoromethyl)isonicotinoyl)-2-azabicyclo[3.1.0]hexane-3-carboxamide | LCMS-ESI (POS.) m/z: 546.2 (M + H)+ | 1H NMR (DMSO-d6) δ: 8.85 (d, J = 4.9 Hz, 1H), 8.56 (d, J = 7.8 Hz, 1H), 7.84 (t, J = 1.1 Hz, 1H), 7.82-7.73 (m, 2H), 7.49 (dd, J = 11.0, 5.4 Hz, 1H), 7.07 (t, J = 54.8 Hz, 1H), 5.05-4.94 (m, 2H), 3.85 (q, J = 7.2 Hz, 1H), 3.25 (td, J = 6.1, 2.5 Hz, 1H), 2.58 (dt, J = 12.3, 6.2 Hz, 1H), 2.38-2.25 (m, 1H), 2.03 (h, J = 7.5, 6.9 Hz, 2H), 1.71 (ddd, J = 15.7, 11.3, 4.7 Hz, 2H), 1.63-1.53 (m, 2H), 1.09 (td, J = 5.1, 2.6 Hz, 1H), 0.75-0.70 (m, 1H) | AE |
| 831 | (1R,3R,5R)-N-((R)-(2,5-difluoro-4-(trifluoromethyl)phenyl)((1r,3R)-3-hydroxycyclobutyl)methyl)-2-(2-(difluoromethyl)isonicotinoyl)-2-azabicyclo[3.1.0]hexane-3-carboxamide | LCMS-ESI (POS.) m/z: 546.2 (M + H)+ | 1H NMR (DMSO-d6) δ: 7.95 (d, J = 4.9 Hz, 1H), 7.14 (s, 1H), 7.01 (dd, J = 5.0, 1.3 Hz, 1H), 6.66 (dd, J = 9.4, 5.8 Hz, 1H), 6.49 (dd, J = 10.7, 5.5 Hz, 1H), 5.95 (t, J = 55.1 Hz, 1H), 4.29 (d, J = 10.8 Hz, 1H), 4.14 (dd, J = 11.4, 4.0 Hz, 1H), 3.54 (p, J = 6.6 Hz, 1H), 2.42 (td, J = 6.2, 2.6 Hz, 1H), 1.82 (ddd, J = 13.6, 11.2, 6.3 Hz, 2H), 1.51 (ddt, J = 11.4, 7.5, 3.9 Hz, 1H), 1.29 (ddd, J = 12.7, 8.8, 6.0 Hz, 1H), 1.24-1.07 (m, 2H), 1.07-0.99 (m, 1H), 0.93 (dd, J = 12.0, 7.4, 4.5 Hz, 1H), 0.36 (td, J = 5.4, 2.7 Hz, 1H), −0.01 (dt, J = 9.0, 5.7 Hz, 1H) | AE |
| 832 | (1R,3R,5R)-N-((S)-(2,5-difluoro-4-(trifluoromethyl)phenyl)(5-oxopyrrolidin-3-yl)methyl)-2-(2-(trifluoromethyl)isonicotinoyl)-2-azabicyclo[3.1.0]hexane-3-carboxamide | LCMS-ESI (POS.) m/z 546.2 (M + H)+ | 1H NMR (DMSO-d6) δ: 8.95 (d, J = 4.9 Hz, 1H), 8.78 (d, J = 8.3 Hz, 1H), 8.00 (t, J = 1.1 Hz, 1H), 7.94 (dd, J = 5.0, 1.4 Hz, 1H), 7.80 (dd, J = 9.3, 5.8 Hz, 1H), 7.62 (dd, J = 10.9, 5.6 Hz, 1H), 7.57 (s, 1H), 5.11 (t, J = 8.5 Hz, 1H), 4.90 (dd, J = 11.4, 3.6 Hz, 1H), 3.30 (dd, J = 6.3, 2.8 Hz, 1H), 3.18-3.04 (m, 1H), 2.97-2.80 (m, 2H), 2.57 (ddd, J = 13.1, 11.3, 6.2 Hz, 1H), 2.26 (dd, J = 16.8, 8.4 Hz, 1H), 2.15 (dd, J = 16.9, 7.7 Hz, 1H), 1.78-1.65 (m, 2H), 1.15 (td, J = 5.0, 2.5 Hz, 1H), 0.76 (dt, J = 8.7, 5.3 Hz, 1H) | AE |

| Ex. # | Structure Name | LCMS-ESI (POS/NEG) m/z: (M + H)+ | NMR Data | Syn. Rte. |
|---|---|---|---|---|
| 833 | 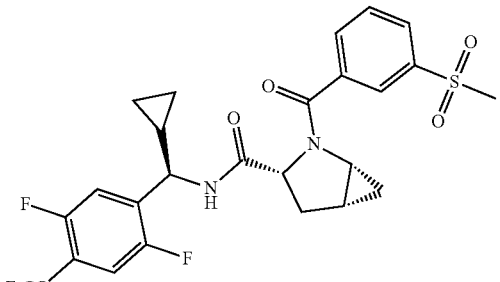<br>(1R,3R,5R)-N-((R)-cyclopropyl(2,5-difluoro-4-(trifluoromethoxy)phenyl)methyl)-2-(3-(methylsulfonyl)benzoyl)-2-azabicyclo[3.1.0]hexane-3-carboxamide | LCMS-ESI (POS.) m/z 577.2 (M + H)$^+$ | 1H NMR (500 MHz, DMSO-d6) δ ppm 8.33-8.66 (m, 1 H), 7.42-8.22 (m, 6 H), 4.09-4.98 (m, 2 H), 3.18-3.79 (m, 4 H), 2.52-2.76 (m, 1 H), 1.51-1.90 (m, 2 H), 0.81-1.27 (m, 2 H),-0.22-0.80 (m, 5 H). | C |

Formulations:

A compound as disclosed herein and water were admixed together. Either 30% wt/vol or 40% wt/vol of hydroxypropyl beta-cyclodextrin (HPBCD) was added and the mixture stirred until dissolved.

In Vitro Model of Dose-Dependent Myofibril ATPase Modulation:

Dose responses were measured using a calcium-buffered, pyruvate kinase and lactate dehydrogenase-coupled ATPase assay containing the following reagents (concentrations expressed are final assay concentrations): Potassium PIPES (12 mM), MgC$_2$ (2 mM), ATP (1 mM), DTT (1 mM), BSA (0.1 mg/ml), NADH (0.5 mM), PEP (1.5 mM), pyruvate kinase (4 U/ml), lactate dehydrogenase (8 U/ml), and antifoam (90 ppm). The pH was adjusted to 6.80 at 22° C. by addition of potassium hydroxide. Calcium levels were controlled by a buffering system containing 0.6 mM EGTA and varying concentrations of calcium, to achieve a free calcium concentration of $1 \times 10^{-4}$ M to $1 \times 10^{-8}$ M.

Bovine cardiac myofibrils were obtained by homogenizing the appropriate tissue in the presence of detergent. Such treatment removes membranes and majority of soluble cytoplasmic proteins but leaves intact cardiac sarcomeric actomyosin apparatus. Concentrations of myofibrils were adjusted to achieve the necessary rate of ATP hydrolysis (typically 0.25-1.0 mg/ml).

Chemical entity dose responses were measured at the calcium concentration corresponding to 25% of maximal ATPase activity (pCa$_{25}$), so a preliminary experiment was performed to test the response of the ATPase activity to free calcium concentrations in the range of $1 \times 10^{-4}$ M to $1 \times 10^{-8}$ M. Subsequently, the assay mixture was adjusted to the pCa$_{25}$. Assays were performed by first preparing a dilution series of test chemical entity, each with an assay mixture containing potassium Pipes, MgCl$_2$, BSA, DTT, pyruvate kinase, lactate dehydrogenase, myofibrils, antifoam, EGTA, CaCl$_2$, and water. The assay was started by adding an equal volume of solution containing potassium Pipes, MgCl$_2$, BSA, DTT, ATP, NADH, PEP, antifoam, and water. ATP hydrolysis was monitored by absorbance at 340 nm. The resulting dose response curve was fit by the 4 parameter equation y=Bottom+((Top-Bottom)/(1+((EC50/X)^Hill))). The AC1.4 is defined as the concentration at which ATPase activity was 1.4-fold higher than the bottom of the dose curve. AC1.4 values reported in the table below are mean values based on a minimum of two independent tests. For compounds for which two independent tests were performed, the individual values were within two-fold of each other. For compounds for which more than two independent tests were performed, the typical error is mean +/−20-30%.

| EX. # | AC$_{1.4}$ (μM) | EX. # | AC$_{1.4}$ (μM) | EX. # | AC$_{1.4}$ (μM) | EX. # | AC$_{1.4}$ (μM) |
|---|---|---|---|---|---|---|---|
| 1 | 0.01405 | 204 | 0.4305 | 407 | 1.427 | 610 | 3.7735 |
| 2 | 0.01475 | 205 | 0.4322 | 408 | 1.479 | 611 | 3.788 |
| 3 | 0.01635 | 206 | 0.43375 | 409 | 1.484 | 612 | 3.527 |
| 4 | 0.01635 | 207 | 0.4436 | 410 | 1.4853 | 613 | 3.8643 |
| 5 | 0.01655 | 208 | 0.4457 | 411 | 1.493 | 614 | 3.8655 |
| 6 | 0.0171 | 209 | 0.4473 | 412 | 1.495 | 615 | 3.8905 |
| 7 | 0.01905 | 210 | 0.4487 | 413 | 1.511 | 616 | 3.5615 |
| 8 | 0.0198 | 211 | 0.4488 | 414 | 1.515 | 617 | 3.626 |
| 9 | 0.01995 | 212 | 0.4557 | 415 | 1.522 | 618 | 3.9205 |
| 10 | 0.02115 | 213 | 0.46035 | 416 | 1.528 | 619 | 3.929 |
| 11 | 0.0215 | 214 | 0.46651 | 417 | 1.53 | 620 | 3.94 |
| 12 | 0.0216 | 215 | 0.46655 | 418 | 1.5305 | 621 | 3.9478 |
| 13 | 0.0219 | 216 | 0.47455 | 419 | 1.542 | 622 | 3.9515 |
| 14 | 0.0227 | 217 | 0.4751 | 420 | 1.5455 | 623 | 3.975 |
| 15 | 0.02315 | 218 | 0.47985 | 421 | 1.4335 | 624 | 3.658 |
| 16 | 0.0238 | 219 | 0.48085 | 422 | 1.5655 | 625 | 4.01 |
| 17 | 0.02445 | 220 | 0.48095 | 423 | 1.5735 | 626 | 4.031 |

-continued

| EX. # | AC$_{1.4}$ (µM) | EX. # | AC$_{1.4}$ (µM) | EX. # | AC$_{1.4}$ (µM) | EX. # | AC$_{1.4}$ (µM) |
|---|---|---|---|---|---|---|---|
| 18 | 0.02455 | 221 | 0.4821 | 424 | 1.5805 | 627 | 4.037 |
| 19 | 0.02495 | 222 | 0.4825 | 425 | 1.5805 | 628 | 3.83 |
| 20 | 0.02545 | 223 | 0.48415 | 426 | 1.4595 | 629 | 4.051 |
| 21 | 0.0266 | 224 | 0.485 | 427 | 1.5865 | 630 | 3.9185 |
| 22 | 0.02715 | 225 | 0.4889 | 428 | 1.606 | 631 | 4.082 |
| 23 | 0.0287 | 226 | 0.49143 | 429 | 1.6075 | 632 | 4.0915 |
| 24 | 0.02875 | 227 | 0.4927 | 430 | 1.474 | 633 | 4.0935 |
| 25 | 0.0289 | 228 | 0.4974 | 431 | 1.6305 | 634 | 4.1045 |
| 26 | 0.0296 | 229 | 0.5053 | 432 | 1.6518 | 635 | 4.1355 |
| 27 | 0.031067 | 230 | 0.5074 | 433 | 1.656 | 636 | 3.919 |
| 28 | 0.03125 | 231 | 0.51875 | 434 | 1.66 | 637 | 3.9795 |
| 29 | 0.03155 | 232 | 0.5201 | 435 | 1.681 | 638 | 4.1835 |
| 30 | 0.0318 | 233 | 0.5241 | 436 | 1.7 | 639 | 4.1855 |
| 31 | 0.03275 | 234 | 0.5321 | 437 | 1.7085 | 640 | 4.2315 |
| 32 | 0.0335 | 235 | 0.5332 | 438 | 1.712 | 641 | 4.262 |
| 33 | 0.03455 | 236 | 0.5579 | 439 | 1.7125 | 642 | 4.2755 |
| 34 | 0.0361 | 237 | 0.55925 | 440 | 1.7235 | 643 | 4.3125 |
| 35 | 0.0372 | 238 | 0.56065 | 441 | 1.7265 | 644 | 4.3367 |
| 36 | 0.03765 | 239 | 0.5676 | 442 | 1.7305 | 645 | 4.351 |
| 37 | 0.0383 | 240 | 0.56845 | 443 | 1.7885 | 646 | 4.377 |
| 38 | 0.0394 | 241 | 0.5692 | 444 | 1.547 | 647 | 4.4125 |
| 39 | 0.0394 | 242 | 0.573 | 445 | 1.823 | 648 | 4.421 |
| 40 | 0.0398 | 243 | 0.5746 | 446 | 1.826 | 649 | 4.4365 |
| 41 | 0.04135 | 244 | 0.57925 | 447 | 1.831 | 650 | 4.0425 |
| 42 | 0.042933 | 245 | 0.582 | 448 | 1.844 | 651 | 4.4705 |
| 43 | 0.043375 | 246 | 0.582 | 449 | 1.845 | 652 | 4.5245 |
| 44 | 0.0434 | 247 | 0.5868 | 450 | 1.8545 | 653 | 4.5245 |
| 45 | 0.0435 | 248 | 0.59145 | 451 | 1.8635 | 654 | 4.538 |
| 46 | 0.0456 | 249 | 0.5932 | 452 | 1.8655 | 655 | 4.5443 |
| 47 | 0.0527 | 250 | 0.5978 | 453 | 1.5515 | 656 | 4.071 |
| 48 | 0.0531 | 251 | 0.60545 | 454 | 1.8665 | 657 | 4.572 |
| 49 | 0.05315 | 252 | 0.6066 | 455 | 1.877 | 658 | 4.159 |
| 50 | 0.0546 | 253 | 0.6092 | 456 | 1.882 | 659 | 4.605 |
| 51 | 0.0553 | 254 | 0.6139 | 457 | 1.8865 | 660 | 4.606 |
| 52 | 0.05535 | 255 | 0.6167 | 458 | 1.5845 | 661 | 4.1595 |
| 53 | 0.0574 | 256 | 0.632 | 459 | 1.8995 | 662 | 4.4365 |
| 54 | 0.0583 | 257 | 0.63215 | 460 | 1.915 | 663 | 4.6285 |
| 55 | 0.0606 | 258 | 0.6326 | 461 | 1.9174 | 664 | 4.669 |
| 56 | 0.06215 | 259 | 0.63725 | 462 | 1.9235 | 665 | 4.554 |
| 57 | 0.06485 | 260 | 0.63895 | 463 | 1.9305 | 666 | 4.7065 |
| 58 | 0.06485 | 261 | 0.64605 | 464 | 1.612 | 667 | 4.708 |
| 59 | 0.06495 | 262 | 0.64675 | 465 | 1.9455 | 668 | 4.71 |
| 60 | 0.0657 | 263 | 0.6526 | 466 | 1.961 | 669 | 4.727 |
| 61 | 0.0687 | 264 | 0.6615 | 467 | 1.9675 | 670 | 4.735 |
| 62 | 0.07198 | 265 | 0.6631 | 468 | 1.9855 | 671 | 4.776 |
| 63 | 0.07385 | 266 | 0.66745 | 469 | 1.9915 | 672 | 4.8355 |
| 64 | 0.0744 | 267 | 0.6696 | 470 | 1.9915 | 673 | 4.897 |
| 65 | 0.0748 | 268 | 0.6764 | 471 | 1.996 | 674 | 4.9025 |
| 66 | 0.0766 | 269 | 0.6767 | 472 | 1.807 | 675 | 4.9395 |
| 67 | 0.077863 | 270 | 0.668 | 473 | 2.035 | 676 | 4.59 |
| 68 | 0.0784 | 271 | 0.68735 | 474 | 2.036 | 677 | 4.987 |
| 69 | 0.08835 | 272 | 0.6904 | 475 | 1.866 | 678 | 4.993 |
| 70 | 0.08855 | 273 | 0.6841 | 476 | 2.071 | 679 | 5.023 |
| 71 | 0.08898 | 274 | 0.6977 | 477 | 2.0765 | 680 | 5.0333 |
| 72 | 0.09025 | 275 | 0.69215 | 478 | 2.082 | 681 | 5.0425 |
| 73 | 0.09745 | 276 | 0.7014 | 479 | 1.887 | 682 | 4.606 |
| 74 | 0.09935 | 277 | 0.7027 | 480 | 2.1525 | 683 | 5.096 |
| 75 | 0.10055 | 278 | 0.7012 | 481 | 2.157 | 684 | 5.1985 |
| 76 | 0.1008 | 279 | 0.70924 | 482 | 1.945 | 685 | 5.246 |
| 77 | 0.1016 | 280 | 0.713 | 483 | 2.168 | 686 | 5.284 |
| 78 | 0.10235 | 281 | 0.7104 | 484 | 2.014 | 687 | 5.299 |
| 79 | 0.10395 | 282 | 0.7195 | 485 | 2.0445 | 688 | 5.317 |
| 80 | 0.10455 | 283 | 0.72885 | 486 | 2.202 | 689 | 5.334 |
| 81 | 0.1048 | 284 | 0.73315 | 487 | 2.218 | 690 | 5.354 |
| 82 | 0.10845 | 285 | 0.73515 | 488 | 2.1245 | 691 | 5.3575 |
| 83 | 0.1146 | 286 | 0.74365 | 489 | 2.2325 | 692 | 5.379 |
| 84 | 0.1147 | 287 | 0.7212 | 490 | 2.1625 | 693 | 5.425 |
| 85 | 0.1157 | 288 | 0.7452 | 491 | 2.181 | 694 | 5.48 |
| 86 | 0.1312 | 289 | 0.7506 | 492 | 2.256 | 695 | 5.5132 |
| 87 | 0.13185 | 290 | 0.7542 | 493 | 2.271 | 696 | 5.525 |
| 88 | 0.13445 | 291 | 0.75595 | 494 | 2.274 | 697 | 5.5445 |
| 89 | 0.1357 | 292 | 0.7577 | 495 | 2.278 | 698 | 5.5675 |
| 90 | 0.13635 | 293 | 0.76035 | 496 | 2.291 | 699 | 5.5865 |
| 91 | 0.1384 | 294 | 0.7619 | 497 | 2.3075 | 700 | 5.588 |
| 92 | 0.13875 | 295 | 0.7671 | 498 | 2.335 | 701 | 5.643 |
| 93 | 0.1413 | 296 | 0.76785 | 499 | 2.344 | 702 | 5.6535 |

-continued

| EX. # | AC$_{1.4}$ (µM) | EX. # | AC$_{1.4}$ (µM) | EX. # | AC$_{1.4}$ (µM) | EX. # | AC$_{1.4}$ (µM) |
|---|---|---|---|---|---|---|---|
| 94 | 0.1425 | 297 | 0.76855 | 500 | 2.346 | 703 | 5.723 |
| 95 | 0.14463 | 298 | 0.7905 | 501 | 2.3495 | 704 | 5.725 |
| 96 | 0.1452 | 299 | 0.79235 | 502 | 2.3515 | 705 | 5.7373 |
| 97 | 0.1466 | 300 | 0.7928 | 503 | 2.3565 | 706 | 5.7465 |
| 98 | 0.14745 | 301 | 0.79429 | 504 | 2.3635 | 707 | 5.821 |
| 99 | 0.14845 | 302 | 0.79435 | 505 | 2.1945 | 708 | 5.8345 |
| 100 | 0.15015 | 303 | 0.79565 | 506 | 2.23 | 709 | 5.865 |
| 101 | 0.1559 | 304 | 0.74385 | 507 | 2.38 | 710 | 5.887 |
| 102 | 0.1574 | 305 | 0.8013 | 508 | 2.3805 | 711 | 5.9075 |
| 103 | 0.15845 | 306 | 0.8057 | 509 | 2.3995 | 712 | 5.9215 |
| 104 | 0.1611 | 307 | 0.8008 | 510 | 2.2505 | 713 | 6.039 |
| 105 | 0.16385 | 308 | 0.8085 | 511 | 2.4195 | 714 | 6.0545 |
| 106 | 0.164 | 309 | 0.822 | 512 | 2.252 | 715 | 6.057 |
| 107 | 0.1642 | 310 | 0.8061 | 513 | 2.3655 | 716 | 6.168 |
| 108 | 0.16885 | 311 | 0.8393 | 514 | 2.433 | 717 | 6.259 |
| 109 | 0.1712 | 312 | 0.841 | 515 | 2.441 | 718 | 6.2625 |
| 110 | 0.1732 | 313 | 0.8424 | 516 | 2.446 | 719 | 6.2628 |
| 111 | 0.1746 | 314 | 0.84602 | 517 | 2.4485 | 720 | 6.27 |
| 112 | 0.1762 | 315 | 0.8574 | 518 | 2.457 | 721 | 6.2885 |
| 113 | 0.17633 | 316 | 0.8325 | 519 | 2.367 | 722 | 6.3585 |
| 114 | 0.17705 | 317 | 0.86185 | 520 | 2.5075 | 723 | 6.4425 |
| 115 | 0.17745 | 318 | 0.86525 | 521 | 2.551 | 724 | 6.475 |
| 116 | 0.17905 | 319 | 0.8692 | 522 | 2.4145 | 725 | 6.507 |
| 117 | 0.17905 | 320 | 0.8613 | 523 | 2.582 | 726 | 6.547 |
| 118 | 0.1795 | 321 | 0.8725 | 524 | 2.583 | 727 | 6.61 |
| 119 | 0.1819 | 322 | 0.87315 | 525 | 2.4285 | 728 | 6.701 |
| 120 | 0.1826 | 323 | 0.87065 | 526 | 2.5923 | 729 | 6.7185 |
| 121 | 0.1828 | 324 | 0.8782 | 527 | 2.5985 | 730 | 6.7333 |
| 122 | 0.18585 | 325 | 0.88831 | 528 | 2.4294 | 731 | 6.763 |
| 123 | 0.189 | 326 | 0.88855 | 529 | 2.4895 | 732 | 6.7885 |
| 124 | 0.19985 | 327 | 0.8893 | 530 | 2.614 | 733 | 6.8025 |
| 125 | 0.20265 | 328 | 0.8776 | 531 | 2.553 | 734 | 6.866 |
| 126 | 0.2062 | 329 | 0.89215 | 532 | 2.6285 | 735 | 7.0265 |
| 127 | 0.2088 | 330 | 0.89718 | 533 | 2.5883 | 736 | 7.041 |
| 128 | 0.2103 | 331 | 0.8976 | 534 | 2.611 | 737 | 7.053 |
| 129 | 0.21185 | 332 | 0.9097 | 535 | 2.69 | 738 | 7.0545 |
| 130 | 0.21395 | 333 | 0.92095 | 536 | 2.696 | 739 | 7.1325 |
| 131 | 0.21584 | 334 | 0.92945 | 537 | 2.7025 | 740 | 7.156 |
| 132 | 0.2176 | 335 | 0.93615 | 538 | 2.6115 | 741 | 7.1615 |
| 133 | 0.2186 | 336 | 0.9372 | 539 | 2.753 | 742 | 7.2 |
| 134 | 0.21985 | 337 | 0.94775 | 540 | 2.7885 | 743 | 7.2015 |
| 135 | 0.22148 | 338 | 0.94805 | 541 | 2.789 | 744 | 7.232 |
| 136 | 0.2235 | 339 | 0.9511 | 542 | 2.806 | 745 | 7.244 |
| 137 | 0.2267 | 340 | 0.88975 | 543 | 2.813 | 746 | 7.268 |
| 138 | 0.2306 | 341 | 0.9606 | 544 | 2.8175 | 747 | 7.287 |
| 139 | 0.232 | 342 | 0.9661 | 545 | 2.818 | 748 | 7.314 |
| 140 | 0.2351 | 343 | 0.9742 | 546 | 2.6257 | 749 | 7.3175 |
| 141 | 0.23655 | 344 | 0.95545 | 547 | 2.836 | 750 | 7.331 |
| 142 | 0.2421 | 345 | 0.9744 | 548 | 2.66 | 751 | 7.3925 |
| 143 | 0.244 | 346 | 1.0139 | 549 | 2.8405 | 752 | 7.417 |
| 144 | 0.2462 | 347 | 1.0255 | 550 | 2.8425 | 753 | 7.42 |
| 145 | 0.24655 | 348 | 1.0273 | 551 | 2.8435 | 754 | 7.453 |
| 146 | 0.2474 | 349 | 1.0296 | 552 | 2.854 | 755 | 7.5435 |
| 147 | 0.248 | 350 | 1.0349 | 553 | 2.873 | 756 | 7.5875 |
| 148 | 0.25685 | 351 | 1.0354 | 554 | 2.688 | 757 | 7.6005 |
| 149 | 0.25885 | 352 | 0.97585 | 555 | 2.893 | 758 | 7.61 |
| 150 | 0.25885 | 353 | 1.0398 | 556 | 2.9075 | 759 | 7.6347 |
| 151 | 0.2616 | 354 | 1.0425 | 557 | 2.9265 | 760 | 7.661 |
| 152 | 0.26235 | 355 | 1.0472 | 558 | 2.928 | 761 | 7.696 |
| 153 | 0.26965 | 356 | 1.0535 | 559 | 2.7115 | 762 | 7.747 |
| 154 | 0.2715 | 357 | 1.0695 | 560 | 2.9638 | 763 | 7.879 |
| 155 | 0.27195 | 358 | 1.0947 | 561 | 2.9935 | 764 | 7.912 |
| 156 | 0.27265 | 359 | 1.1055 | 562 | 3.025 | 765 | 7.9325 |
| 157 | 0.2727 | 360 | 1.11 | 563 | 2.8195 | 766 | 7.933 |
| 158 | 0.27295 | 361 | 1.1125 | 564 | 3.077 | 767 | 8.015 |
| 159 | 0.2735 | 362 | 1.0375 | 565 | 3.077 | 768 | 8.033 |
| 160 | 0.274 | 363 | 1.143 | 566 | 3.0845 | 769 | 8.078 |
| 161 | 0.2746 | 364 | 1.04 | 567 | 3.1075 | 770 | 8.1255 |
| 162 | 0.27675 | 365 | 1.139 | 568 | 3.114 | 771 | 8.1415 |
| 163 | 0.2773 | 366 | 1.1445 | 569 | 3.182 | 772 | 8.175 |
| 164 | 0.27853 | 367 | 1.1962 | 570 | 3.1825 | 773 | 8.21 |
| 165 | 0.2792 | 368 | 1.2 | 571 | 3.1845 | 774 | 8.3045 |
| 166 | 0.28075 | 369 | 1.1795 | 572 | 3.205 | 775 | 8.31 |
| 167 | 0.2813 | 370 | 1.1806 | 573 | 3.224 | 776 | 8.3695 |
| 168 | 0.28755 | 371 | 1.216 | 574 | 3.2325 | 777 | 8.3805 |
| 169 | 0.28915 | 372 | 1.2085 | 575 | 3.245 | 778 | 8.418 |

-continued

| EX. # | AC$_{1.4}$ (μM) | EX. # | AC$_{1.4}$ (μM) | EX. # | AC$_{1.4}$ (μM) | EX. # | AC$_{1.4}$ (μM) |
|---|---|---|---|---|---|---|---|
| 170 | 0.29275 | 373 | 1.2258 | 576 | 2.838 | 779 | 8.423 |
| 171 | 0.29345 | 374 | 1.2265 | 577 | 3.2945 | 780 | 8.4235 |
| 172 | 0.29595 | 375 | 1.2153 | 578 | 3.3475 | 781 | 8.59 |
| 173 | 0.3001 | 376 | 1.2296 | 579 | 3.354 | 782 | 8.6395 |
| 174 | 0.3052 | 377 | 1.216 | 580 | 3.3545 | 783 | 8.7825 |
| 175 | 0.3064 | 378 | 1.227 | 581 | 3.364 | 784 | 8.852 |
| 176 | 0.3085 | 379 | 1.237 | 582 | 3.371 | 785 | 8.8883 |
| 177 | 0.3113 | 380 | 1.257 | 583 | 3.3715 | 786 | 8.9175 |
| 178 | 0.31405 | 381 | 1.268 | 584 | 3.397 | 787 | 8.931 |
| 179 | 0.3231 | 382 | 1.232 | 585 | 3.413 | 788 | 8.9395 |
| 180 | 0.3256 | 383 | 1.2725 | 586 | 3.4335 | 789 | 8.9635 |
| 181 | 0.32785 | 384 | 1.295 | 587 | 3.4385 | 790 | 8.9725 |
| 182 | 0.33249 | 385 | 1.3155 | 588 | 3.447 | 791 | 9.007 |
| 183 | 0.3361 | 386 | 1.3335 | 589 | 2.881 | 792 | 9.071 |
| 184 | 0.33645 | 387 | 1.34 | 590 | 3.4675 | 793 | 9.129 |
| 185 | 0.3371 | 388 | 1.3405 | 591 | 3.476 | 794 | 9.2425 |
| 186 | 0.33723 | 389 | 1.2325 | 592 | 3.477 | 795 | 9.3255 |
| 187 | 0.34095 | 390 | 1.3495 | 593 | 3.49 | 796 | 9.426 |
| 188 | 0.3496 | 391 | 1.3505 | 594 | 3.505 | 797 | 9.447 |
| 189 | 0.35245 | 392 | 1.268 | 595 | 3.5165 | 798 | 9.448 |
| 190 | 0.35695 | 393 | 1.3425 | 596 | 2.9335 | 799 | 9.4535 |
| 191 | 0.35925 | 394 | 1.3725 | 597 | 3.5295 | 800 | 9.537 |
| 192 | 0.3628 | 395 | 1.361 | 598 | 3.0525 | 801 | 9.578 |
| 193 | 0.3676 | 396 | 1.3975 | 599 | 3.5615 | 802 | 9.6005 |
| 194 | 0.38495 | 397 | 1.361 | 600 | 3.6113 | 803 | 9.622 |
| 195 | 0.3859 | 398 | 1.4045 | 601 | 3.276 | 804 | 9.7525 |
| 196 | 0.39065 | 399 | 1.4045 | 602 | 3.4595 | 805 | 9.817 |
| 197 | 0.39635 | 400 | 1.4048 | 603 | 3.6775 | 806 | 10 |
| 198 | 0.4034 | 401 | 1.378 | 604 | 3.679 | 807 | 4.609 |
| 199 | 0.40785 | 402 | 1.381 | 605 | 3.685 | 808 | 4.6765 |
| 200 | 0.40827 | 403 | 1.4025 | 606 | 3.696 | 809 | 4.951 |
| 201 | 0.411 | 404 | 1.4525 | 607 | 3.714 | 810 | 5.084 |
| 202 | 0.4116 | 405 | 1.4065 | 608 | 3.7405 | 811 | 8.7795 |
| 203 | 0.4299 | 406 | 1.4675 | 609 | 3.7443 | 812 | 1.5766 |
| 813 | 0.7101 | 814 | 0.4802 | 815 | 2.39995 | 816 | 2.77505 |
| 817 | 9.11455 | 818 | 4.15535 | 819 | 1.3468 | 820 | 0.9916 |
| 821 | 1.2142 | 822 | 5.894 | 823 | 2.76845 | 824 | 8.87405 |
| 825 | 9.3793 | 826 | 2.62795 | 827 | 0.15 | 828 | 0.1639 |
| 829 | 1.702 | 830 | 0.6694 | 831 | 0.6115 | 832 | 0.657 |
| 833 | 0.7424 | | | | | | |

Echocardiography/Ultrasound Protocol:

Serial echocardiography was conducted with the aid of an imaging system suitable for rodent cardiac ultrasound. Male CD rats (6-10 weeks of age; 6-12 animals per group) were cannulated with a jugular vein catheter to enable delivery of test article by intravenous infusion. Rats were anesthetized with inhaled isoflurane (<1.75%) delivered in oxygen (0.8 L/hr) and positioned on the imaging platform, with limbs appropriately aligned to enable acquisition of the electrocardiogram to enable heart rat determination. Body temperature was maintained between 36-37.5 degrees Celsius and baseline heart rates were maintained minimally at 350 beats per minute. An imaging probe was fixed in position to acquire short axis (SAX), motion (M)-mode images of the left cardiac ventricle at the level of the papillary muscles. Baseline data was acquired prior to initiating test article delivery. Test article (compound as disclosed herein in a HPBCD formulation), or vehicle control, was delivered with the aid of an infusion pump connected to the jugular vein catheter. Infusion rate of test article was increased at 15 min intervals, to a maximum of 5 mL/kg/hr. Ultrasound images were acquired at 5 min intervals. Additionally whole blood (not exceeding 10 uL) was collected via a tail nick at the same 5 min intervals for subsequent exposure determination.

Whole blood samples were analyzed by protein precipitation and liquid chromatography tandem mass spectrometry (LC-MS/MS) using multiple reaction monitoring (MRM) in positive ionization mode. The lower limit of quantitation (LLOQ) in the assay was 1 ng/mL and the upper limit of quantitation (ULOQ) was 10,000 ng/mL. Example 163 was used as an internal standard.

Offline data analysis of the SAX M-mode ultrasound images was conducted to derive measures of left ventricular end diastolic diameter (LVEDD), left ventricular end systolic diameter (LVESD) and subsequent calculation of fractional shortening (% FS) using the following formula: % FS=((LVEDD−LVESD)/LVEDD)*100. Minimally efficacious exposure (MEE) was defined as the exposure at which a 10% increase in % FS from baseline was observed. The MEE was derived by plotting assayed exposures against % FS and using non-linear curve fitting (log(exposure) vs. % FS; variable slope, 4 parameters). Response to vehicle at each time point was averaged and all test article responses were normalized to baseline and subtracted from time matched (averaged) vehicle responses.

Pressure-Volume Loop (PV Loop) Protocol (Invasive Hemodynamics):

Left ventricular catheterization with a pressure-volume transducing catheter was applied as an alternative method to derive pharmacodynamic endpoints. A pressure volume conductance catheter was inserted via the left carotid artery and advanced into the left ventricle. The electrical signal emitted from the volume catheter was used to derive measures of relative volume at 5 min intervals. From these measures, left ventricular end diastolic volume (LVEDV) and left ventricular end systolic volume (LVESV) were derived. Ejection fraction was then derived using the following formula: % EF=((LVEDV−LVESV)/LVEDV)*100. Minimally efficacious exposure (MEE) was defined as the exposure at which a 10% increase in % EF from baseline was observed. The MEE was derived by plotting assayed exposures against % EF and using non-linear curve fitting (log(exposure) vs. % EF; variable slope, 4 parameters). Response to vehicle at each time point was averaged and all test article responses were normalized to baseline and subtracted from time matched (averaged) vehicle responses. Animal preparation, vehicle/test article delivery and blood sampling for exposure determination was as described in Echocardiography/ultrasound protocol.

| Example | MEE* (unbound) | Formulation | Protocol |
|---|---|---|---|
| 67 | 1.05 | 40% HPbCD pH 4 NaOH | PV Loop |
| 91 | 0.04 | 40% HPbCD | PV Loop |
| 113 | 0.04 | 40% HPbCD | PV Loop |
| 135 | 0.05 | 40% HPbCD | PV Loop |
| 200 | 1.02 | 40% HPbCD | PV Loop |
| 214 | 0.12 | 40% HPbCD | Echocardiography |
| 218 | 0.06 | 40% HPbCD | Echocardiography |
| 261 | 0.16 | 40% HPbCD | PV Loop |
| 270 | 0.13 | 40% HPbCD | PV Loop |
| 279 | 0.68 | 40% HPbCD | Echocardiography |
| 287 | 0.47 | 40% HPbCD | PV Loop |
| 301 | 0.19 | 40% HPbCD | PV Loop |
| 314 | 0.16 | 40% HPbCD | Echocardiography |
| 325 | 0.41 | 40% HPbCD | PV Loop |
| 364 | 0.27 | 40% HPbCD | Echocardiography and PV Loop |
| 402 | 0.18 | 40% HPbCD | PV Loop |

*MEE means minimally efficacious exposure. The MEE value has been corrected for rat plasma protein binding.

What is claimed:

1. A compound or pharmaceutically acceptable salt thereof, according to Formula (I):

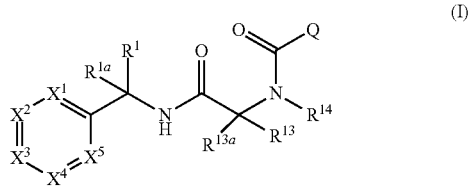

(I)

wherein
Q is

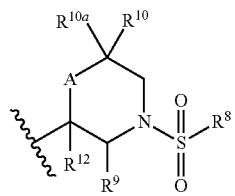

or a 5-member heteroaryl having 1 or 2 ring heteroatoms independently selected from N, O, and S which is optionally substituted with 1 or 2 groups selected from $C_1$-$C_6$alkyl and halo $C_1$-$C_6$alkyl;
A is absent, oxygen, N(H), N($C_1$-$C_6$alkyl) or $CR^{11}R^{11a}$;
$X^1$ is N or $CR^2$;
$X^2$, $X^3$, $X^4$ and $X^5$ are each independently selected from N and $CR^3$ provided that 0, 1, or 2 of $X^1$, $X^2$, $X^3$, $X^4$ and $X^5$ are N and the remainder are $CR^2$ or $CR^3$;
$R^{1a}$ is selected from the group consisting of hydrogen, $C_1$-$C_6$alkyl and halogen;
$R^1$ is selected from the group consisting of hydrogen, $C_1$-$C_6$alkyl, halo $C_1$-$C_6$alkyl, hydroxy $C_1$-$C_6$alkyl, $C_2$-$C_6$alkenyl, $C_2$-$C_6$alkynyl, $C_3$-$C_7$cycloalkyl optionally substituted with 1 or 2 groups selected from hydroxy, halogen, and $C_1$-$C_4$alkyl, hydroxy $C_3$-$C_7$cycloalkyl, $C_3$-$C_7$cycloalkyl$C_1$-$C_4$alkyl, hydroxy $C_3$-$C_7$cycloalkyl$C_1$-$C_4$alkyl, and 4 to 7 member heterocycloalkyl having 1 or 2 ring heteroatoms independently selected from N, O and S, which heterocycloalkyl is optionally substituted with 1 or 2 groups selected from oxo, hydroxy, halogen and $C_1$-$C_4$alkyl;
$R^2$ is selected from the group consisting of hydrogen, halogen, $C_1$-$C_6$alkyl, halo$C_1$-$C_6$alkyl, $C_2$-$C_6$alkenyl, $C_2$-$C_6$alkynyl, $C_3$-$C_7$cycloalkyl, $C_3$-$C_7$cycloalkyl$C_1$-$C_4$alkyl, $C_1$-$C_6$alkoxy, halo$C_1$-$C_6$alkoxy and $SF_5$;
or
$R^1$ and $R^2$, taken in combination, form a divalent group selected from —$CH_2$—, —$CH_2CH_2$—, —$CH_2CH_2CH_2$—, —$OCH_2$—, —$CH_2OCH_2$—, —$OCH_2CH_2$, —$CH_2N(H)CH_2$— and —$CH_2N(C_1$-$C_4$alkyl$)CH_2$—, each of which is optionally substituted with $C_1$-$C_4$alkyl or hydroxy$C_1$-$C_4$alkyl and wherein the oxygen of —$OCH_2CH_2$— or —$OCH_2$— is attached to the $CR^2$ carbon;
$R^3$ is independently selected from the group consisting of hydrogen, halogen, $C_1$-$C_6$alkyl, halo$C_1$-$C_6$alkyl, $C_2$-$C_6$alkenyl, $C_2$-$C_6$alkynyl, $C_3$-$C_7$cycloalkyl, $C_3$-$C_7$cycloalkyl$C_1$-$C_4$alkyl, $C_1$-$C_6$alkoxy, halo$C_1$-$C_6$alkoxy and $SF_5$;
$R^8$ is $C_1$-$C_6$alkyl, $NR^{8d}R^{8e}$, $C_3$-$C_7$cycloalkyl, halo$C_1$-$C_6$alkyl or benzyl, wherein each alkyl, cycloalkyl or haloalkyl is optionally substituted with hydroxy, $CO_2H$, $CO_2C_1$-$C_6$alkyl or $C(O)NH_2$; or
$R^8$ is a group of the formula:

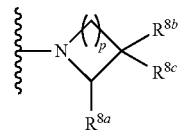

wherein
p is 1 or 2;
$R^{8a}$ is hydrogen, $C_1$-$C_6$alkyl, benzyl, or phenyl optionally substituted with $C_1$-$C_6$alkyl or halogen;
$R^{8b}$ is hydrogen, halogen, $C_1$-$C_6$alkyl, $C_2$-$C_6$alkenyl, $C_2$-$C_6$alkynyl, halo$C_1$-$C_6$alkyl, $C_1$-$C_6$alkoxy, $C_1$-$C_6$alkoxy$C_1$-$C_4$alkyl, $C_3$-$C_7$cycloalkyl, cyano, amino, N(H)C(O)$C_1$-$C_6$alkyl, N(H)C(O)$C_3$-$C_7$cycloalkyl, N(H)C(O)halo$C_1$-$C_6$alkyl, $CO_2H$, C(O)NH$_2$, C(O)NH($C_1$-$C_6$alkyl), C(O)N($C_1$-$C_6$alkyl)$_2$, C(O)$C_1$-$C_6$alkyl, C(O)halo$C_1$-$C_6$alkyl, $SO_2C_1$-$C_6$alkyl, phenyl optionally substituted with halogen, $C_1$-$C_4$alkyl or halo$C_1$-$C_4$alkyl, benzyl optionally substituted with halogen, phenoxy optionally substituted with halogen, 4 to 7 member heterocycloalkyl having 1 or 2 ring heteroatoms selected from N, O and S, or 5 or 6 member heteroaryl having 1 ring heteroatom selected from N, O or S and 0, 1 or 2 additional ring nitrogen atoms, which heteroaryl is optionally substituted with 1 or 2 $C_1$-$C_6$alkyl, and wherein the alkoxy is optionally substituted with halogen, phenyl or halogen-substituted phenyl;

$R^{8c}$ is hydrogen, halogen, hydroxy or $C_1$-$C_6$alkyl; or $CR^{8b}R^{8c}$, taken in combination, forms a spirocyclic 3 to 6 member carboxycle or a 4 to 6 member heterocycle having a ring heteroatom selected from N, O and S, which spirocycle is optionally substituted with hydroxy, $C_1$-$C_4$alkyl, halo$C_1$-$C_4$alkyl or $C_1$-$C_4$alkoxy;

$R^{8d}$ is hydrogen, $C_1$-$C_6$alkyl, halo$C_1$-$C_6$alkyl, $C_3$-$C_7$cycloalkyl, or 4 to 7 member heterocycloalkyl having 1 ring heteroatoms selected from N, O and S and 0 or 1 additional ring nitrogen atoms, which heterocycloalkyl is optionally substituted with 1 or 2 substituents independently selected from hydroxy, halogen, oxo, $C_1$-$C_6$alkyl, and $C_1$-$C_6$alkoxy;

$R^{8e}$ is hydrogen or $C_1$-$C_6$alkyl; or $NR^{8d}R^{8e}$, taken in combination, forms a 4 to 7 member heterocycloalkyl optionally comprising an additional ring heteroatom selected from N, O and S, which heterocycloalkyl is optionally substituted with 1 or 2 substituents independently selected from hydroxy, halogen, oxo, $C_1$-$C_6$alkyl, $C_1$-$C_6$alkoxy and heteroaryl, which heteroaryl has 5 or 6 ring atoms and has one ring heteroatom selected from N, O and S and 0 or 1 additional ring nitrogen atom, or $NR^{8d}R^{8e}$, taken in combination, forms a 5 or 6 member heteroaryl optionally comprising 1 additional ring heteroatom selected from N, O and S;

$R^9$ is hydrogen or $C_1$-$C_6$alkyl;

$R^{10}$ and $R^{10a}$ are each independently selected from the group consisting of hydrogen, halogen and $C_1$-$C_6$alkyl; or $R^9$ and $R^{10}$ taken in combination form a divalent bridge selected from O, $CH_2$, and $CH_2CH_2$ and $R^{10a}$ is hydrogen;

$R^{11a}$ is hydrogen or halogen;

$R^{12}$ is hydrogen or halogen;

$R^{11}$ is selected from the group consisting of hydrogen, halogen, $C_1$-$C_6$alkyl, $N(H)C_1$-$C_6$alkyl and $N(H)C_3$-$C_7$cycloalkyl; or $R^{11}$ and $R^{12}$, taken in combination, form a double bond;

$R^{13a}$ is hydrogen or $C_1$-$C_6$alkyl;

$R^{13}$ is $C_1$-$C_6$alkyl, $C_3$-$C_7$cycloalkyl or $C_3$-$C_7$cycloalkyl$C_1$-$C_6$alkyl;

$R^{14}$ is $C_1$-$C_5$alkyl, $C_3$-$C_7$cycloalkyl or $C_3$-$C_7$cycloalkyl$C_1$-$C_6$alkyl; or $R^{13}$ and $R^{14}$, taken in combination with the interposed C and N atoms, form a saturated or partially unsaturated 4 to 7 member heterocycle which heterocycle further comprises 0 or 1 additional ring heteroatoms selected from N, O and S, which heterocycle is optionally fused to a benzo ring or to a saturated carbocycle having 3 to 7 ring atoms, or which heterocycle is optionally taken together with a saturated carbocyle having 3 to 7 ring atoms to form a spirocyclic ring, and wherein the heterocycle is optionally substituted with 0, 1, 2, or 3 substituents independently selected from the group consisting of halogen, hydroxy, oxo, $C_1$-$C_6$alkyl, $C_2$-$C_6$alkenyl, $C_2$-$C_6$alkynyl, halo$C_1$-$C_5$alkyl, $C_1$-$C_6$alkoxy, $C_3$-$C_7$cycloalkyl, O-A C(O)pyridine substituted with $C_1$-$C_4$alkyl and halo$C_1$-$C_4$alkyl.

2. The compound or salt of claim 1, wherein $X^1$ is $CR^2$, $X^2$ is N or $CR^3$, $X^3$ is $CR^{3a}$, $X^4$ is N or $CR^3$ and $X^5$ is $CR^3$;

$R^2$ is hydrogen, halogen, $C_1$-$C_4$alkyl, cyclopropyl, halo$C_1$-$C_4$alkyl, $C_1$-$C_4$alkoxy or halo$C_1$-$C_4$alkoxy;

$R^3$ is independently selected at each occurrence from the group consisting of hydrogen, halogen, $C_1$-$C_4$alkyl, cyclopropyl, halo$C_1$-$C_4$alkyl, $C_1$-$C_4$alkoxy and halo$C_1$-$C_4$alkoxy; and $R^{3a}$ is halogen, $C_1$-$C_6$alkyl, halo$C_1$-$C_6$alkyl, $C_2$-$C_6$alkenyl, $C_2$-$C_6$alkynyl, $C_3$-$C_7$cycloalkyl, $C_3$-$C_7$cycloalkyl$C_1$-$C_4$alkyl, $C_1$-$C_6$alkoxy, halo$C_1$-$C_6$alkoxy or $SF_5$.

3. The compound or salt of claim 1, wherein $X^1$ is $CR^2$;

$R^2$ is hydrogen, halogen, $C_1$-$C_4$alkyl or $C_1$-$C_4$alkoxy;

$X^2$ is CH or N;

$X^3$ is $CR^{3a}$;

$R^3$ is halogen, $C_1$-$C_4$alkyl, halo$C_1$-$C_4$alkyl, halo$C_1$-$C_6$alkoxy or $SF_5$;

$X^4$ is $CR^3$ or N;

$R^3$ is hydrogen or halogen; and $X^5$ is CH.

4. The compound or salt of claim 1, wherein $X^1$ is $CR^2$;

$R^2$ is hydrogen, halogen, methyl, ethyl, methoxy or ethoxy;

$X^2$ and $X^5$ are each CH;

$X^3$ is $CR^{3a}$;

$R^{3a}$ is halogen, methyl, ethyl, fluoromethyl, difluoromethyl, trifluoromethyl, trifluoromethoxy, or $SF_5$;

$X^4$ is $CR^3$; and $R^3$ is hydrogen or halogen.

5. The compound or salt of claim 1, wherein $R^1$ is selected from the group consisting of hydrogen, $C_1$-$C_6$alkyl, halo $C_1$-$C_6$alkyl, $C_3$-$C_7$cycloalkyl, $C_3$-$C_7$cycloalkylmethyl, and 4 to 6 member heterocycloalkyl having a ring heteroatom selected from N and O, which heterocycloalkyl is optionally substituted with 1 or 2 groups selected from oxo, halogen, and hydroxy, and wherein the alkyl or cycloalkyl is optionally substituted with hydroxy.

6. The compound or salt of claim 1, wherein $R^1$ is $C_1$-$C_4$alkyl, trifluoromethyl, $C_3$-$C_5$cycloalkyl, $C_3$-$C_5$cycloalkylmethyl, oxetanyl, tetrahydrofuryl, or azetidinyl, wherein each alkyl, cycloalkyl, oxetanyl or azetidinyl is optionally substituted with hydroxy or halogen.

7. The compound or salt of claim 1, wherein $R^1$ is methyl, isopropyl, cyclopropyl, cyclopropylmethyl, cyclobutyl, oxetanyl, difluoromethyl, 1-hydroxycyclopropyl, 3-hydroxycyclobutyl, 3-hydroxy-3-methylcyclobutyl, 3-fluorooxetanyl or oxopyrrolidinyl.

8. The compound or salt of claim 1, wherein $R^{13}$ and $R^{14}$ are each independently selected from the group consisting of $C_1$-$C_4$alkyl, $C_3$-$C_5$cycloalkyl and $C_3$-$C_5$cycloalkylmethyl; and $R^{13a}$ is hydrogen.

9. The compound or salt of claim 1, wherein $R^{13}$ and $R^{14}$ are each methyl and $R^{13a}$ is hydrogen.

10. The compound or salt of claim 1, wherein $R^{13a}$ is hydrogen; and $R^{13}$ and $R^{14}$, taken in combination with the interposed C and N atoms, form a saturated or partially unsaturated 4 to 6 member heterocycle, which heterocycle further comprises 0 or 1 additional ring heteroatoms selected from N, O and S, wherein the heterocycle is optionally fused to a saturated carbocycle having 3 to 7 ring atoms, or which heterocycle is optionally taken together with a saturated carbocyle having 3 to 7 ring atoms to form a spirocyclic ring, and wherein the heterocycle is optionally substituted with 0, 1, 2, or 3 substituents independently selected from the group consisting of halogen, hydroxy, $C_1$-$C_6$alkyl, halo$C_1$-$C_6$alkyl, $C_1$-$C_6$alkoxy and $C_3$-$C_7$cycloalkyl.

11. The compound or salt of claim 1, wherein $R^{13a}$ is hydrogen; and $R^{13}$ and $R^{14}$, taken in combination with the interposed C and N atoms, form a heterocyclic ring selected from the group consisting of azetidine, pyrrolidine, thiazolidine, piperidine and morpholine, wherein the heterocyclic ring is optionally fused to a cyclopropyl ring and the heterocyclic ring is further optionally substituted with 1 or 2 substituents independently selected from the group consisting of halogen, hydroxy, methyl, hydroxymethyl, methoxy and cyclopropyl.

12. The compound or salt of claim 1, wherein $R^{13a}$ is hydrogen; and $R^{13}$ and $R^{14}$, taken in combination with the interposed C and N atoms, form a pyrrolidine ring, wherein the pyrrolidine ring is optionally fused to a cyclopropyl ring and the pyrrolidine ring is further optionally substituted with 1 or 2 substituents independently selected from the group consisting of halogen, hydroxy, methyl, hydroxymethyl and cyclopropyl.

13. The compound or salt of any claim 1, wherein Q is

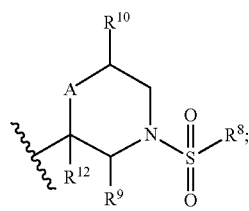

A is oxygen, N(H), or $CHR^{11}$;

$R^8$ is $C_1$-$C_6$alkyl, $NR^{8d}R^{8e}$, $C_3$-$C_7$cycloalkyl, halo$C_1$-$C_6$alkyl or benzyl, and wherein each alkyl, cycloalkyl or haloalkyl is optionally substituted with hydroxy, $CO_2H$, $CO_2C_1$-$C_6$alkyl or $C(O)NH_2$; or $R^8$ is a group of the formula:

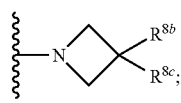

$R^{8b}$ is hydrogen, $C_1$-$C_4$alkyl, halo $C_1$-$C_4$alkyl, $C_1$-$C_4$alkoxy, $C_3$-$C_6$cycloalkyl, cyano, or amino;

$R^{8c}$ is hydrogen, hydroxy or $C_1$-$C_6$alkyl;

$R^{8d}$ is hydrogen, $C_1$-$C_6$alkyl, halo$C_1$-$C_6$alkyl, or $C_3$-$C_7$cycloalkyl;

$R^{8e}$ is hydrogen or $C_1$-$C_6$alkyl;

$R^9$ is hydrogen;

$R^{10}$ is hydrogen; or $R^9$ and $R^{10}$, taken in combination, form a divalent methylene bridge; and $R^{11}$ is hydrogen or $C_1$-$C_6$alkyl.

14. The compound or salt of any claim 1, according to the formula:

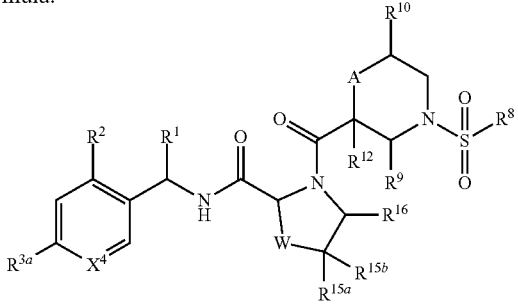

wherein $R^1$ is selected from the group consisting of hydrogen, $C_1$-$C_6$alkyl, halo $C_1$-$C_6$alkyl, $C_3$-$C_7$cycloalkyl, $C_3$-$C_7$cycloalkylmethyl, and 4 to 6 member heterocycloalkyl having a ring heteroatom selected from N and O, which heterocycloalkyl is optionally substituted with 1 or 2 groups selected from oxo and hydroxy, and wherein the alkyl or cycloalkyl is optionally substituted with hydroxy;

$R^2$ is hydrogen, halogen, $C_1$-$C_4$alkyl or $C_1$-$C_4$alkoxy;

$R^{3a}$ is halogen, $C_1$-$C_4$alkyl, halo$C_1$-$C_4$alkyl or $SF_5$;

$X^4$ is $CR^3$ or N;

$R^3$ is hydrogen or halogen;

$Z^2$ is CH or N;

$Z^3$ is CH or N;

$R^8$ is $C_1$-$C_6$alkyl, $C_3$-$C_7$cycloalkyl or halo$C_1$-$C_6$alkyl; or $R^8$ is a group of the formula:

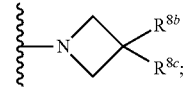

$R^{8b}$ is halogen, $C_1$-$C_4$alkyl, halo$C_1$-$C_4$alkyl, $C_1$-$C_4$alkoxy, $C_3$-$C_5$cycloalkyl, cyano, or amino;

$R^{8c}$ is hydrogen, halogen, hydroxy or $C_1$-$C_6$alkyl; or $CR^{8b}R^{8c}$, taken in combination, forms a spirocyclic 3 to 4 member carboxycle or a 4 or 5 member heterocycle having a ring heteroatom selected from N, O and S, which spirocycle is optionally substituted with hydroxy, $C_1$-$C_4$alkyl, halo$C_1$-$C_4$alkyl or $C_1$-$C_4$alkoxy;

W is a bond, $CH_2$, $CH_2CH_2$ or $CH_2O$, where the oxygen is adjacent to $CR^{15a}R^{15b}$; and $R^{15a}$ and $R^{15b}$ are independently selected from the group consisting of hydrogen, halogen, hydroxy, $C_1$-$C_4$alkyl, hydroxy$C_1$-$C_4$alkyl, $C_1$-$C_4$alkoxy and $C_3$-$C_6$cycloalkyl; or $R^{15a}$ and $R^{15b}$, taken in combination with the carbon to which they are attached, form a spirocyclic cyclopropyl ring; and $R^{16}$ is hydrogen; or $R^{15a}$ and $R^{16}$, taken in combination with the carbon atoms to which they are attached, form a fused cyclopropyl ring, and $R^{15b}$ is selected from the group consisting of hydrogen, halogen, hydroxy, $C_1$-$C_4$alkyl, hydroxy$C_1$-$C_4$alkyl, $C_1$-$C_4$alkoxy and $C_3$-$C_6$cycloalkyl.

15. A compound of claim 1, or a pharmaceutically acceptable salt thereof wherein the compound is selected from the group consisting of:

N-((R)-(4-chloro-2-fluorophenyl)(cyclopropyl)methyl)-1-(((3S)-1-((3-cyano-1-azetidinyl)sulfonyl)-3-piperidinyl) carbonyl)-D-prolinamide;

1-(((3S)-1-(3-cyano-1-azetidinyl)sulfonyl)-3-piperidinyl)carbonyl)-N-MR)-1-(2-fluoro-4-(trifluoromethyl)phenyl)propyl)-D-prolinamide;

1-(((3S)-1-(3-cyano-1-azetidinyl)sulfonyl)-3-piperidinyl)carbonyl)-N-MR)-1-(2-fluoro-4-(trifluoromethyl) phenyl)-2-methylpropyl)-D-prolinamide;

1-(((3S)-1-(3-cyano-1-azetidinyl)sulfonyl)-3-piperidinyl)carbonyl)-N-((R)-cyclopropyl(4-(trifluoromethyl)phenyl)methyl)-D-prolinamide;

1-(((3S)-1-(3-cyano-1-azetidinyl)sulfonyl)-3-piperidinyl)carbonyl)-N-MR)-2-cyclopropyl-1-(4-(trifluoromethyl)phenyl)ethyl)-D-prolinamide;

1-(((3S)-1-(3-cyano-1-azetidinyl)sulfonyl)-3-piperidinyl)carbonyl)-N-MR)-1-(4-(trifluoromethyl)phenyl)propyl)-D-prolinamide;

N-(4-chloro-2,5-difluorobenzyl)-1-(((3S)-1-(3-cyano-1-azetidinyl)sulfonyl)-3-piperidinyl)carbonyl)-D-prolinamide;

1-(((3S)-1-(3-cyano-1-azetidinyl)sulfonyl)-3-piperidinyl)carbonyl)-4,4-difluoro-N-(4-(trifluoromethyl)benzyl)-D-prolinamide;

1-(((3S)-1-(3-cyano-1-azetidinyl)sulfonyl)-3-piperidinyl)carbonyl)-N-MR)-3,3,3-trifluoro-1-(4-(trifluoromethyl)phenyl)propyl)-D- prolinamide;

1-(((3S)-1-(3-cyano-1-azetidinyl)sulfonyl)-3-piperidinyl)carbonyl)-N-MR)-1-(2-fluoro-4-(trifluoromethyl)phenyl)ethyl)-D-prolinamide;

1-(((3S)-1-(3-cyano-1-azetidinyl)sulfonyl)-3-piperidinyl)carbonyl)-N-(3-fluoro-4-(trifluoromethyl)benzyl)-D-prolinamide;

(1R,3R,5R)-2-(((3S)-1-(3-cyano-1-azetidinyl)sulfonyl)-3-piperidinyl)carbonyl)-N-(2-fluoro-4-(trifluoromethyl) benzyl)-2-azabicyclo[3.1.01hexane-3-carboxamide;

1-(((3S)-1-(3-cyano-1-azetidinyl)sulfonyl)-3-piperidinyl)carbonyl)-N-((R)-cyclopropyl(2,5-difluoro-4-(trifluoromethyl)phenyl)methyl)-D- prolinamide;

1-(((3S)-1-(3-cyano-1-azetidinyl)sulfonyl)-3-piperidinyl)carbonyl)-N-MR)-3-hydroxy-1-(4-(trifluoromethyl)phenyl)propyl)-D-prolinamide;

N-(3-chloro-4-(trifluoromethyl)benzyl)-1-(((3S)-1 -(3-cyano-1-azetidinyl)sulfonyl)-3-piperidinyl)carbonyl)-D-prolinamide;

N-((R)-(4-chloro-2,5-difluorophenyl)(cyclopropyl)methyl)-1 -(((3S)-1-((3-cyano-1-azetidinyl)sulfonyl)-3-piperidinyl) carbonyl)-D-prolinamide;

N-((S)-3-azetidinyl(4-chloro-2,5-difluorophenyl)methyl)-1-(((3S)-1-((3-cyano-1-azetidinyl)sulfonyl)-3-piperidinyl)carbonyl)-D-prolinamide;

N-((1R)-1-(4-chloro-2,5-difluorophenypethyl)-1-(((3S)-1-((3-cyano-1-azetidinyl)sulfonyl)-3-piperidinyl)carbonyl)-D-prolinamide;

N-(4-chloro-3-fluorobenzyl)-1-(((3S)-1-(3 -cyano-1-azetidinyl)sulfonyl)-3-piperidinyl)carbonyl)-D-prolinamide;

(3R)-4-(((3S)-1-(3-cyano-1-azetidinyl) sulfonyl)-3-piperidinyl)carbonyl)-N-((1R)-1-(2 -fluoro-4-(trifluoromethyl)phenypethyl)-3-morpholinecarboxamide;

(4S)-1-(((3S)-1-(3-cyano-1-azetidinyl) sulfonyl)-3-piperidinyl)carbonyl)-4-fluoro-N-(4-(trifluoromethyl) benzyl)-D-prolinamide;

1-(((3S)-1-((cis-3-cyanocyclobutylslfonyl)-3-piperidinyl)carbonyl)-N-(4-(trifluoromethyl)benzyl)-D-prolinamide;

1-(((3S)-1-(3-cyano-1-azetidinyl)sulfonyl)-3-piperidinyl)carbonyl)-N-(2-methyl-4-(trifluoromethyl)benzyl)-D-prolinamide;

1-(((3S)-1-(3-cyano-1-azetidinyl)sulfonyl)-3-piperidinyl)carbonyl)-N-(2-fluoro-4-(trifluoromethyl)benzyl)-D-prolinamide;

N-(2-chloro-4-(trifluoromethyl)benzyl)-1-(((3S)-1-((3-cyano-1-azetidinyl) sulfonyl)-3-piperidinyl)carbonyl)-D-prolinamide;

(2R)-1-(((3S)-1-(3-cyano-1-azetidinyl)sulfonyl)-3-piperidinyl) carbonyl)-N-(4-(trifluoromethyl)benzyl)-2-piperidinecarboxamide;

1-(((3S)-1-(3-cyano-1-azetidinyl)sulfonyl)-3-piperidinyl)carbonyl)-N-(4-(trifluoromethyl)benzyl)-D-prolinamide;

1-(((3S)-1-(3-cyano-1-azetidinyl)sulfonyl)-3-piperidinyl)carbonyl)-N-MR)-3-methyl-1-(4-(trifluoromethyl)phenyl)butyl)-D-prolinamide;

N-((1R)-1-(4-chloro-3-fluorophenypethyl)-1-(((3S)-1-((3-cyano-1-azetidinyl) sulfonyl)-3-piperidinyl)carbonyl)-D-prolinamide;

N-(4-chloro-2-fluorobenzyl)-1-(((3S)-1-(3-cyano-1-azetidinyl) sulfonyl)-3-piperidinyl)carbonyl)-D-prolinamide;

1-(((3S)-1-(3-(methylsulfonyl)-1-azetidinyl)sulfonyl)-3-piperidinyl) carbonyl)-N-(4-(trifluoromethyl)benzyl)-D-prolinamide;

1-(((2S)-4-(3-cyano-1-azetidinyl)sulfonyl)-2-morpholinyl) carbonyl)-N-MR)-1-(2-fluoro-4-(trifluoromethyl)phenyl)ethyl)-D-prolinamide;

1-(((3R)-1-(3-cyano-1-azetidinyl)sulfonyl)-5,5-difluoro-3-piperidinyl) carbonyl)-N-(4-(trifluoromethyl)benzyl)-D-prolinamide;

1-(((3S)-1-(3-cyano-1-azetidinyl)sulfonyl)-5,5-difluoro-3-piperidinyl) carbonyl)-N-(4-(trifluoromethyl)benzyl)-D-prolinamide;

N-((1S)-1-(4-chloro-3-fluorophenyl)-2-hydroxyethyl)-1-(((3S)-1-( 3-cyano-1-azetidinyl)sulfonyl)-3-piperidinyl)carbonyl)-D-prolinamide;

1-(((3S,4R)-1-(3-cyano-1-azetidinyl) sulfonyl)-4-methyl-3-piperidinyl)carbonyl)-N-(4-(trifluoromethyl)benzyl)-D-prolinamide;

1-(((3S)-1-(3-cyano-1-azetidinyl)sulfonyl)-3-piperidinyl)carbonyl)-N-MR)-1-(4-(trifluoromethyl)phenyl)ethyl)-D-prolinamide;

1-(((3S)-1-(3-cyano-1-azetidinyl)sulfonyl)-3-piperidinyl)carbonyl)-N-(3-fluoro-4-methylbenzyl)-D-prolinamide;

1-(((3S)-1-(3-cyano-1-azetidinyl)sulfonyl)-3-piperidinyl)carbonyl)-N-MS)-2-hydroxv-1-(4-(trifluoromethyl)phenyl)ethyl)-D-prolinamide;

(1R,2R,5S)-3-(((3S)-1-(3-cyano-1-azetidinyl) sulfonyl)-3-piperidinyl)carbonyl)-N-(4-(trifluoromethyl)benzyl)-3-azabicyclo[3.1.0]hexane-2-carboxamide;

1-(((3S)-1-(3-cyano-1-azetidinyl)sulfonyl)-3-piperidinyl)carbonyl)-N-(3,4-dichlorobenzyl)-D-prolinamide;

N-((1R)-1-(4-chlorophenyl)-2-methoxyethyl)-1-(((3S)-1-( 3-cyano-1-azetidinyl)sulfonyl)-3-piperidinyl)carbonyl)-D-prolinamide;

N-((1S)-1-(4-chlorophenyl)-2-methoxyethyl)-1-(((3S)-1-( 3-cyano-1-azetidinyl)sulfonyl)-3-piperidinyl)carbonyl)-D-prolinamide;

1-(((3S)-1-(3-cyano-1-azetidinyl)sulfonyl)-3-piperidinyl)carbonyl)-N-MR)-1-(2-fluoro-4-methylphenyl)ethyl)-D-prolinamide;

1-(((3S)-1-(3-cyano-1-azetidinyl)sulfonyl)-3-piperidinyl)carbonyl)-N-(2,4-dichlorobenzyl)-D-prolinamide;

1-(((1R,4R,6R)-2-(3-cyano-1-azetidinyl)sulfonyl)-2-azabicyclo[2.2.1hept-6-Y1)carbonyl)-N-(2-fluoro-4-(trifluoromethyl)benzyl)-D-prolinamide;

1-(((3S)-1-(3-cyano-1-azetidinyl)sulfonyl)-3-piperidinyl) carbonyl)-N-MR)-1-(4-(difluoromethyl)-2-fluorophenyl)ethyl)-D-prolinamide;

1-(((3S)-1-(3-cyano-1-azetidinyl)sulfonyl)-3-piperidinyl) carbonyl)-N-((S)-cyclopropyl(4-(trifluoromethyl)phenyl)methyl)-D-prolinamide;

(3R)-4-(((3S)-1-(3-cyano-1-azetidinyl)sulfonyl)-3-piperidinyl) carbonyl)-N-(4-(trifluoromethyl)benzyl)-3-morpholinecarboxamide;

1-(((2S)-4-((3-cyano-1-azetidinyl)sulfonyl)-2-morpholinyl) carbonyl)-N-(2-fluoro-4-(trifluoromethyl)benzyl)-D-prolinamide;

1-(((3S)-1-(3-cyano-1-azetidinyl)sulfonyl)-3-piperidinyl) carbonyl)-N-((R)-cyclopropyl(4-(pentafluoro-lambda~6~-sulfanyl)phenyl)methyl)-D-prolinamide;

N-(4-chloro-2-methylbenzyl)-1-(((3S)-1-(3-cyano-1-azetidinyl) sulfonyl)-3-piperidinyl)carbonyl)-D-prolinamide;

1-((1-((3-cyano-1-azetidinyl)sulfonyl)-1H-pyrazol-4-yl) carbonyl)-N-(4-(trifluoromethyl) benzyl)-D-prolinamide;

N-(3-chloro-4-methylbenzyl)-1-(((3S)-1-(3-cyano-1-azetidinyl) sulfonyl)-3-piperidinyl)carbonyl)-D-prolinamide;

N-((R)-(4-chlorophenyl)((2R)-tetrahydro-2-furanyl) methyl)-1-(((3S)-1-((3-cyano-1-azetidinyl)sulfonyl)-3-piperidinyl) carbonyl)-D-prolinamide & N-((R)-(4-chlorophenyl)((2S)-tetrahydro-2-furanyl) methyl)-1-(((3S)-1-((3-cyano-1-azetidinyl)sulfonyl)-3-piperidinyl) carbonyl)-D-prolinamide & N-((S)-(4-chlorophenyl)((2R)-tetrahydro-2-furanyl) methyl)-1-(((3S)-1-((3-cyano-1-azetidinyl)sulfonyl)-3-piperidinyl) carbonyl)-D-prolinamide & N-((S)-(4-chlorophenyl)((2S)-tetrahydro-2-furanyl) methyl)-1-(((3S)-1-((3-cyano-1-azetidinyl)sulfonyl)-3-piperidinyl)carbonyl)-D-prolinamide;

1-(((3S)-1-(3-cyano-1-azetidinyl)sulfonyl)-3-piperidinyl) carbonyl)-N-MR)-2-hydroxy-1-(4-(trifluoromethyl) phenyl)ethyl)-D-prolinamide;

1-(((3S)-1-(3-cyano-1-azetidinyl)sulfonyl)-3-piperidinyl) carbonyl)-N-MS)-2-hydroxy-1-(4-(trifluoromethyl) phenyl)ethyl)-D-prolinamide;

N-((1R)-1-(4-chlorophenypethyl)-1-(((3S)-1-((3-cyano-1-azetidinyl) sulfonyl)-3-piperidinyl)carbonyl)-D-prolinamide;

N-(4-chloro-3-methylbenzyl)-1-(((3S)-1-(3-cyano-1-azetidinyl) sulfonyl)-3-piperidinyl)carbonyl)-D-prolinamide;

1-(((3S)-1-((3-cyano-1-azetidinyl)sulfonyl)-4,4-difluoro-3-piperidinyl) carbonyl)-N-(4-(trifluoromethyl)benzyl)-D-prolinamide;

1-(((2S)-4-(3-cyano-1-azetidinyl)sulfonyl)-2-piperazinyl) carbonyl)-N-((1R)-1-(2-fluoro-4-(trifluoromethyl)phenyl)ethyl)-D-prolinamide;

1-(((3S)-1-(3-cyano-1-azetidinyl)sulfonyl)-3-piperidinyl) carbonyl)-N-(2-methyl-3-(trifluoromethyl)benzyl)-D-prolinamide;

1-(((2S)-4-(3-cyano-1-azetidinyl)sulfonyl)-2-morpholinyl) carbonyl)-N-(4-(trifluoromethyl)benzyl)-D-prolinamide;

N-((1R)-1-(4-chlorophenypethyl)-1-(((3S)-1-((3-(methylsulfonyl)-1-azetidinyl) sulfonyl)-3-piperidinyl)carbonyl)-D-prolinamide;

N-(2-fluoro-4-(trifluoromethyl)benzyl)-1-(((3S)-1-((3-(1 H-1,2,3-triazol-1-yl)-1-azetidinyl)sulfonyl)-3-piperidinyl)carbonyl)-D-prolinamide;

N-(3-chloro-2-methylbenzyl)-1-(((3S)-1-(3-cyano-1-azetidinyl) sulfonyl)-3-piperidinyl)carbonyl)-D-prolinamide;

1-(((3S)-1-(3-cyano-1-azetidinyl)sulfonyl)-3-piperidinyl) carbonyl)-N-(3,4,5-trifluorobenzyl)-D-prolinamide;

1-(((3S)-1-(3-cyano-1-azetidinyl)sulfonyl)-3-piperidinyl) carbonyl)-N-((1R)-1-(3-fluoro-4-methylphenypethyl)-D-prolinamide;

1-(((3S)-1-(3-cyano-1-azetidinyl)sulfonyl)-3-piperidinyl) carbonyl)-N-MS)-1-(3-fluoro-4-methylphenypethyl)-D-prolinamide;

1-(((3S)-1-(3-cyano-3-methyl-1-azetidinyl)sulfonyl)-3-piperidinyl) carbonyl)-N-(4-(trifluoromethyl)benzyl)-D-prolinamide;

N-(4-chlorobenzyl)-1-(((3S)-1-(3-cyano-1-azetidinyl) sulfonyl)-3-piperidinyl)carbonyl)-D-prolinamide;

1-(((3S)-1-(((2R)-2-(3-fluorophenyl)-1-azetidinyl)sulfonyl)-3-piperidinyl) carbonyl)-N-(4-(trifluoromethyl) benzyl)-D-prolinamide;

1-(((3S)-1-(((2S)-2-(3-fluorophenyl)-1-azetidinyl)sulfonyl)-3-piperidinyl) carbonyl)-N-(4-(trifluoromethyl) benzyl)-D-prolinamide;

1-(1-(3-cyano-1-azetidinyl)sulfonyl)-4-fluoro-1,2,5,6-tetrahydro-3-pyridinyl) carbonyl)-N-(4-(trifluoromethyl) benzyl)-D-prolinamide;

N-((1S)-1-(4-chlorophenyl)-2-hydroxyethyl)-1-(((3S)-1-((3-cyano-1-azetidinyl)sulfonyl)-3-piperidinyl)carbonyl)-D-prolinamide;

1-(((3R,4S)-1-(3-cyano-1-azetidinyl)sulfonyl)-4-methyl-3-piperidinyl) carbonyl)-N-(4-(trifluoromethyl)benzyl)-D-prolinamide;

1-(((3S,4R)-1-(3-cyano-1-azetidinyl)sulfonyl)-4-methyl-3-piperidinyl) carbonyl)-N-(4-(trifluoromethyl)benzyl)-D-prolinamide;

1-((((1R,4R,6R)-2-(3-cyano-1-azetidinyl)sulfonyl)-2-azabicyclo[2.2.1]hept-6-yl)carbonyl)-N-(4-(trifluoromethyl)benzyl)-D-prolinamide;

N-(4-chloro-3-fluorobenzyl)-1-(((2S)-4-(3-cyano-1-azetidinyl) sulfonyl)-2-piperazinyl)carbonyl)-D-prolinamide;

(3R)-4-(((3S)-1-(3-cyano-1-azetidinyl)sulfonyl)-3-piperidinyl) carbonyl)-N-((1R)-1-(4-(trifluoromethyl)phenypethyl)-3-morpholinecarboxamide;

N-(4-chloro-2-methoxybenzyl)-1-(((3S)-1-(3-cyano-1-azetidinyl) sulfonyl)-3-piperidinyl)carbonyl)-D-prolinamide;

(1S,2R,5R)-3-(((3S)-1-(3-cyano-1-azetidinyl)sulfonyl)-3-piperidinyl) carbonyl)- N-(4-(trifluoromethyl)benzyl)-3-azabicyclo[3.1.0]hexane-2-carboxamide;

1-(((3S)-1-(((2R)-2-(3-bromophenyl)-1-azetidinyl)sulfonyl)-3-piperidinyl) carbonyl)-N-(4-(trifluoromethyl) benzyl)-D-prolinamide;

1-(((3S)-1-(((2S)-2-(3-bromophenyl)-1-azetidinyl) sulfonyl)-3-piperidinyl)carbonyl)-N-(4-(trifluoromethyl) benzyl)-D-prolinamide;

1-(((3S)-1-(3-cyano-1-azetidinyl)sulfonyl)-3-piperidinyl) carbonyl)-N-(2-fluoro-4-methylbenzyl)-D-prolinamide;

1-(((3S)-1-(3-cyano-1-azetidinyl)sulfonyl)-3-fluoro-3-piperidinyl) carbonyl)- N-(4-(trifluoromethyl)benzyl)-D-prolinamide or 1-(((3R)-1-(3-cyano-1-azetidinyl) sulfonyl)-3-fluoro-3-piperidinyl)carbonyl)-N-(4-(trifluoromethyl)benzyl)-D-prolinamide;

N-(4-chloro-2-fluorobenzyl)-1-(((2S)-4-(3-cyano-1-azetidinyl) sulfonyl)-2-morpholinyl)carbonyl)-D-prolinamide;

1-(((1R,4R,6R)-2-(3-cyano-1-azetidinyl) sulfonyl)-2-azabicyclo[2.2.1hept-6-yl)carbonyl)-N-(2-fluoro-4-(trifluoromethyl)benzyl)-D-prolinamide;
1-(((1S,4S,6S)-2-(3-cyano-1-azetidinyl) sulfonyl)-2-azabicyclo[2.2.1hept-6-yl)carbonyl)-N-(2-fluoro-4-(trifluoromethyl)benzyl)-D-prolinamide;
N-(2-chloro-4-methylbenzyl)-1-(((3S)-1-(3-cyano-1-azetidinyl) sulfonyl)-3-piperidinyl)carbonyI)-D-prolinamide;
1-(((3S)-1-(((3S)-3-cyano-1-pyrrolidinyl)sulfonyl)-3-piperidinyl) carbonyl)-N-(4-(trifluoromethyl)benzyI)-D-prolinamide;
1-(((3S)-1-(3-cyano-1-azetidinyl)sulfonyl)-3-piperidinyl) carbonyl)-N-MS)-1-(4-(trifluoromethyl)phenyl)propyl)-D-prolinamide;
1-(((3S)-1-(3-ethynyl-3-hydroxy-1-azetidinyl)sulfonyl)-3-piperidinyl) carbonyl)-N-(2-fluoro-4-(trifluoromethyl)benzyl)-D-prolinamide;
1-(((3S)-1-(3-cyano-1-azetidinyl)sulfonyl)-3-piperidinyl) carbonyl)-N-MS)-2,2,2-trifluoro-1-(4-(trifluoromethyl)phenyl)ethyl)-D-prolinamide;
1-(((3S)-1-(3-cyclopropyl-3-hydroxy-1-azetidinyl)sulfonyl)-3-piperidinyl) carbonyl)-N-(2-fluoro-4-(trifluoromethyl)benzyI)-D-prolinamide;
1-(((2S)-4-(3-cyano-1-azetidinyl)sulfonyl)-2-piperazinyl) carbonyl)-N-(2-fluoro-4-(trifluoromethyl)benzyl)-D-prolinamide;
1-(((3S)-1-((3-(1 H-1,2,3-triazol-1-yl)-1-azetidinyl)sulfonyl)-3-piperidinyl) carbonyl)-N-(4-(trifluoromethyl) benzyl)-D-prolinamide;
1-(((3S)-1-(3-cyano-1-azetidinyl)sulfonyl)-3-piperidinyl) carbonyl)-N-(2,3-dichlorobenzyl)-D-prolinamide;
(3S)-1(3-cyano-1-azetidinyl)sulfonyl)-N-((2R)-1-(((1R)-1-(2-fluoro-4-(trifluoromethyl) phenyl)ethyl)amino)-1-oxo-2-propanyl)-N-methyl-3-piperidinecarboxamide;
1-(((3S)-1-(3-(4-chlorobenzyl)oxy)-1-azetidinyl)sulfonyl)-3-piperidinyl) carbonyl)-N-(4-(trifluoromethyl) benzyl)-D-prolinamide;
(4R)-1-(((3S)-14(3-cyano-1-azetidinyl)sulfonyl)-3-piperidinyl) carbonyl)-4-fluoro-N-(4-(trifluoromethyl) benzyl)-D-prolinamide;
1-(((3S)-1(3-cyano-1-azetidinyl)sulfonyl)-3-piperidinyl) carbonyl)-N-(3,4-difluorobenzyl)-D-prolinamide;
1-(((3S)-1-(3-(1,2-oxazol-3-0-1-azetidinyl)sulfonyl)-3-piperidinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-MS)-1-(2-fluoro-4-(trifluoromethyl)phenyl)-2-methylpropyl)-D-prolinamide;
1-(((3S)-1-(3-(2-fluoroethoxy)-1-azetidinyl)sulfonyl)-3-piperidinyl) carbonyl)-N-(2-fluoro-4-(trifluoromethyl)benzyl)-D-prolinamide;
1-(((2S)-4-(3-cyano-1-azetidinyl)sulfonyl)-2-piperazinyl) carbonyl)-N-(4-(trifluoromethyl)benzyl)-D-prolinamide;
(4R)-1-(((3S)-1-(3-cyano-1-azetidinyl)sulfonyl)-3-piperidinyl) carbonyl)-4-hydroxy-N-(4-(trifluoromethyl)benzyl)-D-prolinamide;
1-(((3S)-1-(3-cyano-1-azetidinyl)sulfonyl)-3-piperidinyl) carbonyl)-N-((1R)-4-methoxy-2,3-dihydro-1H-inden-1-yl)-D-prolinamide;
1-(((3S)-1-(3-cyano-1-azetidinyl)sulfonyl)-3-piperidinyl) carbonyl)-N-((1S)-4-methoxy-2,3-dihydro-1H-inden-1-yl)-D-prolinamide;
1-(((3S)-1-(3-cyano-1-azetidinyl)sulfonyl)-3-piperidinyl) carbonyl)-N-(4-methylbenzyl)-D-prolinamide;
1-(((3S)-1-(3-cyano-1-azetidinyl)sulfonyl)-3-piperidinyl) carbonyl)-N-MR)-1-(3,5-difluorophenyl)propyl)-D-prolinamide;
1-(((3S)-1-(3-cyano-1-azetidinyl)sulfonyl)-3-piperidinyl) carbonyl)-N-MR)-1-(4-(difluoromethyl)phenyl)ethyl)-D-prolinamide;
N-((1R)-1-(4-chloro-2-fluorophenypethyl)-1-(((2S)-4-(3-cyano-1-azetidinyl) sulfonyl)-2-piperazinyl)carbonyl)-D-prolinamide;
1-(((3S)-1-(3-cyano-1-azetidinyl)sulfonyl)-3-piperidinyl) carbonyl)-N-(2,4-dimethylbenzyl)-D-prolinamide;
1-(((2S)-4-(3-cyano-1-azetidinyl)sulfonyl)-2-piperazinyl) carbonyl)-N-(3,4-dichlorobenzyl)-D-prolinamide;
1-(((3S)-1-(3-cyano-1-azetidinyl)sulfonyl)-3-piperidinyl) carbonyl)-N-(4-(difluoromethyl)benzyl)-D-prolinamide;
N-((R)-(4-chlorophenyl)(phenyl)methyl)-1-(((3S)-1-((3-cyano-1-azetidinyl) sulfonyl)-3-piperidinyl)carbonyl)-D-prolinamide & N-((S)-(4-chlorophenyl)(phenyl)methyl)-1-(((3S)-1-((3-cyano-1-azetidinyl)sulfonyl)-3-piperidinyl)carbonyl)-D-prolinamide;
1-(((2S,3S)-1-(3-cyano-1-azetidinyl)sulfonyl)-2-methyl-3-piperidinyl) carbonyl)-N-(4-(trifluoromethyl)benzyl)-D-prolinamide;
N-(3-chloro-4-fluorobenzyl)-1-(((3S)-1-(3-cyano-1-azetidinyl) sulfonyl)-3-piperidinyl)carbonyl)-D-prolinamide. 1-(((3S)-1-(3-(difluoromethyl)-1-azetidinyl) sulfonyl)-3-piperidinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-MR,3R)-3-(hydroxymethyl)-2,3-dihydro-1H-inden-1-yl)-D-prolinamide;
1-(((3S)-1-(3-cyano-1-azetidinyl)sulfonyl)-3-piperidinyl) carbonyl)-N-MR,3S)-3-(hydroxymethyl)-2,3-dihydro-1H-inden-1-yl)-D-prolinamide;
1-(((3S)-1-(3-cyano-1-azetidinyl)sulfonyl)-3-piperidinyl) carbonyl)-N-MS,3R)-3-(hydroxymethyl)-2,3-dihydro-1H-inden-1-yl)-D-prolinamide;
1-(((3S)-1-(3-cyano-1-azetidinyl)sulfonyl)-3-piperidinyl) carbonyl)-N-MS,3S)-3-(hydroxymethyl)-2,3-dihydro-1H-inden-1-yl)-D-prolinamide;
N-(2-chloro-4-fluorobenzyl)-1-(((3S)-1-(3-cyano-1-azetidinyl) sulfonyl)-3-piperidinyl)carbonyI)-D-prolinamide;
1-(((3S)-1-(3-cyano-1-azetidinyl)sulfonyl)-3-piperidinyl) carbonyl)-N-MR)-1-(4-methylphenyl)ethyl)-D-prolinamide;
1-(((3S)-1-(3-cyano-1-azetidinyl)sulfonyl)-3-piperidinyl) carbonyl)-N-(3,5-difluorobenzyl)-D-prolinamide;
1-(((3S)-1-(3-cyano-1-azetidinyl)sulfonyl)-3-piperidinyl) carbonyl)-N-(3-fluoro-2-methylbenzyl)-D-prolinamide;
N-(4-chloro-2-fluorobenzyl)-1-(((2S)-4-(3-cyano-1-azetidinyl) sulfonyl)-2-piperazinyl)carbonyI)-D-prolinamide;
N-((1R)-1-(4-chlorophenypethyl)-1-(((2S)-4-(3-cyano-1-azetidinyl) sulfonyl)-2-morpholinyl)carbonyl)-D-prolinamide;
1-(((3S)-1-(3-cyano-1-azetidinyl)sulfonyl)-3-piperidinyl) carbonyl)-N-MS)-1-(2-fluoro-4-(trifluoromethyl)phenyl)propyl)-D-prolinamide;
1-(((3S)-1-(3-(difluoromethyl)-3-hydroxy-1-azetidinyl) sulfonyl)-3-piperidinyl)carbonyl)-N-(2-fluoro-4-(trifluoromethyl)benzyl)-D-prolinamide;
1-(((3S)-1-(3-cyano-1-azetidinyl)sulfonyl)-3-piperidinyl) carbonyl)-N-(4-fluoro-3-(trifluoromethyl)benzyl)-D-prolinamide;

(2S)-4-(3-cyano-1-azetidinyl) sulfonyl)-N-((2R)-1-(((1R)-1-(2-fluoro-4-(trifluoromethyl)phenyl)ethyl)amino)-1-oxo-2-propanyl)-N-methyl-2-morpholinecarboxamide;

1-(((3S)-1-(3-cyano-1-azetidinyl)sulfonyl)-3-piperidinyl) carbonyl)-N-MR)-1-(3,4-difluorophenyl)ethyl)-D-prolinamide;

1-(((3S)-1-(((2R)-2-(2-fluorophenyl)-1-azetidinyl)sulfonyl)-3-piperidinyl) carbonyl)-N-(4-(trifluoromethyl)benzyl)-D-prolinamide;

1-(((3S)-1-(((2S)-2-(2-fluorophenyl)-1-azetidinyl)sulfonyl)-3-piperidinyl) carbonyl)-N-(4-(trifluoromethyl)benzyl)-D-prolinamide;

N-((1S)-1-(4-chlorophenyl)-2,2,2-trifluoroethyl)-1-(((3S)-1-((3-cyano-1-azetidinyl) sulfonyl)-3-piperidinyl)carbonyl)-D-prolinamide;

1-(((3S)-1-(3-(2,2-difluoroethoxy)-1-azetidinyl)sulfonyl)-3-piperidinyl) carbonyl)-N-(4-(trifluoromethyl)benzyl)-D-prolinamide;

N-(3-chloro-5-fluorobenzyl)-1-(((3S)-1-(3-cyano-1-azetidinyl) sulfonyl)-3-piperidinyl)carbonyl)-D-prolinamide;

(3S)-N-((2R)-1-(((1R)-1-(4-chloro-2-fluorophenyl)ethyl)amino)-1-oxo-2-propanyl)-1-((3-cyano-1-azetidinyl) sulfonyl)-N-methyl-3-piperidinecarboxamide;

1-(((3S)-1-(((3R)-3-cyano-1-pyrrolidinyl) sulfonyl)-3-piperidinyl)carbonyl)-N-(4-(trifluoromethyl)benzyl)-D-prolinamide;

N-((1R)-1-(2,4-difluorophenypethyl)-1-(((3S)-1-((3-(methylsulfonyl)-1-azetidinyl) sulfonyl)-3-piperidinyl) carbonyl)-D-prolinamide;

1-(((3S)-1-(3-cyano-1-azetidinyl)sulfonyl)-3-piperidinyl) carbonyl)-N-MR)-1-(2,4-difluorophenypethyl)-D-prolinamide;

(1R,3R,5R)-2-(((3S)-1-(3-cyano-1-azetidinyl)sulfonyl)-3-piperidinyl) carbonyl)-N-((6-(trifluoromethyl)-3-pyridinyl)methyl)-2-azabicyclo]3.1.01[hexane-3-carboxamide;

1-(((3S)-1-(3-cyano-3-fluoro-1-azetidinyl)sulfonyl)-3-piperidinyl) carbonyl)-N-(2-fluoro-4-(trifluoromethyl)benzyl)-D-prolinamide;

N-(2-fluoro-4-(trifluoromethyl)benzyl)-1-(((3S)-1-(3-hydroxy-3-(2-propanyl)-1-azetidinyl) sulfonyl)-3-piperidinyl)carbonyl)-D-prolinamide;

N-(4-chloro-3-(trifluoromethyl)benzyl)-1-(((3S)-1-(3-cyano-1-azetidinyl) sulfonyl)-3-piperidinyl)carbonyl)-D-prolinamide;

1-(((2S)-4(3-cyano-1-azetidinyl)sulfonyl)-2-piperazinyl) carbonyl)-N-(3-fluoro-4-methylbenzyl)-D-prolinamide;

1-(((3S)-1-(3-cyano-1-azetidinyl)sulfonyl)-3-piperidinyl) carbonyl)-N-(2-fluoro-3-(trifluoromethyl)benzyl)-D-prolinamide;

1-(((3S)-1(3-cyano-1-azetidinyl)sulfonyl)-3-piperidinyl) carbonyl)-N-(3,4-dimethylbenzyl)-D-prolinamide;

1-(((3S)-1-(3-cyano-1-azetidinyl)sulfonyl)-3-piperidinyl) carbonyl)-N-(Pentafluorobenzyl)-D-prolinamide;

1-(((3S)-1-(((2R)-2-phenyl-1-azetidinyl)sulfonyl)-3-piperidinyl) carbonyl)-N-(4-(trifluoromethyl)benzyl)-D-prolinamide;

1-(((3S)-1-(((2S)-2-phenyl-1-azetidinyl)sulfonyl)-3-piperidinyl) carbonyl)-N-(4-(trifluoromethyl)benzyl)-D-prolinamide;

1-(((3S)-1-(3-(difluoromethoxy)-1-azetidinyl)sulfonyl)-3-piperidinyl) carbonyl)-N-(4-(trifluoromethyl)benzyl)-D-prolinamide;

(1R,3R,5R)-2-(((3S)-1-(3-cyano-1-azetidinyl)sulfonyl)-3-piperidinyl) carbonyl)-N-1)-N-((5-(trifluoromethyl)-2-pyridinyl)methyl)-2-azabicyclo[3.1.0]hexane-3-carboxamide;

1-(((3S)-1-(3-cyano-1-azetidinyl)sulfonyl)-3-piperidinyl) carbonyl)-N-(3-(trifluoromethyl)benzyl)-D-prolinamide;

1-(((3S)-1(3-cyano-1-azetidinyl)sulfonyl)-3-piperidinyl) carbonyl)-N-(2,3,5-trifluorobenzyl)-D-prolinamide;

1-(((3S)-1-(3-cyano-1-azetidinyl)sulfonyl)-3-piperidinyl) carbonyl)-N-((3R)-4,6-difluoro-2,3-dihydro-1-benzofuran-3-yl)-D-prolinamide;

1-(((3S)-1-(3-cyano-1-azetidinyl)sulfonyl)-3-piperidinyl) carbonyl)-N-((3S)-4,6-difluoro-2,3-dihydro-1-benzofuran-3-yl)-D-prolinamide;

1-(((3S)-1-(3-cyano-1-azetidinyl)sulfonyl)-3-piperidinyl) carbonyl)-N-(3-methyl-5-(trifluoromethyl)benzyl)-D-prolinamide;

1-(((3S)-1-(3-cyano-1-azetidinyl)sulfonyl)-3-piperidinyl) carbonyl)-N-(2,4-difluorobenzyl)-D-prolinamide;

1-(((3S)-1-(3-cyano-1-azetidinyl)sulfonyl)-3-piperidinyl) carbonyl)-N-methyl-N-(4-(trifluoromethyl)benzyl)-D-prolinamide;

1-(((3S)-1-((3-(1H-pyrrol-1-yl)-1-azetidinyl)sulfonyl)-3-piperidinyl) carbonyl)-N-(4-(trifluoromethyl)benzyl)-D-prolinamide;

1-(((3S)-1-(3-hydroxy-3-phenyl-1-azetidinyl)sulfonyl)-3-piperidinyl) arbonyl)-N-(4-(trifluoromethyl)benzyl)-D-prolinamide;

1-(((3S)-1-((3-cyano-1-azetidinyl)sulfonyl)-3-piperidinyl) carbonyl)-N-((5-(trifluoromethyl)-2-pyridinyl)methyl)-D-prolinamide;

1-(((3S)-1-(3-cyano-1-azetidinyl)sulfonyl)-3-piperidinyl) carbonyl)-N-(3-fluoro-5-(trifluoromethyl)benzyl)-D-prolinamide;

1-(((3S)-1-(3-(trifluoromethyl)-1-azetidinyl)sulfonyl)-3-piperidinyl) carbonyl)-N-(4-(trifluoromethyl)benzyl)-D-prolinamide;

1-(((3S)-1-(3-cyano-1-azetidinyl)sulfonyl)-3-piperidinyl) carbonyl)-N-(4-fluoro-2-methylbenzyl)-D-prolinamide;

N-(4-(trifluoromethyl)benzyl)-1-(((3S)-1-(((3S)-3-(trifluoromethyl)-1-pyrrolidinyl) sulfonyl)-3-piperidinyl) carbonyl)-D-prolinamide;

1-(((3S)-1-(3-cyano-1-azetidinyl)sulfonyl)-3-piperidinyl) carbonyl)-N-(3-methoxy-4-methylbenzyl)-D-prolinamide;

1-(((3S)-1-(3-cyano-1-azetidinyl)sulfonyl)-3-piperidinyl) carbonyl)-N-MR)-2-methoxy1-(3-(trifluoromethyl)phenyl)ethyl)-D-prolinamide;

1-(((3S)-1-((3-cyano-1-azetidinyl)sulfonyl)-3-piperidinyl) carbonyl)-N-MS)-2-methoxy-1-(3-(trifluoromethyl)phenyl)ethyl)-D-prolinamide;

1-(((3S)-1-(3-cyano-1-azetidinyl)sulfonyl)-3-piperidinyl) carbonyl)-N-(3,5-dichlorobenzyl)-D-prolinamide;

1-(((3S)-1-(3-cyano-1-azetidinyl)sulfonyl)-3-piperidinyl) carbonyl)-N-MR)-1-(3,5-difluorophenyl)ethyl)-D-prolinamide;

1-(((3S)-1-(3-cyano-1-azetidinyl)sulfonyl)-3-piperidinyl) carbonyl)-N-(2,5-difluorobenzyl)-D-prolinamide;

1-(((3S)-1-(3-(3-chlorophenyl)-1-azetidinyl)sulfonyl)-3-piperidinyl) carbonyl)-N-(4-(trifluoromethyl)benzyl)-D-prolinamide;

1-(((3S)-1-(3-cyano-1-azetidinyl)sulfonyl)-3-piperidinyl) carbonyl)-N-((2-(trifluoromethyl)-5-pyrimidinyl)methyl)-D-prolinamide;

1-(((3S)-1-(3-cyano-1-azetidinyl)sulfonyl)-3-piperidinyl) carbonyl)-N-MS)-2-hydroxy-1-(3-(trifluoromethyl) phenyl)ethyl)-D-prolinamide;
N-(3-chloro-2-fluorobenzyl)-1-(((3S)-1-(3-cyano-1-azetidinyl) sulfonyl)-3-piperidinyl)carbonyl)-D-prolinamide;
1-(((3S)-1-(3-cyano-1-azetidinyl)sulfonyl)-3-piperidinyl) carbonyl)-N-((6-(trifluoromethyl)-3-pyridinyl) methyl)-D-prolinamide;
1-(((3S)-1-(3-cyano-1-azetidinyl)sulfonyl)-3-piperidinyl) carbonyl)-N-(4-(fluoromethyl)benzyl)-D-prolinamide;
(3S)-1-(3-cyano-1-azetidinyl) sulfonyl)-N-methyl-N-MR)-1-methyl-2-oxo-2-(((1R)-1-(4-(trifluoromethyl) phenyl) ethyl)amino)ethyl)-3-piperidinecarboxamide;
1-(((3S)-1-(3-cyano-1-azetidinyl)sulfonyl)-3-piperidinyl) carbonyl)-N-(2-methoxy-4-methylbenzyl)-D-prolinamide;
N-(2-chloro-3-fluorobenzyl)-1-(((3S)-1-(3-cyano-1-azetidinyl) sulfonyl)-3-piperidinyl)carbonyl)-D-prolinamide;
(2S)-N-((2R)-1-(((1R)-1-(4-chloro-2-fluorophenyl)ethyl) amino)-1-oxo-2-propanyl)-4-((3-cyano-1-azetidinyl) sulfonyl)-N-methyl-2-morpholinecarboxamide;
1-(((3S)-1-(3-cyano-1-azetidinyl)sulfonyl)-3-piperidinyl) carbonyl)-N-(2,3,4,6-tetrafluorobenzyl)-D-prolinamide;
1-(((3S)-1-(3-(4-chlorophenoxy)-1-azetidinyl)sulfonyl)-3-piperidinyl) carbonyl)-N-(4-(trifluoromethyl)benzyl)-D-prolinamide;
1-(((3S)-1-((cis-3-carbamoylcyclobutyl)sulfonyl)-3-piperidinyl) carbonyl)-N-(4-(trifluoromethyl)benzyl)-D-prolinamide;
(4S)-1-(((3S)-1-(3-cyano-1-azetidinyl)sulfonyl)-3-piperidinyl) carbonyl)-4-fluoro-N-(3-(trifluoromethyl) benzyl)-D-prolinamide;
1-(((2S)-4-(3-cyano-1-azetidinyl)sulfonyl)-2-piperazinyl) carbonyl)-N-((1R)-1-(4-(trifluoromethyl)phenyl) ethyl)-D-prolinamide;
N-(3,5-difluorobenzyl)-1-(((3S)-1-(3-(methylsulfonyl)-1-azetidinyl) sulfonyl)-3-piperidinyl)carbonyl)-D-prolinamide;
1-(((3S)-1-(3-cyano-1-azetidinyl)sulfonyl)-3-piperidinyl) carbonyl)-N-MS)-1-(4-(trifluoromethyl)phenyl)ethyl)-D-prolinamide;
(3S)-1-(3-cyano-1-azetidinyl)sulfonyl)-N-methyl-N-MR)-1-methyl-2-oxo-2-(4-(trifluoromethyl) benzyl) amino)ethyl)-3-piperidinecarboxamide;
1-(((3S)-1-(3-cyano-1-azetidinyl)sulfonyl)-3-piperidinyl) carbonyl)-N-(2,3-dimethylbenzyl)-D-prolinamide;
1-(((3S)-1-(3-cyano-1-azetidinyl)sulfonyl)-3-piperidinyl) carbonyl)-N-(4-(difluoromethoxy)benzyl)-D-prolinamide;
1-(((3S)-1-(3-cyano-1-azetidinyl)sulfonyl)-3-piperidinyl) carbonyl)-N-(4-fluorobenzyl)-D-prolinamide;
N-(3-chlorobenzyl)-1-(((3S)-1-(3-cyano-1-azetidinyl) sulfonyl)-3-piperidinyl) carbonyl)-D-prolinamide;
1-(((3S)-1-(3-cyano-1-azetidinyl)sulfonyl)-3-piperidinyl) carbonyl)-N-(4-fluoro-3-methylbenzyl)-D-prolinamide;
N-(2-chloro-5-fluorobenzyl)-1-(((3S)-1-(3-cyano-1-azetidinyl) sulfonyl)-3-piperidinyl)carbonyl)-D-prolinamide;
N-((1R)-1-(4-chloro-3-fluorophenyl)-2-hydroxyethyl)-1-(((3S)-1-((3-cyano-1-azetidinyl) sulfonyl)-3-piperidinyl)-D-prolinamide;
1-(((3S)-1-(3-cyano-1-azetidinyl)sulfonyl)-3-piperidinyl) carbonyl)-N-((1R)-2,3-dihydro-1H-inden-1-yl)-D-prolinamide. 1-(((3S)-1-(3-cyano-1-azetidinyl)sulfonyl)-3-piperidinyl) carbonyl)-N-((1S)-2,3-dihydro-1H-inden-1-yl)-D-prolinamide;
N-(3-chloro-5-methylbenzyl)-1-(((3S)-1-(3-cyano-1-azetidinyl) sulfonyl)-3-piperidinyl)carbonyl)-D-prolinamide;
1-(((3S)-1-(3-cyano-1-azetidinyl)sulfonyl)-3-piperidinyl) carbonyl)-N-(4-fluoro-3,5-dimethylbenzyl)-D-prolinamide;
1-(((3S)-1-(3-cyano-1-azetidinyl)sulfonyl)-3-piperidinyl) carbonyl)-N-(4-cyclopropylbenzyl)-D-prolinamide;
(3R)-4-(((3S)-1-(3-cyano-1-azetidinyl)sulfonyl)-3-piperidinyl) carbonyl)-N-(4-(difluoromethyl)benzyl)-3-morpholinecarboxamide;
1-(((3S)-1-(3-cyclopropyl-3-fluoro-1-azetidinyl)sulfonyl)-3-piperidinyl) carbonyl)-N-(4-(trifluoromethyl) benzyl)-D-prolinamide;
1-(((3S)-1-(3-cyano-1-azetidinyl)sulfonyl)-3-piperidinyl) carbonyl)-N-MR)-1-(4-methylphenypethyl)-D-prolinamide;
1-(((3S)-1-(3-cyano-1-azetidinyl)sulfonyl)-3-piperidinyl) carbonyl)-N-MS)-1-(4-methylphenypethyl)-D-prolinamide;
1-(((3S)-1-(3-cyano-1-azetidinyl)sulfonyl)-3-piperidinyl) carbonyl)-N-(3-fluoro-4-methoxybenzyl)-D-prolinamide;
N-((1S)-1-(4-chloro-3-fluorophenypethyl)-1-(((3S)-1-((3-cyano-1-azetidinyl) sulfonyl)-3-piperidinyl)carbonyl)-D-prolinamide;
1-(((3S)-1-(3-fluoro-3-phenyl-1-azetidinyl)sulfonyl)-3-piperidinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-MR)-1-(3-(trifluoromethyl)phenyl)ethyl)-D-prolinamide;
1-(((3S)-1-(3-hydroxy-3-(trifluoromethyl)-1-azetidinyl) sulfonyl)-3-piperidinyl)carbonyl)-N-(4-(trifluoromethyl)benzyl)-D-prolinamide;
1-(((3S)-1-(3-cyano-1-azetidinyl)sulfonyl)-3-piperidinyl) carbonyl)-N-MS)-1-(3,5-difluorophenyl)propyl)-D-prolinamide;
1-(((3S)-1-(3(4-fluorophenyl)amino)-1-azetidinyl)sulfonyl)-3-piperidinyl) carbonyl)-N-(4-(trifluoromethyl) benzyl)-D-prolinamide;
1-(((3S)-1-(3-cyano-1-azetidinyl)sulfonyl)-3-pyrrolidinyl) carbonyl)-N-(2-fluoro-4-(trifluoromethyl)benzyl)-D-prolinamide;
1-(((3S)-1-(((3R)-2-oxo-3-azepanyl)sulfonyl)-3-piperidinyl) carbonyl)-N-(4-(trifluoromethyl)benzyl)-D-prolinamide;
1-(((3S)-1-(((3S)-2-oxo-3-azepanyl)sulfonyl)-3-piperidinyl)carbonyl)-N-(4- (trifluoromethyl)benzyl)-D-prolinamide;
1-(((3S)-1-(3-(4-fluorophenyl)-1-azetidinyl)sulfonyl)-3-piperidinyl) carbonyl)-N-(4-(trifluoromethyl)benzyl)-D-prolinamide;
1-(((3S)-1-(3-cyclobutyl-1-azetidinyl)sulfonyl)-3-piperidinyl) carbonyl)-N-(4-(trifluoromethyl)benzyl)-D-prolinamide;
1-(((3S)-1-(3-((trifluoroacetypamino)-1-azetidinyl)sulfonyl)-3-piperidinyl) carbonyl)-N-(4-(trifluoromethyl) benzyl)-D-prolinamide. 1-(((3S)-1-(3-methoxy-1-azetidinyl)sulfonyl)-3-piperidinyl) carbonyl)-N-(4-(trifluoromethyl)benzyl)-D-prolinamide;
(4S)-1-(((3S)-1-(3-cyano-1-azetidinyl)sulfonyl)-3-piperidinyl) carbonyl)-4-fluoro-N-((1R)-1-(3-(trifluoromethyl)phenyl)ethyl)-D-prolinamide;

1-(((3S)-1-(3-cyano-1-azetidinyl)sulfonyl)-3-piperidinyl) carbonyl)-N-(3-fluorobenzyl)-D-prolinamide;

1-(((3S)-1(3-cyano-1-azetidinyl)sulfonyl)-3-piperidinyl) carbonyl)-N-(3-fluoro-5-methylbenzyl)-D-prolinamide;

1-(((3S)-1-(3-(methylsulfonyl)-1-azetidinyl)sulfonyl)-3-piperidinyl) carbonyl)-N-((5-(trifluoromethyl)-2-pyridinyl)methyl)-D-prolinamide;

1-(((3S)-1-(3-cyano-1-azetidinyl)sulfonyl)-3-piperidinyl) carbonyl)-N-((4R)-3,4-dihydro-2H-chromen-4-yl)-D-prolinamide;

1-(((3S)-1-(3-cyano-1-azetidinyl)sulfonyl)-3-piperidinyl) carbonyl)-N-((4S)-3,4-dihydro-2H-chromen-4-yl)-D-prolinamide;

1-(((1R,4S,5R)-2-(3-cyano-1-azetidinyl) sulfonyl)-2-azabicyclo[3.1.01]hex-4-yl)carbonyl)-N-(4-(trifluoromethyl)benzyl)-D-prolinamide;

1-(((1S,4R,5S)-2-(3-cyano-1-azetidinyl) sulfonyl)-2-azabicyclo[3.1.01]hex-4-yl)carbonyl)-N-(4-(trifluoromethyl)benzyl)-D-prolinamide;

1-(((3S)-1-(3-cyano-1-azetidinyl)sulfonyl)-3-piperidinyl) carbonyl)-N-(5-fluoro-2-methylbenzyl)-D-prolinamide;

1-(((3S)-1-(3-ethyl-3-hydroxy-1-azetidinyl)sulfonyl)-3-piperidinyl) carbonyl)-N-(2-fluoro-4-(trifluoromethyl) benzyl)-D-prolinamide;

N-((1R)-1-(4-chlorophenyl)ethyl)-1-(((2S)-4-((3-cyano-1-azetidinyl) sulfonyl)-2-piperazinyl)carbonyl)-D-prolinamide;

1-(((3R)-1-(3-cyano-1-azetidinyl)sulfonyl)-3-fluoro-3-piperidinyl) carbonyl)-N-(4-(trifluoromethyl)benzyl)-D-prolinamide or 1-(((3S)-1-(3-cyano-1-azetidinyl) sulfonyl)-3-fluoro-3-piperidinyl)carbonyl)-N-(4-(trifluoromethyl)benzyl)-D-prolinamide;

1-(((3S)-1-(3-cyano-1-azetidinyl) sulfonyl)-3-piperidinyl)carbonyl)-N-((3-fluoro-5-(trifluoromethyl)-2-pyridinyl)methyl)-D-prolinamide;

1-(((3S)-1-(3-cyano-1-azetidinyl)sulfonyl)-3-piperidinyl) carbonyl)-N-(2,3-difluorobenzyl)-D-prolinamide;

1-(((2S)-4-(3-cyano-1-azetidinyl)sulfonyl)-2-morpholinyl) carbonyl)-N-(3,5-difluorobenzyl)-D-prolinamide;

methyl cis-3-(((3S)-3-(((2R)-2-((4-(trifluoromethyl)benzyl) carbamoyl)-1-pyrrolidinyl)carbonyl)-1-piperidinyl)sulfonyl)cyclobutanecarboxylate;

methyl trans-3-(((3S)-3-(((2R)-2-((4-(trifluoromethyl)benzyl) carbamoyl)-1-pyrrolidinyl)carbonyl)-1-piperidinyl)sulfonyl)cyclobutanecarboxylate;

1-(((3S)-1-(3-cyano-1-azetidinyl)sulfonyl)-3-piperidinyl) carbonyl)-N-MR)-1-(2,5-difluorophenyl)-2,2-difluoroethyl)-D-prolinamide;

1-(((3S)-1-(3-cyano-1-azetidinyl)sulfonyl)-3-piperidinyl) carbonyl)-N-MS)-1-(2,5-difluorophenyl)-2,2-difluoroethyl)-D-prolinamide;

N-(3-chloro-5-(trifluoromethyl)benzyl)-1-(((3S)-1-(3-cyano-1-azetidinyl) sulfonyl)-3-piperidinyl)carbonyl)-D-prolinamide;

1-(((3S)-1-(3-(trifluoromethoxy)-1-azetidinyl)sulfonyl)-3-piperidinyl) carbonyl)-N-(4-(trifluoromethyl)benzyl)-D-prolinamide;

1-(((3S)-1(3-(Pentyloxy)-1-azetidinyl)sulfonyl)-3-piperidinyl) carbonyl)-N-(4-(trifluoromethyl)benzyl)-D-prolinamide;

1-(((3R)-1-(3-cyano-1-azetidinyl)sulfonyl)-3-piperidinyl) carbonyl)-N-(2-fluoro-4-(trifluoromethyl)benzyl)-D-prolinamide;

1-(((3S)-1-(3-cyano-1-azetidinyl)sulfonyl)-3-piperidinyl) carbonyl)-N-MR)-1-(4-cyanophenyl)ethyl)-D-prolinamide;

1-(((3S)-1-(3-cyano-1-azetidinyl)sulfonyl)-3-piperidinyl) carbonyl)-N-(4-methyl-3-(trifluoromethyl)benzyl)-D-prolinamide;

N-(5-chloro-2-fluorobenzyl)-1-(((3S)-1-(3-cyano-1-azetidinyl) sulfonyl)-3-piperidinyl)carbonyl)-D-prolinamide;

1-(((3S)-1-(3-cyano-1-azetidinyl)sulfonyl)-3-piperidinyl) carbonyl)-N-(4-cyanobenzyl)-D-prolinamide;

1-(((3S)-1-(3-cyano-1-azetidinyl)sulfonyl)-3-piperidinyl) carbonyl)-N-(2-fluoro-4-methoxybenzyl)-D-prolinamide;

N-((R)-3-azetidinyl(4-chloro-2,5-difluorophenyl) methyl)-1-(((3S)-1-((3-cyano-1-azetidinyl)sulfonyl)-3-piperidinyl)carbonyl)-D-prolinamide;

1-(((3S)-1-((3-cyano-1-azetidinyl)sulfonyl)-3-piperidinyl) carbonyl)-N-MR)-2-hydroxy-1-(4-(trifluoromethyl)phenyl)ethyl)-D-prolinamide;

1-(((3S)-1-((3-(1H-imidazol-1-yl)-1-azetidinyl)sulfonyl)-3-piperidinyl) carbonyl)-N-(4-(trifluoromethyl)benzyl)-D-prolinamide;

N4(7S)-bicyclo[4.2.0octa-1,3,5-trien-7-yl)-1-(((3S)-1-((3-cyano-1-azetidinyl) sulfonyl)-3-piperidinyl)carbonyl)-D-prolinamide;

1-(((3S)-1-(3-cyano-1-azetidinyl)sulfonyl)-3-piperidinyl) carbonyl)-N-(2-methylbenzyl)-D-prolinamide;

N-(2-chlorobenzyl)-1-(((3S)-1-(3-cyano-1-azetidinyl) sulfonyl)-3-piperidinyl) carbonyl)-D-prolinamide;

N-((3R)-4-chloro-2,3-dihydro-1-benzofuran-3-yl)-1-(((3S)-1-((3-cyano-1-azetidinyl) sulfonyl)-3-piperidinyl) carbonyl)-D-prolinamide & N4(3S)-4-chloro-2,3-dihydro-1-benzofuran-3-yl)-1-(((3S)-1-(3-cyano-1-azetidinyl) sulfonyl)-3-piperidinyl)carbonyl)-D-prolinamide;

1-(((3S)-1-(3-(4-pyridinyloxy)-1-azetidinyl)sulfonyl)-3-piperidinyl) carbonyl)-N-(4-(trifluoromethyl)benzyl)-D-prolinamide;

(4S)-1-(((3S)-1-(3-cyano-1-azetidinyl)sulfonyl)-3-piperidinyl) carbonyl)-4-hydroxy-N-(4-(trifluoromethyl) benzyl)-D-prolinamide;

1-(((3S)-1-((3-(1H-pyrazol-1-yl)-1-azetidinyl)sulfonyl)-3-piperidinyl) carbonyl)-N-(4-(trifluoromethyl)benzyl)-D-prolinamide;

N-(2-chloro-3-methoxybenzyl)-1-(((3S)-1-(3-cyano-1-azetidinyl) sulfonyl)-3-piperidinyl)carbonyl)-D-prolinamide. 1-(((3S)-1-(3-cyano-1-azetidinyl)sulfonyl)-3-piperidinyl) carbonyl)-N-MR)-1-(3-fluoro-4-methoxyphenyl)ethyl)-D-prolinamide;

1-(((3S)-1-(3-cyano-1-azetidinyl)sulfonyl)-3-piperidinyl) carbonyl)-N-MS)-1-(3-fluoro-4-methoxyphenypethyl)-D-prolinamide;

1-(((3S)-1-((trans-3-cyanocyclobutyl)sulfonyl)-3-piperidinyl) carbonyl)-N-(4-(trifluoromethyl)benzyl)-D-prolinamide;

1-(((3S)-1-(3-cyano-1-azetidinyl)sulfonyl)-3-piperidinyl) carbonyl)-N-((cis-4-(trifluoromethyl)cyclohexyl) methyl)-D-prolinamide;

1-(((3S)-1-(3-cyano-1-azetidinyl)sulfonyl)-3-piperidinyl) carbonyl)-N-((4- (trifluoromethyl)cyclohexyl)methyl)-D-prolinamide;

N-(3-chloro-4-methoxybenzyl)-1-(((3S)-1-(3-cyano-1-azetidinyl) sulfonyl)-3-piperidinyl)carbonyl)-D-prolinamide;

1-(((3S)-1-(3-cyano-1-azetidinyl)sulfonyl)-3-piperidinyl) carbonyl)-N-MR)-1-(4-fluoro-3-methylphenypethyl)-D-prolinamide;
1-(((3S)-1-(3-cyano-1-azetidinyl)sulfonyl)-3-piperidinyl) carbonyl)-N-MS)-1-(4-fluoro-3-methylphenypethyl)-D-prolinamide;
1-(((3S)-1-(3-cyano-1-azetidinyl)sulfonyl)-3-piperidinyl) carbonyl)-N-MR)-1-(4-(difluoromethoxy)phenyl) ethyl)-D-prolinamide;
1-(((3S)-1-(3-cyano-1-azetidinyl)sulfonyl)-3-piperidinyl) carbonyl)-N-MS)-1-(4-(difluoromethoxy)phenyl) ethyl)-D-prolinamide;
N-((1R)-1-(2-fluoro-4-(trifluoromethyl)pheny) ethyl)-1-(((3S)-1-(((3-hydroxy-3-methyl-1-azetidinyl)sulfonyl)-3-piperidinyl) carbonyl)-D-prolinamide;
1-(((3S)-1-(3-cyano-1-azetidinyl)sulfonyl)-3-piperidinyl) carbonyl)-N-(2-fluoro-3-methylbenzyl)-D-prolinamide;
1-(((3S)-1-(3-cyano-1-azetidinyl)sulfonyl)-3-piperidinyl) carbonyl)-N-(2-fluoro-6-methylbenzyl)-D-prolinamide;
N-(2-fluoro-4-(trifluoromethyl)benzyl)-1-(((3S)-1-((3-hydroxy-1-azetidinyl) sulfonyl)-3-piperidinyl)carbonyl)-D-prolinamide;
N-4-6-chloro-3-pyridinyl)methyl)-1-(((3S)-1-((3-cyano-1-azetidinyl) sulfonyl)-3-piperidinyl)carbonyl)-D-prolinamide;
1-(((3S)-1-(3-cyano-1-azetidinyl)sulfonyl)-3-piperidinyl) carbonyl)-N-(4-methoxy-2-methylbenzyl)-D-prolinamide;
N-(5-chloro-2-methylbenzyl)-1-(((3S)-1-(3-cyano-1-azetidinyl) sulfonyl)-3-piperidinyl)carbonyl)-D-prolinamide;
1-(((3S)-1(3-cyano-1-azetidinyl)sulfonyl)-3-piperidinyl) carbonyl)-N-((1R)-5-fluoro-6-methoxy-2,3-dihydro-1H-inden-1-yl)-D-prolinamide;
1-(((3S)-1-(3-cyano-1-azetidinyl)sulfonyl)-3-piperidinyl) carbonyl)-N-((1S)-5-fluoro-6-methoxy-2,3-dihydro-1H-inden-1-yl)-D-prolinamide;
1-(((3S)-1-(3-cyano-1-azetidinyl)sulfonyl)-3-piperidinyl) carbonyl)-N-(2,3,5,6-tetrafluorobenzyl)-D-prolinamide;
1-(((3S)-1-(3-cyano-1-azetidinyl)sulfonyl)-3-piperidinyl) carbonyl)-N-MR)-1-(4-methoxyphenyl)propyl)-D-prolinamide;
1-(((3S)-1-(3-cyano-1-azetidinyl)sulfonyl)-3-piperidinyl) carbonyl)-N-MS)-1-(4-methoxyphenyl)propyl)-D-prolinamide;
1-(((3S)-1-((trans-3-carbamoylcyclobutyl)sulfonyl)-3-piperidinyl) carbonyl)-N-(4-(trifluoromethyl)benzyl)-D-prolinamide;
1-(((3S)-1-(3-hydroxy-1-azetidinyl)sulfonyl)-3-piperidinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-MR)-1-(4-(difluoromethoxy)-3-methoxyphenyl)ethyl)-D-prolinamide;
1-(((3S)-1(3-cyano-1-azetidinyl)sulfonyl)-3-piperidinyl) carbonyl)-N-MS)-1-(4-(difluoromethoxy)-3-methoxyphenypethyl)-D-prolinamide;
1-(((3S)-1-(3-cyano-1-azetidinyl)sulfonyl)-3-piperidinyl) carbonyl)-N-MR)-1-(5-fluoro-2-methoxyphenypethyl)-D-prolinamide;
1-(((3S)-1-(3-cyano-1-azetidinyl)sulfonyl)-3-piperidinyl) carbonyl)-N-MS)-1-(5-fluoro-2-methoxyphenypethyl)-D-prolinamide;
1-(((2R)-4-(3-cyano-1-azetidinyl)sulfonyl)-1-methyl-2-piperazinyl) carbonyl)-N-(4-(trifluoromethyl)benzyl)-D-prolinamide;
1-(((2S)-4-(3-cyano-1-azetidinyl)sulfonyl)-1-methyl-2-piperazinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-(2-fluoro-5-methylbenzyl)-D-prolinamide;
1-(((3S)-1-(3-cyano-1-azetidinyl)sulfonyl)-3-piperidinyl) carbonyl)-N-(3-methylbenzyl)-D-prolinamide;
1-(((3S)-1(1,1-dioxido-3-thietanyl)sulfamoyl)-3-piperidinyl) carbonyl)-N-(4-(trifluoromethyl)benzyl)-D-prolinamide;
1-(((3S)-1-(3-cyano-1-azetidinyl)sulfonyl)-3-pyrrolidinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-(2,5-dichlorobenzyl)-D-prolinamide;
1-(((3S)-1-(3-cyano-1-azetidinyl)sulfonyl)-3-piperidinyl) carbonyl)-N-(4-fluoro-2-(trifluoromethyl)benzyl)-D-prolinamide;
1-(((3S)-1-(1-oxa-6-azaspiro[3.3.1hept-6-ylsulfonyl)-3-piperidinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-((3R)-5-(trifluoromethyl)-2,3-dihydro-1-benzofuran-3-yl)-D-prolinamide & 1-(((3S)-1-(3-cyano-1-azetidinyl) sulfonyl)-3-piperidinyl)carbonyl)-N-((3S)-5-(trifluoromethyl)-2,3-dihydro-1-benzofuran-3-yI)-D-prolinamide;
1-(((3S)-1-(3-cyano-1-azetidinyl)sulfonyl)-3-piperidinyl) carbonyl)-N-(2-fluoro-6-(trifluoromethyl) benzyI)-D-prolinamide;
N-(2-chloro-5-methylbenzyl)-1-(((3S)-1-(3-cyano-1-azetidinyl)sulfonyl)-3-piperidinyl) carbonyI)-D-prolinamide;
N-(4-chloro-3-fluorobenzyl)-1-(((3S)-1-(3-hydroxy-3-methyl-1-azetidinyl) sulfonyl)-3-piperidinyl)carbonyI)-D-prolinamide;
1-(((3S)-1-(3-oxetanylsulfonyl)-3-piperidinyl)carbonyl)-N-(4-(trifluoromethyl)benzyl)-D-prolinamide;
1-(((3S)-1-(3-hydroxy-3-methyl-1-azetidinyl)sulfonyl)-3-piperidinyl) carbonyl)-N-((1R)-1-(4-(trifluoromethyl)phenyl)propyl)-D-prolinamide;
1-(((3S)-1-(3-hydroxy-3-methyl-1-azetidinyl)sulfonyl)-3-piperidinyl) carbonyl)-N-((1S)-1-(4-(trifluoromethyl)phenyl)propyl)-D-prolinamide;
N-(2-fluoro-4-(trifluoromethyl)benzyl)-1-(((3S)-1-(3-hydroxy-3-methyl-1-azetidinyl) sulfonyl)-3-piperidinyl) carbonyl)-D-prolinamide;
1-(((3S)-1-(3-cyano-1-azetidinyl)sulfonyl)-3-piperidinyl) carbonyl)-N-(4-methoxv-3-methylbenzyl)-D-prolinamide;
1-(((3S)-1-(3-cyano-1-azetidinyl)sulfonyl)-3-piperidinyl) carbonyl)-N-(2-fluoro-5-(trifluoromethyl) benzyI)-D-prolinamide;
1-(((3S)-1-((3-(1 H-1,2,4-triazol-1-yl)-1-azetidinyl)sulfonyl)-3-piperidinyl) carbonyl)-N-(4-(trifluoromethyl) benzyI)-D-prolinamide;
1-(((3S)-1(3-cyano-1-azetidinyl)sulfonyl)-3-piperidinyl) carbonyl)-N-(3-fluoro-5-methoxybenzyl)-D-prolinamide;
(4S)-4-fluoro-1-(((3S)-1(3-hydroxy-3-methyl-1-azetidinyl)sulfonyl)-3-piperidinyl) carbonyI)-N-(4-(trifluoromethyl)benzyl)-D-prolinamide;

1-(((3S)-1-(3-cyano-1-azetidinyl)sulfonyl)-3-piperidinyl) carbonyl)-N-(2-fluorobenzyl)-D-prolinamide;
1-(((3S)-1-(3-(3-methyl-1,2,4-oxadiazol-5-0-1-azetidinyl) sulfonyl)-3-piperidinyl)carbonyl)-N-(4-(trifluoromethyl)benzyl)-D-prolinamide;
1-(((3S)-1-(3-((methoxyacetyl)amino)-1-azetidinyl) sulfonyl)-3-piperidinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-(3,5-difluorobenzyl)-L-prolinamide;
1-(((3S)-1-(((2R)-2-(4-chlorophenyl)-1-azetidinyl)sulfonyl)-3-piperidinyl) carbonyl)-N-(4-(trifluoromethyl)benzyl)-D-prolinamide;
1-(((3S)-1-(((2S)-2-(4-chlorophenyl)-1-azetidinyl)sulfonyl)-3-piperidinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-((1R)-1-(2-(difluoromethoxy)-4-fluorophenyethyl)-D-prolinamide;
1-(((3S)-1-(3-(4-chlorobenzyl)-1-azetidinyl)sulfonyl)-3-piperidinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-(5-fluoro-2-methoxybenzyl)-D-prolinamide;
1-(((3S)-1-(3,3-difluoro-1-azetidinyl)sulfonyl)-3-piperidinyl) carbonyl)-N-(4-(trifluoromethyl)benzyl)-D-prolinamide;
N4(7R)-bicyclo[4.2.0]octa-1,3,5-trien-7-yl)-1-(((3S)-1-((3-cyano-1-azetidinyl) sulfonyl)-3-piperidinyl)carbonyl)-D-prolinamide;
N4(7S)-bicyclo[4.2.0]octa-1,3,5-trien-7-yl)-1-(((3S)-1-((3-cyano-1-azetidinyl) sulfonyl)-3-piperidinyl)carbonyl)-D-prolinamide. 1-(((3S)-1-(3-(2-pyridinyl)-1-azetidinyl)sulfonyl)-3-piperidinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-(4-ethoxv-3-fluorobenzyl)-D-prolinamide;
1-(((3S)-1(3-cyano-1-azetidinyl)sulfonyl)-3-piperidinyl) carbonyl)-N-(2,6-dimethylbenzyl)-D-prolinamide;
1-(((3S)-1-(3-((cyclopropylcarbonyl)amino)-1-azetidinyl) sulfonyl)-3-piperidinyl)carbonyl)-N-(4-(trifluoromethyl)benzyl)-D-prolinamide;
1-(((3S)-1-(3-cyano-1-azetidinyl)sulfonyl)-3-piperidinyl) carbonyl)-N-((4R)-2-methyl-1,2,3,4-tetrahydro-4-isoquinolinyl)-D-prolinamide;
1-(((3S)-1-(3-cyano-1-azetidinyl)sulfonyl)-3-piperidinyl) carbonyl)-N-((4S)-2-methyl-1,2,3,4-tetrahydro-4-isoquinolinyl)-D-prolinamide;
1-(((3S)-1-(3-(dimethylcarbamoyl)-1-azetidinyl)sulfonyl)-3-piperidinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-(2-methyl-5-(trifluoromethyl)benzyl)-D-prolinamide;
N-(2-chloro-6-fluorobenzyl)-1-(((3S)-1-(3-cyano-1-azetidinyl) sulfonyl)-3-piperidinyl)carbonyl)-D-prolinamide;
1-(((3S)-1-(((2R)-2-benzyl-1-azetidinyl)sulfonyl)-3-piperidinyl) carbonyl)-N-(4-(trifluoromethyl)benzyl)-D-prolinamide;
1-(((3S)-1-(((2S)-2-benzyl-1-azetidinyl)sulfonyl)-3-piperidinyl) carbonyl)-N-(4-(trifluoromethyl)benzyl)-D-prolinamide;
(1R,3R,5R)-N-((R)-(4-chloro-2,5-difluorophenyl)(cyclopropyl) methyl)-2-(((2S)-4-(methylsulfonyl)-2-piperazinyl) carbonyl)-2-azabicyclo[3.1.0]hexane-3-carboxamide;
1-(((3S)-1-(3-cyano-1-azetidinyl)sulfonyl)-3-piperidinyl) carbonyl)-N-MR)-1-(4-fluorophenypethyl)-D-prolinamide;
1-(((3S)-1-(3-cyano-1-azetidinyl)sulfonyl)-3-piperidinyl) carbonyl)-N-MS)-1-(4-fluorophenypethyl)-D-prolinamide;
1-(((3S)-1-(3-hydroxy-3-methyl-1-azetidinyl)sulfonyl)-3-piperidinyl) carbonyl)-N-(4-(trifluoromethyl)benzyl)-D-prolinamide;
N-((1R)-1-(4-chlorophenyl)-2-hydroxyethyl)-1-(((3S)-1-((3-cyano-1-azetidinyl) sulfonyl)-3-piperidinyl)carbonyl)-D-prolinamide;
1-(((3S)-1-(3-tert-butoxy-1-azetidinyl)sulfonyl)-3-piperidinyl) carbonyl)-N-(4-(trifluoromethyl)benzyl)-D-prolinamide;
1-(((3S)-1-(3-pentyl-1-azetidinyl)sulfonyl)-3-piperidinyl) carbonyl)-N-(4-(trifluoromethyl)benzyl)-D-prolinamide;
1-(((3S)-1-(3-(3R)-tetrahydro-3-furanyl)-1-azetidinyl) sulfonyl)-3-piperidinyl)carbonyl)-N-(4-(trifluoromethyl)benzyl)-D-prolinamide;
1-(((3S)-1-(3-(3S)-tetrahydro-3-furanyl)-1-azetidinyl) sulfonyl)-3-piperidinyl)carbonyl)-N-(4-(trifluoromethyl)benzyl)-D-prolinamide;
1-(((3S)-1-(3-cyano-1-azetidinyl)sulfonyl)-3-piperidinyl) carbonyl)-N-MR)-2,2-dimethyl-1-(4-(trifluoromethyl) phenyl)propyl)-D-prolinamide;
1-(((3S)-1-(3-cyano-1-azetidinyl)sulfonyl)-3-piperidinyl) carbonyl)-N-(5-methyl-2-(trifluoromethyl)benzyl)-D-prolinamide;
1-(((3S)-1(6-hydroxy-6-(trifluoromethyl)-2-azaspiro[3.3.]hept-2-yl) sulfonyl)-3-piperidinyl)carbonyl)-N-(4-(trifluoromethyl)benzyl)-D-prolinamide;
1-(((3S)-1-(dimethylsulfamoyl)-3-piperidinyl)carbonyl)-N-(4-(trifluoromethyl)benzyl)-D- prolinamide;
1-(((3S)-1-(3-cyano-1-azetidinyl)sulfonyl)-3-piperidinyl) carbonyl)-N-(2-(trifluoromethyl)benzyl)-D-prolinamide;
1-(((3S)-1-(((6R)-6-hydroxy-2-azaspiro[3.4loct-2-yl) sulfonyl)-3-piperidinyl)carbonyl)-N-(4-(trifluoromethyl)benzyl)-D-prolinamide;
1-(((3S)-1-(((6S)-6-hydroxy-2-azaspiro[3.4]oct-2-yl) sulfonyl)-3-piperidinyl) carbonyl)-N-(4-(trifluoromethyl)benzyl)-D-prolinamide;
1-(((3S)-1-(3-((cyclobutylcarbonyl)amino)-1-azetidinyl) sulfonyl)-3-piperidinyl)carbonyl)-N-(4-(trifluoromethyl)benzyl)-D-prolinamide;
N-benzyl-1-(((3S)-1-(3-cyano-1-azetidinyl)sulfonyl)-3-piperidinyl) carbonyl)-D-prolinamide;
1-(((3S)-1-(3-fluoro-3-(trifluoromethyl)-1-azetidinyl) sulfonyl)-3-piperidinyl) carbonyl)-N-(4-(trifluoromethyl)benzyl)-D-prolinamide;
1-(((3S)-1-(3-cyano-1-azetidinyl)sulfonyl)-3-piperidinyl) carbonyl)-N-MR)-1-(2,3-difluorophenypethyl)-D-prolinamide;
1-(((3S)-1-(3-cyano-1-azetidinyl)sulfonyl)-3-piperidinyl) carbonyl)-N-MS)-1-(2,3-difluorophenypethyl)-D-prolinamide;
1-(((3S)-1-(3-cyano-1-azetidinyl)sulfonyl)-3-piperidinyl) carbonyl)-N-(2,5-dimethylbenzyl)-D-prolinamide;
1-(((3S)-1-(3R)-tetrahydro-3-furanylsulfonyl)-3-piperidinyl) carbonyl)-N-(4-(trifluoromethyl)benzyl)-D-prolinamide;

1-(((3S)-1-(3S)-tetrahydro-3-furanylsulfonyl)-3-piperidinyl) carbonyl)-N-(4-(trifluoromethyl)benzyl)-D-prolinamide;

1-(((3S)-1-(3-cyano-1-azetidinyl)sulfonyl)-3-piperidinyl) carbonyl)-N-MR)-2,2,2-trifluoro-1-(4-(trifluoromethyl)phenyl)ethyl)-D-prolinamide;

1-(((3S)-1-(((2R)-2-methyl-1-azetidinyl)sulfonyl)-3-piperidinyl) carbonyl)-N-(4-(trifluoromethyl)benzyl)-D-prolinamide;

1-(((3S)-1-(((2S)-2-methyl-1-azetidinyl)sulfonyl)-3-piperidinyl) carbonyl)-N-(4-(trifluoromethyl)benzyl)-D-prolinamide;

N-(5-chloro-2-methoxybenzyl)-1-(((3S)-1-(3-cyano-1-azetidinyl) sulfonyl)-3-piperidinyl)carbonyl)-D-prolinamide;

N-(4-(trifluoromethyl)benzyl)-1-(((3S)-1-(3-(3-(trifluoromethyl) phenyl)-1-azetidinyl)sulfonyl)-3-piperidinyl)carbonyl)-D-prolinamide;

1-(((3S)-1-(3,3-difluoro-1-pyrrolidinyl)sulfonyl)-3-piperidinyl) carbonyl)-N-(4-(trifluoromethyl)benzyl)-D-prolinamide;

1-(((3S)-1-(((5-methyl-1,3,4-oxadiazol-2-yl)methyl)sulfamoyl)-3-piperidinyl) carbonyl)-N-(4-(trifluoromethyl)benzyl)-D-prolinamide;

methyl trans-3-(((3S)-3-(((2R)-2-(4-(trifluoromethyl) benzyl) carbamoyl)-1-pyrrolidinyl)carbonyl)-1-piperidinyl)sulfonyl)cyclobutanecarboxylate;

1-(((3S)-1-(3-cyano-1-azetidinyl)sulfonyl)-3-piperidinyl) carbonyl)-N-MS)-2,2,2-trifluoro-1-(3-fluoro-4-methoxyphenypethyl)-D-prolinamide;

1-(((3S)-1-(cyclobutylsulfonyl)-3-piperidinyl)carbonyl)-N-(4-(trifluoromethyl) benzyl)-D-prolinamide;

1-(((3S)-1-(3-cyano-1-azetidinyl)sulfonyl)-3-piperidinyl) carbonyl)-N-(3-(difluoromethoxy)benzyl)-D-prolinamide;

1-(((3S)-1-(3-(acetylamino)-1-azetidinyl)sulfonyl)-3-piperidinyl) carbonyl)-N-(4-(trifluoromethyl)benzyl)-D-prolinamide;

1-(((3S)-1-(3-cyano-1-azetidinyl)sulfonyl)-3-piperidinyl) carbonyl)-N-((4R)-6-methoxy-3,4-dihydro-2H-chromen-4-yl)-D-prolinamide;

1-(((3S)-1-(3-(2,2,2-trifluoroethyl)-1-azetidinyl)sulfonyl)-3-piperidinyl) carbonyl)-N-(4-(trifluoromethyl)benzyl)-D-prolinamide;

1-(((3S)-1-(3-(methoxymethyl)-1-azetidinyl)sulfonyl)-3-piperidinyl) carbonyl)-N-(4-(trifluoromethyl)benzyl)-D-prolinamide;

1-(((2S)-4-(3-cyano-1-azetidinyl)sulfonyl)-2-piperazinyl) carbonyl)-N-(3,5-dichlorobenzyl)-D-prolinamide;

1-(((3S)-1-(3-cyano-1-azetidinyl)sulfonyl)-3-piperidinyl) carbonyl)-N-MR,2R)-2-(trifluoromethyl)cyclobutyl)-D-prolinamide;

1-(((3S)-1-(3-cyano-1-azetidinyl)sulfonyl)-3-piperidinyl) carbonyl)-N-MR,2S)-2-(trifluoromethyl)cyclobutyl)-D-prolinamide;

1-(((3S)-1(3-cyano-1-azetidinyl)sulfonyl)-3-piperidinyl) carbonyl)-N-MS,2R)-2-(trifluoromethyl)cyclobutyl)-D-prolinamide;

1-(((3S)-1(3-cyano-1-azetidinyl)sulfonyl)-3-piperidinyl) carbonyl)-N-MS,2S)-2-(trifluoromethyl)cyclobutyl)-D-prolinamide;

1-(((3S)-1-(1-azaspiro[3.31]hept-1-ylsulfonyl)-3-piperidinyl) carbonyl)-N-(4-(trifluoromethyl)benzyl)-D-prolinamide;

(1R,3S,5R)-2-(((3S)-1-(3-cyano-1-azetidinyl)sulfonyl)-3-piperidinyl) carbonyl)-N-(4-(trifluoromethyl)benzyl)-2-azabicyclo[3.1.0]hexane-3-carboxamide;

N-((1S)-1-(4-chlorophenyl)ethyl)-1-(((3S)-1-((3-cyano-1-azetidinyl) sulfonyl)-3-piperidinyl)carbonyl)-D-prolinamide;

1-(((3S)-1-(3-cyano-1-azetidinyl)sulfonyl)-3-piperidinyl) carbonyl)-N-MR)-1-(2-methoxyphenyl)propyl)-D-prolinamide;

1-(((3S)-1-(3-cyano-1-azetidinyl)sulfonyl)-3-piperidinyl) carbonyl)-N-MS)-1-(2-methoxyphenyl)propyl)-D-prolinamide;

1-(((3S)-1-(1-acetyl-3-azetidinyl)sulfamoyl)-3-piperidinyl) carbonyl)-N-(4-(trifluoromethyl)benzyl)-D-prolinamide;

(1R,3R,5R)-N-((R)-(2,5-difluoro-4-(trifluoromethyl)phenyl)(oxetan-3-yl) methyl)-2-(5-methylthiophene-2-carbonyl)-2-azabicyclo[3.1.0]hexane-3-carboxamide;

(1R,3R,5R)-N-((R)-(2,5-difluoro-4-(trifluoromethyl)phenyl)(oxetan-3-yl) methyl)-2-(1,4-dimethyl-1H-pyrazole-5-carbonyl)-2-azabicyclo[3.1.0]hexane-3-carboxamide;

(1R,3R,5R)-N-((R)-(2,5-difluoro-4-(trifluoromethyl)phenyl)(oxetan-3-yl) methyl)-2-(5-(trifluoromethyl)isoxazole-3-carbonyl)-2-azabicyclo[3.1.01]hexane-3-carboxamide;

(1R,3R,5R)-N-((R)-(2,5-difluoro-4-(trifluoromethyl)phenyl)(oxetan-3-yl) methyl)-2-(3,4-dimethylisoxazole-5-carbonyl)-2-azabicyclo[3.1.01]hexane-3-carboxamide;

(1R,3R,5R)-N-((R)-(2,5-difluoro-4-(trifluoromethyl)phenyl)(oxetan-3-yl) methyl)-2-(3,5-dimethylisoxazole-4-carbonyl)-2-azabicyclo[3.1.0]hexane-3-carboxamide;

(1R,3R,5R)-N-((R)-(2,5-difluoro-4-(trifluoromethyl)phenyl)(oxetan-3-yl) methyl)-2-(3-(trifluoromethyl)isoxazole-5-carbonyl)-2-azabicyclo[3.1.01]hexane-3-carboxamide; and 1-(((3S)-1-(3-cyano-1-azetidinyl)sulfonyl)-3-piperidinyl) carbonyl)-N-(2-(4-(trifluoromethyl)phenyl)ethyl)-D-prolinamide.

16. A compound of claim 1, or a pharmaceutically acceptable salt thereof, wherein the compound is selected from the group consisting of:

(1R,3R,5R)-2-(((3S)-1-(3-cyano-1-azetidinyl)sulfonyl)-3-piperidinyl)carbonyl)-N-(2-fluoro-4-(trifluoromethyl) benzyl)-2-azabicyclo[3.1.0]hexane-3-carboxamide;

1-(((3S)-1-(3-cyano-1-azetidinyl)sulfonyl)-3-piperidinyl) carbonyl)-N-((R)-cyclopropyl(2,5-difluoro-4-(trifluoromethyl)phenyl) methyl)-D-prolinamide;

1-(((2S)-4-(3-cyano-1-azetidinyl)sulfonyl)-2-piperazinyl) carbonyl)-N-(2-fluoro-4-(trifluoromethyl)benzyl)-D-prolinamide; and 1-(((3S)-1-(3-cyano-1-azetidinyl)sulfonyl)-3-piperidinyl) carbonyl)-N-(3,5-difluorobenzyl)-D-prolinamide..

17. The compound of claim 1 in the form of a pharmaceutically acceptable salt.

18. A pharmaceutical composition comprising a pharmaceutically acceptable excipient, carrier or adjuvant and at least one compound or salt of claim 1.

19. The pharmaceutical composition of claim 18, wherein the composition is formulated in a form selected from the group consisting of an injectable fluid, an aerosol, a tablet, a pill, a capsule, a syrup, a cream, a gel and a transdermal patch.

20. A packaged pharmaceutical composition, comprising a pharmaceutical composition of claim 18 and instructions for using the composition to treat a patient suffering from a heart disease.

21. The packaged pharmaceutical composition of claim 20, wherein the heart disease is heart failure.

22. A method of treating heart disease in a mammal which method comprises administering to the mammal a therapeutically effective amount of at least one compound of claim 1, or a pharmaceutical salt thereof or a pharmaceutical composition thereof.

23. The method of claim 22, wherein the heart disease is heart failure.

24. The method of claim 23, wherein the heart failure is congestive heart failure.

25. The method of claim 23, wherein the heart failure is systolic heart failure.

26. A method for modulating the cardiac sarcomere in a mammal which method comprises administering to the mammal an amount of at least one compound of claim 1 or a pharmaceutical salt thereof or a pharmaceutical composition thereof to modulate the cardiac sarcomere in the mammal.

27. A method for potentiating cardiac myosin in a mammal which method comprises administering to the mammal an amount of at least one compound of claim 1 or a pharmaceutical salt thereof or a pharmaceutical composition thereof to potentiate cardiac myosin in the mammal.

\* \* \* \* \*